(12) United States Patent
Ibrahim et al.

(10) Patent No.: US 7,605,168 B2
(45) Date of Patent: Oct. 20, 2009

(54) PDE4B INHIBITORS

(75) Inventors: Prabha N. Ibrahim, Mountain View, CA (US); Ryan Bremer, Albany, CA (US); Sam Gillette, Oakland, CA (US); Hanna Cho, Oakland, CA (US); Marika Nespi, Berkeley, CA (US); Shumeye Mamo, Oakland, CA (US); Chao Zhang, Moraga, CA (US); Dean R. Artis, Kensington, CA (US); Byunghun Lee, Marina, CA (US); Rebecca Zuckerman, Alameda, CA (US)

(73) Assignee: Plexxikon, Inc., Berkeley, CA (US)

( * ) Notice: Subject to any disclaimer, the term of this patent is extended or adjusted under 35 U.S.C. 154(b) by 579 days.

(21) Appl. No.: 11/219,635

(22) Filed: Sep. 2, 2005

(65) Prior Publication Data

US 2006/0100218 A1    May 11, 2006

Related U.S. Application Data

(60) Provisional application No. 60/607,407, filed on Sep. 3, 2004.

(51) Int. Cl.
*A61K 31/437* (2006.01)
*A61K 31/403* (2006.01)
*C07D 471/02* (2006.01)
*C07D 405/02* (2006.01)

(52) U.S. Cl. .................. 514/300; 514/414; 514/415; 546/113; 548/454; 548/516

(58) Field of Classification Search .................. None
See application file for complete search history.

(56) References Cited

U.S. PATENT DOCUMENTS

| | | | |
|---|---|---|---|
| 4,150,949 A | 4/1979 | Smith | |
| 4,568,649 A | 2/1986 | Bertoglio-Matte | |
| 4,626,513 A | 12/1986 | Burton et al. | |
| 4,861,891 A | 8/1989 | Saccomano et al. | |
| 5,143,854 A | 9/1992 | Pirrung et al. | |
| 5,426,039 A | 6/1995 | Wallace et al. | |
| 5,434,049 A | 7/1995 | Okano et al. | |
| 5,449,614 A | 9/1995 | Danos et al. | |
| 5,474,935 A | 12/1995 | Chatterjee et al. | |
| 5,556,752 A | 9/1996 | Lockhart et al. | |
| 5,580,859 A | 12/1996 | Felgner et al. | |
| 5,631,236 A | 5/1997 | Woo et al. | |
| 5,632,957 A | 5/1997 | Heller et al. | |
| 5,658,775 A | 8/1997 | Gilboa | |
| 5,700,637 A | 12/1997 | Southern | |
| 5,721,118 A | 2/1998 | Scheffler | |
| 5,744,305 A | 4/1998 | Fodor et al. | |
| 5,747,276 A | 5/1998 | Hoch et al. | |
| 5,763,198 A | 6/1998 | Hirth et al. | |
| 5,770,456 A | 6/1998 | Holmes | |
| 5,800,992 A | 9/1998 | Fodor et al. | |
| 5,807,522 A | 9/1998 | Brown et al. | |
| 5,830,645 A | 11/1998 | Pinkel et al. | |
| 5,840,485 A | 11/1998 | Lebl et al. | |
| 5,856,174 A | 1/1999 | Lipshutz et al. | |
| 5,877,007 A | 3/1999 | Housey | |
| 5,922,557 A | 7/1999 | Pon | |
| 5,959,098 A | 9/1999 | Goldberg et al. | |
| 5,965,452 A | 10/1999 | Kovacs | |
| 6,013,440 A | 1/2000 | Lipshutz et al. | |
| 6,022,963 A | 2/2000 | McGall et al. | |
| 6,025,155 A | 2/2000 | Hadlacsky et al. | |
| 6,045,996 A | 4/2000 | Cronin et al. | |
| 6,048,695 A | 4/2000 | Bradley et al. | |
| 6,054,270 A | 4/2000 | Southern | |
| 6,090,912 A | 7/2000 | Lebl et al. | |
| 6,096,718 A | 8/2000 | Weitzman et al. | |
| 6,107,478 A | 8/2000 | Pederson et al. | |
| 6,110,456 A | 8/2000 | During | |
| 6,110,458 A | 8/2000 | Freeman et al. | |
| 6,113,913 A | 9/2000 | Brough et al. | |
| 6,117,681 A | 9/2000 | Salmons et al. | |
| 6,178,384 B1 | 1/2001 | Kolossváry | |
| 6,243,980 B1 | 6/2001 | Bronstein et al. | |
| 6,258,606 B1 | 7/2001 | Kovacs | |
| 6,261,776 B1 | 7/2001 | Pirrung et al. | |
| 6,277,489 B1 | 8/2001 | Abbott et al. | |
| 6,277,628 B1 | 8/2001 | Johann et al. | |
| 6,288,234 B1 | 9/2001 | Griffin | |
| 6,294,330 B1 | 9/2001 | Michnick et al. | |
| 6,500,610 B1 | 12/2002 | Pamukcu et al. | |
| 6,559,168 B2 | 5/2003 | Marfat et al. | |
| 2001/0008765 A1 | 7/2001 | Shinoki et al. | |
| 2001/0012537 A1 | 8/2001 | Anderson et al. | |
| 2001/0014448 A1 | 8/2001 | Chappa et al. | |
| 2001/0014449 A1 | 8/2001 | Nerenberg et al. | |
| 2001/0016322 A1 | 8/2001 | Caren et al. | |
| 2001/0018642 A1 | 8/2001 | Balaban et al. | |
| 2001/0019827 A1 | 9/2001 | Dawson et al. | |
| 2002/0009764 A1 | 1/2002 | Thompson et al. | |
| 2002/0165237 A1 | 11/2002 | Fryburg et al. | |
| 2003/0064374 A1 | 4/2003 | Ait Ikhlef et al. | |
| 2004/0106641 A1 | 6/2004 | Hofgen et al. | |

(Continued)

FOREIGN PATENT DOCUMENTS

EP    0154734    9/1985

(Continued)

OTHER PUBLICATIONS

Spina, D., Br J Pharmacol. 2008, 155(3):308-15.*

(Continued)

*Primary Examiner*—Zinna N Davis
(74) *Attorney, Agent, or Firm*—Foley & Lardner LLP

(57) ABSTRACT

Compounds are described that are active on PDE4. Also described are crystal structures of PDE4B determined using X-ray crystallography, the use of PDE4B crystals and structural information for identifying molecular scaffolds, for developing ligands that bind to and modulate PDE4B, and for identifying improved ligands based on known ligands.

16 Claims, 2 Drawing Sheets

FOREIGN PATENT DOCUMENTS

| | | |
|---|---|---|
| EP | 0 667 345 | 8/1995 |
| EP | 1 166 785 | 1/2002 |
| WO | WO 96/17958 | 6/1996 |
| WO | WO 96/18738 | 6/1996 |
| WO | WO 97/46313 | 12/1997 |
| WO | WO 98/45268 | 10/1998 |
| WO | WO 99/09217 | 4/1999 |
| WO | WO 99/20625 | 4/1999 |
| WO | WO 99/21845 | 5/1999 |
| WO | WO 99/51773 | 10/1999 |
| WO | WO 01/02369 | 1/2001 |
| WO | WO 2005/016924 | 2/2005 |
| WO | WO 02/062290 | 8/2006 |

OTHER PUBLICATIONS

Ghavami et al., Drugs R D. 2006, 7(2):63-71.*
Smith et al., Blood 2005, 105(1):308-16.*
Kim, DH and Lerner, A., Blood 1998, 92(7):2484-94.*
Lee F-Y et al. "Synthesis of 1-benzyl-3-(5'-hydroxymethyl-2'-furyl) indazole Analogues as Novel Antiplatelet Agents" Journal of Med. Chem, Amer. Can Society, vol. 44, 3746-3749, 2001.
Ciattini, P.G. et al. "An efficient synthesis fo 3-substituted indoles by palladium-catalyzed coupling reaction of 3-tributylstannylindoles with organic triflates and halides" Tetrhedron Letters Vo. 35, No. 15, 1994 2405-2408.
PCT International Search Report Form PCT/ISA/210 dated Nov. 6, 2006.
Card et al., Structural basis for the activity of drugs that inhibit phosphodiesterases, 12:2233-2247, 2004.
Dym et al., Molecular docking of competitive phosphodiesterase inhibitors, Molecular Pharmacology, 61:20-25, 2002.
Haddad et al., Immunopharmacological potential of selective phosphodiesterase inhibition. I. Differential regulation of lipopolysaccharide-mediated proinflammatory cytokine (Interleukin-6 and tumor necrosis factor-α) Biosynthesis in alveolar epithelial cells, The Journal of Pharmacology and Experimental Therapeutics, 300:559-566, 2002.
Ho et al., Structure of the GAF domain, a ubiquitous signaling motif and a new class of cyclic GMP receptor, The EMBO Journal, 19(20):5288-5299, 2000.
Huai et al., Three-dimensional structures of PDE4D in complex with rolipram and implication on inhibitor selectivity, Structure, 11:865-873, 2003.
Manning et al., Suppression of human inflammatory cell function by subtype-selective PDE4 inhibitors correlates with inhibition of PDE4A and PDE4B, British Journal of Pharmacology, 128:1393-1398, 1999.
Rascon et al., Cloning and characterization of a cAMP-specific phosphodiesterase (TbPDE2B) from *Trypanosoma brucei*, PNAS, 99(7):4714-4719, 2002.
Sopory et al., Modeling and mutational analysis of the GAF domain of the cGMP-binding, cGMP-specific phosphodiesterase, PDE5, FEBS Letters, 539:161-166, 2003.
Tejada et al., The phosphodiesterase inhibitory selectivity and the in vitro and in vivo potency of the new PDE5 inhibitor vardenafil, International Journal of Impotence Research, 13:282-290, 2001.
Turko et al., Inhibition of cyclic GMP-binding cyclic GMP-specific phosphodiesterase (type 5) by sildenafil and related compounds, Mol Pharmacol, 56:124-130, 1999.
Abdelhamid, et. al., Reactions with Hydrazonoyl Halides. Part 21. Reinvestigation of the Reactions of Hydrazonoyl Bromides with 1,1-Dicyanothioacetanilide, *J. Chem. Res.*, 184-185 (1999).
Alfthan, "Surface plasmon resonance biosensors as a tool in antibody engineering," *Biosensors & Bioelectronics*. 13:653-63 (1998).
al-Obeidi, "Peptide and Petidomimetic Libraries" *Mol Biotechnol* 9(3):205-23 (1998).
Amersdorfer P. Marks JD., "Phage Libraries for Generation of Antibotulinum scFv Antibodies," *Methods in Molecular Biology*, 145:219-40 (2001).

Bartlett et al., "Caveat: A Program to Facilitate the Structure-derived Design of Biologically Active Molecules," in Chemical and Biological Problems in Molecular Recognition, Roberts, S.M.; Ley, S.V.; Campbell, M.M. eds.; *Royal Society of Chemistry*: Cambridge, pp. I82-I96 (1989).
Bagshaw, C.R. and Harris, D.A., "Measurement of Ligand Binding to Proteins," *Spectrophotometry and Spectrofluorometry: A Practical Approach*, Bashford, C.L. and Harris, D.A., eds.; pp. 91-114, IRL Press Ltd., Oxford, U.K., (1987).
Beavo, et al., "Multiple Cyclic Nucleotide Phosphodiesterases," *Mol. Pharmacol.*, 46:399-405 (1994).
Bell, J.E., *Spectroscopy In Biochemistry*, vol. I, pp. 155-194, CRC Press, (1981).
Berthet, et al., "The Assay of Glucagon and Epinephrine with Use of Liver Homogenates," *J. Biol. Chem.*, 229:351-361 (1957).
Blundell et al., "Knowledge-based protein modeling and design." *Eur. J. Biochem.*, 172:513-520 (1988).
Böhm, H., "On the use of LUDI to search the Fine Chemicals Director for ligands of proteins of known three-dimensional structure," *J. Comp. Aided Molec. Design* 8: 623-632 (1994).
Bolger et al., "A Family of Human Phosphodiesterases Homologous to the *dunce* Learning and Memory Gene Product of *Drosophila melanogaster* Are Potential Targets for Antidepressant Drugs," *Mol. Cell. Biol.* 13 (10), 6558-6571 (1993).
Bolger, G.B., "Molecular Biology of the Cyclic AMP-Specific Cyclic Nucleotide Phosphodiesterases: A Diverse Family of Regulatory Enzymes," *Cell Signal*, 6:851-859 (1994).
Borch, et al., "Lithium Cyanohydridoborate, a Versatile New Reagent," *J. Am. Chem. Soc.*, 91, 3996-3997 (1969).
Bowtell, D. "Options available—from start to finish—for obtaining expression data by microarray," *Nature Genetics Supp.* 21:25-32 (1999).
Brenner et al., "Encoded Combinatorial Chemistry," *Proc. Natl. Acad. Sci. USA*, 89, 5381-5383 (1992).
Brünger, A.T., "Free R value: a novel statistical quantity for assessing the accuracy of crystal structures," *Nature* 355:472-475 (1992).
Buchschacher, G.L. and Panganiban, A.T., "Human Immunodeficiency Virus Vectors for Inducible Expression for Foreign Genes," *J. Virol.* 66:2731-2739, (1992).
Burgers, et al., "Stereochemistry of Hydrolysis of Adenosine 3':5'-Cyclic Phosphorothioate by the Cyclic Phosphodiesterase from Beef Heart," *J. Biol. Chem.*, 254:9959-9961 (1979).
Butcher, et al., "Adenosine 3', 5"-Phosphate in Biological Materials," *J. Biol. Chem.*, 237:1244-1250 (1962).
Capon, et al., "Designing CD4 immunoadhesins for AIDS therapy," *Nature* 377:525-531 (1989).
Carell et al., "New promise in combinatorial chemistry: synthesis, characterization, and screening of small-molecule libraries in solution," *Chem. Biol.*, 2:171-183 (1995).
Chabala, J.C., "Solid-phase combinatorial chemistry and novel tagging methods for identifying leads," *Curr Opin Biotechnol* 6(6):633-9 (1995).
Charbonneau, H., "Structure-Function Relationships Among Cyclic Nucleotide Phosphodiesterases," *Cyclic Nucleotide Phosphodiesterases: Structure, Regulation and Drug Action*, Beavo, J., and Houslay, M.D., eds) 267-296 (1990).
Checovich, W. J., et al., "Fluorescence polarization—a new tool for cell and molecular biology," *Nature* 375:254-256 (1995).
Clark et al.,"Pro_Ligand: An approach to de novo molecular design. 1. Application to the design of organic molecules," *J. Comp. Aided Molec. Design* 9:13 (1995).
Coe et al., "Solution-phase combinatorial chemistry," *Mol Divers*;4(1):31-38 (1999).
Colliuod et al., "Oriented and Covalent Immobilization of Target Molecules to Solid Supports: Synthesis and Application of a Light-Activatable and Thiol-Reactive Cross-Linking Reagent." *Bioconjugate Chem.* 4:528-536 (1993).
Colman, P.M., "Structure-based drug design," *Current Opinion in Struc. Biol.* 4:868-874 (1994).
Conti et al. "Cyclic AMP-specific PDE4 Phosphodiesterases as Critical Components of Cyclic AMP Signaling," *J Biol Chem.* 278(8):5493-5496 (2003).

Conti, et al., "Recent Progress in Understanding the Hormonal Regulation of Phosphodiesterases," *Endocr. Rev.*, 16:370-389 (1995).

Creighton, T., "An Empirical Approach to Protein Conformation Stability and Flexibility," *Biopolymers* 22(1):49-58 (1983).

Cwirla et al., "Peptides on phage: A vast library of peptides for identifying ligands," *Biochemistry*, 87, 6378-6382; (1990).

Dandliker, W. B., et al., "Equilibrium and Kinetic Inhibition Assays Based upon Fluorescence Polarization," *Methods in Enzymology* 74:3-28 (1981).

Degerman, et al., "Structure, Localization, and Regulation of cGMP-inhibited Phosphodiesterase (PDE3)," *J. Biol. Chem.*, 272:6823-6826 (1997).

Dobeli, et al., "Recombinant Fusion Proteins for the Industrial Production of Disulfide Bridge Containing Peptides: Purification, Oxidation without Concatamer Formation, and Selective Cleavage," *Protein Expr. Purif.* 12:404-414 (1998).

Dolle et al., "Comprehensive Survey of Combinattorial Library Synthesis: 1998," *J Comb Chem* 1(4):235-282, (1999).

Eliseev, A.V. Lehn JM., (1999) Dynamic Combinatorial Chemistry: Evolutionary Formation and Screening of Molecular Libraries, *Current Topics in Microbiology & Immunology* 243:159-72; Bolger et al., (1991) *Methods Enz.* 203:21-45.

Enjalbal C. et al., "Mass Spectrometry in Combinatorial Chemistry," *Mass Spectrometry Reviews*. 19:139-61 (2000).

Feng et al., "Stable in vivo gene transduction via a novel adenoviral/retroviral chimeric vector." *Nature Biotechnology* 15:866-870 (1997).

Fisher, et al., Isolation and Characterization of PDE9A, a Novel Human cGMP-specific Phosphodiesterase, *J. Biol. Chem.*, 273:15559-15564 (1998).

Fivash et al., BIAcore for macromolecular interaction, Current Opinion in Biotechnology, 9:97-101 (1998).

Florio, et al, Phosphorylation of the 61-kDa Calmodulin-Stimulated Cyclic Nucleotide Phosphodiesterase at Serine 120 Reduces Its Affinity for Calmodulin, *Biochemistry*, 33:8948-8954 (1994).

Francis, et al., "Zinc Interactions and Conserved Motifs of the cGMP-binding cGMP-specific Phosphodiesterase Suggest That It Is a Zinc Hydrolase," *J. Biol. Chem.*, 269:22477-22480 (1994).

Gallop et al., "Applications of Combinatorial Technologies to Drug Discovery. 1. Background and Peptide Combinatorial Libraries," *J. Med. Chem.*, 37(9):1233-1251 (1994).

Gettys, et al., "Short-term Feedback Regulation of cAMP by Accelerated Degradation in Rat Tissues." *J. Biol. Chem.* 262:333-339 (1987).

Goldberg, et al., $^{18}$O-Labeling of Guanosine Monophosphate upon Hydrolysis of Cyclic Guanosine 3':3'-Monophosphate by Phosphodiesterase, *J. Biol. Chem.*, 255:10344-10347 (1980).

Goodford, P.J., "A Computational Procedure for Determining Energetically Favorable Binding Sites on Biologically Important Macromolecules," *J. Med. Chem.* 28:849 (1985).

Goodsell and Olson, "Automated Docking of Substrates to Proteins by Simulated Annealing," *Proteins: Structure, Function, and Genetics*, 8:195 (1990).

Gordon et al., Application of Combinatorial Technologies to Drug Discovery. 2. Combinatorial Organic Synthesis, Library Screening Strategies, and Future Directions. *J. Med. Chem.*, 37, 1385-1401; (1994).

Gram H., "Phage Display in Proteolysis and Signal Transduction," Combinatorial Chemistry & High Throughput Screening, 2:19-28 (1999).

Gravert et al., Synthesis on soluble polymers: new reactions and the construction of small molecules, *Curr Opin Chem Biol* 1(1):107-13 (1997).

Greer, J., "Model Structure for the Inflammatory Protein C5a," *Science* 228:1055; (1985).

Guida, W.C., "Software for structure-based drug design," *Current Opinion in Struc. Biol.* 4: 777 (1994).

Hafner et al., "Isothermal Amplification and Multimerization of DNA by *Bst* Polymerase," *Biotechniques*, 30(4):852-6, 858, 860 passim; (2001).

Hanselman et al., "A cDNA-dependent scintillation proximity assay for quantifying apolipoprotein A-1," *J. Lipid Res.* 38:2365-2373 (1997).

Hansen et al. "Absence of Muscarinic Cholinergic Airway Responses in Mice Deficient in the Cyclic Nucleotide Phosphodiesterase PDE4D," *Proc Natl Acad Sci U S A*, 97(12):6751-6756 (2000).

Heim et al., Engineering green fluorescent protein for improved brightness longer wavelengths and fluorescence resonance energy transfer, *Curr. Biol.* 6:178-182, (1996).

Houghten et al., "Generation and use of synthetic peptide combinatorial libraries for basic research and drug discovery," *Nature*, 354:84-86 (1991).

Houghten, R.A., "Peptide libraries: criteria and trends," *Trends Genet.*, 9, 235-239 (1993).

Houghten, R.A, "Parallel Array and Mixture-Based Synthetic Combinatorial Chemistry: Tools for the Next Millenium," *Annu Rev Pharmacol Toxicol* 40:273-82 (2000).

Houslay, M.D., "Compartmentalization of Cyclic Amp Phosphodiesterases, Signalling 'Crosstalk', Desensitation and the Phosphorylation of $G_i$-2 Add Cell Specific Personalization to the Control of the Levels of the Second Messenger Cyclic Map," *Adv. Enzyme Regul.*, 35:303-338 (1995).

Hughes-Jones et al., Synthesis of Rh Fv phage-antibodies using VH and VL germline genes, *British Journal of Haematology*, 105:811-816 (1999).

Ismail, A.H., "One Pot synthesis of 1-(S-Triazolo[4,3-c] Pyrimidin-3-YL) Substituted Polyols," *Synthetic Communications*, 32(12):1791-1795, (2002).

Iwane et al., "Myosin Subfragment-1 Is Fully Equipped with Factors Essential for Motor Function," *Biophys. Biochem. Res. Comm.* 230:76-80 (1997).

Jin and Conti, "Induction of the cyclic nucleotide phosphodiesterase PDE4B is essential for LPS-activated TNF-α responses," *Proc Natl Acad Sci U S A*, 99:7628-7633 (2002).

Jin et al., "Impaired Growth and Fertility of cAMP-Specific Phosphodiesterase PDE4D-Deficient Mice," *Proc Natl Acad Sci U S A*, 96:11998-12003 (1999).

Jin et al., "Characterization of the Structure of a Low $K_m$, Rolipram-sensitive cAMP Phosphodiesterase," *J. Biol. Chem.*, 267:18929-18939 (1992).

Johann et al., "GLVR1, a Receptor for Gibbon Ape Leukemia Virus, Is Homologous to a Phosphate Permease of *Neurospora crassa* and Is Expressed at High Levels in the Brain and Thymus," *J. Virol.*, 66:1635-1640 (1992).

Johnston, M. "Gene chips: Array of hope for understanding gene regulation," *Curr. Biol.*, 8:R171-R174 (1998).

Joseph-McCarthy D., "Computational approaches to structure-based ligand design," *Pharmacology & Therapeutics*, 84:179-91 (1999).

Kahl et al., "A Multiple-Approach Scintillation Proximity Assay to Measure the Association between Ras and Raf," *Anal. Biochem.* 243:282-283, (1996).

Kanda et al."Synthesis and Structure—Activity Relationships of Potent and Orally Active Sulfonamide $ET_B$ Selective Antagonists," *Bioorganic Medicinal Chemistry*, vol. 9, No. 4, 897-907 (2001).

Kern and Hampton, Direct Hybridization of Large-Insert Genomic Clones in High-Density Gridded cDNA Filter Arrays, *Biotechniques* 23:120-124, (1997).

Khimiya, *?? Russian alphabet ?? Geterotsiklicheskikh Soedinenii*, vol. 8, 1129-1130, (1987).

Kim, H.O. and Kahn, M., A Merger of Rational Drug Design and Combinatorial Chemistry: Development and Application of Peptide Secondary Structure Mimetics, Combinatorial Chemistry & High Throughput Screening 3:167-83, (2000).

Kirkpatrick et al., Structure-based drug design: combinatorial chemistry and molecular modeling, *Combinatorial Chemistry & High Throughput Screening*. 2:211-21, (1999).

Kline et al.,"Studies by $^1$H Nuclear Magnetic Resonance and Distance Geometry of the Solution Conformation of the α-amylase Inhibitor Tendamistat," *J. Mol. Biol.* 189:377-382, (1986).

Knighton et al., "Structural Basis of the Intrasteric Regulation of Myosin Light Chain Kinases,"*Science* 258:130-I35, (1992).

Kolaskar and Tongaonkar, "A semi-empirical method for prediction of antigenic determinants on protein antigens," *FEBS Lett.* 276(1-2):172-174, (1990).

Kroll et al., "A Multifunctional Prokaryotic Protein Expression System: Overproduction, Affinity Purification, and Selective Detection," *DNA Cell. Biol.* 12:441-53, (1993).

Kundu et al., "Combinatorial chemistry: polymer supported synthesis of peptide and non-peptide libraries," *Progress in Drug Research*, 53:89-156, (1999).

Kunkel, T.A., "Rapid and Efficient Site-Specific Mutagenesis without Phenotypic Selection," Proc. Natl. Acad. Sci. 82:488-492, (1985).

Kuntz et al., "Structure-Based Molecular Design," *Acc. Chem. Res.* 27:117, (1994).

Kuntz et al., "A Geometric Aproach to Macromolecule-Ligand Interactions," *J. Mol. Biol. 162*: 269, (1982).

Lam et al., "A new of synthetic peptide library for identifying ligand-binding activity," *Nature*, 354, 82-84, (1991).

Lebl et al., "One-Bead-One-Structure Combinatorial Libraries," *Biopolymers*, 37 177-198, (1995).

Lee et al., "Crystal structure of phosphodiesterase 4D and inhibitor complex," *FEBS Lett*, 530:53-58 WO 00/54759, (2002).

Liparoto, S.F. and Ciardelli, T.L., "Biosensor analysis of the interleukin-2 receptor complex," *Journal of Molecular Recognition*. 12:316-21, (1999).

Lipinski et al., "Experimental and computational approaches to estimate solubility and permeability in drug discovery and development settings," *Advanced Drug Delivery Reviews*, 23 3-25, (1997).

Lipschultz et al., "Experimental Design for Analysis of Complex Kinetics Using Surface Plasmon Resonance," *Methods.* 20(3):310-8, (2000).

Lu et al., "Oriented Immobilization of Fab' Fragments on Silica Surfaces," *Anal. Chem.* 67:83-87, (1995).

Madden et al., "Synthetic combinatorial libraries: Views on techniques and their application," *Perspectives in Drug Discovery and Design*, 2:269-282, (1994).

Malmborg, A. and Borrebaeck, C.A.K., "BIAcore as a tool in antibody engineering," *Journal of Immunological Methods.* 183:7-13, (1995).

Malmqvistl, M. and Karlsson, R., "Biomolecular interaction analysis: affinity biosensor technologies for functional analysis of proteins," *Current Opinion in Chemical Biology.* 1:378-83, (1997).

Malmqvist, M., "BIACORE: an affinity biosensor system for characterization of biomolecular interactions," Biochemical Society Transactions 27:335-40, (1999).

Markiewicz et al., "Synthetic oligonucleotide combinatorial libraries and their applications," *Farmaco.* 55:174-7, (2000).

Martin, Y.C., "Computer-Assisted Rational Drug Design," *Methods Enz.* 203:587-613, (1991).

Masquelin, T. and Obrecht, D., "A new general three component solution-phase synthesis of 2-amino-1,3-thiazole and 2,4-diamino-1,3-thiazole combinatorial libraries," *Tetrahedron*, vol. 57, No. 1, 153-156, (2001).

McAllister-Lucas, et al., "An Essential Aspartic Acid at Each of Two Allosteric cGMP-binding Sites of a cGMP-specific Phosphodiesterase," *J. Biol. Chem.*, 270:30671-30679 (1995).

McCall et al., "Characterization of anti-mouse Fcγ RII single-chain Fv fragments derived from human phage display libraries," *Immunotechnology.* 4:71-87, (1998).

McCasland, G.E. and Tarbell, D.S., "Analogs of Pyridoxine. II. Synthesis of a Pyrimidine Analog," *Journal of American Chemical Society*, 68,:2393-2395, (1946).

Mekonnen, B. and Crank, G., "Friedel-Crafts Reactions of 2-Amino-4-Alkyl or aryl)oxazoles with Acid Chlorides and Acid Anjhydrides: Synthesis of 5-Acyl-2-amino-4-alkyloxazoles," *Journal of Heterocylic Chemistry*, 34(2):567-572, (1997).

McLaughlin et al., "A Low-$K_m$, Rolipram-sensitive, cAMP-specific Phosphodiesterase from Human Brain," *J. Biol. Chem.* 268 (9), 6470-6476, (1993).

McPherson, A., "Current approaches to macromolecular crystallization," John Wiley, New York; McPherson *Eur. J. Biochem.*, 189:1-23, (1990).

Meng et al., "Automated Docking with Grid-Based Energy Evaluation," *J. Compt. Chem. 13*: 505, (1992).

Merritt, A.T., "Solution Phase Combinatorial Chemistry," *Comb Chem High Throughput Screen* 1(2):57-72, (1998).

Michaeli, et al., "Isolation and Characterization of a Previously Undetected Huan cAMP Phosphodiesterase by Complementation of cAMP Phosphodiesterase-deficient *Saccaromyces cervisiae*," *J. Biol. Chem.*, 268:12925-12932, (1993).

Miller et al., "FLOG: A system to select 'quasi-flexible' ligands complementary to a receptor of known three-dimensional structure," *J. Comp. Aided Molec. Design*, 8:153, (1994).

Miranker, A. and Karplus, M., "Functionality Maps of Binding Sites: A Multiple Copy simultaneous Search Method," *Proteins: Structure, Function, and Genetics*, 11:29, (1991).

Mitra et al., "Flurescence resonalce energy transfer between blue-emitting and red-shifted excitation derivatives of the green fluorescent protein," *Gene* 173:13-17, (1996).

Nicolls et al., "Protein Folding and Association: Insights From the Interfacial and Thermodynamic Properties of Hydrocarbons," *Proteins: Structure, Function, and Genetics*, 11:281-295 (1991).

Navaza, J., "AmoRe: an Automated Package for Molecular Replacement," *Acta Cryst.*, A50:157-163, (1994).

Neidle, S. and Jenkins, T.C., "Molecular Modeling to Study DNA Intercalation by Anti-tumor Drugs," *Methods Enz.* 203:433-458, (1991).

Ng et al., "Engineering Protein—Lipid Interactions: Targeting of Histidine-Tagged Proteins to Metal Chelating Lipid Monolayers," *Langmuir*, 11:4048-4055, (1995).

Nicholls *Proteins* 11:281-296, (1994).

Nichols et al., "Development of a Scintillation Proximity Assay for Peroxisome Poliferator-Actiated Receptor γ Ligand Binding Domain," *Anal. Biochem*,.257:112-119, (1998).

O'Shannessy, D.J. and Winzor, D.J., "Interpretation of Deviations from Pseudo-First-Order Kinetic Behavior in the Characterization of Ligand Binding by Biosensor Technology," *Analytical Biochemistry*, 236:275-83, (1996).

O'Shannessy, D.J., "Determination of kinetic rate and equilibrium binding constants for macromolecular interactions: a critique of the surface plasmon resonance literature," *Current Opinions in Biotechnology*, 5:65-71, (1994).

Obernolte et al., "The cDNA of a human lymphocyte cyclic-AMP phosphodiesterase (PDE IV) reveals a multigene family." *Gene* 129 (2), 239-247 (1993).

Okada et al., "Gene therapy against an experimental glioma using adeno-associated virus vectors," *Gene Ther.*, 3:957-964, (1996).

Otwinowski, Z., "Maximum Likelihood Refinement of Heavy Atom Parameters," Daresbury, United Kingdom, 80-86, (1991).

Parker et al., "Development of High Throughput Screening Assays Using Fluorescence Polarization: Nuclear Receptor-Ligand-Binding and Kinase/Phosphatase Assays," *J Biomol Screen.*, 5:77-88, (2000).

Percival, et al., "Zinc Dependent Activation of cAMP-Specific Phosphodiesterase (PDE4A)," *Biochem. Biophys. Res. Commun.*, 241:175-180 (1997).

Perrin, D.M., Nucleic Acids for Recognition and Catalysis: Landmarks, Limitations, and Looking to the Future, *Combinatorial Chemistry & High Throughput Screening* 3:243-69, (2000).

Pflugrath et al., "Crystal Structure Determination, Refinement and the Molecular Model of the α-Amylase Inhibitor Hoe-467A," *J. Mol. Biol.*, 189:383-386; (1986).

Plunkett, M. J., and Ellman, J. A., "A Silicon-Based Linker for Traceless Solid-Phase Synthesis," *J. Org. Chem.*, 60:6006, (1995).

Poul et al., "Selection of tumor-specific internalizing human antibodies from phage libraries," Source *Journal of Molecular Biology*. 301:1149-61, (2000).

Price et al.; Summary report on the ISOBM TD-4 Workshop: Analysis of 56 Monoclonal Antibodies Against the MUC1 mucin. *Tumour Biology*, 19(Suppl 1):1-20, (1998).

Rall, T.W. and Sutherland, E.W., "Formation of a Cyclic Adenine Ribonucleotide by Tissue Particles," *J. Biol. Chem.*, 232:1065-1076 (1958).

*Remington's Pharmaceutical Sciences*, 19th ed., Mack Publishing Co., Easton, PA, vol. 2, p. 1457, (1995).

Roberts et al., "Generation of an antibody with enhanced affinity and specificity for its antigen by protein engineering," *Nature* 328-731; (1987).

Romero-Ortego et al., "Synthesis of 4-Substituted 2-Phenylaminothiazoles from Amidines. A Convenient Route to 4-Trichloromethylthiazoles," *Journal of Organic Chemistry*, 65(21):7244-7247, (2000).

Rosenfeld, M.A., "Human artificial chromosomes get real," *Nat. Genet.*, 15:333-335, (1997).

Saiki, R.K., "Amplification of Genomic DNA" in PCR Protocols, Innis et al., Eds., Academic Press, San Diego, CA, pp. 13-20, (1990).

Schneider et al., "Functional Purification of a Bacterial STP-Binding Cassette Transporter Protein (MalK) from the Cytoplasmic Fraction of an Overproducing Strain," *Protein Expr. Purif.*, 6:10-14, (1995).

Schuhmann et al., "Immobilization of Enzymes on Langmuir-Blodgett Films via a Membrane-Bound Receptor. Possible Applications for Amperometric Biosensors," *Adv. Mater.* 3:388-391, (1991).

Schummer et al., "Inexpensive Handheld Device for the construction of High-Density Nucleic Acid Arrays," *Biotechniques*, 23:1087-1092, (1997).

Schweizer, F. and Hindsgaul, O., "Combinatorial synthesis of carbohydrates," *Curr Opin Chem Biol* 3(3):291-8, (1999).

Selvin et al., "Fluorescence Resonance Energy Transfer," *Meth. Enzymol.* 246:300-345, (1995).

Sheets et al., "Efficient construction of a large nonimmune phage antibody library: the production of high-affinity human single-chain antibodies to protein antigens (published erratum appears in *Proc Natl Acad Sci* USA 1999 96:795, (1998).

Sheth, et al., "Isolation and Regulation of the cGMP-Inhibited cAMP Phosphodiesterase in Human Erythroleukemia Cells," *Throm. Haemostasis*, 77:155-162 (1997).

Shiao, M. and Tarng, K., "A Convenient Synthesis of 2,4'-Dipyridine," *Heterocycles*, vol. 31, No. 4, 637-641, (1990).

Siegel et al., "Mass Spectral Analysis of a Protein Complex using Single-chain Antibodies Selected on a Peptide Target: Applications to Functional Genomics," *Journal of Molecular Biology*, 302:285-93, (2000).

Sigal et al., "A Self-Assembled Monolayer for the Binding and Study of Histidine-Tagged Proteins by Surface Plasmon Resonance," *Anal. Chem.* 68:490-497, (1996).

Smith, et. al., "Necklace-Coded Polymer-Supported Combinatorial Synthesis of 2-Arylaminobenzimidazoles." *J. Comb. Chem.*, 1:368-370, (1999).

Soderling, et al., "Identification and Characterization of a Novel Family of Cyclic Nucleotide Phosphodiesterases," *J. Biol. Chem.*, 273:15553-15558, (1998).

Soderling, et al., "Cloning and Characterization of a cAMP-Specific Cyclic Nucleotide Phosphodiesterase," *Proc. Natl. Acad. Sci. U.S.A.*, 95:8991-8996 (1998).

Solinas-Toldo et al., "Matrix-Baseed Comparative Genomic Hyridization: Biochips to Screen for Genomic Imbalances," *Genes, Chromosomes & Cancer* 20:399-407, (1997).

Sommen, et. al., "An improved method for the synthesis of aminothiphenes precursers of theno[2,3-b]pyrrole," *Tetrahedron Lett.*, 43, 257-259, (2002).

Sonnenberg, et al., "Identification of Inhibitory and Calmodulin-binding Domains of the PDE1A1 and PDE1A2 Calmodulin-stimulated Cyclic Nucleotide Phosphodiesterases," *J. Biol. Chem.*, 270:30989-31000, (1995).

Srivastava, et al., "Effects of magnesium on cyclic GMP hydrolysis by the bovine retinal rod cyclic GMP phosphodiesterase," *Biochem. J.*, 308:653-658 (1995).

Sun, et al., "Design, Synthesis, and Evaluations of Substituted 3-[(3- or 4-Carboxyethylpyrrol-2yl)methylidenl]indolin-2-ones as Inhibitors of VEGF, FGF, and PDGF Receptor Tyrosine Kinases," *J. Med. Chem.*, 42:5120-5130, (1999).

Taylor et al., "The rapid generation of oligonucleotide-directed mutations at high frequency using phosphorothioate-modified DNA," *Nucl. Acids Res.*, 13:8764-8785, (1985).

Thompson, et al, "Regulatory Mechanisms of Particulate Cyclic Nucleotide Phosphodiesterases," *Adv. Second Messenger Phosphoprotein Res.*, 25:165-184, (1992).

Undenfriend et al., "Scintillation Proximity Assay: A Sensitive and Continuous Isotopic Method for Monitoring Ligand/Receptor and Antigen/Antibody Interactions," *Anal. Biochem.* 161:494-500, (1987).

Underwood, et al., "Comparison of Phosphodiesterase III, IV and Dual III/IV Inhibitors on Bronchospasm and Pulmonary Eosinophil Influx in Guinea Pigs," *J. Pharmacol. Exp. Ther.*, 270:250-259, (1994).

Van Regenmortel, M.H.V., "Use of Biosensors to Characterize Recombinant Proteins," *Developments in Biological Standardization.*, 83:143-51, (1994).

Vely F. et al., "BIAcore Analysis to Test Phosphopeptide-SH2 Domain Interactions," *Methods in Molecular Biology*, 121:313-21, (2000).

Wessjohann, L.A., "Synthesis of natural-product-based compound libraries," *Curr Opin Chem Biol* 4(3):303-9, (2000).

Wharam et al., "Specific detection of DNA and RNA targets using a novel isothermal nucleic acid amplification assay based on the formation of a three-way junction structure," *Nucleic Acids Res.*, 1;29(11):e54 ,1-8, (2001).

Williams, "Dissection of the Extracellular Human Interferon γ Receptor α-Chain into two Immunoglobulin-like Domains. Production in an *Escherichia coli* Thioredoxin Gene Fusion Expression System and Recognition by Neutralizing Antibodies," *Biochemistry*, 34:1787-1797, (1995).

Woon et al., "Construction and Characterization of a 10-fold Genome Equivalent Rat P1-Derived Artificial Chromosome Library," *Genomics* 50:306-316, (1998).

Wüthrich, K., "Chapter 10: Three-Dimensional Protein Structures by NMR," *NMR of Proteins and Nucleic Acids*,,John Wiley and Sons, New York:176-199, Zürich, Switzerland, (1986).

Xu et al., "Atomic Structure of PDE4: Insights into Phosphodiesterase Mechanism and Specificity," *Science*, 288, 1822-1825, (2000).

Yamazaki, et al., "Enzyme Regulation and TGP Binding Protein: An Algorithm of Control That Includes Physical Displaceent of an Inhibitory Protein," *Adv. Cyclic Nucleotide Protein Phosphorylation Res.*, 16:381-392 (1984).

Yamazaki, et al., "Cyclic GMP-specific, High Affinity, Noncatalytic Binding Sites on Light-activated Phosphodiesterase," *J. Biol. Chem.*, 255:11619-11624, (1980).

Wolff et al., Burger's Medicinal Chemistry and Drug Discovery, Wiley-Interscience, Fifth Edition, vol. 1: Principles and Practice, p. 975-977, 1994.

* cited by examiner

Ribbon Diagram of PDE4B dimer

Overlay of PDE4B structure with prior proposed PDE4B structure

SEQUENCE LISTING

<160> NUMBER OF SEQ ID NOS: 32

<210> SEQ ID NO 1
<211> LENGTH: 564
<212> TYPE: PRT
<213> ORGANISM: Homo sapiens

<400> SEQUENCE: 1

```
Met Lys Glu His Gly Gly Thr Phe Ser Thr Gly Ile Ser Gly Gly
  1               5                  10                  15

Ser Gly Asp Ser Ala Met Asp Ser Leu Gln Pro Leu Gln Pro Asn Tyr
                 20                  25                  30

Met Pro Val Cys Leu Phe Ala Glu Glu Ser Tyr Gln Lys Leu Ala Met
             35                  40                  45

Glu Thr Leu Glu Glu Leu Asp Trp Cys Leu Asp Gln Leu Glu Thr Ile
         50                  55                  60
```

```
Gln Thr Tyr Arg Ser Val Ser Glu Met Ala Ser Asn Lys Phe Lys Arg
 65                  70                  75                  80

Met Leu Asn Arg Glu Leu Thr His Leu Ser Glu Met Ser Arg Ser Gly
                 85                  90                  95

Asn Gln Val Ser Glu Tyr Ile Ser Asn Thr Phe Leu Asp Lys Gln Asn
            100                 105                 110

Asp Val Glu Ile Pro Ser Pro Thr Gln Lys Asp Arg Glu Lys Lys Lys
        115                 120                 125

Lys Gln Gln Leu Met Thr Gln Ile Ser Gly Val Lys Lys Leu Met His
    130                 135                 140

Ser Ser Ser Leu Asn Asn Thr Ser Ile Ser Arg Phe Gly Val Asn Thr
145                 150                 155                 160

Glu Asn Glu Asp His Leu Ala Lys Glu Leu Glu Asp Leu Asn Lys Trp
                165                 170                 175

Gly Leu Asn Ile Phe Asn Val Ala Gly Tyr Ser His Asn Arg Pro Leu
            180                 185                 190

Thr Cys Ile Met Tyr Ala Ile Phe Gln Glu Arg Asp Leu Leu Lys Thr
        195                 200                 205

Phe Arg Ile Ser Ser Asp Thr Phe Ile Thr Tyr Met Met Thr Leu Glu
    210                 215                 220

Asp His Tyr His Ser Asp Val Ala Tyr His Asn Ser Leu His Ala Ala
225                 230                 235                 240

Asp Val Ala Gln Ser Thr His Val Leu Leu Ser Thr Pro Ala Leu Asp
                245                 250                 255

Ala Val Phe Thr Asp Leu Glu Ile Leu Ala Ala Ile Phe Ala Ala Ala
            260                 265                 270

Ile His Asp Val Asp His Pro Gly Val Ser Asn Gln Phe Leu Ile Asn
        275                 280                 285

Thr Asn Ser Glu Leu Ala Leu Met Tyr Asn Asp Glu Ser Val Leu Glu
    290                 295                 300

Asn His His Leu Ala Val Gly Phe Lys Leu Leu Gln Glu Glu His Cys
305                 310                 315                 320

Asp Ile Phe Met Asn Leu Thr Lys Lys Gln Arg Gln Thr Leu Arg Lys
                325                 330                 335

Met Val Ile Asp Met Val Leu Ala Thr Asp Met Ser Lys His Met Ser
            340                 345                 350

Leu Leu Ala Asp Leu Lys Thr Met Val Glu Thr Lys Lys Val Thr Ser
        355                 360                 365

Ser Gly Val Leu Leu Leu Asp Asn Tyr Thr Asp Arg Ile Gln Val Leu
    370                 375                 380

Arg Asn Met Val His Cys Ala Asp Leu Ser Asn Pro Thr Lys Ser Leu
385                 390                 395                 400

Glu Leu Tyr Arg Gln Trp Thr Asp Arg Ile Met Glu Glu Phe Phe Gln
                405                 410                 415

Gln Gly Asp Lys Glu Arg Glu Arg Gly Met Glu Ile Ser Pro Met Cys
            420                 425                 430

Asp Lys His Thr Ala Ser Val Glu Lys Ser Gln Val Gly Phe Ile Asp
        435                 440                 445

Tyr Ile Val His Pro Leu Trp Glu Thr Trp Ala Asp Leu Val Gln Pro
    450                 455                 460

Asp Ala Gln Asp Ile Leu Asp Thr Leu Glu Asp Asn Arg Asn Trp Tyr
465                 470                 475                 480

Gln Ser Met Ile Pro Gln Ser Pro Ser Pro Pro Leu Asp Glu Gln Asn
```

```
                    485                 490                 495
Arg Asp Cys Gln Gly Leu Met Glu Lys Phe Gln Phe Glu Leu Thr Leu
                500                 505                 510

Asp Glu Glu Asp Ser Glu Gly Pro Glu Lys Glu Gly Glu Gly His Ser
            515                 520                 525

Tyr Phe Ser Ser Thr Lys Thr Leu Cys Val Ile Asp Pro Glu Asn Arg
        530                 535                 540

Asp Ser Leu Gly Glu Thr Asp Ile Asp Ile Ala Thr Glu Asp Lys Ser
545                 550                 555                 560

Pro Val Asp Thr

<210> SEQ ID NO 2
<211> LENGTH: 673
<212> TYPE: PRT
<213> ORGANISM: Homo sapiens

<400> SEQUENCE: 2

Met Met His Val Asn Asn Phe Pro Phe Arg Arg His Ser Trp Ile Cys
  1               5                  10                  15

Phe Asp Val Asp Asn Gly Thr Ser Ala Gly Arg Ser Pro Leu Asp Pro
             20                  25                  30

Met Thr Ser Pro Gly Ser Gly Leu Ile Leu Gln Ala Asn Phe Val His
         35                  40                  45

Ser Gln Arg Arg Glu Ser Phe Leu Tyr Arg Ser Asp Ser Asp Tyr Asp
     50                  55                  60

Leu Ser Pro Lys Ser Met Ser Arg Asn Ser Ser Ile Ala Ser Asp Ile
 65                  70                  75                  80

His Gly Asp Asp Leu Ile Val Thr Pro Phe Ala Gln Val Leu Ala Ser
                 85                  90                  95

Leu Arg Thr Val Arg Asn Asn Phe Ala Ala Leu Thr Asn Leu Gln Asp
            100                 105                 110

Arg Ala Pro Ser Lys Arg Ser Pro Met Cys Asn Gln Pro Ser Ile Asn
        115                 120                 125

Lys Ala Thr Ile Thr Glu Glu Ala Tyr Gln Lys Leu Ala Ser Glu Thr
    130                 135                 140

Leu Glu Glu Leu Asp Trp Cys Leu Asp Gln Leu Glu Thr Leu Gln Thr
145                 150                 155                 160

Arg His Ser Val Ser Glu Met Ala Ser Asn Lys Phe Lys Arg Met Leu
                165                 170                 175

Asn Arg Glu Leu Thr His Leu Ser Glu Met Ser Arg Ser Gly Asn Gln
            180                 185                 190

Val Ser Glu Phe Ile Ser Asn Thr Phe Leu Asp Lys Gln His Glu Val
        195                 200                 205

Glu Ile Pro Ser Pro Thr Gln Lys Glu Lys Glu Lys Lys Lys Arg Pro
    210                 215                 220

Met Ser Gln Ile Ser Gly Val Lys Lys Leu Met His Ser Ser Ser Leu
225                 230                 235                 240

Thr Asn Ser Ser Ile Pro Arg Phe Gly Val Lys Thr Glu Gln Glu Asp
                245                 250                 255

Val Leu Ala Lys Glu Leu Glu Asp Val Asn Lys Trp Gly Leu His Val
            260                 265                 270

Phe Arg Ile Ala Glu Leu Ser Gly Asn Arg Pro Leu Thr Val Ile Met
        275                 280                 285

His Thr Ile Phe Gln Glu Arg Asp Leu Leu Lys Thr Phe Lys Ile Pro
```

```
              290                 295                 300
Val Asp Thr Leu Ile Thr Tyr Leu Met Thr Leu Glu Asp His Tyr His
305                 310                 315                 320

Ala Asp Val Ala Tyr His Asn Asn Ile His Ala Ala Asp Val Val Gln
                325                 330                 335

Ser Thr His Val Leu Leu Ser Thr Pro Ala Leu Glu Ala Val Phe Thr
                340                 345                 350

Asp Leu Glu Ile Leu Ala Ala Ile Phe Ala Ser Ala Ile His Asp Val
            355                 360                 365

Asp His Pro Gly Val Ser Asn Gln Phe Leu Ile Asn Thr Asn Ser Glu
370                 375                 380

Leu Ala Leu Met Tyr Asn Asp Ser Ser Val Leu Glu Asn His His Leu
385                 390                 395                 400

Ala Val Gly Phe Lys Leu Leu Gln Glu Glu Asn Cys Asp Ile Phe Gln
                405                 410                 415

Asn Leu Thr Lys Lys Gln Arg Gln Ser Leu Arg Lys Met Val Ile Asp
                420                 425                 430

Ile Val Leu Ala Thr Asp Met Ser Lys His Met Asn Leu Leu Ala Asp
            435                 440                 445

Leu Lys Thr Met Val Glu Thr Lys Lys Val Thr Ser Ser Gly Val Leu
    450                 455                 460

Leu Leu Asp Asn Tyr Ser Asp Arg Ile Gln Val Leu Gln Asn Met Val
465                 470                 475                 480

His Cys Ala Asp Leu Ser Asn Pro Thr Lys Pro Leu Gln Leu Tyr Arg
                485                 490                 495

Gln Trp Thr Asp Arg Ile Met Glu Glu Phe Phe Arg Gln Gly Asp Arg
                500                 505                 510

Glu Arg Glu Arg Gly Met Glu Ile Ser Pro Met Cys Asp Lys His Asn
            515                 520                 525

Ala Ser Val Glu Lys Ser Gln Val Gly Phe Ile Asp Tyr Ile Val His
    530                 535                 540

Pro Leu Trp Glu Thr Trp Ala Asp Leu Val His Pro Asp Ala Gln Asp
545                 550                 555                 560

Ile Leu Asp Thr Leu Glu Asp Asn Arg Glu Trp Tyr Gln Ser Thr Ile
                565                 570                 575

Pro Gln Ser Pro Ser Pro Ala Pro Asp Asp Pro Glu Glu Gly Arg Gln
                580                 585                 590

Gly Gln Thr Glu Lys Phe Gln Phe Glu Leu Thr Leu Glu Glu Asp Gly
            595                 600                 605

Glu Ser Asp Thr Glu Lys Asp Ser Gly Ser Gln Val Glu Glu Asp Thr
    610                 615                 620

Ser Cys Ser Asp Ser Lys Thr Leu Cys Thr Gln Asp Ser Glu Ser Thr
625                 630                 635                 640

Glu Ile Pro Leu Asp Glu Gln Val Glu Glu Glu Ala Val Gly Glu Glu
                645                 650                 655

Glu Glu Ser Gln Pro Glu Ala Cys Val Ile Asp Asp Arg Ser Pro Asp
                660                 665                 670

Thr

<210> SEQ ID NO 3
<211> LENGTH: 736
<212> TYPE: PRT
<213> ORGANISM: Homo sapiens
```

-continued

```
<400> SEQUENCE: 3

Met Lys Lys Ser Arg Ser Val Met Thr Val Met Ala Asp Asp Asn Val
  1               5                  10                  15

Lys Asp Tyr Phe Glu Cys Ser Leu Ser Lys Ser Tyr Ser Ser Ser Ser
                 20                  25                  30

Asn Thr Leu Gly Ile Asp Leu Trp Arg Gly Arg Arg Cys Cys Ser Gly
             35                  40                  45

Asn Leu Gln Leu Pro Pro Leu Ser Gln Arg Gln Ser Glu Arg Ala Arg
 50                  55                  60

Thr Pro Glu Gly Asp Gly Ile Ser Arg Pro Thr Thr Leu Pro Leu Thr
 65                  70                  75                  80

Thr Leu Pro Ser Ile Ala Ile Thr Thr Val Ser Gln Glu Cys Phe Asp
                 85                  90                  95

Val Glu Asn Gly Pro Ser Pro Gly Arg Ser Pro Leu Asp Pro Gln Ala
             100                 105                 110

Ser Ser Ser Ala Gly Leu Val Leu His Ala Thr Phe Pro Gly His Ser
         115                 120                 125

Gln Arg Arg Glu Ser Phe Leu Tyr Arg Ser Asp Ser Asp Tyr Asp Leu
     130                 135                 140

Ser Pro Lys Ala Met Ser Arg Asn Ser Ser Leu Pro Ser Glu Gln His
145                 150                 155                 160

Gly Asp Asp Leu Ile Val Thr Pro Phe Ala Gln Val Leu Ala Ser Leu
                 165                 170                 175

Arg Ser Val Arg Asn Asn Phe Thr Ile Leu Thr Asn Leu His Gly Thr
             180                 185                 190

Ser Asn Lys Arg Ser Pro Ala Ala Ser Gln Pro Pro Val Ser Arg Val
         195                 200                 205

Asn Pro Gln Glu Glu Ser Tyr Gln Lys Leu Ala Met Glu Thr Leu Glu
     210                 215                 220

Glu Leu Asp Trp Cys Leu Asp Gln Leu Glu Thr Ile Gln Thr Tyr Arg
225                 230                 235                 240

Ser Val Ser Glu Met Ala Ser Asn Lys Phe Lys Arg Met Leu Asn Arg
                 245                 250                 255

Glu Leu Thr His Leu Ser Glu Met Ser Arg Ser Gly Asn Gln Val Ser
             260                 265                 270

Glu Tyr Ile Ser Asn Thr Phe Leu Asp Lys Gln Asn Asp Val Glu Ile
         275                 280                 285

Pro Ser Pro Thr Gln Lys Asp Arg Glu Lys Lys Lys Gln Gln Leu
     290                 295                 300

Met Thr Gln Ile Ser Gly Val Lys Lys Leu Met His Ser Ser Ser Leu
305                 310                 315                 320

Asn Asn Thr Ser Ile Ser Arg Phe Gly Val Asn Thr Glu Asn Glu Asp
                 325                 330                 335

His Leu Ala Lys Glu Leu Glu Asp Leu Asn Lys Trp Gly Leu Asn Ile
             340                 345                 350

Phe Asn Val Ala Gly Tyr Ser His Asn Arg Pro Leu Thr Cys Ile Met
         355                 360                 365

Tyr Ala Ile Phe Gln Glu Arg Asp Leu Leu Lys Thr Phe Arg Ile Ser
     370                 375                 380

Ser Asp Thr Phe Ile Thr Tyr Met Met Thr Leu Glu Asp His Tyr His
385                 390                 395                 400

Ser Asp Val Ala Tyr His Asn Ser Leu His Ala Ala Asp Val Ala Gln
                 405                 410                 415
```

Ser Thr His Val Leu Leu Ser Thr Pro Ala Leu Asp Ala Val Phe Thr
              420                 425                 430

Asp Leu Glu Ile Leu Ala Ala Ile Phe Ala Ala Ile His Asp Val
            435                 440                 445

Asp His Pro Gly Val Ser Asn Gln Phe Leu Ile Asn Thr Asn Ser Glu
              450                 455                 460

Leu Ala Leu Met Tyr Asn Asp Glu Ser Val Leu Glu Asn His His Leu
465                 470                 475                 480

Ala Val Gly Phe Lys Leu Leu Gln Glu Glu His Cys Asp Ile Phe Met
                485                 490                 495

Asn Leu Thr Lys Lys Gln Arg Gln Thr Leu Arg Lys Met Val Ile Asp
              500                 505                 510

Met Val Leu Ala Thr Asp Met Ser Lys His Met Ser Leu Leu Ala Asp
              515                 520                 525

Leu Lys Thr Met Val Glu Thr Lys Lys Val Thr Ser Ser Gly Val Leu
              530                 535                 540

Leu Leu Asp Asn Tyr Thr Asp Arg Ile Gln Val Leu Arg Asn Met Val
545                 550                 555                 560

His Cys Ala Asp Leu Ser Asn Pro Thr Lys Ser Leu Glu Leu Tyr Arg
              565                 570                 575

Gln Trp Thr Asp Arg Ile Met Glu Glu Phe Phe Gln Gln Gly Asp Lys
              580                 585                 590

Glu Arg Glu Arg Gly Met Glu Ile Ser Pro Met Cys Asp Lys His Thr
              595                 600                 605

Ala Ser Val Glu Lys Ser Gln Val Gly Phe Ile Asp Tyr Ile Val His
              610                 615                 620

Pro Leu Trp Glu Thr Trp Ala Asp Leu Val Gln Pro Asp Ala Gln Asp
625                 630                 635                 640

Ile Leu Asp Thr Leu Glu Asp Asn Arg Asn Trp Tyr Gln Ser Met Ile
              645                 650                 655

Pro Gln Ser Pro Ser Pro Leu Asp Glu Gln Asn Arg Asp Cys Gln
              660                 665                 670

Gly Leu Met Glu Lys Phe Gln Phe Glu Leu Thr Leu Asp Glu Glu Asp
              675                 680                 685

Ser Glu Gly Pro Glu Lys Glu Gly Glu Gly His Ser Tyr Phe Ser Ser
              690                 695                 700

Thr Lys Thr Leu Cys Val Ile Asp Pro Glu Asn Arg Asp Ser Leu Gly
705                 710                 715                 720

Glu Thr Asp Ile Asp Ile Ala Thr Glu Asp Lys Ser Pro Val Asp Thr
                725                 730                 735

<210> SEQ ID NO 4
<211> LENGTH: 3186
<212> TYPE: DNA
<213> ORGANISM: Homo sapiens

<400> SEQUENCE: 4
gcggccgcgg cggtgcagca gaggcgcctc gggcaggagg agggcggctt ctgcgagggc         60
agcctgaggt attaaaaagt gtcagcaaac tgcattgaat aacagacatc ctaagagggg        120
atattttcca cctctataat gaagaaaagc aggagtgtga tgacggtgat ggctgatgat        180
aatgttaaag attattttga atgtagcttg agtaaatcct acagttcttc agtaacacac        240
cttgggatcg acctctggag agggagaagg tgttgctcag gaaacttaca gttaccacca        300

```
ctgtctcaaa gacagagtga aagggcaagg actcctgagg gagatggtat ttccaggccg    360
accacactgc ctttgacaac gcttccaagc attgctatta caactgtaag ccaggagtgc    420
tttgatgtgg aaaatggccc ttccccaggt cggagtccac tggatcccca ggccagctct    480
tccgctgggc tggtacttca cgccacctt cctgggcaca gccagcgcag agagtcattt    540
ctctacagat cagacagcga ctatgacttg tcaccaaagg cgatgtcgag aaactcttct    600
cttccaagcg agcaacacgg cgatgacttg attgtaactc cttttgccca ggtccttgcc    660
agcttgcgaa gtgtgagaaa caacttcact atactgacaa accttcatgg tacatctaac    720
aagaggtccc cagctgctag tcagcctcct gtctccagag tcaacccaca agaagaatct    780
tatcaaaaat tagcaatgga aacgctggag gaattagact ggtgtttaga ccagctagag    840
accatacaga cctaccggtc tgtcagtgag atggcttcta caagttcaa aagaatgctg     900
aaccgggagc tgacacacct ctcagagatg agccgatcag ggaaccaggt gtctgaatac    960
atttcaaata ctttcttaga caagcagaat gatgtggaga tcccatctcc tacccagaaa   1020
gacagggaga aaagaaaaa gcagcagctc atgacccaga taagtggagt gaagaaatta   1080
atgcatagtt caagcctaaa caatacaagc atctcacgct ttggagtcaa cactgaaaat   1140
gaagatcacc tggccaagga gctggaagac ctgaacaaat ggggtcttaa catctttaat   1200
gtggctggat attctcacaa tagacccta acatgcatca tgtatgctat attccaggaa   1260
agagacctcc taaagacatt cagaatctca tctgacacat ttataaccta catgatgact   1320
ttagaagacc attaccattc tgacgtggca tatcacaaca gcctgcacgc tgctgatgta   1380
gcccagtcga cccatgttct cctttctaca ccagcattag acgctgtctt cacagatttg   1440
gagatcctgg ctgccatttt tgcagctgcc atccatgacg ttgatcatcc tggagtctcc   1500
aatcagtttc tcatcaacac aaattcagaa cttgctttga tgtataatga tgaatctgtg   1560
ttggaaaatc atcaccttgc tgtgggtttc aaactgctgc aagaagaaca ctgtgacatc   1620
ttcatgaatc tcaccaagaa gcagcgtcag acactcagga agatggttat tgacatggtg   1680
ttagcaactg atatgtctaa acatatgagc ctgctggcag acctgaagac aatggtagaa   1740
acgaagaaag ttacaagttc aggcgttctt ctcctagaca actataccga tcgcattcag   1800
gtccttcgca acatggtaca ctgtgcagac ctgagcaacc ccaccaagtc cttggaattg   1860
tatcggcaat ggacagaccg catcatggag gaatttttcc agcagggaga caaagagcgg   1920
gagaggggaa tggaaattag cccaatgtgt gataaacaca cagcttctgt ggaaaaatcc   1980
caggttggtt tcatcgacta cattgtccat ccattgtggg agacatgggc agatttggta   2040
cagcctgatg ctcaggacat tctcgatacc ttagaagata acaggaactg gtatcagagc   2100
atgatacctc aaagtccctc accaccactg gacgagcaga cagggactg ccagggtctg    2160
atggagaagt ttcagtttga actgactctc gatgaggaag attctgaagg acctgagaag   2220
gagggagagg gacacagcta tttcagcagc acaaagacgc tttgtgtgat tgatccagaa   2280
aacagagatt ccctgggaga gactgacata gacattgcaa cagaagacaa gtcccccgtg   2340
gatacataat ccccctctcc ctgtggagat gaacattcta tccttgatga gcatgccagc   2400
tatgtggtag ggccagccca ccatgggggc caagacctgc acaggacaag ggccacctgg   2460
cctttcagtt acttgagttt ggagtcagaa agcaagacca ggaagcaaat agcagctcag   2520
gaaatcccac ggttgacttg ccttgatggc aagcttggtg gagagggctg aagctgttgc   2580
tggggggccga ttctgatcaa gacacatggc ttgaaaatgg aagacacaaa actgagagat   2640
cattctgcac taagtttcgg gaacttatcc ccgacagtga ctgaactcac tgactaataa   2700
```

-continued

```
cttcatttat gaatcttctc acttgtccct tgtctgcca acctgtgtgc ctttttgta    2760 aaacattttc atgtctttaa aatgcctgtt gaatacctgg agtttagtat caacttctac    2820
acagataagc tttcaaagtt gacaaacttt tttgactctt tctggaaaag ggaagaaaa    2880 tagtcttcct tctttcttgg gcaatatcct tcactttact acagttactt ttgcaaacag    2940
acagaaagga tacacttcta accacatttt acttccttcc cctgttgtcc agtccaactc    3000
cacagtcact cttaaaactt ctctctgttt gcctgcctcc aacagtactt ttaacttttt    3060
gctgtaaaca gaataaaatt gaacaaatta gggggtagaa aggagcagtg gtgtcgttca    3120
ccgtgagagt ctgcatagaa ctcagcagtg tgccctgctg tgtcttggac cctgcaatgc    3180
ggccgc                                                                3186
```

<210> SEQ ID NO 5
<211> LENGTH: 721
<212> TYPE: PRT
<213> ORGANISM: Homo sapiens

<400> SEQUENCE: 5

```
Met Thr Ala Lys Asp Ser Ser Lys Glu Leu Thr Ala Ser Glu Pro Glu
 1               5                  10                  15

Val Cys Ile Lys Thr Phe Lys Glu Gln Met His Leu Glu Leu Glu Leu
             20                  25                  30

Pro Arg Leu Pro Gly Asn Arg Pro Thr Ser Pro Lys Ile Ser Pro Arg
         35                  40                  45

Ser Ser Pro Arg Asn Ser Pro Cys Phe Phe Arg Lys Leu Leu Val Asn
     50                  55                  60

Lys Ser Ile Arg Gln Arg Arg Phe Thr Val Ala His Thr Cys Phe
 65                  70                  75                  80

Asp Val Glu Asn Gly Pro Ser Pro Gly Arg Ser Pro Leu Asp Pro Gln
                 85                  90                  95

Ala Ser Ser Ser Ala Gly Leu Val Leu His Ala Thr Phe Pro Gly His
            100                 105                 110

Ser Gln Arg Arg Glu Ser Phe Leu Tyr Arg Ser Asp Ser Asp Tyr Asp
        115                 120                 125

Leu Ser Pro Lys Ala Met Ser Arg Asn Ser Ser Leu Pro Ser Glu Gln
    130                 135                 140

His Gly Asp Asp Leu Ile Val Thr Pro Phe Ala Gln Val Leu Ala Ser
145                 150                 155                 160

Leu Arg Ser Val Arg Asn Asn Phe Thr Ile Leu Thr Asn Leu His Gly
                165                 170                 175

Thr Ser Asn Lys Arg Ser Pro Ala Ala Ser Gln Pro Pro Val Ser Arg
            180                 185                 190

Val Asn Pro Gln Glu Glu Ser Tyr Gln Lys Leu Ala Met Glu Thr Leu
        195                 200                 205

Glu Glu Leu Asp Trp Cys Leu Asp Gln Leu Glu Thr Ile Gln Thr Tyr
    210                 215                 220

Arg Ser Val Ser Glu Met Ala Ser Asn Lys Phe Lys Arg Met Leu Asn
225                 230                 235                 240

Arg Glu Leu Thr His Leu Ser Glu Met Ser Arg Ser Gly Asn Gln Val
                245                 250                 255

Ser Glu Tyr Ile Ser Asn Thr Phe Leu Asp Lys Gln Asn Asp Val Glu
            260                 265                 270

Ile Pro Ser Pro Thr Gln Lys Asp Arg Glu Lys Lys Lys Lys Gln Gln
```

-continued

```
                275                 280                 285
Leu Met Thr Gln Ile Ser Gly Val Lys Lys Leu Met His Ser Ser Ser
    290                 295                 300
Leu Asn Thr Ser Ile Ser Arg Phe Gly Val Asn Thr Glu Asn Glu
305                 310                 315                 320
Asp His Leu Ala Lys Glu Leu Glu Asp Leu Asn Lys Trp Gly Leu Asn
                325                 330                 335
Ile Phe Asn Val Ala Gly Tyr Ser His Asn Arg Pro Leu Thr Cys Ile
                340                 345                 350
Met Tyr Ala Ile Phe Gln Glu Arg Asp Leu Leu Lys Thr Phe Arg Ile
                355                 360                 365
Ser Ser Asp Thr Phe Ile Thr Tyr Met Met Thr Leu Glu Asp His Tyr
    370                 375                 380
His Ser Asp Val Ala Tyr His Asn Ser Leu His Ala Ala Asp Val Ala
385                 390                 395                 400
Gln Ser Thr His Val Leu Leu Ser Thr Pro Ala Leu Asp Ala Val Phe
                405                 410                 415
Thr Asp Leu Glu Ile Leu Ala Ala Ile Phe Ala Ala Ala Ile His Asp
                420                 425                 430
Val Asp His Pro Gly Val Ser Asn Gln Phe Leu Ile Asn Thr Asn Ser
                435                 440                 445
Glu Leu Ala Leu Met Tyr Asn Asp Glu Ser Val Leu Glu Asn His His
    450                 455                 460
Leu Ala Val Gly Phe Lys Leu Leu Gln Glu Glu His Cys Asp Ile Phe
465                 470                 475                 480
Met Asn Leu Thr Lys Lys Gln Arg Gln Thr Leu Arg Lys Met Val Ile
                485                 490                 495
Asp Met Val Leu Ala Thr Asp Met Ser Lys His Met Ser Leu Leu Ala
                500                 505                 510
Asp Leu Lys Thr Met Val Glu Thr Lys Lys Val Thr Ser Ser Gly Val
                515                 520                 525
Leu Leu Leu Asp Asn Tyr Thr Asp Arg Ile Gln Val Leu Arg Asn Met
    530                 535                 540
Val His Cys Ala Asp Leu Ser Asn Pro Thr Lys Ser Leu Glu Leu Tyr
545                 550                 555                 560
Arg Gln Trp Thr Asp Arg Ile Met Glu Glu Phe Gln Gln Gly Asp
                565                 570                 575
Lys Glu Arg Glu Arg Gly Met Glu Ile Ser Pro Met Cys Asp Lys His
                580                 585                 590
Thr Ala Ser Val Glu Lys Ser Gln Val Gly Phe Ile Asp Tyr Ile Val
                595                 600                 605
His Pro Leu Trp Glu Thr Trp Ala Asp Leu Val Gln Pro Asp Ala Gln
                610                 615                 620
Asp Ile Leu Asp Thr Leu Glu Asp Asn Arg Asn Trp Tyr Gln Ser Met
625                 630                 635                 640
Ile Pro Gln Ser Pro Ser Pro Leu Asp Glu Gln Asn Arg Asp Cys
                645                 650                 655
Gln Gly Leu Met Glu Lys Phe Gln Phe Glu Leu Thr Leu Asp Glu Glu
                660                 665                 670
Asp Ser Glu Gly Pro Glu Lys Glu Gly Glu Gly His Ser Tyr Phe Ser
                675                 680                 685
Ser Thr Lys Thr Leu Cys Val Ile Asp Pro Glu Asn Arg Asp Ser Leu
    690                 695                 700
```

Gly Glu Thr Asp Ile Asp Ile Ala Thr Glu Asp Lys Ser Pro Val Asp
705                 710                 715                 720

Thr

<210> SEQ ID NO 6
<211> LENGTH: 606
<212> TYPE: PRT
<213> ORGANISM: Homo sapiens

<400> SEQUENCE: 6

Ile Thr Asp Thr Ser Ser Arg Arg Gly Val Gly Gly Lys Leu Gly Thr
1               5                   10                  15

Ser His Pro Arg Gln Ser Thr Thr Val Ile Cys Ser Pro Gly Gly Glu
            20                  25                  30

Ser Trp Lys Glu Gly Ala Ser Val Gln Ile Met Lys Glu His Gly Gly
        35                  40                  45

Thr Phe Ser Ser Thr Gly Ile Ser Gly Gly Ser Gly Asp Ser Ala Met
    50                  55                  60

Asp Ser Leu Gln Pro Leu Gln Pro Asn Tyr Met Pro Val Cys Leu Phe
65                  70                  75                  80

Ala Glu Glu Ser Tyr Gln Lys Leu Ala Met Glu Thr Leu Glu Glu Leu
                85                  90                  95

Asp Trp Cys Leu Asp Gln Leu Glu Thr Ile Gln Thr Tyr Arg Ser Val
            100                 105                 110

Ser Glu Met Ala Ser Asn Lys Phe Lys Arg Met Leu Asn Arg Glu Leu
        115                 120                 125

Thr His Leu Ser Glu Met Ser Arg Ser Gly Asn Gln Val Ser Glu Tyr
    130                 135                 140

Ile Ser Asn Thr Phe Leu Asp Lys Gln Asn Asp Val Glu Ile Pro Ser
145                 150                 155                 160

Pro Thr Gln Lys Asp Arg Glu Lys Lys Lys Gln Gln Leu Met Thr
                165                 170                 175

Gln Ile Ser Gly Val Lys Lys Leu Met His Ser Ser Ser Leu Asn Asn
        180                 185                 190

Thr Ser Ile Ser Arg Phe Gly Val Asn Thr Glu Asn Glu Asp His Leu
    195                 200                 205

Ala Lys Glu Leu Glu Asp Leu Asn Lys Trp Gly Leu Asn Ile Phe Asn
210                 215                 220

Val Ala Gly Tyr Ser His Asn Arg Pro Leu Thr Cys Ile Met Tyr Ala
225                 230                 235                 240

Ile Phe Gln Glu Arg Asp Leu Leu Lys Thr Phe Arg Ile Ser Ser Asp
                245                 250                 255

Thr Phe Ile Thr Tyr Met Met Thr Leu Glu Asp His Tyr His Ser Asp
            260                 265                 270

Val Ala Tyr His Asn Ser Leu His Ala Ala Asp Val Ala Gln Ser Thr
        275                 280                 285

His Val Leu Leu Ser Thr Pro Ala Leu Asp Ala Val Phe Thr Asp Leu
    290                 295                 300

Glu Ile Leu Ala Ala Ile Phe Ala Ala Ala Ile His Asp Val Asp His
305                 310                 315                 320

Pro Gly Val Ser Asn Gln Phe Leu Ile Asn Thr Asn Ser Glu Leu Ala
                325                 330                 335

Leu Met Tyr Asn Asp Glu Ser Val Leu Glu Asn His His Leu Ala Val
            340                 345                 350

```
Gly Phe Lys Leu Leu Gln Glu Glu His Cys Asp Ile Phe Met Asn Leu
        355                 360                 365

Thr Lys Lys Gln Arg Gln Thr Leu Arg Lys Met Val Ile Asp Met Val
    370                 375                 380

Leu Ala Thr Asp Met Ser Lys His Met Ser Leu Leu Ala Asp Leu Lys
385                 390                 395                 400

Thr Met Val Glu Thr Lys Lys Val Thr Ser Ser Gly Val Leu Leu Leu
                405                 410                 415

Asp Asn Tyr Thr Asp Arg Ile Gln Val Leu Arg Asn Met Val His Cys
            420                 425                 430

Ala Asp Leu Ser Asn Pro Thr Lys Ser Leu Glu Leu Tyr Arg Gln Trp
        435                 440                 445

Thr Asp Arg Ile Met Glu Glu Phe Phe Gln Gln Gly Asp Lys Glu Arg
    450                 455                 460

Glu Arg Gly Met Glu Ile Ser Pro Met Cys Asp Lys His Thr Ala Ser
465                 470                 475                 480

Val Glu Lys Ser Gln Val Gly Phe Ile Asp Tyr Ile Val His Pro Leu
                485                 490                 495

Trp Glu Thr Trp Ala Asp Leu Val Gln Pro Asp Ala Gln Asp Ile Leu
            500                 505                 510

Asp Thr Leu Glu Asp Asn Arg Asn Trp Tyr Gln Ser Met Ile Pro Gln
        515                 520                 525

Ser Pro Ser Pro Pro Leu Asp Glu Gln Asn Arg Asp Cys Gln Gly Leu
    530                 535                 540

Met Glu Lys Phe Gln Phe Glu Leu Thr Leu Asp Glu Glu Asp Ser Glu
545                 550                 555                 560

Gly Pro Glu Lys Glu Gly Gly His Ser Tyr Phe Ser Ser Thr Lys
                565                 570                 575

Thr Leu Cys Val Ile Asp Pro Glu Asn Arg Asp Ser Leu Gly Glu Thr
            580                 585                 590

Asp Ile Asp Ile Ala Thr Glu Asp Lys Ser Pro Val Asp Thr
        595                 600                 605

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccgaattcat atgagcatct cacgctttgg agtc                              34

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgtgctctcg agttagctgt gtccctctcc ctcc                              34

<210> SEQ ID NO 9
<211> LENGTH: 29
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 9
gatatgtcta aacacatgag cctgctggc                                          29

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gccagcaggc tcatgtgttt agacatatc                                          29

<210> SEQ ID NO 11
<211> LENGTH: 391
<212> TYPE: DNA
<213> ORGANISM: Artificial Sequence
<220> FEATURE:
<223> OTHER INFORMATION: Description of Artificial Sequence: Synthetic
      plasmid sequence
<220> FEATURE:
<221> NAME/KEY: CDS
<222> LOCATION: (108)..(170)

<400> SEQUENCE: 11
agatctcgat cccgcgaaat taatacgact cactataggg gaattgtgag cggataacaa        60
ttcccctcta gaaataattt tgtttaactt taagaaggag atatacc atg ggc agc         116
                                                     Met Gly Ser
                                                       1 agc cat cat cat cat cat cac agc agc ggc ctg gtg ccg cgc ggc agc         164
Ser His His His His His His Ser Ser Gly Leu Val Pro Arg Gly Ser
     5                  10                  15 cat atg ggatccggaa ttcaaaggcc tacgtcgact agagcctgca gtctcgacca          220
His Met
 20 tcatcatcat catcattaat aaaagggcga attccagcac actggcggcc gttactagtg       280 gatccggctg ctaacaaagc ccgaaaggaa gctgagttgg ctgctgccac cgctgagcaa       340 taactagcat aaccccttgg ggcctctaaa cgggtcttga ggggttttt g                 391

<210> SEQ ID NO 12
<211> LENGTH: 21
<212> TYPE: PRT
<213> ORGANISM: Artificial Sequence
<220> FEATURE:
<223> OTHER INFORMATION: Description of Artificial Sequence: Synthetic
      amino acid sequence

<400> SEQUENCE: 12

Met Gly Ser Ser His His His His His His Ser Ser Gly Leu Val Pro
  1               5                  10                  15

Arg Gly Ser His Met
             20

<210> SEQ ID NO 13
<211> LENGTH: 1376
<212> TYPE: DNA
<213> ORGANISM: Artificial Sequence
<220> FEATURE:
```

-continued

<223> OTHER INFORMATION: Description of Artificial Sequence: Synthetic
      plasmid sequence
<220> FEATURE:
<221> NAME/KEY: CDS
<222> LOCATION: (88)..(1281)

<400> SEQUENCE: 13

```
taatacgact cactataggg gaattgtgag cggataacaa ttcccctcta gaaataattt        60
tgtttaactt taagaaggag atatacc atg ggc agc agc cat cat cat cat cat      114
                              Met Gly Ser Ser His His His His His
                              1               5 cac agc agc ggc ctg gtg ccg cgc ggc agc cat atg agc atc tca cgc        162
His Ser Ser Gly Leu Val Pro Arg Gly Ser His Met Ser Ile Ser Arg
 10                  15                  20                  25 ttt gga gtc aac act gaa aat gaa gat cac ctg gcc aag gag ctg gaa        210
Phe Gly Val Asn Thr Glu Asn Glu Asp His Leu Ala Lys Glu Leu Glu
                 30                  35                  40 gac ctg aac aaa tgg ggt ctt aac atc ttt aat gtg gct gga tat tct        258
Asp Leu Asn Lys Trp Gly Leu Asn Ile Phe Asn Val Ala Gly Tyr Ser
             45                  50                  55 cac aat aga ccc cta aca tgc atc atg tat gct ata ttc cag gaa aga        306
His Asn Arg Pro Leu Thr Cys Ile Met Tyr Ala Ile Phe Gln Glu Arg
         60                  65                  70 gac ctc cta aag aca ttc aga atc tca tct gac aca ttt ata acc tac        354
Asp Leu Leu Lys Thr Phe Arg Ile Ser Ser Asp Thr Phe Ile Thr Tyr
     75                  80                  85 atg atg act tta gaa gac cat tac cat tct gac gtg gca tat cac aac        402
Met Met Thr Leu Glu Asp His Tyr His Ser Asp Val Ala Tyr His Asn
 90                  95                 100                 105 agc ctg cac gct gct gat gta gcc cag tcg acc cat gtt ctc ctt tct        450
Ser Leu His Ala Ala Asp Val Ala Gln Ser Thr His Val Leu Leu Ser
                110                 115                 120 aca cca gca tta gac gct gtc ttc aca gat ttg gaa atc ctg gct gcc        498
Thr Pro Ala Leu Asp Ala Val Phe Thr Asp Leu Glu Ile Leu Ala Ala
            125                 130                 135 att ttt gca gct gcc atc cat gac gtt gat cat cct gga gtc tcc aat        546
Ile Phe Ala Ala Ala Ile His Asp Val Asp His Pro Gly Val Ser Asn
        140                 145                 150 cag ttt ctc atc aac aca aat tca gaa ctt gct ttg atg tat aat gat        594
Gln Phe Leu Ile Asn Thr Asn Ser Glu Leu Ala Leu Met Tyr Asn Asp
    155                 160                 165 gaa tct gtg ttg gaa aat cat cac ctt gct gtg ggt ttc aaa ctg ctg        642
Glu Ser Val Leu Glu Asn His His Leu Ala Val Gly Phe Lys Leu Leu
170                 175                 180                 185 caa gaa gaa cac tgt gac atc ttc atg aat ctc acc aag aag cag cgt        690
Gln Glu Glu His Cys Asp Ile Phe Met Asn Leu Thr Lys Lys Gln Arg
                190                 195                 200 cag aca ctc agg aag atg gtt att gac atg gtg tta gca act gat atg        738
Gln Thr Leu Arg Lys Met Val Ile Asp Met Val Leu Ala Thr Asp Met
            205                 210                 215 tct aaa cac atg agc ctg ctg gca gac ctg aag aca atg gta gaa acg        786
Ser Lys His Met Ser Leu Leu Ala Asp Leu Lys Thr Met Val Glu Thr
        220                 225                 230 aag aaa gtt aca agt tca ggc gtt ctt ctc cta gac aac tat acc gat        834
Lys Lys Val Thr Ser Ser Gly Val Leu Leu Leu Asp Asn Tyr Thr Asp
    235                 240                 245 cgc att cag gtc ctt cgc aac atg gta cac tgt gca gac ctg agc aac        882
Arg Ile Gln Val Leu Arg Asn Met Val His Cys Ala Asp Leu Ser Asn
250                 255                 260                 265 ccc acc aag tcc ttg gaa ttg tat cgg caa tgg aca gac gcc atc atg        930
```

-continued

```
Pro Thr Lys Ser Leu Glu Leu Tyr Arg Gln Trp Thr Asp Arg Ile Met
                270                 275                 280 gag gaa ttt ttc cag cag gga gac aaa gag cgg gag agg gga atg gaa      978
Glu Glu Phe Phe Gln Gln Gly Asp Lys Glu Arg Glu Arg Gly Met Glu
            285                 290                 295 att agc cca atg tgt gat aaa cac aca gct tct gtg gaa aaa tcc cag     1026
Ile Ser Pro Met Cys Asp Lys His Thr Ala Ser Val Glu Lys Ser Gln
        300                 305                 310 gtt ggt ttc atc gac tac att gtc cat cca ttg tgg gag aca tgg gca     1074
Val Gly Phe Ile Asp Tyr Ile Val His Pro Leu Trp Glu Thr Trp Ala
    315                 320                 325 gat ttg gta cag cct gat gct cag gac att ctc gat acc tta gaa gat     1122
Asp Leu Val Gln Pro Asp Ala Gln Asp Ile Leu Asp Thr Leu Glu Asp
330                 335                 340                 345 aac agg aac tgg tat cag agc atg ata cct caa agt ccc tca cca cca     1170
Asn Arg Asn Trp Tyr Gln Ser Met Ile Pro Gln Ser Pro Ser Pro Pro
                350                 355                 360 ctg gac gag cag aac agg gac tgc cag ggt ctg atg gag aag ttt cag     1218
Leu Asp Glu Gln Asn Arg Asp Cys Gln Gly Leu Met Glu Lys Phe Gln
            365                 370                 375 ttt gaa ctg act ctc gat gag gaa gat tct gaa gga cct gag aag gag     1266
Phe Glu Leu Thr Leu Asp Glu Glu Asp Ser Glu Gly Pro Glu Lys Glu
        380                 385                 390 gga gag gga cac agc taactcgact agagcctgca gtctcgacca tcatcatcat     1321
Gly Glu Gly His Ser
    395 catcattaat aaaagggcga attccagcac actggcggcc gttactagtg gatcc        1376
```

<210> SEQ ID NO 14
<211> LENGTH: 398
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 14

```
Met Gly Ser Ser His His His His His His Ser Ser Gly Leu Val Pro
1               5                   10                  15

Arg Gly Ser His Met Ser Ile Ser Arg Phe Gly Val Asn Thr Glu Asn
            20                  25                  30

Glu Asp His Leu Ala Lys Glu Leu Glu Asp Leu Asn Lys Trp Gly Leu
        35                  40                  45

Asn Ile Phe Asn Val Ala Gly Tyr Ser His Asn Arg Pro Leu Thr Cys
    50                  55                  60

Ile Met Tyr Ala Ile Phe Gln Glu Arg Asp Leu Leu Lys Thr Phe Arg
65                  70                  75                  80

Ile Ser Ser Asp Thr Phe Ile Thr Tyr Met Met Thr Leu Glu Asp His
                85                  90                  95

Tyr His Ser Asp Val Ala Tyr His Asn Ser Leu His Ala Ala Asp Val
            100                 105                 110

Ala Gln Ser Thr His Val Leu Leu Ser Thr Pro Ala Leu Asp Ala Val
        115                 120                 125

Phe Thr Asp Leu Glu Ile Leu Ala Ala Ile Phe Ala Ala Ala Ile His
    130                 135                 140

Asp Val Asp His Pro Gly Val Ser Asn Gln Phe Leu Ile Asn Thr Asn
145                 150                 155                 160

Ser Glu Leu Ala Leu Met Tyr Asn Asp Glu Ser Val Leu Glu Asn His
```

```
                    165                 170                 175
His Leu Ala Val Gly Phe Lys Leu Leu Gln Glu Glu His Cys Asp Ile
            180                 185                 190

Phe Met Asn Leu Thr Lys Lys Gln Arg Gln Thr Leu Arg Lys Met Val
        195                 200                 205

Ile Asp Met Val Leu Ala Thr Asp Met Ser Lys His Met Ser Leu Leu
    210                 215                 220

Ala Asp Leu Lys Thr Met Val Glu Thr Lys Lys Val Thr Ser Ser Gly
225                 230                 235                 240

Val Leu Leu Leu Asp Asn Tyr Thr Asp Arg Ile Gln Val Leu Arg Asn
                245                 250                 255

Met Val His Cys Ala Asp Leu Ser Asn Pro Thr Lys Ser Leu Glu Leu
            260                 265                 270

Tyr Arg Gln Trp Thr Asp Arg Ile Met Glu Glu Phe Phe Gln Gln Gly
        275                 280                 285

Asp Lys Glu Arg Glu Arg Gly Met Glu Ile Ser Pro Met Cys Asp Lys
    290                 295                 300

His Thr Ala Ser Val Glu Lys Ser Gln Val Gly Phe Ile Asp Tyr Ile
305                 310                 315                 320

Val His Pro Leu Trp Glu Thr Trp Ala Asp Leu Val Gln Pro Asp Ala
                325                 330                 335

Gln Asp Ile Leu Asp Thr Leu Glu Asp Asn Arg Asn Trp Tyr Gln Ser
            340                 345                 350

Met Ile Pro Gln Ser Pro Ser Pro Pro Leu Asp Glu Gln Asn Arg Asp
        355                 360                 365

Cys Gln Gly Leu Met Glu Lys Phe Gln Phe Glu Leu Thr Leu Asp Glu
    370                 375                 380

Glu Asp Ser Glu Gly Pro Glu Lys Glu Gly Glu Gly His Ser
385                 390                 395

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ccgaattcat atgagcatct cacgctttgg agtc                                34

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tgtgctctcg agttagctgt gtccctctcc ctcc                                34

<210> SEQ ID NO 17
<211> LENGTH: 1376
<212> TYPE: DNA
<213> ORGANISM: Artificial Sequence
<220> FEATURE:
<223> OTHER INFORMATION: Description of Artificial Sequence: Synthetic
      plasmid sequence
<220> FEATURE:
```

```
<221> NAME/KEY: CDS
<222> LOCATION: (88)..(1281)

<400> SEQUENCE: 17
taatacgact cactataggg gaattgtgag cggataacaa ttcccctcta gaaataattt      60
tgtttaactt taagaaggag atatacc atg ggc agc agc cat cat cat cat cat    114
                                Met Gly Ser Ser His His His His His
                                 1               5 cac agc agc ggc ctg gtg ccg cgc ggc agc cat atg agt atc cca agg      162
His Ser Ser Gly Leu Val Pro Arg Gly Ser His Met Ser Ile Pro Arg
 10              15                  20                  25 ttt gga gtt aaa act gaa caa gaa gat gtc ctt gcc aag gaa cta gaa      210
Phe Gly Val Lys Thr Glu Gln Glu Asp Val Leu Ala Lys Glu Leu Glu
             30                  35                  40 gat gtg aac aaa tgg ggt ctt cat gtt ttc aga ata gca gag ttg tct      258
Asp Val Asn Lys Trp Gly Leu His Val Phe Arg Ile Ala Glu Leu Ser
         45                  50                  55 ggt aac cgg ccc ttg act gtt atc atg cac acc att ttt cag gaa cgg      306
Gly Asn Arg Pro Leu Thr Val Ile Met His Thr Ile Phe Gln Glu Arg
     60                  65                  70 gat tta tta aaa aca ttt aaa att cca gta gat act tta att aca tat      354
Asp Leu Leu Lys Thr Phe Lys Ile Pro Val Asp Thr Leu Ile Thr Tyr
 75                  80                  85 ctt atg act ctc gaa gac cat tac cat gct gat gtg gcc tat cac aac      402
Leu Met Thr Leu Glu Asp His Tyr His Ala Asp Val Ala Tyr His Asn
 90                  95                 100                 105 aat atc cat gct gca gat gtt gtc cag tct act cat gtg cta tta tct      450
Asn Ile His Ala Ala Asp Val Val Gln Ser Thr His Val Leu Leu Ser
                 110                 115                 120 aca cct gct ttg gag gct gtg ttt aca gat ttg gag att ctt gca gca      498
Thr Pro Ala Leu Glu Ala Val Phe Thr Asp Leu Glu Ile Leu Ala Ala
             125                 130                 135 att ttt gcc agt gca ata cat gat gta gat cat cct ggt gtg tcc aat      546
Ile Phe Ala Ser Ala Ile His Asp Val Asp His Pro Gly Val Ser Asn
         140                 145                 150 caa ttt ctg atc aat aca aac tct gaa ctt gcc ttg atg tac aat gat      594
Gln Phe Leu Ile Asn Thr Asn Ser Glu Leu Ala Leu Met Tyr Asn Asp
 155                 160                 165 tcc tca gtc tta gag aac cat cat ttg gct gtg ggc ttt aaa ttg ctt      642
Ser Ser Val Leu Glu Asn His His Leu Ala Val Gly Phe Lys Leu Leu
170                 175                 180                 185 cag gaa gaa aac tgt gac att ttc cag aat ttg acc aaa aaa caa aga      690
Gln Glu Glu Asn Cys Asp Ile Phe Gln Asn Leu Thr Lys Lys Gln Arg
                 190                 195                 200 caa tct tta agg aaa atg gtc att gac atc gta ctt gca aca gat atg      738
Gln Ser Leu Arg Lys Met Val Ile Asp Ile Val Leu Ala Thr Asp Met
             205                 210                 215 tca aaa cac atg aat cta ctg gct gat ttg aag act atg gtt gaa act      786
Ser Lys His Met Asn Leu Leu Ala Asp Leu Lys Thr Met Val Glu Thr
         220                 225                 230 aag aaa gtg aca agc tct gga gtt ctt ctt gat aat tat tcc gat         834
Lys Lys Val Thr Ser Ser Gly Val Leu Leu Asp Asn Tyr Ser Asp
 235                 240                 245 agg att cag gtt ctt cag aat atg gtg cac tgt gca gat ctg agc aac      882
Arg Ile Gln Val Leu Gln Asn Met Val His Cys Ala Asp Leu Ser Asn
250                 255                 260                 265 cca aca aag cct ctc cag ctg tac cgc cag tgg acg gac cgg ata atg      930
Pro Thr Lys Pro Leu Gln Leu Tyr Arg Gln Trp Thr Asp Arg Ile Met
                 270                 275                 280
```

```
gag gag ttc ttc cgc caa gga gac cga gag agg gaa cgt ggc atg gag      978
Glu Glu Phe Phe Arg Gln Gly Asp Arg Glu Arg Glu Arg Gly Met Glu
            285                 290                 295 ata agc ccc atg tgt gac aag cac aat gct tcc gtg gaa aaa tca cag     1026
Ile Ser Pro Met Cys Asp Lys His Asn Ala Ser Val Glu Lys Ser Gln
        300                 305                 310 gtg ggc ttc ata gac tat att gtt cat ccc ctc tgg gag aca tgg gca     1074
Val Gly Phe Ile Asp Tyr Ile Val His Pro Leu Trp Glu Thr Trp Ala
    315                 320                 325 gac ctc gtc cac cct gac gcc cag gat att ttg gac act ttg gag gac     1122
Asp Leu Val His Pro Asp Ala Gln Asp Ile Leu Asp Thr Leu Glu Asp
330                 335                 340                 345 aat cgt gaa tgg tac cag agc aca atc cct cag agc ccc tct cct gca     1170
Asn Arg Glu Trp Tyr Gln Ser Thr Ile Pro Gln Ser Pro Ser Pro Ala
                350                 355                 360 cct gat gac cca gag gag ggc cgg cag ggt caa act gag aaa ttc cag     1218
Pro Asp Asp Pro Glu Glu Gly Arg Gln Gly Gln Thr Glu Lys Phe Gln
            365                 370                 375 ttt gaa cta act tta gag gaa gat ggt gag tca gac acg gaa aag gac     1266
Phe Glu Leu Thr Leu Glu Glu Asp Gly Glu Ser Asp Thr Glu Lys Asp
        380                 385                 390 agt ggc agt caa gtg taagtcgact agagcctgca gtctcgacca tcatcatcat     1321
Ser Gly Ser Gln Val
    395 catcattaat aaaagggcga attccagcac actggcggcc gttactagtg gatcc         1376

<210> SEQ ID NO 18
<211> LENGTH: 398
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 18

Met Gly Ser Ser His His His His His His Ser Ser Gly Leu Val Pro
 1               5                  10                  15

Arg Gly Ser His Met Ser Ile Pro Arg Phe Gly Val Lys Thr Glu Gln
            20                  25                  30

Glu Asp Val Leu Ala Lys Glu Leu Glu Asp Val Asn Lys Trp Gly Leu
        35                  40                  45

His Val Phe Arg Ile Ala Glu Leu Ser Gly Asn Arg Pro Leu Thr Val
    50                  55                  60

Ile Met His Thr Ile Phe Gln Glu Arg Asp Leu Leu Lys Thr Phe Lys
65                  70                  75                  80

Ile Pro Val Asp Thr Leu Ile Thr Tyr Leu Met Thr Leu Glu Asp His
                85                  90                  95

Tyr His Ala Asp Val Ala Tyr His Asn Asn Ile His Ala Ala Asp Val
            100                 105                 110

Val Gln Ser Thr His Val Leu Leu Ser Thr Pro Ala Leu Glu Ala Val
        115                 120                 125

Phe Thr Asp Leu Glu Ile Leu Ala Ala Ile Phe Ala Ser Ala Ile His
    130                 135                 140

Asp Val Asp His Pro Gly Val Ser Asn Gln Phe Leu Ile Asn Thr Asn
145                 150                 155                 160

Ser Glu Leu Ala Leu Met Tyr Asn Asp Ser Ser Val Leu Glu Asn His
                165                 170                 175

His Leu Ala Val Gly Phe Lys Leu Leu Gln Glu Glu Asn Cys Asp Ile
```

```
              180                 185                 190
Phe Gln Asn Leu Thr Lys Lys Gln Arg Gln Ser Leu Arg Lys Met Val
            195                 200                 205
Ile Asp Ile Val Leu Ala Thr Asp Met Ser Lys His Met Asn Leu Leu
210                 215                 220
Ala Asp Leu Lys Thr Met Val Glu Thr Lys Lys Val Thr Ser Ser Gly
225                 230                 235                 240
Val Leu Leu Leu Asp Asn Tyr Ser Asp Arg Ile Gln Val Leu Gln Asn
                245                 250                 255
Met Val His Cys Ala Asp Leu Ser Asn Pro Thr Lys Pro Leu Gln Leu
            260                 265                 270
Tyr Arg Gln Trp Thr Asp Arg Ile Met Glu Glu Phe Phe Arg Gln Gly
        275                 280                 285
Asp Arg Glu Arg Glu Arg Gly Met Glu Ile Ser Pro Met Cys Asp Lys
    290                 295                 300
His Asn Ala Ser Val Glu Lys Ser Gln Val Gly Phe Ile Asp Tyr Ile
305                 310                 315                 320
Val His Pro Leu Trp Glu Thr Trp Ala Asp Leu Val His Pro Asp Ala
                325                 330                 335
Gln Asp Ile Leu Asp Thr Leu Glu Asp Asn Arg Glu Trp Tyr Gln Ser
            340                 345                 350
Thr Ile Pro Gln Ser Pro Ser Pro Ala Pro Asp Asp Pro Glu Glu Gly
        355                 360                 365
Arg Gln Gly Gln Thr Glu Lys Phe Gln Phe Glu Leu Thr Leu Glu Glu
    370                 375                 380
Asp Gly Glu Ser Asp Thr Glu Lys Asp Ser Gly Ser Gln Val
385                 390                 395

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tctgactcat atgagtatcc caaggtttgg agt                              33

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ctagtgtcga cttacacttg actgccactg tcct                             34

<210> SEQ ID NO 21
<211> LENGTH: 1856
<212> TYPE: DNA
<213> ORGANISM: Artificial Sequence
<220> FEATURE:
<223> OTHER INFORMATION: Description of Artificial Sequence: Synthetic
      plasmid sequence
<220> FEATURE:
<221> NAME/KEY: CDS
<222> LOCATION: (56)..(1822)
```

-continued

```
<400> SEQUENCE: 21
tattccggat tattcatacc gtcccaccat cgggcgcgga tctcggtccg aaacc atg      58
                                                             Met
                                                             1 tcg tac tac cat cac cat cac cat cac gat tac gat atc cca acg acc     106
Ser Tyr Tyr His His His His His His Asp Tyr Asp Ile Pro Thr Thr
          5                  10                  15 gaa aac ctg tat ttt cag ggc cat atg aag gag cac ggg ggc acc ttc     154
Glu Asn Leu Tyr Phe Gln Gly His Met Lys Glu His Gly Gly Thr Phe
             20                  25                  30 agt agc acc gga atc agc ggt ggt agc ggt gac tct gct atg gac agc     202
Ser Ser Thr Gly Ile Ser Gly Gly Ser Gly Asp Ser Ala Met Asp Ser
 35                  40                  45 ctg cag ccg ctc cag cct aac tac atg cct gtg tgt ttg ttt gca gaa     250
Leu Gln Pro Leu Gln Pro Asn Tyr Met Pro Val Cys Leu Phe Ala Glu
 50                  55                  60                  65 gaa tct tat caa aaa tta gca atg gaa acg ctg gag gaa tta gac tgg     298
Glu Ser Tyr Gln Lys Leu Ala Met Glu Thr Leu Glu Glu Leu Asp Trp
                 70                  75                  80 tgt tta gac cag cta gag acc ata cag acc tac cgg tct gtc agt gag     346
Cys Leu Asp Gln Leu Glu Thr Ile Gln Thr Tyr Arg Ser Val Ser Glu
             85                  90                  95 atg gct tct aac aag ttc aaa aga atg ctg aac cgg gag ctg aca cac     394
Met Ala Ser Asn Lys Phe Lys Arg Met Leu Asn Arg Glu Leu Thr His
100                 105                 110 ctc tca gag atg agc cga tca ggg aac cag gtg tct gaa tac att tca     442
Leu Ser Glu Met Ser Arg Ser Gly Asn Gln Val Ser Glu Tyr Ile Ser
    115                 120                 125 aat act ttc tta gac aag cag aat gat gtg gag atc cca tct cct acc     490
Asn Thr Phe Leu Asp Lys Gln Asn Asp Val Glu Ile Pro Ser Pro Thr
130                 135                 140                 145 cag aaa gac agg gag aaa aag aaa aag cag cag ctc atg acc cag ata     538
Gln Lys Asp Arg Glu Lys Lys Lys Lys Gln Gln Leu Met Thr Gln Ile
                150                 155                 160 agt gga gtg aag aaa tta atg cat agt tca agc cta aac aat aca agc     586
Ser Gly Val Lys Lys Leu Met His Ser Ser Ser Leu Asn Asn Thr Ser
            165                 170                 175 atc tca cgc ttt gga gtc aac act gaa aat gaa gat cac ctg gcc aag     634
Ile Ser Arg Phe Gly Val Asn Thr Glu Asn Glu Asp His Leu Ala Lys
        180                 185                 190 gag ctg gaa gac ctg aac aaa tgg ggt ctt aac atc ttt aat gtg gct     682
Glu Leu Glu Asp Leu Asn Lys Trp Gly Leu Asn Ile Phe Asn Val Ala
    195                 200                 205 gga tat tct cac aat aga ccc cta aca tgc atc atg tat gct ata ttc     730
Gly Tyr Ser His Asn Arg Pro Leu Thr Cys Ile Met Tyr Ala Ile Phe
210                 215                 220                 225 cag gaa aga gac ctc cta aag aca ttc aga atc tca tct gac aca ttt     778
Gln Glu Arg Asp Leu Leu Lys Thr Phe Arg Ile Ser Ser Asp Thr Phe
                230                 235                 240 ata acc tac atg atg act tta gaa gac cat tac cat tct gac gtg gca     826
Ile Thr Tyr Met Met Thr Leu Glu Asp His Tyr His Ser Asp Val Ala
            245                 250                 255 tat cac aac agc ctg cac gct gct gat gta gcc cag tcg acc cat gtt     874
Tyr His Asn Ser Leu His Ala Ala Asp Val Ala Gln Ser Thr His Val
        260                 265                 270 ctc ctt tct aca cca gca tta gac gct gtc ttc aca gat ttg gaa atc     922
Leu Leu Ser Thr Pro Ala Leu Asp Ala Val Phe Thr Asp Leu Glu Ile
    275                 280                 285 ctg gct gcc att ttt gca gct gcc atc cat gac gtt gat cat cct gga     970
```

```
Leu Ala Ala Ile Phe Ala Ala Ile His Asp Val Asp His Pro Gly
290                 295                 300                 305 gtc tcc aat cag ttt ctc atc aac aca aat tca gaa ctt gct ttg atg    1018
Val Ser Asn Gln Phe Leu Ile Asn Thr Asn Ser Glu Leu Ala Leu Met
                310                 315                 320 tat aat gat gaa tct gtg ttg gaa aat cat cac ctt gct gtg ggt ttc    1066
Tyr Asn Asp Glu Ser Val Leu Glu Asn His His Leu Ala Val Gly Phe
            325                 330                 335 aaa ctg ctg caa gaa gaa cac tgt gac atc ttc atg aat ctc acc aag    1114
Lys Leu Leu Gln Glu Glu His Cys Asp Ile Phe Met Asn Leu Thr Lys
        340                 345                 350 aag cag cgt cag aca ctc agg aag atg gtt att gac atg gtg tta gca    1162
Lys Gln Arg Gln Thr Leu Arg Lys Met Val Ile Asp Met Val Leu Ala
    355                 360                 365 act gat atg tct aaa cac atg agc ctg ctg gca gac ctg aag aca atg    1210
Thr Asp Met Ser Lys His Met Ser Leu Leu Ala Asp Leu Lys Thr Met
370                 375                 380                 385 gta gaa acg aag aaa gtt aca agt tca ggc gtt ctt ctc cta gac aac    1258
Val Glu Thr Lys Lys Val Thr Ser Ser Gly Val Leu Leu Leu Asp Asn
                390                 395                 400 tat acc gat cgc att cag gtc ctt cgc aac atg gta cac tgt gca gac    1306
Tyr Thr Asp Arg Ile Gln Val Leu Arg Asn Met Val His Cys Ala Asp
            405                 410                 415 ctg agc aac ccc acc aag tcc ttg gaa ttg tat cgg caa tgg aca gac    1354
Leu Ser Asn Pro Thr Lys Ser Leu Glu Leu Tyr Arg Gln Trp Thr Asp
        420                 425                 430 cgc atc atg gag gaa ttt ttc cag cag gga gac aaa gag cgg gag agg    1402
Arg Ile Met Glu Glu Phe Phe Gln Gln Gly Asp Lys Glu Arg Glu Arg
    435                 440                 445 gga atg gaa att agc cca atg tgt gat aaa cac aca gct tct gtg gaa    1450
Gly Met Glu Ile Ser Pro Met Cys Asp Lys His Thr Ala Ser Val Glu
450                 455                 460                 465 aaa tcc cag gtt ggt ttc atc gac tac att gtc cat cca ttg tgg gag    1498
Lys Ser Gln Val Gly Phe Ile Asp Tyr Ile Val His Pro Leu Trp Glu
                470                 475                 480 aca tgg gca gat ttg gta cag cct gat gct cag gac att ctc gat acc    1546
Thr Trp Ala Asp Leu Val Gln Pro Asp Ala Gln Asp Ile Leu Asp Thr
            485                 490                 495 tta gaa gat aac agg aac tgg tat cag agc atg ata cct caa gtc ccc    1594
Leu Glu Asp Asn Arg Asn Trp Tyr Gln Ser Met Ile Pro Gln Ser Pro
        500                 505                 510 tca cca cca ctg gac gag cag aac agg gac tgc cag ggt ctg atg gag    1642
Ser Pro Pro Leu Asp Glu Gln Asn Arg Asp Cys Gln Gly Leu Met Glu
    515                 520                 525 aag ttt cag ttt gaa ctg act ctc gat gag gaa gat tct gaa gga cct    1690
Lys Phe Gln Phe Glu Leu Thr Leu Asp Glu Glu Asp Ser Glu Gly Pro
530                 535                 540                 545 gag aag gag gga gag gga cac agc tat ttc agc agc aca aag acg ctt    1738
Glu Lys Glu Gly Glu Gly His Ser Tyr Phe Ser Ser Thr Lys Thr Leu
                550                 555                 560 tgt gtg att gat cca gaa aac aga gat tcc ctg gga gag act gac ata    1786
Cys Val Ile Asp Pro Glu Asn Arg Asp Ser Leu Gly Glu Thr Asp Ile
            565                 570                 575 gac att gca aca gaa gac aag tcc ccc gtg gat aca taatcccct          1832
Asp Ile Ala Thr Glu Asp Lys Ser Pro Val Asp Thr
        580                 585 ctcgaggcat gcggtaccaa gctt                                         1856

<210> SEQ ID NO 22
```

```
<211> LENGTH: 589
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 22
```

Met Ser Tyr Tyr His His His His His His Asp Tyr Asp Ile Pro Thr
1               5                   10                  15

Thr Glu Asn Leu Tyr Phe Gln Gly His Met Lys Glu His Gly Gly Thr
            20                  25                  30

Phe Ser Ser Thr Gly Ile Ser Gly Ser Gly Asp Ser Ala Met Asp
        35                  40                  45

Ser Leu Gln Pro Leu Gln Pro Asn Tyr Met Pro Val Cys Leu Phe Ala
50                  55                  60

Glu Glu Ser Tyr Gln Lys Leu Ala Met Glu Thr Leu Glu Glu Leu Asp
65                  70                  75                  80

Trp Cys Leu Asp Gln Leu Glu Thr Ile Gln Thr Tyr Arg Ser Val Ser
                85                  90                  95

Glu Met Ala Ser Asn Lys Phe Lys Arg Met Leu Asn Arg Glu Leu Thr
            100                 105                 110

His Leu Ser Glu Met Ser Arg Ser Gly Asn Gln Val Ser Glu Tyr Ile
        115                 120                 125

Ser Asn Thr Phe Leu Asp Lys Gln Asn Asp Val Glu Ile Pro Ser Pro
130                 135                 140

Thr Gln Lys Asp Arg Glu Lys Lys Lys Gln Gln Leu Met Thr Gln
145                 150                 155                 160

Ile Ser Gly Val Lys Lys Leu Met His Ser Ser Leu Asn Asn Thr
                165                 170                 175

Ser Ile Ser Arg Phe Gly Val Asn Thr Glu Asn Glu Asp His Leu Ala
            180                 185                 190

Lys Glu Leu Glu Asp Leu Asn Lys Trp Gly Leu Asn Ile Phe Asn Val
        195                 200                 205

Ala Gly Tyr Ser His Asn Arg Pro Leu Thr Cys Ile Met Tyr Ala Ile
210                 215                 220

Phe Gln Glu Arg Asp Leu Leu Lys Thr Phe Arg Ile Ser Ser Asp Thr
225                 230                 235                 240

Phe Ile Thr Tyr Met Met Thr Leu Glu Asp His Tyr His Ser Asp Val
                245                 250                 255

Ala Tyr His Asn Ser Leu His Ala Ala Asp Val Ala Gln Ser Thr His
            260                 265                 270

Val Leu Leu Ser Thr Pro Ala Leu Asp Ala Val Phe Thr Asp Leu Glu
        275                 280                 285

Ile Leu Ala Ala Ile Phe Ala Ala Ala Ile His Asp Val Asp His Pro
290                 295                 300

Gly Val Ser Asn Gln Phe Leu Ile Asn Thr Asn Ser Glu Leu Ala Leu
305                 310                 315                 320

Met Tyr Asn Asp Glu Ser Val Leu Glu Asn His His Leu Ala Val Gly
                325                 330                 335

Phe Lys Leu Leu Gln Glu Glu His Cys Asp Ile Phe Met Asn Leu Thr
            340                 345                 350

Lys Lys Gln Arg Gln Thr Leu Arg Lys Met Val Ile Asp Met Val Leu
        355                 360                 365

Ala Thr Asp Met Ser Lys His Met Ser Leu Leu Ala Asp Leu Lys Thr

```
                370                 375                 380
Met Val Glu Thr Lys Lys Val Thr Ser Ser Gly Val Leu Leu Asp
385                 390                 395                 400

Asn Tyr Thr Asp Arg Ile Gln Val Leu Arg Asn Met Val His Cys Ala
                405                 410                 415

Asp Leu Ser Asn Pro Thr Lys Ser Leu Glu Leu Tyr Arg Gln Trp Thr
                420                 425                 430

Asp Arg Ile Met Glu Glu Phe Phe Gln Gln Gly Asp Lys Glu Arg Glu
                435                 440                 445

Arg Gly Met Glu Ile Ser Pro Met Cys Asp Lys His Thr Ala Ser Val
450                 455                 460

Glu Lys Ser Gln Val Gly Phe Ile Asp Tyr Ile Val His Pro Leu Trp
465                 470                 475                 480

Glu Thr Trp Ala Asp Leu Val Gln Pro Asp Ala Gln Asp Ile Leu Asp
                485                 490                 495

Thr Leu Glu Asp Asn Arg Asn Trp Tyr Gln Ser Met Ile Pro Gln Ser
                500                 505                 510

Pro Ser Pro Leu Asp Glu Gln Asn Arg Asp Cys Gln Gly Leu Met
                515                 520                 525

Glu Lys Phe Gln Phe Glu Leu Thr Leu Asp Glu Glu Asp Ser Glu Gly
530                 535                 540

Pro Glu Lys Glu Gly Glu Gly His Ser Tyr Phe Ser Ser Thr Lys Thr
545                 550                 555                 560

Leu Cys Val Ile Asp Pro Glu Asn Arg Asp Ser Leu Gly Glu Thr Asp
                565                 570                 575

Ile Asp Ile Ala Thr Glu Asp Lys Ser Pro Val Asp Thr
                580                 585

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cgtgcaacat atgaaggagc acgggggcac                                     30

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tccacctcga gaggggatt atgtatccac                                      30

<210> SEQ ID NO 25
<211> LENGTH: 2413
<212> TYPE: DNA
<213> ORGANISM: Artificial Sequence
<220> FEATURE:
<223> OTHER INFORMATION: Description of Artificial Sequence: Synthetic
      plasmid sequence
<220> FEATURE:
<221> NAME/KEY: CDS
<222> LOCATION: (56)..(2365)
```

<400> SEQUENCE: 25

```
tattccggat tattcatacc gtcccaccat cgggcgcgga tctcggtccg aaacc atg        58
                                                              Met
                                                                1 tcg tac tac cat cac cat cac cat cac gat tac gat atc cca acg acc        106
Ser Tyr Tyr His His His His His His Asp Tyr Asp Ile Pro Thr Thr
          5                  10                  15 gaa aac ctg tat ttt cag ggc cat atg gct cag cag aca agc ccg gac        154
Glu Asn Leu Tyr Phe Gln Gly His Met Ala Gln Gln Thr Ser Pro Asp
             20                  25                  30 act tta aca gta cct gaa gtg gat aat ccg cat tgt cca aac ccg tgg        202
Thr Leu Thr Val Pro Glu Val Asp Asn Pro His Cys Pro Asn Pro Trp
         35                  40                  45 ctg aac gaa gac ctt gtg aaa tcc ttg cga gaa aac ctg ttg cag cat        250
Leu Asn Glu Asp Leu Val Lys Ser Leu Arg Glu Asn Leu Leu Gln His
 50                  55                  60                  65 gag aag tcc aag aca gcg agg aaa tcg gtt tct ccc aag ctc tct ca         298
Glu Lys Ser Lys Thr Ala Arg Lys Ser Val Ser Pro Lys Leu Ser Pro
                 70                  75                  80 gtg atc tct ccg aga aat tcc ccc agg ctt ctg cgc aga atg ct ctc         346
Val Ile Ser Pro Arg Asn Ser Pro Arg Leu Leu Arg Arg Met Leu Leu
             85                  90                  95 agc agc aac atc ccc aaa cag cgg cgt ttc acg gtg gca ca aca tgt        394
Ser Ser Asn Ile Pro Lys Gln Arg Arg Phe Thr Val Ala His Thr Cys
        100                 105                 110 ttt gat gtg gac aat ggc aca tct gcg gga cgg agt cccttg gat ccc        442
Phe Asp Val Asp Asn Gly Thr Ser Ala Gly Arg Ser Pro Leu Asp Pro
115                 120                 125 atg acc agc cca gga tcc ggg cta att ctc caa gca at ttt gtc cac        490
Met Thr Ser Pro Gly Ser Gly Leu Ile Leu Gln Ala Asn Phe Val His
130                 135                 140                 145 agt caa cga cgg gag tcc ttc ctg tat cga tcc gc agc gat tat gac        538
Ser Gln Arg Arg Glu Ser Phe Leu Tyr Arg Ser Asp Ser Asp Tyr Asp
                150                 155                 160 ctc tct cca aag tct atg tcc cgg aac tcc tc att gcc agt gat ata        586
Leu Ser Pro Lys Ser Met Ser Arg Asn Ser Ser Ile Ala Ser Asp Ile
            165                 170                 175 cac gga gat gac ttg att gtg act cca tttgct cag gtc ttg gcc agt        634
His Gly Asp Asp Leu Ile Val Thr Pro Phe Ala Gln Val Leu Ala Ser
        180                 185                 190 ctg cga act gta cga aac aac ttt gct ca tta act aat ttg caa gat        682
Leu Arg Thr Val Arg Asn Asn Phe Ala Ala Leu Thr Asn Leu Gln Asp
    195                 200                 205 cga gca cct agc aaa aga tca ccc ag tgc aac caa cca tcc atc aac        730
Arg Ala Pro Ser Lys Arg Ser Pro Met Cys Asn Gln Pro Ser Ile Asn
210                 215                 220                 225 aaa gcc acc ata aca gag gag gc tac cag aaa ctg gcc agc gag acc        778
Lys Ala Thr Ile Thr Glu Glu Ala Tyr Gln Lys Leu Ala Ser Glu Thr
                230                 235                 240 ctg gag gag ctg gac tgg tgtctg gac cag cta gag acc cta cag acc        826
Leu Glu Glu Leu Asp Trp Cys Leu Asp Gln Leu Glu Thr Leu Gln Thr
            245                 250                 255 agg cac tcc gtc agt gag tg gcc tcc aac aag ttt aaa agg atg ctt        874
Arg His Ser Val Ser Glu Met Ala Ser Asn Lys Phe Lys Arg Met Leu
        260                 265                 270 aat cgg gag ctc acc ct ctc tct gaa atg agt cgg tct gga aat caa        922
Asn Arg Glu Leu Thr His Leu Ser Glu Met Ser Arg Ser Gly Asn Gln
    275                 280                 285 gtg tca gag ttt at tca aac aca ttc tta gat aag caa cat gaa gtg        970
```

```
                                        -continued

Val Ser Glu Phe Ile Ser Asn Thr Phe Leu Asp Lys Gln His Glu Val
290                 295                 300                 305 gaa att cct tct cca act cag aag gaa aag gag aaa aag aaa aga cca      1018
Glu Ile Pro Ser Pro Thr Gln Lys Glu Lys Glu Lys Lys Lys Arg Pro
                310                 315                 320 atg tct cag atc agt gga gtc aag aaa ttg atg cac agc tct agt ctg      1066
Met Ser Gln Ile Ser Gly Val Lys Lys Leu Met His Ser Ser Ser Leu
            325                 330                 335 act aat tca agt atc cca agg ttt gga gtt aaa act gaa caa gaa gat      1114
Thr Asn Ser Ser Ile Pro Arg Phe Gly Val Lys Thr Glu Gln Glu Asp
        340                 345                 350 gtc ctt gcc aag gaa cta gaa gat gtg aac aaa tgg ggt ctt cat gtt      1162
Val Leu Ala Lys Glu Leu Glu Asp Val Asn Lys Trp Gly Leu His Val
    355                 360                 365 ttc aga ata gca gag ttg tct ggt aac cgg ccc ttg act gtt atc atg      1210
Phe Arg Ile Ala Glu Leu Ser Gly Asn Arg Pro Leu Thr Val Ile Met
370                 375                 380                 385 cac acc att ttt cag gaa cgg gat tta tta aaa aca ttt aaa att cca      1258
His Thr Ile Phe Gln Glu Arg Asp Leu Leu Lys Thr Phe Lys Ile Pro
                390                 395                 400 gta gat act tta att aca tat ctt atg act ctc gaa gac cat tac cat      1306
Val Asp Thr Leu Ile Thr Tyr Leu Met Thr Leu Glu Asp His Tyr His
            405                 410                 415 gct gat gtg gcc tat cac aac aat atc cat gct gca gat gtt gtc cag      1354
Ala Asp Val Ala Tyr His Asn Asn Ile His Ala Ala Asp Val Val Gln
        420                 425                 430 tct act cat gtg cta tta tct aca cct gct ttg gag gct gtg ttt aca      1402
Ser Thr His Val Leu Leu Ser Thr Pro Ala Leu Glu Ala Val Phe Thr
    435                 440                 445 gat ttg gag att ctt gca gca att ttt gcc agt gca ata cat gat gta      1450
Asp Leu Glu Ile Leu Ala Ala Ile Phe Ala Ser Ala Ile His Asp Val
450                 455                 460                 465 gat cat cct ggt gtg tcc aat caa ttt ctg atc aat aca aac tct gaa      1498
Asp His Pro Gly Val Ser Asn Gln Phe Leu Ile Asn Thr Asn Ser Glu
                470                 475                 480 ctt gcc ttg atg tac aat gat tcc tca gtc tta gag aac cat cat ttg      1546
Leu Ala Leu Met Tyr Asn Asp Ser Ser Val Leu Glu Asn His His Leu
            485                 490                 495 gct gtg ggc ttt aaa ttg ctt cag gaa gaa aac tgt gac att ttc cag      1594
Ala Val Gly Phe Lys Leu Leu Gln Glu Glu Asn Cys Asp Ile Phe Gln
        500                 505                 510 aat ttg acc aaa aaa caa aga caa tct tta agg aaa atg gtc att gac      1642
Asn Leu Thr Lys Lys Gln Arg Gln Ser Leu Arg Lys Met Val Ile Asp
    515                 520                 525 atc gta ctt gca aca gat atg tca aaa cac atg aat cta ctg gct gat      1690
Ile Val Leu Ala Thr Asp Met Ser Lys His Met Asn Leu Leu Ala Asp
530                 535                 540                 545 ttg aag act atg gtt gaa act aag aaa gtg aca agc tct gga gtt ctt      1738
Leu Lys Thr Met Val Glu Thr Lys Lys Val Thr Ser Ser Gly Val Leu
                550                 555                 560 ctt ctt gat aat tat tcc gat agg att cag gtt ctt cag aat atg gtg      1786
Leu Leu Asp Asn Tyr Ser Asp Arg Ile Gln Val Leu Gln Asn Met Val
            565                 570                 575 cac tgt gca gat ctg agc aac cca aca aag cct ctc cag ctg tac cgc      1834
His Cys Ala Asp Leu Ser Asn Pro Thr Lys Pro Leu Gln Leu Tyr Arg
        580                 585                 590 cag tgg acg gac cgg ata atg gag gag ttc ttc cgc caa gga gac cga      1882
Gln Trp Thr Asp Arg Ile Met Glu Glu Phe Phe Arg Gln Gly Asp Arg
    595                 600                 605
```

```
gag agg gaa cgt ggc atg gag ata agc ccc atg tgt gac aag cac aat    1930
Glu Arg Glu Arg Gly Met Glu Ile Ser Pro Met Cys Asp Lys His Asn
610             615                 620                 625 gct tcc gtg gaa aaa tca cag gtg ggc ttc ata gac tat att gtt cat    1978
Ala Ser Val Glu Lys Ser Gln Val Gly Phe Ile Asp Tyr Ile Val His
                630                 635                 640 ccc ctc tgg gag aca tgg gca gac ctc gtc cac cct gac gcc cag gat    2026
Pro Leu Trp Glu Thr Trp Ala Asp Leu Val His Pro Asp Ala Gln Asp
            645                 650                 655 att ttg gac act ttg gag gac aat cgt gaa tgg tac cag agc aca atc    2074
Ile Leu Asp Thr Leu Glu Asp Asn Arg Glu Trp Tyr Gln Ser Thr Ile
        660                 665                 670 cct cag agc ccc tct cct gca cct gat gac cca gag gag ggc cgg cag    2122
Pro Gln Ser Pro Ser Pro Ala Pro Asp Asp Pro Glu Glu Gly Arg Gln
    675                 680                 685 ggt caa act gag aaa ttc cag ttt gaa cta act tta gag gaa gat ggt    2170
Gly Gln Thr Glu Lys Phe Gln Phe Glu Leu Thr Leu Glu Glu Asp Gly
690                 695                 700                 705 gag tca gac acg gaa aag gac agt ggc agt caa gtg gaa gaa gac act    2218
Glu Ser Asp Thr Glu Lys Asp Ser Gly Ser Gln Val Glu Glu Asp Thr
                710                 715                 720 agc tgc agt gac tcc aag act ctt tgt act caa gac tca gag tct act    2266
Ser Cys Ser Asp Ser Lys Thr Leu Cys Thr Gln Asp Ser Glu Ser Thr
            725                 730                 735 gaa att ccc ctt gat gaa cag gtt gaa gag gag gca gta ggg gaa gaa    2314
Glu Ile Pro Leu Asp Glu Gln Val Glu Glu Glu Ala Val Gly Glu Glu
        740                 745                 750 gag gaa agc cag cct gaa gcc tgt gtc ata gat gat cgt tct cct gac    2362
Glu Glu Ser Gln Pro Glu Ala Cys Val Ile Asp Asp Arg Ser Pro Asp
    755                 760                 765 acg taacagtcga ctagagcctg cagtctcgag gcatgcggta ccaagctt          2413
Thr
770

<210> SEQ ID NO 26
<211> LENGTH: 770
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 26

Met Ser Tyr Tyr His His His His His His Asp Tyr Asp Ile Pro Thr
1               5                   10                  15

Thr Glu Asn Leu Tyr Phe Gln Gly His Met Ala Gln Gln Thr Ser Pro
            20                  25                  30

Asp Thr Leu Thr Val Pro Glu Val Asp Asn Pro His Cys Pro Asn Pro
        35                  40                  45

Trp Leu Asn Glu Asp Leu Val Lys Ser Leu Arg Glu Asn Leu Leu Gln
    50                  55                  60

His Glu Lys Ser Lys Thr Ala Arg Lys Ser Val Ser Pro Lys Leu Ser
65                  70                  75                  80

Pro Val Ile Ser Pro Arg Asn Ser Pro Arg Leu Leu Arg Arg Met Leu
                85                  90                  95

Leu Ser Ser Asn Ile Pro Lys Gln Arg Arg Phe Thr Val Ala His Thr
            100                 105                 110

Cys Phe Asp Val Asp Asn Gly Thr Ser Ala Gly Arg Ser Pro Leu Asp
        115                 120                 125
```

-continued

```
Pro Met Thr Ser Pro Gly Ser Gly Leu Ile Leu Gln Ala Asn Phe Val
    130                 135                 140

His Ser Gln Arg Arg Glu Ser Phe Leu Tyr Arg Ser Asp Ser Asp Tyr
145                 150                 155                 160

Asp Leu Ser Pro Lys Ser Met Ser Arg Asn Ser Ser Ile Ala Ser Asp
                165                 170                 175

Ile His Gly Asp Asp Leu Ile Val Thr Pro Phe Ala Gln Val Leu Ala
            180                 185                 190

Ser Leu Arg Thr Val Arg Asn Asn Phe Ala Ala Leu Thr Asn Leu Gln
        195                 200                 205

Asp Arg Ala Pro Ser Lys Arg Ser Pro Met Cys Asn Gln Pro Ser Ile
    210                 215                 220

Asn Lys Ala Thr Ile Thr Glu Glu Ala Tyr Gln Lys Leu Ala Ser Glu
225                 230                 235                 240

Thr Leu Glu Glu Leu Asp Trp Cys Leu Asp Gln Leu Glu Thr Leu Gln
                245                 250                 255

Thr Arg His Ser Val Ser Glu Met Ala Ser Asn Lys Phe Lys Arg Met
            260                 265                 270

Leu Asn Arg Glu Leu Thr His Leu Ser Glu Met Ser Arg Ser Gly Asn
        275                 280                 285

Gln Val Ser Glu Phe Ile Ser Asn Thr Phe Leu Asp Lys Gln His Glu
    290                 295                 300

Val Glu Ile Pro Ser Pro Thr Gln Lys Glu Lys Glu Lys Lys Lys Arg
305                 310                 315                 320

Pro Met Ser Gln Ile Ser Gly Val Lys Lys Leu Met His Ser Ser Ser
                325                 330                 335

Leu Thr Asn Ser Ser Ile Pro Arg Phe Gly Val Lys Thr Glu Gln Glu
            340                 345                 350

Asp Val Leu Ala Lys Glu Leu Glu Asp Val Asn Lys Trp Gly Leu His
        355                 360                 365

Val Phe Arg Ile Ala Glu Leu Ser Gly Asn Arg Pro Leu Thr Val Ile
    370                 375                 380

Met His Thr Ile Phe Gln Glu Arg Asp Leu Leu Lys Thr Phe Lys Ile
385                 390                 395                 400

Pro Val Asp Thr Leu Ile Thr Tyr Leu Met Thr Leu Glu Asp His Tyr
                405                 410                 415

His Ala Asp Val Ala Tyr His Asn Asn Ile His Ala Ala Asp Val Val
            420                 425                 430

Gln Ser Thr His Val Leu Leu Ser Thr Pro Ala Leu Glu Ala Val Phe
        435                 440                 445

Thr Asp Leu Glu Ile Leu Ala Ala Ile Phe Ala Ser Ala Ile His Asp
    450                 455                 460

Val Asp His Pro Gly Val Ser Asn Gln Phe Leu Ile Asn Thr Asn Ser
465                 470                 475                 480

Glu Leu Ala Leu Met Tyr Asn Asp Ser Ser Val Leu Glu Asn His His
                485                 490                 495

Leu Ala Val Gly Phe Lys Leu Leu Gln Glu Glu Asn Cys Asp Ile Phe
            500                 505                 510

Gln Asn Leu Thr Lys Lys Gln Arg Gln Ser Leu Arg Lys Met Val Ile
        515                 520                 525

Asp Ile Val Leu Ala Thr Asp Met Ser Lys His Met Asn Leu Leu Ala
    530                 535                 540

Asp Leu Lys Thr Met Val Glu Thr Lys Lys Val Thr Ser Ser Gly Val
```

```
                    545                 550                 555                 560
Leu Leu Leu Asp Asn Tyr Ser Asp Arg Ile Gln Val Leu Gln Asn Met
                565                 570                 575
Val His Cys Ala Asp Leu Ser Asn Pro Thr Lys Pro Leu Gln Leu Tyr
                580                 585                 590
Arg Gln Trp Thr Asp Arg Ile Met Glu Glu Phe Phe Arg Gln Gly Asp
                595                 600                 605
Arg Glu Arg Glu Arg Gly Met Glu Ile Ser Pro Met Cys Asp Lys His
            610                 615                 620
Asn Ala Ser Val Glu Lys Ser Gln Val Gly Phe Ile Asp Tyr Ile Val
625                 630                 635                 640
His Pro Leu Trp Glu Thr Trp Ala Asp Leu Val His Pro Asp Ala Gln
                645                 650                 655
Asp Ile Leu Asp Thr Leu Glu Asp Asn Arg Glu Trp Tyr Gln Ser Thr
                660                 665                 670
Ile Pro Gln Ser Pro Ser Pro Ala Pro Asp Asp Pro Glu Glu Gly Arg
                675                 680                 685
Gln Gly Gln Thr Glu Lys Phe Gln Phe Glu Leu Thr Leu Glu Glu Asp
            690                 695                 700
Gly Glu Ser Asp Thr Glu Lys Asp Ser Gly Ser Gln Val Glu Glu Asp
705                 710                 715                 720
Thr Ser Cys Ser Asp Ser Lys Thr Leu Cys Thr Gln Asp Ser Glu Ser
                725                 730                 735
Thr Glu Ile Pro Leu Asp Glu Gln Val Glu Glu Ala Val Gly Glu
                740                 745                 750
Glu Glu Glu Ser Gln Pro Glu Ala Cys Val Ile Asp Asp Arg Ser Pro
            755                 760                 765
Asp Thr
    770

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gaccaggcat atggctcagc agacaagccc                                           30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
agtttgtcga ctgttacgtg tcaggagaac                                           30

<210> SEQ ID NO 29
<211> LENGTH: 1274
<212> TYPE: DNA
<213> ORGANISM: Artificial Sequence
<220> FEATURE:
<223> OTHER INFORMATION: Description of Artificial Sequence: Synthetic
      plasmid sequence
```

```
<400> SEQUENCE: 29
atataccatg ggcagcagcc atcatcatca tcatcacagc agcggcctgg tgccgcgcgg      60
cagccatatg agcatctcac gctttggagt caacactgaa aatgaagatc acctggccaa     120
ggagctggaa gacctgaaca aatggggtct aaacatcttt aatgtggctg gatattctca     180
caatagaccc ctaacatgca tcatgtatgc tatattccag gaaagagacc tcctaaagac     240
attcagaatc tcatctgaca catttataac ctacatgatg actttagaag accattacca     300
ttctgacgtg gcatatcaca cagcctgcca cgctgctgat gtagcccagt cgacccatgt     360
tctcctttct acaccagcat tagacgctgt cttcacagat ttggaaatcc tggctgccat     420
ttttgcagct gccatccatg acgttgatca tcctggagtc tccaatcagt ttctcatcaa     480
cacaaattca gaacttgctt tgatgtataa tgatgaatct gtgttggaaa atcatcacct     540
tgctgtgggt ttcaaactgc tgcaagaaga acactgtgac atcttcatga atctcaccaa     600
gaagcagcgt cagacactca ggaagatggt tattgacatg gtgttagcaa ctgatatgtc     660
taaacacatg agcctgctgg cagacctgaa gacaatggta gaaacgaaga agttacaag     720 ttcaggcgtt cttctcctag acaactatac cgatcgcatt caggtccttc gcaacatggt     780
acactgtgca gacctgagca accccaccaa gtccttggaa ttgtatcggc aatggacaga     840
ccgcatcatg gaggaatttt tccagcaggg agacaaagag cgggagaggg gaatggaaat     900
tagcccaatg tgtgataaac acacagcttc tgtggaaaaa tcccaggttg gtttcatcga     960
ctacattgtc catccattgt gggagacatg ggcagatttg gtacagcctg atgctcagga    1020
cattctcgat accttagaag ataacaggaa ctggtatcag agcatgatac ctcaaagtcc    1080
ctcaccacca ctggacgagc agaacaggga ctgccagggt ctgatggaga gtttcagtt    1140 tgaactgact ctcgatgagg aagattctga aggacctgag aaggagggag agggacacag    1200
ctaactcgac tagagcctgc agtctcgacc atcatcatca tcatcattaa taaaagggcg    1260
aattccagca cact                                                     1274

<210> SEQ ID NO 30
<211> LENGTH: 357
<212> TYPE: PRT
<213> ORGANISM: Homo sapiens

<400> SEQUENCE: 30

Ser Ile Ser Arg Phe Gly Val Asn Thr Glu Asn Glu Asp His Leu Ala
  1               5                  10                  15

Lys Glu Leu Glu Asp Leu Asn Lys Trp Gly Leu Asn Ile Phe Asn Val
             20                  25                  30

Ala Gly Tyr Ser His Asn Arg Pro Leu Thr Cys Ile Met Tyr Ala Ile
         35                  40                  45

Phe Gln Glu Arg Asp Leu Leu Lys Thr Phe Arg Ile Ser Ser Asp Thr
     50                  55                  60

Phe Ile Thr Tyr Met Met Thr Leu Glu Asp His Tyr His Ser Asp Val
 65                  70                  75                  80

Ala Tyr His Asn Ser Leu His Ala Ala Asp Val Ala Gln Ser Thr His
                 85                  90                  95

Val Leu Leu Ser Thr Pro Ala Leu Asp Ala Val Phe Thr Asp Leu Glu
            100                 105                 110

Ile Leu Ala Ala Ile Phe Ala Ala Ala Ile His Asp Val Asp His Pro
        115                 120                 125

Gly Val Ser Asn Gln Phe Leu Ile Asn Thr Asn Ser Glu Leu Ala Leu
```

```
              130                 135                 140
Met Tyr Asn Asp Glu Ser Val Leu Glu Asn His His Leu Ala Val Gly
145                 150                 155                 160

Phe Lys Leu Leu Gln Glu Glu His Cys Asp Ile Phe Met Asn Leu Thr
                165                 170                 175

Lys Lys Gln Arg Gln Thr Leu Arg Lys Met Val Ile Asp Met Val Leu
            180                 185                 190

Ala Thr Asp Met Ser Lys His Met Ser Leu Leu Ala Asp Leu Lys Thr
        195                 200                 205

Met Val Glu Thr Lys Lys Val Thr Ser Ser Gly Val Leu Leu Leu Asp
210                 215                 220

Asn Tyr Thr Asp Arg Ile Gln Val Leu Arg Asn Met Val His Cys Ala
225                 230                 235                 240

Asp Leu Ser Asn Pro Thr Lys Ser Leu Glu Leu Tyr Arg Gln Trp Thr
                245                 250                 255

Asp Arg Ile Met Glu Glu Phe Phe Gln Gln Gly Asp Lys Glu Arg Glu
            260                 265                 270

Arg Gly Met Glu Ile Ser Pro Met Cys Asp Lys His Thr Ala Ser Val
        275                 280                 285

Glu Lys Ser Gln Val Gly Phe Ile Asp Tyr Ile Val His Pro Leu Trp
290                 295                 300

Glu Thr Trp Ala Asp Leu Val Gln Pro Asp Ala Gln Asp Ile Leu Asp
305                 310                 315                 320

Thr Leu Glu Asp Asn Arg Asn Trp Tyr Gln Ser Met Ile Pro Gln Ala
                325                 330                 335

Pro Ala Pro Pro Leu Asp Glu Gln Asn Arg Asp Cys Gln Gly Leu Met
            340                 345                 350

Glu Lys Phe Gln Phe
            355

<210> SEQ ID NO 31
<211> LENGTH: 349
<212> TYPE: PRT
<213> ORGANISM: Homo sapiens

<400> SEQUENCE: 31

Thr Glu Gln Glu Asp Val Leu Ala Lys Glu Leu Glu Asp Val Asn Lys
  1               5                  10                  15

Trp Gly Leu His Val Phe Arg Ile Ala Glu Leu Ser Gly Asn Arg Pro
                20                  25                  30

Leu Thr Val Ile Met His Thr Ile Phe Gln Glu Arg Asp Leu Leu Lys
            35                  40                  45

Thr Phe Lys Ile Pro Val Asp Thr Leu Ile Thr Tyr Leu Met Thr Leu
        50                  55                  60

Glu Asp His Tyr His Ala Asp Val Ala Tyr His Asn Asn Ile His Ala
65                  70                  75                  80

Ala Asp Val Val Gln Ser Thr His Val Leu Leu Ser Thr Pro Ala Leu
                85                  90                  95

Glu Ala Val Phe Thr Asp Leu Glu Ile Leu Ala Ala Ile Phe Ala Ser
            100                 105                 110

Ala Ile His Asp Val Asp His Pro Gly Val Ser Asn Gln Phe Leu Ile
        115                 120                 125

Asn Thr Asn Ser Glu Leu Ala Leu Met Tyr Asn Asp Ser Ser Val Leu
130                 135                 140
```

```
                                                 -continued

Glu Asn His His Leu Ala Val Gly Phe Lys Leu Leu Gln Glu Glu Asn
145                 150                 155                 160

Cys Asp Ile Phe Gln Asn Leu Thr Lys Lys Gln Arg Gln Ser Leu Arg
                165                 170                 175

Lys Met Val Ile Asp Ile Val Leu Ala Thr Asp Met Ser Lys His Met
            180                 185                 190

Asn Leu Leu Ala Asp Leu Lys Thr Met Val Glu Thr Lys Lys Val Thr
        195                 200                 205

Ser Ser Gly Val Leu Leu Leu Asp Asn Tyr Ser Asp Arg Ile Gln Val
    210                 215                 220

Leu Gln Asn Met Val His Cys Ala Asp Leu Ser Asn Pro Thr Lys Pro
225                 230                 235                 240

Leu Gln Leu Tyr Arg Gln Trp Thr Asp Arg Ile Met Glu Glu Phe Phe
                245                 250                 255

Pro Gln Gly Asp Arg Glu Arg Glu Arg Gly Met Glu Ile Ser Pro Met
                260                 265                 270

Cys Asp Lys His Asn Ala Ser Val Glu Lys Ser Gln Val Gly Phe Ile
            275                 280                 285

Asp Tyr Ile Val His Pro Leu Trp Glu Thr Trp Ala Asp Leu Val His
        290                 295                 300

Pro Asp Ala Gln Asp Ile Leu Asp Thr Leu Glu Asp Asn Arg Glu Trp
305                 310                 315                 320

Tyr Gln Ser Thr Ile Pro Gln Ser Pro Ser Pro Ala Pro Asp Asp Pro
                325                 330                 335

Glu Glu Gly Arg Gln Gly Gln Thr Glu Lys Phe Gln Phe
                340                 345

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 32

His His His His His His
  1               5
```

PDE4B INHIBITORS

CROSS-REFERENCE TO RELATED PATENT APPLICATIONS

This application claims the benefit of U.S. Prov. App. No. 60/607,407, filed Sep. 3, 2004, which is incorporated herein by reference in its entirety and for all purposes.

FIELD OF THE INVENTION

This invention relates to the development of ligands for phosphodiesterase PDE4, including for PDE4 isoforms PDE4B and PDE4D, and to the use of crystal structures of PDE4B and/or PDE4D. Additionally, this invention provides compounds with activity toward PDE4, and methods of use thereof.

BACKGROUND OF THE INVENTION

The information provided is intended solely to assist the understanding of the reader. None of the information provided nor references cited is admitted to be prior art to the present invention. Each of the references cited is incorporated herein in its entirety.

Phosphodiesterases (PDEs) were first detected by Sutherland and co-workers (Rall, et al., *J. Biol. Chem.*, 232:1065-1076 (1958), Butcher, et al., *J. Biol. Chem.*, 237:1244-1250 (1962)). The superfamily of PDEs is subdivided into two major classes, class I and class II (Charbonneau, H., *Cyclic Nucleotide Phosphodiesterases: Structure, Regulation and Drug Action*, Beavo, J., and Houslay, M. D., eds) 267-296 John Wiley & Sons, Inc., New York (1990)), which have no recognizable sequence similarity. Class I includes all known mammalian PDEs and is comprised of 11 identified families that are products of separate genes (Beavo, et al., *Mol. Pharmacol.*, 46:399-405 (1994); Conti, et al., *Endocr. Rev.*, 16:370-389 (1995); Degerman, et al., *J. Biol. Chem.*, 272:6823-6826 (1997); Houslay, M. D., *Adv. Enzyme Regul.*, 35:303-338 (1995); Bolger, G. B., *Cell Signal*, 6:851-859 (1994); Thompson, et al, *Adv. Second Messenger Phosphoprotein Res.*, 25:165-184 (1992); Underwood, et al., *J. Pharmacol. Exp. Ther.*, 270:250-259 (1994); Michaeli, et al., *J. Biol. Chem.*, 268:12925-12932 (1993); Soderling, et al., *Proc. Natl. Acad. Sci. U.S.A.*, 95:8991-8996 (1998); Soderling, et al., *J. Biol. Chem.*, 273:15553-15558 (1998); Fisher, et al., *J. Biol. Chem.*, 273:15559-15564 (1998)). Some PDEs are highly specific for hydrolysis of cAMP (PDE4, PDE7, PDE8), some are highly cGMP-specific (PDE5, PDE6, PDE9), and some have mixed specificity (PDE1, PDE2, PDE3, PDE10, PDE11) (Conti, *Molecular Endocrinology*, 14:1317-1327 (2000)).

All of the characterized mammalian PDEs are dimeric, but the importance of the dimeric structure for function in each of the PDEs is unknown. Each PDE has a conserved catalytic domain of ~270 amino acids with a high degree of conservation (25-30%) of amino acid sequence among PDE families, which is located carboxyl-terminal to its regulatory domain. Activators of certain PDEs appear to relieve the influence of autoinhibitory domains located within the enzyme structures (Sonnenberg, et al., *J. Biol. Chem.*, 270:30989-31000 (1995); Jin, et al., *J. Biol. Chem.*, 267:18929-18939 (1992)).

PDEs cleave the cyclic nucleotide phosphodiester bond between the phosphorus and oxygen atoms at the 3'-position with inversion of configuration at the phosphorus atom (Goldberg, et al., *J. Biol. Chem.*, 255:10344-10347 (1980); Burgers, et al., *J. Biol. Chem.*, 254:9959-9961 (1979)). This apparently results from an in-line nucleophilic attack by the OH$^-$ of ionized H$_2$O. It has been proposed that metals bound in the conserved metal binding motifs within PDEs facilitate the production of the attacking OH$^-$ (Francis, et al., *J. Biol. Chem.*, 269:22477-22480 (1994)). The kinetic properties of catalysis are consistent with a random order mechanism with respect to cyclic nucleotide and the divalent cations(s) that are required for catalysis (Srivastava, et al., *Biochem. J*, 308:653-658 (1995)). The catalytic domains of all known mammalian PDEs contain two sequences (HX$_3$ HX$_n$(E/D)) arranged in tandem, each of which resembles the single Zn$^{2+}$-binding site of metalloendoproteases such as thermolysin (Francis, et al., *J. Biol. Chem.*, 269:22477-22480 (1994)). PDE5 specifically binds Zn$^{2+}$, and the catalytic activities of PDE4, PDE5, and PDE6 are supported by submicromolar concentrations of Zn$^{2+}$ (Francis, et al., *J. Biol. Chem.*, 269:22477-22480 (1994); Percival, et al., *Biochem. Biophys. Res. Commun.*, 241:175-180 (1997)). Whether each of the Zn$^{2+}$-binding motifs binds Zn$^{2+}$ independently or whether the two motifs interact to form a novel Zn$^{2+}$-binding site is not known. The catalytic mechanism for cleaving phosphodiester bonds of cyclic nucleotides by PDEs may be similar to that of certain proteases for cleaving the amide ester of peptides, but the presence of two Zn$^{2+}$ motifs arranged in tandem in PDEs is unprecedented.

The group of Sutherland and Rall (Berthet, et al., *J. Biol. Chem.*, 229:351-361 (1957)), in the late 1950s, was the first to realize that at least part of the mechanism(s) whereby caffeine enhanced the effect of glucagon, a stimulator of adenylyl cyclase, on cAMP accumulation and glycogenolysis in liver involved inhibition of cAMP PDE activity. Since that time chemists have synthesized thousands of PDE inhibitors, including the widely used 3-isobutyl-1-methylxanthine (IBMX). Many of these compounds, as well as caffeine, are non-selective and inhibit many of the PDE families. One important advance in PDE research has been the discovery/design of family-specific inhibitors such as the PDE4 inhibitor, rolipram, and the PDE5 inhibitor, sildenafil.

Precise modulation of PDE function in cells is critical for maintaining cyclic nucleotide levels within a narrow rate-limiting range of concentrations. Increases in cGMP of 2-4-fold above the basal level will usually produce a maximum physiological response. There are three general schemes by which PDEs are regulated: (a) regulation by substrate availability, such as by stimulation of PDE activity by mass action after elevation of cyclic nucleotide levels or by alteration in the rate of hydrolysis of one cyclic nucleotide because of competition by another, which can occur with any of the dual specificity PDEs (e.g. PDE1, PDE2, PDE3); (b) regulation by extracellular signals that alter intracellular signaling (e.g. phosphorylation events, Ca$^{2+}$, phosphatidic acid, inositol phosphates, protein-protein interactions, etc.) resulting, for example, in stimulation of PDE3 activity by insulin (Degerman, et al., *J. Biol. Chem.*, 272:6823-6826 (1997)), stimulation of PDE6 activity by photons through the transducin system (Yamazaki, et al., *J. Biol. Chem.*, 255:11619-11624 (1980)), which alters PDE6 interaction with this enzyme, or stimulation of PDE 1 activity by increased interaction with Ca$^{2+}$/calmodulin; (c) feedback regulation, such as by phosphorylation of PDE1, PDE3, or PDE4 catalyzed by PKA after cAmP elevation (Conti, et al., *Endocr. Rev.*, 16:370-389 (1995); Degerman, et al., *J. Biol. Chem.*, 272:6823-6826 (1997); Gettys, et al., *J. Biol. Chem.* 262:333-339 (1987); Florio, et al, *Biochemistry*, 33:8948-8954 (1994)), by allosteric cGMP binding to PDE2 to promote breakdown of cAMP or cGMP after cGMP elevation, or by modulation of PDE protein levels, such as the desensitization that occurs by increased concentrations of PDE3 or PDE4 following chronic exposure of cells to cAMP-elevating agents (Conti, et al., *Endocr. Rev.*, 16:370-389 (1995), Sheth, et al., *Throm. Haemostasis*, 77:155-162 (1997)) or by developmentally related changes in PDE5 content. Other factors that could influence any of the three schemes outlined above are cellular compartmentalization of PDEs (Houslay, M. D., *Adv. Enzyme Regul*, 35:303-338 (1995)) effected by covalent modifications such as prenylation or by specific targeting sequences in the PDE primary structure and perhaps translocation of PDEs between compartments within a cell.

Within the PDE superfamily, four (PDE2, PDE5, PDE6, and PDE10) of the 10 families contain highly cGMP-specific allosteric (non-catalytic) cGMP-binding sites in addition to a catalytic site of varying substrate specificity. Each of the monomers of these dimeric cGMP-binding PDEs contains two homologous cGMP-binding sites of ~110 amino acids arranged in tandem and located in the amino-terminal portion of the protein (Charbonneau, H., *Cyclic Nucleotide Phosphodiesterases: Structure, Regulation and Drug Action*, Beavo, J., and Houslay, M. D., eds) 267-296 (1990); McAllister-Lucas, et al., *J. Biol. Chem.*, 270:30671-30679 (1995)). In PDE2, binding of the cGMP to these sites stimulates the hydrolysis of cAMP at the catalytic site (Beavo, et al., *Mol. Pharmacol.*, 46:399-405 (1994)). PDE2 hydrolyzes cGMP as well as cAMP, and cGMP hydrolysis is stimulated by cGMP binding at the allosteric sites in accordance with positively cooperative kinetics (Manganiello, et al., *Cyclic Nucleotide Phosphodiesterases. Structure, Regulation, and Drug Action*, Beavo, J., and Houslay, M. D., eds, 61-85 John Wiley & Sons, Inc., New York (1990)). This could represent a negative feedback process for regulation of tissue cGMP levels (Manganiello, et al., *Cyclic Nucleotide Phosphodiesterases: Structure, Regulation, and Drug Action*, Beavo, J., and Houslay, M. D., eds, 61-85 John Wiley & Sons, Inc., New York (1990)), which occurs in addition to the cross-talk between cyclic nucleotide pathways represented by cGMP stimulation of cAMP breakdown. Binding of cGMP to the allosteric sites of PDE6 has not been shown to affect catalysis, but this binding may modulate the interaction of PDE6 with the regulatory protein, transducin, and the inhibitory γ subunit of PDE6 (Yamazaki, et al., *Adv. Cyclic Nucleotide Protein Phosphorylation Res.*, 16:381-392 (1984)).

The PDE4 subfamily is comprised of 4 members: PDE4A, PDE4B (SEQ ID NO:1), PDE4C, and PDE4D (SEQ ID NO:2) (Conti et al. (2003) *J Biol. Chem.* 278:5493-5496). The PDE4 enzymes display a preference for cAMP over cGMP as a substrate. These enzymes possess N-terminal regulatory domains that presumably mediate dimerization, which results in optimally regulated PDE activity. In addition, activity is regulated via cAMP-dependent protein kinase phosphorylation sites in this upstream regulatory domain. These enzymes are also rather ubiquitously expressed, but importantly in lymphocytes.

Inhibitors of the PDE4 enzymes have proposed utility in the treatment of inflammatory diseases. Knockout of PDE4B results in viable mice (Jin and Conti (2002) *Proc Natl Acad Sci USA*, 99, 7628-7633), while knockout of PDE4D results in reduced viability (Jin et al. (1999) *Proc Natl Acad Sci USA*, 96, 11998-12003). The PDE4D knockout genotype can be rescued by breeding onto other background mouse strains. Airway epithelial cells from these PDE4D knockout embryos display greatly reduced hypersensitivity to adrenergic agonists, suggesting PDE4D as a therapeutic target in airway inflammatory diseases (Hansen et al. (2000) *Proc Natl Acad Sci USA*, 97, 6751-6756). PDE4B-knockout mice have few symptoms and normal airway hypersensitivity. Delgado et al., (*MedSciMonit*, 2003, 9:BR252-259), report that in view of the increase in PDE4 activity described in blood mononuclear white cells of patients with atopic dermatitis, and the putative relationship between histamine and PDE4 in inflammatory cells, histamine up-regulates PDE4 activity in U-937 cells through $H_2$ receptor stimulation and cAMP increase.

By contrast, monocytes from the PDE4B knockout mice exhibit a reduced response to LPS (Jin and Conti (2002) *Proc Natl Acad Sci USA*, 99, 7628-7633). This suggests that a PDE4B compound with selectivity versus PDE4D could exhibit anti-inflammatory activity with reduced side-effects.

Accordingly, there is a need in the art for more potent and specific inhibitors and modulators of PDE4 such as PDE4B and PDE4D and methods for designing them.

SUMMARY OF THE INVENTION

The present invention provides compounds active on PDE4, e.g., PDE4B and/or PDE4D isoforms. In particular, the invention provides compounds of Formula I, Ia, Ib, Ic, Id, and Ie as described below. Thus, the invention provides compounds that can be used for therapeutic methods involving modulation of PDE4, as well as providing molecular scaffolds for developing additional modulators of PDE4, and other PDEs. The invention further involves the use of structural information about PDE4B to derive additional PDE4B modulators.

In one aspect, the invention provides compounds of Formula I having the following structure:

Formula I

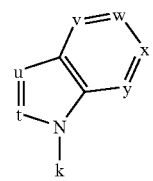

wherein:
k is selected from the group consisting of —$CR^6R^7R^{19}$, —$C(Z)R^8$, —$C(Z)NR^{12}R^{13}$, —$S(O)_2NR^{12}R^{13}$, and —$S(O)_2R^{14}$;

Z is O, S, or $NR^9$;

t, u, v, w, x, and y are each independently N or $CR^1$, provided, however, that no more than one of u and t are N, and no more than two of v, w, x and y are N;

A is selected from the group consisting of substituted aryl and substituted heteroaryl;

$R^1$ at each occurrence is independently selected from the group consisting of hydrogen, halogen, optionally substituted lower alkyl, optionally substituted lower alkenyl, optionally substituted lower alkynyl, optionally substituted cycloalkyl, optionally substituted cycloalkylalkyl, optionally substituted heterocycloalkyl, optionally substituted heterocycloalkylakyl, optionally substituted aralkyl, optionally substituted heteroaralkyl, —$C(Z)R^8$, —$OR^9$, —$SR^9$, —$NR^{10}R^{11}$, —$C(Z)NR^{12}R^{13}$, —$S(O)_2NR^{12}R^{13}$, —$S(O)_2R^{14}$, and A, provided, however, that at least one $R^1$ is A;

$R^6$ and $R^7$ are independently selected from the group consisting of hydrogen, optionally substituted lower alkyl, optionally substituted lower alkenyl, optionally substituted lower alkynyl, optionally substituted cycloalkyl, optionally substituted cycloalkylalkyl, optionally substituted heterocycloalkyl, optionally substituted heterocycloalkylakyl, optionally substituted aryl, optionally substituted aralkyl, optionally substituted heteroaryl, and optionally substituted heteroaralkyl;

$R^8$ at each occurrence is independently selected from the group consisting of —$OR^9$, optionally substituted lower alkyl, optionally substituted lower alkenyl, provided, however, that when $R^8$ is alkenyl, no alkene carbon thereof is bound to C(Z), optionally substituted lower alkynyl, provided, however, that when $R^8$ is alkynyl, no alkyne carbon thereof is bound to C(Z), optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, and optionally substituted heteroaralkyl;

$R^9$ at each occurrence is independently selected from the group consisting of hydrogen, optionally substituted lower alkyl, optionally substituted lower alkenyl, provided, however, that when $R^9$ is alkenyl, no alkene carbon thereof is bound to O, N or S, optionally substituted lower alkynyl, provided, however, that when $R^9$ is alkynyl, no alkyne carbon thereof is bound to O, N or S, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, and optionally substituted heteroaralkyl;

$R^{10}$ and $R^{11}$ at each occurrence are independently selected from the group consisting of hydrogen, optionally substituted lower alkyl, optionally substituted lower alkenyl, provided, however, that when $R^{10}$ and/or $R^{11}$ are alkenyl, no alkene carbon thereof is bound to nitrogen, optionally substituted lower alkynyl, provided, however, that when $R^{10}$ and/or $R^{11}$ are alkynyl, no alkyne carbon thereof is bound to nitrogen, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, optionally substituted heteroaralkyl, —C(Z)$R^8$, —C(Z)N$R^{12}R^{13}$, —S(O)$_2$N$R^{12}R^{13}$, and —S(O)$_2R^{14}$; or $R^{10}$ and $R^{11}$ together with the nitrogen to which they are attached form a 5-7 membered optionally substituted heterocycloalkyl or optionally substituted heteroaryl ring;

$R^{12}$ and $R^{13}$ at each occurrence are independently selected from the group consisting of hydrogen, optionally substituted lower alkyl, optionally substituted lower alkenyl, provided, however, that when $R^{12}$ and/or $R^{13}$ are alkenyl, no alkene carbon thereof is bound to nitrogen, optionally substituted lower alkynyl, provided, however that when $R^{12}$ and/or $R^{13}$ are alkynyl, no alkyne carbon thereof is bound to nitrogen, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, and optionally substituted heteroaralkyl; or $R^{12}$ and $R^{13}$ together with the nitrogen to which they are attached form a 5-7 membered optionally substituted heterocycloalkyl or optionally substituted heteroaryl ring;

$R^{14}$ at each occurrence is independently selected from the group consisting of optionally substituted lower alkyl, optionally substituted lower alkenyl, provided, however, that when $R^{14}$ is alkenyl, no alkene carbon thereof is bound to —S(O)$_2$—, optionally substituted lower alkynyl, provided, however, that when $R^{14}$ is alkynyl, no alkyne carbon thereof is bound to —S(O)$_2$—, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, and optionally substituted heteroaralkyl;

$R^{19}$ is selected from the group consisting of optionally substituted lower alkyl, optionally substituted lower alkenyl, optionally substituted lower alkynyl, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, or optionally substituted heteroaralkyl; and all salts, prodrugs, tautomers and isomers thereof.

In one embodiment of the invention, no more than one of t, u, v, w, x, and y of Formula I is N. In one embodiment, t is N or CH, provided that no more than one of t, u, v, w, x, and y is N. In one embodiment, t, u, v, w, and x are $CR^1$, and y is N or $CR^1$; and in a further embodiment, t is CH. In one embodiment, t is N or CH, y is N or CH, provided t and y are not both N, one of u, v, w, and x is C-A, and the others of u, v, w and x are CH, provided that the compound is not

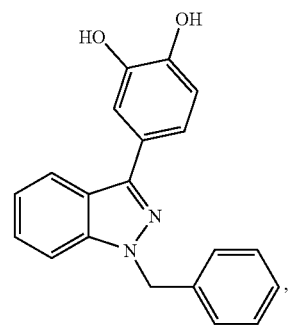

,

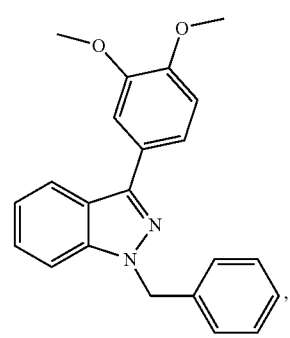

,

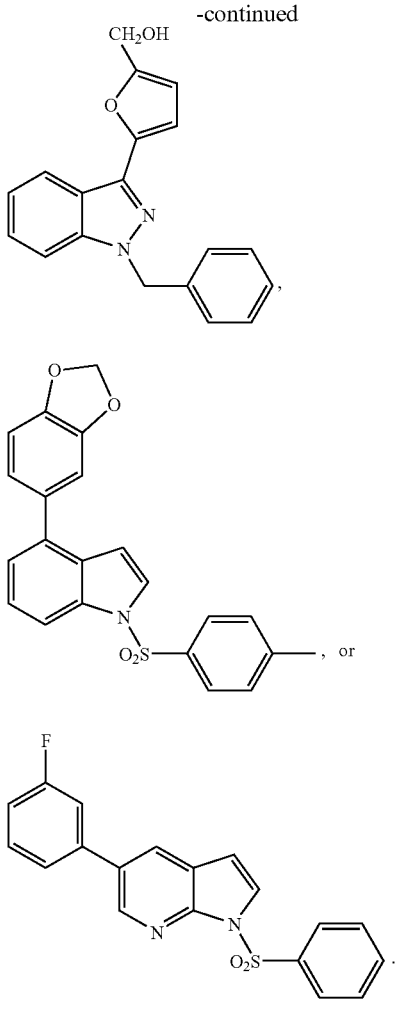

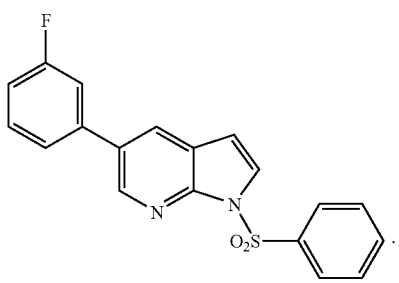

In one embodiment of the invention, t is CH, y is N, one of u, v, w, and x is C-A, and the others of u, v, w and x are CH, provided that the compound is not Further to any of the above embodiments, A of Formula I is selected from the group consisting of substituted phenyl, dialkoxyphenyl, pyrazole carboxylic ester, substituted pyridine, substituted pyrimidine, and substituted thienopyrimidine. In one embodiment, A has a structure of one of the following groups, in which the squiggle line indicates the attachment to the bicyclic core structure of Formula I.

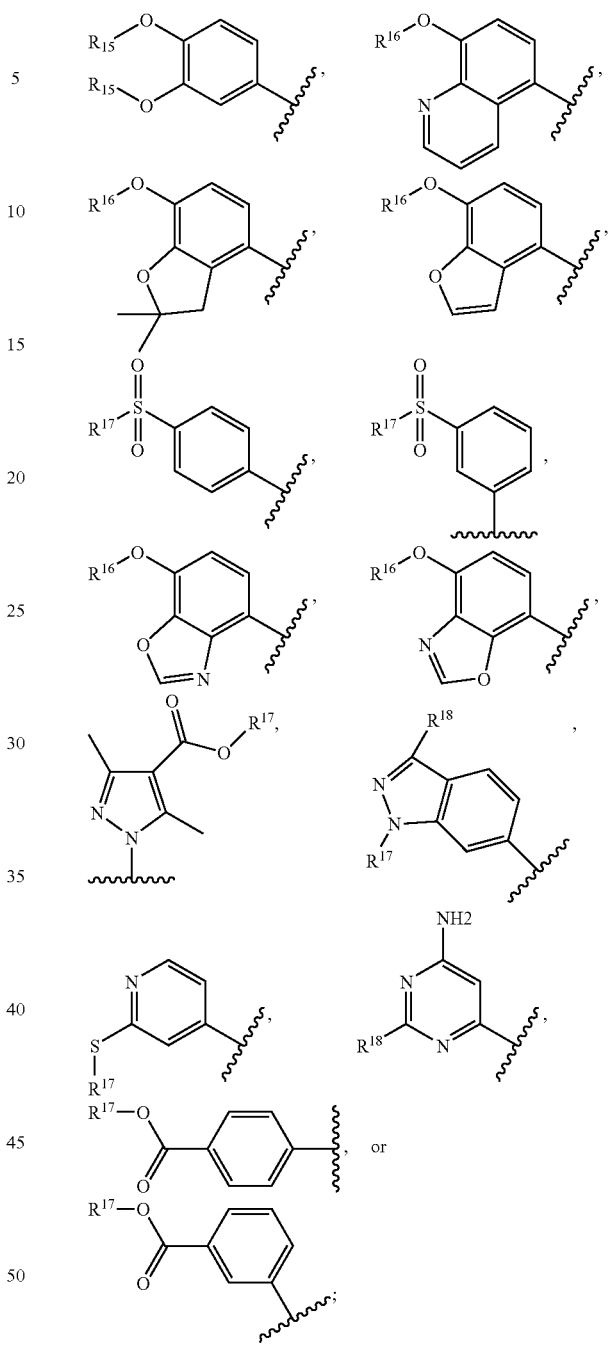

wherein:

R$^{15}$ at each occurrence is independently selected from the group consisting of optionally substituted lower alkyl, optionally substituted lower alkenyl, provided, however, that when R$^{15}$ is alkenyl, no alkene carbon thereof is bound to oxygen, optionally substituted lower alkynyl, provided, however, that when R$^{15}$ is alkynyl, no alkyne carbon thereof is bound to oxygen, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, optionally substituted heteroaralkyl, —C(Z)R⁸, and —C(Z)NR¹²R¹³; or both R¹⁵s along with the oxygens to which they are bound combine to form a 5-7 membered optionally substituted heterocycloalkyl ring fused to the phenyl ring;

R¹⁶ at each occurrence is independently selected from the group consisting of optionally substituted lower alkyl, optionally substituted lower alkenyl, provided, however, that when R¹⁶ is alkenyl, no alkene carbon thereof is bound to oxygen, optionally substituted lower alkynyl, provided, however, that when R¹⁶ is alkynyl, no alkyne carbon thereof is bound to oxygen, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, optionally substituted heteroaralkyl, —C(Z)R⁸, and —C(Z)NR¹²R¹³;

R¹⁷ at each occurrence is independently selected from the group consisting of optionally substituted lower alkyl, optionally substituted lower alkenyl provided, however, that when R¹⁷ is alkenyl, no alkene carbon thereof is bound to N, O, or S, optionally substituted lower alkynyl, provided, however, that when R¹⁷ is alkynyl, no alkyne carbon thereof is bound to N, O, or S, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, and optionally substituted heteroaralkyl;

R¹⁸ at each occurrence is independently selected from the group consisting of optionally substituted lower alkyl, optionally substituted lower alkenyl, optionally substituted lower alkynyl, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, and optionally substituted heteroaralkyl, —C(Z)R⁸, —OR⁹, —SR⁹, —NR¹⁰R¹¹, —C(Z)NR¹²R¹³, —S(O)₂NR¹²R¹³, or —S(O)₂R¹⁴; and all salts, prodrugs, tautomers and isomers thereof.

Further to any of the above embodiments, k of compounds of Formula I is selected from the group consisting of —CH₂R¹⁹, —C(Z)R⁸, —C(Z)NR¹²R¹³, —S(O)₂NR¹²R¹³, and —S(O)₂R¹⁴, wherein R⁸, R¹², R¹³, R¹⁴, and R¹⁹ are selected from the group consisting of optionally substituted lower alkyl, aryl and heteroaryl, wherein aryl and heteroaryl are optionally substituted with 1-3 substituents selected from the group consisting of halogen, optionally substituted lower alkyl, optionally substituted lower alkoxy, optionally substituted lower thioalkyl, optionally substituted aryloxy, optionally substituted heteroaryloxy, optionally substituted amino, optionally substituted carboxyl, optionally substituted alkylsulfonylamino, cyano and nitro.

In certain embodiments of the invention, the compounds of Formula I have a structure of Formula Ia:

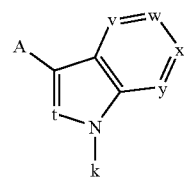

Formula Ia wherein t, v, w, x, y, k and A are as defined in Formula I above; and all salts, prodrugs, tautomers and isomers thereof.

In one embodiment, A of compounds of Formula Ia has a structure of one of the following groups, in which the squiggle line indicates the attachment to the bicyclic core structure of Formula Ia.

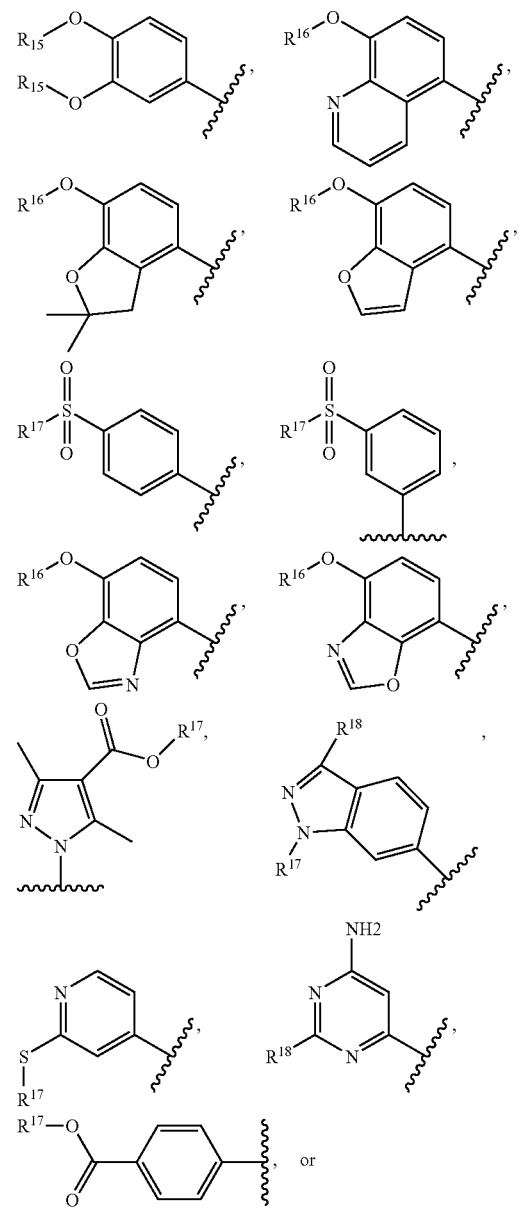

-continued

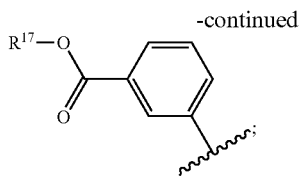

wherein $R^{15}$, $R^{16}$, $R^{17}$ and $R^{18}$ are as defined in Formula I above.

In another embodiment of the invention, no more than one of t, v, w, x, and y is N. In one embodiment, t is N or CH, provided that no more than one of t, u, v, w, x, and y is N. In one embodiment, t, u, v, w, and x are $CR^1$, and y is N or $CR^1$; and in a further embodiment, t is CH. In another embodiment, t is N or CH, y is N or CH, provided t and y are not both N, two of v, w, and x are $CR^1$, and the other of v, w and x is CH. In another embodiment, t is N or CH, y is N or CH, provided t and y are not both N, one of v, w, and x is $CR^1$ and the others of v, w and x are CH. In another embodiment, t is N or CH, y is N or CH, provided t and y are not both N, and v, w, and x are CH. In another embodiment, t, v, w, x and y are CH. In another embodiment, t, v, w and x are CH, and y is N. In another embodiment, t and y are CH, one of v, w, and x is $CR^1$ and the others of v, w and x are CH. In another embodiment, t is CH, y is N, one of v, w, and x is $CR^1$ and the others of v, w and x are CH. Further to any of the above embodiments of Formula Ia, the compound is not

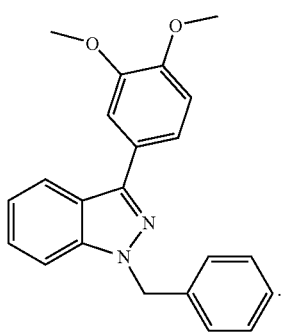

In one emdodiment, k of compounds of Formula Ia is selected from the group consisting of —$CH_2R^{19}$, —$C(Z)R^8$, —$C(Z)NR^{12}R^{13}$, —$S(O)_2NR^{12}R^{13}$, and —$S(O)_2R^{14}$, wherein $R^8$, $R^{12}$, $R^{13}$, $R^{14}$, and $R^{19}$ are selected from the group consisting of optionally substituted lower alkyl, aryl and heteroaryl, wherein aryl and heteroaryl are optionally substituted with 1-3 substituents selected from the group consisting of halogen, optionally substituted lower alkyl, optionally substituted lower alkoxy, optionally substituted lower thioalkyl, optionally substituted aryloxy, optionally substituted heteroaryloxy, optionally substituted amino, optionally substituted carboxyl, optionally substituted alkyl-sulfonylamino, cyano and nitro.

In certain embodiments of the invention, the compounds of Formula I have a structure of Formula Ib:

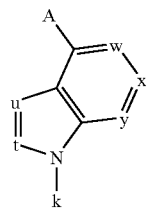

Formula Ib wherein t, u, w, x, y, k and A are as defined in Formula I above; and all salts, prodrugs, tautomers and isomers thereof.

In one embodiment, A of compounds of Formula Ib has a structure of one of the following groups, in which the squiggle line indicates the attachment to the bicyclic core structure of Formula Ib.

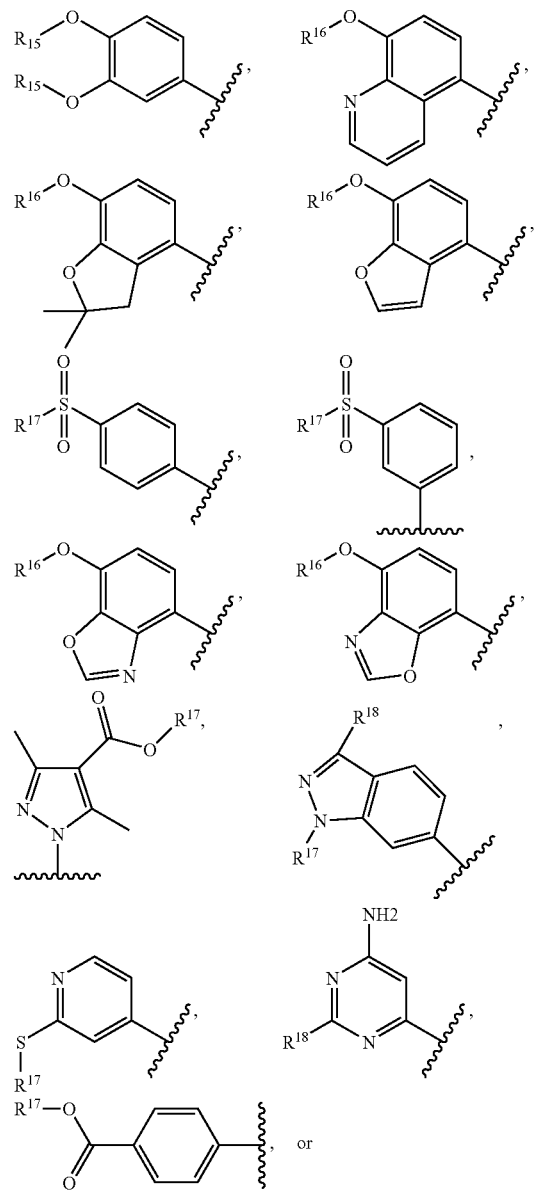

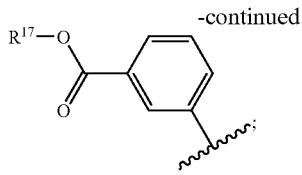

wherein $R^{15}$, $R^{16}$, $R^{17}$ and $R^{18}$ are as defined in Formula I above.

In another embodiment of the invention, no more than one of t, u, w, x, and y is N. In one embodiment, t is N or CH, provided that no more than one of t, u, v, w, x, and y is N. In one embodiment, t, u, v, w, and x are $CR^1$, and y is N or $CR^1$; and in a further embodiment, t is CH. In another embodiment, t is N or CH, y is N or CH, provided t and y are not both N, two of u, w, and x are $CR^1$, and the other of u, w and x is CH. In another embodiment, t is N or CH, y is N or CH, provided t and y are not both N, one of u, w, and x is $CR^1$ and the others of u, w and x are CH. In another embodiment, t is N or CH, y is N or CH, provided that t and y are not both N, and u, w, and x are CH. In another embodiment, t, u, w, x and y are CH. In another embodiment, t is CH, y is N, one of u, w, and x is $CR^1$ and the others of u, w and x are CH. In another embodiment, t, u, w and x are CH and y is N. In another embodiment, t and y are CH, one of u, w, and x is $CR^1$ and the others of u, w and x are CH. Further to any of the above embodiments of Formula Ib, the compound is not

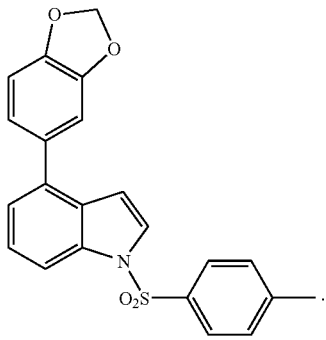

In one emdodiment of the invention, k of compounds of Formula Ib is selected from the group consisting of —$CH_2R^{19}$, —$C(Z)R^8$, —$C(Z)NR^{12}R^{13}$, —$S(O)_2NR^{12}R^{13}$, and —$S(O)_2R^{14}$, wherein $R^8$, $R^{12}$, $R^{13}$, $R^{14}$, and $R^{19}$ are selected from the group consisting of optionally substituted lower alkyl, aryl and heteroaryl, wherein aryl and heteroaryl are optionally substituted with 1-3 substituents selected from the group consisting of halogen, optionally substituted lower alkyl, optionally substituted lower alkoxy, optionally substituted lower thioalkyl, optionally substituted aryloxy, optionally substituted heteroaryloxy, optionally substituted amino, optionally substituted carboxyl, optionally substituted alkylsulfonylamino, cyano and nitro.

In certain embodiments, the compounds of Formula I have a structure of Formula Ic:

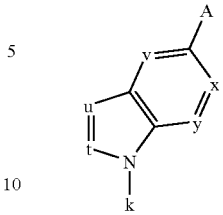

Formula Ic wherein t, u, v, x, y, k and A are as defined in Formula I above; and all salts, prodrugs, tautomers and isomers thereof.

In one embodiment, A of compounds of Formula Ic has a structure of one of the following groups, in which the squiggle line indicates the attachment to the bicyclic core structure of Formula Ic.

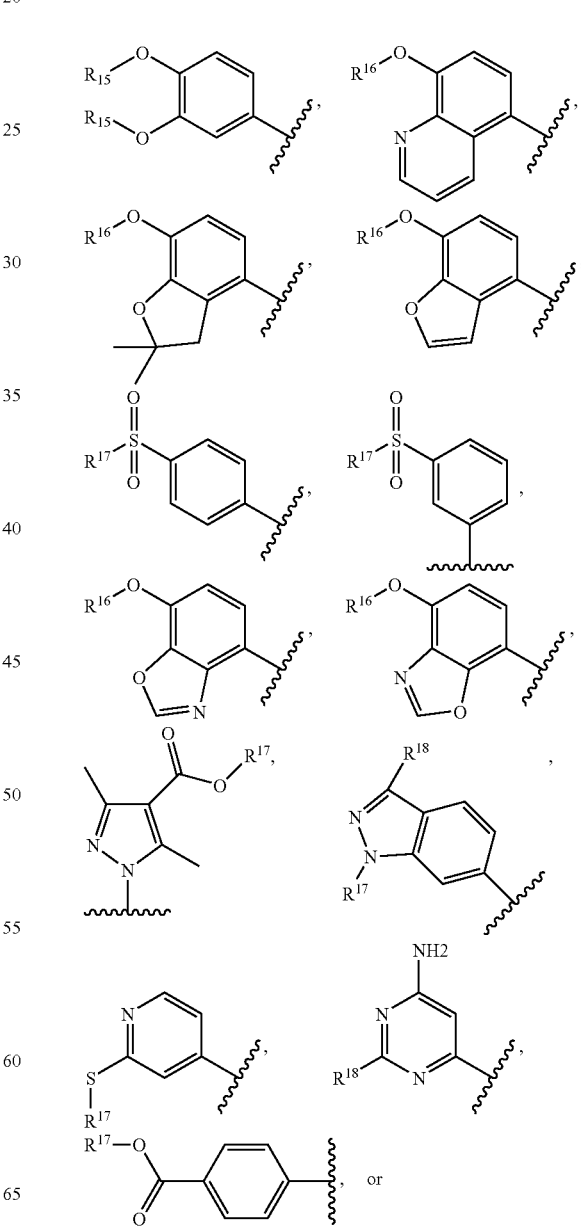

-continued

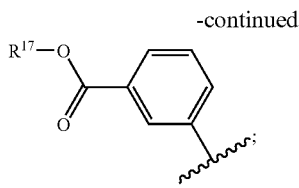

wherein $R^{15}$, $R^{16}$, $R^{17}$, and $R^{18}$ are as defined in Formula I above.

In another embodiment of the invention, no more than one of t, u, v, x, and y is N. In one embodiment, t is N or CH, provided that no more than one of t, u, v, w, x, and y is N. In one embodiment, t, u, v, w, and x are $CR^1$, and y is N or $CR^1$; and in a further embodiment, t is CH. In another embodiment, t is N or CH, y is N or CH, provided t and y are not both N, two of u, v, and x are $CR^1$, and the other of u, v and x is CH. In another embodiment, t is N or CH, y is N or CH, provided t and y are not both N, one of u, v, and x is $CR^1$ and the others of u, v and x are CH. In another embodiment, t is N or CH, y is N or CH, provided t and y are not both N, and u, v, and x are CH. In another embodiment, t, u, v, x and y are CH. In another embodiment, t, u, v and x are CH and y is N. In another embodiment, t and y are CH, one of u, v, and x is $CR^1$ and the others of u, v and x are CH. In another embodiment, t is CH, one of u, v, and x is $CR^1$, the others of u, v, and x are CH, and y is N or CH, provided, however, that when the compound has the structure

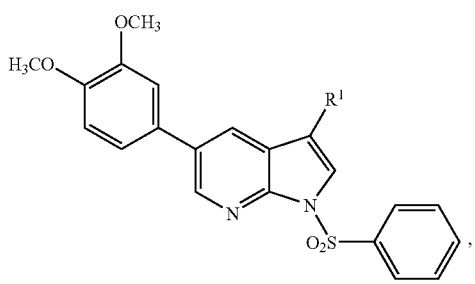

then $R^1$ is selected from the group consisting of hydrogen, F, Cl, Br, optionally substituted lower alkyl, —C(Z)$R^8$, —O$R^9$, —S$R^9$, —C(Z)N$R^{12}R^{13}$, —S(O)$_2$N$R^{12}R^{13}$, and —S(O)$_2R^{14}$.

In one emdodiment of the invention, k of compounds of Formula Ib is selected from the group consisting of —CH$_2R^{19}$, —C(Z)$R^8$, —C(Z)N$R^{12}R^{13}$, —S(O)$_2$N$R^{12}R^{13}$, and —S(O)$_2R^{14}$, wherein $R^8$, $R^{12}$, $R^{13}$, $R^{14}$, and $R^{19}$ are selected from the group consisting of optionally substituted lower alkyl, aryl and heteroaryl, wherein aryl and heteroaryl are optionally substituted with 1-3 substituents selected from the group consisting of halogen, optionally substituted lower alkyl, optionally substituted lower alkoxy, optionally substituted lower thioalkyl, optionally substituted aryloxy, optionally substituted heteroaryloxy, optionally substituted amino, optionally substituted carboxyl, optionally substituted alkylsulfonylamino, cyano and nitro.

In certain embodiments of the invention, the compounds of Formula I have a structure of Formula Id:

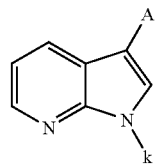

Formula Id wherein k is as defined in Formula I above and A has a structure of one of the following groups, in which the squiggle line indicates the attachment to the bicyclic core structure of Formula Id:

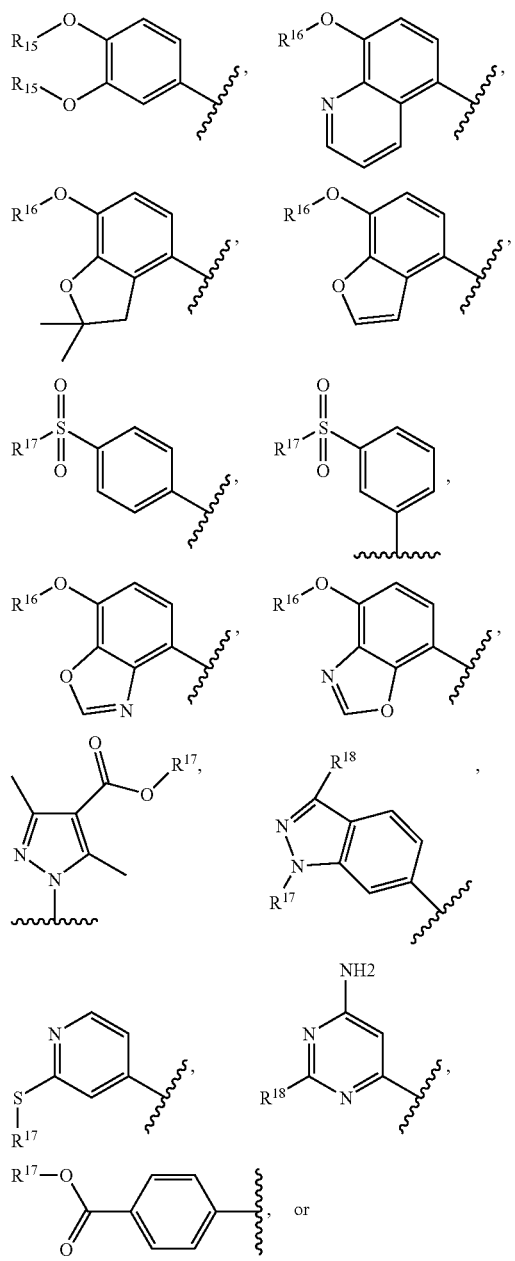

-continued

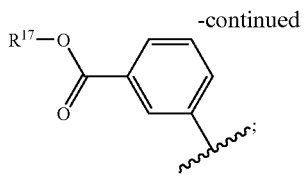

wherein $R^{15}$, $R^{16}$, $R^{17}$ and $R^{18}$ are as defined in Formula I above; and all salts, prodrugs, tautomers and isomers thereof.

In one embodiment of the invention, k of compounds of Formula Id is selected from the group consisting of —$CH_2R^{19}$, —$C(Z)R^8$, —$C(Z)NR^{12}R^{13}$, —$S(O)_2NR^{12}R^{13}$, and —$S(O)_2R^{14}$, wherein $R^8$, $R^{12}$, $R^{13}$, $R^{14}$, and $R^{19}$ are selected from the group consisting of optionally substituted lower alkyl, aryl and heteroaryl, wherein aryl and heteroaryl are optionally substituted with 1-3 substituents selected from the group consisting of halogen, optionally substituted lower alkyl, optionally substituted lower alkoxy, optionally substituted lower thioalkyl, optionally substituted aryloxy, optionally substituted heteroaryloxy, optionally substituted amino, optionally substituted carboxyl, optionally substituted alkylsulfonylamino, cyano and nitro.

In certain embodiments of the invention, the compounds of Formula I have a structure of Formula Ie:

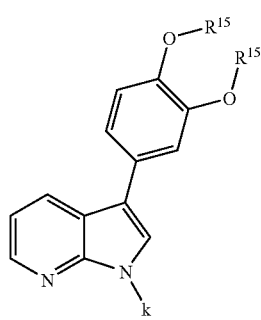

Formula Ie wherein k and $R^{15}$ are as defined in Formula I above; and all salts, prodrugs, tautomers and isomers thereof.

In one embodiment of the invention, k of compounds of Formula Ie is selected from the group consisting of —$CH_2R^{19}$, —$C(Z)R^8$, —$C(Z)NR^{12}R^{13}$, —$S(O)_2NR^{12}R^{13}$, and —$S(O)_2R^{14}$, wherein $R^8$, $R^{12}$, $R^{13}$, $R^{14}$, and $R^{19}$ are selected from the group consisting of optionally substituted lower alkyl, aryl and heteroaryl, wherein aryl and heteroaryl are optionally substituted with 1-3 substituents selected from the group consisting of halogen, optionally substituted lower alkyl, optionally substituted lower alkoxy, optionally substituted lower thioalkyl, optionally substituted aryloxy, optionally substituted heteroaryloxy, optionally substituted amino, optionally substituted carboxyl, optionally substituted alkylsulfonylamino, cyano and nitro, further wherein $R^{15}$ at each occurrence is independently selected from the group consisting of optionally substituted lower alkyl, optionally substituted cycloalkyl, optionally substituted heterocycloalkyl, optionally substituted aryl, and optionally substituted heteroaryl, or each $R^{15}$ along with the oxygens to which they are bound combine to form a 5-7 membered optionally substituted heterocycloalkyl ring fused to the phenyl ring. In a further embodiment, when $R^{15}$ is optionally substituted lower alkyl, the alkyl is optionally substituted with 1-3 substituents selected from the group consisting of fluoro, optionally substituted cycloalkyl, optionally substituted heterocycloalkyl, optionally substituted aryl and optionally substituted heteroaryl.

In certain embodiments of the invention involving compounds of Formula I (for example, compounds of Formula Ia, Formula Ib, and Formula Ic), the bicyclic ring structure shown in Formula I is one of the following:

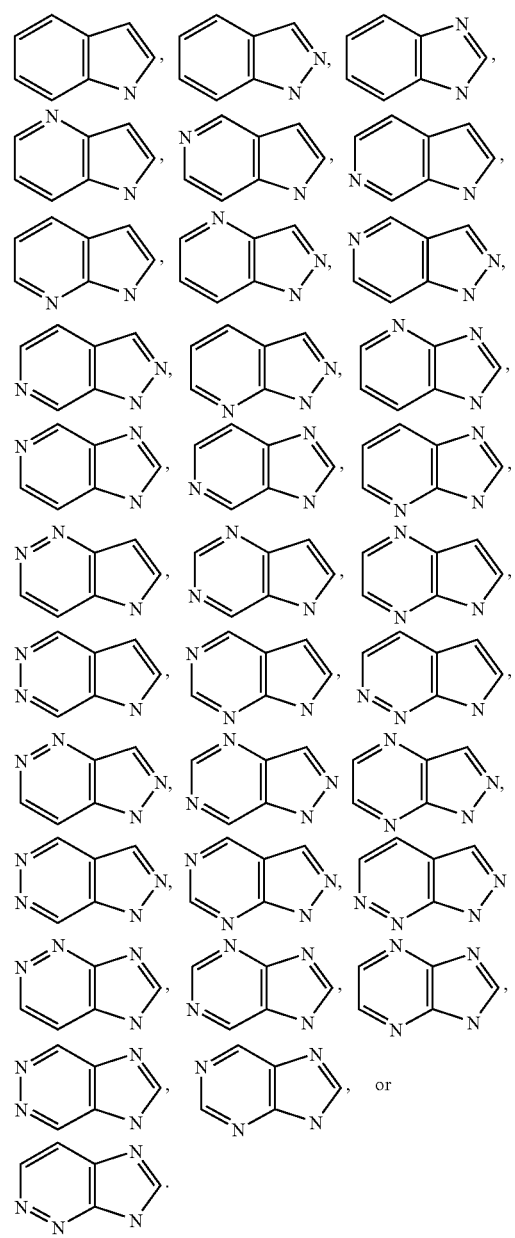

For compounds of Formula I, ring positions are specified as shown in the following indole core, but as used herein, the corresponding numbering also applies to each of the other bicyclic core structures shown above. Reference to a bicyclic core as in Formula I or indication that a compound includes a bicyclic core as in Formula I and phrases of similar import refer to a bicyclic structure or moiety as described herein for embodiments of the invention embracing compounds of Formula I.

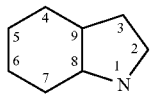

In particular embodiments of the invention, compounds of Formula I (e.g., Formula Ia, Formula Ib, Formula Ic, Formula Id, and Formula Ie) have a substituent at the 1-position as a compound in the Examples; has a substituent at the 3-position as a compound in the Examples; has a substitutent at the 4-position as a compound in the Examples; has a substitutent at the 5-position as a compound in the Examples; has substitutents at the 1- and 3-positions as a compound in the Examples; has substitutents at the 1- and 4-positions as a compound in the Examples; has substitutents at the 1- and 5-positions as a compound in the Examples.

In particular embodiments of the invention, one or more of the bicyclic structures shown above are embraced by Formula I, e.g., any 1, 2, 3, 4, 5, 6, 7, 8, 9, 10, 10, 11, 12, 13, 14, 15, 16, 17, 18, 19, 20, 21, 22, 23, 24, 25, 26, 27, 28, 29, 30, 31, 32, or 33 of the bicyclic core structures shown above are embraced by Formula I.

In certain embodiments of the invention, A of compounds of Formula I (e.g., Formula Ia, Formula Ib, Formula Ic, and Formula Id) is substituted aryl (e.g. phenyl); substituted heteroaryl (such as 5- or 6-membered heteroaryl rings); aryl (e.g., phenyl) substituted with 1, 2, or 3 alkoxy groups (such as methoxy, ethoxy, and propoxy); heteroaryl substituted with 1, 2, or 3 alkoxy groups; aryl substituted with 1, 2, or 3 alkyl ether groups, alkyl thioether groups, or combinations thereof; heteroaryl substituted with 1, 2, or 3 alkyl ether groups, alkyl thioether groups, or combinations thereof; dialkoxyphenyl; dialkylthiophenyl; dialkoxy heteroaryl; dialkylthio heteroaryl; disubstituted aryl (e.g., phenyl) in which the substitutents may be the same or different, e.g., hydroxyl, alkoxy, alkyl ester, —SH, thioether, thioester; disubstituted heteroaryl in which the substitutents may be the same or different, e.g., hydroxyl, alkoxy, alkyl ester, —SH, thioether, thioester. In certain embodiments in which an aryl or heteroaryl is disubstituted, the substitutents are on adjacent ring carbon atoms (e.g., catechols or catechol diethers), for 6-membered rings the two substituents may be meta and para with respect to the linkage of the ring to the remainder of the molecule. In certain embodiments, A is substituted aryl or substituted heteroaryl, with a substitution at the second atom away from the ring atom attached to the remainder of the molecule (e.g., the meta position for 6-membered rings), in certain embodiments, that is the only substitution on the aryl or heteroaryl group.

In certain embodiments of the invention, k of compounds of Formula I (e.g., Formula Ia, Formula Ib, Formula Ic, Formula Id and Formula Ie) comprises optionally substituted aryl; optionally substituted heteroaryl; optionally substituted napthyl; optionally substituted bicyclic heteroaryl; napthyl substituted with alkoxy or alkylthio; heteroaryl substituted with alkoxy or alkylthio. For example $R^6$, $R^7$, $R^8$, $R^9$, $R^{12}$, $R^{13}$ or $R^{14}$ in k is a group so specified. In particular embodiments of the preceding, the alkyl moiety is methyl, ethyl, or propyl.

In particular embodiments, the combination of A and k embraces any A (as specified in [0039]) and any k (as specified in [0040]), e.g., A is substituted phenyl and k comprises optionally substituted napthyl; A is substituted 5- or 6-membered heteroaryl and k comprises optionally substituted napthyl; A is substituted phenyl and k comprises optionally substituted bicyclic heteroaryl; A is substituted 5- or 6-membered heteroaryl and k comprises optionally substituted bicyclic heteraryl, and the like.

In certain embodiments of the invention, compounds are excluded where N, O, S or C(Z) would be bound to a carbon that is also bound to N, O, S, or C(Z) or would be bound to an alkene carbon atom of an alkenyl group or bound to an alkyne atom of an alkynyl group; accordingly, in certain embodiments compounds are excluded from the present invention in which are included linkages such as —NR—$CH_2$—NR—, —O—$CH_2$—NR—, —$S(O)_{0-2}$—$CH_2$—NR—, —C(Z)-$CH_2$—NR—, —NR—$CH_2$—O—, —O—$CH_2$—O—, —$S(O)_{0-2}$—$CH_2$—O—, —C(Z)-$CH_2$—O—, —NR—$CH_2$—$S(O)_{0-2}$—, —O—$CH_2$—$S(O)_{0-2}$—, —$S(O)_{0-2}$—$CH_2$—$S(O)_{0-2}$—, —C(Z)-$CH_2$—$S(O)_{0-2}$—, —NR—$CH_2$—C(Z)-, —O—$CH_2$—C(Z)-, —$S(O)_{0-2}$—$CH_2$—C(Z)-, —C(Z)-$CH_2$—C(Z)-, —NR—CH=CH—, —NR—C≡C—, —O—CH=CH—, —O—C≡C—, —$S(O)_{0-2}$—CH=CH—, —$S(O)_{0-2}$—C≡C—, —C(Z)-CH=CH—, or —C(Z)-C≡—.

Thus, in a first aspect, the invention provides a novel compound of Formulae I, Ia, Ib, Ic, Id, or Ie as described herein.

An additional aspect of this invention provides compositions, which include pharmaceutical formulations, that include a therapeutically effective amount of a compound of Formula I, Ia, Ib, Ic, Id, or Ie (or a compound within a sub-group of compounds within any of those generic formulae) and at least one pharmaceutically acceptable carrier, excipient or diluent.

In particular embodiments, the composition includes a plurality of different pharmacalogically active compounds, which can be a plurality of compounds of Formula I and can also include other compounds in combination with one or more compounds of Formula I. The term "other compounds" in this context denotes compounds that are given to a subject in an effective amount to prevent, alleviate, or ameliorate one or more symptoms of a disease or medical condition, and/or to prolong the survival of the subject being treated, wherein the disease or medical condition is as listed herein.

In a related aspect, the invention provides kits that include a composition as described herein. In particular embodiments, the composition is packaged, e.g., in a vial, bottle, or flask, which may be further packaged, e.g., within a box, envelope, or bag; the composition is a pharmaceutical composition approved by the U.S. Food and Drug Administration or similar regulatory agency for administration to a mammal, e.g., a human; the composition is a pharmaceutical composition approved for administration to a mammal, e.g., a human, for a PDE4-mediated disease or condition; the kit includes written instructions or other indication that the composition is suitable or approved for administration to a mammal, e.g., a human, for a PDE4-mediated disease or condition; the composition is packaged in unit does or single dose form, e.g., single dose pills, capsules, or the like. As used herein, the term "mammal" indicates any mammalian species, and include without limitation, stock animals (e.g., sheep, goats, cattle), domesticated animals (e.g., dogs, cats), research animals (e.g., rats, mice), other primates, and humans.

In another related aspect, compounds of Formula I, Ia, Ib, Ic, Id, or Ie can be used in the preparation of a medicament for the treatment in a subject in need thereof of a PDE4-mediated disease or condition (or a disease or condition mediated by a PDE4 isoform (e.g., a PDE4B- or PDE4D-mediated disease or condition), or a disease or condition in which modulation of PDE4 provides a therapeutic benefit.

In another aspect, the invention provides a method of treating or prophylaxis of a disease or condition in a mammal in need thereof where the disease or condition is a PDE4-mediated disease or condition or a disease or condition in which PDE4 modulation provides a therapeutic benefit, by administering to the mammal a therapeutically effective amount of a compound of Formula I, Ia, Ib, Ic, Id, or Ie, a prodrug of such compound, or a pharmaceutically acceptable salt of such compound or prodrug. The compound can be employed alone or can be part of a pharmaceutical composition.

In aspects and embodiments of the invention involving treatment or prophylaxis of a disease or condition, the disease or condition is, for example without limitation, an acute or chronic pulmonary disease such as obstructive diseases (e.g. asthma, chronic obstructive pulmonary disease (COPD), cystic fibrosis), interstitial lung diseases (e.g. idiopathic pulmonary fibrosis, sarcoidosis), vascular lung diseases (e.g. pulmonary hypertension), bronchitis, allergic bronchitis, or emphysema. Additional diseases or conditions contemplated for treatment by embodiments of the present invention include, for example without limitation, CNS diseases such as Alzheimer's disease, Parkinson's disease and Hunting-ton's chorea; inflammatory autoimmune diseases such as multiple sclerosis, rheumatoid arthritis and Crohn's disease as well as other inflammatory disorders, such as cerebral ischemia, inflammatory bowel disease, ulcerative colitis, and atopic dermatitis; bone disease, such as osteoporosis, osteopetrosis, and Paget's disease; cancers, such as diffuse large-cell B cell lymphoma, chronic lymphocytic leukemia, acute lymphoblastic leukemia; Severe Acute Respiratory Syndrome; and pre-term labor. Specific diseases or disorders which might be treated or prevented include those described herein, and in the references cited therein.

In certain embodiments involving the compounds of the invention and the use thereof, the compound is specific for PDE4B, or an isoform thereof, e.g., PDE4B or PDE4D. In certain embodiments of aspects involving compounds of Formula I, Ia, Ib, Ic, Id, or Ie, the compound is specific for both PDE4B and PDE4D, specific for PDE4B, or specific for PDE4D. Such specificity means that the compound has at least 5-fold greater activity (preferably at least 5-, 10-, 20-, 50-, or 100-fold greater activity, or more) on PDE4B and/or PDE4D than other enzymes, or on PDE4B relative to PDE4D, or PDE4D relative to PDE4B, where the activity is determined using a suitable assay, e.g., any assay known to one skilled in the art or as described herein.

In certain embodiments, a compound of the invention has an $IC_{50}$ of less than 100 nM, less than 50 nM, less than 20 nM, less than 10 nM, less than 5 nM, or less than 1 nM with respect to at least one of PDE4B and PDE4D as determined in a generally accepted PDE4 activity assay. In one embodiment, a compound of Formula I, Ia, Ib, Ic, Id, or Ie will have an $IC_{50}$ of less than 100 nM, less than 50 nM, less than 20 nM, less than 10 nM, less than 5 nM, or less than 1 nM with respect to PDE4B. In one embodiment, a compound of Formula I, Ia, Ib, Ic, Id, or Ie, will have an $IC_{50}$ of less than 100 nM, less than 50 nM, less than 20 nM, less than 10 nM, less than 5 nM, or less than 1 nM with respect to PDE4D. In one embodiment, a compound of Formula I, Ia, Ib, Ic, Id, or Ie will have an $IC_{50}$ of less than 100 nM, less than 50 nM, less than 20 nM, less than 10 nM, less than 5 nM, or less than 1 nM with respect to both PDE4B and PDE4D. Further to any of the above embodiments, a compound of the invention will be a specific inhibitor of either PDE4B or PDE4D, such that the $IC_{50}$ for one of PDE4B and PDE4D will be at least about 5-fold, also 10-fold, also 20-fold, also 50-fold, or at least about 100-fold less than the $IC_{50}$ for the other of PDE4B and PDE4D.

In certain embodiments of the invention, the compounds of Formula I, Ia, Ib, Ic, Id, or Ie, with activity on PDE4 will also have desireable pharmacologic properties. In particular embodiments the desired pharmacologic property is any one or more of serum half-life longer than 2 hr (also longer than 4 hr, also longer than 8 hr), aqueous solubility, and oral bioavailability more than 10% (also more than 20%).

The identification of compounds of Formula I with activity on PDE4, or on isoforms thereof such as PDE4B or PDE4D, also provides a method for identifying or developing additional compounds with activity on PDE4 (or on the respective PDE4 isoform), e.g., improved modulators, by determining whether any of a plurality of test compounds of Formula I with activity on PDE4 provides an improvement in one or more desired pharmacologic properties relative to a reference compound with activity on PDE4, and selecting a compound if any, that has an improvement in the desired pharmacologic property, thereby providing an improved modulator. In certain embodiments, the desired pharmacologic property is at least 2-fold, 4-fold, 6-fold, 8-fold, 10-fold, 20-fold, 50-fold, 100-fold, or more than 100-fold, greater activity on PDE4B than on PDE4D. In further embodiments, the desired pharmacologic property is an $IC_{50}$ of less than 10 μM, less than 1 μM, less than 100 nM, less than 10 nM, or less than 1 nM.

In particular embodiments of the invention embracing modulator development, the desired pharmacologic property is serum half-life longer than 2 hr (or longer than 4 hr or longer than 8 hr), aqueous solubility, oral bioavailability more than 10% (or oral bioavailability more than 20%).

Also in particular embodiments of the invention embracing modulator development, the reference compound is a compound of Formula I. The process can be repeated multiple times, i.e., multiple rounds of preparation of derivatives and/or selection of additional related compounds and evaluation of such further derivatives of related compounds, e.g., 1, 2, 3, 4, 5, 6, 7, 8, 9, 10 or more additional rounds.

In additional aspects, structural information about PDE4B is utilized, e.g., in conjunction with compounds of Formula I or a molecular scaffold or scaffold core of Formula I. In addition, structural information about one or more other PDEs can be utilized, e.g., PDE5A, PDE4D.

The invention also provides a method for developing ligands binding to a PDE4B, where the method includes identifying as molecular scaffolds one or more compounds that bind to a binding site of the PDE; determining the orientation of at least one molecular scaffold in co-crystals with the PDE; identifying chemical structures of one or more of the molecular scaffolds, that, when modified, alter the binding affinity or binding specificity or both between the molecular scaffold and the PDE; and synthesizing a ligand in which one or more of the chemical structures of the molecular scaffold is modified to provide a ligand that binds to the PDE with altered binding affinity or binding specificity or both. Such a scaffold can, for example, be a compound of Formula I, include a scaffold core as in Formula I, or include a bicyclic core as in Formula I.

In an alternative embodiment, the invention provides a method for developing or identifying ligands binding to a PDE4B. The method comprises determining the orientation of at least one molecular scaffold in co-crystals with the PDE wherein the molecular scaffold is contained with one or more compounds that bind to a binding site of the PDE; identifying chemical structures of one or more of the molecular scaffolds, that, when modified, alter the binding affinity or binding specificity or both between the molecular scaffold and the PDE; and modifying the chemical structures so identified to provide a ligand that binds to the PDE with altered binding affinity or binding specificity or both. Such a scaffold can, for example, be a compound of Formula I, include a scaffold core as in Formula I, or include a bicyclic core as in Formula I.

In a related aspect, the invention provides a method for developing ligands specific for PDE4 (or a PDE4 isoform such as PDE4B or PDE4D), where the method involves determining whether a derivative of a compound that binds to a plurality of phosphodiesterases has greater specificity for the particular phosphodiesterase than the parent compound with respect to other phosphodiesterases. In one embodiment, the plurality of phosphodiesterases comprises PDE4B and PDE4D. In another embodiment, the plurality of phosphodiesterases comprises PDE4B and PDE5A. In a further embodiment, the compound that binds to a plurality of phosphodiesterases binds to PDE4B with an affinity at least 2-fold, e.g., 4-fold, 6-fold, 8-fold, 10-fold, 20-fold, 50-fold, or 100-fold, greater than for binding to any of the plurality of phosphodiesterases. In yet another embodiment, the compound that binds to a plurality of phosphodiesterases, binds weakly, wherein "weakly" indicates that the $IC_{50}$ of the compound is greater than 1 µM, e.g., 2 µM, 5 µM, 10 µM, 20 µM, 50 µM, 100 µM, 200 µM, 500 µM, 1 mM, or greater.

In another aspect, the invention provides a method for obtaining improved ligands binding to PDE4B, where the method involves identifying a compound that binds to that particular PDE, determining whether that compound interacts with one or more conserved active site residues, and determining whether a derivative of that compound binds to that PDE with greater affinity or greater specificity or both than the parent binding compound. Binding with greater affinity or greater specificity or both than the parent compound indicates that the derivative is an improved ligand. This process can also be carried out in successive rounds of selection and derivatization and/or with multiple parent compounds to provide a compound or compounds with improved ligand characteristics. Likewise, the derivative compounds can be tested and selected to give high selectivity for that PDE, or to give cross-reactivity to a particular set of targets, for example to a subset of phosphodiesterases that includes PDE4B and/or PDE4D. In particular embodiments, known PDE4B inhibitors can be used, and derivatives with greater affinity and/or greater specificity can be developed, preferably using PDE4B and/or PDE4D structure information; greater specificity for PDE4B relative to PDE4D is developed.

For Formula I, there are multiple scaffold cores described by Formula I. Such a scaffold core includes a bicyclic core as described above for Formula I, with an attached aryl or heteroaryl group of substituent group A as specified above. Thus, for each of the bicyclic cores shown above, there are corresponding scaffold cores for each of the positions of A, and for each aryl and heteroaryl group that is the initial moiety of A linked to the bicyclic core.

In another aspect, structural information about PDE4B can also be used to assist in determining a structure for another phosphodiesterase by creating a homology model from an electronic representation of a PDE4B structure. Such homology model is then equated with the structure of the other phosphodiesterase.

Typically, creating such a homology model involves identifying conserved amino acid residues between the known PDE having known structures, e.g., PDE4B, and the other phosphodiesterase of interest (e.g., PDE5A); transferring the atomic coordinates of a plurality of conserved amino acids in the known structure to the corresponding amino acids of the other phosphodiesterase to provide a rough structure of that phosphodiesterase; and constructing structures representing the remainder of the other phosphodiesterase using electronic representations of the structures of the remaining amino acid residues in the other phosphodiesterase. In particular, for PDE4B, coordinates from Table 1 and 2 can be used. Conserved residues in a binding site can be used.

To assist in developing other portions of the phosphodiesterase structure, the homology model can also utilize, or be fitted with, low resolution x-ray diffraction data from one or more crystals of the phosphodiesterase, e.g., to assist in linking conserved residues and/or to better specify coordinates for terminal portions of a polypeptide.

The PDE4B structural information used can be for a variety of different variants, including full-length wild type, naturally-occurring variants (e.g., allelic variants and splice variants), truncated variants of wild type or naturally-occuring variants, and mutants of full-length or truncated wild-type or naturally-occurring variants (that can be mutated at one or more sites). For example, in order to provide a PDE4B structure closer to a variety of other phosphodiesterase structures, a mutated PDE4B that includes a mutation to a conserved residue in a binding site can be used.

In another aspect, the invention provides a crystal comprising a crystalline form of PDE4B, which may be a reduced length PDE4B such as a phosphodiesterase domain, e.g., having atomic coordinates as described in Tables 1, 2, and 3. The crystalline form can contain one or more heavy metal atoms, for example, atoms useful for X-ray crystallography. The crystal can also include a binding compound in a co-crystal, e.g., a binding compound that interacts with one more conserved active site residues in the PDE, or any two, any three, any four, any five, any six of those residues, and can, for example, be a known PDE inhibitor. Such PDE crystals can be in various environments, e.g., in a crystallography plate, mounted for X-ray crystallography, and/or in an X-ray beam. The PDE may be of various forms, e.g., a wild-type, variant, truncated, and/or mutated form as described herein.

The invention further provides co-crystals of PDE4B, which may be a reduced length PDE, e.g., a phosphodiesterase domain, and a PDE4B binding compound. In certain embodiments, the binding compound within the crystal interacts with one or more conserved PDE4B active site residues. Advantageously, such co-crystals are of sufficient size and quality to allow structural determination of the PDE to at least 3 Angstroms, 2.5 Angstroms, 2.0 Angstroms, 1.8 Angstroms, 1.7 Angstroms, 1.5 Angstroms, 1.4 Angstroms, 1.3 Angstroms, or 1.2 Angstroms. The co-crystals can, for example, be in a crystallography plate, be mounted for X-ray crystallography and/or in an X-ray beam. Such co-crystals are beneficial, for example, for obtaining structural information concerning interaction between the PDE and binding compounds.

In particular embodiments, the binding compound includes the bicyclic core or scaffold core structure as in Formula I, or is a compound of Formula I.

PDE4B binding compounds can include compounds that interact with at least one of conserved active site residues in the PDE, or any 2, 3, 4, 5, or 6 of those residues. Exemplary compounds that bind to PDE4B include compounds described in references cited herein.

Likewise, in additional aspects, methods for obtaining PDE4B crystals and co-crystals are provided. In one aspect, a method for obtaining a crystal of PDE4B phosphodiesterase domain is provided by subjecting PDE4B protein at 5-20 mg/ml, e.g., 8-12 mg/ml, to crystallization conditions substantially equivalent to 30% PEG 400, 0.2M $MgCl_2$, 0.1M Tris pH 8.5, 1 mM binding compound, at 4° C.; or 20% PEG 3000, 0.2M $Ca(OAc)_2$, 0.1M Tris pH 7.0, 1 mM binding compound, 15.9 mg/ml protein at 4° C.; or 1.8M-2.0M ammonium sulphate, 0.1 M CAPS pH 10.0-10.5, 0.2M lithium sulphate.

Crystallization conditions can be initially identified using a screening kit, such as a Hampton Research (Riverside, Calif.) screening kit 1. Conditions resulting in crystals can be selected and crystallization conditions optimized based on the demonstrated crystallization conditions. To assist in subsequent crystallography, the PDE can be seleno-methionine labeled. Also, as indicated above, the PDE may be any of various forms, e.g., truncated to provide a phosphodiesterase domain, which can be selected to be of various lengths.

In another aspect, the identification of compounds active on PDE4B (such as compounds developed using methods described herein) makes it possible for one to modulate the PDE activity by contacting PDE with a compound that binds to PDE and interacts with one more conserved active site residues. The compound is preferably provided at a level sufficient to modulate the activity of the PDE by at least 10%, more preferably at least 20%, 30%, 40%, or 50%. In many embodiments, the compound will be at a concentration of about 1 μM, 100 μM, or 1 mM, or in a range of 1-100 nM, 100-500 nM, 500-1000 nM, 1-100 μM, 100-500 μM, or 500-1000 μM.

In a related aspect, the invention provides a method for treating a subject suffering from a disease or condition characterized by abnormal PDE4 activity (e.g., abnormal PDE4B, PDE4D activity), where the method involves administering to the subject a compound identified by a method as described herein.

Because crystals of PDE4B have been developed and analyzed, and binding modes of ligands determined in such crystals, another aspect of the invention provides an electronic representation of these PDEs (which may be a reduced length PDE), for example, an electronic representation containing atomic coordinate representations for PDE4B corresponding to the coordinates listed for PDE4B in Table 1 and 2, or a schematic representation such as one showing secondary structure and/or chain folding, and may also show conserved active site residues. The PDE may be wild type, an allelic variant, a mutant form, or a modifed form, e.g., as described herein. In particular, the PDE may consist essentially of a PDE4B phosphodiesterase domain.

The electronic representation can also be modified by replacing electronic representations of particular residues with electronic representations of other residues. Thus, for example, an electronic representation containing atomic coordinate representations corresponding to the coordinates for PDE4B listed in Tables 1 or 2 can be modified by the replacement of coordinates for a particular conserved residue in a binding site by a different amino acid. Following a modification or modifications, the representation of the overall structure can be adjusted to allow for the known interactions that would be affected by the modification or modifications. In most cases, a modification involving more than one residue will be performed in an iterative manner.

In addition, an electronic representation of a PDE4B binding compound or a test compound in the binding site can be included, e.g., a non-hydrolyzable cAMP analog or a compound including the core structure of sildenafil.

Likewise, in a related aspect, the invention provides an electronic representation of a portion of PDE4B, which can be a binding site (which can be an active site) or phosphodiesterase domain, for example, PDE4B residues 152-528 of JC1519 (SEQ ID NO:1), or other phosphodiesterase domain described herein. A binding site or phosphodiesterase domain can be represented in various ways, e.g., as representations of atomic coordinates of residues around the binding site and/or as a binding site surface contour, and can include representations of the binding character of particular residues at the binding site, e.g., conserved residues. The binding site preferably includes no more than 1 heavy metal atom; a binding compound or test compound such as a compound including the core structure of Formula I may be present in the binding site; the binding site may be of a wild type, variant, mutant form, or modified form of PDE4B; the electronic representation includes representations coordinates of conserved residues as in Table 1 or 2.

In yet another aspect, the structural and sequence information of PDE4B can be used in a homology model for another PDE. It is helpful if high resolution structural information for PDE4B is used for such a model, e.g., at least 1.7, 1.5, 1.4, 1.3, or 1.2 Angstrom resolution.

In still another aspect, the invention provides an electronic representation of a modified PDE4B crystal structure, that includes an electronic representation of the atomic coordinates of a modified PDE4B based on the atomic coordinates of Table 1 and/or 2. In an exemplary embodiment, atomic coordinates of one of the listed tables can be modified by the replacement of atomic coordinates for a conserved residue with atomic coordinates for a different amino acid. Modifications can include substitutions, deletions (e.g., C-terminal and/or N-terminal detections), insertions (internal, C-terminal, and/or N-terminal) and/or side chain modifications.

In another aspect, the PDE4B structural information provides a method for developing useful biological agents based on PDE4B, by analyzing a PDE4B structure to identify at least one sub-structure for forming the biological agent. Such sub-structures can include epitopes for antibody formation, and the method includes developing antibodies against the epitopes, e.g., by injecting an epitope presenting composition in a mammal such as a rabbit, guinea pig, pig, goat, or horse. The sub-structure can also include a mutation site at which mutation is expected to or is known to alter the activity of the PDE4B, and the method includes creating a mutation at that site. Still further, the sub-structure can include an attachment point for attaching a separate moiety, for example, a peptide, a polypeptide, a solid phase material (e.g., beads, gels, chromatographic media, slides, chips, plates, and well surfaces), a linker, and a label (e.g., a direct label such as a fluorophore or an indirect label, such as biotin or other member of a specific binding pair). The method can include attaching the separate moiety.

In another aspect, the invention provides a method for identifying potential PDE4B binding compounds by fitting at least one electronic representation of a compound in an electronic representation of the PDE binding site. The representation of the binding site may be part of an electronic representation of a larger portion(s) or all of a PDE molecule or may be a representation of only the catalytic domain or of the binding site or active site. The electronic representation may be as described above or otherwise described herein. For PDE4B the electronic representation includes representations of coordinates according to Tables 1 and/or 2 (in particular residues with coordinates differing signficantly from the previously proposed PDE4B structure). In certain embodiments, the compound complexed with PDE4B is an anlog of cGMP which is non-hydrolyzable.

In particular embodiments, the method involves fitting a computer representation of a compound from a computer database with a computer representation of the active site of the PDE, and involves removing a computer representation of a compound complexed with the PDE molecule and identifying compounds that best fit the active site based on favorable geometric fit and energetically favorable complementary interactions as potential binding compounds. In particular embodiments, the compound is a known PDE4B inhibitor, e.g., as described in a reference cited herein, or a derivative thereof.

In other embodiments, the method involves modifying a computer representation of a compound complexed with the PDE molecule, by the deletion or addition or both of one or more chemical groups; fitting a computer representation of a compound from a computer database with a computer representation of the active site of the PDE molecule; and identifying compounds that best fit the active site based on favorable geometric fit and energetically favorable complementary interactions as potential binding compounds. In certain embodiments, the fitting comprises determining whether potential binding compounds interact with one or more of conserved PDE4B active site residues.

In still other embodiments, the method involves removing a computer representation of a compound complexed with the PDE, and searching a database for compounds having structural similarity to the complexed compound using a compound searching computer program or replacing portions of the complexed compound with similar chemical structures using a compound construction computer program.

Fitting a compound can include determining whether a compound will interact with one or more conserved active site residues for the PDE. Compounds selected for fitting or that are complexed with the PDE can, for example, be a known PDE4B inhibitor compound, or a compound including the core structure of such compound.

In another aspect, the invention provides a method for attaching a PDE4B binding compound to an attachment component without substantially changing the binding of the binding compound to PDE4B, as well as a method for identifying attachment sites on a PDE4B binding compound. The method involves identifying energetically allowed sites for attachment of an attachment component for the binding compound bound to a binding site of PDE4B; and attaching the compound or a derivative thereof to the attachment component at the energetically allowed site. In this context, "substantially changing the binding" denotes a change in $IC_{50}$ after attachment of less than 3 log units, e.g., 1 nM to 1 µM. In certain embodiments, the binding compound is a compound of Formula I.

Attachment components can include, for example, linkers (including traceless linkers) for attachment to a solid phase or to another molecule or other moiety. Such attachment can be formed by synthesizing the compound or derivative on the linker attached to a solid phase medium, e.g., in a combinatorial synthesis of a plurality of compounds. Likewise, the attachment to a solid phase medium can provide an affinity medium (e.g., for affinity chromatography).

The attachment component can also include a label, which can be a directly detectable label such as a fluorophore, or an indirectly detectable such as a member of a specific binding pair, e.g., biotin.

The ability to identify energetically allowed sites on a PDE4B binding compound, also, in a related aspect, provides modified binding compounds that have linkers attached, preferably at an energetically allowed site for binding of the modified compound to PDE4B. The linker can be attached to an attachment component as described above.

Another aspect of the invention provides a modified PDE4B polypeptide that includes a modification that makes the modified PDE4B more similar than native PDE4B to another phosphodiesterase, and can also include other mutations or other modifications. In various embodiments, the polypeptide includes a full-length PDE4B polypeptide, includes a modified PDE4B binding site, includes at least 20, 30, 40, 50, 60, 70, or 80 contiguous amino acid residues derived from PDE4B including a conserved site.

Still another aspect of the invention provides a method for developing a ligand for a phosphodiesterase that includes conserved residues matching any one, 2, 3, 4, 5, or 6 of conserved PDE4B active site residues respectively, by determining whether a compound binds to the phosphodiesterase and interacts with such active site residues in a PDE4B crystal or a PDE4B binding model having coordinates as in Table 1 and/or 2. The method can also include determining whether the compound modulates the activity of the phosphodiesterase. Preferably the phosphodiesterase has at least 50, 55, 60, or 70% identity over an equal length phosphodiesterase domain segment. In certain embodiments, the compound is a compound of Formula I.

In yet another aspect, the invention provides a method for developing or identifying a ligand for a phosphodiesterase wherein the phosphodiesterase comprises conserved residues matching one or more PDE4B active site residues. The method comprises determining whether a PDE4B binding compound binds to said phosphodiesterase, and determining whether the PDE4B binding compound interacts with one or more conserved PDE4B active site residues in a crystal structure. In a further embodiment, the method comprises determining whether a PDE4B binding compound which binds to the phosphodiesterase interacts with one or more conserved PDE4B active site residues in a crystal structure.

In particular embodiments, determining includes computer fitting the compound in a binding site of the phosphodiesterase and/or the method includes forming a co-crystal of the phosphodiesterase and the compound. Such co-crystals can be used for determining the binding orientation of the compound with the phosphodiesterase and/or provide structural information on the phosphodiesterase, e.g., on the binding site and interacting amino acid residues. Such binding orientation and/or other structural information can be accomplished using X-ray crystallography.

The invention also provides compounds that bind to and/or modulate (e.g., inhibit) PDE4B phosphodiesterase activity e.g., compounds identified by the methods described herein. Accordingly, in aspects of the invention involving PDE4B binding compounds, molecular scaffolds, and ligands or modulators, the compound is a weak binding compound; a moderate binding compound; a strong binding compound; the compound interacts with one or more conserved active site residues in the PDE; the compound is a small molecule; the compound binds to a plurality of different phosphodiesterases (e.g., at least 2, 3, 4, 5, 7, 10, or more different phosphodiesterases). In particular, the invention provides compounds identified or selected.

In yet another embodiment, the invention provides a method for identifying a compound having selectivity between PDE4B and PDE4D by utilizing particular differential sites. The method involves analyzing whether a compound differentially interacts in PDE4B and PDE4D in at least one of the differential sites, where a differential interaction is indicative of such selectivity. The differential sites are identified from crystal structure comparison. The term "differential site" denotes a site, i.e., a location, where the chemical features of PDE4B and PDE4D interact differently with the compound. The term "chemical feature" is understood by those of skill in the art to denote structural and chemical properties responsible for chemical reactivity (including binding) and include without limitation hydrogen bond donor or acceptors, hydrophobic/lipophilic sites, positively ionizable sites, negatively ionizable sites, charge density, electronegativity, and the like.

In particular embodiments, the analyzing includes fitting an electronic representation of the compound in electronic representations of binding sites of PDE4B and PDE4D, and determining whether the compound differentially interacts based on said fitting; the method involves selecting an initial compound that binds to both PDE4B and PDE4D, fitting an electronic representation of the initial compound in electronic representations of binding sites of PDE4B and PDE4D, modifying the electronic representation of the initial compound with at least one moiety that interacts with at least differentials site, and determining whether the modified compound differentially binds to PDE4B and PDE4D; the modified compound binds differentially to a greater extent than does the initial compound; the method also includes assaying a compound that differentially interacts for differential activity on PDE4B and PDE4D; the initial compound includes the sildenafil scaffold structure; the initial compound can include the sildenafil core. Sildenafil is 1-[4-ethoxy-3-(6,7-dihydro-1-methyl-7-oxo-3-propyl-1H-pyrazolo[4,3-d]pyrimidin-5-yl)phenylsulfonyl]-4-methylpiperazine. In certain emboidments, the binding compound is a compound of Formula I.

In the various aspects described above that involve atomic coordinates for PDE4B in connection with binding compounds, the coordinates provided in Tables 1 or 2 can be used. Those coordinates can then be adjusted using conventional modeling methods to fit compounds having structures different from sildenafil, and can thus be used for development of different PDE4B modulators, relative to currently described PDE4B modulators. PDE4B crystal coordinates provided herein can be used instead of the previously described PDE4B structure coordinate because the present structure coordinates correct apparent errors in the previously described structure (e.g., as shown by the structure overlay in FIG. 4), and thus are better adapted for PDE4B ligand development and other uses of PDE4B structure information such as the uses described herein.

Additional aspects and embodiments will be apparent from the following Detailed Description and from the claims.

DETAILED DESCRIPTION OF THE PREFERRED EMBODIMENTS

Figure 1:
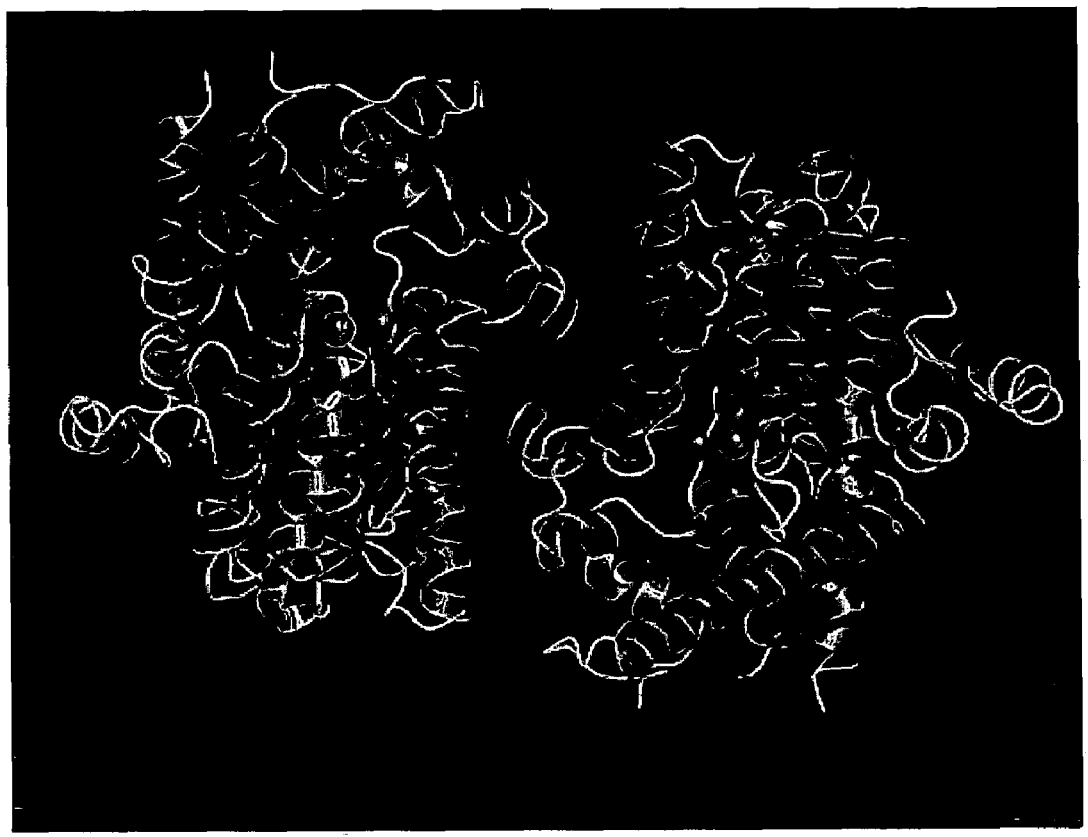
FIG. 1 shows a ribbon diagram schematic representation of PDE4B phosphodiesterase domain having the sequence in Table 3.

Table 1 provides atomic coordinates for human PDE4B phosphodiesterase domain including residues 155-507. In this table, the various columns have the following content, beginning with the left-most column:

ATOM: Refers to the relevant moiety for the table row;
Atom number: Refers to the arbitrary atom number designation within the coordinate table;
Atom Name: Identifier for the atom present at the particular coordinates;
Chain ID: Chain ID refers to one monomer of the protein in the crystal, e.g., chain "A", or to other compound present in the crystal, e.g., HOH for water, and L for a ligand or binding compound. Multiple copies of the protein monomers will have different chain Ids;
Residue Number: The amino acid residue number in the chain;
X, Y, Z: Respectively are the X, Y, and Z coordinate values;
Occupancy: Describes the fraction of time the atom is observed in the crystal. For example, occupancy=1 means that the atom is present all the time; occupancy=0.5 indicates that the atom is present in the location 50% of the time;
B-factor: A measure of the thermal motion of the atom;
Element: Identifier for the element.

Table 2 provides atomic coordinate data for PDE4B phosphodiesterase domain co-crystal with 4-(3,4-dimethoxy-phenyl)-1H-pyrrolo[2,3-b]pyridine 50.

Table 3 provides amino acid and nucleic acid sequences for PDE4B phosphodiesterase domain as used in the work described herein.

Table 4 shows the alignment of the phosphodiesterase domains of PDE4B and PDE4D, with 3 regions that can be exploited for designing selective ligands indicated by filled squares beneath the regions.

Table 5 provides activity of exemplary compounds of Formula I in assays that assess inhibition of PDE4B or PDE4D as described in Examples 145-147.

As used herein the following definitions apply unless otherwise indicated:

"Halo" or "halogen"—alone or in combination means all halogens, that is, chloro (Cl), fluoro (F), bromo (Br), or iodo (I).

"Hydroxyl" refers to the group —OH.

"Thiol" or "mercapto" refers to the group —SH.

"Alkyl"—alone or in combination means an alkane-derived radical containing from 1 to 20, preferably 1 to 15, carbon atoms (unless specifically defined). It is a straight chain alkyl or branched alkyl, and includes a straight chain or branched alkyl group that contains or is interrupted by a cycloalkyl portion. The straight chain or branched alkyl group is attached at any available point to produce a stable compound. Examples of this include, but are not limited to, 4-(isopropyl)-cyclohexylethyl or 2-methyl-cyclopropylpentyl. In many embodiments, an alkyl is a straight or branched alkyl group containing from 1-15, 1-8, 1-6, 1-4, or 1-2, carbon atoms, such as methyl, ethyl, propyl, isopropyl, butyl, t-butyl and the like. "Optionally substituted alkyl" denotes alkyl or alkyl that is independently substituted with 1 to 3 groups or substituents selected from the group consisting of halo, hydroxy, optionally substituted lower alkoxy, optionally substituted acyloxy, optionally substituted aryloxy, optionally substituted heteroaryloxy, optionally substituted cycloalkyloxy, optionally substituted heterocycloalkyloxy, thiol, optionally substituted lower alkylthio, optionally substituted arylthio, optionally substituted heteroarylthio, optionally substituted cycloalkylthio, optionally substituted heterocycloalkylthio, optionally substituted alkylsulfinyl, optionally substituted arylsulfinyl, optionally substituted heteroarylsulfinyl, optionally substituted cycloalkylsulfinyl, optionally substituted heterocycloalkylsulfinyl, optionally substituted alkylsulfonyl, optionally substituted arylsulfonyl, optionally substituted heteroarylsulfonyl, optionally substituted cycloalkylsulfonyl, optionally substituted heterocycloalkylsulfonyl, optionally substituted amino, optionally substituted amido, optionally substituted amidino, optionally substituted urea, optionally substituted aminosulfonyl, optionally substituted alkylsulfonylamino, optionally substituted arylsulfonylamino, optionally substituted heteroarylsulfonylamino, optionally substituted cycloalkylsulfonylamino, optionally substituted heterocycloalkylsulfonylamino, optionally substituted alkylcarbonylamino, optionally substituted arylcarbonylamino, optionally substituted heteroarylcarbonylamino, optionally substituted cycloalkylcarbonylamino, optionally substituted heterocycloalkylcarbonylamino, optionally substituted carboxyl, optionally substituted acyl, optionally substituted cycloalkyl, optionally substituted heterocycloalkyl, optionally substituted aryl, optionally substituted heteroaryl, nitro, and cyano, attached at any available point to produce a stable compound.

"Lower alkyl" refers to an alkyl group having 1-6 carbon atoms. "Optionally substituted lower alkyl" denotes lower alkyl or lower alkyl that is independently substituted with 1 to 3 groups or substituents as defined in [0110] attached at any available point to produce a stable compound.

"Lower alkylene" refers to a divalent alkane-derived radical containing 1-6 carbon atoms, straight chain or branched, from which two hydrogen atoms are taken from the same carbon atom or from different carbon atoms. Examples of lower alkylene include, but are not limited to, —$CH_2$—, —$CH_2CH_2$—, and —$CH_2CH(CH_3)$—.

"Alkenyl"—alone or in combination means a straight, branched, or cyclic hydrocarbon containing 2-20, preferably 2-17, more preferably 2-10, even more preferably 2-8, most preferably 2-4, carbon atoms and at least one, preferably 1-3, more preferably 1-2, most preferably one, carbon to carbon double bond. In the case of a cycloalkenyl group, conjugation of more than one carbon to carbon double bond is not such as to confer aromaticity to the ring. Carbon to carbon double bonds may be either contained within a cycloalkyl portion, with the exception of cyclopropyl, or within a straight chain or branched portion. Examples of alkenyl groups include ethenyl, propenyl, isopropenyl, butenyl, cyclohexenyl, cyclohexenylalkyl and the like. "Optionally substituted alkenyl" denotes alkenyl or alkenyl that is independently substituted with 1 to 3 groups or substituents as defined in [0110] attached at any available point to produce a stable compound.

"Lower alkenyl" refers to an alkenyl group having 1-6 carbon atoms. "Optionally substituted lower alkenyl" denotes lower alkenyl or lower alkenyl that is substituted with 1 to 3 groups or substituents as defined in [0110] attached at any available point to produce a stable compound.

"Alkynyl"—alone or in combination means a straight or branched hydrocarbon containing 2-20, preferably 2-17, more preferably 2-10, even more preferably 2-8, most preferably 2-4, carbon atoms containing at least one, preferably one, carbon to carbon triple bond. Examples of alkynyl groups include ethynyl, propynyl, butynyl and the like. "Optionally substituted alkynyl" denotes alkynyl or alkynyl that is independently substituted with 1 to 3 groups or substituents as defined in [0110] attached at any available point to produce a stable compound.

"Lower alkynyl" refers to an alkynyl group having 1-6 carbon atoms. "Optionally substituted lower alkynyl" denotes lower alkynyl or lower alkynyl that is substituted with 1 to 3 groups or substituents as defined [0110] attached at any available point to produce a stable compound.

"Alkoxy" or "lower alkoxy" denotes the group —$OR^a$, wherein $R^a$ is alkyl or lower alkyl, respectively. "Optionally substituted alkoxy" or "optionally substituted lower alkoxy" denotes alkoxy or lower alkoxy in which $R^a$ is optionally substituted alkyl or optionally substituted lower alkyl, respectively.

"Acyloxy" denotes the group —$OC(O)R^b$, wherein $R^b$ is hydrogen, lower alkyl, cycloalkyl, heterocycloalkyl, aryl, or heteroaryl. "Optionally substituted acyloxy" denotes acyloxy in which Rb is hydrogen, optionally substituted lower alkyl, optionally substituted cycloalkyl, optionally substituted heterocycloalkyl, optionally substituted aryl, or optionally substituted heteroaryl.

"Aryloxy" denotes the group —$OR^c$, wherein $R^c$ is aryl. "Optionally substituted aryloxy" denotes aryloxy or aryloxy in which $R^c$ is optionally substituted aryl.

"Heteroaryloxy" denotes the group —$OR^d$, wherein $R^d$ is heteroaryl. "Optionally substituted heteroaryloxy" denotes heteroaryloxy in which $R^d$ is optionally substituted heteroaryl.

"Cycloalkyloxy" denotes the group —$OR^e$, wherein $R^e$ is cycloalkyl. "Optionally substituted cycloalkyloxy" denotes cycloalkyloxy in which $R^e$ is optionally substituted cycloalkyl.

"Heterocycloalkyloxy" denotes the group —$OR^f$, wherein $R^f$ is heterocycloalkyl. "Optionally substituted heterocycloalkyloxy" denotes heterocycloalkyloxy in which $R^f$ is optionally substituted heterocycloalkyl.

"Alkylthio" or "lower alkylthio" denotes the group —$OR^g$, wherein $R^g$ is alkyl or lower alkyl, respectively. "Optionally substituted alkylthio" or "optionally substituted lower alkylthio" denotes alkylthio or lower alkylthio in which $R^g$ is optionally substituted alkyl or optionally substituted lower alkyl, respectively.

"Arylthio" denotes the group —$SR^h$, wherein $R^h$ is aryl. "Optionally substituted arylthio" denotes arylthio in which $R^h$ is optionally substituted aryl.

"Heteroarylthio" denotes the group —$SR^i$, wherein $R^i$ is heteroaryl. "Optionally substituted heteroarylthio" denotes heteroarylthio in which $R^i$ is optionally substituted heteroaryl.

"Cycloalkylthio" denotes the group —$SR^j$, wherein $R^j$ is cycloalkyl. "Optionally substituted cycloalkylthio" denotes cycloalkylthio in which $R^j$ is optionally substituted cycloalkyl.

"Heterocycloalkylthio" denotes the group —$SR^k$, wherein $R^k$ is heterocycloalkyl. "Optionally substituted heterocycloalkylthio" denotes heterocycloalkylthio in which $R^k$ is optionally substituted heterocycloalkyl.

"Acyl" denotes groups —$C(O)R^L$, wherein $R^L$ is hydrogen, lower alkyl, cycloalkyl, heterocycloalkyl, aryl, or heteroaryl. "Optionally substituted acyl" denotes acyl in which $R^L$ is hydrogen, optionally substituted lower alkyl, optionally substituted cycloalkyl, optionally substituted heterocycloalkyl, optionally substituted aryl, or optionally substituted heteroaryl.

"Optionally substituted amino" denotes the group —$NR^mR^n$, wherein $R^m$ and $R^n$ are independently hydrogen, optionally substituted lower alkyl, optionally substituted cycloalkyl, optionally substituted heterocycloalkyl, optionally substituted aryl, optionally substituted heteroaryl, optionally substituted acyl, or optionally substituted sulfonyl, or, $R^m$ and $R^n$ together with the nitrogen to which they are attached form a 5-7 membered optionally substituted heterocycloalkyl or optionally substituted heteroaryl ring.

"Optionally substituted amido" denotes the group —$C(O)NR^oR^p$, wherein $R^o$ and $R^p$ are independently hydrogen, optionally substituted lower alkyl, optionally substituted cycloalkyl, optionally substituted heterocycloalkyl, optionally substituted aryl, or optionally substituted heteroaryl, or $R^o$ and $R^p$ together with the nitrogen to which they are attached form a 5-7 membered optionally substituted heterocycloalkyl or optionally substituted heteroaryl ring.

"Optionally substituted amidino" denotes the group —$C(=NR^q)NR'R^s$, wherein $R^q$, $R^r$, and $R^s$ are independently hydrogen or optionally substituted lower alkyl.

"Optionally substituted urea" denotes the group —NR$^t$C(O)NR$^u$R$^v$, wherein R$^t$ is hydrogen or optionally substituted lower alkyl, and R$^u$ and R$^v$ are independently hydrogen, optionally substituted lower alkyl, optionally substituted cycloalkyl, optionally substituted heterocycloalkyl, optionally substituted aryl or optionally substituted heteroaryl, or R$^u$ and R$^v$ together with the nitrogen to which they are attached form a 5-7 membered optionally substituted heterocycloalkyl or optionally substituted heteroaryl ring.

"Optionally substituted sulfonyl" denotes the group —S(O)$_2$R$^w$, wherein R$^w$ is optionally substituted lower alkyl, optionally substituted cycloalkyl, optionally substituted heterocycloalkyl, optionally substituted aryl, or optionally substituted heteroaryl.

"Optionally substituted aminosulfonyl" denotes the group —S(O)$_2$NR$^x$R$^y$, wherein R$^x$ and R$^y$ are independently hydrogen, optionally substituted lower alkyl, optionally substituted cycloalkyl, optionally substituted heterocycloalkyl, optionally substituted aryl, or optionally substituted heteroaryl, or R$^x$ and R$^y$ together with the nitrogen to which they are attached form a 5-7 membered optionally substituted heterocycloalkyl or optionally substituted heteroaryl ring.

"Carboxyl" denotes the group —C(O)OR$^z$, wherein R$^z$ is hydrogen, lower alkyl, cycloalkyl, heterocycloalkyl, aryl, or heteroaryl. "Optionally substituted carboxyl" denotes carboxyl wherein R$^z$ is hydrogen, optionally substituted lower alkyl, optionally substituted cycloalkyl, optionally substituted heterocycloalkyl, optionally substituted aryl, or optionally substituted heteroaryl.

"Aryl" refers to a ring system-containing aromatic hydrocarbon such as phenyl or naphthyl, which may be optionally fused with a cycloalkyl of preferably 5-7, more preferably 5-6, ring members. "Optionally substituted aryl" denotes aryl or aryl that is substituted with 1 to 3 groups or substituents as defined in [0110], optionally substituted lower alkyl, optionally substituted lower alkenyl, or optionally substituted lower alkynyl, attached at any available point to produce a stable compound. A "substituted aryl" is aryl that is substituted with 1 to 3 groups or substituents as defined in [0110], or optionally substituted lower alkyl, optionally substituted lower alkenyl, or optionally substituted lower alkynyl, attached at any available point to produce a stable compound.

"Aralkyl" refers to the group —R$^{aa}$—Ar wherein Ar is an aryl group and R$^{aa}$ is lower alkylene. "Optionally substituted aralkyl" denotes aralkyl or aralkyl in which the lower alkylene group is optionally substituted with 1 to 3 groups or substituents as defined in [0110] attached at any available point to produce a stable compound, and in which the aryl group is optionally substituted with 1 to 3 groups or substituents as defined in [0110], optionally substituted lower alkyl, optionally substituted lower alkenyl, or optionally substituted lower alkynyl, attached at any available point to produce a stable compound.

"Heteroaryl" alone or in combination refers to a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group consisting of O, S, and N. Heteroaryl is also intended to include oxidized S or N, such as sulfinyl, sulfonyl, and N-oxide of a tertiary ring nitrogen. A carbon or nitrogen atom is the point of attachment of the heteroaryl ring structure such that a stable aromatic ring is retained. Examples of heteroaryl groups include, but are not limited to, pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, and indolyl. "Optionally substituted heteroaryl" includes heteroaryl or heteroaryl that is substituted with 1 to 3 groups or substituents as defined in [0110], optionally substituted lower alkyl, optionally substituted lower alkenyl, or optionally substituted lower alkynyl, attached at any available carbon or nitrogen to produce a stable compound. "Substituted heteroaryl" denotes heteroaryl that is substituted with 1 to 3 groups or substituents as defined in [0110], or optionally substituted lower alkyl, optionally substituted lower alkenyl, or optionally substituted lower alkynyl, attached at any available carbon or nitrogen to produce a stable compound "Heteroaralkyl" refers to the group —R$^{bb}$-HetAr wherein HetAr is a heteroaryl group, and R$^{bb}$ is lower alkylene. "Optionally substituted heteroaralkyl" denotes heteroaralkyl or heteroaralkyl in which the lower alkylene group is optionally substituted with 1 to 3 groups or substituents as defined in [0110], attached at any available point to produce a stable compound, and in which the heteroaryl group is optionally substituted with 1 to 3 groups or substituents as defined in [0110], optionally substituted lower alkyl, optionally substituted lower alkenyl, or optionally substituted lower alkynyl, attached at any available point to produce a stable compound.

"Cycloalkyl" refers to saturated or unsaturated, non-aromatic monocyclic, bicyclic or tricyclic carbon ring systems of 3-8, more preferably 3-6, ring members per ring, such as cyclopropyl, cyclopentyl, cyclohexyl, adamantyl, and the like. "Optionally substituted cycloalkyl" denotes cycloalkyl or cycloalkyl that is substituted with 1 to 3 groups or substituents as defined in [0110], optionally substituted lower alkyl, optionally substituted lower alkenyl, or optionally substituted lower alkynyl, attached at any available carbon or nitrogen to produce a stable compound.

"Cycloalkylalkyl" refers to the group —R$^{cc}$-Cyc wherein Cyc is a cycloalkyl group, and R$^{cc}$ is a lower alkylene group. "Optionally substituted cycloalkylalkyl" denotes cycloalkylalkyl or cycloalkylalkyl in which the lower alkylene group is optionally substituted with 1 to 3 groups or substituents as defined in [0110], attached at any available point to produce a stable compound, and in which the cycloalkyl group is optionally substituted with 1 to 3 groups or substituents as defined in [0110], optionally substituted lower alkyl, optionally substituted lower alkenyl, or optionally substituted lower alkynyl, attached at any available point to produce a stable compound.

"Heterocycloalkyl" refers to a saturated or unsaturated non-aromatic cycloalkyl group having from 5 to 10 atoms in which from 1 to 3 carbon atoms in the ring are replaced by heteroatoms of O, S or N, and are optionally fused with benzo or heteroaryl of 5-6 ring members. Heterocycloalkyl is also intended to include oxidized S or N, such as sulfinyl, sulfonyl and N-oxide of a tertiary ring nitrogen. The point of attachment of the heterocycloalkyl ring is at a carbon or nitrogen atom such that a stable ring is retained. Examples of heterocycloalkyl groups include, but are not limited to, morpholino, tetrahydrofuranyl, dihydropyridinyl, piperidinyl, pyrrolidinyl, piperazinyl, dihydrobenzofuryl, and dihydroindolyl. "Optionally substituted heterocycloalkyl" denotes heterocycloalkyl or heterocycloalkyl that is substituted with 1 to 3 groups or substituents as defined in [0110], optionally substituted lower alkyl, optionally substituted lower alkenyl, or optionally substituted lower alkynyl, attached at any available carbon or nitrogen to produce a stable compound.

"Heterocycloalkylalkyl" refers to the group —R$^{dd}$-Het wherein Het is a heterocycloalkyl group, and R$^{dd}$ is a lower alkylene group. "Optionally substituted heterocycloalkylalkyl" denotes heterocycloalkylalkyl or heterocycloalkylalkyl in which the lower alkylene group is optionally substituted with 1 to 3 groups or substituents as defined in [0110], attached at any available point to produce a stable compound, and in which the heterocycloalkyl group is optionally substituted with 1 to 3 groups or substituents as defined in [0110], optionally substituted lower alkyl, optionally substituted lower alkenyl, or optionally substituted lower alkynyl, attached at any available point to produce a stable compound.

"Optionally substituted alkylsulfinyl" denotes the group —S(O)$R^{ee}$, wherein $R^{ee}$ is optionally substituted lower alkyl.

"Optionally substituted arylsulfinyl" denotes the group —S(O)$R^{ff}$, wherein $R^{ff}$ is optionally substituted aryl.

"Optionally substituted heteroarylsulfinyl" denotes the group —S(O)$R^{gg}$, wherein $R^{gg}$ is optionally substituted heteroaryl.

"Optionally substituted cycloalkylsulfinyl" denotes the group —S(O)$R^{hh}$, wherein $R^{hh}$ is optionally substituted cycloalkyl.

"Optionally substituted heterocycloalkylsulfinyl" denotes the group —S(O)$R^{ii}$, wherein $R^{ii}$ is optionally substituted heterocycloalkyl.

"Optionally substituted alkylsulfonyl" denotes the group —S(O)$_2R^{jj}$, wherein $R^{jj}$ is optionally substituted lower alkyl.

"Optionally substituted arylsulfonyl" denotes the group —S(O)$_2R^{kk}$, wherein $R^{kk}$ is optionally substituted aryl.

"Optionally substituted heteroarylsulfonyl" denotes the group —S(O)$_2R^{LL}$, wherein $R^{LL}$ is optionally substituted heteroaryl.

"Optionally substituted cycloalkylsulfonyl" denotes the group —S(O)$_2R^{mm}$, wherein $R^{mm}$ is optionally substituted cycloalkyl.

"Optionally substituted heterocycloalkylsulfonyl" denotes the group —S(O)$_2R^{nn}$, wherein $R^{nn}$ is optionally substituted heterocycloalkyl.

"Optionally substituted alkylsulfonylamino" denotes the group —$NR^{oo}S(O)_2R^{pp}$, wherein $R^{pp}$ is optionally substituted lower alkyl, and $R^{oo}$ is hydrogen or optionally substituted lower alkyl.

"Optionally substituted arylsulfonylamino" denotes the group —$NR^{oo}S(O)_2R^{qq}$, wherein $R^{qq}$ is optionally substituted aryl, and $R^{oo}$ is hydrogen or optionally substituted lower alkyl.

"Optionally substituted heteroarylsulfonylamino" denotes the group —$NR^{oo}S(O)_2R^{ss}$, wherein $R^{ss}$ is optionally substituted heteroaryl, and $R^{oo}$ is hydrogen or optionally substituted lower alkyl.

"Optionally substituted cycloalkylsulfonylamino" denotes the group —$NR^{oo}S(O)_2R^{ss}$, wherein $R^{ss}$ is optionally substituted cycloalkyl, and $R^{oo}$ is hydrogen or optionally substituted lower alkyl.

"Optionally substituted heterocycloalkylsulfonylamino" denotes the group —$NR^{oo}S(O)_2R^{rr}$, wherein $R^{rr}$ is optionally substituted heterocycloalkyl, and $R^{oo}$ is hydrogen or optionally substituted lower alkyl.

"Optionally substituted alkylcarbonylamino" denotes the group —$NR^{oo}C(O)R^{uu}$, wherein $R^{uu}$ is optionally substituted lower alkyl, and $R^{oo}$ is hydrogen or optionally substituted lower alkyl.

"Optionally substituted arylcarbonylamino" denotes the group —$NR^{oo}C(O)R^{vv}$, wherein $R^{vv}$ is optionally substituted aryl, and $R^{oo}$ is hydrogen or optionally substituted lower alkyl.

"Optionally substituted heteroarylcarbonylamino" denotes the group —$NR^{oo}C(O)R^{ww}$, wherein $R^{ww}$ is optionally substituted heteroaryl, and $R^{oo}$ is hydrogen or optionally substituted lower alkyl.

"Optionally substituted cycloalkylcarbonylamino" denotes the group —$NR^{oo}C(O)R^{xx}$, wherein $R^{xx}$ is optionally substituted cycloalkyl, and $R^{oo}$ is hydrogen or optionally substituted lower alkyl.

"Optionally substituted heterocycloalkylcarbonylamino" denotes the group —$NR^{oo}C(O)R^{yy}$, wherein $R^{yy}$ is optionally substituted heterocycloalkyl, and $R^{oo}$ is hydrogen or optionally substituted lower alkyl.

As used herein, the terms "composition" and "pharmaceutical composition" refer to a preparation that includes a therapeutically significant quantity of an active agent, that is prepared in a form adapted for administration to a subject. Thus, the preparation does not include any component or components in such quantity that a reasonably prudent medical practitioner would find the preparation unsuitable for administration to a normal subject. In many cases, such a pharmaceutical composition is a sterile preparation.

As used herein in connection with PDE4 modulating compound, binding compounds or ligands, the term "specific for PDE4 phosphodiesterase", "specific for PDE4" and terms of like import mean that a particular compound binds to PDE4 to a statistically greater extent than to other phosphodiesterases that may be present in a particular organism, e.g., at least 2, 3, 4, 5, 10, 20, 50, 100, or 1000-fold. Also, where biological activity other than binding is indicated, the term "specific for PDE4" indicates that a particular compound has greater biological activity associated with binding PDE4 than to other phosphodiesterases (e.g., at a level as indicated for binding specificity). Preferably, the specificity is also with respect to other biomolecules (not limited to phosphodiesterases) that may be present from an organism. Such binding and/or activity specificity may be for a PDE4 isoform, e.g., PDE4A, PDE4B, PDE4C, PDE4D, such that the specificity is also with respect to the other PDE4 isoforms. In the context of ligands interacting with PDE4, the terms "activity on", "activity toward," and like terms mean that such ligands have $IC_{50}$ less than 10 µM, less than 1 µM, less than 100 nM, less than 50 nM, less than 20 nM, less than 10 nM, less than 5 nM, or less than 1 nM with respect to one or more PDE4 as determined in a generally accepted PDE4 activity assay.

As used herein, the term "PDE4-mediated" disease or condition and like terms refer to a disease or condition in which the biological function of PDE4 affects the development and/or course of the disease or condition, and/or in which modulation of PDE4 alters the development, course, and/or symptoms of the disease or condition. Similarly, the phrase "PDE4 modulation provides a therapeutic benefit" indicates that modulation of the level of activity of PDE4 in a subject indicates that such modulation reduces the severity and/or duration of the disease, reduces the likelihood or delays the onset of the disease or condition, and/or causes an improvement in one or more symptoms of the disease or condtion. In some cases the disease or condition may be mediated by one of the PDE4 isoforms, e.g., PDE4B, PDE4C, or PDE4D.

In the present context, the term "therapeutically effective" indicates that the materials or amount of material is effective to prevent, alleviate, or ameliorate one or more symptoms of a disease or medical condition, and/or to prolong the survival of the subject being treated.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectibles.

The term "pharmaceutically acceptable metabolite" refers to a pharmacologically acceptable product, which may be an active product, produced through metabolism of a specified compound (or salt thereof) in the body of a subject or patient. Metabolites of a compound may be identified using routine techniques known in the art, and their activities determined using tests such as those described herein. For example, in some compounds, one or more alkoxy groups can be metabolized to hydroxyl groups while retaining pharmacologic activity and/or carboxyl groups can be esterified, e.g., glucuronidation. In some cases, there can be more than one metabolite, where an intermediate metabolite(s) is further metabolized to provide an active metabolite. For example, in some cases a derivative compound resulting from metabolic glucuronidation may be inactive or of low activity, and can be further metabolized to provide an active metabolite.

"A pharmaceutically acceptable salt" is intended to mean a salt that retains the biological effectiveness of the free acids and bases of the specified compound and that is not biologically or otherwise unacceptable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sodium, chloride, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4 dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma.-hydroxybutyrates, glycollates, tartrates, methane-sulfonates, propanesulfonates, naphthalene-1-sulfonates, naphthalene-2-sulfonates, and mandelates.

The terms "PDE4B phosphodiesterase" and "PDE4B" mean an enzymatically active phosphodiesterase that contains a portion with greater than 90% amino acid sequence identity to amino acid residues 152-528 (S152-S528) with reference to GenBank polypeptide sequence JC1519 (SEQ ID NO:1) of native PDE4B as shown in Table 4, for a maximal alignment over an equal length segment; or that contains a portion with greater than 90% amino acid sequence identity to at least 200 contiguous amino acids from amino acid residues 152-528 of JC1519 (SEQ ID NO:1) of native PDE4B that retains binding to natural PDE4B ligand. Preferably the sequence identity is at least 95, 97, 98, 99, or even 100%. Preferably the specified level of sequence identity is over a sequence at least 300 contiguous amino acid residues in length. The sequence represented by amino acid residues 152-528 of JC1519 (SEQ ID NO:1) is also available as S324 to S700 of NP_002591 (SEQ ID NO:3, encoded by NM_002600, SEQ ID NO:4), S309 to S685 of AAB96381 (SEQ ID NO:5), and S194 to S570 of AAA35643 (SEQ ID NO:6). Therefore, amino acid residues identified in one of the listed sequences can also be expressed as the matching amino acid residue in any other of the listed sequences or other matching sequence.

The term "PDE4B phosphodiesterase domain" refers to a reduced length PDE4B (i.e., shorter than a full-length PDE4B by at least 100 amino acids that includes the phosphodiesterase, catalytic region in PDE4B. Highly preferably for use in this invention, the phosphodiesterase domain retains phosphodiesterase activity, preferably at least 50% the level of phosphodiesterase activity as compared to the native PDE4B, more preferably at least 60, 70, 80, 90, or 100% of the native activity.

As used herein, the terms "ligand" and "modulator" are used equivalently to refer to a compound that modulates the activity of a target biomolecule, e.g., an enzyme such as a kinase or phosphodiesterase. Generally a ligand or modulator will be a small molecule, where "small molecule refers to a compound with a molecular weight of 1500 daltons or less, or preferably 1000 daltons or less, 800 daltons or less, or 600 daltons or less. Thus, an "improved ligand" is one that possesses better pharmacological and/or pharmacokinetic properties than a reference compound, where "better" can be defined by a person for a particular biological system or therapeutic use. In terms of the development of ligands from scaffolds, a ligand is a derivative of a scaffold.

In the context of binding compounds, molecular scaffolds, and ligands, the term "derivative" or "derivative compound" refers to a compound having a chemical structure that contains a common core chemical structure as a parent or reference compound, but differs by having at least one structural difference, e.g., by having one or more substituents added and/or removed and/or substituted, and/or by having one or more atoms substituted with different atoms. Unless clearly indicated to the contrary, the term "derivative" does not mean that the derivative is synthesized using the parent compound as a starting material or as an intermediate, although in some cases, the derivative may be synthesized from the parent.

Thus, the term "parent compound" refers to a reference compound for another compound, having structural features continued in the derivative compound. Often but not always, a parent compound has a simpler chemical structure than the derivative.

By "chemical structure" or "chemical substructure" is meant any definable atom or group of atoms that constitute a part of a molecule. Normally, chemical substructures of a scaffold or ligand can have a role in binding of the scaffold or ligand to a target molecule, or can influence the three-dimensional shape, electrostatic charge, and/or conformational properties of the scaffold or ligand.

The term "binds" in connection with the interaction between a target and a potential binding compound indicates that the potential binding compound associates with the target to a statistically significant degree as compared to association with proteins generally (i.e., non-specific binding). Thus, the term "binding compound" refers to a compound that has a statistically significant association with a target molecule. Preferably a binding compound interacts with a specified target with a dissociation constant ($k_d$) of 1 mM or less. A binding compound can bind with "low affinity", "very low affinity", "extremely low affinity", "moderate affinity", "moderately high affinity", or "high affinity" as described herein.

In the context of compounds binding to a target, the term "greater affinity" indicates that the compound binds more tightly than a reference compound, or than the same compound in a reference condition, i.e., with a lower dissociation constant. In particular embodiments, the greater affinity is at least 2, 3, 4, 5, 8, 10, 50, 100, 200, 400, 500, 1000, or 10,000-fold greater affinity.

Also in the context of compounds binding to a biomolecular target, the term "greater specificity" indicates that a compound binds to a specified target to a greater extent than to another biomolecule or biomolecules that may be present under relevant binding conditions, where binding to such other biomolecules produces a different biological activity than binding to the specified target. Typically, the specificity is with reference to a limited set of other biomolecules, e.g., in the case of PDE4B, other phosphodiesterases (e.g., PDE5A) or other PDE4 isoforms (e.g., PDE4D) or even other type of enzymes. In particular embodiments, the greater specificity is at least 2, 3, 4, 5, 8, 10, 50, 100, 200, 400, 500, or 1000-fold greater specificity.

As used in connection with binding of a compound with a target, the term "interact" indicates that the distance from a bound compound to a particular amino acid residue will be 5.0 angstroms or less. In particular embodiments, the distance from the compound to the particular amino acid residue is 4.5 angstroms or less, 4.0 angstroms or less, or 3.5 angstroms or less. Such distances can be determined, for example, using co-crystallography, or estimated using computer fitting of a compound in an active site.

Reference to particular amino acid residues in PDE4B polypeptide residue number is defined by the numbering corresponding to NCBI protein sequence accession number JC1519 (SEQ ID NO:1), as described, for example, in McLaughlin et al., *J. Biol. Chem.* 268 (9), 6470-6476 (1993); Obernolte et al., *Gene* 129 (2), 239-247 (1993); and Bolger et al., *Mol. Cell. Biol.* 13 (10), 6558-6571 (1993). As indicated above, alternate numbering from other matching PDE4B sequences can also be used.

By "molecular scaffold" or "scaffold" is meant a simple target binding molecule to which one or more additional chemical moieties can be covalently attached, modified, or eliminated to form a plurality of molecules with common structural elements. The moieties can include, but are not limited to, a halogen atom, a hydroxyl group, a methyl group, a nitro group, a carboxyl group, or any other type of molecular group including, but not limited to, those recited in this application. Molecular scaffolds bind to at least one target molecule, preferably to a plurality of molecules in a protein family, and the target molecule can preferably be a enzyme, receptor, or other protein. Preferred characteristics of a scaffold can include binding at a target molecule binding site such that one or more substituents on the scaffold are situated in binding pockets in the target molecule binding site; having chemically tractable structures that can be chemically modified, particularly by synthetic reactions, so that a combinatorial library can be easily constructed; having chemical positions where moieties can be attached that do not interfere with binding of the scaffold to a protein binding site, such that the scaffold or library members can be modified to form ligands, to achieve additional desirable characteristics, e.g., enabling the ligand to be actively transported into cells and/or to specific organs, or enabling the ligand to be attached to a chromatography column for additional analysis. Thus, a molecular scaffold is an identified target binding molecule prior to modification to improve binding affinity and/or specificity, or other pharmacalogic properties.

The term "scaffold core" refers to the core structure of a molecular scaffold onto which various substituents can be attached. Thus, for a number of scaffold molecules of a particular chemical class, the scaffold core is common to all the scaffold molecules. In many cases, the scaffold core will consist of or include one or more ring structures.

By "binding site" is meant an area of a target molecule to which a ligand can bind non-covalently. Binding sites embody particular shapes and often contain multiple binding pockets present within the binding site. The particular shapes are often conserved within a class of molecules, such as a molecular family. Binding sites within a class also can contain conserved structures such as, for example, chemical moieties, the presence of a binding pocket, and/or an electrostatic charge at the binding site or some portion of the binding site, all of which can influence the shape of the binding site.

By "binding pocket" is meant a specific volume within a binding site. A binding pocket can often be a particular shape, indentation, or cavity in the binding site. Binding pockets can contain particular chemical groups or structures that are important in the non-covalent binding of another molecule such as, for example, groups that contribute to ionic, hydrogen bonding, or van der Waals interactions between the molecules.

By "orientation", in reference to a binding compound bound to a target molecule is meant the spatial relationship of the binding compound (which can be defined by reference to at least some of its consitituent atoms) to the binding pocket and/or atoms of the target molecule at least partially defining the binding pocket.

In the context of target molecules in this invention, the term "crystal" refers to a regular assemblage of a target molecule of a type suitable for X-ray crystallography. That is, the assemblage produces an X-ray diffraction pattern when illuminated with a beam of X-rays. Thus, a crystal is distinguished from an aggolmeration or other complex of target molecule that does not give a diffraction pattern.

By "co-crystal" is meant a complex of the compound, molecular scaffold, or ligand bound non-covalently to the target molecule and present in a crystal form appropriate for analysis by X-ray or protein crystallography. In preferred embodiments the target molecule-ligand complex can be a protein-ligand complex.

The phrase "alter the binding affinity or binding specificity" refers to changing the binding constant of a first compound for another, or changing the level of binding of a first compound for a second compound as compared to the level of binding of the first compound for third compounds, respectively. For example, the binding specificity of a compound for a particular protein is increased if the relative level of binding to that particular protein is increased as compared to binding of the compound to unrelated proteins.

As used herein in connection with test compounds, binding compounds, and modulators (ligands), the term "synthesizing" and like terms means chemical synthesis from one or more precursor materials.

The phrase "chemical structure of the molecular scaffold is modified" means that a derivative molecule has a chemical structure that differs from that of the molecular scaffold but still contains common core chemical structural features. The phrase does not necessarily mean that the molecular scaffold is used as a precursor in the synthesis of the derivative.

By "assaying" is meant the creation of experimental conditions and the gathering of data regarding a particular result of the experimental conditions. For example, enzymes can be assayed based on their ability to act upon a detectable substrate. A compound or ligand can be assayed based on its ability to bind to a particular target molecule or molecules.

By a "set" of compounds is meant a collection of compounds. The compounds may or may not be structurally related.

As used herein, the term "modulating" or "modulate" refers to an effect of altering a biological activity, especially a biological activity associated with a particular biomolecule such as PDE4 or an isoform thereof, e.g., PDE4B. For example, an agonist or antagonist of a particular biomolecule modulates the activity of that biomolecule, e.g., an enzyme.

The term "PDE4 activity" refers to a biological activity of PDE4, particularly including phosphodiesterase activity.

Similar terms apply to the particular PDE4 isoforms, e.g., PDE4A, PDE4B, PDE4C, and PDE4D.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

I. General

The present invention provides compounds of Formula that are inhibitors of PDE4B, and methods for the use of PDE4B phosphodiesterase structures, structural information, and related compositions for developing improved compounds with those structures that modulate PDE4B phosphodiesterase activity.

A number of patent publications have concerned PDE4 inhibitors and their use. Most such publications have focused on PDE4D. For example, Marfat et al., U.S. Pat. No. 6,559,168 describes PDE4 inhibitors, especially PDE4D inhibitors, and cites additional patent publications that describe additional PDE4 inhibitors. Such additional publications include Marfat et al., WO 98/45268; Saccoomano et al., U.S. Pat. No. 4,861,891; Pon, U.S. Pat. No. 5,922,557; and Eggleston, WO 99/20625.

Ait Ikhlef et al., U.S. Patent Publ. 20030064374, application Ser. No. 10/983,754 describes compounds active on PDE4B and their use in treatment of neurotoxicity, including treatment in neurodegenerative diseases such as Alzheimers' disease, Parkinson's disease, multiple sclerosis, Huntington's chorea, and cerebral ischemia.

All of the cited references above are incorporated herein by reference in their entireties, including without limitation for the descriptions of inhibitors and their uses as well as for assays, syntheses, and for identification and preparation of the PDEs and derivatives.

Exemplary Diseases Associated with PDE4B.

Modulation of PDE4B has been correlated with treatment of a number of different diseases and conditions. A number of patent publications have described PDE4 inhibitors and their use. Most such publications have focused on PDE4D. For example, Marfat et al., U.S. Pat. No. 6,559,168 describes PDE4 inhibitors, especially PDE4D inhibitors, and cites additional patent publications that describe additional PDE4 inhibitors. Such additional publications include Marfat et al., WO 98/45268; Saccoomano et al., U.S. Pat. No. 4,861,891; Pon, U.S. Pat. No. 5,922,557; and Eggleston, WO 99/20625.

Ait Ikhlef et al., U.S. Patent Publ. 20030064374, application Ser. No. 10/983,754 describes compounds active on PDE4B and their use in treatment of neurotoxicity, including treatment in neurodegenerative diseases such as Alzheimers' disease, Parkinson's disease, multiple sclerosis, Huntington's chorea, and cerebral ischemia.

Thus, PDE4B modulators can be used for treatement or prophylaxis of such conditions correlated with PDE4 and in particular PDE4B. Additional conditions that can be treated include, without limitation, an acute or chronic pulmonary disease such as obstructive diseases (e.g. asthma, chronic obstructive pulmonary disease (COPD), cystic fibrosis), interstitial lung diseases (e.g. idiopathic pulmonary fibrosis, sarcoidosis), vascular lung diseases (e.g. pulmonary hypertension), bronchitis, allergic bronchitis, and emphysema. Additional diseases or conditions contemplated for treatment by embodiments of the present invention include for example, without limitation, CNS diseases such as Alzheimer's disease, Parkinson's disease and Huntington's chorea; inflammatory autoimmune diseases such as multiple sclerosis, rheumatoid arthritis and Crohn's disease as well as other inflammatory disorders, such as cerebral ischemia, inflammatory bowel disease, ulcerative colitis, and atopic dermatitis; bone disease, such as osteoporosis, osteopetrosis, and Paget's disease; cancers, such as diffuse large-cell B cell lymphoma, chronic lymphocytic leukemia, acute lymphoblastic leukemia; Severe Acute Respiratory Syndrome; and pre-term labor.

II. Crystalline PDE4B

Crystalline PDE4B includes native crystals, phosphodiesterase domain crystals, derivative crystals and co-crystals. The native crystals generally comprise substantially pure polypeptides corresponding to PDE4B in crystalline form. PDE4B phosphodiesterase domain crystals generally comprise substantially pure PDE4B phosphodiesterase domain in crystalline form. In connection with the development of inhibitors of PDE4B phosphodiesterase function, it is advantageous to use PDE4B phosphodiesterase domain respectively for structural determination, because use of the reduced sequence simplifies structure determination. To be useful for this purpose, the phosphodiesterase domain should be active and/or retain native-type binding, thus indicating that the phosphodiesterase domain takes on substantially normal 3D structure.

It is to be understood that the crystalline phosphodiesterases and phosphodiesterase domains of the invention are not limited to naturally occurring or native phosphodiesterase. Indeed, the crystals of the invention include crystals of mutants of native phosphodiesterases. Mutants of native phosphodiesterases are obtained by replacing at least one amino acid residue in a native phosphodiesterase with a different amino acid residue, or by adding or deleting amino acid residues within the native polypeptide or at the N- or C-terminus of the native polypeptide, and have substantially the same three-dimensional structure as the native phosphodiesterase from which the mutant is derived.

By having substantially the same three-dimensional structure is meant having a set of atomic structure coordinates that have a root-mean-square deviation of less than or equal to about 2 Å when superimposed with the atomic structure coordinates of the native phosphodiesterase from which the mutant is derived when at least about 50% to 100% of the Cα atoms of the native phosphodiesterase domain are included in the superposition.

Amino acid substitutions, deletions and additions which do not significantly interfere with the three-dimensional structure of the phosphodiesterase will depend, in part, on the region of the phosphodiesterase where the substitution, addition or deletion occurs. In highly variable regions of the molecule, non-conservative substitutions as well as conservative substitutions may be tolerated without significantly disrupting the three-dimensional, structure of the molecule. In highly conserved regions, or regions containing significant secondary structure, conservative amino acid substitutions are preferred. Such conserved and variable regions can be identified by sequence alignment of PDE4B with other phosphodiesterases.

Conservative amino acid substitutions are well known in the art, and include substitutions made on the basis of similarity in polarity, charge, solubility, hydrophobicity, hydrophilicity and/or the amphipathic nature of the amino acid residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine. Other conservative amino acid substitutions are well known in the art.

For phosphodiesterases obtained in whole or in part by chemical synthesis, the selection of amino acids available for substitution or addition is not limited to the genetically encoded amino acids. Indeed, the mutants described herein may contain non-genetically encoded amino acids. Conservative amino acid substitutions for many of the commonly known non-genetically encoded amino acids are well known in the art. Conservative substitutions for other amino acids can be determined based on their physical properties as compared to the properties of the genetically encoded amino acids.

In some instances, it may be particularly advantageous or convenient to substitute, delete and/or add amino acid residues to a native phosphodiesterase in order to provide convenient cloning sites in cDNA encoding the polypeptide, to aid in purification of the polypeptide, and for crystallization of the polypeptide. Such substitutions, deletions and/or additions which do not substantially alter the three dimensional structure of the native phosphodiesterase domain will be apparent to those of ordinary skill in the art.

It should be noted that the mutants contemplated herein need not all exhibit phosphodiesterase activity. Indeed, amino acid substitutions, additions or deletions that interfere with the phosphodiesterase activity but which do not significantly alter the three-dimensional structure of the domain are specifically contemplated by the invention. Such crystalline polypeptides, or the atomic structure coordinates obtained therefrom, can be used to identify compounds that bind to the native domain. These compounds can affect the activity of the native domain.

The derivative crystals of the invention can comprise a crystalline phosphodiesterase polypeptide in covalent association with one or more heavy metal atoms. The polypeptide may correspond to a native or a mutated phosphodiesterase. Heavy metal atoms useful for providing derivative crystals include, by way of example and not limitation, gold, mercury, selenium, etc.

The co-crystals of the invention generally comprise a crystalline phosphodiesterase domain polypeptide in association with one or more compounds. The association may be covalent or non-covalent. Such compounds include, but are not limited to, cofactors, substrates, substrate analogues, inhibitors, allosteric effectors, etc.

III. Three Dimensional Structure Determination Using X-Ray Crystallography

X-ray crystallography is a method of solving the three dimensional structures of molecules. The structure of a molecule is calculated from X-ray diffraction patterns using a crystal as a diffraction grating. Three dimensional structures of protein molecules arise from crystals grown from a concentrated aqueous solution of that protein. The process of X-ray crystallography can include the following steps:

(a) synthesizing and isolating (or otherwise obtaining) a polypeptide;
(b) growing a crystal from an aqueous solution comprising the polypeptide with or without a modulator; and
(c) collecting X-ray diffraction patterns from the crystals, determining unit cell dimensions and symmetry, determining electron density, fitting the amino acid sequence of the polypeptide to the electron density, and refining the structure.

Production of Polypeptides

The native and mutated phosphodiesterase polypeptides described herein may be chemically synthesized in whole or part using techniques that are well-known in the art (see, e.g., Creighton (1983) *Biopolymers* 22(1):49-58).

Alternatively, methods which are well known to those skilled in the art can be used to construct expression vectors containing the native or mutated phosphodiesterase polypeptide coding sequence and appropriate transcriptional/translational control signals. These methods include in vitro recombinant DNA techniques, synthetic techniques and in vivo recombination/genetic recombination. See, for example, the techniques described in Maniatis, T (1989). *Molecular cloning: A laboratory Manual*. Cold Spring Harbor Laboratory, New York. Cold Spring Harbor Laboratory Press; and Ausubel, F. M. et al. (1994) *Current Protocols in Molecular Biology*. John Wiley & Sons, Secaucus, N.J.

A variety of host-expression vector systems may be utilized to express the phosphodiesterase coding sequence. These include but are not limited to microorganisms such as bacteria transformed with recombinant bacteriophage DNA, plasmid DNA or cosmid DNA expression vectors containing the phosphodiesterase domain coding sequence; yeast transformed with recombinant yeast expression vectors containing the phosphodiesterase domain coding sequence; insect cell systems infected with recombinant virus expression vectors (e.g., baculovirus) containing the phosphodiesterase domain coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the phosphodiesterase domain coding sequence; or animal cell systems. The expression elements of these systems vary in their strength and specificities.

Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the $^{35}$S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the phosphodiesterase domain DNA, SV40-, BPV- and EBV-based vectors may be used with an appropriate selectable marker.

Exemplary methods describing methods of DNA manipulation, vectors, various types of cells used, methods of incorporating the vectors into the cells, expression techniques, protein purification and isolation methods, and protein concentration methods are disclosed in detail in PCT publication WO 96/18738. This publication is incorporated herein by reference in its entirety, including any drawings. Those skilled in the art will appreciate that such descriptions are applicable to the present invention and can be easily adapted to it.

Crystal Growth

Crystals are grown from an aqueous solution containing the purified and concentrated polypeptide by a variety of techniques. These techniques include batch, liquid, bridge, dialysis, vapor diffusion, and hanging drop methods. McPherson (1982) John Wiley, New York; McPherson (1990) *Eur. J. Biochem.* 189:1-23; Webber (1991) *Adv. Protein Chem.* 41:1-36, incorporated by reference herein in their entireties, including all figures, tables, and drawings.

The native crystals of the invention are, in general, grown by adding precipitants to the concentrated solution of the polypeptide. The precipitants are added at a concentration just below that necessary to precipitate the protein. Water is removed by controlled evaporation to produce precipitating conditions, which are maintained until crystal growth ceases.

For crystals of the invention, exemplary crystallization conditions are described in the Examples. Those of ordinary skill in the art will recognize that the exemplary crystallization conditions can be varied. Such variations may be used alone or in combination. In addition, other crystallization conditions may be found, e.g., by using crystallization screening plates to identify such other conditions. Those alternate conditions can then be optimized if needed to provide larger or better quality crystals.

Derivative crystals of the invention can be obtained by soaking native crystals in mother liquor containing salts of heavy metal atoms. It has been found that soaking a native crystal in a solution containing about 0.1 mM to about 5 mM thimerosal, 4-chloromeruribenzoic acid or $KAu(CN)_2$ for about 2 hr to about 72 hr provides derivative crystals suitable for use as isomorphous replacements in determining the X-ray crystal structure.

Co-crystals of the invention can be obtained by soaking a native crystal in mother liquor containing compound that binds the phosphodiesterase, or can be obtained by co-crystallizing the phosphodiesterase polypeptide in the presence of a binding compound.

Generally, co-crystallization of phosphodiesterase and binding compound can be accomplished using conditions identified for crystallizing the corresponding phosphodiesterase without binding compound. It is advantageous if a plurality of different crystallization conditions have been identified for the phosphodiesterase, and these can be tested to determine which condition gives the best co-crystals. It may also be benficial to optimize the conditions for co-crystallization. Alternatively, new crystallization conditions can be determined for obtaining co-crystals, e.g., by screening for crystallization and then optimizing those conditions. Exemplary co-crystallization conditions are provided in the Examples.

Determining Unit Cell Dimensions and the Three Dimensional Structure of a Polypeptide or Polypeptide Complex Once the crystal is grown, it can be placed in a glass capillary tube or other mounting device and mounted onto a holding device connected to an X-ray generator and an X-ray detection device. Collection of X-ray diffraction patterns are well documented by those in the art. See, e.g., Ducruix and Geige, (1992), IRL Press, Oxford, England, and references cited therein. A beam of X-rays enters the crystal and then diffracts from the crystal. An X-ray detection device can be utilized to record the diffraction patterns emanating from the crystal. Although the X-ray detection device on older models of these instruments is a piece of film, modern instruments digitally record X-ray diffraction scattering. X-ray sources can be of various types, but advantageously, a high intensity source is used, e.g., a synchrotron beam source.

Methods for obtaining the three dimensional structure of the crystalline form of a peptide molecule or molecule complex are well known in the art. See, e.g., Ducruix and Geige, (1992), IRL Press, Oxford, England, and references cited therein. The following are steps in the process of determining the three dimensional structure of a molecule or complex from X-ray diffraction data.

After the X-ray diffraction patterns are collected from the crystal, the unit cell dimensions and orientation in the crystal can be determined. They can be determined from the spacing between the diffraction emissions as well as the patterns made from these emissions. The unit cell dimensions are characterized in three dimensions in units of Angstroms (one $Å=10^{-10}$ meters) and by angles at each vertices. The symmetry of the unit cell in the crystals is also characterized at this stage. The symmetry of the unit cell in the crystal simplifies the complexity of the collected data by identifying repeating patterns. Application of the symmetry and dimensions of the unit cell is described below.

Each diffraction pattern emission is characterized as a vector and the data collected at this stage of the method determines the amplitude of each vector. The phases of the vectors can be determined using multiple techniques. In one method, heavy atoms can be soaked into a crystal, a method called isomorphous replacement, and the phases of the vectors can be determined by using these heavy atoms as reference points in the X-ray analysis. (Otwinowski, (1991), Daresbury, United Kingdom, 80-86). The isomorphous replacement method usually utilizes more than one heavy atom derivative.

In another method, the amplitudes and phases of vectors from a crystalline polypeptide with an already determined structure can be applied to the amplitudes of the vectors from a crystalline polypeptide of unknown structure and consequently determine the phases of these vectors. This second method is known as molecular replacement and the protein structure which is used as a reference must have a closely related structure to the protein of interest. (Naraza (1994) *Proteins* 11:281-296). Thus, the vector information from a phosphodiesterase of known structure, such as those reported herein, are useful for the molecular replacement analysis of another phosphodiesterase with unknown structure.

Once the phases of the vectors describing the unit cell of a crystal are determined, the vector amplitudes and phases, unit cell dimensions, and unit cell symmetry can be used as terms in a Fourier transform function. The Fourier transform function calculates the electron density in the unit cell from these measurements. The electron density that describes one of the molecules or one of the molecule complexes in the unit cell can be referred to as an electron density map. The amino acid structures of the sequence or the molecular structures of compounds complexed with the crystalline polypeptide may then be fitted to the electron density using a variety of computer programs. This step of the process is sometimes referred to as model building and can be accomplished by using computer programs such as Turbo/FRODO or "O". (Jones (1985) *Methods in Enzymology* 115:157-171).

A theoretical electron density map can then be calculated from the amino acid structures fit to the experimentally determined electron density. The theoretical and experimental electron density maps can be compared to one another and the agreement between these two maps can be described by a parameter called an R-factor. A low value for an R-factor describes a high degree of overlapping electron density between a theoretical and experimental electron density map.

The R-factor is then minimized by using computer programs that refine the theoretical electron density map. A computer program such as X-PLOR can be used for model refinement by those skilled in the art. (Brunger (1992) *Nature* 355:472-475.) Refinement may be achieved in an iterative process. A first step can entail altering the conformation of atoms defined in an electron density map. The conformations of the atoms can be altered by simulating a rise in temperature, which will increase the vibrational frequency of the bonds and modify positions of atoms in the structure. At a particular point in the atomic perturbation process, a force field, which typically defines interactions between atoms in terms of allowed bond angles and bond lengths, Van der Waals interactions, hydrogen bonds, ionic interactions, and hydrophobic interactions, can be applied to the system of atoms. Favorable interactions may be described in terms of free energy and the atoms can be moved over many iterations until a free energy minimum is achieved. The refinement process can be iterated until the R-factor reaches a minimum value.

The three dimensional structure of the molecule or molecule complex is described by atoms that fit the theoretical electron density characterized by a minimum R-value. A file can then be created for the three dimensional structure that defines each atom by coordinates in three dimensions. An example of such a structural coordinate file is shown in Table 1.

IV. Structures of PDE4B

High-resolution three-dimensional structures and atomic structure coordinates of crystalline PDE4B phosphodiesterase domain and PDE4B phosphodiesterase domain co-complexed with exemplary binding compounds are described. The methods used to obtain the structure coordinates are provided in the examples. The atomic structure coordinates of crystalline PDE4B phosphodiesterase domain are listed in Table 1. Co-crystal coordinates can be used in the same way, e.g., in the various aspects described herein, as coordinates for the protein by itself, but can be advantageous because such co-crystals demonstrate or confirm the binding mode of binding compound, and can also include shifts of protein atoms in response to the presence of the binding compound.

Those having skill in the art will recognize that atomic structure coordinates as determined by X-ray crystallography are not without error. Thus, it is to be understood that generally any set of structure coordinates obtained for crystals of PDE, whether native crystals, phosphodiesterase domain crystals, derivative crystals or co-crystals, that have a root mean square deviation ("r.m.s.d.") of less than or equal to about 1.5 Å when superimposed, using backbone atoms (N, $C_\alpha$, C and O), on the structure coordinates listed in a coordinate table herein are considered to be identical with the structure coordinates listed in that table when at least about 50% to 100% of the backbone atoms of the crystallized protein are included in the superposition.

V. Uses of the Crystals and Atomic Structure Coordinates

The crystals of the invention, and particularly the atomic structure coordinates obtained therefrom, have a wide variety of uses. For example, the crystals described herein can be used as a starting point in any of the methods of use for phosphodiesterases known in the art or later developed. Such methods of use include, for example, identifying molecules that bind to the native or mutated catalytic domain of phosphodiesterases. The crystals and structure coordinates are particularly useful for identifying ligands that modulate phosphodiesterase activity as an approach towards developing new therapeutic agents. In particular, the crystals and structural information are useful in methods for ligand development utilizing molecular scaffolds.

The structure coordinates described herein can be used as phasing models for determining the crystal structures of additional phosphodiesterases, as well as the structures of co-crystals of such phosphodiesterases with ligands such as inhibitors, agonists, antagonists, and other molecules. The structure coordinates, as well as models of the three-dimensional structures obtained therefrom, can also be used to aid the elucidation of solution-based structures of native or mutated phosphodiesterases, such as those obtained via NMR.

VI. Electronic Representations of Phosphodiesterase Structures

Structural information of phosphodiesterases or portions of phosphodiesterases (e.g., phosphodiesterase active sites) can be represented in many different ways. Particularly useful are electronic representations, as such representations allow rapid and convenient data manipulations and structural modifications. Electronic representations can be embedded in many different storage or memory media, frequently computer readable media. Examples include without limitations, computer random access memory (RAM), floppy disk, magnetic hard drive, magnetic tape (analog or digital), compact disk (CD), optical disk, CD-ROM, memory card, digital video disk (DVD), and others. The storage medium can be separate or part of a computer system. Such a computer system may be a dedicated, special purpose, or embedded system, such as a computer system that forms part of an X-ray crystallography system, or may be a general purpose computer (which may have data connection with other equipment such as a sensor device in an X-ray crystallographic system. In many cases, the information provided by such electronic representations can also be represented physically or visually in two or three dimensions, e.g., on paper, as a visual display (e.g., on a computer monitor as a two dimensional or pseudo-three dimensional image) or as a three dimensional physical model. Such physical representations can also be used, alone or in connection with electronic representations. Exemplary useful representations include, but are not limited to, the following:

Atomic Coordinate Representation

One type of representation is a list or table of atomic coordinates representing positions of particular atoms in a molecular structure, portions of a structure, or complex (e.g., a co-crystal). Such a representation may also include additional information, for example, information about occupancy of particular coordinates. One such atomic coordinate representation contains the coordinate information of Table 1 in electronic form.

Energy Surface or Surface of Interaction Representation

Another representation is an energy surface representation, e.g., of an active site or other binding site, representing an energy surface for electronic and steric interactions. Such a representation may also include other features. An example is the inclusion of representation of a particular amino acid residue(s) or group(s) on a particular amino acid residue(s), e.g., a residue or group that can participate in H-bonding or ionic interaction. Such energy surface representations can be readily generated from atomic coordinate representations using any of a variety of available computer programs.

Structural Representation

Still another representation is a structural representation, i.e., a physical representation or an electronic representation of such a physical representation. Such a structural representation includes representations of relative positions of particular features of a molecule or complex, often with linkage between structural features. For example, a structure can be represented in which all atoms are linked; atoms other than hydrogen are linked; backbone atoms, with or without representation of sidechain atoms that could participate in significant electronic interaction, are linked; among others. However, not all features need to be linked. For example, for structural representations of portions of a molecule or complex, structural features significant for that feature may be represented (e.g., atoms of amino acid residues that can have significant binding interation with a ligand at a binding site. Those amino acid residues may not be linked with each other.

Figure 2:
FIG. 2 shows an overlay of ribbon diagram schematic representations of the present PDE4B structure and the previously reported PDE4B crystal structure, and shows significant structure differences.

A structural representation can also be a schematic representation. For example, a schematic representation can represent secondary and/or tertiary structure in a schematic manner. Within such a schematic representation of a polypeptide, a particular amino acid residue(s) or group(s) on a residue(s) can be included, e.g., conserved residues in a binding site, and/or residue(s) or group(s) that may interact with binding compounds. Electronic structural representations can be generated, for example, from atomic coordinate information using computer programs designed for that function and/or by constructing an electronic representation with manual input based on interpretation of another form of structural information. Physical representations can be created, for example, by printing an image of a computer-generated image or by constructing a 3D model. An example of such a printed representation is the ribbon diagram presented in FIG. 2.

VII. Structure Determination for Phosphodiesterases with Unknown Structure Using Structural Coordinates Structural coordinates, such as those set forth in Table 1, can be used to determine the three dimensional structures of phosphodiesterases with unknown structure. The methods described below can apply structural coordinates of a polypeptide with known structure to another data set, such as an amino acid sequence, X-ray crystallographic diffraction data, or nuclear magnetic resonance (NMR) data. Preferred embodiments of the invention relate to determining the three dimensional structures of modified phosphodiesterases, other native phosphodiesterases, and related polypeptides.

Structures Using Amino Acid Homology

Homology modeling is a method of applying structural coordinates of a polypeptide of known structure to the amino acid sequence of a polypeptide of unknown structure. This method is accomplished using a computer representation of the three dimensional structure of a polypeptide or polypeptide complex, the computer representation of amino acid sequences of the polypeptides with known and unknown structures, and standard computer representations of the structures of amino acids. Homology modeling generally involves (a) aligning the amino acid sequences of the polypeptides with and without known structure; (b) transferring the coordinates of the conserved amino acids in the known structure to the corresponding amino acids of the polypeptide of unknown structure; refining the subsequent three dimensional structure; and (d) constructing structures of the rest of the polypeptide. One skilled in the art recognizes that conserved amino acids between two proteins can be determined from the sequence alignment step in step (a).

The above method is well known to those skilled in the art. (Greer (1985) *Science* 228:1055; Blundell et al. *A*(1988) *Eur. J. Biochem.* 172:513. An exemplary computer program that can be utilized for homology modeling by those skilled in the art is the Homology module in the Insight II modeling package distributed by Accelerys Inc.

Alignment of the amino acid sequence is accomplished by first placing the computer representation of the amino acid sequence of a polypeptide with known structure above the amino acid sequence of the polypeptide of unknown structure. Amino acids in the sequences are then compared and groups of amino acids that are homologous (e.g., amino acid side chains that are similar in chemical nature—aliphatic, aromatic, polar, or charged) are grouped together. This method will detect conserved regions of the polypeptides and account for amino acid insertions or deletions. Such alignment and/or can also be performed fully computationally using sequence alignment and analysis software.

Once the amino acid sequences of the polypeptides with known and unknown structures are aligned, the structures of the conserved amino acids in the computer representation of the polypeptide with known structure are transferred to the corresponding amino acids of the polypeptide whose structure is unknown. For example, a tyrosine in the amino acid sequence of known structure may be replaced by a phenylalanine, the corresponding homologous amino acid in the amino acid sequence of unknown structure.

The structures of amino acids located in non-conserved regions are to be assigned manually by either using standard peptide geometries or molecular simulation techniques, such as molecular dynamics. The final step in the process is accomplished by refining the entire structure using molecular dynamics and/or energy minimization. The homology modeling method is well known to those skilled in the art and has been practiced using different protein molecules. For example, the three dimensional structure of the polypeptide corresponding to the catalytic domain of a serine/threonine protein kinase, myosin light chain protein kinase, was homology modeled from the cAMP-dependent protein kinase catalytic subunit. (Knighton et al. (1992) *Science* 258:130-135.)

Structures Using Molecular Replacement

Molecular replacement is a method of applying the X-ray diffraction data of a polypeptide of known structure to the X-ray diffraction data of a polypeptide of unknown sequence. This method can be utilized to define the phases describing the X-ray diffraction data of a polypeptide of unknown structure when only the amplitudes are known. X-PLOR is a commonly utilized computer software package used for molecular replacement. Brünger (1992) *Nature* 355:472-475. AMORE is another program used for molecular replacement. Navaza (1994) *Acta Crystallogr. A*50: 157-163. Preferably, the resulting structure does not exhibit a root-mean-square deviation of more than 3 Å.

A goal of molecular replacement is to align the positions of atoms in the unit cell by matching electron diffraction data from two crystals. A program such as X-PLOR can involve four steps. A first step can be to determine the number of molecules in the unit cell and define the angles between them. A second step can involve rotating the diffraction data to define the orientation of the molecules in the unit cell. A third step can be to translate the electron density in three dimensions to correctly position the molecules in the unit cell. Once the amplitudes and phases of the X-ray diffraction data is determined, an R-factor can be calculated by comparing electron diffraction maps calculated experimentally from the reference data set and calculated from the new data set. An R-factor between 30-50% indicates that the orientations of the atoms in the unit cell are reasonably determined by this method. A fourth step in the process can be to decrease the R-factor to roughly 20% by refining the new electron density map using iterative refinement techniques described herein and known to those or ordinary skill in the art.

Structures Using NMR Data

Structural coordinates of a polypeptide or polypeptide complex derived from X-ray crystallographic techniques can be applied towards the elucidation of three dimensional structures of polypeptides from nuclear magnetic resonance (NMR) data. This method is used by those skilled in the art. (Wuthrich, (1986), John Wiley and Sons, New York:176-199; Pflugrath et al. (1986) *J. Mol. Biol.* 189:383-386; Kline et al. (1986) *J. Mol. Biol.* 189:377-382.) While the secondary structure of a polypeptide is often readily determined by utilizing two-dimensional NMR data, the spatial connections between individual pieces of secondary structure are not as readily determinable. The coordinates defining a three-dimensional structure of a polypeptide derived from X-ray crystallographic techniques can guide the NMR spectroscopist to an understanding of these spatial interactions between secondary structural elements in a polypeptide of related structure.

The knowledge of spatial interactions between secondary structural elements can greatly simplify Nuclear Overhauser Effect (NOE) data from two-dimensional NMR experiments. Additionally, applying the crystallographic coordinates after the determination of secondary structure by NMR techniques only simplifies the assignment of NOEs relating to particular amino acids in the polypeptide sequence and does not greatly bias the NMR analysis of polypeptide structure. Conversely, using the crystallographic coordinates to simplify NOE data while determining secondary structure of the polypeptide would bias the NMR analysis of protein structure.

VIII. Structure-Based Design of Modulators of Phosphodiesterase Function Utilizing Structural Coordinates Structure-based modulator design and identification methods are powerful techniques that can involve searches of computer databases containing a wide variety of potential modulators and chemical functional groups. The computerized design and identification of modulators is useful as the computer databases contain more compounds than the chemical libraries, often by an order of magnitude. For reviews of structure-based drug design and identification (see Kuntz et al. (1994), *Acc. Chem. Res.* 27:117; Guida (1994) *Current Opinion in Struc. Biol.* 4: 777; Colman (1994) *Current Opinion in Struc. Biol.* 4: 868).

The three dimensional structure of a polypeptide defined by structural coordinates can be utilized by these design methods, for example, the structural coordinates of Table 1. In addition, the three dimensional structures of phosphodiesterases determined by the homology, molecular replacement, and NMR techniques described herein can also be applied to modulator design and identification methods.

For identifying modulators, structural information for a native phosphodiesterase, in particular, structural information for the active site of the phosphodiesterase, can be used. However, it may be advantageous to utilize structural information from one or more co-crystals of the phosphodiesterase with one or more binding compounds. It can also be advantageous if the binding compound has a structural core in common with test compounds.

Design by Searching Molecular Data Bases

One method of rational design searches for modulators by docking the computer representations of compounds from a database of molecules. Publicly available databases include, for example:

a) ACD from Molecular Designs Limited
b) NCI from National Cancer Institute
c) CCDC from Cambridge Crystallographic Data Center
d) CAST from Chemical Abstract Service
e) Derwent from Derwent Information Limited
f) Maybridge from Maybridge Chemical Company LTD
g) Aldrich from Aldrich Chemical Company
h) Directory of Natural Products from Chapman & Hall One such data base (ACD distributed by Molecular Designs Limited Information Systems) contains compounds that are synthetically derived or are natural products. Methods available to those skilled in the art can convert a data set represented in two dimensions to one represented in three dimensions. These methods are enabled by such computer programs as CONCORD from Tripos Associates or DE-Converter from Molecular Simulations Limited.

Multiple methods of structure-based modulator design are known to those in the art. (Kuntz et al., (1982), *J. Mol. Biol.* 162: 269; Kuntz et aZ., (1994), *Acc. Chern. Res.* 27:117; Meng et al., (1992), *J. Compt. Chem.* 13:505; Bohm, (1994), *J. Comp. Aided Molec. Design* 8: 623.)

A computer program widely utilized by those skilled in the art of rational modulator design is DOCK from the University of California in San Francisco. The general methods utilized by this computer program and programs like it are described in three applications below. More detailed information regarding some of these techniques can be found in the Accelerys User Guide, 1995. A typical computer program used for this purpose can perform a processes comprising the following steps or functions:

(a) remove the existing compound from the protein;
(b) dock the structure of another compound into the active-site using the computer program (such as DOCK) or by interactively moving the compound into the active-site;
(c) characterize the space between the compound and the active-site atoms;
(d) search libraries for molecular fragments which (i) can fit into the empty space between the compound and the active-site, and (ii) can be linked to the compound; and
(e) link the fragments found above to the compound and evaluate the new modified compound.

Part (c) refers to characterizing the geometry and the complementary interactions formed between the atoms of the active site and the compounds. A favorable geometric fit is attained when a significant surface area is shared between the compound and active-site atoms without forming unfavorable steric interactions. One skilled in the art would note that the method can be performed by skipping parts (d) and (e) and screening a database of many compounds.

Structure-based design and identification of modulators of phosphodiesterase function can be used in conjunction with assay screening. As large computer databases of compounds (around 10,000 compounds) can be searched in a matter of hours or even less, the computer-based method can narrow the compounds tested as potential modulators of phosphodiesterase function in biochemical or cellular assays.

The above descriptions of structure-based modulator design are not all encompassing and other methods are reported in the literature and can be used, e.g.:

(1) CAVEAT: Bartlett et al., (1989), in Chemical and Biological Problems in Molecular Recognition, Roberts, S. M.; Ley, S. V.; Campbell, M. M. eds.; *Royal Society of Chemistry*: Cambridge, pp. 182-196.
(2) FLOG: Miller et al., (1994), *J. Comp. Aided Molec. Design* 8:153.
(3) PRO Modulator: Clark et al., (1995), *J. Comp. Aided Molec. Design* 9:13.
(4) MCSS: Miranker and Karplus, (1991), *Proteins: Structure, Function, and Genetics* 11:29.
(5) AUTODOCK: Goodsell and Olson, (1990), *Proteins: Structure, Function, and Genetics* 8:195.
(6) GRID: Goodford, (1985), *J. Med. Chem.* 28:849.

Design by Modifying Compounds in Complex with PDE4B

Another way of identifying compounds as potential modulators is to modify an existing modulator in the polypeptide active site. For example, the computer representation of modulators can be modified within the computer representation of a PDE4B active site. Detailed instructions for this technique can be found, for example, in the Accelerys User Manual, 1995 in LUDI. The computer representation of the modulator is typically modified by the deletion of a chemical group or groups or by the addition of a chemical group or groups.

Upon each modification to the compound, the atoms of the modified compound and active site can be shifted in conformation and the distance between the modulator and the active-site atoms may be scored along with any complementary interactions formed between the two molecules. Scoring can be complete when a favorable geometric fit and favorable complementary interactions are attained. Compounds that have favorable scores are potential modulators.

Design by Modifying the Structure of Compounds that Bind PDE4B

A third method of structure-based modulator design is to screen compounds designed by a modulator building or modulator searching computer program. Examples of these types of programs can be found in the Molecular Simulations Package, Catalyst. Descriptions for using this program are documented in the Molecular Simulations User Guide (1995). Other computer programs used in this application are ISIS/HOST, ISIS/BASE, ISIS/DRAW) from Molecular Designs Limited and UNITY from Tripos Associates.

These programs can be operated on the structure of a compound that has been removed from the active site of the three dimensional structure of a compound-phosphodiesterase complex. Operating the program on such a compound is preferable since it is in a biologically active conformation.

A modulator construction computer program is a computer program that may be used to replace computer representations of chemical groups in a compound complexed with a phosphodiesterase or other biomolecule with groups from a computer database. A modulator searching computer program is a computer program that may be used to search computer representations of compounds from a computer data base that have similar three dimensional structures and similar chemical groups as compound bound to a particular biomolecule.

A typical program can operate by using the following general steps:
  (a) map the compounds by chemical features such as by hydrogen bond donors or acceptors, hydrophobic/lipophilic sites, positively ionizable sites, or negatively ionizable sites;
  (b) add geometric constraints to the mapped features; and
  (c) search databases with the model generated in (b).

Those skilled in the art also recognize that not all of the possible chemical features of the compound need be present in the model of (b). One can use any subset of the model to generate different models for data base searches.

Modulator Design Using Molecular Scaffolds

The present invention can also advantageously utilize methods for designing compounds, designated as molecular scaffolds, that can act broadly across families of molecules and/or for using a molecular scaffold to design ligands that target individual or multiple members of those families. Such design using molecular scaffolds is described in Hirth and Milburn, U.S. patent application Ser. No. 10/377,268, which is incorporated herein by reference in its entirety. Such design and development using molecular scaffolds is described, in part, below.

In preferred embodiments, the molecules can be proteins and a set of chemical compounds can be assembled that have properties such that they are 1) chemically designed to act on certain protein families and/or 2) behave more like molecular scaffolds, meaning that they have chemical substructures that make them specific for binding to one or more proteins in a family of interest. Alternatively, molecular scaffolds can be designed that are preferentially active on an individual target molecule.

Useful chemical properties of molecular scaffolds can include one or more of the following characteristics, but are not limited thereto: an average molecular weight below about 350 daltons, or between from about 150 to about 350 daltons, or from about 150 to about 300 daltons; having a clogP below 3; a number of rotatable bonds of less than 4; a number of hydrogen bond donors and acceptors below 5 or below 4; a polar surface area of less than 50 Å$^2$; binding at protein binding sites in an orientation so that chemical substituents from a combinatorial library that are attached to the scaffold can be projected into pockets in the protein binding site; and possessing chemically tractable structures at its substituent attachment points that can be modified, thereby enabling rapid library construction.

By "clog P" is meant the calculated log P of a compound, "P" referring to the partition coefficient between octanol and water.

The term "Molecular Polar Surface Area (PSA)" refers to the sum of surface contributions of polar atoms (usually oxygens, nitrogens and attached hydrogens) in a molecule. The polar surface area has been shown to correlate well with drug transport properties, such as intestinal absorption, or blood-brain barrier penetration.

Additional useful chemical properties of distinct compounds for inclusion in a combinatorial library include the ability to attach chemical moieties to the compound that will not interfere with binding of the compound to at least one protein of interest, and that will impart desirable properties to the library members, for example, causing the library members to be actively transported to cells and/or organs of interest, or the ability to attach to a device such as a chromatography column (e.g., a streptavidin column through a molecule such as biotin) for uses such as tissue and proteomics profiling purposes.

A person of ordinary skill in the art will realize other properties that can be desirable for the scaffold or library members to have depending on the particular requirements of the use, and that compounds with these properties can also be sought and identified in like manner. Methods of selecting compounds for assay are known to those of ordinary skill in the art, for example, methods and compounds described in U.S. Pat. Nos. 6,288,234, 6,090,912, 5,840,485, each of which is hereby incorporated by reference in its entirety, including all charts and drawings.

In various embodiments, the present invention provides methods of designing ligands that bind to a plurality of members of a molecular family, where the ligands contain a common molecular scaffold. Thus, a compound set can be assayed for binding to a plurality of members of a molecular family, e.g., a protein family. One or more compounds that bind to a plurality of family members can be identified as molecular scaffolds. When the orientation of the scaffold at the binding site of the target molecules has been determined and chemically tractable structures have been identified, a set of ligands can be synthesized starting with one or a few molecular scaffolds to arrive at a plurality of ligands, wherein each ligand binds to a separate target molecule of the molecular family with altered or changed binding affinity or binding specificity relative to the scaffold. Thus, a plurality of drug lead molecules can be designed to preferentially target individual members of a molecular family based on the same molecular scaffold, and act on them in a specific manner.

IX. Binding Assays

The methods of the present invention can involve assays that are able to detect the binding of compounds to a target molecule. Such binding is at a statistically significant level, preferably with a confidence level of at least 90%, more preferably at least 95, 97, 98, 99% or greater confidence level that the assay signal represents binding to the target molecule, i.e., is distinguished from background. Preferably controls are used to distinguish target binding from non-specific binding. The assays of the present invention can also include assaying compounds for low affinity binding to the target molecule. A large variety of assays indicative of binding are known for different target types and can be used for this invention. Compounds that act broadly across protein families are not likely to have a high affinity against individual targets, due to the broad nature of their binding. Thus, assays described herein allow for the identification of compounds that bind with low affinity, very low affinity, and extremely low affinity. Therefore, potency (or binding affinity) is not the primary, nor even the most important, indicia of identification of a potentially useful binding compound. Rather, even those compounds that bind with low affinity, very low affinity, or extremely low affinity can be considered as molecular scaffolds that can continue to the next phase of the ligand design process.

By binding with "low affinity" is meant binding to the target molecule with a dissociation constant ($k_d$) of greater than 1 µM under standard conditions. By binding with "very low affinity" is meant binding with a $k_d$ of above about 100 µM under standard conditions. By binding with "extremely low affinity" is meant binding at a $k_d$ of above about 1 mM under standard conditions. By "moderate affinity" is meant binding with a $k_d$ of from about 200 nM to about 1 µM under standard conditions. By "moderately high affinity" is meant binding at a $k_d$ of from about 1 nM to about 200 nM. By binding at "high affinity" is meant binding at a $k_d$ of below about 1 nM under standard conditions. For example, low affinity binding can occur because of a poorer fit into the binding site of the target molecule or because of a smaller number of non-covalent bonds, or weaker covalent bonds present to cause binding of the scaffold or ligand to the binding site of the target molecule relative to instances where higher affinity binding occurs. The standard conditions for binding are at pH 7.2 at 37° C. for one hour. For example, 100 µl/well can be used in HEPES 50 mM buffer at pH 7.2, NaCl 15 mM, ATP 2 µM, and bovine serum albumin 1 ug/well, 37° C. for one hour.

Binding compounds can also be characterized by their effect on the activity of the target molecule. Thus, a "low activity" compound has an inhibitory concentration ($IC_{50}$) or excitation concentration ($EC_{50}$) of greater than 1 µM under standard conditions. By "very low activity" is meant an $IC_{50}$ or $EC_{50}$ of above 100 µM under standard conditions. By "extremely low activity" is meant an $IC_{50}$ or $EC_{50}$ of above 1 mM under standard conditions. By "moderate activity" is meant an $IC_{50}$ or $EC_{50}$ of 200 nM to 1 µM under standard conditions. By "moderately high activity" is meant an $IC_{50}$ or $EC_{50}$ of 1 nM to 200 nM. By "high activity" is meant an $IC_{50}$ or $EC_{50}$ of below 1 nM under standard conditions. The $IC_{50}$ (or $EC_{50}$) is defined as the concentration of compound at which 50% of the activity of the target molecule (e.g., enzyme or other protein) activity being measured is lost (or gained) relative to activity when no compound is present. Activity can be measured using methods known to those of ordinary skill in the art, e.g., by measuring any detectable product or signal produced by occurrence of an enzymatic reaction, or other activity by a protein being measured.

By "background signal" in reference to a binding assay is meant the signal that is recorded under standard conditions for the particular assay in the absence of a test compound, molecular scaffold, or ligand that binds to the target molecule. Persons of ordinary skill in the art will realize that accepted methods exist and are widely available for determining background signal.

By "standard deviation" is meant the square root of the variance. The variance is a measure of how spread out a distribution is. It is computed as the average squared deviation of each number from its mean. For example, for the numbers 1, 2, and 3, the mean is 2 and the variance is:

$$\sigma^2 = \frac{(1-2)^2 + (2-2)^2 + (3-2)^2}{3} = 0.667$$

To design or discover scaffolds that act broadly across protein families, proteins of interest can be assayed against a compound collection or set. The assays can preferably be enzymatic or binding assays. In some embodiments it may be desirable to enhance the solubility of the compounds being screened and then analyze all compounds that show activity in the assay, including those that bind with low affinity or produce a signal with greater than about three times the standard deviation of the background signal. The assays can be any suitable assay such as, for example, binding assays that measure the binding affinity between two binding partners. Various types of screening assays that can be useful in the practice of the present invention are known in the art, such as those described in U.S. Pat. Nos. 5,763,198, 5,747,276, 5,877,007, 6,243,980, 6,294,330, and 6,294,330, each of which is hereby incorporated by reference in its entirety, including all charts and drawings.

In various embodiments of the assays at least one compound, at least about 5%, at least about 10%, at least about 15%, at least about 20%, or at least about 25% of the compounds can bind with low affinity. In general, up to about 20% of the compounds can show activity in the screening assay and these compounds can then be analyzed directly with high-throughput co-crystallography, computational analysis to group the compounds into classes with common structural properties (e.g., structural core and/or shape and polarity characteristics), and the identification of common chemical structures between compounds that show activity.

The person of ordinary skill in the art will realize that decisions can be based on criteria that are appropriate for the needs of the particular situation, and that the decisions can be made by computer software programs. Classes can be created containing almost any number of scaffolds, and the criteria selected can be based on increasingly exacting criteria until an arbitrary number of scaffolds is arrived at for each class that is deemed to be advantageous.

Surface Plasmon Resonance

Binding parameters can be measured using surface plasmon resonance, for example, with a BIAcore® chip (Biacore, Japan) coated with immobilized binding components. Surface plasmon resonance is used to characterize the microscopic association and dissociation constants of reaction between an sFv or other ligand directed against target molecules. Such methods are generally described in the following references which are incorporated herein by reference. Vely F. et al., (2000) BIAcore® analysis to test phosphopeptide-SH2 domain interactions, *Methods in Molecular Biology.* 121: 313-21; Liparoto et al., (1999) Biosensor analysis of the interleukin-2 receptor complex, *Journal of Molecular Recognition.* 12:316-21; Lipschultz et al., (2000) Experimental design for analysis of complex kinetics using surface plasmon resonance, *Methods.* 20(3):310-8; Malmqvist., (1999) BIACORE: an affinity biosensor system for characterization of biomolecular interactions, Biochemical Society Transactions 27:335-40; Alfthan, (1998) Surface plasmon resonance biosensors as a tool in antibody engineering, *Biosensors & Bioelectronics.* 13:653-63; Fivash et al., (1998) BIAcore for macromolecular interaction, Current Opinion in Biotechnology. 9:97-101; Price et al.; (1998) Summary report on the ISOBM TD-4 Workshop: analysis of 56 monoclonal antibodies against the MUC1 mucin. *Tumour Biology* 19 Suppl 1:1-20; Malmqvist et al, (1997) Biomolecular interaction analysis: affinity biosensor technologies for functional analysis of proteins, *Current Opinion in Chemical Biology.* 1:378-83; O'Shannessy et al., (1996) Interpretation of deviations from pseudo-first-order kinetic behavior in the characterization of ligand binding by biosensor technology, *Analytical Biochemistry.* 236:275-83; Malmborg et al., (1995) BIAcore as a tool in antibody engineering, *Journal of Immunological Methods.* 183:7-13; Van Regenmortel, (1994) Use of biosensors to characterize recombinant proteins, *Developments in Biological Standardization.* 83:143-51; and O'Shannessy, (1994) Determination of kinetic rate and equilibrium binding constants for macromolecular interactions: a critique of the surface plasmon resonance literature, *Current Opinions in Biotechnology.* 5:65-71.

BIAcore® uses the optical properties of surface plasmon resonance (SPR) to detect alterations in protein concentration bound to a dextran matrix lying on the surface of a gold/glass sensor chip interface, a dextran biosensor matrix. In brief, proteins are covalently bound to the dextran matrix at a known concentration and a ligand for the protein is injected through the dextran matrix. Near infrared light, directed onto the opposite side of the sensor chip surface is reflected and also induces an evanescent wave in the gold film, which in turn, causes an intensity dip in the reflected light at a particular angle known as the resonance angle. If the refractive index of the sensor chip surface is altered (e.g., by ligand binding to the bound protein) a shift occurs in the resonance angle. This angle shift can be measured and is expressed as resonance units (RUs) such that 1000 RUs is equivalent to a change in surface protein concentration of 1 ng/mm$^2$. These changes are displayed with respect to time along the y-axis of a sensorgram, which depicts the association and dissociation of any biological reaction.

High Throughput Screening (HTS) Assays

HTS typically uses automated assays to search through large numbers of compounds for a desired activity. Typically HTS assays are used to find new drugs by screening for chemicals that act on a particular enzyme or molecule. For example, if a chemical inactivates an enzyme it might prove to be effective in preventing a process in a cell which causes a disease. High throughput methods enable researchers to assay thousands of different chemicals against each target molecule very quickly using robotic handling systems and automated analysis of results.

As used herein, "high throughput screening" or "HTS" refers to the rapid in vitro screening of large numbers of compounds (libraries); generally tens to hundreds of thousands of compounds, using robotic screening assays. Ultra high-throughput Screening (uHTS) generally refers to the high-throughput screening accelerated to greater than 100,000 tests per day.

To achieve high-throughput screening, it is advantageous to house samples on a multicontainer carrier or platform. A multicontainer carrier facilitates measuring reactions of a plurality of candidate compounds simultaneously. Multi-well microplates may be used as the carrier. Such multi-well microplates, and methods for their use in numerous assays, are both known in the art and commercially available.

Screening assays may include controls for purposes of calibration and confirmation of proper manipulation of the components of the assay. Blank wells that contain all of the reactants but no member of the chemical library are usually included. As another example, a known inhibitor (or activator) of an enzyme for which modulators are sought, can be incubated with one sample of the assay, and the resulting decrease (or increase) in the enzyme activity used as a comparator or control. It will be appreciated that modulators can also be combined with the enzyme activators or inhibitors to find modulators which inhibit the enzyme activation or repression that is otherwise caused by the presence of the known the enzyme modulator. Similarly, when ligands to a sphingolipid target are sought, known ligands of the target can be present in control/calibration assay wells.

Measuring Enzymatic and Binding Reactions During Screening Assays

Techniques for measuring the progression of enzymatic and binding reactions, e.g., in multicontainer carriers, are known in the art and include, but are not limited to, the following.

Spectrophotometric and spectrofluorometric assays are well known in the art. Examples of such assays include the use of colorimetric assays for the detection of peroxides, as described in Gordon, A. J. and Ford, R. A., (1972) *The Chemist's Companion: A Handbook Of Practical Data, Techniques, And References*, John Wiley and Sons, N.Y., Page 437.

Fluorescence spectrometry may be used to monitor the generation of reaction products. Fluorescence methodology is generally more sensitive than the absorption methodology. The use of fluorescent probes is well known to those skilled in the art. For reviews, see Bashford et al., (1987) *Spectrophotometry and Spectrofluorometry: A Practical Approach*, pp. 91-114, IRL Press Ltd.; and Bell, (1981) *Spectroscopy In Biochemistry*, Vol. I, pp. 155-194, CRC Press.

In spectrofluorometric methods, enzymes are exposed to substrates that change their intrinsic fluorescence when processed by the target enzyme. Typically, the substrate is non-fluorescent and is converted to a fluorophore through one or more reactions. As a non-limiting example, SMase activity can be detected using the Amplex® Red reagent (Molecular Probes, Eugene, Oreg.). In order to measure sphingomyelinase activity using Amplex® Red, the following reactions occur. First, SMase hydrolyzes sphingomyelin to yield ceramide and phosphorylcholine. Second, alkaline phosphatase hydrolyzes phosphorylcholine to yield choline. Third, choline is oxidized by choline oxidase to betaine. Finally, $H_2O_2$, in the presence of horseradish peroxidase, reacts with Amplex® Red to produce the fluorescent product, Resorufin, and the signal therefrom is detected using spectrofluorometry.

Fluorescence polarization (FP) is based on a decrease in the speed of molecular rotation of a fluorophore that occurs upon binding to a larger molecule, such as a receptor protein, allowing for polarized fluorescent emission by the bound ligand. FP is empirically determined by measuring the vertical and horizontal components of fluorophore emission following excitation with plane polarized light. Polarized emission is increased when the molecular rotation of a fluorophore is reduced. A fluorophore produces a larger polarized signal when it is bound to a larger molecule (i.e. a receptor), slowing molecular rotation of the fluorophore. The magnitude of the polarized signal relates quantitatively to the extent of fluorescent ligand binding. Accordingly, polarization of the "bound" signal depends on maintenance of high affinity binding.

FP is a homogeneous technology and reactions are very rapid, taking seconds to minutes to reach equilibrium. The reagents are stable, and large batches may be prepared, resulting in high reproducibility. Because of these properties, FP has proven to be highly automatable, often performed with a single incubation with a single, premixed, tracer-receptor reagent. For a review, see Owickiet al., (1997), Application of Fluorescence Polarization Assays in High-Throughput Screening, *Genetic Engineering News,* 17:27.

FP is particularly desirable since its readout is independent of the emission intensity (Checovich, W. J., et al., (1995) *Nature* 375:254-256; Dandliker, W. B., et al., (1981) *Methods in Enzymology* 74:3-28) and is thus insensitive to the presence of colored compounds that quench fluorescence emission. FP and FRET (see below) are well-suited for identifying compounds that block interactions between sphingolipid receptors and their ligands. See, for example, Parker et al., (2000) Development of high throughput screening assays using fluorescence polarization: nuclear receptor-ligand-binding and kinase/phosphatase assays, J Biomol Screen 5:77-88.

Fluorophores derived from sphingolipids that may be used in FP assays are commercially available. For example, Molecular Probes (Eugene, Oreg.) currently sells sphingomyelin and one ceramide flurophores. These are, respectively, N-(4,4-difluoro-5,7-dimethyl-4-bora-3a,4a-diaza-s-indacene-3-pentanoyl)sphingosyl phosphocholine (BODIPY® FL C5-sphingomyelin); N-(4,4-difluoro-5,7-dimethyl-4-bora-3a,4a-diaza-s-indacene-3-dodecanoyl)sphingosyl phosphocholine (BODIPY® FL C12-sphingomyelin); and N-(4,4-difluoro-5,7-dimethyl-4-bora-3a,4a-diaza-s-indacene-3-pentanoyl)sphingosine (BODIPY® FL C5-ceramide). U.S. Pat. No. 4,150,949, (Immunoassay for gentamicin), discloses fluorescein-labelled gentamicins, including fluoresceinthiocarbanyl gentamicin. Additional fluorophores may be prepared using methods well known to the skilled artisan.

Exemplary normal-and-polarized fluorescence readers include the POLARION® fluorescence polarization system (Tecan A G, Hombrechtikon, Switzerland). General multiwell plate readers for other assays are available, such as the VERSAMAX™ reader and the SPECTRAMAX® multiwell plate spectrophotometer (both from Molecular Devices).

Fluorescence resonance energy transfer (FRET) is another useful assay for detecting interaction and has been described. See, e.g., Heim et al., (1996) *Curr. Biol.* 6:178-182; Mitra et al., (1996) *Gene* 173:13-17; and Selvin et al., (1995) *Meth. Enzymol.* 246:300-345. FRET detects the transfer of energy between two fluorescent substances in close proximity, having known excitation and emission wavelengths. As an example, a protein can be expressed as a fusion protein with green fluorescent protein (GFP). When two fluorescent proteins are in proximity, such as when a protein specifically interacts with a target molecule, the resonance energy can be transferred from one excited molecule to the other. As a result, the emission spectrum of the sample shifts, which can be measured by a fluorometer, such as a FMAX multiwell fluorometer (Molecular Devices, Sunnyvale Calif.).

Scintillation proximity assay (SPA) is a particularly useful assay for detecting an interaction with the target molecule. SPA is widely used in the pharmaceutical industry and has been described (Hanselman et al., (1997) *J. Lipid Res.* 38:2365-2373; Kahl et al., (1996) *Anal. Biochem.* 243:282-283; Undenfriend et al., (1987) *Anal. Biochem.* 161:494-500). See also U.S. Pat. Nos. 4,626,513 and 4,568,649, and European Patent No. 0,154,734. One commercially available system uses FLASHPLATE® scintillant-coated plates (NEN Life Science Products, Boston, Mass.).

The target molecule can be bound to the scintillator plates by a variety of well known means. Scintillant plates are available that are derivatized to bind to fusion proteins such as GST, His6 (SEQ ID NO: 32) or Flag fusion proteins. Where the target molecule is a protein complex or a multimer, one protein or subunit can be attached to the plate first, then the other components of the complex added later under binding conditions, resulting in a bound complex.

In a typical SPA assay, the gene products in the expression pool will have been radiolabeled and added to the wells, and allowed to interact with the solid phase, which is the immobilized target molecule and scintillant coating in the wells. The assay can be measured immediately or allowed to reach equilibrium. Either way, when a radiolabel becomes sufficiently close to the scintillant coating, it produces a signal detectable by a device such as a TOPCOUNT NXT® microplate scintillation counter (Packard BioScience Co., Meriden Conn.). If a radiolabeled expression product binds to the target molecule, the radiolabel remains in proximity to the scintillant long enough to produce a detectable signal.

In contrast, the labeled proteins that do not bind to the target molecule, or bind only briefly, will not remain near the scintillant long enough to produce a signal above background. Any time spent near the scintillant caused by random Brownian motion will also not result in a significant amount of signal. Likewise, residual unincorporated radiolabel used during the expression step may be present, but will not generate significant signal because it will be in solution rather than interacting with the target molecule. These non-binding interactions will therefore cause a certain level of background signal that can be mathematically removed. If too many signals are obtained, salt or other modifiers can be added directly to the assay plates until the desired specificity is obtained (Nichols et al., (1998) *Anal. Biochem.* 257:112-119).

Assay Compounds and Molecular Scaffolds

Preferred characteristics of a scaffold include being of low molecular weight (e.g., less than 350 Da, or from about 100 to about 350 daltons, or from about 150 to about 300 daltons). Preferably clog P of a scaffold is from −1 to 8, more preferably less than 6, 5, or 4, most preferably less than 3. In particular embodiments the clogP is in a range −1 to an upper limit of 2, 3, 4, 5, 6, or 8; or is in a range of 0 to an upper limit of 2, 3, 4, 5, 6, or 8. Preferably the number of rotatable bonds is less than 5, more preferably less than 4. Preferably the number of hydrogen bond donors and acceptors is below 6, more preferably below 5. An additional criterion that can be useful is a polar surface area of less than 5. Guidance that can be useful in identifying criteria for a particular application can be found in Lipinski et al., (1997) *Advanced Drug Delivery Reviews* 23 3-25, which is hereby incorporated by reference in its entirety.

A scaffold may preferably bind to a given protein binding site in a configuration that causes substituent moieties of the scaffold to be situated in pockets of the protein binding site. Also, possessing chemically tractable groups that can be chemically modified, particularly through synthetic reactions, to easily create a combinatorial library can be a preferred characteristic of the scaffold. Also preferred can be having positions on the scaffold to which other moieties can be attached, which do not interfere with binding of the scaffold to the protein(s) of interest but do cause the scaffold to achieve a desirable property, for example, active transport of the scaffold to cells and/or organs, enabling the scaffold to be attached to a chromatographic column to facilitate analysis, or another desirable property. A molecular scaffold can bind to a target molecule with any affinity, such as binding at high affinity, moderate affinity, low affinity, very low affinity, or extremely low affinity.

Thus, the above criteria can be utilized to select many compounds for testing that have the desired attributes. Many compounds having the criteria described are available in the commercial market, and may be selected for assaying depending on the specific needs to which the methods are to be applied.

A "compound library" or "library" is a collection of different compounds having different chemical structures. A compound library is screenable, that is, the compound library members therein may be subject to screening assays. In preferred embodiments, the library members can have a molecular weight of from about 100 to about 350 daltons, or from about 150 to about 350 daltons. Examples of libraries are provided aove.

Libraries of the present invention can contain at least one compound than binds to the target molecule at low affinity. Libraries of candidate compounds can be assayed by many different assays, such as those described above, e.g., a fluorescence polarization assay. Libraries may consist of chemically synthesized peptides, peptidomimetics, or arrays of combinatorial chemicals that are large or small, focused or nonfocused. By "focused" it is meant that the collection of compounds is prepared using the structure of previously characterized compounds and/or pharmacophores.

Compound libraries may contain molecules isolated from natural sources, artificially synthesized molecules, or molecules synthesized, isolated, or otherwise prepared in such a manner so as to have one or more moieties variable, e.g., moieties that are independently isolated or randomly synthesized. Types of molecules in compound libraries include but are not limited to organic compounds, polypeptides and nucleic acids as those terms are used herein, and derivatives, conjugates and mixtures thereof.

Compound libraries of the invention may be purchased on the commercial market or prepared or obtained by any means including, but not limited to, combinatorial chemistry techniques, fermentation methods, plant and cellular extraction procedures and the like (see, e.g., Cwirla et al., (1990) *Biochemistry*, 87, 6378-6382; Houghten et al., (1991) *Nature*, 354, 84-86; Lan et al., (1991) *Nature*, 354, 82-84; Brenner et al., (1992) *Proc. Natl. Acad. Sci. USA*, 89, 5381-5383; R. A. Houghten, (1993) *Trends Genet.*, 9, 235-239; E. R. Felder, (1994) *Chimia*, 48, 512-541; Gallop et al., (1994) *J. Med. Chem.*, 37, 1233-1251; Gordon et al., (1994) *J. Med. Chem.*, 37, 1385-1401; Carell et al., (1995) *Chem. Biol.*, 3, 171-183; Madden et al., *Perspectives in Drug Discovery and Design* 2, 269-282; Lebl et al., (1995) *Biopolymers*, 37 177-198); small molecules assembled around a shared molecular structure; collections of chemicals that have been assembled by various commercial and noncommercial groups, natural products; extracts of marine organisms, fungi, bacteria, and plants.

Preferred libraries can be prepared in a homogenous reaction mixture, and separation of unreacted reagents from members of the library is not required prior to screening. Although many combinatorial chemistry approaches are based on solid state chemistry, liquid phase combinatorial chemistry is capable of generating libraries (Sun C M., (1999) Recent advances in liquid-phase combinatorial chemistry, *Combinatorial Chemistry & High Throughput Screening*. 2:299-318).

Libraries of a variety of types of molecules are prepared in order to obtain members therefrom having one or more preselected attributes that can be prepared by a variety of techniques, including but not limited to parallel array synthesis (Houghton, (2000) *Annu Rev Pharmacol Toxicol* 40:273-82, Parallel array and mixture-based synthetic combinatorial chemistry; solution-phase combinatorial chemistry (Merritt, (1998) *Comb Chem High Throughput Screen* 1(2):57-72, Solution phase combinatorial chemistry, Coe et al., (1998-99) *Mol Divers;* 4(1):31-8, Solution-phase combinatorial chemistry, Sun, (1999) *Comb Chem High Throughput Screen* 2(6): 299-318, Recent advances in liquid-phase combinatorial chemistry); synthesis on soluble polymer (Gravert et al., (1997) *Curr Opin Chem Biol* 1(1):107-13, Synthesis on soluble polymers: new reactions and the construction of small molecules); and the like. See, e.g., Dolle et al., (1999) *J Comb Chem* 1(4):235-82, Comprehensive survey of cominatorial library synthesis: 1998. Freidinger R M., (1999) Nonpeptidic ligands for peptide and protein receptors, Current Opinion in Chemical Biology; and Kundu et al., *Prog Drug Res;* 53:89-156, Combinatorial chemistry: polymer supported synthesis of peptide and non-peptide libraries). Compounds may be clinically tagged for ease of identification (Chabala, (1995) *Curr Opin Biotechnol* 6(6):633-9, Solid-phase combinatorial chemistry and novel tagging methods for identifying leads).

The combinatorial synthesis of carbohydrates and libraries containing oligosaccharides have been described (Schweizer et al., (1999) *Curr Opin Chem Biol* 3(3):291-8, Combinatorial synthesis of carbohydrates). The synthesis of natural-product based compound libraries has been described (Wessjohann, (2000) *Curr Opin Chem Biol* 4(3):303-9, Synthesis of natural-product based compound libraries).

Libraries of nucleic acids are prepared by various techniques, including by way of non-limiting example the ones described herein, for the isolation of aptamers. Libraries that include oligonucleotides and polyaminooligonucleotides (Markiewicz et al., (2000) Synthetic oligonucleotide combinatorial libraries and their applications, *Farmaco*. 55:174-7) displayed on streptavidin magnetic beads are known. Nucleic acid libraries are known that can be coupled to parallel sampling and be deconvoluted without complex procedures such as automated mass spectrometry (Enjalbal C. Martinez J. Aubagnac J L, (2000) Mass spectrometry in combinatorial chemistry, *Mass Spectrometry Reviews*. 19:139-61) and parallel tagging. (Perrin D M., Nucleic acids for recognition and catalysis: landmarks, limitations, and looking to the future, *Combinatorial Chemistry & High Throughput Screening* 3:243-69).

Peptidomimetics are identified using combinatorial chemistry and solid phase synthesis (Kim H O. Kahn M., (2000) A merger of rational drug design and combinatorial chemistry: development and application of peptide secondary structure mimetics, Combinatorial Chemistry & High Throughput Screening 3:167-83; al-Obeidi, (1998) *Mol Biotechnol* 9(3): 205-23, Peptide and peptidomimetric libraries. Molecular diversity and drug design). The synthesis may be entirely random or based in part on a known polypeptide.

Polypeptide libraries can be prepared according to various techniques. In brief, phage display techniques can be used to produce polypeptide ligands (Gram H., (1999) Phage display in proteolysis and signal transduction, Combinatorial Chemistry & High Throughput Screening. 2:19-28) that may be used as the basis for synthesis of peptidomimetics. Polypeptides, constrained peptides, proteins, protein domains, antibodies, single chain antibody fragments, antibody fragments, and antibody combining regions are displayed on filamentous phage for selection.

Large libraries of individual variants of human single chain Fv antibodies have been produced. See, e.g., Siegel R W. Allen B. Pavlik P. Marks J D. Bradbury A., (2000) Mass spectral analysis of a protein complex using single-chain antibodies selected on a peptide target: applications to functional genomics, *Journal of Molecular Biology* 302:285-93; Poul M A. Becerril B. Nielsen U B. Morisson P. Marks J D., (2000) Selection of tumor-specific internalizing human antibodies from phage libraries. Source *Journal of Molecular Biology.* 301:1149-61; Amersdorfer P. Marks J D., (2001) Phage libraries for generation of anti-botulinum scFv antibodies, *Methods in Molecular Biology.* 145:219-40; Hughes-Jones N C. Bye J M. Gorick B D. Marks J D. Ouwehand W H., (1999) Synthesis of Rh Fv phage-antibodies using VH and VL germline genes, *British Journal of Haematology.* 105: 811-6; McCall A M. Amoroso A R. Sautes C. Marks J D. Weiner L M., (1998) Characterization of anti-mouse Fc gamma RII single-chain Fv fragments derived from human phage display libraries, *Immunotechnology.* 4:71-87; Sheets M D. Amersdorfer P. Finnern R. Sargent P. Lindquist E. Schier R. Hemingsen G. Wong C. Gerhart J C. Marks J D. Lindquist E., (1998) Efficient construction of a large nonimmune phage antibody library: the production of high-affinity human single-chain antibodies to protein antigens (published erratum appears in *Proc Natl Acad Sci USA* 1999 96:795), *Proc Natl Acad Sci USA* 95:6157-62).

Focused or smart chemical and pharmacophore libraries can be designed with the help of sophisticated strategies involving computational chemistry (e.g., Kundu B. Khare S K. Rastogi S K., (1999) Combinatorial chemistry: polymer supported synthesis of peptide and non-peptide libraries, *Progress in Drug Research* 53:89-156) and the use of structure-based ligands using database searching and docking, de novo drug design and estimation of ligand binding affinities (Joseph-McCarthy D., (1999) Computational approaches to structure-based ligand design, *Pharmacology & Therapeutics* 84:179-91; Kirkpatrick D L. Watson S. Ulhaq S., (1999) Structure-based drug design: combinatorial chemistry and molecular modeling, *Combinatorial Chemistry & High Throughput Screening.* 2:211-21; Eliseev A V. Lehn J M., (1999) Dynamic combinatorial chemistry: evolutionary formation and screening of molecular libraries, *Current Topics in Microbiology & Immunology* 243:159-72; Bolger et al., (1991) *Methods Enz.* 203:21-45; Martin, (1991) *Methods Enz.* 203:587-613; Neidle et al., (1991) *Methods Enz.* 203: 433-458; U.S. Pat. No. 6,178,384).

X. Crystallography

After binding compounds have been determined, the orientation of compound bound to target is determined. Preferably this determination involves crystallography on co-crystals of molecular scaffold compounds with target. Most protein crystallographic platforms can preferably be designed to analyze up to about 500 co-complexes of compounds, ligands, or molecular scaffolds bound to protein targets due to the physical parameters of the instruments and convenience of operation. If the number of scaffolds that have binding activity exceeds a number convenient for the application of crystallography methods, the scaffolds can be placed into groups based on having at least one common chemical structure or other desirable characteristics, and representative compounds can be selected from one or more of the classes. Classes can be made with increasingly exacting criteria until a desired number of classes (e.g., 500) is obtained. The classes can be based on chemical structure similarities between molecular scaffolds in the class, e.g., all possess a pyrrole ring, benzene ring, or other chemical feature. Likewise, classes can be based on shape characteristics, e.g., space-filling characteristics.

The co-crystallography analysis can be performed by co-complexing each scaffold with its target at concentrations of the scaffold that showed activity in the screening assay. This co-complexing can be accomplished with the use of low percentage organic solvents with the target molecule and then concentrating the target with each of the scaffolds. In preferred embodiments these solvents are less than 5% organic solvent such as dimethyl sulfoxide (DMSO), ethanol, methanol, or ethylene glycol in water or another aqueous solvent. Each scaffold complexed to the target molecule can then be screened with a suitable number of crystallization screening conditions at both 4 and 20 degrees. In preferred embodiments, about 96 crystallization screening conditions can be performed in order to obtain sufficient information about the co-complexation and crystallization conditions, and the orientation of the scaffold at the binding site of the target molecule. Crystal structures can then be analyzed to determine how the bound scaffold is oriented physically within the binding site or within one or more binding pockets of the molecular family member.

It is desirable to determine the atomic coordinates of the compounds bound to the target proteins in order to determine which is a most suitable scaffold for the protein family. X-ray crystallographic analysis is therefore most preferable for determining the atomic coordinates. Those compounds selected can be further tested with the application of medicinal chemistry. Compounds can be selected for medicinal chemistry testing based on their binding position in the target molecule. For example, when the compound binds at a binding site, the compound's binding position in the binding site of the target molecule can be considered with respect to the chemistry that can be performed on chemically tractable structures or sub-structures of the compound, and how such modifications on the compound might interact with structures or sub-structures on the binding site of the target. Thus, one can explore the binding site of the target and the chemistry of the scaffold in order to make decisions on how to modify the scaffold to arrive at a ligand with higher potency and/or selectivity. This process allows for more direct design of ligands, by utilizing structural and chemical information obtained directly from the co-complex, thereby enabling one to more efficiently and quickly design lead compounds that are likely to lead to beneficial drug products. In various embodiments it may be desirable to perform co-crystallography on all scaffolds that bind, or only those that bind with a particular affinity, for example, only those that bind with high affinity, moderate affinity, low affinity, very low affinity, or extremely low affinity. It may also be advantageous to perform co-crystallography on a selection of scaffolds that bind with any combination of affinities.

Standard X-ray protein diffraction studies such as by using a Rigaku RU-200® (Rigaku, Tokyo, Japan) with an X-ray imaging plate detector or a synchrotron beam-line can be performed on co-crystals and the diffraction data measured on a standard X-ray detector, such as a CCD detector or an X-ray imaging plate detector.

Performing X-ray crystallography on about 200 co-crystals should generally lead to about 50 co-crystals structures, which should provide about 10 scaffolds for validation in chemistry, which should finally result in about 5 selective leads for target molecules.

Virtual Assays

Commercially available software that generates three-dimensional graphical representations of the complexed target and compound from a set of coordinates provided can be used to illustrate and study how a compound is oriented when bound to a target. (e.g., QUANTA®, Accelerys, San Diego, Calif.). Thus, the existence of binding pockets at the binding site of the targets can be particularly useful in the present invention. These binding pockets are revealed by the crystallographic structure determination and show the precise chemical interactions involved in binding the compound to the binding site of the target. The person of ordinary skill will realize that the illustrations can also be used to decide where chemical groups might be added, substituted, modified, or deleted from the scaffold to enhance binding or another desirable effect, by considering where unoccupied space is located in the complex and which chemical substructures might have suitable size and/or charge characteristics to fill it. The person of ordinary skill will also realize that regions within the binding site can be flexible and its properties can change as a result of scaffold binding, and that chemical groups can be specifically targeted to those regions to achieve a desired effect. Specific locations on the molecular scaffold can be considered with reference to where a suitable chemical substructure can be attached and in which conformation, and which site has the most advantageous chemistry available.

An understanding of the forces that bind the compounds to the target proteins reveals which compounds can most advantageously be used as scaffolds, and which properties can most effectively be manipulated in the design of ligands. The person of ordinary skill will realize that steric, ionic, hydrogen bond, and other forces can be considered for their contribution to the maintenance or enhancement of the target-compound complex. Additional data can be obtained with automated computational methods, such as docking and/or Free Energy Perturbations (FEP), to account for other energetic effects such as desolvation penalties. The compounds selected can be used to generate information about the chemical interactions with the target or for elucidating chemical modifications that can enhance selectivity of binding of the compound.

Computer models, such as homology models (i.e., based on a known, experimentally derived structure) can be constructed using data from the co-crystal structures. When the target molecule is a protein or enzyme, preferred co-crystal structures for making homology models contain high sequence identity in the binding site of the protein sequence being modeled, and the proteins will preferentially also be within the same class and/or fold family. Knowledge of conserved residues in active sites of a protein class can be used to select homology models that accurately represent the binding site. Homology models can also be used to map structural information from a surrogate protein where an apo or co-crystal structure exists to the target protein.

Virtual screening methods, such as docking, can also be used to predict the binding configuration and affinity of scaffolds, compounds, and/or combinatorial library members to homology models. Using this data, and carrying out "virtual experiments" using computer software can save substantial resources and allow the person of ordinary skill to make decisions about which compounds can be suitable scaffolds or ligands, without having to actually synthesize the ligand and perform co-crystallization. Decisions thus can be made about which compounds merit actual synthesis and co-crystallization. An understanding of such chemical interactions aids in the discovery and design of drugs that interact more advantageously with target proteins and/or are more selective for one protein family member over others. Thus, applying these principles, compounds with superior properties can be discovered.

Additives that promote co-crystallization can of course be included in the target molecule formulation in order to enhance the formation of co-crystals. In the case of proteins or enzymes, the scaffold to be tested can be added to the protein formulation, which is preferably present at a concentration of approximately 1 mg/ml. The formulation can also contain between 0%-10% (v/v) organic solvent, e.g. DMSO, methanol, ethanol, propane diol, or 1,3 dimethyl propane diol (MPD) or some combination of those organic solvents. Compounds are preferably solubilized in the organic solvent at a concentration of about 10 mM and added to the protein sample at a concentration of about 100 mM. The protein-compound complex is then concentrated to a final concentration of protein of from about 5 to about 20 mg/ml. The complexation and concentration steps can conveniently be performed using a 96-well formatted concentration apparatus (e.g., Amicon Inc., Piscataway, N.J.). Buffers and other reagents present in the formulation being crystallized can contain other components that promote crystallization or are compatible with crystallization conditions, such as DTT, propane diol, glycerol.

The crystallization experiment can be set-up by placing small aliquots of the concentrated protein-compound complex (1 µl) in a 96 well format and sampling under 96 crystallization conditions. (Other screening formats can also be used, e.g., plates with greater than 96 wells.) Crystals can typically be obtained using standard crystallization protocols that can involve the 96 well crystallization plate being placed at different temperatures. Co-crystallization varying factors other than temperature can also be considered for each protein-compound complex if desirable. For example, atmospheric pressure, the presence or absence of light or oxygen, a change in gravity, and many other variables can all be tested. The person of ordinary skill in the art will realize other variables that can advantageously be varied and considered.

Ligand Design and Preparation

The design and preparation of ligands can be performed with or without structural and/or co-crystallization data by considering the chemical structures in common between the active scaffolds of a set. In this process structure-activity hypotheses can be formed and those chemical structures found to be present in a substantial number of the scaffolds, including those that bind with low affinity, can be presumed to have some effect on the binding of the scaffold. This binding can be presumed to induce a desired biochemical effect when it occurs in a biological system (e.g., a treated mammal). New or modified scaffolds or combinatorial libraries derived from scaffolds can be tested to disprove the maximum number of binding and/or structure-activity hypotheses. The remaining hypotheses can then be used to design ligands that achieve a desired binding and biochemical effect.

But in many cases it will be preferred to have co-crystallography data for consideration of how to modify the scaffold to achieve the desired binding effect (e.g., binding at higher affinity or with higher selectivity). Using the case of proteins and enzymes, co-crystallography data shows the binding pocket of the protein with the molecular scaffold bound to the binding site, and it will be apparent that a modification can be made to a chemically tractable group on the scaffold. For example, a small volume of space at a protein binding site or pocket might be filled by modifying the scaffold to include a small chemical group that fills the volume. Filling the void volume can be expected to result in a greater binding affinity, or the loss of undesirable binding to another member of the protein family. Similarly, the co-crystallography data may show that deletion of a chemical group on the scaffold may decrease a hindrance to binding and result in greater binding affinity or specificity.

It can be desirable to take advantage of the presence of a charged chemical group located at the binding site or pocket of the protein. For example, a positively charged group can be complemented with a negatively charged group introduced on the molecular scaffold. This can be expected to increase binding affinity or binding specificity, thereby resulting in a more desirable ligand. In many cases, regions of protein binding sites or pockets are known to vary from one family member to another based on the amino acid differences in those regions. Chemical additions in such regions can result in the creation or elimination of certain interactions (e.g., hydrophobic, electrostatic, or entropic) that allow a compound to be more specific for one protein target over another or to bind with greater affinity, thereby enabling one to synthesize a compound with greater selectivity or affinity for a particular family member. Additionally, certain regions can contain amino acids that are known to be more flexible than others. This often occurs in amino acids contained in loops connecting elements of the secondary structure of the protein, such as alpha helices or beta strands. Additions of chemical moieties can also be directed to these flexible regions in order to increase the likelihood of a specific interaction occurring between the protein target of interest and the compound. Virtual screening methods can also be conducted in silico to assess the effect of chemical additions, subtractions, modifications, and/or substitutions on compounds with respect to members of a protein family or class.

The addition, subtraction, or modification of a chemical structure or sub-structure to a scaffold can be performed with any suitable chemical moiety. For example the following moieties, which are provided by way of example and are not intended to be limiting, can be utilized: hydrogen, alkyl, alkoxy, phenoxy, alkenyl, alkynyl, phenylalkyl, hydroxyalkyl, haloalkyl, aryl, arylalkyl, alkyloxy, alkylthio, alkenylthio, phenyl, phenylalkyl, phenylalkylthio, hydroxyalkyl-thio, alkylthiocarbbamylthio, cyclohexyl, pyridyl, piperidinyl, alkylamino, amino, nitro, mercapto, cyano, hydroxyl, a halogen atom, halomethyl, an oxygen atom (e.g., forming a ketone or N-oxide) or a sulphur atom (e.g., forming a thiol, thione, di-alkylsulfoxide or sulfone) are all examples of moieties that can be utilized.

Additional examples of structures or sub-structures that may be utilized are an aryl optionally substituted with one, two, or three substituents independently selected from the group consisting of alkyl, alkoxy, halogen, trihalomethyl, carboxylate, carboxamide, nitro, and ester moieties; an amine of formula —$NX_2X_3$, where $X_2$ and $X_3$ are independently selected from the group consisting of hydrogen, saturated or unsaturated alkyl, and homocyclic or heterocyclic ring moieties; halogen or trihalomethyl; a ketone of formula —$COX_4$, where $X_4$ is selected from the group consisting of alkyl and homocyclic or heterocyclic ring moieties; a carboxylic acid of formula —$(X_5)_n$COOH or ester of formula $(X_6)_n$COO$X_7$, where $X_5$, $X_6$, and $X_7$ and are independently selected from the group consisting of alkyl and homocyclic or heterocyclic ring moieties and where n is 0 or 1; an alcohol of formula $(X_8)_n$OH or an alkoxy moiety of formula —$(X_8)_n$O$X_9$, where $X_8$ and $X_9$ are independently selected from the group consisting of saturated or unsaturated alkyl and homocyclic or heterocyclic ring moieties, wherein said ring is optionally substituted with one or more substituents independently selected from the group consisting of alkyl, alkoxy, halogen, trihalomethyl, carboxylate, nitro, and ester and where n is 0 or 1; an amide of formula NHCO$X_{10}$, where $X_{10}$ is selected from the group consisting of alkyl, hydroxyl, and homocyclic or heterocyclic ring moieties, wherein said ring is optionally substituted with one or more substituents independently selected from the group consisting of alkyl, alkoxy, halogen, trihalomethyl, carboxylate, nitro, and ester; $SO_2$, $NX_{11}$, $X_{12}$, where $X_{11}$ and $X_{12}$ are selected from the group consisting of hydrogen, alkyl, and homocyclic or heterocyclic ring moieties; a homocyclic or heterocyclic ring moiety optionally substituted with one, two, or three substituents independently selected from the group consisting of alkyl, alkoxy, halogen, trihalomethyl, carboxylate, carboxamide, nitro, and ester moieties; an aldehyde of formula —CHO; a sulfone of formula —$SO_2X_{13}$, where $X_{13}$ is selected from the group consisting of saturated or unsaturated alkyl and homocyclic or heterocyclic ring moieties; and a nitro of formula —$NO_2$.

Identification of Attachment Sites on Molecular Scaffolds and Ligands

In addition to the identification and development of ligands for phosphodiesterases and other enzymes, determination of the orientation of a molecular scaffold or other binding compound in a binding site allows identification of energetically allowed sites for attachment of the binding molecule to another component. For such sites, any free energy change associated with the presence of the attached component should not destabilize the binding of the compound to the phosphodiesterase to an extent that will disrupt the binding. Preferably, the binding energy with the attachment should be at least 4 kcal/mol., more preferably at least 6, 8, 10, 12, 15, or 20 kcal/mol. Preferably, the presence of the attachment at the particular site reduces binding energy by no more than 3, 4, 5, 8, 10, 12, or 15 kcal/mol.

In many cases, suitable attachment sites will be those that are exposed to solvent when the binding compound is bound in the binding site. In some cases, attachment sites can be used that will result in small displacements of a portion of the enzyme without an excessive energetic cost. Exposed sites can be identified in various ways. For example, exposed sites can be identified using a graphic display or 3-dimensional model. In a grahic display, such as a computer display, an image of a compound bound in a binding site can be visually inspected to reveal atoms or groups on the compound that are exposed to solvent and oriented such that attachment at such atom or group would not preclude binding of the enzyme and binding compound. Energetic costs of attachment can be calculated based on changes or distortions that would be caused by the attachment as well as entropic changes.

Many different types of components can be attached. Persons with skill are familiar with the chemistries used for various attachments. Examples of components that can be attached include, without limitation: solid phase components such as beads, plates, chips, and wells; a dlrect or indirect label; a linker, which may be a traceless linker; among others. Such linkers can themselves be attached to other components, e.g., to solid phase media, labels, and/or binding moieties.

The binding energy of a compound and the effects on binding energy for attaching the molecule to another component can be calculated approximately using any of a variety of available software or by manual calculation. An example is the following:

Calculations were performed to estimate binding energies of different organic molecules to two Kinases: PIM-1 and CDK2. The organic molecules considered included Staurosporine, identified compounds that bind to PDE5A, and several linkers.

Calculated binding energies between protein-ligand complexes were obtained using the FlexX score (an implementation of the Bohm scoring function) within the Tripos software suite. The form for that equation is shown in the equation below:

$$\Delta G\text{bind} = \Delta G tr + \Delta G hb + \Delta G ion + \Delta G lipo + \Delta G arom + \Delta G rot$$

wherein: $\Delta G tr$ is a constant term that accounts for the overall loss of rotational and translational entropy of the lignand, $\Delta G hb$ accounts for hydrogen bonds formed between the ligand and protein, $\Delta G ion$ accounts for the ionic interactions between the ligand and protein, $\Delta G lipo$ accounts for the lipophilic interaction that corresponds to the protein-ligand contact surface, $\Delta G arom$ accounts for interactions between aromatic rings in the protein and ligand, and $\Delta G rot$ accounts for the entropic penalty of restricting rotatable bonds in the ligand upon binding.

This method estimates the free energy that a lead compound should have to a target protein for which there is a crystal structure, and it accounts for the entropic penalty of flexible linkers. It can therefore be used to estimate the free energy penalty incurred by attaching linkers to molecules being screened and the binding energy that a lead compound should have in order to overcome the free energy penalty of the linker. The method does not account for solvation and the entropic penalty is likely overestimated for cases where the linker is bound to a solid phase through another binding complex, such as a biotin:streptavidin complex.

Co-crystals were aligned by superimposing residues of PIM-1 with corresponding residues in CDK2. The PIM-1 structure used for these calculations was a co-crystal of PIM-1 with a binding compound. The CDK2:Staurosporine co-crystal used was from the Brookhaven database file 1aq1. Hydrogen atoms were added to the proteins and atomic charges were assigned using the AMBER95 parameters within Sybyl. Modifications to the compounds described were made within the Sybyl modeling suite from Tripos.

These calcualtions indicate that the calculated binding energy for compounds that bind strongly to a given target (such as Staurosporine:CDK2) can be lower than −25 kcal/mol, while the calculated binding affinity for a good scaffold or an unoptimized binding compound can be in the range of −15 to −20. The free energy penalty for attachment to a linker such as the ethylene glycol or hexatriene is estimated as typically being in the range of +5 to +15 kcal/mol.

Linkers

Linkers suitable for use in the invention can be of many different types. Linkers can be selected for particular applications based on factors such as linker chemistry compatible for attachment to a binding compound and to another component utilized in the particular application. Additional factors can include, without limitation, linker length, linker stability, and ability to remove the linker at an appropriate time. Exemplary linkers include, but are not limited to, hexyl, hexatrienyl, ethylene glycol, and peptide linkers. Traceless linkers can also be used, e.g., as described in Plunkett, M. J., and Ellman, J. A., (1995), *J. Org. Chem.*, 60:6006.

Typical functional groups, that are utilized to link binding compound(s), include, but not limited to, carboxylic acid, amine, hydroxyl, and thiol. (Examples can be found in Solid-supported combinatorial and parallel synthesis of small molecular weight compound libraries; (1998) Tetrahedron organic chemistry series Vol. 17; Pergamon; p85).

Labels

As indicated above, labels can also be attached to a binding compound or to a linker attached to a binding compound. Such attachment may be direct (attached directly to the binding compound) or indirect (attached to a component that is directly or indirectly attached to the binding compound). Such labels allow detection of the compound either directly or indirectly. Attachement of labels can be performed using conventional chemistries. Labels can include, for example, fluorescent labels, radiolabels, light scattering particles, light absorbent particles, magnetic particles, enzymes, and specific binding agents (e.g., biotin or an antibody target moiety).

Solid Phase Media

Additional examples of components that can be attached directly or indirectly to a binding compound include various solid phase media. Similar to attachment of linkers and labels, attachment to solid phase media can be performed using conventional chemistries. Such solid phase media can include, for example, small components such as beads, nanoparticles, and fibers (e.g., in suspension or in a gel or chromatographic matrix). Likewise, solid phase media can include larger objects such as plates, chips, slides, and tubes. In many cases, the binding compound will be attached in only a portion of such an objects, e.g., in a spot or other local element on a generally flat surface or in a well or portion of a well.

Identification of Biological Agents

The posession of structural information about a protein also provides for the identification of useful biological agents, such as epitpose for development of antibodies, identification of mutation sites expected to affect activity, and identification of attachment sites allowing attachment of the protein to materials such as labels, linkers, peptides, and solid phase media.

Antibodies (Abs) finds multiple applications in a variety of areas including biotechnology, medicine and diagnosis, and indeed they are one of the most powerful tools for life science research. Abs directed against protein antigens can recognize either linear or native three-dimensional (3D) epitopes. The obtention of Abs that recognize 3D epitopes require the use of whole native protein (or of a portion that assumes a native conformation) as immunogens. Unfortunately, this not always a choice due to various technical reasons: for example the native protein is just not available, the protein is toxic, or its is desirable to utilize a high density antigen presentation. In such cases, immunization with peptides is the alternative. Of course, Abs generated in this manner will recognize linear epitopes, and they might or might not recognize the source native protein, but yet they will be useful for standard laboratory applications such as western blots. The selection of peptides to use as immunogens can be accomplished by following particular selection rules and/or use of epitope prediction software.

Though methods to predict antigenic peptides are not infallible, there are several rules that can be followed to determine what peptide fragments from a protein are likely to be antigenic. These rules are also dictated to increase the likelihood that an Ab to a particular peptide will recognize the native protein.

1. Antigenic peptides should be located in solvent accessible regions and contain both hydrophobic and hydrophilic residues.

For proteins of known 3D structure, solvent accessibility can be determined using a variety of programs such as DSSP, NACESS, or WHATIF, among others.

If the 3D structure is not known, use any of the following web servers to predict accessibilities: PHD, JPRED, PredAcc (c) ACCpro 2. Preferably select peptides lying in long loops connecting Secondary Structure (SS) motifs, avoiding peptides located in helical regions. This will increase the odds that the Ab recognizes the native protein. Such peptides can, for example, be identified from a crystal structure or crystal structure-based homology model.

For protein with known 3D coordinates, SS can be obtained from the sequence link of the relevant entry at the Brookhaven data bank. The PDBsum server also offer SS analysis of pdb records.

When no structure is available secondary structure predictions can be obtained from any of the following servers: PHD, JPRED, PSI-PRED, NNSP, etc 3. When possible, choose peptides that are in the N- and C-terminal region of the protein. Because the N- and C-terminal regions of proteins are usually solvent accessible and unstructured, Abs against those regions are also likely to recognize the native protein.

4. For cell surface glycoproteins, eliminate from initial peptides those containing consesus sites for N-glycosilation.

N-glycosilation sites can be detected using Scanoprosite, or NetNGlyc

In addition, several methods based on various physiochemical properties of experimental determined epitopes (flexibility, hydrophibility, accessibility) have been published for the prediction of antigenic determinants and can be used. The antigenic index and Preditop are example.

Perhaps the simplest method for the prediction of antigenic determinants is that of Kolaskar and Tongaonkar, which is based on the occurrence of amino acid residues in experimentally determined epitopes. (Kolaskar and Tongaonkar (1990) A semi-empirical method for prediction of antigenic determinants on protein antigens. *FEBBS Lett.* 276(1-2):172-174.) The prediction algorithm works as follows:

1. Calculate the average propensity for each overlapping 7-mer and assign the result to the central residue (i+3) of the 7-mer.
2. Calculate the average for the whole protein.
3. (a) If the average for the whole protein is above 1.0 then all residues having average propensity above 1.0 are potentially antigenic.
4. (b) If the average for the whole protein is below 1.0 then all residues having above the average for the whole protein are potentially antigenic.
5. Find 8-mers where all residues are selected by step 3 above (6-mers in the original paper)

The Kolaskar and Tongaonkar method is also available from the GCG package, and it runs using the command egcg.

Crystal structures also allow identification of residues at which mutation is likely to alter the activity of the protein. Such residues include, for example, residues that interact with susbtrate, conserved active site residues, and residues that are in a region of ordered secondary structure of involved in tertiary interactions. The mutations that are likely to affect activity will vary for different molecular contexts. Mutations in an active site that will affect activity are typically substitutions or deletions that eliminate a charge-charge or hydrogen bonding interaction, or introduce a steric interference. Mutations in secondary structure regions or molecular interaction regions that are likely to affect activity include, for example, substitutions that alter the hydrophobicity/hydrophilicity of a region, or that introduce a sufficient strain in a region near or including the active site so that critical residue(s) in the active site are displaced. Such substitutions and/or deletions and/or insertions are recognized, and the predicted structural and/or energetic effects of mutations can be calculated using conventional software.

XI. Phosphodiesterase Activity Assays

A number of different assays for phosphodiesterase activity can be utilized for assaying for active modulators and/or determining specificity of a modulator for a particular phosphodiesterase or group or phosphodiesterases. In addition to the assay mentioned in the Examples below, one of ordinary skill in the art will know of other assays that can be utilized and can modify an assay for a particular application. For example, numerous papers concerning PDEs described assays that can be used. For example, useful assays are described in Fryburg et al., U.S. Patent Application Publication 2002/0165237, Thompson et al., U.S. Patent Application Publication 2002/0009764, Pamukcu et al., U.S. patent application Ser. No. 09/046,739, and Pamukcu et al., U.S. Pat. No. 6,500,610.

An assay for phosphodiesterase activity that can be used for PDE4B, can be performed according to the following procedure using purified PDE4B using the procedure described in the Examples.

Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phosphor-specific antibody.

XII. Organic Synthetic Techniques

The versatility of computer-based modulator design and identification lies in the diversity of structures screened by the computer programs. The computer programs can search databases that contain very large numbers of molecules and can modify modulators already complexed with the enzyme with a wide variety of chemical functional groups. A consequence of this chemical diversity is that a potential modulator of phosphodiesterase function may take a chemical form that is not predictable. A wide array of organic synthetic techniques exist in the art to meet the challenge of constructing these potential modulators. Many of these organic synthetic methods are described in detail in standard reference sources utilized by those skilled in the art. One example of suh a reference is March, 1994, *Advanced Organic Chemistry; Reactions, Mechanisms and Structure*, New York, McGraw Hill. Thus, the techniques useful to synthesize a potential modulator of phosphodiesterase function identified by computer-based methods are readily available to those skilled in the art of organic chemical synthesis.

XIII. Isomers, Prodrugs, and Active Metabolites

The present compounds are described herein with generic formulas and specific compounds. In addition, the present compounds may exist in a number of different forms or derivatives, all within the scope of the present invention. These include, for example, tautomers, enantiomers, stereoisomers, racemic mixtures, regioisomers, salts, prodrugs (e.g., carboxylic acid esters), solvated forms, different crystal forms or polymorphs, and active metabolites A. Tautomers, Stereoisomers, Regioisomers, and Solvated Forms It is understood that certain compounds may exhibit tautomerism. In such cases, the formula drawings within this specification expressly depict only one of the possible tautomeric forms. It is therefore to be understood that within the invention the formulas are intended to represent any tautomeric form of the depicted compounds and are not to be limited merely to the specific tautomeric form depicted by the formula drawings.

Likewise, some of the present compounds may contain one or more chiral centers, and therefore, may exist in two or more stereoisomeric forms. Thus, such compounds may be present as single stereoisomers (i.e., essentially free of other stereoisomers), racemates, and/or mixtures of enantiomers and/or diastereomers. All such single stereoisomers, racemates and mixtures thereof are intended to be within the scope of the present invention. Unless specified to the contrary, all such steroisomeric forms are included within the formulas provided herein.

In certain embodiments, a chiral compound of the present invention is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In certain embodiments, the compound is present in optically pure form.

For compounds is which synthesis involves addition of a single group at a double bond, particularly a carbon-carbon double bond, the addition may occur at either of the double bond-linked atoms. For such compounds, the present invention includes both such regioisomers.

Additionally, the formulas are intended to cover solvated as well as unsolvated forms of the identified structures. For example, the indicated structures include both both hydrated and non-hydrated forms. Other examples of solvates include the structures in combination with isopropanol, ethanol, methanol, DMSO, ethyl acetate, acetic acid, or ethanol amine.

B. Prodrugs and Metabolites

In addition to the present formulas and compounds described herein, the invention also includes prodrugs (generally pharmaceutically acceptable prodrugs), active metabolic derivatives (active metabolites), and their pharmaceutically acceptable salts.

In this context, prodrugs are compounds that may be converted under physiological conditions or by solvolysis to the specified compound or to a pharmaceutically acceptable salt of such a compound. A common example is an alkyl ester of a carboxylic acid.

As described in *The Practice of Medicinal Chemistry*, Ch. 31-32 (Ed. Wermuth, Academic Press, San Diego, Calif., 2001), prodrugs can be conceptually divided into two non-exclusive categories, bioprecursor prodrugs and carrier prodrugs. Generally, bioprecursor prodrugs are compounds are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the follow types:

Oxidative reactions, such as oxidation of alcohol, carbonyl, and acid functions, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-delakylation, oxidative O- and S-delakylation, oxidative deamination, as well as other oxidative reactions.

Reductive reactions, such as reduction of carbonyl groups, reduction of alcoholic groups and carbon-carbon double bonds, reduction of nitrogen-containing functions groups, and other reduction reactions.

Reactions without change in the state of oxidation, such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety in intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent publ. 20040077595, application Ser. No. 10/656,838, incorporated herein by reference.) Such carrier prodrugs are often advantageous for orally administered drugs. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, *The Practice of Medicinal Chemistry*, Ch. 31-32, Ed. Wermuth, Academic Press, San Diego, Calif., 2001.

Prodrugs may proceed from prodrug form to active form in a single step or may have one or more intermediate forms which may themselves have activity or may be inactive.

Metabolites, e.g., active metabolites overlap with prodrugs as described above, e.g., bioprecursor prodrugs. Thus, such metabolites are pharmacologically active compounds or compounds that further metabolize to pharmacologically active compounds that are derivatives resulting from metabolic process in the body of a subject or patient. Of these, active metabolites are such pharmacologically active derivative compounds. For prodrugs, the prodrug compounds is generally inactive or of lower activity than the metabolic product. For active metabolites, the parent compound may be either an active compound or may be an inactive prodrug.

Prodrugs and active metabolites may be identified using routine techniques know in the art. See, e.g., Bertolini et al, 1997, *J Med Chem* 40:2011-2016; Shan et al., *J Pharm Sci* 86:756-757; Bagshawe, 1995, *Drug Dev Res* 34:220-230; Wermuth, *The Practice of Medicinal Chemistry*, Ch. 31-32, Academic Press, San Diego, Calif., 2001.

C. Pharmaceutically Acceptable Salts

Compounds can be formulated as or be in the form of pharmaceutically acceptable salts. Pharmaceutically acceptable salts are non-toxic salts in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug.

Pharmaceutically acceptable salts include acid addition salts such as those containing sulfate, chloride, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see *Remington's Pharmaceutical Sciences*, 19$^{th}$ ed., Mack Publishing Co., Easton, Pa., Vol. 2, p. 1457, 1995. Such salts can be prepared using the appropriate corresponding bases.

Pharmaceutically acceptable salts can be prepared by standard techniques. For example, the free-base form of a compound is dissolved in a suitable solvent, such as an aqueous or aqueous-alcohol in solution containing the appropriate acid and then isolated by evaporating the solution. In another example, a salt is prepared by reacting the free base and acid in an organic solvent.

Thus, for example, if the particular compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

Similarly, if the particular compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The pharmaceutically acceptable salt of the different compounds may be present as a complex. Examples of complexes include 8-chlorotheophylline complex (analogous to, e.g., dimenhydrinate: diphenhydramine 8-chlorotheophylline (1:1) complex; Dramamine) and various cyclodextrin inclusion complexes.

Unless specified to the contrary, specification of a compound herein includes pharmaceutically acceptable salts of such compound.

D. Polymorphic Forms

In the case of agents that are solids, it is understood by those skilled in the art that the compounds and salts may exist in different crystal or polymorphic forms, all of which are intended to be within the scope of the present invention and specified formulas.

XIV. Administration

The methods and compounds will typically be used in therapy for human subjects or patients. However, they may also be used to treat similar or identical diseases in other vertebrates such as other primates, sports animals, and pets such as horses, dogs and cats.

Suitable dosage forms, in part, depend upon the use or the route of administration, for example, oral, transdermal, transmucosal, inhalant, or by injection (parenteral). Such dosage forms should allow the compound to reach target cells. Other factors are well known in the art, and include considerations such as toxicity and dosage forms that retard the compound or composition from exerting its effects. Techniques and formulations generally may be found in Remington: *The Science and Practice of Pharmacy*, 21$^{st}$ edition, Lippincott, Williams and Wilkins, Philadelphia, Pa., 2005 (hereby incorporated by reference herein).

Compounds can be formulated as pharmaceutically acceptable salts. Pharmaceutically acceptable salts are non-toxic salts in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug.

Pharmaceutically acceptable salts include acid addition salts such as those containing sulfate, chloride, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see *Remington's Pharmaceutical Sciences*, 19$^{th}$ ed., Mack Publishing Co., Easton, Pa., Vol. 2, p. 1457, 1995. Such salts can be prepared using the appropriate corresponding bases.

Pharmaceutically acceptable salts can be prepared by standard techniques. For example, the free-base form of a compound is dissolved in a suitable solvent, such as an aqueous or aqueous-alcohol in solution containing the appropriate acid and then isolated by evaporating the solution. In another example, a salt is prepared by reacting the free base and acid in an organic solvent.

The pharmaceutically acceptable salt of the different compounds may be present as a complex. Examples of complexes include 8-chlorotheophylline complex (analogous to, e.g., dimenhydrinate: diphenhydramine 8-chlorotheophylline (1:1) complex; Dramamine) and various cyclodextrin inclusion complexes.

Carriers or excipients can be used to produce compositions. The carriers or excipients can be chosen to facilitate administration of the compound. Examples of carriers include calcium carbonate, calcium phosphate, various sugars such as lactose, glucose, or sucrose, or types of starch, cellulose derivatives, gelatin, vegetable oils, polyethylene glycols and physiologically compatible solvents. Examples of physiologically compatible solvents include sterile solutions of water for injection (WFI), saline solution, and dextrose.

The compounds can be administered by different routes including intravenous, intraperitoneal, subcutaneous, intramuscular, oral, transmucosal, rectal, inhalant or transdermal. For oral administration, for example, the compounds can be formulated into conventional oral dosage forms such as capsules, tablets, and liquid preparations such as syrups, elixirs, and concentrated drops.

Pharmaceutical preparations for oral use can be obtained, for example, by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone). If desired, disintegrating agents may be added, such as the cross-linked polyvinylpyrrolidone, agar, or alginic acid, or a salt thereof such as sodium alginate.

Dragee cores are provided with suitable coatings. For this purpose, concentrated sugar solutions may be used, which may optionally contain, for example, gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Alternatively, injection (parenteral administration) may be used, e.g., intramuscular, intravenous, intraperitoneal, and/or subcutaneous. For injection, the compounds of the invention are formulated in sterile liquid solutions, preferably in physiologically compatible buffers or solutions, such as saline solution, Hank's solution, or Ringer's solution. In addition, the compounds may be formulated in solid form and redissolved or suspended immediately prior to use. Lyophilized forms can also be produced.

Administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal).

For inhalants, compounds of the invention may be formulated as dry powder or a suitable solution, suspension, or aerosol. Powders and solutions may be formulated with suitable additives known in the art. For example, powders may include a suitable powder base such as lacatose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer and the like. The compounds of the invention may also be used in combination with other inhaled therapies, for example corticosteroids such as fluticasone proprionate, beclomethasone dipropionate, triamcinolone acetonide, budesonide, and mometasone furoate; beta agonists such as albuterol, salmeterol, and formoterol; anticholinergic agents such as ipratroprium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

It is understood that use in combination for any route of administration includes delivery of compounds of the invention and one or more other therapeutics delivered by the same route of administration together in any formulation, including formulations where the two compounds are chemically linked such that they maintain their therapeutic activity when administered. Combination use includes administration of co-formulations or formulations of chemically joined compounds, or co-administration of the compounds in separate formulations. Separate formulations may be co-administered by delivery via one device, for example the same inhalant device, the same syringe, etc., or can be co-administered from separate devices, where co-administration in this case means administered within a short time of each other. Co-formulations of a compound of the invention and one or more additional therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

The amounts of various compound to be administered can be determined by standard procedures taking into account factors such as the compound $IC_{50}$, the biological half-life of the compound, the age, size, and weight of the subject, and the disorder associated with the subject. The importance of these and other factors are well known to those of ordinary skill in the art. Generally, a dose will be between about 0.01 and 50 mg/kg, preferably 0.1 and 20 mg/kg of the subject being treated. Multiple doses may be used.

XV. Manipulation of PDE4B

As the full-length coding sequence and amino acid sequence of PDE4B from various mammals including human is known, cloning, construction of recombinant PDE4B, production and purification of recombinant protein, introduction of PDE4B into other organisms, and other molecular biological manipulations of PDE4B are readily performed.

Techniques for the manipulation of nucleic acids, such as, e.g., subcloning, labeling probes (e.g., random-primer labeling using Klenow polymerase, nick translation, amplification), sequencing, hybridization and the like are well disclosed in the scientific and patent literature, see, e.g., Sambrook, ed., Molecular Cloning: a Laboratory Manual (2nd ed.), Vols. 1-3, Cold Spring Harbor Laboratory, (1989); Current Protocols in Molecular Biology, Ausubel, ed. John Wiley & Sons, Inc., New York (1997); Laboratory Techniques in Biochemistry and Molecular Biology: Hybridization With Nucleic Acid Probes, Part I. Theory and Nucleic Acid Preparation, Tijssen, ed. Elsevier, N.Y. (1993).

Nucleic acid sequences can be amplified as necessary for further use using amplification methods, such as PCR, isothermal methods, rolling circle methods, etc., are well known to the skilled artisan. See, e.g., Saiki, "Amplification of Genomic DNA" in PCR Protocols, Innis et al., Eds., Academic Press, San Diego, Calif. 1990, pp 13-20; Wharam et al., *Nucleic Acids Res.* 2001 Jun. 1; 29(11):E54-E54; Haffner et al., *Biotechniques* 2001 April; 30(4):852-6, 858, 860 passim; Zhong et al., *Biotechniques* 2001 April; 30(4):852-6, 858, 860 passim.

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immuno-electrophoresis, radioimmunoassays (RIAs), enzyme-linked immunosorbent assays (ELISAs), immuno-fluorescent assays, Southern analysis, Northern analysis, dot-blot analysis, gel electrophoresis (e.g., SDS-PAGE), nucleic acid or target or signal amplification methods, radiolabeling, scintillation counting, and affinity chromatography.

Obtaining and manipulating nucleic acids used to practice the methods of the invention can be performed by cloning from genomic samples, and, if desired, screening and re-cloning inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) *Nat. Genet.* 15:333-335; yeast artificial chromosomes (YAC); bacterial artificial chromosomes (BAC); P1 artificial chromosomes, see, e.g., Woon (1998) *Genomics* 50:306-316; P1-derived vectors (PACs), see, e.g., Kern (1997) *Biotechniques* 23:120-124; cosmids, recombinant viruses, phages or plasmids.

The nucleic acids of the invention can be operatively linked to a promoter. A promoter can be one motif or an array of nucleic acid control sequences which direct transcription of a nucleic acid. A promoter can include necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter which is active under most environmental and developmental conditions. An "inducible" promoter is a promoter which is under environmental or developmental regulation. A "tissue specific" promoter is active in certain tissue types of an organism, but not in other tissue types from the same organism. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The nucleic acids of the invention can also be provided in expression vectors and cloning vehicles, e.g., sequences encoding the polypeptides of the invention. Expression vectors and cloning vehicles of the invention can comprise viral particles, baculovirus, phage, plasmids, phagemids, cosmids, fosmids, bacterial artificial chromosomes, viral DNA (e.g., vaccinia, adenovirus, foul pox virus, pseudorabies and derivatives of SV40), P1-based artificial chromosomes, yeast plasmids, yeast artificial chromosomes, and any other vectors specific for specific hosts of interest (such as *bacillus*, *Aspergillus* and yeast). Vectors of the invention can include chromosomal, non-chromosomal and synthetic DNA sequences. Large numbers of suitable vectors are known to those of skill in the art, and are commercially available.

The nucleic acids of the invention can be cloned, if desired, into any of a variety of vectors using routine molecular biological methods; methods for cloning in vitro amplified nucleic acids are disclosed, e.g., U.S. Pat. No. 5,426,039. To facilitate cloning of amplified sequences, restriction enzyme sites can be "built into" a PCR primer pair. Vectors may be introduced into a genome or into the cytoplasm or a nucleus of a cell and expressed by a variety of conventional techniques, well described in the scientific and patent literature. See, e.g., Roberts (1987) *Nature* 328:731; Schneider (1995) *Protein Expr. Purif.* 6435:10; Sambrook, Tijssen or Ausubel. The vectors can be isolated from natural sources, obtained from such sources as ATCC or GenBank libraries, or prepared by synthetic or recombinant methods. For example, the nucleic acids of the invention can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required.

The nucleic acids can be administered in vivo for in situ expression of the peptides or polypeptides of the invention. The nucleic acids can be administered as "naked DNA" (see, e.g., U.S. Pat. No. 5,580,859) or in the form of an expression vector, e.g., a recombinant virus. The nucleic acids can be administered by any route, including peri- or intra-tumorally, as described below. Vectors administered in vivo can be derived from viral genomes, including recombinantly modified enveloped or non-enveloped DNA and RNA viruses, preferably selected from baculoviridiae, parvoviridiae, picornoviridiae, herpesveridiae, poxyiridae, adenoviridiae, or picornnaviridiae. Chimeric vectors may also be employed which exploit advantageous merits of each of the parent vector properties (See e.g., Feng (1997) *Nature Biotechnology* 15:866-870). Such viral genomes may be modified by recombinant DNA techniques to include the nucleic acids of the invention; and may be further engineered to be replication deficient, conditionally replicating or replication competent.

In alternative aspects, vectors are derived from the adenoviral (e.g., replication incompetent vectors derived from the human adenovirus genome, see, e.g., U.S. Pat. Nos. 6,096, 718; 6,110,458; 6,113,913; 5,631,236); adeno-associated viral and retroviral genomes. Retroviral vectors can include those based upon murine leukemia virus (MuLV), gibbon ape leukemia virus (GaLV), Simian Immuno deficiency virus (SIV), human immuno deficiency virus (HIV), and combinations thereof; see, e.g., U.S. Pat. Nos. 6,117,681; 6,107,478; 5,658,775; 5,449,614; Buchscher (1992) *J. Virol.* 66:2731-2739; Johann (1992) *J. Virol.* 66:1635-1640). Adeno-associated virus (AAV)-based vectors can be used to transduce cells with target nucleic acids, e.g., in the in vitro production of nucleic acids and peptides, and in in vivo and ex vivo gene therapy procedures; see, e.g., U.S. Pat. Nos. 6,110,456; 5,474,935; Okada (1996) *Gene Ther.* 3:957-964.

The present invention also relates to fusion proteins, and nucleic acids encoding them. A polypeptide of the invention can be fused to a heterologous peptide or polypeptide, such as N-terminal identification peptides which impart desired characteristics, such as increased stability or simplified purification. Peptides and polypeptides of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) *Biochemistry* 34:1787-1797; Dobeli (1998) *Protein Expr. Purif.* 12:404-414). The histidine residues facilitate detection and purification while the enterokinase cleavage site provides a means for purifying the epitope from the remainder of the fusion protein. In one aspect, a nucleic acid encoding a polypeptide of the invention is assembled in appropriate phase with a leader sequence capable of directing secretion of the translated polypeptide or fragment thereof. Technology pertaining to vectors encoding fusion proteins and application of fusion proteins are well disclosed in the scientific and patent literature, see e.g., Kroll (1993) *DNA Cell. Biol.* 12:441-53.

The nucleic acids and polypeptides of the invention can be bound to a solid support, e.g., for use in screening and diagnostic methods. Solid supports can include, e.g., membranes (e.g., nitrocellulose or nylon), a microtiter dish (e.g., PVC, polypropylene, or polystyrene), a test tube (glass or plastic), a dip stick (e.g., glass, PVC, polypropylene, polystyrene, latex and the like), a microfuge tube, or a glass, silica, plastic, metallic or polymer bead or other substrate such as paper. One solid support uses a metal (e.g., cobalt or nickel)-comprising column which binds with specificity to a histidine tag engineered onto a peptide.

Adhesion of molecules to a solid support can be direct (i.e., the molecule contacts the solid support) or indirect (a "linker" is bound to the support and the molecule of interest binds to this linker). Molecules can be immobilized either covalently (e.g., utilizing single reactive thiol groups of cysteine residues (see, e.g., Colliuod (1993) *Bioconjugate Chem.* 4:528-536) or non-covalently but specifically (e.g., via immobilized antibodies (see, e.g., Schuhmann (1991) *Adv. Mater.* 3:388-391; Lu (1995) *Anal. Chem.* 67:83-87; the biotin/strepavidin system (see, e.g., Iwane (1997) *Biophys. Biochem. Res. Comm.* 230:76-80); metal chelating, e.g., Langmuir-Blodgett films (see, e.g., Ng (1995) *Langmuir* 11:4048-55); metal-chelating self-assembled monolayers (see, e.g., Sigal (1996) *Anal. Chem.* 68:490-497) for binding of polyhistidine fusions.

Indirect binding can be achieved using a variety of linkers which are commercially available. The reactive ends can be any of a variety of functionalities including, but not limited to: amino reacting ends such as N-hydroxysuccinimide (NHS) active esters, imidoesters, aldehydes, epoxides, sulfonyl halides, isocyanate, isothiocyanate, and nitroaryl halides; and thiol reacting ends such as pyridyl disulfides, maleimides, thiophthalimides, and active halogens. The heterobifunctional crosslinking reagents have two different reactive ends, e.g., an amino-reactive end and a thiol-reactive end, while homobifunctional reagents have two similar reactive ends, e.g., bismaleimidohexane (BMH) which permits the cross-linking of sulfhydryl-containing compounds. The spacer can be of varying length and be aliphatic or aromatic. Examples of commercially available homobifunctional cross-linking reagents include, but are not limited to, the imidoesters such as dimethyl adipimidate dihydrochloride (DMA); dimethyl pimelimidate dihydrochloride (DMP); and dimethyl suberimidate dihydrochloride (DMS). Heterobifunctional reagents include commercially available active halogen-NHS active esters coupling agents such as N-succinimidyl bromoacetate and N-succinimidyl (4-iodoacetyl)aminobenzoate (SIAB) and the sulfosuccinimidyl derivatives such as sulfosuccinimidyl(4-iodoacetyl)aminobenzoate (sulfo-SIAB) (Pierce). Another group of coupling agents is the heterobifunctional and thiol cleavable agents such as N-succinimidyl 3-(2-pyridyldithio)propionate (SPDP) (Pierce Chemicals, Rockford, Ill.).

Antibodies can also be used for binding polypeptides and peptides of the invention to a solid support. This can be done directly by binding peptide-specific antibodies to the column or it can be done by creating fusion protein chimeras comprising motif-containing peptides linked to, e.g., a known epitope (e.g., a tag (e.g., FLAG, myc) or an appropriate immunoglobulin constant domain sequence (an "immunoadhesin," see, e.g., Capon (1989) *Nature* 377:525-531 (1989).

Nucleic acids or polypeptides of the invention can be immobilized to or applied to an array. Arrays can be used to screen for or monitor libraries of compositions (e.g., small molecules, antibodies, nucleic acids, etc.) for their ability to bind to or modulate the activity of a nucleic acid or a polypeptide of the invention. For example, in one aspect of the invention, a monitored parameter is transcript expression of a gene comprising a nucleic acid of the invention. One or more, or, all the transcripts of a cell can be measured by hybridization of a sample comprising transcripts of the cell, or, nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the invention. Polypeptide arrays" can also be used to simultaneously quantify a plurality of proteins.

The terms "array" or "microarray" or "biochip" or "chip" as used herein is a plurality of target elements, each target element comprising a defined amount of one or more polypeptides (including antibodies) or nucleic acids immobilized onto a defined area of a substrate surface. In practicing the methods of the invention, any known array and/or method of making and using arrays can be incorporated in whole or in part, or variations thereof, as disclosed, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) *Curr. Biol.* 8:R171-R174; Schummer (1997) *Biotechniques* 23:1087-1092; Kern (1997) *Biotechniques* 23:120-124; Solinas-Toldo (1997) *Genes, Chromosomes & Cancer* 20:399-407; Bowtell (1999) *Nature Genetics Supp.* 21:25-32. See also published U.S. patent applications Nos. 20010018642; 20010019827; 20010016322; 20010014449; 20010014448; 20010012537; 20010008765.

Host Cells and Transformed Cells

The invention also provides a transformed cell comprising a nucleic acid sequence of the invention, e.g., a sequence encoding a polypeptide of the invention, or a vector of the invention. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include *E. coli, Streptomyces, Bacillus subtilis, Salmonella typhimurium* and various species within the genera *Pseudomonas, Streptomyces*, and *Staphylococcus*. Exemplary insect cells include *Drosophila* S2 and *Spodoptera* Sf9. Exemplary animal cells include CHO, COS or Bowes melanoma or any mouse or human cell line. The selection of an appropriate host is within the abilities of those skilled in the art.

Vectors may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation.

Engineered host cells can be cultured in conventional nutrient media modified as appropriate for activating promoters, selecting transformants or amplifying the genes of the invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides of the invention may or may not also include an initial methionine amino acid residue.

Cell-free translation systems can also be employed to produce a polypeptide of the invention. Cell-free translation systems can use mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

For transient expression in mammalian cells, cDNA encoding a polypeptide of interest may be incorporated into a mammalian expression vector, e.g. pcDNA1, which is available commercially from Invitrogen Corporation (San Diego, Calif., U.S.A.; catalogue number V490-20). This is a multifunctional 4.2 kb plasmid vector designed for cDNA expression in eukaryotic systems, and cDNA analysis in prokaryotes, incorporated on the vector are the CMV promoter and enhancer, splice segment and polyadenylation signal, an SV40 and Polyoma virus origin of replication, and M13 origin to rescue single strand DNA for sequencing and mutagenesis, Sp6 and T7 RNA promoters for the production of sense and anti-sense RNA transcripts and a Col E1-like high copy plasmid origin. A polylinker is located appropriately downstream of the CMV promoter (and 3' of the T7 promoter).

The cDNA insert may be first released from the above phagemid incorporated at appropriate restriction sites in the pcDNAI polylinker. Sequencing across the junctions may be performed to confirm proper insert orientation in pcDNAI. The resulting plasmid may then be introduced for transient expression into a selected mammalian cell host, for example, the monkey-derived, fibroblast like cells of the COS-1 lineage (available from the American Type Culture Collection, Rockville, Md. as ATCC CRL 1650).

For transient expression of the protein-encoding DNA, for example, COS-1 cells may be transfected with approximately 8 μg DNA per $10^6$ COS cells, by DEAE-mediated DNA transfection and treated with chloroquine according to the procedures described by Sambrook et al, Molecular Cloning: A Laboratory Manual, 1989, Cold Spring Harbor Laboratory Press, Cold Spring Harbor N.Y, pp. 16.30-16.37. An exemplary method is as follows. Briefly, COS-1 cells are plated at a density of $5\times10^6$ cells/dish and then grown for 24 hours in FBS-supplemented DMEM/F12 medium. Medium is then removed and cells are washed in PBS and then in medium. A transfection solution containing DEAE dextran (0.4 mg/ml), 100 μM chloroquine, 10% NuSerum, DNA (0.4 mg/ml) in DMEM/F12 medium is then applied on the cells 10 ml volume. After incubation for 3 hours at 37° C., cells are washed in PBS and medium as just described and then shocked for 1 minute with 10% DMSO in DMEM/F12 medium. Cells are allowed to grow for 2-3 days in 10% FBS-supplemented medium, and at the end of incubation dishes are placed on ice, washed with ice cold PBS and then removed by scraping. Cells are then harvested by centrifugation at 1000 rpm for 10 minutes and the cellular pellet is frozen in liquid nitrogen, for subsequent use in protein expression. Northern blot analysis of a thawed aliquot of frozen cells may be used to confirm expression of receptor-encoding cDNA in cells under storage.

In a like manner, stably transfected cell lines can also prepared, for example, using two different cell types as host: CHO K1 and CHO Pro5. To construct these cell lines, cDNA coding for the relevant protein may be incorporated into the mammalian expression vector pRC/CMV (Invitrogen), which enables stable expression. Insertion at this site places the cDNA under the expression control of the cytomegalovirus promoter and upstream of the polyadenylation site and terminator of the bovine growth hormone gene, and into a vector background comprising the neomycin resistance gene (driven by the SV40 early promoter) as selectable marker.

An exemplary protocol to introduce plasmids constructed as described above is as follows. The host CHO cells are first seeded at a density of $5 \times 10^5$ in 10% FBS-supplemented MEM medium. After growth for 24 hours, fresh medium is added to the plates and three hours later, the cells are transfected using the calcium phosphate-DNA co-precipitation procedure (Sambrook et al, supra). Briefly, 3 μg of DNA is mixed and incubated with buffered calcium solution for 10 minutes at room temperature. An equal volume of buffered phosphate solution is added and the suspension is incubated for 15 minutes at room temperature. Next, the incubated suspension is applied to the cells for 4 hours, removed and cells were shocked with medium containing 15% glycerol. Three minutes later, cells are washed with medium and incubated for 24 hours at normal growth conditions. Cells resistant to neomycin are selected in 10% FBS-supplemented alpha-MEM medium containing G418 (1 mg/ml). Individual colonies of G418-resistant cells are isolated about 2-3 weeks later, clonally selected and then propagated for assay purposes.

EXAMPLES

A number of examples involved in the present invention are described below. In most cases, alternative techniques could also be used. The examples are intended to be illustrative and are not limiting or restrictive to the scope of the invention.

Example 1

Synthesis of Compounds of Formula Ia

Scheme - 1

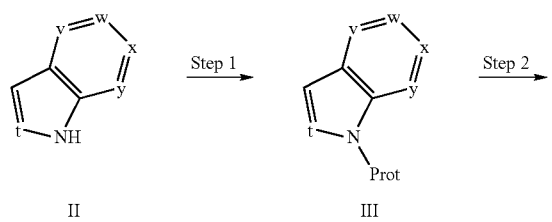

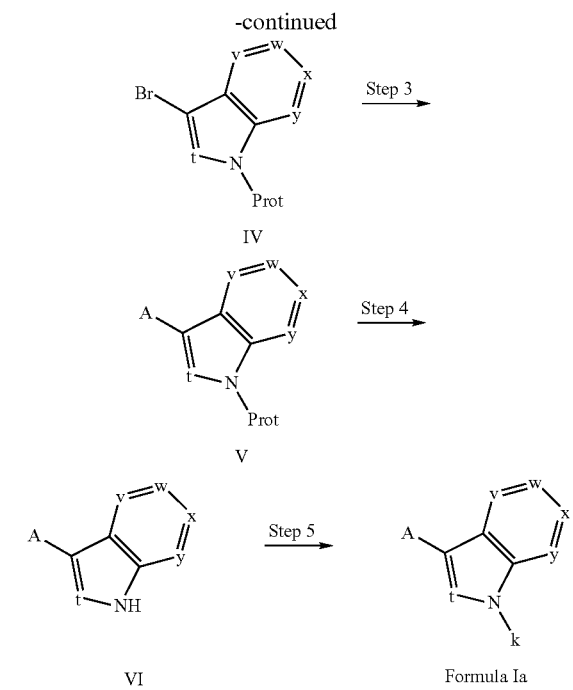

Step-1 Synthesis of Formula III

Compound of Formula III can be prepared from commercially available compound II by reacting with a reagent containing a leaving group, e.g. chloro, tosyl, etc., in presence of a base, e.g. triethyl amine, pyridine, aqueous hydroxides, etc., in a polar solvent, e.g, dimethylformamide (DMF), or water (Greene, T. W.; Wuts, P.G.M. *Protective Groups in Organic Synthesis*, 3$^{rd}$ ed.; John Wiley & Sons: New York, 1999). The product can be isolated by conventional work up procedure, e.g. extraction of the product with an organic solvent and evaporation.

Step-2 Synthesis of Formula IV

Compound of Formula IV can be prepared from compound III by reacting with bromine in carbon tetrachloride or N-bromosuccinimide in THF. The product can be isolated by conventional work up procedure, e.g. extraction of the product with an organic solvent and purifying by column chromatography.

Step-3 Synthesis of Formula V

Compound of Formula V can be prepared from compound IV by reacting with boronic acids under Suzuki reaction conditions (Smith M. B.; March, J. *March's Advanced Organic Chemistry: Reactions, Mechanisms, and Structure*, 5$^{th}$ ed.; John Wiley & Sons: New York, 2001 p 868). Alternately, compound IV can also be reacted with tin, zinc, or copper reagents, under Stille, Negishi or cuprate coupling reaction conditions, respectively (Smith M. B.; March, J. *March's Advanced Organic Chemistry: Reactions, Mechanisms, and Structure*, 5$^{th}$ ed.; John Wiley & Sons: New York, 2001 p 931), to provide compound V. The product can be isolated by conventional work up procedure, e.g. extraction of the product with an organic solvent and purifying by column chromatography.

Step-4 Synthesis of Formula VI

Compound of formula VI can be prepared by reacting compound V with fluorides (for silyl protecting groups—tetrabutyl ammonium fluoride or ammonium fluoride) (Greene, T. W.; Wuts, P.G.M. *Protective Groups in Organic Synthesis*, $3^{rd}$ ed.; John Wiley & Sons: New York, 1999, p 620), base (for aryl sulfone protecting groups—aqueous potassium hydroxide) (Greene, T. W.; Wuts, P.G.M. *Protective Groups in Organic Synthesis*, 3rd ed.; John Wiley & Sons: New York, 1999, p 615), or an acid (for carbamates—trifluoroacetic acid) (Greene, T. W.; Wuts, P.G.M. *Protective Groups in Organic Synthesis*, $3^{rd}$ ed.; John Wiley & Sons: New York, 1999, p 272) and isolating the product following standard workup procedures, e.g. extraction of the product with organic solvent and purifying by column chromatography.

Step-5 Synthesis of Formula Ia

Compounds of Formula Ia can be prepared by reacting compound VI with nucleophilic reagents, e.g. acid chlorides, sulfonyl chlorides, isocyanates, isothiocyanates, alkyl halides, benzyl halides, etc., under basic conditions (General reference: Smith M. B.; March, J. *March's Advanced Organic Chemistry: Reactions, Mechanisms, and Structure*, $5^{th}$ ed.; John Wiley & Sons: New York, 2001). The product can be isolated by following standard workup procedures, e.g. extraction of the product with organic solvent and purifying by column chromatography.

Example 2

Alternate Synthesis of Compounds of Formula Ia

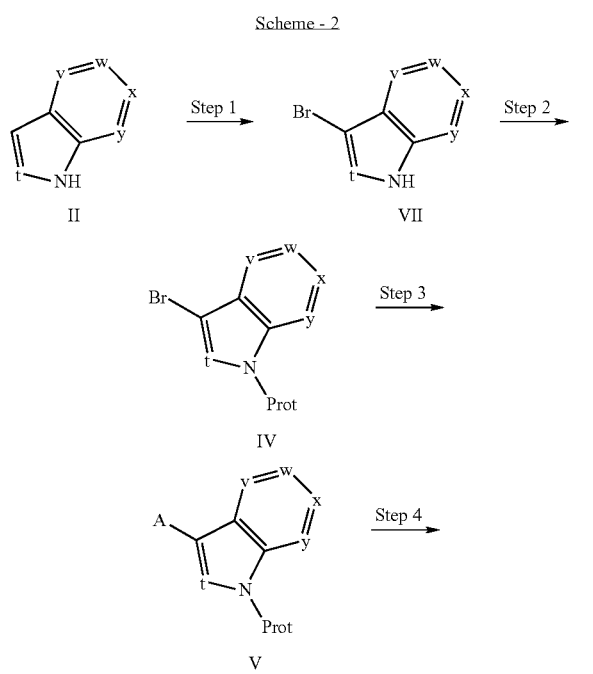

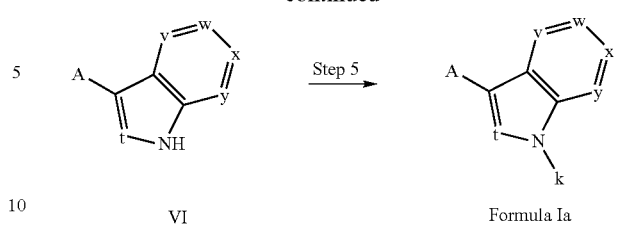

Step-1 Synthesis of Formula VII

Compound of Formula VII can be prepared from commercially available compound II by reacting with bromine in carbon tetrachloride at low temperature, for example −20° C., or N-bromosuccinimide in THF. The product can be isolated by conventional work up procedure, e.g. extraction of the product with an organic solvent and purifying by column chromatography.

Step-2 Synthesis of Formula IV

Compound of Formula IV can be prepared from compound VII by reacting with a reagent containing a leaving group, e.g. chloro, tosyl, etc., in presence of a base, e.g. triethyl amine, pyridine, aqueous hydroxides, etc., in a polar solvent, e.g, dimethylformamide (DMF), or water. The product can be isolated by conventional work up procedure, e.g. extraction of the product with an organic solvent and evaporation.

Step-3 Synthesis of Formula V

Compound of Formula V can be prepared from compound IV by reacting with boronic acids under Suzuki reaction conditions. Alternately, compound IV can also be reacted with tin, zinc, or copper reagents, under Stille, Negishi or cuprate coupling reaction conditions respectively, to provide compound V. The product can be isolated by conventional work up procedure, e.g. extraction of the product with an organic solvent and purifying by column chromatography.

Step-4 Synthesis of Formula VI

Compound of Formula VI can be prepared by reacting compound V with fluorides (for silyl protecting groups—tetrabutyl ammonium fluoride, or ammonium fluoride), base (for aryl sulfone protecting groups—aqueous potassium hydroxide), or an acid (for carbamates—trifluoroacetic acid) and isolating the product following standard workup procedures, e.g. extraction of the product with organic solvent and purifying by column chromatography.

Step-5 Synthesis of Formula Ia

Compound of Formula Ia can be prepared by reacting compound VI with nucleophilic reagents, e.g. acid chlorides, sulfonyl chlorides, isocyanates, isothiocyanates, etc., under basic conditions. The product can be isolated by following standard workup procedures, e.g. extraction of the product with organic solvent and purifying by column chromatography.

Example 3

Alternate Synthesis of Compounds of Formula Ia

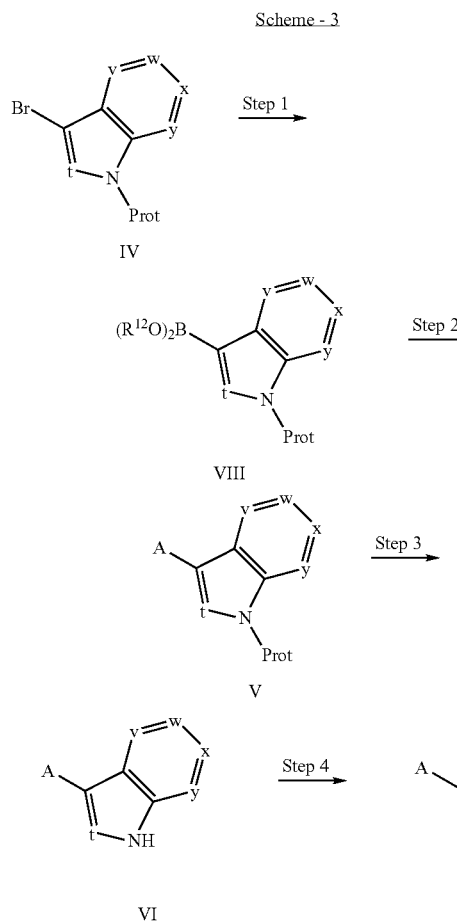

Step-1 Synthesis of Formula VIII

Compound of Formula VIII can be prepared from compound IV by reacting with the tributyl ester of boronic acid as described by Gilman et al. in J. Am. Chem. Soc., 1957, 79, 3077. The product can be isolated by conventional work up procedure, e.g. extraction of the product with an organic solvent and purifying by column chromatography.

Step-2 Synthesis of Formula V

Compound of Formula V can be prepared by reacting compound VIII with compounds of Formula A-Br or A-I under Suzuki reaction conditions and isolating the product following standard workup procedures, e.g. extraction of the product with organic solvent and purifying by column chromatography.

Step-3 Synthesis of Formula VI

Compound of Formula VI can be prepared by reacting compound V with fluorides (for silyl protecting groups—tetrabutyl ammonium fluoride, or ammonium fluoride), base (for aryl sulfone protecting groups—aqueous potassium hydroxide), or an acid (for carbamates—trifluoroacetic acid) and isolating the product following standard workup procedures, e.g. extraction of the product with organic solvent and purifying by column chromatography

Step-4 Synthesis of Formula Ia

Compound of Formula Ia can be prepared by reacting compound VI with nucleophilic reagents, e.g. acid chlorides, sulfonyl chlorides, isocyanates, isothiocyanates, etc., under basic conditions. The product can be isolated by following standard workup procedures, e.g. extraction of the product with organic solvent and purifying by column chromatography.

Example 4

Alternate Synthesis of Compounds of Formula Ia

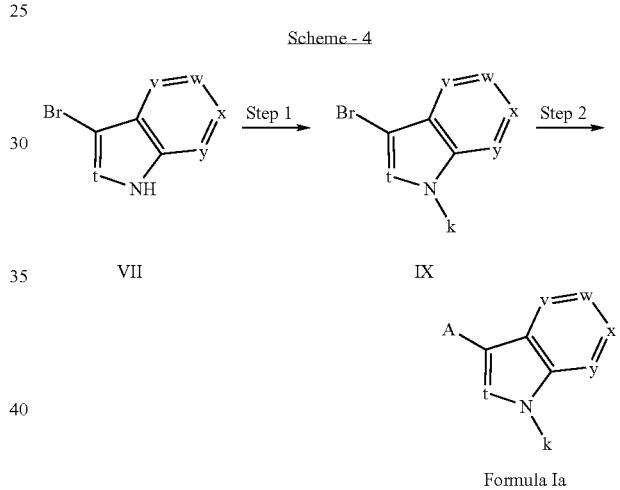

Step-1 Synthesis of Formula IX

Compound of Formula IX can be prepared by reacting compound VII with nucleophilic reagents, e.g. acid chlorides, sulfonyl chlorides, isocyanates, isothiocyanates, alkyl halides, benzyl halides, etc., under basic conditions. The product can be isolated by following standard workup procedures, e.g. extraction of the product with organic solvent and purifying by column chromatography.

Step-2 Synthesis of Formula Ia

Compound of Formula Ia can be prepared from compound IX by reacting with boronic acids under Suzuki reaction conditions (aqueous base and Pd(0) catalyst or anhydrous conditions with KF in dioxane with Pd(0) catalyst). Alternately, compound IX can also be reacted with a tin reagent, zinc reagent or copper reagent, under Stille, Negishi or cuprate coupling reaction conditions respectively, to provide compound Ia. The product can be isolated by conventional work up procedure, e.g. extraction of the product with an organic solvent and purifying by column chromatography.

Example 5

Alternate Synthesis of Compounds of Formula Ia

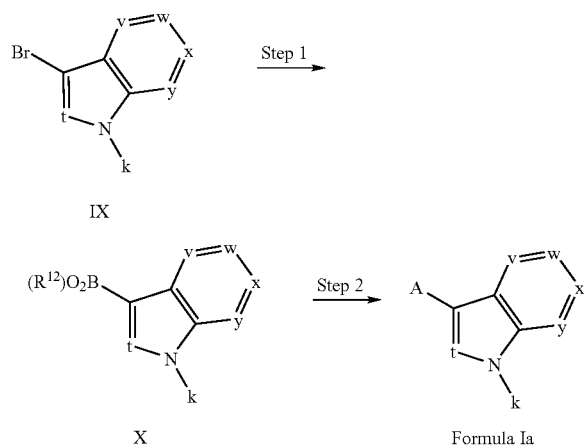

Scheme - 5

Step-1 Synthesis of Formula X

Compound of Formula X can be prepared from compound IX by reacting with tributyl ester of boronic acid as described by Gilman et. al. in *J. Am. Chem. Soc.,* 1957, 79, 3077. The product can be isolated by conventional work up procedure, e.g. extraction of the product with an organic solvent and purifying by column chromatography.

Step-2 Synthesis of Formula Ia

Compound of Formula Ia can be prepared by reacting compound X with compounds of Formula A-Br or A-I under Suzuki reaction conditions and isolating the product following standard workup procedures, e.g. extraction of the product with organic solvent and purifying by column chromatography.

Example 6

Alternate Synthesis of Compounds of Formula Ia

Scheme - 6

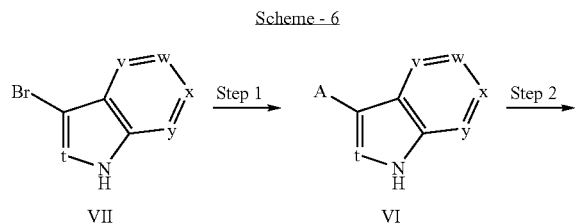

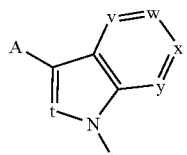

Formula Ia

Step-1 Synthesis of Formula VI

Compound of Formula VI can be prepared from compound VII by reacting with boronic acids under Suzuki reaction conditions (aqueous base and Pd(0) catalyst or anhydrous conditions with KF in dioxane with Pd(0) catalyst). Alternately, compound VII can also be reacted with a tin reagent, zinc reagent or copper reagent, under Stille, Negishi or cuprate coupling reaction conditions respectively, to provide compound VI. The product can be isolated by conventional work up procedure, e.g. extraction of the product with an organic solvent and purifying by column chromatography.

Step-2 Synthesis of Formula Ia

Compound of Formula Ia can be prepared by reacting compound VI with nucleophilic reagents, e.g. acid chlorides, sulfonyl chlorides, isocyanates, isothiocyanates, alkyl halides, benzyl halides, etc., under basic conditions. The product can be isolated by following standard workup procedures, e.g. extraction of the product with organic solvent and purifying by column chromatography.

Example 7

Synthesis of Intermediate
3-(3,4-dimethoxy-phenyl)-1H-pyrrolo[2,3-b]pyridine 1

Scheme - 7

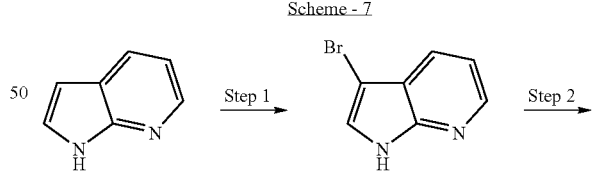

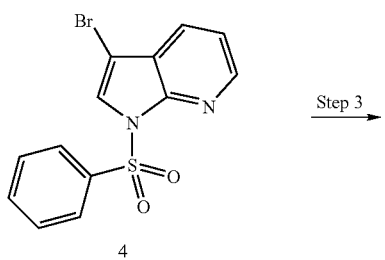

-continued

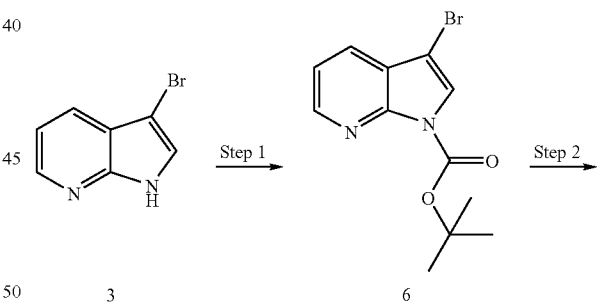

5

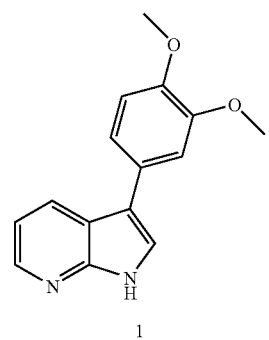

1

Step 1—Preparation of 3-bromo-1H-pyrrolo[2,3-b]pyridine 3

7-Azaindole (2, 3.57 g, 30.2 mmol) was dissolved in tetrahydrofuran (240 mL) under an atmosphere of nitrogen. At −40° C., N-bromosuccinimide (5.38 g, 30.2 mmol) in tetrahydrofuran was added under an atmosphere of nitrogen. The reaction mixture was stirred for a few hours as it was gradually warmed to room temperature and the reaction was followed by TLC. The reaction was quenched with sodium thiosulfate pentahydrate (7.50 g, 30.2 mmol) in water (1M). Two layers were separated, and the aqueous layer was extracted with ethyl acetate. The combined organic layers were washed with water, brine, dried with anhydrous sodium sulfate, and evaporated to dryness. The crude material was purified by column chromatography (25-40% ethyl acetate in hexanes) to yield the desired product as a white solid, 3, (4.20 g, 21.3 mmol). MS(ESI) $[M+H^+]^+$=198.5.

Step 2—Preparation of 1-benzenesulfonyl-3-bromo-1H-pyrrolo[2,3-b]pyridine 4

3-Bromo-1H-pyrrolo[2,3-b]pyridine (3, 280 mg, 1.4 mmol) was dissolved in acetone (15 mL) and potassium carbonate (220 mg, 1.6 mmol) was added, followed by benzenesulfonyl chloride (0.2 mL, 1.6 mmol). The reaction mixture was heated to reflux overnight, filtered and concentrated under reduced pressure. The resulting solid was purified by flash chromatography (5%-20% ethyl acetate:hexanes) to provide the desired product, 4, (300 mg, 47%). MS(ESI) $[M+H^+]^+$=455.0.

Step 3—Preparation of 1-benzenesulfonyl-3-(3,4-dimethoxy-phenyl)-1H-pyrrolo[2,3-b]pyridine 5

1-Benzenesulfonyl-3-bromo-1H-pyrrolo[2,3-b]pyridine (4, 1.00 g, 2.96 mmol) was dissolved in tetrahydrofuran (16 mL) and 3,4-dimethoxyphenyl boronic acid (1.35 g, 7.41 mmol), tetrakis(triphenylphosphine)palladium(0) (200 mg, 0.1 mmol), and 1 M potassium carbonate (8 mL) were added. The reaction mixture was heated in a CEM Discover microwave at 120° C. for 10 minutes. The reaction mixture was concentrated under reduced pressure and partitioned between ethyl acetate and water. The organic portions were dried with anhydrous magnesium sulfate, filtered, and the filtrate was adsorbed onto silica. The mixture was purified by flash chromatography (30% ethyl acetate:hexanes) to provide the desired product, 5, (909 mg, 78%). MS(ESI) $[M+H^+]^+$=394.9.

Step 4—Preparation of 3-(3,4-dimethoxy-phenyl)-1H-pyrrolo[2,3-b]pyridine 1

1-Benzenesulfonyl-3-(3,4-dimethoxy-phenyl)-1H-pyrrolo[2,3-b]pyridine (5, 290 mg, 0.74 mmol) was dissolved in ethanol (4 mL) and potassium hydroxide pellets (330 mg, 5.9 mmol) were added. The reaction was heated in a CEM Discover microwave instrument at 120° C. for 10 minutes. The reaction mixture was concentrated to dryness and the residue was partitioned between ethyl acetate and saturated sodium bicarbonate. The organic portions were dried with anhydrous magnesium sulfate, filtered and the filtrate concentrated to provide the desired product, 1, which was used without further purification (191 mg). MS(ESI) $[M+H^+]^+$=255.1.

Example 8

Alternative Synthesis of the Key Intermediate 3-(3,4-dimethoxy-phenyl)-1H-pyrrolo[2,3-b]pyridine 1

Scheme - 8

Step-1 Preparation of 3-Bromo-pyrrolo[2,3-b]pyridine-1-carboxylic acid tert-butyl ester 6

Into a round bottom flask was added 3-bromo-7-azaindole (3, 2.6 g, 13.0 mmol) and N,N-dimethylformamide (50 mL) and sodium hydride (60% dispersion in mineral oil) (550 mg, 14.0 mmol) under an atmosphere of nitrogen. The reaction mixture was stirred at room temperature for 30 minutes, followed by addition of di-tert-butyldicarbonate (4.0 g, 18.0 mmol). The reaction mixture was stirred at room temperature overnight and was poured into water and extracted into ethyl acetate. The organic layer was washed with brine and dried over anhydrous sodium sulfate. The crude material was purified by column chromatography (30% ethyl acetate in hexane) to yield the desired product, 6, as a solid (3.0 g, 10.1 mmol).

Step 2—Preparation of 3-(3,4-dimethoxy-phenyl)-1H-pyrrolo[2,3-b]pyridine 1

Into a round bottom flask was added 3-Bromo-pyrrolo[2,3-b]pyridine-1-carboxylic acid tert-butyl ester (6, 2.8 g, 9.4 mmol) and tetrahydrofuran (100 mL). Tetrakis(triphenylphosphine)palladium(0) (500 mg, 0.50 mmol), 3,4-dimethoxyphenylboronic acid (2.1 g, 11 mmol) and 1 M $K_2CO_3$ solution (50 mL) The reaction mixture was stirred at 65° C. overnight. The reaction mixture was poured into water and extracted into ethyl acetate. The organic layer was washed with brine and dried over anhydrous magnesium sulfate. The crude material was purified by column chromatography (gradient system of hexanes and ethyl acetate) to yield the titled compound, 1, (500 mg, 2 mmol, 20%) and 3-(3,4-dimethoxy-phenyl)-pyrrolo[2,4-b]pyridine-1-carboxylic acid tert-butyl ester (2.1 g, 5.9 mmol, 63%). The later compound can be easily converted to the desired compound, 1 by treatment with acid reagents such as TFA or HCl.

Example 9

Synthesis of 8-[3-(3,4-dimethoxy-phenyl)-pyrrolo[2,3-b]pyridine-1-sulfonyl]-quinoline 7

Scheme - 9

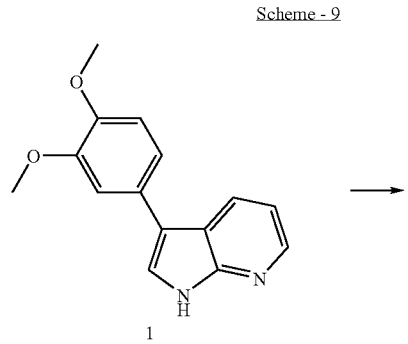

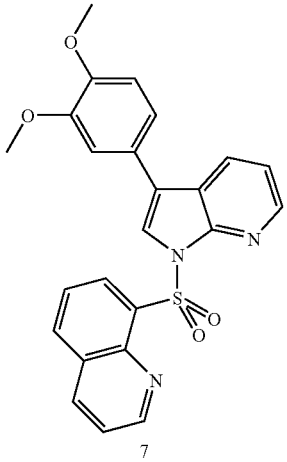

Preparation of 8-[3-(3,4-dimethoxy-phenyl)-pyrrolo[2,3-b]pyridine-1-sulfonyl]-quinoline 7

3-(3,4-Dimethoxy-phenyl)-1H-pyrrolo-[2,3-b]pyridine, 1, (50 mg, 0.20 mmol) was dissolved in methylene chloride (4 mL). Aqueous potassium hydroxide (50% wt/vol, 300 μL) and tetrabutylammonium hydrogen sulfate (2 mg, 0.007 mmol) were added. The reaction mixture was stirred for 10 minutes at room temperature. Into the reaction was added 8-quinoline-sulfonyl chloride (48 mg, 0.21 mmol) and the reaction mixture was stirred for 2 hours at room temperature. The reaction mixture was concentrated and the residue was washed with brine and ethyl acetate. The organic portion was dried with anhydrous sodium sulfate and filtered. The filtrate was concentrated and purified by preparative TLC (75% ethyl acetate:hexanes). The product was eluted from the silica with ethyl acetate and filtration. The filtrate was concentrated to provide 7 (14 mg, 16%). MS(ESI) $[M+H^+]^+=445.9$.

Example 10

Synthesis of 3-(3,4-dimethoxy-phenyl)-1-phenyl-methanesulfonyl-1H-pyrrolo[2,3-b]pyridine 8

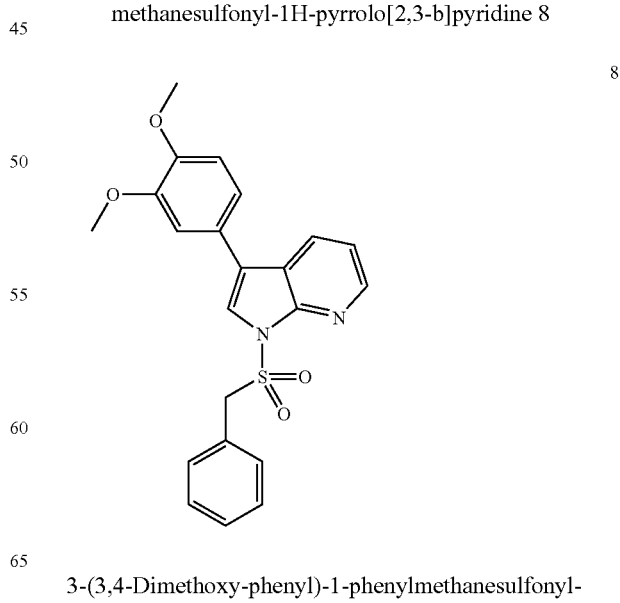

3-(3,4-Dimethoxy-phenyl)-1-phenylmethanesulfonyl-1H-pyrrolo[2,3-b]pyridine 8 was prepared using the same protocol as described in Example 9, substituting 8-quinoline-sulfonyl chloride with phenyl-methanesulfonyl chloride. MS(ESI) [M+H$^+$]$^+$=409.0.

Example 11

Synthesis of 1-(3-chloro-phenylmethanesulfonyl)-3-(3,4-dimethoxy-phenyl)-1H-pyrrolo[2,3-b]pyridine 9

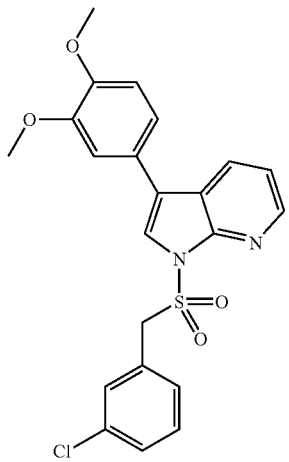

9

1-(3-Chloro-phenylmethanesulfonyl)-3-(3,4-dimethoxy-phenyl)-1H-pyrrolo[2,3-b]pyridine 9 was prepared using the same protocol as described in Example 9, substituting 8-quinoline-sulfonyl chloride with (3-chlorophenyl)-methanesulfonyl chloride. MS(ESI) [M+H$^+$]$^+$=443.3.

Example 12

Synthesis of 1-(Biphenyl-4-sulfonyl)-3-(3,4-dimethoxy-phenyl)-1H-pyrrolo[2,3-b]pyridine 10

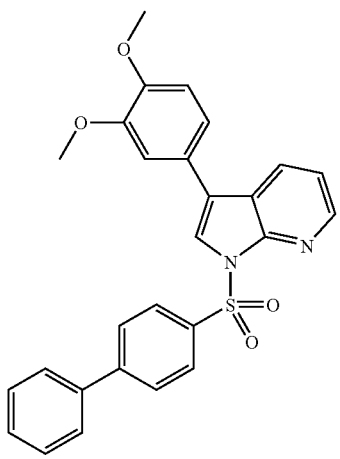

10

1-(Biphenyl-4-sulfonyl)-3-(3,4-dimethoxy-phenyl)-1H-pyrrolo[2,3-b]pyridine 10 was prepared using the same protocol as described in Example 9, substituting 8-quinoline sulfonyl chloride with biphenyl-4-sulfonyl chloride. The crude material was purified by preparative TLC (50% ethyl acetate:hexanes). The compound was eluted from silica with ethyl acetate and concentrated to provide an oil. The oil was washed with a minimum of methanol and a white precipitate was collected by filtration to provide 10. MS(ESI) [M+H$^+$]$^+$=471.0.

Example 13

Synthesis of 3-(3,4-Dimethoxy-phenyl)-1-(naphthalene-2-sulfonyl)-1H-pyrrolo[2,3-b]pyridine 11

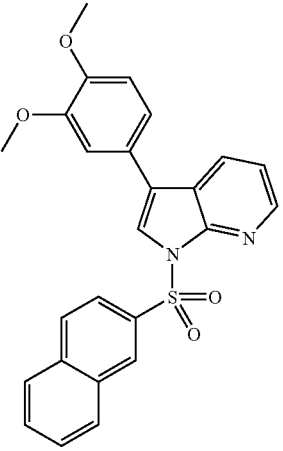

11

3-(3,4-Dimethoxy-phenyl)-1-(naphthalene-2-sulfonyl)-1H-pyrrolo[2,3-b]pyridine 11 was prepared using the same protocol as described in Example 9, substituting 8-quinoline sulfonyl chloride with 2-naphthalene-sulfonyl chloride. The crude material was purified by preparative TLC (50% ethyl acetate:hexanes). The compound was eluted from silica with ethyl acetate and concentrated to provide an oil. The oil was washed with a minimum of methanol and a white precipitate was collected by filtration to provide 11. MS(ESI) [M+H$^+$]$^+$=445.0.

Example 14

Synthesis of 3-(3,4-Dimethoxy-phenyl)-1-(4-methyl-naphthalene-1-sulfonyl)-1H-pyrrolo[2,3-b]pyridine 12

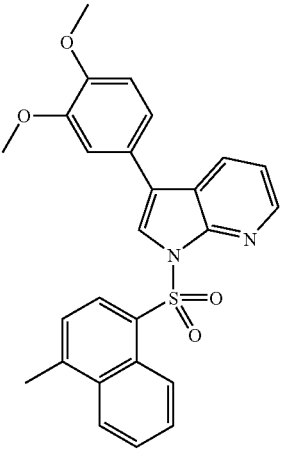

12

3-(3,4-Dimethoxy-phenyl)-1-(4-methyl-naphthalene-1-sulfonyl)-1H-pyrrolo[2,3-b]pyridine 12 was prepared using the same protocol as described in Example 9, substituting 8-quinoline sulfonyl chloride with 4-methyl-naphthalene-1-sulfonyl chloride. The crude oil was washed with ethyl acetate, which provided a solid that was washed with acetonitrile: water and methanol:methylene chloride to provide 12. MS(ESI) [M+H⁺]⁺=458.9.

Example 15

Synthesis of 8-[3-(3,4-Dimethoxy-phenyl)-pyrrolo[2,3-b]pyridine-1-sulfonyl]-3-methyl-quinoline 13

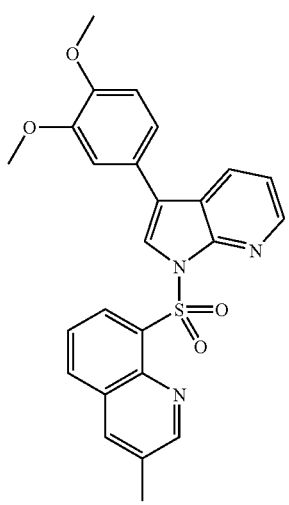

13

8-[3-(3,4-Dimethoxy-phenyl)-pyrrolo[2,3-b]pyridine-1-sulfonyl]-3-methyl-quinoline 13 was prepared using the same protocol as described in Example 9, substituting 8-quinoline sulfonyl chloride with 3-methyl-quinoline-8-sulfonyl chloride. The crude oil was washed with ethyl acetate, which provided a solid that was washed with acetonitrile, methanol and methylene chloride to provide 13. MS(ESI) [M+H⁺]⁺=460.0.

Example 16

Synthesis of 5-[3-(3,4-Dimethoxy-phenyl)-pyrrolo[2,3-b]pyridine-1-sulfonyl]-isoquinoline 14

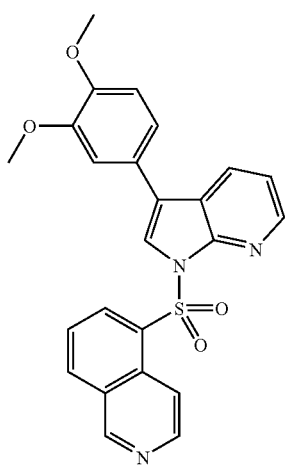

14

5-[3-(3,4-Dimethoxy-phenyl)-pyrrolo[2,3-b]pyridine-1-sulfonyl]-isoquinoline 14 was prepared using the same protocol as described in Example 9, substituting 8-quinoline sulfonyl chloride with isoquinoline-5-sulfonyl chloride. The crude mixture was purified by preparative TLC in two subsequent runs of 75% ethyl acetate:hexanes and 50% ethyl acetate: hexanes to provide 14. MS(ESI) [M+H⁺]⁺=446.0.

Example 17

Synthesis of 3-(3,4-Dimethoxy-phenyl)-1-(4-phenoxy-benzenesulfonyl)-1H-pyrrolo[2,3-b]pyridine 15

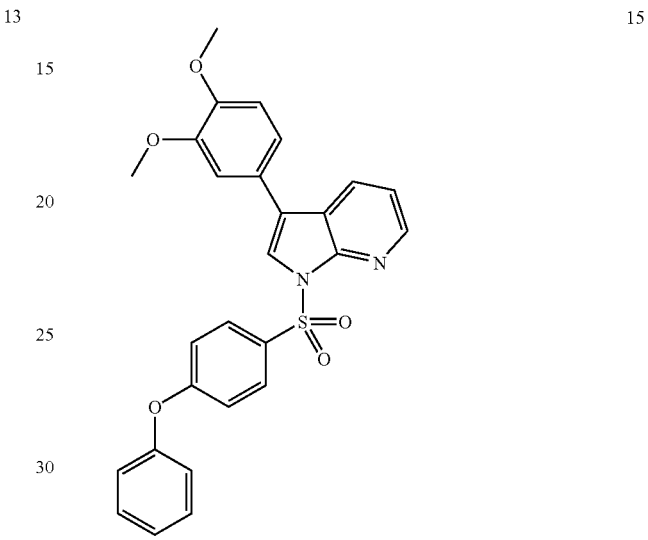

15

3-(3,4-Dimethoxy-phenyl)-1-(4-phenoxy-benzenesulfonyl)-1H-pyrrolo[2,3-b]pyridine 15 was prepared using the same protocol as described in Example 9, substituting 8-quinoline sulfonyl chloride with 4-phenoxy-benzenesulfonyl chloride. The crude mixture was crystallized from acetonitrile to provide 15. MS(ESI) [M+H⁺]⁺=487.1.

Example 18

Synthesis of 3-(3,4-Dimethoxy-phenyl)-1-(naphthalene-1-sulfonyl)-1H-pyrrolo[2,3-b]pyridine 16

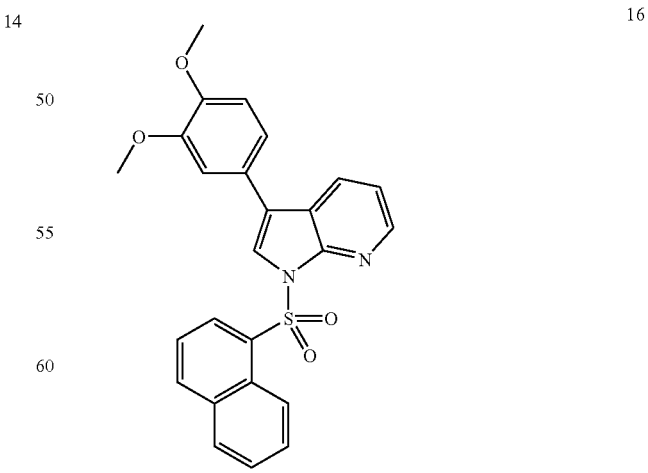

16

3-(3,4-Dimethoxy-phenyl)-1-(naphthalene-1-sulfonyl)-1H-pyrrolo[2,3-b]pyridine 16 was prepared using the same protocol as described in Example 9, substituting 8-quinoline sulfonyl chloride with 1-naphthalenesulfonyl chloride. MS(ESI) [M+H⁺]⁺=445.5.

Example 19

Synthesis of 1-(4-chloro-phenylmethanesulfonyl)-3-(3,4-dimethoxy-phenyl)-1H-pyrrolo[2,3-b]pyridine 17

Scheme - 10

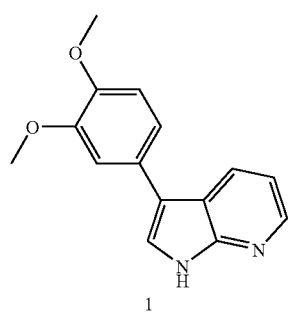

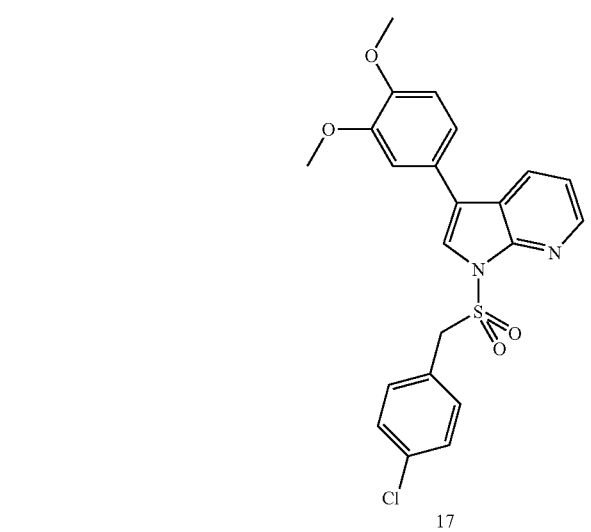

Preparation of 1-(4-chloro-phenylmethanesulfonyl)-3-(3,4-dimethoxy-phenyl)-1H-pyrrolo[2,3-b]pyridine 17

3-(3,4-Dimethoxy-phenyl)-1H-pyrrolo-[2,3-b]pyridine 1 (40 mg, 0.16 mmol) was dissolved in tetrahydrofuran (3.5 mL). Sodium hydride (60% dispersion in mineral oil, 10 mg, 0.24 mmol) was added. The reaction was stirred for 15 minutes. Into the reaction mixture was added (4-chloro-phenyl)-methanesulfonyl chloride (40 mg, 0.18 mmol). The mixture was stirred overnight, concentrated, and partitioned between brine and ethyl acetate. The organic portions was dried with anhydrous sodium sulfate, filtered, and concentrated. The product was purified by reverse phase HPLC with 40-100% acetonitrile: 0.1% aqueous formic acid. The appropriate fractions were lyophilized to provide 17 as the formate salt (7.5 mg, 11%). MS(ESI) [M+H⁺]⁺=443.0.

Example 20

Synthesis of 3-(3,4-dimethoxy-phenyl)-1-(3-nitro-phenylmethanesulfonyl)-1H-pyrrolo[2,3-b]pyridine 18

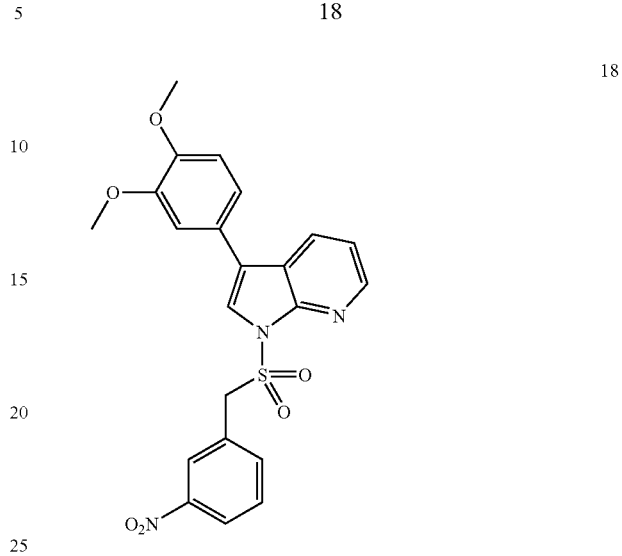

3-(3,4-Dimethoxy-phenyl)-1-(3-nitro-phenylmethanesulfonyl)-1H-pyrrolo[2,3-b]pyridine 18 was prepared using the same protocol as described in Example 19, substituting (4-chloro-phenyl)-methanesulfonyl chloride with (3-nitro-pheny)-methanesulfonyl chloride. The crude material was purified by preperative TLC (50% ethyl acetate:hexanes). MS(ESI) [M+H⁺]⁺=454.0.

Example 21

Synthesis of 1-benzenesulfonyl-3-(3,4-dimethoxy-phenyl)-1H-indole 19

Scheme - 11

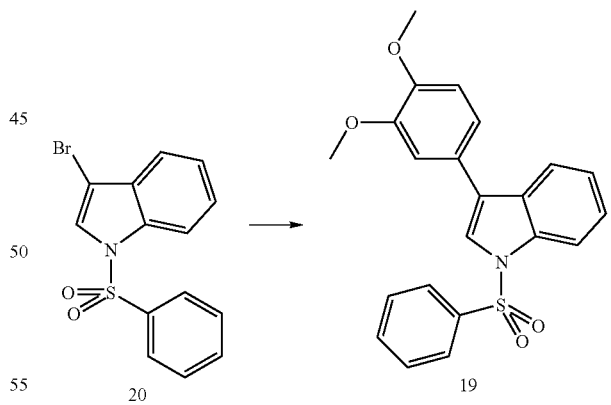

1-Benzenesulfonyl-3-bromoindole 20 (350 mg, 1.0 mmol) was dissolved in tetrahydrofuran (6 mL). Into the solution was added 3,4-dimethoxyphenyl boronic acid (379 mg, 2.1 mmol), tetrakis(triphenylphosphine)palladium(0) (60 mg, 0.05 mmol) and 1 M potassium carbonate (3 mL). The reaction mixture was heated in a CEM Discover microwave instrument at 120° C. for 10 minutes. The reaction mixture was concentrated under reduced pressure and partioned between ethyl acetate and saturated sodium bicabonate. The organic portion was dried over anhydrous magnesium sulfate, and filtered. The filtrate was adsorbed onto silica gel and purified by flash chromatography (5%-50% ethyl acetate: hexanes) to provide the desired product, 19, (359 mg, 88%).

Example 22

Synthesis of 8-[3-(3,4-dimethoxy-phenyl)-indole-1-sulfonyl]-quinoline 21

Scheme - 12

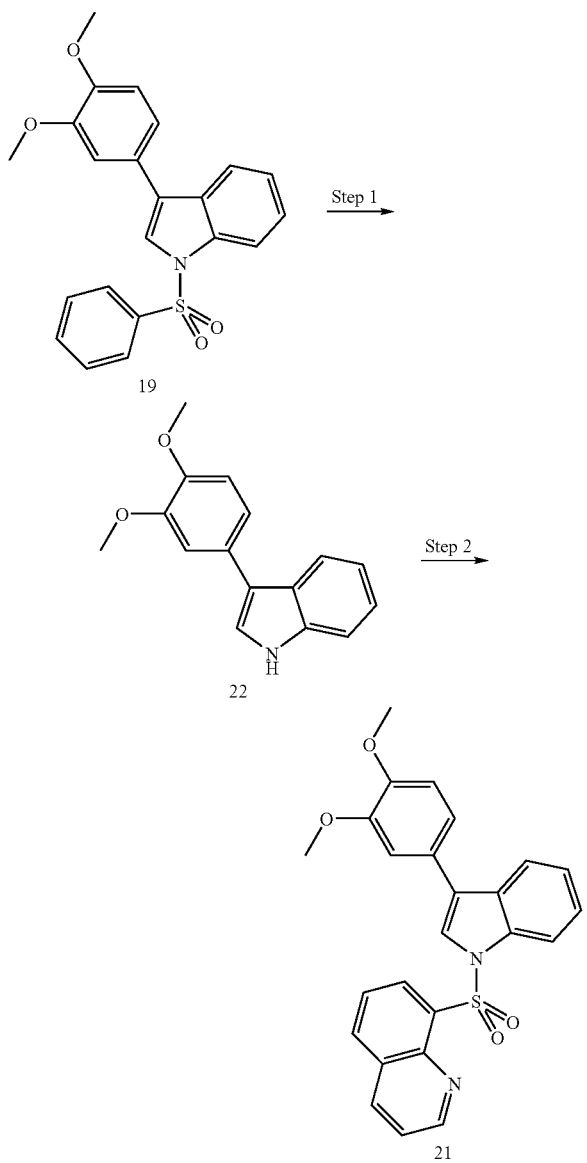

Step 1—Preparation of 3-(3,4-dimethoxy-phenyl)-indole 22

1-Benzenesulfonyl-3-(3,4-dimethoxy-phenyl)-indole (350 mg, 0.89 mmol) 19 was dissolved in ethanol (3 mL) and potassium hydroxide pellets (385 mg, 6.9 mmol) were added. The reaction mixture was heated in a CEM Discover microwave instrument at 120° C. for 10 minutes. The reaction mixture was concentrated to dryness and the residue was partitioned between ethyl acetate and saturated sodium bicarbonate. The organic portion was dried with anhydrous magnesium sulfate, filtered and the filtrate concentrated to provide the desired product 22, which was used without further purification (208 mg, 92%)

Step 2—Preparation of 8-[3-(3,4-dimethoxy-phenyl)-indole-1-sulfonyl]-quinoline 21

3-(3,4-Dimethoxy-phenyl)-indole 22 (70 mg, 0.28 mmol) was dissolved in methylene chloride (5.0 mL). Tetra-N-butylammonium bromide (3 mg, 0.01 mmol) and aqueous potassium hydroxide (50% wt/vol, 500 µL) were added. The reaction mixture was stirred for 5 minutes. 8-quinoline-sulfonyl chloride (89.5 mg, 0.39 mmol) was added and the reaction mixture was stirred for 2 hours. The product was extracted with 2 N lithium hydroxide and methylene chloride. The organic portion was dried over anhydrous magnesium sulfate and filtered. The filtrate was concentrated and purified by flash chromatography (ethyl acetate:hexanes 0%-50%). The appropriate fractions were combined and concentrated to provide 21, (76.1 mg, 90%). MS(ESI) [M+H$^+$]$^+$=445.0.

Example 23

Synthesis of 8-[3-(3,4-dimethoxy-phenyl)-pyrrolo[2,3-b]pyridine-1-sulfonyl]-3-methyl-quinoline 24

Scheme - 13

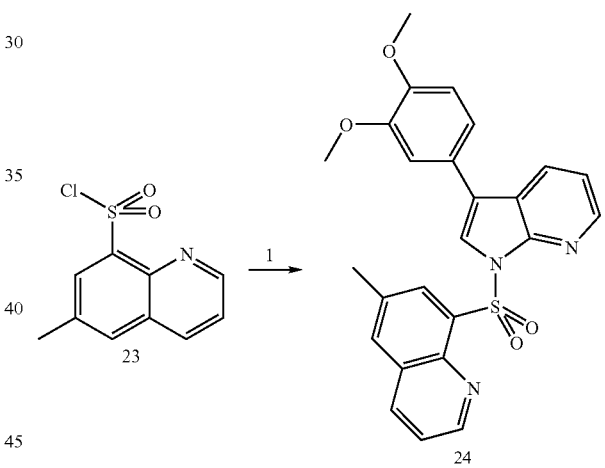

Preparation of 8-[3-(3,4-dimethoxy-phenyl)-pyrrolo[2,3-b]pyridine-1-sulfonyl]-3-methyl-quinoline 24

3-(3,4-Dimethoxy-phenyl)-1H-pyrrolo-[2,3-b]pyridine, 1, (40 mg, 0.1 mmol) was dissolved in methylene chloride (4 mL). Aqueous potassium hydroxide (50% wt/vol, 300 µL) and tetrabutylammonium hydrogen sulfate (20 mg, 0.007 mmol) were added. The reaction mixture was stirred for 10 minutes at room temperature. Into the reaction was added 6-methyl-quinoline-8-sulfonyl chloride (68 mg, 0.28 mmol), prepared as described (Lubenets, V. I.; Stadnitskaya, N. E.; Novikov, V. P.; Russ. *J. Org. Chem.;* 36; 2000; 851-853) and the reaction mixture was stirred for 2 hours at room temperature. The reaction mixture was concentrated and the residue was washed with brine and ethyl acetate. The organic portion was dried with anhydrous sodium sulfate and filtered. The filtrate was concentrated and the resulting solid was washed with acetonitrile to provide 24 (43 mg, 60%). MS(ESI) [M+H$^+$]$^+$=460.1.

Example 24

Synthesis of 8-[3-(3,4-dimethoxy-phenyl)-indole-1-sulfonyl]-3-methyl-quinoline 25

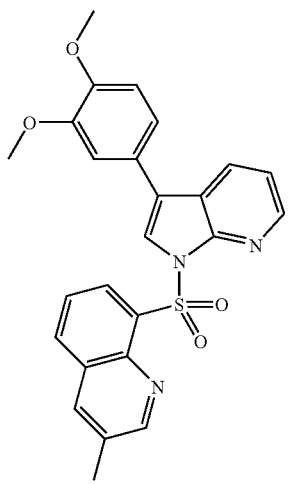

8-[3-(3,4-Dimethoxy-phenyl)-indole-1-sulfonyl]-3-methyl-quinoline 25 was prepared using the same protocol as described in Example 22, substituting 8-quinoline-sulfonyl chloride with 6-methyl-quinoline-8-sulfonyl chloride. After the crude material was concentrated, acetonitrile was added to the oil and let stand. The resulting precipitate was filtered and further washed with acetonitrile and dried in vacuo to provide the desired product 25. MS(ESI) [M+H$^+$]$^+$=459.1.

Example 25

Synthesis of 3-(3,4-dimethoxy-phenyl)-pyrrolo[2,3-b]pyridine-1-carboxylic acid (4-chloro-phenyl)-amide 26

Scheme - 14

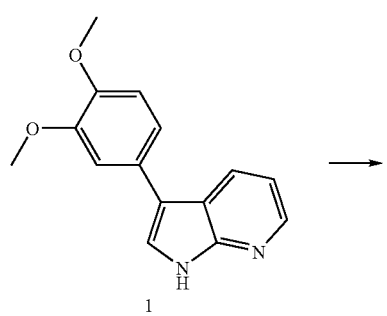

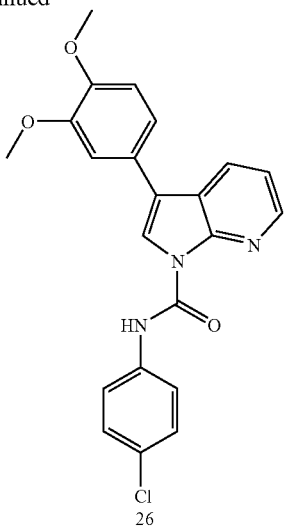

Preparation of 3-(3,4-dimethoxy-phenyl)-pyrrolo[2,3-b]pyridine-1-carboxylic acid (4-chloro-phenyl)-amide 26

3-(3,4-Dimethoxy-phenyl)-1H-pyrrolo-[2,3-b]pyridine 1 (40 mg, 0.16 mmol) was dissolved in benzene and 4-chlorophenyl isocyanate (36 mg, 0.24 mol) dissolved in tetrahydrofuran (4 mL) was added. 4-Dimethylaminopyridine (20 mg, polymer bound) was added. The reaction was heated in a CEM Discover microwave at 200° C. for 10 minutes. The mixture was filtered and concentrated. The resulting solid was washed with a minimum of methanol, filtered, and then washed with dichloromethane to provide 26, (26 mg, 40%). MS(ESI) [M+H$^+$]$^+$=408.4.

Example 26

Synthesis of 3-(3,4-Dimethoxy-phenyl)-pyrrolo[2,3-b]pyridine-1-carboxylic acid (3-chloro-4-methoxy-phenyl)-amide 27

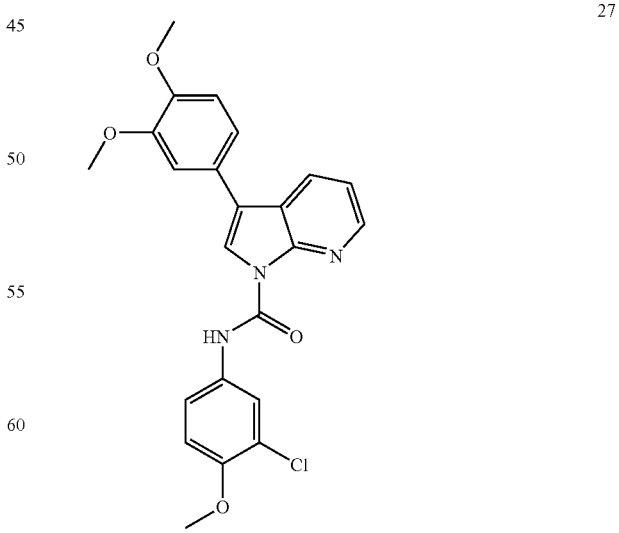

3-(3,4-Dimethoxy-phenyl)-pyrrolo[2,3-b]pyridine-1-carboxylic acid (3-chloro-4-methoxy-phenyl)-amide 27 was prepared using the same protocol as described in Example 25, substituting 4-chlorophenyl isocyanate with 3-chloro-4-methoxyphenyl isocyanate. MS(ESI) [M+H$^+$]$^+$=438.4.

Example 27

Synthesis of 3-(3,4-Dimethoxy-phenyl)-pyrrolo[2,3-b]pyridine-1-carboxylic acid phenylamide 28

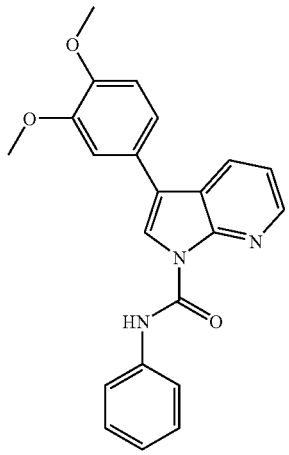

28

3-(3,4-Dimethoxy-phenyl)-pyrrolo[2,3-b]pyridine-1-carboxylic acid phenylamide 28 was prepared using the same protocol as described in Example 25, substituting 4-chlorophenyl isocyanate with phenylisocyanate. After an initial heating at 120° C. for 15 minutes, additional phenyl isocyanate was added (500 μL) and the reaction was heated again in the microwave for 30 minutes at 180° C. The concentrated solid was washed with a minimum of acetonitrile and purified by reverse phase HPLC (0.1% formic acid: acetonitrile) to provide the desired product 28. MS(ESI) [M+H$^+$]$^+$=374.3.

Example 28

Synthesis of 3-(3,4-Dimethoxy-phenyl)-pyrrolo[2,3-b]pyridine-1-carboxylic acid (3,5-dimethoxy-phenyl)-amide 29

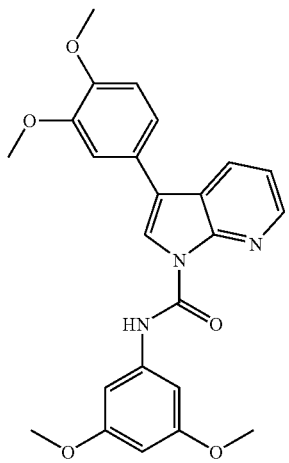

29

3-(3,4-Dimethoxy-phenyl)-pyrrolo[2,3-b]pyridine-1-carboxylic acid (3,5-dimethoxy-phenyl)-amide 29 was prepared using the same protocol as described in Example 25, substituting 4-chlorophenyl isocyanate with 3,5-dimethoxyphenyl isocyanate and microwave heating for 20 minutes at 200° C. MS(ESI) [M+H$^+$]$^+$=434.2.

Example 29

Synthesis of 3-[3-(3,4-Dimethoxy-phenyl)-pyrrolo[2,3-b]pyridine-1-carbonyl]-amino-benzoic acid ethyl ester 30

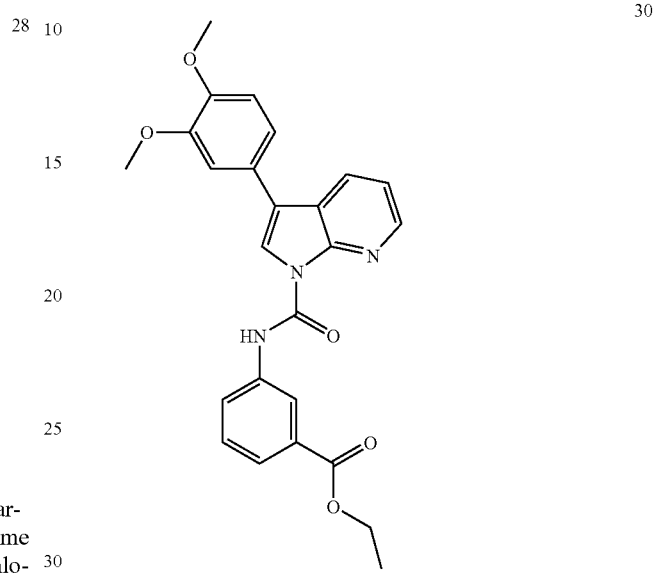

30

3-[3-(3,4-Dimethoxy-phenyl)-pyrrolo[2,3-b]pyridine-1-carbonyl]-amino-benzoic acid ethyl ester 30 was prepared using the same protocol as described in Example 25, substituting 4-chlorophenyl isocyanate with 3-isocyanato-benzoic acid ethyl ester and microwave heating for 20 minutes at 200° C. After washing with a minimum of methanol and methylene chloride, the reaction mixture was diluted with methanol: methylene chloride (95:5) and let stand. The resulting precipitate was isolated by filtration and dried in vacuo to provide 30. MS(ESI) [M+H$^+$]$^+$=446.5.

Example 30

Synthesis of 3-(3,4-Dimethoxy-phenyl)-pyrrolo[2,3-b]pyridine-1-carboxylic acid (4-fluoro-3-nitro-phenyl)-amide 31

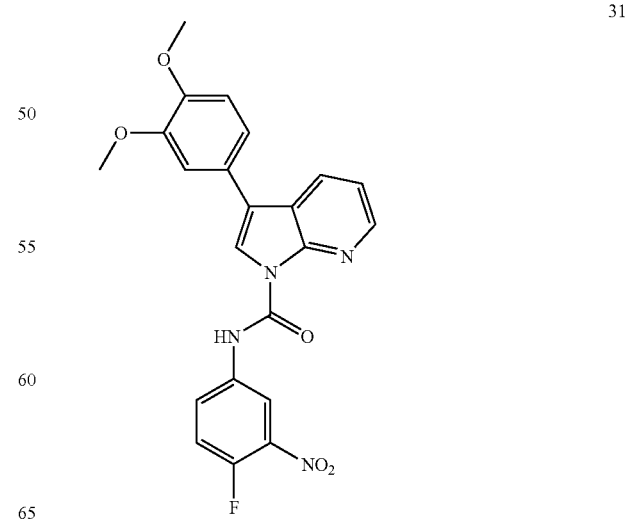

31

3-(3,4-Dimethoxy-phenyl)-pyrrolo[2,3-b]pyridine-1-carboxylic acid (4-fluoro-3-nitro-phenyl)-amide 31 was pre pared using the same protocol as described in Example 25, substituting 4-chlorophenyl isocyanate with 1-fluoro-4-isocyanato-2-nitro-benzene and reacting at room temperature for two hours. The resulting precipitate was washed with methanol and dichloromethane and dried in vacuo to provide 31. MS(ESI) [M+H⁺]⁺=437.5.

Example 31

Synthesis of 3-(3,4-Dimethoxy-phenyl)-pyrrolo[2,3-b]pyridine-1-carboxylic acid (3-methoxy-phenyl)-amide 32

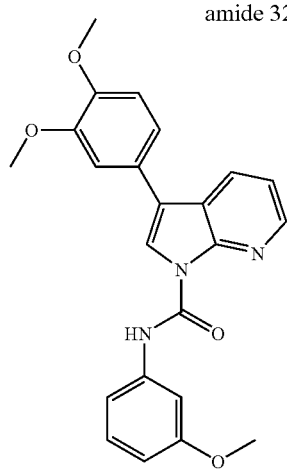

3-(3,4-Dimethoxy-phenyl)-pyrrolo[2,3-b]pyridine-1-carboxylic acid (3-methoxy-phenyl)-amide 32 was prepared using the same protocol as described in Example 25, substituting 4-chlorophenyl isocyanate with 3-methoxy-phenyl isocyanate. After filtration and concentration, the reaction mixture was redissolved in acetonitrile and a minimum of water and let stand. The resulting precipitate was collected by filtration and dried in vacuo to provide 32. MS(ESI) [M+H⁺]⁺= 404.4.

Example 32

Synthesis of 4-[3-(3,4-Dimethoxy-phenyl)-pyrrolo[2,3-b]pyridine-1-carbonyl]-amino-benzoic acid ethyl ester 33

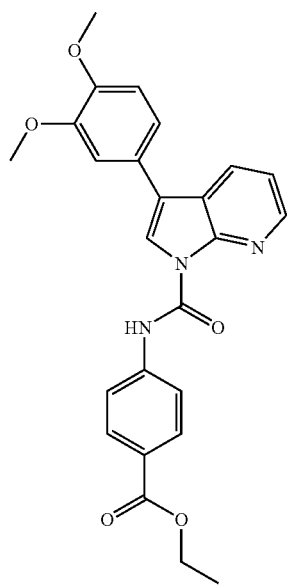

4-[3-(3,4-Dimethoxy-phenyl)-pyrrolo[2,3-b]pyridine-1-carbonyl]-amino-benzoic acid ethyl ester 33 was prepared using the same protocol as described in Example 25, substituting 4-chlorophenyl isocyanate with 4-isocyanato-benzoic acid ethyl ester.

Example 33

Synthesis of 3-(3,4-Dimethoxy-phenyl)-pyrrolo[2,3-b]pyridine-1-carboxylic acid (3-acetyl-phenyl)-amide 34

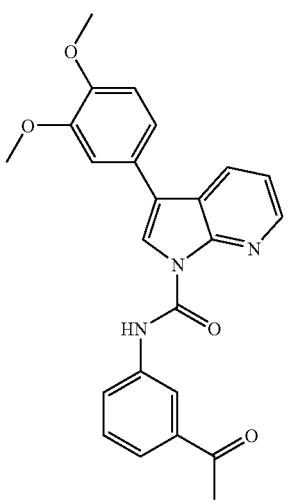

3-(3,4-Dimethoxy-phenyl)-pyrrolo[2,3-b]pyridine-1-carboxylic acid (3-acetyl-phenyl)-amide 34 was prepared using the same protocol as described in Example 25, substituting 4-chlorophenyl isocyanate with 3-acetyl-phenyl isocyanate. MS(ESI) [M+H⁺]⁺=416.3.

Example 34

Synthesis of 3-(3,4-Dimethoxy-phenyl)-pyrrolo[2,3-b]pyridine-1-carboxylic acid(3-fluoro-phenyl)-amide 35

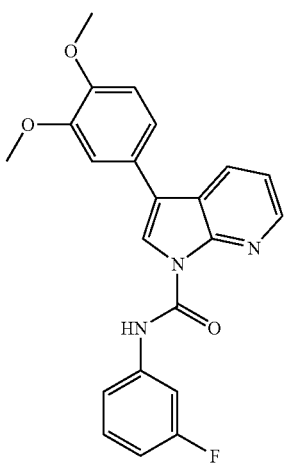

3-(3,4-Dimethoxy-phenyl)-pyrrolo[2,3-b]pyridine-1-carboxylic acid(3-fluoro-phenyl)-amide 35 was prepared using the same protocol as described in Example 25, substituting 4-chlorophenyl isocyanate with 3-fluoro-isocyanato-benzene. MS(ESI) [M+H⁺]⁺=392.0.

Example 35

Synthesis of 3-(3,4-Dimethoxy-phenyl)-pyrrolo[2,3-b]pyridine-1-carboxylic acidbenzo[1,3]dioxol-5-ylamide 36

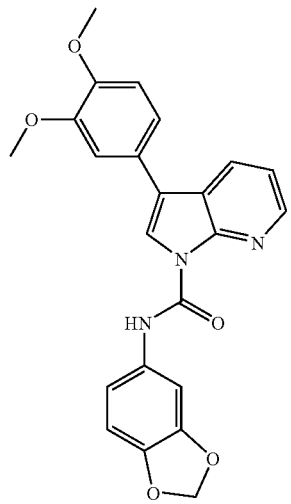

3-(3,4-Dimethoxy-phenyl)-pyrrolo[2,3-b]pyridine-1-carboxylic acidbenzo[1,3]dioxol-5-ylamide 36 was prepared using the same protocol as described in Example 25, substituting 4-chlorophenyl isocyanate with 5-isocyanato-benzo[1,3]dioxole. After the initial microwave heating, the reaction was heated again in the microwave for 10 minutes at 210° C. The crude material was recrystallized from methanol:methylene chloride to provide 36. MS(ESI) $[M+H^+]^+$=418.5.

Example 36

Synthesis of 3-(3,4-Dimethoxy-phenyl)-pyrrolo[2,3-b]pyridine-1-carboxylic acid (3,4-dichloro-phenyl)-amide 37

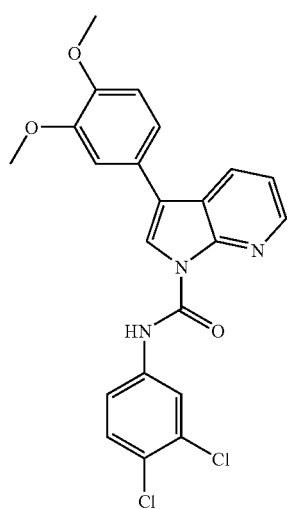

3-(3,4-Dimethoxy-phenyl)-pyrrolo[2,3-b]pyridine-1-carboxylic acid (3,4-dichloro-phenyl)-amide 37 was prepared using the same protocol as described in Example 25, substituting 4-chlorophenyl isocyanate with 1,2-dichloro-4-isocyanato-benzene. MS(ESI) $[M+H^+]^+$=443.5.

Example 37

Synthesis of 3-(3,4-Dimethoxy-phenyl)-pyrrolo[2,3-b]pyridine-1-carboxylic acid (3-nitro-phenyl)-amide 38

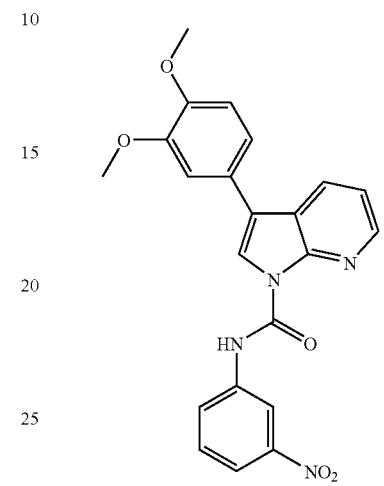

3-(3,4-Dimethoxy-phenyl)-pyrrolo[2,3-b]pyridine-1-carboxylic acid (3-nitro-phenyl)-amide 38 was prepared using the same protocol as described in Example 25, substituting 4-chlorophenyl isocyanate with 1-isocyanato-3-nitro-benzene. After the initial microwave heating, the reaction was heated again in a CEM Discover microwave for 6 minutes at 200° C. with an additional equivalent of 1-isocyanato-3-nitro-benzene. MS(ESI) $[M+H^+]^+$=419.2.

Example 38

Synthesis of 3-(3,4-Dimethoxy-phenyl)-pyrrolo[2,3-b]pyridine-1-carboxylic acid (4-methoxy-phenyl)-amide 39

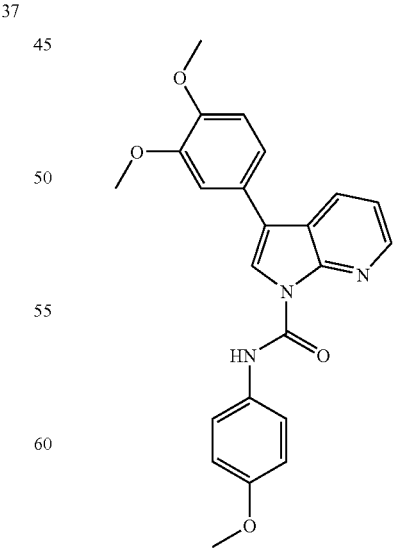

3-(3,4-Dimethoxy-phenyl)-pyrrolo[2,3-b]pyridine-1-carboxylic acid (4-methoxy-phenyl)-amide 39 was prepared using the same protocol as described in Example 25, substituting 4-chlorophenyl isocyanate with 4-methoxyphenyl isocyanate. After the initial microwave heating, the reaction was heated again in the microwave for 5 minutes at 190° C. MS(ESI) [M+H$^+$]$^+$=404.2.

Example 39

Synthesis of 3-(3,4-Dimethoxy-phenyl)-pyrrolo[2,3-b]pyridine-1-carboxylic acid (4-acetyl-phenyl)-amide 40

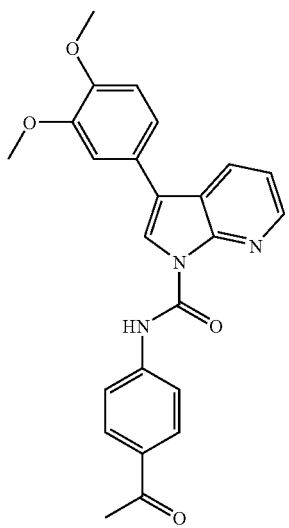

40

3-(3,4-Dimethoxy-phenyl)-pyrrolo[2,3-b]pyridine-1-carboxylic acid (4-acetyl-phenyl)-amide 40 was prepared using the same protocol as described in Example 25, substituting 4-chlorophenyl isocyanate with 4-acetylphenyl isocyanate. After the initial microwave heating, the reaction was heated again in the microwave for 20 minutes at 220° C. MS(ESI) [M+H$^+$]$^+$=416.2.

Example 40

Synthesis of 3-(3,4-dimethoxy-phenyl)-pyrrolo[2,3-b]pyridine-1-carbothioic acid phenylamide 41

Scheme - 15

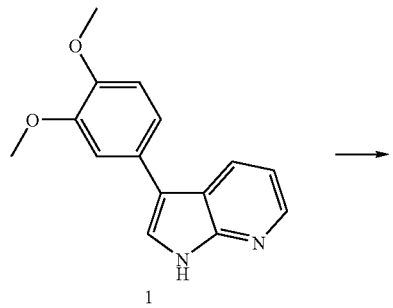

1

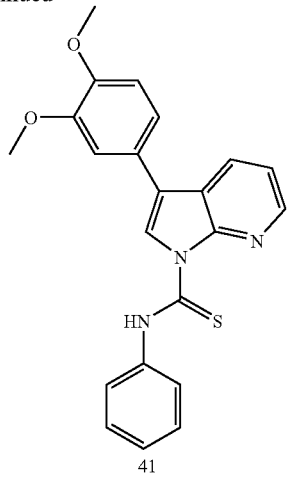

41

Preparation of 3-(3,4-dimethoxy-phenyl)-pyrrolo[2,3-b]pyridine-1-carbothioic acid phenylamide 41

3-(3,4-Dimethoxy-phenyl)-1H-pyrrolo-[2,3-b]pyridine 1 (50 mg, 0.20 mmol) was dissolved in N,N-dimethylformamide (4 mL). Sodium hydride (10 mg, 0.24 mmol, 60% dispersion in mineral oil) was added. The reaction mixture was stirred for 15 minutes at room temperature. 1-Isothiocyanatobenzene (35 µL, 0.29 mmol) was added and the reaction mixture was stirred for 40 minutes at room temperature. The product was concentrated and the residue was partitioned between brine and ethyl acetate. The organic portion was dried over anhydrous sodium sulfate, filtered, and concentrated to provide a solid. The solid was washed with a minimum of methanol and dried in vacuo to provide 41, (38 mg, 49%). MS(ESI) [M+H$^+$]$^+$=390.2.

Example 41

3-(3,4-dimethoxy-phenyl)-pyrrolo[2,3-b]pyridine-1-carbothioic acid (3-methoxy-phenyl)-amide 42

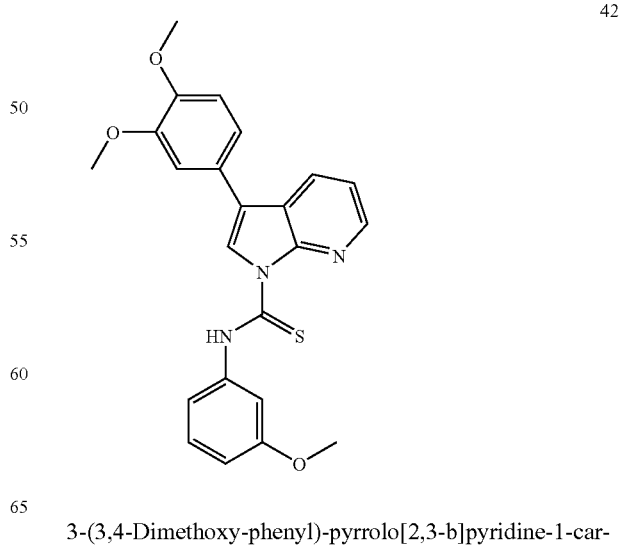

42

3-(3,4-Dimethoxy-phenyl)-pyrrolo[2,3-b]pyridine-1-carbothioic acid (3-methoxy-phenyl)-amide 42 was prepared using the same protocol as described in Example 40, substituting 1-isothiocyanatobenzene with 1-chloro-4-isothiocyanatobenzene.

Example 42

Synthesis of 8-[3-(2-methoxy-pyrimidin-5-yl)-pyrrolo[2,3-b]pyridine-1-sulfonyl]-quinoline 43

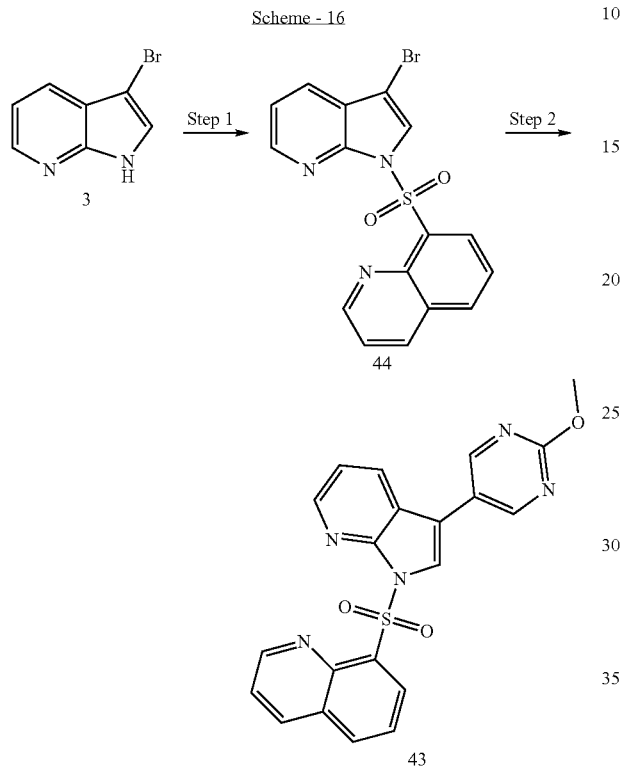

Step-1 Preparation of 8-(3-bromo-pyrrolo[2,3-b]pyridine-1-sulfonyl)-quinoline 44

Into a round bottom flask was added 3-bromo-7-azaindole (3, 1.18 g, 5.99 mmol) and tetra-N-butylammonium bromide (193 mg, 0.600 mmol), and 5.0 M sodium hydroxide (15.4 mL). 8-Quinoline-sulfonyl chloride (1.64 g, 7.19 mmol) in dichloromethane (5.9 mL) was added dropwise at room temperature. After a few hours, all starting materials were gone. After 30 mL of dichlormethane was added, two layers were separated. The aqueous layer was washed with dichloromethane. The combined organic layers were washed with 1 M sodium bicarbonate, water, and brine and dried over anhydrous sodium sulfate. The crude material was concentrated under reduced pressure and was purified by column chromatography (55-80% ethyl acetate in hexane) to yield the desired product as a light yellow colored solid (44, 1.72 g, 4.43 mmol). MS(ESI) [M+H$^+$]$^+$=389.4.

Step-2 Preparation of 8-[3-(2-methoxy-pyrimidin-5-yl)-pyrrolo[2,3-b]pyridine-1-sulfonyl]-quinoline 43

In a microwave reaction tube, 8-(3-bromo-pyrrolo[2,3-b]pyridine-1-sulfonyl)-quinoline (44, 68 mg, 0.18 mmol), 2-methoxy-pyrimidine-4-boronic acid (67.4 mg, 0.438 mmol), and tetrakis(triphenylphosphine)palladium(0) (10 mg, 0.0088 mmol) were mixed in 1.0 M of potassium carbonate (0.52 mL) and tetrahydrofuran (0.84 mL). The resulting mixture was heated at 120° C. in a CEM Discover microwave unit for 10 minutes. Ethyl acetate and water were added and two layers were separated. The aqueous layer was extracted with ethyl acetate and the combined organic layers were washed with brine and dried over sodium sulfate. The product was concentrated under reduced pressure and the resultant crude material was purified by column chromatography (80-90% ethyl acetate in hexane) to yield the desired product as a white solid (43, 0.005 g, 0.01 mmol). MS(ESI) [M+H$^+$]$^+$= 417.8.

Example 43

Synthesis of 3-(2-Methoxy-pyrimidin-5-yl)-1-phenylmethanesulfonyl-1H-pyrrolo[2,3-b]pyridine 45

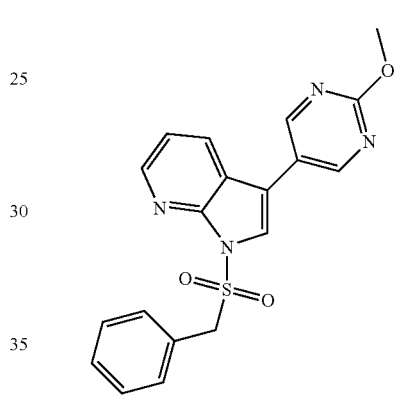

3-(2-Methoxy-pyrimidin-5-yl)-1-phenylmethanesulfonyl-1H-pyrrolo[2,3-b]pyridine 45 was prepared using the same protocol as described in Example 42, substituting 8-quinoline-sulfonyl chloride with phenyl methanesulfonyl chloride. MS(ESI) [M+H$^+$]$^+$=381.2.

Example 44

Synthesis of 8-[3-(2-Methylsulfanyl-pyrimidin-4-yl)-pyrrolo[2,3-b]pyridine-1-sulfonyl]-quinoline 46

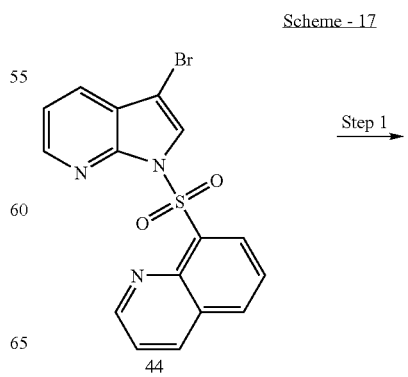

-continued

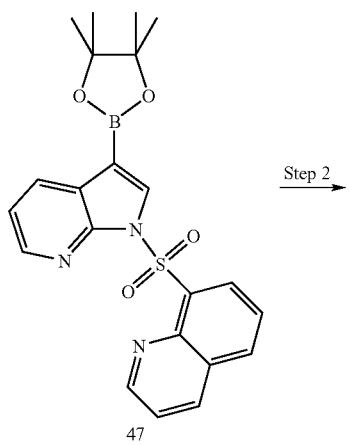

47

Step-1 Preparation of 8-[3-(4,4,5,5-tetramethyl-[1,3,2]dioxaborolan-2-yl)-pyrrolo[2,3-b]pyridine-1-sulfonyl]-quinoline 47

Into a round bottom flask, 8-(3-bromo-pyrrolo[2,3-b]pyridine-1-sulfonyl)-quinoline (44, 335 mg, 0.863 mmol), diboron pinacol ester (263 mg, 1.04 mmol), and bis(triphenylphosphine)palladium(II) chloride (18 mg, 0.026 mmol) were added. Under an atmosphere of nitrogen, N,N-dimethylformamide (4.0 mL) was added. The mixture was thoroughly degassed by alternately connecting the flask to vacuum and nitrogen source. The resulting mixture was heated to 100° C. overnight. After the reaction mixture was cooled to room temperature, it was poured into water and extracted with ethyl acetate twice. The combined organic layers were washed with water and brine and dried over anhydrous sodium sulfate. The product was concentraqted under reduced pressure and the crude material was purified by column chromatography (55% ethyl acetate in hexane) to yield the desired product as a white solid (47, 70 mg, 0.16 mmol). MS(ESI) [M+H$^+$]$^+$=435.8.

Step-2 Preparation of 8-[3-(2-Methylsulfanyl-pyrimidin-4-yl)-pyrrolo[2,3-b]pyridine-1-sulfonyl]-quinoline 46

In a microwave reaction tube, 8-[3-(4,4,5,5-tetramethyl-[1,3,2]dioxaborolan-2-yl)-pyrrolo[2,3-b]pyridine-1-sulfonyl]-quinoline (47, 70 mg, 0.16 mmol), 4-iodo-2-methylsulfanyl-pyrimidine (101 mg, 0.402 mmol), and tetrakis (triphenylphosphine)palladium(0) (9.3 mg, 0.008 mmol) were mixed in 1.0 M potassium carbonate in water (0.48 mL) and tetrahydrofuran (0.77 mL). The resulting mixture was heated at 120° C. in a CEM Discover microwave unit for 10 minutes. Ethyl acetate and water were added, and the two layers were separated. The aqueous layer was extracted with ethyl acetate. The combined organic layers were washed with brine and dried over sodium sulfate. Concentration under reduced pressure afforded the crude material, which was purified by column chromatography (50% ethyl acetate in hexane) to yield the desired product in light yellow solid (46, 10 mg, 0.023 mmol). MS(ESI) [M+H$^+$]$^+$=434.0.

Example 45

Synthesis of [3-(3,4-Dimethoxy-phenyl)-pyrrolo[2,3-b]pyridin-1-yl]-(2-ethoxy-naphthalen-1-yl)-methanone 52

Scheme - 18

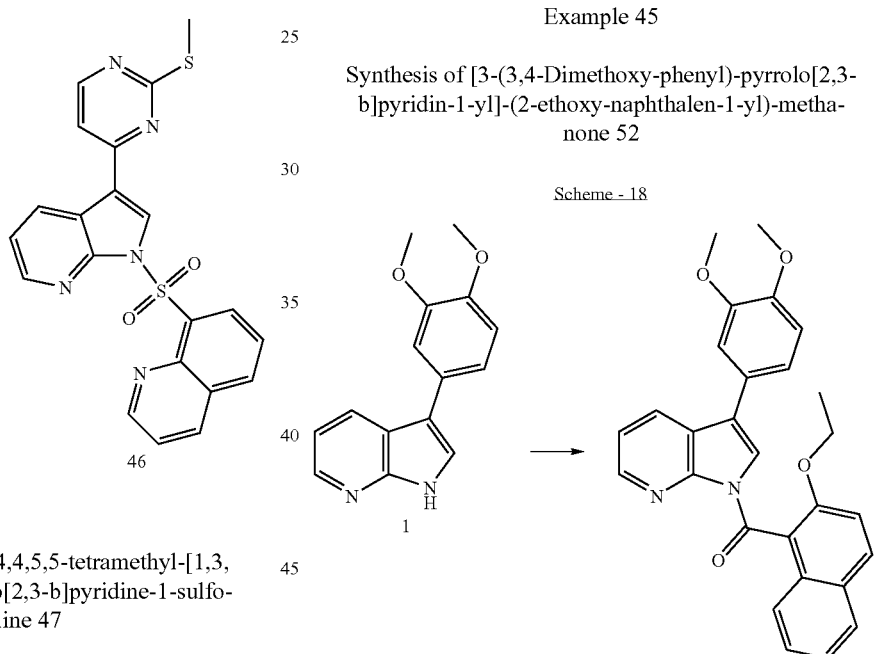

3-(3,4-Dimethoxy-phenyl)-1H-pyrrolo[2,3-b]pyridine 1 (638 mg, 2.51 mmole) was dissolved in DMF (30 mL) and sodium hydride (60% dispersion in mineral oil, 100 mg, 2.50 mmole) was added in small portions to the reaction mixture. After stirring for 30 minutes, 2-ethoxy-1-naphthoyl chloride (646 mg, 2.76 mmole) was added and the reaction was stirred for 4 hours. The reaction mixture was poured into 200 mL of ice water and was extracted with ethyl acetate. The organic layer was washed with saturated bicarbonate solution followed by saturated potassium hydrogen sulfate and then brine. The resulting solution was dried over anhydrous magnesium sulfate, filtered and concentrated under reduced pressure. The residue was purified by silica gel chromatography (30% ethyl acetate:hexanes) to yield 800 mg (70%) of the titled compound as a white solid MS(ESI) [M+H$^+$]$^+$=453.06.

Example 46

Synthesis of 3-(3,4-Dimethoxy-phenyl)-1-(3-nitro-benzyl)-1H-pyrrolo[2,3-b]pyridine 53

Scheme - 19

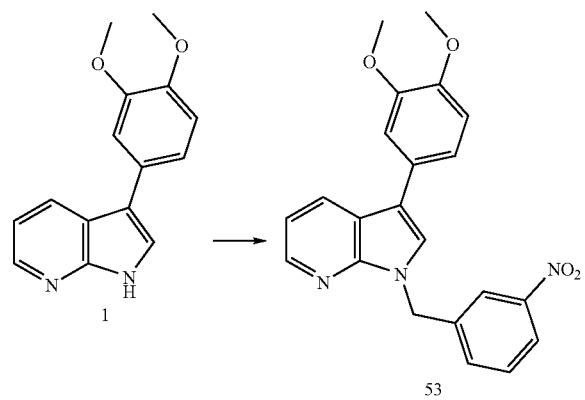

3-(3,4-Dimethoxy-phenyl)-1H-pyrrolo[2,3-b]pyridine 1 (35 mg, 0.14 mmole) was dissolved in 15 mL of DMF and sodium hydride (60% dispersion in mineral oil, 10 mg, 0.25 mmol) was added in small portion to the reaction mixture. After stirring for 30 minutes, m-nitro-benzyl chloride (30 mg, 0.14 mmole) was added to the reaction mixture and was stirred for 2 hours. The reaction mixture was poured into 50 mL of ice water and was extracted with ethyl acetate. The organic layer was washed with saturated sodium bicarbonate followed by saturated potassium bisulfate and then brine. The resulting solution was dried over anhydrous magnesium sulfate, filtered and concentrated under reduced pressure. The residue was purified by silica gel chromatography (30% ethyl acetate in hexanes) to yield 42 mg (71%) of the titled compound as a white solid. MS(ESI) [M+H$^+$]$^+$=390.1.

Example 47

Synthesis of [3-(3,4-Dimethoxy-phenyl)-pyrrolo[2,3-b]pyridin-1-yl]-(2-ethoxy-4-nitro-phenyl)-methanone 54

Scheme - 20

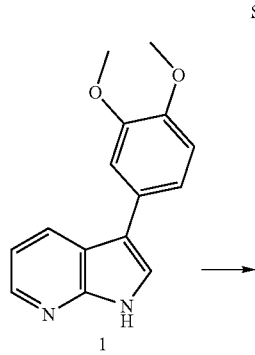

-continued

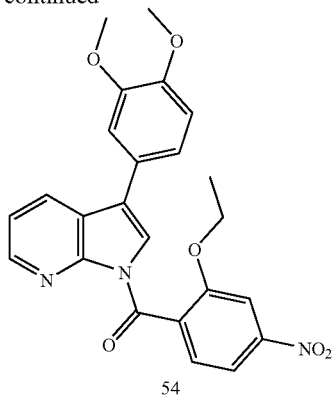

3-(3,4-Dimethoxy-phenyl)-1H-pyrrolo[2,3-b]pyridine 1(250 mg, 0.98 mmole) was dissolved in 50 mL of CH$_2$Cl$_2$. N,N-diethylisopropylamine (205 uL, 1.2 mmol), 2-ethoxy-4-nitro-benzoic acid (228 mg, 1.1 mmol) and bromotris(pyrolodino)phoshonium hexafluorophosphate (550 mg, 1.1 mmol) were added to the stirring reaction mixture. The mixture was stirred at ambient temperature for 4 h and washed consecutively with saturated sodium bicarbonate and saturated potassium bisulfate solution. The resulting solution was dried over anhydrous magnesium sulfate, filtered and concentrated under reduced pressure. The residue was purified by silica gel chromatography (30% ethyl acetate in hexanes) to yield 340 mg (77%) of the titled compound as a yellow solid. MS(ESI) [M+H$^+$]$^+$=448.2.

Example 48

Synthesis of [3-(3,4-Dimethoxy-phenyl)-pyrrolo[2,3-b]pyridin-1-yl]phenylmethanone-amide 55

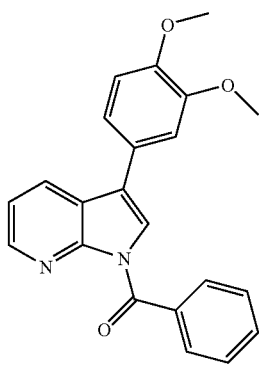

[3-(3,4-Dimethoxy-phenyl)-pyrrolo[2,3-b]pyridin-1-yl] phenylmethanone-amide 55 was prepared using the same protocol as described for Example 45, substituting 2-ethoxy-1-naphthalene carbonyl chloride with benzoyl chloride. MS(ESI) [M+H$^+$]$^+$=359.2.

Example 49

Synthesis of [3-(3,4-Dimethoxy-phenyl)-pyrrolo[2,3-b]pyridin-1-yl]-(3-pyridylyl)-methanone-amide 56

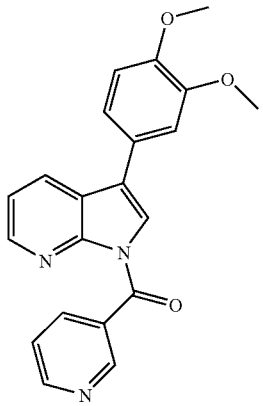

[3-(3,4-Dimethoxy-phenyl)-pyrrolo[2,3-b]pyridin-1-yl]-(3-pyridylyl)-methanone-amide 56 was prepared using the same protocol as described for Example 45, substituting 2-ethoxy-1-naphthalene carbonyl chloride with pyridine-3-carbonyl chloride. MS(ESI) $[M+H^+]^+=360.0$.

Example 50

Synthesis of [3-(3,4-Dimethoxy-phenyl)-pyrrolo[2,3-b]pyridin-1-yl]-(4-trifluoromethypyridn-3-yl)-methanone-amide 57

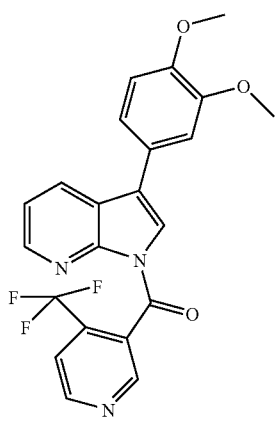

[3-(3,4-Dimethoxy-phenyl)-pyrrolo[2,3-b]pyridin-1-yl]-(4-trifluoromethypyridn-3-yl)-methanone-amide 57 was prepared using the same protocol as described for Example 45 substituting 2-ethoxy-1-naphthalene carbonyl chloride with 4-trifluoromethylpyridine-3-carbonyl chloride. MS(ESI) $[M+H^+]^+=428.0$.

Example 51

Synthesis of [3-(3,4-Dimethoxy-phenyl)-pyrrolo[2,3-b]pyridin-1-yl]-(1-naphthyl)-methanone-amide 58

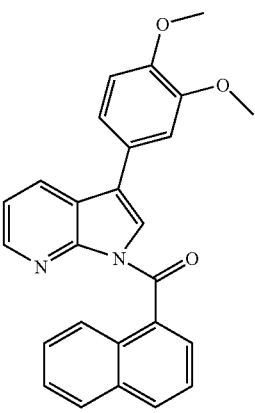

[3-(3,4-Dimethoxy-phenyl)-pyrrolo[2,3-b]pyridin-1-yl]-(1-naphthyl)-methanone amide 58 was prepared using the same protocol as described for Example 45, substituting 2-ethoxy-1-naphthalene carbonyl chloride with naphthylene-1-carbonyl chloride. MS(ESI) $[M+H^+]^+=409.1$.

Example 52

Synthesis of [3-(3,4-Dimethoxy-phenyl)-pyrrolo[2,3-b]pyridin-1-yl]-(2-chloropyridin-3-yl)-methanone-amide 59

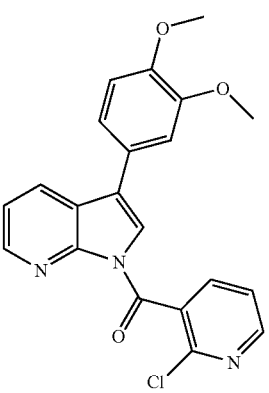

[3-(3,4-Dimethoxy-phenyl)-pyrrolo[2,3-b]pyridin-1-yl]-(2-chloropyridn-3-yl)-methanone—amide 59 was prepared using the same protocol as described for Example 45, substituting 2-ethoxy-1-naphthalene carbonyl chloride with 2-chloropyridine-3-carbonyl chloride. MS(ESI) $[M+H^+]^+=393.9$.

Example 53

Synthesis of 1-[3-(3,4-Dimethoxy-phenyl)-pyrrolo[2,3-b]pyridin-1-yl]-2-(4-methoxy-phenyl)-ethanone-amide 60

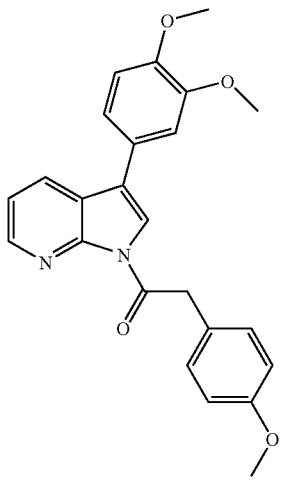

1-[3-(3,4-Dimethoxy-phenyl)-pyrrolo[2,3-b]pyridin-1-yl]-2-(4-methoxy-phenyl)-ethanone-amide 60 was prepared using the same protocol as described for Example 45, substituting 2-ethoxy-1-naphthalene carbonyl chloride with (4-methoxy-phenyl)-acetyl chloride. MS(ESI) [M+H$^+$]$^+$=403.0.

Example 54

Synthesis of [3-(3,4-Dimethoxy-phenyl)-pyrrolo[2,3-b]pyridin-1-yl]-(2-ethoxy-phenyl)-methanone-amide 61

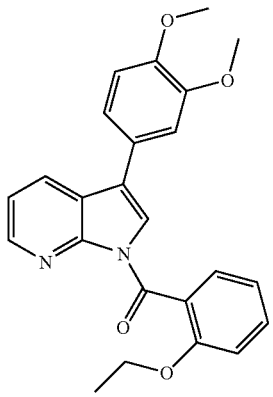

[3-(3,4-Dimethoxy-phenyl)-pyrrolo[2,3-b]pyridin-1-yl]-(2-ethoxy-phenyl)-methanone-amide 61 was prepared using the same protocol as described for Example 45 substituting 2-ethoxy-1-naphthalene carbonyl chloride with 2-ethoxy-benzoyl chloride. MS(ESI) [M+H$^+$]$^+$=403.5.

Example 55

Synthesis of Acetic acid 6-[3-(3,4-dimethoxy-phenyl)-pyrrolo[2,3-b]pyridine-1-carbonyl]-naphthalen-1-yl ester-amide 62

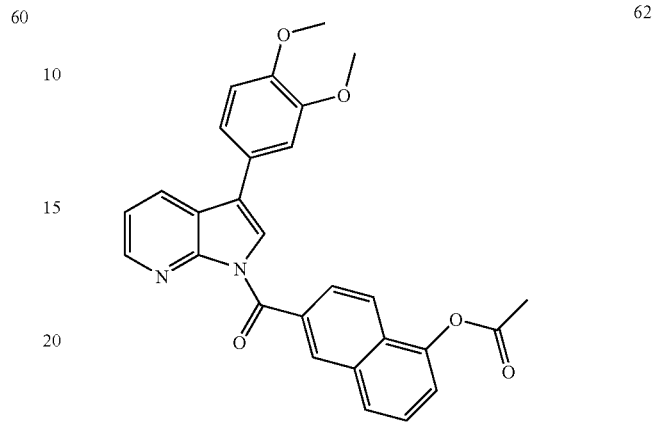

Acetic acid 6-[3-(3,4-dimethoxy-phenyl)-pyrrolo[2,3-b]pyridine-1-carbonyl]-naphthalen-1-yl ester-amide 62 was prepared using the same protocol as described for Example 47, substituting 2-ethoxy-4-nitrobenzoic acid with 5-acetoxy-naphthalene-2-carboxylic acid. MS(ESI) [M+H$^+$]$^+$=467.5.

Example 56

Synthesis of Benzo[b]thiophen-3-yl-[3-(3,4-dimethoxy-phenyl)-pyrrolo[2,3-b]pyridin-1-yl]-methanone 63

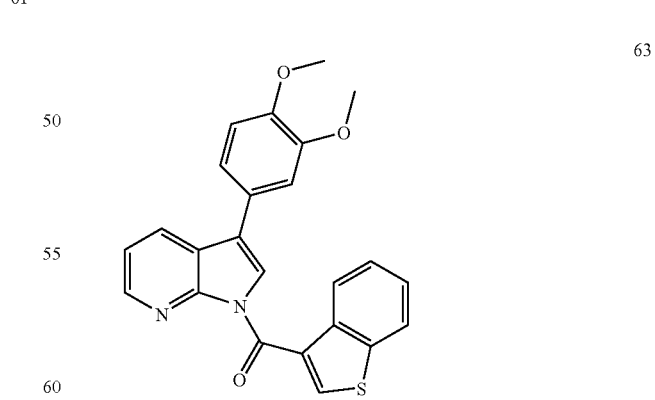

Benzo[b]thiophen-3-yl-[3-(3,4-dimethoxy-phenyl)-pyrrolo[2,3-b]pyridin-1-yl]-methanone 63 was prepared using the same protocol as described for Example 45, substituting 2-ethoxy-1-naphthalene carbonyl chloride with benzo[b]thiophene-3-carbonyl chloride.

Example 57

Synthesis of [3-(3,4-Dimethoxy-phenyl)-pyrrolo[2,3-b]pyridin-1-yl]-(4-fluoro-naphthalen-1-yl)-methanone 64

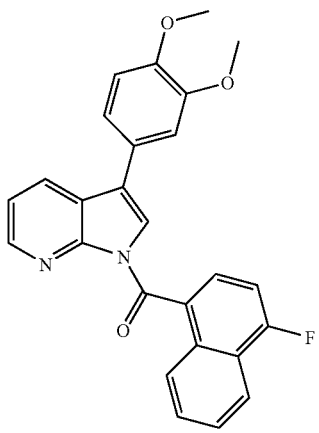

[3-(3,4-Dimethoxy-phenyl)-pyrrolo[2,3-b]pyridin-1-yl]-(4-fluoro-naphthalen-1-yl)-methanone 64 was prepared using the same protocol as described for Example 47, substituting 2-ethoxy-4-nitrobenzoic acid with 4-fluoro-naphthalene-1-carboxylic acid. MS(ESI) [M+H$^+$]$^+$=427.5.

Example 58

Synthesis of [3-(3,4-Dimethoxy-phenyl)-pyrrolo[2,3-b]pyridin-1-yl]-(5-methoxynaphthalen-1-yl)-methanone 65

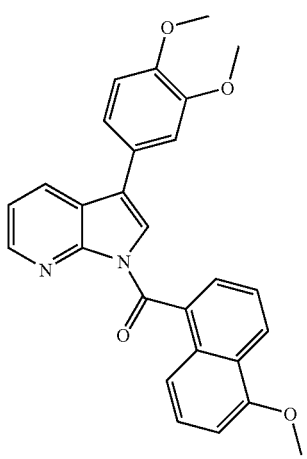

[3-(3,4-Dimethoxy-phenyl)-pyrrolo[2,3-b]pyridin-1-yl]-(5-methoxynaphthalen-1-yl)-methanone 65 was prepared using the same protocol as described for Example 47, substituting 2-ethoxy-4-nitrobenzoic acid with 5-methoxy-naphthalene-2-carboxylic acid.

Example 59

Synthesis of [3-(3,4-Dimethoxy-phenyl)-pyrrolo[2,3-b]pyridin-1-yl]-isoquinolin-8-yl-methanone 66

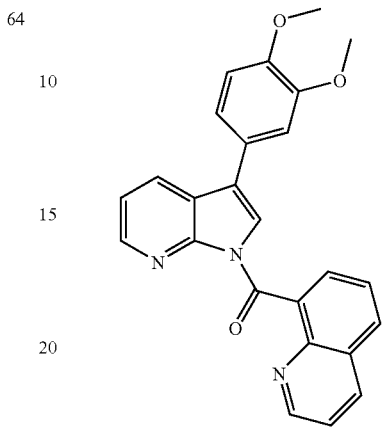

[3-(3,4-Dimethoxy-phenyl)-pyrrolo[2,3-b]pyridin-1-yl]-isoquinolin-8-yl-methanone 66 was prepared using the same protocol as described for Example 47, substituting 2-ethoxy-4-nitrobenzoic acid with quinolin-8-carboxylic acid. MS(ESI) [M+H$^+$]$^+$=410.5.

Example 60

Synthesis of 1-[3-(3,4-Dimethoxy-phenyl)-pyrrolo[2,3-b]pyridin-1-yl]-ethanone 67

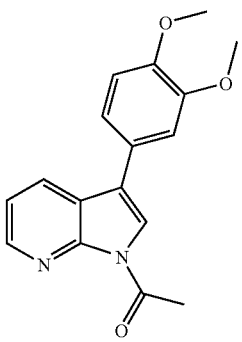

1-[3-(3,4-Dimethoxy-phenyl)-pyrrolo[2,3-b]pyridin-1-yl]-ethanone 67 was prepared using the same protocol as described for Example 45, substituting 2-ethoxy-1-naphthalene carbonyl chloride with acetyl chloride. MS(ESI) [M+H$^+$]$^+$=279.2.

Example 61

Synthesis of [3-(3,4-Dimethoxy-phenyl)-pyrrolo[2,3-b]pyridin-1-yl]-(2-methoxyphenyl)-methanone 68

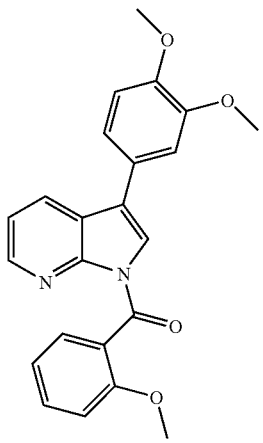

[3-(3,4-Dimethoxy-phenyl)-pyrrolo[2,3-b]pyridin-1-yl]-(2-methoxyphenyl)-methanone 68 was prepared using the same protocol as described for Example 45, substituting 2-ethoxy-1-naphthalene carbonyl chloride with 2-methoxybenzoyl chloride. MS(ESI) [M+H$^+$]$^+$=389.15.

Example 62

Synthesis of 3-(3,4-Dimethoxy-phenyl)-1-[4-(3-methyl-pyridin-4-yl)-benzenesulfonyl]-1H-pyrrolo[2,3-b]pyridine 69

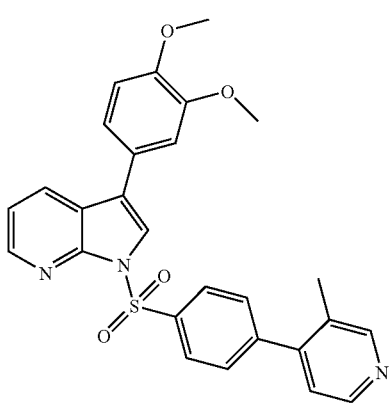

3-(3,4-Dimethoxy-phenyl)-1-[4-(3-methyl-pyridin-4-yl)-benzenesulfonyl]-1H-pyrrolo[2,3-b]pyridine 69 was prepared using the same protocol as described in Example 9, substituting 8-quinoline-sulfonyl chloride with 4-(3-methyl-pyridin-4-yl)-benzenesulfonyl chloride. MS(ESI) [M+H$^+$]$^+$=487.0.

Example 63

Synthesis of 3-(3,4-Dimethoxy-phenyl)-1-(4-oxazol-5-yl-benzenesulfonyl)-1H-pyrrolo[2,3-b]pyridine 70

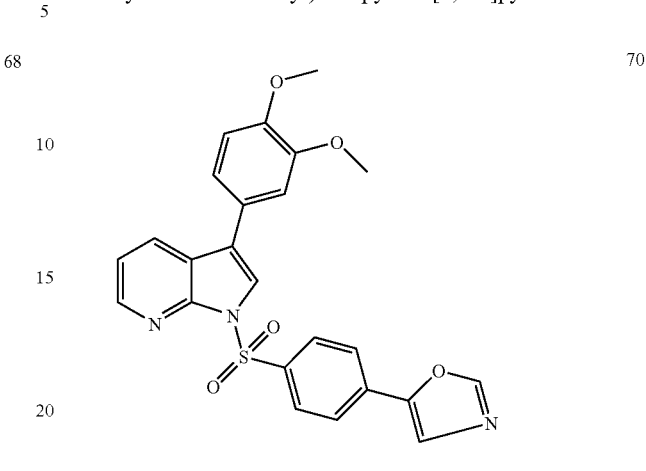

3-(3,4-Dimethoxy-phenyl)-1-(4-oxazol-5-yl-benzenesulfonyl)-1H-pyrrolo[2,3-b]pyridine 70 was prepared using the same protocol as described in Example 9, substituting 8-quinoline-sulfonyl chloride with 4-oxazol-5-yl-benzenesulfonyl chloride. MS(ESI) [M+H$^+$]$^+$=462.0.

Example 64

Synthesis of 3-(3,4-Dimethoxy-phenyl)-1-(4-pyrazol-1-yl-benzenesulfonyl)-1H-pyrrolo[2,3-b]pyridine 71

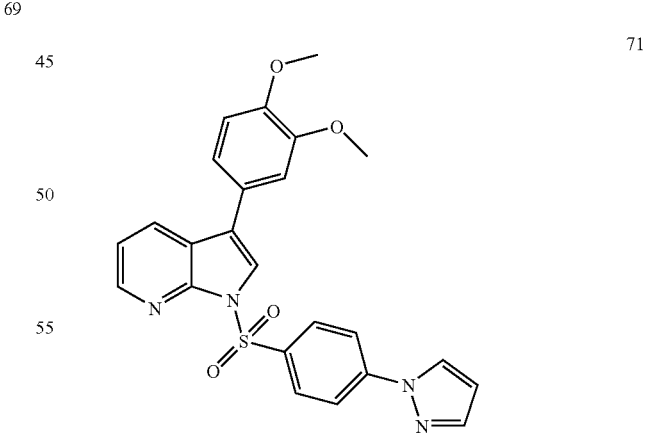

3-(3,4-Dimethoxy-phenyl)-1-(4-pyrazol-1-yl-benzenesulfonyl)-1H-pyrrolo[2,3-b]pyridine 71 was prepared using the same protocol as described in Example 9, substituting 8-quinoline-sulfonyl chloride with 4-pyrazol-1-yl-benzenesulfonyl chloride. MS(ESI) [M+H$^+$]$^+$=461.0.

Example 65

Synthesis of 3-(3,4-Dimethoxy-phenyl)-1-(3-oxazol-5-yl-benzenesulfonyl)-1H-pyrrolo[2,3-b]pyridine 72

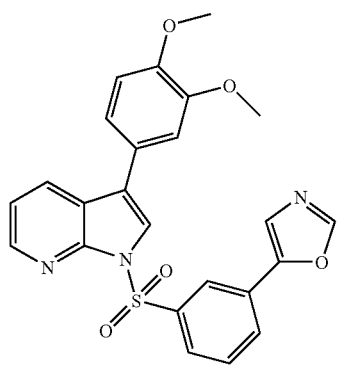

72

3-(3,4-Dimethoxy-phenyl)-1-(3-oxazol-5-yl-benzenesulfonyl)-1H-pyrrolo[2,3-b]pyridine 72 was prepared using the same protocol as described in Example 9, substituting 8-quinoline-sulfonyl chloride with 3-oxazol-5-yl-benzenesulfonyl chloride. MS(ESI) [M+H$^+$]$^+$=462.0.

Example 66

Synthesis of 3-(3,4-Dimethoxy-phenyl)-1-[4-(5-methyl-[1,3,4]oxadiazol-2-yl)-benzenesulfonyl]-1H-pyrrolo[2,3-b]pyridine 73

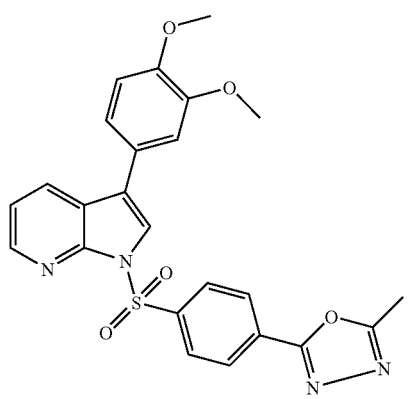

73

3-(3,4-Dimethoxy-phenyl)-1-[4-(5-methyl-[1,3,4]oxadiazol-2-yl)-benzenesulfonyl]-1H-pyrrolo[2,3-b]pyridine 73 was prepared using the same protocol as described in Example 9, substituting 8-quinoline-sulfonyl chloride with 3-oxazol-5-yl-benzenesulfonyl chloride. MS(ESI) [M+H$^+$]$^+$= 477.0.

Example 67

Synthesis of 1-(2-Benzenesulfonylmethyl-benzyl)-3-(3,4-dimethoxy-phenyl)-1H-pyrrolo[2,3-b]pyridine 74

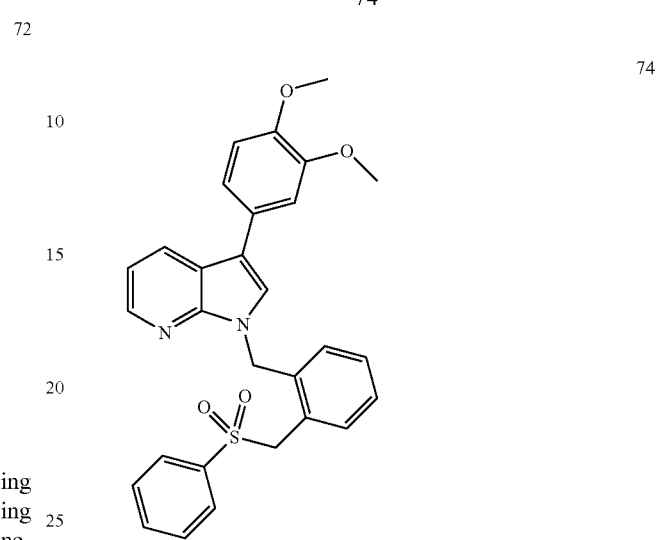

74

1-(2-Benzenesulfonylmethyl-benzyl)-3-(3,4-dimethoxy-phenyl)-1H-pyrrolo[2,3-b]pyridine 74 was prepared using the same protocol as described in Example 46, substituting m-nitro-benzyl chloride with 1-benzenesulfonylmethyl-2-chloromethyl-benzene. MS(ESI) [M+H$^+$]$^+$=499.1.

Example 68

Synthesis of 1-Benzyl-3-(3,4-dimethoxy-phenyl)-1H-pyrrolo[2,3-b]pyridine 75

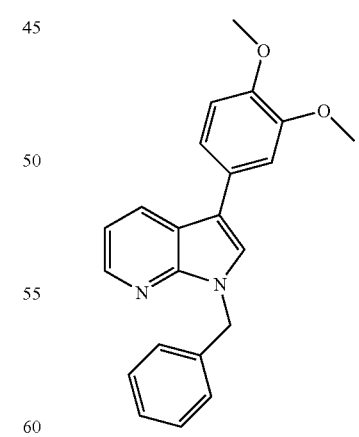

75

1-Benzyl-3-(3,4-dimethoxy-phenyl)-1H-pyrrolo[2,3-b]pyridine 75 was prepared using the same protocol as described in Example 46, substituting m-nitro-benzyl chloride with benzyl chloride. MS(ESI) [M+H$^+$]$^+$= 345.1.

Example 69

Synthesis of 3-(3,4-Dimethoxy-phenyl)-1-(2-methyl-naphthalen-1-ylmethyl)-1H-pyrrolo[2,3-b]pyridine 76

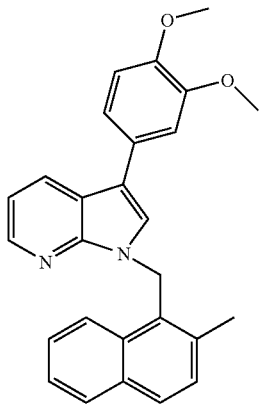

3-(3,4-Dimethoxy-phenyl)-1-(2-methyl-naphthalen-1-ylmethyl)-1H-pyrrolo[2,3-b]pyridine 76 was prepared using the same protocol as described in Example 46, substituting m-nitro-benzyl chloride with 1-chloromethyl-2-methyl-naphthalene.

Example 70

Synthesis of 4-[3-(3,4-Dimethoxy-phenyl)-pyrrolo[2,3-b]pyridin-1-ylmethyl]-benzonitrile 77

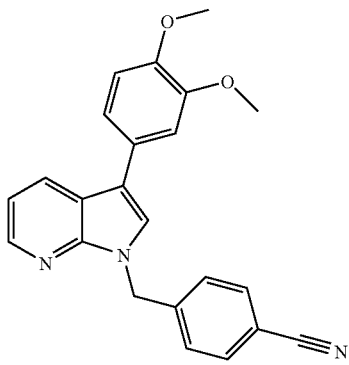

4-[3-(3,4-Dimethoxy-phenyl)-pyrrolo[2,3-b]pyridin-1-ylmethyl]-benzonitrile 77 was prepared using the same protocol as described in Example 46, substituting m-nitro-benzyl chloride with 4-chloromethylbenzonitrile. MS(ESI) [M+H$^+$]$^+$=370.2.

Example 71

Synthesis of 1-Biphenyl-2-ylmethyl-3-(3,4-dimethoxy-phenyl)-1H-pyrrolo[2,3-b]pyridine 78

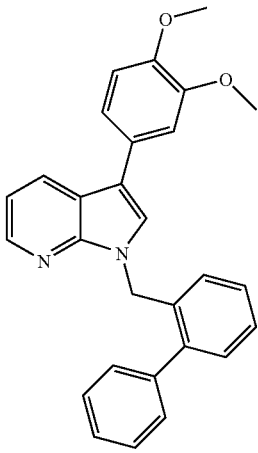

1-Biphenyl-2-ylmethyl-3-(3,4-dimethoxy-phenyl)-1H-pyrrolo[2,3-b]pyridine 78 was prepared using the same protocol as described in Example 46, substituting m-nitro-benzyl chloride with 2-phenylbenzyl chloride.

Example 72

Synthesis of 3-(3,4-Dimethoxy-phenyl)-1-(3-trifluoromethyl-benzyl)-1H-pyrrolo[2,3-b]pyridine 79

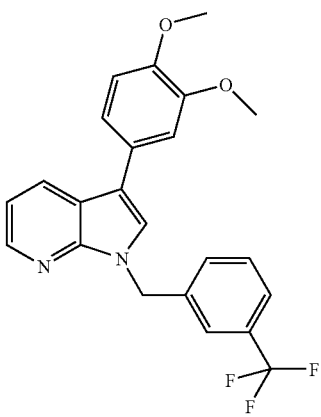

3-(3,4-Dimethoxy-phenyl)-1-(3-trifluoromethyl-benzyl)-1H-pyrrolo[2,3-b]pyridine 79 was prepared using the same protocol as described in Example 46, substituting m-nitro-benzyl chloride with m-trifluoromethylbenzyl chloride. MS(ESI) [M+H$^+$]$^+$=413.0.

Example 73

Synthesis of Compounds of Formula Ib

Scheme - 21

[Scheme showing compound XI → XII → Formula Ib via Step1 and Step2]

Step-1 Synthesis of Formula XII

Compound XI can be prepared from 7-azaindole following published procedure (Schneller, S. W.; Luo, Jiann-Kuan. *J. Org. Chem.* 1980, 45, 4045-4048), and compound of Formula XII can prepared from compound XI by reacting with boronic acids under Suzuki reaction conditions (aqueous base and Pd(0) catalyst or anhydrous conditions with KF in dioxane with Pd(0) catalyst). Alternately, compound XI can also be reacted with a tin reagent, zinc reagent or copper reagent, under Stille, Negishi or cuprate coupling reaction conditions respectively, to provide compound XII. The product can isolated by conventional work up procedure, e.g. extraction of the product with an organic solvent and purifying by column chromatography.

Step-2 Synthesis of Formula Ib

Compound of Formula Ib can be prepared by reacting compound XII with nucleophilic reagents, e.g. acid chlorides, sulfonyl chlorides, isocyanates, isothiocyanates, alkyl halides, benzyl halides, etc., under basic conditions. The product can be isolated by following standard workup procedures, e.g. extraction of the product with organic solvent and purifying by column chromatography.

Example 74

Synthesis of [4-(3,4-Dimethoxy-phenyl)-pyrrolo[2,3-b]pyridin-1-yl]-(2-ethoxy-naphthalen-1-yl)-methanone 48

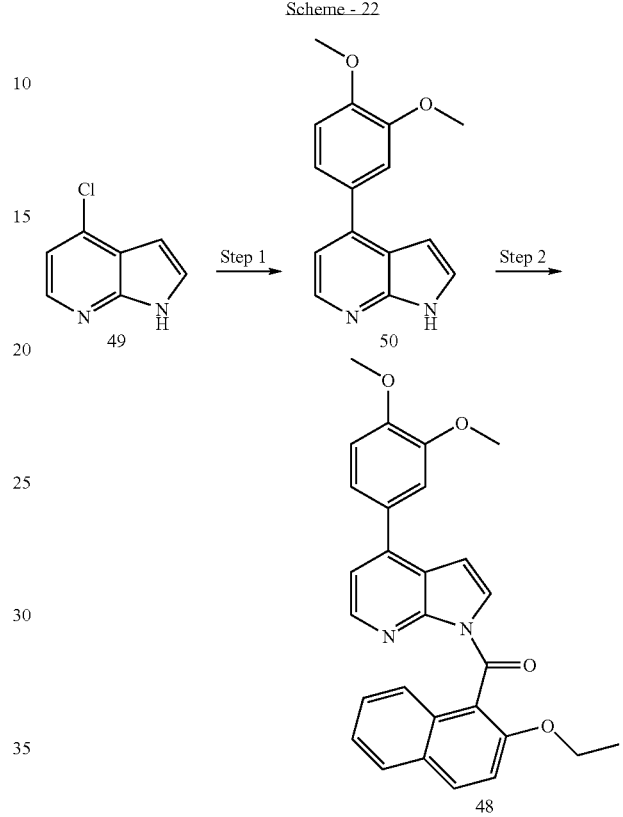

Step-1 Preparation of 4-(3,4-Dimethoxy-phenyl)-1H-pyrrolo[2,3-b]pyridine 50

In a microwave reaction tube, 4-chloro-7-azaindole (49, 1.362 g, 8.926 mmol), prepared from 7-azaindole following published procedure (Schneller, S. W.; Luo, Jiann-Kuan. *J. Org. Chem.* 1980, 45, 4045-4048), 3,4-dimethoxyphenyl boronic acid (4.06 g, 22.3 mmol), and tetrakis(triphenylphosphine)palladium(0) (52 mg, 0.45 mmol) were mixed in 1.0 M potassium carbonate in water (27 mL) and tetrahydrofuran (43 mL). The resulting mixture was heated at 150° C. in a CEM Discover microwave unit for 20 minutes. Ethyl acetate and water were added, and the two layers were separated. The aqueous layer was extracted with ethyl acetate. The combined organic layers were washed with brine and dried over anhydrous sodium sulfate. Concentration under reduced pressure afforded the crude material, which was purified by column chromatography (40-70% ethyl acetate in hexane) to yield the desired product in light yellow solid (50, 974 mg, 3.83 mmol). MS(ESI) $[M+H^+]^+=255.2$.

Step-2 Preparation of [4-(3,4-Dimethoxy-phenyl)-pyrrolo[2,3-b]pyridin-1-yl]-(2-ethoxy-naphthalen-1-yl)-methanone 48

Sodium hydride (60% dispersion in mineral oil, 39.9 mg, 0.997 mmol) was washed with hexane and put under an atmosphere of nitrogen, and 1 mL of tetrahydrofuran was added. 4-(3,4-dimethoxy-phenyl)-1H-pyrrolo[2,3-b]pyridine (50, 195 mg, 0.767 mmol) in tetrahydrofuran (6.2 mL) was added, and the resulting mixture was stirred for 10 minutes at room temperature. 2-ethoxy naphthoyl chloride (202 mg, 0.844 mmol) in tetrahydrofuran was added. After two hours, the reaction was quenched with water, and the two layers were separated. The aqueous layer was extracted with ethyl acetate. The combined organic layers were washed with brine and dried over anhydrous sodium sulfate. Concentration under reduced pressure afforded the crude material, which was purified by column chromatography (35-60% ethyl acetate in hexane) to yield the desired product in light yellow solid (48, 262 mg, 0.579 mmol). MS(ESI) [M+H$^+$]$^+$= 453.2.

Example 75

Synthesis of [4-(3,4-Dimethoxy-phenyl)-pyrrolo[2,3-b]pyridin-1-yl]-(2-ethoxy-phenyl)-methanone 51

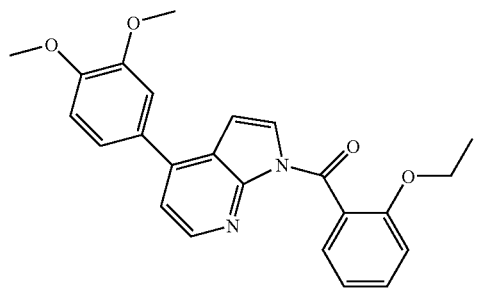

51

[4-(3,4-Dimethoxy-phenyl)-pyrrolo[2,3-b]pyridin-1-yl]-(2-ethoxy-phenyl)-methanone 51 was prepared using the same protocol as described in Example 74, substituting 2-ethoxy naphthoyl chloride with 2-ethoxy-benzoyl chloride. MS(ESI) [M+H$^+$]$^+$=403.3.

Example 76

Synthesis of Compounds of Formula Ic

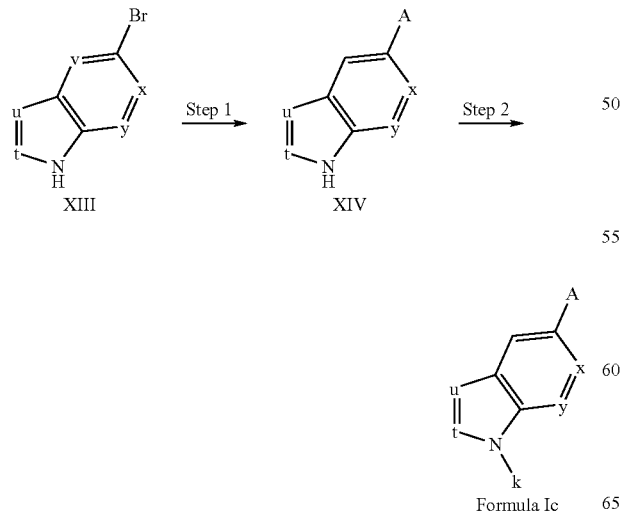

Step-1 Synthesis of Formula XIV

Compound XIII can be prepared from 7-azaindole following published procedure (Marie-Claude, Viaud, Heterocycles, 1999, 50, 1065-1080), and compound of Formula XIV can be prepared from compound XIII by reacting with boronic acids under Suzuki reaction conditions (aqueous base and Pd(0) catalyst or anhydrous conditions with KF in dioxane with Pd(0) catalyst). Alternately, compound XIII can also be reacted with a tin reagent, zinc reagent or copper reagent, under Stille, Negishi or cuprate coupling reaction conditions respectively, to provide compound XIV. The product can be isolated by conventional work up procedure, e.g. extraction of the product with an organic solvent and purifying by column chromatography.

Step-2 Synthesis of Formula Ic

Compound of Formula Ic can be prepared by reacting compound XIV with nucleophilic reagents, e.g. acid chlorides, sulfonyl chlorides, isocyanates, isothiocyanates, alkyl halides, benzyl halides, etc., under basic conditions. The product can be isolated by following standard workup procedures, e.g. extraction of the product with organic solvent and purifying by column chromatography.

Example 77

Synthesis of [5-(3,4-Dimethoxy-phenyl)-pyrrolo[2,3-b]pyridin-1-yl]-(2-ethoxy-naphthalen-1-yl)-methanone 80

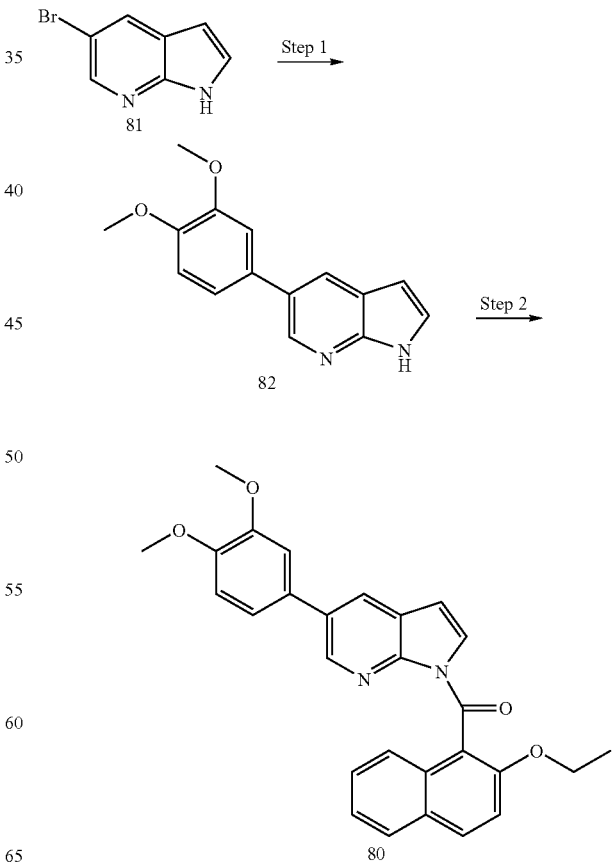

Step-1 Preparation of 5-(3,4-Dimethoxy-phenyl)-1H-pyrrolo[2,3-b]pyridine 82

In a microwave safe tube, 5-bromo-7-azaindole (81, 392 mg, 1.99 mmol), prepared from 7-azaindole following the published procedure (Marie-Claude, Viaud, *Heterocycles*, 1999, 50, 1065-1080), 3,4-dimethoxyphenyl boronic acid (905 mg, 4.97 mmol), and tetrakis(triphenylphosphine)palladium(0) (11 mg, 0.099 mol) were mixed in 1.0 M of potassium carbonate (6.0 mL) and tetrahydrofuran (9.5 mL, 0.12 mol). The resulting mixture was heated at 120° C. in a CEM Discover microwave unit for 10 minutes. Ethyl acetate and water were added, and the two layers were separated. The aqueous layer was extracted with ethyl acetate. The combined organic layers were washed with brine and dried over anhydrous sodium sulfate. Concentration under reduced pressure afforded the crude material, which was purified by column chromatography (40-70% ethyl acetate:hexanes) to yield the desired product as a light yellow solid (82, 207 mg, 41%). MS(ESI) $[M+H^+]^+=255.2$.

Step-2 Preparation of [5-(3,4-Dimethoxy-phenyl)-pyrrolo[2,3-b]pyridin-1-yl]-(2-ethoxy-naphthalen-1-yl)-methanone 80

Sodium hydride (60% dispersion in mineral oil, 10.1 mg, 0.252 mmol) was washed with hexane and put under an atmosphere of nitrogen, and 1 mL of tetrahydrofuran was added. 5-(3,4-Dimethoxy-phenyl)-1H-pyrrolo[2,3-b]pyridine (82, 49.3 mg, 0.194 mmol) in tetrahydrofuran (1.6 mL) was added, and the resulting mixture was stirred for 30 minutes at room temperature. 2-Ethoxy naphthoyol chloride (51.1 mg, 0.213 mmol) in THF was added. After two hours, the reaction was quenched with water, and the two layers were seperated. The aqueous layer was extracted with ethyl acetate. The combined organic layers were washed with brine and dried over anhydrous sodium sulfate. Concentration under reduced pressure afforde the crude, which was purified by column chromatography (40-55% ethyl acetate in hexane) to yield the desired product as a liquid (80, 61 mg, 70%). MS(ESI) $[M+H^+]^+=453.2$.

Example 78

Synthesis of [5-(3,4-Dimethoxy-phenyl)-pyrrolo[2,3-b]pyridin-1-yl]-(2-ethoxy-phenyl)-methanone 83

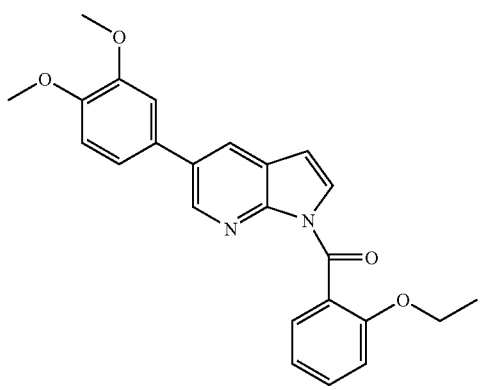

83

[5-(3,4-Dimethoxy-phenyl)-pyrrolo[2,3-b]pyridin-1-yl]-(2-ethoxy-phenyl)-methanone 83 was prepared using the same protocol as described in Example 77, substituting 2-ethoxy naphthoyol chloride with 2-ethoxy-benzoyl chloride. MS(ESI) $[M+H^+]^+=403.2$.

Example 79

Synthesis of (2-Ethoxy-naphthalen-1-yl)-[3-(4-methanesulfonyl-phenyl)-pyrrolo[2,3-b]pyridin-1-yl]-methanone 84

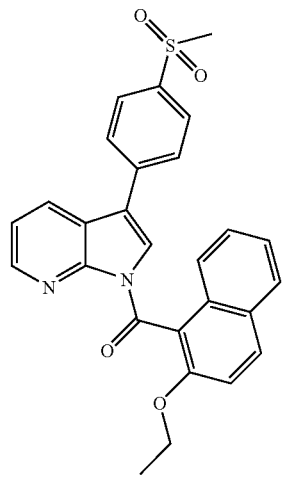

84

Scheme - 25

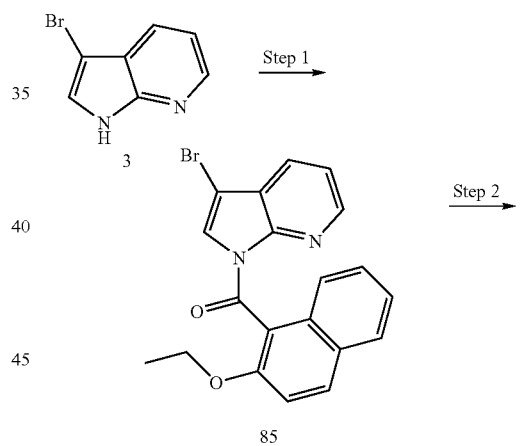

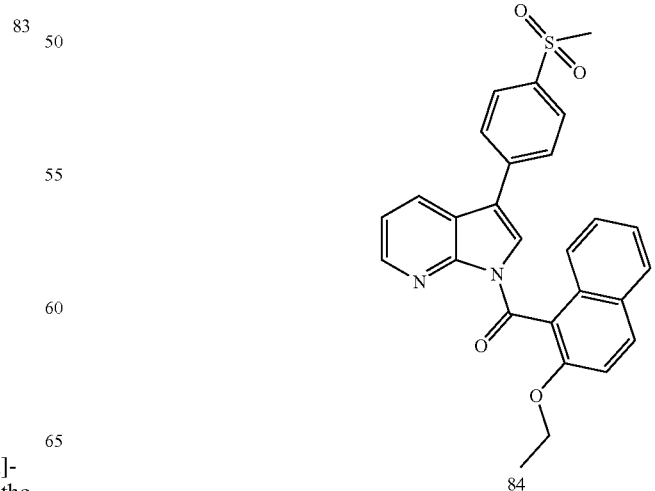

84

Step 1—Preparation of (3-Bromo-pyrrolo[2,3-b]pyridin-1-yl)-(2-ethoxy-naphthalen-1-yl)-methanone 85

3-Bromo-7-azaindole (500 mg, 2.0 mmol) 3 was dissolved in N,N-dimethylformamide (50 mL) and sodium hydride (210 mg, 5.3 mmol, 60% dispersion in mineral oil) and 2-Ethoxy-naphthalene-1-carbonyl chloride (710 mg, 3.0 mmol) were added. The reaction mixture was stirred at ambient temperature for 30 min, cast into ice water (100 mL) and extracted into ethyl acetate. The organic portion was dried with anhydrous magnesium sulfate, filtered and the filtrate concentrated. Purification via column chromatography (10% Ethyl acetate in hexanes) provided the desired product 85 (800 mg, 80%).

Step 2—Preparation of (2-Ethoxy-naphthalen-1-yl)-[3-(4-methanesulfonyl-phenyl)-pyrrolo[2,3-b]pyridin-1-yl]-methanone 84

(3-Bromo-pyrrolo[2,3-b]pyridin-1-yl)-(2-ethoxy-naphthalen-1-yl)-methanone 85 (35 mg, 0.0088 mmol), 4-Methanesulfonyl-phenylboronic acid (35 mg, 0.18 mmol) and tetrakis(triphenylphosphine)palladium(0) (5 mg) were stirred in tetrahydrofuran (16 mL) and potassium carbonate solution (8.0 mL, 1 M aqueous). The reaction mixture was stirred over night at 60° C. The reaction mixture was concentrated under reduced pressure and partitioned between ethyl acetate and brine. The organic portion was dried over anhydrous magnesium sulfate and filtered. The filtrate was concentrated and purified by flash chromatography (ethyl acetate:hexanes 20%-100%). The desired product, 84 was obtained as a pale yellow powder (10 mg, 20%).

Example 80

Synthesis of (2-Ethoxy-naphthalen-1-yl)-[3-(3-methanesulfonyl-phenyl)-pyrrolo[2,3-b]pyridin-1-yl]-methanone 86

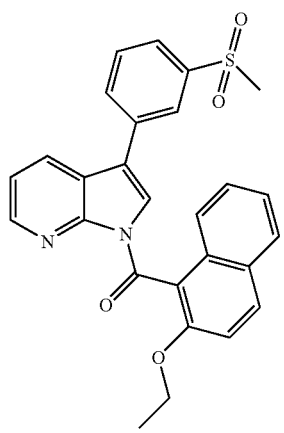

86

(2-Ethoxy-naphthalen-1-yl)-[3-(3-methanesulfonyl-phenyl)-pyrrolo[2,3-b]pyridin-1-yl]-methanone 86 was prepared using the same protocol as described in Example 79, substituting 4-Methanesulfonyl-phenylboronic acid with 3-Methanesulfonyl-phenylboronic acid.

Example 81

Synthesis of 3-[1-(2-Ethoxy-naphthalene-1-carbonyl)-1H-pyrrolo[2,3-b]pyridin-3-yl]-benzoic acid benzyl ester 87

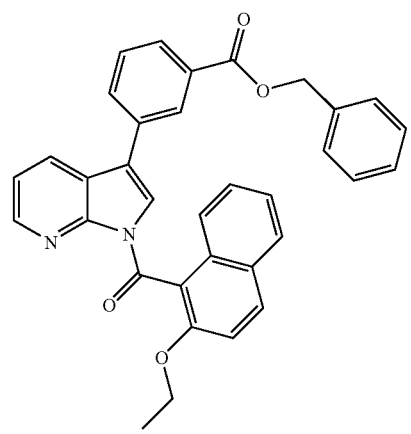

87

3-[1-(2-Ethoxy-naphthalene-1-carbonyl)-1H-pyrrolo[2,3-b]pyridin-3-yl]-benzoic acid benzyl ester 87 was prepared using the same protocol as described in Example 79, substituting 4-Methanesulfonyl-phenylboronic acid with 3-carbobenzyloxy-phenylboronic acid.

Example 82

Synthesis of 3-(3-Cyclopentyloxy-4-methoxy-phenyl)-1H-pyrrolo[2,3-b]pyridine 88

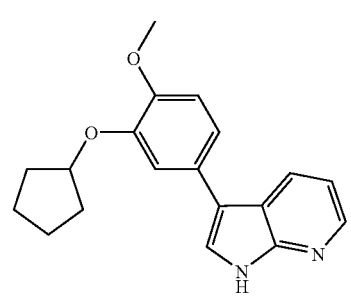

88

3-(3-Cyclopentyloxy-4-methoxy-phenyl)-1H-pyrrolo[2,3-b]pyridine 88 was prepared using the same protocol as described in Example 7, substituting 3,4-dimethoxyphenylboronic acid with 3-cyclopentyloxy,4-methoxy-phenylboronic acid. MS(ESI) $[M+H^+]^+$=309.20.

Example 83

Synthesis of 3-(3-Benzyloxy-4-methoxy-phenyl)-1H-pyrrolo[2,3-b]pyridine 89

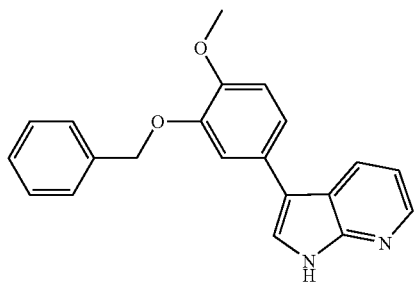

89

3-(3-Benzyloxy-4-methoxy-phenyl)-1H-pyrrolo[2,3-b]pyridine 89 was prepared using the same protocol as described in Example 7, substituting 3,4-dimethoxyphenylboronic acid with 3-benzyloxy,4-methoxy-phenylboronic acid.

Example 84

Synthesis of 3-Benzo[1,3]dioxol-5-yl-1H-pyrrolo[2,3-b]pyridine 90

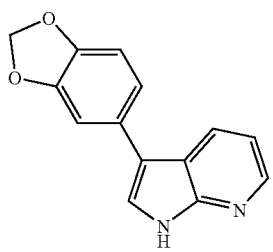

90

3-Benzo[1,3]dioxol-5-yl-1H-pyrrolo[2,3-b]pyridine 90 was prepared using the same protocol as described in Example 7, substituting 3,4-dimethoxyphenylboronic acid with 3,4-methylenedioxybenzene boronic acid.

Example 85

Synthesis of 1-(Benzo[b]thiophene-3-sulfonyl)-3-(3,4-dimethoxy-phenyl)-1H-pyrrolo[2,3-b]pyridine 91

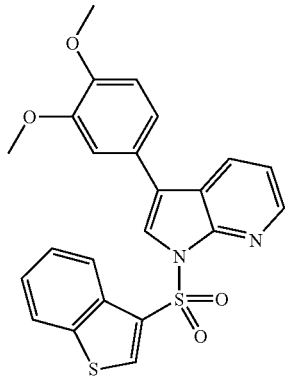

91

1-(Benzo[b]thiophene-3-sulfonyl)-3-(3,4-dimethoxy-phenyl)-1H-pyrrolo[2,3-b]pyridine 91 was prepared using the same protocol as described in Example 9, substituting 8-quinoline-sulfonyl chloride with Benzo[b]thiophene-3-sulfonyl chloride. MS(ESI) [M+H$^+$]$^+$=450.97.

Example 86

Synthesis of 8-[3-(3,4-Dimethoxy-phenyl)-5-methoxy-indole-1-sulfonyl]-quinoline 92

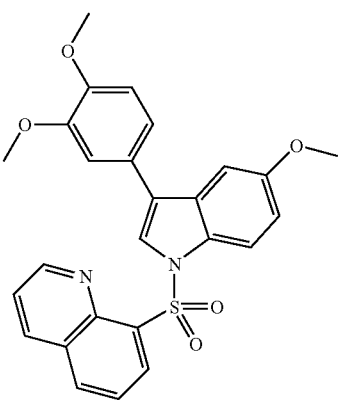

92

8-[3-(3,4-Dimethoxy-phenyl)-5-methoxy-indole-1-sulfonyl]-quinoline 92 was prepared using the same protocol as described in Examples 21 and 22, substituting 1-benzenesulfonyl-3-bromoindole with 1-Benzenesulfonyl-3-bromo-5-methoxyindole.

MS(ESI) [M+H$^+$]$^+$=475.10.

Example 87

Synthesis of 8-[3-(3,4-Dimethoxy-phenyl)-5-chloro-indole-1-sulfonyl]-quinoline 93

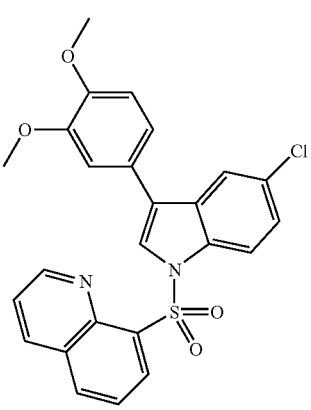

93

8-[3-(3,4-Dimethoxy-phenyl)-5-chloro-indole-1-sulfonyl]-quinoline 93 was prepared using the same protocol as described in Examples 21 and 22, substituting 1-Benzenesulfonyl-3-bromoindole with 1-Benzenesulfonyl-3-bromo-5-chloroindole. MS(ESI) [M+H$^+$]$^+$=479.10.

Example 88

Synthesis of 8-[3-(3,4-Dimethoxy-phenyl)-5-methoxy-indole-1-sulfonyl]-3-methyl-quinoline 94

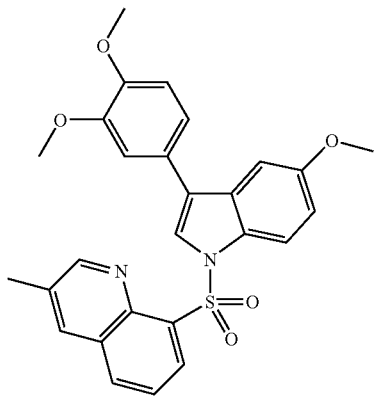

8-[3-(3,4-Dimethoxy-phenyl)-5-methoxy-indole-1-sulfonyl]-3-methyl-quinoline 94 was prepared using the same protocol as described in Examples 21 and 22, substituting 8-quinoline-sulfonyl chloride with 3-methyl-quinoline-8-sulfonyl chloride. MS(ESI) [M+H⁺]⁺=489.10.

Example 89

Synthesis of 8-[5-Chloro-3-(3-cyclopentyloxy-4-methoxy-phenyl)-indole-1-sulfonyl]-3-methyl-quinoline 95

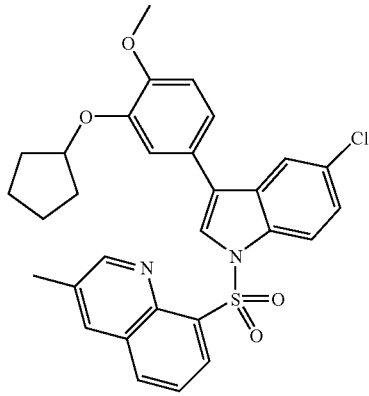

8-[5-Chloro-3-(3-cyclopentyloxy-4-methoxy-phenyl)-indole-1-sulfonyl]-3-methyl-quinoline 95 was prepared using the same protocol as described in Examples 21 and 22, substituting 8-quinoline-sulfonyl chloride, 1-Benzenesulfonyl-3-bromoindole and 3,4-dimethoxyphenyl boronic acid with 3-methyl-quinoline-8-sulfonyl chloride, 1-Benzenesulfonyl-3-bromo-5-chloro-indole and 3-cyclopentyloxy-4-methoxy-phenylboronic acid respectively. MS(ESI) [M+H⁺]⁺=547.10.

Example 90

Synthesis of 8-[5-Chloro-3-(3,4-Dimethoxy-phenyl)-indole-1-sulfonyl]-3-methyl-quinoline 96

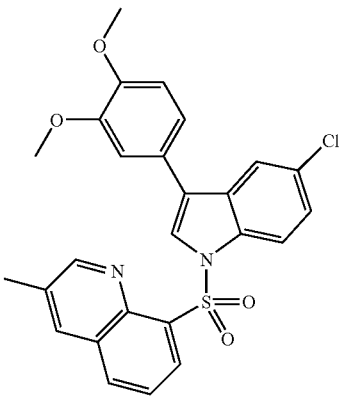

8-[5-Chloro-3-(3,4-Dimethoxy-phenyl)-indole-1-sulfonyl]-3-methyl-quinoline 96 was prepared using the same protocol as described in Examples 21 and 22, substituting 8-quinoline-sulfonyl chloride and 1-Benzenesulfonyl-3-bromoindole with 3-methyl-quinoline-8-sulfonyl chloride and 1-benzenesulfonyl-3-bromo-5-methoxy-indole respectively. MS(ESI) [M+H⁺]⁺=493.00.

Example 91

Synthesis of 8-[5-Methoxy-3-(3-cyclopentyloxy-4-methoxy-phenyl)-indole-1-sulfonyl]-3-methyl-quinoline 97

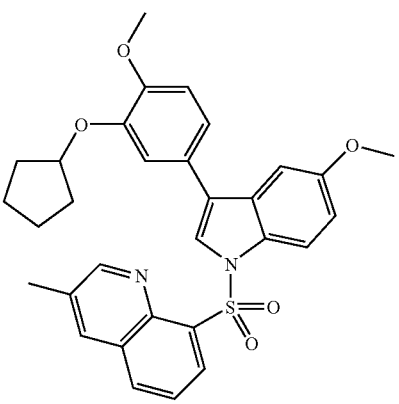

8-[5-Methoxy-3-(3-cyclopentyloxy-4-methoxy-phenyl)-indole-1-sulfonyl]-3-methyl-quinoline 97 was prepared using the same protocol as described in Examples 21 and 22, substituting 8-quinoline-sulfonyl chloride, 1-Benzenesulfonyl-3-bromoindole and 3,4-dimethoxyphenyl boronic acid with 3-methyl-quinoline-8-sulfonyl chloride, 1-benzenesulfonyl-3-bromo-5-methoxy-indole and 3-cyclopentyloxy-4-methoxy-phenylboronic acid respectively. MS(ESI) [M+H⁺]⁺=543.20.

Example 92

3-(3-Cyclopentyloxy-4-methoxy-phenyl)-pyrrolo[2,3-b]pyridine-1-carboxylic acid (3-nitro-4-fluoro-phenyl)-amide 98

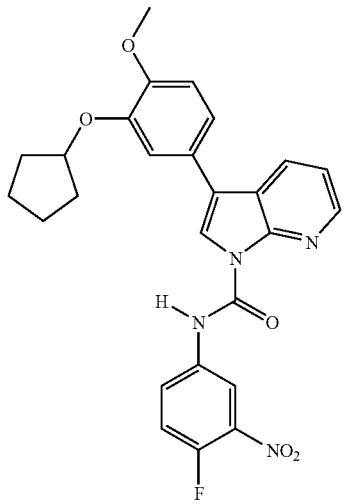

3-(3-Cyclopentyloxy-4-methoxy-phenyl)-pyrrolo[2,3-b]pyridine-1-carboxylic acid (3-nitro-4-fluoro-phenyl)-amide 98 was prepared using the same protocol as described in Example 25, substituting 3-(3,4-dimethoxy-phenyl)-1H-pyrrolo[2,3-b]pyridine 1 and 4-chlorophenyl isocyanate with 3-(3-Cyclopentyloxy-4-methoxy-phenyl)-1H-pyrrolo[2,3-b]pyridine 88 and 4-fluoro-3-nitrophenyl isocyanate respectively. MS(ESI) $[M+H^+]^+=491.10$.

Example 93

1-Benzenesulfonyl-3-(3-cyclopentyloxy-4-methoxy-phenyl)-1H-indole 99

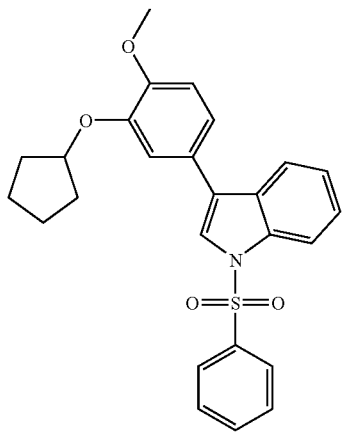

1-Benzenesulfonyl-3-(3-cyclopentyloxy-4-methoxy-phenyl)-1H-indole 99 was prepared using the same protocol as described in Example 21, substituting 3,4-dimethoxyphenyl boronic acid with 3-cyclopentyloxy-4-methoxy-phenyl boronic acid. MS(ESI) $[M+H^+]^+=448.31$.

Example 94

8-[3-(3-Cyclopentyloxy-4-methoxy-phenyl)-indole-1-sulfonyl]-quinoline 100

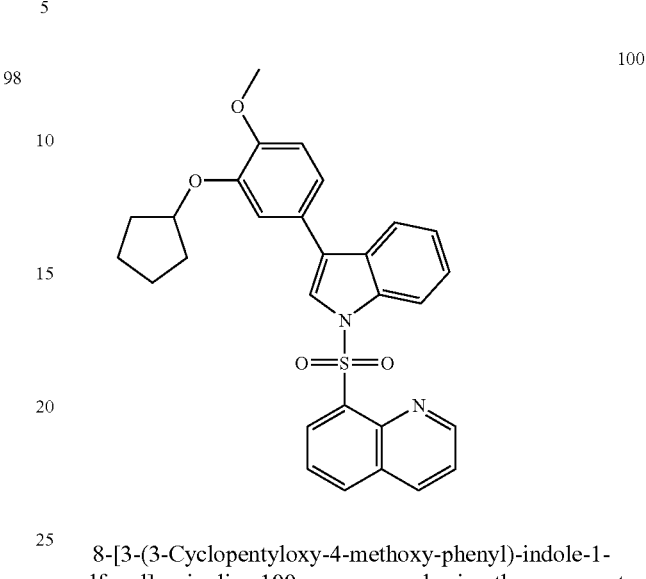

8-[3-(3-Cyclopentyloxy-4-methoxy-phenyl)-indole-1-sulfonyl]-quinoline 100 was prepared using the same protocol as described in Examples 21 and 22, substituting 3,4-dimethoxyphenyl boronic acid and benxene sulfonyl chloride with 3-cyclopentyloxy-4-methoxy-phenyl boronic acid and 8-quinoline sulfonyl chloride respectively. MS(ESI) $[M+H^+]^+=499.09$.

Example 95

1-Benzenesulfonyl-3-(3-cyclopentyloxy-4-methoxy-phenyl)-1H-pyrrolo[2,3-b]pyridine 101

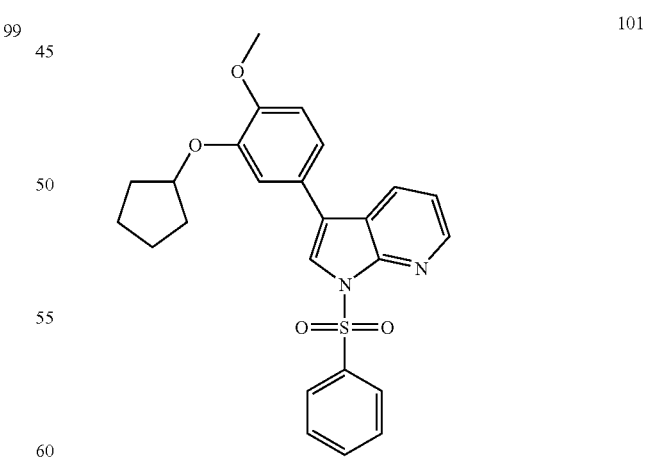

1-Benzenesulfonyl-3-(3-cyclopentyloxy-4-methoxy-phenyl)-1H-pyrrolo[2,3-b]pyridine 101 was prepared using the same protocol as described in Example 7, substituting 3,4-dimethoxyphenyl boronic acid with 3-cyclopentyloxy-4-methoxy-phenyl boronic acid. MS(ESI) $[M+H^+]^+=449.13$.

Example 96

8-[3-(3-Cyclopentyloxy-4-methoxy-phenyl)-pyrrolo[2,3-b]pyridine-1-sulfonyl]-quinoline 102

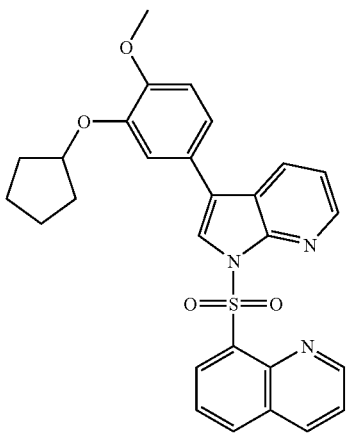

8-[3-(3-Cyclopentyloxy-4-methoxy-phenyl)-pyrrolo[2,3-b]pyridine-1-sulfonyl]-quinoline 102 was prepared using the same protocol as described in Example 42, substituting 2-methoxy-pyrimidine-4-boronic acid with 3-cyclopentyloxy-4-methoxy-phenyl boronic acid. MS(ESI) [M+H$^+$]$^+$= 500.20.

Example 97

1-Benzenesulfonyl-3-(3-benzyloxy-4-methoxy-phenyl)-1H-pyrrolo[2,3-b]pyridine 103

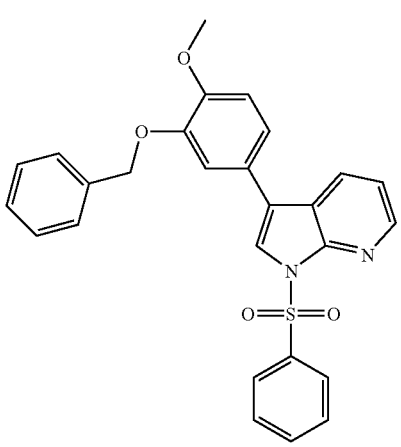

1-Benzenesulfonyl-3-(3-benzyloxy-4-methoxy-phenyl)-1H-pyrrolo[2,3-b]pyridine 103 was prepared using the same protocol as described in Example 42, substituting 2-methoxy-pyrimidine-4-boronic acid and quinoline-8-sulfonyl chloride with 3-cyclopentyloxy-4-methoxy-phenyl boronic acid and benzene sulfonyl chloride respectively.

Example 98

3-(3,4-Dimethoxy-phenyl)-1-(3-phenyl-isoxazol-5-ylmethyl)-1H-pyrrolo[2,3-b]pyridine 104

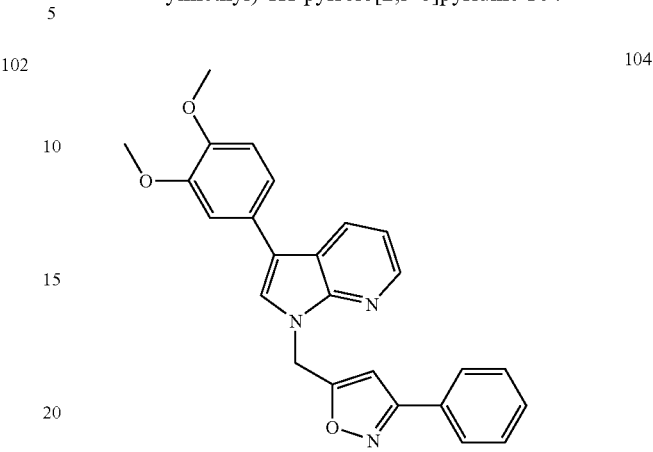

3-(3,4-Dimethoxy-phenyl)-1-(3-phenyl-isoxazol-5-ylmethyl)-1H-pyrrolo[2,3-b]pyridine 104 was prepared using the same protocol as described in Example 46, substituting m-nitro-benzyl chloride with 5-Chloromethyl-3-phenyl-isoxazole. MS(ESI) [M+H$^+$]$^+$=412.23.

Example 99

[3-(3,4-Dimethoxy-phenyl)-pyrrolo[2,3-b]pyridin-1-yl]-[5-(3-iodo-phenyl)-isoxazol-3-yl]-methanone 105

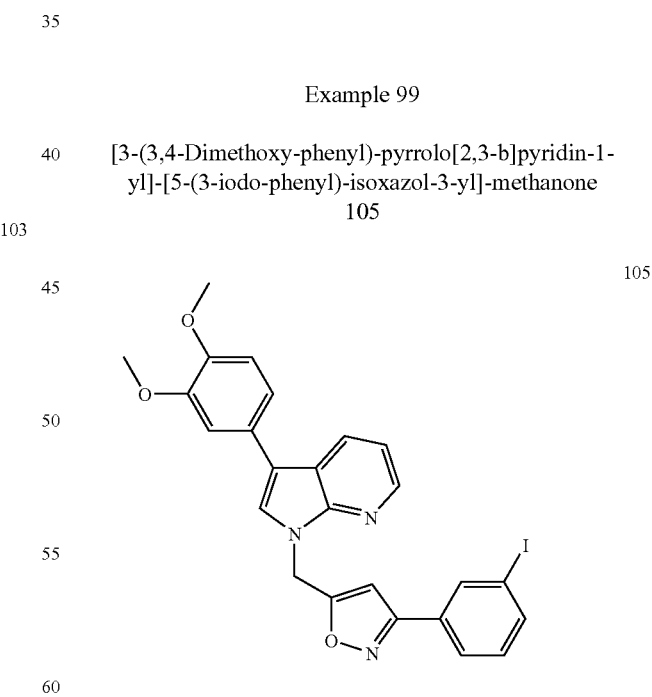

[3-(3,4-Dimethoxy-phenyl)-pyrrolo[2,3-b]pyridin-1-yl]-[5-(3-iodo-phenyl)-isoxazol-3-yl]-methanone 105 was prepared using the same protocol as described in Example 45, substituting 2-ethoxy-1-naphthoyl chloride with 3-(3-Iodo-phenyl)-isoxazole-5-carbonyl chloride.

Example 100

4-[3-(3,4-Dimethoxy-phenyl)-pyrrolo[2,3-b]pyridine-1-carbonyl]-benzonitrile 106

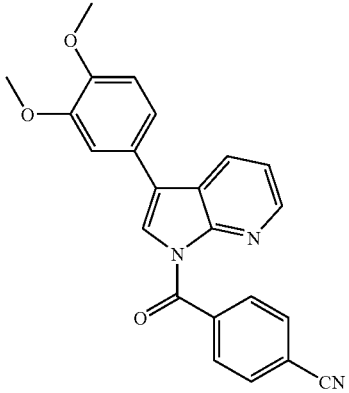

4-[3-(3,4-Dimethoxy-phenyl)-pyrrolo[2,3-b]pyridine-1-carbonyl]-benzonitrile 106 was prepared using the same protocol as described in Example 45, substituting 2-ethoxy-1-naphthoyl chloride with 4-cyano-benzoyl chloride. MS(ESI) [M+H$^+$]$^+$=384.20.

Example 101

(6-Chloro-pyridin-3-yl)-[3-(3,4-dimethoxy-phenyl)-pyrrolo[2,3-b]pyridin-1-yl]-methanone 107

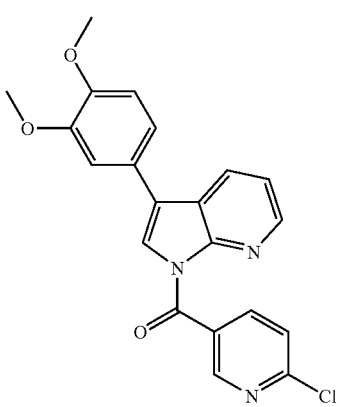

(6-Chloro-pyridin-3-yl)-[3-(3,4-dimethoxy-phenyl)-pyrrolo[2,3-b]pyridin-1-yl]-methanone 107 was prepared using the same protocol as described in Example 45, substituting 2-ethoxy-1-naphthoyl chloride with 2-chloro nicotinoyl chloride. MS(ESI) [M+H$^+$]$^+$=394.10.

Example 102

[3-(3,4-Dimethoxy-phenyl)-pyrrolo[2,3-b]pyridin-1-yl]-((1R,2R)-2-phenyl-trans-cyclopropyl)-methanone 108

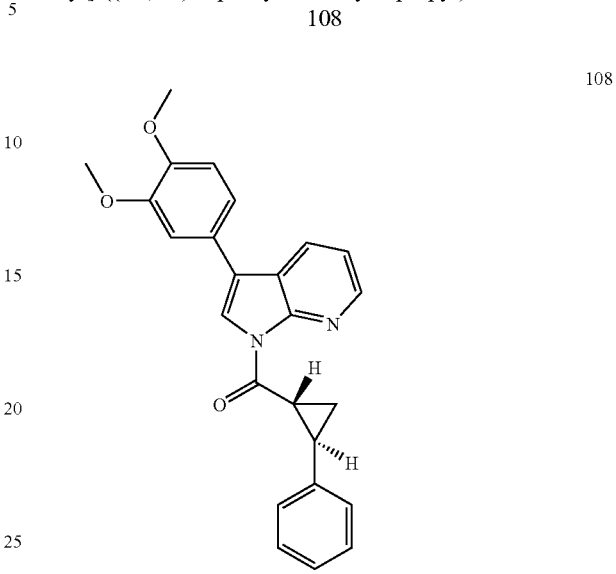

[3-(3,4-Dimethoxy-phenyl)-pyrrolo[2,3-b]pyridin-1-yl]-((1R,2R)-2-phenyl-trans-cyclopropyl)-methanone 108 was prepared using the same protocol as described in Example 45, substituting 2-ethoxy-1-naphthoyl chloride with trans-2-phenylcyclopropane-carbonyl chloride. MS(ESI) [M+H$^+$]$^+$=399.17.

Example 103

[3-(3,4-Dimethoxy-phenyl)-pyrrolo[2,3-b]pyridin-1-yl]-(4-dimethylamino-naphthalen-1-yl)-methanone 109

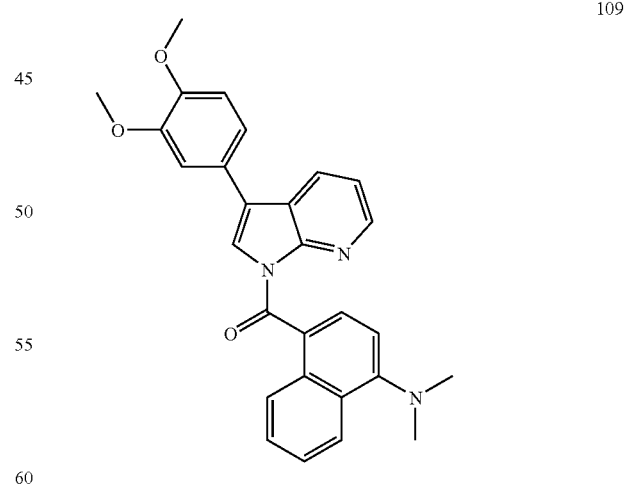

[3-(3,4-Dimethoxy-phenyl)-pyrrolo[2,3-b]pyridin-1-yl]-(4-dimethylamino-naphthalen-1-yl)-methanone 109 was prepared using the same protocol as described in Example 45, substituting 2-ethoxy-1-naphthoyl chloride with 4-Dimethylamino-naphthalene-1-carbonyl chloride. MS(ESI) [M+H$^+$]$^+$=452.20.

Example 104

Acetic acid 2-[3-(3,4-dimethoxy-phenyl)-pyrrolo[2,3-b]pyridine-1-carbonyl]-phenyl ester 110

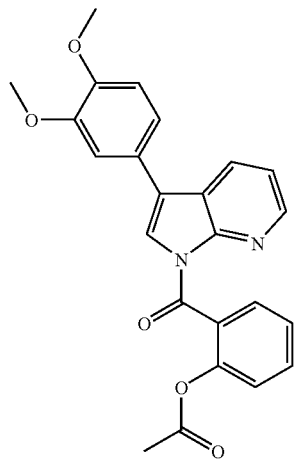

Acetic acid 2-[3-(3,4-dimethoxy-phenyl)-pyrrolo[2,3-b]pyridine-1-carbonyl]-phenyl ester 110 was prepared using the same protocol as described in Example 45, substituting 2-ethoxy-1-naphthoyl chloride with Acetic acid 2-chlorocarbonyl-phenyl ester. MS(ESI) [M+H$^+$]$^+$=417.20.

Example 105

(2,4-Diethoxy-phenyl)-[3-(3,4-dimethoxy-phenyl)-pyrrolo[2,3-b]pyridin-1-yl]-methanone 111

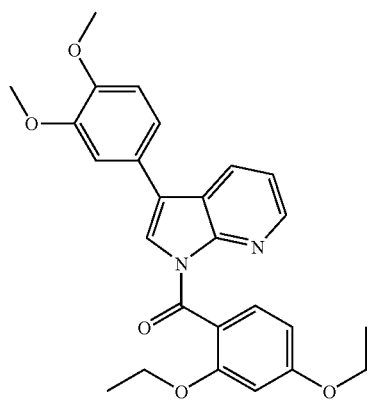

(2,4-Diethoxy-phenyl)-[3-(3,4-dimethoxy-phenyl)-pyrrolo[2,3-b]pyridin-1-yl]-methanone 111 was prepared using the same protocol as described in Example 45, substituting 2-ethoxy-1-naphthoyl chloride with 2,4-dimethoxy-benzoyl chloride. MS(ESI) [M+H$^+$]$^+$=447.20.

Example 106

[3-(3,4-Dimethoxy-phenyl)-pyrrolo[2,3-b]pyridin-1-yl]-[2-(2,2,2-trifluoro-ethoxy)-naphthalen-1-yl]-methanone 112

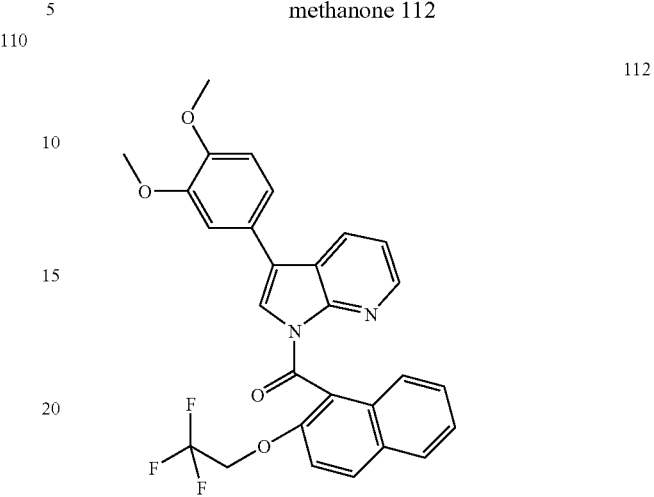

[3-(3,4-Dimethoxy-phenyl)-pyrrolo[2,3-b]pyridin-1-yl]-[2-(2,2,2-trifluoro-ethoxy)-naphthalen-1-yl]-methanone 112 was prepared using the same protocol as described in Example 47, substituting 2-ethoxy-4-nitro-benzoic acid with 2-(2,2,2-Trifluoro-ethoxy)-naphthalene-1-carboxylic acid. MS(ESI) [M+H$^+$]$^+$=507.10.

Example 107

[3-(3,4-Dimethoxy-phenyl)-pyrrolo[2,3-b]pyridin-1-yl]-(2-propoxy-phenyl)-methanone 113

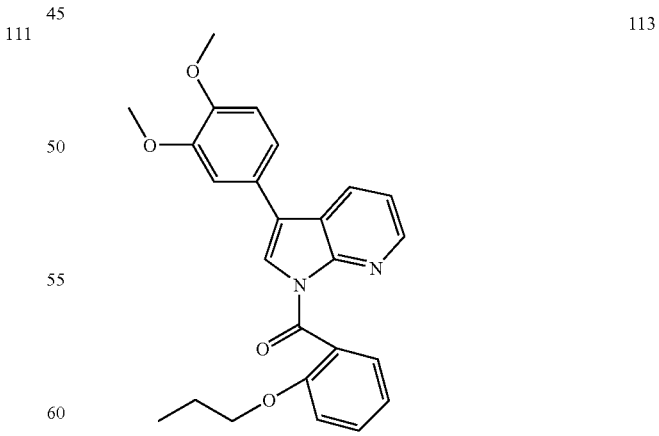

[3-(3,4-Dimethoxy-phenyl)-pyrrolo[2,3-b]pyridin-1-yl]-(2-propoxy-phenyl)-methanone 113 was prepared using the same protocol as described in Example 47, substituting 2-ethoxy-4-nitro-benzoic acid with 2-propoxy-naphthalene-1-carboxylic acid. MS(ESI) [M+H$^+$]$^+$=417.20.

Example 108

[3-(3,4-Dimethoxy-phenyl)-pyrrolo[2,3-b]pyridin-1-yl]-(4-methyl-naphthalen-1-yl)-methanone 114

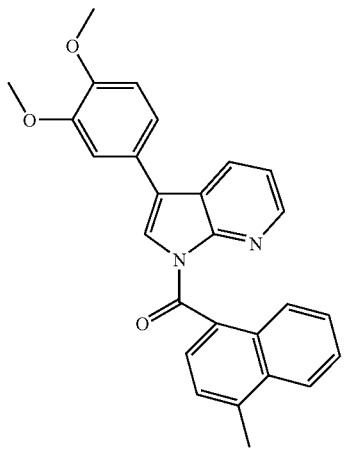

[3-(3,4-Dimethoxy-phenyl)-pyrrolo[2,3-b]pyridin-1-yl]-(4-methyl-naphthalen-1-yl)-methanone 114 was prepared using the same protocol as described in Example 47, substituting 2-ethoxy-4-nitro-benzoic acid with 4-methyl-naphthalene-1-carboxylic acid. MS(ESI) [M+H$^+$]$^+$=423.20.

Example 109

[3-(3,4-Dimethoxy-phenyl)-pyrrolo[2,3-b]pyridin-1-yl]-quinolin-4-yl-methanone 115

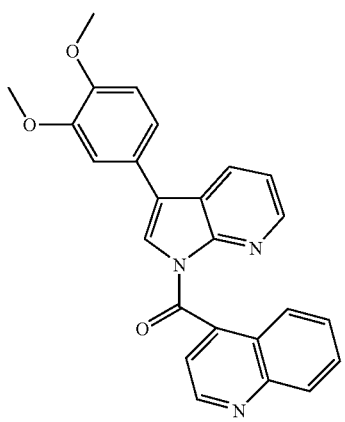

[3-(3,4-Dimethoxy-phenyl)-pyrrolo[2,3-b]pyridin-1-yl]-quinolin-4-yl-methanone 115 was prepared using the same protocol as described in Example 47, substituting 2-ethoxy-4-nitro-benzoic acid with quinoline-4-carboxylic acid. MS(ESI) [M+H$^+$]$^+$=410.20.

Example 110

[3-(3,4-Dimethoxy-phenyl)-pyrrolo[2,3-b]pyridin-1-yl]-(2-methyl-quinolin-4-yl)-methanone 116

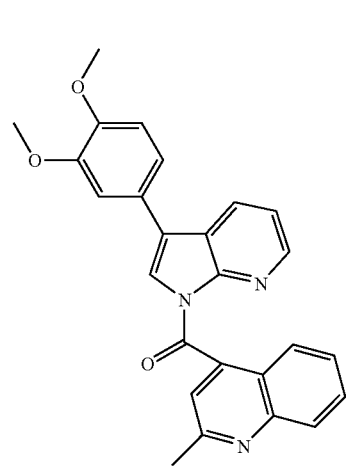

[3-(3,4-Dimethoxy-phenyl)-pyrrolo[2,3-b]pyridin-1-yl]-(2-methyl-quinolin-4-yl)-methanone 116 was prepared using the same protocol as described in Example 47, substituting 2-ethoxy-4-nitro-benzoic acid with 2-methyl-quinoline-4-carboxylic acid. MS(ESI) [M+H$^+$]$^+$=424.20.

Example 111

[3-(3,4-Dimethoxy-phenyl)-pyrrolo[2,3-b]pyridin-1-yl]-(3-phenyl-quinolin-4-yl)-methanone 117

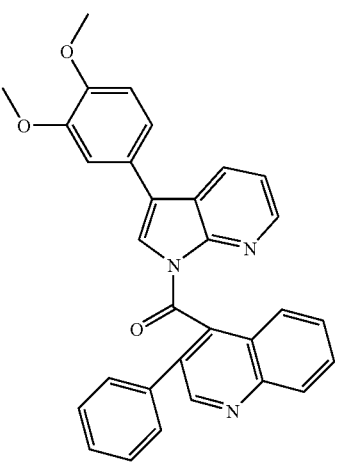

[3-(3,4-Dimethoxy-phenyl)-pyrrolo[2,3-b]pyridin-1-yl]-(3-phenyl-quinolin-4-yl)-methanone 117 was prepared using the same protocol as described in Example 47, substituting 2-ethoxy-4-nitro-benzoic acid with 3-phenyl-quinoline-4-carboxylic acid. MS(ESI) [M+H$^+$]$^+$=486.20.

Example 112

[3-(3,4-Dimethoxy-phenyl)-pyrrolo[2,3-b]pyridin-1-yl]-(2-phenoxy-phenyl)-methanone 118

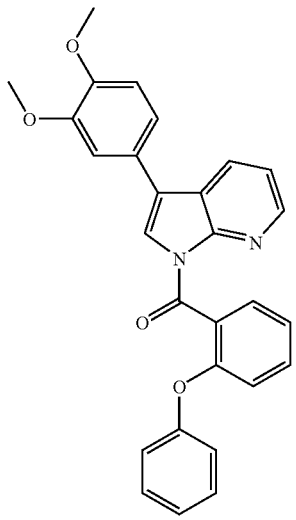

[3-(3,4-Dimethoxy-phenyl)-pyrrolo[2,3-b]pyridin-1-yl]-(2-phenoxy-phenyl)-methanone 118 was prepared using the same protocol as described in Example 47, substituting 2-ethoxy-4-nitro-benzoic acid with 2-phenoxy-benxoic acid. MS(ESI) [M+H$^+$]$^+$=451.16.

Example 113

[3-(3-Cyclopentyloxy-4-methoxy-phenyl)-pyrrolo[2,3-b]pyridin-1-yl]-(2-ethoxy-naphthalen-1-yl)-methanone 119

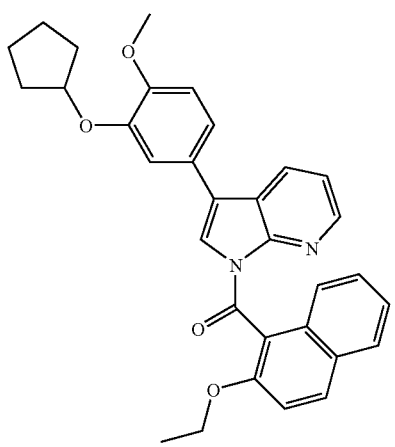

[3-(3-Cyclopentyloxy-4-methoxy-phenyl)-pyrrolo[2,3-b]pyridin-1-yl]-(2-ethoxy-naphthalen-1-yl)-methanone 119 was prepared using the same protocol as described in Example 79, substituting 4-Methanesulfonyl-phenylboronic acid with 3-cyclopentoxy-4-methoxy phenyl boronic acid. MS(ESI) [M+H$^+$]$^+$=507.30.

Example 114

3-[1-(2-Ethoxy-naphthalene-1-carbonyl)-1H-pyrrolo[2,3-b]pyridin-3-yl]-benzoic acid methyl ester 120

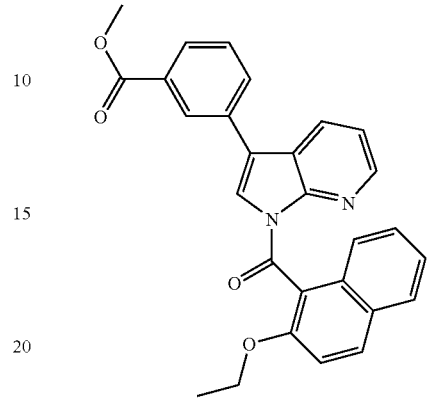

3-[1-(2-Ethoxy-naphthalene-1-carbonyl)-1H-pyrrolo[2,3-b]pyridin-3-yl]-benzoic acid methyl ester 120 was prepared using the same protocol as described in Example 79, substituting 4-Methanesulfonyl-phenylboronic acid with 3-methoxycarbonyl phenyl boronic acid. MS(ESI) [M+H$^+$]$^+$=451.14.

Example 115

3-[1-(2-Ethoxy-naphthalene-1-carbonyl)-1H-pyrrolo[2,3-b]pyridin-3-yl]-benzamide 121

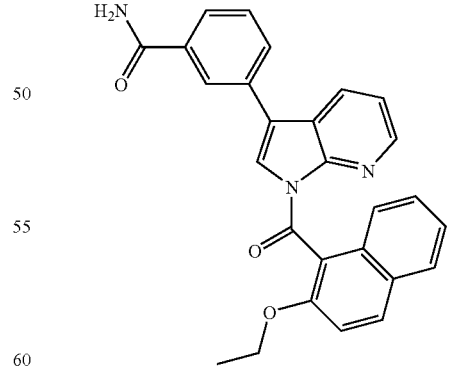

3-[1-(2-Ethoxy-naphthalene-1-carbonyl)-1H-pyrrolo[2,3-b]pyridin-3-yl]-benzamide 121 was prepared using the same protocol as described in Example 79, substituting 4-Methanesulfonyl-phenylboronic acid with 3-amido phenyl boronic acid. MS(ESI) [M+H$^+$]$^+$=436.14.

Example 116

N-{3-[1-(2-Ethoxy-naphthalene-1-carbonyl)-1H-pyrrolo[2,3-b]pyridin-3-yl]-phenyl}-methanesulfonamide 122

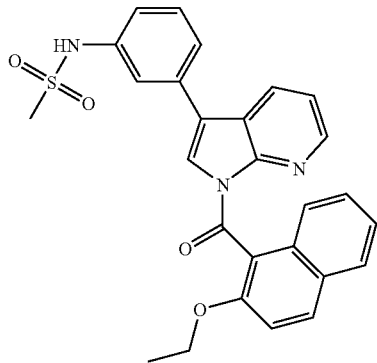

N-{3-[1-(2-Ethoxy-naphthalene-1-carbonyl)-1H-pyrrolo[2,3-b]pyridin-3-yl]-phenyl}-methanesulfonamide 122 was prepared using the same protocol as described in Example 79, substituting 4-Methanesulfonyl-phenylboronic acid with 3-N-methanesulfonamide phenyl boronic acid. MS(ESI) [M+H+]+=486.10.

Example 117

(2-Ethoxy-naphthalen-1-yl)-[3-(4-hydroxy-3-methoxy-phenyl)-pyrrolo[2,3-b]pyridin-1-yl]-methanone 123

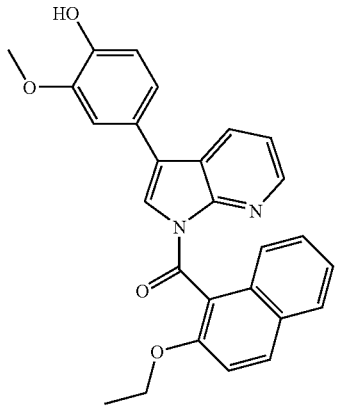

(2-Ethoxy-naphthalen-1-yl)-[3-(4-hydroxy-3-methoxy-phenyl)-pyrrolo[2,3-b]pyridin-1-yl]-methanone 123 was prepared using the same protocol as described in Example 79, substituting 4-Methanesulfonyl-phenylboronic acid with 2-Methoxy-4-(4,4,5,5-tetramethyl-[1,3,2]dioxaborolan-2-yl)-phenol. MS(ESI) [M+H+]+=439.17.

Example 118

[3-(3-Cyclopentyloxy-4-methoxy-phenyl)-pyrrolo[2,3-b]pyridin-1-yl]-[2-(2,2,2-trifluoro-ethoxy)-naphthalen-1-yl]-methanone 124

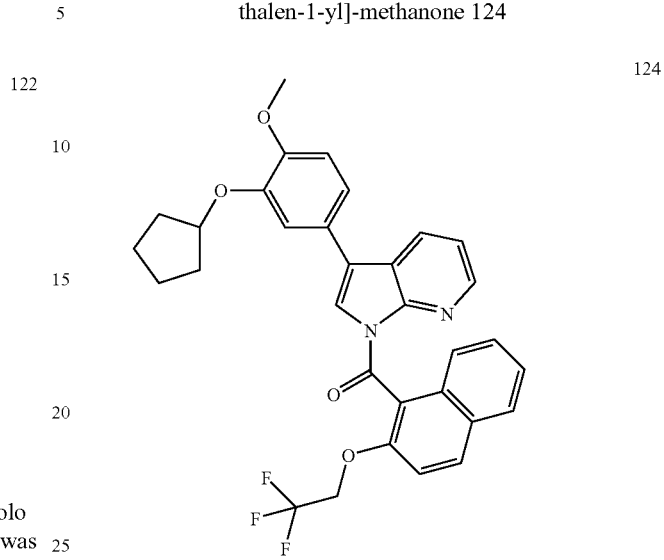

[3-(3-Cyclopentyloxy-4-methoxy-phenyl)-pyrrolo[2,3-b]pyridin-1-yl]-[2-(2,2,2-trifluoro-ethoxy)-naphthalen-1-yl]-methanone 124 was prepared using the same protocol as described in Example 47, substituting 2-ethoxy-4-nitro-benzoic acid and 3-(3,4-Dimethoxy-phenyl)-1H-pyrrolo[2,3-b]pyridine with 2-(2,2,2-Trifluoro-ethoxy)-naphthalene-1-carboxylic acid and 3-(3-cyclopentoxy-4-methoxy-phenyl)-1H-pyrrolo[2,3-b]pyridine. MS(ESI) [M+H+]+=561.10.

Example 119

1-Benzenesulfonyl-3-[3-methoxy-4-(3-phenyl-isoxazol-5-ylmethoxy)-phenyl]-1H-pyrrolo[2,3-b]pyridine 125

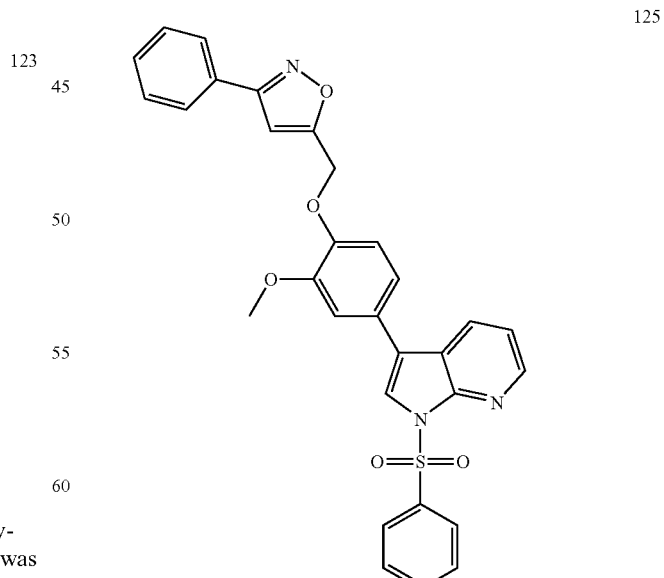

1-Benzenesulfonyl-3-[3-methoxy-4-(3-phenyl-isoxazol-5-ylmethoxy)-phenyl]-1H-pyrrolo[2,3-b]pyridine 125 was prepared using the same protocol as described in Example 7, substituting 2,3-dimethoxy-phenyl boronic acid with 5-[2-Methoxy-4-(4,4,5,5-tetramethyl-[1,3,2]dioxaborolan-2-yl)-phenoxymethyl]-3-phenyl-isoxazole. MS(ESI) [M+H$^+$]$^+$= 538.06.

Example 120

1-Benzenesulfonyl-3-[3-methoxy-4-(3-phenyl-isoxazol-5-ylmethoxy)-phenyl]-1H-pyrrolo[2,3-b]pyridine 126

Scheme - 26

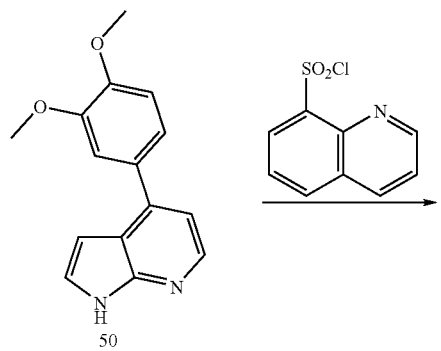

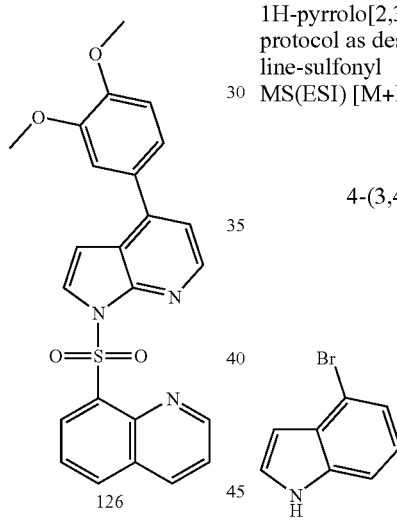

Preparation of 8-[4-(3,4-Dimethoxy-phenyl)-pyrrolo[2,3-b]pyridine-1-sulfonyl]-quinoline 126

Into a Round bottom flask was added 4-(3,4-Dimethoxy-phenyl)-1H-pyrrolo[2,3-b]pyridine (0.222 g, 0.000873 mol), 50 and Tetra-N-butylammonium bromide (0.0282 g, 0.0000874 mol), and 5.000 M of Sodium hydroxide in Water (2.25 mL). 8-quinoline-sulfonyl chloride (0.238 g, 0.00105 mol) dissolved in Methylene chloride (0.616 mL, 0.00960 mol) was added dropwise at 0 Celsius. The reaction was stirred at ambient temperature for 3 h and the reaction mixture was diliuted with an addional 25 mL of methylene chloride. The organic layer was washed with 1 M sodium bicarbonate (aq.) (30 ml×2) and then with brine. The separated organic layer was dried over anhydrous sodium sulfate, filtered and concentrated under reduced pressure. The residue was purified by silica gel chromatography (30% ethyl acetate in hexanes) to yield the titled compound as a white solid. MS(ESI) [M+H$^+$]$^+$=446.20.

Example 121

4-(3,4-Dimethoxy-phenyl)-1-phenylmethanesulfonyl-1H-pyrrolo[2,3-b]pyridine 127

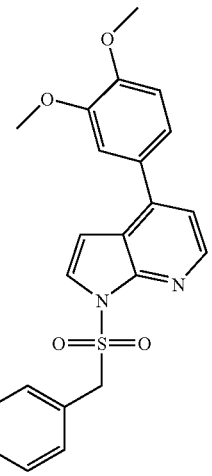

4-(3,4-Dimethoxy-phenyl)-1-phenylmethanesulfonyl-1H-pyrrolo[2,3-b]pyridine 127 was prepared using the same protocol as described in Example 120, substituting 8-quinoline-sulfonyl chloride with benzyl sulfonyl chloride. MS(ESI) [M+H$^+$]$^+$=409.20.

Example 122

4-(3,4-Dimethoxy-phenyl)-1H-indole 128

Scheme - 27

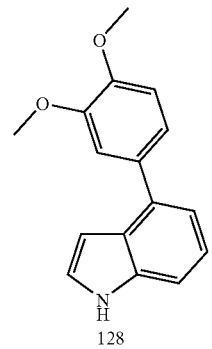

Synthesis of 4-(3,4-Dimethoxy-phenyl)-1H-indole 128

In a microwave safe tube, 4-Bromoindole (1.383 g, 0.007054 mol), 3,4-dimethoxyphenyl boronic acid (3.21 g, 0.0176 mol), and Tetrakis(triphenylphosphine)palladium(0)

(0.41 g, 0.00035 mol) were mixed in 1.00 M of Potassium carbonate in Water (21 mL) and Tetrahydrofuran (34 mL, 0.42 mol). The resulting mixture was heated at 100° Celsius in the microwave for 10 minutes. The reaction mixture was partitioned between water and ethyl acetate. The aqueous layer was extracted with ethyl acetate and the organic layers were combined, washed with brine and dried over sodium sulfate. The reaction mixture was concentrated under reduced pressure and the residue was purified by silica gel chromatography (30% ethyl acetate in hexanes) to the yield 1.02 g of the titled compound as a light green solid. MS(ESI) [M+H$^+$]$^+$= 254.20.

Example 123

5-(3,4-Dimethoxy-phenyl)-1H-indole 129

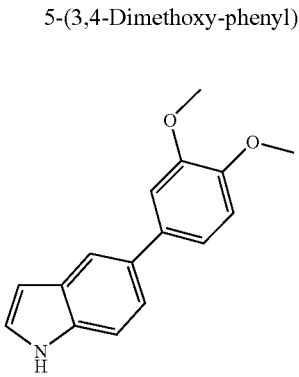

129

5-(3,4-Dimethoxy-phenyl)-1H-indole 129 was prepared using the same protocol as described in Example 122, substituting 4-bromoindole with 5-bromoindole. MS(ESI) [M+H$^+$]$^+$=254.20

Example 124

8-[5-(3,4-Dimethoxy-phenyl)-indole-1-sulfonyl]-quinoline 130

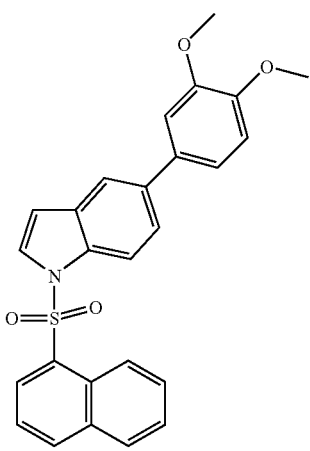

130

8-[5-(3,4-Dimethoxy-phenyl)-indole-1-sulfonyl]-quinoline 130 was prepared using the same protocol as described in Example 9, substituting 3-(3,4-Dimethoxy-phenyl)-1H-pyr- rolo-[2,3-b]pyridine with 5-(3,4-Dimethoxy-phenyl)-1H-indole. MS(ESI) [M+H$^+$]$^+$=445.20

Example 125

8-[4-(3,4-Dimethoxy-phenyl)-indole-1-sulfonyl]-quinoline 131

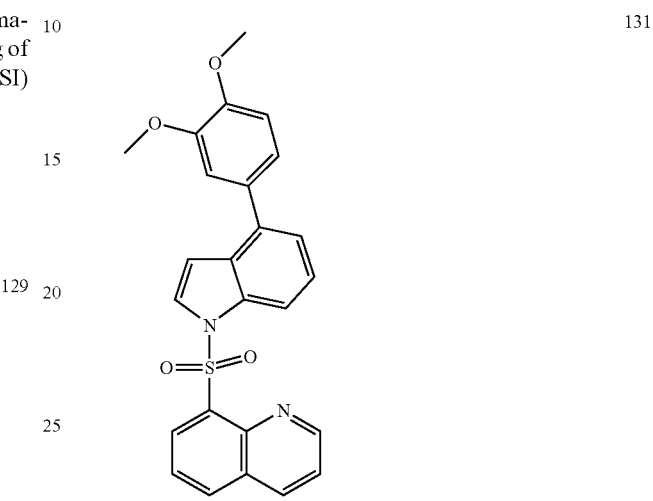

131

8-[4-(3,4-Dimethoxy-phenyl)-indole-1-sulfonyl]-quinoline 131 was prepared using the same protocol as described in Example 9, substituting 3-(3,4-Dimethoxy-phenyl)-1H-pyrrolo-[2,3-b]pyridine with 4-(3,4-Dimethoxy-phenyl)-1H-indole. MS(ESI) [M+H$^+$]$^+$=445.10

Example 126

1-Benzenesulfonyl-5-(3,4-dimethoxy-phenyl)-1H-pyrrolo[2,3-b]pyridine 132

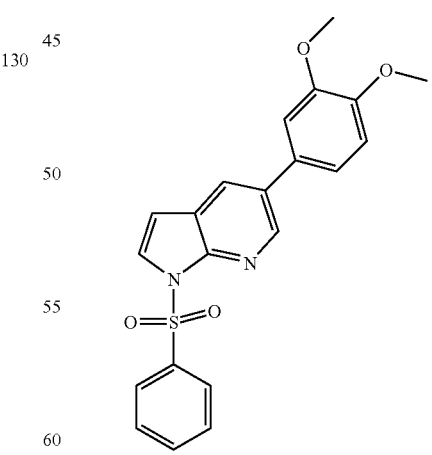

132

1-Benzenesulfonyl-5-(3,4-dimethoxy-phenyl)-1H-pyrrolo[2,3-b]pyridine 132 was prepared using the same protocol as described in Example 9, substituting 3-(3,4-Dimethoxy-phenyl)-1H-pyrrolo-[2,3-b]pyridine and quioline-8-sulfonyl chloride with 5-(3,4-Dimethoxy-phenyl)-1H-pyrrolo-[2,3-b]pyridine and benzene sulfonyl chloride respectively. MS(ESI) [M+H⁺]⁺=395.20

Example 127

4-[1-Benzenesulfonyl-5-(3,4-dimethoxy-phenyl)-1H-pyrrolo[2,3-b]pyridin-3-ylethynyl]-benzoic acid ethyl ester 135

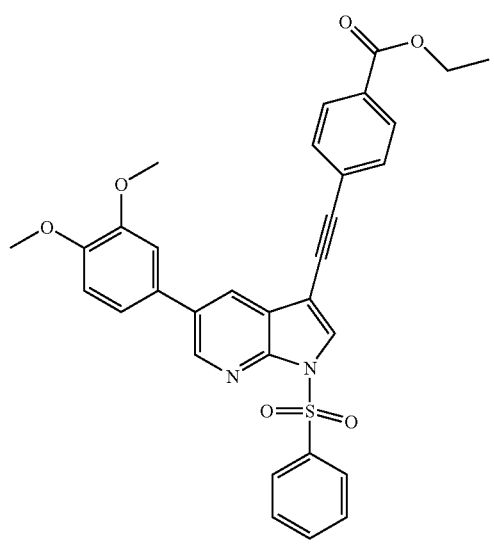

Scheme - 28

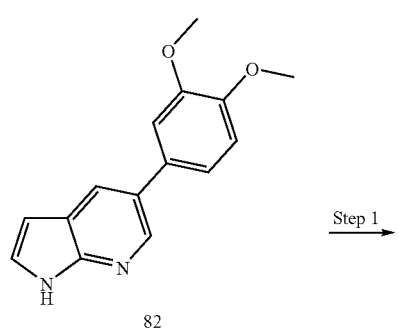

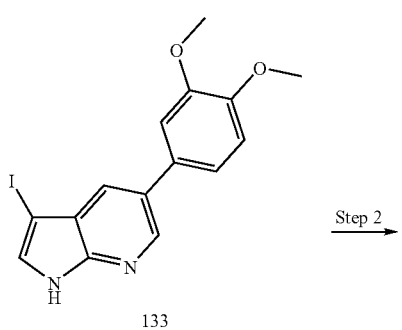

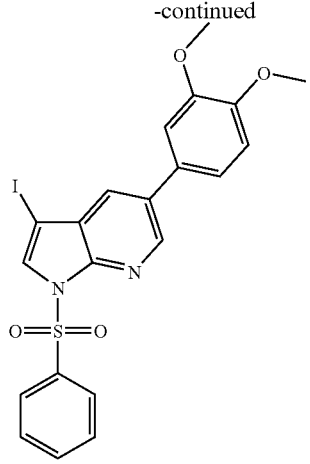

-continued

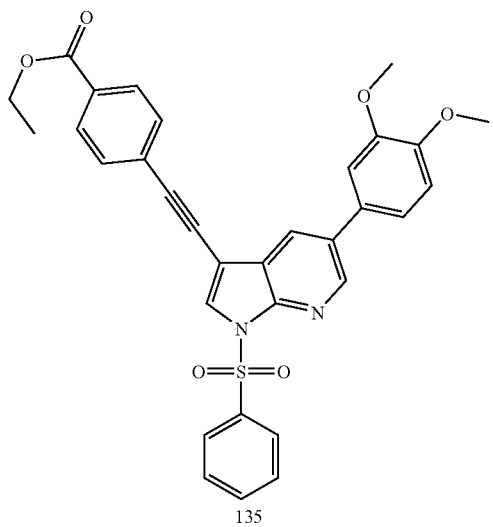

Step 1—Preparation of 5-(3,4-Dimethoxy-phenyl)-3-iodo-1H-pyrrolo[2,3-b]pyridine 133

5-(3,4-Dimethoxy-phenyl)-1H-pyrrolo[2,3-b]pyridine, 82, (0.270 g, 0.00106 mol) was dissolved in Tetrahydrofuran (8.5 mL, 0.10 mol) under an atmosphere of Nitrogen. The solution was stirred at −40° C. and Iodine (0.269 g, 0.00106 mol) dissolved in 2.5 mL of Tetrahydrofuran was added. The chilled reaction mixture was stirred for 2 h and was then quenched with the addition of Sodium thiosulfate, pentahydrate (0.13 g, 0.00053 mol) in water (1M). The reaction mixture was partitioned between water (20 mL and ethyl acetate (30 mL). The two layers were seperated, and the aquous layer was extracted with ethyl acetate. The organic layers were washed with water and brine, dried with sodium sulfate, then concentrated under reduced pressure. The dark colored crude residue was carried onto the next reaction without further purification.

Step 2—Preparation of 1-Benzenesulfonyl-5-(3,4-dimethoxy-phenyl)-3-iodo-1H-pyrrolo[2,3-b]pyridine 134

Into a Round bottom flask was added 5-(3,4-Dimethoxy-phenyl)-3-iodo-1H-pyrrolo[2,3-b]pyridine, 133, (0.403 g, 0.00106 mol) and Tetra-N-butylammonium bromide (0.0342 g, 0.000106 mol), in 5.000 M of Sodium hydroxide in Water (2.73 mL). Benzenesulfonyl chloride (0.225 g, 0.00127 mol) in Methylene chloride (0.747 mL, 0.0116 mol) was added dropwise. After 2 h, 30 mL of Methylene chloride and 30 mL of water were added. The organic layer was separated and washed with 1M sodium bicarbonate (aq.) (30 ml×2) followed by water (30 ml) and brine (30 mL). The organic layer was collected and dried over anhydrous sodium sulfate, then concentrated under reduced pressure. The residue was purified by chromatography (Silica gel, ethyl acetate/hexanes) to give 295 mg of the desired product as a white solid. MS(ESI) [M+H$^+$]$^+$=521.04

Step 3—Preparation of 4-[1-Benzenesulfonyl-5-(3,4-dimethoxy-phenyl)-1H-pyrrolo[2,3-b]pyridin-3-yl-ethynyl]-benzoic acid ethyl ester 135

1-Benzenesulfonyl-5-(3,4-dimethoxy-phenyl)-3-iodo-1H-pyrrolo[2,3-b]pyridine (0.0800 g, 0.000151 mol), 4-Ethynyl-benzoic acid ethyl ester (0.0321 g, 0.000181 mol), Bis(triphenylphosphine)palladium(II) chloride (0.0048 g, 0.0000069 mol), and Copper(I) iodide (0.00024 g, 0.0000013 mol) were dissolved in Triethylamine (0.8 mL, 0.005 mol) under an atmosphere of Nitrogen. The resulting mixture was heated to 60° C. and stirred under an atmosphere of Nitrogen for 2 hours. The reaction mixture was was concentrated under reduced pressure and water (30 mL) was added to the residue. This slurry was extracted with ether. (20 mL 2×). The combined organic layers were washed with brine, dried over sodium sulfate and concentrated under reduced pressure. The crude was purified by chromatography (Silica gel, ethyl acetate/hexanes to give 85 mg of the titled product as a pale orange solid. MS(ESI) [M+H$^+$]$^+$=567.10

Example 128

1-Benzenesulfonyl-5-(3,4-dimethoxy-phenyl)-3-phenylethynyl-1H-pyrrolo[2,3-b]pyridine 136

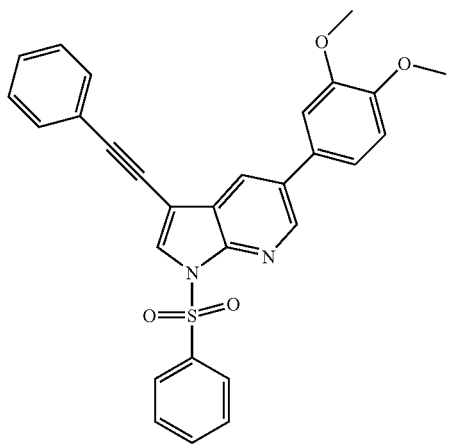

1-Benzenesulfonyl-5-(3,4-dimethoxy-phenyl)-3-phenyl-ethynyl-1H-pyrrolo[2,3-b]pyridine 136 was prepared using the same protocol as described in Example 127, substituting 4-Ethynyl-benzoic acid ethyl ester with Ethynyl-benzene. MS(ESI) [M+H$^+$]$^+$=495.20

Example 129

3-[1-Benzenesulfonyl-5-(3,4-dimethoxy-phenyl)-1H-pyrrolo[2,3-b]pyridin-3-ylethynyl]-benzoic acid methyl ester 137

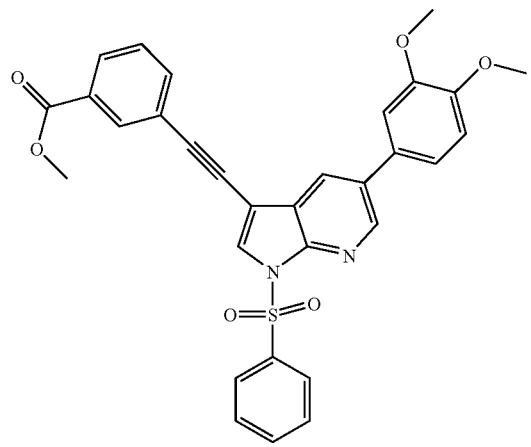

3-[1-Benzenesulfonyl-5-(3,4-dimethoxy-phenyl)-1H-pyrrolo[2,3-b]pyridin-3-ylethynyl]-benzoic acid methyl ester 137 was prepared using the same protocol as described in Example 127, substituting 4-Ethynyl-benzoic acid ethyl ester with 3-Ethynyl-benzoic acid methy ester. MS(ESI) [M+H$^+$]$^+$= 553.10

Example 130

5-(3,4-Dimethoxy-phenyl)-3-phenylethynyl-1H-pyrrolo[2,3-b]pyridine 138

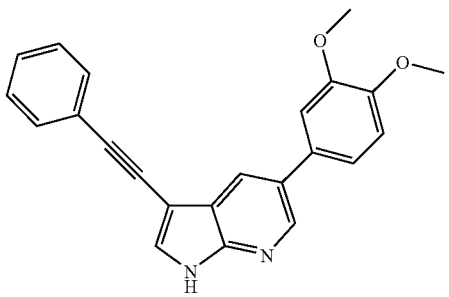

5-(3,4-Dimethoxy-phenyl)-3-phenylethynyl-1H-pyrrolo[2,3-b]pyridine 138 was prepared using the same protocol as described in Example 7, substituting 1-Benzenesulfonyl-3-(3,4-dimethoxy-phenyl)-1H-pyrrolo[2,3-b]pyridine with 1-Benzenesulfonyl-5-(3,4-dimethoxy-phenyl)-3-phenyl-ethynyl-1H-pyrrolo[2,3-b]pyridine. MS(ESI) [M+H$^+$]$^+$= 355.20

Example 131

3-[5-(3,4-Dimethoxy-phenyl)-1H-pyrrolo[2,3-b]pyridin-3-ylethynyl]-benzoic acid methyl ester 139

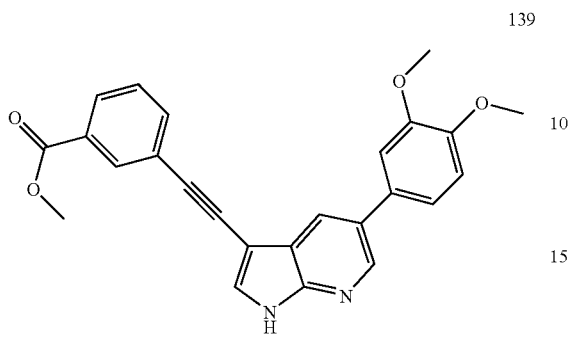

3-[5-(3,4-Dimethoxy-phenyl)-1H-pyrrolo[2,3-b]pyridin-3-ylethynyl]-benzoic acid methyl ester 139 was prepared using the same protocol as described in Example 7, substituting 1-Benzenesulfonyl-3-(3,4-dimethoxy-phenyl)-1H-pyrrolo[2,3-b]pyridine with 3-[1-Benzenesulfonyl-5-(3,4-dimethoxy-phenyl)-1H-pyrrolo[2,3-b]pyridin-3-ylethynyl]-benzoic acid methyl ester. MS(ESI) $[M+H^+]^+=413.20$

Example 132

3-[5-(3,4-Dimethoxy-phenyl)-1H-pyrrolo[2,3-b]pyridin-3-ylethynyl]-benzoic acid 140

Scheme - 29

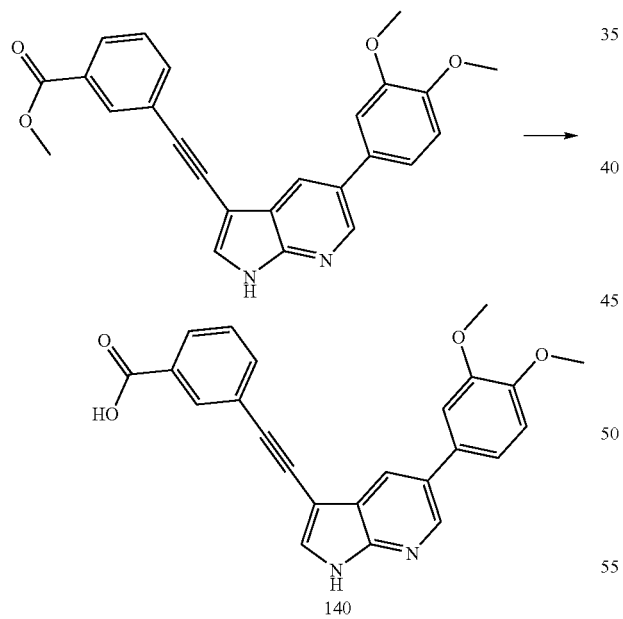

Preparation of 3-[5-(3,4-Dimethoxy-phenyl)-1H-pyrrolo[2,3-b]pyridin-3-ylethynyl]-benzoic acid 140

Into a microwave safe tube, 3-[5-(3,4-Dimethoxy-phenyl)-1H-pyrrolo[2,3-b]pyridin-3-ylethynyl]-benzoic acid methyl ester (0.049 g, 0.00012 mol) was dissolved in 5.00 M of Sodium hydroxide in Water (1.78 mL) and Methanol (7.1 mL, 0.18 mol). The reaction was warmed at 60 watts to 100° C. for 10 minutes. The resulting clear yellow solution was concentrated under reduced pressure. The resulting aqueous slurry was acidified to pH 5 with 1 M HCl (aq) and was extracted into ethyl acetate. The organic layer was washed with brine, dried over anhydrous sodium sulfate, then concentrated under reduced pressure. The resulting residue was recrystalized from ethyl acetate and methanol to yield the titled compound as a white solid. MS(ESI) $[M+H^+]^+=399.20$

Example 133

5-(1-Benzenesulfonyl-1H-pyrrolo[2,3-b]pyridin-3-yl)-2-methoxy-phenol 141

Scheme - 30

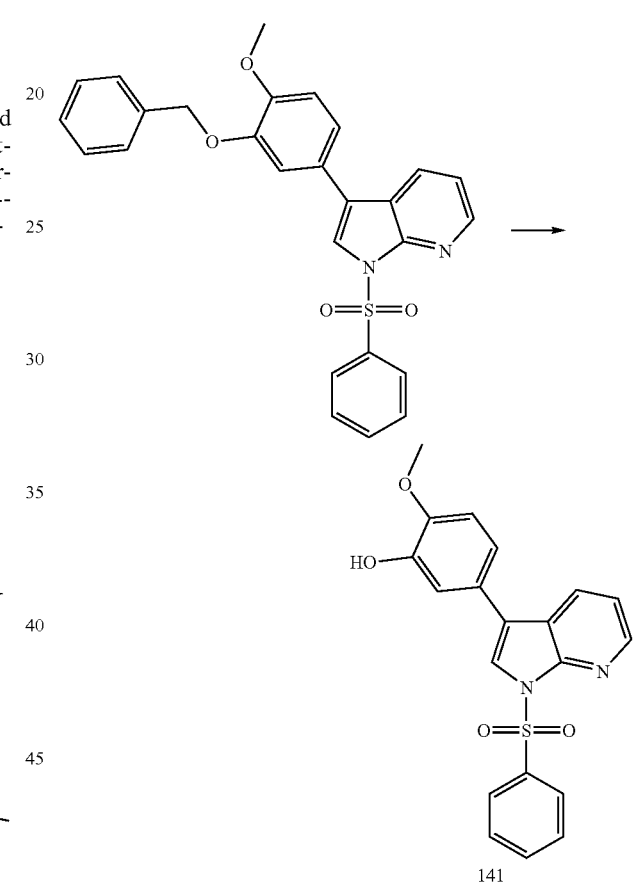

Preparation of 5-(1-Benzenesulfonyl-1H-pyrrolo[2,3-b]pyridin-3-yl)-2-methoxy-phenol 141

Into a Parr pressure reactor 1-Benzenesulfonyl-3-(3-benzyloxy-4-methoxy-phenyl)-1H-pyrrolo[2,3-b]pyridine (92 mg, 0.00020 mol) was placed with Palladium (50 mg, 0.00005 mol) 10%, tetrahydrofuran (15 mL, 0.18 mol) and Methanol (1 mL, 0.02 mol) and HCl solution (3 mL, 0.04 mol). The reaction was shaken under an atmosphere of hydrogen at 50 psi for 4 hours. The mixture reaction was filtered through Celite™ and concentrated under reduced pressure. The residue was purified by preparative TLC (ethyl acetate/hexanes 1:1) to give 31 mg of the titled product. MS(ESI) $[M+H^+]^+=381.11$.

Example 134

3-Benzo[1,3]dioxol-5-yl-2-methyl-1H-pyrrolo[2,3-b]pyridine 142

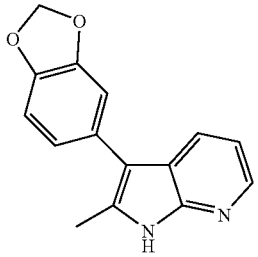

142

3-Benzo[1,3]dioxol-5-yl-2-methyl-1H-pyrrolo[2,3-b]pyridine 142 was prepared using the same protocol as described in Example 8, substituting 3-Bromo-1H-pyrrolo[2,3-b]pyridine and 3,4-dimethoxy-phenyl boronic acid with 3-Bromo-2-methyl-1H-pyrrolo[2,3-b]pyridine and 5-(4,4,5,5-Tetramethyl-[1,3,2]dioxaborolan-2-yl)-benzo[1,3]dioxole respectively.

Example 135

3-(3,4-Dimethoxy-phenyl)-2-methyl-1H-pyrrolo[2,3-b]pyridine 143

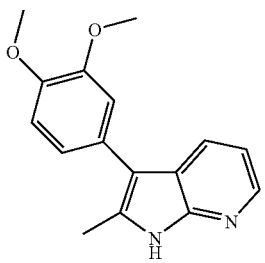

143

3-(3,4-Dimethoxy-phenyl)-2-methyl-1H-pyrrolo[2,3-b]pyridine 143 was prepared using the same protocol as described in Example 8, substituting 3-Bromo-1H-pyrrolo[2,3-b]pyridine with 3-Bromo-2-methyl-1H-pyrrolo[2,3-b]pyridine.

Example 136

(4-Amino-2-ethoxy-phenyl)-[3-(3,4-dimethoxy-phenyl)-pyrrolo[2,3-b]pyridin-1-yl]-methanone 144

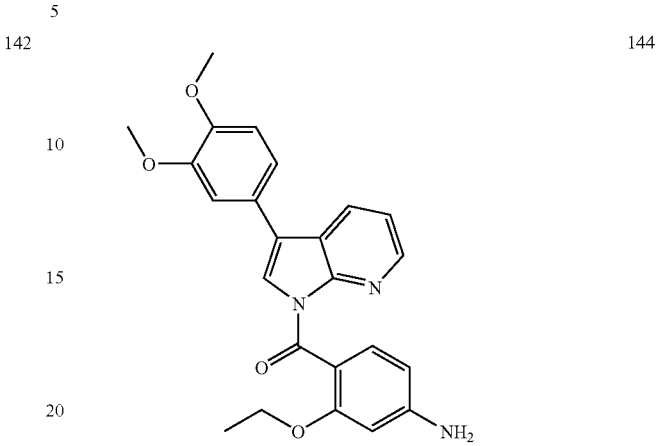

144

[3-(3,4-dimethoxy-phenyl)-pyrrolo[2,3-b]pyridine-1-yl]-(2-ethoxy-4-nitro-phenyl)-methanone, 54, (100 mg, 0.22 mmol) was dissolved in EtOAc (30 mL). A catalytic amount of 10% Pd/C (7 mg) was added and the flask capped with rubber septa. The flask was evacuated and back filled with hydrogen twice. Finally, the reaction was stirred overnight under a hydrogen gas atmosphere (balloon). The reaction mixture was filtered over Celite®, rinsed generously with EtOAc (2×75 mL) and concentrated under reduced pressure to give the titled compound. (56 mg, 60%) MS(ESI) [M+H$^+$]$^+$= 418.24

Example 137

N-{4-[3-(3,4-Dimethoxy-phenyl)-pyrrolo[2,3-b]pyridine-1-carbonyl]-3-ethoxy-phenyl}-methanesulfonamide 145

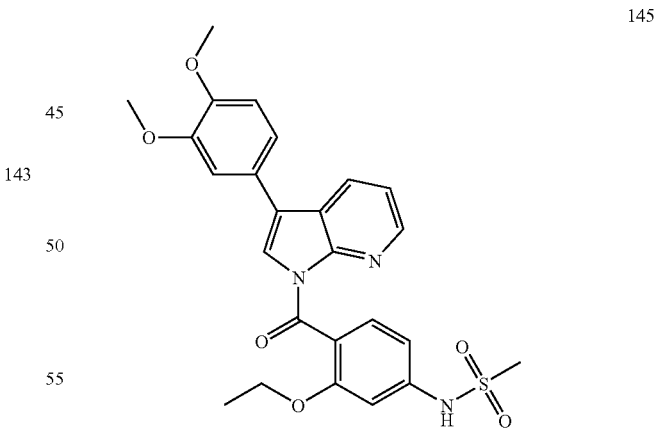

145

Into a round bottom flask was (4-amino-2-ethoxyphenyl) [3-(3,4-dimethoxyphenyl)-pyrrolo[2,3-b]pyridin-1-yl]methonone (56 mg, 0.00013 mol) in tetrahydrofuran (15 mL). Sodium hydride (4.8 mg, 0.00020 mol, 60% dispersion in mineral oil) was added and Methanesulfonyl chloride (38 mg, 0.00034 mol) was added to reaction mixture, which was then stirred at room temperature over night. Top of FormColumn chromatoghraphy purification (silica gel) gave the titled compoundBottom of Form. MS(ESI) [M+H$^+$]$^+$=496.08

Example 138

Cloning of PDE4B Phosphodiesterase Domain

PDE4B cDNA sequence was amplified from a Human Brain, hippocampus QUICK-Clone cDNA library (Clontech, #7169-1) by PCR using the following primers:

```
PDE4B-S:
                                          (SEQ ID NO: 7)
5'-CCGAATT CATATG AGCATCTCACGCTTTGGAGTC-3'   34 mer PDE4B-A:
                                          (SEQ ID NO: 8)
5'-TGTGCT CTCGAG TTA GCTGTGTCCCTCTCCCTCC-3'  34 mer
```

An internal NdeI site was then engineered out by site directed mutagenesis using the following primers:

```
    PDE4B-NDE1:
                                          (SEQ ID NO: 9)
    5'-GATATGTCTAAACACATGAGCCTGCTGGC-3'  29 mer PDE4B-NDE2:
                                          (SEQ ID NO: 10)
    5'-GCCAGCAGGCTCATGTGTTTAGACATATC-3'  29 mer
```

The resulting PCR fragment was digested with NdeI and SalI and subcloned into the pET15S vector.

In this expression plasmid, residues 152-528 of PDE4B (NCBI sequence JC1519, SEQ ID NO:1) are in frame with an N-terminal His-tag followed by a thrombin cleavage site.

The sequence of pET15S, with multi-cloning site is shown below (SEQ ID NOS: 11 and 12):

```
T7 promoter
AGATCTCGATCCCGCGAAATTAATACGACTCACTATAGGGGAATTGTGAGCGGATAACAATTCCCC

RBS
TCTAGAAATAATTTTGTTTAACTTTAAGAAGGAGATATACC

NdeI
ATGGGCAGCAGCCATCATCATCATCATCACAGCAGCGGCCTGGTGCCGCGCGGCAGCCATATGGGATCCGG
  M   G   S   S   H   H   H   H   H   H   S   S   G   L   V   P   R   G   S   H   M --------

StuI      SalI
AATTCAAAGGCCTACGTCGACTAGAGCCTGCAGTCTCGACCATCATCATCATCATCATTAATAAAAGGGCG
----------------------- *

SpeI   BamHI
AATTCCAGCACACTGGCGGCCGTTACTAGTGGATCCGGCTGCTAACAAAGCCCGAAAGGAAGCTGAGTTGG
   IVEX-3 Primer Bpu1102 I                     T7 terminator
CTGCTGCCACCGCTGAGCAATAACTAGCATAACCCCTTGGGGCCTCTAAACGGGTCTTGAGGGGTTTTTG
               3'-PET Primer
``` pET15S vector is derived from pET15b vector (Novagen) for bacterial expression to produce the proteins with N-terminal His6 (SEQ ID NO: 32). This vector was modified by replacement of NdeI-BamHI fragment to others to create a SalI site and stop codon (TAG). Vector size is 5814 bp. Insertion can be performed using NdeI-SalI site. The amino acid and nucleic acid sequences for the PDE4B phosphodiesterase domain utilized are provided in Table 3.

Example 139

Purification of PDE4B

PDE4B is purified from E. coli cells [BL21 (DE3) Codon Plus (RIL) (Novagen)] grown in Terrific broth that has been supplemented with 0.2 mM Zinc Acetate and 1 mM MgCl2 and induced for 16-20 h with 1 mM IPTG at 22° C. The centrifuged bacterial pellet (typically 200-250 g from 16 L) is suspended in lysis buffer (0.1 M potassium phosphate buffer, pH 8.0, 10% glycerol, 1 mM PMSF). 100 ug/ml of lysozyme is added to the lysate and the cells are lysed in a Cell Disruptor (MicroFluidics). The cell extract is clarified at 5000 rpm in a Sorvall SA6000 rotor for 1 h, and the supernatant is recentrifuged for another hour at 17000 rpm in a Sorvall SA 600 rotor. 5 mM imidazole (pH 8.0) is added to the clarified supernatant and 2 ml of cobalt beads (50% slurry) is added to each 35 ml of extract. The beads are mixed at 4 C for 3-4 h on a Nutator and the beads are recovered by centrifugation at 4000 rpm for 3 min. The pelleted beads are washed several times with lysis buffer and the beads are packed on a BioRad disposable column. The bound protein is eluted with 3-4 column volumes of 0.1M imidazole followed by 0.25M imidazole, both prepared in lysis buffer. The protein eluted from the cobalt beads is concentrated on Centriprep-10 membranes (Amicon) and separated on a Pharmacia Superdex 200 column (26/60) in low salt buffer (25 mM Tris-HCl, pH 8.0, 150 mM NaCl, 14 mM beta-mercaptoethanol). At this stage the PDE proteins are treated with thrombin for 16-20 hours at room temperature. The PDE proteins are further purified by anion exchange chromatography on a Pharmacia Source Q column (10/10) in 20 mM Tris-HCl pH 8 and 14 mM beta-mercaptoethanol using a NaCl gradient in an AKTA-FPLC (Pharmacia).

Example 140

Crystallization of PDE4B Phosphodiesterase Domain

Crystals of PDE4B were grown in 30% PEG 400, 0.2M $MgCl_2$, 0.1M Tris pH 8.5, 1 mM binding ligand, 15.9 mg/ml protein at 4° C., using an Intelliplate (Robbins Scientific, Hampton) by mixing one microliter of protein with one microliter of precipitant. Data was collected to 1.4 Å.

Additionally, PDE4B crystals were grown in 20% PEG 3000, 0.2M $Ca(OAc)_2$, 0.1M Tris pH 7.0, 1 mM binding ligand, 15.9 mg/ml protein at 4° C., using an Intelliplate (Robbins Scientific, Hampton) by mixing one microliter of protein with one microliter of precipitant. Data was collected to 1.7 Å

Example 141

Structure Determination of PDE4B

The structure of PDE4B was solved using molecular replacement, using the previously deposited coordinates for .

PDE4B. The atomic coordinates for the PDE4B structure determined are provided in Table 1 (coordinates for a co-crystal structure is provided in Table 2).

Example 142

PDE Binding Assays

Binding assays can be performed in a variety of ways, including a variety of ways known in the art. For example, as indicated above, binding assays can be performed using fluorescence resonance energy transfer (FRET) format, or using an AlphaScreen Alternatively, any method which can measure binding of a ligand to the cAMP-binding site can be used. For example, a fluorescent ligand can be used. When bound to PDE4B, the emitted fluorescence is polarized. Once displaced by inhibitor binding, the polarization decreases.

Determination of $IC_{50}$ for compounds by competitive binding assays. (Note that $K_I$, is the dissociation constant for inhibitor binding; $K_D$ is the dissociation constant for substrate binding.) For this system, the IC50, inhibitor binding constant and substrate binding constant can be interrelated according to the following formula:

When using radiolabeled substrate, $$K_I = \frac{IC_{50}}{1 + [L^*]/K_D},$$

and the $IC_{50} \sim K_I$, when there is a small amount of labeled substrate.

Example 143

PDE Activity Assay

As an exemplary phosphodiesterase assay, the effect of potential modulators phosphodiesterase activity of PDE4B, PDE5A, and other PDEs was measured in the following assay format:

Reagents
Assay Buffer
50 mM Tris, 7.5
8.3 mM $MgCl_2$
1.7 mM EGTA
0.01% BSA
Store @ 4 degrees
RNA binding YSi SPA beads
Beads are 100 mg/ml in water. Dilute to 5 mg/ml in 18 mM Zn using 1 M ZnAcetate/$ZnSO_4$ solution (3:1) and water. Store @ 4 degrees.

| Low control compounds | Concentration of 20X DMSO Stock |
|---|---|
| PDE1B: 8-methoxymethyl IBMX | 20 mM |
| PDE2A: EHNA | 10 mM |
| PDE3B: Milrinone | 2 mM |
| PDE4D: Rolipram | 10 mM |
| PDE5A: Zaprinast | 10 mM |
| PDE7B: IBMX | 40 mM |
| PDE10A: Dipyridamole | 4 mM |

Enzyme concentrations (2× final concentration. Diluted in assay buffer)
PDE1B 50 ng/ml
PDE2A 50 ng/ml
PDE3B 10 ng/ml
PDE4D 5 ng/ml
PDE5A 20 ng/ml
PDE7B 25 ng/ml
PDE10A 5 ng/ml)

Radioligands
[$^3$H] cAMP (Amersham TRK559). Dilute 2000× in assay buffer.
[$^3$H] cGMP (Amersham TRK392). For PDE5A assay only. Dilute 2000× in assay buffer.

Protocol
Make assay plates from 2 mM, 96 well master plates by transferring 1 ul of
compound to 384 well plate using BiomekFx. Final concentration of compounds will be ~100 μM. Duplicate assay plates are prepared from each master plate so that compounds are assayed in duplicate.
To column 23 of the assay plate add 1 ul of 20× DMSO stock of appropriate control compound. These will be the low controls.
Columns 1 and 2 of Chembridge library assay plates and columns 21 and 22 of the Maybridge library assay plates have 1 ul DMSO. These are the high controls.
Using BiomekFx, pipet 10 μl of radioligand into each assay well, then, using the same tips, pipet 10 μl of enzyme into each well.
Seal assay plate with transparent cover. Centrifuge briefly @ 1000 RPM, them mix on plate shaker for 10 s.
Incubate @ 30° for 30 min.
Using BiomekFx, add 10 μl of bead mixture to each assay well. Mix beads thoroughly in reservoir immediately prior to each assay plate addition.
Re-seal plate with fresh transparent cover. Mix on plate shaker for 10 s, then centrifuge for 1 min. @1000 RPM.
Place plates in counting racks. Let stand for ≧30 min, then count on Wallac TriLux using program 8.
Analyze data as % inhibition of enzyme activity. Average of high controls=0% inhibition. Average of low controls=100% inhibition.

Example 144

Expression and purification of PPARs for use in biochemical and cell assays Genetic Engineering Plasmids encoding the human phosphodiesterases (PDEs) 4B and 4D were engineered using common polymerase chain reaction (PCR) methods. Both the full-length PDEs and truncated versions harboring just the PDE catalytic domains were engineered for heterologous expression. The relevant DNA sequences and encoded protein sequences used are shown for each (see below). The human PDE4B and PDE4D genes have several splice variants; the splice variants chosen for full-length expression are PDE4B2 (NCBI accession gi 292387) and PDE4D5 (NCBI accession gi 2735856). Complementary DNA cloned from various human tissues were purchased from Invitrogen, and these were used as substrates in the PCR reactions. Specific custom synthetic oligonucleotide primers (Invitrogen, see below) were designed to initiate the PCR product, and also to provide the appropriate restriction enzyme cleavage sites for ligation with the plasmids.

The plasmid used for ligation with the catalytic domain-encoding PDE4B and PDE4D inserts was derived from pET15 (Novagen) for expression using *E. coli*. The plasmid used for ligation of the full-length PDE4B and PDE4D inserts was pFastBacHT (Invitrogen). In all of these cases the PDE was engineered to include a Histidine tag for purification using metal affinity chromatography.

Protein Expression and Purification of PDE4 Catalytic domains in E. coli:

For protein expression, plasmids containing genes of interest were transformed into E. coli strains BL21 (DE3) RIL and transformants selected for on LB agar plates containing appropriate antibiotics. Single colonies were grown for 4 hrs at 37° C. in 200 ml LB media. For PDE4B and PDE4D all protein expression was performed by large scale fermentation using a 30L bioreactor. 400 ml of starter culture was added to 30L TB culture and allowed to grow at 37° C. until an OD600 nm of 2-5 was obtained. The culture was cooled to 20° C. and 0.5 mM IPTG, 1 mM MgCl2 and 0.2 mM ZnOAc added, the culture was allowed to grow for a further 18 hrs.

For protein purificatio all operations were carried out at 4° C. Frozen E. coli cell pellets were resuspended in lysis buffer and lysed using standard mechanical methods. Soluble proteins were purified via poly-Histidine tags using immobilized metal affinity purification (IMAC). For each of the PDE's purification was achieved using a 3 step purification process utilizing; IMAC, size exclusion chromatography and ion exchange chromatography. For both PDE4B and PDE4D, the poly-Histidine tag was removed using Thrombin (Calbiochem) before the final purification step.

For proteins provided for assay purposes, the above described expression conditions were carried out except purification was only 2-steps and the poly-histidine tag was not removed. Enzymes were stored in 50% glycerol.

Protein Expression and Purification of full length PDE4 isoforms in insect cells using Baculovirus PDE's Expressed Using Standard Protocols.

PDE4B2: The full-length human PDE4B2 isozyme with an N-terminal His6 tag (SEQ ID NO: 32) and TEV cleavage site expressed in baculovirus infected insect cells. The enzyme was not purified from the cell lysates, so enzyme concentrations were not determined. Enzyme was stored in 50% glycerol at −20°.

PDE4D5: The full-length human PDE4D5 isozyme with an N-terminal His6 tag (SEQ ID NO: 32) and TEV cleavage site expressed in baculovirus infected insect cells. The enzyme was not purified from the cell lysates, so enzyme concentrations were not determined. Enzyme was stored in 50% glycerol at −20°.

Plasmid Sequence and PCR Primer Information:
PDE4B:

```
P457. pET15S PDE4B S152-S528-X (SEQ ID NOS: 13 and 14)

taatacgactcactatagggaattgt gagcggataacaattcccctctagaaataattttgtttaactttaagaaggagatatacc atgggcagcagccatcatcatcatcatcacagcagcggcctggtgccgcgcggcagccat
 M   G   S   S   H   H   H   H   H   H   S   S   G   L   V   P   R   G   S   H atgagcatctcacgctttggagtcaacactgaaaatgaagatcacctggccaaggagctg
 M   S   I   S   R   F   G   V   N   T   E   N   E   D   H   L   A   K   E   L gaagacctgaacaaatggggtcttaacatctttaatgtggctggatattctcacaataga
 E   D   L   N   K   W   G   L   N   I   F   N   V   A   G   Y   S   H   N   R cccctaacatgcatcatgtatgctatattccaggaaagagacctcctaaagacattcaga
 P   L   T   C   I   M   Y   A   I   F   Q   E   R   D   L   L   K   T   F   R atctcatctgacacatttataacctacatgatgactttagaagaccattaccattctgac
 I   S   S   D   T   F   I   T   Y   M   M   T   L   E   D   H   Y   H   S   D gtggcatatcacaacagcctgcacgctgctgatgtagcccagtcgacccatgttctcctt
 V   A   Y   H   N   S   L   H   A   A   D   V   A   Q   S   T   H   V   L   L tctacaccagcattagacgctgtcttcacagatttggaaatcctggctgccattttgca
 S   T   P   A   L   D   A   V   F   T   D   L   E   I   L   A   A   I   F   A gctgccatccatgacgttgatcatcctggagtctccaatcagtttctcatcaacacaaat
 A   A   I   H   D   V   D   H   P   G   V   S   N   Q   F   L   I   N   T   N tcagaacttgctttgatgtataatgatgaatctgtgttggaaaatcatcaccttgctgtg
 S   E   L   A   L   M   Y   N   D   E   S   V   L   E   N   H   H   L   A   V ggtttcaaactgctgcaagaagaacactgtgacatcttcatgaatctcaccaagaagcag
 G   F   K   L   L   Q   E   E   H   C   D   I   F   M   N   L   T   K   K   Q cgtcagacactcaggaagatggttattgacatggtgttagcaactgatatgtctaaacac
 R   Q   T   L   R   K   M   V   I   D   M   V   L   A   T   D   M   S   K   H atgagcctgctggcagacctgaagacaatggtagaaacgaagaaagttacaagttcaggc
 M   S   L   L   A   D   L   K   T   M   V   E   T   K   K   V   T   S   S   G gttcttctcctagacaactataccgatcgcattcaggtccttcgcaacatggtacactgt
 V   L   L   D   N   Y   T   D   R   I   Q   V   L   R   N   M   V   H   C gcagacctgagcaaccccaccaagtccttggaattgtatcggcaatggacagaccgcatc
 A   D   L   S   N   P   T   K   S   L   E   L   Y   R   Q   W   T   D   R   I
```

P457. pET15S PDE4B S152-S528-X (SEQ ID NOS: 13 and 14)

```
atggaggaattttccagcagggagacaaagagcgggagaggggaatggaaattagccca
 M  E  E  F  F  Q  Q  G  D  K  E  R  E  R  G  M  E  I  S  P atgtgtgataaacacacagcttctgtggaaaaatcccaggttggtttcatcgactacatt
 M  C  D  K  H  T  A  S  V  E  K  S  Q  V  G  F  I  D  Y  I gtccatccattgtgggagacatgggcagatttggtacagcctgatgctcaggacattctc
 V  H  P  L  W  E  T  W  A  D  L  V  Q  P  D  A  Q  D  I  L gataccttagaagataacaggaactggtatcagagcatgatacctcaaagtccctcacca
 D  T  L  E  D  N  R  N  W  Y  Q  S  M  I  P  Q  S  P  S  P ccactggacgagcagaacagggactgccagggtctgatggagaagtttcagtttgaactg
 P  L  D  E  Q  N  R  D  C  Q  G  L  M  E  K  F  Q  F  E  L actctcgatgaggaagattctgaaggacctgagaaggagggagagggacacagctaactc
 T  L  D  E  E  D  S  E  G  P  E  K  E  G  E  G  H  S  - gactagagcctgcagtctcgaccatcatcatcatcatcattaataaaagggcgaattcca gcacactggcggccgttactagtggatcc
```

PCR Primers:

PDE4B

```
                                              (SEQ ID NO: 15)
PDE4-S    CCGAATTCATATGAGCATCTCACGCTTTGGAGTC  316
                                              (SEQ ID NO: 16)
PDE4B-A   TGTGCTCTCGAGTTAGCTGTGTCCCTCTCCCTCC   317
```

PDE4D:

P4437. pET15S PDE4D S316-V692-X (SEQ ID NOS: 17 and 18)

```
                   taatacgactcactatagggGaattgt gagcggataacaattcccctctagaaataattttgtttaactttaagaaggagatatacc atgggcagcagccatcatcatcatcatcatagcagcggcctggtgccgcgcggcagccat
 M  G  S  S  H  H  H  H  H  H  S  S  G  L  V  P  R  G  S  H atgagtatcccaaggtttggagttaaaactgaacaagaagatgtccttgccaaggaacta
 M  S  I  P  R  F  G  V  K  T  E  Q  E  D  V  L  A  K  E  L gaagatgtgaacaaatggggtcttcatgttttcagaatagcagagttgtctggtaaccgg
 E  D  V  N  K  W  G  L  H  V  F  R  I  A  E  L  S  G  N  R cccttgactgttatcatgcacaccatttttcaggaacgggatttattaaaaacatttaaa
 P  L  T  V  I  M  H  T  I  F  Q  E  R  D  L  L  K  T  F  K attccagtagatactttaattacatatcttatgactctcgaagaccattaccatgctgat
 I  P  V  D  T  L  I  T  Y  L  M  T  L  E  D  H  Y  H  A  D gtggcctatcacaacaatatccatgctgcagatgttgtccagtctactcatgtgctatta
 V  A  Y  H  N  N  I  H  A  A  D  V  V  Q  S  T  H  V  L  L tctacacctgctttggaggctgtgtttacagatttggagattcttgcagcaatttttgcc
 S  T  P  A  L  E  A  V  F  T  D  L  E  I  L  A  A  I  F  A agtgcaatacatgatgtagatcatcctggtgtgtccaatcaatttctgatcaatacaaac
 S  A  I  H  D  V  D  H  P  G  V  S  N  Q  F  L  I  N  T  N tctgaacttgccttgatgtacaatgattcctcagtcttagagaaccatcatttggctgtg
 S  E  L  A  L  M  Y  N  D  S  S  V  L  E  N  H  H  L  A  V
```

-continued

| P4437. pET15S PDE4D S316-V692-X (SEQ ID NOS: 17 and 18) |
|---|
| ggctttaaattgcttcaggaagaaaactgtgacattttccagaatttgaccaaaaacaa<br> G  F  K  L  L  Q  E  E  N  C  D  I  F  Q  N  L  T  K  K  Q |
| agacaatctttaaggaaaatggtcattgacatcgtacttgcaacagatatgtcaaaacac<br> R  Q  S  L  R  K  M  V  I  D  I  V  L  A  T  D  M  S  K  H |
| atgaatctactggctgatttgaagactatggttgaaactaagaaagtgacaagctctgga<br> M  N  L  L  A  D  L  K  T  M  V  E  T  K  K  V  T  S  S  G |
| gttcttcttcttgataattattccgataggattcaggttcttcagaatatggtgcactgt<br> V  L  L  L  D  N  Y  S  D  R  I  Q  V  L  Q  N  M  V  H  C |
| gcagatctgagcaacccaacaaagcctctccagctgtaccgccagtggacggaccggata<br> A  D  L  S  N  P  T  K  P  L  Q  L  Y  R  Q  W  T  D  R  I |
| atggaggagttcttccgccaaggagaccgagagagggaacgtggcatggagataagcccc<br> M  E  E  F  F  R  Q  G  D  R  E  R  E  R  G  M  E  I  S  P |
| atgtgtgacaagcacaatgcttccgtggaaaaatcacaggtgggcttcatagactatatt<br> M  C  D  K  H  N  A  S  V  E  K  S  Q  V  G  F  I  D  Y  I |
| gttcatcccctctgggagacatgggcagacctcgtccaccctgacgcccaggatattttg<br> V  H  P  L  W  E  T  W  A  D  L  V  H  P  D  A  Q  D  I  L |
| gacactttggaggacaatcgtgaatggtaccagagcacaatccctcagagcccctctcct<br> D  T  L  E  D  N  R  E  W  Y  Q  S  T  I  P  Q  S  P  S  P |
| gcacctgatgacccagaggagggccggcagggtcaaactgagaaattccagtttgaacta<br> A  P  D  D  P  E  E  G  R  Q  G  Q  T  E  K  F  Q  F  E  L |
| actttagaggaagatggtgagtcagacacggaaaaggacagtggcagtcaagtgtaagtc<br> T  L  E  E  D  G  E  S  D  T  E  K  D  S  G  S  Q  V  - |
| gactagagcctgcagtctcgaccatcatcatcatcatcattaataaaagggcgaattcca |
| gcacactggcggccgttactagtggatcc |

PCR Primers:

| PDE4D |
|---|
| (SEQ ID NO: 19)<br>PDE4D-S  TCTGACTCATATGAGTATCCCAAGGTTTGGAGT    323 |
| (SEQ ID NO: 20)<br>PDE4D-A  CTAGTGTCGACTTACACTTGACTGCCACTGTCCT   324 |

PDE4B2:

| P4477. pFastBac PDE4B2 M1-T564-X (SEQ ID NOS: 21 and 22) |
|---|
| tattccggattattcataccgtcccaccatcgggcgcggatctcggtccgaaacc |
| atgtcgtactaccatcaccatcaccatcacgattacgatatcccaacgaccgaaaacctg<br> M  S  Y  Y  H  H  H  H  H  H  D  Y  D  I  P  T  T  E  N  L |
| tattttcagggccatatgaaggagcacggggggcaccttcagtagcaccggaatcagcggt<br> Y  F  Q  G  H  M  K  E  H  G  G  T  F  S  S  T  G  I  S  G |
| ggtagcggtgactctgctatggacagcctgcagccgctccagcctaactacatgcctgtg<br> G  S  G  D  S  A  M  D  S  L  Q  P  L  Q  P  N  Y  M  P  V |
| tgtttgtttgcagaagaatcttatcaaaaattagcaatggaaacgctggaggaattagac<br> C  L  F  A  E  E  S  Y  Q  K  L  A  M  E  T  L  E  E  L  D |
| tggtgtttagaccagctagagaccatacagacctaccggtctgtcagtgagatggcttct<br> W  C  L  D  Q  L  E  T  I  Q  T  Y  R  S  V  S  E  M  A  S |

-continued

P4477. pFastBac PDE4B2 M1-T564-X (SEQ ID NOS: 21 and 22)

```
aacaagttcaaaagaatgctgaaccgggagctgacacacctctcagagatgagccgatca
 N   K   F   K   R   M   L   N   R   E   L   T   H   L   S   E   M   S   R   S gggaaccaggtgtctgaatacatttcaaatactttcttagacaagcagaatgatgtggag
 G   N   Q   V   S   E   Y   I   S   N   T   F   L   D   K   Q   N   D   V   E atcccatctcctacccagaaagacagggagaaaaagaaaaagcagcagctcatgaccag
 I   P   S   P   T   Q   K   D   R   E   K   K   K   K   Q   Q   L   M   T   Q ataagtggagtgaagaaattaatgcatagttcaagcctaaacaatacaagcatctcacgc
 I   S   G   V   K   K   L   M   H   S   S   S   L   N   N   T   S   I   S   R tttggagtcaacactgaaaatgaagatcacctggccaaggagctggaagacctgaacaaa
 F   G   V   N   T   E   N   E   D   H   L   A   K   E   L   E   D   L   N   K tggggtcttaacatctttaatgtggctggatattctcacaatagaccctaacatgcatc
 W   G   L   N   I   F   N   V   A   G   Y   S   H   N   R   P   L   T   C   I atgtatgctatattccaggaaagagacctcctaaagacattcagaatctcatctgacaca
 M   Y   A   I   F   Q   E   R   D   L   L   K   T   F   R   I   S   S   D   T tttataacctacatgatgactttagaagaccattaccattctgacgtggcatatcacaac
 F   I   T   Y   M   M   T   L   E   D   H   Y   H   S   D   V   A   Y   H   N agcctgcacgctgctgatgtagcccagtcgacccatgttctcctttctacaccagcatta
 S   L   H   A   A   D   V   A   Q   S   T   H   V   L   L   S   T   P   A   L gacgctgtcttcacagatttggaaatcctggctgccattttgcagctgccatccatgac
 D   A   V   F   T   D   L   E   I   L   A   A   I   F   A   A   A   I   H   D gttgatcatcctggagtctccaatcagtttctcatcaacacaaattcagaacttgctttg
 V   D   H   P   G   V   S   N   Q   F   L   I   N   T   N   S   E   L   A   L atgtataatgatgaatctgtgttggaaaatcatcaccttgctgtgggttttcaaactgctg
 M   Y   N   D   E   S   V   L   E   N   H   H   L   A   V   G   F   K   L   L caagaagaacactgtgacatcttcatgaatctcaccaagaagcagcgtcagacactcagg
 Q   E   E   H   C   D   I   F   M   N   L   T   K   K   Q   R   Q   T   L   R aagatggttattgacatggtgttagcaactgatatgtctaaacacatgagcctgctggca
 K   M   V   I   D   M   V   L   A   T   D   M   S   K   H   M   S   L   L   A gacctgaagacaatggtagaaacgaagaaagttacaagttcaggcgttcttctcctagac
 D   L   K   T   M   V   E   T   K   K   V   T   S   S   G   V   L   L   L   D aactataccgatcgcattcaggtccttcgcaacatggtacactgtgcagacctgagcaac
 N   Y   T   D   R   I   Q   V   L   R   N   M   V   H   C   A   D   L   S   N cccaccaagtccttggaattgtatcggcaatggacagaccgcatcatggaggaattttc
 P   T   K   S   L   E   L   Y   R   Q   W   T   D   R   I   M   E   E   F   F cagcagggagacaaagagcgggagaggggaatggaaattagcccaatgtgtgataaacac
 Q   Q   G   D   K   E   R   E   R   G   M   E   I   S   P   M   C   D   K   H acagcttctgtggaaaaatcccaggttggtttcatcgactacattgtccatccattgtgg
 T   A   S   V   E   K   S   Q   V   G   F   I   D   Y   I   V   H   P   L   W gagacatgggcagatttggtacagcctgatgctcaggacattctcgataccttagaagat
 E   T   W   A   D   L   V   Q   P   D   A   Q   D   I   L   D   T   L   E   D aacaggaactggtatcagagcatgatacctcaaagtccctcaccaccactggacgagcag
 N   R   N   W   Y   Q   S   M   I   P   Q   S   P   S   P   P   L   D   E   Q aacagggactgccagggtctgatggagaagtttcagtttgaactgactctcgatgaggaa
 N   R   D   C   Q   G   L   M   E   K   F   Q   F   E   L   T   L   D   E   E gattctgaaggacctgagaaggagggagagggacacagctatttcagcagcacaaagacg
 D   S   E   G   P   E   K   E   G   E   G   H   S   Y   F   S   S   T   K   T ctttgtgtgattgatccagaaaacagagattccctgggagagactgacatagacattgca
 L   C   V   I   D   P   E   N   R   D   S   L   G   E   T   D   I   D   I   A acagaagacaagtcccccgtggatacataatccccctctcgaggcatgcggtaccaagct
 T   E   D   K   S   P   V   D   T   - t
```

PCR primers:

| PDE4B | |
|---|---|
| PDE4B2-S    CGTGCAACATATGAAGGAGCACGGGGGCAC 3734 | (SEQ ID NO: 23) |
| PDE4BFULL-A TCCACCTCGAGAGGGGGATTATGTATCCAC 1898 | (SEQ ID NO: 24) |

PDE4D5:

P4478. pFastBac PDE4D5 M1-T745-X (SEQ ID NOS: 25 and 26)

```
    tattccggattattcataccgtcccaccatcgggcgcggatctcggtccgaaacc atgtcgtactaccatcaccatcaccatcacgattacgatatcccaacgaccgaaaacctg
 M  S  Y  Y  H  H  H  H  H  H  D  Y  D  I  P  T  T  E  N  L tattttcagggccatatggctcagcagacaagcccggacactttaacagtacctgaagtg
 Y  F  Q  G  H  M  A  Q  Q  T  S  P  D  T  L  T  V  P  E  V gataatccgcattgtccaaacccgtggctgaacgaagaccttgtgaaatccttgcgagaa
 D  N  P  H  C  P  N  P  W  L  N  E  D  L  V  K  S  L  R  E aacctgttgcagcatgagaagtccaagacagcgaggaaatcggtttctcccaagctctct
 N  L  L  Q  H  E  K  S  K  T  A  R  K  S  V  S  P  K  L  S ccagtgatctctccgagaaattcccccaggcttctgcgcagaatgcttctcagcagcaac
 P  V  I  S  P  R  N  S  P  R  L  L  R  R  M  L  L  S  S  N atccccaaacagcggcgtttcacggtggcacatacatgttttgatgtggacaatggcaca
 I  P  K  Q  R  R  F  T  V  A  H  T  C  F  D  V  D  N  G  T tctgcgggacggagtcccttggatcccatgaccagcccaggatccgggctaattctccaa
 S  A  G  R  S  P  L  D  P  M  T  S  P  G  S  G  L  I  L  Q gcaaattttgtccacagtcaacgacgggagtccttcctgtatcgatccgacagcgattat
 A  N  F  V  H  S  Q  R  R  E  S  F  L  Y  R  S  D  S  D  Y gacctctctccaaagtctatgtcccggaactcctccattgccagtgatatacacggagat
 D  L  S  P  K  S  M  S  R  N  S  S  I  A  S  D  I  H  G  D gacttgattgtgactccatttgctcaggtcttggccagtctgcgaactgtacgaaacaac
 D  L  I  V  T  P  F  A  Q  V  L  A  S  L  R  T  V  R  N  N tttgctgcattaactaatttgcaagatcgagcacctagcaaaagatcacccatgtgcaac
 F  A  A  L  T  N  L  Q  D  R  A  P  S  K  R  S  P  M  C  N caaccatccatcaacaaagccaccataacagaggaggcctaccagaaactggccagcgag
 Q  P  S  I  N  K  A  T  I  T  E  E  A  Y  Q  K  L  A  S  E accctggaggagctggactggtgtctggaccagctagagaccctacagaccaggcactcc
 T  L  E  E  L  D  W  C  L  D  Q  L  E  T  L  Q  T  R  H  S gtcagtgagatggcctccaacaagtttaaaaggatgcttaatcgggagctcacccatctc
 V  S  E  M  A  S  N  K  F  K  R  M  L  N  R  E  L  T  H  L tctgaaatgagtcggtctggaaatcaagtgtcagagtttatatcaaacacattcttagat
 S  E  M  S  R  S  G  N  Q  V  S  E  F  I  S  N  T  F  L  D aagcaacatgaagtggaaattccttctccaactcagaaggaaaaggagaaaaagaaaaga
 K  Q  H  E  V  E  I  P  S  P  T  Q  K  E  K  E  K  K  K  R ccaatgtctcagatcagtggagtcaagaaattgatgcacagctctagtctgactaattca
 P  M  S  Q  I  S  G  V  K  K  L  M  H  S  S  S  L  T  N  S agtatccccaaggtttggagttaaaactgaacaagaagatgtccttgccaaggaactagaa
 S  I  P  R  F  G  V  K  T  E  Q  E  D  V  L  A  K  E  L  E gatgtgaacaaatggggtcttcatgtttttcagaatagcagagttgtctggtaaccggccc
 D  V  N  K  W  G  L  H  V  F  R  I  A  E  L  S  G  N  R  P ttgactgttatcatgcacaccatttttcaggaacgggatttattaaaaacatttaaaatt
 L  T  V  I  M  H  T  I  F  Q  E  R  D  L  L  K  T  F  K  I
```

-continued

P4478. pFastBac PDE4D5 M1-T745-X (SEQ ID NOS: 25 and 26)

```
ccagtagatactttaattacatatcttatgactctcgaagaccattaccatgctgatgtg
 P  V  D  T  L  I  T  Y  L  M  T  L  E  D  H  Y  A  D  V gcctatcacaacaatatccatgctgcagatgttgtccagtctactcatgtgctattatct
 A  Y  H  N  N  I  H  A  A  D  V  V  Q  S  T  H  V  L  L  S acacctgctttggaggctgtgtttacagatttggagattcttgcagcaattttttgccagt
 T  P  A  L  E  A  V  F  T  D  L  E  I  L  A  A  I  F  A  S gcaatacatgatgtagatcatcctggtgtgtccaatcaatttctgatcaatacaaactct
 A  I  H  D  V  D  H  P  G  V  S  N  Q  F  L  I  N  T  N  S gaacttgccttgatgtacaatgattcctcagtcttagagaaccatcatttggctgtgggc
 E  L  A  L  M  Y  N  D  S  S  V  L  E  N  H  H  L  A  V  G tttaaattgcttcaggaagaaaactgtgacattttccagaatttgaccaaaaaacaaaga
 F  K  L  L  Q  E  E  N  C  D  I  F  Q  N  L  T  K  K  Q  R caatctttaaggaaaatggtcattgacatcgtacttgcaacagatatgtcaaaacacatg
 Q  S  L  R  K  M  V  I  D  I  V  L  A  T  D  M  S  K  H  M aatctactggctgatttgaagactatggttgaaactaagaaagtgacaagctctggagtt
 N  L  L  A  D  L  K  T  M  V  E  T  K  K  V  T  S  S  G  V cttcttcttgataattattccgataggattcaggttcttcagaatatggtgcactgtgca
 L  L  L  D  N  Y  S  D  R  I  Q  V  L  Q  N  M  V  H  C  A gatctgagcaacccaacaaagcctctccagctgtaccgccagtggacggaccggataatg
 D  L  S  N  P  T  K  P  L  Q  L  Y  R  Q  W  T  D  R  I  M gaggagttcttccgccaaggagaccgagagagggaacgtggcatggagataagccccatg
 E  E  F  R  Q  G  D  R  E  R  E  R  G  M  E  I  S  P  M tgtgacaagcacaatgcttccgtggaaaaatcacaggtgggcttcatagactatattgtt
 C  D  K  H  N  A  S  V  E  K  S  Q  V  G  F  I  D  Y  I  V catcccctctgggagacatgggcagacctcgtccaccctgacgcccaggatattttggac
 H  P  L  W  E  T  W  A  D  L  V  H  P  D  A  Q  D  I  L  D actttggaggacaatcgtgaatggtaccagagcacaatccctcagagccccctctcctgca
 T  L  E  D  N  R  E  W  Y  Q  S  T  I  P  Q  S  P  S  P  A cctgatgacccagaggagggccggcagggtcaaactgagaaattccagtttgaactaact
 P  D  D  P  E  E  G  R  Q  G  Q  T  E  K  F  Q  F  E  L  T ttagaggaagatggtgagtcagacacggaaaaggacagtggcagtcaagtggaagaagac
 L  E  E  D  G  E  S  D  T  E  K  D  S  G  S  Q  V  E  E  D actagctgcagtgactccaagactcttttgtactcaagactcagagtctactgaaattccc
 T  S  C  S  D  S  K  T  L  C  T  Q  D  S  E  S  T  E  I  P cttgatgaacaggttgaagaggaggcagtaggggaagaagaggaaagccagcctgaagcc
 L  D  E  Q  V  E  E  E  A  V  G  E  E  E  E  S  Q  P  E  A tgtgtcatagatgatcgttctcctgacacgtaacagtcgactagagcctgcagtctcgag
 C  V  I  D  D  R  S  P  D  T  - gcatgcggtaccaagctt
```

PCR Primers:

| PDE4D | | |
|---|---|---|
| | (SEQ ID NO: 27) | |
| PDE4DFULL-S GACCAGGCATATGGCTCAGCAGACAAGCCC | | 1911 |
| | (SEQ ID NO: 28) | |
| PDE4DFULL-A AGTTTGTCGACTGTTACGTGTCAGGAGAAC | | 1912 |

Example 145

PDE4 $IC_{50}$ Determinations $IC_{50}$s were determined by Scintillation Proximity Assay (SPA). The principle of the assay is based on the fact that cAMP, the PDE4 substrate, binds weakly to Yittrium Silicate SPA beads, whereas AMP, the product of PDE4 hydrolysis binds strongly. Thus, the extent of PDE4 hydrolysis of a sample of [$^3$H]cAMP can be measured because only the [$^3$H] AMP produced by PDE4 hydrolysis will bind to the SPA beads and produce a scintillation signal.

PDE4 Enzymes Used for $IC_{50}$ Assays:

PDE4B: The catalytic domain of human PDE4B from S152-S528 with an N-terminal His6 tag (SEQ ID NO: 32) and thrombin cleavage site, expressed in *E. coli* and purified by metal ion affinity chromatography. Enzyme was stored in 50% glycerol at −20°. See Example 144.

PDE4D: The catalytic domain of human PDE4B from S316-V692 with an N-terminal His6 tag (SEQ ID NO: 32) and thrombin cleavage site, expressed in *E. coli* and purified by metal ion affinity chromatography. Enzyme was stored in 50% glycerol at −20°. See Example 144.

PDE4B2: see Example 144.

PDE4D5: see Example 144.

$IC_{50}$ Procedure:

Compounds tested (see Tables 5 for compounds and results) were 3-fold serially diluted 11 times in DMSO from a starting concentration of 4 mM or 40 μM, depending on compound potency. 1 μl of each dilution was transferred into duplicate wells of a white polystyrene 384-well assay plate (Corning #3710). In addition to the compound dilutions, each assay plate contained control wells with 1 μl of DMSO (to define 0% enzyme inhibition) or 1 μl of 200 μM roflumilast (to define 100% enzyme inhibition). Using a Beckman FX robot, 10 μl of [$^3$H] cAMP (Amersham TRK559) at 2 mCi/ml in assay buffer (50 mM Tris, pH 7.5; 8.3 mM MgCl; 1.7 mM EGTA; 0.01% BSA) was transferred to each assay well. Next, 10 μl of PDE4 enzyme in assay buffer was added and the plates were shaken for 30 s. at 1000 rpm to start the cAMP hydrolysis reaction. The concentrations of enzyme used were: PDE4B, 80 ng/ml; PDE4D, 4 ng/ml; PDE4B2, 2.5 μl of 50% glycerol stock/ml; PDE4D5 0.083 μl of 50% glycerol stock/ml. Assay plates were covered and incubated for 30 min. at 30° C. Reactions were stopped by robotic addition of 10 μl of 5 mg/ml SPA beads (Amersham RPNQ0013) in 18 mM $ZnSO_4$. The assay plates were covered with clear plastic film, centrifuged for 1 min. at 1000 RPM to settle the SPA beads, and counted using a Wallac TriLux scintillation counter. $IC_{50}$'s were calculated from the raw assay data by non-linear regression curve fitting using the Assay Explorer software package from MDL.

Example 146

$IC_{50}$ Determinations assessed by TNF alpha production upon stimulation of whole blood cultures with LPS.

Compounds were assayed to generate $IC_{50}$ numbers based on the inhibition of TNF-α release from whole blood cultures, using the following assay protocol (see Table 5 for compounds tested and results). Inhibition of PDE4B results in the inhibition of TNF-α release by whole blood cultures stimulated with lipopolysaccharide (LPS). The measurement of TNF-α release was used to assess compounds as PDE4B inhibitors.

Compounds were provided in DMSO at 20 mM and 2 μl per well was added to one row of a dilution plate. Added 98 μl of RPMI 1640 media with 2.5% heat inactivated FBS to each well containing compound. The same media with 2% DMSO was prepared and 60 μl was added to each of the empty wells in the dilution plate. The compound was serially diluted 1:3 (30 μl to 60 μl of media) for a total of 8 concentrations per compound. Wells were also prepared with 50 μM roflumilast and piclamilast as 100% inhibition controls, and 2% DMSO in media was used as 0% inhibition control. A 20 μl aliquot of each sample was transferred to an assay plate in duplicate.

Human buffy coat was obtained from the Stanford Medical School Blood Center and diluted with 7 volumes of RPMI 1640 media with 1% penicillin/streptomycin and 2.5% heat inactivated FBS. A 160 μl aliquot of the diluted blood was added to each well of the assay plates, mixed and incubated for 1 hour at 37° C. in 5% $CO_2$. LPS (Sigma catalog number L2637) that had been diluted to 1 mg/ml in PBS and stored as 20 μl aliquots at −20° C. was thawed and diluted 1000× to 1 μg/ml. A 20 μl aliquot of this was added to each sample (final concentration 100 ng/ml LPS) after the 1 hour incubation. A background sample was prepared without addition of LPS as well. The samples were mixed on a shaker for one minute at 900 RPM and incubated for 4 hours at 37° C. in 5% $CO_2$. The plates were then put on a shaker for one minute at 900 RPM, followed by centrifuging at 100×g for 10 minutes, deceleration setting of 5. The top 75 μl of supernatant was carefully pipetted to a new plate and frozen at −20° C.

A 50 μl aliquot of incubation buffer (Biosource International Immunoassay Kit:Human TNF-α catalog number KHC3011) was added to each well of a plate coated with monoclonal antibody specific for hTNF-α (Biosource kit). The supernatant blood samples were thawed and a 50 μl aliquot along with 50 μl of diluent buffer (Biosource kit) were added to incubation buffer and the samples were incubated for 2 hours at room temperature. The samples were washed 4 times with 300 μl/well wash buffer (Biosource kit). A 100 μl aliquot of biotinylated anti-TNFalpha (Biosource kit) was added and the samples incubated for 1 hour at room temperature. The samples were washed 4 times with 300 μl/well wash buffer. A 100 μl aliquot of Streptavidin-HRP solution (BioSource kit) was added and the samples incubated for 30 minutes at room temperature. The samples were washed 4 times with 300 μl/well wash buffer. A 100 μl aliquot of Chromagen (Biosource kit) was added and the samples incubated in the dark for 30 minutes. A 100 μl aliquot of stop solution (2N $H_2SO_4$) was added to each sample and samples were read at 450 nm on a WallacVictor for 0.1 sec/well.

Example 147

Rat Inhibition Studies

All studies were done with male rats CD (SD) IGS BR (Crl) (Charles River, France), which were grouped in to 5 animal groups. Compound doses were as indicated in Table 5.

At the end of the acclimatization period, the non-fasted rats were weighed, individually identified on the tail with a permanent marker and administered by oral (po) or interperitoneal (ip) route with either vehicle, reference or test compound in a volume of 10 mL/kg adapted to the body weight. The animals were gathered in groups of 5 animals in a polystyrene labeled cage with sawdust covered floors. 2-hours after vehicle, reference or test substance administration, rats received an intravenous (iv) injection of 0.1 mg/kg LPS in a volume of 1 mL/kg of body weight. 2 h after LPS challenge (or as indicated in Tables 3B and 4B), blood samples were collected into tubes without anticoagulant by retro-orbital puncture under gas (isoflurane) anesthesia. Samples were allowed to clot at room temperature for 5 to 10 min then put on ice until there were prepared by centrifugation (6000×g for 3 min at 4° C.) and stored at −20° C. until use. TNFα levels were measured in serum samples in duplicate by ELISA technique according to the manufacturer's procedure (Rat TNFα kit Quantikine M (RTA00, R&D System, France)). Data are reported as percent decrease in observed TNFα levels versus TNFα levels observed for vehicle dosed animal groups.

Example 148

Site-directed Mutagenesis of PDE4B

Mutagenesis of PDE4B can be carried out according to the following procedure as described in Molecular Biology: Current Innovations and Future Trends. Eds. A. M. Griffin and H. G. Griffin. (1995) ISBN 1-898486-01-8, Horizon Scientific Press, PO Box 1, Wymondham, Norfolk, U.K., among others.

In vitro site-directed mutagenesis is an invaluable technique for studying protein structure-function relationships, gene expression and vector modification. Several methods have appeared in the literature, but many of these methods require single-stranded DNA as the template. The reason for this, historically, has been the need for separating the complementary strands to prevent reannealing. Use of PCR in site-directed mutagenesis accomplishes strand separation by using a denaturing step to separate the complementing strands and allowing efficient polymerization of the PCR primers. PCR site-directed methods thus allow site-specific mutations to be incorporated in virtually any double-stranded plasmid; eliminating the need for M13-based vectors or single-stranded rescue.

It is often desirable to reduce the number of cycles during PCR when performing PCR-based site-directed mutagenesis to prevent clonal expansion of any (undesired) second-site mutations. Limited cycling which would result in reduced product yield, is offset by increasing the starting template concentration. A selection is used to reduce the number of parental molecules coming through the reaction. Also, in order to use a single PCR primer set, it is desirable to optimize the long PCR method. Further, because of the extendase activity of some thermostable polymerases it is often necessary to incorporate an end-polishing step into the procedure prior to end-to-end ligation of the PCR-generated product containing the incorporated mutations in one or both PCR primers.

The following protocol provides a facile method for site-directed mutagenesis and accomplishes the above desired features by the incorporation of the following steps: (i) increasing template concentration approximately 1000-fold over conventional PCR conditions; (ii) reducing the number of cycles from 25-30 to 5-10; (iii) adding the restriction endonuclease DpnI (recognition target sequence: 5-Gm6ATC-3, where the A residue is methylated) to select against parental DNA (note: DNA isolated from almost all common strains of E. coli is Dam-methylated at the sequence 5-GATC-3); (iv) using Taq Extender in the PCR mix for increased reliability for PCR to 10 kb; (v) using Pfu DNA polymerase to polish the ends of the PCR product, and (vi) efficient intramolecular ligation in the presence of T4 DNA ligase.

Plasmid template DNA (approximately 0.5 pmole) is added to a PCR cocktail containing, in 25 ul of 1× mutagenesis buffer: (20 mM Tris HCl, pH 7.5; 8 mM MgCl2; 40 ug/ml BSA); 12-20 pmole of each primer (one of which must contain a 5-prime phosphate), 250 uM each dNTP, 2.5 U Taq DNA polymerase, 2.5 U of Taq Extender (Stratagene).

The PCR cycling parameters are 1 cycle of: 4 min at 94° C., 2 min at 50 C and 2 min at 72° C.; followed by 5-10 cycles of 1 min at 94° C., 2 min at 54 C and 1 min at 72° C. (step 1).

The parental template DNA and the linear, mutagenesis-primer incorporating newly synthesized DNA are treated with DpnI (10 U) and Pfu DNA polymerase (2.5 U). This results in the DpnI digestion of the in vivo methylated parental template and hybrid DNA and the removal, by Pfu DNA polymerase, of the Taq DNA polymerase-extended base(s) on the linear PCR product.

The reaction is incubated at 37° C. for 30 min and then transferred to 72° C. for an additional 30 min (step 2).

Mutagenesis buffer (1×, 115 ul, containing 0.5 mM ATP) is added to the DpnI-digested, Pfu DNA polymerase-polished PCR products.

The solution is mixed and 10 ul is removed to a new microfuge tube and T4 DNA ligase (2-4 U) added.

The ligation is incubated for greater than 60 min at 37° C. (step 3).

The treated solution is transformed into competent E. coli (step 4).

In addition to the PCR-based site-directed mutagenesis described above, other methods are available. Examples include those described in Kunkel (1985) *Proc. Natl. Acad. Sci.* 82:488-492; Eckstein et al. (1985) *Nucl. Acids Res.* 13:8764-8785; and using the GeneEditor™ Site-Directed Mutageneis Sytem from Promega.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, variations can be made to crystallization or co-crystallization conditions for PDE4B proteins and/or various phosphodiesterase domain sequences can be used. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

TABLE 1

| | | | | | | | | | | |
|---|---|---|---|---|---|---|---|---|---|---|
| REMARK Written by O version 8.0.11 | | | | | | | | | | |
| CRYST1 | 1.000 | 1.000 | 1.000 | 90.00 | 90.00 | 90.00 | | | | |
| ORIGX1 | 1.000000 | 0.000000 | 0.000000 | | 0.00000 | | | | | |
| ORIGX2 | 0.000000 | 1.000000 | 0.000000 | | 0.00000 | | | | | |
| ORIGX3 | 0.000000 | 0.000000 | 1.000000 | | 0.00000 | | | | | |
| SCALE1 | 1.000000 | −0.000026 | −0.000026 | | 0.00000 | | | | | |
| SCALE2 | 0.000000 | 1.000000 | −0.000026 | | 0.00000 | | | | | |
| SCALE3 | 0.000000 | 0.000000 | 1.000000 | | 0.00000 | | | | | |
| ATOM | 1 | CB | ARG | A | 155 | 79.971 | 64.880 | 65.907 | 1.00 | 23.05 A |
| ATOM | 2 | CG | ARG | A | 155 | 80.613 | 63.882 | 66.857 | 1.00 | 22.25 A |
| ATOM | 3 | CD | ARG | A | 155 | 81.907 | 63.327 | 66.300 | 1.00 | 21.47 A |
| ATOM | 4 | NE | ARG | A | 155 | 82.378 | 62.172 | 67.060 | 1.00 | 22.64 A |
| ATOM | 5 | CZ | ARG | A | 155 | 82.051 | 60.910 | 66.792 | 1.00 | 20.30 A |
| ATOM | 6 | NH1 | ARG | A | 155 | 81.248 | 60.626 | 65.775 | 1.00 | 20.18 A |
| ATOM | 7 | NH2 | ARG | A | 155 | 82.533 | 59.927 | 67.542 | 1.00 | 21.88 A |
| ATOM | 8 | C | ARG | A | 155 | 80.084 | 66.914 | 64.494 | 1.00 | 22.90 A |
| ATOM | 9 | O | ARG | A | 155 | 80.453 | 66.813 | 63.325 | 1.00 | 22.93 A |
| ATOM | 10 | N | ARG | A | 155 | 80.953 | 66.971 | 66.838 | 1.00 | 22.95 A |
| ATOM | 11 | CA | ARG | A | 155 | 80.788 | 66.143 | 65.606 | 1.00 | 22.82 A |
| ATOM | 12 | N | PHE | A | 156 | 79.060 | 67.679 | 64.859 | 1.00 | 22.91 A |
| ATOM | 13 | CA | PHE | A | 156 | 78.296 | 68.439 | 63.879 | 1.00 | 22.30 A |
| ATOM | 14 | CB | PHE | A | 156 | 76.906 | 68.746 | 64.434 | 1.00 | 22.43 A |
| ATOM | 15 | CG | PHE | A | 156 | 75.997 | 67.556 | 64.464 | 1.00 | 22.09 A |
| ATOM | 16 | CD1 | PHE | A | 156 | 75.372 | 67.121 | 63.306 | 1.00 | 22.60 A |
| ATOM | 17 | CD2 | PHE | A | 156 | 75.786 | 66.858 | 65.641 | 1.00 | 23.79 A |
| ATOM | 18 | CE1 | PHE | A | 156 | 74.550 | 66.009 | 63.325 | 1.00 | 23.14 A |
| ATOM | 19 | CE2 | PHE | A | 156 | 74.966 | 65.747 | 65.667 | 1.00 | 23.39 A |
| ATOM | 20 | CZ | PHE | A | 156 | 74.348 | 65.322 | 64.506 | 1.00 | 23.54 A |
| ATOM | 21 | C | PHE | A | 156 | 78.966 | 69.728 | 63.423 | 1.00 | 23.31 A |
| ATOM | 22 | O | PHE | A | 156 | 78.749 | 70.177 | 62.300 | 1.00 | 23.75 A |
| ATOM | 23 | N | GLY | A | 157 | 79.776 | 70.321 | 64.295 | 1.00 | 22.97 A |
| ATOM | 24 | CA | GLY | A | 157 | 80.459 | 71.552 | 63.943 | 1.00 | 24.05 A |
| ATOM | 25 | C | GLY | A | 157 | 79.526 | 72.691 | 63.579 | 1.00 | 24.76 A |
| ATOM | 26 | O | GLY | A | 157 | 79.888 | 73.562 | 62.786 | 1.00 | 26.86 A |
| ATOM | 27 | N | VAL | A | 158 | 78.328 | 72.693 | 64.157 | 1.00 | 25.15 A |
| ATOM | 28 | CA | VAL | A | 158 | 77.349 | 73.742 | 63.880 | 1.00 | 24.88 A |
| ATOM | 29 | CB | VAL | A | 158 | 76.019 | 73.475 | 64.612 | 1.00 | 24.20 A |
| ATOM | 30 | CG1 | VAL | A | 158 | 75.028 | 74.583 | 64.304 | 1.00 | 23.49 A |
| ATOM | 31 | CG2 | VAL | A | 158 | 75.453 | 72.128 | 64.191 | 1.00 | 25.00 A |
| ATOM | 32 | C | VAL | A | 158 | 77.876 | 75.105 | 64.319 | 1.00 | 26.65 A |
| ATOM | 33 | O | VAL | A | 158 | 78.278 | 75.286 | 65.471 | 1.00 | 27.38 A |
| ATOM | 34 | N | ASN | A | 159 | 77.872 | 76.059 | 63.392 | 1.00 | 27.36 A |
| ATOM | 35 | CA | ASN | A | 159 | 78.351 | 77.407 | 63.669 | 1.00 | 28.38 A |
| ATOM | 36 | C | ASN | A | 159 | 77.553 | 78.037 | 64.806 | 1.00 | 29.46 A |
| ATOM | 37 | O | ASN | A | 159 | 76.329 | 77.907 | 64.867 | 1.00 | 29.12 A |
| ATOM | 38 | CB | ASN | A | 159 | 78.275 | 78.271 | 62.410 | 1.00 | 28.09 A |
| ATOM | 39 | CG | ASN | A | 159 | 79.112 | 77.719 | 61.273 | 1.00 | 20.00 A |
| ATOM | 40 | OD1 | ASN | A | 159 | 80.222 | 77.234 | 61.486 | 1.00 | 20.00 A |
| ATOM | 41 | ND2 | ASN | A | 159 | 78.581 | 77.793 | 60.059 | 1.00 | 20.00 A |
| ATOM | 42 | N | THR | A | 160 | 78.258 | 78.720 | 65.701 | 1.00 | 27.70 A |
| ATOM | 43 | CA | THR | A | 160 | 77.631 | 79.364 | 66.849 | 1.00 | 27.94 A |
| ATOM | 44 | C | THR | A | 160 | 76.431 | 80.212 | 66.451 | 1.00 | 28.14 A |
| ATOM | 45 | O | THR | A | 160 | 75.420 | 80.236 | 67.152 | 1.00 | 28.28 A |
| ATOM | 46 | CB | THR | A | 160 | 78.615 | 80.269 | 67.590 | 1.00 | 26.10 A |
| ATOM | 47 | OG1 | THR | A | 160 | 79.724 | 79.492 | 68.058 | 1.00 | 20.00 A |
| ATOM | 48 | CG2 | THR | A | 160 | 77.938 | 80.929 | 68.782 | 1.00 | 20.00 A |
| ATOM | 49 | N | GLU | A | 161 | 76.543 | 80.906 | 65.323 | 1.00 | 27.39 A |
| ATOM | 50 | CA | GLU | A | 161 | 75.466 | 81.765 | 64.847 | 1.00 | 28.03 A |
| ATOM | 51 | C | GLU | A | 161 | 74.271 | 80.974 | 64.322 | 1.00 | 27.84 A |
| ATOM | 52 | O | GLU | A | 161 | 73.218 | 81.546 | 64.041 | 1.00 | 28.36 A |
| ATOM | 53 | CB | GLU | A | 161 | 75.970 | 82.692 | 63.740 | 1.00 | 28.29 A |
| ATOM | 54 | CG | GLU | A | 161 | 77.100 | 83.612 | 64.168 | 1.00 | 20.00 A |
| ATOM | 55 | CD | GLU | A | 161 | 77.573 | 84.515 | 63.046 | 1.00 | 20.00 A |
| ATOM | 56 | OE1 | GLU | A | 161 | 77.016 | 84.420 | 61.933 | 1.00 | 20.00 A |
| ATOM | 57 | OE2 | GLU | A | 161 | 78.500 | 85.317 | 63.280 | 1.00 | 20.00 A |
| ATOM | 58 | N | ASN | A | 162 | 74.431 | 79.662 | 64.191 | 1.00 | 26.56 A |
| ATOM | 59 | CA | ASN | A | 162 | 73.348 | 78.824 | 63.688 | 1.00 | 26.62 A |
| ATOM | 60 | CB | ASN | A | 162 | 73.838 | 77.996 | 62.497 | 1.00 | 25.54 A |
| ATOM | 61 | CG | ASN | A | 162 | 74.307 | 78.863 | 61.343 | 1.00 | 25.39 A |
| ATOM | 62 | OD1 | ASN | A | 162 | 73.613 | 79.796 | 60.935 | 1.00 | 27.84 A |
| ATOM | 63 | ND2 | ASN | A | 162 | 75.486 | 78.561 | 60.811 | 1.00 | 27.27 A |
| ATOM | 64 | C | ASN | A | 162 | 72.762 | 77.911 | 64.757 | 1.00 | 26.85 A |

TABLE 1-continued

| ATOM | 65 | O | ASN | A | 162 | 71.782 | 77.202 | 64.512 | 1.00 | 27.85 | A |
| ATOM | 66 | N | GLU | A | 163 | 73.356 | 77.938 | 65.945 | 1.00 | 26.44 | A |
| ATOM | 67 | CA | GLU | A | 163 | 72.887 | 77.118 | 67.054 | 1.00 | 26.49 | A |
| ATOM | 68 | CB | GLU | A | 163 | 73.726 | 77.382 | 68.306 | 1.00 | 26.50 | A |
| ATOM | 69 | CG | GLU | A | 163 | 74.517 | 76.184 | 68.788 | 1.00 | 28.58 | A |
| ATOM | 70 | CD | GLU | A | 163 | 75.856 | 76.049 | 68.098 | 1.00 | 29.98 | A |
| ATOM | 71 | OE1 | GLU | A | 163 | 75.896 | 76.082 | 66.849 | 1.00 | 32.90 | A |
| ATOM | 72 | OE2 | GLU | A | 163 | 76.874 | 75.904 | 68.810 | 1.00 | 31.77 | A |
| ATOM | 73 | C | GLU | A | 163 | 71.425 | 77.396 | 67.375 | 1.00 | 25.70 | A |
| ATOM | 74 | O | GLU | A | 163 | 70.598 | 76.481 | 67.392 | 1.00 | 25.71 | A |
| ATOM | 75 | N | ASP | A | 164 | 71.116 | 78.665 | 67.636 | 1.00 | 25.48 | A |
| ATOM | 76 | CA | ASP | A | 164 | 69.759 | 79.084 | 67.968 | 1.00 | 25.27 | A |
| ATOM | 77 | CB | ASP | A | 164 | 69.740 | 80.566 | 68.359 | 1.00 | 27.36 | A |
| ATOM | 78 | CG | ASP | A | 164 | 70.568 | 80.854 | 69.597 | 1.00 | 29.80 | A |
| ATOM | 79 | OD1 | ASP | A | 164 | 70.276 | 80.264 | 70.659 | 1.00 | 32.25 | A |
| ATOM | 80 | OD2 | ASP | A | 164 | 71.508 | 81.674 | 69.508 | 1.00 | 32.26 | A |
| ATOM | 81 | C | ASP | A | 164 | 68.777 | 78.862 | 66.827 | 1.00 | 24.21 | A |
| ATOM | 82 | O | ASP | A | 164 | 67.622 | 78.506 | 67.056 | 1.00 | 24.88 | A |
| ATOM | 83 | N | HIS | A | 165 | 69.234 | 79.081 | 65.599 | 1.00 | 22.75 | A |
| ATOM | 84 | CA | HIS | A | 165 | 68.371 | 78.906 | 64.438 | 1.00 | 23.18 | A |
| ATOM | 85 | CB | HIS | A | 165 | 69.054 | 79.453 | 63.184 | 1.00 | 24.09 | A |
| ATOM | 86 | CG | HIS | A | 165 | 69.299 | 80.930 | 63.228 | 1.00 | 25.46 | A |
| ATOM | 87 | CD2 | HIS | A | 165 | 70.440 | 81.648 | 63.102 | 1.00 | 26.59 | A |
| ATOM | 88 | ND1 | HIS | A | 165 | 68.291 | 81.846 | 63.443 | 1.00 | 27.36 | A |
| ATOM | 89 | CE1 | HIS | A | 165 | 68.802 | 83.065 | 63.449 | 1.00 | 26.84 | A |
| ATOM | 90 | NE2 | HIS | A | 165 | 70.104 | 82.972 | 63.245 | 1.00 | 27.21 | A |
| ATOM | 91 | C | HIS | A | 165 | 68.014 | 77.438 | 64.244 | 1.00 | 22.85 | A |
| ATOM | 92 | O | HIS | A | 165 | 66.886 | 77.110 | 63.880 | 1.00 | 23.63 | A |
| ATOM | 93 | N | LEU | A | 166 | 68.977 | 76.558 | 64.499 | 1.00 | 22.36 | A |
| ATOM | 94 | CA | LEU | A | 166 | 68.755 | 75.122 | 64.360 | 1.00 | 22.41 | A |
| ATOM | 95 | CB | LEU | A | 166 | 70.078 | 74.362 | 64.487 | 1.00 | 22.69 | A |
| ATOM | 96 | CG | LEU | A | 166 | 70.342 | 73.168 | 63.563 | 1.00 | 24.72 | A |
| ATOM | 97 | CD1 | LEU | A | 166 | 71.318 | 72.236 | 64.258 | 1.00 | 24.38 | A |
| ATOM | 98 | CD2 | LEU | A | 166 | 69.052 | 72.430 | 63.226 | 1.00 | 23.56 | A |
| ATOM | 99 | C | LEU | A | 166 | 67.793 | 74.633 | 65.446 | 1.00 | 22.38 | A |
| ATOM | 100 | O | LEU | A | 166 | 66.851 | 73.896 | 65.165 | 1.00 | 21.57 | A |
| ATOM | 101 | N | ALA | A | 167 | 68.032 | 75.042 | 66.689 | 1.00 | 22.78 | A |
| ATOM | 102 | CA | ALA | A | 167 | 67.175 | 74.624 | 67.796 | 1.00 | 22.78 | A |
| ATOM | 103 | CB | ALA | A | 167 | 67.727 | 75.156 | 69.117 | 1.00 | 23.00 | A |
| ATOM | 104 | C | ALA | A | 167 | 65.739 | 75.104 | 67.595 | 1.00 | 22.72 | A |
| ATOM | 105 | O | ALA | A | 167 | 64.784 | 74.422 | 67.968 | 1.00 | 23.75 | A |
| ATOM | 106 | N | LYS | A | 168 | 65.595 | 76.287 | 67.006 | 1.00 | 23.26 | A |
| ATOM | 107 | CA | LYS | A | 168 | 64.281 | 76.857 | 66.738 | 1.00 | 24.03 | A |
| ATOM | 108 | CB | LYS | A | 168 | 64.444 | 78.258 | 66.145 | 1.00 | 23.60 | A |
| ATOM | 109 | CG | LYS | A | 168 | 63.155 | 78.955 | 65.751 | 1.00 | 25.93 | A |
| ATOM | 110 | CD | LYS | A | 168 | 63.468 | 80.312 | 65.117 | 1.00 | 27.10 | A |
| ATOM | 111 | CE | LYS | A | 168 | 64.440 | 80.154 | 63.949 | 1.00 | 29.33 | A |
| ATOM | 112 | NZ | LYS | A | 168 | 64.847 | 81.450 | 63.326 | 1.00 | 29.14 | A |
| ATOM | 113 | C | LYS | A | 168 | 63.524 | 75.958 | 65.760 | 1.00 | 22.83 | A |
| ATOM | 114 | O | LYS | A | 168 | 62.334 | 75.700 | 65.932 | 1.00 | 24.33 | A |
| ATOM | 115 | N | GLU | A | 169 | 64.225 | 75.483 | 64.735 | 1.00 | 23.15 | A |
| ATOM | 116 | CA | GLU | A | 169 | 63.614 | 74.611 | 63.735 | 1.00 | 22.21 | A |
| ATOM | 117 | CB | GLU | A | 169 | 64.583 | 74.350 | 62.572 | 1.00 | 21.88 | A |
| ATOM | 118 | CG | GLU | A | 169 | 65.003 | 75.569 | 61.750 | 1.00 | 25.15 | A |
| ATOM | 119 | CD | GLU | A | 169 | 63.844 | 76.254 | 61.043 | 1.00 | 25.44 | A |
| ATOM | 120 | OE1 | GLU | A | 169 | 62.900 | 75.557 | 60.607 | 1.00 | 28.94 | A |
| ATOM | 121 | OE2 | GLU | A | 169 | 63.889 | 77.497 | 60.904 | 1.00 | 28.04 | A |
| ATOM | 122 | C | GLU | A | 169 | 63.229 | 73.272 | 64.356 | 1.00 | 22.48 | A |
| ATOM | 123 | O | GLU | A | 169 | 62.154 | 72.737 | 64.088 | 1.00 | 23.05 | A |
| ATOM | 124 | N | LEU | A | 170 | 64.114 | 72.736 | 65.192 | 1.00 | 21.62 | A |
| ATOM | 125 | CA | LEU | A | 170 | 63.878 | 71.447 | 65.824 | 1.00 | 21.58 | A |
| ATOM | 126 | CB | LEU | A | 170 | 65.175 | 70.934 | 66.457 | 1.00 | 20.64 | A |
| ATOM | 127 | CG | LEU | A | 170 | 66.293 | 70.607 | 65.460 | 1.00 | 21.61 | A |
| ATOM | 128 | CD1 | LEU | A | 170 | 67.567 | 70.244 | 66.211 | 1.00 | 21.59 | A |
| ATOM | 129 | CD2 | LEU | A | 170 | 65.853 | 69.461 | 64.554 | 1.00 | 21.25 | A |
| ATOM | 130 | C | LEU | A | 170 | 62.742 | 71.415 | 66.843 | 1.00 | 21.28 | A |
| ATOM | 131 | O | LEU | A | 170 | 62.343 | 70.342 | 67.293 | 1.00 | 22.17 | A |
| ATOM | 132 | N | GLU | A | 171 | 62.216 | 72.578 | 67.214 | 1.00 | 21.88 | A |
| ATOM | 133 | CA | GLU | A | 171 | 61.105 | 72.602 | 68.160 | 1.00 | 22.83 | A |
| ATOM | 134 | CB | GLU | A | 171 | 60.757 | 74.035 | 68.572 | 1.00 | 23.48 | A |
| ATOM | 135 | CG | GLU | A | 171 | 61.792 | 74.710 | 69.453 | 1.00 | 25.17 | A |
| ATOM | 136 | CD | GLU | A | 171 | 61.249 | 75.956 | 70.128 | 1.00 | 28.89 | A |
| ATOM | 137 | OE1 | GLU | A | 171 | 60.748 | 76.853 | 69.415 | 1.00 | 31.29 | A |
| ATOM | 138 | OE2 | GLU | A | 171 | 61.322 | 76.037 | 71.373 | 1.00 | 31.71 | A |
| ATOM | 139 | C | GLU | A | 171 | 59.887 | 71.959 | 67.501 | 1.00 | 22.17 | A |
| ATOM | 140 | O | GLU | A | 171 | 58.942 | 71.553 | 68.175 | 1.00 | 22.98 | A |
| ATOM | 141 | N | ASP | A | 172 | 59.928 | 71.865 | 66.175 | 1.00 | 21.31 | A |
| ATOM | 142 | CA | ASP | A | 172 | 58.838 | 71.278 | 65.404 | 1.00 | 20.32 | A |
| ATOM | 143 | CB | ASP | A | 172 | 58.596 | 72.116 | 64.149 | 1.00 | 21.90 | A |

TABLE 1-continued

| ATOM | 144 | CG | ASP | A | 172 | 58.305 | 73.568 | 64.476 | 1.00 | 26.96 | A |
|------|-----|-----|-----|---|-----|--------|--------|--------|------|-------|---|
| ATOM | 145 | OD1 | ASP | A | 172 | 57.361 | 73.815 | 65.257 | 1.00 | 27.29 | A |
| ATOM | 146 | OD2 | ASP | A | 172 | 59.021 | 74.456 | 63.962 | 1.00 | 29.99 | A |
| ATOM | 147 | C | ASP | A | 172 | 59.128 | 69.826 | 65.017 | 1.00 | 18.25 | A |
| ATOM | 148 | O | ASP | A | 172 | 58.494 | 69.274 | 64.122 | 1.00 | 19.05 | A |
| ATOM | 149 | N | LEU | A | 173 | 60.078 | 69.214 | 65.714 | 1.00 | 17.76 | A |
| ATOM | 150 | CA | LEU | A | 173 | 60.468 | 67.831 | 65.458 | 1.00 | 17.09 | A |
| ATOM | 151 | CB | LEU | A | 173 | 61.434 | 67.353 | 66.546 | 1.00 | 17.23 | A |
| ATOM | 152 | CG | LEU | A | 173 | 61.953 | 65.918 | 66.406 | 1.00 | 18.22 | A |
| ATOM | 153 | CD1 | LEU | A | 173 | 62.842 | 65.820 | 65.174 | 1.00 | 18.47 | A |
| ATOM | 154 | CD2 | LEU | A | 173 | 62.726 | 65.525 | 67.663 | 1.00 | 19.38 | A |
| ATOM | 155 | C | LEU | A | 173 | 59.290 | 66.863 | 65.380 | 1.00 | 17.63 | A |
| ATOM | 156 | O | LEU | A | 173 | 59.252 | 65.991 | 64.511 | 1.00 | 18.15 | A |
| ATOM | 157 | N | ASN | A | 174 | 58.328 | 67.013 | 66.285 | 1.00 | 17.68 | A |
| ATOM | 158 | CA | ASN | A | 174 | 57.177 | 66.118 | 66.310 | 1.00 | 18.34 | A |
| ATOM | 159 | CB | ASN | A | 174 | 56.713 | 65.899 | 67.754 | 1.00 | 20.61 | A |
| ATOM | 160 | CG | ASN | A | 174 | 57.847 | 65.512 | 68.682 | 1.00 | 22.17 | A |
| ATOM | 161 | OD1 | ASN | A | 174 | 58.672 | 64.667 | 68.347 | 1.00 | 22.67 | A |
| ATOM | 162 | ND2 | ASN | A | 174 | 57.886 | 66.124 | 69.865 | 1.00 | 23.82 | A |
| ATOM | 163 | C | ASN | A | 174 | 55.985 | 66.591 | 65.481 | 1.00 | 18.49 | A |
| ATOM | 164 | O | ASN | A | 174 | 54.876 | 66.089 | 65.657 | 1.00 | 19.70 | A |
| ATOM | 165 | N | LYS | A | 175 | 56.212 | 67.534 | 64.571 | 1.00 | 18.41 | A |
| ATOM | 166 | CA | LYS | A | 175 | 55.131 | 68.078 | 63.748 | 1.00 | 18.38 | A |
| ATOM | 167 | CB | LYS | A | 175 | 55.036 | 69.591 | 63.945 | 1.00 | 20.31 | A |
| ATOM | 168 | CG | LYS | A | 175 | 54.789 | 70.030 | 65.379 | 1.00 | 22.09 | A |
| ATOM | 169 | CD | LYS | A | 175 | 54.812 | 71.545 | 65.469 | 1.00 | 23.35 | A |
| ATOM | 170 | CE | LYS | A | 175 | 54.558 | 72.034 | 66.883 | 1.00 | 26.61 | A |
| ATOM | 171 | NZ | LYS | A | 175 | 54.612 | 73.524 | 66.946 | 1.00 | 28.25 | A |
| ATOM | 172 | C | LYS | A | 175 | 55.310 | 67.790 | 62.263 | 1.00 | 17.31 | A |
| ATOM | 173 | O | LYS | A | 175 | 56.430 | 67.706 | 61.768 | 1.00 | 17.36 | A |
| ATOM | 174 | N | TRP | A | 176 | 54.191 | 67.657 | 61.556 | 1.00 | 18.04 | A |
| ATOM | 175 | CA | TRP | A | 176 | 54.206 | 67.390 | 60.122 | 1.00 | 17.86 | A |
| ATOM | 176 | CB | TRP | A | 176 | 52.776 | 67.092 | 59.648 | 1.00 | 17.14 | A |
| ATOM | 177 | CG | TRP | A | 176 | 52.654 | 66.297 | 58.372 | 1.00 | 15.60 | A |
| ATOM | 178 | CD2 | TRP | A | 176 | 53.051 | 64.933 | 58.162 | 1.00 | 15.09 | A |
| ATOM | 179 | CE2 | TRP | A | 176 | 52.659 | 64.579 | 56.855 | 1.00 | 14.34 | A |
| ATOM | 180 | CE3 | TRP | A | 176 | 53.697 | 63.977 | 58.953 | 1.00 | 15.37 | A |
| ATOM | 181 | CD1 | TRP | A | 176 | 52.060 | 66.703 | 57.208 | 1.00 | 15.68 | A |
| ATOM | 182 | NE1 | TRP | A | 176 | 52.057 | 65.676 | 56.295 | 1.00 | 14.60 | A |
| ATOM | 183 | CZ2 | TRP | A | 176 | 52.889 | 63.311 | 56.323 | 1.00 | 14.99 | A |
| ATOM | 184 | CZ3 | TRP | A | 176 | 53.925 | 62.717 | 58.423 | 1.00 | 16.21 | A |
| ATOM | 185 | CH2 | TRP | A | 176 | 53.521 | 62.395 | 57.121 | 1.00 | 15.03 | A |
| ATOM | 186 | C | TRP | A | 176 | 54.757 | 68.622 | 59.402 | 1.00 | 18.06 | A |
| ATOM | 187 | O | TRP | A | 176 | 55.260 | 68.525 | 58.283 | 1.00 | 18.52 | A |
| ATOM | 188 | N | GLY | A | 177 | 54.686 | 69.773 | 60.068 | 1.00 | 19.48 | A |
| ATOM | 189 | CA | GLY | A | 177 | 55.153 | 71.016 | 59.477 | 1.00 | 20.36 | A |
| ATOM | 190 | C | GLY | A | 177 | 56.632 | 71.350 | 59.577 | 1.00 | 20.93 | A |
| ATOM | 191 | O | GLY | A | 177 | 57.061 | 72.396 | 59.094 | 1.00 | 22.82 | A |
| ATOM | 192 | N | LEU | A | 178 | 57.419 | 70.482 | 60.202 | 1.00 | 19.75 | A |
| ATOM | 193 | CA | LEU | A | 178 | 58.854 | 70.724 | 60.323 | 1.00 | 18.09 | A |
| ATOM | 194 | CB | LEU | A | 178 | 59.529 | 69.499 | 60.950 | 1.00 | 18.68 | A |
| ATOM | 195 | CG | LEU | A | 178 | 61.044 | 69.487 | 61.175 | 1.00 | 18.87 | A |
| ATOM | 196 | CD1 | LEU | A | 178 | 61.380 | 68.476 | 62.253 | 1.00 | 22.51 | A |
| ATOM | 197 | CD2 | LEU | A | 178 | 61.767 | 69.143 | 59.886 | 1.00 | 19.56 | A |
| ATOM | 198 | C | LEU | A | 178 | 59.450 | 71.012 | 58.945 | 1.00 | 17.28 | A |
| ATOM | 199 | O | LEU | A | 178 | 59.044 | 70.407 | 57.953 | 1.00 | 19.08 | A |
| ATOM | 200 | N | ASN | A | 179 | 60.402 | 71.940 | 58.879 | 1.00 | 17.34 | A |
| ATOM | 201 | CA | ASN | A | 179 | 61.037 | 72.285 | 57.607 | 1.00 | 17.56 | A |
| ATOM | 202 | CB | ASN | A | 179 | 61.126 | 73.803 | 57.440 | 1.00 | 18.95 | A |
| ATOM | 203 | CG | ASN | A | 179 | 61.540 | 74.204 | 56.042 | 1.00 | 19.70 | A |
| ATOM | 204 | OD1 | ASN | A | 179 | 62.490 | 73.654 | 55.486 | 1.00 | 21.00 | A |
| ATOM | 205 | ND2 | ASN | A | 179 | 60.831 | 75.167 | 55.464 | 1.00 | 21.60 | A |
| ATOM | 206 | C | ASN | A | 179 | 62.436 | 71.696 | 57.566 | 1.00 | 17.32 | A |
| ATOM | 207 | O | ASN | A | 179 | 63.385 | 72.287 | 58.085 | 1.00 | 17.55 | A |
| ATOM | 208 | N | ILE | A | 180 | 62.563 | 70.537 | 56.930 | 1.00 | 17.15 | A |
| ATOM | 209 | CA | ILE | A | 180 | 63.845 | 69.851 | 56.859 | 1.00 | 16.59 | A |
| ATOM | 210 | CB | ILE | A | 180 | 63.655 | 68.418 | 56.316 | 1.00 | 16.15 | A |
| ATOM | 211 | CG2 | ILE | A | 180 | 63.407 | 68.457 | 54.818 | 1.00 | 16.84 | A |
| ATOM | 212 | CG1 | ILE | A | 180 | 64.876 | 67.563 | 56.658 | 1.00 | 16.30 | A |
| ATOM | 213 | CD1 | ILE | A | 180 | 65.048 | 67.323 | 58.152 | 1.00 | 18.04 | A |
| ATOM | 214 | C | ILE | A | 180 | 64.883 | 70.605 | 56.027 | 1.00 | 15.54 | A |
| ATOM | 215 | O | ILE | A | 180 | 66.085 | 70.429 | 56.223 | 1.00 | 16.30 | A |
| ATOM | 216 | N | PHE | A | 181 | 64.416 | 71.449 | 55.110 | 1.00 | 15.72 | A |
| ATOM | 217 | CA | PHE | A | 181 | 65.307 | 72.244 | 54.271 | 1.00 | 16.55 | A |
| ATOM | 218 | CB | PHE | A | 181 | 64.499 | 73.038 | 53.239 | 1.00 | 16.12 | A |
| ATOM | 219 | CG | PHE | A | 181 | 63.813 | 72.176 | 52.212 | 1.00 | 17.03 | A |
| ATOM | 220 | CD1 | PHE | A | 181 | 64.529 | 71.609 | 51.170 | 1.00 | 18.63 | A |
| ATOM | 221 | CD2 | PHE | A | 181 | 62.459 | 71.907 | 52.313 | 1.00 | 17.82 | A |
| ATOM | 222 | CE1 | PHE | A | 181 | 63.903 | 70.786 | 50.247 | 1.00 | 20.00 | A |

TABLE 1-continued

| | | | | | | | | | | |
|---|---|---|---|---|---|---|---|---|---|---|
| ATOM | 223 | CE2 | PHE | A | 181 | 61.829 | 71.085 | 51.395 | 1.00 | 17.51 | A |
| ATOM | 224 | CZ | PHE | A | 181 | 62.554 | 70.523 | 50.360 | 1.00 | 17.36 | A |
| ATOM | 225 | C | PHE | A | 181 | 66.109 | 73.206 | 55.146 | 1.00 | 15.85 | A |
| ATOM | 226 | O | PHE | A | 181 | 67.302 | 73.410 | 54.924 | 1.00 | 17.31 | A |
| ATOM | 227 | N | ASN | A | 182 | 65.456 | 73.794 | 56.143 | 1.00 | 17.65 | A |
| ATOM | 228 | CA | ASN | A | 182 | 66.161 | 74.713 | 57.027 | 1.00 | 18.69 | A |
| ATOM | 229 | CB | ASN | A | 182 | 65.183 | 75.544 | 57.854 | 1.00 | 19.86 | A |
| ATOM | 230 | CG | ASN | A | 182 | 64.335 | 76.457 | 56.997 | 1.00 | 21.86 | A |
| ATOM | 231 | OD1 | ASN | A | 182 | 64.759 | 76.892 | 55.924 | 1.00 | 23.94 | A |
| ATOM | 232 | ND2 | ASN | A | 182 | 63.134 | 76.765 | 57.473 | 1.00 | 23.53 | A |
| ATOM | 233 | C | ASN | A | 182 | 67.089 | 73.935 | 57.944 | 1.00 | 19.19 | A |
| ATOM | 234 | O | ASN | A | 182 | 68.163 | 74.417 | 58.302 | 1.00 | 20.79 | A |
| ATOM | 235 | N | VAL | A | 183 | 66.678 | 72.731 | 58.328 | 1.00 | 18.83 | A |
| ATOM | 236 | CA | VAL | A | 183 | 67.522 | 71.901 | 59.184 | 1.00 | 17.82 | A |
| ATOM | 237 | CB | VAL | A | 183 | 66.815 | 70.580 | 59.555 | 1.00 | 17.94 | A |
| ATOM | 238 | CG1 | VAL | A | 183 | 67.799 | 69.624 | 60.219 | 1.00 | 18.47 | A |
| ATOM | 239 | CG2 | VAL | A | 183 | 65.639 | 70.868 | 60.473 | 1.00 | 17.83 | A |
| ATOM | 240 | C | VAL | A | 183 | 68.829 | 71.585 | 58.457 | 1.00 | 17.58 | A |
| ATOM | 241 | O | VAL | A | 183 | 69.907 | 71.628 | 59.048 | 1.00 | 18.65 | A |
| ATOM | 242 | N | ALA | A | 184 | 68.734 | 71.274 | 57.167 | 1.00 | 17.48 | A |
| ATOM | 243 | CA | ALA | A | 184 | 69.918 | 70.959 | 56.377 | 1.00 | 17.45 | A |
| ATOM | 244 | CB | ALA | A | 184 | 69.505 | 70.479 | 54.985 | 1.00 | 16.66 | A |
| ATOM | 245 | C | ALA | A | 184 | 70.819 | 72.182 | 56.262 | 1.00 | 17.80 | A |
| ATOM | 246 | O | ALA | A | 184 | 72.047 | 72.079 | 56.329 | 1.00 | 19.06 | A |
| ATOM | 247 | N | GLY | A | 185 | 70.201 | 73.347 | 56.104 | 1.00 | 18.60 | A |
| ATOM | 248 | CA | GLY | A | 185 | 70.965 | 74.571 | 55.971 | 1.00 | 19.69 | A |
| ATOM | 249 | C | GLY | A | 185 | 71.758 | 74.958 | 57.203 | 1.00 | 20.68 | A |
| ATOM | 250 | O | GLY | A | 185 | 72.854 | 75.502 | 57.087 | 1.00 | 22.71 | A |
| ATOM | 251 | N | TYR | A | 186 | 71.217 | 74.678 | 58.383 | 1.00 | 20.79 | A |
| ATOM | 252 | CA | TYR | A | 186 | 71.897 | 75.031 | 59.627 | 1.00 | 21.00 | A |
| ATOM | 253 | CB | TYR | A | 186 | 70.870 | 75.458 | 60.685 | 1.00 | 20.43 | A |
| ATOM | 254 | CG | TYR | A | 186 | 70.115 | 76.730 | 60.348 | 1.00 | 21.83 | A |
| ATOM | 255 | CD1 | TYR | A | 186 | 70.793 | 77.917 | 60.100 | 1.00 | 21.59 | A |
| ATOM | 256 | CE1 | TYR | A | 186 | 70.110 | 79.085 | 59.798 | 1.00 | 24.25 | A |
| ATOM | 257 | CD2 | TYR | A | 186 | 68.730 | 76.745 | 60.286 | 1.00 | 22.13 | A |
| ATOM | 258 | CE2 | TYR | A | 186 | 68.035 | 77.910 | 59.984 | 1.00 | 23.32 | A |
| ATOM | 259 | CZ | TYR | A | 186 | 68.733 | 79.076 | 59.741 | 1.00 | 24.49 | A |
| ATOM | 260 | OH | TYR | A | 186 | 68.055 | 80.239 | 59.441 | 1.00 | 27.87 | A |
| ATOM | 261 | C | TYR | A | 186 | 72.776 | 73.918 | 60.195 | 1.00 | 21.63 | A |
| ATOM | 262 | O | TYR | A | 186 | 73.418 | 74.103 | 61.229 | 1.00 | 23.64 | A |
| ATOM | 263 | N | SER | A | 187 | 72.819 | 72.769 | 59.526 | 1.00 | 20.69 | A |
| ATOM | 264 | CA | SER | A | 187 | 73.631 | 71.655 | 60.017 | 1.00 | 19.57 | A |
| ATOM | 265 | CB | SER | A | 187 | 72.745 | 70.432 | 60.265 | 1.00 | 18.38 | A |
| ATOM | 266 | OG | SER | A | 187 | 72.187 | 69.951 | 59.048 | 1.00 | 18.57 | A |
| ATOM | 267 | C | SER | A | 187 | 74.767 | 71.261 | 59.081 | 1.00 | 20.33 | A |
| ATOM | 268 | O | SER | A | 187 | 75.240 | 70.126 | 59.120 | 1.00 | 20.31 | A |
| ATOM | 269 | N | HIS | A | 188 | 75.216 | 72.195 | 58.248 | 1.00 | 20.86 | A |
| ATOM | 270 | CA | HIS | A | 188 | 76.293 | 71.917 | 57.304 | 1.00 | 21.53 | A |
| ATOM | 271 | CB | HIS | A | 188 | 77.581 | 71.576 | 58.051 | 1.00 | 22.29 | A |
| ATOM | 272 | CG | HIS | A | 188 | 78.127 | 72.719 | 58.844 | 1.00 | 23.94 | A |
| ATOM | 273 | CD2 | HIS | A | 188 | 78.417 | 72.835 | 60.162 | 1.00 | 24.48 | A |
| ATOM | 274 | ND1 | HIS | A | 188 | 78.440 | 73.934 | 58.273 | 1.00 | 25.01 | A |
| ATOM | 275 | CE1 | HIS | A | 188 | 78.899 | 74.750 | 59.205 | 1.00 | 25.13 | A |
| ATOM | 276 | NE2 | HIS | A | 188 | 78.896 | 74.108 | 60.360 | 1.00 | 24.90 | A |
| ATOM | 277 | C | HIS | A | 188 | 75.913 | 70.776 | 56.373 | 1.00 | 19.79 | A |
| ATOM | 278 | O | HIS | A | 188 | 76.726 | 69.906 | 56.058 | 1.00 | 20.06 | A |
| ATOM | 279 | N | ASN | A | 189 | 74.657 | 70.791 | 55.949 | 1.00 | 19.07 | A |
| ATOM | 280 | CA | ASN | A | 189 | 74.116 | 69.793 | 55.044 | 1.00 | 18.96 | A |
| ATOM | 281 | CB | ASN | A | 189 | 74.795 | 69.895 | 53.673 | 1.00 | 20.86 | A |
| ATOM | 282 | CG | ASN | A | 189 | 74.035 | 69.143 | 52.591 | 1.00 | 24.63 | A |
| ATOM | 283 | OD1 | ASN | A | 189 | 72.823 | 69.312 | 52.439 | 1.00 | 28.24 | A |
| ATOM | 284 | ND2 | ASN | A | 189 | 74.745 | 68.312 | 51.831 | 1.00 | 26.51 | A |
| ATOM | 285 | C | ASN | A | 189 | 74.207 | 68.365 | 55.569 | 1.00 | 17.10 | A |
| ATOM | 286 | O | ASN | A | 189 | 74.555 | 67.442 | 54.834 | 1.00 | 18.62 | A |
| ATOM | 287 | N | ARG | A | 190 | 73.893 | 68.191 | 56.849 | 1.00 | 16.40 | A |
| ATOM | 288 | CA | ARG | A | 190 | 73.878 | 66.870 | 57.466 | 1.00 | 15.56 | A |
| ATOM | 289 | CB | ARG | A | 190 | 74.990 | 66.743 | 58.513 | 1.00 | 17.82 | A |
| ATOM | 290 | CG | ARG | A | 190 | 76.401 | 66.702 | 57.926 | 1.00 | 19.21 | A |
| ATOM | 291 | CD | ARG | A | 190 | 76.527 | 65.600 | 56.875 | 1.00 | 22.29 | A |
| ATOM | 292 | NE | ARG | A | 190 | 77.918 | 65.295 | 56.546 | 1.00 | 24.25 | A |
| ATOM | 293 | CZ | ARG | A | 190 | 78.295 | 64.497 | 55.551 | 1.00 | 23.85 | A |
| ATOM | 294 | NH1 | ARG | A | 190 | 77.383 | 63.920 | 54.773 | 1.00 | 23.57 | A |
| ATOM | 295 | NH2 | ARG | A | 190 | 79.586 | 64.270 | 55.336 | 1.00 | 25.08 | A |
| ATOM | 296 | C | ARG | A | 190 | 72.507 | 66.686 | 58.126 | 1.00 | 14.09 | A |
| ATOM | 297 | O | ARG | A | 190 | 72.404 | 66.341 | 59.302 | 1.00 | 14.55 | A |
| ATOM | 298 | N | PRO | A | 191 | 71.426 | 66.894 | 57.356 | 1.00 | 12.43 | A |
| ATOM | 299 | CD | PRO | A | 191 | 71.393 | 67.152 | 55.906 | 1.00 | 12.36 | A |
| ATOM | 300 | CA | PRO | A | 191 | 70.068 | 66.756 | 57.887 | 1.00 | 12.25 | A |
| ATOM | 301 | CB | PRO | A | 191 | 69.193 | 67.206 | 56.719 | 1.00 | 10.84 | A |

TABLE 1-continued

| ATOM | 302 | CG  | PRO | A | 191 | 69.984 | 66.732 | 55.536 | 1.00 | 11.01 | A |
| ATOM | 303 | C   | PRO | A | 191 | 69.681 | 65.373 | 58.391 | 1.00 | 11.81 | A |
| ATOM | 304 | O   | PRO | A | 191 | 68.944 | 65.260 | 59.363 | 1.00 | 12.80 | A |
| ATOM | 305 | N   | LEU | A | 192 | 70.160 | 64.320 | 57.739 | 1.00 | 12.56 | A |
| ATOM | 306 | CA  | LEU | A | 192 | 69.799 | 62.981 | 58.186 | 1.00 | 12.47 | A |
| ATOM | 307 | CB  | LEU | A | 192 | 70.233 | 61.936 | 57.154 | 1.00 | 12.79 | A |
| ATOM | 308 | CG  | LEU | A | 192 | 69.905 | 60.480 | 57.487 | 1.00 | 13.72 | A |
| ATOM | 309 | CD1 | LEU | A | 192 | 68.399 | 60.294 | 57.658 | 1.00 | 12.53 | A |
| ATOM | 310 | CD2 | LEU | A | 192 | 70.437 | 59.592 | 56.376 | 1.00 | 15.24 | A |
| ATOM | 311 | C   | LEU | A | 192 | 70.408 | 62.659 | 59.544 | 1.00 | 12.15 | A |
| ATOM | 312 | O   | LEU | A | 192 | 69.730 | 62.130 | 60.422 | 1.00 | 13.07 | A |
| ATOM | 313 | N   | THR | A | 193 | 71.685 | 62.983 | 59.724 | 1.00 | 13.19 | A |
| ATOM | 314 | CA  | THR | A | 193 | 72.336 | 62.711 | 60.998 | 1.00 | 13.74 | A |
| ATOM | 315 | CB  | THR | A | 193 | 73.855 | 62.968 | 60.907 | 1.00 | 14.07 | A |
| ATOM | 316 | OG1 | THR | A | 193 | 74.427 | 62.083 | 59.936 | 1.00 | 15.87 | A |
| ATOM | 317 | CG2 | THR | A | 193 | 74.524 | 62.717 | 62.253 | 1.00 | 15.95 | A |
| ATOM | 318 | C   | THR | A | 193 | 71.725 | 63.584 | 62.088 | 1.00 | 13.16 | A |
| ATOM | 319 | O   | THR | A | 193 | 71.447 | 63.114 | 63.191 | 1.00 | 13.24 | A |
| ATOM | 320 | N   | CYS | A | 194 | 71.505 | 64.854 | 61.768 | 1.00 | 13.77 | A |
| ATOM | 321 | CA  | CYS | A | 194 | 70.920 | 65.789 | 62.716 | 1.00 | 14.71 | A |
| ATOM | 322 | CB  | CYS | A | 194 | 70.856 | 67.184 | 62.089 | 1.00 | 16.72 | A |
| ATOM | 323 | SG  | CYS | A | 194 | 70.205 | 68.462 | 63.179 | 1.00 | 21.33 | A |
| ATOM | 324 | C   | CYS | A | 194 | 69.519 | 65.355 | 63.150 | 1.00 | 14.33 | A |
| ATOM | 325 | O   | CYS | A | 194 | 69.229 | 65.250 | 64.344 | 1.00 | 14.68 | A |
| ATOM | 326 | N   | ILE | A | 195 | 68.646 | 65.090 | 62.184 | 1.00 | 13.98 | A |
| ATOM | 327 | CA  | ILE | A | 195 | 67.286 | 64.701 | 62.520 | 1.00 | 14.07 | A |
| ATOM | 328 | CB  | ILE | A | 195 | 66.361 | 64.719 | 61.264 | 1.00 | 14.75 | A |
| ATOM | 329 | CG2 | ILE | A | 195 | 66.402 | 63.384 | 60.535 | 1.00 | 16.38 | A |
| ATOM | 330 | CG1 | ILE | A | 195 | 64.926 | 65.024 | 61.693 | 1.00 | 17.02 | A |
| ATOM | 331 | CD1 | ILE | A | 195 | 64.765 | 66.403 | 62.288 | 1.00 | 18.15 | A |
| ATOM | 332 | C   | ILE | A | 195 | 67.230 | 63.335 | 63.202 | 1.00 | 12.83 | A |
| ATOM | 333 | O   | ILE | A | 195 | 66.420 | 63.126 | 64.107 | 1.00 | 14.09 | A |
| ATOM | 334 | N   | MET | A | 196 | 68.098 | 62.407 | 62.801 | 1.00 | 13.45 | A |
| ATOM | 335 | CA  | MET | A | 196 | 68.081 | 61.091 | 63.431 | 1.00 | 11.19 | A |
| ATOM | 336 | CB  | MET | A | 196 | 68.973 | 60.106 | 62.669 | 1.00 | 12.34 | A |
| ATOM | 337 | CG  | MET | A | 196 | 68.335 | 59.567 | 61.381 | 1.00 | 12.99 | A |
| ATOM | 338 | SD  | MET | A | 196 | 66.881 | 58.516 | 61.676 | 1.00 | 14.52 | A |
| ATOM | 339 | CE  | MET | A | 196 | 67.676 | 56.931 | 62.036 | 1.00 | 15.62 | A |
| ATOM | 340 | C   | MET | A | 196 | 68.519 | 61.175 | 64.894 | 1.00 | 12.03 | A |
| ATOM | 341 | O   | MET | A | 196 | 67.968 | 60.485 | 65.749 | 1.00 | 14.36 | A |
| ATOM | 342 | N   | TYR | A | 197 | 69.511 | 62.011 | 65.179 | 1.00 | 12.60 | A |
| ATOM | 343 | CA  | TYR | A | 197 | 69.977 | 62.169 | 66.556 | 1.00 | 13.57 | A |
| ATOM | 344 | CB  | TYR | A | 197 | 71.221 | 63.060 | 66.590 | 1.00 | 15.15 | A |
| ATOM | 345 | CG  | TYR | A | 197 | 71.881 | 63.190 | 67.946 | 1.00 | 18.18 | A |
| ATOM | 346 | CD1 | TYR | A | 197 | 72.287 | 62.070 | 68.656 | 1.00 | 20.05 | A |
| ATOM | 347 | CE1 | TYR | A | 197 | 72.937 | 62.193 | 69.878 | 1.00 | 21.76 | A |
| ATOM | 348 | CD2 | TYR | A | 197 | 72.137 | 64.440 | 68.491 | 1.00 | 21.37 | A |
| ATOM | 349 | CE2 | TYR | A | 197 | 72.784 | 64.573 | 69.704 | 1.00 | 23.24 | A |
| ATOM | 350 | CZ  | TYR | A | 197 | 73.181 | 63.449 | 70.391 | 1.00 | 23.94 | A |
| ATOM | 351 | OH  | TYR | A | 197 | 73.832 | 63.589 | 71.597 | 1.00 | 26.71 | A |
| ATOM | 352 | C   | TYR | A | 197 | 68.852 | 62.785 | 67.389 | 1.00 | 13.72 | A |
| ATOM | 353 | O   | TYR | A | 197 | 68.581 | 62.343 | 68.504 | 1.00 | 16.14 | A |
| ATOM | 354 | N   | ALA | A | 198 | 68.194 | 63.801 | 66.835 | 1.00 | 14.59 | A |
| ATOM | 355 | CA  | ALA | A | 198 | 67.086 | 64.466 | 67.526 | 1.00 | 15.09 | A |
| ATOM | 356 | CB  | ALA | A | 198 | 66.577 | 65.638 | 66.687 | 1.00 | 14.63 | A |
| ATOM | 357 | C   | ALA | A | 198 | 65.947 | 63.484 | 67.802 | 1.00 | 15.02 | A |
| ATOM | 358 | O   | ALA | A | 198 | 65.384 | 63.454 | 68.905 | 1.00 | 16.63 | A |
| ATOM | 359 | N   | ILE | A | 199 | 65.604 | 62.684 | 66.798 | 1.00 | 14.17 | A |
| ATOM | 360 | CA  | ILE | A | 199 | 64.536 | 61.699 | 66.931 | 1.00 | 14.10 | A |
| ATOM | 361 | CB  | ILE | A | 199 | 64.274 | 60.980 | 65.585 | 1.00 | 15.41 | A |
| ATOM | 362 | CG2 | ILE | A | 199 | 63.413 | 59.741 | 65.808 | 1.00 | 15.83 | A |
| ATOM | 363 | CG1 | ILE | A | 199 | 63.595 | 61.939 | 64.606 | 1.00 | 14.55 | A |
| ATOM | 364 | CD1 | ILE | A | 199 | 63.509 | 61.406 | 63.190 | 1.00 | 16.04 | A |
| ATOM | 365 | C   | ILE | A | 199 | 64.886 | 60.660 | 67.985 | 1.00 | 14.55 | A |
| ATOM | 366 | O   | ILE | A | 199 | 64.077 | 60.351 | 68.856 | 1.00 | 14.78 | A |
| ATOM | 367 | N   | PHE | A | 200 | 66.100 | 60.127 | 67.914 | 1.00 | 15.53 | A |
| ATOM | 368 | CA  | PHE | A | 200 | 66.518 | 59.121 | 68.878 | 1.00 | 16.28 | A |
| ATOM | 369 | CB  | PHE | A | 200 | 67.865 | 58.523 | 68.475 | 1.00 | 16.28 | A |
| ATOM | 370 | CG  | PHE | A | 200 | 67.737 | 57.332 | 67.566 | 1.00 | 15.69 | A |
| ATOM | 371 | CD1 | PHE | A | 200 | 67.066 | 57.441 | 66.358 | 1.00 | 16.24 | A |
| ATOM | 372 | CD2 | PHE | A | 200 | 68.259 | 56.098 | 67.929 | 1.00 | 17.07 | A |
| ATOM | 373 | CE1 | PHE | A | 200 | 66.916 | 56.343 | 65.531 | 1.00 | 17.37 | A |
| ATOM | 374 | CE2 | PHE | A | 200 | 68.112 | 54.998 | 67.105 | 1.00 | 16.68 | A |
| ATOM | 375 | CZ  | PHE | A | 200 | 67.439 | 55.120 | 65.903 | 1.00 | 17.14 | A |
| ATOM | 376 | C   | PHE | A | 200 | 66.565 | 59.654 | 70.305 | 1.00 | 17.38 | A |
| ATOM | 377 | O   | PHE | A | 200 | 66.274 | 58.918 | 71.249 | 1.00 | 19.01 | A |
| ATOM | 378 | N   | GLN | A | 201 | 66.927 | 60.923 | 70.469 | 1.00 | 17.67 | A |
| ATOM | 379 | CA  | GLN | A | 201 | 66.955 | 61.512 | 71.805 | 1.00 | 18.69 | A |
| ATOM | 380 | CB  | GLN | A | 201 | 67.711 | 62.845 | 71.810 | 1.00 | 19.36 | A |

TABLE 1-continued

| ATOM | 381 | CG | GLN | A | 201 | 69.223 | 62.701 | 71.788 | 1.00 | 22.43 | A |
| --- | --- | --- | --- | --- | --- | --- | --- | --- | --- | --- | --- |
| ATOM | 382 | CD | GLN | A | 201 | 69.925 | 63.945 | 72.299 | 1.00 | 27.24 | A |
| ATOM | 383 | OE1 | GLN | A | 201 | 71.139 | 63.946 | 72.512 | 1.00 | 30.40 | A |
| ATOM | 384 | NE2 | GLN | A | 201 | 69.162 | 65.014 | 72.501 | 1.00 | 28.68 | A |
| ATOM | 385 | C | GLN | A | 201 | 65.521 | 61.733 | 72.282 | 1.00 | 18.52 | A |
| ATOM | 386 | O | GLN | A | 201 | 65.193 | 61.460 | 73.433 | 1.00 | 19.29 | A |
| ATOM | 387 | N | GLU | A | 202 | 64.670 | 62.211 | 71.378 | 1.00 | 18.30 | A |
| ATOM | 388 | CA | GLU | A | 202 | 63.263 | 62.473 | 71.680 | 1.00 | 18.52 | A |
| ATOM | 389 | CB | GLU | A | 202 | 62.572 | 63.031 | 70.432 | 1.00 | 19.84 | A |
| ATOM | 390 | CG | GLU | A | 202 | 61.058 | 63.185 | 70.517 | 1.00 | 22.00 | A |
| ATOM | 391 | CD | GLU | A | 202 | 60.620 | 64.238 | 71.514 | 1.00 | 25.77 | A |
| ATOM | 392 | OE1 | GLU | A | 202 | 61.382 | 65.203 | 71.735 | 1.00 | 27.93 | A |
| ATOM | 393 | OE2 | GLU | A | 202 | 59.502 | 64.107 | 72.063 | 1.00 | 27.98 | A |
| ATOM | 394 | C | GLU | A | 202 | 62.531 | 61.219 | 72.155 | 1.00 | 18.79 | A |
| ATOM | 395 | O | GLU | A | 202 | 61.699 | 61.285 | 73.061 | 1.00 | 20.57 | A |
| ATOM | 396 | N | ARG | A | 203 | 62.850 | 60.080 | 71.546 | 1.00 | 17.76 | A |
| ATOM | 397 | CA | ARG | A | 203 | 62.215 | 58.810 | 71.888 | 1.00 | 17.84 | A |
| ATOM | 398 | CB | ARG | A | 203 | 61.961 | 57.990 | 70.619 | 1.00 | 17.24 | A |
| ATOM | 399 | CG | ARG | A | 203 | 60.875 | 58.568 | 69.718 | 1.00 | 16.56 | A |
| ATOM | 400 | CD | ARG | A | 203 | 60.683 | 57.741 | 68.456 | 1.00 | 16.79 | A |
| ATOM | 401 | NE | ARG | A | 203 | 59.524 | 58.200 | 67.691 | 1.00 | 15.23 | A |
| ATOM | 402 | CZ | ARG | A | 203 | 58.259 | 57.935 | 68.009 | 1.00 | 17.65 | A |
| ATOM | 403 | NH1 | ARG | A | 203 | 57.974 | 57.201 | 69.078 | 1.00 | 16.96 | A |
| ATOM | 404 | NH2 | ARG | A | 203 | 57.275 | 58.417 | 67.262 | 1.00 | 16.00 | A |
| ATOM | 405 | C | ARG | A | 203 | 63.019 | 57.971 | 72.875 | 1.00 | 17.96 | A |
| ATOM | 406 | O | ARG | A | 203 | 62.615 | 56.861 | 73.218 | 1.00 | 18.80 | A |
| ATOM | 407 | N | ASP | A | 204 | 64.155 | 58.499 | 73.319 | 1.00 | 18.40 | A |
| ATOM | 408 | CA | ASP | A | 204 | 65.011 | 57.792 | 74.270 | 1.00 | 18.83 | A |
| ATOM | 409 | CB | ASP | A | 204 | 64.275 | 57.597 | 75.599 | 1.00 | 21.85 | A |
| ATOM | 410 | CG | ASP | A | 204 | 64.028 | 58.903 | 76.325 | 1.00 | 26.06 | A |
| ATOM | 411 | OD1 | ASP | A | 204 | 65.015 | 59.614 | 76.615 | 1.00 | 28.65 | A |
| ATOM | 412 | OD2 | ASP | A | 204 | 62.851 | 59.218 | 76.610 | 1.00 | 29.13 | A |
| ATOM | 413 | C | ASP | A | 204 | 65.474 | 56.437 | 73.748 | 1.00 | 17.57 | A |
| ATOM | 414 | O | ASP | A | 204 | 65.700 | 55.507 | 74.521 | 1.00 | 18.95 | A |
| ATOM | 415 | N | LEU | A | 205 | 65.628 | 56.323 | 72.433 | 1.00 | 16.01 | A |
| ATOM | 416 | CA | LEU | A | 205 | 66.060 | 55.064 | 71.843 | 1.00 | 16.61 | A |
| ATOM | 417 | CB | LEU | A | 205 | 65.874 | 55.103 | 70.324 | 1.00 | 17.33 | A |
| ATOM | 418 | CG | LEU | A | 205 | 64.421 | 55.006 | 69.843 | 1.00 | 19.09 | A |
| ATOM | 419 | CD1 | LEU | A | 205 | 64.346 | 55.298 | 68.346 | 1.00 | 17.19 | A |
| ATOM | 420 | CD2 | LEU | A | 205 | 63.877 | 53.617 | 70.141 | 1.00 | 18.49 | A |
| ATOM | 421 | C | LEU | A | 205 | 67.506 | 54.723 | 72.188 | 1.00 | 16.22 | A |
| ATOM | 422 | O | LEU | A | 205 | 67.863 | 53.548 | 72.287 | 1.00 | 17.42 | A |
| ATOM | 423 | N | LEU | A | 206 | 68.338 | 55.745 | 72.373 | 1.00 | 17.08 | A |
| ATOM | 424 | CA | LEU | A | 206 | 69.739 | 55.510 | 72.717 | 1.00 | 17.81 | A |
| ATOM | 425 | CB | LEU | A | 206 | 70.525 | 56.826 | 72.711 | 1.00 | 18.79 | A |
| ATOM | 426 | CG | LEU | A | 206 | 70.599 | 57.603 | 71.394 | 1.00 | 19.14 | A |
| ATOM | 427 | CD1 | LEU | A | 206 | 71.435 | 58.856 | 71.591 | 1.00 | 20.05 | A |
| ATOM | 428 | CD2 | LEU | A | 206 | 71.207 | 56.726 | 70.308 | 1.00 | 20.42 | A |
| ATOM | 429 | C | LEU | A | 206 | 69.825 | 54.865 | 74.098 | 1.00 | 18.22 | A |
| ATOM | 430 | O | LEU | A | 206 | 70.646 | 53.980 | 74.331 | 1.00 | 18.94 | A |
| ATOM | 431 | N | LYS | A | 207 | 68.966 | 55.306 | 75.012 | 1.00 | 18.45 | A |
| ATOM | 432 | CA | LYS | A | 207 | 68.953 | 54.757 | 76.364 | 1.00 | 18.71 | A |
| ATOM | 433 | CB | LYS | A | 207 | 68.138 | 55.653 | 77.296 | 1.00 | 19.50 | A |
| ATOM | 434 | CG | LYS | A | 207 | 68.716 | 57.040 | 77.483 | 1.00 | 22.32 | A |
| ATOM | 435 | CD | LYS | A | 207 | 67.788 | 57.909 | 78.313 | 1.00 | 25.07 | A |
| ATOM | 436 | CE | LYS | A | 207 | 67.516 | 57.281 | 79.671 | 1.00 | 25.35 | A |
| ATOM | 437 | NZ | LYS | A | 207 | 68.773 | 57.077 | 80.444 | 1.00 | 28.80 | A |
| ATOM | 438 | C | LYS | A | 207 | 68.360 | 53.355 | 76.382 | 1.00 | 18.50 | A |
| ATOM | 439 | O | LYS | A | 207 | 68.910 | 52.444 | 76.999 | 1.00 | 20.56 | A |
| ATOM | 440 | N | THR | A | 208 | 67.234 | 53.190 | 75.697 | 1.00 | 17.44 | A |
| ATOM | 441 | CA | THR | A | 208 | 66.542 | 51.911 | 75.641 | 1.00 | 17.30 | A |
| ATOM | 442 | CB | THR | A | 208 | 65.281 | 52.018 | 74.767 | 1.00 | 18.22 | A |
| ATOM | 443 | OG1 | THR | A | 208 | 64.394 | 52.993 | 75.329 | 1.00 | 21.21 | A |
| ATOM | 444 | CG2 | THR | A | 208 | 64.575 | 50.677 | 74.688 | 1.00 | 19.32 | A |
| ATOM | 445 | C | THR | A | 208 | 67.398 | 50.770 | 75.111 | 1.00 | 17.28 | A |
| ATOM | 446 | O | THR | A | 208 | 67.307 | 49.635 | 75.588 | 1.00 | 18.99 | A |
| ATOM | 447 | N | PHE | A | 209 | 68.236 | 51.069 | 74.127 | 1.00 | 16.89 | A |
| ATOM | 448 | CA | PHE | A | 209 | 69.074 | 50.044 | 73.527 | 1.00 | 17.34 | A |
| ATOM | 449 | CB | PHE | A | 209 | 68.799 | 50.001 | 72.020 | 1.00 | 15.74 | A |
| ATOM | 450 | CG | PHE | A | 209 | 67.400 | 49.568 | 71.686 | 1.00 | 15.73 | A |
| ATOM | 451 | CD1 | PHE | A | 209 | 67.016 | 48.246 | 71.851 | 1.00 | 16.26 | A |
| ATOM | 452 | CD2 | PHE | A | 209 | 66.456 | 50.488 | 71.253 | 1.00 | 14.45 | A |
| ATOM | 453 | CE1 | PHE | A | 209 | 65.715 | 47.845 | 71.592 | 1.00 | 16.69 | A |
| ATOM | 454 | CE2 | PHE | A | 209 | 65.150 | 50.095 | 70.991 | 1.00 | 15.08 | A |
| ATOM | 455 | CZ | PHE | A | 209 | 64.779 | 48.773 | 71.161 | 1.00 | 16.27 | A |
| ATOM | 456 | C | PHE | A | 209 | 70.563 | 50.227 | 73.811 | 1.00 | 17.36 | A |
| ATOM | 457 | O | PHE | A | 209 | 71.407 | 49.653 | 73.123 | 1.00 | 18.33 | A |
| ATOM | 458 | N | ARG | A | 210 | 70.873 | 51.018 | 74.836 | 1.00 | 17.44 | A |
| ATOM | 459 | CA | ARG | A | 210 | 72.255 | 51.279 | 75.234 | 1.00 | 17.78 | A |

TABLE 1-continued

| | | | | | | | | | | |
|---|---|---|---|---|---|---|---|---|---|---|
| ATOM | 460 | CB | ARG | A | 210 | 72.816 | 50.085 | 76.015 | 1.00 | 19.77 | A |
| ATOM | 461 | CG | ARG | A | 210 | 72.240 | 49.913 | 77.422 | 1.00 | 21.38 | A |
| ATOM | 462 | CD | ARG | A | 210 | 72.813 | 50.926 | 78.405 | 1.00 | 21.06 | A |
| ATOM | 463 | NE | ARG | A | 210 | 72.315 | 50.709 | 79.763 | 1.00 | 22.04 | A |
| ATOM | 464 | CZ | ARG | A | 210 | 72.738 | 51.373 | 80.835 | 1.00 | 21.09 | A |
| ATOM | 465 | NH1 | ARG | A | 210 | 73.676 | 52.306 | 80.720 | 1.00 | 20.83 | A |
| ATOM | 466 | NH2 | ARG | A | 210 | 72.222 | 51.105 | 82.028 | 1.00 | 23.00 | A |
| ATOM | 467 | C | ARG | A | 210 | 73.171 | 51.592 | 74.057 | 1.00 | 17.17 | A |
| ATOM | 468 | O | ARG | A | 210 | 74.240 | 50.995 | 73.904 | 1.00 | 17.95 | A |
| ATOM | 469 | N | ILE | A | 211 | 72.751 | 52.533 | 73.223 | 1.00 | 16.87 | A |
| ATOM | 470 | CA | ILE | A | 211 | 73.558 | 52.924 | 72.078 | 1.00 | 15.09 | A |
| ATOM | 471 | CB | ILE | A | 211 | 72.683 | 53.313 | 70.867 | 1.00 | 16.27 | A |
| ATOM | 472 | CG2 | ILE | A | 211 | 73.570 | 53.588 | 69.663 | 1.00 | 16.35 | A |
| ATOM | 473 | CG1 | ILE | A | 211 | 71.685 | 52.201 | 70.560 | 1.00 | 15.77 | A |
| ATOM | 474 | CD1 | ILE | A | 211 | 70.651 | 52.584 | 69.501 | 1.00 | 13.41 | A |
| ATOM | 475 | C | ILE | A | 211 | 74.350 | 54.148 | 72.488 | 1.00 | 16.35 | A |
| ATOM | 476 | O | ILE | A | 211 | 73.769 | 55.157 | 72.885 | 1.00 | 17.22 | A |
| ATOM | 477 | N | SER | A | 212 | 75.673 | 54.063 | 72.413 | 1.00 | 15.50 | A |
| ATOM | 478 | CA | SER | A | 212 | 76.496 | 55.205 | 72.769 | 1.00 | 15.44 | A |
| ATOM | 479 | CB | SER | A | 212 | 77.963 | 54.790 | 72.866 | 1.00 | 17.53 | A |
| ATOM | 480 | OG | SER | A | 212 | 78.147 | 53.929 | 73.976 | 1.00 | 17.99 | A |
| ATOM | 481 | C | SER | A | 212 | 76.315 | 56.287 | 71.710 | 1.00 | 16.65 | A |
| ATOM | 482 | O | SER | A | 212 | 76.189 | 55.992 | 70.520 | 1.00 | 15.73 | A |
| ATOM | 483 | N | SER | A | 213 | 76.287 | 57.539 | 72.145 | 1.00 | 17.02 | A |
| ATOM | 484 | CA | SER | A | 213 | 76.105 | 58.652 | 71.226 | 1.00 | 18.62 | A |
| ATOM | 485 | CB | SER | A | 213 | 76.047 | 59.971 | 71.997 | 1.00 | 20.29 | A |
| ATOM | 486 | OG | SER | A | 213 | 74.867 | 60.041 | 72.778 | 1.00 | 26.41 | A |
| ATOM | 487 | C | SER | A | 213 | 77.191 | 58.729 | 70.161 | 1.00 | 17.78 | A |
| ATOM | 488 | O | SER | A | 213 | 76.901 | 59.044 | 69.002 | 1.00 | 18.48 | A |
| ATOM | 489 | N | ASP | A | 214 | 78.438 | 58.453 | 70.534 | 1.00 | 17.39 | A |
| ATOM | 490 | CA | ASP | A | 214 | 79.500 | 58.520 | 69.544 | 1.00 | 16.63 | A |
| ATOM | 491 | CB | ASP | A | 214 | 80.897 | 58.424 | 70.190 | 1.00 | 17.62 | A |
| ATOM | 492 | CG | ASP | A | 214 | 81.013 | 57.330 | 71.239 | 1.00 | 18.25 | A |
| ATOM | 493 | OD1 | ASP | A | 214 | 80.167 | 56.413 | 71.280 | 1.00 | 20.25 | A |
| ATOM | 494 | OD2 | ASP | A | 214 | 81.990 | 57.390 | 72.022 | 1.00 | 21.51 | A |
| ATOM | 495 | C | ASP | A | 214 | 79.320 | 57.455 | 68.470 | 1.00 | 15.62 | A |
| ATOM | 496 | O | ASP | A | 214 | 79.527 | 57.725 | 67.288 | 1.00 | 16.48 | A |
| ATOM | 497 | N | THR | A | 215 | 78.923 | 56.253 | 68.876 | 1.00 | 14.14 | A |
| ATOM | 498 | CA | THR | A | 215 | 78.694 | 55.165 | 67.931 | 1.00 | 14.08 | A |
| ATOM | 499 | CB | THR | A | 215 | 78.267 | 53.882 | 68.662 | 1.00 | 16.27 | A |
| ATOM | 500 | OG1 | THR | A | 215 | 79.252 | 53.551 | 69.650 | 1.00 | 17.56 | A |
| ATOM | 501 | CG2 | THR | A | 215 | 78.129 | 52.729 | 67.676 | 1.00 | 16.78 | A |
| ATOM | 502 | C | THR | A | 215 | 77.575 | 55.566 | 66.978 | 1.00 | 12.71 | A |
| ATOM | 503 | O | THR | A | 215 | 77.692 | 55.430 | 65.753 | 1.00 | 13.36 | A |
| ATOM | 504 | N | PHE | A | 216 | 76.485 | 56.068 | 67.548 | 1.00 | 12.54 | A |
| ATOM | 505 | CA | PHE | A | 216 | 75.334 | 56.474 | 66.750 | 1.00 | 11.93 | A |
| ATOM | 506 | CB | PHE | A | 216 | 74.229 | 57.026 | 67.657 | 1.00 | 11.50 | A |
| ATOM | 507 | CG | PHE | A | 216 | 72.953 | 57.335 | 66.928 | 1.00 | 13.94 | A |
| ATOM | 508 | CD1 | PHE | A | 216 | 72.127 | 56.314 | 66.500 | 1.00 | 15.73 | A |
| ATOM | 509 | CD2 | PHE | A | 216 | 72.596 | 58.640 | 66.654 | 1.00 | 14.80 | A |
| ATOM | 510 | CE1 | PHE | A | 216 | 70.958 | 56.590 | 65.803 | 1.00 | 19.14 | A |
| ATOM | 511 | CE2 | PHE | A | 216 | 71.430 | 58.924 | 65.959 | 1.00 | 17.38 | A |
| ATOM | 512 | CZ | PHE | A | 216 | 70.613 | 57.896 | 65.535 | 1.00 | 15.37 | A |
| ATOM | 513 | C | PHE | A | 216 | 75.702 | 57.529 | 65.717 | 1.00 | 11.99 | A |
| ATOM | 514 | O | PHE | A | 216 | 75.375 | 57.398 | 64.536 | 1.00 | 12.76 | A |
| ATOM | 515 | N | ILE | A | 217 | 76.388 | 58.577 | 66.159 | 1.00 | 13.73 | A |
| ATOM | 516 | CA | ILE | A | 217 | 76.769 | 59.645 | 65.251 | 1.00 | 14.45 | A |
| ATOM | 517 | CB | ILE | A | 217 | 77.380 | 60.837 | 66.017 | 1.00 | 16.01 | A |
| ATOM | 518 | CG2 | ILE | A | 217 | 77.907 | 61.877 | 65.036 | 1.00 | 17.64 | A |
| ATOM | 519 | CG1 | ILE | A | 217 | 76.312 | 61.464 | 66.917 | 1.00 | 17.42 | A |
| ATOM | 520 | CD1 | ILE | A | 217 | 76.810 | 62.595 | 67.780 | 1.00 | 20.00 | A |
| ATOM | 521 | C | ILE | A | 217 | 77.735 | 59.153 | 64.179 | 1.00 | 12.59 | A |
| ATOM | 522 | O | ILE | A | 217 | 77.615 | 59.529 | 63.014 | 1.00 | 14.27 | A |
| ATOM | 523 | N | THR | A | 218 | 78.685 | 58.302 | 64.556 | 1.00 | 12.06 | A |
| ATOM | 524 | CA | THR | A | 218 | 79.627 | 57.791 | 63.569 | 1.00 | 11.98 | A |
| ATOM | 525 | CB | THR | A | 218 | 80.711 | 56.909 | 64.221 | 1.00 | 12.77 | A |
| ATOM | 526 | OG1 | THR | A | 218 | 81.393 | 57.666 | 65.232 | 1.00 | 15.65 | A |
| ATOM | 527 | CG2 | THR | A | 218 | 81.725 | 56.456 | 63.184 | 1.00 | 11.72 | A |
| ATOM | 528 | C | THR | A | 218 | 78.875 | 56.986 | 62.503 | 1.00 | 11.22 | A |
| ATOM | 529 | O | THR | A | 218 | 79.144 | 57.129 | 61.315 | 1.00 | 12.99 | A |
| ATOM | 530 | N | TYR | A | 219 | 77.925 | 56.154 | 62.918 | 1.00 | 11.49 | A |
| ATOM | 531 | CA | TYR | A | 219 | 77.168 | 55.379 | 61.936 | 1.00 | 10.29 | A |
| ATOM | 532 | CB | TYR | A | 219 | 76.205 | 54.382 | 62.593 | 1.00 | 11.04 | A |
| ATOM | 533 | CG | TYR | A | 219 | 75.303 | 53.713 | 61.568 | 1.00 | 12.11 | A |
| ATOM | 534 | CD1 | TYR | A | 219 | 75.751 | 52.638 | 60.819 | 1.00 | 12.70 | A |
| ATOM | 535 | CE1 | TYR | A | 219 | 74.979 | 52.080 | 59.820 | 1.00 | 10.61 | A |
| ATOM | 536 | CD2 | TYR | A | 219 | 74.040 | 54.216 | 61.291 | 1.00 | 12.48 | A |
| ATOM | 537 | CE2 | TYR | A | 219 | 73.260 | 53.670 | 60.287 | 1.00 | 13.01 | A |
| ATOM | 538 | CZ | TYR | A | 219 | 73.738 | 52.602 | 59.557 | 1.00 | 10.75 | A |

TABLE 1-continued

| | | | | | | | | | | |
|---|---|---|---|---|---|---|---|---|---|---|
| ATOM | 539 | OH | TYR | A | 219 | 72.981 | 52.054 | 58.548 | 1.00 | 13.24 | A |
| ATOM | 540 | C | TYR | A | 219 | 76.350 | 56.294 | 61.038 | 1.00 | 10.64 | A |
| ATOM | 541 | O | TYR | A | 219 | 76.395 | 56.167 | 59.817 | 1.00 | 11.75 | A |
| ATOM | 542 | N | MET | A | 220 | 75.608 | 57.218 | 61.643 | 1.00 | 10.51 | A |
| ATOM | 543 | CA | MET | A | 220 | 74.766 | 58.118 | 60.859 | 1.00 | 11.01 | A |
| ATOM | 544 | CB | MET | A | 220 | 73.922 | 59.004 | 61.778 | 1.00 | 12.90 | A |
| ATOM | 545 | CG | MET | A | 220 | 72.818 | 58.250 | 62.513 | 1.00 | 14.37 | A |
| ATOM | 546 | SD | MET | A | 220 | 71.716 | 57.345 | 61.396 | 1.00 | 14.85 | A |
| ATOM | 547 | CE | MET | A | 220 | 71.340 | 58.626 | 60.167 | 1.00 | 16.89 | A |
| ATOM | 548 | C | MET | A | 220 | 75.550 | 58.978 | 59.882 | 1.00 | 11.47 | A |
| ATOM | 549 | O | MET | A | 220 | 75.116 | 59.177 | 58.746 | 1.00 | 12.12 | A |
| ATOM | 550 | N | MET | A | 221 | 76.704 | 59.485 | 60.312 | 1.00 | 12.71 | A |
| ATOM | 551 | CA | MET | A | 221 | 77.538 | 60.307 | 59.441 | 1.00 | 12.31 | A |
| ATOM | 552 | CB | MET | A | 221 | 78.717 | 60.891 | 60.229 | 1.00 | 11.59 | A |
| ATOM | 553 | CG | MET | A | 221 | 78.327 | 62.007 | 61.177 | 1.00 | 14.51 | A |
| ATOM | 554 | SD | MET | A | 221 | 77.825 | 63.499 | 60.295 | 1.00 | 18.63 | A |
| ATOM | 555 | CE | MET | A | 221 | 77.867 | 64.734 | 61.640 | 1.00 | 19.55 | A |
| ATOM | 556 | C | MET | A | 221 | 78.058 | 59.463 | 58.285 | 1.00 | 12.18 | A |
| ATOM | 557 | O | MET | A | 221 | 78.195 | 59.950 | 57.161 | 1.00 | 13.98 | A |
| ATOM | 558 | N | THR | A | 222 | 78.345 | 58.196 | 58.567 | 1.00 | 11.39 | A |
| ATOM | 559 | CA | THR | A | 222 | 78.845 | 57.280 | 57.542 | 1.00 | 11.46 | A |
| ATOM | 560 | CB | THR | A | 222 | 79.353 | 55.984 | 58.195 | 1.00 | 11.09 | A |
| ATOM | 561 | OG1 | THR | A | 222 | 80.460 | 56.301 | 59.050 | 1.00 | 12.56 | A |
| ATOM | 562 | CG2 | THR | A | 222 | 79.794 | 54.979 | 57.142 | 1.00 | 13.19 | A |
| ATOM | 563 | C | THR | A | 222 | 77.721 | 56.976 | 56.553 | 1.00 | 11.41 | A |
| ATOM | 564 | O | THR | A | 222 | 77.924 | 56.992 | 55.338 | 1.00 | 12.33 | A |
| ATOM | 565 | N | LEU | A | 223 | 76.529 | 56.730 | 57.083 | 1.00 | 12.04 | A |
| ATOM | 566 | CA | LEU | A | 223 | 75.361 | 56.438 | 56.255 | 1.00 | 11.51 | A |
| ATOM | 567 | CB | LEU | A | 223 | 74.159 | 56.111 | 57.147 | 1.00 | 11.24 | A |
| ATOM | 568 | CG | LEU | A | 223 | 72.842 | 55.825 | 56.417 | 1.00 | 14.00 | A |
| ATOM | 569 | CD1 | LEU | A | 223 | 72.962 | 54.525 | 55.643 | 1.00 | 13.15 | A |
| ATOM | 570 | CD2 | LEU | A | 223 | 71.706 | 55.725 | 57.429 | 1.00 | 14.69 | A |
| ATOM | 571 | C | LEU | A | 223 | 75.028 | 57.647 | 55.385 | 1.00 | 11.28 | A |
| ATOM | 572 | O | LEU | A | 223 | 74.789 | 57.514 | 54.183 | 1.00 | 11.76 | A |
| ATOM | 573 | N | GLU | A | 224 | 75.016 | 58.831 | 55.993 | 1.00 | 12.39 | A |
| ATOM | 574 | CA | GLU | A | 224 | 74.692 | 60.046 | 55.252 | 1.00 | 13.02 | A |
| ATOM | 575 | CB | GLU | A | 224 | 74.654 | 61.253 | 56.197 | 1.00 | 16.60 | A |
| ATOM | 576 | CG | GLU | A | 224 | 74.243 | 62.561 | 55.527 | 1.00 | 19.20 | A |
| ATOM | 577 | CD | GLU | A | 224 | 73.410 | 63.458 | 56.431 | 1.00 | 19.14 | A |
| ATOM | 578 | OE1 | GLU | A | 224 | 73.662 | 63.486 | 57.654 | 1.00 | 19.02 | A |
| ATOM | 579 | OE2 | GLU | A | 224 | 72.508 | 64.153 | 55.915 | 1.00 | 17.18 | A |
| ATOM | 580 | C | GLU | A | 224 | 75.677 | 60.281 | 54.108 | 1.00 | 12.19 | A |
| ATOM | 581 | O | GLU | A | 224 | 75.289 | 60.755 | 53.035 | 1.00 | 12.42 | A |
| ATOM | 582 | N | ASP | A | 225 | 76.941 | 59.931 | 54.327 | 1.00 | 11.04 | A |
| ATOM | 583 | CA | ASP | A | 225 | 77.967 | 60.090 | 53.302 | 1.00 | 14.95 | A |
| ATOM | 584 | CB | ASP | A | 225 | 79.363 | 59.868 | 53.884 | 1.00 | 19.81 | A |
| ATOM | 585 | CG | ASP | A | 225 | 80.041 | 61.159 | 54.273 | 1.00 | 25.16 | A |
| ATOM | 586 | OD1 | ASP | A | 225 | 79.746 | 62.198 | 53.643 | 1.00 | 28.81 | A |
| ATOM | 587 | OD2 | ASP | A | 225 | 80.886 | 61.135 | 55.192 | 1.00 | 25.73 | A |
| ATOM | 588 | C | ASP | A | 225 | 77.779 | 59.137 | 52.133 | 1.00 | 13.03 | A |
| ATOM | 589 | O | ASP | A | 225 | 78.395 | 59.310 | 51.081 | 1.00 | 16.08 | A |
| ATOM | 590 | N | HIS | A | 226 | 76.947 | 58.118 | 52.316 | 1.00 | 12.65 | A |
| ATOM | 591 | CA | HIS | A | 226 | 76.710 | 57.165 | 51.250 | 1.00 | 12.26 | A |
| ATOM | 592 | CB | HIS | A | 226 | 76.582 | 55.748 | 51.807 | 1.00 | 14.14 | A |
| ATOM | 593 | CG | HIS | A | 226 | 77.902 | 55.110 | 52.111 | 1.00 | 16.55 | A |
| ATOM | 594 | CD2 | HIS | A | 226 | 78.603 | 54.155 | 51.455 | 1.00 | 16.59 | A |
| ATOM | 595 | ND1 | HIS | A | 226 | 78.686 | 55.496 | 53.177 | 1.00 | 17.29 | A |
| ATOM | 596 | CE1 | HIS | A | 226 | 79.815 | 54.808 | 53.163 | 1.00 | 18.97 | A |
| ATOM | 597 | NE2 | HIS | A | 226 | 79.790 | 53.988 | 52.128 | 1.00 | 17.99 | A |
| ATOM | 598 | C | HIS | A | 226 | 75.521 | 57.536 | 50.380 | 1.00 | 12.17 | A |
| ATOM | 599 | O | HIS | A | 226 | 75.175 | 56.811 | 49.453 | 1.00 | 12.03 | A |
| ATOM | 600 | N | TYR | A | 227 | 74.885 | 58.660 | 50.701 | 1.00 | 11.39 | A |
| ATOM | 601 | CA | TYR | A | 227 | 73.812 | 59.172 | 49.861 | 1.00 | 11.26 | A |
| ATOM | 602 | CB | TYR | A | 227 | 72.777 | 59.980 | 50.656 | 1.00 | 12.86 | A |
| ATOM | 603 | CG | TYR | A | 227 | 71.664 | 59.146 | 51.251 | 1.00 | 9.91 | A |
| ATOM | 604 | CD1 | TYR | A | 227 | 71.803 | 58.540 | 52.494 | 1.00 | 10.75 | A |
| ATOM | 605 | CE1 | TYR | A | 227 | 70.802 | 57.748 | 53.016 | 1.00 | 8.76 | A |
| ATOM | 606 | CD2 | TYR | A | 227 | 70.482 | 58.930 | 50.549 | 1.00 | 10.92 | A |
| ATOM | 607 | CE2 | TYR | A | 227 | 69.477 | 58.133 | 51.060 | 1.00 | 9.51 | A |
| ATOM | 608 | CZ | TYR | A | 227 | 69.641 | 57.543 | 52.297 | 1.00 | 7.54 | A |
| ATOM | 609 | OH | TYR | A | 227 | 68.643 | 56.746 | 52.805 | 1.00 | 9.94 | A |
| ATOM | 610 | C | TYR | A | 227 | 74.594 | 60.104 | 48.939 | 1.00 | 12.03 | A |
| ATOM | 611 | O | TYR | A | 227 | 75.581 | 60.707 | 49.358 | 1.00 | 15.36 | A |
| ATOM | 612 | N | HIS | A | 228 | 74.174 | 60.205 | 47.685 | 1.00 | 13.80 | A |
| ATOM | 613 | CA | HIS | A | 228 | 74.853 | 61.061 | 46.721 | 1.00 | 15.41 | A |
| ATOM | 614 | CB | HIS | A | 228 | 74.696 | 60.473 | 45.321 | 1.00 | 16.36 | A |
| ATOM | 615 | CG | HIS | A | 228 | 75.417 | 59.178 | 45.132 | 1.00 | 20.91 | A |
| ATOM | 616 | CD2 | HIS | A | 228 | 74.962 | 57.904 | 45.072 | 1.00 | 22.59 | A |
| ATOM | 617 | ND1 | HIS | A | 228 | 76.788 | 59.102 | 45.002 | 1.00 | 24.71 | A |

TABLE 1-continued

| | | | | | | | | | | |
|---|---|---|---|---|---|---|---|---|---|---|
| ATOM | 618 | CE1 | HIS | A | 228 | 77.146 | 57.837 | 44.869 | 1.00 | 24.66 | A |
| ATOM | 619 | NE2 | HIS | A | 228 | 76.056 | 57.090 | 44.908 | 1.00 | 24.98 | A |
| ATOM | 620 | C | HIS | A | 228 | 74.288 | 62.476 | 46.753 | 1.00 | 16.73 | A |
| ATOM | 621 | O | HIS | A | 228 | 73.129 | 62.700 | 46.410 | 1.00 | 18.52 | A |
| ATOM | 622 | N | SER | A | 229 | 75.111 | 63.441 | 47.141 | 1.00 | 18.38 | A |
| ATOM | 623 | CA | SER | A | 229 | 74.640 | 64.818 | 47.217 | 1.00 | 19.25 | A |
| ATOM | 624 | CB | SER | A | 229 | 75.646 | 65.677 | 47.984 | 1.00 | 21.64 | A |
| ATOM | 625 | OG | SER | A | 229 | 76.889 | 65.726 | 47.311 | 1.00 | 24.89 | A |
| ATOM | 626 | C | SER | A | 229 | 74.361 | 65.448 | 45.855 | 1.00 | 18.22 | A |
| ATOM | 627 | O | SER | A | 229 | 73.638 | 66.440 | 45.772 | 1.00 | 20.39 | A |
| ATOM | 628 | N | ASP | A | 230 | 74.918 | 64.869 | 44.793 | 1.00 | 17.49 | A |
| ATOM | 629 | CA | ASP | A | 230 | 74.721 | 65.392 | 43.443 | 1.00 | 18.82 | A |
| ATOM | 630 | CB | ASP | A | 230 | 75.918 | 65.044 | 42.555 | 1.00 | 22.61 | A |
| ATOM | 631 | CG | ASP | A | 230 | 76.154 | 63.552 | 42.462 | 1.00 | 24.85 | A |
| ATOM | 632 | OD1 | ASP | A | 230 | 76.454 | 62.934 | 43.506 | 1.00 | 28.07 | A |
| ATOM | 633 | OD2 | ASP | A | 230 | 76.039 | 62.998 | 41.348 | 1.00 | 30.23 | A |
| ATOM | 634 | C | ASP | A | 230 | 73.438 | 64.888 | 42.787 | 1.00 | 18.02 | A |
| ATOM | 635 | O | ASP | A | 230 | 73.090 | 65.314 | 41.683 | 1.00 | 19.13 | A |
| ATOM | 636 | N | VAL | A | 231 | 72.742 | 63.970 | 43.451 | 1.00 | 16.44 | A |
| ATOM | 637 | CA | VAL | A | 231 | 71.474 | 63.471 | 42.922 | 1.00 | 15.58 | A |
| ATOM | 638 | CB | VAL | A | 231 | 71.159 | 62.059 | 43.467 | 1.00 | 16.63 | A |
| ATOM | 639 | CG1 | VAL | A | 231 | 69.745 | 61.646 | 43.094 | 1.00 | 18.43 | A |
| ATOM | 640 | CG2 | VAL | A | 231 | 72.158 | 61.062 | 42.890 | 1.00 | 17.55 | A |
| ATOM | 641 | C | VAL | A | 231 | 70.453 | 64.495 | 43.413 | 1.00 | 14.08 | A |
| ATOM | 642 | O | VAL | A | 231 | 70.442 | 64.845 | 44.586 | 1.00 | 15.21 | A |
| ATOM | 643 | N | ALA | A | 232 | 69.601 | 64.978 | 42.517 | 1.00 | 13.51 | A |
| ATOM | 644 | CA | ALA | A | 232 | 68.643 | 66.020 | 42.871 | 1.00 | 12.81 | A |
| ATOM | 645 | CB | ALA | A | 232 | 67.901 | 66.476 | 41.619 | 1.00 | 14.69 | A |
| ATOM | 646 | C | ALA | A | 232 | 67.637 | 65.737 | 43.974 | 1.00 | 11.78 | A |
| ATOM | 647 | O | ALA | A | 232 | 67.407 | 66.584 | 44.839 | 1.00 | 14.83 | A |
| ATOM | 648 | N | TYR | A | 233 | 67.024 | 64.565 | 43.947 | 1.00 | 10.72 | A |
| ATOM | 649 | CA | TYR | A | 233 | 66.010 | 64.254 | 44.946 | 1.00 | 8.52 | A |
| ATOM | 650 | CB | TYR | A | 233 | 64.720 | 63.832 | 44.241 | 1.00 | 10.59 | A |
| ATOM | 651 | CG | TYR | A | 233 | 63.578 | 63.475 | 45.165 | 1.00 | 11.48 | A |
| ATOM | 652 | CD1 | TYR | A | 233 | 62.720 | 64.452 | 45.656 | 1.00 | 13.78 | A |
| ATOM | 653 | CE1 | TYR | A | 233 | 61.646 | 64.119 | 46.467 | 1.00 | 11.86 | A |
| ATOM | 654 | CD2 | TYR | A | 233 | 63.336 | 62.156 | 45.517 | 1.00 | 10.75 | A |
| ATOM | 655 | CE2 | TYR | A | 233 | 62.272 | 61.812 | 46.324 | 1.00 | 11.05 | A |
| ATOM | 656 | CZ | TYR | A | 233 | 61.425 | 62.796 | 46.794 | 1.00 | 9.98 | A |
| ATOM | 657 | OH | TYR | A | 233 | 60.333 | 62.438 | 47.555 | 1.00 | 10.85 | A |
| ATOM | 658 | C | TYR | A | 233 | 66.417 | 63.186 | 45.942 | 1.00 | 10.01 | A |
| ATOM | 659 | O | TYR | A | 233 | 66.295 | 63.384 | 47.147 | 1.00 | 11.44 | A |
| ATOM | 660 | N | HIS | A | 234 | 66.900 | 62.058 | 45.437 | 1.00 | 10.22 | A |
| ATOM | 661 | CA | HIS | A | 234 | 67.281 | 60.962 | 46.312 | 1.00 | 10.33 | A |
| ATOM | 662 | CB | HIS | A | 234 | 67.209 | 59.639 | 45.547 | 1.00 | 11.41 | A |
| ATOM | 663 | CG | HIS | A | 234 | 65.811 | 59.245 | 45.176 | 1.00 | 9.67 | A |
| ATOM | 664 | CD2 | HIS | A | 234 | 64.793 | 58.773 | 45.934 | 1.00 | 10.89 | A |
| ATOM | 665 | ND1 | HIS | A | 234 | 65.317 | 59.348 | 43.893 | 1.00 | 12.98 | A |
| ATOM | 666 | CE1 | HIS | A | 234 | 64.056 | 58.953 | 43.877 | 1.00 | 11.92 | A |
| ATOM | 667 | NE2 | HIS | A | 234 | 63.713 | 58.600 | 45.102 | 1.00 | 12.52 | A |
| ATOM | 668 | C | HIS | A | 234 | 68.619 | 61.116 | 47.015 | 1.00 | 11.24 | A |
| ATOM | 669 | O | HIS | A | 234 | 69.513 | 60.281 | 46.883 | 1.00 | 13.22 | A |
| ATOM | 670 | N | ASN | A | 235 | 68.735 | 62.197 | 47.776 | 1.00 | 11.39 | A |
| ATOM | 671 | CA | ASN | A | 235 | 69.936 | 62.473 | 48.552 | 1.00 | 10.27 | A |
| ATOM | 672 | CB | ASN | A | 235 | 70.496 | 63.855 | 48.209 | 1.00 | 11.41 | A |
| ATOM | 673 | CG | ASN | A | 235 | 69.437 | 64.928 | 48.228 | 1.00 | 12.84 | A |
| ATOM | 674 | OD1 | ASN | A | 235 | 68.772 | 65.133 | 49.239 | 1.00 | 14.78 | A |
| ATOM | 675 | ND2 | ASN | A | 235 | 69.268 | 65.617 | 47.103 | 1.00 | 12.83 | A |
| ATOM | 676 | C | ASN | A | 235 | 69.537 | 62.386 | 50.025 | 1.00 | 10.06 | A |
| ATOM | 677 | O | ASN | A | 235 | 68.392 | 62.053 | 50.335 | 1.00 | 10.99 | A |
| ATOM | 678 | N | SER | A | 236 | 70.462 | 62.694 | 50.930 | 1.00 | 10.36 | A |
| ATOM | 679 | CA | SER | A | 236 | 70.165 | 62.568 | 52.357 | 1.00 | 9.20 | A |
| ATOM | 680 | CB | SER | A | 236 | 71.433 | 62.785 | 53.202 | 1.00 | 9.86 | A |
| ATOM | 681 | OG | SER | A | 236 | 71.790 | 64.147 | 53.303 | 1.00 | 13.00 | A |
| ATOM | 682 | C | SER | A | 236 | 69.031 | 63.440 | 52.878 | 1.00 | 10.04 | A |
| ATOM | 683 | O | SER | A | 236 | 68.472 | 63.150 | 53.930 | 1.00 | 10.71 | A |
| ATOM | 684 | N | LEU | A | 237 | 68.679 | 64.495 | 52.151 | 1.00 | 10.84 | A |
| ATOM | 685 | CA | LEU | A | 237 | 67.580 | 65.356 | 52.589 | 1.00 | 11.27 | A |
| ATOM | 686 | CB | LEU | A | 237 | 67.501 | 66.615 | 51.719 | 1.00 | 13.43 | A |
| ATOM | 687 | CG | LEU | A | 237 | 66.576 | 67.705 | 52.261 | 1.00 | 18.43 | A |
| ATOM | 688 | CD1 | LEU | A | 237 | 67.091 | 68.191 | 53.609 | 1.00 | 18.80 | A |
| ATOM | 689 | CD2 | LEU | A | 237 | 66.513 | 68.859 | 51.272 | 1.00 | 19.22 | A |
| ATOM | 690 | C | LEU | A | 237 | 66.264 | 64.578 | 52.507 | 1.00 | 10.32 | A |
| ATOM | 691 | O | LEU | A | 237 | 65.404 | 64.686 | 53.382 | 1.00 | 11.99 | A |
| ATOM | 692 | N | HIS | A | 238 | 66.103 | 63.799 | 51.443 | 1.00 | 9.70 | A |
| ATOM | 693 | CA | HIS | A | 238 | 64.898 | 62.997 | 51.302 | 1.00 | 9.52 | A |
| ATOM | 694 | CB | HIS | A | 238 | 64.879 | 62.342 | 49.917 | 1.00 | 9.43 | A |
| ATOM | 695 | CG | HIS | A | 238 | 63.864 | 61.250 | 49.774 | 1.00 | 10.25 | A |
| ATOM | 696 | CD2 | HIS | A | 238 | 64.018 | 59.922 | 49.569 | 1.00 | 10.24 | A |

TABLE 1-continued

| | | | | | | | | | | |
|---|---|---|---|---|---|---|---|---|---|---|
| ATOM | 697 | ND1 | HIS | A | 238 | 62.504 | 61.472 | 49.845 | 1.00 | 9.33 A |
| ATOM | 698 | CE1 | HIS | A | 238 | 61.867 | 60.326 | 49.689 | 1.00 | 9.88 A |
| ATOM | 699 | NE2 | HIS | A | 238 | 62.762 | 59.371 | 49.520 | 1.00 | 10.04 A |
| ATOM | 700 | C | HIS | A | 238 | 64.837 | 61.941 | 52.412 | 1.00 | 9.29 A |
| ATOM | 701 | O | HIS | A | 238 | 63.782 | 61.712 | 53.005 | 1.00 | 9.64 A |
| ATOM | 702 | N | ALA | A | 239 | 65.970 | 61.308 | 52.707 | 1.00 | 9.53 A |
| ATOM | 703 | CA | ALA | A | 239 | 66.008 | 60.297 | 53.759 | 1.00 | 9.61 A |
| ATOM | 704 | CB | ALA | A | 239 | 67.396 | 59.666 | 53.835 | 1.00 | 10.48 A |
| ATOM | 705 | C | ALA | A | 239 | 65.644 | 60.916 | 55.111 | 1.00 | 8.43 A |
| ATOM | 706 | O | ALA | A | 239 | 64.906 | 60.317 | 55.892 | 1.00 | 10.38 A |
| ATOM | 707 | N | ALA | A | 240 | 66.172 | 62.105 | 55.384 | 1.00 | 10.61 A |
| ATOM | 708 | CA | ALA | A | 240 | 65.873 | 62.787 | 56.644 | 1.00 | 9.33 A |
| ATOM | 709 | CB | ALA | A | 240 | 66.664 | 64.093 | 56.738 | 1.00 | 11.23 A |
| ATOM | 710 | C | ALA | A | 240 | 64.371 | 63.069 | 56.717 | 1.00 | 10.00 A |
| ATOM | 711 | O | ALA | A | 240 | 63.738 | 62.864 | 57.746 | 1.00 | 11.21 A |
| ATOM | 712 | N | ASP | A | 241 | 63.808 | 63.539 | 55.608 | 1.00 | 9.95 A |
| ATOM | 713 | CA | ASP | A | 241 | 62.388 | 63.837 | 55.532 | 1.00 | 10.00 A |
| ATOM | 714 | CB | ASP | A | 241 | 62.065 | 64.407 | 54.151 | 1.00 | 11.71 A |
| ATOM | 715 | CG | ASP | A | 241 | 60.588 | 64.699 | 53.969 | 1.00 | 14.13 A |
| ATOM | 716 | OD1 | ASP | A | 241 | 59.972 | 65.281 | 54.888 | 1.00 | 16.35 A |
| ATOM | 717 | OD2 | ASP | A | 241 | 60.049 | 64.351 | 52.903 | 1.00 | 15.16 A |
| ATOM | 718 | C | ASP | A | 241 | 61.541 | 62.596 | 55.801 | 1.00 | 9.21 A |
| ATOM | 719 | O | ASP | A | 241 | 60.597 | 62.639 | 56.593 | 1.00 | 10.80 A |
| ATOM | 720 | N | VAL | A | 242 | 61.884 | 61.488 | 55.151 | 1.00 | 9.21 A |
| ATOM | 721 | CA | VAL | A | 242 | 61.127 | 60.260 | 55.346 | 1.00 | 9.40 A |
| ATOM | 722 | CB | VAL | A | 242 | 61.567 | 59.161 | 54.343 | 1.00 | 8.76 A |
| ATOM | 723 | CG1 | VAL | A | 242 | 60.802 | 57.869 | 54.602 | 1.00 | 9.67 A |
| ATOM | 724 | CG2 | VAL | A | 242 | 61.277 | 59.624 | 52.927 | 1.00 | 9.44 A |
| ATOM | 725 | C | VAL | A | 242 | 61.249 | 59.763 | 56.790 | 1.00 | 9.12 A |
| ATOM | 726 | O | VAL | A | 242 | 60.271 | 59.277 | 57.358 | 1.00 | 11.25 A |
| ATOM | 727 | N | ALA | A | 243 | 62.433 | 59.899 | 57.386 | 1.00 | 11.03 A |
| ATOM | 728 | CA | ALA | A | 243 | 62.636 | 59.475 | 58.769 | 1.00 | 10.54 A |
| ATOM | 729 | CB | ALA | A | 243 | 64.118 | 59.564 | 59.144 | 1.00 | 13.23 A |
| ATOM | 730 | C | ALA | A | 243 | 61.806 | 60.329 | 59.732 | 1.00 | 10.95 A |
| ATOM | 731 | O | ALA | A | 243 | 61.154 | 59.806 | 60.637 | 1.00 | 12.73 A |
| ATOM | 732 | N | GLN | A | 244 | 61.836 | 61.644 | 59.537 | 1.00 | 11.47 A |
| ATOM | 733 | CA | GLN | A | 244 | 61.085 | 62.551 | 60.402 | 1.00 | 11.53 A |
| ATOM | 734 | CB | GLN | A | 244 | 61.472 | 64.000 | 60.102 | 1.00 | 11.85 A |
| ATOM | 735 | CG | GLN | A | 244 | 60.948 | 65.042 | 61.096 | 1.00 | 13.27 A |
| ATOM | 736 | CD | GLN | A | 244 | 59.581 | 65.569 | 60.730 | 1.00 | 13.24 A |
| ATOM | 737 | OE1 | GLN | A | 244 | 59.236 | 65.675 | 59.552 | 1.00 | 15.07 A |
| ATOM | 738 | NE2 | GLN | A | 244 | 58.803 | 65.934 | 61.739 | 1.00 | 12.75 A |
| ATOM | 739 | C | GLN | A | 244 | 59.587 | 62.346 | 60.209 | 1.00 | 9.52 A |
| ATOM | 740 | O | GLN | A | 244 | 58.817 | 62.433 | 61.162 | 1.00 | 12.02 A |
| ATOM | 741 | N | SER | A | 245 | 59.171 | 62.060 | 58.978 | 1.00 | 10.84 A |
| ATOM | 742 | CA | SER | A | 245 | 57.757 | 61.828 | 58.708 | 1.00 | 11.18 A |
| ATOM | 743 | CB | SER | A | 245 | 57.502 | 61.773 | 57.202 | 1.00 | 9.69 A |
| ATOM | 744 | OG | SER | A | 245 | 57.856 | 63.008 | 56.601 | 1.00 | 12.01 A |
| ATOM | 745 | C | SER | A | 245 | 57.296 | 60.530 | 59.366 | 1.00 | 10.42 A |
| ATOM | 746 | O | SER | A | 245 | 56.184 | 60.455 | 59.876 | 1.00 | 12.31 A |
| ATOM | 747 | N | THR | A | 246 | 58.157 | 59.513 | 59.358 | 1.00 | 11.70 A |
| ATOM | 748 | CA | THR | A | 246 | 57.828 | 58.233 | 59.979 | 1.00 | 12.28 A |
| ATOM | 749 | CB | THR | A | 246 | 58.913 | 57.174 | 59.650 | 1.00 | 12.43 A |
| ATOM | 750 | OG1 | THR | A | 246 | 58.922 | 56.944 | 58.238 | 1.00 | 12.38 A |
| ATOM | 751 | CG2 | THR | A | 246 | 58.633 | 55.851 | 60.358 | 1.00 | 12.81 A |
| ATOM | 752 | C | THR | A | 246 | 57.726 | 58.449 | 61.487 | 1.00 | 12.48 A |
| ATOM | 753 | O | THR | A | 246 | 56.854 | 57.882 | 62.154 | 1.00 | 12.79 A |
| ATOM | 754 | N | HIS | A | 247 | 58.618 | 59.285 | 62.012 | 1.00 | 12.34 A |
| ATOM | 755 | CA | HIS | A | 247 | 58.639 | 59.614 | 63.432 | 1.00 | 12.74 A |
| ATOM | 756 | CB | HIS | A | 247 | 59.770 | 60.609 | 63.709 | 1.00 | 14.22 A |
| ATOM | 757 | CG | HIS | A | 247 | 59.662 | 61.298 | 65.033 | 1.00 | 15.48 A |
| ATOM | 758 | CD2 | HIS | A | 247 | 59.492 | 62.605 | 65.344 | 1.00 | 16.84 A |
| ATOM | 759 | ND1 | HIS | A | 247 | 59.725 | 60.623 | 66.233 | 1.00 | 15.80 A |
| ATOM | 760 | CE1 | HIS | A | 247 | 59.598 | 61.485 | 67.226 | 1.00 | 17.07 A |
| ATOM | 761 | NE2 | HIS | A | 247 | 59.455 | 62.694 | 66.715 | 1.00 | 16.99 A |
| ATOM | 762 | C | HIS | A | 247 | 57.291 | 60.205 | 63.854 | 1.00 | 13.52 A |
| ATOM | 763 | O | HIS | A | 247 | 56.757 | 59.869 | 64.910 | 1.00 | 16.35 A |
| ATOM | 764 | N | VAL | A | 248 | 56.734 | 61.073 | 63.018 | 1.00 | 13.83 A |
| ATOM | 765 | CA | VAL | A | 248 | 55.447 | 61.685 | 63.326 | 1.00 | 14.65 A |
| ATOM | 766 | CB | VAL | A | 248 | 55.154 | 62.883 | 62.397 | 1.00 | 15.01 A |
| ATOM | 767 | CG1 | VAL | A | 248 | 53.755 | 63.416 | 62.670 | 1.00 | 14.97 A |
| ATOM | 768 | CG2 | VAL | A | 248 | 56.172 | 63.980 | 62.622 | 1.00 | 15.35 A |
| ATOM | 769 | C | VAL | A | 248 | 54.306 | 60.674 | 63.204 | 1.00 | 15.22 A |
| ATOM | 770 | O | VAL | A | 248 | 53.427 | 60.619 | 64.068 | 1.00 | 16.97 A |
| ATOM | 771 | N | LEU | A | 249 | 54.316 | 59.880 | 62.135 | 1.00 | 15.01 A |
| ATOM | 772 | CA | LEU | A | 249 | 53.271 | 58.882 | 61.922 | 1.00 | 14.68 A |
| ATOM | 773 | CB | LEU | A | 249 | 53.463 | 58.176 | 60.573 | 1.00 | 15.30 A |
| ATOM | 774 | CG | LEU | A | 249 | 53.177 | 59.045 | 59.344 | 1.00 | 14.95 A |
| ATOM | 775 | CD1 | LEU | A | 249 | 53.534 | 58.297 | 58.065 | 1.00 | 16.15 A |

TABLE 1-continued

| | | | | | | | | | | |
|---|---|---|---|---|---|---|---|---|---|---|
| ATOM | 776 | CD2 | LEU | A | 249 | 51.706 | 59.434 | 59.339 | 1.00 | 16.99 | A |
| ATOM | 777 | C | LEU | A | 249 | 53.231 | 57.852 | 63.048 | 1.00 | 15.22 | A |
| ATOM | 778 | O | LEU | A | 249 | 52.163 | 57.355 | 63.408 | 1.00 | 16.74 | A |
| ATOM | 779 | N | LEU | A | 250 | 54.390 | 57.530 | 63.610 | 1.00 | 16.48 | A |
| ATOM | 780 | CA | LEU | A | 250 | 54.440 | 56.560 | 64.698 | 1.00 | 16.69 | A |
| ATOM | 781 | CB | LEU | A | 250 | 55.892 | 56.221 | 65.042 | 1.00 | 16.80 | A |
| ATOM | 782 | CG | LEU | A | 250 | 56.590 | 55.275 | 64.063 | 1.00 | 17.60 | A |
| ATOM | 783 | CD1 | LEU | A | 250 | 58.092 | 55.365 | 64.239 | 1.00 | 17.25 | A |
| ATOM | 784 | CD2 | LEU | A | 250 | 56.092 | 53.853 | 64.294 | 1.00 | 19.47 | A |
| ATOM | 785 | C | LEU | A | 250 | 53.727 | 57.060 | 65.951 | 1.00 | 17.62 | A |
| ATOM | 786 | O | LEU | A | 250 | 53.306 | 56.261 | 66.788 | 1.00 | 19.32 | A |
| ATOM | 787 | N | SER | A | 251 | 53.591 | 58.376 | 66.078 | 1.00 | 18.59 | A |
| ATOM | 788 | CA | SER | A | 251 | 52.937 | 58.949 | 67.249 | 1.00 | 19.38 | A |
| ATOM | 789 | CB | SER | A | 251 | 53.673 | 60.212 | 67.695 | 1.00 | 20.39 | A |
| ATOM | 790 | OG | SER | A | 251 | 54.932 | 59.888 | 68.259 | 1.00 | 24.83 | A |
| ATOM | 791 | C | SER | A | 251 | 51.457 | 59.266 | 67.058 | 1.00 | 19.49 | A |
| ATOM | 792 | O | SER | A | 251 | 50.855 | 59.945 | 67.892 | 1.00 | 21.68 | A |
| ATOM | 793 | N | THR | A | 252 | 50.865 | 58.781 | 65.972 | 1.00 | 19.34 | A |
| ATOM | 794 | CA | THR | A | 252 | 49.446 | 59.025 | 65.737 | 1.00 | 20.18 | A |
| ATOM | 795 | CB | THR | A | 252 | 48.974 | 58.393 | 64.421 | 1.00 | 22.38 | A |
| ATOM | 796 | OG1 | THR | A | 252 | 49.063 | 56.969 | 64.513 | 1.00 | 26.69 | A |
| ATOM | 797 | CG2 | THR | A | 252 | 49.839 | 58.864 | 63.273 | 1.00 | 20.24 | A |
| ATOM | 798 | C | THR | A | 252 | 48.662 | 58.400 | 66.884 | 1.00 | 19.56 | A |
| ATOM | 799 | O | THR | A | 252 | 48.908 | 57.253 | 67.266 | 1.00 | 20.24 | A |
| ATOM | 800 | N | PRO | A | 253 | 47.706 | 59.147 | 67.453 | 1.00 | 20.06 | A |
| ATOM | 801 | CD | PRO | A | 253 | 47.332 | 60.525 | 67.093 | 1.00 | 20.20 | A |
| ATOM | 802 | CA | PRO | A | 253 | 46.884 | 58.662 | 68.567 | 1.00 | 19.84 | A |
| ATOM | 803 | CB | PRO | A | 253 | 45.778 | 59.709 | 68.649 | 1.00 | 20.71 | A |
| ATOM | 804 | CG | PRO | A | 253 | 46.500 | 60.954 | 68.293 | 1.00 | 19.86 | A |
| ATOM | 805 | C | PRO | A | 253 | 46.332 | 57.253 | 68.375 | 1.00 | 19.89 | A |
| ATOM | 806 | O | PRO | A | 253 | 46.320 | 56.450 | 69.306 | 1.00 | 20.48 | A |
| ATOM | 807 | N | ALA | A | 254 | 45.879 | 56.956 | 67.163 | 1.00 | 19.86 | A |
| ATOM | 808 | CA | ALA | A | 254 | 45.319 | 55.648 | 66.860 | 1.00 | 20.86 | A |
| ATOM | 809 | CB | ALA | A | 254 | 44.783 | 55.635 | 65.439 | 1.00 | 21.87 | A |
| ATOM | 810 | C | ALA | A | 254 | 46.309 | 54.502 | 67.052 | 1.00 | 21.49 | A |
| ATOM | 811 | O | ALA | A | 254 | 45.906 | 53.363 | 67.264 | 1.00 | 22.33 | A |
| ATOM | 812 | N | LEU | A | 255 | 47.602 | 54.800 | 66.983 | 1.00 | 21.67 | A |
| ATOM | 813 | CA | LEU | A | 255 | 48.619 | 53.763 | 67.134 | 1.00 | 22.22 | A |
| ATOM | 814 | CB | LEU | A | 255 | 49.622 | 53.858 | 65.981 | 1.00 | 21.71 | A |
| ATOM | 815 | CG | LEU | A | 255 | 49.038 | 53.721 | 64.571 | 1.00 | 21.23 | A |
| ATOM | 816 | CD1 | LEU | A | 255 | 50.117 | 53.999 | 63.535 | 1.00 | 20.15 | A |
| ATOM | 817 | CD2 | LEU | A | 255 | 48.468 | 52.330 | 64.384 | 1.00 | 21.31 | A |
| ATOM | 818 | C | LEU | A | 255 | 49.360 | 53.836 | 68.468 | 1.00 | 22.79 | A |
| ATOM | 819 | O | LEU | A | 255 | 50.472 | 53.323 | 68.597 | 1.00 | 23.35 | A |
| ATOM | 820 | N | ASP | A | 256 | 48.745 | 54.462 | 69.464 | 1.00 | 23.64 | A |
| ATOM | 821 | CA | ASP | A | 256 | 49.384 | 54.591 | 70.767 | 1.00 | 24.21 | A |
| ATOM | 822 | CB | ASP | A | 256 | 48.577 | 55.527 | 71.672 | 1.00 | 25.02 | A |
| ATOM | 823 | CG | ASP | A | 256 | 49.185 | 55.662 | 73.058 | 1.00 | 28.18 | A |
| ATOM | 824 | OD1 | ASP | A | 256 | 50.372 | 56.044 | 73.158 | 1.00 | 29.88 | A |
| ATOM | 825 | OD2 | ASP | A | 256 | 48.477 | 55.388 | 74.051 | 1.00 | 30.80 | A |
| ATOM | 826 | C | ASP | A | 256 | 49.578 | 53.253 | 71.475 | 1.00 | 24.00 | A |
| ATOM | 827 | O | ASP | A | 256 | 48.650 | 52.453 | 71.578 | 1.00 | 24.48 | A |
| ATOM | 828 | N | ALA | A | 257 | 50.798 | 53.026 | 71.954 | 1.00 | 23.88 | A |
| ATOM | 829 | CA | ALA | A | 257 | 51.153 | 51.811 | 72.681 | 1.00 | 24.43 | A |
| ATOM | 830 | CB | ALA | A | 257 | 50.301 | 51.701 | 73.940 | 1.00 | 25.23 | A |
| ATOM | 831 | C | ALA | A | 257 | 51.033 | 50.529 | 71.865 | 1.00 | 24.05 | A |
| ATOM | 832 | O | ALA | A | 257 | 51.139 | 49.428 | 72.411 | 1.00 | 25.34 | A |
| ATOM | 833 | N | VAL | A | 258 | 50.821 | 50.663 | 70.561 | 1.00 | 21.49 | A |
| ATOM | 834 | CA | VAL | A | 258 | 50.685 | 49.498 | 69.696 | 1.00 | 21.01 | A |
| ATOM | 835 | CB | VAL | A | 258 | 49.992 | 49.877 | 68.368 | 1.00 | 20.43 | A |
| ATOM | 836 | CG1 | VAL | A | 258 | 50.111 | 48.739 | 67.370 | 1.00 | 22.15 | A |
| ATOM | 837 | CG2 | VAL | A | 258 | 48.523 | 50.197 | 68.621 | 1.00 | 22.44 | A |
| ATOM | 838 | C | VAL | A | 258 | 52.007 | 48.806 | 69.366 | 1.00 | 19.79 | A |
| ATOM | 839 | O | VAL | A | 258 | 52.084 | 47.576 | 69.348 | 1.00 | 20.97 | A |
| ATOM | 840 | N | PHE | A | 259 | 53.051 | 49.591 | 69.118 | 1.00 | 19.04 | A |
| ATOM | 841 | CA | PHE | A | 259 | 54.342 | 49.018 | 68.744 | 1.00 | 18.35 | A |
| ATOM | 842 | CB | PHE | A | 259 | 54.939 | 49.823 | 67.587 | 1.00 | 18.36 | A |
| ATOM | 843 | CG | PHE | A | 259 | 54.085 | 49.830 | 66.352 | 1.00 | 17.46 | A |
| ATOM | 844 | CD1 | PHE | A | 259 | 53.876 | 48.668 | 65.630 | 1.00 | 17.34 | A |
| ATOM | 845 | CD2 | PHE | A | 259 | 53.477 | 50.996 | 65.925 | 1.00 | 18.87 | A |
| ATOM | 846 | CE1 | PHE | A | 259 | 53.071 | 48.668 | 64.500 | 1.00 | 17.24 | A |
| ATOM | 847 | CE2 | PHE | A | 259 | 52.671 | 51.006 | 64.796 | 1.00 | 19.53 | A |
| ATOM | 848 | CZ | PHE | A | 259 | 52.468 | 49.839 | 64.084 | 1.00 | 19.84 | A |
| ATOM | 849 | C | PHE | A | 259 | 55.371 | 48.914 | 69.857 | 1.00 | 17.62 | A |
| ATOM | 850 | O | PHE | A | 259 | 55.384 | 49.719 | 70.787 | 1.00 | 19.41 | A |
| ATOM | 851 | N | THR | A | 260 | 56.237 | 47.912 | 69.745 | 1.00 | 17.89 | A |
| ATOM | 852 | CA | THR | A | 260 | 57.303 | 47.701 | 70.718 | 1.00 | 17.06 | A |
| ATOM | 853 | CB | THR | A | 260 | 57.888 | 46.283 | 70.623 | 1.00 | 19.51 | A |
| ATOM | 854 | OG1 | THR | A | 260 | 58.512 | 46.115 | 69.344 | 1.00 | 20.56 | A |

TABLE 1-continued

| | | | | | | | | | | |
|---|---|---|---|---|---|---|---|---|---|---|
| ATOM | 855 | CG2 | THR | A | 260 | 56.794 | 45.238 | 70.780 | 1.00 | 20.22 | A |
| ATOM | 856 | C | THR | A | 260 | 58.419 | 48.683 | 70.389 | 1.00 | 16.31 | A |
| ATOM | 857 | O | THR | A | 260 | 58.455 | 49.250 | 69.290 | 1.00 | 15.49 | A |
| ATOM | 858 | N | ASP | A | 261 | 59.331 | 48.890 | 71.328 | 1.00 | 15.94 | A |
| ATOM | 859 | CA | ASP | A | 261 | 60.432 | 49.806 | 71.074 | 1.00 | 17.24 | A |
| ATOM | 860 | CB | ASP | A | 261 | 61.286 | 49.996 | 72.331 | 1.00 | 20.48 | A |
| ATOM | 861 | CG | ASP | A | 261 | 60.523 | 50.682 | 73.452 | 1.00 | 24.85 | A |
| ATOM | 862 | OD1 | ASP | A | 261 | 59.665 | 51.539 | 73.151 | 1.00 | 26.79 | A |
| ATOM | 863 | OD2 | ASP | A | 261 | 60.790 | 50.374 | 74.632 | 1.00 | 26.08 | A |
| ATOM | 864 | C | ASP | A | 261 | 61.290 | 49.298 | 69.913 | 1.00 | 16.71 | A |
| ATOM | 865 | O | ASP | A | 261 | 61.841 | 50.095 | 69.156 | 1.00 | 17.84 | A |
| ATOM | 866 | N | LEU | A | 262 | 61.385 | 47.979 | 69.759 | 1.00 | 16.16 | A |
| ATOM | 867 | CA | LEU | A | 262 | 62.175 | 47.404 | 68.672 | 1.00 | 15.49 | A |
| ATOM | 868 | CB | LEU | A | 262 | 62.284 | 45.879 | 68.817 | 1.00 | 16.17 | A |
| ATOM | 869 | CG | LEU | A | 262 | 63.203 | 45.190 | 67.798 | 1.00 | 17.54 | A |
| ATOM | 870 | CD1 | LEU | A | 262 | 64.645 | 45.594 | 68.053 | 1.00 | 17.57 | A |
| ATOM | 871 | CD2 | LEU | A | 262 | 63.051 | 43.684 | 67.889 | 1.00 | 20.05 | A |
| ATOM | 872 | C | LEU | A | 262 | 61.553 | 47.743 | 67.316 | 1.00 | 15.26 | A |
| ATOM | 873 | O | LEU | A | 262 | 62.263 | 48.048 | 66.363 | 1.00 | 15.71 | A |
| ATOM | 874 | N | GLU | A | 263 | 60.229 | 47.683 | 67.233 | 1.00 | 15.63 | A |
| ATOM | 875 | CA | GLU | A | 263 | 59.532 | 47.988 | 65.988 | 1.00 | 15.51 | A |
| ATOM | 876 | CB | GLU | A | 263 | 58.055 | 47.580 | 66.110 | 1.00 | 17.38 | A |
| ATOM | 877 | CG | GLU | A | 263 | 57.912 | 46.087 | 66.432 | 1.00 | 19.32 | A |
| ATOM | 878 | CD | GLU | A | 263 | 56.487 | 45.630 | 66.695 | 1.00 | 21.46 | A |
| ATOM | 879 | OE1 | GLU | A | 263 | 55.721 | 46.366 | 67.349 | 1.00 | 21.68 | A |
| ATOM | 880 | OE2 | GLU | A | 263 | 56.141 | 44.511 | 66.264 | 1.00 | 23.34 | A |
| ATOM | 881 | C | GLU | A | 263 | 59.690 | 49.474 | 65.659 | 1.00 | 14.63 | A |
| ATOM | 882 | O | GLU | A | 263 | 59.839 | 49.848 | 64.492 | 1.00 | 15.41 | A |
| ATOM | 883 | N | ILE | A | 264 | 59.664 | 50.321 | 66.685 | 1.00 | 14.27 | A |
| ATOM | 884 | CA | ILE | A | 264 | 59.844 | 51.758 | 66.491 | 1.00 | 14.47 | A |
| ATOM | 885 | CB | ILE | A | 264 | 59.605 | 52.512 | 67.822 | 1.00 | 15.75 | A |
| ATOM | 886 | CG2 | ILE | A | 264 | 60.112 | 53.944 | 67.733 | 1.00 | 14.96 | A |
| ATOM | 887 | CG1 | ILE | A | 264 | 58.112 | 52.470 | 68.151 | 1.00 | 15.55 | A |
| ATOM | 888 | CD1 | ILE | A | 264 | 57.764 | 52.974 | 69.534 | 1.00 | 17.94 | A |
| ATOM | 889 | C | ILE | A | 264 | 61.265 | 52.002 | 65.964 | 1.00 | 14.06 | A |
| ATOM | 890 | O | ILE | A | 264 | 61.464 | 52.743 | 64.993 | 1.00 | 14.36 | A |
| ATOM | 891 | N | LEU | A | 265 | 62.245 | 51.366 | 66.599 | 1.00 | 14.04 | A |
| ATOM | 892 | CA | LEU | A | 265 | 63.642 | 51.479 | 66.183 | 1.00 | 13.62 | A |
| ATOM | 893 | CB | LEU | A | 265 | 64.525 | 50.583 | 67.056 | 1.00 | 14.83 | A |
| ATOM | 894 | CG | LEU | A | 265 | 66.014 | 50.518 | 66.700 | 1.00 | 16.23 | A |
| ATOM | 895 | CD1 | LEU | A | 265 | 66.685 | 51.832 | 67.054 | 1.00 | 17.52 | A |
| ATOM | 896 | CD2 | LEU | A | 265 | 66.672 | 49.370 | 67.466 | 1.00 | 15.63 | A |
| ATOM | 897 | C | LEU | A | 265 | 63.787 | 51.039 | 64.727 | 1.00 | 12.86 | A |
| ATOM | 898 | O | LEU | A | 265 | 64.416 | 51.722 | 63.916 | 1.00 | 14.63 | A |
| ATOM | 899 | N | ALA | A | 266 | 63.193 | 49.895 | 64.403 | 1.00 | 13.09 | A |
| ATOM | 900 | CA | ALA | A | 266 | 63.270 | 49.348 | 63.050 | 1.00 | 12.95 | A |
| ATOM | 901 | CB | ALA | A | 266 | 62.581 | 47.989 | 62.997 | 1.00 | 13.61 | A |
| ATOM | 902 | C | ALA | A | 266 | 62.661 | 50.273 | 62.007 | 1.00 | 12.42 | A |
| ATOM | 903 | O | ALA | A | 266 | 63.234 | 50.464 | 60.932 | 1.00 | 13.61 | A |
| ATOM | 904 | N | ALA | A | 267 | 61.508 | 50.849 | 62.328 | 1.00 | 12.74 | A |
| ATOM | 905 | CA | ALA | A | 267 | 60.822 | 51.745 | 61.402 | 1.00 | 12.46 | A |
| ATOM | 906 | CB | ALA | A | 267 | 59.456 | 52.143 | 61.970 | 1.00 | 13.39 | A |
| ATOM | 907 | C | ALA | A | 267 | 61.637 | 52.993 | 61.084 | 1.00 | 12.23 | A |
| ATOM | 908 | O | ALA | A | 267 | 61.765 | 53.376 | 59.922 | 1.00 | 14.13 | A |
| ATOM | 909 | N | ILE | A | 268 | 62.190 | 53.631 | 62.111 | 1.00 | 12.39 | A |
| ATOM | 910 | CA | ILE | A | 268 | 62.977 | 54.835 | 61.890 | 1.00 | 12.16 | A |
| ATOM | 911 | CB | ILE | A | 268 | 63.218 | 55.585 | 63.220 | 1.00 | 13.76 | A |
| ATOM | 912 | CG2 | ILE | A | 268 | 64.085 | 56.814 | 62.983 | 1.00 | 16.04 | A |
| ATOM | 913 | CG1 | ILE | A | 268 | 61.865 | 56.008 | 63.809 | 1.00 | 16.47 | A |
| ATOM | 914 | CD1 | ILE | A | 268 | 61.951 | 56.633 | 65.197 | 1.00 | 17.84 | A |
| ATOM | 915 | C | ILE | A | 268 | 64.297 | 54.505 | 61.189 | 1.00 | 10.99 | A |
| ATOM | 916 | O | ILE | A | 268 | 64.751 | 55.251 | 60.321 | 1.00 | 12.73 | A |
| ATOM | 917 | N | PHE | A | 269 | 64.906 | 53.382 | 61.556 | 1.00 | 10.98 | A |
| ATOM | 918 | CA | PHE | A | 269 | 66.148 | 52.964 | 60.915 | 1.00 | 11.22 | A |
| ATOM | 919 | CB | PHE | A | 269 | 66.684 | 51.688 | 61.573 | 1.00 | 12.29 | A |
| ATOM | 920 | CG | PHE | A | 269 | 67.942 | 51.163 | 60.942 | 1.00 | 13.65 | A |
| ATOM | 921 | CD1 | PHE | A | 269 | 69.153 | 51.809 | 61.131 | 1.00 | 14.62 | A |
| ATOM | 922 | CD2 | PHE | A | 269 | 67.912 | 50.024 | 60.154 | 1.00 | 14.97 | A |
| ATOM | 923 | CE1 | PHE | A | 269 | 70.313 | 51.326 | 60.547 | 1.00 | 15.18 | A |
| ATOM | 924 | CE2 | PHE | A | 269 | 69.065 | 49.538 | 59.567 | 1.00 | 13.83 | A |
| ATOM | 925 | CZ | PHE | A | 269 | 70.266 | 50.191 | 59.766 | 1.00 | 15.15 | A |
| ATOM | 926 | C | PHE | A | 269 | 65.866 | 52.696 | 59.436 | 1.00 | 10.84 | A |
| ATOM | 927 | O | PHE | A | 269 | 66.619 | 53.126 | 58.557 | 1.00 | 11.96 | A |
| ATOM | 928 | N | ALA | A | 270 | 64.781 | 51.979 | 59.164 | 1.00 | 10.96 | A |
| ATOM | 929 | CA | ALA | A | 270 | 64.416 | 51.660 | 57.786 | 1.00 | 10.59 | A |
| ATOM | 930 | CB | ALA | A | 270 | 63.133 | 50.837 | 57.758 | 1.00 | 12.22 | A |
| ATOM | 931 | C | ALA | A | 270 | 64.245 | 52.936 | 56.964 | 1.00 | 9.83 | A |
| ATOM | 932 | O | ALA | A | 270 | 64.720 | 53.019 | 55.832 | 1.00 | 10.53 | A |
| ATOM | 933 | N | ALA | A | 271 | 63.565 | 53.932 | 57.527 | 1.00 | 10.99 | A |

TABLE 1-continued

| | | | | | | | | | | |
|---|---|---|---|---|---|---|---|---|---|---|
| ATOM | 934 | CA | ALA | A | 271 | 63.362 | 55.184 | 56.807 | 1.00 | 9.90 | A |
| ATOM | 935 | CB | ALA | A | 271 | 62.463 | 56.115 | 57.623 | 1.00 | 13.45 | A |
| ATOM | 936 | C | ALA | A | 271 | 64.702 | 55.857 | 56.513 | 1.00 | 9.51 | A |
| ATOM | 937 | O | ALA | A | 271 | 64.928 | 56.378 | 55.420 | 1.00 | 10.70 | A |
| ATOM | 938 | N | ALA | A | 272 | 65.608 | 55.836 | 57.486 | 1.00 | 9.89 | A |
| ATOM | 939 | CA | ALA | A | 272 | 66.914 | 56.458 | 57.302 | 1.00 | 8.82 | A |
| ATOM | 940 | CB | ALA | A | 272 | 67.688 | 56.434 | 58.619 | 1.00 | 10.73 | A |
| ATOM | 941 | C | ALA | A | 272 | 67.762 | 55.822 | 56.193 | 1.00 | 8.10 | A |
| ATOM | 942 | O | ALA | A | 272 | 68.461 | 56.527 | 55.461 | 1.00 | 10.85 | A |
| ATOM | 943 | N | ILE | A | 273 | 67.705 | 54.499 | 56.067 | 1.00 | 8.73 | A |
| ATOM | 944 | CA | ILE | A | 273 | 68.515 | 53.817 | 55.055 | 1.00 | 8.22 | A |
| ATOM | 945 | CB | ILE | A | 273 | 69.077 | 52.450 | 55.559 | 1.00 | 8.56 | A |
| ATOM | 946 | CG2 | ILE | A | 273 | 69.778 | 52.619 | 56.890 | 1.00 | 11.42 | A |
| ATOM | 947 | CG1 | ILE | A | 273 | 67.946 | 51.423 | 55.677 | 1.00 | 10.89 | A |
| ATOM | 948 | CD1 | ILE | A | 273 | 68.441 | 49.992 | 55.779 | 1.00 | 11.69 | A |
| ATOM | 949 | C | ILE | A | 273 | 67.775 | 53.482 | 53.776 | 1.00 | 9.67 | A |
| ATOM | 950 | O | ILE | A | 273 | 68.398 | 53.016 | 52.830 | 1.00 | 11.43 | A |
| ATOM | 951 | N | HIS | A | 274 | 66.469 | 53.745 | 53.723 | 1.00 | 9.87 | A |
| ATOM | 952 | CA | HIS | A | 274 | 65.680 | 53.317 | 52.575 | 1.00 | 9.09 | A |
| ATOM | 953 | CB | HIS | A | 274 | 64.196 | 53.638 | 52.800 | 1.00 | 9.86 | A |
| ATOM | 954 | CG | HIS | A | 274 | 63.757 | 54.929 | 52.195 | 1.00 | 11.74 | A |
| ATOM | 955 | CD2 | HIS | A | 274 | 63.070 | 55.188 | 51.057 | 1.00 | 9.64 | A |
| ATOM | 956 | ND1 | HIS | A | 274 | 64.048 | 56.152 | 52.757 | 1.00 | 10.74 | A |
| ATOM | 957 | CE1 | HIS | A | 274 | 63.561 | 57.111 | 51.991 | 1.00 | 11.82 | A |
| ATOM | 958 | NE2 | HIS | A | 274 | 62.962 | 56.552 | 50.952 | 1.00 | 7.53 | A |
| ATOM | 959 | C | HIS | A | 274 | 66.086 | 53.692 | 51.151 | 1.00 | 8.60 | A |
| ATOM | 960 | O | HIS | A | 274 | 65.671 | 53.007 | 50.216 | 1.00 | 9.73 | A |
| ATOM | 961 | N | ASP | A | 275 | 66.882 | 54.746 | 50.968 | 1.00 | 7.82 | A |
| ATOM | 962 | CA | ASP | A | 275 | 67.336 | 55.133 | 49.619 | 1.00 | 7.44 | A |
| ATOM | 963 | CB | ASP | A | 275 | 66.679 | 56.443 | 49.154 | 1.00 | 9.89 | A |
| ATOM | 964 | CG | ASP | A | 275 | 65.359 | 56.223 | 48.460 | 1.00 | 8.90 | A |
| ATOM | 965 | OD1 | ASP | A | 275 | 65.178 | 55.155 | 47.849 | 1.00 | 9.38 | A |
| ATOM | 966 | OD2 | ASP | A | 275 | 64.507 | 57.130 | 48.504 | 1.00 | 8.55 | A |
| ATOM | 967 | C | ASP | A | 275 | 68.848 | 55.332 | 49.566 | 1.00 | 7.74 | A |
| ATOM | 968 | O | ASP | A | 275 | 69.358 | 55.982 | 48.660 | 1.00 | 9.34 | A |
| ATOM | 969 | N | VAL | A | 276 | 69.580 | 54.771 | 50.522 | 1.00 | 7.75 | A |
| ATOM | 970 | CA | VAL | A | 276 | 71.017 | 55.001 | 50.532 | 1.00 | 8.61 | A |
| ATOM | 971 | CB | VAL | A | 276 | 71.661 | 54.414 | 51.810 | 1.00 | 10.03 | A |
| ATOM | 972 | CG1 | VAL | A | 276 | 71.584 | 52.914 | 51.787 | 1.00 | 11.00 | A |
| ATOM | 973 | CG2 | VAL | A | 276 | 73.099 | 54.910 | 51.942 | 1.00 | 9.13 | A |
| ATOM | 974 | C | VAL | A | 276 | 71.737 | 54.495 | 49.282 | 1.00 | 8.35 | A |
| ATOM | 975 | O | VAL | A | 276 | 71.423 | 53.435 | 48.746 | 1.00 | 10.58 | A |
| ATOM | 976 | N | ASP | A | 277 | 72.686 | 55.301 | 48.817 | 1.00 | 9.55 | A |
| ATOM | 977 | CA | ASP | A | 277 | 73.485 | 55.013 | 47.629 | 1.00 | 9.67 | A |
| ATOM | 978 | CB | ASP | A | 277 | 74.290 | 53.720 | 47.812 | 1.00 | 12.86 | A |
| ATOM | 979 | CG | ASP | A | 277 | 75.454 | 53.614 | 46.835 | 1.00 | 15.64 | A |
| ATOM | 980 | OD1 | ASP | A | 277 | 76.021 | 54.666 | 46.464 | 1.00 | 17.72 | A |
| ATOM | 981 | OD2 | ASP | A | 277 | 75.818 | 52.483 | 46.452 | 1.00 | 18.03 | A |
| ATOM | 982 | C | ASP | A | 277 | 72.625 | 54.932 | 46.371 | 1.00 | 9.98 | A |
| ATOM | 983 | O | ASP | A | 277 | 72.902 | 54.157 | 45.462 | 1.00 | 12.40 | A |
| ATOM | 984 | N | HIS | A | 278 | 71.576 | 55.745 | 46.332 | 1.00 | 10.37 | A |
| ATOM | 985 | CA | HIS | A | 278 | 70.679 | 55.792 | 45.181 | 1.00 | 10.87 | A |
| ATOM | 986 | CB | HIS | A | 278 | 69.407 | 56.557 | 45.564 | 1.00 | 10.73 | A |
| ATOM | 987 | CG | HIS | A | 278 | 68.266 | 56.351 | 44.617 | 1.00 | 12.83 | A |
| ATOM | 988 | CD2 | HIS | A | 278 | 67.054 | 55.773 | 44.796 | 1.00 | 12.74 | A |
| ATOM | 989 | ND1 | HIS | A | 278 | 68.300 | 56.772 | 43.306 | 1.00 | 11.18 | A |
| ATOM | 990 | CE1 | HIS | A | 278 | 67.158 | 56.462 | 42.717 | 1.00 | 12.18 | A |
| ATOM | 991 | NE2 | HIS | A | 278 | 66.385 | 55.854 | 43.599 | 1.00 | 12.59 | A |
| ATOM | 992 | C | HIS | A | 278 | 71.437 | 56.527 | 44.071 | 1.00 | 10.98 | A |
| ATOM | 993 | O | HIS | A | 278 | 71.980 | 57.600 | 44.301 | 1.00 | 11.48 | A |
| ATOM | 994 | N | PRO | A | 279 | 71.499 | 55.945 | 42.858 | 1.00 | 12.29 | A |
| ATOM | 995 | CD | PRO | A | 279 | 71.055 | 54.576 | 42.541 | 1.00 | 13.89 | A |
| ATOM | 996 | CA | PRO | A | 279 | 72.199 | 56.544 | 41.714 | 1.00 | 12.49 | A |
| ATOM | 997 | CB | PRO | A | 279 | 72.476 | 55.341 | 40.820 | 1.00 | 13.95 | A |
| ATOM | 998 | CG | PRO | A | 279 | 71.268 | 54.499 | 41.033 | 1.00 | 14.11 | A |
| ATOM | 999 | C | PRO | A | 279 | 71.461 | 57.654 | 40.966 | 1.00 | 12.54 | A |
| ATOM | 1000 | O | PRO | A | 279 | 72.026 | 58.279 | 40.061 | 1.00 | 14.01 | A |
| ATOM | 1001 | N | GLY | A | 280 | 70.209 | 57.902 | 41.335 | 1.00 | 12.41 | A |
| ATOM | 1002 | CA | GLY | A | 280 | 69.459 | 58.951 | 40.669 | 1.00 | 13.96 | A |
| ATOM | 1003 | C | GLY | A | 280 | 68.738 | 58.498 | 39.417 | 1.00 | 15.21 | A |
| ATOM | 1004 | O | GLY | A | 280 | 68.302 | 59.324 | 38.613 | 1.00 | 15.91 | A |
| ATOM | 1005 | N | VAL | A | 281 | 68.634 | 57.187 | 39.237 | 1.00 | 14.73 | A |
| ATOM | 1006 | CA | VAL | A | 281 | 67.923 | 56.619 | 38.101 | 1.00 | 13.66 | A |
| ATOM | 1007 | CB | VAL | A | 281 | 68.885 | 56.032 | 37.042 | 1.00 | 13.41 | A |
| ATOM | 1008 | CG1 | VAL | A | 281 | 69.755 | 57.147 | 36.458 | 1.00 | 14.56 | A |
| ATOM | 1009 | CG2 | VAL | A | 281 | 69.738 | 54.936 | 37.654 | 1.00 | 15.72 | A |
| ATOM | 1010 | C | VAL | A | 281 | 67.010 | 55.522 | 38.628 | 1.00 | 13.42 | A |
| ATOM | 1011 | O | VAL | A | 281 | 67.209 | 55.006 | 39.735 | 1.00 | 14.31 | A |
| ATOM | 1012 | N | SER | A | 282 | 66.015 | 55.164 | 37.827 | 1.00 | 12.82 | A |

TABLE 1-continued

| ATOM | 1013 | CA | SER | A | 282 | 65.027 | 54.158 | 38.202 | 1.00 | 11.61 | A |
|---|---|---|---|---|---|---|---|---|---|---|---|
| ATOM | 1014 | CB | SER | A | 282 | 63.785 | 54.334 | 37.340 | 1.00 | 14.29 | A |
| ATOM | 1015 | OG | SER | A | 282 | 64.083 | 53.957 | 36.006 | 1.00 | 14.59 | A |
| ATOM | 1016 | C | SER | A | 282 | 65.494 | 52.713 | 38.058 | 1.00 | 9.29 | A |
| ATOM | 1017 | O | SER | A | 282 | 66.514 | 52.434 | 37.426 | 1.00 | 10.99 | A |
| ATOM | 1018 | N | ASN | A | 283 | 64.716 | 51.790 | 38.622 | 1.00 | 10.33 | A |
| ATOM | 1019 | CA | ASN | A | 283 | 65.043 | 50.376 | 38.511 | 1.00 | 10.12 | A |
| ATOM | 1020 | CB | ASN | A | 283 | 64.017 | 49.513 | 39.252 | 1.00 | 10.66 | A |
| ATOM | 1021 | CG | ASN | A | 283 | 64.278 | 49.452 | 40.730 | 1.00 | 12.46 | A |
| ATOM | 1022 | OD1 | ASN | A | 283 | 65.422 | 49.554 | 41.168 | 1.00 | 14.88 | A |
| ATOM | 1023 | ND2 | ASN | A | 283 | 63.221 | 49.262 | 41.513 | 1.00 | 12.08 | A |
| ATOM | 1024 | C | ASN | A | 283 | 65.065 | 49.969 | 37.044 | 1.00 | 10.47 | A |
| ATOM | 1025 | O | ASN | A | 283 | 65.911 | 49.190 | 36.623 | 1.00 | 12.66 | A |
| ATOM | 1026 | N | GLN | A | 284 | 64.125 | 50.498 | 36.269 | 1.00 | 12.15 | A |
| ATOM | 1027 | CA | GLN | A | 284 | 64.053 | 50.161 | 34.853 | 1.00 | 11.81 | A |
| ATOM | 1028 | CB | GLN | A | 284 | 62.813 | 50.790 | 34.214 | 1.00 | 15.62 | A |
| ATOM | 1029 | CG | GLN | A | 284 | 62.480 | 50.202 | 32.855 | 1.00 | 22.18 | A |
| ATOM | 1030 | CD | GLN | A | 284 | 62.331 | 48.691 | 32.910 | 1.00 | 24.03 | A |
| ATOM | 1031 | OE1 | GLN | A | 284 | 61.589 | 48.157 | 33.741 | 1.00 | 25.53 | A |
| ATOM | 1032 | NE2 | GLN | A | 284 | 63.036 | 47.994 | 32.026 | 1.00 | 26.67 | A |
| ATOM | 1033 | C | GLN | A | 284 | 65.309 | 50.611 | 34.114 | 1.00 | 12.41 | A |
| ATOM | 1034 | O | GLN | A | 284 | 65.772 | 49.940 | 33.196 | 1.00 | 13.25 | A |
| ATOM | 1035 | N | PHE | A | 285 | 65.870 | 51.744 | 34.522 | 1.00 | 12.41 | A |
| ATOM | 1036 | CA | PHE | A | 285 | 67.077 | 52.242 | 33.879 | 1.00 | 11.68 | A |
| ATOM | 1037 | CB | PHE | A | 285 | 67.435 | 53.624 | 34.437 | 1.00 | 11.83 | A |
| ATOM | 1038 | CG | PHE | A | 285 | 68.660 | 54.237 | 33.814 | 1.00 | 10.72 | A |
| ATOM | 1039 | CD1 | PHE | A | 285 | 69.927 | 53.892 | 34.257 | 1.00 | 10.38 | A |
| ATOM | 1040 | CD2 | PHE | A | 285 | 68.546 | 55.147 | 32.772 | 1.00 | 11.44 | A |
| ATOM | 1041 | CE1 | PHE | A | 285 | 71.062 | 54.442 | 33.678 | 1.00 | 13.14 | A |
| ATOM | 1042 | CE2 | PHE | A | 285 | 69.680 | 55.703 | 32.186 | 1.00 | 12.75 | A |
| ATOM | 1043 | CZ | PHE | A | 285 | 70.938 | 55.349 | 32.641 | 1.00 | 13.30 | A |
| ATOM | 1044 | C | PHE | A | 285 | 68.214 | 51.253 | 34.108 | 1.00 | 10.36 | A |
| ATOM | 1045 | O | PHE | A | 285 | 68.955 | 50.918 | 33.181 | 1.00 | 12.82 | A |
| ATOM | 1046 | N | LEU | A | 286 | 68.346 | 50.779 | 35.345 | 1.00 | 11.39 | A |
| ATOM | 1047 | CA | LEU | A | 286 | 69.392 | 49.821 | 35.696 | 1.00 | 12.33 | A |
| ATOM | 1048 | CB | LEU | A | 286 | 69.391 | 49.565 | 37.204 | 1.00 | 14.20 | A |
| ATOM | 1049 | CG | LEU | A | 286 | 69.708 | 50.785 | 38.066 | 1.00 | 15.06 | A |
| ATOM | 1050 | CD1 | LEU | A | 286 | 69.510 | 50.430 | 39.528 | 1.00 | 14.27 | A |
| ATOM | 1051 | CD2 | LEU | A | 286 | 71.126 | 51.248 | 37.798 | 1.00 | 15.73 | A |
| ATOM | 1052 | C | LEU | A | 286 | 69.192 | 48.501 | 34.963 | 1.00 | 12.49 | A |
| ATOM | 1053 | O | LEU | A | 286 | 70.153 | 47.840 | 34.574 | 1.00 | 14.41 | A |
| ATOM | 1054 | N | ILE | A | 287 | 67.938 | 48.112 | 34.781 | 1.00 | 13.50 | A |
| ATOM | 1055 | CA | ILE | A | 287 | 67.635 | 46.870 | 34.095 | 1.00 | 14.65 | A |
| ATOM | 1056 | CB | ILE | A | 287 | 66.141 | 46.517 | 34.267 | 1.00 | 14.38 | A |
| ATOM | 1057 | CG2 | ILE | A | 287 | 65.738 | 45.406 | 33.305 | 1.00 | 16.15 | A |
| ATOM | 1058 | CG1 | ILE | A | 287 | 65.888 | 46.104 | 35.720 | 1.00 | 14.21 | A |
| ATOM | 1059 | CD1 | ILE | A | 287 | 64.425 | 45.994 | 36.082 | 1.00 | 14.40 | A |
| ATOM | 1060 | C | ILE | A | 287 | 67.993 | 46.986 | 32.619 | 1.00 | 14.47 | A |
| ATOM | 1061 | O | ILE | A | 287 | 68.615 | 46.085 | 32.049 | 1.00 | 14.94 | A |
| ATOM | 1062 | N | ASN | A | 288 | 67.623 | 48.111 | 32.012 | 1.00 | 13.61 | A |
| ATOM | 1063 | CA | ASN | A | 288 | 67.896 | 48.342 | 30.597 | 1.00 | 15.19 | A |
| ATOM | 1064 | CB | ASN | A | 288 | 67.163 | 49.592 | 30.114 | 1.00 | 15.01 | A |
| ATOM | 1065 | CG | ASN | A | 288 | 65.663 | 49.419 | 30.125 | 1.00 | 19.03 | A |
| ATOM | 1066 | OD1 | ASN | A | 288 | 65.159 | 48.298 | 30.051 | 1.00 | 20.46 | A |
| ATOM | 1067 | ND2 | ASN | A | 288 | 64.936 | 50.530 | 30.204 | 1.00 | 21.63 | A |
| ATOM | 1068 | C | ASN | A | 288 | 69.377 | 48.466 | 30.265 | 1.00 | 14.72 | A |
| ATOM | 1069 | O | ASN | A | 288 | 69.789 | 48.171 | 29.141 | 1.00 | 18.40 | A |
| ATOM | 1070 | N | THR | A | 289 | 70.180 | 48.903 | 31.229 | 1.00 | 14.21 | A |
| ATOM | 1071 | CA | THR | A | 289 | 71.614 | 49.052 | 30.991 | 1.00 | 13.57 | A |
| ATOM | 1072 | CB | THR | A | 289 | 72.180 | 50.284 | 31.732 | 1.00 | 14.64 | A |
| ATOM | 1073 | OG1 | THR | A | 289 | 71.852 | 50.201 | 33.124 | 1.00 | 16.00 | A |
| ATOM | 1074 | CG2 | THR | A | 289 | 71.608 | 51.568 | 31.151 | 1.00 | 14.01 | A |
| ATOM | 1075 | C | THR | A | 289 | 72.418 | 47.816 | 31.398 | 1.00 | 13.31 | A |
| ATOM | 1076 | O | THR | A | 289 | 73.646 | 47.800 | 31.288 | 1.00 | 14.55 | A |
| ATOM | 1077 | N | ASN | A | 290 | 71.721 | 46.773 | 31.837 | 1.00 | 13.87 | A |
| ATOM | 1078 | CA | ASN | A | 290 | 72.374 | 45.541 | 32.272 | 1.00 | 15.12 | A |
| ATOM | 1079 | CB | ASN | A | 290 | 73.137 | 44.881 | 31.121 | 1.00 | 17.91 | A |
| ATOM | 1080 | CG | ASN | A | 290 | 72.225 | 44.433 | 30.010 | 1.00 | 23.51 | A |
| ATOM | 1081 | OD1 | ASN | A | 290 | 71.158 | 43.867 | 30.259 | 1.00 | 27.23 | A |
| ATOM | 1082 | ND2 | ASN | A | 290 | 72.641 | 44.668 | 28.771 | 1.00 | 26.45 | A |
| ATOM | 1083 | C | ASN | A | 290 | 73.336 | 45.810 | 33.415 | 1.00 | 15.07 | A |
| ATOM | 1084 | O | ASN | A | 290 | 74.436 | 45.258 | 33.459 | 1.00 | 16.56 | A |
| ATOM | 1085 | N | SER | A | 291 | 72.909 | 46.664 | 34.338 | 1.00 | 15.07 | A |
| ATOM | 1086 | CA | SER | A | 291 | 73.707 | 47.006 | 35.506 | 1.00 | 14.92 | A |
| ATOM | 1087 | CB | SER | A | 291 | 72.971 | 48.038 | 36.361 | 1.00 | 17.76 | A |
| ATOM | 1088 | OG | SER | A | 291 | 73.583 | 48.166 | 37.636 | 1.00 | 25.05 | A |
| ATOM | 1089 | C | SER | A | 291 | 73.997 | 45.775 | 36.353 | 1.00 | 13.85 | A |
| ATOM | 1090 | O | SER | A | 291 | 73.175 | 44.865 | 36.447 | 1.00 | 13.51 | A |
| ATOM | 1091 | N | GLU | A | 292 | 75.172 | 45.758 | 36.974 | 1.00 | 15.67 | A |

TABLE 1-continued

| | | | | | | | | | | |
|---|---|---|---|---|---|---|---|---|---|---|
| ATOM | 1092 | CA | GLU | A | 292 | 75.570 | 44.645 | 37.830 | 1.00 | 16.78 | A |
| ATOM | 1093 | CB | GLU | A | 292 | 76.915 | 44.951 | 38.493 | 1.00 | 19.65 | A |
| ATOM | 1094 | CG | GLU | A | 292 | 77.358 | 43.921 | 39.521 | 1.00 | 24.88 | A |
| ATOM | 1095 | CD | GLU | A | 292 | 78.737 | 44.217 | 40.087 | 1.00 | 27.13 | A |
| ATOM | 1096 | OE1 | GLU | A | 292 | 78.952 | 45.347 | 40.575 | 1.00 | 29.29 | A |
| ATOM | 1097 | OE2 | GLU | A | 292 | 79.606 | 43.320 | 40.046 | 1.00 | 30.31 | A |
| ATOM | 1098 | C | GLU | A | 292 | 74.516 | 44.389 | 38.905 | 1.00 | 15.63 | A |
| ATOM | 1099 | O | GLU | A | 292 | 74.250 | 43.239 | 39.263 | 1.00 | 15.23 | A |
| ATOM | 1100 | N | LEU | A | 293 | 73.917 | 45.465 | 39.411 | 1.00 | 15.27 | A |
| ATOM | 1101 | CA | LEU | A | 293 | 72.891 | 45.349 | 40.446 | 1.00 | 14.59 | A |
| ATOM | 1102 | CB | LEU | A | 293 | 72.475 | 46.734 | 40.947 | 1.00 | 16.52 | A |
| ATOM | 1103 | CG | LEU | A | 293 | 73.424 | 47.464 | 41.899 | 1.00 | 19.49 | A |
| ATOM | 1104 | CD1 | LEU | A | 293 | 74.779 | 47.650 | 41.257 | 1.00 | 24.10 | A |
| ATOM | 1105 | CD2 | LEU | A | 293 | 72.817 | 48.805 | 42.269 | 1.00 | 20.66 | A |
| ATOM | 1106 | C | LEU | A | 293 | 71.659 | 44.608 | 39.940 | 1.00 | 13.51 | A |
| ATOM | 1107 | O | LEU | A | 293 | 71.095 | 43.768 | 40.639 | 1.00 | 14.29 | A |
| ATOM | 1108 | N | ALA | A | 294 | 71.240 | 44.916 | 38.720 | 1.00 | 13.49 | A |
| ATOM | 1109 | CA | ALA | A | 294 | 70.067 | 44.264 | 38.161 | 1.00 | 14.10 | A |
| ATOM | 1110 | CB | ALA | A | 294 | 69.683 | 44.915 | 36.832 | 1.00 | 15.46 | A |
| ATOM | 1111 | C | ALA | A | 294 | 70.334 | 42.775 | 37.970 | 1.00 | 14.31 | A |
| ATOM | 1112 | O | ALA | A | 294 | 69.462 | 41.937 | 38.207 | 1.00 | 15.96 | A |
| ATOM | 1113 | N | LEU | A | 295 | 71.546 | 42.441 | 37.544 | 1.00 | 14.87 | A |
| ATOM | 1114 | CA | LEU | A | 295 | 71.889 | 41.045 | 37.337 | 1.00 | 15.39 | A |
| ATOM | 1115 | CB | LEU | A | 295 | 73.251 | 40.941 | 36.644 | 1.00 | 16.41 | A |
| ATOM | 1116 | CG | LEU | A | 295 | 73.257 | 41.520 | 35.225 | 1.00 | 20.94 | A |
| ATOM | 1117 | CD1 | LEU | A | 295 | 74.638 | 41.376 | 34.618 | 1.00 | 21.57 | A |
| ATOM | 1118 | CD2 | LEU | A | 295 | 72.221 | 40.801 | 34.372 | 1.00 | 22.86 | A |
| ATOM | 1119 | C | LEU | A | 295 | 71.895 | 40.294 | 38.668 | 1.00 | 16.39 | A |
| ATOM | 1120 | O | LEU | A | 295 | 71.376 | 39.185 | 38.765 | 1.00 | 18.29 | A |
| ATOM | 1121 | N | MET | A | 296 | 72.462 | 40.912 | 39.697 | 1.00 | 16.33 | A |
| ATOM | 1122 | CA | MET | A | 296 | 72.530 | 40.296 | 41.020 | 1.00 | 17.98 | A |
| ATOM | 1123 | CB | MET | A | 296 | 73.257 | 41.220 | 41.996 | 1.00 | 24.29 | A |
| ATOM | 1124 | CG | MET | A | 296 | 74.705 | 41.495 | 41.691 | 1.00 | 29.41 | A |
| ATOM | 1125 | SD | MET | A | 296 | 75.292 | 42.798 | 42.788 | 1.00 | 31.48 | A |
| ATOM | 1126 | CE | MET | A | 296 | 74.627 | 42.251 | 44.337 | 1.00 | 29.53 | A |
| ATOM | 1127 | C | MET | A | 296 | 71.156 | 39.997 | 41.616 | 1.00 | 15.96 | A |
| ATOM | 1128 | O | MET | A | 296 | 70.931 | 38.932 | 42.203 | 1.00 | 16.23 | A |
| ATOM | 1129 | N | TYR | A | 297 | 70.243 | 40.950 | 41.473 | 1.00 | 14.24 | A |
| ATOM | 1130 | CA | TYR | A | 297 | 68.918 | 40.809 | 42.051 | 1.00 | 12.86 | A |
| ATOM | 1131 | CB | TYR | A | 297 | 68.525 | 42.131 | 42.725 | 1.00 | 13.61 | A |
| ATOM | 1132 | CG | TYR | A | 297 | 69.411 | 42.453 | 43.903 | 1.00 | 13.90 | A |
| ATOM | 1133 | CD1 | TYR | A | 297 | 69.460 | 41.607 | 45.002 | 1.00 | 13.95 | A |
| ATOM | 1134 | CE1 | TYR | A | 297 | 70.315 | 41.855 | 46.057 | 1.00 | 15.30 | A |
| ATOM | 1135 | CD2 | TYR | A | 297 | 70.240 | 43.567 | 43.892 | 1.00 | 14.98 | A |
| ATOM | 1136 | CE2 | TYR | A | 297 | 71.101 | 43.824 | 44.947 | 1.00 | 18.07 | A |
| ATOM | 1137 | CZ | TYR | A | 297 | 71.131 | 42.962 | 46.023 | 1.00 | 16.45 | A |
| ATOM | 1138 | OH | TYR | A | 297 | 71.985 | 43.209 | 47.075 | 1.00 | 20.50 | A |
| ATOM | 1139 | C | TYR | A | 297 | 67.829 | 40.340 | 41.095 | 1.00 | 11.93 | A |
| ATOM | 1140 | O | TYR | A | 297 | 66.642 | 40.446 | 41.392 | 1.00 | 12.79 | A |
| ATOM | 1141 | N | ASN | A | 298 | 68.244 | 39.803 | 39.954 | 1.00 | 11.89 | A |
| ATOM | 1142 | CA | ASN | A | 298 | 67.305 | 39.289 | 38.970 | 1.00 | 11.45 | A |
| ATOM | 1143 | CB | ASN | A | 298 | 66.748 | 37.945 | 39.452 | 1.00 | 12.91 | A |
| ATOM | 1144 | CG | ASN | A | 298 | 67.845 | 36.906 | 39.619 | 1.00 | 14.01 | A |
| ATOM | 1145 | OD1 | ASN | A | 298 | 68.662 | 36.721 | 38.723 | 1.00 | 15.20 | A |
| ATOM | 1146 | ND2 | ASN | A | 298 | 67.874 | 36.235 | 40.767 | 1.00 | 14.19 | A |
| ATOM | 1147 | C | ASN | A | 298 | 66.186 | 40.257 | 38.609 | 1.00 | 10.25 | A |
| ATOM | 1148 | O | ASN | A | 298 | 65.016 | 39.885 | 38.507 | 1.00 | 12.39 | A |
| ATOM | 1149 | N | ASP | A | 299 | 66.579 | 41.512 | 38.414 | 1.00 | 12.68 | A |
| ATOM | 1150 | CA | ASP | A | 299 | 65.676 | 42.585 | 38.013 | 1.00 | 12.14 | A |
| ATOM | 1151 | CB | ASP | A | 299 | 65.122 | 42.307 | 36.606 | 1.00 | 13.25 | A |
| ATOM | 1152 | CG | ASP | A | 299 | 66.218 | 42.165 | 35.551 | 1.00 | 16.79 | A |
| ATOM | 1153 | OD1 | ASP | A | 299 | 67.349 | 42.648 | 35.768 | 1.00 | 16.70 | A |
| ATOM | 1154 | OD2 | ASP | A | 299 | 65.936 | 41.582 | 34.480 | 1.00 | 17.81 | A |
| ATOM | 1155 | C | ASP | A | 299 | 64.512 | 42.875 | 38.960 | 1.00 | 12.75 | A |
| ATOM | 1156 | O | ASP | A | 299 | 63.593 | 43.609 | 38.598 | 1.00 | 15.43 | A |
| ATOM | 1157 | N | GLU | A | 300 | 64.555 | 42.328 | 40.170 | 1.00 | 13.14 | A |
| ATOM | 1158 | CA | GLU | A | 300 | 63.466 | 42.543 | 41.131 | 1.00 | 14.50 | A |
| ATOM | 1159 | CB | GLU | A | 300 | 63.027 | 41.203 | 41.722 | 1.00 | 16.17 | A |
| ATOM | 1160 | CG | GLU | A | 300 | 62.008 | 41.337 | 42.845 | 1.00 | 21.34 | A |
| ATOM | 1161 | CD | GLU | A | 300 | 60.614 | 41.692 | 42.349 | 1.00 | 27.09 | A |
| ATOM | 1162 | OE1 | GLU | A | 300 | 60.483 | 42.598 | 41.496 | 1.00 | 29.87 | A |
| ATOM | 1163 | OE2 | GLU | A | 300 | 59.641 | 41.069 | 42.825 | 1.00 | 30.80 | A |
| ATOM | 1164 | C | GLU | A | 300 | 63.831 | 43.498 | 42.268 | 1.00 | 13.55 | A |
| ATOM | 1165 | O | GLU | A | 300 | 64.785 | 43.247 | 43.006 | 1.00 | 15.42 | A |
| ATOM | 1166 | N | SER | A | 301 | 63.054 | 44.574 | 42.419 | 1.00 | 12.92 | A |
| ATOM | 1167 | CA | SER | A | 301 | 63.301 | 45.578 | 43.465 | 1.00 | 11.80 | A |
| ATOM | 1168 | CB | SER | A | 301 | 62.759 | 45.093 | 44.816 | 1.00 | 13.57 | A |
| ATOM | 1169 | OG | SER | A | 301 | 61.351 | 44.933 | 44.774 | 1.00 | 14.63 | A |
| ATOM | 1170 | C | SER | A | 301 | 64.804 | 45.810 | 43.558 | 1.00 | 10.78 | A |

TABLE 1-continued

| | | | | | | | | | | |
|---|---|---|---|---|---|---|---|---|---|---|
| ATOM | 1171 | O | SER | A | 301 | 65.394 | 45.807 | 44.637 | 1.00 | 12.22 | A |
| ATOM | 1172 | N | VAL | A | 302 | 65.418 | 46.045 | 42.407 | 1.00 | 11.02 | A |
| ATOM | 1173 | CA | VAL | A | 302 | 66.861 | 46.211 | 42.354 | 1.00 | 10.12 | A |
| ATOM | 1174 | CB | VAL | A | 302 | 67.319 | 46.536 | 40.926 | 1.00 | 11.34 | A |
| ATOM | 1175 | CG1 | VAL | A | 302 | 68.837 | 46.697 | 40.891 | 1.00 | 11.71 | A |
| ATOM | 1176 | CG2 | VAL | A | 302 | 66.869 | 45.422 | 39.985 | 1.00 | 13.02 | A |
| ATOM | 1177 | C | VAL | A | 302 | 67.452 | 47.236 | 43.308 | 1.00 | 9.28 | A |
| ATOM | 1178 | O | VAL | A | 302 | 68.333 | 46.909 | 44.108 | 1.00 | 12.15 | A |
| ATOM | 1179 | N | LEU | A | 303 | 66.980 | 48.473 | 43.234 | 1.00 | 11.21 | A |
| ATOM | 1180 | CA | LEU | A | 303 | 67.523 | 49.510 | 44.098 | 1.00 | 10.85 | A |
| ATOM | 1181 | CB | LEU | A | 303 | 67.016 | 50.890 | 43.664 | 1.00 | 14.89 | A |
| ATOM | 1182 | CG | LEU | A | 303 | 67.774 | 51.471 | 42.467 | 1.00 | 18.24 | A |
| ATOM | 1183 | CD1 | LEU | A | 303 | 67.149 | 52.779 | 42.024 | 1.00 | 21.91 | A |
| ATOM | 1184 | CD2 | LEU | A | 303 | 69.235 | 51.673 | 42.861 | 1.00 | 17.26 | A |
| ATOM | 1185 | C | LEU | A | 303 | 67.209 | 49.286 | 45.565 | 1.00 | 10.37 | A |
| ATOM | 1186 | O | LEU | A | 303 | 68.065 | 49.495 | 46.418 | 1.00 | 11.02 | A |
| ATOM | 1187 | N | GLU | A | 304 | 65.986 | 48.856 | 45.854 | 1.00 | 10.15 | A |
| ATOM | 1188 | CA | GLU | A | 304 | 65.576 | 48.620 | 47.232 | 1.00 | 10.99 | A |
| ATOM | 1189 | CB | GLU | A | 304 | 64.098 | 48.222 | 47.275 | 1.00 | 13.64 | A |
| ATOM | 1190 | CG | GLU | A | 304 | 63.117 | 49.329 | 46.828 | 1.00 | 14.71 | A |
| ATOM | 1191 | CD | GLU | A | 304 | 63.172 | 49.652 | 45.334 | 1.00 | 15.64 | A |
| ATOM | 1192 | OE1 | GLU | A | 304 | 63.510 | 48.760 | 44.526 | 1.00 | 13.16 | A |
| ATOM | 1193 | OE2 | GLU | A | 304 | 62.847 | 50.802 | 44.960 | 1.00 | 15.63 | A |
| ATOM | 1194 | C | GLU | A | 304 | 66.451 | 47.546 | 47.891 | 1.00 | 10.98 | A |
| ATOM | 1195 | O | GLU | A | 304 | 66.809 | 47.662 | 49.066 | 1.00 | 12.37 | A |
| ATOM | 1196 | N | ASN | A | 305 | 66.801 | 46.504 | 47.144 | 1.00 | 10.94 | A |
| ATOM | 1197 | CA | ASN | A | 305 | 67.666 | 45.463 | 47.697 | 1.00 | 10.24 | A |
| ATOM | 1198 | CB | ASN | A | 305 | 67.753 | 44.273 | 46.736 | 1.00 | 11.47 | A |
| ATOM | 1199 | CG | ASN | A | 305 | 66.638 | 43.276 | 46.959 | 1.00 | 13.72 | A |
| ATOM | 1200 | OD1 | ASN | A | 305 | 66.591 | 42.613 | 47.992 | 1.00 | 16.46 | A |
| ATOM | 1201 | ND2 | ASN | A | 305 | 65.729 | 43.173 | 46.001 | 1.00 | 15.40 | A |
| ATOM | 1202 | C | ASN | A | 305 | 69.054 | 46.038 | 47.950 | 1.00 | 9.96 | A |
| ATOM | 1203 | O | ASN | A | 305 | 69.711 | 45.705 | 48.938 | 1.00 | 12.28 | A |
| ATOM | 1204 | N | HIS | A | 306 | 69.509 | 46.904 | 47.054 | 1.00 | 12.09 | A |
| ATOM | 1205 | CA | HIS | A | 306 | 70.812 | 47.525 | 47.230 | 1.00 | 11.27 | A |
| ATOM | 1206 | CB | HIS | A | 306 | 71.189 | 48.331 | 45.986 | 1.00 | 13.44 | A |
| ATOM | 1207 | CG | HIS | A | 306 | 72.535 | 48.975 | 46.079 | 1.00 | 13.87 | A |
| ATOM | 1208 | CD2 | HIS | A | 306 | 72.908 | 50.276 | 46.038 | 1.00 | 15.76 | A |
| ATOM | 1209 | ND1 | HIS | A | 306 | 73.691 | 48.249 | 46.270 | 1.00 | 15.82 | A |
| ATOM | 1210 | CE1 | HIS | A | 306 | 74.718 | 49.076 | 46.345 | 1.00 | 17.17 | A |
| ATOM | 1211 | NE2 | HIS | A | 306 | 74.271 | 50.312 | 46.208 | 1.00 | 15.59 | A |
| ATOM | 1212 | C | HIS | A | 306 | 70.816 | 48.438 | 48.459 | 1.00 | 10.63 | A |
| ATOM | 1213 | O | HIS | A | 306 | 71.772 | 48.435 | 49.229 | 1.00 | 10.64 | A |
| ATOM | 1214 | N | HIS | A | 307 | 69.745 | 49.211 | 48.651 | 1.00 | 10.21 | A |
| ATOM | 1215 | CA | HIS | A | 307 | 69.676 | 50.112 | 49.807 | 1.00 | 10.36 | A |
| ATOM | 1216 | CB | HIS | A | 307 | 68.350 | 50.894 | 49.830 | 1.00 | 10.66 | A |
| ATOM | 1217 | CG | HIS | A | 307 | 68.074 | 51.673 | 48.578 | 1.00 | 8.93 | A |
| ATOM | 1218 | CD2 | HIS | A | 307 | 66.937 | 51.816 | 47.855 | 1.00 | 9.54 | A |
| ATOM | 1219 | ND1 | HIS | A | 307 | 69.032 | 52.432 | 47.941 | 1.00 | 10.97 | A |
| ATOM | 1220 | CE1 | HIS | A | 307 | 68.498 | 53.006 | 46.875 | 1.00 | 10.16 | A |
| ATOM | 1221 | NE2 | HIS | A | 307 | 67.229 | 52.648 | 46.801 | 1.00 | 10.25 | A |
| ATOM | 1222 | C | HIS | A | 307 | 69.806 | 49.309 | 51.101 | 1.00 | 9.63 | A |
| ATOM | 1223 | O | HIS | A | 307 | 70.486 | 49.720 | 52.040 | 1.00 | 10.40 | A |
| ATOM | 1224 | N | LEU | A | 308 | 69.138 | 48.163 | 51.149 | 1.00 | 9.63 | A |
| ATOM | 1225 | CA | LEU | A | 308 | 69.205 | 47.294 | 52.318 | 1.00 | 10.46 | A |
| ATOM | 1226 | CB | LEU | A | 308 | 68.249 | 46.112 | 52.144 | 1.00 | 11.26 | A |
| ATOM | 1227 | CG | LEU | A | 308 | 66.771 | 46.427 | 52.386 | 1.00 | 11.84 | A |
| ATOM | 1228 | CD1 | LEU | A | 308 | 65.916 | 45.314 | 51.814 | 1.00 | 14.13 | A |
| ATOM | 1229 | CD2 | LEU | A | 308 | 66.521 | 46.596 | 53.883 | 1.00 | 14.79 | A |
| ATOM | 1230 | C | LEU | A | 308 | 70.622 | 46.774 | 52.531 | 1.00 | 10.29 | A |
| ATOM | 1231 | O | LEU | A | 308 | 71.152 | 46.828 | 53.642 | 1.00 | 12.51 | A |
| ATOM | 1232 | N | ALA | A | 309 | 71.240 | 46.287 | 51.458 | 1.00 | 10.48 | A |
| ATOM | 1233 | CA | ALA | A | 309 | 72.595 | 45.750 | 51.543 | 1.00 | 11.75 | A |
| ATOM | 1234 | CB | ALA | A | 309 | 73.062 | 45.274 | 50.165 | 1.00 | 11.23 | A |
| ATOM | 1235 | C | ALA | A | 309 | 73.571 | 46.782 | 52.091 | 1.00 | 10.51 | A |
| ATOM | 1236 | O | ALA | A | 309 | 74.357 | 46.482 | 52.991 | 1.00 | 13.69 | A |
| ATOM | 1237 | N | VAL | A | 310 | 73.518 | 47.996 | 51.552 | 1.00 | 10.84 | A |
| ATOM | 1238 | CA | VAL | A | 310 | 74.413 | 49.065 | 51.987 | 1.00 | 11.11 | A |
| ATOM | 1239 | CB | VAL | A | 310 | 74.295 | 50.297 | 51.062 | 1.00 | 11.70 | A |
| ATOM | 1240 | CG1 | VAL | A | 310 | 75.127 | 51.440 | 51.612 | 1.00 | 10.20 | A |
| ATOM | 1241 | CG2 | VAL | A | 310 | 74.759 | 49.933 | 49.659 | 1.00 | 11.55 | A |
| ATOM | 1242 | C | VAL | A | 310 | 74.138 | 49.492 | 53.423 | 1.00 | 11.21 | A |
| ATOM | 1243 | O | VAL | A | 310 | 75.052 | 49.572 | 54.246 | 1.00 | 12.91 | A |
| ATOM | 1244 | N | GLY | A | 311 | 72.872 | 49.767 | 53.720 | 1.00 | 10.62 | A |
| ATOM | 1245 | CA | GLY | A | 311 | 72.502 | 50.173 | 55.066 | 1.00 | 11.56 | A |
| ATOM | 1246 | C | GLY | A | 311 | 72.999 | 49.224 | 56.145 | 1.00 | 12.62 | A |
| ATOM | 1247 | O | GLY | A | 311 | 73.504 | 49.665 | 57.186 | 1.00 | 14.88 | A |
| ATOM | 1248 | N | PHE | A | 312 | 72.860 | 47.921 | 55.916 | 1.00 | 12.70 | A |
| ATOM | 1249 | CA | PHE | A | 312 | 73.317 | 46.949 | 56.905 | 1.00 | 13.65 | A |

TABLE 1-continued

| ATOM | 1250 | CB | PHE | A | 312 | 72.570 | 45.624 | 56.728 | 1.00 | 15.16 | A |
| --- | --- | --- | --- | --- | --- | --- | --- | --- | --- | --- | --- |
| ATOM | 1251 | CG | PHE | A | 312 | 71.208 | 45.619 | 57.365 | 1.00 | 18.03 | A |
| ATOM | 1252 | CD1 | PHE | A | 312 | 71.081 | 45.581 | 58.744 | 1.00 | 19.84 | A |
| ATOM | 1253 | CD2 | PHE | A | 312 | 70.062 | 45.688 | 56.592 | 1.00 | 20.32 | A |
| ATOM | 1254 | CE1 | PHE | A | 312 | 69.836 | 45.613 | 59.344 | 1.00 | 22.38 | A |
| ATOM | 1255 | CE2 | PHE | A | 312 | 68.812 | 45.721 | 57.186 | 1.00 | 20.03 | A |
| ATOM | 1256 | CZ | PHE | A | 312 | 68.700 | 45.684 | 58.563 | 1.00 | 20.47 | A |
| ATOM | 1257 | C | PHE | A | 312 | 74.826 | 46.729 | 56.884 | 1.00 | 13.35 | A |
| ATOM | 1258 | O | PHE | A | 312 | 75.441 | 46.517 | 57.929 | 1.00 | 14.74 | A |
| ATOM | 1259 | N | LYS | A | 313 | 75.423 | 46.789 | 55.700 | 1.00 | 12.71 | A |
| ATOM | 1260 | CA | LYS | A | 313 | 76.868 | 46.613 | 55.566 | 1.00 | 13.38 | A |
| ATOM | 1261 | CB | LYS | A | 313 | 77.250 | 46.689 | 54.083 | 1.00 | 15.99 | A |
| ATOM | 1262 | CG | LYS | A | 313 | 78.730 | 46.724 | 53.785 | 1.00 | 22.93 | A |
| ATOM | 1263 | CD | LYS | A | 313 | 78.959 | 46.889 | 52.282 | 1.00 | 25.29 | A |
| ATOM | 1264 | CE | LYS | A | 313 | 78.294 | 48.160 | 51.758 | 1.00 | 25.27 | A |
| ATOM | 1265 | NZ | LYS | A | 313 | 78.389 | 48.302 | 50.274 | 1.00 | 29.05 | A |
| ATOM | 1266 | C | LYS | A | 313 | 77.642 | 47.672 | 56.361 | 1.00 | 12.46 | A |
| ATOM | 1267 | O | LYS | A | 313 | 78.683 | 47.381 | 56.965 | 1.00 | 12.84 | A |
| ATOM | 1268 | N | LEU | A | 314 | 77.131 | 48.900 | 56.374 | 1.00 | 12.42 | A |
| ATOM | 1269 | CA | LEU | A | 314 | 77.805 | 49.989 | 57.070 | 1.00 | 13.48 | A |
| ATOM | 1270 | CB | LEU | A | 314 | 77.144 | 51.325 | 56.724 | 1.00 | 13.87 | A |
| ATOM | 1271 | CG | LEU | A | 314 | 77.324 | 51.741 | 55.259 | 1.00 | 14.33 | A |
| ATOM | 1272 | CD1 | LEU | A | 314 | 76.597 | 53.052 | 55.003 | 1.00 | 16.01 | A |
| ATOM | 1273 | CD2 | LEU | A | 314 | 78.807 | 51.878 | 54.944 | 1.00 | 13.72 | A |
| ATOM | 1274 | C | LEU | A | 314 | 77.881 | 49.817 | 58.580 | 1.00 | 12.65 | A |
| ATOM | 1275 | O | LEU | A | 314 | 78.688 | 50.479 | 59.231 | 1.00 | 13.97 | A |
| ATOM | 1276 | N | LEU | A | 315 | 77.055 | 48.932 | 59.132 | 1.00 | 14.31 | A |
| ATOM | 1277 | CA | LEU | A | 315 | 77.080 | 48.676 | 60.569 | 1.00 | 14.85 | A |
| ATOM | 1278 | CB | LEU | A | 315 | 75.934 | 47.745 | 60.968 | 1.00 | 15.84 | A |
| ATOM | 1279 | CG | LEU | A | 315 | 74.518 | 48.319 | 60.892 | 1.00 | 15.66 | A |
| ATOM | 1280 | CD1 | LEU | A | 315 | 73.509 | 47.194 | 61.031 | 1.00 | 17.27 | A |
| ATOM | 1281 | CD2 | LEU | A | 315 | 74.332 | 49.363 | 61.981 | 1.00 | 15.76 | A |
| ATOM | 1282 | C | LEU | A | 315 | 78.406 | 48.022 | 60.929 | 1.00 | 15.95 | A |
| ATOM | 1283 | O | LEU | A | 315 | 78.816 | 48.025 | 62.093 | 1.00 | 17.54 | A |
| ATOM | 1284 | N | GLN | A | 316 | 79.079 | 47.474 | 59.920 | 1.00 | 15.51 | A |
| ATOM | 1285 | CA | GLN | A | 316 | 80.358 | 46.796 | 60.119 | 1.00 | 16.62 | A |
| ATOM | 1286 | CB | GLN | A | 316 | 80.480 | 45.629 | 59.139 | 1.00 | 17.82 | A |
| ATOM | 1287 | CG | GLN | A | 316 | 79.479 | 44.516 | 59.391 | 1.00 | 21.80 | A |
| ATOM | 1288 | CD | GLN | A | 316 | 79.541 | 43.438 | 58.331 | 1.00 | 23.44 | A |
| ATOM | 1289 | OE1 | GLN | A | 316 | 80.623 | 43.073 | 57.870 | 1.00 | 27.65 | A |
| ATOM | 1290 | NE2 | GLN | A | 316 | 78.381 | 42.913 | 57.944 | 1.00 | 26.55 | A |
| ATOM | 1291 | C | GLN | A | 316 | 81.594 | 47.680 | 60.014 | 1.00 | 16.29 | A |
| ATOM | 1292 | O | GLN | A | 316 | 82.711 | 47.213 | 60.259 | 1.00 | 17.60 | A |
| ATOM | 1293 | N | GLU | A | 317 | 81.421 | 48.946 | 59.646 | 1.00 | 15.99 | A |
| ATOM | 1294 | CA | GLU | A | 317 | 82.577 | 49.826 | 59.575 | 1.00 | 15.21 | A |
| ATOM | 1295 | CB | GLU | A | 317 | 82.250 | 51.121 | 58.820 | 1.00 | 16.42 | A |
| ATOM | 1296 | CG | GLU | A | 317 | 81.944 | 50.874 | 57.336 | 1.00 | 19.70 | A |
| ATOM | 1297 | CD | GLU | A | 317 | 82.405 | 51.999 | 56.411 | 1.00 | 21.20 | A |
| ATOM | 1298 | OE1 | GLU | A | 317 | 82.750 | 53.094 | 56.899 | 1.00 | 21.55 | A |
| ATOM | 1299 | OE2 | GLU | A | 317 | 82.412 | 51.784 | 55.180 | 1.00 | 22.14 | A |
| ATOM | 1300 | C | GLU | A | 317 | 83.020 | 50.103 | 61.011 | 1.00 | 15.05 | A |
| ATOM | 1301 | O | GLU | A | 317 | 82.270 | 49.861 | 61.961 | 1.00 | 15.02 | A |
| ATOM | 1302 | N | GLU | A | 318 | 84.242 | 50.590 | 61.170 | 1.00 | 16.70 | A |
| ATOM | 1303 | CA | GLU | A | 318 | 84.783 | 50.830 | 62.502 | 1.00 | 17.84 | A |
| ATOM | 1304 | CB | GLU | A | 318 | 86.208 | 51.374 | 62.387 | 1.00 | 21.34 | A |
| ATOM | 1305 | CG | GLU | A | 318 | 87.077 | 51.104 | 63.611 | 1.00 | 24.40 | A |
| ATOM | 1306 | CD | GLU | A | 318 | 87.429 | 49.633 | 63.775 | 1.00 | 26.61 | A |
| ATOM | 1307 | OE1 | GLU | A | 318 | 86.513 | 48.813 | 64.004 | 1.00 | 30.14 | A |
| ATOM | 1308 | OE2 | GLU | A | 318 | 88.630 | 49.295 | 63.671 | 1.00 | 30.43 | A |
| ATOM | 1309 | C | GLU | A | 318 | 83.937 | 51.758 | 63.367 | 1.00 | 17.27 | A |
| ATOM | 1310 | O | GLU | A | 318 | 83.556 | 52.843 | 62.935 | 1.00 | 17.34 | A |
| ATOM | 1311 | N | HIS | A | 319 | 83.651 | 51.301 | 64.588 | 1.00 | 17.50 | A |
| ATOM | 1312 | CA | HIS | A | 319 | 82.875 | 52.048 | 65.580 | 1.00 | 17.25 | A |
| ATOM | 1313 | CB | HIS | A | 319 | 83.651 | 53.298 | 65.990 | 1.00 | 18.02 | A |
| ATOM | 1314 | CG | HIS | A | 319 | 85.082 | 53.025 | 66.332 | 1.00 | 20.07 | A |
| ATOM | 1315 | CD2 | HIS | A | 319 | 85.640 | 52.129 | 67.181 | 1.00 | 20.84 | A |
| ATOM | 1316 | ND1 | HIS | A | 319 | 86.131 | 53.691 | 65.735 | 1.00 | 22.42 | A |
| ATOM | 1317 | CE1 | HIS | A | 319 | 87.273 | 53.215 | 66.199 | 1.00 | 22.47 | A |
| ATOM | 1318 | NE2 | HIS | A | 319 | 87.003 | 52.266 | 67.076 | 1.00 | 21.94 | A |
| ATOM | 1319 | C | HIS | A | 319 | 81.503 | 52.443 | 65.065 | 1.00 | 16.26 | A |
| ATOM | 1320 | O | HIS | A | 319 | 80.958 | 53.479 | 65.442 | 1.00 | 18.84 | A |
| ATOM | 1321 | N | CYS | A | 320 | 80.924 | 51.586 | 64.236 | 1.00 | 17.29 | A |
| ATOM | 1322 | CA | CYS | A | 320 | 79.641 | 51.885 | 63.625 | 1.00 | 20.46 | A |
| ATOM | 1323 | CB | CYS | A | 320 | 79.839 | 51.855 | 62.107 | 1.00 | 26.05 | A |
| ATOM | 1324 | SG | CYS | A | 320 | 78.587 | 52.657 | 61.131 | 1.00 | 39.75 | A |
| ATOM | 1325 | C | CYS | A | 320 | 78.481 | 50.965 | 64.015 | 1.00 | 16.87 | A |
| ATOM | 1326 | O | CYS | A | 320 | 77.366 | 51.150 | 63.535 | 1.00 | 17.20 | A |
| ATOM | 1327 | N | ASP | A | 321 | 78.710 | 49.989 | 64.890 | 1.00 | 16.43 | A |
| ATOM | 1328 | CA | ASP | A | 321 | 77.622 | 49.073 | 65.228 | 1.00 | 16.32 | A |

TABLE 1-continued

| | | | | | | | | | | |
|---|---|---|---|---|---|---|---|---|---|---|
| ATOM | 1329 | CB | ASP | A | 321 | 78.175 | 47.711 | 65.650 | 1.00 | 18.66 | A |
| ATOM | 1330 | CG | ASP | A | 321 | 77.087 | 46.654 | 65.750 | 1.00 | 21.06 | A |
| ATOM | 1331 | OD1 | ASP | A | 321 | 75.950 | 46.924 | 65.300 | 1.00 | 20.72 | A |
| ATOM | 1332 | OD2 | ASP | A | 321 | 77.365 | 45.553 | 66.265 | 1.00 | 23.53 | A |
| ATOM | 1333 | C | ASP | A | 321 | 76.644 | 49.572 | 66.281 | 1.00 | 15.84 | A |
| ATOM | 1334 | O | ASP | A | 321 | 76.808 | 49.322 | 67.479 | 1.00 | 17.01 | A |
| ATOM | 1335 | N | ILE | A | 322 | 75.605 | 50.263 | 65.827 | 1.00 | 15.83 | A |
| ATOM | 1336 | CA | ILE | A | 322 | 74.606 | 50.790 | 66.744 | 1.00 | 15.80 | A |
| ATOM | 1337 | CB | ILE | A | 322 | 73.722 | 51.855 | 66.068 | 1.00 | 15.39 | A |
| ATOM | 1338 | CG2 | ILE | A | 322 | 74.569 | 53.053 | 65.691 | 1.00 | 13.98 | A |
| ATOM | 1339 | CG1 | ILE | A | 322 | 73.023 | 51.265 | 64.846 | 1.00 | 15.35 | A |
| ATOM | 1340 | CD1 | ILE | A | 322 | 72.015 | 52.209 | 64.217 | 1.00 | 16.08 | A |
| ATOM | 1341 | C | ILE | A | 322 | 73.703 | 49.708 | 67.323 | 1.00 | 15.57 | A |
| ATOM | 1342 | O | ILE | A | 322 | 72.931 | 49.972 | 68.245 | 1.00 | 17.56 | A |
| ATOM | 1343 | N | PHE | A | 323 | 73.797 | 48.490 | 66.797 | 1.00 | 16.02 | A |
| ATOM | 1344 | CA | PHE | A | 323 | 72.962 | 47.406 | 67.312 | 1.00 | 15.98 | A |
| ATOM | 1345 | CB | PHE | A | 323 | 72.281 | 46.659 | 66.164 | 1.00 | 16.58 | A |
| ATOM | 1346 | CG | PHE | A | 323 | 71.388 | 47.526 | 65.317 | 1.00 | 16.40 | A |
| ATOM | 1347 | CD1 | PHE | A | 323 | 70.567 | 48.476 | 65.898 | 1.00 | 16.29 | A |
| ATOM | 1348 | CD2 | PHE | A | 323 | 71.347 | 47.365 | 63.940 | 1.00 | 16.51 | A |
| ATOM | 1349 | CE1 | PHE | A | 323 | 69.720 | 49.250 | 65.124 | 1.00 | 18.27 | A |
| ATOM | 1350 | CE2 | PHE | A | 323 | 70.501 | 48.137 | 63.160 | 1.00 | 17.82 | A |
| ATOM | 1351 | CZ | PHE | A | 323 | 69.688 | 49.078 | 63.751 | 1.00 | 16.29 | A |
| ATOM | 1352 | C | PHE | A | 323 | 73.748 | 46.423 | 68.173 | 1.00 | 17.19 | A |
| ATOM | 1353 | O | PHE | A | 323 | 73.273 | 45.331 | 68.483 | 1.00 | 17.72 | A |
| ATOM | 1354 | N | MET | A | 324 | 74.947 | 46.831 | 68.570 | 1.00 | 18.03 | A |
| ATOM | 1355 | CA | MET | A | 324 | 75.816 | 46.000 | 69.388 | 1.00 | 19.94 | A |
| ATOM | 1356 | CB | MET | A | 324 | 77.042 | 46.803 | 69.827 | 1.00 | 21.36 | A |
| ATOM | 1357 | CG | MET | A | 324 | 77.957 | 46.047 | 70.774 | 1.00 | 24.50 | A |
| ATOM | 1358 | SD | MET | A | 324 | 79.345 | 47.044 | 71.328 | 1.00 | 26.18 | A |
| ATOM | 1359 | CE | MET | A | 324 | 78.534 | 48.149 | 72.480 | 1.00 | 27.81 | A |
| ATOM | 1360 | C | MET | A | 324 | 75.143 | 45.410 | 70.624 | 1.00 | 19.21 | A |
| ATOM | 1361 | O | MET | A | 324 | 75.384 | 44.256 | 70.970 | 1.00 | 21.99 | A |
| ATOM | 1362 | N | ASN | A | 325 | 74.298 | 46.188 | 71.292 | 1.00 | 19.81 | A |
| ATOM | 1363 | CA | ASN | A | 325 | 73.662 | 45.678 | 72.495 | 1.00 | 19.35 | A |
| ATOM | 1364 | CB | ASN | A | 325 | 73.616 | 46.774 | 73.558 | 1.00 | 20.17 | A |
| ATOM | 1365 | CG | ASN | A | 325 | 75.001 | 47.113 | 74.081 | 1.00 | 21.13 | A |
| ATOM | 1366 | OD1 | ASN | A | 325 | 75.766 | 46.220 | 74.451 | 1.00 | 23.54 | A |
| ATOM | 1367 | ND2 | ASN | A | 325 | 75.333 | 48.396 | 74.110 | 1.00 | 24.33 | A |
| ATOM | 1368 | C | ASN | A | 325 | 72.301 | 45.017 | 72.327 | 1.00 | 19.91 | A |
| ATOM | 1369 | O | ASN | A | 325 | 71.643 | 44.676 | 73.311 | 1.00 | 21.09 | A |
| ATOM | 1370 | N | LEU | A | 326 | 71.870 | 44.837 | 71.084 | 1.00 | 18.05 | A |
| ATOM | 1371 | CA | LEU | A | 326 | 70.614 | 44.144 | 70.841 | 1.00 | 17.42 | A |
| ATOM | 1372 | CB | LEU | A | 326 | 70.075 | 44.455 | 69.442 | 1.00 | 19.27 | A |
| ATOM | 1373 | CG | LEU | A | 326 | 69.235 | 45.724 | 69.239 | 1.00 | 21.05 | A |
| ATOM | 1374 | CD1 | LEU | A | 326 | 67.943 | 45.606 | 70.015 | 1.00 | 24.37 | A |
| ATOM | 1375 | CD2 | LEU | A | 326 | 70.017 | 46.947 | 69.681 | 1.00 | 21.56 | A |
| ATOM | 1376 | C | LEU | A | 326 | 70.984 | 42.666 | 70.926 | 1.00 | 16.65 | A |
| ATOM | 1377 | O | LEU | A | 326 | 72.110 | 42.290 | 70.594 | 1.00 | 17.37 | A |
| ATOM | 1378 | N | THR | A | 327 | 70.060 | 41.833 | 71.390 | 1.00 | 16.29 | A |
| ATOM | 1379 | CA | THR | A | 327 | 70.334 | 40.405 | 71.468 | 1.00 | 17.21 | A |
| ATOM | 1380 | CB | THR | A | 327 | 69.244 | 39.651 | 72.261 | 1.00 | 17.28 | A |
| ATOM | 1381 | OG1 | THR | A | 327 | 67.975 | 39.818 | 71.616 | 1.00 | 19.02 | A |
| ATOM | 1382 | CG2 | THR | A | 327 | 69.157 | 40.179 | 73.683 | 1.00 | 18.40 | A |
| ATOM | 1383 | C | THR | A | 327 | 70.330 | 39.893 | 70.037 | 1.00 | 17.93 | A |
| ATOM | 1384 | O | THR | A | 327 | 69.813 | 40.566 | 69.144 | 1.00 | 16.92 | A |
| ATOM | 1385 | N | LYS | A | 328 | 70.912 | 38.719 | 69.808 | 1.00 | 19.42 | A |
| ATOM | 1386 | CA | LYS | A | 328 | 70.933 | 38.152 | 68.462 | 1.00 | 20.02 | A |
| ATOM | 1387 | CB | LYS | A | 328 | 71.576 | 36.762 | 68.465 | 1.00 | 21.62 | A |
| ATOM | 1388 | CG | LYS | A | 328 | 73.087 | 36.776 | 68.551 | 1.00 | 23.65 | A |
| ATOM | 1389 | CD | LYS | A | 328 | 73.709 | 37.382 | 67.301 | 1.00 | 26.20 | A |
| ATOM | 1390 | CE | LYS | A | 328 | 75.228 | 37.386 | 67.393 | 1.00 | 26.95 | A |
| ATOM | 1391 | NZ | LYS | A | 328 | 75.879 | 37.925 | 66.164 | 1.00 | 28.12 | A |
| ATOM | 1392 | C | LYS | A | 328 | 69.506 | 38.052 | 67.941 | 1.00 | 19.58 | A |
| ATOM | 1393 | O | LYS | A | 328 | 69.239 | 38.330 | 66.775 | 1.00 | 19.40 | A |
| ATOM | 1394 | N | LYS | A | 329 | 68.594 | 37.658 | 68.824 | 1.00 | 19.59 | A |
| ATOM | 1395 | CA | LYS | A | 329 | 67.186 | 37.523 | 68.479 | 1.00 | 19.05 | A |
| ATOM | 1396 | CB | LYS | A | 329 | 66.411 | 36.990 | 69.683 | 1.00 | 19.28 | A |
| ATOM | 1397 | CG | LYS | A | 329 | 64.908 | 36.962 | 69.507 | 1.00 | 20.82 | A |
| ATOM | 1398 | CD | LYS | A | 329 | 64.484 | 35.930 | 68.485 | 1.00 | 22.28 | A |
| ATOM | 1399 | CE | LYS | A | 329 | 62.974 | 35.898 | 68.358 | 1.00 | 23.96 | A |
| ATOM | 1400 | NZ | LYS | A | 329 | 62.320 | 35.634 | 69.674 | 1.00 | 27.59 | A |
| ATOM | 1401 | C | LYS | A | 329 | 66.592 | 38.858 | 68.030 | 1.00 | 18.15 | A |
| ATOM | 1402 | O | LYS | A | 329 | 65.920 | 38.931 | 66.999 | 1.00 | 19.42 | A |
| ATOM | 1403 | N | GLN | A | 330 | 66.828 | 39.911 | 68.807 | 1.00 | 16.59 | A |
| ATOM | 1404 | CA | GLN | A | 330 | 66.309 | 41.230 | 68.450 | 1.00 | 16.88 | A |
| ATOM | 1405 | CB | GLN | A | 330 | 66.648 | 42.262 | 69.526 | 1.00 | 16.08 | A |
| ATOM | 1406 | CG | GLN | A | 330 | 65.909 | 42.082 | 70.841 | 1.00 | 16.71 | A |
| ATOM | 1407 | CD | GLN | A | 330 | 66.338 | 43.108 | 71.867 | 1.00 | 14.27 | A |

TABLE 1-continued

| | | | | | | | | | | |
|---|---|---|---|---|---|---|---|---|---|---|
| ATOM | 1408 | OE1 | GLN | A | 330 | 67.525 | 43.260 | 72.136 | 1.00 | 15.49 | A |
| ATOM | 1409 | NE2 | GLN | A | 330 | 65.374 | 43.820 | 72.445 | 1.00 | 17.15 | A |
| ATOM | 1410 | C | GLN | A | 330 | 66.897 | 41.685 | 67.116 | 1.00 | 15.88 | A |
| ATOM | 1411 | O | GLN | A | 330 | 66.201 | 42.277 | 66.299 | 1.00 | 16.92 | A |
| ATOM | 1412 | N | ARG | A | 331 | 68.182 | 41.414 | 66.907 | 1.00 | 16.85 | A |
| ATOM | 1413 | CA | ARG | A | 331 | 68.844 | 41.796 | 65.665 | 1.00 | 17.39 | A |
| ATOM | 1414 | CB | ARG | A | 331 | 70.321 | 41.396 | 65.688 | 1.00 | 17.37 | A |
| ATOM | 1415 | CG | ARG | A | 331 | 71.218 | 42.258 | 66.540 | 1.00 | 20.72 | A |
| ATOM | 1416 | CD | ARG | A | 331 | 72.345 | 42.808 | 65.683 | 1.00 | 23.49 | A |
| ATOM | 1417 | NE | ARG | A | 331 | 73.583 | 42.991 | 66.427 | 1.00 | 27.97 | A |
| ATOM | 1418 | CZ | ARG | A | 331 | 74.657 | 43.600 | 65.935 | 1.00 | 23.57 | A |
| ATOM | 1419 | NH1 | ARG | A | 331 | 74.637 | 44.088 | 64.699 | 1.00 | 28.18 | A |
| ATOM | 1420 | NH2 | ARG | A | 331 | 75.753 | 43.706 | 66.669 | 1.00 | 27.70 | A |
| ATOM | 1421 | C | ARG | A | 331 | 68.180 | 41.121 | 64.472 | 1.00 | 17.42 | A |
| ATOM | 1422 | O | ARG | A | 331 | 67.972 | 41.745 | 63.430 | 1.00 | 17.91 | A |
| ATOM | 1423 | N | GLN | A | 332 | 67.862 | 39.838 | 64.625 | 1.00 | 17.79 | A |
| ATOM | 1424 | CA | GLN | A | 332 | 67.220 | 39.079 | 63.559 | 1.00 | 19.81 | A |
| ATOM | 1425 | CB | GLN | A | 332 | 67.100 | 37.605 | 63.947 | 1.00 | 20.35 | A |
| ATOM | 1426 | CG | GLN | A | 332 | 68.418 | 36.866 | 64.027 | 1.00 | 24.70 | A |
| ATOM | 1427 | CD | GLN | A | 332 | 68.222 | 35.378 | 64.239 | 1.00 | 26.39 | A |
| ATOM | 1428 | OE1 | GLN | A | 332 | 69.186 | 34.620 | 64.341 | 1.00 | 29.23 | A |
| ATOM | 1429 | NE2 | GLN | A | 332 | 66.963 | 34.951 | 64.300 | 1.00 | 28.58 | A |
| ATOM | 1430 | C | GLN | A | 332 | 65.834 | 39.628 | 63.264 | 1.00 | 18.60 | A |
| ATOM | 1431 | O | GLN | A | 332 | 65.459 | 39.805 | 62.105 | 1.00 | 19.38 | A |
| ATOM | 1432 | N | THR | A | 333 | 65.076 | 39.888 | 64.323 | 1.00 | 17.51 | A |
| ATOM | 1433 | CA | THR | A | 333 | 63.726 | 40.416 | 64.187 | 1.00 | 17.83 | A |
| ATOM | 1434 | CB | THR | A | 333 | 63.046 | 40.546 | 65.561 | 1.00 | 18.75 | A |
| ATOM | 1435 | OG1 | THR | A | 333 | 63.038 | 39.267 | 66.208 | 1.00 | 20.67 | A |
| ATOM | 1436 | CG2 | THR | A | 333 | 61.615 | 41.037 | 65.404 | 1.00 | 19.79 | A |
| ATOM | 1437 | C | THR | A | 333 | 63.756 | 41.783 | 63.520 | 1.00 | 15.62 | A |
| ATOM | 1438 | O | THR | A | 333 | 62.942 | 42.070 | 62.639 | 1.00 | 15.43 | A |
| ATOM | 1439 | N | LEU | A | 334 | 64.696 | 42.625 | 63.938 | 1.00 | 15.88 | A |
| ATOM | 1440 | CA | LEU | A | 334 | 64.812 | 43.953 | 63.359 | 1.00 | 14.77 | A |
| ATOM | 1441 | CB | LEU | A | 334 | 65.869 | 44.779 | 64.099 | 1.00 | 15.78 | A |
| ATOM | 1442 | CG | LEU | A | 334 | 66.103 | 46.180 | 63.524 | 1.00 | 17.62 | A |
| ATOM | 1443 | CD1 | LEU | A | 334 | 66.384 | 47.165 | 64.643 | 1.00 | 18.10 | A |
| ATOM | 1444 | CD2 | LEU | A | 334 | 67.250 | 46.131 | 62.524 | 1.00 | 18.31 | A |
| ATOM | 1445 | C | LEU | A | 334 | 65.167 | 43.861 | 61.878 | 1.00 | 14.30 | A |
| ATOM | 1446 | O | LEU | A | 334 | 64.592 | 44.574 | 61.058 | 1.00 | 15.17 | A |
| ATOM | 1447 | N | ARG | A | 335 | 66.107 | 42.981 | 61.535 | 1.00 | 14.04 | A |
| ATOM | 1448 | CA | ARG | A | 335 | 66.504 | 42.826 | 60.135 | 1.00 | 14.97 | A |
| ATOM | 1449 | CB | ARG | A | 335 | 67.600 | 41.767 | 60.001 | 1.00 | 17.59 | A |
| ATOM | 1450 | CG | ARG | A | 335 | 68.266 | 41.758 | 58.632 | 1.00 | 21.60 | A |
| ATOM | 1451 | CD | ARG | A | 335 | 69.141 | 40.530 | 58.433 | 1.00 | 25.47 | A |
| ATOM | 1452 | NE | ARG | A | 335 | 69.938 | 40.628 | 57.211 | 1.00 | 27.46 | A |
| ATOM | 1453 | CZ | ARG | A | 335 | 71.033 | 41.374 | 57.095 | 1.00 | 27.50 | A |
| ATOM | 1454 | NH1 | ARG | A | 335 | 71.464 | 42.084 | 58.129 | 1.00 | 28.88 | A |
| ATOM | 1455 | NH2 | ARG | A | 335 | 71.698 | 41.413 | 55.949 | 1.00 | 28.61 | A |
| ATOM | 1456 | C | ARG | A | 335 | 65.299 | 42.427 | 59.278 | 1.00 | 14.29 | A |
| ATOM | 1457 | O | ARG | A | 335 | 65.075 | 42.988 | 58.207 | 1.00 | 14.75 | A |
| ATOM | 1458 | N | LYS | A | 336 | 64.520 | 41.462 | 59.754 | 1.00 | 14.67 | A |
| ATOM | 1459 | CA | LYS | A | 336 | 63.347 | 41.012 | 59.014 | 1.00 | 15.65 | A |
| ATOM | 1460 | CB | LYS | A | 336 | 62.658 | 39.865 | 59.758 | 1.00 | 18.14 | A |
| ATOM | 1461 | CG | LYS | A | 336 | 61.402 | 39.339 | 59.077 | 1.00 | 21.81 | A |
| ATOM | 1462 | CD | LYS | A | 336 | 60.729 | 38.258 | 59.920 | 1.00 | 25.00 | A |
| ATOM | 1463 | CE | LYS | A | 336 | 60.349 | 38.790 | 61.297 | 1.00 | 26.92 | A |
| ATOM | 1464 | NZ | LYS | A | 336 | 59.713 | 37.760 | 62.169 | 1.00 | 28.12 | A |
| ATOM | 1465 | C | LYS | A | 336 | 62.358 | 42.159 | 58.803 | 1.00 | 14.53 | A |
| ATOM | 1466 | O | LYS | A | 336 | 61.824 | 42.334 | 57.706 | 1.00 | 16.71 | A |
| ATOM | 1467 | N | MET | A | 337 | 62.120 | 42.945 | 59.849 | 1.00 | 13.58 | A |
| ATOM | 1468 | CA | MET | A | 337 | 61.191 | 44.068 | 59.749 | 1.00 | 13.55 | A |
| ATOM | 1469 | CB | MET | A | 337 | 60.914 | 44.654 | 61.135 | 1.00 | 15.02 | A |
| ATOM | 1470 | CG | MET | A | 337 | 60.264 | 43.663 | 62.078 | 1.00 | 16.48 | A |
| ATOM | 1471 | SD | MET | A | 337 | 59.612 | 44.466 | 63.545 | 1.00 | 19.72 | A |
| ATOM | 1472 | CE | MET | A | 337 | 61.104 | 44.844 | 64.429 | 1.00 | 16.64 | A |
| ATOM | 1473 | C | MET | A | 337 | 61.691 | 45.165 | 58.812 | 1.00 | 12.92 | A |
| ATOM | 1474 | O | MET | A | 337 | 60.917 | 45.711 | 58.016 | 1.00 | 14.56 | A |
| ATOM | 1475 | N | VAL | A | 338 | 62.975 | 45.490 | 58.905 | 1.00 | 13.04 | A |
| ATOM | 1476 | CA | VAL | A | 338 | 63.551 | 46.532 | 58.056 | 1.00 | 12.15 | A |
| ATOM | 1477 | CB | VAL | A | 338 | 65.013 | 46.827 | 58.463 | 1.00 | 11.84 | A |
| ATOM | 1478 | CG1 | VAL | A | 338 | 65.638 | 47.829 | 57.503 | 1.00 | 12.54 | A |
| ATOM | 1479 | CG2 | VAL | A | 338 | 65.039 | 47.387 | 59.876 | 1.00 | 12.66 | A |
| ATOM | 1480 | C | VAL | A | 338 | 63.489 | 46.116 | 56.592 | 1.00 | 10.73 | A |
| ATOM | 1481 | O | VAL | A | 338 | 63.187 | 46.928 | 55.720 | 1.00 | 11.90 | A |
| ATOM | 1482 | N | ILE | A | 339 | 63.763 | 44.846 | 56.322 | 1.00 | 11.30 | A |
| ATOM | 1483 | CA | ILE | A | 339 | 63.704 | 44.358 | 54.950 | 1.00 | 13.40 | A |
| ATOM | 1484 | CB | ILE | A | 339 | 64.062 | 42.861 | 54.873 | 1.00 | 13.14 | A |
| ATOM | 1485 | CG2 | ILE | A | 339 | 63.655 | 42.289 | 53.514 | 1.00 | 14.90 | A |
| ATOM | 1486 | CG1 | ILE | A | 339 | 65.559 | 42.680 | 55.121 | 1.00 | 13.93 | A |

TABLE 1-continued

| | | | | | | | | | | |
|---|---|---|---|---|---|---|---|---|---|---|
| ATOM | 1487 | CD1 | ILE | A | 339 | 65.997 | 41.236 | 55.167 | 1.00 | 16.14 | A |
| ATOM | 1488 | C | ILE | A | 339 | 62.299 | 44.569 | 54.386 | 1.00 | 13.56 | A |
| ATOM | 1489 | O | ILE | A | 339 | 62.135 | 45.103 | 53.288 | 1.00 | 15.35 | A |
| ATOM | 1490 | N | ASP | A | 340 | 61.280 | 44.170 | 55.143 | 1.00 | 13.87 | A |
| ATOM | 1491 | CA | ASP | A | 340 | 59.908 | 44.331 | 54.669 | 1.00 | 14.97 | A |
| ATOM | 1492 | CB | ASP | A | 340 | 58.922 | 43.698 | 55.654 | 1.00 | 19.82 | A |
| ATOM | 1493 | CG | ASP | A | 340 | 59.130 | 42.203 | 55.801 | 1.00 | 25.42 | A |
| ATOM | 1494 | OD1 | ASP | A | 340 | 59.288 | 41.520 | 54.765 | 1.00 | 26.97 | A |
| ATOM | 1495 | OD2 | ASP | A | 340 | 59.129 | 41.707 | 56.950 | 1.00 | 28.82 | A |
| ATOM | 1496 | C | ASP | A | 340 | 59.539 | 45.795 | 54.441 | 1.00 | 13.75 | A |
| ATOM | 1497 | O | ASP | A | 340 | 58.844 | 46.117 | 53.484 | 1.00 | 15.77 | A |
| ATOM | 1498 | N | MET | A | 341 | 60.011 | 46.686 | 55.307 | 1.00 | 12.85 | A |
| ATOM | 1499 | CA | MET | A | 341 | 59.680 | 48.098 | 55.153 | 1.00 | 12.32 | A |
| ATOM | 1500 | CB | MET | A | 341 | 59.991 | 48.865 | 56.438 | 1.00 | 14.73 | A |
| ATOM | 1501 | CG | MET | A | 341 | 58.991 | 48.565 | 57.543 | 1.00 | 15.86 | A |
| ATOM | 1502 | SD | MET | A | 341 | 59.246 | 49.537 | 59.028 | 1.00 | 21.36 | A |
| ATOM | 1503 | CE | MET | A | 341 | 60.489 | 48.572 | 59.825 | 1.00 | 18.20 | A |
| ATOM | 1504 | C | MET | A | 341 | 60.369 | 48.756 | 53.962 | 1.00 | 12.29 | A |
| ATOM | 1505 | O | MET | A | 341 | 59.743 | 49.517 | 53.227 | 1.00 | 12.72 | A |
| ATOM | 1506 | N | VAL | A | 342 | 61.648 | 48.463 | 53.759 | 1.00 | 12.16 | A |
| ATOM | 1507 | CA | VAL | A | 342 | 62.351 | 49.061 | 52.634 | 1.00 | 11.71 | A |
| ATOM | 1508 | CB | VAL | A | 342 | 63.875 | 48.852 | 52.751 | 1.00 | 11.04 | A |
| ATOM | 1509 | CG1 | VAL | A | 342 | 64.575 | 49.416 | 51.518 | 1.00 | 11.66 | A |
| ATOM | 1510 | CG2 | VAL | A | 342 | 64.392 | 49.555 | 53.992 | 1.00 | 10.71 | A |
| ATOM | 1511 | C | VAL | A | 342 | 61.844 | 48.497 | 51.306 | 1.00 | 11.79 | A |
| ATOM | 1512 | O | VAL | A | 342 | 61.702 | 49.232 | 50.325 | 1.00 | 12.78 | A |
| ATOM | 1513 | N | LEU | A | 343 | 61.555 | 47.202 | 51.262 | 1.00 | 12.33 | A |
| ATOM | 1514 | CA | LEU | A | 343 | 61.051 | 46.620 | 50.024 | 1.00 | 13.51 | A |
| ATOM | 1515 | CB | LEU | A | 343 | 60.976 | 45.092 | 50.129 | 1.00 | 14.60 | A |
| ATOM | 1516 | CG | LEU | A | 343 | 62.313 | 44.349 | 50.121 | 1.00 | 17.95 | A |
| ATOM | 1517 | CD1 | LEU | A | 343 | 62.067 | 42.851 | 50.148 | 1.00 | 16.78 | A |
| ATOM | 1518 | CD2 | LEU | A | 343 | 63.099 | 44.733 | 48.880 | 1.00 | 19.17 | A |
| ATOM | 1519 | C | LEU | A | 343 | 59.673 | 47.189 | 49.695 | 1.00 | 12.86 | A |
| ATOM | 1520 | O | LEU | A | 343 | 59.256 | 47.200 | 48.537 | 1.00 | 14.40 | A |
| ATOM | 1521 | N | ALA | A | 344 | 58.967 | 47.671 | 50.713 | 1.00 | 13.89 | A |
| ATOM | 1522 | CA | ALA | A | 344 | 57.639 | 48.239 | 50.503 | 1.00 | 14.80 | A |
| ATOM | 1523 | CB | ALA | A | 344 | 56.879 | 48.312 | 51.829 | 1.00 | 16.07 | A |
| ATOM | 1524 | C | ALA | A | 344 | 57.710 | 49.622 | 49.859 | 1.00 | 14.06 | A |
| ATOM | 1525 | O | ALA | A | 344 | 56.681 | 50.194 | 49.489 | 1.00 | 16.21 | A |
| ATOM | 1526 | N | THR | A | 345 | 58.917 | 50.166 | 49.718 | 1.00 | 13.00 | A |
| ATOM | 1527 | CA | THR | A | 345 | 59.055 | 51.475 | 49.091 | 1.00 | 13.04 | A |
| ATOM | 1528 | CB | THR | A | 345 | 60.222 | 52.305 | 49.695 | 1.00 | 11.75 | A |
| ATOM | 1529 | OG1 | THR | A | 345 | 61.466 | 51.626 | 49.496 | 1.00 | 14.32 | A |
| ATOM | 1530 | CG2 | THR | A | 345 | 59.995 | 52.529 | 51.191 | 1.00 | 12.17 | A |
| ATOM | 1531 | C | THR | A | 345 | 59.238 | 51.344 | 47.578 | 1.00 | 13.13 | A |
| ATOM | 1532 | O | THR | A | 345 | 59.377 | 52.343 | 46.877 | 1.00 | 15.04 | A |
| ATOM | 1533 | N | ASP | A | 346 | 59.235 | 50.111 | 47.080 | 1.00 | 15.13 | A |
| ATOM | 1534 | CA | ASP | A | 346 | 59.343 | 49.871 | 45.641 | 1.00 | 16.12 | A |
| ATOM | 1535 | CB | ASP | A | 346 | 59.647 | 48.394 | 45.361 | 1.00 | 17.10 | A |
| ATOM | 1536 | CG | ASP | A | 346 | 59.748 | 48.080 | 43.872 | 1.00 | 19.43 | A |
| ATOM | 1537 | OD1 | ASP | A | 346 | 59.300 | 48.898 | 43.046 | 1.00 | 20.70 | A |
| ATOM | 1538 | OD2 | ASP | A | 346 | 60.271 | 47.002 | 43.525 | 1.00 | 18.76 | A |
| ATOM | 1539 | C | ASP | A | 346 | 57.969 | 50.225 | 45.071 | 1.00 | 16.26 | A |
| ATOM | 1540 | O | ASP | A | 346 | 56.984 | 49.537 | 45.342 | 1.00 | 16.33 | A |
| ATOM | 1541 | N | MET | A | 347 | 57.903 | 51.298 | 44.290 | 1.00 | 18.28 | A |
| ATOM | 1542 | CA | MET | A | 347 | 56.640 | 51.741 | 43.705 | 1.00 | 21.29 | A |
| ATOM | 1543 | CB | MET | A | 347 | 56.858 | 52.997 | 42.861 | 1.00 | 25.96 | A |
| ATOM | 1544 | CG | MET | A | 347 | 56.796 | 54.281 | 43.657 | 1.00 | 31.87 | A |
| ATOM | 1545 | SD | MET | A | 347 | 55.132 | 54.562 | 44.281 | 1.00 | 34.25 | A |
| ATOM | 1546 | CE | MET | A | 347 | 54.435 | 55.496 | 42.943 | 1.00 | 34.55 | A |
| ATOM | 1547 | C | MET | A | 347 | 55.913 | 50.700 | 42.864 | 1.00 | 21.27 | A |
| ATOM | 1548 | O | MET | A | 347 | 54.694 | 50.768 | 42.719 | 1.00 | 21.62 | A |
| ATOM | 1549 | N | SER | A | 348 | 56.648 | 49.740 | 42.311 | 1.00 | 21.21 | A |
| ATOM | 1550 | CA | SER | A | 348 | 56.023 | 48.712 | 41.486 | 1.00 | 22.59 | A |
| ATOM | 1551 | CB | SER | A | 348 | 57.092 | 47.866 | 40.787 | 1.00 | 22.39 | A |
| ATOM | 1552 | OG | SER | A | 348 | 57.782 | 47.038 | 41.705 | 1.00 | 26.83 | A |
| ATOM | 1553 | C | SER | A | 348 | 55.105 | 47.810 | 42.313 | 1.00 | 23.21 | A |
| ATOM | 1554 | O | SER | A | 348 | 54.302 | 47.051 | 41.762 | 1.00 | 24.23 | A |
| ATOM | 1555 | N | LYS | A | 349 | 55.214 | 47.905 | 43.635 | 1.00 | 22.03 | A |
| ATOM | 1556 | CA | LYS | A | 349 | 54.401 | 47.091 | 44.534 | 1.00 | 21.97 | A |
| ATOM | 1557 | CB | LYS | A | 349 | 55.267 | 46.529 | 45.665 | 1.00 | 22.74 | A |
| ATOM | 1558 | CG | LYS | A | 349 | 56.581 | 45.901 | 45.223 | 1.00 | 23.77 | A |
| ATOM | 1559 | CD | LYS | A | 349 | 56.363 | 44.711 | 44.308 | 1.00 | 24.27 | A |
| ATOM | 1560 | CE | LYS | A | 349 | 57.693 | 44.118 | 43.855 | 1.00 | 24.59 | A |
| ATOM | 1561 | NZ | LYS | A | 349 | 57.493 | 42.948 | 42.957 | 1.00 | 25.73 | A |
| ATOM | 1562 | C | LYS | A | 349 | 53.262 | 47.897 | 45.157 | 1.00 | 20.67 | A |
| ATOM | 1563 | O | LYS | A | 349 | 52.535 | 47.394 | 46.009 | 1.00 | 21.69 | A |
| ATOM | 1564 | N | HIS | A | 350 | 53.107 | 49.145 | 44.730 | 1.00 | 19.53 | A |
| ATOM | 1565 | CA | HIS | A | 350 | 52.074 | 50.008 | 45.287 | 1.00 | 19.27 | A |

TABLE 1-continued

| | | | | | | | | | | |
|---|---|---|---|---|---|---|---|---|---|---|
| ATOM | 1566 | CB | HIS | A | 350 | 52.067 | 51.360 | 44.579 | 1.00 | 19.99 | A |
| ATOM | 1567 | CG | HIS | A | 350 | 50.965 | 52.263 | 45.036 | 1.00 | 22.05 | A |
| ATOM | 1568 | CD2 | HIS | A | 350 | 49.843 | 52.689 | 44.408 | 1.00 | 22.13 | A |
| ATOM | 1569 | ND1 | HIS | A | 350 | 50.915 | 52.791 | 46.308 | 1.00 | 24.88 | A |
| ATOM | 1570 | CE1 | HIS | A | 350 | 49.810 | 53.504 | 46.445 | 1.00 | 24.84 | A |
| ATOM | 1571 | NE2 | HIS | A | 350 | 49.142 | 53.458 | 45.307 | 1.00 | 25.02 | A |
| ATOM | 1572 | C | HIS | A | 350 | 50.650 | 49.455 | 45.288 | 1.00 | 19.80 | A |
| ATOM | 1573 | O | HIS | A | 350 | 49.968 | 49.511 | 46.308 | 1.00 | 20.38 | A |
| ATOM | 1574 | N | MET | A | 351 | 50.198 | 48.933 | 44.154 | 1.00 | 20.02 | A |
| ATOM | 1575 | CA | MET | A | 351 | 48.838 | 48.412 | 44.063 | 1.00 | 21.53 | A |
| ATOM | 1576 | CB | MET | A | 351 | 48.521 | 48.004 | 42.621 | 1.00 | 24.75 | A |
| ATOM | 1577 | CG | MET | A | 351 | 48.551 | 49.148 | 41.617 | 1.00 | 28.47 | A |
| ATOM | 1578 | SD | MET | A | 351 | 47.436 | 50.522 | 42.021 | 1.00 | 31.24 | A |
| ATOM | 1579 | CE | MET | A | 351 | 48.411 | 51.925 | 41.465 | 1.00 | 33.64 | A |
| ATOM | 1580 | C | MET | A | 351 | 48.576 | 47.237 | 44.999 | 1.00 | 21.50 | A |
| ATOM | 1581 | O | MET | A | 351 | 47.512 | 47.159 | 45.619 | 1.00 | 22.29 | A |
| ATOM | 1582 | N | SER | A | 352 | 49.536 | 46.324 | 45.105 | 1.00 | 22.13 | A |
| ATOM | 1583 | CA | SER | A | 352 | 49.373 | 45.163 | 45.977 | 1.00 | 23.14 | A |
| ATOM | 1584 | CB | SER | A | 352 | 50.514 | 44.159 | 45.764 | 1.00 | 23.45 | A |
| ATOM | 1585 | OG | SER | A | 352 | 51.763 | 44.714 | 46.134 | 1.00 | 27.89 | A |
| ATOM | 1586 | C | SER | A | 352 | 49.342 | 45.608 | 47.434 | 1.00 | 23.14 | A |
| ATOM | 1587 | O | SER | A | 352 | 48.574 | 45.080 | 48.240 | 1.00 | 25.17 | A |
| ATOM | 1588 | N | LEU | A | 353 | 50.183 | 46.583 | 47.768 | 1.00 | 21.80 | A |
| ATOM | 1589 | CA | LEU | A | 353 | 50.243 | 47.110 | 49.125 | 1.00 | 20.98 | A |
| ATOM | 1590 | CB | LEU | A | 353 | 51.374 | 48.126 | 49.258 | 1.00 | 21.58 | A |
| ATOM | 1591 | CG | LEU | A | 353 | 52.727 | 47.642 | 49.770 | 1.00 | 24.48 | A |
| ATOM | 1592 | CD1 | LEU | A | 353 | 53.639 | 48.848 | 49.925 | 1.00 | 23.12 | A |
| ATOM | 1593 | CD2 | LEU | A | 353 | 52.559 | 46.925 | 51.107 | 1.00 | 23.65 | A |
| ATOM | 1594 | C | LEU | A | 353 | 48.942 | 47.785 | 49.533 | 1.00 | 20.87 | A |
| ATOM | 1595 | O | LEU | A | 353 | 48.447 | 47.573 | 50.642 | 1.00 | 22.05 | A |
| ATOM | 1596 | N | LEU | A | 354 | 48.401 | 48.605 | 48.636 | 1.00 | 20.35 | A |
| ATOM | 1597 | CA | LEU | A | 354 | 47.160 | 49.328 | 48.899 | 1.00 | 19.81 | A |
| ATOM | 1598 | CB | LEU | A | 354 | 46.850 | 50.285 | 47.748 | 1.00 | 19.95 | A |
| ATOM | 1599 | CG | LEU | A | 354 | 45.583 | 51.122 | 47.927 | 1.00 | 19.89 | A |
| ATOM | 1600 | CD1 | LEU | A | 354 | 45.732 | 51.995 | 49.160 | 1.00 | 21.73 | A |
| ATOM | 1601 | CD2 | LEU | A | 354 | 45.344 | 51.966 | 46.687 | 1.00 | 22.26 | A |
| ATOM | 1602 | C | LEU | A | 354 | 45.996 | 48.369 | 49.074 | 1.00 | 20.65 | A |
| ATOM | 1603 | O | LEU | A | 354 | 45.183 | 48.526 | 49.985 | 1.00 | 21.97 | A |
| ATOM | 1604 | N | ALA | A | 355 | 45.920 | 47.379 | 48.191 | 1.00 | 22.24 | A |
| ATOM | 1605 | CA | ALA | A | 355 | 44.848 | 46.391 | 48.246 | 1.00 | 22.74 | A |
| ATOM | 1606 | CB | ALA | A | 355 | 45.022 | 45.370 | 47.129 | 1.00 | 23.99 | A |
| ATOM | 1607 | C | ALA | A | 355 | 44.844 | 45.693 | 49.597 | 1.00 | 23.62 | A |
| ATOM | 1608 | O | ALA | A | 355 | 43.791 | 45.512 | 50.212 | 1.00 | 24.76 | A |
| ATOM | 1609 | N | ASP | A | 356 | 46.024 | 45.304 | 50.065 | 1.00 | 25.25 | A |
| ATOM | 1610 | CA | ASP | A | 356 | 46.129 | 44.623 | 51.345 | 1.00 | 25.56 | A |
| ATOM | 1611 | CB | ASP | A | 356 | 47.510 | 43.977 | 51.489 | 1.00 | 27.12 | A |
| ATOM | 1612 | CG | ASP | A | 356 | 47.688 | 42.775 | 50.572 | 1.00 | 28.99 | A |
| ATOM | 1613 | OD1 | ASP | A | 356 | 46.830 | 41.864 | 50.609 | 1.00 | 31.04 | A |
| ATOM | 1614 | OD2 | ASP | A | 356 | 48.682 | 42.735 | 49.817 | 1.00 | 32.31 | A |
| ATOM | 1615 | C | ASP | A | 356 | 45.840 | 45.554 | 52.520 | 1.00 | 25.60 | A |
| ATOM | 1616 | O | ASP | A | 356 | 45.326 | 45.116 | 53.549 | 1.00 | 27.10 | A |
| ATOM | 1617 | N | LEU | A | 357 | 46.157 | 46.837 | 52.369 | 1.00 | 23.87 | A |
| ATOM | 1618 | CA | LEU | A | 357 | 45.892 | 47.798 | 53.437 | 1.00 | 23.13 | A |
| ATOM | 1619 | CB | LEU | A | 357 | 46.545 | 49.150 | 53.130 | 1.00 | 21.87 | A |
| ATOM | 1620 | CG | LEU | A | 357 | 46.349 | 50.231 | 54.199 | 1.00 | 21.26 | A |
| ATOM | 1621 | CD1 | LEU | A | 357 | 46.965 | 49.768 | 55.510 | 1.00 | 22.31 | A |
| ATOM | 1622 | CD2 | LEU | A | 357 | 46.980 | 51.539 | 53.747 | 1.00 | 22.11 | A |
| ATOM | 1623 | C | LEU | A | 357 | 44.381 | 47.980 | 53.566 | 1.00 | 22.69 | A |
| ATOM | 1624 | O | LEU | A | 357 | 43.856 | 48.161 | 54.662 | 1.00 | 23.96 | A |
| ATOM | 1625 | N | LYS | A | 358 | 43.687 | 47.933 | 52.436 | 1.00 | 22.86 | A |
| ATOM | 1626 | CA | LYS | A | 358 | 42.240 | 48.082 | 52.430 | 1.00 | 23.64 | A |
| ATOM | 1627 | CB | LYS | A | 358 | 41.726 | 48.186 | 50.994 | 1.00 | 21.78 | A |
| ATOM | 1628 | CG | LYS | A | 358 | 41.931 | 49.542 | 50.354 | 1.00 | 22.04 | A |
| ATOM | 1629 | CD | LYS | A | 358 | 41.424 | 49.537 | 48.922 | 1.00 | 23.04 | A |
| ATOM | 1630 | CE | LYS | A | 358 | 41.465 | 50.927 | 48.302 | 1.00 | 24.68 | A |
| ATOM | 1631 | NZ | LYS | A | 358 | 40.536 | 51.871 | 48.981 | 1.00 | 27.46 | A |
| ATOM | 1632 | C | LYS | A | 358 | 41.564 | 46.912 | 53.133 | 1.00 | 24.81 | A |
| ATOM | 1633 | O | LYS | A | 358 | 40.571 | 47.095 | 53.838 | 1.00 | 26.10 | A |
| ATOM | 1634 | N | THR | A | 359 | 42.101 | 45.711 | 52.944 | 1.00 | 25.35 | A |
| ATOM | 1635 | CA | THR | A | 359 | 41.530 | 44.527 | 53.579 | 1.00 | 26.13 | A |
| ATOM | 1636 | CB | THR | A | 359 | 42.245 | 43.237 | 53.135 | 1.00 | 25.56 | A |
| ATOM | 1637 | OG1 | THR | A | 359 | 42.075 | 43.053 | 51.723 | 1.00 | 27.97 | A |
| ATOM | 1638 | CG2 | THR | A | 359 | 41.665 | 42.033 | 53.870 | 1.00 | 25.58 | A |
| ATOM | 1639 | C | THR | A | 359 | 41.664 | 44.660 | 55.089 | 1.00 | 26.66 | A |
| ATOM | 1640 | O | THR | A | 359 | 40.722 | 44.382 | 55.834 | 1.00 | 27.49 | A |
| ATOM | 1641 | N | MET | A | 360 | 42.843 | 45.086 | 55.531 | 1.00 | 26.06 | A |
| ATOM | 1642 | CA | MET | A | 360 | 43.116 | 45.281 | 56.948 | 1.00 | 26.88 | A |
| ATOM | 1643 | CB | MET | A | 360 | 44.524 | 45.852 | 57.131 | 1.00 | 29.78 | A |
| ATOM | 1644 | CG | MET | A | 360 | 44.905 | 46.149 | 58.571 | 1.00 | 32.95 | A |

TABLE 1-continued

| | | | | | | | | | | |
|---|---|---|---|---|---|---|---|---|---|---|
| ATOM | 1645 | SD | MET | A | 360 | 45.119 | 44.644 | 59.542 | 1.00 | 35.82 | A |
| ATOM | 1646 | CE | MET | A | 360 | 46.859 | 44.343 | 59.301 | 1.00 | 34.82 | A |
| ATOM | 1647 | C | MET | A | 360 | 42.091 | 46.256 | 57.515 | 1.00 | 26.89 | A |
| ATOM | 1648 | O | MET | A | 360 | 41.520 | 46.033 | 58.584 | 1.00 | 27.79 | A |
| ATOM | 1649 | N | VAL | A | 361 | 41.861 | 47.337 | 56.777 | 1.00 | 25.45 | A |
| ATOM | 1650 | CA | VAL | A | 361 | 40.914 | 48.372 | 57.172 | 1.00 | 25.13 | A |
| ATOM | 1651 | CB | VAL | A | 361 | 40.822 | 49.462 | 56.099 | 1.00 | 24.50 | A |
| ATOM | 1652 | CG1 | VAL | A | 361 | 39.820 | 50.527 | 56.518 | 1.00 | 24.68 | A |
| ATOM | 1653 | CG2 | VAL | A | 361 | 42.194 | 50.049 | 55.858 | 1.00 | 26.07 | A |
| ATOM | 1654 | C | VAL | A | 361 | 39.513 | 47.831 | 57.404 | 1.00 | 24.97 | A |
| ATOM | 1655 | O | VAL | A | 361 | 38.875 | 48.147 | 58.406 | 1.00 | 25.84 | A |
| ATOM | 1656 | N | GLU | A | 362 | 39.031 | 47.021 | 56.468 | 1.00 | 25.15 | A |
| ATOM | 1657 | CA | GLU | A | 362 | 37.694 | 46.456 | 56.579 | 1.00 | 25.35 | A |
| ATOM | 1658 | CB | GLU | A | 362 | 37.391 | 45.588 | 55.358 | 1.00 | 24.73 | A |
| ATOM | 1659 | CG | GLU | A | 362 | 37.456 | 46.347 | 54.045 | 1.00 | 26.70 | A |
| ATOM | 1660 | CD | GLU | A | 362 | 36.929 | 45.539 | 52.877 | 1.00 | 28.52 | A |
| ATOM | 1661 | OE1 | GLU | A | 362 | 37.434 | 44.419 | 52.647 | 1.00 | 31.92 | A |
| ATOM | 1662 | OE2 | GLU | A | 362 | 36.009 | 46.029 | 52.187 | 1.00 | 31.50 | A |
| ATOM | 1663 | C | GLU | A | 362 | 37.498 | 45.646 | 57.857 | 1.00 | 26.32 | A |
| ATOM | 1664 | O | GLU | A | 362 | 36.404 | 45.631 | 58.422 | 1.00 | 27.35 | A |
| ATOM | 1665 | N | THR | A | 363 | 38.551 | 44.973 | 58.308 | 1.00 | 26.81 | A |
| ATOM | 1666 | CA | THR | A | 363 | 38.477 | 44.173 | 59.527 | 1.00 | 27.78 | A |
| ATOM | 1667 | CB | THR | A | 363 | 39.234 | 42.836 | 59.374 | 1.00 | 27.80 | A |
| ATOM | 1668 | OG1 | THR | A | 363 | 40.613 | 43.097 | 59.083 | 1.00 | 30.57 | A |
| ATOM | 1669 | CG2 | THR | A | 363 | 38.628 | 42.003 | 58.254 | 1.00 | 27.64 | A |
| ATOM | 1670 | C | THR | A | 363 | 39.076 | 44.936 | 60.704 | 1.00 | 27.86 | A |
| ATOM | 1671 | O | THR | A | 363 | 39.502 | 44.337 | 61.693 | 1.00 | 28.85 | A |
| ATOM | 1672 | N | LYS | A | 364 | 39.102 | 46.260 | 60.586 | 1.00 | 26.86 | A |
| ATOM | 1673 | CA | LYS | A | 364 | 39.643 | 47.133 | 61.623 | 1.00 | 26.45 | A |
| ATOM | 1674 | CB | LYS | A | 364 | 39.460 | 48.598 | 61.215 | 1.00 | 24.94 | A |
| ATOM | 1675 | CG | LYS | A | 364 | 39.867 | 49.609 | 62.276 | 1.00 | 25.85 | A |
| ATOM | 1676 | CD | LYS | A | 364 | 39.610 | 51.036 | 61.812 | 1.00 | 25.30 | A |
| ATOM | 1677 | CE | LYS | A | 364 | 40.031 | 52.047 | 62.871 | 1.00 | 26.07 | A |
| ATOM | 1678 | NZ | LYS | A | 364 | 39.796 | 53.458 | 62.446 | 1.00 | 27.15 | A |
| ATOM | 1679 | C | LYS | A | 364 | 38.983 | 46.899 | 62.980 | 1.00 | 27.09 | A |
| ATOM | 1680 | O | LYS | A | 364 | 37.763 | 46.752 | 63.075 | 1.00 | 27.70 | A |
| ATOM | 1681 | N | LYS | A | 365 | 39.803 | 46.867 | 64.026 | 1.00 | 26.80 | A |
| ATOM | 1682 | CA | LYS | A | 365 | 39.318 | 46.671 | 65.387 | 1.00 | 27.07 | A |
| ATOM | 1683 | CB | LYS | A | 365 | 39.648 | 45.260 | 65.878 | 1.00 | 26.82 | A |
| ATOM | 1684 | CG | LYS | A | 365 | 39.000 | 44.149 | 65.068 | 1.00 | 27.96 | A |
| ATOM | 1685 | CD | LYS | A | 365 | 39.389 | 42.780 | 65.608 | 1.00 | 28.82 | A |
| ATOM | 1686 | CE | LYS | A | 365 | 38.814 | 41.661 | 64.755 | 1.00 | 28.89 | A |
| ATOM | 1687 | NZ | LYS | A | 365 | 39.274 | 40.320 | 65.220 | 1.00 | 29.93 | A |
| ATOM | 1688 | C | LYS | A | 365 | 40.002 | 47.694 | 66.284 | 1.00 | 27.63 | A |
| ATOM | 1689 | O | LYS | A | 365 | 41.222 | 47.864 | 66.218 | 1.00 | 27.67 | A |
| ATOM | 1690 | N | VAL | A | 366 | 39.220 | 48.378 | 67.113 | 1.00 | 26.47 | A |
| ATOM | 1691 | CA | VAL | A | 366 | 39.776 | 49.380 | 68.011 | 1.00 | 25.96 | A |
| ATOM | 1692 | CB | VAL | A | 366 | 39.481 | 50.811 | 67.508 | 1.00 | 24.10 | A |
| ATOM | 1693 | CG1 | VAL | A | 366 | 40.035 | 50.994 | 66.103 | 1.00 | 24.03 | A |
| ATOM | 1694 | CG2 | VAL | A | 366 | 37.984 | 51.075 | 67.530 | 1.00 | 24.00 | A |
| ATOM | 1695 | C | VAL | A | 366 | 39.246 | 49.256 | 69.434 | 1.00 | 26.37 | A |
| ATOM | 1696 | O | VAL | A | 366 | 38.172 | 48.694 | 69.664 | 1.00 | 28.22 | A |
| ATOM | 1697 | N | THR | A | 367 | 40.017 | 49.781 | 70.383 | 1.00 | 26.43 | A |
| ATOM | 1698 | CA | THR | A | 367 | 39.653 | 49.771 | 71.798 | 1.00 | 27.54 | A |
| ATOM | 1699 | CB | THR | A | 367 | 40.452 | 48.719 | 72.598 | 1.00 | 27.71 | A |
| ATOM | 1700 | OG1 | THR | A | 367 | 41.857 | 48.908 | 72.377 | 1.00 | 28.47 | A |
| ATOM | 1701 | CG2 | THR | A | 367 | 40.049 | 47.314 | 72.186 | 1.00 | 28.59 | A |
| ATOM | 1702 | C | THR | A | 367 | 39.955 | 51.138 | 72.397 | 1.00 | 26.70 | A |
| ATOM | 1703 | O | THR | A | 367 | 41.101 | 51.589 | 72.377 | 1.00 | 26.71 | A |
| ATOM | 1704 | N | GLY | A | 370 | 40.510 | 55.504 | 71.435 | 1.00 | 25.74 | A |
| ATOM | 1705 | CA | GLY | A | 370 | 40.309 | 55.041 | 70.077 | 1.00 | 27.88 | A |
| ATOM | 1706 | C | GLY | A | 370 | 41.547 | 54.357 | 69.535 | 1.00 | 28.02 | A |
| ATOM | 1707 | O | GLY | A | 370 | 41.620 | 54.032 | 68.351 | 1.00 | 29.88 | A |
| ATOM | 1708 | N | VAL | A | 371 | 41.968 | 53.301 | 69.825 | 1.00 | 27.21 | A |
| ATOM | 1709 | CA | VAL | A | 371 | 43.286 | 52.750 | 69.527 | 1.00 | 25.97 | A |
| ATOM | 1710 | CB | VAL | A | 371 | 44.092 | 52.494 | 70.818 | 1.00 | 24.86 | A |
| ATOM | 1711 | CG1 | VAL | A | 371 | 45.403 | 51.799 | 70.481 | 1.00 | 23.86 | A |
| ATOM | 1712 | CG2 | VAL | A | 371 | 44.360 | 53.808 | 71.534 | 1.00 | 25.07 | A |
| ATOM | 1713 | C | VAL | A | 371 | 43.163 | 51.438 | 68.764 | 1.00 | 25.29 | A |
| ATOM | 1714 | O | VAL | A | 371 | 42.406 | 50.548 | 69.153 | 1.00 | 25.40 | A |
| ATOM | 1715 | N | LEU | A | 372 | 43.917 | 51.321 | 67.677 | 1.00 | 24.10 | A |
| ATOM | 1716 | CA | LEU | A | 372 | 43.888 | 50.120 | 66.856 | 1.00 | 24.56 | A |
| ATOM | 1717 | CB | LEU | A | 372 | 44.783 | 50.301 | 65.627 | 1.00 | 24.29 | A |
| ATOM | 1718 | CG | LEU | A | 372 | 44.276 | 51.289 | 64.579 | 1.00 | 24.78 | A |
| ATOM | 1719 | CD1 | LEU | A | 372 | 45.336 | 51.496 | 63.512 | 1.00 | 25.56 | A |
| ATOM | 1720 | CD2 | LEU | A | 372 | 42.996 | 50.758 | 63.965 | 1.00 | 24.78 | A |
| ATOM | 1721 | C | LEU | A | 372 | 44.326 | 48.877 | 67.614 | 1.00 | 24.79 | A |
| ATOM | 1722 | O | LEU | A | 372 | 45.168 | 48.942 | 68.512 | 1.00 | 25.30 | A |
| ATOM | 1723 | N | LEU | A | 373 | 43.741 | 47.744 | 67.243 | 1.00 | 24.44 | A |

TABLE 1-continued

| ATOM | 1724 | CA | LEU | A | 373 | 44.075 | 46.468 | 67.853 | 1.00 | 25.16 | A |
| ATOM | 1725 | CB | LEU | A | 373 | 42.808 | 45.717 | 68.271 | 1.00 | 25.33 | A |
| ATOM | 1726 | CG | LEU | A | 373 | 42.048 | 46.268 | 69.475 | 1.00 | 24.87 | A |
| ATOM | 1727 | CD1 | LEU | A | 373 | 40.831 | 45.395 | 69.737 | 1.00 | 26.12 | A |
| ATOM | 1728 | CD2 | LEU | A | 373 | 42.962 | 46.292 | 70.695 | 1.00 | 26.02 | A |
| ATOM | 1729 | C | LEU | A | 373 | 44.856 | 45.628 | 66.853 | 1.00 | 25.04 | A |
| ATOM | 1730 | O | LEU | A | 373 | 44.280 | 45.046 | 65.931 | 1.00 | 25.70 | A |
| ATOM | 1731 | N | LEU | A | 374 | 46.171 | 45.590 | 67.039 | 1.00 | 24.97 | A |
| ATOM | 1732 | CA | LEU | A | 374 | 47.066 | 44.823 | 66.183 | 1.00 | 25.46 | A |
| ATOM | 1733 | CB | LEU | A | 374 | 48.139 | 45.736 | 65.594 | 1.00 | 23.98 | A |
| ATOM | 1734 | CG | LEU | A | 374 | 47.590 | 46.881 | 64.741 | 1.00 | 23.68 | A |
| ATOM | 1735 | CD1 | LEU | A | 374 | 48.740 | 47.699 | 64.173 | 1.00 | 24.31 | A |
| ATOM | 1736 | CD2 | LEU | A | 374 | 46.739 | 46.314 | 63.620 | 1.00 | 22.68 | A |
| ATOM | 1737 | C | LEU | A | 374 | 47.700 | 43.750 | 67.059 | 1.00 | 26.45 | A |
| ATOM | 1738 | O | LEU | A | 374 | 48.868 | 43.837 | 67.444 | 1.00 | 27.79 | A |
| ATOM | 1739 | N | ASP | A | 375 | 46.897 | 42.738 | 67.363 | 1.00 | 26.61 | A |
| ATOM | 1740 | CA | ASP | A | 375 | 47.284 | 41.621 | 68.213 | 1.00 | 27.28 | A |
| ATOM | 1741 | CB | ASP | A | 375 | 46.082 | 40.688 | 68.379 | 1.00 | 27.38 | A |
| ATOM | 1742 | CG | ASP | A | 375 | 45.435 | 40.336 | 67.052 | 1.00 | 28.74 | A |
| ATOM | 1743 | OD1 | ASP | A | 375 | 46.094 | 39.674 | 66.223 | 1.00 | 31.27 | A |
| ATOM | 1744 | OD2 | ASP | A | 375 | 44.269 | 40.731 | 66.832 | 1.00 | 31.82 | A |
| ATOM | 1745 | C | ASP | A | 375 | 48.499 | 40.803 | 67.789 | 1.00 | 27.98 | A |
| ATOM | 1746 | O | ASP | A | 375 | 49.298 | 40.403 | 68.637 | 1.00 | 28.80 | A |
| ATOM | 1747 | N | ASN | A | 376 | 48.641 | 40.542 | 66.493 | 1.00 | 26.01 | A |
| ATOM | 1748 | CA | ASN | A | 376 | 49.764 | 39.737 | 66.027 | 1.00 | 24.81 | A |
| ATOM | 1749 | CB | ASN | A | 376 | 49.255 | 38.518 | 65.251 | 1.00 | 25.46 | A |
| ATOM | 1750 | CG | ASN | A | 376 | 48.438 | 38.898 | 64.030 | 1.00 | 26.39 | A |
| ATOM | 1751 | OD1 | ASN | A | 376 | 48.913 | 39.613 | 63.149 | 1.00 | 30.51 | A |
| ATOM | 1752 | ND2 | ASN | A | 376 | 47.201 | 38.414 | 63.971 | 1.00 | 28.24 | A |
| ATOM | 1753 | C | ASN | A | 376 | 50.785 | 40.483 | 65.179 | 1.00 | 25.28 | A |
| ATOM | 1754 | O | ASN | A | 376 | 50.506 | 41.552 | 64.633 | 1.00 | 25.65 | A |
| ATOM | 1755 | N | TYR | A | 377 | 51.972 | 39.892 | 65.081 | 1.00 | 23.91 | A |
| ATOM | 1756 | CA | TYR | A | 377 | 53.079 | 40.451 | 64.312 | 1.00 | 23.31 | A |
| ATOM | 1757 | CB | TYR | A | 377 | 54.264 | 39.486 | 64.344 | 1.00 | 22.27 | A |
| ATOM | 1758 | CG | TYR | A | 377 | 55.371 | 39.853 | 63.385 | 1.00 | 21.76 | A |
| ATOM | 1759 | CD1 | TYR | A | 377 | 56.234 | 40.904 | 63.661 | 1.00 | 22.68 | A |
| ATOM | 1760 | CE1 | TYR | A | 377 | 57.222 | 41.271 | 62.764 | 1.00 | 22.82 | A |
| ATOM | 1761 | CD2 | TYR | A | 377 | 55.527 | 39.173 | 62.183 | 1.00 | 20.93 | A |
| ATOM | 1762 | CE2 | TYR | A | 377 | 56.510 | 39.534 | 61.280 | 1.00 | 22.74 | A |
| ATOM | 1763 | CZ | TYR | A | 377 | 57.354 | 40.585 | 61.575 | 1.00 | 22.76 | A |
| ATOM | 1764 | OH | TYR | A | 377 | 58.319 | 40.967 | 60.669 | 1.00 | 24.97 | A |
| ATOM | 1765 | C | TYR | A | 377 | 52.692 | 40.718 | 62.860 | 1.00 | 22.84 | A |
| ATOM | 1766 | O | TYR | A | 377 | 52.975 | 41.788 | 62.315 | 1.00 | 23.96 | A |
| ATOM | 1767 | N | THR | A | 378 | 52.051 | 39.736 | 62.237 | 1.00 | 23.38 | A |
| ATOM | 1768 | CA | THR | A | 378 | 51.636 | 39.846 | 60.845 | 1.00 | 23.80 | A |
| ATOM | 1769 | CB | THR | A | 378 | 50.734 | 38.661 | 60.446 | 1.00 | 25.48 | A |
| ATOM | 1770 | OG1 | THR | A | 378 | 51.446 | 37.433 | 60.651 | 1.00 | 29.10 | A |
| ATOM | 1771 | CG2 | THR | A | 378 | 50.325 | 38.772 | 58.980 | 1.00 | 26.98 | A |
| ATOM | 1772 | C | THR | A | 378 | 50.897 | 41.145 | 60.543 | 1.00 | 22.83 | A |
| ATOM | 1773 | O | THR | A | 378 | 51.166 | 41.798 | 59.533 | 1.00 | 24.33 | A |
| ATOM | 1774 | N | ASP | A | 379 | 49.963 | 41.516 | 61.412 | 1.00 | 22.53 | A |
| ATOM | 1775 | CA | ASP | A | 379 | 49.197 | 42.742 | 61.220 | 1.00 | 22.43 | A |
| ATOM | 1776 | CB | ASP | A | 379 | 47.948 | 42.736 | 62.108 | 1.00 | 24.36 | A |
| ATOM | 1777 | CG | ASP | A | 379 | 46.893 | 41.756 | 61.626 | 1.00 | 27.03 | A |
| ATOM | 1778 | OD1 | ASP | A | 379 | 47.198 | 40.550 | 61.518 | 1.00 | 30.79 | A |
| ATOM | 1779 | OD2 | ASP | A | 379 | 45.756 | 42.194 | 61.355 | 1.00 | 30.32 | A |
| ATOM | 1780 | C | ASP | A | 379 | 50.028 | 43.985 | 61.519 | 1.00 | 21.23 | A |
| ATOM | 1781 | O | ASP | A | 379 | 49.892 | 45.006 | 60.845 | 1.00 | 21.56 | A |
| ATOM | 1782 | N | ARG | A | 380 | 50.889 | 43.902 | 62.527 | 1.00 | 20.84 | A |
| ATOM | 1783 | CA | ARG | A | 380 | 51.716 | 45.042 | 62.885 | 1.00 | 19.89 | A |
| ATOM | 1784 | CB | ARG | A | 380 | 52.470 | 44.779 | 64.195 | 1.00 | 20.64 | A |
| ATOM | 1785 | CG | ARG | A | 380 | 51.550 | 44.664 | 65.414 | 1.00 | 22.66 | A |
| ATOM | 1786 | CD | ARG | A | 380 | 52.262 | 45.041 | 66.703 | 1.00 | 23.15 | A |
| ATOM | 1787 | NE | ARG | A | 380 | 53.374 | 44.152 | 67.013 | 1.00 | 25.09 | A |
| ATOM | 1788 | CZ | ARG | A | 380 | 53.245 | 42.870 | 67.342 | 1.00 | 24.87 | A |
| ATOM | 1789 | NH1 | ARG | A | 380 | 52.041 | 42.316 | 67.408 | 1.00 | 25.24 | A |
| ATOM | 1790 | NH2 | ARG | A | 380 | 54.322 | 42.143 | 67.608 | 1.00 | 27.04 | A |
| ATOM | 1791 | C | ARG | A | 380 | 52.697 | 45.390 | 61.773 | 1.00 | 18.86 | A |
| ATOM | 1792 | O | ARG | A | 380 | 52.841 | 46.557 | 61.418 | 1.00 | 19.07 | A |
| ATOM | 1793 | N | ILE | A | 381 | 53.361 | 44.386 | 61.212 | 1.00 | 18.19 | A |
| ATOM | 1794 | CA | ILE | A | 381 | 54.318 | 44.647 | 60.140 | 1.00 | 19.09 | A |
| ATOM | 1795 | CB | ILE | A | 381 | 55.142 | 43.382 | 59.787 | 1.00 | 18.39 | A |
| ATOM | 1796 | CG2 | ILE | A | 381 | 54.259 | 42.347 | 59.108 | 1.00 | 20.45 | A |
| ATOM | 1797 | CG1 | ILE | A | 381 | 56.316 | 43.769 | 58.885 | 1.00 | 19.91 | A |
| ATOM | 1798 | CD1 | ILE | A | 381 | 57.230 | 44.806 | 59.501 | 1.00 | 21.55 | A |
| ATOM | 1799 | C | ILE | A | 381 | 53.608 | 45.166 | 58.889 | 1.00 | 18.80 | A |
| ATOM | 1800 | O | ILE | A | 381 | 54.187 | 45.918 | 58.106 | 1.00 | 19.63 | A |
| ATOM | 1801 | N | GLN | A | 382 | 52.353 | 44.773 | 58.705 | 1.00 | 19.73 | A |
| ATOM | 1802 | CA | GLN | A | 382 | 51.581 | 45.232 | 57.553 | 1.00 | 20.03 | A |

TABLE 1-continued

| | | | | | | | | | | |
|---|---|---|---|---|---|---|---|---|---|---|
| ATOM | 1803 | CB | GLN | A | 382 | 50.231 | 44.515 | 57.498 | 1.00 | 21.35 | A |
| ATOM | 1804 | CG | GLN | A | 382 | 49.439 | 44.788 | 56.232 | 1.00 | 24.59 | A |
| ATOM | 1805 | CD | GLN | A | 382 | 50.016 | 44.085 | 55.021 | 1.00 | 27.65 | A |
| ATOM | 1806 | OE1 | GLN | A | 382 | 49.460 | 44.157 | 53.926 | 1.00 | 31.64 | A |
| ATOM | 1807 | NE2 | GLN | A | 382 | 51.136 | 43.396 | 55.211 | 1.00 | 29.16 | A |
| ATOM | 1808 | C | GLN | A | 382 | 51.354 | 46.735 | 57.692 | 1.00 | 20.05 | A |
| ATOM | 1809 | O | GLN | A | 382 | 51.412 | 47.480 | 56.719 | 1.00 | 21.36 | A |
| ATOM | 1810 | N | VAL | A | 383 | 51.092 | 47.177 | 58.916 | 1.00 | 19.07 | A |
| ATOM | 1811 | CA | VAL | A | 383 | 50.872 | 48.591 | 59.168 | 1.00 | 18.28 | A |
| ATOM | 1812 | CB | VAL | A | 383 | 50.283 | 48.819 | 60.579 | 1.00 | 18.81 | A |
| ATOM | 1813 | CG1 | VAL | A | 383 | 50.235 | 50.306 | 60.891 | 1.00 | 18.02 | A |
| ATOM | 1814 | CG2 | VAL | A | 383 | 48.879 | 48.225 | 60.645 | 1.00 | 20.64 | A |
| ATOM | 1815 | C | VAL | A | 383 | 52.185 | 49.361 | 59.019 | 1.00 | 17.24 | A |
| ATOM | 1816 | O | VAL | A | 383 | 52.222 | 50.426 | 58.406 | 1.00 | 17.10 | A |
| ATOM | 1817 | N | LEU | A | 384 | 53.265 | 48.808 | 59.559 | 1.00 | 16.44 | A |
| ATOM | 1818 | CA | LEU | A | 384 | 54.569 | 49.457 | 59.471 | 1.00 | 16.62 | A |
| ATOM | 1819 | CB | LEU | A | 384 | 55.603 | 48.692 | 60.301 | 1.00 | 18.15 | A |
| ATOM | 1820 | CG | LEU | A | 384 | 55.409 | 48.726 | 61.818 | 1.00 | 20.02 | A |
| ATOM | 1821 | CD1 | LEU | A | 384 | 56.434 | 47.821 | 62.472 | 1.00 | 22.12 | A |
| ATOM | 1822 | CD2 | LEU | A | 384 | 55.550 | 50.155 | 62.332 | 1.00 | 21.97 | A |
| ATOM | 1823 | C | LEU | A | 384 | 55.051 | 49.580 | 58.032 | 1.00 | 15.97 | A |
| ATOM | 1824 | O | LEU | A | 384 | 55.636 | 50.595 | 57.659 | 1.00 | 18.19 | A |
| ATOM | 1825 | N | ARG | A | 385 | 54.816 | 48.555 | 57.218 | 1.00 | 15.80 | A |
| ATOM | 1826 | CA | ARG | A | 385 | 55.245 | 48.620 | 55.824 | 1.00 | 16.02 | A |
| ATOM | 1827 | CB | ARG | A | 385 | 55.020 | 47.278 | 55.117 | 1.00 | 18.31 | A |
| ATOM | 1828 | CG | ARG | A | 385 | 53.577 | 46.903 | 54.890 | 1.00 | 24.03 | A |
| ATOM | 1829 | CD | ARG | A | 385 | 53.460 | 45.456 | 54.414 | 1.00 | 26.25 | A |
| ATOM | 1830 | NE | ARG | A | 385 | 54.272 | 45.201 | 53.229 | 1.00 | 27.51 | A |
| ATOM | 1831 | CZ | ARG | A | 385 | 54.291 | 44.047 | 52.569 | 1.00 | 27.90 | A |
| ATOM | 1832 | NH1 | ARG | A | 385 | 53.542 | 43.032 | 52.980 | 1.00 | 30.71 | A |
| ATOM | 1833 | NH2 | ARG | A | 385 | 55.051 | 43.911 | 51.490 | 1.00 | 28.89 | A |
| ATOM | 1834 | C | ARG | A | 385 | 54.482 | 49.733 | 55.110 | 1.00 | 15.36 | A |
| ATOM | 1835 | O | ARG | A | 385 | 55.051 | 50.477 | 54.314 | 1.00 | 16.46 | A |
| ATOM | 1836 | N | ASN | A | 386 | 53.195 | 49.864 | 55.405 | 1.00 | 16.28 | A |
| ATOM | 1837 | CA | ASN | A | 386 | 52.400 | 50.910 | 54.777 | 1.00 | 16.79 | A |
| ATOM | 1838 | CB | ASN | A | 386 | 50.910 | 50.605 | 54.941 | 1.00 | 18.73 | A |
| ATOM | 1839 | CG | ASN | A | 386 | 50.412 | 49.613 | 53.905 | 1.00 | 22.47 | A |
| ATOM | 1840 | OD1 | ASN | A | 386 | 50.233 | 49.960 | 52.737 | 1.00 | 24.09 | A |
| ATOM | 1841 | ND2 | ASN | A | 386 | 50.207 | 48.369 | 54.321 | 1.00 | 24.87 | A |
| ATOM | 1842 | C | ASN | A | 386 | 52.737 | 52.293 | 55.327 | 1.00 | 15.78 | A |
| ATOM | 1843 | O | ASN | A | 386 | 52.603 | 53.298 | 54.627 | 1.00 | 15.65 | A |
| ATOM | 1844 | N | MET | A | 387 | 53.190 | 52.344 | 56.576 | 1.00 | 16.58 | A |
| ATOM | 1845 | CA | MET | A | 387 | 53.551 | 53.613 | 57.191 | 1.00 | 15.91 | A |
| ATOM | 1846 | CB | MET | A | 387 | 53.853 | 53.425 | 58.675 | 1.00 | 17.75 | A |
| ATOM | 1847 | CG | MET | A | 387 | 54.162 | 54.722 | 59.398 | 1.00 | 18.40 | A |
| ATOM | 1848 | SD | MET | A | 387 | 54.685 | 54.438 | 61.097 | 1.00 | 21.99 | A |
| ATOM | 1849 | CE | MET | A | 387 | 53.127 | 54.046 | 61.856 | 1.00 | 19.64 | A |
| ATOM | 1850 | C | MET | A | 387 | 54.765 | 54.212 | 56.502 | 1.00 | 15.41 | A |
| ATOM | 1851 | O | MET | A | 387 | 54.766 | 55.390 | 56.146 | 1.00 | 15.59 | A |
| ATOM | 1852 | N | VAL | A | 388 | 55.804 | 53.402 | 56.315 | 1.00 | 16.37 | A |
| ATOM | 1853 | CA | VAL | A | 388 | 57.016 | 53.888 | 55.663 | 1.00 | 15.81 | A |
| ATOM | 1854 | CB | VAL | A | 388 | 58.155 | 52.853 | 55.749 | 1.00 | 17.43 | A |
| ATOM | 1855 | CG1 | VAL | A | 388 | 59.375 | 53.356 | 54.990 | 1.00 | 18.43 | A |
| ATOM | 1856 | CG2 | VAL | A | 388 | 58.521 | 52.618 | 57.208 | 1.00 | 18.17 | A |
| ATOM | 1857 | C | VAL | A | 388 | 56.719 | 54.211 | 54.203 | 1.00 | 15.38 | A |
| ATOM | 1858 | O | VAL | A | 388 | 57.279 | 55.153 | 53.641 | 1.00 | 14.00 | A |
| ATOM | 1859 | N | HIS | A | 389 | 55.828 | 53.433 | 53.594 | 1.00 | 14.57 | A |
| ATOM | 1860 | CA | HIS | A | 389 | 55.440 | 53.670 | 52.207 | 1.00 | 15.93 | A |
| ATOM | 1861 | CB | HIS | A | 389 | 54.499 | 52.555 | 51.733 | 1.00 | 17.19 | A |
| ATOM | 1862 | CG | HIS | A | 389 | 53.998 | 52.730 | 50.332 | 1.00 | 18.34 | A |
| ATOM | 1863 | CD2 | HIS | A | 389 | 52.760 | 52.575 | 49.805 | 1.00 | 19.82 | A |
| ATOM | 1864 | ND1 | HIS | A | 389 | 54.818 | 53.086 | 49.284 | 1.00 | 19.86 | A |
| ATOM | 1865 | CE1 | HIS | A | 389 | 54.107 | 53.144 | 48.171 | 1.00 | 21.07 | A |
| ATOM | 1866 | NE2 | HIS | A | 389 | 52.855 | 52.838 | 48.461 | 1.00 | 19.96 | A |
| ATOM | 1867 | C | HIS | A | 389 | 54.758 | 55.040 | 52.124 | 1.00 | 14.29 | A |
| ATOM | 1868 | O | HIS | A | 389 | 55.019 | 55.819 | 51.206 | 1.00 | 15.16 | A |
| ATOM | 1869 | N | CYS | A | 390 | 53.896 | 55.334 | 53.096 | 1.00 | 14.65 | A |
| ATOM | 1870 | CA | CYS | A | 390 | 53.203 | 56.624 | 53.146 | 1.00 | 14.68 | A |
| ATOM | 1871 | CB | CYS | A | 390 | 52.181 | 56.641 | 54.284 | 1.00 | 15.22 | A |
| ATOM | 1872 | SG | CYS | A | 390 | 50.637 | 55.757 | 53.923 | 1.00 | 23.86 | A |
| ATOM | 1873 | C | CYS | A | 390 | 54.195 | 57.764 | 53.358 | 1.00 | 12.43 | A |
| ATOM | 1874 | O | CYS | A | 390 | 54.095 | 58.819 | 52.733 | 1.00 | 12.71 | A |
| ATOM | 1875 | N | ALA | A | 391 | 55.149 | 57.550 | 54.257 | 1.00 | 12.70 | A |
| ATOM | 1876 | CA | ALA | A | 391 | 56.159 | 58.558 | 54.539 | 1.00 | 11.72 | A |
| ATOM | 1877 | CB | ALA | A | 391 | 57.104 | 58.053 | 55.621 | 1.00 | 10.94 | A |
| ATOM | 1878 | C | ALA | A | 391 | 56.941 | 58.873 | 53.258 | 1.00 | 11.76 | A |
| ATOM | 1879 | O | ALA | A | 391 | 57.231 | 60.032 | 52.967 | 1.00 | 13.79 | A |
| ATOM | 1880 | N | ASP | A | 392 | 57.264 | 57.832 | 52.495 | 1.00 | 12.11 | A |
| ATOM | 1881 | CA | ASP | A | 392 | 58.008 | 57.982 | 51.246 | 1.00 | 12.04 | A |

TABLE 1-continued

| | | | | | | | | | | |
|---|---|---|---|---|---|---|---|---|---|---|
| ATOM | 1882 | CB | ASP | A | 392 | 58.327 | 56.598 | 50.669 | 1.00 | 12.06 | A |
| ATOM | 1883 | CG | ASP | A | 392 | 59.425 | 56.629 | 49.616 | 1.00 | 13.56 | A |
| ATOM | 1884 | OD1 | ASP | A | 392 | 59.398 | 55.754 | 48.724 | 1.00 | 17.06 | A |
| ATOM | 1885 | OD2 | ASP | A | 392 | 60.318 | 57.500 | 49.687 | 1.00 | 9.21 | A |
| ATOM | 1886 | C | ASP | A | 392 | 57.190 | 58.789 | 50.234 | 1.00 | 12.05 | A |
| ATOM | 1887 | O | ASP | A | 392 | 57.744 | 59.526 | 49.419 | 1.00 | 14.41 | A |
| ATOM | 1888 | N | LEU | A | 393 | 55.867 | 58.649 | 50.298 | 1.00 | 11.58 | A |
| ATOM | 1889 | CA | LEU | A | 393 | 54.974 | 59.363 | 49.386 | 1.00 | 13.19 | A |
| ATOM | 1890 | CB | LEU | A | 393 | 53.978 | 58.383 | 48.755 | 1.00 | 15.37 | A |
| ATOM | 1891 | CG | LEU | A | 393 | 54.579 | 57.277 | 47.883 | 1.00 | 17.56 | A |
| ATOM | 1892 | CD1 | LEU | A | 393 | 53.466 | 56.395 | 47.334 | 1.00 | 18.60 | A |
| ATOM | 1893 | CD2 | LEU | A | 393 | 55.377 | 57.896 | 46.748 | 1.00 | 21.35 | A |
| ATOM | 1894 | C | LEU | A | 393 | 54.216 | 60.465 | 50.120 | 1.00 | 12.25 | A |
| ATOM | 1895 | O | LEU | A | 393 | 53.040 | 60.714 | 49.845 | 1.00 | 15.76 | A |
| ATOM | 1896 | N | SER | A | 394 | 54.897 | 61.136 | 51.044 | 1.00 | 11.49 | A |
| ATOM | 1897 | CA | SER | A | 394 | 54.271 | 62.192 | 51.830 | 1.00 | 11.54 | A |
| ATOM | 1898 | CB | SER | A | 394 | 54.760 | 62.113 | 53.279 | 1.00 | 13.05 | A |
| ATOM | 1899 | OG | SER | A | 394 | 56.151 | 62.373 | 53.371 | 1.00 | 13.21 | A |
| ATOM | 1900 | C | SER | A | 394 | 54.470 | 63.617 | 51.310 | 1.00 | 11.78 | A |
| ATOM | 1901 | O | SER | A | 394 | 53.823 | 64.540 | 51.802 | 1.00 | 13.70 | A |
| ATOM | 1902 | N | ASN | A | 395 | 55.344 | 63.800 | 50.322 | 1.00 | 12.05 | A |
| ATOM | 1903 | CA | ASN | A | 395 | 55.609 | 65.134 | 49.782 | 1.00 | 12.13 | A |
| ATOM | 1904 | CB | ASN | A | 395 | 56.431 | 65.055 | 48.487 | 1.00 | 13.30 | A |
| ATOM | 1905 | CG | ASN | A | 395 | 57.866 | 64.607 | 48.710 | 1.00 | 14.95 | A |
| ATOM | 1906 | OD1 | ASN | A | 395 | 58.606 | 64.412 | 47.746 | 1.00 | 15.49 | A |
| ATOM | 1907 | ND2 | ASN | A | 395 | 58.269 | 64.455 | 49.969 | 1.00 | 15.39 | A |
| ATOM | 1908 | C | ASN | A | 395 | 54.347 | 65.957 | 49.498 | 1.00 | 11.87 | A |
| ATOM | 1909 | O | ASN | A | 395 | 54.237 | 67.099 | 49.937 | 1.00 | 11.96 | A |
| ATOM | 1910 | N | PRO | A | 396 | 53.378 | 65.383 | 48.765 | 1.00 | 12.62 | A |
| ATOM | 1911 | CD | PRO | A | 396 | 53.404 | 64.106 | 48.035 | 1.00 | 14.02 | A |
| ATOM | 1912 | CA | PRO | A | 396 | 52.150 | 66.126 | 48.452 | 1.00 | 12.71 | A |
| ATOM | 1913 | CB | PRO | A | 396 | 51.441 | 65.218 | 47.448 | 1.00 | 14.17 | A |
| ATOM | 1914 | CG | PRO | A | 396 | 52.571 | 64.431 | 46.833 | 1.00 | 14.79 | A |
| ATOM | 1915 | C | PRO | A | 396 | 51.251 | 66.464 | 49.633 | 1.00 | 12.40 | A |
| ATOM | 1916 | O | PRO | A | 396 | 50.334 | 67.275 | 49.492 | 1.00 | 13.43 | A |
| ATOM | 1917 | N | THR | A | 397 | 51.496 | 65.845 | 50.785 | 1.00 | 13.56 | A |
| ATOM | 1918 | CA | THR | A | 397 | 50.681 | 66.093 | 51.972 | 1.00 | 12.40 | A |
| ATOM | 1919 | CB | THR | A | 397 | 50.506 | 64.813 | 52.816 | 1.00 | 13.47 | A |
| ATOM | 1920 | OG1 | THR | A | 397 | 51.730 | 64.516 | 53.502 | 1.00 | 14.03 | A |
| ATOM | 1921 | CG2 | THR | A | 397 | 50.120 | 63.644 | 51.935 | 1.00 | 13.51 | A |
| ATOM | 1922 | C | THR | A | 397 | 51.284 | 67.163 | 52.876 | 1.00 | 11.50 | A |
| ATOM | 1923 | O | THR | A | 397 | 50.691 | 67.541 | 53.884 | 1.00 | 12.93 | A |
| ATOM | 1924 | N | LYS | A | 398 | 52.469 | 67.642 | 52.521 | 1.00 | 12.26 | A |
| ATOM | 1925 | CA | LYS | A | 398 | 53.142 | 68.662 | 53.312 | 1.00 | 13.58 | A |
| ATOM | 1926 | CB | LYS | A | 398 | 54.661 | 68.560 | 53.125 | 1.00 | 14.82 | A |
| ATOM | 1927 | CG | LYS | A | 398 | 55.246 | 67.231 | 53.555 | 1.00 | 15.74 | A |
| ATOM | 1928 | CD | LYS | A | 398 | 55.033 | 66.994 | 55.042 | 1.00 | 16.62 | A |
| ATOM | 1929 | CE | LYS | A | 398 | 55.539 | 65.623 | 55.481 | 1.00 | 17.02 | A |
| ATOM | 1930 | NZ | LYS | A | 398 | 57.019 | 65.472 | 55.402 | 1.00 | 15.70 | A |
| ATOM | 1931 | C | LYS | A | 398 | 52.689 | 70.055 | 52.912 | 1.00 | 14.25 | A |
| ATOM | 1932 | O | LYS | A | 398 | 52.058 | 70.240 | 51.872 | 1.00 | 14.15 | A |
| ATOM | 1933 | N | SER | A | 399 | 53.022 | 71.035 | 53.743 | 1.00 | 15.69 | A |
| ATOM | 1934 | CA | SER | A | 399 | 52.673 | 72.418 | 53.454 | 1.00 | 17.71 | A |
| ATOM | 1935 | CB | SER | A | 399 | 53.396 | 73.346 | 54.431 | 1.00 | 20.09 | A |
| ATOM | 1936 | OG | SER | A | 399 | 52.806 | 74.634 | 54.445 | 1.00 | 26.34 | A |
| ATOM | 1937 | C | SER | A | 399 | 53.136 | 72.676 | 52.020 | 1.00 | 16.54 | A |
| ATOM | 1938 | O | SER | A | 399 | 54.171 | 72.164 | 51.598 | 1.00 | 16.94 | A |
| ATOM | 1939 | N | LEU | A | 400 | 52.371 | 73.462 | 51.271 | 1.00 | 16.60 | A |
| ATOM | 1940 | CA | LEU | A | 400 | 52.700 | 73.741 | 49.879 | 1.00 | 16.02 | A |
| ATOM | 1941 | CB | LEU | A | 400 | 51.666 | 74.702 | 49.282 | 1.00 | 16.60 | A |
| ATOM | 1942 | CG | LEU | A | 400 | 51.808 | 74.998 | 47.785 | 1.00 | 17.23 | A |
| ATOM | 1943 | CD1 | LEU | A | 400 | 51.687 | 73.715 | 46.978 | 1.00 | 18.46 | A |
| ATOM | 1944 | CD2 | LEU | A | 400 | 50.734 | 75.987 | 47.367 | 1.00 | 16.33 | A |
| ATOM | 1945 | C | LEU | A | 400 | 54.112 | 74.271 | 49.615 | 1.00 | 15.55 | A |
| ATOM | 1946 | O | LEU | A | 400 | 54.708 | 73.933 | 48.589 | 1.00 | 16.70 | A |
| ATOM | 1947 | N | GLU | A | 401 | 54.658 | 75.082 | 50.520 | 1.00 | 15.65 | A |
| ATOM | 1948 | CA | GLU | A | 401 | 56.001 | 75.618 | 50.302 | 1.00 | 16.97 | A |
| ATOM | 1949 | CB | GLU | A | 401 | 56.358 | 76.679 | 51.355 | 1.00 | 19.54 | A |
| ATOM | 1950 | CG | GLU | A | 401 | 56.793 | 76.125 | 52.699 | 1.00 | 21.98 | A |
| ATOM | 1951 | CD | GLU | A | 401 | 55.632 | 75.885 | 53.636 | 1.00 | 24.19 | A |
| ATOM | 1952 | OE1 | GLU | A | 401 | 54.513 | 75.664 | 53.137 | 1.00 | 26.88 | A |
| ATOM | 1953 | OE2 | GLU | A | 401 | 55.842 | 75.906 | 54.870 | 1.00 | 26.57 | A |
| ATOM | 1954 | C | GLU | A | 401 | 57.044 | 74.499 | 50.311 | 1.00 | 15.71 | A |
| ATOM | 1955 | O | GLU | A | 401 | 58.086 | 74.607 | 49.661 | 1.00 | 17.68 | A |
| ATOM | 1956 | N | LEU | A | 402 | 56.759 | 73.424 | 51.041 | 1.00 | 14.61 | A |
| ATOM | 1957 | CA | LEU | A | 402 | 57.677 | 72.293 | 51.106 | 1.00 | 14.28 | A |
| ATOM | 1958 | CB | LEU | A | 402 | 57.445 | 71.482 | 52.385 | 1.00 | 15.31 | A |
| ATOM | 1959 | CG | LEU | A | 402 | 57.764 | 72.187 | 53.708 | 1.00 | 18.56 | A |
| ATOM | 1960 | CD1 | LEU | A | 402 | 57.346 | 71.313 | 54.887 | 1.00 | 20.28 | A |

TABLE 1-continued

| | | | | | | | | | | |
|---|---|---|---|---|---|---|---|---|---|---|
| ATOM | 1961 | CD2 | LEU | A | 402 | 59.257 | 72.492 | 53.761 | 1.00 | 22.05 | A |
| ATOM | 1962 | C | LEU | A | 402 | 57.455 | 71.406 | 49.889 | 1.00 | 12.37 | A |
| ATOM | 1963 | O | LEU | A | 402 | 58.402 | 71.000 | 49.217 | 1.00 | 13.91 | A |
| ATOM | 1964 | N | TYR | A | 403 | 56.189 | 71.120 | 49.601 | 1.00 | 13.12 | A |
| ATOM | 1965 | CA | TYR | A | 403 | 55.833 | 70.280 | 48.467 | 1.00 | 13.06 | A |
| ATOM | 1966 | CB | TYR | A | 403 | 54.308 | 70.151 | 48.413 | 1.00 | 11.94 | A |
| ATOM | 1967 | CG | TYR | A | 403 | 53.740 | 69.369 | 47.248 | 1.00 | 12.99 | A |
| ATOM | 1968 | CD1 | TYR | A | 403 | 54.446 | 68.332 | 46.648 | 1.00 | 12.79 | A |
| ATOM | 1969 | CE1 | TYR | A | 403 | 53.885 | 67.584 | 45.618 | 1.00 | 14.80 | A |
| ATOM | 1970 | CD2 | TYR | A | 403 | 52.460 | 69.639 | 46.787 | 1.00 | 13.78 | A |
| ATOM | 1971 | CE2 | TYR | A | 403 | 51.892 | 68.901 | 45.769 | 1.00 | 14.19 | A |
| ATOM | 1972 | CZ | TYR | A | 403 | 52.604 | 67.877 | 45.187 | 1.00 | 14.54 | A |
| ATOM | 1973 | OH | TYR | A | 403 | 52.023 | 67.143 | 44.171 | 1.00 | 16.68 | A |
| ATOM | 1974 | C | TYR | A | 403 | 56.402 | 70.846 | 47.162 | 1.00 | 12.98 | A |
| ATOM | 1975 | O | TYR | A | 403 | 56.929 | 70.098 | 46.333 | 1.00 | 15.47 | A |
| ATOM | 1976 | N | ARG | A | 404 | 56.310 | 72.164 | 46.992 | 1.00 | 13.53 | A |
| ATOM | 1977 | CA | ARG | A | 404 | 56.838 | 72.832 | 45.802 | 1.00 | 14.31 | A |
| ATOM | 1978 | CB | ARG | A | 404 | 56.656 | 74.350 | 45.923 | 1.00 | 17.96 | A |
| ATOM | 1979 | CG | ARG | A | 404 | 55.242 | 74.858 | 45.681 | 1.00 | 22.47 | A |
| ATOM | 1980 | CD | ARG | A | 404 | 54.940 | 75.064 | 44.198 | 1.00 | 24.43 | A |
| ATOM | 1981 | NE | ARG | A | 404 | 55.787 | 76.089 | 43.587 | 1.00 | 27.85 | A |
| ATOM | 1982 | CZ | ARG | A | 404 | 57.029 | 75.886 | 43.153 | 1.00 | 28.36 | A |
| ATOM | 1983 | NH1 | ARG | A | 404 | 57.589 | 74.687 | 43.251 | 1.00 | 31.22 | A |
| ATOM | 1984 | NH2 | ARG | A | 404 | 57.717 | 76.887 | 42.623 | 1.00 | 29.23 | A |
| ATOM | 1985 | C | ARG | A | 404 | 58.328 | 72.533 | 45.611 | 1.00 | 13.28 | A |
| ATOM | 1986 | O | ARG | A | 404 | 58.783 | 72.298 | 44.495 | 1.00 | 14.00 | A |
| ATOM | 1987 | N | GLN | A | 405 | 59.084 | 72.563 | 46.704 | 1.00 | 12.67 | A |
| ATOM | 1988 | CA | GLN | A | 405 | 60.516 | 72.298 | 46.639 | 1.00 | 14.09 | A |
| ATOM | 1989 | CB | GLN | A | 405 | 61.190 | 72.704 | 47.955 | 1.00 | 16.67 | A |
| ATOM | 1990 | CG | GLN | A | 405 | 61.106 | 74.202 | 48.232 | 1.00 | 19.03 | A |
| ATOM | 1991 | CD | GLN | A | 405 | 61.787 | 74.606 | 49.527 | 1.00 | 19.85 | A |
| ATOM | 1992 | OE1 | GLN | A | 405 | 63.013 | 74.578 | 49.632 | 1.00 | 21.13 | A |
| ATOM | 1993 | NE2 | GLN | A | 405 | 60.991 | 74.977 | 50.521 | 1.00 | 21.41 | A |
| ATOM | 1994 | C | GLN | A | 405 | 60.811 | 70.837 | 46.318 | 1.00 | 12.92 | A |
| ATOM | 1995 | O | GLN | A | 405 | 61.751 | 70.535 | 45.573 | 1.00 | 14.19 | A |
| ATOM | 1996 | N | TRP | A | 406 | 60.018 | 69.928 | 46.875 | 1.00 | 11.59 | A |
| ATOM | 1997 | CA | TRP | A | 406 | 60.218 | 68.513 | 46.603 | 1.00 | 11.37 | A |
| ATOM | 1998 | CB | TRP | A | 406 | 59.309 | 67.649 | 47.481 | 1.00 | 10.72 | A |
| ATOM | 1999 | CG | TRP | A | 406 | 59.683 | 67.635 | 48.931 | 1.00 | 11.12 | A |
| ATOM | 2000 | CD2 | TRP | A | 406 | 60.949 | 67.261 | 49.497 | 1.00 | 13.39 | A |
| ATOM | 2001 | CE2 | TRP | A | 406 | 60.839 | 67.402 | 50.894 | 1.00 | 13.47 | A |
| ATOM | 2002 | CE3 | TRP | A | 406 | 62.161 | 66.821 | 48.958 | 1.00 | 13.67 | A |
| ATOM | 2003 | CD1 | TRP | A | 406 | 58.882 | 67.976 | 49.980 | 1.00 | 11.18 | A |
| ATOM | 2004 | NE1 | TRP | A | 406 | 59.568 | 67.839 | 51.166 | 1.00 | 12.80 | A |
| ATOM | 2005 | CZ2 | TRP | A | 406 | 61.895 | 67.119 | 51.759 | 1.00 | 14.28 | A |
| ATOM | 2006 | CZ3 | TRP | A | 406 | 63.210 | 66.540 | 49.819 | 1.00 | 14.66 | A |
| ATOM | 2007 | CH2 | TRP | A | 406 | 63.070 | 66.691 | 51.204 | 1.00 | 12.75 | A |
| ATOM | 2008 | C | TRP | A | 406 | 59.922 | 68.224 | 45.137 | 1.00 | 11.97 | A |
| ATOM | 2009 | O | TRP | A | 406 | 60.637 | 67.460 | 44.497 | 1.00 | 14.63 | A |
| ATOM | 2010 | N | THR | A | 407 | 58.867 | 68.840 | 44.610 | 1.00 | 12.63 | A |
| ATOM | 2011 | CA | THR | A | 407 | 58.479 | 68.635 | 43.217 | 1.00 | 13.93 | A |
| ATOM | 2012 | CB | THR | A | 407 | 57.145 | 69.366 | 42.908 | 1.00 | 14.39 | A |
| ATOM | 2013 | OG1 | THR | A | 407 | 56.092 | 68.785 | 43.686 | 1.00 | 17.39 | A |
| ATOM | 2014 | CG2 | THR | A | 407 | 56.790 | 69.243 | 41.439 | 1.00 | 16.94 | A |
| ATOM | 2015 | C | THR | A | 407 | 59.562 | 69.109 | 42.254 | 1.00 | 13.54 | A |
| ATOM | 2016 | O | THR | A | 407 | 59.867 | 68.438 | 41.265 | 1.00 | 14.07 | A |
| ATOM | 2017 | N | ASP | A | 408 | 60.156 | 70.258 | 42.543 | 1.00 | 15.33 | A |
| ATOM | 2018 | CA | ASP | A | 408 | 61.213 | 70.778 | 41.683 | 1.00 | 16.70 | A |
| ATOM | 2019 | CB | ASP | A | 408 | 61.642 | 72.171 | 42.148 | 1.00 | 20.83 | A |
| ATOM | 2020 | CG | ASP | A | 408 | 60.554 | 73.211 | 41.937 | 1.00 | 27.28 | A |
| ATOM | 2021 | OD1 | ASP | A | 408 | 60.054 | 73.320 | 40.798 | 1.00 | 30.78 | A |
| ATOM | 2022 | OD2 | ASP | A | 408 | 60.196 | 73.918 | 42.903 | 1.00 | 31.50 | A |
| ATOM | 2023 | C | ASP | A | 408 | 62.406 | 69.826 | 41.675 | 1.00 | 15.96 | A |
| ATOM | 2024 | O | ASP | A | 408 | 63.041 | 69.628 | 40.641 | 1.00 | 17.76 | A |
| ATOM | 2025 | N | ARG | A | 409 | 62.694 | 69.225 | 42.826 | 1.00 | 14.51 | A |
| ATOM | 2026 | CA | ARG | A | 409 | 63.806 | 68.287 | 42.926 | 1.00 | 13.79 | A |
| ATOM | 2027 | CB | ARG | A | 409 | 64.131 | 67.991 | 44.391 | 1.00 | 14.84 | A |
| ATOM | 2028 | CG | ARG | A | 409 | 64.785 | 69.160 | 45.097 | 1.00 | 15.68 | A |
| ATOM | 2029 | CD | ARG | A | 409 | 65.115 | 68.849 | 46.538 | 1.00 | 17.95 | A |
| ATOM | 2030 | NE | ARG | A | 409 | 65.868 | 69.949 | 47.134 | 1.00 | 18.15 | A |
| ATOM | 2031 | CZ | ARG | A | 409 | 66.935 | 69.786 | 47.904 | 1.00 | 18.97 | A |
| ATOM | 2032 | NH1 | ARG | A | 409 | 67.373 | 68.563 | 48.174 | 1.00 | 19.30 | A |
| ATOM | 2033 | NH2 | ARG | A | 409 | 67.574 | 70.843 | 48.392 | 1.00 | 21.46 | A |
| ATOM | 2034 | C | ARG | A | 409 | 63.544 | 66.984 | 42.191 | 1.00 | 12.51 | A |
| ATOM | 2035 | O | ARG | A | 409 | 64.435 | 66.456 | 41.530 | 1.00 | 13.34 | A |
| ATOM | 2036 | N | ILE | A | 410 | 62.330 | 66.455 | 42.294 | 1.00 | 12.18 | A |
| ATOM | 2037 | CA | ILE | A | 410 | 62.047 | 65.209 | 41.607 | 1.00 | 14.64 | A |
| ATOM | 2038 | CB | ILE | A | 410 | 60.692 | 64.609 | 42.052 | 1.00 | 17.58 | A |
| ATOM | 2039 | CG2 | ILE | A | 410 | 59.542 | 65.387 | 41.449 | 1.00 | 20.89 | A |

TABLE 1-continued

| ATOM | 2040 | CG1 | ILE | A | 410 | 60.619 | 63.145 | 41.626 | 1.00 | 19.91 | A |
| --- | --- | --- | --- | --- | --- | --- | --- | --- | --- | --- | --- |
| ATOM | 2041 | CD1 | ILE | A | 410 | 61.793 | 62.313 | 42.112 | 1.00 | 22.03 | A |
| ATOM | 2042 | C | ILE | A | 410 | 62.058 | 65.457 | 40.098 | 1.00 | 13.55 | A |
| ATOM | 2043 | O | ILE | A | 410 | 62.538 | 64.627 | 39.331 | 1.00 | 13.62 | A |
| ATOM | 2044 | N | MET | A | 411 | 61.560 | 66.617 | 39.681 | 1.00 | 13.62 | A |
| ATOM | 2045 | CA | MET | A | 411 | 61.543 | 66.951 | 38.261 | 1.00 | 15.59 | A |
| ATOM | 2046 | CB | MET | A | 411 | 60.853 | 68.299 | 38.030 | 1.00 | 20.43 | A |
| ATOM | 2047 | CG | MET | A | 411 | 59.342 | 68.238 | 38.164 | 1.00 | 29.99 | A |
| ATOM | 2048 | SD | MET | A | 411 | 58.603 | 66.797 | 37.357 | 1.00 | 33.22 | A |
| ATOM | 2049 | CE | MET | A | 411 | 58.946 | 67.148 | 35.632 | 1.00 | 34.66 | A |
| ATOM | 2050 | C | MET | A | 411 | 62.976 | 67.017 | 37.751 | 1.00 | 14.15 | A |
| ATOM | 2051 | O | MET | A | 411 | 63.280 | 66.517 | 36.669 | 1.00 | 14.88 | A |
| ATOM | 2052 | N | GLU | A | 412 | 63.862 | 67.626 | 38.538 | 1.00 | 13.96 | A |
| ATOM | 2053 | CA | GLU | A | 412 | 65.261 | 67.732 | 38.134 | 1.00 | 15.05 | A |
| ATOM | 2054 | CB | GLU | A | 412 | 66.058 | 68.567 | 39.137 | 1.00 | 17.37 | A |
| ATOM | 2055 | CG | GLU | A | 412 | 67.528 | 68.746 | 38.765 | 1.00 | 22.75 | A |
| ATOM | 2056 | CD | GLU | A | 412 | 67.723 | 69.271 | 37.350 | 1.00 | 28.08 | A |
| ATOM | 2057 | OE1 | GLU | A | 412 | 67.911 | 68.451 | 36.418 | 1.00 | 29.97 | A |
| ATOM | 2058 | OE2 | GLU | A | 412 | 67.680 | 70.510 | 37.167 | 1.00 | 31.57 | A |
| ATOM | 2059 | C | GLU | A | 412 | 65.892 | 66.351 | 37.999 | 1.00 | 14.34 | A |
| ATOM | 2060 | O | GLU | A | 412 | 66.659 | 66.107 | 37.069 | 1.00 | 15.05 | A |
| ATOM | 2061 | N | GLU | A | 413 | 65.567 | 65.441 | 38.913 | 1.00 | 14.81 | A |
| ATOM | 2062 | CA | GLU | A | 413 | 66.133 | 64.103 | 38.829 | 1.00 | 15.36 | A |
| ATOM | 2063 | CB | GLU | A | 413 | 65.848 | 63.303 | 40.105 | 1.00 | 16.73 | A |
| ATOM | 2064 | CG | GLU | A | 413 | 66.713 | 62.050 | 40.208 | 1.00 | 17.93 | A |
| ATOM | 2065 | CD | GLU | A | 413 | 66.647 | 61.385 | 41.565 | 1.00 | 17.74 | A |
| ATOM | 2066 | OE1 | GLU | A | 413 | 66.896 | 62.075 | 42.574 | 1.00 | 15.92 | A |
| ATOM | 2067 | OE2 | GLU | A | 413 | 66.365 | 60.170 | 41.616 | 1.00 | 18.42 | A |
| ATOM | 2068 | C | GLU | A | 413 | 65.576 | 63.383 | 37.598 | 1.00 | 14.66 | A |
| ATOM | 2069 | O | GLU | A | 413 | 66.294 | 62.632 | 36.940 | 1.00 | 15.21 | A |
| ATOM | 2070 | N | PHE | A | 414 | 64.304 | 63.623 | 37.283 | 1.00 | 14.54 | A |
| ATOM | 2071 | CA | PHE | A | 414 | 63.681 | 63.017 | 36.102 | 1.00 | 15.60 | A |
| ATOM | 2072 | CB | PHE | A | 414 | 62.245 | 63.520 | 35.913 | 1.00 | 16.81 | A |
| ATOM | 2073 | CG | PHE | A | 414 | 61.180 | 62.567 | 36.377 | 1.00 | 22.22 | A |
| ATOM | 2074 | CD1 | PHE | A | 414 | 60.802 | 62.514 | 37.709 | 1.00 | 23.33 | A |
| ATOM | 2075 | CD2 | PHE | A | 414 | 60.512 | 61.765 | 35.465 | 1.00 | 22.65 | A |
| ATOM | 2076 | CE1 | PHE | A | 414 | 59.772 | 61.682 | 38.122 | 1.00 | 23.93 | A |
| ATOM | 2077 | CE2 | PHE | A | 414 | 59.482 | 60.929 | 35.871 | 1.00 | 24.24 | A |
| ATOM | 2078 | CZ | PHE | A | 414 | 59.110 | 60.889 | 37.200 | 1.00 | 23.76 | A |
| ATOM | 2079 | C | PHE | A | 414 | 64.476 | 63.438 | 34.868 | 1.00 | 15.94 | A |
| ATOM | 2080 | O | PHE | A | 414 | 64.818 | 62.616 | 34.016 | 1.00 | 16.80 | A |
| ATOM | 2081 | N | PHE | A | 415 | 64.747 | 64.737 | 34.776 | 1.00 | 15.83 | A |
| ATOM | 2082 | CA | PHE | A | 415 | 65.496 | 65.284 | 33.649 | 1.00 | 18.64 | A |
| ATOM | 2083 | CB | PHE | A | 415 | 65.536 | 66.815 | 33.711 | 1.00 | 19.60 | A |
| ATOM | 2084 | CG | PHE | A | 415 | 64.189 | 67.462 | 33.589 | 1.00 | 22.12 | A |
| ATOM | 2085 | CD1 | PHE | A | 415 | 63.137 | 66.797 | 32.983 | 1.00 | 22.28 | A |
| ATOM | 2086 | CD2 | PHE | A | 415 | 63.979 | 68.749 | 34.067 | 1.00 | 24.06 | A |
| ATOM | 2087 | CE1 | PHE | A | 415 | 61.897 | 67.400 | 32.854 | 1.00 | 23.90 | A |
| ATOM | 2088 | CE2 | PHE | A | 415 | 62.743 | 69.358 | 33.940 | 1.00 | 21.91 | A |
| ATOM | 2089 | CZ | PHE | A | 415 | 61.699 | 68.681 | 33.332 | 1.00 | 23.33 | A |
| ATOM | 2090 | C | PHE | A | 415 | 66.916 | 64.747 | 33.616 | 1.00 | 19.13 | A |
| ATOM | 2091 | O | PHE | A | 415 | 67.486 | 64.570 | 32.537 | 1.00 | 20.54 | A |
| ATOM | 2092 | N | GLN | A | 416 | 67.491 | 64.502 | 34.792 | 1.00 | 18.16 | A |
| ATOM | 2093 | CA | GLN | A | 416 | 68.846 | 63.965 | 34.876 | 1.00 | 18.89 | A |
| ATOM | 2094 | CB | GLN | A | 416 | 69.304 | 63.810 | 36.333 | 1.00 | 19.84 | A |
| ATOM | 2095 | CG | GLN | A | 416 | 69.381 | 65.098 | 37.147 | 1.00 | 24.89 | A |
| ATOM | 2096 | CD | GLN | A | 416 | 70.277 | 64.963 | 38.374 | 1.00 | 25.70 | A |
| ATOM | 2097 | OE1 | GLN | A | 416 | 71.455 | 65.328 | 38.335 | 1.00 | 30.88 | A |
| ATOM | 2098 | NE2 | GLN | A | 416 | 69.729 | 64.419 | 39.462 | 1.00 | 21.09 | A |
| ATOM | 2099 | C | GLN | A | 416 | 68.866 | 62.594 | 34.211 | 1.00 | 17.56 | A |
| ATOM | 2100 | O | GLN | A | 416 | 69.767 | 62.283 | 33.435 | 1.00 | 17.86 | A |
| ATOM | 2101 | N | GLN | A | 417 | 67.876 | 61.765 | 34.525 | 1.00 | 15.75 | A |
| ATOM | 2102 | CA | GLN | A | 417 | 67.818 | 60.434 | 33.935 | 1.00 | 14.60 | A |
| ATOM | 2103 | CB | GLN | A | 417 | 66.685 | 59.603 | 34.546 | 1.00 | 13.97 | A |
| ATOM | 2104 | CG | GLN | A | 417 | 66.639 | 58.182 | 33.995 | 1.00 | 14.64 | A |
| ATOM | 2105 | CD | GLN | A | 417 | 65.635 | 57.293 | 34.700 | 1.00 | 13.58 | A |
| ATOM | 2106 | OE1 | GLN | A | 417 | 65.527 | 57.313 | 35.925 | 1.00 | 16.51 | A |
| ATOM | 2107 | NE2 | GLN | A | 417 | 64.903 | 56.495 | 33.931 | 1.00 | 16.85 | A |
| ATOM | 2108 | C | GLN | A | 417 | 67.609 | 60.557 | 32.432 | 1.00 | 15.37 | A |
| ATOM | 2109 | O | GLN | A | 417 | 68.182 | 59.799 | 31.651 | 1.00 | 17.14 | A |
| ATOM | 2110 | N | GLY | A | 418 | 66.781 | 61.515 | 32.030 | 1.00 | 15.76 | A |
| ATOM | 2111 | CA | GLY | A | 418 | 66.536 | 61.715 | 30.614 | 1.00 | 16.90 | A |
| ATOM | 2112 | C | GLY | A | 418 | 67.838 | 62.025 | 29.898 | 1.00 | 16.88 | A |
| ATOM | 2113 | O | GLY | A | 418 | 68.061 | 61.566 | 28.776 | 1.00 | 19.30 | A |
| ATOM | 2114 | N | ASP | A | 419 | 68.703 | 62.798 | 30.545 | 1.00 | 17.22 | A |
| ATOM | 2115 | CA | ASP | A | 419 | 69.987 | 63.141 | 29.947 | 1.00 | 18.10 | A |
| ATOM | 2116 | CB | ASP | A | 419 | 70.727 | 64.178 | 30.795 | 1.00 | 22.23 | A |
| ATOM | 2117 | CG | ASP | A | 419 | 70.039 | 65.535 | 30.792 | 1.00 | 26.68 | A |
| ATOM | 2118 | OD1 | ASP | A | 419 | 69.594 | 65.977 | 29.713 | 1.00 | 29.27 | A |

TABLE 1-continued

| | | | | | | | | | | |
|---|---|---|---|---|---|---|---|---|---|---|
| ATOM | 2119 | OD2 | ASP | A | 419 | 69.954 | 66.167 | 31.865 | 1.00 | 29.97 | A |
| ATOM | 2120 | C | ASP | A | 419 | 70.847 | 61.889 | 29.799 | 1.00 | 17.38 | A |
| ATOM | 2121 | O | ASP | A | 419 | 71.489 | 61.698 | 28.770 | 1.00 | 17.54 | A |
| ATOM | 2122 | N | LYS | A | 420 | 70.850 | 61.033 | 30.818 | 1.00 | 16.19 | A |
| ATOM | 2123 | CA | LYS | A | 420 | 71.647 | 59.809 | 30.763 | 1.00 | 15.05 | A |
| ATOM | 2124 | CB | LYS | A | 420 | 71.631 | 59.084 | 32.116 | 1.00 | 14.57 | A |
| ATOM | 2125 | CG | LYS | A | 420 | 72.204 | 59.882 | 33.283 | 1.00 | 17.19 | A |
| ATOM | 2126 | CD | LYS | A | 420 | 72.174 | 59.057 | 34.569 | 1.00 | 18.24 | A |
| ATOM | 2127 | CE | LYS | A | 420 | 72.356 | 59.928 | 35.807 | 1.00 | 22.24 | A |
| ATOM | 2128 | NZ | LYS | A | 420 | 73.628 | 60.690 | 35.777 | 1.00 | 24.88 | A |
| ATOM | 2129 | C | LYS | A | 420 | 71.142 | 58.862 | 29.680 | 1.00 | 13.72 | A |
| ATOM | 2130 | O | LYS | A | 420 | 71.937 | 58.226 | 28.982 | 1.00 | 15.98 | A |
| ATOM | 2131 | N | GLU | A | 421 | 69.825 | 58.767 | 29.530 | 1.00 | 13.82 | A |
| ATOM | 2132 | CA | GLU | A | 421 | 69.262 | 57.879 | 28.522 | 1.00 | 15.82 | A |
| ATOM | 2133 | CB | GLU | A | 421 | 67.734 | 57.855 | 28.630 | 1.00 | 16.66 | A |
| ATOM | 2134 | CG | GLU | A | 421 | 67.254 | 57.462 | 30.023 | 1.00 | 18.54 | A |
| ATOM | 2135 | CD | GLU | A | 421 | 65.744 | 57.420 | 30.150 | 1.00 | 22.50 | A |
| ATOM | 2136 | OE1 | GLU | A | 421 | 65.068 | 58.272 | 29.531 | 1.00 | 25.22 | A |
| ATOM | 2137 | OE2 | GLU | A | 421 | 65.234 | 56.542 | 30.883 | 1.00 | 23.66 | A |
| ATOM | 2138 | C | GLU | A | 421 | 69.712 | 58.328 | 27.133 | 1.00 | 16.59 | A |
| ATOM | 2139 | O | GLU | A | 421 | 70.044 | 57.499 | 26.284 | 1.00 | 18.60 | A |
| ATOM | 2140 | N | ARG | A | 422 | 69.744 | 59.639 | 26.912 | 1.00 | 18.06 | A |
| ATOM | 2141 | CA | ARG | A | 422 | 70.187 | 60.169 | 25.625 | 1.00 | 19.52 | A |
| ATOM | 2142 | CB | ARG | A | 422 | 69.891 | 61.666 | 25.531 | 1.00 | 21.06 | A |
| ATOM | 2143 | CG | ARG | A | 422 | 70.514 | 62.339 | 24.316 | 1.00 | 24.66 | A |
| ATOM | 2144 | CD | ARG | A | 422 | 71.685 | 63.207 | 24.731 | 1.00 | 24.97 | A |
| ATOM | 2145 | NE | ARG | A | 422 | 71.242 | 64.306 | 25.584 | 1.00 | 25.82 | A |
| ATOM | 2146 | CZ | ARG | A | 422 | 72.052 | 65.087 | 26.291 | 1.00 | 24.05 | A |
| ATOM | 2147 | NH1 | ARG | A | 422 | 73.368 | 64.901 | 26.256 | 1.00 | 22.03 | A |
| ATOM | 2148 | NH2 | ARG | A | 422 | 71.541 | 66.053 | 27.039 | 1.00 | 26.82 | A |
| ATOM | 2149 | C | ARG | A | 422 | 71.683 | 59.928 | 25.440 | 1.00 | 18.68 | A |
| ATOM | 2150 | O | ARG | A | 422 | 72.124 | 59.477 | 24.379 | 1.00 | 21.26 | A |
| ATOM | 2151 | N | GLU | A | 423 | 72.462 | 60.221 | 26.477 | 1.00 | 17.69 | A |
| ATOM | 2152 | CA | GLU | A | 423 | 73.909 | 60.034 | 26.422 | 1.00 | 16.75 | A |
| ATOM | 2153 | CB | GLU | A | 423 | 74.547 | 60.401 | 27.770 | 1.00 | 18.92 | A |
| ATOM | 2154 | CG | GLU | A | 423 | 74.351 | 61.853 | 28.183 | 1.00 | 20.70 | A |
| ATOM | 2155 | CD | GLU | A | 423 | 74.874 | 62.138 | 29.578 | 1.00 | 22.80 | A |
| ATOM | 2156 | OE1 | GLU | A | 423 | 74.815 | 61.225 | 30.429 | 1.00 | 23.73 | A |
| ATOM | 2157 | OE2 | GLU | A | 423 | 75.332 | 63.274 | 29.831 | 1.00 | 24.67 | A |
| ATOM | 2158 | C | GLU | A | 423 | 74.280 | 58.595 | 26.073 | 1.00 | 16.25 | A |
| ATOM | 2159 | O | GLU | A | 423 | 75.246 | 58.356 | 25.351 | 1.00 | 16.81 | A |
| ATOM | 2160 | N | ARG | A | 424 | 73.506 | 57.642 | 26.582 | 1.00 | 15.35 | A |
| ATOM | 2161 | CA | ARG | A | 424 | 73.785 | 56.230 | 26.351 | 1.00 | 16.43 | A |
| ATOM | 2162 | CB | ARG | A | 424 | 73.517 | 55.443 | 27.634 | 1.00 | 15.39 | A |
| ATOM | 2163 | CG | ARG | A | 424 | 74.309 | 55.977 | 28.812 | 1.00 | 16.51 | A |
| ATOM | 2164 | CD | ARG | A | 424 | 74.112 | 55.142 | 30.052 | 1.00 | 16.22 | A |
| ATOM | 2165 | NE | ARG | A | 424 | 74.601 | 55.843 | 31.236 | 1.00 | 16.27 | A |
| ATOM | 2166 | CZ | ARG | A | 424 | 74.771 | 55.273 | 32.423 | 1.00 | 15.17 | A |
| ATOM | 2167 | NH1 | ARG | A | 424 | 74.501 | 53.985 | 32.587 | 1.00 | 16.11 | A |
| ATOM | 2168 | NH2 | ARG | A | 424 | 75.184 | 56.000 | 33.452 | 1.00 | 13.90 | A |
| ATOM | 2169 | C | ARG | A | 424 | 73.015 | 55.610 | 25.192 | 1.00 | 17.91 | A |
| ATOM | 2170 | O | ARG | A | 424 | 73.048 | 54.392 | 25.002 | 1.00 | 19.16 | A |
| ATOM | 2171 | N | GLY | A | 425 | 72.323 | 56.451 | 24.431 | 1.00 | 20.78 | A |
| ATOM | 2172 | CA | GLY | A | 425 | 71.554 | 55.981 | 23.288 | 1.00 | 22.94 | A |
| ATOM | 2173 | C | GLY | A | 425 | 70.571 | 54.867 | 23.598 | 1.00 | 24.03 | A |
| ATOM | 2174 | O | GLY | A | 425 | 70.403 | 53.943 | 22.800 | 1.00 | 24.64 | A |
| ATOM | 2175 | N | MET | A | 426 | 69.908 | 54.958 | 24.748 | 1.00 | 22.23 | A |
| ATOM | 2176 | CA | MET | A | 426 | 68.943 | 53.945 | 25.174 | 1.00 | 23.17 | A |
| ATOM | 2177 | C | MET | A | 426 | 67.724 | 53.866 | 24.256 | 1.00 | 23.48 | A |
| ATOM | 2178 | O | MET | A | 426 | 67.153 | 54.886 | 23.871 | 1.00 | 24.45 | A |
| ATOM | 2179 | CB | MET | A | 426 | 68.608 | 54.189 | 26.638 | 1.00 | 22.64 | A |
| ATOM | 2180 | CG | MET | A | 426 | 69.821 | 54.381 | 27.547 | 1.00 | 20.00 | A |
| ATOM | 2181 | SD | MET | A | 426 | 69.405 | 54.178 | 29.293 | 1.00 | 20.00 | A |
| ATOM | 2182 | CE | MET | A | 426 | 67.864 | 53.279 | 29.170 | 1.00 | 20.00 | A |
| ATOM | 2183 | N | GLU | A | 427 | 67.471 | 52.497 | 23.897 | 1.00 | 23.43 | A |
| ATOM | 2184 | CA | GLU | A | 427 | 66.410 | 52.171 | 22.949 | 1.00 | 24.49 | A |
| ATOM | 2185 | C | GLU | A | 427 | 65.011 | 52.254 | 23.557 | 1.00 | 25.24 | A |
| ATOM | 2186 | O | GLU | A | 427 | 64.314 | 51.245 | 23.673 | 1.00 | 26.50 | A |
| ATOM | 2187 | CB | GLU | A | 427 | 66.611 | 50.765 | 22.383 | 1.00 | 24.34 | A |
| ATOM | 2188 | CG | GLU | A | 427 | 67.924 | 50.576 | 21.644 | 1.00 | 20.00 | A |
| ATOM | 2189 | CD | GLU | A | 427 | 68.088 | 49.171 | 21.098 | 1.00 | 20.00 | A |
| ATOM | 2190 | OE1 | GLU | A | 427 | 67.134 | 48.661 | 20.475 | 1.00 | 20.00 | A |
| ATOM | 2191 | OE2 | GLU | A | 427 | 69.171 | 48.581 | 21.293 | 1.00 | 20.00 | A |
| ATOM | 2192 | N | ILE | A | 428 | 64.608 | 53.461 | 23.939 | 1.00 | 25.29 | A |
| ATOM | 2193 | CA | ILE | A | 428 | 63.290 | 53.695 | 24.523 | 1.00 | 25.05 | A |
| ATOM | 2194 | CB | ILE | A | 428 | 63.295 | 53.512 | 26.060 | 1.00 | 24.97 | A |
| ATOM | 2195 | CG2 | ILE | A | 428 | 63.583 | 52.064 | 26.416 | 1.00 | 24.93 | A |
| ATOM | 2196 | CG1 | ILE | A | 428 | 64.327 | 54.444 | 26.696 | 1.00 | 22.21 | A |
| ATOM | 2197 | CD1 | ILE | A | 428 | 62.427 | 55.289 | 24.202 | 1.00 | 24.76 | A |

TABLE 1-continued

| ATOM | 2198 | C   | ILE | A | 428 | 62.845 | 55.118 | 24.211 | 1.00 | 26.65 | A |
| ATOM | 2199 | O   | ILE | A | 428 | 63.651 | 55.943 | 23.780 | 1.00 | 26.59 | A |
| ATOM | 2200 | N   | ALA | A | 437 | 56.662 | 70.439 | 30.126 | 1.00 | 27.00 | A |
| ATOM | 2201 | CA  | ALA | A | 437 | 56.829 | 69.117 | 30.715 | 1.00 | 26.16 | A |
| ATOM | 2202 | CB  | ALA | A | 437 | 58.028 | 69.115 | 31.650 | 1.00 | 24.91 | A |
| ATOM | 2203 | C   | ALA | A | 437 | 55.572 | 68.702 | 31.472 | 1.00 | 26.13 | A |
| ATOM | 2204 | O   | ALA | A | 437 | 55.456 | 67.560 | 31.927 | 1.00 | 27.05 | A |
| ATOM | 2205 | N   | SER | A | 438 | 54.634 | 69.637 | 31.601 | 1.00 | 25.02 | A |
| ATOM | 2206 | CA  | SER | A | 438 | 53.380 | 69.387 | 32.298 | 1.00 | 24.02 | A |
| ATOM | 2207 | CB  | SER | A | 438 | 52.609 | 68.256 | 31.615 | 1.00 | 24.69 | A |
| ATOM | 2208 | OG  | SER | A | 438 | 52.322 | 68.578 | 30.264 | 1.00 | 27.74 | A |
| ATOM | 2209 | C   | SER | A | 438 | 53.611 | 69.029 | 33.760 | 1.00 | 22.54 | A |
| ATOM | 2210 | O   | SER | A | 438 | 53.019 | 68.080 | 34.270 | 1.00 | 22.65 | A |
| ATOM | 2211 | N   | VAL | A | 439 | 54.467 | 69.793 | 34.434 | 1.00 | 21.81 | A |
| ATOM | 2212 | CA  | VAL | A | 439 | 54.764 | 69.543 | 35.840 | 1.00 | 22.02 | A |
| ATOM | 2213 | CB  | VAL | A | 439 | 55.733 | 70.601 | 36.412 | 1.00 | 22.20 | A |
| ATOM | 2214 | CG1 | VAL | A | 439 | 55.988 | 70.328 | 37.886 | 1.00 | 23.44 | A |
| ATOM | 2215 | CG2 | VAL | A | 439 | 57.030 | 70.589 | 35.636 | 1.00 | 23.59 | A |
| ATOM | 2216 | C   | VAL | A | 439 | 53.496 | 69.560 | 36.683 | 1.00 | 21.35 | A |
| ATOM | 2217 | O   | VAL | A | 439 | 53.251 | 68.646 | 37.472 | 1.00 | 20.99 | A |
| ATOM | 2218 | N   | GLU | A | 440 | 52.691 | 70.604 | 36.508 | 1.00 | 21.61 | A |
| ATOM | 2219 | CA  | GLU | A | 440 | 51.450 | 70.745 | 37.262 | 1.00 | 21.11 | A |
| ATOM | 2220 | CB  | GLU | A | 440 | 50.753 | 72.060 | 36.897 | 1.00 | 22.04 | A |
| ATOM | 2221 | CG  | GLU | A | 440 | 51.607 | 73.293 | 37.145 | 1.00 | 23.80 | A |
| ATOM | 2222 | CD  | GLU | A | 440 | 52.283 | 73.804 | 35.886 | 1.00 | 27.53 | A |
| ATOM | 2223 | OE1 | GLU | A | 440 | 52.820 | 72.981 | 35.115 | 1.00 | 26.96 | A |
| ATOM | 2224 | OE2 | GLU | A | 440 | 52.280 | 75.037 | 35.670 | 1.00 | 31.26 | A |
| ATOM | 2225 | C   | GLU | A | 440 | 50.499 | 69.580 | 37.016 | 1.00 | 21.18 | A |
| ATOM | 2226 | O   | GLU | A | 440 | 50.033 | 68.940 | 37.959 | 1.00 | 21.38 | A |
| ATOM | 2227 | N   | LYS | A | 441 | 50.212 | 69.307 | 35.747 | 1.00 | 20.82 | A |
| ATOM | 2228 | CA  | LYS | A | 441 | 49.312 | 68.217 | 35.400 | 1.00 | 21.66 | A |
| ATOM | 2229 | CB  | LYS | A | 441 | 49.110 | 68.165 | 33.881 | 1.00 | 22.41 | A |
| ATOM | 2230 | CG  | LYS | A | 441 | 48.183 | 67.057 | 33.409 | 1.00 | 24.36 | A |
| ATOM | 2231 | CD  | LYS | A | 441 | 47.424 | 67.480 | 32.161 | 1.00 | 24.61 | A |
| ATOM | 2232 | CE  | LYS | A | 441 | 48.344 | 68.123 | 31.133 | 1.00 | 25.36 | A |
| ATOM | 2233 | NZ  | LYS | A | 441 | 49.377 | 67.187 | 30.605 | 1.00 | 27.46 | A |
| ATOM | 2234 | C   | LYS | A | 441 | 49.853 | 66.887 | 35.912 | 1.00 | 21.45 | A |
| ATOM | 2235 | O   | LYS | A | 441 | 49.088 | 66.003 | 36.305 | 1.00 | 22.14 | A |
| ATOM | 2236 | N   | SER | A | 442 | 51.174 | 66.753 | 35.915 | 1.00 | 21.15 | A |
| ATOM | 2237 | CA  | SER | A | 442 | 51.806 | 65.532 | 36.388 | 1.00 | 20.90 | A |
| ATOM | 2238 | CB  | SER | A | 442 | 53.318 | 65.590 | 36.161 | 1.00 | 21.81 | A |
| ATOM | 2239 | OG  | SER | A | 442 | 53.946 | 66.320 | 37.200 | 1.00 | 27.97 | A |
| ATOM | 2240 | C   | SER | A | 442 | 51.514 | 65.292 | 37.863 | 1.00 | 19.02 | A |
| ATOM | 2241 | O   | SER | A | 442 | 51.263 | 64.161 | 38.270 | 1.00 | 19.71 | A |
| ATOM | 2242 | N   | GLN | A | 443 | 51.541 | 66.351 | 38.663 | 1.00 | 19.25 | A |
| ATOM | 2243 | CA  | GLN | A | 443 | 51.272 | 66.208 | 40.089 | 1.00 | 17.82 | A |
| ATOM | 2244 | CB  | GLN | A | 443 | 51.636 | 67.492 | 40.836 | 1.00 | 19.26 | A |
| ATOM | 2245 | CG  | GLN | A | 443 | 53.130 | 67.760 | 40.874 | 1.00 | 17.81 | A |
| ATOM | 2246 | CD  | GLN | A | 443 | 53.924 | 66.544 | 41.316 | 1.00 | 18.23 | A |
| ATOM | 2247 | OE1 | GLN | A | 443 | 53.732 | 66.024 | 42.416 | 1.00 | 19.26 | A |
| ATOM | 2248 | NE2 | GLN | A | 443 | 54.824 | 66.084 | 40.455 | 1.00 | 21.49 | A |
| ATOM | 2249 | C   | GLN | A | 443 | 49.816 | 65.844 | 40.350 | 1.00 | 17.57 | A |
| ATOM | 2250 | O   | GLN | A | 443 | 49.514 | 65.045 | 41.233 | 1.00 | 18.11 | A |
| ATOM | 2251 | N   | VAL | A | 444 | 48.904 | 66.438 | 39.589 | 1.00 | 17.31 | A |
| ATOM | 2252 | CA  | VAL | A | 444 | 47.497 | 66.119 | 39.763 | 1.00 | 17.48 | A |
| ATOM | 2253 | CB  | VAL | A | 444 | 46.611 | 66.953 | 38.811 | 1.00 | 17.80 | A |
| ATOM | 2254 | CG1 | VAL | A | 444 | 45.149 | 66.553 | 38.975 | 1.00 | 18.89 | A |
| ATOM | 2255 | CG2 | VAL | A | 444 | 46.791 | 68.434 | 39.109 | 1.00 | 18.60 | A |
| ATOM | 2256 | C   | VAL | A | 444 | 47.309 | 64.633 | 39.470 | 1.00 | 17.11 | A |
| ATOM | 2257 | O   | VAL | A | 444 | 46.638 | 63.919 | 40.218 | 1.00 | 20.12 | A |
| ATOM | 2258 | N   | GLY | A | 445 | 47.920 | 64.174 | 38.383 | 1.00 | 17.96 | A |
| ATOM | 2259 | CA  | GLY | A | 445 | 47.814 | 62.774 | 38.007 | 1.00 | 18.54 | A |
| ATOM | 2260 | C   | GLY | A | 445 | 48.439 | 61.850 | 39.035 | 1.00 | 18.10 | A |
| ATOM | 2261 | O   | GLY | A | 445 | 47.877 | 60.810 | 39.379 | 1.00 | 19.74 | A |
| ATOM | 2262 | N   | PHE | A | 446 | 49.611 | 62.232 | 39.528 | 1.00 | 18.18 | A |
| ATOM | 2263 | CA  | PHE | A | 446 | 50.319 | 61.438 | 40.525 | 1.00 | 17.21 | A |
| ATOM | 2264 | CB  | PHE | A | 446 | 51.666 | 62.099 | 40.850 | 1.00 | 16.65 | A |
| ATOM | 2265 | CG  | PHE | A | 446 | 52.487 | 61.352 | 41.868 | 1.00 | 16.58 | A |
| ATOM | 2266 | CD1 | PHE | A | 446 | 52.708 | 59.991 | 41.736 | 1.00 | 16.98 | A |
| ATOM | 2267 | CD2 | PHE | A | 446 | 53.053 | 62.019 | 42.944 | 1.00 | 17.14 | A |
| ATOM | 2268 | CE1 | PHE | A | 446 | 53.481 | 59.302 | 42.661 | 1.00 | 17.13 | A |
| ATOM | 2269 | CE2 | PHE | A | 446 | 53.828 | 61.336 | 43.874 | 1.00 | 18.97 | A |
| ATOM | 2270 | CZ  | PHE | A | 446 | 54.040 | 59.977 | 43.730 | 1.00 | 17.95 | A |
| ATOM | 2271 | C   | PHE | A | 446 | 49.475 | 61.305 | 41.786 | 1.00 | 16.79 | A |
| ATOM | 2272 | O   | PHE | A | 446 | 49.341 | 60.221 | 42.353 | 1.00 | 15.56 | A |
| ATOM | 2273 | N   | ILE | A | 447 | 48.897 | 62.416 | 42.223 | 1.00 | 16.42 | A |
| ATOM | 2274 | CA  | ILE | A | 447 | 48.069 | 62.415 | 43.416 | 1.00 | 16.48 | A |
| ATOM | 2275 | CB  | ILE | A | 447 | 47.676 | 63.859 | 43.808 | 1.00 | 17.35 | A |
| ATOM | 2276 | CG2 | ILE | A | 447 | 46.676 | 63.845 | 44.950 | 1.00 | 16.77 | A |

TABLE 1-continued

| | | | | | | | | | | |
|---|---|---|---|---|---|---|---|---|---|---|
| ATOM | 2277 | CG1 | ILE | A | 447 | 48.931 | 64.645 | 44.199 | 1.00 | 17.64 | A |
| ATOM | 2278 | CD1 | ILE | A | 447 | 48.667 | 66.095 | 44.531 | 1.00 | 19.00 | A |
| ATOM | 2279 | C | ILE | A | 447 | 46.809 | 61.566 | 43.234 | 1.00 | 15.76 | A |
| ATOM | 2280 | O | ILE | A | 447 | 46.490 | 60.726 | 44.071 | 1.00 | 16.55 | A |
| ATOM | 2281 | N | ASP | A | 448 | 46.094 | 61.771 | 42.133 | 1.00 | 16.95 | A |
| ATOM | 2282 | CA | ASP | A | 448 | 44.875 | 61.003 | 41.904 | 1.00 | 18.92 | A |
| ATOM | 2283 | CB | ASP | A | 448 | 44.108 | 61.558 | 40.700 | 1.00 | 20.70 | A |
| ATOM | 2284 | CG | ASP | A | 448 | 43.544 | 62.943 | 40.951 | 1.00 | 23.82 | A |
| ATOM | 2285 | OD1 | ASP | A | 448 | 43.289 | 63.285 | 42.125 | 1.00 | 24.89 | A |
| ATOM | 2286 | OD2 | ASP | A | 448 | 43.333 | 63.686 | 39.970 | 1.00 | 25.78 | A |
| ATOM | 2287 | C | ASP | A | 448 | 45.113 | 59.511 | 41.692 | 1.00 | 19.53 | A |
| ATOM | 2288 | O | ASP | A | 448 | 44.313 | 58.679 | 42.124 | 1.00 | 22.34 | A |
| ATOM | 2289 | N | TYR | A | 449 | 46.216 | 59.175 | 41.036 | 1.00 | 19.46 | A |
| ATOM | 2290 | CA | TYR | A | 449 | 46.535 | 57.786 | 40.734 | 1.00 | 20.81 | A |
| ATOM | 2291 | CB | TYR | A | 449 | 47.400 | 57.729 | 39.472 | 1.00 | 22.34 | A |
| ATOM | 2292 | CG | TYR | A | 449 | 47.595 | 56.337 | 38.908 | 1.00 | 25.79 | A |
| ATOM | 2293 | CD1 | TYR | A | 449 | 46.512 | 55.591 | 38.457 | 1.00 | 25.80 | A |
| ATOM | 2294 | CE1 | TYR | A | 449 | 46.686 | 54.326 | 37.926 | 1.00 | 27.69 | A |
| ATOM | 2295 | CD2 | TYR | A | 449 | 48.863 | 55.776 | 38.812 | 1.00 | 25.27 | A |
| ATOM | 2296 | CE2 | TYR | A | 449 | 49.047 | 54.509 | 38.281 | 1.00 | 27.63 | A |
| ATOM | 2297 | CZ | TYR | A | 449 | 47.955 | 53.790 | 37.840 | 1.00 | 27.04 | A |
| ATOM | 2298 | OH | TYR | A | 449 | 48.125 | 52.527 | 37.319 | 1.00 | 31.23 | A |
| ATOM | 2299 | C | TYR | A | 449 | 47.228 | 56.999 | 41.844 | 1.00 | 20.67 | A |
| ATOM | 2300 | O | TYR | A | 449 | 46.946 | 55.813 | 42.032 | 1.00 | 20.46 | A |
| ATOM | 2301 | N | ILE | A | 450 | 48.119 | 57.653 | 42.585 | 1.00 | 19.13 | A |
| ATOM | 2302 | CA | ILE | A | 450 | 48.882 | 56.966 | 43.626 | 1.00 | 17.88 | A |
| ATOM | 2303 | CB | ILE | A | 450 | 50.393 | 56.992 | 43.294 | 1.00 | 19.39 | A |
| ATOM | 2304 | CG2 | ILE | A | 450 | 51.168 | 56.209 | 44.346 | 1.00 | 19.89 | A |
| ATOM | 2305 | CG1 | ILE | A | 450 | 50.649 | 56.412 | 41.902 | 1.00 | 20.97 | A |
| ATOM | 2306 | CD1 | ILE | A | 450 | 50.374 | 54.937 | 41.800 | 1.00 | 22.24 | A |
| ATOM | 2307 | C | ILE | A | 450 | 48.757 | 57.493 | 45.053 | 1.00 | 15.95 | A |
| ATOM | 2308 | O | ILE | A | 450 | 48.404 | 56.759 | 45.980 | 1.00 | 17.81 | A |
| ATOM | 2309 | N | VAL | A | 451 | 49.065 | 58.772 | 45.225 | 1.00 | 15.28 | A |
| ATOM | 2310 | CA | VAL | A | 451 | 49.082 | 59.384 | 46.544 | 1.00 | 14.64 | A |
| ATOM | 2311 | CB | VAL | A | 451 | 49.722 | 60.768 | 46.456 | 1.00 | 13.97 | A |
| ATOM | 2312 | CG1 | VAL | A | 451 | 50.050 | 61.273 | 47.844 | 1.00 | 13.25 | A |
| ATOM | 2313 | CG2 | VAL | A | 451 | 50.984 | 60.689 | 45.595 | 1.00 | 14.44 | A |
| ATOM | 2314 | C | VAL | A | 451 | 47.760 | 59.479 | 47.292 | 1.00 | 14.72 | A |
| ATOM | 2315 | O | VAL | A | 451 | 47.676 | 59.082 | 48.455 | 1.00 | 15.41 | A |
| ATOM | 2316 | N | HIS | A | 452 | 46.730 | 59.998 | 46.636 | 1.00 | 16.82 | A |
| ATOM | 2317 | CA | HIS | A | 452 | 45.429 | 60.127 | 47.274 | 1.00 | 17.91 | A |
| ATOM | 2318 | CB | HIS | A | 452 | 44.468 | 60.882 | 46.357 | 1.00 | 19.59 | A |
| ATOM | 2319 | CG | HIS | A | 452 | 43.125 | 61.129 | 46.968 | 1.00 | 22.77 | A |
| ATOM | 2320 | CD2 | HIS | A | 452 | 41.883 | 60.776 | 46.562 | 1.00 | 23.93 | A |
| ATOM | 2321 | ND1 | HIS | A | 452 | 42.961 | 61.825 | 48.146 | 1.00 | 25.09 | A |
| ATOM | 2322 | CE1 | HIS | A | 452 | 41.674 | 61.892 | 48.438 | 1.00 | 26.34 | A |
| ATOM | 2323 | NE2 | HIS | A | 452 | 40.999 | 61.263 | 47.493 | 1.00 | 25.97 | A |
| ATOM | 2324 | C | HIS | A | 452 | 44.820 | 58.779 | 47.680 | 1.00 | 17.05 | A |
| ATOM | 2325 | O | HIS | A | 452 | 44.364 | 58.618 | 48.809 | 1.00 | 19.16 | A |
| ATOM | 2326 | N | PRO | A | 453 | 44.803 | 57.795 | 46.767 | 1.00 | 18.47 | A |
| ATOM | 2327 | CD | PRO | A | 453 | 45.173 | 57.836 | 45.341 | 1.00 | 19.12 | A |
| ATOM | 2328 | CA | PRO | A | 453 | 44.230 | 56.490 | 47.121 | 1.00 | 18.21 | A |
| ATOM | 2329 | CB | PRO | A | 453 | 44.498 | 55.650 | 45.877 | 1.00 | 18.94 | A |
| ATOM | 2330 | CG | PRO | A | 453 | 44.411 | 56.660 | 44.776 | 1.00 | 19.04 | A |
| ATOM | 2331 | C | PRO | A | 453 | 44.891 | 55.900 | 48.365 | 1.00 | 17.61 | A |
| ATOM | 2332 | O | PRO | A | 453 | 44.230 | 55.324 | 49.232 | 1.00 | 18.57 | A |
| ATOM | 2333 | N | LEU | A | 454 | 46.206 | 56.057 | 48.444 | 1.00 | 16.41 | A |
| ATOM | 2334 | CA | LEU | A | 454 | 46.970 | 55.545 | 49.567 | 1.00 | 16.49 | A |
| ATOM | 2335 | CB | LEU | A | 454 | 48.468 | 55.670 | 49.272 | 1.00 | 16.31 | A |
| ATOM | 2336 | CG | LEU | A | 454 | 49.424 | 55.307 | 50.410 | 1.00 | 18.71 | A |
| ATOM | 2337 | CD1 | LEU | A | 454 | 49.218 | 53.853 | 50.808 | 1.00 | 20.00 | A |
| ATOM | 2338 | CD2 | LEU | A | 454 | 50.865 | 55.547 | 49.969 | 1.00 | 18.02 | A |
| ATOM | 2339 | C | LEU | A | 454 | 46.645 | 56.259 | 50.876 | 1.00 | 15.50 | A |
| ATOM | 2340 | O | LEU | A | 454 | 46.304 | 55.618 | 51.871 | 1.00 | 16.68 | A |
| ATOM | 2341 | N | TRP | A | 455 | 46.749 | 57.584 | 50.879 | 1.00 | 16.34 | A |
| ATOM | 2342 | CA | TRP | A | 455 | 46.483 | 58.348 | 52.092 | 1.00 | 15.60 | A |
| ATOM | 2343 | CB | TRP | A | 455 | 46.938 | 59.797 | 51.924 | 1.00 | 16.50 | A |
| ATOM | 2344 | CG | TRP | A | 455 | 48.416 | 59.950 | 52.113 | 1.00 | 15.47 | A |
| ATOM | 2345 | CD2 | TRP | A | 455 | 49.112 | 60.002 | 53.360 | 1.00 | 15.27 | A |
| ATOM | 2346 | CE2 | TRP | A | 455 | 50.485 | 60.114 | 53.068 | 1.00 | 14.82 | A |
| ATOM | 2347 | CE3 | TRP | A | 455 | 48.706 | 59.964 | 54.698 | 1.00 | 16.51 | A |
| ATOM | 2348 | CD1 | TRP | A | 455 | 49.368 | 60.030 | 51.138 | 1.00 | 15.88 | A |
| ATOM | 2349 | NE1 | TRP | A | 455 | 50.616 | 60.130 | 51.704 | 1.00 | 15.63 | A |
| ATOM | 2350 | CZ2 | TRP | A | 455 | 51.456 | 60.190 | 54.065 | 1.00 | 16.36 | A |
| ATOM | 2351 | CZ3 | TRP | A | 455 | 49.673 | 60.040 | 55.688 | 1.00 | 18.58 | A |
| ATOM | 2352 | CH2 | TRP | A | 455 | 51.031 | 60.152 | 55.364 | 1.00 | 18.21 | A |
| ATOM | 2353 | C | TRP | A | 455 | 45.038 | 58.305 | 52.554 | 1.00 | 16.69 | A |
| ATOM | 2354 | O | TRP | A | 455 | 44.764 | 58.412 | 53.747 | 1.00 | 18.08 | A |
| ATOM | 2355 | N | GLU | A | 456 | 44.118 | 58.150 | 51.613 | 1.00 | 17.85 | A |

TABLE 1-continued

| ATOM | 2356 | CA | GLU | A | 456 | 42.707 | 58.071 | 51.959 | 1.00 | 19.00 | A |
|---|---|---|---|---|---|---|---|---|---|---|---|
| ATOM | 2357 | CB | GLU | A | 456 | 41.861 | 58.044 | 50.685 | 1.00 | 19.73 | A |
| ATOM | 2358 | CG | GLU | A | 456 | 40.366 | 58.016 | 50.916 | 1.00 | 24.82 | A |
| ATOM | 2359 | CD | GLU | A | 456 | 39.591 | 58.123 | 49.618 | 1.00 | 27.41 | A |
| ATOM | 2360 | OE1 | GLU | A | 456 | 39.805 | 57.270 | 48.729 | 1.00 | 29.58 | A |
| ATOM | 2361 | OE2 | GLU | A | 456 | 38.771 | 59.060 | 49.486 | 1.00 | 31.04 | A |
| ATOM | 2362 | C | GLU | A | 456 | 42.490 | 56.795 | 52.766 | 1.00 | 18.98 | A |
| ATOM | 2363 | O | GLU | A | 456 | 41.706 | 56.770 | 53.714 | 1.00 | 21.23 | A |
| ATOM | 2364 | N | THR | A | 457 | 43.204 | 55.741 | 52.389 | 1.00 | 19.38 | A |
| ATOM | 2365 | CA | THR | A | 457 | 43.091 | 54.460 | 53.072 | 1.00 | 19.63 | A |
| ATOM | 2366 | CB | THR | A | 457 | 43.706 | 53.338 | 52.220 | 1.00 | 20.45 | A |
| ATOM | 2367 | OG1 | THR | A | 457 | 43.095 | 53.345 | 50.923 | 1.00 | 21.84 | A |
| ATOM | 2368 | CG2 | THR | A | 457 | 43.488 | 51.985 | 52.878 | 1.00 | 21.06 | A |
| ATOM | 2369 | C | THR | A | 457 | 43.779 | 54.517 | 54.434 | 1.00 | 19.60 | A |
| ATOM | 2370 | O | THR | A | 457 | 43.281 | 53.962 | 55.413 | 1.00 | 20.03 | A |
| ATOM | 2371 | N | TRP | A | 458 | 44.926 | 55.185 | 54.502 | 1.00 | 18.12 | A |
| ATOM | 2372 | CA | TRP | A | 458 | 45.631 | 55.306 | 55.768 | 1.00 | 17.21 | A |
| ATOM | 2373 | CB | TRP | A | 458 | 46.987 | 55.995 | 55.565 | 1.00 | 17.17 | A |
| ATOM | 2374 | CG | TRP | A | 458 | 47.695 | 56.298 | 56.858 | 1.00 | 17.09 | A |
| ATOM | 2375 | CD2 | TRP | A | 458 | 48.540 | 55.408 | 57.596 | 1.00 | 17.34 | A |
| ATOM | 2376 | CE2 | TRP | A | 458 | 48.948 | 56.088 | 58.762 | 1.00 | 17.95 | A |
| ATOM | 2377 | CE3 | TRP | A | 458 | 48.990 | 54.101 | 57.384 | 1.00 | 18.88 | A |
| ATOM | 2378 | CD1 | TRP | A | 458 | 47.626 | 57.449 | 57.583 | 1.00 | 17.40 | A |
| ATOM | 2379 | NE1 | TRP | A | 458 | 48.378 | 57.333 | 58.732 | 1.00 | 16.65 | A |
| ATOM | 2380 | CZ2 | TRP | A | 458 | 49.785 | 55.504 | 59.714 | 1.00 | 18.09 | A |
| ATOM | 2381 | CZ3 | TRP | A | 458 | 49.823 | 53.522 | 58.331 | 1.00 | 19.06 | A |
| ATOM | 2382 | CH2 | TRP | A | 458 | 50.210 | 54.223 | 59.479 | 1.00 | 18.64 | A |
| ATOM | 2383 | C | TRP | A | 458 | 44.763 | 56.117 | 56.731 | 1.00 | 16.76 | A |
| ATOM | 2384 | O | TRP | A | 458 | 44.670 | 55.805 | 57.917 | 1.00 | 16.18 | A |
| ATOM | 2385 | N | ALA | A | 459 | 44.117 | 57.151 | 56.203 | 1.00 | 17.73 | A |
| ATOM | 2386 | CA | ALA | A | 459 | 43.247 | 58.007 | 57.000 | 1.00 | 18.94 | A |
| ATOM | 2387 | CB | ALA | A | 459 | 42.693 | 59.130 | 56.136 | 1.00 | 19.79 | A |
| ATOM | 2388 | C | ALA | A | 459 | 42.102 | 57.203 | 57.606 | 1.00 | 20.49 | A |
| ATOM | 2389 | O | ALA | A | 459 | 41.685 | 57.459 | 58.734 | 1.00 | 21.34 | A |
| ATOM | 2390 | N | ASP | A | 460 | 41.593 | 56.230 | 56.856 | 1.00 | 21.63 | A |
| ATOM | 2391 | CA | ASP | A | 460 | 40.500 | 55.402 | 57.353 | 1.00 | 22.89 | A |
| ATOM | 2392 | CB | ASP | A | 460 | 39.924 | 54.523 | 56.234 | 1.00 | 25.00 | A |
| ATOM | 2393 | CG | ASP | A | 460 | 39.316 | 55.328 | 55.100 | 1.00 | 28.11 | A |
| ATOM | 2394 | OD1 | ASP | A | 460 | 38.497 | 56.233 | 55.375 | 1.00 | 30.44 | A |
| ATOM | 2395 | OD2 | ASP | A | 460 | 39.648 | 55.046 | 53.927 | 1.00 | 32.29 | A |
| ATOM | 2396 | C | ASP | A | 460 | 40.996 | 54.506 | 58.485 | 1.00 | 23.03 | A |
| ATOM | 2397 | O | ASP | A | 460 | 40.273 | 54.241 | 59.444 | 1.00 | 23.84 | A |
| ATOM | 2398 | N | LEU | A | 461 | 42.240 | 54.048 | 58.372 | 1.00 | 21.32 | A |
| ATOM | 2399 | CA | LEU | A | 461 | 42.825 | 53.170 | 59.376 | 1.00 | 20.64 | A |
| ATOM | 2400 | CB | LEU | A | 461 | 44.184 | 52.647 | 58.900 | 1.00 | 19.34 | A |
| ATOM | 2401 | CG | LEU | A | 461 | 44.865 | 51.648 | 59.840 | 1.00 | 20.72 | A |
| ATOM | 2402 | CD1 | LEU | A | 461 | 44.074 | 50.340 | 59.837 | 1.00 | 19.53 | A |
| ATOM | 2403 | CD2 | LEU | A | 461 | 46.303 | 51.403 | 59.397 | 1.00 | 21.88 | A |
| ATOM | 2404 | C | LEU | A | 461 | 43.004 | 53.852 | 60.725 | 1.00 | 20.88 | A |
| ATOM | 2405 | O | LEU | A | 461 | 42.713 | 53.264 | 61.763 | 1.00 | 21.41 | A |
| ATOM | 2406 | N | VAL | A | 462 | 43.481 | 55.092 | 60.705 | 1.00 | 20.72 | A |
| ATOM | 2407 | CA | VAL | A | 462 | 43.726 | 55.836 | 61.933 | 1.00 | 20.37 | A |
| ATOM | 2408 | CB | VAL | A | 462 | 45.153 | 56.419 | 61.930 | 1.00 | 20.38 | A |
| ATOM | 2409 | CG1 | VAL | A | 462 | 46.168 | 55.299 | 61.778 | 1.00 | 20.34 | A |
| ATOM | 2410 | CG2 | VAL | A | 462 | 45.302 | 57.418 | 60.792 | 1.00 | 19.63 | A |
| ATOM | 2411 | C | VAL | A | 462 | 42.746 | 56.982 | 62.175 | 1.00 | 21.10 | A |
| ATOM | 2412 | O | VAL | A | 462 | 43.007 | 57.857 | 62.999 | 1.00 | 22.25 | A |
| ATOM | 2413 | N | GLN | A | 463 | 41.617 | 56.975 | 61.474 | 1.00 | 21.86 | A |
| ATOM | 2414 | CA | GLN | A | 463 | 40.632 | 58.042 | 61.629 | 1.00 | 22.64 | A |
| ATOM | 2415 | CB | GLN | A | 463 | 39.306 | 57.654 | 60.971 | 1.00 | 23.80 | A |
| ATOM | 2416 | CG | GLN | A | 463 | 38.686 | 56.379 | 61.509 | 1.00 | 26.52 | A |
| ATOM | 2417 | CD | GLN | A | 463 | 37.270 | 56.171 | 61.007 | 1.00 | 27.52 | A |
| ATOM | 2418 | OE1 | GLN | A | 463 | 36.659 | 55.126 | 61.246 | 1.00 | 31.57 | A |
| ATOM | 2419 | NE2 | GLN | A | 463 | 36.735 | 57.172 | 60.314 | 1.00 | 28.38 | A |
| ATOM | 2420 | C | GLN | A | 463 | 40.385 | 58.405 | 63.090 | 1.00 | 23.04 | A |
| ATOM | 2421 | O | GLN | A | 463 | 40.306 | 57.533 | 63.956 | 1.00 | 23.18 | A |
| ATOM | 2422 | N | PRO | A | 464 | 40.255 | 59.708 | 63.378 | 1.00 | 23.68 | A |
| ATOM | 2423 | CD | PRO | A | 464 | 39.630 | 60.181 | 64.629 | 1.00 | 23.90 | A |
| ATOM | 2424 | CA | PRO | A | 464 | 40.334 | 60.802 | 62.405 | 1.00 | 23.00 | A |
| ATOM | 2425 | CB | PRO | A | 464 | 39.180 | 61.688 | 62.828 | 1.00 | 23.85 | A |
| ATOM | 2426 | CG | PRO | A | 464 | 39.337 | 61.652 | 64.325 | 1.00 | 24.65 | A |
| ATOM | 2427 | C | PRO | A | 464 | 41.665 | 61.550 | 62.507 | 1.00 | 23.08 | A |
| ATOM | 2428 | O | PRO | A | 464 | 41.746 | 62.735 | 62.188 | 1.00 | 24.27 | A |
| ATOM | 2429 | N | ASP | A | 465 | 42.707 | 60.855 | 62.946 | 1.00 | 22.95 | A |
| ATOM | 2430 | CA | ASP | A | 465 | 44.011 | 61.477 | 63.132 | 1.00 | 23.05 | A |
| ATOM | 2431 | CB | ASP | A | 465 | 44.931 | 60.512 | 63.880 | 1.00 | 25.13 | A |
| ATOM | 2432 | CG | ASP | A | 465 | 44.428 | 60.205 | 65.274 | 1.00 | 27.12 | A |
| ATOM | 2433 | OD1 | ASP | A | 465 | 44.205 | 61.163 | 66.046 | 1.00 | 30.09 | A |
| ATOM | 2434 | OD2 | ASP | A | 465 | 44.253 | 59.013 | 65.596 | 1.00 | 29.50 | A |

TABLE 1-continued

| ATOM | 2435 | C | ASP | A | 465 | 44.726 | 62.008 | 61.893 | 1.00 | 23.27 | A |
|---|---|---|---|---|---|---|---|---|---|---|---|
| ATOM | 2436 | O | ASP | A | 465 | 45.592 | 62.873 | 62.006 | 1.00 | 24.33 | A |
| ATOM | 2437 | N | ALA | A | 466 | 44.366 | 61.515 | 60.715 | 1.00 | 21.56 | A |
| ATOM | 2438 | CA | ALA | A | 466 | 45.025 | 61.974 | 59.497 | 1.00 | 21.08 | A |
| ATOM | 2439 | CB | ALA | A | 466 | 45.517 | 60.774 | 58.691 | 1.00 | 19.38 | A |
| ATOM | 2440 | C | ALA | A | 466 | 44.151 | 62.865 | 58.621 | 1.00 | 21.07 | A |
| ATOM | 2441 | O | ALA | A | 466 | 44.452 | 63.067 | 57.445 | 1.00 | 22.35 | A |
| ATOM | 2442 | N | GLN | A | 467 | 43.077 | 63.409 | 59.184 | 1.00 | 21.16 | A |
| ATOM | 2443 | CA | GLN | A | 467 | 42.196 | 64.266 | 58.401 | 1.00 | 20.54 | A |
| ATOM | 2444 | CB | GLN | A | 467 | 40.965 | 64.668 | 59.213 | 1.00 | 21.53 | A |
| ATOM | 2445 | CG | GLN | A | 467 | 39.902 | 65.358 | 58.370 | 1.00 | 23.82 | A |
| ATOM | 2446 | CD | GLN | A | 467 | 39.518 | 64.538 | 57.147 | 1.00 | 25.04 | A |
| ATOM | 2447 | OE1 | GLN | A | 467 | 39.103 | 63.385 | 57.265 | 1.00 | 27.25 | A |
| ATOM | 2448 | NE2 | GLN | A | 467 | 39.657 | 65.131 | 55.966 | 1.00 | 26.57 | A |
| ATOM | 2449 | C | GLN | A | 467 | 42.903 | 65.520 | 57.900 | 1.00 | 20.69 | A |
| ATOM | 2450 | O | GLN | A | 467 | 42.684 | 65.944 | 56.766 | 1.00 | 21.24 | A |
| ATOM | 2451 | N | ASP | A | 468 | 43.740 | 66.118 | 58.744 | 1.00 | 20.82 | A |
| ATOM | 2452 | CA | ASP | A | 468 | 44.469 | 67.327 | 58.370 | 1.00 | 21.77 | A |
| ATOM | 2453 | CB | ASP | A | 468 | 45.255 | 67.864 | 59.566 | 1.00 | 23.31 | A |
| ATOM | 2454 | CG | ASP | A | 468 | 44.364 | 68.190 | 60.747 | 1.00 | 27.59 | A |
| ATOM | 2455 | OD1 | ASP | A | 468 | 43.435 | 69.009 | 60.585 | 1.00 | 30.16 | A |
| ATOM | 2456 | OD2 | ASP | A | 468 | 44.595 | 67.628 | 61.838 | 1.00 | 29.99 | A |
| ATOM | 2457 | C | ASP | A | 468 | 45.426 | 67.054 | 57.213 | 1.00 | 20.85 | A |
| ATOM | 2458 | O | ASP | A | 468 | 45.630 | 67.905 | 56.347 | 1.00 | 21.91 | A |
| ATOM | 2459 | N | ILE | A | 469 | 46.011 | 65.863 | 57.206 | 1.00 | 20.82 | A |
| ATOM | 2460 | CA | ILE | A | 469 | 46.929 | 65.480 | 56.144 | 1.00 | 20.02 | A |
| ATOM | 2461 | CB | ILE | A | 469 | 47.619 | 64.134 | 56.470 | 1.00 | 19.73 | A |
| ATOM | 2462 | CG2 | ILE | A | 469 | 48.365 | 63.616 | 55.246 | 1.00 | 22.81 | A |
| ATOM | 2463 | CG1 | ILE | A | 469 | 48.580 | 64.320 | 57.649 | 1.00 | 21.01 | A |
| ATOM | 2464 | CD1 | ILE | A | 469 | 49.276 | 63.038 | 58.093 | 1.00 | 19.17 | A |
| ATOM | 2465 | C | ILE | A | 469 | 46.151 | 65.368 | 54.830 | 1.00 | 19.76 | A |
| ATOM | 2466 | O | ILE | A | 469 | 46.618 | 65.817 | 53.781 | 1.00 | 19.64 | A |
| ATOM | 2467 | N | LEU | A | 470 | 44.958 | 64.785 | 54.898 | 1.00 | 19.07 | A |
| ATOM | 2468 | CA | LEU | A | 470 | 44.113 | 64.634 | 53.718 | 1.00 | 19.45 | A |
| ATOM | 2469 | CB | LEU | A | 470 | 42.880 | 63.785 | 54.035 | 1.00 | 20.05 | A |
| ATOM | 2470 | CG | LEU | A | 470 | 43.013 | 62.262 | 54.008 | 1.00 | 20.72 | A |
| ATOM | 2471 | CD1 | LEU | A | 470 | 41.642 | 61.650 | 54.265 | 1.00 | 22.80 | A |
| ATOM | 2472 | CD2 | LEU | A | 470 | 43.539 | 61.806 | 52.654 | 1.00 | 22.28 | A |
| ATOM | 2473 | C | LEU | A | 470 | 43.654 | 65.990 | 53.190 | 1.00 | 18.98 | A |
| ATOM | 2474 | O | LEU | A | 470 | 43.591 | 66.203 | 51.977 | 1.00 | 18.71 | A |
| ATOM | 2475 | N | ASP | A | 471 | 43.325 | 66.902 | 54.101 | 1.00 | 19.76 | A |
| ATOM | 2476 | CA | ASP | A | 471 | 42.873 | 68.231 | 53.703 | 1.00 | 19.53 | A |
| ATOM | 2477 | CB | ASP | A | 471 | 42.417 | 69.040 | 54.920 | 1.00 | 21.75 | A |
| ATOM | 2478 | CG | ASP | A | 471 | 41.141 | 68.503 | 55.532 | 1.00 | 24.97 | A |
| ATOM | 2479 | OD1 | ASP | A | 471 | 40.375 | 67.823 | 54.815 | 1.00 | 27.27 | A |
| ATOM | 2480 | OD2 | ASP | A | 471 | 40.894 | 68.776 | 56.725 | 1.00 | 27.42 | A |
| ATOM | 2481 | C | ASP | A | 471 | 43.964 | 68.997 | 52.963 | 1.00 | 18.18 | A |
| ATOM | 2482 | O | ASP | A | 471 | 43.693 | 69.698 | 51.992 | 1.00 | 18.06 | A |
| ATOM | 2483 | N | THR | A | 472 | 45.202 | 68.862 | 53.424 | 1.00 | 17.25 | A |
| ATOM | 2484 | CA | THR | A | 472 | 46.316 | 69.539 | 52.778 | 1.00 | 15.40 | A |
| ATOM | 2485 | CB | THR | A | 472 | 47.590 | 69.443 | 53.630 | 1.00 | 15.27 | A |
| ATOM | 2486 | OG1 | THR | A | 472 | 47.367 | 70.089 | 54.888 | 1.00 | 17.72 | A |
| ATOM | 2487 | CG2 | THR | A | 472 | 48.757 | 70.115 | 52.919 | 1.00 | 14.24 | A |
| ATOM | 2488 | C | THR | A | 472 | 46.586 | 68.915 | 51.413 | 1.00 | 14.97 | A |
| ATOM | 2489 | O | THR | A | 472 | 46.874 | 69.620 | 50.445 | 1.00 | 16.05 | A |
| ATOM | 2490 | N | LEU | A | 473 | 46.488 | 67.590 | 51.339 | 1.00 | 15.60 | A |
| ATOM | 2491 | CA | LEU | A | 473 | 46.714 | 66.888 | 50.084 | 1.00 | 15.63 | A |
| ATOM | 2492 | CB | LEU | A | 473 | 46.537 | 65.380 | 50.273 | 1.00 | 16.14 | A |
| ATOM | 2493 | CG | LEU | A | 473 | 46.760 | 64.530 | 49.020 | 1.00 | 15.16 | A |
| ATOM | 2494 | CD1 | LEU | A | 473 | 48.170 | 64.754 | 48.486 | 1.00 | 15.86 | A |
| ATOM | 2495 | CD2 | LEU | A | 473 | 46.538 | 63.063 | 49.349 | 1.00 | 18.27 | A |
| ATOM | 2496 | C | LEU | A | 473 | 45.722 | 67.398 | 49.048 | 1.00 | 15.41 | A |
| ATOM | 2497 | O | LEU | A | 473 | 46.086 | 67.677 | 47.908 | 1.00 | 16.02 | A |
| ATOM | 2498 | N | GLU | A | 474 | 44.467 | 67.525 | 49.470 | 1.00 | 17.29 | A |
| ATOM | 2499 | CA | GLU | A | 474 | 43.395 | 68.006 | 48.608 | 1.00 | 17.12 | A |
| ATOM | 2500 | CB | GLU | A | 474 | 42.066 | 67.936 | 49.361 | 1.00 | 19.50 | A |
| ATOM | 2501 | CG | GLU | A | 474 | 40.859 | 68.470 | 48.605 | 1.00 | 23.04 | A |
| ATOM | 2502 | CD | GLU | A | 474 | 40.510 | 67.650 | 47.377 | 1.00 | 26.60 | A |
| ATOM | 2503 | OE1 | GLU | A | 474 | 40.794 | 66.433 | 47.364 | 1.00 | 28.66 | A |
| ATOM | 2504 | OE2 | GLU | A | 474 | 39.932 | 68.221 | 46.428 | 1.00 | 29.77 | A |
| ATOM | 2505 | C | GLU | A | 474 | 43.667 | 69.438 | 48.152 | 1.00 | 16.00 | A |
| ATOM | 2506 | O | GLU | A | 474 | 43.547 | 69.749 | 46.965 | 1.00 | 16.27 | A |
| ATOM | 2507 | N | ASP | A | 475 | 44.032 | 70.305 | 49.094 | 1.00 | 16.49 | A |
| ATOM | 2508 | CA | ASP | A | 475 | 44.328 | 71.698 | 48.767 | 1.00 | 16.91 | A |
| ATOM | 2509 | CB | ASP | A | 475 | 44.652 | 72.509 | 50.027 | 1.00 | 18.92 | A |
| ATOM | 2510 | CG | ASP | A | 475 | 43.435 | 72.753 | 50.904 | 1.00 | 22.25 | A |
| ATOM | 2511 | OD1 | ASP | A | 475 | 42.295 | 72.576 | 50.421 | 1.00 | 24.34 | A |
| ATOM | 2512 | OD2 | ASP | A | 475 | 43.625 | 73.137 | 52.080 | 1.00 | 25.35 | A |
| ATOM | 2513 | C | ASP | A | 475 | 45.499 | 71.815 | 47.794 | 1.00 | 16.28 | A |

TABLE 1-continued

| | | | | | | | | | | |
|---|---|---|---|---|---|---|---|---|---|---|
| ATOM | 2514 | O | ASP | A | 475 | 45.434 | 72.577 | 46.829 | 1.00 | 17.72 | A |
| ATOM | 2515 | N | ASN | A | 476 | 46.573 | 71.069 | 48.046 | 1.00 | 14.25 | A |
| ATOM | 2516 | CA | ASN | A | 476 | 47.732 | 71.124 | 47.163 | 1.00 | 13.50 | A |
| ATOM | 2517 | CB | ASN | A | 476 | 48.905 | 70.322 | 47.743 | 1.00 | 13.93 | A |
| ATOM | 2518 | CG | ASN | A | 476 | 49.477 | 70.947 | 49.003 | 1.00 | 14.86 | A |
| ATOM | 2519 | OD1 | ASN | A | 476 | 49.270 | 72.127 | 49.275 | 1.00 | 16.38 | A |
| ATOM | 2520 | ND2 | ASN | A | 476 | 50.220 | 70.154 | 49.773 | 1.00 | 13.48 | A |
| ATOM | 2521 | C | ASN | A | 476 | 47.395 | 70.601 | 45.770 | 1.00 | 13.52 | A |
| ATOM | 2522 | O | ASN | A | 476 | 47.861 | 71.143 | 44.771 | 1.00 | 14.91 | A |
| ATOM | 2523 | N | ARG | A | 477 | 46.592 | 69.543 | 45.709 | 1.00 | 13.19 | A |
| ATOM | 2524 | CA | ARG | A | 477 | 46.193 | 68.971 | 44.427 | 1.00 | 14.37 | A |
| ATOM | 2525 | CB | ARG | A | 477 | 45.291 | 67.757 | 44.637 | 1.00 | 17.12 | A |
| ATOM | 2526 | CG | ARG | A | 477 | 44.700 | 67.224 | 43.338 | 1.00 | 18.32 | A |
| ATOM | 2527 | CD | ARG | A | 477 | 43.466 | 66.371 | 43.596 | 1.00 | 21.12 | A |
| ATOM | 2528 | NE | ARG | A | 477 | 42.925 | 65.816 | 42.357 | 1.00 | 22.13 | A |
| ATOM | 2529 | CZ | ARG | A | 477 | 42.224 | 66.501 | 41.456 | 1.00 | 22.06 | A |
| ATOM | 2530 | NH1 | ARG | A | 477 | 41.952 | 67.787 | 41.641 | 1.00 | 21.09 | A |
| ATOM | 2531 | NH2 | ARG | A | 477 | 41.808 | 65.894 | 40.354 | 1.00 | 22.91 | A |
| ATOM | 2532 | C | ARG | A | 477 | 45.423 | 70.009 | 43.616 | 1.00 | 15.11 | A |
| ATOM | 2533 | O | ARG | A | 477 | 45.706 | 70.235 | 42.437 | 1.00 | 15.63 | A |
| ATOM | 2534 | N | ASN | A | 478 | 44.442 | 70.630 | 44.259 | 1.00 | 15.73 | A |
| ATOM | 2535 | CA | ASN | A | 478 | 43.621 | 71.631 | 43.593 | 1.00 | 16.96 | A |
| ATOM | 2536 | CB | ASN | A | 478 | 42.434 | 72.021 | 44.478 | 1.00 | 18.15 | A |
| ATOM | 2537 | CG | ASN | A | 478 | 41.481 | 70.863 | 44.707 | 1.00 | 18.54 | A |
| ATOM | 2538 | OD1 | ASN | A | 478 | 41.353 | 69.975 | 43.862 | 1.00 | 20.76 | A |
| ATOM | 2539 | ND2 | ASN | A | 478 | 40.797 | 70.872 | 45.845 | 1.00 | 22.28 | A |
| ATOM | 2540 | C | ASN | A | 478 | 44.429 | 72.861 | 43.207 | 1.00 | 16.90 | A |
| ATOM | 2541 | O | ASN | A | 478 | 44.149 | 73.500 | 42.193 | 1.00 | 18.68 | A |
| ATOM | 2542 | N | TRP | A | 479 | 45.437 | 73.194 | 44.006 | 1.00 | 17.18 | A |
| ATOM | 2543 | CA | TRP | A | 479 | 46.268 | 74.345 | 43.694 | 1.00 | 17.07 | A |
| ATOM | 2544 | CB | TRP | A | 479 | 47.273 | 74.618 | 44.815 | 1.00 | 17.06 | A |
| ATOM | 2545 | CG | TRP | A | 479 | 48.108 | 75.835 | 44.549 | 1.00 | 18.72 | A |
| ATOM | 2546 | CD2 | TRP | A | 479 | 49.377 | 75.875 | 43.887 | 1.00 | 20.43 | A |
| ATOM | 2547 | CE2 | TRP | A | 479 | 49.758 | 77.230 | 43.793 | 1.00 | 20.82 | A |
| ATOM | 2548 | CE3 | TRP | A | 479 | 50.228 | 74.897 | 43.360 | 1.00 | 20.34 | A |
| ATOM | 2549 | CD1 | TRP | A | 479 | 47.781 | 77.131 | 44.827 | 1.00 | 19.83 | A |
| ATOM | 2550 | NE1 | TRP | A | 479 | 48.767 | 77.977 | 44.375 | 1.00 | 20.62 | A |
| ATOM | 2551 | CZ2 | TRP | A | 479 | 50.953 | 77.631 | 43.194 | 1.00 | 20.76 | A |
| ATOM | 2552 | CZ3 | TRP | A | 479 | 51.413 | 75.298 | 42.765 | 1.00 | 21.63 | A |
| ATOM | 2553 | CH2 | TRP | A | 479 | 51.763 | 76.653 | 42.688 | 1.00 | 20.93 | A |
| ATOM | 2554 | C | TRP | A | 479 | 47.022 | 74.058 | 42.401 | 1.00 | 16.94 | A |
| ATOM | 2555 | O | TRP | A | 479 | 47.030 | 74.875 | 41.480 | 1.00 | 18.18 | A |
| ATOM | 2556 | N | TYR | A | 480 | 47.659 | 72.892 | 42.333 | 1.00 | 16.87 | A |
| ATOM | 2557 | CA | TYR | A | 480 | 48.406 | 72.523 | 41.140 | 1.00 | 17.45 | A |
| ATOM | 2558 | CB | TYR | A | 480 | 49.139 | 71.194 | 41.356 | 1.00 | 17.97 | A |
| ATOM | 2559 | CG | TYR | A | 480 | 50.594 | 71.365 | 41.729 | 1.00 | 18.22 | A |
| ATOM | 2560 | CD1 | TYR | A | 480 | 51.489 | 71.951 | 40.845 | 1.00 | 19.46 | A |
| ATOM | 2561 | CE1 | TYR | A | 480 | 52.825 | 72.100 | 41.170 | 1.00 | 20.17 | A |
| ATOM | 2562 | CD2 | TYR | A | 480 | 51.076 | 70.933 | 42.958 | 1.00 | 19.67 | A |
| ATOM | 2563 | CE2 | TYR | A | 480 | 52.414 | 71.078 | 43.291 | 1.00 | 20.51 | A |
| ATOM | 2564 | CZ | TYR | A | 480 | 53.281 | 71.660 | 42.392 | 1.00 | 20.12 | A |
| ATOM | 2565 | OH | TYR | A | 480 | 54.613 | 71.789 | 42.707 | 1.00 | 22.48 | A |
| ATOM | 2566 | C | TYR | A | 480 | 47.518 | 72.436 | 39.906 | 1.00 | 17.60 | A |
| ATOM | 2567 | O | TYR | A | 480 | 47.934 | 72.811 | 38.809 | 1.00 | 19.22 | A |
| ATOM | 2568 | N | GLN | A | 481 | 46.295 | 71.948 | 40.078 | 1.00 | 17.95 | A |
| ATOM | 2569 | CA | GLN | A | 481 | 45.387 | 71.840 | 38.943 | 1.00 | 18.98 | A |
| ATOM | 2570 | CB | GLN | A | 481 | 44.106 | 71.102 | 39.339 | 1.00 | 17.87 | A |
| ATOM | 2571 | CG | GLN | A | 481 | 43.209 | 70.782 | 38.146 | 1.00 | 19.28 | A |
| ATOM | 2572 | CD | GLN | A | 481 | 42.073 | 69.844 | 38.492 | 1.00 | 19.66 | A |
| ATOM | 2573 | OE1 | GLN | A | 481 | 41.888 | 68.810 | 37.845 | 1.00 | 21.59 | A |
| ATOM | 2574 | NE2 | GLN | A | 481 | 41.303 | 70.198 | 39.511 | 1.00 | 18.91 | A |
| ATOM | 2575 | C | GLN | A | 481 | 45.045 | 73.230 | 38.418 | 1.00 | 19.80 | A |
| ATOM | 2576 | O | GLN | A | 481 | 44.938 | 73.434 | 37.209 | 1.00 | 21.26 | A |
| ATOM | 2577 | N | SER | A | 482 | 44.893 | 74.189 | 39.325 | 1.00 | 20.93 | A |
| ATOM | 2578 | CA | SER | A | 482 | 44.557 | 75.557 | 38.932 | 1.00 | 22.05 | A |
| ATOM | 2579 | CB | SER | A | 482 | 44.059 | 76.357 | 40.139 | 1.00 | 20.51 | A |
| ATOM | 2580 | OG | SER | A | 482 | 45.125 | 76.687 | 41.015 | 1.00 | 23.08 | A |
| ATOM | 2581 | C | SER | A | 482 | 45.741 | 76.286 | 38.306 | 1.00 | 22.53 | A |
| ATOM | 2582 | O | SER | A | 482 | 45.570 | 77.337 | 37.683 | 1.00 | 24.61 | A |
| ATOM | 2583 | N | MET | A | 483 | 46.938 | 75.730 | 38.465 | 1.00 | 22.77 | A |
| ATOM | 2584 | CA | MET | A | 483 | 48.143 | 76.345 | 37.915 | 1.00 | 22.53 | A |
| ATOM | 2585 | CB | MET | A | 483 | 49.306 | 76.203 | 38.898 | 1.00 | 21.83 | A |
| ATOM | 2586 | CG | MET | A | 483 | 49.141 | 76.998 | 40.182 | 1.00 | 24.67 | A |
| ATOM | 2587 | SD | MET | A | 483 | 49.123 | 78.781 | 39.907 | 1.00 | 24.46 | A |
| ATOM | 2588 | CE | MET | A | 483 | 50.853 | 79.097 | 39.558 | 1.00 | 27.42 | A |
| ATOM | 2589 | C | MET | A | 483 | 48.545 | 75.756 | 36.570 | 1.00 | 23.15 | A |
| ATOM | 2590 | O | MET | A | 483 | 49.557 | 76.155 | 35.989 | 1.00 | 24.17 | A |
| ATOM | 2591 | N | ILE | A | 484 | 47.767 | 74.798 | 36.080 | 1.00 | 22.82 | A |
| ATOM | 2592 | CA | ILE | A | 484 | 48.064 | 74.194 | 34.787 | 1.00 | 24.95 | A |

TABLE 1-continued

| ATOM | 2593 | CB | ILE | A | 484 | 47.072 | 73.058 | 34.444 | 1.00 | 23.62 | A |
|------|------|-----|-----|---|-----|--------|--------|--------|------|-------|---|
| ATOM | 2594 | CG2 | ILE | A | 484 | 47.307 | 72.572 | 33.026 | 1.00 | 24.43 | A |
| ATOM | 2595 | CG1 | ILE | A | 484 | 47.238 | 71.899 | 35.428 | 1.00 | 22.63 | A |
| ATOM | 2596 | CD1 | ILE | A | 484 | 46.251 | 70.775 | 35.221 | 1.00 | 20.73 | A |
| ATOM | 2597 | C | ILE | A | 484 | 47.943 | 75.295 | 33.739 | 1.00 | 25.95 | A |
| ATOM | 2598 | O | ILE | A | 484 | 46.938 | 76.000 | 33.682 | 1.00 | 25.99 | A |
| ATOM | 2599 | N | PRO | A | 485 | 48.982 | 75.468 | 32.909 | 1.00 | 25.89 | A |
| ATOM | 2600 | CD | PRO | A | 485 | 50.237 | 74.695 | 32.922 | 1.00 | 26.30 | A |
| ATOM | 2601 | CA | PRO | A | 485 | 49.007 | 76.487 | 31.855 | 1.00 | 26.49 | A |
| ATOM | 2602 | CB | PRO | A | 485 | 50.229 | 76.092 | 31.035 | 1.00 | 26.74 | A |
| ATOM | 2603 | CG | PRO | A | 485 | 51.158 | 75.560 | 32.087 | 1.00 | 26.49 | A |
| ATOM | 2604 | C | PRO | A | 485 | 47.729 | 76.519 | 31.019 | 1.00 | 27.33 | A |
| ATOM | 2605 | O | PRO | A | 485 | 47.446 | 75.591 | 30.257 | 1.00 | 28.98 | A |
| ATOM | 2606 | N | GLN | A | 500 | 57.823 | 61.166 | 25.823 | 1.00 | 27.23 | A |
| ATOM | 2607 | CA | GLN | A | 500 | 56.906 | 60.889 | 26.925 | 1.00 | 27.11 | A |
| ATOM | 2608 | CB | GLN | A | 500 | 57.203 | 59.535 | 27.562 | 1.00 | 26.34 | A |
| ATOM | 2609 | CG | GLN | A | 500 | 56.914 | 58.342 | 26.657 | 1.00 | 26.66 | A |
| ATOM | 2610 | CD | GLN | A | 500 | 57.025 | 57.026 | 27.409 | 1.00 | 28.35 | A |
| ATOM | 2611 | OE1 | GLN | A | 500 | 57.979 | 56.804 | 28.133 | 1.00 | 28.45 | A |
| ATOM | 2612 | NE2 | GLN | A | 500 | 56.166 | 56.009 | 27.357 | 1.00 | 29.09 | A |
| ATOM | 2613 | C | GLN | A | 500 | 56.949 | 61.974 | 27.995 | 1.00 | 27.94 | A |
| ATOM | 2614 | O | GLN | A | 500 | 58.022 | 62.391 | 28.427 | 1.00 | 28.09 | A |
| ATOM | 2615 | N | GLY | A | 501 | 55.770 | 62.423 | 28.419 | 1.00 | 27.36 | A |
| ATOM | 2616 | CA | GLY | A | 501 | 55.688 | 63.453 | 29.439 | 1.00 | 27.32 | A |
| ATOM | 2617 | C | GLY | A | 501 | 56.098 | 62.919 | 30.799 | 1.00 | 27.53 | A |
| ATOM | 2618 | O | GLY | A | 501 | 56.269 | 61.721 | 30.950 | 1.00 | 27.48 | A |
| ATOM | 2619 | N | LEU | A | 502 | 56.218 | 63.771 | 31.790 | 1.00 | 25.91 | A |
| ATOM | 2620 | CA | LEU | A | 502 | 56.512 | 63.326 | 33.137 | 1.00 | 25.00 | A |
| ATOM | 2621 | C | LEU | A | 502 | 55.686 | 62.081 | 33.495 | 1.00 | 25.16 | A |
| ATOM | 2622 | O | LEU | A | 502 | 56.218 | 60.995 | 33.676 | 1.00 | 25.33 | A |
| ATOM | 2623 | CB | LEU | A | 502 | 56.189 | 64.430 | 34.157 | 1.00 | 24.37 | A |
| ATOM | 2624 | CG | LEU | A | 502 | 57.152 | 65.640 | 34.297 | 1.00 | 20.00 | A |
| ATOM | 2625 | CD1 | LEU | A | 502 | 56.648 | 66.625 | 35.340 | 1.00 | 20.00 | A |
| ATOM | 2626 | CD2 | LEU | A | 502 | 58.549 | 65.154 | 34.650 | 1.00 | 20.00 | A |
| ATOM | 2627 | N | MET | A | 503 | 54.414 | 62.336 | 33.603 | 1.00 | 24.22 | A |
| ATOM | 2628 | CA | MET | A | 503 | 53.511 | 61.306 | 33.995 | 1.00 | 24.40 | A |
| ATOM | 2629 | CB | MET | A | 503 | 52.078 | 61.835 | 34.086 | 1.00 | 26.37 | A |
| ATOM | 2630 | CG | MET | A | 503 | 51.082 | 60.804 | 34.575 | 1.00 | 29.12 | A |
| ATOM | 2631 | SD | MET | A | 503 | 51.581 | 60.069 | 36.144 | 1.00 | 29.58 | A |
| ATOM | 2632 | CE | MET | A | 503 | 51.097 | 61.354 | 37.299 | 1.00 | 31.34 | A |
| ATOM | 2633 | C | MET | A | 503 | 53.554 | 60.104 | 33.057 | 1.00 | 24.49 | A |
| ATOM | 2634 | O | MET | A | 503 | 53.471 | 58.960 | 33.502 | 1.00 | 24.24 | A |
| ATOM | 2635 | N | GLU | A | 504 | 53.680 | 60.363 | 31.759 | 1.00 | 24.16 | A |
| ATOM | 2636 | CA | GLU | A | 504 | 53.740 | 59.279 | 30.783 | 1.00 | 24.81 | A |
| ATOM | 2637 | C | GLU | A | 504 | 54.938 | 58.385 | 31.090 | 1.00 | 25.80 | A |
| ATOM | 2638 | O | GLU | A | 504 | 54.813 | 57.160 | 31.152 | 1.00 | 26.68 | A |
| ATOM | 2639 | CB | GLU | A | 504 | 53.788 | 59.840 | 29.362 | 1.00 | 24.38 | A |
| ATOM | 2640 | CG | GLU | A | 504 | 52.586 | 60.691 | 28.990 | 1.00 | 20.00 | A |
| ATOM | 2641 | CD | GLU | A | 504 | 52.669 | 61.230 | 27.575 | 1.00 | 20.00 | A |
| ATOM | 2642 | OE1 | GLU | A | 504 | 53.667 | 60.937 | 26.886 | 1.00 | 20.00 | A |
| ATOM | 2643 | OE2 | GLU | A | 504 | 51.726 | 61.928 | 27.150 | 1.00 | 20.00 | A |
| ATOM | 2644 | N | LYS | A | 505 | 56.030 | 58.881 | 31.278 | 1.00 | 25.07 | A |
| ATOM | 2645 | CA | LYS | A | 505 | 57.326 | 58.286 | 31.598 | 1.00 | 24.86 | A |
| ATOM | 2646 | C | LYS | A | 505 | 57.176 | 57.297 | 32.750 | 1.00 | 24.44 | A |
| ATOM | 2647 | O | LYS | A | 505 | 57.437 | 56.100 | 32.603 | 1.00 | 24.95 | A |
| ATOM | 2648 | CB | LYS | A | 505 | 58.352 | 59.375 | 31.913 | 1.00 | 23.71 | A |
| ATOM | 2649 | CG | LYS | A | 505 | 58.594 | 60.348 | 30.772 | 1.00 | 20.00 | A |
| ATOM | 2650 | CD | LYS | A | 505 | 59.787 | 61.245 | 31.055 | 1.00 | 20.00 | A |
| ATOM | 2651 | CE | LYS | A | 505 | 60.028 | 62.218 | 29.914 | 1.00 | 20.00 | A |
| ATOM | 2652 | NZ | LYS | A | 505 | 61.195 | 63.104 | 30.177 | 1.00 | 20.00 | A |
| ATOM | 2653 | N | PHE | A | 506 | 56.589 | 58.121 | 33.897 | 1.00 | 23.30 | A |
| ATOM | 2654 | CA | PHE | A | 506 | 56.349 | 57.467 | 35.176 | 1.00 | 23.05 | A |
| ATOM | 2655 | CB | PHE | A | 506 | 55.595 | 58.411 | 36.113 | 1.00 | 22.73 | A |
| ATOM | 2656 | CG | PHE | A | 506 | 55.268 | 57.805 | 37.447 | 1.00 | 22.31 | A |
| ATOM | 2657 | CD1 | PHE | A | 506 | 56.253 | 57.627 | 38.404 | 1.00 | 22.89 | A |
| ATOM | 2658 | CD2 | PHE | A | 506 | 53.977 | 57.394 | 37.735 | 1.00 | 22.89 | A |
| ATOM | 2659 | CE1 | PHE | A | 506 | 55.957 | 57.048 | 39.625 | 1.00 | 23.23 | A |
| ATOM | 2660 | CE2 | PHE | A | 506 | 53.674 | 56.815 | 38.951 | 1.00 | 22.14 | A |
| ATOM | 2661 | CZ | PHE | A | 506 | 54.666 | 56.642 | 39.896 | 1.00 | 22.20 | A |
| ATOM | 2662 | C | PHE | A | 506 | 55.527 | 56.196 | 34.970 | 1.00 | 24.17 | A |
| ATOM | 2663 | O | PHE | A | 506 | 55.915 | 55.114 | 35.415 | 1.00 | 24.62 | A |
| ATOM | 2664 | N | GLN | A | 507 | 54.394 | 56.336 | 34.288 | 1.00 | 24.03 | A |
| ATOM | 2665 | CA | GLN | A | 507 | 53.512 | 55.205 | 34.023 | 1.00 | 25.65 | A |
| ATOM | 2666 | C | GLN | A | 507 | 54.185 | 54.150 | 33.149 | 1.00 | 26.46 | A |
| ATOM | 2667 | O | GLN | A | 507 | 54.005 | 52.951 | 33.364 | 1.00 | 28.00 | A |
| ATOM | 2668 | CB | GLN | A | 507 | 52.215 | 55.680 | 33.366 | 1.00 | 26.09 | A |
| ATOM | 2669 | CG | GLN | A | 507 | 51.260 | 56.383 | 34.315 | 1.00 | 20.00 | A |
| ATOM | 2670 | CD | GLN | A | 507 | 50.230 | 55.442 | 34.907 | 1.00 | 20.00 | A |
| ATOM | 2671 | OE1 | GLN | A | 507 | 50.222 | 54.248 | 34.610 | 1.00 | 20.00 | A |

TABLE 1-continued

| | | | | | | | | | | |
|---|---|---|---|---|---|---|---|---|---|---|
| ATOM | 2672 | NE2 | GLN | A | 507 | 49.269 | 55.764 | 35.764 | 1.00 | 20.00 | A |
| ATOM | 2673 | N | PHE | A | 508 | 54.962 | 54.601 | 32.168 | 1.00 | 26.64 | A |
| ATOM | 2674 | CA | PHE | A | 508 | 55.662 | 53.700 | 31.257 | 1.00 | 26.96 | A |
| ATOM | 2675 | C | PHE | A | 508 | 56.637 | 52.780 | 31.990 | 1.00 | 26.74 | A |
| ATOM | 2676 | O | PHE | A | 508 | 56.581 | 51.559 | 31.836 | 1.00 | 27.49 | A |
| ATOM | 2677 | CB | PHE | A | 508 | 56.426 | 54.496 | 30.198 | 1.00 | 25.48 | A |
| ATOM | 2678 | CG | PHE | A | 508 | 56.589 | 53.770 | 28.895 | 1.00 | 20.00 | A |
| ATOM | 2679 | CD1 | PHE | A | 508 | 55.486 | 53.433 | 28.131 | 1.00 | 20.00 | A |
| ATOM | 2680 | CD2 | PHE | A | 508 | 57.859 | 53.423 | 28.434 | 1.00 | 20.00 | A |
| ATOM | 2681 | CE1 | PHE | A | 508 | 55.636 | 52.765 | 26.932 | 1.00 | 20.00 | A |
| ATOM | 2682 | CE2 | PHE | A | 508 | 58.009 | 52.755 | 27.235 | 1.00 | 20.00 | A |
| ATOM | 2683 | CZ | PHE | A | 508 | 56.898 | 52.426 | 26.484 | 1.00 | 20.00 | A |
| ATOM | 2684 | N | GLU | A | 509 | 57.375 | 53.138 | 32.892 | 1.00 | 26.57 | A |
| ATOM | 2685 | CA | GLU | A | 509 | 58.236 | 52.244 | 33.658 | 1.00 | 26.37 | A |
| ATOM | 2686 | CB | GLU | A | 509 | 59.300 | 53.031 | 34.426 | 1.00 | 25.10 | A |
| ATOM | 2687 | CG | GLU | A | 509 | 60.275 | 53.824 | 33.575 | 1.00 | 26.10 | A |
| ATOM | 2688 | CD | GLU | A | 509 | 61.477 | 54.282 | 34.382 | 1.00 | 25.19 | A |
| ATOM | 2689 | OE1 | GLU | A | 509 | 61.303 | 54.568 | 35.584 | 1.00 | 29.75 | A |
| ATOM | 2690 | OE2 | GLU | A | 509 | 62.588 | 54.366 | 33.818 | 1.00 | 27.78 | A |
| ATOM | 2691 | C | GLU | A | 509 | 57.449 | 51.401 | 34.651 | 1.00 | 28.55 | A |
| ATOM | 2692 | O | GLU | A | 509 | 57.540 | 50.173 | 34.643 | 1.00 | 29.93 | A |
| ATOM | 2693 | N | THR | A | 510 | 56.686 | 52.064 | 35.515 | 1.00 | 28.05 | A |
| ATOM | 2694 | CA | THR | A | 510 | 55.895 | 51.362 | 36.521 | 1.00 | 28.54 | A |
| ATOM | 2695 | CB | THR | A | 510 | 55.042 | 52.346 | 37.356 | 1.00 | 27.27 | A |
| ATOM | 2696 | OG1 | THR | A | 510 | 54.443 | 51.649 | 38.457 | 1.00 | 29.38 | A |
| ATOM | 2697 | CG2 | THR | A | 510 | 53.952 | 52.964 | 36.504 | 1.00 | 26.53 | A |
| ATOM | 2698 | C | THR | A | 510 | 54.982 | 50.322 | 35.872 | 1.00 | 29.49 | A |
| ATOM | 2699 | O | THR | A | 510 | 54.894 | 49.202 | 36.416 | 1.00 | 29.59 | A |
| ATOM | 2700 | OXT | THR | A | 510 | 54.364 | 50.638 | 34.832 | 1.00 | 28.89 | A |
| ATOM | 2701 | CB | ARG | B | 155 | 85.015 | 19.003 | 21.577 | 1.00 | 24.19 | B |
| ATOM | 2702 | CG | ARG | B | 155 | 84.934 | 20.238 | 22.448 | 1.00 | 23.50 | B |
| ATOM | 2703 | CD | ARG | B | 155 | 84.822 | 21.492 | 21.606 | 1.00 | 21.83 | B |
| ATOM | 2704 | NE | ARG | B | 155 | 84.724 | 22.687 | 22.435 | 1.00 | 19.82 | B |
| ATOM | 2705 | CZ | ARG | B | 155 | 84.571 | 23.918 | 21.957 | 1.00 | 19.67 | B |
| ATOM | 2706 | NH1 | ARG | B | 155 | 84.498 | 24.120 | 20.645 | 1.00 | 21.34 | B |
| ATOM | 2707 | NH2 | ARG | B | 155 | 84.491 | 24.945 | 22.791 | 1.00 | 20.32 | B |
| ATOM | 2708 | C | ARG | B | 155 | 84.244 | 17.539 | 23.451 | 1.00 | 24.29 | B |
| ATOM | 2709 | O | ARG | B | 155 | 84.400 | 18.070 | 24.551 | 1.00 | 25.28 | B |
| ATOM | 2710 | N | ARG | B | 155 | 85.300 | 16.557 | 21.415 | 1.00 | 26.08 | B |
| ATOM | 2711 | CA | ARG | B | 155 | 85.285 | 17.714 | 22.350 | 1.00 | 24.35 | B |
| ATOM | 2712 | N | PHE | B | 156 | 83.188 | 16.786 | 23.155 | 1.00 | 22.89 | B |
| ATOM | 2713 | CA | PHE | B | 156 | 82.122 | 16.538 | 24.124 | 1.00 | 21.98 | B |
| ATOM | 2714 | CB | PHE | B | 156 | 80.862 | 16.043 | 23.410 | 1.00 | 19.58 | B |
| ATOM | 2715 | CG | PHE | B | 156 | 80.162 | 17.100 | 22.613 | 1.00 | 19.92 | B |
| ATOM | 2716 | CD1 | PHE | B | 156 | 79.307 | 18.002 | 23.233 | 1.00 | 20.93 | B |
| ATOM | 2717 | CD2 | PHE | B | 156 | 80.366 | 17.206 | 21.249 | 1.00 | 22.26 | B |
| ATOM | 2718 | CE1 | PHE | B | 156 | 78.671 | 18.988 | 22.505 | 1.00 | 21.48 | B |
| ATOM | 2719 | CE2 | PHE | B | 156 | 79.731 | 18.193 | 20.512 | 1.00 | 23.50 | B |
| ATOM | 2720 | CZ | PHE | B | 156 | 78.883 | 19.084 | 21.142 | 1.00 | 22.42 | B |
| ATOM | 2721 | C | PHE | B | 156 | 82.550 | 15.509 | 25.159 | 1.00 | 22.86 | B |
| ATOM | 2722 | O | PHE | B | 156 | 81.908 | 15.357 | 26.202 | 1.00 | 24.31 | B |
| ATOM | 2723 | N | GLY | B | 157 | 83.638 | 14.804 | 24.868 | 1.00 | 23.36 | B |
| ATOM | 2724 | CA | GLY | B | 157 | 84.126 | 13.796 | 25.790 | 1.00 | 23.56 | B |
| ATOM | 2725 | C | GLY | B | 157 | 83.679 | 12.396 | 25.411 | 1.00 | 24.97 | B |
| ATOM | 2726 | O | GLY | B | 157 | 83.722 | 11.477 | 26.232 | 1.00 | 26.71 | B |
| ATOM | 2727 | N | VAL | B | 158 | 83.248 | 12.229 | 24.164 | 1.00 | 24.24 | B |
| ATOM | 2728 | CA | VAL | B | 158 | 82.795 | 10.927 | 23.688 | 1.00 | 23.64 | B |
| ATOM | 2729 | CB | VAL | B | 158 | 81.580 | 11.067 | 22.741 | 1.00 | 22.81 | B |
| ATOM | 2730 | CG1 | VAL | B | 158 | 81.103 | 9.692 | 22.295 | 1.00 | 22.53 | B |
| ATOM | 2731 | CG2 | VAL | B | 158 | 80.457 | 11.813 | 23.438 | 1.00 | 23.22 | B |
| ATOM | 2732 | C | VAL | B | 158 | 83.907 | 10.189 | 22.948 | 1.00 | 24.16 | B |
| ATOM | 2733 | O | VAL | B | 158 | 84.453 | 10.686 | 21.961 | 1.00 | 25.45 | B |
| ATOM | 2734 | N | ASN | B | 159 | 84.245 | 9.001 | 23.438 | 1.00 | 23.84 | B |
| ATOM | 2735 | CA | ASN | B | 159 | 85.277 | 8.184 | 22.812 | 1.00 | 24.89 | B |
| ATOM | 2736 | CB | ASN | B | 159 | 85.534 | 6.925 | 23.645 | 1.00 | 25.27 | B |
| ATOM | 2737 | CG | ASN | B | 159 | 86.188 | 7.230 | 24.984 | 1.00 | 27.41 | B |
| ATOM | 2738 | OD1 | ASN | B | 159 | 86.201 | 6.391 | 25.887 | 1.00 | 31.29 | B |
| ATOM | 2739 | ND2 | ASN | B | 159 | 86.746 | 8.429 | 25.113 | 1.00 | 29.14 | B |
| ATOM | 2740 | C | ASN | B | 159 | 84.789 | 7.797 | 21.420 | 1.00 | 24.42 | B |
| ATOM | 2741 | O | ASN | B | 159 | 83.622 | 7.449 | 21.238 | 1.00 | 24.56 | B |
| ATOM | 2742 | N | THR | B | 160 | 85.681 | 7.867 | 20.438 | 1.00 | 25.41 | B |
| ATOM | 2743 | CA | THR | B | 160 | 85.327 | 7.528 | 19.065 | 1.00 | 25.78 | B |
| ATOM | 2744 | CB | THR | B | 160 | 86.583 | 7.452 | 18.177 | 1.00 | 26.84 | B |
| ATOM | 2745 | OG1 | THR | B | 160 | 87.179 | 8.752 | 18.086 | 1.00 | 30.04 | B |
| ATOM | 2746 | CG2 | THR | B | 160 | 86.224 | 6.965 | 16.784 | 1.00 | 27.12 | B |
| ATOM | 2747 | C | THR | B | 160 | 84.571 | 6.206 | 18.964 | 1.00 | 25.75 | B |
| ATOM | 2748 | O | THR | B | 160 | 83.667 | 6.056 | 18.141 | 1.00 | 26.05 | B |
| ATOM | 2749 | N | GLU | B | 161 | 84.940 | 5.254 | 19.814 | 1.00 | 24.76 | B |
| ATOM | 2750 | CA | GLU | B | 161 | 84.313 | 3.938 | 19.817 | 1.00 | 25.15 | B |

TABLE 1-continued

| | | | | | | | | | | |
|---|---|---|---|---|---|---|---|---|---|---|
| ATOM | 2751 | C | GLU | B | 161 | 82.869 | 3.935 | 20.310 | 1.00 | 25.80 | B |
| ATOM | 2752 | O | GLU | B | 161 | 82.123 | 2.994 | 20.035 | 1.00 | 25.86 | B |
| ATOM | 2753 | CB | GLU | B | 161 | 85.098 | 2.973 | 20.706 | 1.00 | 24.94 | B |
| ATOM | 2754 | CG | GLU | B | 161 | 86.539 | 2.764 | 20.274 | 1.00 | 20.00 | B |
| ATOM | 2755 | CD | GLU | B | 161 | 87.285 | 1.803 | 21.178 | 1.00 | 20.00 | B |
| ATOM | 2756 | OE1 | GLU | B | 161 | 86.674 | 1.300 | 22.143 | 1.00 | 20.00 | B |
| ATOM | 2757 | OE2 | GLU | B | 161 | 88.480 | 1.553 | 20.921 | 1.00 | 20.00 | B |
| ATOM | 2758 | N | ASN | B | 162 | 82.469 | 4.977 | 21.034 | 1.00 | 24.54 | B |
| ATOM | 2759 | CA | ASN | B | 162 | 81.106 | 5.050 | 21.558 | 1.00 | 23.42 | B |
| ATOM | 2760 | CB | ASN | B | 162 | 81.113 | 5.526 | 23.013 | 1.00 | 24.01 | B |
| ATOM | 2761 | CG | ASN | B | 162 | 81.716 | 4.510 | 23.959 | 1.00 | 24.31 | B |
| ATOM | 2762 | OD1 | ASN | B | 162 | 81.408 | 3.321 | 23.888 | 1.00 | 28.88 | B |
| ATOM | 2763 | ND2 | ASN | B | 162 | 82.569 | 4.977 | 24.864 | 1.00 | 25.80 | B |
| ATOM | 2764 | C | ASN | B | 162 | 80.167 | 5.943 | 20.752 | 1.00 | 23.07 | B |
| ATOM | 2765 | O | ASN | B | 162 | 79.006 | 6.115 | 21.123 | 1.00 | 23.17 | B |
| ATOM | 2766 | N | GLU | B | 163 | 80.656 | 6.502 | 19.651 | 1.00 | 22.51 | B |
| ATOM | 2767 | CA | GLU | B | 163 | 79.832 | 7.371 | 18.817 | 1.00 | 24.08 | B |
| ATOM | 2768 | C | GLU | B | 163 | 78.535 | 6.686 | 18.391 | 1.00 | 25.06 | B |
| ATOM | 2769 | O | GLU | B | 163 | 77.478 | 7.320 | 18.335 | 1.00 | 25.48 | B |
| ATOM | 2770 | CB | GLU | B | 163 | 80.613 | 7.828 | 17.585 | 1.00 | 23.35 | B |
| ATOM | 2771 | CG | GLU | B | 163 | 81.746 | 8.793 | 17.892 | 1.00 | 20.00 | B |
| ATOM | 2772 | CD | GLU | B | 163 | 81.255 | 10.201 | 18.162 | 1.00 | 20.00 | B |
| ATOM | 2773 | OE1 | GLU | B | 163 | 80.028 | 10.422 | 18.110 | 1.00 | 20.00 | B |
| ATOM | 2774 | OE2 | GLU | B | 163 | 82.098 | 11.083 | 18.427 | 1.00 | 20.00 | B |
| ATOM | 2775 | N | ASP | B | 164 | 78.618 | 5.391 | 18.097 | 1.00 | 24.90 | B |
| ATOM | 2776 | CA | ASP | B | 164 | 77.451 | 4.621 | 17.673 | 1.00 | 26.01 | B |
| ATOM | 2777 | CB | ASP | B | 164 | 77.893 | 3.295 | 17.049 | 1.00 | 27.20 | B |
| ATOM | 2778 | CG | ASP | B | 164 | 78.609 | 3.488 | 15.728 | 1.00 | 29.72 | B |
| ATOM | 2779 | OD1 | ASP | B | 164 | 78.016 | 4.110 | 14.819 | 1.00 | 32.07 | B |
| ATOM | 2780 | OD2 | ASP | B | 164 | 79.761 | 3.022 | 15.596 | 1.00 | 32.92 | B |
| ATOM | 2781 | C | ASP | B | 164 | 76.457 | 4.351 | 18.799 | 1.00 | 25.49 | B |
| ATOM | 2782 | O | ASP | B | 164 | 75.246 | 4.438 | 18.597 | 1.00 | 27.12 | B |
| ATOM | 2783 | N | HIS | B | 165 | 76.965 | 4.010 | 19.979 | 1.00 | 24.39 | B |
| ATOM | 2784 | CA | HIS | B | 165 | 76.098 | 3.743 | 21.120 | 1.00 | 24.02 | B |
| ATOM | 2785 | CB | HIS | B | 165 | 76.912 | 3.225 | 22.308 | 1.00 | 24.80 | B |
| ATOM | 2786 | CG | HIS | B | 165 | 77.365 | 1.806 | 22.158 | 1.00 | 26.39 | B |
| ATOM | 2787 | CD2 | HIS | B | 165 | 77.176 | 0.911 | 21.161 | 1.00 | 26.51 | B |
| ATOM | 2788 | ND1 | HIS | B | 165 | 78.095 | 1.152 | 23.128 | 1.00 | 26.98 | B |
| ATOM | 2789 | CE1 | HIS | B | 165 | 78.333 | −0.086 | 22.735 | 1.00 | 25.33 | B |
| ATOM | 2790 | NE2 | HIS | B | 165 | 77.786 | −0.259 | 21.545 | 1.00 | 26.97 | B |
| ATOM | 2791 | C | HIS | B | 165 | 75.376 | 5.020 | 21.527 | 1.00 | 23.78 | B |
| ATOM | 2792 | O | HIS | B | 165 | 74.185 | 5.008 | 21.842 | 1.00 | 23.93 | B |
| ATOM | 2793 | N | LEU | B | 166 | 76.108 | 6.126 | 21.521 | 1.00 | 23.16 | B |
| ATOM | 2794 | CA | LEU | B | 166 | 75.531 | 7.408 | 21.895 | 1.00 | 22.75 | B |
| ATOM | 2795 | CB | LEU | B | 166 | 76.631 | 8.470 | 21.976 | 1.00 | 22.64 | B |
| ATOM | 2796 | CG | LEU | B | 166 | 76.197 | 9.870 | 22.418 | 1.00 | 21.89 | B |
| ATOM | 2797 | CD1 | LEU | B | 166 | 75.537 | 10.584 | 21.261 | 1.00 | 25.50 | B |
| ATOM | 2798 | CD2 | LEU | B | 166 | 75.257 | 9.764 | 23.612 | 1.00 | 22.26 | B |
| ATOM | 2799 | C | LEU | B | 166 | 74.453 | 7.825 | 20.900 | 1.00 | 22.78 | B |
| ATOM | 2800 | O | LEU | B | 166 | 73.352 | 8.203 | 21.295 | 1.00 | 21.99 | B |
| ATOM | 2801 | N | ALA | B | 167 | 74.766 | 7.751 | 19.610 | 1.00 | 22.22 | B |
| ATOM | 2802 | CA | ALA | B | 167 | 73.802 | 8.128 | 18.581 | 1.00 | 22.86 | B |
| ATOM | 2803 | CB | ALA | B | 167 | 74.422 | 7.972 | 17.198 | 1.00 | 21.86 | B |
| ATOM | 2804 | C | ALA | B | 167 | 72.548 | 7.267 | 18.699 | 1.00 | 23.08 | B |
| ATOM | 2805 | O | ALA | B | 167 | 71.435 | 7.728 | 18.450 | 1.00 | 24.20 | B |
| ATOM | 2806 | N | LYS | B | 168 | 72.743 | 6.012 | 19.087 | 1.00 | 23.38 | B |
| ATOM | 2807 | CA | LYS | B | 168 | 71.649 | 5.065 | 19.258 | 1.00 | 24.21 | B |
| ATOM | 2808 | CB | LYS | B | 168 | 72.215 | 3.706 | 19.676 | 1.00 | 24.39 | B |
| ATOM | 2809 | CG | LYS | B | 168 | 71.192 | 2.712 | 20.194 | 1.00 | 24.92 | B |
| ATOM | 2810 | CD | LYS | B | 168 | 71.832 | 1.839 | 21.269 | 1.00 | 27.56 | B |
| ATOM | 2811 | CE | LYS | B | 168 | 72.373 | 2.709 | 22.404 | 1.00 | 25.91 | B |
| ATOM | 2812 | NZ | LYS | B | 168 | 73.151 | 1.960 | 23.423 | 1.00 | 29.53 | B |
| ATOM | 2813 | C | LYS | B | 168 | 70.681 | 5.575 | 20.321 | 1.00 | 23.73 | B |
| ATOM | 2814 | O | LYS | B | 168 | 69.471 | 5.630 | 20.098 | 1.00 | 25.71 | B |
| ATOM | 2815 | N | GLU | B | 169 | 71.223 | 5.949 | 21.476 | 1.00 | 23.38 | B |
| ATOM | 2816 | CA | GLU | B | 169 | 70.408 | 6.463 | 22.571 | 1.00 | 22.17 | B |
| ATOM | 2817 | CB | GLU | B | 169 | 71.275 | 6.741 | 23.800 | 1.00 | 22.63 | B |
| ATOM | 2818 | CG | GLU | B | 169 | 71.129 | 5.730 | 24.928 | 1.00 | 26.70 | B |
| ATOM | 2819 | CD | GLU | B | 169 | 69.678 | 5.436 | 25.276 | 1.00 | 26.56 | B |
| ATOM | 2820 | OE1 | GLU | B | 169 | 68.859 | 6.381 | 25.325 | 1.00 | 30.37 | B |
| ATOM | 2821 | OE2 | GLU | B | 169 | 69.356 | 4.252 | 25.509 | 1.00 | 29.65 | B |
| ATOM | 2822 | C | GLU | B | 169 | 69.693 | 7.748 | 22.170 | 1.00 | 20.80 | B |
| ATOM | 2823 | O | GLU | B | 169 | 68.511 | 7.929 | 22.461 | 1.00 | 21.00 | B |
| ATOM | 2824 | N | LEU | B | 170 | 70.414 | 8.642 | 21.502 | 1.00 | 21.11 | B |
| ATOM | 2825 | CA | LEU | B | 170 | 69.840 | 9.911 | 21.081 | 1.00 | 21.11 | B |
| ATOM | 2826 | CB | LEU | B | 170 | 70.929 | 10.822 | 20.514 | 1.00 | 20.36 | B |
| ATOM | 2827 | CG | LEU | B | 170 | 71.924 | 11.313 | 21.567 | 1.00 | 20.03 | B |
| ATOM | 2828 | CD1 | LEU | B | 170 | 72.894 | 12.289 | 20.933 | 1.00 | 19.84 | B |
| ATOM | 2829 | CD2 | LEU | B | 170 | 71.168 | 11.978 | 22.712 | 1.00 | 20.21 | B |

TABLE 1-continued

| ATOM | 2830 | C | LEU | B | 170 | 68.705 | 9.761 | 20.078 | 1.00 | 21.80 | B |
|---|---|---|---|---|---|---|---|---|---|---|---|
| ATOM | 2831 | O | LEU | B | 170 | 68.011 | 10.731 | 19.767 | 1.00 | 22.98 | B |
| ATOM | 2832 | N | GLU | B | 171 | 68.510 | 8.551 | 19.566 | 1.00 | 22.07 | B |
| ATOM | 2833 | CA | GLU | B | 171 | 67.422 | 8.323 | 18.625 | 1.00 | 22.54 | B |
| ATOM | 2834 | CB | GLU | B | 171 | 67.398 | 6.866 | 18.157 | 1.00 | 23.58 | B |
| ATOM | 2835 | CG | GLU | B | 171 | 68.431 | 6.527 | 17.104 | 1.00 | 25.26 | B |
| ATOM | 2836 | CD | GLU | B | 171 | 68.258 | 5.118 | 16.564 | 1.00 | 28.30 | B |
| ATOM | 2837 | OE1 | GLU | B | 171 | 67.140 | 4.790 | 16.112 | 1.00 | 30.60 | B |
| ATOM | 2838 | OE2 | GLU | B | 171 | 69.238 | 4.341 | 16.590 | 1.00 | 31.63 | B |
| ATOM | 2839 | C | GLU | B | 171 | 66.109 | 8.643 | 19.326 | 1.00 | 21.58 | B |
| ATOM | 2840 | O | GLU | B | 171 | 65.120 | 8.996 | 18.686 | 1.00 | 22.06 | B |
| ATOM | 2841 | N | ASP | B | 172 | 66.114 | 8.523 | 20.650 | 1.00 | 21.60 | B |
| ATOM | 2842 | CA | ASP | B | 172 | 64.924 | 8.787 | 21.450 | 1.00 | 20.55 | B |
| ATOM | 2843 | CB | ASP | B | 172 | 64.809 | 7.756 | 22.575 | 1.00 | 23.36 | B |
| ATOM | 2844 | CG | ASP | B | 172 | 64.723 | 6.333 | 22.057 | 1.00 | 27.58 | B |
| ATOM | 2845 | OD1 | ASP | B | 172 | 63.862 | 6.062 | 21.193 | 1.00 | 30.94 | B |
| ATOM | 2846 | OD2 | ASP | B | 172 | 65.514 | 5.484 | 22.521 | 1.00 | 30.56 | B |
| ATOM | 2847 | C | ASP | B | 172 | 64.901 | 10.192 | 22.049 | 1.00 | 19.21 | B |
| ATOM | 2848 | O | ASP | B | 172 | 64.195 | 10.443 | 23.025 | 1.00 | 20.00 | B |
| ATOM | 2849 | N | LEU | B | 173 | 65.664 | 11.103 | 21.453 | 1.00 | 18.97 | B |
| ATOM | 2850 | CA | LEU | B | 173 | 65.733 | 12.481 | 21.927 | 1.00 | 17.67 | B |
| ATOM | 2851 | CB | LEU | B | 173 | 66.581 | 13.322 | 20.974 | 1.00 | 18.94 | B |
| ATOM | 2852 | CG | LEU | B | 173 | 66.725 | 14.793 | 21.363 | 1.00 | 19.48 | B |
| ATOM | 2853 | CD1 | LEU | B | 173 | 67.480 | 14.884 | 22.676 | 1.00 | 20.01 | B |
| ATOM | 2854 | CD2 | LEU | B | 173 | 67.453 | 15.554 | 20.267 | 1.00 | 21.37 | B |
| ATOM | 2855 | C | LEU | B | 173 | 64.364 | 13.143 | 22.076 | 1.00 | 17.35 | B |
| ATOM | 2856 | O | LEU | B | 173 | 64.129 | 13.887 | 23.024 | 1.00 | 17.56 | B |
| ATOM | 2857 | N | ASN | B | 174 | 63.461 | 12.874 | 21.140 | 1.00 | 17.52 | B |
| ATOM | 2858 | CA | ASN | B | 174 | 62.140 | 13.491 | 21.185 | 1.00 | 18.76 | B |
| ATOM | 2859 | CB | ASN | B | 174 | 61.650 | 13.783 | 19.760 | 1.00 | 18.55 | B |
| ATOM | 2860 | CG | ASN | B | 174 | 62.678 | 14.535 | 18.928 | 1.00 | 19.92 | B |
| ATOM | 2861 | OD1 | ASN | B | 174 | 63.334 | 15.457 | 19.411 | 1.00 | 21.88 | B |
| ATOM | 2862 | ND2 | ASN | B | 174 | 62.813 | 14.148 | 17.665 | 1.00 | 24.47 | B |
| ATOM | 2863 | C | ASN | B | 174 | 61.099 | 12.657 | 21.922 | 1.00 | 18.50 | B |
| ATOM | 2864 | O | ASN | B | 174 | 59.901 | 12.928 | 21.830 | 1.00 | 19.21 | B |
| ATOM | 2865 | N | LYS | B | 175 | 61.557 | 11.661 | 22.673 | 1.00 | 19.03 | B |
| ATOM | 2866 | CA | LYS | B | 175 | 60.646 | 10.791 | 23.404 | 1.00 | 19.39 | B |
| ATOM | 2867 | CB | LYS | B | 175 | 60.831 | 9.341 | 22.960 | 1.00 | 21.10 | B |
| ATOM | 2868 | CG | LYS | B | 175 | 60.706 | 9.132 | 21.466 | 1.00 | 22.98 | B |
| ATOM | 2869 | CD | LYS | B | 175 | 60.873 | 7.669 | 21.121 | 1.00 | 24.14 | B |
| ATOM | 2870 | CE | LYS | B | 175 | 60.807 | 7.439 | 19.623 | 1.00 | 25.74 | B |
| ATOM | 2871 | NZ | LYS | B | 175 | 60.977 | 5.994 | 19.308 | 1.00 | 28.38 | B |
| ATOM | 2872 | C | LYS | B | 175 | 60.824 | 10.872 | 24.910 | 1.00 | 17.95 | B |
| ATOM | 2873 | O | LYS | B | 175 | 61.913 | 11.147 | 25.413 | 1.00 | 19.34 | B |
| ATOM | 2874 | N | TRP | B | 176 | 59.735 | 10.613 | 25.622 | 1.00 | 18.25 | B |
| ATOM | 2875 | CA | TRP | B | 176 | 59.715 | 10.639 | 27.077 | 1.00 | 17.79 | B |
| ATOM | 2876 | CB | TRP | B | 176 | 58.267 | 10.496 | 27.553 | 1.00 | 16.96 | B |
| ATOM | 2877 | CG | TRP | B | 176 | 57.983 | 11.021 | 28.929 | 1.00 | 16.64 | B |
| ATOM | 2878 | CD2 | TRP | B | 176 | 58.033 | 12.390 | 29.351 | 1.00 | 16.66 | B |
| ATOM | 2879 | CE2 | TRP | B | 176 | 57.610 | 12.427 | 30.696 | 1.00 | 16.99 | B |
| ATOM | 2880 | CE3 | TRP | B | 176 | 58.392 | 13.588 | 28.721 | 1.00 | 17.54 | B |
| ATOM | 2881 | CD1 | TRP | B | 176 | 57.553 | 10.305 | 30.007 | 1.00 | 17.09 | B |
| ATOM | 2882 | NE1 | TRP | B | 176 | 57.324 | 11.141 | 31.072 | 1.00 | 17.25 | B |
| ATOM | 2883 | CZ2 | TRP | B | 176 | 57.535 | 13.613 | 31.422 | 1.00 | 15.39 | B |
| ATOM | 2884 | CZ3 | TRP | B | 176 | 58.317 | 14.766 | 29.443 | 1.00 | 17.16 | B |
| ATOM | 2885 | CH2 | TRP | B | 176 | 57.891 | 14.770 | 30.780 | 1.00 | 14.84 | B |
| ATOM | 2886 | C | TRP | B | 176 | 60.567 | 9.496 | 27.625 | 1.00 | 18.34 | B |
| ATOM | 2887 | O | TRP | B | 176 | 61.042 | 9.550 | 28.757 | 1.00 | 20.26 | B |
| ATOM | 2888 | N | GLY | B | 177 | 60.778 | 8.474 | 26.801 | 1.00 | 20.21 | B |
| ATOM | 2889 | CA | GLY | B | 177 | 61.549 | 7.323 | 27.233 | 1.00 | 20.19 | B |
| ATOM | 2890 | C | GLY | B | 177 | 63.059 | 7.386 | 27.109 | 1.00 | 20.06 | B |
| ATOM | 2891 | O | GLY | B | 177 | 63.735 | 6.392 | 27.362 | 1.00 | 22.63 | B |
| ATOM | 2892 | N | LEU | B | 178 | 63.603 | 8.530 | 26.710 | 1.00 | 19.92 | B |
| ATOM | 2893 | CA | LEU | B | 178 | 65.051 | 8.643 | 26.591 | 1.00 | 18.61 | B |
| ATOM | 2894 | CB | LEU | B | 178 | 65.445 | 10.059 | 26.161 | 1.00 | 18.69 | B |
| ATOM | 2895 | CG | LEU | B | 178 | 66.950 | 10.318 | 26.027 | 1.00 | 20.59 | B |
| ATOM | 2896 | CD1 | LEU | B | 178 | 67.224 | 11.134 | 24.785 | 1.00 | 21.10 | B |
| ATOM | 2897 | CD2 | LEU | B | 178 | 67.465 | 11.032 | 27.266 | 1.00 | 18.71 | B |
| ATOM | 2898 | C | LEU | B | 178 | 65.695 | 8.311 | 27.932 | 1.00 | 18.99 | B |
| ATOM | 2899 | O | LEU | B | 178 | 65.155 | 8.647 | 28.986 | 1.00 | 20.22 | B |
| ATOM | 2900 | N | ASN | B | 179 | 66.839 | 7.633 | 27.892 | 1.00 | 19.59 | B |
| ATOM | 2901 | CA | ASN | B | 179 | 67.554 | 7.268 | 29.112 | 1.00 | 19.00 | B |
| ATOM | 2902 | CB | ASN | B | 179 | 68.039 | 5.818 | 29.042 | 1.00 | 19.91 | B |
| ATOM | 2903 | CG | ASN | B | 179 | 68.558 | 5.312 | 30.378 | 1.00 | 20.81 | B |
| ATOM | 2904 | OD1 | ASN | B | 179 | 69.379 | 5.960 | 31.022 | 1.00 | 20.85 | B |
| ATOM | 2905 | ND2 | ASN | B | 179 | 68.079 | 4.147 | 30.799 | 1.00 | 22.81 | B |
| ATOM | 2906 | C | ASN | B | 179 | 68.749 | 8.200 | 29.243 | 1.00 | 18.92 | B |
| ATOM | 2907 | O | ASN | B | 179 | 69.782 | 7.994 | 28.605 | 1.00 | 19.10 | B |
| ATOM | 2908 | N | ILE | B | 180 | 68.610 | 9.219 | 30.082 | 1.00 | 18.12 | B |

TABLE 1-continued

| | | | | | | | | | | |
|---|---|---|---|---|---|---|---|---|---|---|
| ATOM | 2909 | CA | ILE | B | 180 | 69.678 | 10.193 | 30.260 | 1.00 | 16.99 | B |
| ATOM | 2910 | CB | ILE | B | 180 | 69.154 | 11.453 | 31.008 | 1.00 | 17.99 | B |
| ATOM | 2911 | CG2 | ILE | B | 180 | 68.982 | 11.156 | 32.483 | 1.00 | 17.57 | B |
| ATOM | 2912 | CG1 | ILE | B | 180 | 70.119 | 12.623 | 30.801 | 1.00 | 17.99 | B |
| ATOM | 2913 | CD1 | ILE | B | 180 | 70.199 | 13.104 | 29.350 | 1.00 | 20.60 | B |
| ATOM | 2914 | C | ILE | B | 180 | 70.888 | 9.603 | 30.989 | 1.00 | 15.91 | B |
| ATOM | 2915 | O | ILE | B | 180 | 72.007 | 10.095 | 30.845 | 1.00 | 17.37 | B |
| ATOM | 2916 | N | PHE | B | 181 | 70.668 | 8.544 | 31.762 | 1.00 | 17.29 | B |
| ATOM | 2917 | CA | PHE | B | 181 | 71.760 | 7.901 | 32.488 | 1.00 | 17.59 | B |
| ATOM | 2918 | CB | PHE | B | 181 | 71.219 | 6.787 | 33.383 | 1.00 | 17.20 | B |
| ATOM | 2919 | CG | PHE | B | 181 | 70.374 | 7.286 | 34.513 | 1.00 | 18.19 | B |
| ATOM | 2920 | CD1 | PHE | B | 181 | 70.959 | 7.796 | 35.660 | 1.00 | 19.64 | B |
| ATOM | 2921 | CD2 | PHE | B | 181 | 68.995 | 7.287 | 34.411 | 1.00 | 20.43 | B |
| ATOM | 2922 | CE1 | PHE | B | 181 | 70.183 | 8.301 | 36.682 | 1.00 | 20.68 | B |
| ATOM | 2923 | CE2 | PHE | B | 181 | 68.212 | 7.790 | 35.430 | 1.00 | 20.48 | B |
| ATOM | 2924 | CZ | PHE | B | 181 | 68.809 | 8.299 | 36.567 | 1.00 | 19.24 | B |
| ATOM | 2925 | C | PHE | B | 181 | 72.763 | 7.326 | 31.498 | 1.00 | 18.24 | B |
| ATOM | 2926 | O | PHE | B | 181 | 73.970 | 7.374 | 31.729 | 1.00 | 20.46 | B |
| ATOM | 2927 | N | ASN | B | 182 | 72.260 | 6.784 | 30.390 | 1.00 | 19.24 | B |
| ATOM | 2928 | CA | ASN | B | 182 | 73.141 | 6.219 | 29.376 | 1.00 | 19.37 | B |
| ATOM | 2929 | CB | ASN | B | 182 | 72.349 | 5.398 | 28.358 | 1.00 | 19.84 | B |
| ATOM | 2930 | CG | ASN | B | 182 | 71.730 | 4.158 | 28.970 | 1.00 | 22.83 | B |
| ATOM | 2931 | OD1 | ASN | B | 182 | 72.260 | 3.596 | 29.930 | 1.00 | 24.83 | B |
| ATOM | 2932 | ND2 | ASN | B | 182 | 70.610 | 3.716 | 28.408 | 1.00 | 24.12 | B |
| ATOM | 2933 | C | ASN | B | 182 | 73.904 | 7.322 | 28.661 | 1.00 | 19.41 | B |
| ATOM | 2934 | O | ASN | B | 182 | 75.088 | 7.180 | 28.380 | 1.00 | 19.81 | B |
| ATOM | 2935 | N | VAL | B | 183 | 73.219 | 8.424 | 28.366 | 1.00 | 19.07 | B |
| ATOM | 2936 | CA | VAL | B | 183 | 73.864 | 9.547 | 27.699 | 1.00 | 18.04 | B |
| ATOM | 2937 | CB | VAL | B | 183 | 72.884 | 10.730 | 27.517 | 1.00 | 18.09 | B |
| ATOM | 2938 | CG1 | VAL | B | 183 | 73.593 | 11.888 | 26.820 | 1.00 | 20.77 | B |
| ATOM | 2939 | CG2 | VAL | B | 183 | 71.664 | 10.282 | 26.712 | 1.00 | 17.63 | B |
| ATOM | 2940 | C | VAL | B | 183 | 75.064 | 10.019 | 28.518 | 1.00 | 17.93 | B |
| ATOM | 2941 | O | VAL | B | 183 | 76.127 | 10.315 | 27.972 | 1.00 | 19.33 | B |
| ATOM | 2942 | N | ALA | B | 184 | 74.894 | 10.084 | 29.835 | 1.00 | 17.20 | B |
| ATOM | 2943 | CA | ALA | B | 184 | 75.966 | 10.521 | 30.723 | 1.00 | 18.84 | B |
| ATOM | 2944 | CB | ALA | B | 184 | 75.456 | 10.602 | 32.159 | 1.00 | 20.06 | B |
| ATOM | 2945 | C | ALA | B | 184 | 77.150 | 9.563 | 30.645 | 1.00 | 19.77 | B |
| ATOM | 2946 | O | ALA | B | 184 | 78.303 | 9.988 | 30.590 | 1.00 | 19.55 | B |
| ATOM | 2947 | N | GLY | B | 185 | 76.857 | 8.268 | 30.631 | 1.00 | 19.84 | B |
| ATOM | 2948 | CA | GLY | B | 185 | 77.917 | 7.279 | 30.560 | 1.00 | 20.49 | B |
| ATOM | 2949 | C | GLY | B | 185 | 78.765 | 7.358 | 29.303 | 1.00 | 21.38 | B |
| ATOM | 2950 | O | GLY | B | 185 | 79.970 | 7.119 | 29.350 | 1.00 | 23.91 | B |
| ATOM | 2951 | N | TYR | B | 186 | 78.146 | 7.692 | 28.176 | 1.00 | 21.11 | B |
| ATOM | 2952 | CA | TYR | B | 186 | 78.873 | 7.785 | 26.915 | 1.00 | 21.18 | B |
| ATOM | 2953 | CB | TYR | B | 186 | 77.938 | 7.508 | 25.734 | 1.00 | 21.47 | B |
| ATOM | 2954 | CG | TYR | B | 186 | 77.361 | 6.113 | 25.709 | 1.00 | 22.97 | B |
| ATOM | 2955 | CD1 | TYR | B | 186 | 78.181 | 4.999 | 25.830 | 1.00 | 24.76 | B |
| ATOM | 2956 | CE1 | TYR | B | 186 | 77.658 | 3.716 | 25.782 | 1.00 | 25.32 | B |
| ATOM | 2957 | CD2 | TYR | B | 186 | 75.997 | 5.909 | 25.539 | 1.00 | 24.05 | B |
| ATOM | 2958 | CE2 | TYR | B | 186 | 75.465 | 4.633 | 25.490 | 1.00 | 24.48 | B |
| ATOM | 2959 | CZ | TYR | B | 186 | 76.300 | 3.541 | 25.612 | 1.00 | 26.33 | B |
| ATOM | 2960 | OH | TYR | B | 186 | 75.774 | 2.270 | 25.561 | 1.00 | 28.76 | B |
| ATOM | 2961 | C | TYR | B | 186 | 79.552 | 9.127 | 26.686 | 1.00 | 21.96 | B |
| ATOM | 2962 | O | TYR | B | 186 | 80.395 | 9.249 | 25.801 | 1.00 | 20.82 | B |
| ATOM | 2963 | N | SER | B | 187 | 79.198 | 10.132 | 27.481 | 1.00 | 20.97 | B |
| ATOM | 2964 | CA | SER | B | 187 | 79.772 | 11.464 | 27.303 | 1.00 | 22.17 | B |
| ATOM | 2965 | CB | SER | B | 187 | 78.647 | 12.491 | 27.171 | 1.00 | 21.61 | B |
| ATOM | 2966 | OG | SER | B | 187 | 77.867 | 12.524 | 28.354 | 1.00 | 21.70 | B |
| ATOM | 2967 | C | SER | B | 187 | 80.741 | 11.933 | 28.387 | 1.00 | 22.18 | B |
| ATOM | 2968 | O | SER | B | 187 | 80.903 | 13.137 | 28.587 | 1.00 | 21.91 | B |
| ATOM | 2969 | N | HIS | B | 188 | 81.385 | 11.002 | 29.082 | 1.00 | 22.65 | B |
| ATOM | 2970 | CA | HIS | B | 188 | 82.332 | 11.380 | 30.129 | 1.00 | 22.66 | B |
| ATOM | 2971 | CB | HIS | B | 188 | 83.542 | 12.087 | 29.501 | 1.00 | 24.04 | B |
| ATOM | 2972 | CG | HIS | B | 188 | 84.709 | 12.240 | 30.427 | 1.00 | 26.08 | B |
| ATOM | 2973 | CD2 | HIS | B | 188 | 85.953 | 11.706 | 30.387 | 1.00 | 26.32 | B |
| ATOM | 2974 | ND1 | HIS | B | 188 | 84.665 | 13.019 | 31.564 | 1.00 | 27.31 | B |
| ATOM | 2975 | CE1 | HIS | B | 188 | 85.830 | 12.957 | 32.184 | 1.00 | 27.44 | B |
| ATOM | 2976 | NE2 | HIS | B | 188 | 86.629 | 12.167 | 31.490 | 1.00 | 27.75 | B |
| ATOM | 2977 | C | HIS | B | 188 | 81.644 | 12.306 | 31.138 | 1.00 | 22.22 | B |
| ATOM | 2978 | O | HIS | B | 188 | 82.181 | 13.344 | 31.521 | 1.00 | 23.24 | B |
| ATOM | 2979 | N | ASN | B | 189 | 80.443 | 11.919 | 31.552 | 1.00 | 21.13 | B |
| ATOM | 2980 | CA | ASN | B | 189 | 79.657 | 12.678 | 32.517 | 1.00 | 20.73 | B |
| ATOM | 2981 | CB | ASN | B | 189 | 80.296 | 12.602 | 33.903 | 1.00 | 22.75 | B |
| ATOM | 2982 | CG | ASN | B | 189 | 79.963 | 11.314 | 34.618 | 1.00 | 24.95 | B |
| ATOM | 2983 | OD1 | ASN | B | 189 | 78.793 | 10.936 | 34.720 | 1.00 | 28.51 | B |
| ATOM | 2984 | ND2 | ASN | B | 189 | 80.984 | 10.633 | 35.123 | 1.00 | 28.38 | B |
| ATOM | 2985 | C | ASN | B | 189 | 79.378 | 14.131 | 32.168 | 1.00 | 20.22 | B |
| ATOM | 2986 | O | ASN | B | 189 | 79.447 | 15.010 | 33.025 | 1.00 | 20.71 | B |
| ATOM | 2987 | N | ARG | B | 190 | 79.064 | 14.379 | 30.901 | 1.00 | 18.69 | B |

TABLE 1-continued

| | | | | | | | | | | |
|---|---|---|---|---|---|---|---|---|---|---|
| ATOM | 2988 | CA | ARG | B | 190 | 78.712 | 15.717 | 30.445 | 1.00 | 17.54 | B |
| ATOM | 2989 | CB | ARG | B | 190 | 79.756 | 16.267 | 29.473 | 1.00 | 18.78 | B |
| ATOM | 2990 | CG | ARG | B | 190 | 81.078 | 16.665 | 30.112 | 1.00 | 20.73 | B |
| ATOM | 2991 | CD | ARG | B | 190 | 80.874 | 17.610 | 31.293 | 1.00 | 20.81 | B |
| ATOM | 2992 | NE | ARG | B | 190 | 82.112 | 18.302 | 31.637 | 1.00 | 21.75 | B |
| ATOM | 2993 | CZ | ARG | B | 190 | 82.312 | 18.981 | 32.761 | 1.00 | 23.62 | B |
| ATOM | 2994 | NH1 | ARG | B | 190 | 81.353 | 19.064 | 33.673 | 1.00 | 23.18 | B |
| ATOM | 2995 | NH2 | ARG | B | 190 | 83.475 | 19.588 | 32.966 | 1.00 | 24.69 | B |
| ATOM | 2996 | C | ARG | B | 190 | 77.372 | 15.587 | 29.731 | 1.00 | 15.48 | B |
| ATOM | 2997 | O | ARG | B | 190 | 77.232 | 15.972 | 28.573 | 1.00 | 15.70 | B |
| ATOM | 2998 | N | PRO | B | 191 | 76.364 | 15.036 | 30.423 | 1.00 | 15.29 | B |
| ATOM | 2999 | CD | PRO | B | 191 | 76.361 | 14.613 | 31.837 | 1.00 | 15.47 | B |
| ATOM | 3000 | CA | PRO | B | 191 | 75.040 | 14.859 | 29.825 | 1.00 | 14.51 | B |
| ATOM | 3001 | CB | PRO | B | 191 | 74.293 | 14.048 | 30.877 | 1.00 | 13.89 | B |
| ATOM | 3002 | CG | PRO | B | 191 | 74.884 | 14.554 | 32.161 | 1.00 | 16.30 | B |
| ATOM | 3003 | C | PRO | B | 191 | 74.309 | 16.143 | 29.481 | 1.00 | 13.52 | B |
| ATOM | 3004 | O | PRO | B | 191 | 73.562 | 16.192 | 28.506 | 1.00 | 15.32 | B |
| ATOM | 3005 | N | LEU | B | 192 | 74.508 | 17.181 | 30.282 | 1.00 | 12.45 | B |
| ATOM | 3006 | CA | LEU | B | 192 | 73.811 | 18.431 | 30.018 | 1.00 | 11.68 | B |
| ATOM | 3007 | CB | LEU | B | 192 | 73.994 | 19.402 | 31.186 | 1.00 | 13.81 | B |
| ATOM | 3008 | CG | LEU | B | 192 | 73.285 | 20.750 | 31.029 | 1.00 | 14.64 | B |
| ATOM | 3009 | CD1 | LEU | B | 192 | 71.785 | 20.551 | 30.853 | 1.00 | 15.86 | B |
| ATOM | 3010 | CD2 | LEU | B | 192 | 73.568 | 21.591 | 32.255 | 1.00 | 13.92 | B |
| ATOM | 3011 | C | LEU | B | 192 | 74.281 | 19.071 | 28.727 | 1.00 | 10.06 | B |
| ATOM | 3012 | O | LEU | B | 192 | 73.462 | 19.467 | 27.902 | 1.00 | 11.66 | B |
| ATOM | 3013 | N | THR | B | 193 | 75.595 | 19.175 | 28.543 | 1.00 | 11.24 | B |
| ATOM | 3014 | CA | THR | B | 193 | 76.122 | 19.775 | 27.321 | 1.00 | 11.61 | B |
| ATOM | 3015 | CB | THR | B | 193 | 77.658 | 19.919 | 27.378 | 1.00 | 12.91 | B |
| ATOM | 3016 | OG1 | THR | B | 193 | 78.012 | 20.820 | 28.435 | 1.00 | 16.19 | B |
| ATOM | 3017 | CG2 | THR | B | 193 | 78.190 | 20.466 | 26.060 | 1.00 | 13.79 | B |
| ATOM | 3018 | C | THR | B | 193 | 75.744 | 18.926 | 26.112 | 1.00 | 12.24 | B |
| ATOM | 3019 | O | THR | B | 193 | 75.334 | 19.449 | 25.071 | 1.00 | 13.82 | B |
| ATOM | 3020 | N | CYS | B | 194 | 75.866 | 17.611 | 26.259 | 1.00 | 12.71 | B |
| ATOM | 3021 | CA | CYS | B | 194 | 75.540 | 16.698 | 25.173 | 1.00 | 13.72 | B |
| ATOM | 3022 | CB | CYS | B | 194 | 75.856 | 15.257 | 25.587 | 1.00 | 16.41 | B |
| ATOM | 3023 | SG | CYS | B | 194 | 75.559 | 14.034 | 24.288 | 1.00 | 21.35 | B |
| ATOM | 3024 | C | CYS | B | 194 | 74.078 | 16.791 | 24.749 | 1.00 | 13.33 | B |
| ATOM | 3025 | O | CYS | B | 194 | 73.777 | 16.995 | 23.571 | 1.00 | 13.97 | B |
| ATOM | 3026 | N | ILE | B | 195 | 73.169 | 16.649 | 25.709 | 1.00 | 13.46 | B |
| ATOM | 3027 | CA | ILE | B | 195 | 71.750 | 16.695 | 25.392 | 1.00 | 13.88 | B |
| ATOM | 3028 | CB | ILE | B | 195 | 70.881 | 16.242 | 26.604 | 1.00 | 15.55 | B |
| ATOM | 3029 | CG2 | ILE | B | 195 | 70.542 | 17.420 | 27.507 | 1.00 | 17.85 | B |
| ATOM | 3030 | CG1 | ILE | B | 195 | 69.585 | 15.610 | 26.092 | 1.00 | 18.57 | B |
| ATOM | 3031 | CD1 | ILE | B | 195 | 69.809 | 14.372 | 25.243 | 1.00 | 19.03 | B |
| ATOM | 3032 | C | ILE | B | 195 | 71.310 | 18.075 | 24.910 | 1.00 | 13.24 | B |
| ATOM | 3033 | O | ILE | B | 195 | 70.450 | 18.176 | 24.036 | 1.00 | 14.65 | B |
| ATOM | 3034 | N | MET | B | 196 | 71.899 | 19.137 | 25.456 | 1.00 | 11.86 | B |
| ATOM | 3035 | CA | MET | B | 196 | 71.522 | 20.482 | 25.031 | 1.00 | 11.58 | B |
| ATOM | 3036 | CB | MET | B | 196 | 72.135 | 21.544 | 25.954 | 1.00 | 11.62 | B |
| ATOM | 3037 | CG | MET | B | 196 | 71.402 | 21.676 | 27.292 | 1.00 | 13.56 | B |
| ATOM | 3038 | SD | MET | B | 196 | 69.755 | 22.411 | 27.117 | 1.00 | 14.36 | B |
| ATOM | 3039 | CE | MET | B | 196 | 70.219 | 24.137 | 26.857 | 1.00 | 12.74 | B |
| ATOM | 3040 | C | MET | B | 196 | 71.959 | 20.717 | 23.594 | 1.00 | 11.56 | B |
| ATOM | 3041 | O | MET | B | 196 | 71.246 | 21.349 | 22.819 | 1.00 | 13.66 | B |
| ATOM | 3042 | N | TYR | B | 197 | 73.131 | 20.204 | 23.232 | 1.00 | 12.14 | B |
| ATOM | 3043 | CA | TYR | B | 197 | 73.597 | 20.370 | 21.865 | 1.00 | 13.19 | B |
| ATOM | 3044 | CB | TYR | B | 197 | 75.029 | 19.845 | 21.704 | 1.00 | 16.11 | B |
| ATOM | 3045 | CG | TYR | B | 197 | 75.664 | 20.235 | 20.384 | 1.00 | 19.16 | B |
| ATOM | 3046 | CD1 | TYR | B | 197 | 76.023 | 21.553 | 20.129 | 1.00 | 19.15 | B |
| ATOM | 3047 | CE1 | TYR | B | 197 | 76.598 | 21.922 | 18.927 | 1.00 | 20.63 | B |
| ATOM | 3048 | CD2 | TYR | B | 197 | 75.895 | 19.291 | 19.396 | 1.00 | 21.73 | B |
| ATOM | 3049 | CE2 | TYR | B | 197 | 76.473 | 19.651 | 18.184 | 1.00 | 22.58 | B |
| ATOM | 3050 | CZ | TYR | B | 197 | 76.821 | 20.969 | 17.961 | 1.00 | 22.00 | B |
| ATOM | 3051 | OH | TYR | B | 197 | 77.394 | 21.338 | 16.766 | 1.00 | 25.29 | B |
| ATOM | 3052 | C | TYR | B | 197 | 72.660 | 19.601 | 20.935 | 1.00 | 12.79 | B |
| ATOM | 3053 | O | TYR | B | 197 | 72.290 | 20.092 | 19.871 | 1.00 | 14.13 | B |
| ATOM | 3054 | N | ALA | B | 198 | 72.268 | 18.397 | 21.337 | 1.00 | 12.79 | B |
| ATOM | 3055 | CA | ALA | B | 198 | 71.370 | 17.589 | 20.511 | 1.00 | 13.49 | B |
| ATOM | 3056 | CB | ALA | B | 198 | 71.183 | 16.202 | 21.137 | 1.00 | 15.13 | B |
| ATOM | 3057 | C | ALA | B | 198 | 70.018 | 18.276 | 20.323 | 1.00 | 13.07 | B |
| ATOM | 3058 | O | ALA | B | 198 | 69.467 | 18.293 | 19.219 | 1.00 | 14.87 | B |
| ATOM | 3059 | N | ILE | B | 199 | 69.490 | 18.848 | 21.400 | 1.00 | 14.66 | B |
| ATOM | 3060 | CA | ILE | B | 199 | 68.208 | 19.544 | 21.360 | 1.00 | 13.61 | B |
| ATOM | 3061 | CB | ILE | B | 199 | 67.773 | 19.963 | 22.781 | 1.00 | 13.70 | B |
| ATOM | 3062 | CG2 | ILE | B | 199 | 66.611 | 20.943 | 22.704 | 1.00 | 14.17 | B |
| ATOM | 3063 | CG1 | ILE | B | 199 | 67.415 | 18.720 | 23.603 | 1.00 | 13.10 | B |
| ATOM | 3064 | CD1 | ILE | B | 199 | 67.159 | 19.016 | 25.079 | 1.00 | 15.18 | B |
| ATOM | 3065 | C | ILE | B | 199 | 68.277 | 20.788 | 20.482 | 1.00 | 14.02 | B |
| ATOM | 3066 | O | ILE | B | 199 | 67.387 | 21.037 | 19.661 | 1.00 | 15.67 | B |

TABLE 1-continued

| ATOM | 3067 | N | PHE | B | 200 | 69.330 | 21.577 | 20.646 | 1.00 | 13.42 | B |
|---|---|---|---|---|---|---|---|---|---|---|---|
| ATOM | 3068 | CA | PHE | B | 200 | 69.457 | 22.782 | 19.839 | 1.00 | 14.38 | B |
| ATOM | 3069 | CB | PHE | B | 200 | 70.610 | 23.638 | 20.355 | 1.00 | 14.15 | B |
| ATOM | 3070 | CG | PHE | B | 200 | 70.203 | 24.591 | 21.444 | 1.00 | 14.10 | B |
| ATOM | 3071 | CD1 | PHE | B | 200 | 69.589 | 24.126 | 22.595 | 1.00 | 14.95 | B |
| ATOM | 3072 | CD2 | PHE | B | 200 | 70.420 | 25.951 | 21.307 | 1.00 | 15.05 | B |
| ATOM | 3073 | CE1 | PHE | B | 200 | 69.196 | 25.003 | 23.592 | 1.00 | 16.14 | B |
| ATOM | 3074 | CE2 | PHE | B | 200 | 70.030 | 26.836 | 22.301 | 1.00 | 16.54 | B |
| ATOM | 3075 | CZ | PHE | B | 200 | 69.418 | 26.361 | 23.443 | 1.00 | 15.94 | B |
| ATOM | 3076 | C | PHE | B | 200 | 69.615 | 22.467 | 18.354 | 1.00 | 15.97 | B |
| ATOM | 3077 | O | PHE | B | 200 | 69.102 | 23.198 | 17.503 | 1.00 | 17.75 | B |
| ATOM | 3078 | N | GLN | B | 201 | 70.316 | 21.382 | 18.041 | 1.00 | 16.45 | B |
| ATOM | 3079 | CA | GLN | B | 201 | 70.492 | 20.975 | 16.648 | 1.00 | 17.39 | B |
| ATOM | 3080 | CB | GLN | B | 201 | 71.487 | 19.814 | 16.556 | 1.00 | 18.95 | B |
| ATOM | 3081 | CG | GLN | B | 201 | 72.933 | 20.219 | 16.764 | 1.00 | 21.95 | B |
| ATOM | 3082 | CD | GLN | B | 201 | 73.575 | 20.741 | 15.496 | 1.00 | 25.50 | B |
| ATOM | 3083 | OE1 | GLN | B | 201 | 73.034 | 21.624 | 14.827 | 1.00 | 27.92 | B |
| ATOM | 3084 | NE2 | GLN | B | 201 | 74.738 | 20.195 | 15.157 | 1.00 | 28.48 | B |
| ATOM | 3085 | C | GLN | B | 201 | 69.142 | 20.530 | 16.092 | 1.00 | 18.10 | B |
| ATOM | 3086 | O | GLN | B | 201 | 68.764 | 20.889 | 14.975 | 1.00 | 18.77 | B |
| ATOM | 3087 | N | GLU | B | 202 | 68.413 | 19.753 | 16.890 | 1.00 | 16.96 | B |
| ATOM | 3088 | CA | GLU | B | 202 | 67.104 | 19.243 | 16.494 | 1.00 | 18.57 | B |
| ATOM | 3089 | CB | GLU | B | 202 | 66.542 | 18.353 | 17.614 | 1.00 | 19.51 | B |
| ATOM | 3090 | CG | GLU | B | 202 | 65.111 | 17.844 | 17.418 | 1.00 | 21.80 | B |
| ATOM | 3091 | CD | GLU | B | 202 | 64.980 | 16.823 | 16.302 | 1.00 | 26.27 | B |
| ATOM | 3092 | OE1 | GLU | B | 202 | 65.882 | 15.971 | 16.157 | 1.00 | 28.81 | B |
| ATOM | 3093 | OE2 | GLU | B | 202 | 63.959 | 16.859 | 15.579 | 1.00 | 28.69 | B |
| ATOM | 3094 | C | GLU | B | 202 | 66.125 | 20.373 | 16.189 | 1.00 | 18.30 | B |
| ATOM | 3095 | O | GLU | B | 202 | 65.340 | 20.285 | 15.243 | 1.00 | 19.71 | B |
| ATOM | 3096 | N | ARG | B | 203 | 66.172 | 21.435 | 16.987 | 1.00 | 17.58 | B |
| ATOM | 3097 | CA | ARG | B | 203 | 65.267 | 22.565 | 16.803 | 1.00 | 16.55 | B |
| ATOM | 3098 | CB | ARG | B | 203 | 64.840 | 23.111 | 18.167 | 1.00 | 16.38 | B |
| ATOM | 3099 | CG | ARG | B | 203 | 63.924 | 22.170 | 18.935 | 1.00 | 17.22 | B |
| ATOM | 3100 | CD | ARG | B | 203 | 63.510 | 22.753 | 20.277 | 1.00 | 15.58 | B |
| ATOM | 3101 | NE | ARG | B | 203 | 62.545 | 21.897 | 20.955 | 1.00 | 14.62 | B |
| ATOM | 3102 | CZ | ARG | B | 203 | 61.255 | 21.817 | 20.635 | 1.00 | 15.74 | B |
| ATOM | 3103 | NH1 | ARG | B | 203 | 60.763 | 22.555 | 19.648 | 1.00 | 18.09 | B |
| ATOM | 3104 | NH2 | ARG | B | 203 | 60.459 | 20.976 | 21.282 | 1.00 | 16.38 | B |
| ATOM | 3105 | C | ARG | B | 203 | 65.834 | 23.694 | 15.946 | 1.00 | 15.84 | B |
| ATOM | 3106 | O | ARG | B | 203 | 65.185 | 24.723 | 15.759 | 1.00 | 16.66 | B |
| ATOM | 3107 | N | ASP | B | 204 | 67.040 | 23.488 | 15.424 | 1.00 | 16.75 | B |
| ATOM | 3108 | CA | ASP | B | 204 | 67.716 | 24.466 | 14.577 | 1.00 | 16.33 | B |
| ATOM | 3109 | CB | ASP | B | 204 | 66.920 | 24.691 | 13.288 | 1.00 | 18.57 | B |
| ATOM | 3110 | CG | ASP | B | 204 | 67.782 | 25.213 | 12.158 | 1.00 | 22.21 | B |
| ATOM | 3111 | OD1 | ASP | B | 204 | 67.233 | 25.841 | 11.228 | 1.00 | 27.95 | B |
| ATOM | 3112 | OD2 | ASP | B | 204 | 69.009 | 24.984 | 12.193 | 1.00 | 25.64 | B |
| ATOM | 3113 | C | ASP | B | 204 | 67.903 | 25.800 | 15.294 | 1.00 | 17.15 | B |
| ATOM | 3114 | O | ASP | B | 204 | 67.976 | 26.856 | 14.661 | 1.00 | 16.89 | B |
| ATOM | 3115 | N | LEU | B | 205 | 67.995 | 25.749 | 16.618 | 1.00 | 15.64 | B |
| ATOM | 3116 | CA | LEU | B | 205 | 68.159 | 26.963 | 17.408 | 1.00 | 16.23 | B |
| ATOM | 3117 | CB | LEU | B | 205 | 67.936 | 26.656 | 18.891 | 1.00 | 15.88 | B |
| ATOM | 3118 | CG | LEU | B | 205 | 66.484 | 26.412 | 19.312 | 1.00 | 16.04 | B |
| ATOM | 3119 | CD1 | LEU | B | 205 | 66.455 | 25.906 | 20.749 | 1.00 | 17.66 | B |
| ATOM | 3120 | CD2 | LEU | B | 205 | 65.680 | 27.705 | 19.170 | 1.00 | 17.91 | B |
| ATOM | 3121 | C | LEU | B | 205 | 69.499 | 27.671 | 17.226 | 1.00 | 14.59 | B |
| ATOM | 3122 | O | LEU | B | 205 | 69.571 | 28.895 | 17.356 | 1.00 | 14.90 | B |
| ATOM | 3123 | N | LEU | B | 206 | 70.561 | 26.924 | 16.932 | 1.00 | 15.05 | B |
| ATOM | 3124 | CA | LEU | B | 206 | 71.859 | 27.563 | 16.743 | 1.00 | 13.63 | B |
| ATOM | 3125 | CB | LEU | B | 206 | 72.971 | 26.524 | 16.569 | 1.00 | 14.65 | B |
| ATOM | 3126 | CG | LEU | B | 206 | 73.267 | 25.588 | 17.741 | 1.00 | 17.27 | B |
| ATOM | 3127 | CD1 | LEU | B | 206 | 74.465 | 24.720 | 17.381 | 1.00 | 18.31 | B |
| ATOM | 3128 | CD2 | LEU | B | 206 | 73.557 | 26.388 | 18.999 | 1.00 | 18.18 | B |
| ATOM | 3129 | C | LEU | B | 206 | 71.823 | 28.477 | 15.521 | 1.00 | 14.30 | B |
| ATOM | 3130 | O | LEU | B | 206 | 72.265 | 29.622 | 15.576 | 1.00 | 15.32 | B |
| ATOM | 3131 | N | LYS | B | 207 | 71.280 | 27.974 | 14.419 | 1.00 | 15.44 | B |
| ATOM | 3132 | CA | LYS | B | 207 | 71.196 | 28.765 | 13.194 | 1.00 | 17.00 | B |
| ATOM | 3133 | CB | LYS | B | 207 | 70.775 | 27.880 | 12.021 | 1.00 | 20.27 | B |
| ATOM | 3134 | CG | LYS | B | 207 | 71.628 | 26.645 | 11.807 | 1.00 | 22.82 | B |
| ATOM | 3135 | CD | LYS | B | 207 | 73.060 | 26.994 | 11.474 | 1.00 | 23.24 | B |
| ATOM | 3136 | CE | LYS | B | 207 | 73.611 | 26.057 | 10.401 | 1.00 | 25.60 | B |
| ATOM | 3137 | NZ | LYS | B | 207 | 73.358 | 24.623 | 10.717 | 1.00 | 27.60 | B |
| ATOM | 3138 | C | LYS | B | 207 | 70.192 | 29.907 | 13.327 | 1.00 | 15.29 | B |
| ATOM | 3139 | O | LYS | B | 207 | 70.448 | 31.028 | 12.897 | 1.00 | 16.50 | B |
| ATOM | 3140 | N | THR | B | 208 | 69.043 | 29.613 | 13.922 | 1.00 | 15.28 | B |
| ATOM | 3141 | CA | THR | B | 208 | 68.001 | 30.618 | 14.090 | 1.00 | 15.47 | B |
| ATOM | 3142 | CB | THR | B | 208 | 66.784 | 30.030 | 14.838 | 1.00 | 14.55 | B |
| ATOM | 3143 | OG1 | THR | B | 208 | 66.194 | 28.997 | 14.041 | 1.00 | 17.60 | B |
| ATOM | 3144 | CG2 | THR | B | 208 | 65.742 | 31.108 | 15.114 | 1.00 | 17.27 | B |
| ATOM | 3145 | C | THR | B | 208 | 68.477 | 31.864 | 14.829 | 1.00 | 15.11 | B |

TABLE 1-continued

| ATOM | 3146 | O | THR | B | 208 | 68.185 | 32.989 | 14.418 | 1.00 | 17.42 | B |
|---|---|---|---|---|---|---|---|---|---|---|---|
| ATOM | 3147 | N | PHE | B | 209 | 69.218 | 31.665 | 15.916 | 1.00 | 15.59 | B |
| ATOM | 3148 | CA | PHE | B | 209 | 69.704 | 32.783 | 16.715 | 1.00 | 15.09 | B |
| ATOM | 3149 | CB | PHE | B | 209 | 69.387 | 32.526 | 18.189 | 1.00 | 15.53 | B |
| ATOM | 3150 | CG | PHE | B | 209 | 67.923 | 32.562 | 18.491 | 1.00 | 13.57 | B |
| ATOM | 3151 | CD1 | PHE | B | 209 | 67.234 | 33.762 | 18.480 | 1.00 | 15.65 | B |
| ATOM | 3152 | CD2 | PHE | B | 209 | 67.221 | 31.394 | 18.732 | 1.00 | 14.27 | B |
| ATOM | 3153 | CE1 | PHE | B | 209 | 65.871 | 33.799 | 18.702 | 1.00 | 16.18 | B |
| ATOM | 3154 | CE2 | PHE | B | 209 | 65.856 | 31.423 | 18.953 | 1.00 | 14.95 | B |
| ATOM | 3155 | CZ | PHE | B | 209 | 65.181 | 32.629 | 18.938 | 1.00 | 16.57 | B |
| ATOM | 3156 | C | PHE | B | 209 | 71.188 | 33.084 | 16.545 | 1.00 | 14.79 | B |
| ATOM | 3157 | O | PHE | B | 209 | 71.777 | 33.805 | 17.348 | 1.00 | 14.76 | B |
| ATOM | 3158 | N | ARG | B | 210 | 71.776 | 32.531 | 15.490 | 1.00 | 14.65 | B |
| ATOM | 3159 | CA | ARG | B | 210 | 73.186 | 32.724 | 15.175 | 1.00 | 15.09 | B |
| ATOM | 3160 | CB | ARG | B | 210 | 73.413 | 34.124 | 14.598 | 1.00 | 16.89 | B |
| ATOM | 3161 | CG | ARG | B | 210 | 72.658 | 34.367 | 13.295 | 1.00 | 21.59 | B |
| ATOM | 3162 | CD | ARG | B | 210 | 73.165 | 33.451 | 12.184 | 1.00 | 23.89 | B |
| ATOM | 3163 | NE | ARG | B | 210 | 72.395 | 33.593 | 10.950 | 1.00 | 27.05 | B |
| ATOM | 3164 | CZ | ARG | B | 210 | 72.737 | 33.043 | 9.788 | 1.00 | 26.76 | B |
| ATOM | 3165 | NH1 | ARG | B | 210 | 73.840 | 32.314 | 9.697 | 1.00 | 28.04 | B |
| ATOM | 3166 | NH2 | ARG | B | 210 | 71.977 | 33.222 | 8.715 | 1.00 | 26.92 | B |
| ATOM | 3167 | C | ARG | B | 210 | 74.117 | 32.491 | 16.356 | 1.00 | 14.01 | B |
| ATOM | 3168 | O | ARG | B | 210 | 74.960 | 33.328 | 16.672 | 1.00 | 16.29 | B |
| ATOM | 3169 | N | ILE | B | 211 | 73.948 | 31.345 | 17.002 | 1.00 | 14.62 | B |
| ATOM | 3170 | CA | ILE | B | 211 | 74.794 | 30.961 | 18.121 | 1.00 | 13.55 | B |
| ATOM | 3171 | CB | ILE | B | 211 | 74.008 | 30.211 | 19.204 | 1.00 | 13.69 | B |
| ATOM | 3172 | CG2 | ILE | B | 211 | 74.885 | 30.028 | 20.436 | 1.00 | 12.94 | B |
| ATOM | 3173 | CG1 | ILE | B | 211 | 72.746 | 30.991 | 19.577 | 1.00 | 15.10 | B |
| ATOM | 3174 | CD1 | ILE | B | 211 | 71.828 | 30.235 | 20.510 | 1.00 | 14.24 | B |
| ATOM | 3175 | C | ILE | B | 211 | 75.797 | 29.988 | 17.515 | 1.00 | 13.29 | B |
| ATOM | 3176 | O | ILE | B | 211 | 75.413 | 28.912 | 17.057 | 1.00 | 14.84 | B |
| ATOM | 3177 | N | SER | B | 212 | 77.071 | 30.366 | 17.485 | 1.00 | 12.75 | B |
| ATOM | 3178 | CA | SER | B | 212 | 78.079 | 29.476 | 16.930 | 1.00 | 13.87 | B |
| ATOM | 3179 | CB | SER | B | 212 | 79.441 | 30.170 | 16.894 | 1.00 | 17.08 | B |
| ATOM | 3180 | OG | SER | B | 212 | 79.395 | 31.331 | 16.084 | 1.00 | 25.78 | B |
| ATOM | 3181 | C | SER | B | 212 | 78.162 | 28.223 | 17.791 | 1.00 | 14.02 | B |
| ATOM | 3182 | O | SER | B | 212 | 77.945 | 28.279 | 19.004 | 1.00 | 13.97 | B |
| ATOM | 3183 | N | SER | B | 213 | 78.467 | 27.086 | 17.173 | 1.00 | 14.06 | B |
| ATOM | 3184 | CA | SER | B | 213 | 78.587 | 25.860 | 17.944 | 1.00 | 14.77 | B |
| ATOM | 3185 | CB | SER | B | 213 | 78.908 | 24.677 | 17.034 | 1.00 | 14.51 | B |
| ATOM | 3186 | OG | SER | B | 213 | 77.763 | 24.305 | 16.287 | 1.00 | 19.92 | B |
| ATOM | 3187 | C | SER | B | 213 | 79.675 | 26.017 | 18.998 | 1.00 | 13.32 | B |
| ATOM | 3188 | O | SER | B | 213 | 79.532 | 25.523 | 20.116 | 1.00 | 13.15 | B |
| ATOM | 3189 | N | ASP | B | 214 | 80.759 | 26.709 | 18.652 | 1.00 | 13.09 | B |
| ATOM | 3190 | CA | ASP | B | 214 | 81.844 | 26.903 | 19.607 | 1.00 | 13.63 | B |
| ATOM | 3191 | CB | ASP | B | 214 | 83.012 | 27.666 | 18.978 | 1.00 | 16.13 | B |
| ATOM | 3192 | CG | ASP | B | 214 | 84.123 | 27.934 | 19.975 | 1.00 | 18.90 | B |
| ATOM | 3193 | OD1 | ASP | B | 214 | 84.774 | 26.964 | 20.420 | 1.00 | 22.48 | B |
| ATOM | 3194 | OD2 | ASP | B | 214 | 84.336 | 29.113 | 20.323 | 1.00 | 22.40 | B |
| ATOM | 3195 | C | ASP | B | 214 | 81.371 | 27.662 | 20.835 | 1.00 | 12.29 | B |
| ATOM | 3196 | O | ASP | B | 214 | 81.677 | 27.271 | 21.961 | 1.00 | 14.25 | B |
| ATOM | 3197 | N | THR | B | 215 | 80.621 | 28.742 | 20.622 | 1.00 | 11.07 | B |
| ATOM | 3198 | CA | THR | B | 215 | 80.125 | 29.542 | 21.741 | 1.00 | 11.42 | B |
| ATOM | 3199 | CB | THR | B | 215 | 79.372 | 30.786 | 21.249 | 1.00 | 11.51 | B |
| ATOM | 3200 | OG1 | THR | B | 215 | 80.233 | 31.547 | 20.400 | 1.00 | 14.55 | B |
| ATOM | 3201 | CG2 | THR | B | 215 | 78.936 | 31.656 | 22.424 | 1.00 | 13.98 | B |
| ATOM | 3202 | C | THR | B | 215 | 79.168 | 28.728 | 22.584 | 1.00 | 9.02 | B |
| ATOM | 3203 | O | THR | B | 215 | 79.232 | 28.741 | 23.810 | 1.00 | 10.90 | B |
| ATOM | 3204 | N | PHE | B | 216 | 78.267 | 28.014 | 21.923 | 1.00 | 10.45 | B |
| ATOM | 3205 | CA | PHE | B | 216 | 77.296 | 27.213 | 22.647 | 1.00 | 8.91 | B |
| ATOM | 3206 | CB | PHE | B | 216 | 76.332 | 26.533 | 21.681 | 1.00 | 12.68 | B |
| ATOM | 3207 | CG | PHE | B | 216 | 75.185 | 25.860 | 22.366 | 1.00 | 16.02 | B |
| ATOM | 3208 | CD1 | PHE | B | 216 | 74.181 | 26.614 | 22.953 | 1.00 | 17.00 | B |
| ATOM | 3209 | CD2 | PHE | B | 216 | 75.121 | 24.483 | 22.452 | 1.00 | 17.44 | B |
| ATOM | 3210 | CE1 | PHE | B | 216 | 73.131 | 26.004 | 23.617 | 1.00 | 18.37 | B |
| ATOM | 3211 | CE2 | PHE | B | 216 | 74.072 | 23.868 | 23.115 | 1.00 | 17.00 | B |
| ATOM | 3212 | CZ | PHE | B | 216 | 73.081 | 24.630 | 23.695 | 1.00 | 15.22 | B |
| ATOM | 3213 | C | PHE | B | 216 | 77.965 | 26.149 | 23.505 | 1.00 | 9.66 | B |
| ATOM | 3214 | O | PHE | B | 216 | 77.617 | 25.970 | 24.667 | 1.00 | 11.34 | B |
| ATOM | 3215 | N | ILE | B | 217 | 78.927 | 25.438 | 22.926 | 1.00 | 9.00 | B |
| ATOM | 3216 | CA | ILE | B | 217 | 79.620 | 24.397 | 23.663 | 1.00 | 9.44 | B |
| ATOM | 3217 | CB | ILE | B | 217 | 80.524 | 23.569 | 22.730 | 1.00 | 12.02 | B |
| ATOM | 3218 | CG2 | ILE | B | 217 | 81.324 | 22.551 | 23.542 | 1.00 | 13.95 | B |
| ATOM | 3219 | CG1 | ILE | B | 217 | 79.653 | 22.843 | 21.699 | 1.00 | 14.93 | B |
| ATOM | 3220 | CD1 | ILE | B | 217 | 80.434 | 22.217 | 20.552 | 1.00 | 17.33 | B |
| ATOM | 3221 | C | ILE | B | 217 | 80.444 | 24.976 | 24.811 | 1.00 | 9.65 | B |
| ATOM | 3222 | O | ILE | B | 217 | 80.468 | 24.410 | 25.909 | 1.00 | 11.30 | B |
| ATOM | 3223 | N | THR | B | 218 | 81.096 | 26.109 | 24.575 | 1.00 | 9.00 | B |
| ATOM | 3224 | CA | THR | B | 218 | 81.902 | 26.728 | 25.617 | 1.00 | 9.70 | B |

TABLE 1-continued

| | | | | | | | | | | |
|---|---|---|---|---|---|---|---|---|---|---|
| ATOM | 3225 | CB | THR | B | 218 | 82.638 | 27.971 | 25.082 | 1.00 | 10.90 | B |
| ATOM | 3226 | OG1 | THR | B | 218 | 83.504 | 27.581 | 24.010 | 1.00 | 13.11 | B |
| ATOM | 3227 | CG2 | THR | B | 218 | 83.460 | 28.624 | 26.183 | 1.00 | 12.91 | B |
| ATOM | 3228 | C | THR | B | 218 | 81.018 | 27.121 | 26.794 | 1.00 | 7.92 | B |
| ATOM | 3229 | O | THR | B | 218 | 81.350 | 26.844 | 27.950 | 1.00 | 9.92 | B |
| ATOM | 3230 | N | TYR | B | 219 | 79.885 | 27.754 | 26.508 | 1.00 | 8.85 | B |
| ATOM | 3231 | CA | TYR | B | 219 | 78.969 | 28.153 | 27.575 | 1.00 | 7.47 | B |
| ATOM | 3232 | CB | TYR | B | 219 | 77.785 | 28.973 | 27.034 | 1.00 | 8.03 | B |
| ATOM | 3233 | CG | TYR | B | 219 | 76.761 | 29.259 | 28.120 | 1.00 | 9.13 | B |
| ATOM | 3234 | CD1 | TYR | B | 219 | 76.955 | 30.288 | 29.035 | 1.00 | 11.36 | B |
| ATOM | 3235 | CE1 | TYR | B | 219 | 76.068 | 30.488 | 30.091 | 1.00 | 11.08 | B |
| ATOM | 3236 | CD2 | TYR | B | 219 | 75.647 | 28.438 | 28.287 | 1.00 | 11.17 | B |
| ATOM | 3237 | CE2 | TYR | B | 219 | 74.759 | 28.627 | 29.337 | 1.00 | 10.37 | B |
| ATOM | 3238 | CZ | TYR | B | 219 | 74.975 | 29.652 | 30.235 | 1.00 | 9.68 | B |
| ATOM | 3239 | OH | TYR | B | 219 | 74.103 | 29.831 | 31.286 | 1.00 | 10.38 | B |
| ATOM | 3240 | C | TYR | B | 219 | 78.408 | 26.935 | 28.299 | 1.00 | 8.12 | B |
| ATOM | 3241 | O | TYR | B | 219 | 78.413 | 26.883 | 29.526 | 1.00 | 11.39 | B |
| ATOM | 3242 | N | MET | B | 220 | 77.923 | 25.952 | 27.547 | 1.00 | 8.60 | B |
| ATOM | 3243 | CA | MET | B | 220 | 77.342 | 24.771 | 28.178 | 1.00 | 9.02 | B |
| ATOM | 3244 | CB | MET | B | 220 | 76.727 | 23.847 | 27.123 | 1.00 | 10.53 | B |
| ATOM | 3245 | CG | MET | B | 220 | 75.423 | 24.381 | 26.515 | 1.00 | 14.14 | B |
| ATOM | 3246 | SD | MET | B | 220 | 74.151 | 24.829 | 27.748 | 1.00 | 13.79 | B |
| ATOM | 3247 | CE | MET | B | 220 | 74.167 | 23.361 | 28.781 | 1.00 | 18.84 | B |
| ATOM | 3248 | C | MET | B | 220 | 78.327 | 24.004 | 29.050 | 1.00 | 8.93 | B |
| ATOM | 3249 | O | MET | B | 220 | 77.965 | 23.557 | 30.135 | 1.00 | 10.27 | B |
| ATOM | 3250 | N | MET | B | 221 | 79.569 | 23.869 | 28.587 | 1.00 | 10.22 | B |
| ATOM | 3251 | CA | MET | B | 221 | 80.592 | 23.170 | 29.364 | 1.00 | 10.08 | B |
| ATOM | 3252 | CB | MET | B | 221 | 81.863 | 22.989 | 28.528 | 1.00 | 12.14 | B |
| ATOM | 3253 | CG | MET | B | 221 | 81.739 | 21.903 | 27.468 | 1.00 | 14.95 | B |
| ATOM | 3254 | SD | MET | B | 221 | 81.567 | 20.264 | 28.205 | 1.00 | 19.05 | B |
| ATOM | 3255 | CE | MET | B | 221 | 81.815 | 19.218 | 26.735 | 1.00 | 19.61 | B |
| ATOM | 3256 | C | MET | B | 221 | 80.905 | 23.955 | 30.636 | 1.00 | 9.04 | B |
| ATOM | 3257 | O | MET | B | 221 | 81.157 | 23.369 | 31.693 | 1.00 | 12.49 | B |
| ATOM | 3258 | N | THR | B | 222 | 80.889 | 25.279 | 30.529 | 1.00 | 9.15 | B |
| ATOM | 3259 | CA | THR | B | 222 | 81.141 | 26.143 | 31.673 | 1.00 | 9.03 | B |
| ATOM | 3260 | CB | THR | B | 222 | 81.285 | 27.617 | 31.211 | 1.00 | 8.98 | B |
| ATOM | 3261 | OG1 | THR | B | 222 | 82.397 | 27.723 | 30.312 | 1.00 | 11.02 | B |
| ATOM | 3262 | CG2 | THR | B | 222 | 81.515 | 28.538 | 32.396 | 1.00 | 10.19 | B |
| ATOM | 3263 | C | THR | B | 222 | 79.972 | 25.999 | 32.659 | 1.00 | 9.26 | B |
| ATOM | 3264 | O | THR | B | 222 | 80.174 | 25.817 | 33.864 | 1.00 | 9.87 | B |
| ATOM | 3265 | N | LEU | B | 223 | 78.748 | 26.055 | 32.141 | 1.00 | 10.23 | B |
| ATOM | 3266 | CA | LEU | B | 223 | 77.565 | 25.913 | 32.987 | 1.00 | 8.74 | B |
| ATOM | 3267 | CB | LEU | B | 223 | 76.286 | 26.047 | 32.149 | 1.00 | 9.44 | B |
| ATOM | 3268 | CG | LEU | B | 223 | 74.963 | 25.876 | 32.908 | 1.00 | 10.37 | B |
| ATOM | 3269 | CD1 | LEU | B | 223 | 74.679 | 27.117 | 33.738 | 1.00 | 13.51 | B |
| ATOM | 3270 | CD2 | LEU | B | 223 | 73.823 | 25.633 | 31.922 | 1.00 | 10.73 | B |
| ATOM | 3271 | C | LEU | B | 223 | 77.570 | 24.553 | 33.676 | 1.00 | 9.68 | B |
| ATOM | 3272 | O | LEU | B | 223 | 77.361 | 24.464 | 34.890 | 1.00 | 10.59 | B |
| ATOM | 3273 | N | GLU | B | 224 | 77.820 | 23.498 | 32.904 | 1.00 | 11.60 | B |
| ATOM | 3274 | CA | GLU | B | 224 | 77.821 | 22.153 | 33.461 | 1.00 | 12.62 | B |
| ATOM | 3275 | CB | GLU | B | 224 | 78.054 | 21.109 | 32.362 | 1.00 | 14.95 | B |
| ATOM | 3276 | CG | GLU | B | 224 | 77.913 | 19.669 | 32.858 | 1.00 | 15.75 | B |
| ATOM | 3277 | CD | GLU | B | 224 | 77.398 | 18.713 | 31.794 | 1.00 | 16.89 | B |
| ATOM | 3278 | OE1 | GLU | B | 224 | 77.634 | 18.964 | 30.592 | 1.00 | 15.87 | B |
| ATOM | 3279 | OE2 | GLU | B | 224 | 76.763 | 17.698 | 32.160 | 1.00 | 14.54 | B |
| ATOM | 3280 | C | GLU | B | 224 | 78.856 | 22.008 | 34.567 | 1.00 | 12.74 | B |
| ATOM | 3281 | O | GLU | B | 224 | 78.618 | 21.316 | 35.558 | 1.00 | 15.06 | B |
| ATOM | 3282 | N | ASP | B | 225 | 79.998 | 22.673 | 34.409 | 1.00 | 12.14 | B |
| ATOM | 3283 | CA | ASP | B | 225 | 81.048 | 22.609 | 35.421 | 1.00 | 14.65 | B |
| ATOM | 3284 | CB | ASP | B | 225 | 82.337 | 23.261 | 34.921 | 1.00 | 18.41 | B |
| ATOM | 3285 | CG | ASP | B | 225 | 83.400 | 22.247 | 34.575 | 1.00 | 23.04 | B |
| ATOM | 3286 | OD1 | ASP | B | 225 | 83.409 | 21.168 | 35.205 | 1.00 | 24.72 | B |
| ATOM | 3287 | OD2 | ASP | B | 225 | 84.234 | 22.536 | 33.691 | 1.00 | 24.18 | B |
| ATOM | 3288 | C | ASP | B | 225 | 80.639 | 23.298 | 36.709 | 1.00 | 13.84 | B |
| ATOM | 3289 | O | ASP | B | 225 | 81.281 | 23.109 | 37.744 | 1.00 | 15.90 | B |
| ATOM | 3290 | N | HIS | B | 226 | 79.587 | 24.109 | 36.650 | 1.00 | 12.52 | B |
| ATOM | 3291 | CA | HIS | B | 226 | 79.121 | 24.803 | 37.844 | 1.00 | 12.52 | B |
| ATOM | 3292 | CB | HIS | B | 226 | 78.644 | 26.214 | 37.501 | 1.00 | 13.34 | B |
| ATOM | 3293 | CG | HIS | B | 226 | 79.770 | 27.188 | 37.348 | 1.00 | 16.73 | B |
| ATOM | 3294 | CD2 | HIS | B | 226 | 80.178 | 28.211 | 38.135 | 1.00 | 18.20 | B |
| ATOM | 3295 | ND1 | HIS | B | 226 | 80.683 | 27.108 | 36.318 | 1.00 | 18.23 | B |
| ATOM | 3296 | CE1 | HIS | B | 226 | 81.609 | 28.037 | 36.481 | 1.00 | 19.31 | B |
| ATOM | 3297 | NE2 | HIS | B | 226 | 81.327 | 28.719 | 37.576 | 1.00 | 20.80 | B |
| ATOM | 3298 | C | HIS | B | 226 | 78.066 | 24.034 | 38.620 | 1.00 | 11.11 | B |
| ATOM | 3299 | O | HIS | B | 226 | 77.548 | 24.512 | 39.631 | 1.00 | 13.59 | B |
| ATOM | 3300 | N | TYR | B | 227 | 77.731 | 22.848 | 38.124 | 1.00 | 11.83 | B |
| ATOM | 3301 | CA | TYR | B | 227 | 76.823 | 21.965 | 38.844 | 1.00 | 11.89 | B |
| ATOM | 3302 | CB | TYR | B | 227 | 76.035 | 21.059 | 37.892 | 1.00 | 11.76 | B |
| ATOM | 3303 | CG | TYR | B | 227 | 74.735 | 21.667 | 37.415 | 1.00 | 7.86 | B |

TABLE 1-continued

| ATOM | 3304 | CD1 | TYR | B | 227 | 74.689 | 22.487 | 36.289 | 1.00 | 11.31 | B |
|------|------|-----|-----|---|-----|--------|--------|--------|------|-------|---|
| ATOM | 3305 | CE1 | TYR | B | 227 | 73.498 | 23.060 | 35.869 | 1.00 | 11.23 | B |
| ATOM | 3306 | CD2 | TYR | B | 227 | 73.552 | 21.439 | 38.106 | 1.00 | 7.51 | B |
| ATOM | 3307 | CE2 | TYR | B | 227 | 72.357 | 22.011 | 37.693 | 1.00 | 9.51 | B |
| ATOM | 3308 | CZ | TYR | B | 227 | 72.339 | 22.821 | 36.572 | 1.00 | 9.15 | B |
| ATOM | 3309 | OH | TYR | B | 227 | 71.151 | 23.395 | 36.154 | 1.00 | 11.04 | B |
| ATOM | 3310 | C | TYR | B | 227 | 77.800 | 21.129 | 39.679 | 1.00 | 14.10 | B |
| ATOM | 3311 | O | TYR | B | 227 | 78.899 | 20.827 | 39.220 | 1.00 | 16.43 | B |
| ATOM | 3312 | N | HIS | B | 228 | 77.421 | 20.777 | 40.903 | 1.00 | 14.97 | B |
| ATOM | 3313 | CA | HIS | B | 228 | 78.304 | 19.994 | 41.769 | 1.00 | 16.33 | B |
| ATOM | 3314 | CB | HIS | B | 228 | 77.999 | 20.269 | 43.244 | 1.00 | 18.10 | B |
| ATOM | 3315 | CG | HIS | B | 228 | 78.094 | 21.711 | 43.635 | 1.00 | 21.87 | B |
| ATOM | 3316 | CD2 | HIS | B | 228 | 78.179 | 22.837 | 42.889 | 1.00 | 23.53 | B |
| ATOM | 3317 | ND1 | HIS | B | 228 | 78.089 | 22.122 | 44.951 | 1.00 | 24.44 | B |
| ATOM | 3318 | CE1 | HIS | B | 228 | 78.169 | 23.439 | 44.999 | 1.00 | 24.66 | B |
| ATOM | 3319 | NE2 | HIS | B | 228 | 78.225 | 23.898 | 43.761 | 1.00 | 24.22 | B |
| ATOM | 3320 | C | HIS | B | 228 | 78.131 | 18.503 | 41.513 | 1.00 | 15.58 | B |
| ATOM | 3321 | O | HIS | B | 228 | 77.074 | 17.945 | 41.802 | 1.00 | 17.45 | B |
| ATOM | 3322 | N | SER | B | 229 | 79.165 | 17.845 | 41.000 | 1.00 | 17.16 | B |
| ATOM | 3323 | CA | SER | B | 229 | 79.055 | 16.421 | 40.713 | 1.00 | 18.30 | B |
| ATOM | 3324 | CB | SER | B | 229 | 80.221 | 15.964 | 39.826 | 1.00 | 19.82 | B |
| ATOM | 3325 | OG | SER | B | 229 | 81.474 | 16.185 | 40.448 | 1.00 | 23.03 | B |
| ATOM | 3326 | C | SER | B | 229 | 78.983 | 15.565 | 41.978 | 1.00 | 19.26 | B |
| ATOM | 3327 | O | SER | B | 229 | 78.559 | 14.412 | 41.928 | 1.00 | 22.10 | B |
| ATOM | 3328 | N | ASP | B | 230 | 79.379 | 16.141 | 43.110 | 1.00 | 18.39 | B |
| ATOM | 3329 | CA | ASP | B | 230 | 79.360 | 15.436 | 44.390 | 1.00 | 20.29 | B |
| ATOM | 3330 | CB | ASP | B | 230 | 80.375 | 16.068 | 45.351 | 1.00 | 23.12 | B |
| ATOM | 3331 | CG | ASP | B | 230 | 80.154 | 17.559 | 45.536 | 1.00 | 26.32 | B |
| ATOM | 3332 | OD1 | ASP | B | 230 | 80.282 | 18.307 | 44.545 | 1.00 | 29.20 | B |
| ATOM | 3333 | OD2 | ASP | B | 230 | 79.851 | 17.986 | 46.673 | 1.00 | 31.52 | B |
| ATOM | 3334 | C | ASP | B | 230 | 77.973 | 15.432 | 45.032 | 1.00 | 19.11 | B |
| ATOM | 3335 | O | ASP | B | 230 | 77.712 | 14.657 | 45.956 | 1.00 | 21.35 | B |
| ATOM | 3336 | N | VAL | B | 231 | 77.086 | 16.303 | 44.552 | 1.00 | 16.59 | B |
| ATOM | 3337 | CA | VAL | B | 231 | 75.723 | 16.367 | 45.075 | 1.00 | 15.74 | B |
| ATOM | 3338 | CB | VAL | B | 231 | 75.062 | 17.715 | 44.713 | 1.00 | 16.21 | B |
| ATOM | 3339 | CG1 | VAL | B | 231 | 73.601 | 17.717 | 45.111 | 1.00 | 16.50 | B |
| ATOM | 3340 | CG2 | VAL | B | 231 | 75.793 | 18.846 | 45.432 | 1.00 | 16.71 | B |
| ATOM | 3341 | C | VAL | B | 231 | 74.981 | 15.198 | 44.424 | 1.00 | 15.11 | B |
| ATOM | 3342 | O | VAL | B | 231 | 75.015 | 15.037 | 43.212 | 1.00 | 16.08 | B |
| ATOM | 3343 | N | ALA | B | 232 | 74.316 | 14.383 | 45.237 | 1.00 | 14.78 | B |
| ATOM | 3344 | CA | ALA | B | 232 | 73.630 | 13.190 | 44.745 | 1.00 | 14.78 | B |
| ATOM | 3345 | CB | ALA | B | 232 | 73.053 | 12.410 | 45.925 | 1.00 | 17.07 | B |
| ATOM | 3346 | C | ALA | B | 232 | 72.551 | 13.349 | 43.673 | 1.00 | 12.72 | B |
| ATOM | 3347 | O | ALA | B | 232 | 72.533 | 12.598 | 42.694 | 1.00 | 14.91 | B |
| ATOM | 3348 | N | TYR | B | 233 | 71.653 | 14.308 | 43.852 | 1.00 | 13.10 | B |
| ATOM | 3349 | CA | TYR | B | 233 | 70.571 | 14.493 | 42.892 | 1.00 | 10.73 | B |
| ATOM | 3350 | CB | TYR | B | 233 | 69.228 | 14.513 | 43.632 | 1.00 | 12.23 | B |
| ATOM | 3351 | CG | TYR | B | 233 | 68.015 | 14.694 | 42.744 | 1.00 | 12.27 | B |
| ATOM | 3352 | CD1 | TYR | B | 233 | 67.359 | 13.598 | 42.200 | 1.00 | 13.49 | B |
| ATOM | 3353 | CE1 | TYR | B | 233 | 66.239 | 13.756 | 41.407 | 1.00 | 13.18 | B |
| ATOM | 3354 | CD2 | TYR | B | 233 | 67.519 | 15.959 | 42.464 | 1.00 | 11.96 | B |
| ATOM | 3355 | CE2 | TYR | B | 233 | 66.398 | 16.129 | 41.666 | 1.00 | 12.76 | B |
| ATOM | 3356 | CZ | TYR | B | 233 | 65.763 | 15.023 | 41.145 | 1.00 | 11.14 | B |
| ATOM | 3357 | OH | TYR | B | 233 | 64.639 | 15.179 | 40.371 | 1.00 | 12.48 | B |
| ATOM | 3358 | C | TYR | B | 233 | 70.698 | 15.752 | 42.038 | 1.00 | 10.96 | B |
| ATOM | 3359 | O | TYR | B | 233 | 70.626 | 15.681 | 40.813 | 1.00 | 12.54 | B |
| ATOM | 3360 | N | HIS | B | 234 | 70.885 | 16.895 | 42.687 | 1.00 | 11.58 | B |
| ATOM | 3361 | CA | HIS | B | 234 | 70.981 | 18.160 | 41.972 | 1.00 | 11.81 | B |
| ATOM | 3362 | CB | HIS | B | 234 | 70.614 | 19.311 | 42.909 | 1.00 | 12.44 | B |
| ATOM | 3363 | CG | HIS | B | 234 | 69.167 | 19.330 | 43.286 | 1.00 | 11.54 | B |
| ATOM | 3364 | CD2 | HIS | B | 234 | 68.069 | 19.672 | 42.570 | 1.00 | 10.42 | B |
| ATOM | 3365 | ND1 | HIS | B | 234 | 68.710 | 18.933 | 44.523 | 1.00 | 13.88 | B |
| ATOM | 3366 | CE1 | HIS | B | 234 | 67.392 | 19.029 | 44.554 | 1.00 | 12.19 | B |
| ATOM | 3367 | NE2 | HIS | B | 234 | 66.979 | 19.474 | 43.381 | 1.00 | 12.46 | B |
| ATOM | 3368 | C | HIS | B | 234 | 72.306 | 18.446 | 41.279 | 1.00 | 12.18 | B |
| ATOM | 3369 | O | HIS | B | 234 | 72.941 | 19.473 | 41.521 | 1.00 | 14.48 | B |
| ATOM | 3370 | N | ASN | B | 235 | 72.710 | 17.525 | 40.412 | 1.00 | 11.91 | B |
| ATOM | 3371 | CA | ASN | B | 235 | 73.933 | 17.665 | 39.634 | 1.00 | 11.80 | B |
| ATOM | 3372 | CB | ASN | B | 235 | 74.814 | 16.423 | 39.795 | 1.00 | 13.03 | B |
| ATOM | 3373 | CG | ASN | B | 235 | 74.045 | 15.137 | 39.605 | 1.00 | 15.08 | B |
| ATOM | 3374 | OD1 | ASN | B | 235 | 73.464 | 14.910 | 38.550 | 1.00 | 16.15 | B |
| ATOM | 3375 | ND2 | ASN | B | 235 | 74.033 | 14.288 | 40.632 | 1.00 | 14.23 | B |
| ATOM | 3376 | C | ASN | B | 235 | 73.499 | 17.859 | 38.179 | 1.00 | 11.93 | B |
| ATOM | 3377 | O | ASN | B | 235 | 72.302 | 17.952 | 37.907 | 1.00 | 12.50 | B |
| ATOM | 3378 | N | SER | B | 236 | 74.447 | 17.914 | 37.247 | 1.00 | 11.66 | B |
| ATOM | 3379 | CA | SER | B | 236 | 74.076 | 18.159 | 35.851 | 1.00 | 10.65 | B |
| ATOM | 3380 | CB | SER | B | 236 | 75.323 | 18.424 | 35.000 | 1.00 | 11.10 | B |
| ATOM | 3381 | OG | SER | B | 236 | 76.040 | 17.240 | 34.710 | 1.00 | 15.22 | B |
| ATOM | 3382 | C | SER | B | 236 | 73.197 | 17.101 | 35.177 | 1.00 | 10.03 | B |

TABLE 1-continued

| | | | | | | | | | | |
|---|---|---|---|---|---|---|---|---|---|---|
| ATOM | 3383 | O | SER | B | 236 | 72.570 | 17.390 | 34.155 | 1.00 | 11.40 | B |
| ATOM | 3384 | N | LEU | B | 237 | 73.136 | 15.892 | 35.731 | 1.00 | 10.91 | B |
| ATOM | 3385 | CA | LEU | B | 237 | 72.288 | 14.860 | 35.136 | 1.00 | 12.41 | B |
| ATOM | 3386 | CB | LEU | B | 237 | 72.541 | 13.491 | 35.783 | 1.00 | 16.51 | B |
| ATOM | 3387 | CG | LEU | B | 237 | 71.830 | 12.326 | 35.078 | 1.00 | 19.49 | B |
| ATOM | 3388 | CD1 | LEU | B | 237 | 72.397 | 12.165 | 33.674 | 1.00 | 20.59 | B |
| ATOM | 3389 | CD2 | LEU | B | 237 | 72.012 | 11.035 | 35.868 | 1.00 | 23.14 | B |
| ATOM | 3390 | C | LEU | B | 237 | 70.823 | 15.260 | 35.313 | 1.00 | 11.44 | B |
| ATOM | 3391 | O | LEU | B | 237 | 69.999 | 15.046 | 34.418 | 1.00 | 13.26 | B |
| ATOM | 3392 | N | HIS | B | 238 | 70.490 | 15.834 | 36.468 | 1.00 | 11.16 | B |
| ATOM | 3393 | CA | HIS | B | 238 | 69.119 | 16.278 | 36.716 | 1.00 | 11.09 | B |
| ATOM | 3394 | CB | HIS | B | 238 | 68.958 | 16.735 | 38.173 | 1.00 | 10.62 | B |
| ATOM | 3395 | CG | HIS | B | 238 | 67.696 | 17.500 | 38.436 | 1.00 | 10.96 | B |
| ATOM | 3396 | CD2 | HIS | B | 238 | 67.503 | 18.777 | 38.840 | 1.00 | 12.08 | B |
| ATOM | 3397 | ND1 | HIS | B | 238 | 66.438 | 16.958 | 38.270 | 1.00 | 9.61 | B |
| ATOM | 3398 | CE1 | HIS | B | 238 | 65.527 | 17.869 | 38.558 | 1.00 | 11.19 | B |
| ATOM | 3399 | NE2 | HIS | B | 238 | 66.147 | 18.982 | 38.905 | 1.00 | 11.36 | B |
| ATOM | 3400 | C | HIS | B | 238 | 68.770 | 17.417 | 35.759 | 1.00 | 9.75 | B |
| ATOM | 3401 | O | HIS | B | 238 | 67.681 | 17.447 | 35.188 | 1.00 | 12.78 | B |
| ATOM | 3402 | N | ALA | B | 239 | 69.698 | 18.353 | 35.580 | 1.00 | 9.80 | B |
| ATOM | 3403 | CA | ALA | B | 239 | 69.462 | 19.473 | 34.670 | 1.00 | 8.47 | B |
| ATOM | 3404 | CB | ALA | B | 239 | 70.647 | 20.453 | 34.713 | 1.00 | 9.70 | B |
| ATOM | 3405 | C | ALA | B | 239 | 69.253 | 18.958 | 33.241 | 1.00 | 8.87 | B |
| ATOM | 3406 | O | ALA | B | 239 | 68.380 | 19.441 | 32.526 | 1.00 | 10.68 | B |
| ATOM | 3407 | N | ALA | B | 240 | 70.062 | 17.988 | 32.831 | 1.00 | 7.68 | B |
| ATOM | 3408 | CA | ALA | B | 240 | 69.939 | 17.416 | 31.487 | 1.00 | 8.79 | B |
| ATOM | 3409 | CB | ALA | B | 240 | 71.031 | 16.393 | 31.262 | 1.00 | 9.79 | B |
| ATOM | 3410 | C | ALA | B | 240 | 68.570 | 16.762 | 31.336 | 1.00 | 9.08 | B |
| ATOM | 3411 | O | ALA | B | 240 | 67.928 | 16.861 | 30.288 | 1.00 | 10.69 | B |
| ATOM | 3412 | N | ASP | B | 241 | 68.128 | 16.096 | 32.397 | 1.00 | 9.20 | B |
| ATOM | 3413 | CA | ASP | B | 241 | 66.837 | 15.428 | 32.402 | 1.00 | 10.07 | B |
| ATOM | 3414 | CB | ASP | B | 241 | 66.688 | 14.630 | 33.696 | 1.00 | 11.27 | B |
| ATOM | 3415 | CG | ASP | B | 241 | 65.346 | 13.950 | 33.807 | 1.00 | 14.16 | B |
| ATOM | 3416 | OD1 | ASP | B | 241 | 64.935 | 13.286 | 32.829 | 1.00 | 15.44 | B |
| ATOM | 3417 | OD2 | ASP | B | 241 | 64.710 | 14.077 | 34.872 | 1.00 | 16.88 | B |
| ATOM | 3418 | C | ASP | B | 241 | 65.693 | 16.432 | 32.259 | 1.00 | 9.75 | B |
| ATOM | 3419 | O | ASP | B | 241 | 64.779 | 16.235 | 31.451 | 1.00 | 12.81 | B |
| ATOM | 3420 | N | VAL | B | 242 | 65.741 | 17.509 | 33.035 | 1.00 | 10.84 | B |
| ATOM | 3421 | CA | VAL | B | 242 | 64.698 | 18.526 | 32.969 | 1.00 | 9.51 | B |
| ATOM | 3422 | CB | VAL | B | 242 | 64.868 | 19.557 | 34.114 | 1.00 | 10.60 | B |
| ATOM | 3423 | CG1 | VAL | B | 242 | 63.853 | 20.689 | 33.979 | 1.00 | 11.72 | B |
| ATOM | 3424 | CG2 | VAL | B | 242 | 64.683 | 18.852 | 35.454 | 1.00 | 12.98 | B |
| ATOM | 3425 | C | VAL | B | 242 | 64.689 | 19.210 | 31.594 | 1.00 | 9.02 | B |
| ATOM | 3426 | O | VAL | B | 242 | 63.619 | 19.481 | 31.037 | 1.00 | 12.09 | B |
| ATOM | 3427 | N | ALA | B | 243 | 65.869 | 19.479 | 31.043 | 1.00 | 8.32 | B |
| ATOM | 3428 | CA | ALA | B | 243 | 65.959 | 20.101 | 29.723 | 1.00 | 8.47 | B |
| ATOM | 3429 | CB | ALA | B | 243 | 67.405 | 20.430 | 29.388 | 1.00 | 11.98 | B |
| ATOM | 3430 | C | ALA | B | 243 | 65.368 | 19.203 | 28.638 | 1.00 | 10.40 | B |
| ATOM | 3431 | O | ALA | B | 243 | 64.612 | 19.671 | 27.786 | 1.00 | 11.59 | B |
| ATOM | 3432 | N | GLN | B | 244 | 65.714 | 17.917 | 28.665 | 1.00 | 11.84 | B |
| ATOM | 3433 | CA | GLN | B | 244 | 65.205 | 16.981 | 27.665 | 1.00 | 11.95 | B |
| ATOM | 3434 | CB | GLN | B | 244 | 65.939 | 15.641 | 27.794 | 1.00 | 13.74 | B |
| ATOM | 3435 | CG | GLN | B | 244 | 65.692 | 14.656 | 26.655 | 1.00 | 14.26 | B |
| ATOM | 3436 | CD | GLN | B | 244 | 64.497 | 13.765 | 26.899 | 1.00 | 14.50 | B |
| ATOM | 3437 | OE1 | GLN | B | 244 | 64.195 | 13.415 | 28.038 | 1.00 | 15.47 | B |
| ATOM | 3438 | NE2 | GLN | B | 244 | 63.822 | 13.367 | 25.823 | 1.00 | 14.81 | B |
| ATOM | 3439 | C | GLN | B | 244 | 63.692 | 16.790 | 27.812 | 1.00 | 10.88 | B |
| ATOM | 3440 | O | GLN | B | 244 | 62.971 | 16.686 | 26.816 | 1.00 | 13.33 | B |
| ATOM | 3441 | N | SER | B | 245 | 63.212 | 16.768 | 29.052 | 1.00 | 11.10 | B |
| ATOM | 3442 | CA | SER | B | 245 | 61.787 | 16.605 | 29.314 | 1.00 | 10.90 | B |
| ATOM | 3443 | CB | SER | B | 245 | 61.532 | 16.407 | 30.809 | 1.00 | 11.12 | B |
| ATOM | 3444 | OG | SER | B | 245 | 62.145 | 15.218 | 31.271 | 1.00 | 13.86 | B |
| ATOM | 3445 | C | SER | B | 245 | 61.027 | 17.828 | 28.830 | 1.00 | 11.68 | B |
| ATOM | 3446 | O | SER | B | 245 | 59.923 | 17.715 | 28.297 | 1.00 | 13.98 | B |
| ATOM | 3447 | N | THR | B | 246 | 61.619 | 19.001 | 29.031 | 1.00 | 12.22 | B |
| ATOM | 3448 | CA | THR | B | 246 | 61.006 | 20.245 | 28.593 | 1.00 | 12.39 | B |
| ATOM | 3449 | CB | THR | B | 246 | 61.841 | 21.454 | 29.065 | 1.00 | 12.58 | B |
| ATOM | 3450 | OG1 | THR | B | 246 | 61.779 | 21.536 | 30.493 | 1.00 | 13.59 | B |
| ATOM | 3451 | CG2 | THR | B | 246 | 61.307 | 22.744 | 28.471 | 1.00 | 14.72 | B |
| ATOM | 3452 | C | THR | B | 246 | 60.923 | 20.223 | 27.066 | 1.00 | 12.97 | B |
| ATOM | 3453 | O | THR | B | 246 | 59.929 | 20.654 | 26.478 | 1.00 | 14.54 | B |
| ATOM | 3454 | N | HIS | B | 247 | 61.971 | 19.703 | 26.437 | 1.00 | 11.92 | B |
| ATOM | 3455 | CA | HIS | B | 247 | 62.027 | 19.593 | 24.984 | 1.00 | 12.49 | B |
| ATOM | 3456 | CB | HIS | B | 247 | 63.370 | 18.977 | 24.576 | 1.00 | 13.03 | B |
| ATOM | 3457 | CG | HIS | B | 247 | 63.425 | 18.521 | 23.153 | 1.00 | 13.55 | B |
| ATOM | 3458 | CD2 | HIS | B | 247 | 63.563 | 17.283 | 22.624 | 1.00 | 13.60 | B |
| ATOM | 3459 | ND1 | HIS | B | 247 | 63.324 | 19.386 | 22.085 | 1.00 | 14.08 | B |
| ATOM | 3460 | CE1 | HIS | B | 247 | 63.398 | 18.700 | 20.958 | 1.00 | 14.38 | B |
| ATOM | 3461 | NE2 | HIS | B | 247 | 63.541 | 17.421 | 21.257 | 1.00 | 15.75 | B |

TABLE 1-continued

| ATOM | 3462 | C | HIS | B | 247 | 60.862 | 18.741 | 24.479 | 1.00 | 13.03 | B |
|---|---|---|---|---|---|---|---|---|---|---|---|
| ATOM | 3463 | O | HIS | B | 247 | 60.205 | 19.087 | 23.497 | 1.00 | 13.30 | B |
| ATOM | 3464 | N | VAL | B | 248 | 60.592 | 17.633 | 25.159 | 1.00 | 12.52 | B |
| ATOM | 3465 | CA | VAL | B | 248 | 59.490 | 16.771 | 24.748 | 1.00 | 12.82 | B |
| ATOM | 3466 | CB | VAL | B | 248 | 59.519 | 15.432 | 25.512 | 1.00 | 14.39 | B |
| ATOM | 3467 | CG1 | VAL | B | 248 | 58.285 | 14.613 | 25.174 | 1.00 | 17.07 | B |
| ATOM | 3468 | CG2 | VAL | B | 248 | 60.774 | 14.658 | 25.139 | 1.00 | 14.54 | B |
| ATOM | 3469 | C | VAL | B | 248 | 58.139 | 17.455 | 24.974 | 1.00 | 12.57 | B |
| ATOM | 3470 | O | VAL | B | 248 | 57.266 | 17.429 | 24.105 | 1.00 | 14.95 | B |
| ATOM | 3471 | N | LEU | B | 249 | 57.963 | 18.074 | 26.136 | 1.00 | 14.53 | B |
| ATOM | 3472 | CA | LEU | B | 249 | 56.703 | 18.752 | 26.437 | 1.00 | 15.02 | B |
| ATOM | 3473 | CB | LEU | B | 249 | 56.728 | 19.314 | 27.861 | 1.00 | 17.50 | B |
| ATOM | 3474 | CG | LEU | B | 249 | 56.742 | 18.255 | 28.969 | 1.00 | 16.08 | B |
| ATOM | 3475 | CD1 | LEU | B | 249 | 56.855 | 18.931 | 30.321 | 1.00 | 17.15 | B |
| ATOM | 3476 | CD2 | LEU | B | 249 | 55.480 | 17.410 | 28.900 | 1.00 | 19.85 | B |
| ATOM | 3477 | C | LEU | B | 249 | 56.387 | 19.867 | 25.439 | 1.00 | 15.17 | B |
| ATOM | 3478 | O | LEU | B | 249 | 55.228 | 20.085 | 25.090 | 1.00 | 17.12 | B |
| ATOM | 3479 | N | LEU | B | 250 | 57.416 | 20.571 | 24.980 | 1.00 | 16.33 | B |
| ATOM | 3480 | CA | LEU | B | 250 | 57.218 | 21.649 | 24.017 | 1.00 | 16.67 | B |
| ATOM | 3481 | CB | LEU | B | 250 | 58.530 | 22.400 | 23.780 | 1.00 | 17.65 | B |
| ATOM | 3482 | CG | LEU | B | 250 | 58.951 | 23.425 | 24.832 | 1.00 | 18.41 | B |
| ATOM | 3483 | CD1 | LEU | B | 250 | 60.403 | 23.821 | 24.611 | 1.00 | 19.35 | B |
| ATOM | 3484 | CD2 | LEU | B | 250 | 58.040 | 24.644 | 24.750 | 1.00 | 18.88 | B |
| ATOM | 3485 | C | LEU | B | 250 | 56.696 | 21.126 | 22.681 | 1.00 | 17.21 | B |
| ATOM | 3486 | O | LEU | B | 250 | 56.080 | 21.873 | 21.920 | 1.00 | 19.20 | B |
| ATOM | 3487 | N | SER | B | 251 | 56.932 | 19.847 | 22.403 | 1.00 | 18.15 | B |
| ATOM | 3488 | CA | SER | B | 251 | 56.499 | 19.253 | 21.142 | 1.00 | 19.87 | B |
| ATOM | 3489 | CB | SER | B | 251 | 57.522 | 18.215 | 20.669 | 1.00 | 21.48 | B |
| ATOM | 3490 | OG | SER | B | 251 | 58.756 | 18.826 | 20.328 | 1.00 | 27.10 | B |
| ATOM | 3491 | C | SER | B | 251 | 55.112 | 18.618 | 21.162 | 1.00 | 20.31 | B |
| ATOM | 3492 | O | SER | B | 251 | 54.655 | 18.117 | 20.135 | 1.00 | 20.88 | B |
| ATOM | 3493 | N | THR | B | 252 | 54.445 | 18.639 | 22.312 | 1.00 | 19.49 | B |
| ATOM | 3494 | CA | THR | B | 252 | 53.108 | 18.058 | 22.421 | 1.00 | 20.53 | B |
| ATOM | 3495 | CB | THR | B | 252 | 52.479 | 18.349 | 23.797 | 1.00 | 21.36 | B |
| ATOM | 3496 | OG1 | THR | B | 252 | 52.292 | 19.760 | 23.949 | 1.00 | 26.25 | B |
| ATOM | 3497 | CG2 | THR | B | 252 | 53.382 | 17.846 | 24.907 | 1.00 | 22.53 | B |
| ATOM | 3498 | C | THR | B | 252 | 52.217 | 18.659 | 21.336 | 1.00 | 20.15 | B |
| ATOM | 3499 | O | THR | B | 252 | 52.245 | 19.864 | 21.099 | 1.00 | 20.80 | B |
| ATOM | 3500 | N | PRO | B | 253 | 51.418 | 17.823 | 20.658 | 1.00 | 21.10 | B |
| ATOM | 3501 | CD | PRO | B | 253 | 51.260 | 16.373 | 20.863 | 1.00 | 21.07 | B |
| ATOM | 3502 | CA | PRO | B | 253 | 50.526 | 18.295 | 19.593 | 1.00 | 20.74 | B |
| ATOM | 3503 | CB | PRO | B | 253 | 49.643 | 17.079 | 19.329 | 1.00 | 21.86 | B |
| ATOM | 3504 | CG | PRO | B | 253 | 50.575 | 15.945 | 19.581 | 1.00 | 21.58 | B |
| ATOM | 3505 | C | PRO | B | 253 | 49.712 | 19.535 | 19.957 | 1.00 | 21.53 | B |
| ATOM | 3506 | O | PRO | B | 253 | 49.552 | 20.443 | 19.142 | 1.00 | 22.03 | B |
| ATOM | 3507 | N | ALA | B | 254 | 49.210 | 19.573 | 21.185 | 1.00 | 20.69 | B |
| ATOM | 3508 | CA | ALA | B | 254 | 48.402 | 20.693 | 21.650 | 1.00 | 21.13 | B |
| ATOM | 3509 | CB | ALA | B | 254 | 47.831 | 20.379 | 23.030 | 1.00 | 21.75 | B |
| ATOM | 3510 | C | ALA | B | 254 | 49.152 | 22.024 | 21.688 | 1.00 | 21.24 | B |
| ATOM | 3511 | O | ALA | B | 254 | 48.536 | 23.087 | 21.714 | 1.00 | 22.02 | B |
| ATOM | 3512 | N | LEU | B | 255 | 50.479 | 21.972 | 21.694 | 1.00 | 21.50 | B |
| ATOM | 3513 | CA | LEU | B | 255 | 51.264 | 23.200 | 21.736 | 1.00 | 20.88 | B |
| ATOM | 3514 | CB | LEU | B | 255 | 52.281 | 23.125 | 22.874 | 1.00 | 19.80 | B |
| ATOM | 3515 | CG | LEU | B | 255 | 51.654 | 22.886 | 24.248 | 1.00 | 19.98 | B |
| ATOM | 3516 | CD1 | LEU | B | 255 | 52.740 | 22.640 | 25.277 | 1.00 | 22.12 | B |
| ATOM | 3517 | CD2 | LEU | B | 255 | 50.806 | 24.091 | 24.633 | 1.00 | 17.78 | B |
| ATOM | 3518 | C | LEU | B | 255 | 51.981 | 23.449 | 20.417 | 1.00 | 22.61 | B |
| ATOM | 3519 | O | LEU | B | 255 | 52.959 | 24.195 | 20.362 | 1.00 | 23.66 | B |
| ATOM | 3520 | N | ASP | B | 256 | 51.476 | 22.828 | 19.357 | 1.00 | 23.28 | B |
| ATOM | 3521 | CA | ASP | B | 256 | 52.057 | 22.956 | 18.025 | 1.00 | 24.28 | B |
| ATOM | 3522 | CB | ASP | B | 256 | 51.319 | 22.022 | 17.059 | 1.00 | 25.93 | B |
| ATOM | 3523 | CG | ASP | B | 256 | 51.996 | 21.918 | 15.710 | 1.00 | 27.96 | B |
| ATOM | 3524 | OD1 | ASP | B | 256 | 53.190 | 21.546 | 15.668 | 1.00 | 31.17 | B |
| ATOM | 3525 | OD2 | ASP | B | 256 | 51.333 | 22.201 | 14.689 | 1.00 | 31.35 | B |
| ATOM | 3526 | C | ASP | B | 256 | 51.991 | 24.397 | 17.520 | 1.00 | 24.79 | B |
| ATOM | 3527 | O | ASP | B | 256 | 50.913 | 24.985 | 17.426 | 1.00 | 24.58 | B |
| ATOM | 3528 | N | ALA | B | 257 | 53.155 | 24.958 | 17.205 | 1.00 | 24.40 | B |
| ATOM | 3529 | CA | ALA | B | 257 | 53.261 | 26.325 | 16.699 | 1.00 | 25.31 | B |
| ATOM | 3530 | CB | ALA | B | 257 | 52.530 | 26.442 | 15.356 | 1.00 | 25.56 | B |
| ATOM | 3531 | C | ALA | B | 257 | 52.737 | 27.380 | 17.670 | 1.00 | 25.05 | B |
| ATOM | 3532 | O | ALA | B | 257 | 52.572 | 28.543 | 17.297 | 1.00 | 27.16 | B |
| ATOM | 3533 | N | VAL | B | 258 | 52.488 | 26.981 | 18.914 | 1.00 | 23.37 | B |
| ATOM | 3534 | CA | VAL | B | 258 | 51.980 | 27.904 | 19.924 | 1.00 | 21.82 | B |
| ATOM | 3535 | CB | VAL | B | 258 | 51.441 | 27.148 | 21.156 | 1.00 | 22.18 | B |
| ATOM | 3536 | CG1 | VAL | B | 258 | 51.170 | 28.127 | 22.288 | 1.00 | 22.06 | B |
| ATOM | 3537 | CG2 | VAL | B | 258 | 50.172 | 26.394 | 20.791 | 1.00 | 21.84 | B |
| ATOM | 3538 | C | VAL | B | 258 | 53.032 | 28.891 | 20.415 | 1.00 | 20.88 | B |
| ATOM | 3539 | O | VAL | B | 258 | 52.732 | 30.056 | 20.656 | 1.00 | 22.53 | B |
| ATOM | 3540 | N | PHE | B | 259 | 54.265 | 28.421 | 20.570 | 1.00 | 19.20 | B |

TABLE 1-continued

| ATOM | 3541 | CA | PHE | B | 259 | 55.337 | 29.278 | 21.060 | 1.00 | 18.21 | B |
|---|---|---|---|---|---|---|---|---|---|---|---|
| ATOM | 3542 | CB | PHE | B | 259 | 56.087 | 28.561 | 22.184 | 1.00 | 18.51 | B |
| ATOM | 3543 | CG | PHE | B | 259 | 55.224 | 28.221 | 23.361 | 1.00 | 16.16 | B |
| ATOM | 3544 | CD1 | PHE | B | 259 | 54.723 | 29.220 | 24.179 | 1.00 | 17.57 | B |
| ATOM | 3545 | CD2 | PHE | B | 259 | 54.893 | 26.905 | 23.639 | 1.00 | 16.17 | B |
| ATOM | 3546 | CE1 | PHE | B | 259 | 53.906 | 28.913 | 25.252 | 1.00 | 18.74 | B |
| ATOM | 3547 | CE2 | PHE | B | 259 | 54.077 | 26.592 | 24.710 | 1.00 | 16.38 | B |
| ATOM | 3548 | CZ | PHE | B | 259 | 53.583 | 27.595 | 25.517 | 1.00 | 20.21 | B |
| ATOM | 3549 | C | PHE | B | 259 | 56.325 | 29.704 | 19.983 | 1.00 | 17.88 | B |
| ATOM | 3550 | O | PHE | B | 259 | 56.598 | 28.961 | 19.049 | 1.00 | 19.56 | B |
| ATOM | 3551 | N | THR | B | 260 | 56.858 | 30.912 | 20.128 | 1.00 | 17.99 | B |
| ATOM | 3552 | CA | THR | B | 260 | 57.837 | 31.442 | 19.185 | 1.00 | 16.82 | B |
| ATOM | 3553 | CB | THR | B | 260 | 58.041 | 32.949 | 19.376 | 1.00 | 16.92 | B |
| ATOM | 3554 | OG1 | THR | B | 260 | 58.521 | 33.188 | 20.703 | 1.00 | 18.74 | B |
| ATOM | 3555 | CG2 | THR | B | 260 | 56.739 | 33.705 | 19.160 | 1.00 | 19.40 | B |
| ATOM | 3556 | C | THR | B | 260 | 59.184 | 30.771 | 19.440 | 1.00 | 15.28 | B |
| ATOM | 3557 | O | THR | B | 260 | 59.373 | 30.124 | 20.467 | 1.00 | 15.52 | B |
| ATOM | 3558 | N | ASP | B | 261 | 60.123 | 30.936 | 18.515 | 1.00 | 15.66 | B |
| ATOM | 3559 | CA | ASP | B | 261 | 61.444 | 30.341 | 18.693 | 1.00 | 14.73 | B |
| ATOM | 3560 | CB | ASP | B | 261 | 62.339 | 30.607 | 17.477 | 1.00 | 18.37 | B |
| ATOM | 3561 | CG | ASP | B | 261 | 61.789 | 30.000 | 16.203 | 1.00 | 23.43 | B |
| ATOM | 3562 | OD1 | ASP | B | 261 | 61.251 | 28.874 | 16.267 | 1.00 | 24.71 | B |
| ATOM | 3563 | OD2 | ASP | B | 261 | 61.908 | 30.643 | 15.136 | 1.00 | 24.78 | B |
| ATOM | 3564 | C | ASP | B | 261 | 62.114 | 30.912 | 19.939 | 1.00 | 13.61 | B |
| ATOM | 3565 | O | ASP | B | 261 | 62.843 | 30.209 | 20.635 | 1.00 | 15.14 | B |
| ATOM | 3566 | N | LEU | B | 262 | 61.864 | 32.187 | 20.218 | 1.00 | 13.37 | B |
| ATOM | 3567 | CA | LEU | B | 262 | 62.458 | 32.839 | 21.381 | 1.00 | 13.88 | B |
| ATOM | 3568 | CB | LEU | B | 262 | 62.159 | 34.340 | 21.363 | 1.00 | 13.41 | B |
| ATOM | 3569 | CG | LEU | B | 262 | 62.871 | 35.171 | 22.439 | 1.00 | 17.34 | B |
| ATOM | 3570 | CD1 | LEU | B | 262 | 64.375 | 35.104 | 22.217 | 1.00 | 17.39 | B |
| ATOM | 3571 | CD2 | LEU | B | 262 | 62.389 | 36.613 | 22.388 | 1.00 | 19.73 | B |
| ATOM | 3572 | C | LEU | B | 262 | 61.935 | 32.232 | 22.677 | 1.00 | 12.72 | B |
| ATOM | 3573 | O | LEU | B | 262 | 62.694 | 32.045 | 23.630 | 1.00 | 14.39 | B |
| ATOM | 3574 | N | GLU | B | 263 | 60.640 | 31.930 | 22.716 | 1.00 | 13.10 | B |
| ATOM | 3575 | CA | GLU | B | 263 | 60.032 | 31.345 | 23.902 | 1.00 | 13.47 | B |
| ATOM | 3576 | CB | GLU | B | 263 | 58.502 | 31.374 | 23.772 | 1.00 | 15.74 | B |
| ATOM | 3577 | CG | GLU | B | 263 | 57.949 | 32.802 | 23.714 | 1.00 | 16.99 | B |
| ATOM | 3578 | CD | GLU | B | 263 | 56.461 | 32.869 | 23.413 | 1.00 | 20.70 | B |
| ATOM | 3579 | OE1 | GLU | B | 263 | 55.999 | 32.134 | 22.516 | 1.00 | 22.06 | B |
| ATOM | 3580 | OE2 | GLU | B | 263 | 55.754 | 33.670 | 24.063 | 1.00 | 22.68 | B |
| ATOM | 3581 | C | GLU | B | 263 | 60.548 | 29.919 | 24.101 | 1.00 | 12.75 | B |
| ATOM | 3582 | O | GLU | B | 263 | 60.744 | 29.471 | 25.235 | 1.00 | 13.64 | B |
| ATOM | 3583 | N | ILE | B | 264 | 60.773 | 29.209 | 22.997 | 1.00 | 12.68 | B |
| ATOM | 3584 | CA | ILE | B | 264 | 61.295 | 27.850 | 23.063 | 1.00 | 12.55 | B |
| ATOM | 3585 | CB | ILE | B | 264 | 61.262 | 27.177 | 21.671 | 1.00 | 14.12 | B |
| ATOM | 3586 | CG2 | ILE | B | 264 | 62.131 | 25.935 | 21.659 | 1.00 | 14.08 | B |
| ATOM | 3587 | CG1 | ILE | B | 264 | 59.817 | 26.817 | 21.313 | 1.00 | 15.80 | B |
| ATOM | 3588 | CD1 | ILE | B | 264 | 59.634 | 26.352 | 19.881 | 1.00 | 20.14 | B |
| ATOM | 3589 | C | ILE | B | 264 | 62.730 | 27.921 | 23.582 | 1.00 | 12.33 | B |
| ATOM | 3590 | O | ILE | B | 264 | 63.122 | 27.138 | 24.451 | 1.00 | 12.84 | B |
| ATOM | 3591 | N | LEU | B | 265 | 63.500 | 28.872 | 23.055 | 1.00 | 11.54 | B |
| ATOM | 3592 | CA | LEU | B | 265 | 64.887 | 29.073 | 23.477 | 1.00 | 12.06 | B |
| ATOM | 3593 | CB | LEU | B | 265 | 65.497 | 30.265 | 22.733 | 1.00 | 13.23 | B |
| ATOM | 3594 | CG | LEU | B | 265 | 66.881 | 30.718 | 23.203 | 1.00 | 13.80 | B |
| ATOM | 3595 | CD1 | LEU | B | 265 | 67.883 | 29.587 | 23.020 | 1.00 | 15.33 | B |
| ATOM | 3596 | CD2 | LEU | B | 265 | 67.312 | 31.950 | 22.431 | 1.00 | 13.99 | B |
| ATOM | 3597 | C | LEU | B | 265 | 64.933 | 29.342 | 24.981 | 1.00 | 12.16 | B |
| ATOM | 3598 | O | LEU | B | 265 | 65.746 | 28.768 | 25.698 | 1.00 | 11.75 | B |
| ATOM | 3599 | N | ALA | B | 266 | 64.047 | 30.217 | 25.447 | 1.00 | 12.67 | B |
| ATOM | 3600 | CA | ALA | B | 266 | 63.984 | 30.573 | 26.858 | 1.00 | 11.14 | B |
| ATOM | 3601 | CB | ALA | B | 266 | 62.955 | 31.686 | 27.066 | 1.00 | 11.89 | B |
| ATOM | 3602 | C | ALA | B | 266 | 63.645 | 29.391 | 27.757 | 1.00 | 10.09 | B |
| ATOM | 3603 | O | ALA | B | 266 | 64.267 | 29.205 | 28.802 | 1.00 | 11.77 | B |
| ATOM | 3604 | N | ALA | B | 267 | 62.653 | 28.599 | 27.357 | 1.00 | 10.44 | B |
| ATOM | 3605 | CA | ALA | B | 267 | 62.225 | 27.456 | 28.156 | 1.00 | 10.99 | B |
| ATOM | 3606 | CB | ALA | B | 267 | 60.982 | 26.817 | 27.533 | 1.00 | 12.27 | B |
| ATOM | 3607 | C | ALA | B | 267 | 63.320 | 26.410 | 28.313 | 1.00 | 11.14 | B |
| ATOM | 3608 | O | ALA | B | 267 | 63.574 | 25.916 | 29.414 | 1.00 | 12.10 | B |
| ATOM | 3609 | N | ILE | B | 268 | 63.973 | 26.067 | 27.211 | 1.00 | 11.40 | B |
| ATOM | 3610 | CA | ILE | B | 268 | 65.028 | 25.067 | 27.269 | 1.00 | 12.32 | B |
| ATOM | 3611 | CB | ILE | B | 268 | 65.433 | 24.617 | 25.852 | 1.00 | 14.56 | B |
| ATOM | 3612 | CG2 | ILE | B | 268 | 66.489 | 23.528 | 25.931 | 1.00 | 16.64 | B |
| ATOM | 3613 | CG1 | ILE | B | 268 | 64.203 | 24.054 | 25.129 | 1.00 | 16.27 | B |
| ATOM | 3614 | CD1 | ILE | B | 268 | 64.454 | 23.659 | 23.680 | 1.00 | 19.23 | B |
| ATOM | 3615 | C | ILE | B | 268 | 66.234 | 25.596 | 28.044 | 1.00 | 11.25 | B |
| ATOM | 3616 | O | ILE | B | 268 | 66.850 | 24.850 | 28.809 | 1.00 | 12.03 | B |
| ATOM | 3617 | N | PHE | B | 269 | 66.553 | 26.878 | 27.867 | 1.00 | 11.57 | B |
| ATOM | 3618 | CA | PHE | B | 269 | 67.672 | 27.492 | 28.587 | 1.00 | 10.70 | B |
| ATOM | 3619 | CB | PHE | B | 269 | 67.906 | 28.925 | 28.093 | 1.00 | 11.45 | B |

TABLE 1-continued

| | | | | | | | | | | |
|---|---|---|---|---|---|---|---|---|---|---|
| ATOM | 3620 | CG | PHE | B | 269 | 68.996 | 29.658 | 28.835 | 1.00 | 12.99 | B |
| ATOM | 3621 | CD1 | PHE | B | 269 | 70.333 | 29.354 | 28.624 | 1.00 | 14.49 | B |
| ATOM | 3622 | CD2 | PHE | B | 269 | 68.677 | 30.653 | 29.744 | 1.00 | 13.23 | B |
| ATOM | 3623 | CE1 | PHE | B | 269 | 71.333 | 30.038 | 29.311 | 1.00 | 14.66 | B |
| ATOM | 3624 | CE2 | PHE | B | 269 | 69.666 | 31.337 | 30.434 | 1.00 | 13.64 | B |
| ATOM | 3625 | CZ | PHE | B | 269 | 70.995 | 31.029 | 30.215 | 1.00 | 13.99 | B |
| ATOM | 3626 | C | PHE | B | 269 | 67.345 | 27.512 | 30.080 | 1.00 | 10.43 | B |
| ATOM | 3627 | O | PHE | B | 269 | 68.188 | 27.185 | 30.922 | 1.00 | 9.52 | B |
| ATOM | 3628 | N | ALA | B | 270 | 66.116 | 27.896 | 30.408 | 1.00 | 10.31 | B |
| ATOM | 3629 | CA | ALA | B | 270 | 65.703 | 27.934 | 31.804 | 1.00 | 9.54 | B |
| ATOM | 3630 | CB | ALA | B | 270 | 64.247 | 28.397 | 31.915 | 1.00 | 10.92 | B |
| ATOM | 3631 | C | ALA | B | 270 | 65.879 | 26.552 | 32.427 | 1.00 | 9.80 | B |
| ATOM | 3632 | O | ALA | B | 270 | 66.402 | 26.425 | 33.530 | 1.00 | 11.73 | B |
| ATOM | 3633 | N | ALA | B | 271 | 65.446 | 25.509 | 31.721 | 1.00 | 10.57 | B |
| ATOM | 3634 | CA | ALA | B | 271 | 65.596 | 24.154 | 32.242 | 1.00 | 10.67 | B |
| ATOM | 3635 | CB | ALA | B | 271 | 64.967 | 23.149 | 31.268 | 1.00 | 13.41 | B |
| ATOM | 3636 | C | ALA | B | 271 | 67.072 | 23.805 | 32.482 | 1.00 | 9.22 | B |
| ATOM | 3637 | O | ALA | B | 271 | 67.422 | 23.216 | 33.502 | 1.00 | 11.13 | B |
| ATOM | 3638 | N | ALA | B | 272 | 67.946 | 24.173 | 31.550 | 1.00 | 8.45 | B |
| ATOM | 3639 | CA | ALA | B | 272 | 69.368 | 23.865 | 31.694 | 1.00 | 8.29 | B |
| ATOM | 3640 | CB | ALA | B | 272 | 70.115 | 24.252 | 30.414 | 1.00 | 9.71 | B |
| ATOM | 3641 | C | ALA | B | 272 | 70.048 | 24.518 | 32.902 | 1.00 | 9.17 | B |
| ATOM | 3642 | O | ALA | B | 272 | 70.889 | 23.904 | 33.544 | 1.00 | 11.32 | B |
| ATOM | 3643 | N | ILE | B | 273 | 69.676 | 25.755 | 33.214 | 1.00 | 9.92 | B |
| ATOM | 3644 | CA | ILE | B | 273 | 70.299 | 26.470 | 34.330 | 1.00 | 10.55 | B |
| ATOM | 3645 | CB | ILE | B | 273 | 70.510 | 27.967 | 34.007 | 1.00 | 11.17 | B |
| ATOM | 3646 | CG2 | ILE | B | 273 | 71.200 | 28.134 | 32.660 | 1.00 | 12.80 | B |
| ATOM | 3647 | CG1 | ILE | B | 273 | 69.160 | 28.688 | 34.000 | 1.00 | 10.79 | B |
| ATOM | 3648 | CD1 | ILE | B | 273 | 69.282 | 30.209 | 34.026 | 1.00 | 10.44 | B |
| ATOM | 3649 | C | ILE | B | 273 | 69.497 | 26.471 | 35.617 | 1.00 | 9.63 | B |
| ATOM | 3650 | O | ILE | B | 273 | 69.980 | 26.958 | 36.636 | 1.00 | 11.91 | B |
| ATOM | 3651 | N | HIS | B | 274 | 68.292 | 25.917 | 35.591 | 1.00 | 10.09 | B |
| ATOM | 3652 | CA | HIS | B | 274 | 67.421 | 25.998 | 36.758 | 1.00 | 8.74 | B |
| ATOM | 3653 | CB | HIS | B | 274 | 66.060 | 25.356 | 36.447 | 1.00 | 9.43 | B |
| ATOM | 3654 | CG | HIS | B | 274 | 65.952 | 23.925 | 36.864 | 1.00 | 10.96 | B |
| ATOM | 3655 | CD2 | HIS | B | 274 | 65.392 | 23.360 | 37.960 | 1.00 | 8.81 | B |
| ATOM | 3656 | ND1 | HIS | B | 274 | 66.509 | 22.891 | 36.141 | 1.00 | 10.16 | B |
| ATOM | 3657 | CE1 | HIS | B | 274 | 66.300 | 21.752 | 36.777 | 1.00 | 10.39 | B |
| ATOM | 3658 | NE2 | HIS | B | 274 | 65.625 | 22.010 | 37.884 | 1.00 | 7.84 | B |
| ATOM | 3659 | C | HIS | B | 274 | 67.915 | 25.539 | 38.131 | 1.00 | 8.71 | B |
| ATOM | 3660 | O | HIS | B | 274 | 67.319 | 25.929 | 39.147 | 1.00 | 9.75 | B |
| ATOM | 3661 | N | ASP | B | 275 | 68.972 | 24.725 | 38.182 | 1.00 | 8.42 | B |
| ATOM | 3662 | CA | ASP | B | 275 | 69.531 | 24.258 | 39.466 | 1.00 | 8.17 | B |
| ATOM | 3663 | CB | ASP | B | 275 | 69.221 | 22.769 | 39.711 | 1.00 | 8.97 | B |
| ATOM | 3664 | CG | ASP | B | 275 | 67.884 | 22.541 | 40.381 | 1.00 | 10.33 | B |
| ATOM | 3665 | OD1 | ASP | B | 275 | 67.447 | 23.412 | 41.148 | 1.00 | 10.14 | B |
| ATOM | 3666 | OD2 | ASP | B | 275 | 67.274 | 21.475 | 40.161 | 1.00 | 9.86 | B |
| ATOM | 3667 | C | ASP | B | 275 | 71.055 | 24.433 | 39.548 | 1.00 | 8.46 | B |
| ATOM | 3668 | O | ASP | B | 275 | 71.708 | 23.825 | 40.404 | 1.00 | 9.88 | B |
| ATOM | 3669 | N | VAL | B | 276 | 71.630 | 25.255 | 38.675 | 1.00 | 9.20 | B |
| ATOM | 3670 | CA | VAL | B | 276 | 73.083 | 25.425 | 38.680 | 1.00 | 8.98 | B |
| ATOM | 3671 | CB | VAL | B | 276 | 73.541 | 26.351 | 37.523 | 1.00 | 10.25 | B |
| ATOM | 3672 | CG1 | VAL | B | 276 | 73.086 | 27.779 | 37.756 | 1.00 | 11.35 | B |
| ATOM | 3673 | CG2 | VAL | B | 276 | 75.045 | 26.265 | 37.367 | 1.00 | 11.42 | B |
| ATOM | 3674 | C | VAL | B | 276 | 73.672 | 25.907 | 40.011 | 1.00 | 8.42 | B |
| ATOM | 3675 | O | VAL | B | 276 | 73.123 | 26.778 | 40.680 | 1.00 | 8.82 | B |
| ATOM | 3676 | N | ASP | B | 277 | 74.794 | 25.305 | 40.391 | 1.00 | 9.58 | B |
| ATOM | 3677 | CA | ASP | B | 277 | 75.500 | 25.624 | 41.634 | 1.00 | 10.27 | B |
| ATOM | 3678 | CB | ASP | B | 277 | 75.943 | 27.096 | 41.638 | 1.00 | 13.36 | B |
| ATOM | 3679 | CG | ASP | B | 277 | 77.058 | 27.368 | 42.637 | 1.00 | 16.91 | B |
| ATOM | 3680 | OD1 | ASP | B | 277 | 77.885 | 26.458 | 42.865 | 1.00 | 17.94 | B |
| ATOM | 3681 | OD2 | ASP | B | 277 | 77.123 | 28.494 | 43.181 | 1.00 | 17.97 | B |
| ATOM | 3682 | C | ASP | B | 277 | 74.672 | 25.298 | 42.884 | 1.00 | 10.70 | B |
| ATOM | 3683 | O | ASP | B | 277 | 74.793 | 25.956 | 43.915 | 1.00 | 13.58 | B |
| ATOM | 3684 | N | HIS | B | 278 | 73.841 | 24.266 | 42.779 | 1.00 | 10.79 | B |
| ATOM | 3685 | CA | HIS | B | 278 | 73.005 | 23.806 | 43.887 | 1.00 | 10.24 | B |
| ATOM | 3686 | CB | HIS | B | 278 | 71.975 | 22.790 | 43.378 | 1.00 | 9.80 | B |
| ATOM | 3687 | CG | HIS | B | 278 | 70.826 | 22.562 | 44.313 | 1.00 | 10.59 | B |
| ATOM | 3688 | CD2 | HIS | B | 278 | 69.500 | 22.783 | 44.158 | 1.00 | 12.43 | B |
| ATOM | 3689 | ND1 | HIS | B | 278 | 70.981 | 22.031 | 45.577 | 1.00 | 13.40 | B |
| ATOM | 3690 | CE1 | HIS | B | 278 | 69.798 | 21.935 | 46.159 | 1.00 | 11.93 | B |
| ATOM | 3691 | NE2 | HIS | B | 278 | 68.882 | 22.384 | 45.319 | 1.00 | 12.85 | B |
| ATOM | 3692 | C | HIS | B | 278 | 73.946 | 23.133 | 44.880 | 1.00 | 9.88 | B |
| ATOM | 3693 | O | HIS | B | 278 | 74.720 | 22.247 | 44.510 | 1.00 | 12.94 | B |
| ATOM | 3694 | N | PRO | B | 279 | 73.900 | 23.552 | 46.151 | 1.00 | 11.89 | B |
| ATOM | 3695 | CD | PRO | B | 279 | 73.131 | 24.699 | 46.664 | 1.00 | 12.25 | B |
| ATOM | 3696 | CA | PRO | B | 279 | 74.760 | 22.985 | 47.192 | 1.00 | 12.36 | B |
| ATOM | 3697 | CB | PRO | B | 279 | 74.794 | 24.094 | 48.239 | 1.00 | 13.43 | B |
| ATOM | 3698 | CG | PRO | B | 279 | 73.418 | 24.651 | 48.151 | 1.00 | 13.68 | B |

TABLE 1-continued

| ATOM | 3699 | C | PRO | B | 279 | 74.307 | 21.648 | 47.774 | 1.00 | 12.90 | B |
|------|------|-----|-----|---|-----|--------|--------|--------|------|-------|---|
| ATOM | 3700 | O | PRO | B | 279 | 75.002 | 21.076 | 48.612 | 1.00 | 14.71 | B |
| ATOM | 3701 | N | GLY | B | 280 | 73.155 | 21.151 | 47.333 | 1.00 | 12.90 | B |
| ATOM | 3702 | CA | GLY | B | 280 | 72.670 | 19.876 | 47.837 | 1.00 | 13.10 | B |
| ATOM | 3703 | C | GLY | B | 280 | 71.915 | 19.957 | 49.150 | 1.00 | 13.99 | B |
| ATOM | 3704 | O | GLY | B | 280 | 71.732 | 18.942 | 49.824 | 1.00 | 14.55 | B |
| ATOM | 3705 | N | VAL | B | 281 | 71.500 | 21.164 | 49.523 | 1.00 | 14.58 | B |
| ATOM | 3706 | CA | VAL | B | 281 | 70.721 | 21.380 | 50.741 | 1.00 | 14.37 | B |
| ATOM | 3707 | CB | VAL | B | 281 | 71.567 | 22.041 | 51.861 | 1.00 | 15.47 | B |
| ATOM | 3708 | CG1 | VAL | B | 281 | 72.657 | 21.084 | 52.319 | 1.00 | 16.54 | B |
| ATOM | 3709 | CG2 | VAL | B | 281 | 72.182 | 23.336 | 51.363 | 1.00 | 17.92 | B |
| ATOM | 3710 | C | VAL | B | 281 | 69.533 | 22.277 | 50.392 | 1.00 | 14.06 | B |
| ATOM | 3711 | O | VAL | B | 281 | 69.571 | 23.022 | 49.409 | 1.00 | 15.98 | B |
| ATOM | 3712 | N | SER | B | 282 | 68.480 | 22.204 | 51.199 | 1.00 | 12.90 | B |
| ATOM | 3713 | CA | SER | B | 282 | 67.261 | 22.979 | 50.972 | 1.00 | 12.27 | B |
| ATOM | 3714 | CB | SER | B | 282 | 66.129 | 22.405 | 51.818 | 1.00 | 15.81 | B |
| ATOM | 3715 | OG | SER | B | 282 | 66.389 | 22.624 | 53.197 | 1.00 | 16.87 | B |
| ATOM | 3716 | C | SER | B | 282 | 67.393 | 24.463 | 51.296 | 1.00 | 11.54 | B |
| ATOM | 3717 | O | SER | B | 282 | 68.340 | 24.886 | 51.958 | 1.00 | 13.10 | B |
| ATOM | 3718 | N | ASN | B | 283 | 66.427 | 25.252 | 50.832 | 1.00 | 12.56 | B |
| ATOM | 3719 | CA | ASN | B | 283 | 66.432 | 26.681 | 51.111 | 1.00 | 10.95 | B |
| ATOM | 3720 | CB | ASN | B | 283 | 65.208 | 27.381 | 50.504 | 1.00 | 12.93 | B |
| ATOM | 3721 | CG | ASN | B | 283 | 65.400 | 27.741 | 49.044 | 1.00 | 13.52 | B |
| ATOM | 3722 | OD1 | ASN | B | 283 | 66.492 | 28.116 | 48.626 | 1.00 | 17.03 | B |
| ATOM | 3723 | ND2 | ASN | B | 283 | 64.327 | 27.655 | 48.267 | 1.00 | 14.50 | B |
| ATOM | 3724 | C | ASN | B | 283 | 66.391 | 26.863 | 52.623 | 1.00 | 11.55 | B |
| ATOM | 3725 | O | ASN | B | 283 | 67.085 | 27.709 | 53.174 | 1.00 | 12.29 | B |
| ATOM | 3726 | N | GLN | B | 284 | 65.577 | 26.054 | 53.292 | 1.00 | 12.65 | B |
| ATOM | 3727 | CA | GLN | B | 284 | 65.453 | 26.178 | 54.740 | 1.00 | 13.65 | B |
| ATOM | 3728 | CB | GLN | B | 284 | 64.423 | 25.188 | 55.284 | 1.00 | 16.47 | B |
| ATOM | 3729 | CG | GLN | B | 284 | 63.922 | 25.560 | 56.675 | 1.00 | 22.61 | B |
| ATOM | 3730 | CD | GLN | B | 284 | 63.376 | 26.980 | 56.733 | 1.00 | 23.14 | B |
| ATOM | 3731 | OE1 | GLN | B | 284 | 62.491 | 27.351 | 55.961 | 1.00 | 25.00 | B |
| ATOM | 3732 | NE2 | GLN | B | 284 | 63.905 | 27.780 | 57.649 | 1.00 | 23.80 | B |
| ATOM | 3733 | C | GLN | B | 284 | 66.794 | 25.972 | 55.439 | 1.00 | 12.32 | B |
| ATOM | 3734 | O | GLN | B | 284 | 67.103 | 26.654 | 56.409 | 1.00 | 13.35 | B |
| ATOM | 3735 | N | PHE | B | 285 | 67.588 | 25.030 | 54.945 | 1.00 | 12.52 | B |
| ATOM | 3736 | CA | PHE | B | 285 | 68.902 | 24.781 | 55.537 | 1.00 | 11.32 | B |
| ATOM | 3737 | CB | PHE | B | 285 | 69.572 | 23.593 | 54.829 | 1.00 | 11.69 | B |
| ATOM | 3738 | CG | PHE | B | 285 | 70.931 | 23.237 | 55.371 | 1.00 | 12.84 | B |
| ATOM | 3739 | CD1 | PHE | B | 285 | 72.053 | 23.978 | 55.026 | 1.00 | 15.56 | B |
| ATOM | 3740 | CD2 | PHE | B | 285 | 71.094 | 22.134 | 56.195 | 1.00 | 14.79 | B |
| ATOM | 3741 | CE1 | PHE | B | 285 | 73.310 | 23.623 | 55.487 | 1.00 | 14.41 | B |
| ATOM | 3742 | CE2 | PHE | B | 285 | 72.352 | 21.776 | 56.660 | 1.00 | 12.95 | B |
| ATOM | 3743 | CZ | PHE | B | 285 | 73.456 | 22.519 | 56.304 | 1.00 | 14.80 | B |
| ATOM | 3744 | C | PHE | B | 285 | 69.765 | 26.041 | 55.407 | 1.00 | 11.25 | B |
| ATOM | 3745 | O | PHE | B | 285 | 70.441 | 26.443 | 56.351 | 1.00 | 12.39 | B |
| ATOM | 3746 | N | LEU | B | 286 | 69.745 | 26.659 | 54.230 | 1.00 | 11.60 | B |
| ATOM | 3747 | CA | LEU | B | 286 | 70.527 | 27.868 | 53.995 | 1.00 | 11.39 | B |
| ATOM | 3748 | CB | LEU | B | 286 | 70.412 | 28.289 | 52.531 | 1.00 | 13.01 | B |
| ATOM | 3749 | CG | LEU | B | 286 | 71.005 | 27.298 | 51.530 | 1.00 | 15.88 | B |
| ATOM | 3750 | CD1 | LEU | B | 286 | 70.748 | 27.802 | 50.118 | 1.00 | 16.02 | B |
| ATOM | 3751 | CD2 | LEU | B | 286 | 72.495 | 27.136 | 51.775 | 1.00 | 16.17 | B |
| ATOM | 3752 | C | LEU | B | 286 | 70.056 | 28.999 | 54.903 | 1.00 | 11.62 | B |
| ATOM | 3753 | O | LEU | B | 286 | 70.861 | 29.754 | 55.450 | 1.00 | 13.36 | B |
| ATOM | 3754 | N | ILE | B | 287 | 68.746 | 29.114 | 55.067 | 1.00 | 12.47 | B |
| ATOM | 3755 | CA | ILE | B | 287 | 68.195 | 30.156 | 55.919 | 1.00 | 13.31 | B |
| ATOM | 3756 | CB | ILE | B | 287 | 66.659 | 30.190 | 55.819 | 1.00 | 14.28 | B |
| ATOM | 3757 | CG2 | ILE | B | 287 | 66.090 | 31.169 | 56.843 | 1.00 | 13.43 | B |
| ATOM | 3758 | CG1 | ILE | B | 287 | 66.242 | 30.594 | 54.405 | 1.00 | 15.88 | B |
| ATOM | 3759 | CD1 | ILE | B | 287 | 64.766 | 30.403 | 54.119 | 1.00 | 15.36 | B |
| ATOM | 3760 | C | ILE | B | 287 | 68.598 | 29.909 | 57.377 | 1.00 | 12.47 | B |
| ATOM | 3761 | O | ILE | B | 287 | 69.023 | 30.833 | 58.073 | 1.00 | 14.12 | B |
| ATOM | 3762 | N | ASN | B | 288 | 68.488 | 28.662 | 57.825 | 1.00 | 13.80 | B |
| ATOM | 3763 | CA | ASN | B | 288 | 68.821 | 28.314 | 59.210 | 1.00 | 15.32 | B |
| ATOM | 3764 | CB | ASN | B | 288 | 68.394 | 26.877 | 59.523 | 1.00 | 16.95 | B |
| ATOM | 3765 | CG | ASN | B | 288 | 66.888 | 26.709 | 59.561 | 1.00 | 19.11 | B |
| ATOM | 3766 | OD1 | ASN | B | 288 | 66.149 | 27.676 | 59.739 | 1.00 | 21.37 | B |
| ATOM | 3767 | ND2 | ASN | B | 288 | 66.426 | 25.472 | 59.411 | 1.00 | 22.68 | B |
| ATOM | 3768 | C | ASN | B | 288 | 70.296 | 28.476 | 59.568 | 1.00 | 15.24 | B |
| ATOM | 3769 | O | ASN | B | 288 | 70.634 | 28.699 | 60.734 | 1.00 | 18.51 | B |
| ATOM | 3770 | N | THR | B | 289 | 71.172 | 28.353 | 58.577 | 1.00 | 14.49 | B |
| ATOM | 3771 | CA | THR | B | 289 | 72.603 | 28.490 | 58.815 | 1.00 | 14.96 | B |
| ATOM | 3772 | CB | THR | B | 289 | 73.416 | 27.516 | 57.923 | 1.00 | 14.70 | B |
| ATOM | 3773 | OG1 | THR | B | 289 | 73.073 | 27.714 | 56.546 | 1.00 | 14.76 | B |
| ATOM | 3774 | CG2 | THR | B | 289 | 73.123 | 26.082 | 58.309 | 1.00 | 16.87 | B |
| ATOM | 3775 | C | THR | B | 289 | 73.097 | 29.914 | 58.587 | 1.00 | 14.30 | B |
| ATOM | 3776 | O | THR | B | 289 | 74.296 | 30.186 | 58.675 | 1.00 | 16.29 | B |
| ATOM | 3777 | N | ASN | B | 290 | 72.170 | 30.823 | 58.295 | 1.00 | 15.22 | B |

TABLE 1-continued

| | | | | | | | | | | |
|---|---|---|---|---|---|---|---|---|---|---|
| ATOM | 3778 | CA | ASN | B | 290 | 72.508 | 32.222 | 58.058 | 1.00 | 16.21 | B |
| ATOM | 3779 | CB | ASN | B | 290 | 73.103 | 32.840 | 59.327 | 1.00 | 18.93 | B |
| ATOM | 3780 | CG | ASN | B | 290 | 73.337 | 34.334 | 59.200 | 1.00 | 23.38 | B |
| ATOM | 3781 | OD1 | ASN | B | 290 | 74.347 | 34.860 | 59.679 | 1.00 | 26.84 | B |
| ATOM | 3782 | ND2 | ASN | B | 290 | 72.398 | 35.028 | 58.567 | 1.00 | 23.94 | B |
| ATOM | 3783 | C | ASN | B | 290 | 73.520 | 32.319 | 56.924 | 1.00 | 15.21 | B |
| ATOM | 3784 | O | ASN | B | 290 | 74.451 | 33.122 | 56.972 | 1.00 | 16.68 | B |
| ATOM | 3785 | N | SER | B | 291 | 73.342 | 31.492 | 55.903 | 1.00 | 15.31 | B |
| ATOM | 3786 | CA | SER | B | 291 | 74.258 | 31.503 | 54.771 | 1.00 | 16.41 | B |
| ATOM | 3787 | CB | SER | B | 291 | 73.915 | 30.368 | 53.811 | 1.00 | 18.28 | B |
| ATOM | 3788 | OG | SER | B | 291 | 72.647 | 30.585 | 53.228 | 1.00 | 23.19 | B |
| ATOM | 3789 | C | SER | B | 291 | 74.217 | 32.830 | 54.017 | 1.00 | 14.89 | B |
| ATOM | 3790 | O | SER | B | 291 | 73.197 | 33.522 | 54.001 | 1.00 | 15.57 | B |
| ATOM | 3791 | N | GLU | B | 292 | 75.339 | 33.174 | 53.391 | 1.00 | 16.31 | B |
| ATOM | 3792 | CA | GLU | B | 292 | 75.457 | 34.404 | 52.614 | 1.00 | 17.02 | B |
| ATOM | 3793 | CB | GLU | B | 292 | 76.840 | 34.471 | 51.962 | 1.00 | 19.06 | B |
| ATOM | 3794 | CG | GLU | B | 292 | 77.040 | 35.642 | 51.018 | 1.00 | 23.64 | B |
| ATOM | 3795 | CD | GLU | B | 292 | 78.446 | 35.690 | 50.450 | 1.00 | 26.32 | B |
| ATOM | 3796 | OE1 | GLU | B | 292 | 78.893 | 34.671 | 49.876 | 1.00 | 28.58 | B |
| ATOM | 3797 | OE2 | GLU | B | 292 | 79.104 | 36.745 | 50.579 | 1.00 | 29.58 | B |
| ATOM | 3798 | C | GLU | B | 292 | 74.373 | 34.506 | 51.546 | 1.00 | 16.12 | B |
| ATOM | 3799 | O | GLU | B | 292 | 73.885 | 35.597 | 51.259 | 1.00 | 17.12 | B |
| ATOM | 3800 | N | LEU | B | 293 | 73.985 | 33.374 | 50.963 | 1.00 | 16.26 | B |
| ATOM | 3801 | CA | LEU | B | 293 | 72.944 | 33.383 | 49.932 | 1.00 | 15.17 | B |
| ATOM | 3802 | CB | LEU | B | 293 | 72.841 | 32.020 | 49.244 | 1.00 | 17.78 | B |
| ATOM | 3803 | CG | LEU | B | 293 | 73.959 | 31.654 | 48.272 | 1.00 | 19.61 | B |
| ATOM | 3804 | CD1 | LEU | B | 293 | 73.661 | 30.292 | 47.664 | 1.00 | 22.08 | B |
| ATOM | 3805 | CD2 | LEU | B | 293 | 74.066 | 32.721 | 47.190 | 1.00 | 23.02 | B |
| ATOM | 3806 | C | LEU | B | 293 | 71.580 | 33.749 | 50.500 | 1.00 | 15.21 | B |
| ATOM | 3807 | O | LEU | B | 293 | 70.816 | 34.493 | 49.876 | 1.00 | 15.20 | B |
| ATOM | 3808 | N | ALA | B | 294 | 71.269 | 33.222 | 51.681 | 1.00 | 13.95 | B |
| ATOM | 3809 | CA | ALA | B | 294 | 69.987 | 33.518 | 52.311 | 1.00 | 14.53 | B |
| ATOM | 3810 | CB | ALA | B | 294 | 69.800 | 32.674 | 53.574 | 1.00 | 14.29 | B |
| ATOM | 3811 | C | ALA | B | 294 | 69.914 | 34.999 | 52.649 | 1.00 | 15.22 | B |
| ATOM | 3812 | O | ALA | B | 294 | 68.865 | 35.621 | 52.509 | 1.00 | 16.21 | B |
| ATOM | 3813 | N | LEU | B | 295 | 71.029 | 35.571 | 53.096 | 1.00 | 15.84 | B |
| ATOM | 3814 | CA | LEU | B | 295 | 71.045 | 36.993 | 53.421 | 1.00 | 16.78 | B |
| ATOM | 3815 | CB | LEU | B | 295 | 72.331 | 37.363 | 54.164 | 1.00 | 17.35 | B |
| ATOM | 3816 | CG | LEU | B | 295 | 72.378 | 36.975 | 55.640 | 1.00 | 19.95 | B |
| ATOM | 3817 | CD1 | LEU | B | 295 | 73.696 | 37.422 | 56.239 | 1.00 | 23.50 | B |
| ATOM | 3818 | CD2 | LEU | B | 295 | 71.220 | 37.627 | 56.369 | 1.00 | 22.71 | B |
| ATOM | 3819 | C | LEU | B | 295 | 70.943 | 37.809 | 52.140 | 1.00 | 16.38 | B |
| ATOM | 3820 | O | LEU | B | 295 | 70.273 | 38.841 | 52.092 | 1.00 | 18.26 | B |
| ATOM | 3821 | N | MET | B | 296 | 71.601 | 37.329 | 51.094 | 1.00 | 16.17 | B |
| ATOM | 3822 | CA | MET | B | 296 | 71.591 | 38.012 | 49.809 | 1.00 | 16.75 | B |
| ATOM | 3823 | CB | MET | B | 296 | 72.461 | 37.243 | 48.811 | 1.00 | 19.70 | B |
| ATOM | 3824 | CG | MET | B | 296 | 73.648 | 38.026 | 48.285 | 1.00 | 28.48 | B |
| ATOM | 3825 | SD | MET | B | 296 | 73.137 | 39.457 | 47.313 | 1.00 | 24.77 | B |
| ATOM | 3826 | CE | MET | B | 296 | 73.324 | 38.831 | 45.628 | 1.00 | 30.08 | B |
| ATOM | 3827 | C | MET | B | 296 | 70.190 | 38.172 | 49.231 | 1.00 | 15.03 | B |
| ATOM | 3828 | O | MET | B | 296 | 69.848 | 39.229 | 48.693 | 1.00 | 16.71 | B |
| ATOM | 3829 | N | TYR | B | 297 | 69.378 | 37.126 | 49.353 | 1.00 | 14.35 | B |
| ATOM | 3830 | CA | TYR | B | 297 | 68.031 | 37.141 | 48.799 | 1.00 | 12.40 | B |
| ATOM | 3831 | CB | TYR | B | 297 | 67.868 | 35.926 | 47.876 | 1.00 | 12.95 | B |
| ATOM | 3832 | CG | TYR | B | 297 | 68.806 | 36.003 | 46.694 | 1.00 | 12.48 | B |
| ATOM | 3833 | CD1 | TYR | B | 297 | 68.680 | 37.024 | 45.762 | 1.00 | 13.15 | B |
| ATOM | 3834 | CE1 | TYR | B | 297 | 69.573 | 37.158 | 44.715 | 1.00 | 12.70 | B |
| ATOM | 3835 | CD2 | TYR | B | 297 | 69.859 | 35.104 | 46.543 | 1.00 | 12.71 | B |
| ATOM | 3836 | CE2 | TYR | B | 297 | 70.766 | 35.234 | 45.493 | 1.00 | 13.85 | B |
| ATOM | 3837 | CZ | TYR | B | 297 | 70.613 | 36.267 | 44.585 | 1.00 | 12.18 | B |
| ATOM | 3838 | OH | TYR | B | 297 | 71.509 | 36.432 | 43.548 | 1.00 | 15.45 | B |
| ATOM | 3839 | C | TYR | B | 297 | 66.885 | 37.228 | 49.812 | 1.00 | 12.43 | B |
| ATOM | 3840 | O | TYR | B | 297 | 65.746 | 36.876 | 49.510 | 1.00 | 13.42 | B |
| ATOM | 3841 | N | ASN | B | 298 | 67.196 | 37.719 | 51.008 | 1.00 | 13.10 | B |
| ATOM | 3842 | CA | ASN | B | 298 | 66.192 | 37.891 | 52.059 | 1.00 | 14.27 | B |
| ATOM | 3843 | CB | ASN | B | 298 | 65.269 | 39.064 | 51.706 | 1.00 | 15.38 | B |
| ATOM | 3844 | CG | ASN | B | 298 | 66.036 | 40.317 | 51.330 | 1.00 | 18.06 | B |
| ATOM | 3845 | OD1 | ASN | B | 298 | 66.935 | 40.754 | 52.052 | 1.00 | 21.15 | B |
| ATOM | 3846 | ND2 | ASN | B | 298 | 65.675 | 40.911 | 50.196 | 1.00 | 20.44 | B |
| ATOM | 3847 | C | ASN | B | 298 | 65.335 | 36.658 | 52.363 | 1.00 | 15.06 | B |
| ATOM | 3848 | O | ASN | B | 298 | 64.132 | 36.775 | 52.614 | 1.00 | 17.05 | B |
| ATOM | 3849 | N | ASP | B | 299 | 65.961 | 35.486 | 52.345 | 1.00 | 15.30 | B |
| ATOM | 3850 | CA | ASP | B | 299 | 65.286 | 34.219 | 52.627 | 1.00 | 16.00 | B |
| ATOM | 3851 | CB | ASP | B | 299 | 64.708 | 34.211 | 54.051 | 1.00 | 17.15 | B |
| ATOM | 3852 | CG | ASP | B | 299 | 65.753 | 34.464 | 55.124 | 1.00 | 20.00 | B |
| ATOM | 3853 | OD1 | ASP | B | 299 | 66.954 | 34.219 | 54.886 | 1.00 | 21.27 | B |
| ATOM | 3854 | OD2 | ASP | B | 299 | 65.359 | 34.895 | 56.234 | 1.00 | 23.31 | B |
| ATOM | 3855 | C | ASP | B | 299 | 64.162 | 33.844 | 51.661 | 1.00 | 15.85 | B |
| ATOM | 3856 | O | ASP | B | 299 | 63.413 | 32.904 | 51.927 | 1.00 | 17.12 | B |

TABLE 1-continued

| ATOM | 3857 | N | GLU | B | 300 | 64.043 | 34.561 | 50.544 | 1.00 | 15.59 | B |
| --- | --- | --- | --- | --- | --- | --- | --- | --- | --- | --- | --- |
| ATOM | 3858 | CA | GLU | B | 300 | 62.987 | 34.287 | 49.568 | 1.00 | 17.14 | B |
| ATOM | 3859 | CB | GLU | B | 300 | 62.287 | 35.592 | 49.189 | 1.00 | 19.40 | B |
| ATOM | 3860 | CG | GLU | B | 300 | 61.459 | 36.203 | 50.307 | 1.00 | 24.35 | B |
| ATOM | 3861 | CD | GLU | B | 300 | 60.060 | 35.624 | 50.381 | 1.00 | 28.50 | B |
| ATOM | 3862 | OE1 | GLU | B | 300 | 59.924 | 34.396 | 50.572 | 1.00 | 30.02 | B |
| ATOM | 3863 | OE2 | GLU | B | 300 | 59.091 | 36.403 | 50.242 | 1.00 | 31.25 | B |
| ATOM | 3864 | C | GLU | B | 300 | 63.538 | 33.614 | 48.316 | 1.00 | 16.27 | B |
| ATOM | 3865 | O | GLU | B | 300 | 64.393 | 34.178 | 47.638 | 1.00 | 17.16 | B |
| ATOM | 3866 | N | SER | B | 301 | 63.030 | 32.419 | 48.010 | 1.00 | 15.30 | B |
| ATOM | 3867 | CA | SER | B | 301 | 63.492 | 31.647 | 46.854 | 1.00 | 14.03 | B |
| ATOM | 3868 | CB | SER | B | 301 | 62.819 | 32.138 | 45.573 | 1.00 | 14.54 | B |
| ATOM | 3869 | OG | SER | B | 301 | 61.420 | 31.942 | 45.648 | 1.00 | 17.57 | B |
| ATOM | 3870 | C | SER | B | 301 | 64.999 | 31.799 | 46.733 | 1.00 | 11.76 | B |
| ATOM | 3871 | O | SER | B | 301 | 65.521 | 32.126 | 45.671 | 1.00 | 13.15 | B |
| ATOM | 3872 | N | VAL | B | 302 | 65.696 | 31.541 | 47.835 | 1.00 | 12.29 | B |
| ATOM | 3873 | CA | VAL | B | 302 | 67.142 | 31.694 | 47.886 | 1.00 | 11.28 | B |
| ATOM | 3874 | CB | VAL | B | 302 | 67.683 | 31.263 | 49.260 | 1.00 | 12.31 | B |
| ATOM | 3875 | CG1 | VAL | B | 302 | 69.182 | 31.475 | 49.318 | 1.00 | 12.16 | B |
| ATOM | 3876 | CG2 | VAL | B | 302 | 66.992 | 32.064 | 50.358 | 1.00 | 13.10 | B |
| ATOM | 3877 | C | VAL | B | 302 | 67.899 | 30.946 | 46.792 | 1.00 | 11.14 | B |
| ATOM | 3878 | O | VAL | B | 302 | 68.670 | 31.549 | 46.045 | 1.00 | 12.80 | B |
| ATOM | 3879 | N | LEU | B | 303 | 67.681 | 29.639 | 46.700 | 1.00 | 11.29 | B |
| ATOM | 3880 | CA | LEU | B | 303 | 68.355 | 28.820 | 45.695 | 1.00 | 12.12 | B |
| ATOM | 3881 | CB | LEU | B | 303 | 67.984 | 27.344 | 45.879 | 1.00 | 14.58 | B |
| ATOM | 3882 | CG | LEU | B | 303 | 68.611 | 26.624 | 47.076 | 1.00 | 17.98 | B |
| ATOM | 3883 | CD1 | LEU | B | 303 | 67.884 | 25.308 | 47.324 | 1.00 | 19.99 | B |
| ATOM | 3884 | CD2 | LEU | B | 303 | 70.080 | 26.392 | 46.804 | 1.00 | 19.30 | B |
| ATOM | 3885 | C | LEU | B | 303 | 68.000 | 29.242 | 44.274 | 1.00 | 10.31 | B |
| ATOM | 3886 | O | LEU | B | 303 | 68.876 | 29.414 | 43.429 | 1.00 | 11.10 | B |
| ATOM | 3887 | N | GLU | B | 304 | 66.708 | 29.396 | 44.014 | 1.00 | 10.04 | B |
| ATOM | 3888 | CA | GLU | B | 304 | 66.250 | 29.775 | 42.687 | 1.00 | 9.51 | B |
| ATOM | 3889 | CB | GLU | B | 304 | 64.723 | 29.770 | 42.671 | 1.00 | 11.48 | B |
| ATOM | 3890 | CG | GLU | B | 304 | 64.110 | 28.379 | 42.943 | 1.00 | 12.15 | B |
| ATOM | 3891 | CD | GLU | B | 304 | 64.255 | 27.885 | 44.387 | 1.00 | 14.37 | B |
| ATOM | 3892 | OE1 | GLU | B | 304 | 64.325 | 28.719 | 45.318 | 1.00 | 14.49 | B |
| ATOM | 3893 | OE2 | GLU | B | 304 | 64.271 | 26.646 | 44.591 | 1.00 | 15.25 | B |
| ATOM | 3894 | C | GLU | B | 304 | 66.823 | 31.119 | 42.216 | 1.00 | 9.19 | B |
| ATOM | 3895 | O | GLU | B | 304 | 67.180 | 31.270 | 41.049 | 1.00 | 12.10 | B |
| ATOM | 3896 | N | ASN | B | 305 | 66.919 | 32.098 | 43.115 | 1.00 | 10.01 | B |
| ATOM | 3897 | CA | ASN | B | 305 | 67.508 | 33.381 | 42.737 | 1.00 | 10.32 | B |
| ATOM | 3898 | CB | ASN | B | 305 | 67.394 | 34.386 | 43.880 | 1.00 | 11.91 | B |
| ATOM | 3899 | CG | ASN | B | 305 | 66.110 | 35.184 | 43.827 | 1.00 | 12.96 | B |
| ATOM | 3900 | OD1 | ASN | B | 305 | 65.898 | 35.976 | 42.911 | 1.00 | 14.58 | B |
| ATOM | 3901 | ND2 | ASN | B | 305 | 65.243 | 34.976 | 44.810 | 1.00 | 14.47 | B |
| ATOM | 3902 | C | ASN | B | 305 | 68.986 | 33.186 | 42.391 | 1.00 | 10.29 | B |
| ATOM | 3903 | O | ASN | B | 305 | 69.514 | 33.820 | 41.474 | 1.00 | 11.48 | B |
| ATOM | 3904 | N | HIS | B | 306 | 69.649 | 32.309 | 43.135 | 1.00 | 8.94 | B |
| ATOM | 3905 | CA | HIS | B | 306 | 71.057 | 32.027 | 42.897 | 1.00 | 9.84 | B |
| ATOM | 3906 | CB | HIS | B | 306 | 71.619 | 31.185 | 44.045 | 1.00 | 10.55 | B |
| ATOM | 3907 | CG | HIS | B | 306 | 73.086 | 30.927 | 43.933 | 1.00 | 13.66 | B |
| ATOM | 3908 | CD2 | HIS | B | 306 | 73.785 | 29.771 | 43.854 | 1.00 | 15.08 | B |
| ATOM | 3909 | ND1 | HIS | B | 306 | 74.015 | 31.943 | 43.881 | 1.00 | 15.44 | B |
| ATOM | 3910 | CE1 | HIS | B | 306 | 75.224 | 31.423 | 43.775 | 1.00 | 16.32 | B |
| ATOM | 3911 | NE2 | HIS | B | 306 | 75.112 | 30.106 | 43.756 | 1.00 | 14.88 | B |
| ATOM | 3912 | C | HIS | B | 306 | 71.293 | 31.315 | 41.562 | 1.00 | 8.93 | B |
| ATOM | 3913 | O | HIS | B | 306 | 72.241 | 31.636 | 40.842 | 1.00 | 10.07 | B |
| ATOM | 3914 | N | HIS | B | 307 | 70.436 | 30.351 | 41.228 | 1.00 | 7.61 | B |
| ATOM | 3915 | CA | HIS | B | 307 | 70.598 | 29.623 | 39.972 | 1.00 | 7.78 | B |
| ATOM | 3916 | CB | HIS | B | 307 | 69.495 | 28.569 | 39.811 | 1.00 | 7.06 | B |
| ATOM | 3917 | CG | HIS | B | 307 | 69.414 | 27.598 | 40.950 | 1.00 | 7.95 | B |
| ATOM | 3918 | CD2 | HIS | B | 307 | 68.347 | 27.046 | 41.577 | 1.00 | 8.54 | B |
| ATOM | 3919 | ND1 | HIS | B | 307 | 70.532 | 27.057 | 41.549 | 1.00 | 9.97 | B |
| ATOM | 3920 | CE1 | HIS | B | 307 | 70.157 | 26.214 | 42.495 | 1.00 | 9.57 | B |
| ATOM | 3921 | NE2 | HIS | B | 307 | 68.837 | 26.187 | 42.531 | 1.00 | 9.41 | B |
| ATOM | 3922 | C | HIS | B | 307 | 70.540 | 30.619 | 38.818 | 1.00 | 6.60 | B |
| ATOM | 3923 | O | HIS | B | 307 | 71.338 | 30.551 | 37.878 | 1.00 | 10.13 | B |
| ATOM | 3924 | N | LEU | B | 308 | 69.584 | 31.539 | 38.895 | 1.00 | 8.24 | B |
| ATOM | 3925 | CA | LEU | B | 308 | 69.421 | 32.566 | 37.875 | 1.00 | 9.36 | B |
| ATOM | 3926 | CB | LEU | B | 308 | 68.185 | 33.418 | 38.177 | 1.00 | 11.02 | B |
| ATOM | 3927 | CG | LEU | B | 308 | 66.838 | 32.790 | 37.804 | 1.00 | 11.82 | B |
| ATOM | 3928 | CD1 | LEU | B | 308 | 65.699 | 33.580 | 38.437 | 1.00 | 11.51 | B |
| ATOM | 3929 | CD2 | LEU | B | 308 | 66.694 | 32.766 | 36.287 | 1.00 | 11.00 | B |
| ATOM | 3930 | C | LEU | B | 308 | 70.651 | 33.462 | 37.794 | 1.00 | 10.02 | B |
| ATOM | 3931 | O | LEU | B | 308 | 71.168 | 33.722 | 36.711 | 1.00 | 11.77 | B |
| ATOM | 3932 | N | ALA | B | 309 | 71.128 | 33.932 | 38.941 | 1.00 | 10.08 | B |
| ATOM | 3933 | CA | ALA | B | 309 | 72.302 | 34.801 | 38.953 | 1.00 | 9.46 | B |
| ATOM | 3934 | CB | ALA | B | 309 | 72.626 | 35.212 | 40.386 | 1.00 | 13.55 | B |
| ATOM | 3935 | C | ALA | B | 309 | 73.518 | 34.121 | 38.315 | 1.00 | 9.19 | B |

TABLE 1-continued

| ATOM | 3936 | O   | ALA | B | 309 | 74.223 | 34.722 | 37.506 | 1.00 | 11.81 | B |
| --- | --- | --- | --- | --- | --- | --- | --- | --- | --- | --- | --- |
| ATOM | 3937 | N   | VAL | B | 310 | 73.769 | 32.874 | 38.691 | 1.00 | 8.85  | B |
| ATOM | 3938 | CA  | VAL | B | 310 | 74.893 | 32.126 | 38.146 | 1.00 | 9.84  | B |
| ATOM | 3939 | CB  | VAL | B | 310 | 75.058 | 30.783 | 38.874 | 1.00 | 9.88  | B |
| ATOM | 3940 | CG1 | VAL | B | 310 | 76.119 | 29.939 | 38.182 | 1.00 | 12.31 | B |
| ATOM | 3941 | CG2 | VAL | B | 310 | 75.447 | 31.034 | 40.328 | 1.00 | 9.44  | B |
| ATOM | 3942 | C   | VAL | B | 310 | 74.715 | 31.865 | 36.649 | 1.00 | 8.84  | B |
| ATOM | 3943 | O   | VAL | B | 310 | 75.632 | 32.085 | 35.852 | 1.00 | 11.09 | B |
| ATOM | 3944 | N   | GLY | B | 311 | 73.533 | 31.398 | 36.266 | 1.00 | 9.94  | B |
| ATOM | 3945 | CA  | GLY | B | 311 | 73.279 | 31.119 | 34.863 | 1.00 | 9.44  | B |
| ATOM | 3946 | C   | GLY | B | 311 | 73.538 | 32.293 | 33.941 | 1.00 | 9.57  | B |
| ATOM | 3947 | O   | GLY | B | 311 | 74.132 | 32.131 | 32.876 | 1.00 | 12.62 | B |
| ATOM | 3948 | N   | PHE | B | 312 | 73.089 | 33.482 | 34.330 | 1.00 | 9.82  | B |
| ATOM | 3949 | CA  | PHE | B | 312 | 73.298 | 34.661 | 33.502 | 1.00 | 10.22 | B |
| ATOM | 3950 | CB  | PHE | B | 312 | 72.262 | 35.735 | 33.852 | 1.00 | 10.84 | B |
| ATOM | 3951 | CG  | PHE | B | 312 | 70.918 | 35.501 | 33.219 | 1.00 | 13.46 | B |
| ATOM | 3952 | CD1 | PHE | B | 312 | 70.669 | 35.923 | 31.924 | 1.00 | 16.17 | B |
| ATOM | 3953 | CD2 | PHE | B | 312 | 69.918 | 34.835 | 33.906 | 1.00 | 13.89 | B |
| ATOM | 3954 | CE1 | PHE | B | 312 | 69.443 | 35.685 | 31.319 | 1.00 | 17.03 | B |
| ATOM | 3955 | CE2 | PHE | B | 312 | 68.691 | 34.594 | 33.309 | 1.00 | 16.20 | B |
| ATOM | 3956 | CZ  | PHE | B | 312 | 68.456 | 35.020 | 32.012 | 1.00 | 14.78 | B |
| ATOM | 3957 | C   | PHE | B | 312 | 74.715 | 35.223 | 33.613 | 1.00 | 10.33 | B |
| ATOM | 3958 | O   | PHE | B | 312 | 75.270 | 35.721 | 32.633 | 1.00 | 12.29 | B |
| ATOM | 3959 | N   | LYS | B | 313 | 75.312 | 35.124 | 34.795 | 1.00 | 10.83 | B |
| ATOM | 3960 | CA  | LYS | B | 313 | 76.668 | 35.627 | 34.991 | 1.00 | 11.41 | B |
| ATOM | 3961 | CB  | LYS | B | 313 | 77.081 | 35.448 | 36.453 | 1.00 | 14.45 | B |
| ATOM | 3962 | CG  | LYS | B | 313 | 78.577 | 35.503 | 36.681 | 1.00 | 21.16 | B |
| ATOM | 3963 | CD  | LYS | B | 313 | 79.062 | 34.278 | 37.455 | 1.00 | 25.23 | B |
| ATOM | 3964 | CE  | LYS | B | 313 | 80.584 | 34.213 | 37.510 | 1.00 | 26.04 | B |
| ATOM | 3965 | NZ  | LYS | B | 313 | 81.088 | 33.027 | 38.264 | 1.00 | 26.66 | B |
| ATOM | 3966 | C   | LYS | B | 313 | 77.677 | 34.915 | 34.090 | 1.00 | 10.58 | B |
| ATOM | 3967 | O   | LYS | B | 313 | 78.608 | 35.535 | 33.565 | 1.00 | 12.82 | B |
| ATOM | 3968 | N   | LEU | B | 314 | 77.484 | 33.613 | 33.905 | 1.00 | 11.34 | B |
| ATOM | 3969 | CA  | LEU | B | 314 | 78.401 | 32.824 | 33.093 | 1.00 | 12.08 | B |
| ATOM | 3970 | CB  | LEU | B | 314 | 78.090 | 31.335 | 33.246 | 1.00 | 13.36 | B |
| ATOM | 3971 | CG  | LEU | B | 314 | 78.323 | 30.821 | 34.669 | 1.00 | 14.77 | B |
| ATOM | 3972 | CD1 | LEU | B | 314 | 78.053 | 29.325 | 34.729 | 1.00 | 15.52 | B |
| ATOM | 3973 | CD2 | LEU | B | 314 | 79.762 | 31.119 | 35.097 | 1.00 | 14.52 | B |
| ATOM | 3974 | C   | LEU | B | 314 | 78.419 | 33.220 | 31.623 | 1.00 | 11.72 | B |
| ATOM | 3975 | O   | LEU | B | 314 | 79.347 | 32.867 | 30.897 | 1.00 | 13.02 | B |
| ATOM | 3976 | N   | LEU | B | 315 | 77.406 | 33.960 | 31.182 | 1.00 | 12.36 | B |
| ATOM | 3977 | CA  | LEU | B | 315 | 77.366 | 34.413 | 29.791 | 1.00 | 12.72 | B |
| ATOM | 3978 | CB  | LEU | B | 315 | 76.039 | 35.121 | 29.489 | 1.00 | 15.01 | B |
| ATOM | 3979 | CG  | LEU | B | 315 | 74.762 | 34.275 | 29.535 | 1.00 | 15.56 | B |
| ATOM | 3980 | CD1 | LEU | B | 315 | 73.532 | 35.178 | 29.560 | 1.00 | 14.05 | B |
| ATOM | 3981 | CD2 | LEU | B | 315 | 74.726 | 33.353 | 28.327 | 1.00 | 14.45 | B |
| ATOM | 3982 | C   | LEU | B | 315 | 78.511 | 35.390 | 29.525 | 1.00 | 13.88 | B |
| ATOM | 3983 | O   | LEU | B | 315 | 78.868 | 35.632 | 28.374 | 1.00 | 15.43 | B |
| ATOM | 3984 | N   | GLN | B | 316 | 79.088 | 35.931 | 30.597 | 1.00 | 13.99 | B |
| ATOM | 3985 | CA  | GLN | B | 316 | 80.172 | 36.911 | 30.494 | 1.00 | 14.97 | B |
| ATOM | 3986 | CB  | GLN | B | 316 | 80.116 | 37.873 | 31.683 | 1.00 | 17.02 | B |
| ATOM | 3987 | CG  | GLN | B | 316 | 78.831 | 38.682 | 31.760 | 1.00 | 20.82 | B |
| ATOM | 3988 | CD  | GLN | B | 316 | 78.676 | 39.650 | 30.598 | 1.00 | 24.71 | B |
| ATOM | 3989 | OE1 | GLN | B | 316 | 77.681 | 40.369 | 30.501 | 1.00 | 30.41 | B |
| ATOM | 3990 | NE2 | GLN | B | 316 | 79.663 | 39.675 | 29.710 | 1.00 | 26.01 | B |
| ATOM | 3991 | C   | GLN | B | 316 | 81.580 | 36.336 | 30.387 | 1.00 | 13.92 | B |
| ATOM | 3992 | O   | GLN | B | 316 | 82.541 | 37.078 | 30.163 | 1.00 | 15.76 | B |
| ATOM | 3993 | N   | GLU | B | 317 | 81.722 | 35.027 | 30.549 | 1.00 | 13.60 | B |
| ATOM | 3994 | CA  | GLU | B | 317 | 83.045 | 34.444 | 30.446 | 1.00 | 13.06 | B |
| ATOM | 3995 | CB  | GLU | B | 317 | 83.086 | 33.062 | 31.111 | 1.00 | 13.46 | B |
| ATOM | 3996 | CG  | GLU | B | 317 | 82.845 | 33.149 | 32.623 | 1.00 | 16.79 | B |
| ATOM | 3997 | CD  | GLU | B | 317 | 83.437 | 31.990 | 33.418 | 1.00 | 17.51 | B |
| ATOM | 3998 | OE1 | GLU | B | 317 | 83.984 | 31.049 | 32.809 | 1.00 | 21.08 | B |
| ATOM | 3999 | OE2 | GLU | B | 317 | 83.351 | 32.026 | 34.668 | 1.00 | 22.18 | B |
| ATOM | 4000 | C   | GLU | B | 317 | 83.454 | 34.387 | 28.979 | 1.00 | 11.87 | B |
| ATOM | 4001 | O   | GLU | B | 317 | 82.631 | 34.592 | 28.085 | 1.00 | 12.62 | B |
| ATOM | 4002 | N   | GLU | B | 318 | 84.734 | 34.135 | 28.742 | 1.00 | 13.06 | B |
| ATOM | 4003 | CA  | GLU | B | 318 | 85.294 | 34.092 | 27.393 | 1.00 | 12.91 | B |
| ATOM | 4004 | CB  | GLU | B | 318 | 86.749 | 33.623 | 27.482 | 1.00 | 14.54 | B |
| ATOM | 4005 | CG  | GLU | B | 318 | 87.510 | 33.570 | 26.161 | 1.00 | 19.93 | B |
| ATOM | 4006 | CD  | GLU | B | 318 | 87.740 | 34.936 | 25.539 | 1.00 | 23.14 | B |
| ATOM | 4007 | OE1 | GLU | B | 318 | 87.625 | 35.955 | 26.255 | 1.00 | 25.31 | B |
| ATOM | 4008 | OE2 | GLU | B | 318 | 88.054 | 34.989 | 24.330 | 1.00 | 25.14 | B |
| ATOM | 4009 | C   | GLU | B | 318 | 84.521 | 33.215 | 26.410 | 1.00 | 12.40 | B |
| ATOM | 4010 | O   | GLU | B | 318 | 84.414 | 32.003 | 26.602 | 1.00 | 12.87 | B |
| ATOM | 4011 | N   | HIS | B | 319 | 84.005 | 33.847 | 25.353 | 1.00 | 13.22 | B |
| ATOM | 4012 | CA  | HIS | B | 319 | 83.245 | 33.177 | 24.296 | 1.00 | 14.33 | B |
| ATOM | 4013 | CB  | HIS | B | 319 | 84.179 | 32.306 | 23.449 | 1.00 | 17.18 | B |
| ATOM | 4014 | CG  | HIS | B | 319 | 84.908 | 33.070 | 22.386 | 1.00 | 21.38 | B |

TABLE 1-continued

| ATOM | 4015 | CD2 | HIS | B | 319 | 86.167 | 33.568 | 22.349 | 1.00 | 21.55 | B |
|------|------|-----|-----|---|-----|--------|--------|--------|------|-------|---|
| ATOM | 4016 | ND1 | HIS | B | 319 | 84.306 | 33.462 | 21.209 | 1.00 | 23.34 | B |
| ATOM | 4017 | CE1 | HIS | B | 319 | 85.163 | 34.170 | 20.493 | 1.00 | 23.04 | B |
| ATOM | 4018 | NE2 | HIS | B | 319 | 86.299 | 34.249 | 21.163 | 1.00 | 23.31 | B |
| ATOM | 4019 | C | HIS | B | 319 | 82.070 | 32.353 | 24.798 | 1.00 | 12.69 | B |
| ATOM | 4020 | O | HIS | B | 319 | 81.772 | 31.282 | 24.264 | 1.00 | 14.01 | B |
| ATOM | 4021 | N | CYS | B | 320 | 81.383 | 32.880 | 25.807 | 1.00 | 12.48 | B |
| ATOM | 4022 | CA | CYS | B | 320 | 80.230 | 32.202 | 26.398 | 1.00 | 12.79 | B |
| ATOM | 4023 | CB | CYS | B | 320 | 80.416 | 32.068 | 27.906 | 1.00 | 13.70 | B |
| ATOM | 4024 | SG | CYS | B | 320 | 81.609 | 30.844 | 28.403 | 1.00 | 15.20 | B |
| ATOM | 4025 | C | CYS | B | 320 | 78.887 | 32.881 | 26.184 | 1.00 | 12.28 | B |
| ATOM | 4026 | O | CYS | B | 320 | 77.869 | 32.364 | 26.642 | 1.00 | 12.58 | B |
| ATOM | 4027 | N | ASP | B | 321 | 78.860 | 34.027 | 25.510 | 1.00 | 12.99 | B |
| ATOM | 4028 | CA | ASP | B | 321 | 77.586 | 34.724 | 25.343 | 1.00 | 13.34 | B |
| ATOM | 4029 | CB | ASP | B | 321 | 77.810 | 36.224 | 25.156 | 1.00 | 16.45 | B |
| ATOM | 4030 | CG | ASP | B | 321 | 76.513 | 37.021 | 25.238 | 1.00 | 18.42 | B |
| ATOM | 4031 | OD1 | ASP | B | 321 | 75.454 | 36.431 | 25.556 | 1.00 | 18.37 | B |
| ATOM | 4032 | OD2 | ASP | B | 321 | 76.554 | 38.244 | 24.990 | 1.00 | 20.55 | B |
| ATOM | 4033 | C | ASP | B | 321 | 76.727 | 34.187 | 24.211 | 1.00 | 11.89 | B |
| ATOM | 4034 | O | ASP | B | 321 | 76.766 | 34.674 | 23.078 | 1.00 | 12.81 | B |
| ATOM | 4035 | N | ILE | B | 322 | 75.923 | 33.188 | 24.539 | 1.00 | 12.38 | B |
| ATOM | 4036 | CA | ILE | B | 322 | 75.055 | 32.577 | 23.551 | 1.00 | 12.72 | B |
| ATOM | 4037 | CB | ILE | B | 322 | 74.478 | 31.254 | 24.080 | 1.00 | 13.28 | B |
| ATOM | 4038 | CG2 | ILE | B | 322 | 75.615 | 30.263 | 24.320 | 1.00 | 12.30 | B |
| ATOM | 4039 | CG1 | ILE | B | 322 | 73.713 | 31.487 | 25.381 | 1.00 | 15.33 | B |
| ATOM | 4040 | CD1 | ILE | B | 322 | 72.842 | 30.316 | 25.768 | 1.00 | 17.45 | B |
| ATOM | 4041 | C | ILE | B | 322 | 73.911 | 33.484 | 23.101 | 1.00 | 12.48 | B |
| ATOM | 4042 | O | ILE | B | 322 | 73.214 | 33.166 | 22.136 | 1.00 | 14.99 | B |
| ATOM | 4043 | N | PHE | B | 323 | 73.709 | 34.609 | 23.781 | 1.00 | 10.92 | B |
| ATOM | 4044 | CA | PHE | B | 323 | 72.620 | 35.514 | 23.397 | 1.00 | 11.83 | B |
| ATOM | 4045 | CB | PHE | B | 323 | 71.783 | 35.896 | 24.622 | 1.00 | 12.94 | B |
| ATOM | 4046 | CG | PHE | B | 323 | 71.193 | 34.722 | 25.349 | 1.00 | 12.55 | B |
| ATOM | 4047 | CD1 | PHE | B | 323 | 70.560 | 33.706 | 24.658 | 1.00 | 14.31 | B |
| ATOM | 4048 | CD2 | PHE | B | 323 | 71.247 | 34.652 | 26.733 | 1.00 | 15.08 | B |
| ATOM | 4049 | CE1 | PHE | B | 323 | 69.989 | 32.639 | 25.333 | 1.00 | 15.13 | B |
| ATOM | 4050 | CE2 | PHE | B | 323 | 70.679 | 33.591 | 27.412 | 1.00 | 14.23 | B |
| ATOM | 4051 | CZ | PHE | B | 323 | 70.049 | 32.585 | 26.712 | 1.00 | 16.33 | B |
| ATOM | 4052 | C | PHE | B | 323 | 73.139 | 36.781 | 22.731 | 1.00 | 12.57 | B |
| ATOM | 4053 | O | PHE | B | 323 | 72.388 | 37.738 | 22.516 | 1.00 | 14.13 | B |
| ATOM | 4054 | N | MET | B | 324 | 74.422 | 36.773 | 22.389 | 1.00 | 13.99 | B |
| ATOM | 4055 | CA | MET | B | 324 | 75.071 | 37.922 | 21.775 | 1.00 | 16.76 | B |
| ATOM | 4056 | CB | MET | B | 324 | 76.524 | 37.573 | 21.456 | 1.00 | 19.95 | B |
| ATOM | 4057 | CG | MET | B | 324 | 77.282 | 38.672 | 20.747 | 1.00 | 25.77 | B |
| ATOM | 4058 | SD | MET | B | 324 | 78.987 | 38.188 | 20.483 | 1.00 | 27.92 | B |
| ATOM | 4059 | CE | MET | B | 324 | 78.779 | 36.913 | 19.248 | 1.00 | 28.30 | B |
| ATOM | 4060 | C | MET | B | 324 | 74.396 | 38.458 | 20.523 | 1.00 | 16.65 | B |
| ATOM | 4061 | O | MET | B | 324 | 74.339 | 39.672 | 20.310 | 1.00 | 19.06 | B |
| ATOM | 4062 | N | ASN | B | 325 | 73.875 | 37.564 | 19.696 | 1.00 | 16.12 | B |
| ATOM | 4063 | CA | ASN | B | 325 | 73.252 | 37.994 | 18.458 | 1.00 | 18.27 | B |
| ATOM | 4064 | CB | ASN | B | 325 | 73.684 | 37.059 | 17.331 | 1.00 | 18.26 | B |
| ATOM | 4065 | CG | ASN | B | 325 | 75.169 | 37.177 | 17.036 | 1.00 | 19.25 | B |
| ATOM | 4066 | OD1 | ASN | B | 325 | 75.709 | 38.285 | 16.988 | 1.00 | 18.80 | B |
| ATOM | 4067 | ND2 | ASN | B | 325 | 75.836 | 36.046 | 16.838 | 1.00 | 18.97 | B |
| ATOM | 4068 | C | ASN | B | 325 | 71.745 | 38.183 | 18.480 | 1.00 | 18.60 | B |
| ATOM | 4069 | O | ASN | B | 325 | 71.090 | 38.170 | 17.433 | 1.00 | 21.64 | B |
| ATOM | 4070 | N | LEU | B | 326 | 71.188 | 38.363 | 19.672 | 1.00 | 17.83 | B |
| ATOM | 4071 | CA | LEU | B | 326 | 69.758 | 38.615 | 19.784 | 1.00 | 18.05 | B |
| ATOM | 4072 | CB | LEU | B | 326 | 69.155 | 37.977 | 21.044 | 1.00 | 17.78 | B |
| ATOM | 4073 | CG | LEU | B | 326 | 69.411 | 36.526 | 21.460 | 1.00 | 22.39 | B |
| ATOM | 4074 | CD1 | LEU | B | 326 | 68.223 | 36.068 | 22.311 | 1.00 | 18.54 | B |
| ATOM | 4075 | CD2 | LEU | B | 326 | 69.592 | 35.620 | 20.253 | 1.00 | 19.72 | B |
| ATOM | 4076 | C | LEU | B | 326 | 69.622 | 40.128 | 19.906 | 1.00 | 17.08 | B |
| ATOM | 4077 | O | LEU | B | 326 | 70.551 | 40.804 | 20.356 | 1.00 | 18.70 | B |
| ATOM | 4078 | N | THR | B | 327 | 68.476 | 40.664 | 19.504 | 1.00 | 16.57 | B |
| ATOM | 4079 | CA | THR | B | 327 | 68.244 | 42.098 | 19.614 | 1.00 | 17.15 | B |
| ATOM | 4080 | CB | THR | B | 327 | 66.973 | 42.527 | 18.865 | 1.00 | 18.05 | B |
| ATOM | 4081 | OG1 | THR | B | 327 | 65.829 | 41.938 | 19.494 | 1.00 | 18.55 | B |
| ATOM | 4082 | CG2 | THR | B | 327 | 67.026 | 42.070 | 17.412 | 1.00 | 19.49 | B |
| ATOM | 4083 | C | THR | B | 327 | 68.035 | 42.409 | 21.093 | 1.00 | 17.29 | B |
| ATOM | 4084 | O | THR | B | 327 | 67.818 | 41.497 | 21.895 | 1.00 | 16.82 | B |
| ATOM | 4085 | N | LYS | B | 328 | 68.090 | 43.687 | 21.452 | 1.00 | 18.57 | B |
| ATOM | 4086 | CA | LYS | B | 328 | 67.887 | 44.085 | 22.840 | 1.00 | 18.80 | B |
| ATOM | 4087 | CB | LYS | B | 328 | 67.995 | 45.608 | 22.984 | 1.00 | 20.11 | B |
| ATOM | 4088 | CG | LYS | B | 328 | 67.709 | 46.132 | 24.388 | 1.00 | 21.15 | B |
| ATOM | 4089 | CD | LYS | B | 328 | 68.653 | 45.524 | 25.419 | 1.00 | 19.48 | B |
| ATOM | 4090 | CE | LYS | B | 328 | 68.493 | 46.184 | 26.786 | 1.00 | 21.73 | B |
| ATOM | 4091 | NZ | LYS | B | 328 | 69.392 | 45.574 | 27.810 | 1.00 | 22.39 | B |
| ATOM | 4092 | C | LYS | B | 328 | 66.508 | 43.619 | 23.287 | 1.00 | 17.93 | B |
| ATOM | 4093 | O | LYS | B | 328 | 66.353 | 43.069 | 24.378 | 1.00 | 18.23 | B |

TABLE 1-continued

| ATOM | 4094 | N | LYS | B | 329 | 65.508 | 43.836 | 22.439 | 1.00 | 17.61 | B |
|---|---|---|---|---|---|---|---|---|---|---|---|
| ATOM | 4095 | CA | LYS | B | 329 | 64.146 | 43.427 | 22.754 | 1.00 | 18.07 | B |
| ATOM | 4096 | CB | LYS | B | 329 | 63.193 | 43.820 | 21.621 | 1.00 | 21.51 | B |
| ATOM | 4097 | CG | LYS | B | 329 | 61.800 | 43.220 | 21.739 | 1.00 | 24.23 | B |
| ATOM | 4098 | CD | LYS | B | 329 | 61.149 | 43.568 | 23.067 | 1.00 | 26.69 | B |
| ATOM | 4099 | CE | LYS | B | 329 | 59.760 | 42.947 | 23.193 | 1.00 | 27.55 | B |
| ATOM | 4100 | NZ | LYS | B | 329 | 58.804 | 43.458 | 22.166 | 1.00 | 28.85 | B |
| ATOM | 4101 | C | LYS | B | 329 | 64.057 | 41.927 | 22.997 | 1.00 | 15.68 | B |
| ATOM | 4102 | O | LYS | B | 329 | 63.385 | 41.479 | 23.924 | 1.00 | 16.02 | B |
| ATOM | 4103 | N | GLN | B | 330 | 64.737 | 41.146 | 22.166 | 1.00 | 14.21 | B |
| ATOM | 4104 | CA | GLN | B | 330 | 64.707 | 39.702 | 22.333 | 1.00 | 12.93 | B |
| ATOM | 4105 | CB | GLN | B | 330 | 65.383 | 39.018 | 21.149 | 1.00 | 14.31 | B |
| ATOM | 4106 | CG | GLN | B | 330 | 64.601 | 39.172 | 19.860 | 1.00 | 16.24 | B |
| ATOM | 4107 | CD | GLN | B | 330 | 65.317 | 38.557 | 18.686 | 1.00 | 17.61 | B |
| ATOM | 4108 | OE1 | GLN | B | 330 | 66.520 | 38.735 | 18.522 | 1.00 | 17.18 | B |
| ATOM | 4109 | NE2 | GLN | B | 330 | 64.576 | 37.843 | 17.849 | 1.00 | 22.41 | B |
| ATOM | 4110 | C | GLN | B | 330 | 65.384 | 39.291 | 23.631 | 1.00 | 12.56 | B |
| ATOM | 4111 | O | GLN | B | 330 | 64.878 | 38.424 | 24.346 | 1.00 | 14.49 | B |
| ATOM | 4112 | N | ARG | B | 331 | 66.518 | 39.916 | 23.928 | 1.00 | 13.05 | B |
| ATOM | 4113 | CA | ARG | B | 331 | 67.258 | 39.617 | 25.153 | 1.00 | 11.28 | B |
| ATOM | 4114 | CB | ARG | B | 331 | 68.618 | 40.322 | 25.140 | 1.00 | 12.67 | B |
| ATOM | 4115 | CG | ARG | B | 331 | 69.620 | 39.631 | 24.221 | 1.00 | 14.32 | B |
| ATOM | 4116 | CD | ARG | B | 331 | 71.005 | 40.267 | 24.238 | 1.00 | 17.39 | B |
| ATOM | 4117 | NE | ARG | B | 331 | 71.068 | 41.512 | 23.474 | 1.00 | 21.56 | B |
| ATOM | 4118 | CZ | ARG | B | 331 | 71.232 | 42.712 | 24.019 | 1.00 | 23.04 | B |
| ATOM | 4119 | NH1 | ARG | B | 331 | 71.348 | 42.830 | 25.334 | 1.00 | 23.04 | B |
| ATOM | 4120 | NH2 | ARG | B | 331 | 71.295 | 43.790 | 23.248 | 1.00 | 24.96 | B |
| ATOM | 4121 | C | ARG | B | 331 | 66.470 | 40.000 | 26.401 | 1.00 | 12.65 | B |
| ATOM | 4122 | O | ARG | B | 331 | 66.478 | 39.264 | 27.385 | 1.00 | 14.69 | B |
| ATOM | 4123 | N | GLN | B | 332 | 65.782 | 41.138 | 26.361 | 1.00 | 12.97 | B |
| ATOM | 4124 | CA | GLN | B | 332 | 64.989 | 41.565 | 27.514 | 1.00 | 14.99 | B |
| ATOM | 4125 | CB | GLN | B | 332 | 64.456 | 42.983 | 27.312 | 1.00 | 18.01 | B |
| ATOM | 4126 | CG | GLN | B | 332 | 65.517 | 44.053 | 27.174 | 1.00 | 22.96 | B |
| ATOM | 4127 | CD | GLN | B | 332 | 64.922 | 45.400 | 26.789 | 1.00 | 25.86 | B |
| ATOM | 4128 | OE1 | GLN | B | 332 | 64.256 | 46.054 | 27.590 | 1.00 | 29.95 | B |
| ATOM | 4129 | NE2 | GLN | B | 332 | 65.152 | 45.811 | 25.550 | 1.00 | 29.01 | B |
| ATOM | 4130 | C | GLN | B | 332 | 63.809 | 40.629 | 27.733 | 1.00 | 13.63 | B |
| ATOM | 4131 | O | GLN | B | 332 | 63.468 | 40.297 | 28.871 | 1.00 | 14.25 | B |
| ATOM | 4132 | N | THR | B | 333 | 63.171 | 40.218 | 26.643 | 1.00 | 13.54 | B |
| ATOM | 4133 | CA | THR | B | 333 | 62.030 | 39.322 | 26.736 | 1.00 | 14.24 | B |
| ATOM | 4134 | CB | THR | B | 333 | 61.333 | 39.164 | 25.377 | 1.00 | 16.89 | B |
| ATOM | 4135 | OG1 | THR | B | 333 | 60.849 | 40.441 | 24.942 | 1.00 | 19.33 | B |
| ATOM | 4136 | CG2 | THR | B | 333 | 60.168 | 38.195 | 25.489 | 1.00 | 18.79 | B |
| ATOM | 4137 | C | THR | B | 333 | 62.453 | 37.945 | 27.233 | 1.00 | 11.97 | B |
| ATOM | 4138 | O | THR | B | 333 | 61.807 | 37.370 | 28.101 | 1.00 | 13.23 | B |
| ATOM | 4139 | N | LEU | B | 334 | 63.543 | 37.418 | 26.689 | 1.00 | 12.75 | B |
| ATOM | 4140 | CA | LEU | B | 334 | 64.012 | 36.106 | 27.110 | 1.00 | 12.28 | B |
| ATOM | 4141 | CB | LEU | B | 334 | 65.231 | 35.681 | 26.284 | 1.00 | 12.74 | B |
| ATOM | 4142 | CG | LEU | B | 334 | 65.871 | 34.354 | 26.714 | 1.00 | 16.14 | B |
| ATOM | 4143 | CD1 | LEU | B | 334 | 66.292 | 33.549 | 25.491 | 1.00 | 15.44 | B |
| ATOM | 4144 | CD2 | LEU | B | 334 | 67.059 | 34.639 | 27.624 | 1.00 | 16.21 | B |
| ATOM | 4145 | C | LEU | B | 334 | 64.359 | 36.103 | 28.596 | 1.00 | 11.81 | B |
| ATOM | 4146 | O | LEU | B | 334 | 63.983 | 35.186 | 29.324 | 1.00 | 12.70 | B |
| ATOM | 4147 | N | ARG | B | 335 | 65.058 | 37.137 | 29.049 | 1.00 | 12.68 | B |
| ATOM | 4148 | CA | ARG | B | 335 | 65.442 | 37.208 | 30.452 | 1.00 | 12.57 | B |
| ATOM | 4149 | CB | ARG | B | 335 | 66.328 | 38.427 | 30.707 | 1.00 | 14.43 | B |
| ATOM | 4150 | CG | ARG | B | 335 | 66.859 | 38.521 | 32.137 | 1.00 | 15.50 | B |
| ATOM | 4151 | CD | ARG | B | 335 | 67.902 | 39.626 | 32.257 | 1.00 | 18.20 | B |
| ATOM | 4152 | NE | ARG | B | 335 | 68.093 | 40.075 | 33.636 | 1.00 | 16.42 | B |
| ATOM | 4153 | CZ | ARG | B | 335 | 68.747 | 39.401 | 34.575 | 1.00 | 16.13 | B |
| ATOM | 4154 | NH1 | ARG | B | 335 | 69.296 | 38.221 | 34.305 | 1.00 | 17.56 | B |
| ATOM | 4155 | NH2 | ARG | B | 335 | 68.856 | 39.915 | 35.794 | 1.00 | 16.59 | B |
| ATOM | 4156 | C | ARG | B | 335 | 64.221 | 37.245 | 31.363 | 1.00 | 12.91 | B |
| ATOM | 4157 | O | ARG | B | 335 | 64.192 | 36.570 | 32.389 | 1.00 | 13.50 | B |
| ATOM | 4158 | N | LYS | B | 336 | 63.214 | 38.032 | 30.992 | 1.00 | 13.24 | B |
| ATOM | 4159 | CA | LYS | B | 336 | 61.996 | 38.124 | 31.794 | 1.00 | 13.73 | B |
| ATOM | 4160 | CB | LYS | B | 336 | 61.021 | 39.125 | 31.157 | 1.00 | 17.57 | B |
| ATOM | 4161 | CG | LYS | B | 336 | 59.744 | 39.354 | 31.949 | 1.00 | 21.59 | B |
| ATOM | 4162 | CD | LYS | B | 336 | 58.777 | 40.271 | 31.205 | 1.00 | 23.84 | B |
| ATOM | 4163 | CE | LYS | B | 336 | 59.409 | 41.622 | 30.885 | 1.00 | 26.40 | B |
| ATOM | 4164 | NZ | LYS | B | 336 | 58.466 | 42.531 | 30.156 | 1.00 | 29.30 | B |
| ATOM | 4165 | C | LYS | B | 336 | 61.323 | 36.760 | 31.924 | 1.00 | 12.56 | B |
| ATOM | 4166 | O | LYS | B | 336 | 60.849 | 36.388 | 33.000 | 1.00 | 14.48 | B |
| ATOM | 4167 | N | MET | B | 337 | 61.294 | 36.010 | 30.828 | 1.00 | 12.18 | B |
| ATOM | 4168 | CA | MET | B | 337 | 60.675 | 34.689 | 30.826 | 1.00 | 12.03 | B |
| ATOM | 4169 | CB | MET | B | 337 | 60.472 | 34.199 | 29.389 | 1.00 | 14.61 | B |
| ATOM | 4170 | CG | MET | B | 337 | 59.546 | 35.084 | 28.565 | 1.00 | 14.43 | B |
| ATOM | 4171 | SD | MET | B | 337 | 59.141 | 34.333 | 26.971 | 1.00 | 20.06 | B |
| ATOM | 4172 | CE | MET | B | 337 | 60.653 | 34.602 | 26.072 | 1.00 | 16.67 | B |

TABLE 1-continued

| | | | | | | | | | | |
|---|---|---|---|---|---|---|---|---|---|---|
| ATOM | 4173 | C | MET | B | 337 | 61.488 | 33.667 | 31.604 | 1.00 | 10.79 | B |
| ATOM | 4174 | O | MET | B | 337 | 60.925 | 32.857 | 32.339 | 1.00 | 11.96 | B |
| ATOM | 4175 | N | VAL | B | 338 | 62.810 | 33.705 | 31.444 | 1.00 | 11.38 | B |
| ATOM | 4176 | CA | VAL | B | 338 | 63.684 | 32.765 | 32.145 | 1.00 | 10.26 | B |
| ATOM | 4177 | CB | VAL | B | 338 | 65.149 | 32.902 | 31.674 | 1.00 | 11.09 | B |
| ATOM | 4178 | CG1 | VAL | B | 338 | 66.063 | 32.056 | 32.553 | 1.00 | 10.25 | B |
| ATOM | 4179 | CG2 | VAL | B | 338 | 65.261 | 32.447 | 30.224 | 1.00 | 13.39 | B |
| ATOM | 4180 | C | VAL | B | 338 | 63.607 | 32.972 | 33.651 | 1.00 | 10.54 | B |
| ATOM | 4181 | O | VAL | B | 338 | 63.543 | 32.009 | 34.415 | 1.00 | 10.69 | B |
| ATOM | 4182 | N | ILE | B | 339 | 63.619 | 34.230 | 34.080 | 1.00 | 11.45 | B |
| ATOM | 4183 | CA | ILE | B | 339 | 63.508 | 34.523 | 35.503 | 1.00 | 12.36 | B |
| ATOM | 4184 | CB | ILE | B | 339 | 63.567 | 36.044 | 35.759 | 1.00 | 13.62 | B |
| ATOM | 4185 | CG2 | ILE | B | 339 | 63.068 | 36.369 | 37.163 | 1.00 | 14.22 | B |
| ATOM | 4186 | CG1 | ILE | B | 339 | 65.003 | 36.531 | 35.559 | 1.00 | 12.80 | B |
| ATOM | 4187 | CD1 | ILE | B | 339 | 65.143 | 38.036 | 35.518 | 1.00 | 14.30 | B |
| ATOM | 4188 | C | ILE | B | 339 | 62.182 | 33.962 | 36.010 | 1.00 | 11.93 | B |
| ATOM | 4189 | O | ILE | B | 339 | 62.130 | 33.306 | 37.045 | 1.00 | 13.25 | B |
| ATOM | 4190 | N | ASP | B | 340 | 61.109 | 34.194 | 35.262 | 1.00 | 12.17 | B |
| ATOM | 4191 | CA | ASP | B | 340 | 59.796 | 33.701 | 35.662 | 1.00 | 14.63 | B |
| ATOM | 4192 | CB | ASP | B | 340 | 58.750 | 34.203 | 34.659 | 1.00 | 18.60 | B |
| ATOM | 4193 | CG | ASP | B | 340 | 57.332 | 33.858 | 35.059 | 1.00 | 24.99 | B |
| ATOM | 4194 | OD1 | ASP | B | 340 | 56.412 | 34.613 | 34.667 | 1.00 | 27.67 | B |
| ATOM | 4195 | OD2 | ASP | B | 340 | 57.129 | 32.835 | 35.748 | 1.00 | 29.69 | B |
| ATOM | 4196 | C | ASP | B | 340 | 59.763 | 32.170 | 35.773 | 1.00 | 13.41 | B |
| ATOM | 4197 | O | ASP | B | 340 | 59.252 | 31.619 | 36.749 | 1.00 | 15.37 | B |
| ATOM | 4198 | N | MET | B | 341 | 60.324 | 31.482 | 34.784 | 1.00 | 13.28 | B |
| ATOM | 4199 | CA | MET | B | 341 | 60.335 | 30.024 | 34.798 | 1.00 | 12.36 | B |
| ATOM | 4200 | CB | MET | B | 341 | 60.776 | 29.492 | 33.439 | 1.00 | 13.00 | B |
| ATOM | 4201 | CG | MET | B | 341 | 59.742 | 29.763 | 32.361 | 1.00 | 13.75 | B |
| ATOM | 4202 | SD | MET | B | 341 | 60.183 | 28.997 | 30.802 | 1.00 | 18.05 | B |
| ATOM | 4203 | CE | MET | B | 341 | 61.110 | 30.308 | 30.018 | 1.00 | 18.82 | B |
| ATOM | 4204 | C | MET | B | 341 | 61.191 | 29.405 | 35.895 | 1.00 | 10.99 | B |
| ATOM | 4205 | O | MET | B | 341 | 60.787 | 28.429 | 36.511 | 1.00 | 12.88 | B |
| ATOM | 4206 | N | VAL | B | 342 | 62.372 | 29.959 | 36.144 | 1.00 | 10.39 | B |
| ATOM | 4207 | CA | VAL | B | 342 | 63.223 | 29.387 | 37.184 | 1.00 | 9.91 | B |
| ATOM | 4208 | CB | VAL | B | 342 | 64.674 | 29.935 | 37.093 | 1.00 | 10.89 | B |
| ATOM | 4209 | CG1 | VAL | B | 342 | 65.535 | 29.359 | 38.232 | 1.00 | 10.35 | B |
| ATOM | 4210 | CG2 | VAL | B | 342 | 65.273 | 29.548 | 35.739 | 1.00 | 7.84 | B |
| ATOM | 4211 | C | VAL | B | 342 | 62.647 | 29.640 | 38.572 | 1.00 | 10.51 | B |
| ATOM | 4212 | O | VAL | B | 342 | 62.687 | 28.758 | 39.434 | 1.00 | 12.03 | B |
| ATOM | 4213 | N | LEU | B | 343 | 62.106 | 30.832 | 38.805 | 1.00 | 11.15 | B |
| ATOM | 4214 | CA | LEU | B | 343 | 61.520 | 31.115 | 40.111 | 1.00 | 13.09 | B |
| ATOM | 4215 | CB | LEU | B | 343 | 61.106 | 32.583 | 40.211 | 1.00 | 14.49 | B |
| ATOM | 4216 | CG | LEU | B | 343 | 62.254 | 33.585 | 40.347 | 1.00 | 15.74 | B |
| ATOM | 4217 | CD1 | LEU | B | 343 | 61.690 | 34.995 | 40.349 | 1.00 | 17.13 | B |
| ATOM | 4218 | CD2 | LEU | B | 343 | 63.032 | 33.315 | 41.636 | 1.00 | 17.13 | B |
| ATOM | 4219 | C | LEU | B | 343 | 60.309 | 30.215 | 40.354 | 1.00 | 12.86 | B |
| ATOM | 4220 | O | LEU | B | 343 | 59.956 | 29.940 | 41.501 | 1.00 | 15.07 | B |
| ATOM | 4221 | N | ALA | B | 344 | 59.683 | 29.755 | 39.274 | 1.00 | 13.38 | B |
| ATOM | 4222 | CA | ALA | B | 344 | 58.521 | 28.878 | 39.377 | 1.00 | 15.55 | B |
| ATOM | 4223 | CB | ALA | B | 344 | 57.773 | 28.832 | 38.041 | 1.00 | 17.97 | B |
| ATOM | 4224 | C | ALA | B | 344 | 58.900 | 27.461 | 39.812 | 1.00 | 16.01 | B |
| ATOM | 4225 | O | ALA | B | 344 | 58.020 | 26.635 | 40.069 | 1.00 | 17.73 | B |
| ATOM | 4226 | N | THR | B | 345 | 60.199 | 27.170 | 39.895 | 1.00 | 13.61 | B |
| ATOM | 4227 | CA | THR | B | 345 | 60.627 | 25.840 | 40.320 | 1.00 | 13.51 | B |
| ATOM | 4228 | CB | THR | B | 345 | 61.954 | 25.396 | 39.640 | 1.00 | 13.32 | B |
| ATOM | 4229 | OG1 | THR | B | 345 | 63.013 | 26.300 | 39.978 | 1.00 | 14.23 | B |
| ATOM | 4230 | CG2 | THR | B | 345 | 61.783 | 25.363 | 38.125 | 1.00 | 12.12 | B |
| ATOM | 4231 | C | THR | B | 345 | 60.769 | 25.755 | 41.839 | 1.00 | 13.71 | B |
| ATOM | 4232 | O | THR | B | 345 | 61.078 | 24.694 | 42.373 | 1.00 | 15.12 | B |
| ATOM | 4233 | N | ASP | B | 346 | 60.537 | 26.872 | 42.523 | 1.00 | 14.53 | B |
| ATOM | 4234 | CA | ASP | B | 346 | 60.588 | 26.908 | 43.988 | 1.00 | 16.09 | B |
| ATOM | 4235 | CB | ASP | B | 346 | 60.599 | 28.358 | 44.488 | 1.00 | 17.44 | B |
| ATOM | 4236 | CG | ASP | B | 346 | 60.628 | 28.458 | 46.008 | 1.00 | 18.92 | B |
| ATOM | 4237 | OD1 | ASP | B | 346 | 60.336 | 27.452 | 46.687 | 1.00 | 19.45 | B |
| ATOM | 4238 | OD2 | ASP | B | 346 | 60.934 | 29.556 | 46.522 | 1.00 | 21.94 | B |
| ATOM | 4239 | C | ASP | B | 346 | 59.302 | 26.223 | 44.450 | 1.00 | 16.67 | B |
| ATOM | 4240 | O | ASP | B | 346 | 58.210 | 26.723 | 44.197 | 1.00 | 17.40 | B |
| ATOM | 4241 | N | MET | B | 347 | 59.434 | 25.085 | 45.124 | 1.00 | 18.66 | B |
| ATOM | 4242 | CA | MET | B | 347 | 58.270 | 24.332 | 45.590 | 1.00 | 20.96 | B |
| ATOM | 4243 | CB | MET | B | 347 | 58.726 | 23.073 | 46.327 | 1.00 | 25.61 | B |
| ATOM | 4244 | CG | MET | B | 347 | 59.158 | 21.956 | 45.401 | 1.00 | 30.18 | B |
| ATOM | 4245 | SD | MET | B | 347 | 57.819 | 21.483 | 44.287 | 1.00 | 32.66 | B |
| ATOM | 4246 | CE | MET | B | 347 | 56.850 | 20.433 | 45.351 | 1.00 | 33.61 | B |
| ATOM | 4247 | C | MET | B | 347 | 57.282 | 25.101 | 46.462 | 1.00 | 20.74 | B |
| ATOM | 4248 | O | MET | B | 347 | 56.113 | 24.731 | 46.545 | 1.00 | 20.20 | B |
| ATOM | 4249 | N | SER | B | 348 | 57.736 | 26.169 | 47.108 | 1.00 | 20.21 | B |
| ATOM | 4250 | CA | SER | B | 348 | 56.849 | 26.954 | 47.960 | 1.00 | 22.42 | B |
| ATOM | 4251 | CB | SER | B | 348 | 57.658 | 27.971 | 48.772 | 1.00 | 22.55 | B |

TABLE 1-continued

| ATOM | 4252 | OG | SER | B | 348 | 58.121 | 29.024 | 47.945 | 1.00 | 26.08 | B |
| ATOM | 4253 | C | SER | B | 348 | 55.781 | 27.686 | 47.143 | 1.00 | 22.99 | B |
| ATOM | 4254 | O | SER | B | 348 | 54.849 | 28.270 | 47.701 | 1.00 | 24.44 | B |
| ATOM | 4255 | N | LYS | B | 349 | 55.912 | 27.650 | 45.820 | 1.00 | 21.70 | B |
| ATOM | 4256 | CA | LYS | B | 349 | 54.959 | 28.323 | 44.944 | 1.00 | 20.97 | B |
| ATOM | 4257 | CB | LYS | B | 349 | 55.716 | 29.196 | 43.944 | 1.00 | 22.27 | B |
| ATOM | 4258 | CG | LYS | B | 349 | 56.626 | 30.217 | 44.612 | 1.00 | 24.07 | B |
| ATOM | 4259 | CD | LYS | B | 349 | 57.595 | 30.845 | 43.628 | 1.00 | 27.13 | B |
| ATOM | 4260 | CE | LYS | B | 349 | 58.561 | 31.783 | 44.345 | 1.00 | 27.13 | B |
| ATOM | 4261 | NZ | LYS | B | 349 | 59.668 | 32.259 | 43.464 | 1.00 | 26.22 | B |
| ATOM | 4262 | C | LYS | B | 349 | 54.081 | 27.324 | 44.196 | 1.00 | 20.14 | B |
| ATOM | 4263 | O | LYS | B | 349 | 53.256 | 27.705 | 43.366 | 1.00 | 20.48 | B |
| ATOM | 4264 | N | HIS | B | 350 | 54.255 | 26.045 | 44.506 | 1.00 | 19.62 | B |
| ATOM | 4265 | CA | HIS | B | 350 | 53.501 | 24.990 | 43.843 | 1.00 | 18.30 | B |
| ATOM | 4266 | CB | HIS | B | 350 | 53.871 | 23.629 | 44.418 | 1.00 | 19.20 | B |
| ATOM | 4267 | CG | HIS | B | 350 | 52.991 | 22.523 | 43.931 | 1.00 | 21.03 | B |
| ATOM | 4268 | CD2 | HIS | B | 350 | 51.978 | 21.858 | 44.537 | 1.00 | 21.77 | B |
| ATOM | 4269 | ND1 | HIS | B | 350 | 53.062 | 22.025 | 42.648 | 1.00 | 21.79 | B |
| ATOM | 4270 | CE1 | HIS | B | 350 | 52.131 | 21.102 | 42.484 | 1.00 | 23.24 | B |
| ATOM | 4271 | NE2 | HIS | B | 350 | 51.459 | 20.982 | 43.615 | 1.00 | 21.47 | B |
| ATOM | 4272 | C | HIS | B | 350 | 51.982 | 25.133 | 43.894 | 1.00 | 18.09 | B |
| ATOM | 4273 | O | HIS | B | 350 | 51.316 | 25.019 | 42.868 | 1.00 | 19.07 | B |
| ATOM | 4274 | N | MET | B | 351 | 51.432 | 25.362 | 45.083 | 1.00 | 19.00 | B |
| ATOM | 4275 | CA | MET | B | 351 | 49.985 | 25.489 | 45.211 | 1.00 | 19.07 | B |
| ATOM | 4276 | CB | MET | B | 351 | 49.588 | 25.672 | 46.677 | 1.00 | 22.89 | B |
| ATOM | 4277 | CG | MET | B | 351 | 49.862 | 24.458 | 47.542 | 1.00 | 27.86 | B |
| ATOM | 4278 | SD | MET | B | 351 | 49.122 | 22.952 | 46.870 | 1.00 | 30.18 | B |
| ATOM | 4279 | CE | MET | B | 351 | 47.454 | 23.072 | 47.510 | 1.00 | 33.02 | B |
| ATOM | 4280 | C | MET | B | 351 | 49.440 | 26.640 | 44.378 | 1.00 | 18.38 | B |
| ATOM | 4281 | O | MET | B | 351 | 48.416 | 26.499 | 43.705 | 1.00 | 20.26 | B |
| ATOM | 4282 | N | SER | B | 352 | 50.122 | 27.778 | 44.425 | 1.00 | 20.06 | B |
| ATOM | 4283 | CA | SER | B | 352 | 49.697 | 28.946 | 43.665 | 1.00 | 21.40 | B |
| ATOM | 4284 | CB | SER | B | 352 | 50.558 | 30.156 | 44.034 | 1.00 | 22.89 | B |
| ATOM | 4285 | OG | SER | B | 352 | 51.915 | 29.946 | 43.687 | 1.00 | 27.77 | B |
| ATOM | 4286 | C | SER | B | 352 | 49.783 | 28.673 | 42.163 | 1.00 | 21.26 | B |
| ATOM | 4287 | O | SER | B | 352 | 48.926 | 29.113 | 41.395 | 1.00 | 21.96 | B |
| ATOM | 4288 | N | LEU | B | 353 | 50.819 | 27.945 | 41.751 | 1.00 | 20.42 | B |
| ATOM | 4289 | CA | LEU | B | 353 | 51.010 | 27.600 | 40.342 | 1.00 | 20.75 | B |
| ATOM | 4290 | CB | LEU | B | 353 | 52.345 | 26.878 | 40.137 | 1.00 | 21.75 | B |
| ATOM | 4291 | CG | LEU | B | 353 | 53.587 | 27.764 | 40.041 | 1.00 | 22.69 | B |
| ATOM | 4292 | CD1 | LEU | B | 353 | 54.846 | 26.903 | 40.037 | 1.00 | 22.86 | B |
| ATOM | 4293 | CD2 | LEU | B | 353 | 53.500 | 28.611 | 38.778 | 1.00 | 24.05 | B |
| ATOM | 4294 | C | LEU | B | 353 | 49.886 | 26.702 | 39.853 | 1.00 | 19.96 | B |
| ATOM | 4295 | O | LEU | B | 353 | 49.272 | 26.962 | 38.818 | 1.00 | 21.02 | B |
| ATOM | 4296 | N | LEU | B | 354 | 49.625 | 25.643 | 40.609 | 1.00 | 20.41 | B |
| ATOM | 4297 | CA | LEU | B | 354 | 48.576 | 24.696 | 40.260 | 1.00 | 19.93 | B |
| ATOM | 4298 | CB | LEU | B | 354 | 48.516 | 23.575 | 41.299 | 1.00 | 21.11 | B |
| ATOM | 4299 | CG | LEU | B | 354 | 47.458 | 22.489 | 41.087 | 1.00 | 21.75 | B |
| ATOM | 4300 | CD1 | LEU | B | 354 | 47.654 | 21.833 | 39.731 | 1.00 | 21.99 | B |
| ATOM | 4301 | CD2 | LEU | B | 354 | 47.558 | 21.464 | 42.203 | 1.00 | 23.16 | B |
| ATOM | 4302 | C | LEU | B | 354 | 47.220 | 25.390 | 40.164 | 1.00 | 19.92 | B |
| ATOM | 4303 | O | LEU | B | 354 | 46.440 | 25.125 | 39.250 | 1.00 | 18.98 | B |
| ATOM | 4304 | N | ALA | B | 355 | 46.942 | 26.282 | 41.108 | 1.00 | 20.81 | B |
| ATOM | 4305 | CA | ALA | B | 355 | 45.674 | 27.006 | 41.108 | 1.00 | 21.29 | B |
| ATOM | 4306 | CB | ALA | B | 355 | 45.631 | 27.981 | 42.275 | 1.00 | 22.14 | B |
| ATOM | 4307 | C | ALA | B | 355 | 45.489 | 27.760 | 39.795 | 1.00 | 22.53 | B |
| ATOM | 4308 | O | ALA | B | 355 | 44.425 | 27.700 | 39.175 | 1.00 | 23.24 | B |
| ATOM | 4309 | N | ASP | B | 356 | 46.533 | 28.466 | 39.374 | 1.00 | 22.60 | B |
| ATOM | 4310 | CA | ASP | B | 356 | 46.488 | 29.237 | 38.139 | 1.00 | 23.34 | B |
| ATOM | 4311 | CB | ASP | B | 356 | 47.736 | 30.109 | 38.015 | 1.00 | 26.39 | B |
| ATOM | 4312 | CG | ASP | B | 356 | 47.797 | 31.184 | 39.077 | 1.00 | 28.28 | B |
| ATOM | 4313 | OD1 | ASP | B | 356 | 46.835 | 31.978 | 39.174 | 1.00 | 31.46 | B |
| ATOM | 4314 | OD2 | ASP | B | 356 | 48.804 | 31.237 | 39.811 | 1.00 | 31.83 | B |
| ATOM | 4315 | C | ASP | B | 356 | 46.359 | 28.353 | 36.908 | 1.00 | 23.37 | B |
| ATOM | 4316 | O | ASP | B | 356 | 45.710 | 28.729 | 35.931 | 1.00 | 25.25 | B |
| ATOM | 4317 | N | LEU | B | 357 | 46.976 | 27.179 | 36.954 | 1.00 | 22.52 | B |
| ATOM | 4318 | CA | LEU | B | 357 | 46.908 | 26.252 | 35.837 | 1.00 | 22.17 | B |
| ATOM | 4319 | CB | LEU | B | 357 | 47.893 | 25.099 | 36.044 | 1.00 | 21.00 | B |
| ATOM | 4320 | CG | LEU | B | 357 | 48.015 | 24.092 | 34.896 | 1.00 | 21.28 | B |
| ATOM | 4321 | CD1 | LEU | B | 357 | 48.478 | 24.807 | 33.640 | 1.00 | 23.48 | B |
| ATOM | 4322 | CD2 | LEU | B | 357 | 48.982 | 22.984 | 35.277 | 1.00 | 20.86 | B |
| ATOM | 4323 | C | LEU | B | 357 | 45.479 | 25.716 | 35.718 | 1.00 | 21.85 | B |
| ATOM | 4324 | O | LEU | B | 357 | 44.937 | 25.604 | 34.617 | 1.00 | 21.70 | B |
| ATOM | 4325 | N | LYS | B | 358 | 44.868 | 25.391 | 36.854 | 1.00 | 21.49 | B |
| ATOM | 4326 | CA | LYS | B | 358 | 43.501 | 24.879 | 36.846 | 1.00 | 21.52 | B |
| ATOM | 4327 | CB | LYS | B | 358 | 43.066 | 24.478 | 38.256 | 1.00 | 20.57 | B |
| ATOM | 4328 | CG | LYS | B | 358 | 43.717 | 23.203 | 38.748 | 1.00 | 21.35 | B |
| ATOM | 4329 | CD | LYS | B | 358 | 43.217 | 22.820 | 40.131 | 1.00 | 22.67 | B |
| ATOM | 4330 | CE | LYS | B | 358 | 43.847 | 21.518 | 40.588 | 1.00 | 22.52 | B |

TABLE 1-continued

| ATOM | 4331 | NZ  | LYS | B | 358 | 43.462 | 21.182 | 41.983 | 1.00 | 26.60 | B |
| ATOM | 4332 | C   | LYS | B | 358 | 42.529 | 25.902 | 36.281 | 1.00 | 22.13 | B |
| ATOM | 4333 | O   | LYS | B | 358 | 41.591 | 25.544 | 35.571 | 1.00 | 22.90 | B |
| ATOM | 4334 | N   | THR | B | 359 | 42.754 | 27.174 | 36.593 | 1.00 | 23.17 | B |
| ATOM | 4335 | CA  | THR | B | 359 | 41.888 | 28.240 | 36.095 | 1.00 | 25.41 | B |
| ATOM | 4336 | CB  | THR | B | 359 | 42.245 | 29.596 | 36.729 | 1.00 | 25.26 | B |
| ATOM | 4337 | OG1 | THR | B | 359 | 41.966 | 29.553 | 38.134 | 1.00 | 28.14 | B |
| ATOM | 4338 | CG2 | THR | B | 359 | 41.432 | 30.717 | 36.086 | 1.00 | 26.90 | B |
| ATOM | 4339 | C   | THR | B | 359 | 42.018 | 28.361 | 34.582 | 1.00 | 26.56 | B |
| ATOM | 4340 | O   | THR | B | 359 | 41.036 | 28.610 | 33.878 | 1.00 | 27.23 | B |
| ATOM | 4341 | N   | MET | B | 360 | 43.237 | 28.176 | 34.089 | 1.00 | 26.18 | B |
| ATOM | 4342 | CA  | MET | B | 360 | 43.511 | 28.255 | 32.661 | 1.00 | 26.69 | B |
| ATOM | 4343 | CB  | MET | B | 360 | 45.019 | 28.223 | 32.427 | 1.00 | 28.98 | B |
| ATOM | 4344 | CG  | MET | B | 360 | 45.432 | 28.248 | 30.975 | 1.00 | 32.30 | B |
| ATOM | 4345 | SD  | MET | B | 360 | 47.169 | 28.695 | 30.835 | 1.00 | 33.61 | B |
| ATOM | 4346 | CE  | MET | B | 360 | 47.033 | 30.441 | 30.474 | 1.00 | 33.17 | B |
| ATOM | 4347 | C   | MET | B | 360 | 42.837 | 27.116 | 31.903 | 1.00 | 26.03 | B |
| ATOM | 4348 | O   | MET | B | 360 | 42.376 | 27.296 | 30.777 | 1.00 | 26.23 | B |
| ATOM | 4349 | N   | VAL | B | 361 | 42.787 | 25.941 | 32.521 | 1.00 | 24.54 | B |
| ATOM | 4350 | CA  | VAL | B | 361 | 42.151 | 24.786 | 31.900 | 1.00 | 23.54 | B |
| ATOM | 4351 | CB  | VAL | B | 361 | 42.386 | 23.501 | 32.729 | 1.00 | 23.28 | B |
| ATOM | 4352 | CG1 | VAL | B | 361 | 41.511 | 22.375 | 32.205 | 1.00 | 23.92 | B |
| ATOM | 4353 | CG2 | VAL | B | 361 | 43.848 | 23.100 | 32.660 | 1.00 | 22.62 | B |
| ATOM | 4354 | C   | VAL | B | 361 | 40.644 | 25.015 | 31.778 | 1.00 | 23.84 | B |
| ATOM | 4355 | O   | VAL | B | 361 | 40.031 | 24.651 | 30.774 | 1.00 | 24.39 | B |
| ATOM | 4356 | N   | GLU | B | 362 | 40.057 | 25.625 | 32.803 | 1.00 | 24.20 | B |
| ATOM | 4357 | CA  | GLU | B | 362 | 38.618 | 25.894 | 32.821 | 1.00 | 24.75 | B |
| ATOM | 4358 | C   | GLU | B | 362 | 38.154 | 26.813 | 31.691 | 1.00 | 25.92 | B |
| ATOM | 4359 | O   | GLU | B | 362 | 37.030 | 26.683 | 31.201 | 1.00 | 26.55 | B |
| ATOM | 4360 | CB  | GLU | B | 362 | 38.208 | 26.427 | 34.196 | 1.00 | 24.69 | B |
| ATOM | 4361 | CG  | GLU | B | 362 | 38.093 | 25.347 | 35.264 | 1.00 | 20.00 | B |
| ATOM | 4362 | CD  | GLU | B | 362 | 37.766 | 23.970 | 34.718 | 1.00 | 20.00 | B |
| ATOM | 4363 | OE1 | GLU | B | 362 | 37.784 | 23.803 | 33.482 | 1.00 | 20.00 | B |
| ATOM | 4364 | OE2 | GLU | B | 362 | 37.493 | 23.061 | 35.527 | 1.00 | 20.00 | B |
| ATOM | 4365 | N   | THR | B | 363 | 39.016 | 27.737 | 31.279 | 1.00 | 25.10 | B |
| ATOM | 4366 | CA  | THR | B | 363 | 38.689 | 28.676 | 30.208 | 1.00 | 25.86 | B |
| ATOM | 4367 | CB  | THR | B | 363 | 39.072 | 30.111 | 30.600 | 1.00 | 26.65 | B |
| ATOM | 4368 | OG1 | THR | B | 363 | 40.494 | 30.196 | 30.752 | 1.00 | 29.84 | B |
| ATOM | 4369 | CG2 | THR | B | 363 | 38.404 | 30.501 | 31.917 | 1.00 | 28.17 | B |
| ATOM | 4370 | C   | THR | B | 363 | 39.431 | 28.320 | 28.922 | 1.00 | 24.53 | B |
| ATOM | 4371 | O   | THR | B | 363 | 39.560 | 29.143 | 28.016 | 1.00 | 25.32 | B |
| ATOM | 4372 | N   | LYS | B | 364 | 39.912 | 27.084 | 28.856 | 1.00 | 23.47 | B |
| ATOM | 4373 | CA  | LYS | B | 364 | 40.659 | 26.578 | 27.708 | 1.00 | 22.75 | B |
| ATOM | 4374 | CB  | LYS | B | 364 | 41.005 | 25.107 | 27.956 | 1.00 | 21.78 | B |
| ATOM | 4375 | CG  | LYS | B | 364 | 41.600 | 24.369 | 26.774 | 1.00 | 22.48 | B |
| ATOM | 4376 | CD  | LYS | B | 364 | 41.795 | 22.901 | 27.125 | 1.00 | 24.94 | B |
| ATOM | 4377 | CE  | LYS | B | 364 | 42.339 | 22.107 | 25.954 | 1.00 | 25.23 | B |
| ATOM | 4378 | NZ  | LYS | B | 364 | 42.414 | 20.651 | 26.265 | 1.00 | 28.14 | B |
| ATOM | 4379 | C   | LYS | B | 364 | 39.951 | 26.709 | 26.357 | 1.00 | 23.08 | B |
| ATOM | 4380 | O   | LYS | B | 364 | 38.764 | 26.418 | 26.235 | 1.00 | 23.91 | B |
| ATOM | 4381 | N   | LYS | B | 365 | 40.704 | 27.146 | 25.351 | 1.00 | 22.10 | B |
| ATOM | 4382 | CA  | LYS | B | 365 | 40.206 | 27.295 | 23.982 | 1.00 | 21.58 | B |
| ATOM | 4383 | CB  | LYS | B | 365 | 40.001 | 28.766 | 23.619 | 1.00 | 22.27 | B |
| ATOM | 4384 | CG  | LYS | B | 365 | 38.801 | 29.442 | 24.249 | 1.00 | 24.62 | B |
| ATOM | 4385 | CD  | LYS | B | 365 | 38.634 | 30.832 | 23.653 | 1.00 | 25.50 | B |
| ATOM | 4386 | CE  | LYS | B | 365 | 37.391 | 31.535 | 24.171 | 1.00 | 27.07 | B |
| ATOM | 4387 | NZ  | LYS | B | 365 | 37.211 | 32.861 | 23.503 | 1.00 | 26.97 | B |
| ATOM | 4388 | C   | LYS | B | 365 | 41.246 | 26.715 | 23.029 | 1.00 | 20.02 | B |
| ATOM | 4389 | O   | LYS | B | 365 | 42.449 | 26.902 | 23.229 | 1.00 | 20.96 | B |
| ATOM | 4390 | N   | VAL | B | 366 | 40.788 | 26.014 | 21.996 | 1.00 | 19.27 | B |
| ATOM | 4391 | CA  | VAL | B | 366 | 41.692 | 25.432 | 21.012 | 1.00 | 19.35 | B |
| ATOM | 4392 | CB  | VAL | B | 366 | 41.743 | 23.890 | 21.105 | 1.00 | 18.93 | B |
| ATOM | 4393 | CG1 | VAL | B | 366 | 42.296 | 23.463 | 22.454 | 1.00 | 19.64 | B |
| ATOM | 4394 | CG2 | VAL | B | 366 | 40.354 | 23.307 | 20.882 | 1.00 | 20.93 | B |
| ATOM | 4395 | C   | VAL | B | 366 | 41.245 | 25.802 | 19.604 | 1.00 | 19.74 | B |
| ATOM | 4396 | O   | VAL | B | 366 | 40.110 | 26.229 | 19.399 | 1.00 | 21.18 | B |
| ATOM | 4397 | N   | THR | B | 367 | 42.152 | 25.642 | 18.646 | 1.00 | 20.37 | B |
| ATOM | 4398 | CA  | THR | B | 367 | 41.865 | 25.932 | 17.244 | 1.00 | 21.68 | B |
| ATOM | 4399 | CB  | THR | B | 367 | 43.158 | 26.225 | 16.454 | 1.00 | 21.58 | B |
| ATOM | 4400 | OG1 | THR | B | 367 | 43.979 | 25.051 | 16.438 | 1.00 | 23.31 | B |
| ATOM | 4401 | CG2 | THR | B | 367 | 43.933 | 27.365 | 17.090 | 1.00 | 22.24 | B |
| ATOM | 4402 | C   | THR | B | 367 | 41.201 | 24.703 | 16.627 | 1.00 | 22.34 | B |
| ATOM | 4403 | O   | THR | B | 367 | 41.013 | 23.689 | 17.297 | 1.00 | 22.37 | B |
| ATOM | 4404 | N   | SER | B | 368 | 40.846 | 24.790 | 15.348 | 1.00 | 22.64 | B |
| ATOM | 4405 | CA  | SER | B | 368 | 40.212 | 23.662 | 14.671 | 1.00 | 24.90 | B |
| ATOM | 4406 | CB  | SER | B | 368 | 39.763 | 24.064 | 13.260 | 1.00 | 23.55 | B |
| ATOM | 4407 | OG  | SER | B | 368 | 40.865 | 24.457 | 12.461 | 1.00 | 29.14 | B |
| ATOM | 4408 | C   | SER | B | 368 | 41.184 | 22.490 | 14.588 | 1.00 | 25.00 | B |
| ATOM | 4409 | O   | SER | B | 368 | 40.771 | 21.343 | 14.409 | 1.00 | 25.86 | B |

TABLE 1-continued

| ATOM | 4410 | N | SER | B | 369 | 42.474 | 22.789 | 14.725 | 1.00 | 25.16 | B |
|---|---|---|---|---|---|---|---|---|---|---|---|
| ATOM | 4411 | CA | SER | B | 369 | 43.518 | 21.771 | 14.671 | 1.00 | 25.79 | B |
| ATOM | 4412 | CB | SER | B | 369 | 44.815 | 22.372 | 14.126 | 1.00 | 25.48 | B |
| ATOM | 4413 | OG | SER | B | 369 | 44.641 | 22.838 | 12.798 | 1.00 | 30.80 | B |
| ATOM | 4414 | C | SER | B | 369 | 43.775 | 21.172 | 16.051 | 1.00 | 25.75 | B |
| ATOM | 4415 | O | SER | B | 369 | 44.599 | 20.270 | 16.200 | 1.00 | 27.06 | B |
| ATOM | 4416 | N | GLY | B | 370 | 43.071 | 21.682 | 17.056 | 1.00 | 24.62 | B |
| ATOM | 4417 | CA | GLY | B | 370 | 43.233 | 21.171 | 18.404 | 1.00 | 24.16 | B |
| ATOM | 4418 | C | GLY | B | 370 | 44.362 | 21.824 | 19.174 | 1.00 | 23.75 | B |
| ATOM | 4419 | O | GLY | B | 370 | 44.673 | 21.418 | 20.295 | 1.00 | 26.28 | B |
| ATOM | 4420 | N | VAL | B | 371 | 44.977 | 22.838 | 18.576 | 1.00 | 22.85 | B |
| ATOM | 4421 | CA | VAL | B | 371 | 46.078 | 23.555 | 19.209 | 1.00 | 21.91 | B |
| ATOM | 4422 | CB | VAL | B | 371 | 46.957 | 24.243 | 18.143 | 1.00 | 22.12 | B |
| ATOM | 4423 | CG1 | VAL | B | 371 | 48.069 | 25.019 | 18.805 | 1.00 | 24.36 | B |
| ATOM | 4424 | CG2 | VAL | B | 371 | 47.525 | 23.201 | 17.195 | 1.00 | 22.92 | B |
| ATOM | 4425 | C | VAL | B | 371 | 45.568 | 24.607 | 20.194 | 1.00 | 22.02 | B |
| ATOM | 4426 | O | VAL | B | 371 | 44.603 | 25.320 | 19.914 | 1.00 | 22.35 | B |
| ATOM | 4427 | N | LEU | B | 372 | 46.216 | 24.700 | 21.353 | 1.00 | 22.00 | B |
| ATOM | 4428 | CA | LEU | B | 372 | 45.821 | 25.665 | 22.373 | 1.00 | 21.94 | B |
| ATOM | 4429 | CB | LEU | B | 372 | 46.700 | 25.518 | 23.620 | 1.00 | 22.47 | B |
| ATOM | 4430 | CG | LEU | B | 372 | 46.317 | 24.431 | 24.622 | 1.00 | 23.07 | B |
| ATOM | 4431 | CD1 | LEU | B | 372 | 47.369 | 24.355 | 25.716 | 1.00 | 26.51 | B |
| ATOM | 4432 | CD2 | LEU | B | 372 | 44.956 | 24.745 | 25.219 | 1.00 | 24.69 | B |
| ATOM | 4433 | C | LEU | B | 372 | 45.904 | 27.104 | 21.884 | 1.00 | 21.69 | B |
| ATOM | 4434 | O | LEU | B | 372 | 46.847 | 27.484 | 21.193 | 1.00 | 22.75 | B |
| ATOM | 4435 | N | LEU | B | 373 | 44.936 | 27.869 | 22.248 | 1.00 | 21.67 | B |
| ATOM | 4436 | CA | LEU | B | 373 | 44.813 | 29.243 | 21.903 | 1.00 | 22.49 | B |
| ATOM | 4437 | CB | LEU | B | 373 | 43.324 | 29.529 | 21.597 | 1.00 | 22.33 | B |
| ATOM | 4438 | CG | LEU | B | 373 | 42.959 | 30.379 | 20.392 | 1.00 | 23.99 | B |
| ATOM | 4439 | CD1 | LEU | B | 373 | 43.914 | 30.107 | 19.235 | 1.00 | 23.77 | B |
| ATOM | 4440 | CD2 | LEU | B | 373 | 41.531 | 30.113 | 19.951 | 1.00 | 23.76 | B |
| ATOM | 4441 | C | LEU | B | 373 | 45.304 | 30.143 | 23.066 | 1.00 | 22.88 | B |
| ATOM | 4442 | O | LEU | B | 373 | 44.567 | 30.315 | 24.044 | 1.00 | 24.02 | B |
| ATOM | 4443 | N | LEU | B | 374 | 46.501 | 30.716 | 22.992 | 1.00 | 23.28 | B |
| ATOM | 4444 | CA | LEU | B | 374 | 47.007 | 31.558 | 24.070 | 1.00 | 24.01 | B |
| ATOM | 4445 | CB | LEU | B | 374 | 48.417 | 31.115 | 24.471 | 1.00 | 22.94 | B |
| ATOM | 4446 | CG | LEU | B | 374 | 48.474 | 29.700 | 25.062 | 1.00 | 21.11 | B |
| ATOM | 4447 | CD1 | LEU | B | 374 | 49.903 | 29.349 | 25.441 | 1.00 | 21.54 | B |
| ATOM | 4448 | CD2 | LEU | B | 374 | 47.569 | 29.618 | 26.281 | 1.00 | 22.57 | B |
| ATOM | 4449 | C | LEU | B | 374 | 46.994 | 33.007 | 23.587 | 1.00 | 26.69 | B |
| ATOM | 4450 | O | LEU | B | 374 | 47.893 | 33.449 | 22.869 | 1.00 | 27.62 | B |
| ATOM | 4451 | N | ASP | B | 375 | 45.948 | 33.724 | 23.986 | 1.00 | 26.40 | B |
| ATOM | 4452 | CA | ASP | B | 375 | 45.724 | 35.116 | 23.605 | 1.00 | 26.83 | B |
| ATOM | 4453 | CB | ASP | B | 375 | 44.548 | 35.693 | 24.402 | 1.00 | 27.45 | B |
| ATOM | 4454 | CG | ASP | B | 375 | 43.258 | 34.929 | 24.173 | 1.00 | 29.74 | B |
| ATOM | 4455 | OD1 | ASP | B | 375 | 42.897 | 34.723 | 22.995 | 1.00 | 32.20 | B |
| ATOM | 4456 | OD2 | ASP | B | 375 | 42.603 | 34.542 | 25.169 | 1.00 | 32.56 | B |
| ATOM | 4457 | C | ASP | B | 375 | 46.909 | 36.064 | 23.732 | 1.00 | 26.74 | B |
| ATOM | 4458 | O | ASP | B | 375 | 47.267 | 36.748 | 22.772 | 1.00 | 27.89 | B |
| ATOM | 4459 | N | ASN | B | 376 | 47.515 | 36.119 | 24.912 | 1.00 | 24.79 | B |
| ATOM | 4460 | CA | ASN | B | 376 | 48.634 | 37.025 | 25.116 | 1.00 | 24.26 | B |
| ATOM | 4461 | CB | ASN | B | 376 | 48.136 | 38.317 | 25.757 | 1.00 | 25.14 | B |
| ATOM | 4462 | CG | ASN | B | 376 | 47.329 | 38.062 | 27.006 | 1.00 | 27.01 | B |
| ATOM | 4463 | OD1 | ASN | B | 376 | 47.784 | 37.375 | 27.919 | 1.00 | 30.31 | B |
| ATOM | 4464 | ND2 | ASN | B | 376 | 46.119 | 38.611 | 27.054 | 1.00 | 30.81 | B |
| ATOM | 4465 | C | ASN | B | 376 | 49.767 | 36.455 | 25.955 | 1.00 | 23.55 | B |
| ATOM | 4466 | O | ASN | B | 376 | 49.786 | 35.268 | 26.290 | 1.00 | 22.98 | B |
| ATOM | 4467 | N | TYR | B | 377 | 50.704 | 37.335 | 26.292 | 1.00 | 23.59 | B |
| ATOM | 4468 | CA | TYR | B | 377 | 51.880 | 36.981 | 27.073 | 1.00 | 22.88 | B |
| ATOM | 4469 | CB | TYR | B | 377 | 52.732 | 38.225 | 27.323 | 1.00 | 22.47 | B |
| ATOM | 4470 | CG | TYR | B | 377 | 53.968 | 37.932 | 28.134 | 1.00 | 21.51 | B |
| ATOM | 4471 | CD1 | TYR | B | 377 | 55.039 | 37.244 | 27.577 | 1.00 | 22.22 | B |
| ATOM | 4472 | CE1 | TYR | B | 377 | 56.153 | 36.921 | 28.334 | 1.00 | 21.70 | B |
| ATOM | 4473 | CD2 | TYR | B | 377 | 54.045 | 38.294 | 29.470 | 1.00 | 21.33 | B |
| ATOM | 4474 | CE2 | TYR | B | 377 | 55.153 | 37.974 | 30.236 | 1.00 | 21.80 | B |
| ATOM | 4475 | CZ | TYR | B | 377 | 56.201 | 37.286 | 29.663 | 1.00 | 21.43 | B |
| ATOM | 4476 | OH | TYR | B | 377 | 57.292 | 36.944 | 30.428 | 1.00 | 23.80 | B |
| ATOM | 4477 | C | TYR | B | 377 | 51.585 | 36.308 | 28.409 | 1.00 | 23.07 | B |
| ATOM | 4478 | O | TYR | B | 377 | 52.157 | 35.264 | 28.718 | 1.00 | 23.13 | B |
| ATOM | 4479 | N | THR | B | 378 | 50.705 | 36.906 | 29.207 | 1.00 | 22.87 | B |
| ATOM | 4480 | CA | THR | B | 378 | 50.376 | 36.339 | 30.510 | 1.00 | 23.44 | B |
| ATOM | 4481 | CB | THR | B | 378 | 49.257 | 37.142 | 31.202 | 1.00 | 23.67 | B |
| ATOM | 4482 | OG1 | THR | B | 378 | 48.137 | 37.268 | 30.320 | 1.00 | 28.32 | B |
| ATOM | 4483 | CG2 | THR | B | 378 | 49.760 | 38.525 | 31.579 | 1.00 | 24.54 | B |
| ATOM | 4484 | C | THR | B | 378 | 49.956 | 34.877 | 30.400 | 1.00 | 22.21 | B |
| ATOM | 4485 | O | THR | B | 378 | 50.386 | 34.037 | 31.194 | 1.00 | 23.98 | B |
| ATOM | 4486 | N | ASP | B | 379 | 49.124 | 34.571 | 29.410 | 1.00 | 21.16 | B |
| ATOM | 4487 | CA | ASP | B | 379 | 48.673 | 33.202 | 29.206 | 1.00 | 21.21 | B |
| ATOM | 4488 | CB | ASP | B | 379 | 47.587 | 33.147 | 28.126 | 1.00 | 24.16 | B |

TABLE 1-continued

| | | | | | | | | | | |
|---|---|---|---|---|---|---|---|---|---|---|
| ATOM | 4489 | CG | ASP | B | 379 | 46.365 | 33.972 | 28.482 | 1.00 | 27.17 | B |
| ATOM | 4490 | OD1 | ASP | B | 379 | 46.444 | 35.219 | 28.418 | 1.00 | 30.31 | B |
| ATOM | 4491 | OD2 | ASP | B | 379 | 45.325 | 33.374 | 28.831 | 1.00 | 30.32 | B |
| ATOM | 4492 | C | ASP | B | 379 | 49.849 | 32.321 | 28.784 | 1.00 | 20.03 | B |
| ATOM | 4493 | O | ASP | B | 379 | 50.019 | 31.213 | 29.290 | 1.00 | 20.59 | B |
| ATOM | 4494 | N | ARG | B | 380 | 50.664 | 32.822 | 27.862 | 1.00 | 19.56 | B |
| ATOM | 4495 | CA | ARG | B | 380 | 51.809 | 32.060 | 27.376 | 1.00 | 19.24 | B |
| ATOM | 4496 | CB | ARG | B | 380 | 52.483 | 32.798 | 26.218 | 1.00 | 19.92 | B |
| ATOM | 4497 | CG | ARG | B | 380 | 51.605 | 32.859 | 24.982 | 1.00 | 22.15 | B |
| ATOM | 4498 | CD | ARG | B | 380 | 52.404 | 33.101 | 23.719 | 1.00 | 22.26 | B |
| ATOM | 4499 | NE | ARG | B | 380 | 51.601 | 32.767 | 22.549 | 1.00 | 26.39 | B |
| ATOM | 4500 | CZ | ARG | B | 380 | 52.096 | 32.579 | 21.333 | 1.00 | 26.41 | B |
| ATOM | 4501 | NH1 | ARG | B | 380 | 53.401 | 32.694 | 21.122 | 1.00 | 26.03 | B |
| ATOM | 4502 | NH2 | ARG | B | 380 | 51.283 | 32.258 | 20.332 | 1.00 | 27.29 | B |
| ATOM | 4503 | C | ARG | B | 380 | 52.842 | 31.723 | 28.442 | 1.00 | 18.48 | B |
| ATOM | 4504 | O | ARG | B | 380 | 53.274 | 30.576 | 28.547 | 1.00 | 17.97 | B |
| ATOM | 4505 | N | ILE | B | 381 | 53.241 | 32.709 | 29.237 | 1.00 | 18.59 | B |
| ATOM | 4506 | CA | ILE | B | 381 | 54.234 | 32.445 | 30.265 | 1.00 | 18.81 | B |
| ATOM | 4507 | CB | ILE | B | 381 | 54.787 | 33.754 | 30.876 | 1.00 | 19.63 | B |
| ATOM | 4508 | CG2 | ILE | B | 381 | 53.703 | 34.467 | 31.666 | 1.00 | 20.49 | B |
| ATOM | 4509 | CG1 | ILE | B | 381 | 55.990 | 33.438 | 31.769 | 1.00 | 18.74 | B |
| ATOM | 4510 | CD1 | ILE | B | 381 | 57.113 | 32.703 | 31.055 | 1.00 | 20.24 | B |
| ATOM | 4511 | C | ILE | B | 381 | 53.670 | 31.551 | 31.367 | 1.00 | 18.10 | B |
| ATOM | 4512 | O | ILE | B | 381 | 54.408 | 30.802 | 31.998 | 1.00 | 17.97 | B |
| ATOM | 4513 | N | GLN | B | 382 | 52.361 | 31.621 | 31.592 | 1.00 | 18.43 | B |
| ATOM | 4514 | CA | GLN | B | 382 | 51.714 | 30.788 | 32.601 | 1.00 | 18.93 | B |
| ATOM | 4515 | CB | GLN | B | 382 | 50.216 | 31.102 | 32.655 | 1.00 | 20.01 | B |
| ATOM | 4516 | CG | GLN | B | 382 | 49.448 | 30.354 | 33.734 | 1.00 | 23.78 | B |
| ATOM | 4517 | CD | GLN | B | 382 | 49.751 | 30.865 | 35.130 | 1.00 | 26.17 | B |
| ATOM | 4518 | OE1 | GLN | B | 382 | 50.805 | 30.576 | 35.698 | 1.00 | 30.04 | B |
| ATOM | 4519 | NE2 | GLN | B | 382 | 48.827 | 31.642 | 35.687 | 1.00 | 29.93 | B |
| ATOM | 4520 | C | GLN | B | 382 | 51.913 | 29.319 | 32.228 | 1.00 | 18.43 | B |
| ATOM | 4521 | O | GLN | B | 382 | 52.244 | 28.482 | 33.072 | 1.00 | 20.15 | B |
| ATOM | 4522 | N | VAL | B | 383 | 51.702 | 29.012 | 30.952 | 1.00 | 18.33 | B |
| ATOM | 4523 | CA | VAL | B | 383 | 51.869 | 27.651 | 30.463 | 1.00 | 17.67 | B |
| ATOM | 4524 | CB | VAL | B | 383 | 51.365 | 27.516 | 29.011 | 1.00 | 18.08 | B |
| ATOM | 4525 | CG1 | VAL | B | 383 | 51.704 | 26.141 | 28.459 | 1.00 | 17.19 | B |
| ATOM | 4526 | CG2 | VAL | B | 383 | 49.857 | 27.736 | 28.968 | 1.00 | 19.59 | B |
| ATOM | 4527 | C | VAL | B | 383 | 53.336 | 27.235 | 30.520 | 1.00 | 16.86 | B |
| ATOM | 4528 | O | VAL | B | 383 | 53.651 | 26.121 | 30.932 | 1.00 | 17.82 | B |
| ATOM | 4529 | N | LEU | B | 384 | 54.230 | 28.136 | 30.115 | 1.00 | 16.13 | B |
| ATOM | 4530 | CA | LEU | B | 384 | 55.659 | 27.832 | 30.123 | 1.00 | 15.24 | B |
| ATOM | 4531 | CB | LEU | B | 384 | 56.454 | 28.953 | 29.452 | 1.00 | 15.85 | B |
| ATOM | 4532 | CG | LEU | B | 384 | 56.329 | 29.008 | 27.931 | 1.00 | 17.94 | B |
| ATOM | 4533 | CD1 | LEU | B | 384 | 57.154 | 30.158 | 27.387 | 1.00 | 20.53 | B |
| ATOM | 4534 | CD2 | LEU | B | 384 | 56.799 | 27.686 | 27.342 | 1.00 | 19.47 | B |
| ATOM | 4535 | C | LEU | B | 384 | 56.205 | 27.598 | 31.525 | 1.00 | 14.25 | B |
| ATOM | 4536 | O | LEU | B | 384 | 56.989 | 26.673 | 31.740 | 1.00 | 15.40 | B |
| ATOM | 4537 | N | ARG | B | 385 | 55.800 | 28.429 | 32.480 | 1.00 | 16.44 | B |
| ATOM | 4538 | CA | ARG | B | 385 | 56.279 | 28.269 | 33.848 | 1.00 | 17.29 | B |
| ATOM | 4539 | CB | ARG | B | 385 | 55.783 | 29.420 | 34.733 | 1.00 | 20.20 | B |
| ATOM | 4540 | CG | ARG | B | 385 | 54.302 | 29.378 | 35.022 | 1.00 | 22.35 | B |
| ATOM | 4541 | CD | ARG | B | 385 | 53.792 | 30.692 | 35.598 | 1.00 | 25.95 | B |
| ATOM | 4542 | NE | ARG | B | 385 | 54.453 | 31.057 | 36.847 | 1.00 | 27.19 | B |
| ATOM | 4543 | CZ | ARG | B | 385 | 53.976 | 31.960 | 37.698 | 1.00 | 27.61 | B |
| ATOM | 4544 | NH1 | ARG | B | 385 | 52.835 | 32.583 | 37.431 | 1.00 | 28.55 | B |
| ATOM | 4545 | NH2 | ARG | B | 385 | 54.637 | 32.239 | 38.816 | 1.00 | 29.24 | B |
| ATOM | 4546 | C | ARG | B | 385 | 55.797 | 26.930 | 34.398 | 1.00 | 16.55 | B |
| ATOM | 4547 | O | ARG | B | 385 | 56.538 | 26.231 | 35.086 | 1.00 | 16.50 | B |
| ATOM | 4548 | N | ASN | B | 386 | 54.559 | 26.563 | 34.081 | 1.00 | 16.88 | B |
| ATOM | 4549 | CA | ASN | B | 386 | 54.020 | 25.296 | 34.552 | 1.00 | 16.42 | B |
| ATOM | 4550 | CB | ASN | B | 386 | 52.502 | 25.257 | 34.354 | 1.00 | 19.24 | B |
| ATOM | 4551 | CG | ASN | B | 386 | 51.754 | 25.904 | 35.508 | 1.00 | 20.62 | B |
| ATOM | 4552 | OD1 | ASN | B | 386 | 51.613 | 25.311 | 36.578 | 1.00 | 22.06 | B |
| ATOM | 4553 | ND2 | ASN | B | 386 | 51.291 | 27.131 | 35.304 | 1.00 | 22.88 | B |
| ATOM | 4554 | C | ASN | B | 386 | 54.686 | 24.118 | 33.847 | 1.00 | 16.02 | B |
| ATOM | 4555 | O | ASN | B | 386 | 54.878 | 23.061 | 34.446 | 1.00 | 15.23 | B |
| ATOM | 4556 | N | MET | B | 387 | 55.055 | 24.309 | 32.585 | 1.00 | 16.21 | B |
| ATOM | 4557 | CA | MET | B | 387 | 55.716 | 23.254 | 31.823 | 1.00 | 17.17 | B |
| ATOM | 4558 | CB | MET | B | 387 | 55.930 | 23.700 | 30.377 | 1.00 | 19.11 | B |
| ATOM | 4559 | CG | MET | B | 387 | 56.586 | 22.649 | 29.511 | 1.00 | 19.74 | B |
| ATOM | 4560 | SD | MET | B | 387 | 56.966 | 23.307 | 27.888 | 1.00 | 22.71 | B |
| ATOM | 4561 | CE | MET | B | 387 | 55.374 | 23.287 | 27.132 | 1.00 | 23.09 | B |
| ATOM | 4562 | C | MET | B | 387 | 57.065 | 22.882 | 32.444 | 1.00 | 16.24 | B |
| ATOM | 4563 | O | MET | B | 387 | 57.369 | 21.702 | 32.625 | 1.00 | 17.43 | B |
| ATOM | 4564 | N | VAL | B | 388 | 57.879 | 23.886 | 32.760 | 1.00 | 15.74 | B |
| ATOM | 4565 | CA | VAL | B | 388 | 59.189 | 23.639 | 33.361 | 1.00 | 14.72 | B |
| ATOM | 4566 | CB | VAL | B | 388 | 60.017 | 24.944 | 33.422 | 1.00 | 15.94 | B |
| ATOM | 4567 | CG1 | VAL | B | 388 | 61.332 | 24.705 | 34.139 | 1.00 | 18.40 | B |

TABLE 1-continued

| | | | | | | | | | | |
|---|---|---|---|---|---|---|---|---|---|---|
| ATOM | 4568 | CG2 | VAL | B | 388 | 60.284 | 25.439 | 32.010 | 1.00 | 16.79 | B |
| ATOM | 4569 | C | VAL | B | 388 | 59.028 | 23.051 | 34.764 | 1.00 | 13.30 | B |
| ATOM | 4570 | O | VAL | B | 388 | 59.840 | 22.238 | 35.215 | 1.00 | 13.93 | B |
| ATOM | 4571 | N | HIS | B | 389 | 57.972 | 23.461 | 35.452 | 1.00 | 15.28 | B |
| ATOM | 4572 | CA | HIS | B | 389 | 57.693 | 22.951 | 36.786 | 1.00 | 15.30 | B |
| ATOM | 4573 | CB | HIS | B | 389 | 56.530 | 23.742 | 37.404 | 1.00 | 17.02 | B |
| ATOM | 4574 | CG | HIS | B | 389 | 56.124 | 23.275 | 38.769 | 1.00 | 19.73 | B |
| ATOM | 4575 | CD2 | HIS | B | 389 | 54.902 | 23.009 | 39.287 | 1.00 | 20.45 | B |
| ATOM | 4576 | ND1 | HIS | B | 389 | 57.025 | 23.070 | 39.792 | 1.00 | 20.38 | B |
| ATOM | 4577 | CE1 | HIS | B | 389 | 56.376 | 22.696 | 40.881 | 1.00 | 20.53 | B |
| ATOM | 4578 | NE2 | HIS | B | 389 | 55.086 | 22.652 | 40.602 | 1.00 | 20.40 | B |
| ATOM | 4579 | C | HIS | B | 389 | 57.351 | 21.463 | 36.655 | 1.00 | 14.86 | B |
| ATOM | 4580 | O | HIS | B | 389 | 57.801 | 20.634 | 37.452 | 1.00 | 16.52 | B |
| ATOM | 4581 | N | CYS | B | 390 | 56.571 | 21.126 | 35.632 | 1.00 | 15.02 | B |
| ATOM | 4582 | CA | CYS | B | 390 | 56.197 | 19.734 | 35.387 | 1.00 | 15.93 | B |
| ATOM | 4583 | CB | CYS | B | 390 | 55.203 | 19.633 | 34.223 | 1.00 | 17.36 | B |
| ATOM | 4584 | SG | CYS | B | 390 | 53.474 | 20.014 | 34.651 | 1.00 | 24.78 | B |
| ATOM | 4585 | C | CYS | B | 390 | 57.439 | 18.912 | 35.051 | 1.00 | 13.96 | B |
| ATOM | 4586 | O | CYS | B | 390 | 57.587 | 17.779 | 35.501 | 1.00 | 14.82 | B |
| ATOM | 4587 | N | ALA | B | 391 | 58.330 | 19.489 | 34.252 | 1.00 | 13.12 | B |
| ATOM | 4588 | CA | ALA | B | 391 | 59.556 | 18.799 | 33.866 | 1.00 | 12.95 | B |
| ATOM | 4589 | CB | ALA | B | 391 | 60.331 | 19.638 | 32.865 | 1.00 | 12.04 | B |
| ATOM | 4590 | C | ALA | B | 391 | 60.413 | 18.534 | 35.098 | 1.00 | 10.96 | B |
| ATOM | 4591 | O | ALA | B | 391 | 61.022 | 17.472 | 35.230 | 1.00 | 13.44 | B |
| ATOM | 4592 | N | ASP | B | 392 | 60.448 | 19.507 | 36.003 | 1.00 | 11.78 | B |
| ATOM | 4593 | CA | ASP | B | 392 | 61.228 | 19.386 | 37.226 | 1.00 | 13.07 | B |
| ATOM | 4594 | CB | ASP | B | 392 | 61.226 | 20.731 | 37.963 | 1.00 | 13.80 | B |
| ATOM | 4595 | CG | ASP | B | 392 | 62.260 | 20.797 | 39.079 | 1.00 | 13.78 | B |
| ATOM | 4596 | OD1 | ASP | B | 392 | 63.370 | 20.249 | 38.911 | 1.00 | 10.77 | B |
| ATOM | 4597 | OD2 | ASP | B | 392 | 61.965 | 21.416 | 40.120 | 1.00 | 21.06 | B |
| ATOM | 4598 | C | ASP | B | 392 | 60.660 | 18.280 | 38.116 | 1.00 | 12.46 | B |
| ATOM | 4599 | O | ASP | B | 392 | 61.394 | 17.639 | 38.865 | 1.00 | 15.24 | B |
| ATOM | 4600 | N | LEU | B | 393 | 59.350 | 18.063 | 38.025 | 1.00 | 13.52 | B |
| ATOM | 4601 | CA | LEU | B | 393 | 58.676 | 17.029 | 38.812 | 1.00 | 14.76 | B |
| ATOM | 4602 | CB | LEU | B | 393 | 57.448 | 17.619 | 39.504 | 1.00 | 18.22 | B |
| ATOM | 4603 | CG | LEU | B | 393 | 57.710 | 18.720 | 40.530 | 1.00 | 19.43 | B |
| ATOM | 4604 | CD1 | LEU | B | 393 | 56.381 | 19.239 | 41.070 | 1.00 | 20.84 | B |
| ATOM | 4605 | CD2 | LEU | B | 393 | 58.571 | 18.171 | 41.652 | 1.00 | 22.46 | B |
| ATOM | 4606 | C | LEU | B | 393 | 58.235 | 15.874 | 37.912 | 1.00 | 14.12 | B |
| ATOM | 4607 | O | LEU | B | 393 | 57.152 | 15.314 | 38.096 | 1.00 | 17.10 | B |
| ATOM | 4608 | N | SER | B | 394 | 59.079 | 15.503 | 36.955 | 1.00 | 13.23 | B |
| ATOM | 4609 | CA | SER | B | 394 | 58.730 | 14.434 | 36.021 | 1.00 | 14.35 | B |
| ATOM | 4610 | CB | SER | B | 394 | 59.184 | 14.816 | 34.608 | 1.00 | 15.22 | B |
| ATOM | 4611 | OG | SER | B | 394 | 60.599 | 14.889 | 34.527 | 1.00 | 14.55 | B |
| ATOM | 4612 | C | SER | B | 394 | 59.277 | 13.048 | 36.359 | 1.00 | 14.48 | B |
| ATOM | 4613 | O | SER | B | 394 | 58.912 | 12.072 | 35.707 | 1.00 | 16.13 | B |
| ATOM | 4614 | N | ASN | B | 395 | 60.136 | 12.952 | 37.372 | 1.00 | 15.43 | B |
| ATOM | 4615 | CA | ASN | B | 395 | 60.726 | 11.665 | 37.742 | 1.00 | 14.41 | B |
| ATOM | 4616 | CB | ASN | B | 395 | 61.536 | 11.786 | 39.045 | 1.00 | 15.01 | B |
| ATOM | 4617 | CG | ASN | B | 395 | 62.818 | 12.602 | 38.889 | 1.00 | 15.76 | B |
| ATOM | 4618 | OD1 | ASN | B | 395 | 63.497 | 12.867 | 39.876 | 1.00 | 17.66 | B |
| ATOM | 4619 | ND2 | ASN | B | 395 | 63.157 | 12.988 | 37.663 | 1.00 | 14.75 | B |
| ATOM | 4620 | C | ASN | B | 395 | 59.708 | 10.526 | 37.903 | 1.00 | 14.34 | B |
| ATOM | 4621 | O | ASN | B | 395 | 59.889 | 9.445 | 37.353 | 1.00 | 14.64 | B |
| ATOM | 4622 | N | PRO | B | 396 | 58.628 | 10.754 | 38.666 | 1.00 | 14.59 | B |
| ATOM | 4623 | CD | PRO | B | 396 | 58.362 | 11.894 | 39.559 | 1.00 | 15.46 | B |
| ATOM | 4624 | CA | PRO | B | 396 | 57.625 | 9.700 | 38.862 | 1.00 | 15.54 | B |
| ATOM | 4625 | CB | PRO | B | 396 | 56.718 | 10.281 | 39.949 | 1.00 | 15.67 | B |
| ATOM | 4626 | CG | PRO | B | 396 | 57.621 | 11.232 | 40.692 | 1.00 | 16.27 | B |
| ATOM | 4627 | C | PRO | B | 396 | 56.837 | 9.321 | 37.608 | 1.00 | 16.19 | B |
| ATOM | 4628 | O | PRO | B | 396 | 56.080 | 8.345 | 37.619 | 1.00 | 16.47 | B |
| ATOM | 4629 | N | THR | B | 397 | 57.006 | 10.085 | 36.535 | 1.00 | 16.18 | B |
| ATOM | 4630 | CA | THR | B | 397 | 56.285 | 9.807 | 35.294 | 1.00 | 16.59 | B |
| ATOM | 4631 | CB | THR | B | 397 | 55.802 | 11.099 | 34.615 | 1.00 | 17.26 | B |
| ATOM | 4632 | OG1 | THR | B | 397 | 56.914 | 11.762 | 34.004 | 1.00 | 17.78 | B |
| ATOM | 4633 | CG2 | THR | B | 397 | 55.157 | 12.025 | 35.630 | 1.00 | 18.25 | B |
| ATOM | 4634 | C | THR | B | 397 | 57.112 | 9.033 | 34.277 | 1.00 | 17.22 | B |
| ATOM | 4635 | O | THR | B | 397 | 56.615 | 8.684 | 33.205 | 1.00 | 17.65 | B |
| ATOM | 4636 | N | LYS | B | 398 | 58.373 | 8.773 | 34.602 | 1.00 | 16.95 | B |
| ATOM | 4637 | CA | LYS | B | 398 | 59.249 | 8.031 | 33.705 | 1.00 | 17.56 | B |
| ATOM | 4638 | CB | LYS | B | 398 | 60.703 | 8.468 | 33.913 | 1.00 | 18.01 | B |
| ATOM | 4639 | CG | LYS | B | 398 | 60.946 | 9.953 | 33.668 | 1.00 | 18.84 | B |
| ATOM | 4640 | CD | LYS | B | 398 | 60.604 | 10.332 | 32.234 | 1.00 | 19.47 | B |
| ATOM | 4641 | CE | LYS | B | 398 | 60.702 | 11.835 | 31.996 | 1.00 | 18.84 | B |
| ATOM | 4642 | NZ | LYS | B | 398 | 62.092 | 12.349 | 32.149 | 1.00 | 18.45 | B |
| ATOM | 4643 | C | LYS | B | 398 | 59.097 | 6.537 | 34.000 | 1.00 | 17.51 | B |
| ATOM | 4644 | O | LYS | B | 398 | 58.430 | 6.158 | 34.964 | 1.00 | 18.04 | B |
| ATOM | 4645 | N | SER | B | 399 | 59.707 | 5.695 | 33.169 | 1.00 | 18.98 | B |
| ATOM | 4646 | CA | SER | B | 399 | 59.632 | 4.249 | 33.370 | 1.00 | 20.36 | B |

TABLE 1-continued

| ATOM | 4647 | CB | SER | B | 399 | 60.514 | 3.517 | 32.359 | 1.00 | 21.38 | B |
|---|---|---|---|---|---|---|---|---|---|---|---|
| ATOM | 4648 | OG | SER | B | 399 | 61.887 | 3.772 | 32.603 | 1.00 | 27.87 | B |
| ATOM | 4649 | C | SER | B | 399 | 60.109 | 3.926 | 34.780 | 1.00 | 19.68 | B |
| ATOM | 4650 | O | SER | B | 399 | 60.998 | 4.593 | 35.307 | 1.00 | 20.18 | B |
| ATOM | 4651 | N | LEU | B | 400 | 59.523 | 2.898 | 35.386 | 1.00 | 20.04 | B |
| ATOM | 4652 | CA | LEU | B | 400 | 59.889 | 2.513 | 36.744 | 1.00 | 19.16 | B |
| ATOM | 4653 | CB | LEU | B | 400 | 59.187 | 1.205 | 37.135 | 1.00 | 20.53 | B |
| ATOM | 4654 | CG | LEU | B | 400 | 59.389 | 0.737 | 38.581 | 1.00 | 19.46 | B |
| ATOM | 4655 | CD1 | LEU | B | 400 | 58.888 | 1.806 | 39.547 | 1.00 | 22.22 | B |
| ATOM | 4656 | CD2 | LEU | B | 400 | 58.641 | −0.571 | 38.807 | 1.00 | 21.21 | B |
| ATOM | 4657 | C | LEU | B | 400 | 61.398 | 2.370 | 36.932 | 1.00 | 19.35 | B |
| ATOM | 4658 | O | LEU | B | 400 | 61.934 | 2.767 | 37.964 | 1.00 | 20.59 | B |
| ATOM | 4659 | N | GLU | B | 401 | 62.080 | 1.810 | 35.937 | 1.00 | 20.33 | B |
| ATOM | 4660 | CA | GLU | B | 401 | 63.528 | 1.625 | 36.013 | 1.00 | 21.53 | B |
| ATOM | 4661 | CB | GLU | B | 401 | 64.046 | 1.002 | 34.715 | 1.00 | 23.36 | B |
| ATOM | 4662 | CG | GLU | B | 401 | 65.561 | 0.941 | 34.611 | 1.00 | 26.96 | B |
| ATOM | 4663 | CD | GLU | B | 401 | 66.030 | 0.448 | 33.252 | 1.00 | 29.79 | B |
| ATOM | 4664 | OE1 | GLU | B | 401 | 67.261 | 0.374 | 33.030 | 1.00 | 31.18 | B |
| ATOM | 4665 | OE2 | GLU | B | 401 | 65.166 | 0.137 | 32.403 | 1.00 | 32.01 | B |
| ATOM | 4666 | C | GLU | B | 401 | 64.253 | 2.944 | 36.268 | 1.00 | 21.64 | B |
| ATOM | 4667 | O | GLU | B | 401 | 65.155 | 3.013 | 37.106 | 1.00 | 23.41 | B |
| ATOM | 4668 | N | LEU | B | 402 | 63.859 | 3.985 | 35.541 | 1.00 | 20.35 | B |
| ATOM | 4669 | CA | LEU | B | 402 | 64.472 | 5.302 | 35.692 | 1.00 | 19.60 | B |
| ATOM | 4670 | CB | LEU | B | 402 | 64.106 | 6.194 | 34.505 | 1.00 | 19.88 | B |
| ATOM | 4671 | CG | LEU | B | 402 | 64.620 | 5.720 | 33.145 | 1.00 | 20.91 | B |
| ATOM | 4672 | CD1 | LEU | B | 402 | 64.231 | 6.720 | 32.075 | 1.00 | 23.11 | B |
| ATOM | 4673 | CD2 | LEU | B | 402 | 66.129 | 5.550 | 33.202 | 1.00 | 22.90 | B |
| ATOM | 4674 | C | LEU | B | 402 | 64.030 | 5.973 | 36.989 | 1.00 | 18.77 | B |
| ATOM | 4675 | O | LEU | B | 402 | 64.844 | 6.537 | 37.722 | 1.00 | 18.98 | B |
| ATOM | 4676 | N | TYR | B | 403 | 62.735 | 5.904 | 37.270 | 1.00 | 17.08 | B |
| ATOM | 4677 | CA | TYR | B | 403 | 62.178 | 6.508 | 38.466 | 1.00 | 16.30 | B |
| ATOM | 4678 | CB | TYR | B | 403 | 60.671 | 6.228 | 38.519 | 1.00 | 15.79 | B |
| ATOM | 4679 | CG | TYR | B | 403 | 59.946 | 6.799 | 39.716 | 1.00 | 15.74 | B |
| ATOM | 4680 | CD1 | TYR | B | 403 | 60.435 | 7.909 | 40.398 | 1.00 | 15.43 | B |
| ATOM | 4681 | CE1 | TYR | B | 403 | 59.749 | 8.441 | 41.480 | 1.00 | 17.13 | B |
| ATOM | 4682 | CD2 | TYR | B | 403 | 58.753 | 6.241 | 40.147 | 1.00 | 16.57 | B |
| ATOM | 4683 | CE2 | TYR | B | 403 | 58.061 | 6.764 | 41.217 | 1.00 | 18.48 | B |
| ATOM | 4684 | CZ | TYR | B | 403 | 58.561 | 7.862 | 41.883 | 1.00 | 18.05 | B |
| ATOM | 4685 | OH | TYR | B | 403 | 57.865 | 8.368 | 42.954 | 1.00 | 19.16 | B |
| ATOM | 4686 | C | TYR | B | 403 | 62.874 | 6.006 | 39.727 | 1.00 | 16.60 | B |
| ATOM | 4687 | O | TYR | B | 403 | 63.218 | 6.792 | 40.609 | 1.00 | 16.10 | B |
| ATOM | 4688 | N | ARG | B | 404 | 63.093 | 4.701 | 39.819 | 1.00 | 17.32 | B |
| ATOM | 4689 | CA | ARG | B | 404 | 63.760 | 4.158 | 40.994 | 1.00 | 18.47 | B |
| ATOM | 4690 | CB | ARG | B | 404 | 63.802 | 2.632 | 40.925 | 1.00 | 20.53 | B |
| ATOM | 4691 | CG | ARG | B | 404 | 62.424 | 2.002 | 40.871 | 1.00 | 22.62 | B |
| ATOM | 4692 | CD | ARG | B | 404 | 62.505 | 0.502 | 41.045 | 1.00 | 26.02 | B |
| ATOM | 4693 | NE | ARG | B | 404 | 63.062 | 0.151 | 42.348 | 1.00 | 26.64 | B |
| ATOM | 4694 | CZ | ARG | B | 404 | 63.348 | −1.089 | 42.730 | 1.00 | 27.47 | B |
| ATOM | 4695 | NH1 | ARG | B | 404 | 63.131 | −2.104 | 41.905 | 1.00 | 28.66 | B |
| ATOM | 4696 | NH2 | ARG | B | 404 | 63.847 | −1.313 | 43.938 | 1.00 | 27.37 | B |
| ATOM | 4697 | C | ARG | B | 404 | 65.170 | 4.725 | 41.133 | 1.00 | 16.94 | B |
| ATOM | 4698 | O | ARG | B | 404 | 65.639 | 4.957 | 42.249 | 1.00 | 18.36 | B |
| ATOM | 4699 | N | GLN | B | 405 | 65.843 | 4.948 | 40.005 | 1.00 | 16.57 | B |
| ATOM | 4700 | CA | GLN | B | 405 | 67.191 | 5.508 | 40.039 | 1.00 | 15.94 | B |
| ATOM | 4701 | CB | GLN | B | 405 | 67.835 | 5.473 | 38.648 | 1.00 | 17.43 | B |
| ATOM | 4702 | CG | GLN | B | 405 | 68.132 | 4.070 | 38.155 | 1.00 | 20.32 | B |
| ATOM | 4703 | CD | GLN | B | 405 | 68.847 | 4.055 | 36.818 | 1.00 | 21.15 | B |
| ATOM | 4704 | OE1 | GLN | B | 405 | 70.020 | 4.429 | 36.719 | 1.00 | 24.86 | B |
| ATOM | 4705 | NE2 | GLN | B | 405 | 68.142 | 3.628 | 35.778 | 1.00 | 22.02 | B |
| ATOM | 4706 | C | GLN | B | 405 | 67.145 | 6.940 | 40.558 | 1.00 | 16.02 | B |
| ATOM | 4707 | O | GLN | B | 405 | 68.009 | 7.356 | 41.323 | 1.00 | 16.85 | B |
| ATOM | 4708 | N | TRP | B | 406 | 66.137 | 7.696 | 40.137 | 1.00 | 14.97 | B |
| ATOM | 4709 | CA | TRP | B | 406 | 65.994 | 9.074 | 40.595 | 1.00 | 14.32 | B |
| ATOM | 4710 | CB | TRP | B | 406 | 64.888 | 9.792 | 39.814 | 1.00 | 13.61 | B |
| ATOM | 4711 | CG | TRP | B | 406 | 65.247 | 10.098 | 38.389 | 1.00 | 13.33 | B |
| ATOM | 4712 | CD2 | TRP | B | 406 | 66.365 | 10.868 | 37.930 | 1.00 | 13.27 | B |
| ATOM | 4713 | CE2 | TRP | B | 406 | 66.294 | 10.907 | 36.522 | 1.00 | 13.99 | B |
| ATOM | 4714 | CE3 | TRP | B | 406 | 67.417 | 11.528 | 38.571 | 1.00 | 15.08 | B |
| ATOM | 4715 | CD1 | TRP | B | 406 | 64.564 | 9.713 | 37.272 | 1.00 | 15.01 | B |
| ATOM | 4716 | NE1 | TRP | B | 406 | 65.186 | 10.195 | 36.148 | 1.00 | 13.61 | B |
| ATOM | 4717 | CZ2 | TRP | B | 406 | 67.235 | 11.579 | 35.744 | 1.00 | 13.07 | B |
| ATOM | 4718 | CZ3 | TRP | B | 406 | 68.351 | 12.197 | 37.795 | 1.00 | 14.21 | B |
| ATOM | 4719 | CH2 | TRP | B | 406 | 68.253 | 12.217 | 36.398 | 1.00 | 15.23 | B |
| ATOM | 4720 | C | TRP | B | 406 | 65.666 | 9.103 | 42.084 | 1.00 | 15.21 | B |
| ATOM | 4721 | O | TRP | B | 406 | 66.178 | 9.941 | 42.824 | 1.00 | 15.30 | B |
| ATOM | 4722 | N | THR | B | 407 | 64.810 | 8.186 | 42.521 | 1.00 | 15.80 | B |
| ATOM | 4723 | CA | THR | B | 407 | 64.427 | 8.117 | 43.926 | 1.00 | 16.58 | B |
| ATOM | 4724 | CB | THR | B | 407 | 63.359 | 7.030 | 44.159 | 1.00 | 16.95 | B |
| ATOM | 4725 | OG1 | THR | B | 407 | 62.182 | 7.350 | 43.406 | 1.00 | 18.84 | B |

TABLE 1-continued

| | | | | | | | | | | |
|---|---|---|---|---|---|---|---|---|---|---|
| ATOM | 4726 | CG2 | THR | B | 407 | 62.996 | 6.945 | 45.631 | 1.00 | 18.45 | B |
| ATOM | 4727 | C | THR | B | 407 | 65.638 | 7.820 | 44.806 | 1.00 | 16.46 | B |
| ATOM | 4728 | O | THR | B | 407 | 65.790 | 8.400 | 45.884 | 1.00 | 17.79 | B |
| ATOM | 4729 | N | ASP | B | 408 | 66.501 | 6.916 | 44.353 | 1.00 | 16.64 | B |
| ATOM | 4730 | CA | ASP | B | 408 | 67.691 | 6.586 | 45.131 | 1.00 | 17.11 | B |
| ATOM | 4731 | CB | ASP | B | 408 | 68.504 | 5.476 | 44.456 | 1.00 | 20.31 | B |
| ATOM | 4732 | CG | ASP | B | 408 | 67.807 | 4.128 | 44.496 | 1.00 | 25.13 | B |
| ATOM | 4733 | OD1 | ASP | B | 408 | 66.915 | 3.935 | 45.350 | 1.00 | 28.10 | B |
| ATOM | 4734 | OD2 | ASP | B | 408 | 68.168 | 3.254 | 43.680 | 1.00 | 28.21 | B |
| ATOM | 4735 | C | ASP | B | 408 | 68.570 | 7.822 | 45.294 | 1.00 | 15.90 | B |
| ATOM | 4736 | O | ASP | B | 408 | 69.152 | 8.047 | 46.354 | 1.00 | 16.44 | B |
| ATOM | 4737 | N | ARG | B | 409 | 68.658 | 8.629 | 44.241 | 1.00 | 14.72 | B |
| ATOM | 4738 | CA | ARG | B | 409 | 69.479 | 9.834 | 44.293 | 1.00 | 14.16 | B |
| ATOM | 4739 | CB | ARG | B | 409 | 69.686 | 10.397 | 42.885 | 1.00 | 14.73 | B |
| ATOM | 4740 | CG | ARG | B | 409 | 70.545 | 9.513 | 42.015 | 1.00 | 14.13 | B |
| ATOM | 4741 | CD | ARG | B | 409 | 70.863 | 10.175 | 40.691 | 1.00 | 16.12 | B |
| ATOM | 4742 | NE | ARG | B | 409 | 71.781 | 9.363 | 39.898 | 1.00 | 16.95 | B |
| ATOM | 4743 | CZ | ARG | B | 409 | 72.770 | 9.861 | 39.164 | 1.00 | 17.75 | B |
| ATOM | 4744 | NH1 | ARG | B | 409 | 72.975 | 11.173 | 39.119 | 1.00 | 19.60 | B |
| ATOM | 4745 | NH2 | ARG | B | 409 | 73.559 | 9.048 | 38.477 | 1.00 | 19.46 | B |
| ATOM | 4746 | C | ARG | B | 409 | 68.901 | 10.912 | 45.198 | 1.00 | 14.05 | B |
| ATOM | 4747 | O | ARG | B | 409 | 69.630 | 11.535 | 45.970 | 1.00 | 15.29 | B |
| ATOM | 4748 | N | ILE | B | 410 | 67.594 | 11.141 | 45.125 | 1.00 | 14.65 | B |
| ATOM | 4749 | CA | ILE | B | 410 | 67.027 | 12.171 | 45.977 | 1.00 | 15.66 | B |
| ATOM | 4750 | CB | ILE | B | 410 | 65.555 | 12.472 | 45.625 | 1.00 | 17.16 | B |
| ATOM | 4751 | CG2 | ILE | B | 410 | 64.671 | 11.306 | 46.008 | 1.00 | 19.34 | B |
| ATOM | 4752 | CG1 | ILE | B | 410 | 65.103 | 13.743 | 46.354 | 1.00 | 20.62 | B |
| ATOM | 4753 | CD1 | ILE | B | 410 | 65.885 | 14.993 | 45.964 | 1.00 | 21.23 | B |
| ATOM | 4754 | C | ILE | B | 410 | 67.142 | 11.748 | 47.437 | 1.00 | 15.22 | B |
| ATOM | 4755 | O | ILE | B | 410 | 67.372 | 12.582 | 48.309 | 1.00 | 15.77 | B |
| ATOM | 4756 | N | MET | B | 411 | 67.005 | 10.453 | 47.707 | 1.00 | 15.96 | B |
| ATOM | 4757 | CA | MET | B | 411 | 67.117 | 9.983 | 49.083 | 1.00 | 16.37 | B |
| ATOM | 4758 | CB | MET | B | 411 | 66.686 | 8.518 | 49.207 | 1.00 | 17.92 | B |
| ATOM | 4759 | CG | MET | B | 411 | 65.184 | 8.299 | 49.074 | 1.00 | 21.37 | B |
| ATOM | 4760 | SD | MET | B | 411 | 64.210 | 9.363 | 50.172 | 1.00 | 23.38 | B |
| ATOM | 4761 | CE | MET | B | 411 | 64.689 | 8.730 | 51.781 | 1.00 | 26.58 | B |
| ATOM | 4762 | C | MET | B | 411 | 68.545 | 10.151 | 49.584 | 1.00 | 16.11 | B |
| ATOM | 4763 | O | MET | B | 411 | 68.757 | 10.524 | 50.733 | 1.00 | 15.72 | B |
| ATOM | 4764 | N | GLU | B | 412 | 69.528 | 9.884 | 48.731 | 1.00 | 15.83 | B |
| ATOM | 4765 | CA | GLU | B | 412 | 70.909 | 10.048 | 49.164 | 1.00 | 16.01 | B |
| ATOM | 4766 | CB | GLU | B | 412 | 71.892 | 9.544 | 48.107 | 1.00 | 18.76 | B |
| ATOM | 4767 | CG | GLU | B | 412 | 73.348 | 9.699 | 48.538 | 1.00 | 24.44 | B |
| ATOM | 4768 | CD | GLU | B | 412 | 73.593 | 9.196 | 49.957 | 1.00 | 28.55 | B |
| ATOM | 4769 | OE1 | GLU | B | 412 | 73.394 | 7.986 | 50.203 | 1.00 | 31.15 | B |
| ATOM | 4770 | OE2 | GLU | B | 412 | 73.981 | 10.011 | 50.830 | 1.00 | 30.92 | B |
| ATOM | 4771 | C | GLU | B | 412 | 71.188 | 11.518 | 49.466 | 1.00 | 15.59 | B |
| ATOM | 4772 | O | GLU | B | 412 | 71.873 | 11.834 | 50.432 | 1.00 | 15.30 | B |
| ATOM | 4773 | N | GLU | B | 413 | 70.653 | 12.425 | 48.652 | 1.00 | 15.53 | B |
| ATOM | 4774 | CA | GLU | B | 413 | 70.888 | 13.840 | 48.910 | 1.00 | 15.73 | B |
| ATOM | 4775 | CB | GLU | B | 413 | 70.364 | 14.707 | 47.759 | 1.00 | 17.43 | B |
| ATOM | 4776 | CG | GLU | B | 413 | 70.796 | 16.163 | 47.876 | 1.00 | 17.34 | B |
| ATOM | 4777 | CD | GLU | B | 413 | 70.518 | 16.968 | 46.624 | 1.00 | 16.08 | B |
| ATOM | 4778 | OE1 | GLU | B | 413 | 70.874 | 16.491 | 45.531 | 1.00 | 15.68 | B |
| ATOM | 4779 | OE2 | GLU | B | 413 | 69.959 | 18.081 | 46.734 | 1.00 | 17.21 | B |
| ATOM | 4780 | C | GLU | B | 413 | 70.194 | 14.219 | 50.215 | 1.00 | 14.75 | B |
| ATOM | 4781 | O | GLU | B | 413 | 70.707 | 15.016 | 51.005 | 1.00 | 15.01 | B |
| ATOM | 4782 | N | PHE | B | 414 | 69.023 | 13.635 | 50.438 | 1.00 | 15.31 | B |
| ATOM | 4783 | CA | PHE | B | 414 | 68.264 | 13.887 | 51.654 | 1.00 | 16.35 | B |
| ATOM | 4784 | CB | PHE | B | 414 | 66.974 | 13.070 | 51.637 | 1.00 | 18.25 | B |
| ATOM | 4785 | CG | PHE | B | 414 | 66.113 | 13.267 | 52.847 | 1.00 | 19.73 | B |
| ATOM | 4786 | CD1 | PHE | B | 414 | 65.244 | 14.345 | 52.932 | 1.00 | 21.35 | B |
| ATOM | 4787 | CD2 | PHE | B | 414 | 66.165 | 12.368 | 53.899 | 1.00 | 21.69 | B |
| ATOM | 4788 | CE1 | PHE | B | 414 | 64.441 | 14.518 | 54.047 | 1.00 | 21.92 | B |
| ATOM | 4789 | CE2 | PHE | B | 414 | 65.363 | 12.538 | 55.019 | 1.00 | 23.22 | B |
| ATOM | 4790 | CZ | PHE | B | 414 | 64.502 | 13.611 | 55.091 | 1.00 | 22.82 | B |
| ATOM | 4791 | C | PHE | B | 414 | 69.114 | 13.473 | 52.853 | 1.00 | 15.56 | B |
| ATOM | 4792 | O | PHE | B | 414 | 69.238 | 14.217 | 53.829 | 1.00 | 16.70 | B |
| ATOM | 4793 | N | PHE | B | 415 | 69.695 | 12.278 | 52.779 | 1.00 | 16.39 | B |
| ATOM | 4794 | CA | PHE | B | 415 | 70.536 | 11.787 | 53.867 | 1.00 | 17.16 | B |
| ATOM | 4795 | CB | PHE | B | 415 | 70.883 | 10.309 | 53.669 | 1.00 | 18.13 | B |
| ATOM | 4796 | CG | PHE | B | 415 | 69.685 | 9.405 | 53.657 | 1.00 | 20.02 | B |
| ATOM | 4797 | CD1 | PHE | B | 415 | 68.632 | 9.616 | 54.531 | 1.00 | 20.58 | B |
| ATOM | 4798 | CD2 | PHE | B | 415 | 69.617 | 8.334 | 52.778 | 1.00 | 21.28 | B |
| ATOM | 4799 | CE1 | PHE | B | 415 | 67.530 | 8.776 | 54.529 | 1.00 | 22.08 | B |
| ATOM | 4800 | CE2 | PHE | B | 415 | 68.519 | 7.493 | 52.772 | 1.00 | 22.18 | B |
| ATOM | 4801 | CZ | PHE | B | 415 | 67.475 | 7.714 | 53.647 | 1.00 | 22.75 | B |
| ATOM | 4802 | C | PHE | B | 415 | 71.811 | 12.609 | 53.982 | 1.00 | 16.85 | B |
| ATOM | 4803 | O | PHE | B | 415 | 72.351 | 12.764 | 55.079 | 1.00 | 19.53 | B |
| ATOM | 4804 | N | GLN | B | 416 | 72.295 | 13.129 | 52.856 | 1.00 | 17.47 | B |

TABLE 1-continued

| | | | | | | | | | | |
|---|---|---|---|---|---|---|---|---|---|---|
| ATOM | 4805 | CA | GLN | B | 416 | 73.492 | 13.969 | 52.862 | 1.00 | 18.09 | B |
| ATOM | 4806 | CB | GLN | B | 416 | 73.873 | 14.421 | 51.443 | 1.00 | 20.52 | B |
| ATOM | 4807 | CG | GLN | B | 416 | 74.443 | 13.341 | 50.528 | 1.00 | 23.74 | B |
| ATOM | 4808 | CD | GLN | B | 416 | 75.009 | 13.902 | 49.219 | 1.00 | 24.94 | B |
| ATOM | 4809 | OE1 | GLN | B | 416 | 74.299 | 14.537 | 48.426 | 1.00 | 22.81 | B |
| ATOM | 4810 | NE2 | GLN | B | 416 | 76.298 | 13.664 | 48.988 | 1.00 | 27.78 | B |
| ATOM | 4811 | C | GLN | B | 416 | 73.193 | 15.206 | 53.705 | 1.00 | 17.10 | B |
| ATOM | 4812 | O | GLN | B | 416 | 74.019 | 15.633 | 54.508 | 1.00 | 16.92 | B |
| ATOM | 4813 | N | GLN | B | 417 | 72.012 | 15.791 | 53.513 | 1.00 | 16.24 | B |
| ATOM | 4814 | CA | GLN | B | 417 | 71.652 | 16.973 | 54.282 | 1.00 | 14.43 | B |
| ATOM | 4815 | CB | GLN | B | 417 | 70.357 | 17.612 | 53.769 | 1.00 | 14.92 | B |
| ATOM | 4816 | CG | GLN | B | 417 | 70.012 | 18.893 | 54.518 | 1.00 | 15.40 | B |
| ATOM | 4817 | CD | GLN | B | 417 | 68.786 | 19.598 | 53.970 | 1.00 | 17.07 | B |
| ATOM | 4818 | OE1 | GLN | B | 417 | 68.614 | 19.716 | 52.757 | 1.00 | 20.04 | B |
| ATOM | 4819 | NE2 | GLN | B | 417 | 67.932 | 20.087 | 54.866 | 1.00 | 18.86 | B |
| ATOM | 4820 | C | GLN | B | 417 | 71.489 | 16.595 | 55.747 | 1.00 | 15.00 | B |
| ATOM | 4821 | O | GLN | B | 417 | 71.876 | 17.354 | 56.630 | 1.00 | 14.67 | B |
| ATOM | 4822 | N | GLY | B | 418 | 70.918 | 15.419 | 55.995 | 1.00 | 14.72 | B |
| ATOM | 4823 | CA | GLY | B | 418 | 70.742 | 14.962 | 57.361 | 1.00 | 17.03 | B |
| ATOM | 4824 | C | GLY | B | 418 | 72.083 | 14.870 | 58.066 | 1.00 | 17.70 | B |
| ATOM | 4825 | O | GLY | B | 418 | 72.210 | 15.257 | 59.230 | 1.00 | 18.70 | B |
| ATOM | 4826 | N | ASP | B | 419 | 73.091 | 14.359 | 57.363 | 1.00 | 17.59 | B |
| ATOM | 4827 | CA | ASP | B | 419 | 74.426 | 14.241 | 57.945 | 1.00 | 16.79 | B |
| ATOM | 4828 | CB | ASP | B | 419 | 75.396 | 13.557 | 56.980 | 1.00 | 20.08 | B |
| ATOM | 4829 | CG | ASP | B | 419 | 75.103 | 12.078 | 56.794 | 1.00 | 23.86 | B |
| ATOM | 4830 | OD1 | ASP | B | 419 | 74.450 | 11.473 | 57.672 | 1.00 | 27.08 | B |
| ATOM | 4831 | OD2 | ASP | B | 419 | 75.548 | 11.518 | 55.770 | 1.00 | 26.34 | B |
| ATOM | 4832 | C | ASP | B | 419 | 74.970 | 15.622 | 58.296 | 1.00 | 16.64 | B |
| ATOM | 4833 | O | ASP | B | 419 | 75.540 | 15.815 | 59.370 | 1.00 | 17.12 | B |
| ATOM | 4834 | N | LYS | B | 420 | 74.790 | 16.581 | 57.392 | 1.00 | 15.93 | B |
| ATOM | 4835 | CA | LYS | B | 420 | 75.272 | 17.940 | 57.628 | 1.00 | 15.87 | B |
| ATOM | 4836 | CB | LYS | B | 420 | 75.019 | 18.827 | 56.405 | 1.00 | 16.54 | B |
| ATOM | 4837 | CG | LYS | B | 420 | 75.692 | 18.363 | 55.133 | 1.00 | 17.29 | B |
| ATOM | 4838 | CD | LYS | B | 420 | 75.342 | 19.297 | 53.988 | 1.00 | 18.16 | B |
| ATOM | 4839 | CE | LYS | B | 420 | 75.749 | 18.714 | 52.642 | 1.00 | 20.09 | B |
| ATOM | 4840 | NZ | LYS | B | 420 | 77.214 | 18.482 | 52.536 | 1.00 | 23.94 | B |
| ATOM | 4841 | C | LYS | B | 420 | 74.594 | 18.569 | 58.840 | 1.00 | 15.08 | B |
| ATOM | 4842 | O | LYS | B | 420 | 75.244 | 19.241 | 59.639 | 1.00 | 16.59 | B |
| ATOM | 4843 | N | GLU | B | 421 | 73.287 | 18.358 | 58.977 | 1.00 | 16.23 | B |
| ATOM | 4844 | CA | GLU | B | 421 | 72.563 | 18.928 | 60.107 | 1.00 | 16.38 | B |
| ATOM | 4845 | CB | GLU | B | 421 | 71.058 | 18.660 | 59.974 | 1.00 | 16.78 | B |
| ATOM | 4846 | CG | GLU | B | 421 | 70.469 | 19.194 | 58.671 | 1.00 | 20.21 | B |
| ATOM | 4847 | CD | GLU | B | 421 | 68.952 | 19.132 | 58.623 | 1.00 | 23.10 | B |
| ATOM | 4848 | OE1 | GLU | B | 421 | 68.374 | 18.157 | 59.146 | 1.00 | 28.17 | B |
| ATOM | 4849 | OE2 | GLU | B | 421 | 68.335 | 20.053 | 58.042 | 1.00 | 23.93 | B |
| ATOM | 4850 | C | GLU | B | 421 | 73.106 | 18.347 | 61.410 | 1.00 | 17.38 | B |
| ATOM | 4851 | O | GLU | B | 421 | 73.243 | 19.058 | 62.404 | 1.00 | 19.24 | B |
| ATOM | 4852 | N | ARG | B | 422 | 73.428 | 17.059 | 61.399 | 1.00 | 16.44 | B |
| ATOM | 4853 | CA | ARG | B | 422 | 73.971 | 16.409 | 62.591 | 1.00 | 16.90 | B |
| ATOM | 4854 | CB | ARG | B | 422 | 74.006 | 14.890 | 62.397 | 1.00 | 19.02 | B |
| ATOM | 4855 | CG | ARG | B | 422 | 74.700 | 14.121 | 63.522 | 1.00 | 21.25 | B |
| ATOM | 4856 | CD | ARG | B | 422 | 76.075 | 13.649 | 63.081 | 1.00 | 23.84 | B |
| ATOM | 4857 | NE | ARG | B | 422 | 75.977 | 12.760 | 61.927 | 1.00 | 25.31 | B |
| ATOM | 4858 | CZ | ARG | B | 422 | 77.004 | 12.395 | 61.169 | 1.00 | 23.60 | B |
| ATOM | 4859 | NH1 | ARG | B | 422 | 78.224 | 12.840 | 61.436 | 1.00 | 23.19 | B |
| ATOM | 4860 | NH2 | ARG | B | 422 | 76.807 | 11.590 | 60.133 | 1.00 | 26.79 | B |
| ATOM | 4861 | C | ARG | B | 422 | 75.374 | 16.930 | 62.901 | 1.00 | 16.03 | B |
| ATOM | 4862 | O | ARG | B | 422 | 75.686 | 17.254 | 64.048 | 1.00 | 17.62 | B |
| ATOM | 4863 | N | GLU | B | 423 | 76.212 | 17.016 | 61.873 | 1.00 | 16.45 | B |
| ATOM | 4864 | CA | GLU | B | 423 | 77.583 | 17.498 | 62.029 | 1.00 | 16.45 | B |
| ATOM | 4865 | CB | GLU | B | 423 | 78.314 | 17.470 | 60.687 | 1.00 | 17.30 | B |
| ATOM | 4866 | CG | GLU | B | 423 | 78.393 | 16.106 | 60.029 | 1.00 | 19.66 | B |
| ATOM | 4867 | CD | GLU | B | 423 | 79.018 | 16.169 | 58.647 | 1.00 | 21.26 | B |
| ATOM | 4868 | OE1 | GLU | B | 423 | 78.750 | 17.146 | 57.914 | 1.00 | 21.02 | B |
| ATOM | 4869 | OE2 | GLU | B | 423 | 79.767 | 15.237 | 58.288 | 1.00 | 22.31 | B |
| ATOM | 4870 | C | GLU | B | 423 | 77.635 | 18.923 | 62.569 | 1.00 | 16.02 | B |
| ATOM | 4871 | O | GLU | B | 423 | 78.561 | 19.287 | 63.291 | 1.00 | 16.28 | B |
| ATOM | 4872 | N | ARG | B | 424 | 76.642 | 19.731 | 62.215 | 1.00 | 16.63 | B |
| ATOM | 4873 | CA | ARG | B | 424 | 76.613 | 21.121 | 62.656 | 1.00 | 16.78 | B |
| ATOM | 4874 | CB | ARG | B | 424 | 76.151 | 22.018 | 61.502 | 1.00 | 17.21 | B |
| ATOM | 4875 | CG | ARG | B | 424 | 76.998 | 21.846 | 60.250 | 1.00 | 17.15 | B |
| ATOM | 4876 | CD | ARG | B | 424 | 76.641 | 22.839 | 59.160 | 1.00 | 16.99 | B |
| ATOM | 4877 | NE | ARG | B | 424 | 77.217 | 22.445 | 57.878 | 1.00 | 14.15 | B |
| ATOM | 4878 | CZ | ARG | B | 424 | 77.211 | 23.205 | 56.789 | 1.00 | 14.42 | B |
| ATOM | 4879 | NH1 | ARG | B | 424 | 76.667 | 24.414 | 56.824 | 1.00 | 13.44 | B |
| ATOM | 4880 | NH2 | ARG | B | 424 | 77.733 | 22.747 | 55.658 | 1.00 | 15.50 | B |
| ATOM | 4881 | C | ARG | B | 424 | 75.747 | 21.359 | 63.888 | 1.00 | 17.47 | B |
| ATOM | 4882 | O | ARG | B | 424 | 75.601 | 22.493 | 64.339 | 1.00 | 17.85 | B |
| ATOM | 4883 | N | GLY | B | 425 | 75.181 | 20.286 | 64.429 | 1.00 | 17.45 | B |

TABLE 1-continued

| ATOM | 4884 | CA  | GLY | B | 425 | 74.339 | 20.407 | 65.608 | 1.00 | 19.21 | B |
| ATOM | 4885 | C   | GLY | B | 425 | 73.057 | 21.185 | 65.380 | 1.00 | 19.98 | B |
| ATOM | 4886 | O   | GLY | B | 425 | 72.625 | 21.953 | 66.240 | 1.00 | 21.81 | B |
| ATOM | 4887 | N   | MET | B | 426 | 72.434 | 20.982 | 64.225 | 1.00 | 21.07 | B |
| ATOM | 4888 | CA  | MET | B | 426 | 71.192 | 21.669 | 63.897 | 1.00 | 23.10 | B |
| ATOM | 4889 | CB  | MET | B | 426 | 71.147 | 21.968 | 62.399 | 1.00 | 23.78 | B |
| ATOM | 4890 | CG  | MET | B | 426 | 72.235 | 22.911 | 61.928 | 1.00 | 24.54 | B |
| ATOM | 4891 | SD  | MET | B | 426 | 72.368 | 22.932 | 60.137 | 1.00 | 24.34 | B |
| ATOM | 4892 | CE  | MET | B | 426 | 70.892 | 23.846 | 59.690 | 1.00 | 23.10 | B |
| ATOM | 4893 | C   | MET | B | 426 | 69.983 | 20.828 | 64.291 | 1.00 | 24.62 | B |
| ATOM | 4894 | O   | MET | B | 426 | 70.129 | 19.715 | 64.796 | 1.00 | 27.07 | B |
| ATOM | 4895 | N   | PRO | B | 430 | 65.182 | 16.336 | 63.873 | 1.00 | 27.03 | B |
| ATOM | 4896 | CD  | PRO | B | 430 | 64.953 | 15.879 | 65.253 | 1.00 | 27.42 | B |
| ATOM | 4897 | CA  | PRO | B | 430 | 66.114 | 15.440 | 63.181 | 1.00 | 27.93 | B |
| ATOM | 4898 | CB  | PRO | B | 430 | 66.613 | 14.535 | 64.299 | 1.00 | 26.76 | B |
| ATOM | 4899 | CG  | PRO | B | 430 | 65.419 | 14.437 | 65.192 | 1.00 | 27.07 | B |
| ATOM | 4900 | C   | PRO | B | 430 | 65.449 | 14.653 | 62.061 | 1.00 | 28.19 | B |
| ATOM | 4901 | O   | PRO | B | 430 | 64.374 | 14.077 | 62.242 | 1.00 | 28.28 | B |
| ATOM | 4902 | N   | MET | B | 431 | 66.097 | 14.632 | 60.902 | 1.00 | 26.69 | B |
| ATOM | 4903 | CA  | MET | B | 431 | 65.572 | 13.911 | 59.755 | 1.00 | 26.46 | B |
| ATOM | 4904 | C   | MET | B | 431 | 65.874 | 12.428 | 59.919 | 1.00 | 26.35 | B |
| ATOM | 4905 | O   | MET | B | 431 | 66.810 | 12.049 | 60.624 | 1.00 | 25.40 | B |
| ATOM | 4906 | CB  | MET | B | 431 | 66.144 | 14.481 | 58.457 | 1.00 | 26.67 | B |
| ATOM | 4907 | CG  | MET | B | 431 | 66.915 | 15.777 | 58.635 | 1.00 | 20.00 | B |
| ATOM | 4908 | SD  | MET | B | 431 | 67.585 | 16.408 | 57.085 | 1.00 | 20.00 | B |
| ATOM | 4909 | CE  | MET | B | 431 | 66.902 | 15.233 | 55.919 | 1.00 | 20.00 | B |
| ATOM | 4910 | N   | CYS | B | 432 | 65.076 | 11.587 | 59.273 | 1.00 | 26.28 | B |
| ATOM | 4911 | CA  | CYS | B | 432 | 65.288 | 10.151 | 59.349 | 1.00 | 28.69 | B |
| ATOM | 4912 | CB  | CYS | B | 432 | 64.088 | 9.397  | 58.768 | 1.00 | 31.65 | B |
| ATOM | 4913 | SG  | CYS | B | 432 | 62.528 | 9.642  | 59.642 | 1.00 | 36.54 | B |
| ATOM | 4914 | C   | CYS | B | 432 | 66.534 | 9.797  | 58.550 | 1.00 | 26.43 | B |
| ATOM | 4915 | O   | CYS | B | 432 | 66.972 | 10.565 | 57.690 | 1.00 | 26.50 | B |
| ATOM | 4916 | N   | ASP | B | 433 | 67.107 | 8.635  | 58.848 | 1.00 | 25.64 | B |
| ATOM | 4917 | CA  | ASP | B | 433 | 68.286 | 8.161  | 58.140 | 1.00 | 24.43 | B |
| ATOM | 4918 | CB  | ASP | B | 433 | 69.408 | 7.809  | 59.124 | 1.00 | 26.05 | B |
| ATOM | 4919 | CG  | ASP | B | 433 | 68.946 | 6.882  | 60.236 | 1.00 | 27.55 | B |
| ATOM | 4920 | OD1 | ASP | B | 433 | 67.853 | 6.292  | 60.111 | 1.00 | 28.87 | B |
| ATOM | 4921 | OD2 | ASP | B | 433 | 69.683 | 6.737  | 61.233 | 1.00 | 30.52 | B |
| ATOM | 4922 | C   | ASP | B | 433 | 67.895 | 6.931  | 57.330 | 1.00 | 25.37 | B |
| ATOM | 4923 | O   | ASP | B | 433 | 66.711 | 6.621  | 57.193 | 1.00 | 24.40 | B |
| ATOM | 4924 | N   | LYS | B | 434 | 68.891 | 6.229  | 56.801 | 1.00 | 24.86 | B |
| ATOM | 4925 | CA  | LYS | B | 434 | 68.649 | 5.043  | 55.990 | 1.00 | 25.53 | B |
| ATOM | 4926 | C   | LYS | B | 434 | 67.943 | 3.912  | 56.737 | 1.00 | 25.70 | B |
| ATOM | 4927 | O   | LYS | B | 434 | 67.331 | 3.043  | 56.115 | 1.00 | 26.03 | B |
| ATOM | 4928 | CB  | LYS | B | 434 | 69.967 | 4.482  | 55.455 | 1.00 | 26.67 | B |
| ATOM | 4929 | CG  | LYS | B | 434 | 70.744 | 5.452  | 54.581 | 1.00 | 20.00 | B |
| ATOM | 4930 | CD  | LYS | B | 434 | 71.907 | 4.762  | 53.889 | 1.00 | 20.00 | B |
| ATOM | 4931 | CE  | LYS | B | 434 | 72.684 | 5.731  | 53.015 | 1.00 | 20.00 | B |
| ATOM | 4932 | NZ  | LYS | B | 434 | 73.826 | 5.068  | 52.331 | 1.00 | 20.00 | B |
| ATOM | 4933 | N   | HIS | B | 435 | 68.016 | 3.925  | 58.065 | 1.00 | 24.99 | B |
| ATOM | 4934 | CA  | HIS | B | 435 | 67.392 | 2.874  | 58.863 | 1.00 | 25.11 | B |
| ATOM | 4935 | CB  | HIS | B | 435 | 68.236 | 2.574  | 60.110 | 1.00 | 24.53 | B |
| ATOM | 4936 | CG  | HIS | B | 435 | 69.691 | 2.356  | 59.828 | 1.00 | 25.99 | B |
| ATOM | 4937 | CD2 | HIS | B | 435 | 70.436 | 1.224  | 59.807 | 1.00 | 25.65 | B |
| ATOM | 4938 | ND1 | HIS | B | 435 | 70.557 | 3.388  | 59.537 | 1.00 | 26.95 | B |
| ATOM | 4939 | CE1 | HIS | B | 435 | 71.772 | 2.903  | 59.351 | 1.00 | 27.05 | B |
| ATOM | 4940 | NE2 | HIS | B | 435 | 71.726 | 1.593  | 59.509 | 1.00 | 28.53 | B |
| ATOM | 4941 | C   | HIS | B | 435 | 65.965 | 3.195  | 59.308 | 1.00 | 25.42 | B |
| ATOM | 4942 | O   | HIS | B | 435 | 65.189 | 2.290  | 59.609 | 1.00 | 26.16 | B |
| ATOM | 4943 | N   | THR | B | 436 | 65.615 | 4.475  | 59.347 | 1.00 | 25.13 | B |
| ATOM | 4944 | CA  | THR | B | 436 | 64.284 | 4.874  | 59.793 | 1.00 | 26.22 | B |
| ATOM | 4945 | CB  | THR | B | 436 | 64.387 | 5.921  | 60.930 | 1.00 | 26.95 | B |
| ATOM | 4946 | OG1 | THR | B | 436 | 65.059 | 5.340  | 62.054 | 1.00 | 29.28 | B |
| ATOM | 4947 | CG2 | THR | B | 436 | 63.004 | 6.389  | 61.361 | 1.00 | 27.82 | B |
| ATOM | 4948 | C   | THR | B | 436 | 63.380 | 5.431  | 58.696 | 1.00 | 25.36 | B |
| ATOM | 4949 | O   | THR | B | 436 | 62.155 | 5.395  | 58.819 | 1.00 | 26.67 | B |
| ATOM | 4950 | N   | ALA | B | 437 | 63.981 | 5.935  | 57.625 | 1.00 | 24.30 | B |
| ATOM | 4951 | CA  | ALA | B | 437 | 63.219 | 6.515  | 56.522 | 1.00 | 23.39 | B |
| ATOM | 4952 | CB  | ALA | B | 437 | 64.171 | 7.029  | 55.450 | 1.00 | 22.09 | B |
| ATOM | 4953 | C   | ALA | B | 437 | 62.208 | 5.554  | 55.899 | 1.00 | 25.05 | B |
| ATOM | 4954 | O   | ALA | B | 437 | 62.389 | 4.334  | 55.925 | 1.00 | 25.85 | B |
| ATOM | 4955 | N   | SER | B | 438 | 61.140 | 6.126  | 55.346 | 1.00 | 24.33 | B |
| ATOM | 4956 | CA  | SER | B | 438 | 60.082 | 5.365  | 54.684 | 1.00 | 24.47 | B |
| ATOM | 4957 | CB  | SER | B | 438 | 58.739 | 5.616  | 55.368 | 1.00 | 24.80 | B |
| ATOM | 4958 | OG  | SER | B | 438 | 58.790 | 5.269  | 56.741 | 1.00 | 30.21 | B |
| ATOM | 4959 | C   | SER | B | 438 | 60.016 | 5.860  | 53.243 | 1.00 | 22.58 | B |
| ATOM | 4960 | O   | SER | B | 438 | 59.084 | 6.568  | 52.863 | 1.00 | 23.92 | B |
| ATOM | 4961 | N   | VAL | B | 439 | 61.014 | 5.484  | 52.451 | 1.00 | 21.58 | B |
| ATOM | 4962 | CA  | VAL | B | 439 | 61.104 | 5.910  | 51.060 | 1.00 | 21.48 | B |

TABLE 1-continued

| ATOM | 4963 | CB | VAL | B | 439 | 62.280 | 5.216 | 50.352 | 1.00 | 21.97 | B |
| --- | --- | --- | --- | --- | --- | --- | --- | --- | --- | --- | --- |
| ATOM | 4964 | CG1 | VAL | B | 439 | 62.363 | 5.679 | 48.907 | 1.00 | 21.61 | B |
| ATOM | 4965 | CG2 | VAL | B | 439 | 63.578 | 5.534 | 51.081 | 1.00 | 22.65 | B |
| ATOM | 4966 | C | VAL | B | 439 | 59.837 | 5.684 | 50.240 | 1.00 | 21.37 | B |
| ATOM | 4967 | O | VAL | B | 439 | 59.349 | 6.601 | 49.577 | 1.00 | 21.09 | B |
| ATOM | 4968 | N | GLU | B | 440 | 59.311 | 4.465 | 50.277 | 1.00 | 21.33 | B |
| ATOM | 4969 | CA | GLU | B | 440 | 58.103 | 4.143 | 49.526 | 1.00 | 21.00 | B |
| ATOM | 4970 | CB | GLU | B | 440 | 57.707 | 2.679 | 49.744 | 1.00 | 21.40 | B |
| ATOM | 4971 | CG | GLU | B | 440 | 58.732 | 1.647 | 49.298 | 1.00 | 25.73 | B |
| ATOM | 4972 | CD | GLU | B | 440 | 59.993 | 1.663 | 50.138 | 1.00 | 26.72 | B |
| ATOM | 4973 | OE1 | GLU | B | 440 | 59.886 | 1.813 | 51.375 | 1.00 | 28.64 | B |
| ATOM | 4974 | OE2 | GLU | B | 440 | 61.091 | 1.512 | 49.560 | 1.00 | 30.19 | B |
| ATOM | 4975 | C | GLU | B | 440 | 56.934 | 5.034 | 49.932 | 1.00 | 19.70 | B |
| ATOM | 4976 | O | GLU | B | 440 | 56.283 | 5.649 | 49.084 | 1.00 | 20.00 | B |
| ATOM | 4977 | N | LYS | B | 441 | 56.668 | 5.094 | 51.232 | 1.00 | 20.78 | B |
| ATOM | 4978 | CA | LYS | B | 441 | 55.572 | 5.894 | 51.758 | 1.00 | 20.87 | B |
| ATOM | 4979 | CB | LYS | B | 441 | 55.502 | 5.738 | 53.281 | 1.00 | 22.00 | B |
| ATOM | 4980 | CG | LYS | B | 441 | 54.241 | 6.301 | 53.920 | 1.00 | 24.30 | B |
| ATOM | 4981 | CD | LYS | B | 441 | 54.129 | 5.844 | 55.367 | 1.00 | 25.49 | B |
| ATOM | 4982 | CE | LYS | B | 441 | 52.836 | 6.320 | 56.009 | 1.00 | 27.95 | B |
| ATOM | 4983 | NZ | LYS | B | 441 | 52.667 | 5.774 | 57.387 | 1.00 | 29.48 | B |
| ATOM | 4984 | C | LYS | B | 441 | 55.714 | 7.367 | 51.380 | 1.00 | 20.92 | B |
| ATOM | 4985 | O | LYS | B | 441 | 54.721 | 8.035 | 51.092 | 1.00 | 21.68 | B |
| ATOM | 4986 | N | SER | B | 442 | 56.943 | 7.873 | 51.372 | 1.00 | 21.09 | B |
| ATOM | 4987 | CA | SER | B | 442 | 57.162 | 9.273 | 51.021 | 1.00 | 21.29 | B |
| ATOM | 4988 | CB | SER | B | 442 | 58.575 | 9.713 | 51.400 | 1.00 | 22.18 | B |
| ATOM | 4989 | OG | SER | B | 442 | 58.706 | 9.805 | 52.808 | 1.00 | 27.11 | B |
| ATOM | 4990 | C | SER | B | 442 | 56.916 | 9.537 | 49.543 | 1.00 | 19.41 | B |
| ATOM | 4991 | O | SER | B | 442 | 56.381 | 10.580 | 49.179 | 1.00 | 20.24 | B |
| ATOM | 4992 | N | GLN | B | 443 | 57.295 | 8.597 | 48.684 | 1.00 | 19.71 | B |
| ATOM | 4993 | CA | GLN | B | 443 | 57.070 | 8.794 | 47.259 | 1.00 | 19.47 | B |
| ATOM | 4994 | CB | GLN | B | 443 | 57.812 | 7.740 | 46.434 | 1.00 | 19.23 | B |
| ATOM | 4995 | CG | GLN | B | 443 | 59.309 | 7.968 | 46.375 | 1.00 | 19.88 | B |
| ATOM | 4996 | CD | GLN | B | 443 | 59.660 | 9.358 | 45.874 | 1.00 | 20.06 | B |
| ATOM | 4997 | OE1 | GLN | B | 443 | 59.267 | 9.755 | 44.776 | 1.00 | 20.39 | B |
| ATOM | 4998 | NE2 | GLN | B | 443 | 60.398 | 10.107 | 46.682 | 1.00 | 23.73 | B |
| ATOM | 4999 | C | GLN | B | 443 | 55.581 | 8.755 | 46.946 | 1.00 | 19.06 | B |
| ATOM | 5000 | O | GLN | B | 443 | 55.104 | 9.497 | 46.094 | 1.00 | 19.58 | B |
| ATOM | 5001 | N | VAL | B | 444 | 54.838 | 7.897 | 47.636 | 1.00 | 18.31 | B |
| ATOM | 5002 | CA | VAL | B | 444 | 53.405 | 7.831 | 47.390 | 1.00 | 17.94 | B |
| ATOM | 5003 | CB | VAL | B | 444 | 52.745 | 6.645 | 48.129 | 1.00 | 18.38 | B |
| ATOM | 5004 | CG1 | VAL | B | 444 | 51.232 | 6.728 | 47.986 | 1.00 | 19.96 | B |
| ATOM | 5005 | CG2 | VAL | B | 444 | 53.256 | 5.326 | 47.554 | 1.00 | 19.96 | B |
| ATOM | 5006 | C | VAL | B | 444 | 52.761 | 9.135 | 47.848 | 1.00 | 16.98 | B |
| ATOM | 5007 | O | VAL | B | 444 | 51.897 | 9.675 | 47.166 | 1.00 | 18.03 | B |
| ATOM | 5008 | N | GLY | B | 445 | 53.191 | 9.642 | 49.001 | 1.00 | 17.64 | B |
| ATOM | 5009 | CA | GLY | B | 445 | 52.640 | 10.892 | 49.496 | 1.00 | 18.57 | B |
| ATOM | 5010 | C | GLY | B | 445 | 52.977 | 12.032 | 48.550 | 1.00 | 18.61 | B |
| ATOM | 5011 | O | GLY | B | 445 | 52.131 | 12.869 | 48.231 | 1.00 | 20.44 | B |
| ATOM | 5012 | N | PHE | B | 446 | 54.231 | 12.059 | 48.110 | 1.00 | 19.28 | B |
| ATOM | 5013 | CA | PHE | B | 446 | 54.728 | 13.070 | 47.181 | 1.00 | 18.59 | B |
| ATOM | 5014 | CB | PHE | B | 446 | 56.199 | 12.759 | 46.862 | 1.00 | 19.29 | B |
| ATOM | 5015 | CG | PHE | B | 446 | 56.817 | 13.654 | 45.823 | 1.00 | 20.78 | B |
| ATOM | 5016 | CD1 | PHE | B | 446 | 56.772 | 15.032 | 45.950 | 1.00 | 21.49 | B |
| ATOM | 5017 | CD2 | PHE | B | 446 | 57.494 | 13.108 | 44.743 | 1.00 | 20.82 | B |
| ATOM | 5018 | CE1 | PHE | B | 446 | 57.395 | 15.851 | 45.016 | 1.00 | 19.12 | B |
| ATOM | 5019 | CE2 | PHE | B | 446 | 58.119 | 13.920 | 43.808 | 1.00 | 22.01 | B |
| ATOM | 5020 | CZ | PHE | B | 446 | 58.067 | 15.294 | 43.948 | 1.00 | 20.81 | B |
| ATOM | 5021 | C | PHE | B | 446 | 53.878 | 13.062 | 45.909 | 1.00 | 17.64 | B |
| ATOM | 5022 | O | PHE | B | 446 | 53.497 | 14.117 | 45.393 | 1.00 | 18.63 | B |
| ATOM | 5023 | N | ILE | B | 447 | 53.566 | 11.866 | 45.417 | 1.00 | 17.72 | B |
| ATOM | 5024 | CA | ILE | B | 447 | 52.758 | 11.715 | 44.209 | 1.00 | 17.84 | B |
| ATOM | 5025 | CB | ILE | B | 447 | 52.793 | 10.253 | 43.689 | 1.00 | 17.28 | B |
| ATOM | 5026 | CG2 | ILE | B | 447 | 51.767 | 10.059 | 42.573 | 1.00 | 17.54 | B |
| ATOM | 5027 | CG1 | ILE | B | 447 | 54.198 | 9.919 | 43.190 | 1.00 | 16.87 | B |
| ATOM | 5028 | CD1 | ILE | B | 447 | 54.306 | 8.556 | 42.549 | 1.00 | 19.49 | B |
| ATOM | 5029 | C | ILE | B | 447 | 51.298 | 12.122 | 44.410 | 1.00 | 18.44 | B |
| ATOM | 5030 | O | ILE | B | 447 | 50.722 | 12.822 | 43.578 | 1.00 | 19.21 | B |
| ATOM | 5031 | N | ASP | B | 448 | 50.697 | 11.686 | 45.511 | 1.00 | 19.97 | B |
| ATOM | 5032 | CA | ASP | B | 448 | 49.300 | 12.015 | 45.774 | 1.00 | 20.91 | B |
| ATOM | 5033 | CB | ASP | B | 448 | 48.757 | 11.180 | 46.936 | 1.00 | 22.76 | B |
| ATOM | 5034 | CG | ASP | B | 448 | 48.710 | 9.695 | 46.631 | 1.00 | 25.37 | B |
| ATOM | 5035 | OD1 | ASP | B | 448 | 48.705 | 9.314 | 45.440 | 1.00 | 27.38 | B |
| ATOM | 5036 | OD2 | ASP | B | 448 | 48.657 | 8.905 | 47.600 | 1.00 | 28.31 | B |
| ATOM | 5037 | C | ASP | B | 448 | 49.072 | 13.485 | 46.105 | 1.00 | 21.83 | B |
| ATOM | 5038 | O | ASP | B | 448 | 48.056 | 14.069 | 45.725 | 1.00 | 23.14 | B |
| ATOM | 5039 | N | TYR | B | 449 | 50.023 | 14.079 | 46.812 | 1.00 | 21.08 | B |
| ATOM | 5040 | CA | TYR | B | 449 | 49.907 | 15.463 | 47.252 | 1.00 | 21.18 | B |
| ATOM | 5041 | CB | TYR | B | 449 | 50.637 | 15.605 | 48.594 | 1.00 | 22.08 | B |

TABLE 1-continued

| | | | | | | | | | | |
|---|---|---|---|---|---|---|---|---|---|---|
| ATOM | 5042 | CG | TYR | B | 449 | 50.540 | 16.958 | 49.273 | 1.00 | 24.85 | B |
| ATOM | 5043 | CD1 | TYR | B | 449 | 51.679 | 17.723 | 49.504 | 1.00 | 25.33 | B |
| ATOM | 5044 | CE1 | TYR | B | 449 | 51.609 | 18.932 | 50.180 | 1.00 | 25.55 | B |
| ATOM | 5045 | CD2 | TYR | B | 449 | 49.322 | 17.443 | 49.732 | 1.00 | 25.73 | B |
| ATOM | 5046 | CE2 | TYR | B | 449 | 49.241 | 18.651 | 50.407 | 1.00 | 26.01 | B |
| ATOM | 5047 | CZ | TYR | B | 449 | 50.388 | 19.389 | 50.630 | 1.00 | 26.99 | B |
| ATOM | 5048 | OH | TYR | B | 449 | 50.310 | 20.582 | 51.314 | 1.00 | 30.67 | B |
| ATOM | 5049 | C | TYR | B | 449 | 50.421 | 16.509 | 46.269 | 1.00 | 19.84 | B |
| ATOM | 5050 | O | TYR | B | 449 | 49.865 | 17.601 | 46.183 | 1.00 | 19.90 | B |
| ATOM | 5051 | N | ILE | B | 450 | 51.460 | 16.169 | 45.514 | 1.00 | 18.97 | B |
| ATOM | 5052 | CA | ILE | B | 450 | 52.065 | 17.124 | 44.594 | 1.00 | 18.60 | B |
| ATOM | 5053 | CB | ILE | B | 450 | 53.532 | 17.397 | 45.005 | 1.00 | 19.72 | B |
| ATOM | 5054 | CG2 | ILE | B | 450 | 54.178 | 18.351 | 44.022 | 1.00 | 19.65 | B |
| ATOM | 5055 | CG1 | ILE | B | 450 | 53.590 | 17.952 | 46.431 | 1.00 | 21.74 | B |
| ATOM | 5056 | CD1 | ILE | B | 450 | 52.857 | 19.256 | 46.614 | 1.00 | 24.04 | B |
| ATOM | 5057 | C | ILE | B | 450 | 52.076 | 16.766 | 43.111 | 1.00 | 17.20 | B |
| ATOM | 5058 | O | ILE | B | 450 | 51.505 | 17.473 | 42.284 | 1.00 | 18.08 | B |
| ATOM | 5059 | N | VAL | B | 451 | 52.741 | 15.665 | 42.785 | 1.00 | 16.44 | B |
| ATOM | 5060 | CA | VAL | B | 451 | 52.895 | 15.242 | 41.406 | 1.00 | 16.45 | B |
| ATOM | 5061 | CB | VAL | B | 451 | 53.874 | 14.064 | 41.325 | 1.00 | 15.82 | B |
| ATOM | 5062 | CG1 | VAL | B | 451 | 54.182 | 13.746 | 39.875 | 1.00 | 17.68 | B |
| ATOM | 5063 | CG2 | VAL | B | 451 | 55.151 | 14.417 | 42.077 | 1.00 | 14.69 | B |
| ATOM | 5064 | C | VAL | B | 451 | 51.632 | 14.905 | 40.623 | 1.00 | 16.23 | B |
| ATOM | 5065 | O | VAL | B | 451 | 51.437 | 15.419 | 39.523 | 1.00 | 17.38 | B |
| ATOM | 5066 | N | HIS | B | 452 | 50.772 | 14.054 | 41.170 | 1.00 | 17.09 | B |
| ATOM | 5067 | CA | HIS | B | 452 | 49.561 | 13.694 | 40.442 | 1.00 | 17.75 | B |
| ATOM | 5068 | CB | HIS | B | 452 | 48.818 | 12.562 | 41.155 | 1.00 | 20.20 | B |
| ATOM | 5069 | CG | HIS | B | 452 | 47.732 | 11.948 | 40.328 | 1.00 | 22.18 | B |
| ATOM | 5070 | CD2 | HIS | B | 452 | 47.759 | 10.921 | 39.444 | 1.00 | 23.54 | B |
| ATOM | 5071 | ND1 | HIS | B | 452 | 46.441 | 12.427 | 40.318 | 1.00 | 24.45 | B |
| ATOM | 5072 | CE1 | HIS | B | 452 | 45.718 | 11.723 | 39.464 | 1.00 | 24.32 | B |
| ATOM | 5073 | NE2 | HIS | B | 452 | 46.494 | 10.804 | 38.920 | 1.00 | 24.60 | B |
| ATOM | 5074 | C | HIS | B | 452 | 48.624 | 14.879 | 40.197 | 1.00 | 16.75 | B |
| ATOM | 5075 | O | HIS | B | 452 | 48.117 | 15.044 | 39.092 | 1.00 | 17.68 | B |
| ATOM | 5076 | N | PRO | B | 453 | 48.373 | 15.715 | 41.218 | 1.00 | 17.21 | B |
| ATOM | 5077 | CD | PRO | B | 453 | 48.739 | 15.584 | 42.639 | 1.00 | 17.66 | B |
| ATOM | 5078 | CA | PRO | B | 453 | 47.483 | 16.865 | 41.012 | 1.00 | 17.79 | B |
| ATOM | 5079 | CB | PRO | B | 453 | 47.519 | 17.572 | 42.362 | 1.00 | 18.28 | B |
| ATOM | 5080 | CG | PRO | B | 453 | 47.695 | 16.435 | 43.320 | 1.00 | 19.39 | B |
| ATOM | 5081 | C | PRO | B | 453 | 47.997 | 17.760 | 39.881 | 1.00 | 17.19 | B |
| ATOM | 5082 | O | PRO | B | 453 | 47.226 | 18.267 | 39.064 | 1.00 | 19.35 | B |
| ATOM | 5083 | N | LEU | B | 454 | 49.313 | 17.945 | 39.839 | 1.00 | 17.54 | B |
| ATOM | 5084 | CA | LEU | B | 454 | 49.929 | 18.771 | 38.812 | 1.00 | 17.68 | B |
| ATOM | 5085 | CB | LEU | B | 454 | 51.410 | 18.979 | 39.128 | 1.00 | 18.11 | B |
| ATOM | 5086 | CG | LEU | B | 454 | 52.200 | 19.791 | 38.103 | 1.00 | 18.15 | B |
| ATOM | 5087 | CD1 | LEU | B | 454 | 51.584 | 21.176 | 37.949 | 1.00 | 19.06 | B |
| ATOM | 5088 | CD2 | LEU | B | 454 | 53.653 | 19.884 | 38.558 | 1.00 | 19.51 | B |
| ATOM | 5089 | C | LEU | B | 454 | 49.797 | 18.146 | 37.429 | 1.00 | 17.12 | B |
| ATOM | 5090 | O | LEU | B | 454 | 49.318 | 18.784 | 36.492 | 1.00 | 17.37 | B |
| ATOM | 5091 | N | TRP | B | 455 | 50.225 | 16.895 | 37.298 | 1.00 | 17.17 | B |
| ATOM | 5092 | CA | TRP | B | 455 | 50.162 | 16.231 | 36.006 | 1.00 | 17.92 | B |
| ATOM | 5093 | CB | TRP | B | 455 | 50.984 | 14.940 | 36.024 | 1.00 | 18.19 | B |
| ATOM | 5094 | CG | TRP | B | 455 | 52.452 | 15.198 | 35.820 | 1.00 | 18.53 | B |
| ATOM | 5095 | CD2 | TRP | B | 455 | 53.107 | 15.432 | 34.569 | 1.00 | 18.74 | B |
| ATOM | 5096 | CE2 | TRP | B | 455 | 54.470 | 15.672 | 34.845 | 1.00 | 18.32 | B |
| ATOM | 5097 | CE3 | TRP | B | 455 | 52.673 | 15.462 | 33.239 | 1.00 | 19.35 | B |
| ATOM | 5098 | CD1 | TRP | B | 455 | 53.417 | 15.304 | 36.783 | 1.00 | 19.27 | B |
| ATOM | 5099 | NE1 | TRP | B | 455 | 54.634 | 15.589 | 36.203 | 1.00 | 18.33 | B |
| ATOM | 5100 | CZ2 | TRP | B | 455 | 55.400 | 15.938 | 33.840 | 1.00 | 18.01 | B |
| ATOM | 5101 | CZ3 | TRP | B | 455 | 53.599 | 15.726 | 32.244 | 1.00 | 19.40 | B |
| ATOM | 5102 | CH2 | TRP | B | 455 | 54.947 | 15.960 | 32.551 | 1.00 | 19.94 | B |
| ATOM | 5103 | C | TRP | B | 455 | 48.749 | 15.952 | 35.515 | 1.00 | 17.23 | B |
| ATOM | 5104 | O | TRP | B | 455 | 48.511 | 15.891 | 34.310 | 1.00 | 16.47 | B |
| ATOM | 5105 | N | GLU | B | 456 | 47.813 | 15.786 | 36.443 | 1.00 | 18.33 | B |
| ATOM | 5106 | CA | GLU | B | 456 | 46.432 | 15.530 | 36.055 | 1.00 | 19.11 | B |
| ATOM | 5107 | CB | GLU | B | 456 | 45.586 | 15.212 | 37.288 | 1.00 | 20.89 | B |
| ATOM | 5108 | CG | GLU | B | 456 | 44.146 | 14.849 | 36.974 | 1.00 | 25.41 | B |
| ATOM | 5109 | CD | GLU | B | 456 | 43.371 | 14.439 | 38.212 | 1.00 | 27.79 | B |
| ATOM | 5110 | OE1 | GLU | B | 456 | 43.172 | 15.293 | 39.104 | 1.00 | 30.79 | B |
| ATOM | 5111 | OE2 | GLU | B | 456 | 42.963 | 13.260 | 38.294 | 1.00 | 29.77 | B |
| ATOM | 5112 | C | GLU | B | 456 | 45.907 | 16.784 | 35.375 | 1.00 | 19.66 | B |
| ATOM | 5113 | O | GLU | B | 456 | 45.179 | 16.716 | 34.380 | 1.00 | 20.67 | B |
| ATOM | 5114 | N | THR | B | 457 | 46.300 | 17.933 | 35.917 | 1.00 | 19.00 | B |
| ATOM | 5115 | CA | THR | B | 457 | 45.882 | 19.218 | 35.387 | 1.00 | 19.68 | B |
| ATOM | 5116 | CB | THR | B | 457 | 46.195 | 20.334 | 36.391 | 1.00 | 20.58 | B |
| ATOM | 5117 | OG1 | THR | B | 457 | 45.609 | 20.001 | 37.655 | 1.00 | 20.84 | B |
| ATOM | 5118 | CG2 | THR | B | 457 | 45.629 | 21.660 | 35.916 | 1.00 | 20.77 | B |
| ATOM | 5119 | C | THR | B | 457 | 46.566 | 19.506 | 34.054 | 1.00 | 18.55 | B |
| ATOM | 5120 | O | THR | B | 457 | 45.947 | 20.045 | 33.139 | 1.00 | 19.14 | B |

TABLE 1-continued

| ATOM | 5121 | N | TRP | B | 458 | 47.842 | 19.146 | 33.940 | 1.00 | 16.85 | B |
|---|---|---|---|---|---|---|---|---|---|---|---|
| ATOM | 5122 | CA | TRP | B | 458 | 48.557 | 19.363 | 32.692 | 1.00 | 16.61 | B |
| ATOM | 5123 | CB | TRP | B | 458 | 50.045 | 19.045 | 32.865 | 1.00 | 16.42 | B |
| ATOM | 5124 | CG | TRP | B | 458 | 50.825 | 19.176 | 31.590 | 1.00 | 17.28 | B |
| ATOM | 5125 | CD2 | TRP | B | 458 | 51.384 | 20.378 | 31.045 | 1.00 | 17.02 | B |
| ATOM | 5126 | CE2 | TRP | B | 458 | 51.978 | 20.040 | 29.813 | 1.00 | 17.51 | B |
| ATOM | 5127 | CE3 | TRP | B | 458 | 51.437 | 21.709 | 31.477 | 1.00 | 18.21 | B |
| ATOM | 5128 | CD1 | TRP | B | 458 | 51.097 | 18.187 | 30.692 | 1.00 | 17.63 | B |
| ATOM | 5129 | NE1 | TRP | B | 458 | 51.790 | 18.697 | 29.623 | 1.00 | 17.38 | B |
| ATOM | 5130 | CZ2 | TRP | B | 458 | 52.619 | 20.981 | 29.008 | 1.00 | 18.10 | B |
| ATOM | 5131 | CZ3 | TRP | B | 458 | 52.078 | 22.647 | 30.671 | 1.00 | 18.66 | B |
| ATOM | 5132 | CH2 | TRP | B | 458 | 52.658 | 22.275 | 29.452 | 1.00 | 16.55 | B |
| ATOM | 5133 | C | TRP | B | 458 | 47.949 | 18.475 | 31.604 | 1.00 | 17.34 | B |
| ATOM | 5134 | O | TRP | B | 458 | 47.795 | 18.896 | 30.454 | 1.00 | 18.38 | B |
| ATOM | 5135 | N | ALA | B | 459 | 47.595 | 17.250 | 31.977 | 1.00 | 19.06 | B |
| ATOM | 5136 | CA | ALA | B | 459 | 46.997 | 16.312 | 31.033 | 1.00 | 19.79 | B |
| ATOM | 5137 | CB | ALA | B | 459 | 46.732 | 14.980 | 31.713 | 1.00 | 20.69 | B |
| ATOM | 5138 | C | ALA | B | 459 | 45.699 | 16.887 | 30.477 | 1.00 | 20.51 | B |
| ATOM | 5139 | O | ALA | B | 459 | 45.388 | 16.713 | 29.299 | 1.00 | 21.52 | B |
| ATOM | 5140 | N | ASP | B | 460 | 44.947 | 17.576 | 31.328 | 1.00 | 21.05 | B |
| ATOM | 5141 | CA | ASP | B | 460 | 43.687 | 18.187 | 30.913 | 1.00 | 22.22 | B |
| ATOM | 5142 | CB | ASP | B | 460 | 42.949 | 18.754 | 32.127 | 1.00 | 24.28 | B |
| ATOM | 5143 | CG | ASP | B | 460 | 42.193 | 17.691 | 32.897 | 1.00 | 27.84 | B |
| ATOM | 5144 | OD1 | ASP | B | 460 | 41.729 | 17.981 | 34.020 | 1.00 | 31.06 | B |
| ATOM | 5145 | OD2 | ASP | B | 460 | 42.052 | 16.566 | 32.372 | 1.00 | 29.36 | B |
| ATOM | 5146 | C | ASP | B | 460 | 43.936 | 19.300 | 29.904 | 1.00 | 21.91 | B |
| ATOM | 5147 | O | ASP | B | 460 | 43.207 | 19.441 | 28.920 | 1.00 | 24.01 | B |
| ATOM | 5148 | N | LEU | B | 461 | 44.972 | 20.092 | 30.157 | 1.00 | 21.20 | B |
| ATOM | 5149 | CA | LEU | B | 461 | 45.322 | 21.199 | 29.284 | 1.00 | 20.14 | B |
| ATOM | 5150 | CB | LEU | B | 461 | 46.509 | 21.970 | 29.872 | 1.00 | 19.58 | B |
| ATOM | 5151 | CG | LEU | B | 461 | 46.953 | 23.206 | 29.090 | 1.00 | 19.24 | B |
| ATOM | 5152 | CD1 | LEU | B | 461 | 45.863 | 24.265 | 29.164 | 1.00 | 18.64 | B |
| ATOM | 5153 | CD2 | LEU | B | 461 | 48.260 | 23.739 | 29.663 | 1.00 | 20.49 | B |
| ATOM | 5154 | C | LEU | B | 461 | 45.668 | 20.755 | 27.863 | 1.00 | 19.88 | B |
| ATOM | 5155 | O | LEU | B | 461 | 45.243 | 21.382 | 26.892 | 1.00 | 20.26 | B |
| ATOM | 5156 | N | VAL | B | 462 | 46.432 | 19.671 | 27.745 | 1.00 | 19.93 | B |
| ATOM | 5157 | CA | VAL | B | 462 | 46.866 | 19.168 | 26.443 | 1.00 | 20.06 | B |
| ATOM | 5158 | CB | VAL | B | 462 | 48.407 | 19.006 | 26.409 | 1.00 | 19.82 | B |
| ATOM | 5159 | CG1 | VAL | B | 462 | 49.084 | 20.325 | 26.753 | 1.00 | 17.51 | B |
| ATOM | 5160 | CG2 | VAL | B | 462 | 48.835 | 17.929 | 27.399 | 1.00 | 17.17 | B |
| ATOM | 5161 | C | VAL | B | 462 | 46.252 | 17.826 | 26.044 | 1.00 | 21.22 | B |
| ATOM | 5162 | O | VAL | B | 462 | 46.760 | 17.155 | 25.144 | 1.00 | 22.36 | B |
| ATOM | 5163 | N | GLN | B | 463 | 45.160 | 17.437 | 26.696 | 1.00 | 22.11 | B |
| ATOM | 5164 | CA | GLN | B | 463 | 44.526 | 16.154 | 26.404 | 1.00 | 22.79 | B |
| ATOM | 5165 | CB | GLN | B | 463 | 43.189 | 16.037 | 27.141 | 1.00 | 24.10 | B |
| ATOM | 5166 | CG | GLN | B | 463 | 42.197 | 17.132 | 26.827 | 1.00 | 25.15 | B |
| ATOM | 5167 | CD | GLN | B | 463 | 40.899 | 16.961 | 27.589 | 1.00 | 28.06 | B |
| ATOM | 5168 | OE1 | GLN | B | 463 | 40.207 | 15.950 | 27.440 | 1.00 | 29.83 | B |
| ATOM | 5169 | NE2 | GLN | B | 463 | 40.561 | 17.948 | 28.416 | 1.00 | 29.25 | B |
| ATOM | 5170 | C | GLN | B | 463 | 44.318 | 15.900 | 24.916 | 1.00 | 23.35 | B |
| ATOM | 5171 | O | GLN | B | 463 | 43.954 | 16.803 | 24.164 | 1.00 | 23.62 | B |
| ATOM | 5172 | N | PRO | B | 464 | 44.538 | 14.651 | 24.478 | 1.00 | 23.00 | B |
| ATOM | 5173 | CD | PRO | B | 464 | 44.052 | 14.136 | 23.184 | 1.00 | 22.82 | B |
| ATOM | 5174 | CA | PRO | B | 464 | 44.956 | 13.541 | 25.341 | 1.00 | 23.37 | B |
| ATOM | 5175 | CB | PRO | B | 464 | 44.088 | 12.406 | 24.838 | 1.00 | 22.05 | B |
| ATOM | 5176 | CG | PRO | B | 464 | 44.196 | 12.619 | 23.348 | 1.00 | 23.79 | B |
| ATOM | 5177 | C | PRO | B | 464 | 46.440 | 13.210 | 25.188 | 1.00 | 22.96 | B |
| ATOM | 5178 | O | PRO | B | 464 | 46.866 | 12.089 | 25.466 | 1.00 | 24.81 | B |
| ATOM | 5179 | N | ASP | B | 465 | 47.222 | 14.193 | 24.754 | 1.00 | 23.55 | B |
| ATOM | 5180 | CA | ASP | B | 465 | 48.646 | 14.010 | 24.515 | 1.00 | 22.84 | B |
| ATOM | 5181 | CB | ASP | B | 465 | 49.226 | 15.281 | 23.885 | 1.00 | 24.36 | B |
| ATOM | 5182 | CG | ASP | B | 465 | 48.469 | 15.711 | 22.637 | 1.00 | 27.27 | B |
| ATOM | 5183 | OD1 | ASP | B | 465 | 48.281 | 14.871 | 21.728 | 1.00 | 28.54 | B |
| ATOM | 5184 | OD2 | ASP | B | 465 | 48.064 | 16.891 | 22.561 | 1.00 | 27.95 | B |
| ATOM | 5185 | C | ASP | B | 465 | 49.506 | 13.601 | 25.711 | 1.00 | 22.82 | B |
| ATOM | 5186 | O | ASP | B | 465 | 50.665 | 13.230 | 25.534 | 1.00 | 24.18 | B |
| ATOM | 5187 | N | ALA | B | 466 | 48.956 | 13.663 | 26.919 | 1.00 | 22.40 | B |
| ATOM | 5188 | CA | ALA | B | 466 | 49.727 | 13.297 | 28.103 | 1.00 | 21.54 | B |
| ATOM | 5189 | CB | ALA | B | 466 | 49.827 | 14.495 | 29.046 | 1.00 | 21.44 | B |
| ATOM | 5190 | C | ALA | B | 466 | 49.158 | 12.099 | 28.851 | 1.00 | 20.90 | B |
| ATOM | 5191 | O | ALA | B | 466 | 49.636 | 11.749 | 29.927 | 1.00 | 21.04 | B |
| ATOM | 5192 | N | GLN | B | 467 | 48.144 | 11.453 | 28.286 | 1.00 | 22.02 | B |
| ATOM | 5193 | CA | GLN | B | 467 | 47.543 | 10.312 | 28.963 | 1.00 | 22.43 | B |
| ATOM | 5194 | CB | GLN | B | 467 | 46.379 | 9.755 | 28.142 | 1.00 | 23.24 | B |
| ATOM | 5195 | CG | GLN | B | 467 | 45.563 | 8.720 | 28.902 | 1.00 | 24.41 | B |
| ATOM | 5196 | CD | GLN | B | 467 | 45.154 | 9.206 | 30.284 | 1.00 | 25.34 | B |
| ATOM | 5197 | OE1 | GLN | B | 467 | 44.488 | 10.232 | 30.424 | 1.00 | 28.95 | B |
| ATOM | 5198 | NE2 | GLN | B | 467 | 45.556 | 8.469 | 31.313 | 1.00 | 27.41 | B |
| ATOM | 5199 | C | GLN | B | 467 | 48.542 | 9.196 | 29.273 | 1.00 | 21.75 | B |

TABLE 1-continued

| ATOM | 5200 | O   | GLN | B | 467 | 48.473 | 8.575  | 30.332 | 1.00 | 22.56 | B |
|------|------|-----|-----|---|-----|--------|--------|--------|------|-------|---|
| ATOM | 5201 | N   | ASP | B | 468 | 49.473 | 8.949  | 28.358 | 1.00 | 21.45 | B |
| ATOM | 5202 | CA  | ASP | B | 468 | 50.468 | 7.901  | 28.561 | 1.00 | 21.34 | B |
| ATOM | 5203 | CB  | ASP | B | 468 | 51.313 | 7.732  | 27.300 | 1.00 | 23.95 | B |
| ATOM | 5204 | CG  | ASP | B | 468 | 50.472 | 7.388  | 26.086 | 1.00 | 27.18 | B |
| ATOM | 5205 | OD1 | ASP | B | 468 | 49.745 | 6.372  | 26.136 | 1.00 | 29.17 | B |
| ATOM | 5206 | OD2 | ASP | B | 468 | 50.533 | 8.136  | 25.084 | 1.00 | 32.05 | B |
| ATOM | 5207 | C   | ASP | B | 468 | 51.365 | 8.213  | 29.756 | 1.00 | 21.11 | B |
| ATOM | 5208 | O   | ASP | B | 468 | 51.753 | 7.318  | 30.507 | 1.00 | 22.01 | B |
| ATOM | 5209 | N   | ILE | B | 469 | 51.694 | 9.488  | 29.924 | 1.00 | 20.48 | B |
| ATOM | 5210 | CA  | ILE | B | 469 | 52.532 | 9.912  | 31.034 | 1.00 | 20.29 | B |
| ATOM | 5211 | CB  | ILE | B | 469 | 52.954 | 11.392 | 30.873 | 1.00 | 19.95 | B |
| ATOM | 5212 | CG2 | ILE | B | 469 | 53.725 | 11.854 | 32.095 | 1.00 | 21.52 | B |
| ATOM | 5213 | CG1 | ILE | B | 469 | 53.823 | 11.546 | 29.623 | 1.00 | 21.77 | B |
| ATOM | 5214 | CD1 | ILE | B | 469 | 54.267 | 12.972 | 29.346 | 1.00 | 20.40 | B |
| ATOM | 5215 | C   | ILE | B | 469 | 51.761 | 9.721  | 32.339 | 1.00 | 19.56 | B |
| ATOM | 5216 | O   | ILE | B | 469 | 52.328 | 9.300  | 33.348 | 1.00 | 20.58 | B |
| ATOM | 5217 | N   | LEU | B | 470 | 50.464 | 10.021 | 32.316 | 1.00 | 20.03 | B |
| ATOM | 5218 | CA  | LEU | B | 470 | 49.626 | 9.855  | 33.500 | 1.00 | 20.59 | B |
| ATOM | 5219 | CB  | LEU | B | 470 | 48.231 | 10.446 | 33.276 | 1.00 | 22.31 | B |
| ATOM | 5220 | CG  | LEU | B | 470 | 47.955 | 11.847 | 33.819 | 1.00 | 23.87 | B |
| ATOM | 5221 | CD1 | LEU | B | 470 | 46.471 | 12.157 | 33.671 | 1.00 | 23.62 | B |
| ATOM | 5222 | CD2 | LEU | B | 470 | 48.353 | 11.923 | 35.288 | 1.00 | 22.41 | B |
| ATOM | 5223 | C   | LEU | B | 470 | 49.486 | 8.385  | 33.871 | 1.00 | 20.52 | B |
| ATOM | 5224 | O   | LEU | B | 470 | 49.552 | 8.028  | 35.046 | 1.00 | 20.81 | B |
| ATOM | 5225 | N   | ASP | B | 471 | 49.286 | 7.534  | 32.867 | 1.00 | 21.29 | B |
| ATOM | 5226 | CA  | ASP | B | 471 | 49.146 | 6.103  | 33.116 | 1.00 | 21.33 | B |
| ATOM | 5227 | CB  | ASP | B | 471 | 48.961 | 5.331  | 31.804 | 1.00 | 23.74 | B |
| ATOM | 5228 | CG  | ASP | B | 471 | 47.658 | 5.665  | 31.103 | 1.00 | 26.63 | B |
| ATOM | 5229 | OD1 | ASP | B | 471 | 46.666 | 5.982  | 31.794 | 1.00 | 28.17 | B |
| ATOM | 5230 | OD2 | ASP | B | 471 | 47.623 | 5.592  | 29.854 | 1.00 | 29.66 | B |
| ATOM | 5231 | C   | ASP | B | 471 | 50.385 | 5.585  | 33.830 | 1.00 | 21.13 | B |
| ATOM | 5232 | O   | ASP | B | 471 | 50.284 | 4.837  | 34.805 | 1.00 | 20.90 | B |
| ATOM | 5233 | N   | THR | B | 472 | 51.554 | 5.985  | 33.339 | 1.00 | 19.58 | B |
| ATOM | 5234 | CA  | THR | B | 472 | 52.816 | 5.567  | 33.939 | 1.00 | 18.79 | B |
| ATOM | 5235 | CB  | THR | B | 472 | 54.021 | 6.127  | 33.158 | 1.00 | 19.82 | B |
| ATOM | 5236 | OG1 | THR | B | 472 | 53.981 | 5.653  | 31.805 | 1.00 | 20.95 | B |
| ATOM | 5237 | CG2 | THR | B | 472 | 55.326 | 5.689  | 33.811 | 1.00 | 20.67 | B |
| ATOM | 5238 | C   | THR | B | 472 | 52.895 | 6.060  | 35.382 | 1.00 | 18.33 | B |
| ATOM | 5239 | O   | THR | B | 472 | 53.298 | 5.320  | 36.282 | 1.00 | 18.91 | B |
| ATOM | 5240 | N   | LEU | B | 473 | 52.510 | 7.315  | 35.599 | 1.00 | 18.12 | B |
| ATOM | 5241 | CA  | LEU | B | 473 | 52.534 | 7.896  | 36.937 | 1.00 | 18.39 | B |
| ATOM | 5242 | CB  | LEU | B | 473 | 52.006 | 9.333  | 36.904 | 1.00 | 19.36 | B |
| ATOM | 5243 | CG  | LEU | B | 473 | 51.948 | 10.074 | 38.245 | 1.00 | 17.63 | B |
| ATOM | 5244 | CD1 | LEU | B | 473 | 53.327 | 10.077 | 38.888 | 1.00 | 16.45 | B |
| ATOM | 5245 | CD2 | LEU | B | 473 | 51.457 | 11.498 | 38.022 | 1.00 | 18.85 | B |
| ATOM | 5246 | C   | LEU | B | 473 | 51.682 | 7.063  | 37.887 | 1.00 | 18.43 | B |
| ATOM | 5247 | O   | LEU | B | 473 | 52.097 | 6.765  | 39.006 | 1.00 | 17.70 | B |
| ATOM | 5248 | N   | GLU | B | 474 | 50.491 | 6.686  | 37.432 | 1.00 | 18.93 | B |
| ATOM | 5249 | CA  | GLU | B | 474 | 49.590 | 5.889  | 38.249 | 1.00 | 19.85 | B |
| ATOM | 5250 | CB  | GLU | B | 474 | 48.210 | 5.802  | 37.592 | 1.00 | 21.27 | B |
| ATOM | 5251 | CG  | GLU | B | 474 | 47.463 | 7.126  | 37.569 | 1.00 | 24.02 | B |
| ATOM | 5252 | CD  | GLU | B | 474 | 45.996 | 6.968  | 37.214 | 1.00 | 28.80 | B |
| ATOM | 5253 | OE1 | GLU | B | 474 | 45.696 | 6.454  | 36.114 | 1.00 | 30.31 | B |
| ATOM | 5254 | OE2 | GLU | B | 474 | 45.140 | 7.359  | 38.039 | 1.00 | 32.18 | B |
| ATOM | 5255 | C   | GLU | B | 474 | 50.145 | 4.491  | 38.497 | 1.00 | 19.17 | B |
| ATOM | 5256 | O   | GLU | B | 474 | 50.020 | 3.958  | 39.599 | 1.00 | 19.57 | B |
| ATOM | 5257 | N   | ASP | B | 475 | 50.763 | 3.907  | 37.475 | 1.00 | 18.82 | B |
| ATOM | 5258 | CA  | ASP | B | 475 | 51.347 | 2.577  | 37.602 | 1.00 | 19.26 | B |
| ATOM | 5259 | CB  | ASP | B | 475 | 51.853 | 2.084  | 36.246 | 1.00 | 21.20 | B |
| ATOM | 5260 | CG  | ASP | B | 475 | 52.255 | 0.623  | 36.276 | 1.00 | 25.59 | B |
| ATOM | 5261 | OD1 | ASP | B | 475 | 51.412 | −0.215 | 36.666 | 1.00 | 28.39 | B |
| ATOM | 5262 | OD2 | ASP | B | 475 | 53.409 | 0.309  | 35.908 | 1.00 | 28.36 | B |
| ATOM | 5263 | C   | ASP | B | 475 | 52.501 | 2.598  | 38.603 | 1.00 | 18.34 | B |
| ATOM | 5264 | O   | ASP | B | 475 | 52.611 | 1.720  | 39.452 | 1.00 | 19.23 | B |
| ATOM | 5265 | N   | ASN | B | 476 | 53.359 | 3.608  | 38.507 | 1.00 | 17.44 | B |
| ATOM | 5266 | CA  | ASN | B | 476 | 54.489 | 3.715  | 39.424 | 1.00 | 16.68 | B |
| ATOM | 5267 | CB  | ASN | B | 476 | 55.439 | 4.826  | 38.976 | 1.00 | 17.90 | B |
| ATOM | 5268 | CG  | ASN | B | 476 | 56.183 | 4.474  | 37.705 | 1.00 | 19.41 | B |
| ATOM | 5269 | OD1 | ASN | B | 476 | 56.257 | 3.305  | 37.318 | 1.00 | 20.94 | B |
| ATOM | 5270 | ND2 | ASN | B | 476 | 56.758 | 5.481  | 37.057 | 1.00 | 18.88 | B |
| ATOM | 5271 | C   | ASN | B | 476 | 54.020 | 3.974  | 40.848 | 1.00 | 16.33 | B |
| ATOM | 5272 | O   | ASN | B | 476 | 54.632 | 3.515  | 41.809 | 1.00 | 17.72 | B |
| ATOM | 5273 | N   | ARG | B | 477 | 52.928 | 4.715  | 40.978 | 1.00 | 17.45 | B |
| ATOM | 5274 | CA  | ARG | B | 477 | 52.370 | 5.013  | 42.283 | 1.00 | 18.80 | B |
| ATOM | 5275 | CB  | ARG | B | 477 | 51.191 | 5.973  | 42.119 | 1.00 | 19.31 | B |
| ATOM | 5276 | CG  | ARG | B | 477 | 50.631 | 6.546  | 43.404 | 1.00 | 22.88 | B |
| ATOM | 5277 | CD  | ARG | B | 477 | 49.604 | 5.627  | 44.028 | 1.00 | 24.47 | B |
| ATOM | 5278 | NE  | ARG | B | 477 | 48.948 | 6.260  | 45.169 | 1.00 | 26.03 | B |

TABLE 1-continued

| ATOM | 5279 | CZ | ARG | B | 477 | 48.090 | 5.642 | 45.972 | 1.00 | 26.03 | B |
| --- | --- | --- | --- | --- | --- | --- | --- | --- | --- | --- | --- |
| ATOM | 5280 | NH1 | ARG | B | 477 | 47.781 | 4.370 | 45.758 | 1.00 | 25.82 | B |
| ATOM | 5281 | NH2 | ARG | B | 477 | 47.548 | 6.294 | 46.992 | 1.00 | 27.12 | B |
| ATOM | 5282 | C | ARG | B | 477 | 51.926 | 3.696 | 42.924 | 1.00 | 19.28 | B |
| ATOM | 5283 | O | ARG | B | 477 | 52.170 | 3.456 | 44.107 | 1.00 | 20.69 | B |
| ATOM | 5284 | N | ASN | B | 478 | 51.294 | 2.835 | 42.130 | 1.00 | 19.49 | B |
| ATOM | 5285 | CA | ASN | B | 478 | 50.836 | 1.542 | 42.632 | 1.00 | 19.61 | B |
| ATOM | 5286 | CB | ASN | B | 478 | 49.930 | 0.847 | 41.610 | 1.00 | 20.31 | B |
| ATOM | 5287 | CG | ASN | B | 478 | 48.594 | 1.546 | 41.447 | 1.00 | 21.54 | B |
| ATOM | 5288 | OD1 | ASN | B | 478 | 48.080 | 2.153 | 42.386 | 1.00 | 25.02 | B |
| ATOM | 5289 | ND2 | ASN | B | 478 | 48.015 | 1.445 | 40.256 | 1.00 | 23.73 | B |
| ATOM | 5290 | C | ASN | B | 478 | 51.997 | 0.621 | 42.982 | 1.00 | 19.75 | B |
| ATOM | 5291 | O | ASN | B | 478 | 51.910 | −0.165 | 43.927 | 1.00 | 20.26 | B |
| ATOM | 5292 | N | TRP | B | 479 | 53.085 | 0.706 | 42.223 | 1.00 | 18.76 | B |
| ATOM | 5293 | CA | TRP | B | 479 | 54.236 | −0.134 | 42.509 | 1.00 | 18.48 | B |
| ATOM | 5294 | CB | TRP | B | 479 | 55.270 | −0.047 | 41.382 | 1.00 | 19.78 | B |
| ATOM | 5295 | CG | TRP | B | 479 | 54.860 | −0.817 | 40.160 | 1.00 | 24.00 | B |
| ATOM | 5296 | CD2 | TRP | B | 479 | 54.674 | −2.235 | 40.061 | 1.00 | 24.72 | B |
| ATOM | 5297 | CE2 | TRP | B | 479 | 54.249 | −2.510 | 38.745 | 1.00 | 25.38 | B |
| ATOM | 5298 | CE3 | TRP | B | 479 | 54.824 | −3.299 | 40.959 | 1.00 | 25.87 | B |
| ATOM | 5299 | CD1 | TRP | B | 479 | 54.551 | −0.306 | 38.933 | 1.00 | 24.73 | B |
| ATOM | 5300 | NE1 | TRP | B | 479 | 54.183 | −1.315 | 38.077 | 1.00 | 25.30 | B |
| ATOM | 5301 | CZ2 | TRP | B | 479 | 53.971 | −3.805 | 38.303 | 1.00 | 26.23 | B |
| ATOM | 5302 | CZ3 | TRP | B | 479 | 54.548 | −4.585 | 40.517 | 1.00 | 27.15 | B |
| ATOM | 5303 | CH2 | TRP | B | 479 | 54.126 | −4.825 | 39.200 | 1.00 | 25.76 | B |
| ATOM | 5304 | C | TRP | B | 479 | 54.853 | 0.286 | 43.836 | 1.00 | 17.45 | B |
| ATOM | 5305 | O | TRP | B | 479 | 55.160 | −0.556 | 44.677 | 1.00 | 18.45 | B |
| ATOM | 5306 | N | TYR | B | 480 | 55.020 | 1.588 | 44.042 | 1.00 | 17.98 | B |
| ATOM | 5307 | CA | TYR | B | 480 | 55.601 | 2.046 | 45.296 | 1.00 | 18.47 | B |
| ATOM | 5308 | CB | TYR | B | 480 | 55.912 | 3.545 | 45.234 | 1.00 | 19.02 | B |
| ATOM | 5309 | CG | TYR | B | 480 | 57.346 | 3.843 | 44.849 | 1.00 | 20.86 | B |
| ATOM | 5310 | CD1 | TYR | B | 480 | 58.372 | 3.732 | 45.777 | 1.00 | 22.06 | B |
| ATOM | 5311 | CE1 | TYR | B | 480 | 59.690 | 3.967 | 45.421 | 1.00 | 22.53 | B |
| ATOM | 5312 | CD2 | TYR | B | 480 | 57.677 | 4.198 | 43.549 | 1.00 | 22.14 | B |
| ATOM | 5313 | CE2 | TYR | B | 480 | 58.988 | 4.431 | 43.184 | 1.00 | 23.18 | B |
| ATOM | 5314 | CZ | TYR | B | 480 | 59.990 | 4.314 | 44.119 | 1.00 | 21.70 | B |
| ATOM | 5315 | OH | TYR | B | 480 | 61.296 | 4.535 | 43.740 | 1.00 | 25.76 | B |
| ATOM | 5316 | C | TYR | B | 480 | 54.693 | 1.744 | 46.486 | 1.00 | 18.70 | B |
| ATOM | 5317 | O | TYR | B | 480 | 55.167 | 1.325 | 47.540 | 1.00 | 18.77 | B |
| ATOM | 5318 | N | GLN | B | 481 | 53.389 | 1.938 | 46.321 | 1.00 | 18.52 | B |
| ATOM | 5319 | CA | GLN | B | 481 | 52.463 | 1.672 | 47.415 | 1.00 | 19.42 | B |
| ATOM | 5320 | CB | GLN | B | 481 | 51.028 | 2.034 | 47.009 | 1.00 | 19.97 | B |
| ATOM | 5321 | CG | GLN | B | 481 | 49.989 | 1.687 | 48.071 | 1.00 | 23.88 | B |
| ATOM | 5322 | CD | GLN | B | 481 | 48.756 | 2.564 | 48.001 | 1.00 | 27.99 | B |
| ATOM | 5323 | OE1 | GLN | B | 481 | 48.821 | 3.766 | 48.266 | 1.00 | 30.97 | B |
| ATOM | 5324 | NE2 | GLN | B | 481 | 47.622 | 1.969 | 47.646 | 1.00 | 30.63 | B |
| ATOM | 5325 | C | GLN | B | 481 | 52.520 | 0.216 | 47.872 | 1.00 | 18.56 | B |
| ATOM | 5326 | O | GLN | B | 481 | 52.417 | −0.073 | 49.066 | 1.00 | 20.44 | B |
| ATOM | 5327 | N | SER | B | 482 | 52.703 | −0.697 | 46.926 | 1.00 | 19.51 | B |
| ATOM | 5328 | CA | SER | B | 482 | 52.765 | −2.118 | 47.250 | 1.00 | 19.42 | B |
| ATOM | 5329 | CB | SER | B | 482 | 52.754 | −2.958 | 45.970 | 1.00 | 20.18 | B |
| ATOM | 5330 | OG | SER | B | 482 | 53.962 | −2.814 | 45.245 | 1.00 | 22.40 | B |
| ATOM | 5331 | C | SER | B | 482 | 54.009 | −2.449 | 48.062 | 1.00 | 19.34 | B |
| ATOM | 5332 | O | SER | B | 482 | 54.074 | −3.491 | 48.705 | 1.00 | 20.35 | B |
| ATOM | 5333 | N | MET | B | 483 | 54.993 | −1.553 | 48.041 | 1.00 | 19.66 | B |
| ATOM | 5334 | CA | MET | B | 483 | 56.235 | −1.779 | 48.770 | 1.00 | 21.33 | B |
| ATOM | 5335 | CB | MET | B | 483 | 57.425 | −1.272 | 47.950 | 1.00 | 23.33 | B |
| ATOM | 5336 | CG | MET | B | 483 | 57.626 | −1.986 | 46.625 | 1.00 | 25.96 | B |
| ATOM | 5337 | SD | MET | B | 483 | 57.802 | −3.775 | 46.805 | 1.00 | 27.94 | B |
| ATOM | 5338 | CE | MET | B | 483 | 59.283 | −3.873 | 47.787 | 1.00 | 28.55 | B |
| ATOM | 5339 | C | MET | B | 483 | 56.262 | −1.134 | 50.151 | 1.00 | 21.40 | B |
| ATOM | 5340 | O | MET | B | 483 | 57.279 | −1.173 | 50.841 | 1.00 | 22.44 | B |
| ATOM | 5341 | N | ILE | B | 484 | 55.146 | −0.544 | 50.561 | 1.00 | 21.22 | B |
| ATOM | 5342 | CA | ILE | B | 484 | 55.085 | 0.095 | 51.866 | 1.00 | 22.56 | B |
| ATOM | 5343 | CB | ILE | B | 484 | 53.919 | 1.095 | 51.933 | 1.00 | 20.73 | B |
| ATOM | 5344 | CG2 | ILE | B | 484 | 53.760 | 1.617 | 53.354 | 1.00 | 21.50 | B |
| ATOM | 5345 | CG1 | ILE | B | 484 | 54.178 | 2.245 | 50.960 | 1.00 | 21.80 | B |
| ATOM | 5346 | CD1 | ILE | B | 484 | 53.062 | 3.260 | 50.903 | 1.00 | 21.06 | B |
| ATOM | 5347 | C | ILE | B | 484 | 54.931 | −0.935 | 52.978 | 1.00 | 24.13 | B |
| ATOM | 5348 | O | ILE | B | 484 | 53.948 | −1.674 | 53.018 | 1.00 | 24.81 | B |
| ATOM | 5349 | N | PRO | B | 485 | 55.910 | −0.995 | 53.899 | 1.00 | 24.73 | B |
| ATOM | 5350 | CD | PRO | B | 485 | 57.110 | −0.141 | 53.942 | 1.00 | 24.09 | B |
| ATOM | 5351 | CA | PRO | B | 485 | 55.903 | −1.934 | 55.026 | 1.00 | 25.60 | B |
| ATOM | 5352 | CB | PRO | B | 485 | 57.024 | −1.406 | 55.915 | 1.00 | 24.57 | B |
| ATOM | 5353 | CG | PRO | B | 485 | 58.002 | −0.885 | 54.923 | 1.00 | 24.79 | B |
| ATOM | 5354 | C | PRO | B | 485 | 54.564 | −1.989 | 55.753 | 1.00 | 26.40 | B |
| ATOM | 5355 | O | PRO | B | 485 | 54.086 | −3.067 | 56.113 | 1.00 | 28.41 | B |
| ATOM | 5356 | N | GLN | B | 500 | 61.987 | 12.714 | 61.050 | 1.00 | 28.08 | B |
| ATOM | 5357 | CA | GLN | B | 500 | 61.217 | 13.364 | 59.985 | 1.00 | 27.45 | B |

TABLE 1-continued

| ATOM | 5358 | C | GLN | B | 500 | 61.591 | 12.824 | 58.605 | 1.00 | 28.09 | B |
| ATOM | 5359 | O | GLN | B | 500 | 62.744 | 12.927 | 58.181 | 1.00 | 27.45 | B |
| ATOM | 5360 | CB | GLN | B | 500 | 61.533 | 14.856 | 59.944 | 1.00 | 27.23 | B |
| ATOM | 5361 | CG | GLN | B | 500 | 60.475 | 15.751 | 60.558 | 1.00 | 20.00 | B |
| ATOM | 5362 | CD | GLN | B | 500 | 60.661 | 17.222 | 60.211 | 1.00 | 20.00 | B |
| ATOM | 5363 | OE1 | GLN | B | 500 | 61.471 | 17.586 | 59.360 | 1.00 | 20.00 | B |
| ATOM | 5364 | NE2 | GLN | B | 500 | 60.003 | 18.235 | 60.761 | 1.00 | 20.00 | B |
| ATOM | 5365 | N | GLY | B | 501 | 60.608 | 12.253 | 57.910 | 1.00 | 26.90 | B |
| ATOM | 5366 | CA | GLY | B | 501 | 60.848 | 11.702 | 56.588 | 1.00 | 26.66 | B |
| ATOM | 5367 | C | GLY | B | 501 | 60.922 | 12.761 | 55.505 | 1.00 | 27.87 | B |
| ATOM | 5368 | O | GLY | B | 501 | 60.749 | 13.950 | 55.780 | 1.00 | 28.76 | B |
| ATOM | 5369 | N | LEU | B | 502 | 61.213 | 12.399 | 54.241 | 1.00 | 26.62 | B |
| ATOM | 5370 | CA | LEU | B | 502 | 61.283 | 13.393 | 53.153 | 1.00 | 26.54 | B |
| ATOM | 5371 | C | LEU | B | 502 | 59.922 | 14.015 | 52.902 | 1.00 | 27.16 | B |
| ATOM | 5372 | O | LEU | B | 502 | 59.806 | 15.185 | 52.518 | 1.00 | 28.67 | B |
| ATOM | 5373 | CB | LEU | B | 502 | 61.599 | 12.779 | 51.786 | 1.00 | 25.13 | B |
| ATOM | 5374 | CG | LEU | B | 502 | 62.105 | 13.665 | 50.633 | 1.00 | 20.00 | B |
| ATOM | 5375 | CD1 | LEU | B | 502 | 62.892 | 14.847 | 51.172 | 1.00 | 20.00 | B |
| ATOM | 5376 | CD2 | LEU | B | 502 | 62.946 | 12.860 | 49.650 | 1.00 | 20.00 | B |
| ATOM | 5377 | N | MET | B | 503 | 58.873 | 13.358 | 53.255 | 1.00 | 26.97 | B |
| ATOM | 5378 | CA | MET | B | 503 | 57.561 | 13.968 | 53.123 | 1.00 | 27.04 | B |
| ATOM | 5379 | CB | MET | B | 503 | 56.484 | 12.883 | 53.100 | 1.00 | 27.98 | B |
| ATOM | 5380 | CG | MET | B | 503 | 55.164 | 13.348 | 52.523 | 1.00 | 29.39 | B |
| ATOM | 5381 | SD | MET | B | 503 | 55.352 | 13.902 | 50.819 | 1.00 | 31.66 | B |
| ATOM | 5382 | CE | MET | B | 503 | 55.176 | 15.663 | 51.007 | 1.00 | 30.79 | B |
| ATOM | 5383 | C | MET | B | 503 | 57.305 | 14.928 | 54.278 | 1.00 | 26.05 | B |
| ATOM | 5384 | O | MET | B | 503 | 56.895 | 16.071 | 54.071 | 1.00 | 27.13 | B |
| ATOM | 5385 | N | GLU | B | 504 | 57.551 | 14.454 | 55.497 | 1.00 | 25.99 | B |
| ATOM | 5386 | CA | GLU | B | 504 | 57.346 | 15.266 | 56.691 | 1.00 | 25.56 | B |
| ATOM | 5387 | C | GLU | B | 504 | 58.306 | 16.451 | 56.726 | 1.00 | 25.67 | B |
| ATOM | 5388 | O | GLU | B | 504 | 57.924 | 17.558 | 57.108 | 1.00 | 26.20 | B |
| ATOM | 5389 | CB | GLU | B | 504 | 57.467 | 14.421 | 57.969 | 1.00 | 25.55 | B |
| ATOM | 5390 | CG | GLU | B | 504 | 56.325 | 13.444 | 58.168 | 1.00 | 20.00 | B |
| ATOM | 5391 | CD | GLU | B | 504 | 56.221 | 12.883 | 59.572 | 1.00 | 20.00 | B |
| ATOM | 5392 | OE1 | GLU | B | 504 | 56.848 | 13.455 | 60.487 | 1.00 | 20.00 | B |
| ATOM | 5393 | OE2 | GLU | B | 504 | 55.513 | 11.872 | 59.756 | 1.00 | 20.00 | B |
| ATOM | 5394 | N | LYS | B | 505 | 59.554 | 16.216 | 56.334 | 1.00 | 25.04 | B |
| ATOM | 5395 | CA | LYS | B | 505 | 60.553 | 17.277 | 56.321 | 1.00 | 25.73 | B |
| ATOM | 5396 | C | LYS | B | 505 | 60.132 | 18.340 | 55.318 | 1.00 | 26.05 | B |
| ATOM | 5397 | O | LYS | B | 505 | 60.192 | 19.534 | 55.608 | 1.00 | 26.62 | B |
| ATOM | 5398 | CB | LYS | B | 505 | 61.938 | 16.705 | 56.018 | 1.00 | 25.46 | B |
| ATOM | 5399 | CG | LYS | B | 505 | 63.069 | 17.707 | 56.166 | 1.00 | 20.00 | B |
| ATOM | 5400 | CD | LYS | B | 505 | 64.424 | 17.020 | 56.132 | 1.00 | 20.00 | B |
| ATOM | 5401 | CE | LYS | B | 505 | 65.529 | 17.956 | 56.589 | 1.00 | 20.00 | B |
| ATOM | 5402 | NZ | LYS | B | 505 | 65.142 | 18.721 | 57.805 | 1.00 | 20.00 | B |
| ATOM | 5403 | N | PHE | B | 506 | 59.703 | 17.898 | 54.138 | 1.00 | 25.21 | B |
| ATOM | 5404 | CA | PHE | B | 506 | 59.255 | 18.817 | 53.099 | 1.00 | 25.83 | B |
| ATOM | 5405 | CB | PHE | B | 506 | 58.765 | 18.044 | 51.874 | 1.00 | 24.31 | B |
| ATOM | 5406 | CG | PHE | B | 506 | 58.037 | 18.900 | 50.875 | 1.00 | 23.84 | B |
| ATOM | 5407 | CD1 | PHE | B | 506 | 58.691 | 19.931 | 50.217 | 1.00 | 26.06 | B |
| ATOM | 5408 | CD2 | PHE | B | 506 | 56.692 | 18.694 | 50.618 | 1.00 | 25.52 | B |
| ATOM | 5409 | CE1 | PHE | B | 506 | 58.016 | 20.742 | 49.321 | 1.00 | 25.41 | B |
| ATOM | 5410 | CE2 | PHE | B | 506 | 56.006 | 19.502 | 49.721 | 1.00 | 25.43 | B |
| ATOM | 5411 | CZ | PHE | B | 506 | 56.669 | 20.527 | 49.072 | 1.00 | 26.16 | B |
| ATOM | 5412 | C | PHE | B | 506 | 58.119 | 19.673 | 53.640 | 1.00 | 26.29 | B |
| ATOM | 5413 | O | PHE | B | 506 | 58.161 | 20.902 | 53.569 | 1.00 | 27.79 | B |
| ATOM | 5414 | N | GLN | B | 507 | 57.100 | 19.013 | 54.181 | 1.00 | 26.93 | B |
| ATOM | 5415 | CA | GLN | B | 507 | 55.950 | 19.708 | 54.743 | 1.00 | 28.06 | B |
| ATOM | 5416 | C | GLN | B | 507 | 56.399 | 20.626 | 55.878 | 1.00 | 29.45 | B |
| ATOM | 5417 | O | GLN | B | 507 | 56.057 | 21.828 | 55.835 | 1.00 | 29.64 | B |
| ATOM | 5418 | CB | GLN | B | 507 | 54.892 | 18.706 | 55.205 | 1.00 | 26.71 | B |
| ATOM | 5419 | CG | GLN | B | 507 | 54.359 | 17.812 | 54.099 | 1.00 | 20.00 | B |
| ATOM | 5420 | CD | GLN | B | 507 | 53.313 | 16.832 | 54.594 | 1.00 | 20.00 | B |
| ATOM | 5421 | OE1 | GLN | B | 507 | 52.977 | 16.814 | 55.778 | 1.00 | 20.00 | B |
| ATOM | 5422 | NE2 | GLN | B | 507 | 52.671 | 15.930 | 53.864 | 1.00 | 20.00 | B |
| ATOM | 5423 | ZN | ZN | A | 1001 | 62.421 | 57.290 | 48.974 | 1.00 | 14.33 | A |
| ATOM | 5424 | MG | MG | A | 1002 | 63.429 | 54.325 | 46.970 | 1.00 | 15.21 | A |
| ATOM | 5425 | O | HOH | A | 1003 | 64.844 | 53.271 | 45.635 | 1.00 | 9.95 | A |
| ATOM | 5426 | O | HOH | A | 1004 | 63.637 | 52.752 | 48.555 | 1.00 | 10.74 | A |
| ATOM | 5427 | O | HOH | A | 1005 | 61.832 | 53.112 | 46.103 | 1.00 | 12.26 | A |
| ATOM | 5428 | O | HOH | A | 1006 | 63.187 | 55.819 | 45.251 | 1.00 | 11.49 | A |
| ATOM | 5429 | O | HOH | A | 1007 | 61.906 | 55.337 | 48.085 | 1.00 | 11.74 | A |
| ATOM | 5430 | O | HOH | A | 1008 | 61.653 | 58.020 | 47.023 | 1.00 | 10.26 | A |
| ATOM | 5431 | O | HOH | A | 1009 | 59.519 | 59.747 | 47.246 | 1.00 | 11.90 | A |
| ATOM | 5432 | O | HOH | A | 1010 | 56.667 | 61.920 | 48.376 | 1.00 | 16.95 | A |
| ATOM | 5433 | O | HOH | A | 1011 | 63.770 | 54.989 | 42.907 | 1.00 | 17.86 | A |
| ATOM | 5434 | O | HOH | A | 1012 | 65.312 | 58.258 | 39.951 | 1.00 | 21.46 | A |
| ATOM | 5435 | O | HOH | A | 1013 | 62.335 | 52.427 | 40.119 | 1.00 | 19.32 | A |
| ATOM | 5436 | O | HOH | A | 1014 | 65.063 | 59.386 | 37.638 | 1.00 | 24.88 | A |

TABLE 1-continued

| | | | | | | | | | | |
|---|---|---|---|---|---|---|---|---|---|---|
| ATOM | 5437 | O | HOH | A | 1015 | 55.711 | 64.303 | 43.279 | 1.00 | 25.94 | A |
| ATOM | 5438 | O | HOH | A | 1016 | 59.942 | 53.329 | 43.358 | 1.00 | 26.51 | A |
| ATOM | 5439 | O | HOH | A | 1017 | 62.055 | 23.101 | 45.361 | 1.00 | 29.29 | A |
| ATOM | 5440 | O | HOH | A | 1018 | 63.345 | 56.571 | 41.019 | 1.00 | 26.07 | A |
| ATOM | 5441 | O | HOH | A | 1019 | 61.439 | 54.987 | 39.710 | 1.00 | 28.55 | A |
| ATOM | 5442 | ZN | ZN | B | 1001 | 65.316 | 20.842 | 39.708 | 1.00 | 11.81 | B |
| ATOM | 5443 | MG | MG | B | 1002 | 65.563 | 23.679 | 42.142 | 1.00 | 14.15 | B |
| ATOM | 5444 | O | HOH | B | 1003 | 66.623 | 24.883 | 43.618 | 1.00 | 9.14 | B |
| ATOM | 5445 | O | HOH | B | 1004 | 65.397 | 25.488 | 40.804 | 1.00 | 10.50 | B |
| ATOM | 5446 | O | HOH | B | 1005 | 63.709 | 24.379 | 43.069 | 1.00 | 12.14 | B |
| ATOM | 5447 | O | HOH | B | 1006 | 65.670 | 21.998 | 43.594 | 1.00 | 12.44 | B |
| ATOM | 5448 | O | HOH | B | 1007 | 66.097 | 22.510 | 46.080 | 1.00 | 15.81 | B |
| ATOM | 5449 | O | HOH | B | 1008 | 64.405 | 22.384 | 40.832 | 1.00 | 11.54 | B |
| ATOM | 5450 | O | HOH | B | 1009 | 64.843 | 19.672 | 41.529 | 1.00 | 11.66 | B |
| ATOM | 5451 | O | HOH | B | 1010 | 63.136 | 17.566 | 41.056 | 1.00 | 16.37 | B |
| ATOM | 5452 | O | HOH | W | 1 | 61.217 | 63.887 | 50.587 | 1.00 | 11.31 | W |
| ATOM | 5453 | O | HOH | W | 2 | 77.279 | 17.559 | 37.853 | 1.00 | 13.71 | W |
| ATOM | 5454 | O | HOH | W | 3 | 73.109 | 63.623 | 50.242 | 1.00 | 12.32 | W |
| ATOM | 5455 | O | HOH | W | 4 | 59.025 | 67.770 | 53.976 | 1.00 | 13.81 | W |
| ATOM | 5456 | O | HOH | W | 5 | 65.850 | 14.336 | 37.279 | 1.00 | 13.62 | W |
| ATOM | 5457 | O | HOH | W | 6 | 85.798 | 30.506 | 28.430 | 1.00 | 14.98 | W |
| ATOM | 5458 | O | HOH | W | 7 | 74.914 | 21.441 | 41.796 | 1.00 | 12.58 | W |
| ATOM | 5459 | O | HOH | W | 8 | 66.306 | 65.869 | 48.337 | 1.00 | 17.57 | W |
| ATOM | 5460 | O | HOH | W | 9 | 71.193 | 13.440 | 39.194 | 1.00 | 15.22 | W |
| ATOM | 5461 | O | HOH | W | 10 | 71.947 | 58.849 | 46.828 | 1.00 | 13.01 | W |
| ATOM | 5462 | O | HOH | W | 11 | 64.554 | 10.579 | 33.279 | 1.00 | 16.51 | W |
| ATOM | 5463 | O | HOH | W | 12 | 78.048 | 32.858 | 18.724 | 1.00 | 17.61 | W |
| ATOM | 5464 | O | HOH | W | 13 | 73.301 | 34.616 | 19.768 | 1.00 | 15.53 | W |
| ATOM | 5465 | O | HOH | W | 14 | 57.457 | 64.797 | 52.612 | 1.00 | 14.62 | W |
| ATOM | 5466 | O | HOH | W | 15 | 82.925 | 55.049 | 58.860 | 1.00 | 17.55 | W |
| ATOM | 5467 | O | HOH | W | 16 | 84.505 | 29.569 | 30.769 | 1.00 | 12.79 | W |
| ATOM | 5468 | O | HOH | W | 17 | 60.706 | 66.445 | 57.103 | 1.00 | 14.62 | W |
| ATOM | 5469 | O | HOH | W | 19 | 62.382 | 12.863 | 34.961 | 1.00 | 18.71 | W |
| ATOM | 5470 | O | HOH | W | 20 | 84.256 | 22.725 | 31.263 | 1.00 | 19.87 | W |
| ATOM | 5471 | O | HOH | W | 21 | 63.587 | 46.233 | 39.940 | 1.00 | 16.58 | W |
| ATOM | 5472 | O | HOH | W | 22 | 61.465 | 51.549 | 37.407 | 1.00 | 17.91 | W |
| ATOM | 5473 | O | HOH | W | 23 | 81.341 | 54.222 | 72.435 | 1.00 | 18.06 | W |
| ATOM | 5474 | O | HOH | W | 24 | 80.983 | 36.647 | 26.935 | 1.00 | 16.19 | W |
| ATOM | 5475 | O | HOH | W | 25 | 65.873 | 12.739 | 30.263 | 1.00 | 15.25 | W |
| ATOM | 5476 | O | HOH | W | 26 | 76.150 | 33.874 | 20.336 | 1.00 | 17.69 | W |
| ATOM | 5477 | O | HOH | W | 27 | 73.028 | 48.784 | 70.790 | 1.00 | 22.12 | W |
| ATOM | 5478 | O | HOH | W | 28 | 60.940 | 14.884 | 39.445 | 1.00 | 20.30 | W |
| ATOM | 5479 | O | HOH | W | 29 | 81.165 | 61.424 | 57.518 | 1.00 | 19.08 | W |
| ATOM | 5480 | O | HOH | W | 30 | 60.112 | 37.962 | 35.163 | 1.00 | 20.83 | W |
| ATOM | 5481 | O | HOH | W | 31 | 60.175 | 68.944 | 56.100 | 1.00 | 17.12 | W |
| ATOM | 5482 | O | HOH | W | 32 | 84.521 | 54.377 | 60.981 | 1.00 | 22.12 | W |
| ATOM | 5483 | O | HOH | W | 33 | 61.521 | 24.318 | 17.530 | 1.00 | 18.85 | W |
| ATOM | 5484 | O | HOH | W | 34 | 75.498 | 62.759 | 51.417 | 1.00 | 18.73 | W |
| ATOM | 5485 | O | HOH | W | 35 | 63.976 | 30.416 | 50.265 | 1.00 | 17.10 | W |
| ATOM | 5486 | O | HOH | W | 36 | 81.200 | 47.241 | 55.619 | 1.00 | 19.56 | W |
| ATOM | 5487 | O | HOH | W | 37 | 63.184 | 41.981 | 18.149 | 1.00 | 22.04 | W |
| ATOM | 5488 | O | HOH | W | 39 | 68.641 | 39.691 | 54.058 | 1.00 | 19.20 | W |
| ATOM | 5489 | O | HOH | W | 40 | 64.454 | 37.647 | 47.154 | 1.00 | 23.72 | W |
| ATOM | 5490 | O | HOH | W | 41 | 71.087 | 41.622 | 49.467 | 1.00 | 19.16 | W |
| ATOM | 5491 | O | HOH | W | 42 | 66.038 | 10.116 | 30.997 | 1.00 | 17.30 | W |
| ATOM | 5492 | O | HOH | W | 43 | 57.397 | 32.668 | 38.429 | 1.00 | 24.83 | W |
| ATOM | 5493 | O | HOH | W | 44 | 37.815 | 25.290 | 22.278 | 1.00 | 23.57 | W |
| ATOM | 5494 | O | HOH | W | 45 | 59.246 | 55.897 | 71.402 | 1.00 | 20.72 | W |
| ATOM | 5495 | O | HOH | W | 46 | 81.078 | 47.997 | 63.426 | 1.00 | 22.60 | W |
| ATOM | 5496 | O | HOH | W | 47 | 79.316 | 19.117 | 36.851 | 1.00 | 20.84 | W |
| ATOM | 5497 | O | HOH | W | 48 | 63.517 | 41.194 | 33.561 | 1.00 | 22.97 | W |
| ATOM | 5498 | O | HOH | W | 49 | 72.580 | 37.731 | 72.094 | 1.00 | 24.60 | W |
| ATOM | 5499 | O | HOH | W | 50 | 48.465 | 59.435 | 60.810 | 1.00 | 21.15 | W |
| ATOM | 5500 | O | HOH | W | 51 | 68.999 | 43.096 | 49.936 | 1.00 | 22.59 | W |
| ATOM | 5501 | O | HOH | W | 52 | 63.408 | 41.382 | 46.415 | 1.00 | 21.87 | W |
| ATOM | 5502 | O | HOH | W | 53 | 64.040 | 41.979 | 31.006 | 1.00 | 21.71 | W |
| ATOM | 5503 | O | HOH | W | 54 | 63.251 | 39.785 | 48.554 | 1.00 | 21.61 | W |
| ATOM | 5504 | O | HOH | W | 55 | 62.821 | 39.864 | 69.161 | 1.00 | 23.95 | W |
| ATOM | 5505 | O | HOH | W | 56 | 57.262 | 36.212 | 24.689 | 1.00 | 24.45 | W |
| ATOM | 5506 | O | HOH | W | 59 | 57.043 | 10.568 | 24.061 | 1.00 | 24.29 | W |
| ATOM | 5507 | O | HOH | W | 60 | 65.526 | 45.564 | 20.042 | 1.00 | 25.24 | W |
| ATOM | 5508 | O | HOH | W | 61 | 63.272 | 24.634 | 52.077 | 1.00 | 19.89 | W |
| ATOM | 5509 | O | HOH | W | 62 | 58.704 | 8.001 | 61.144 | 1.00 | 33.82 | W |
| ATOM | 5510 | O | HOH | W | 63 | 80.208 | 51.710 | 71.478 | 1.00 | 25.38 | W |
| ATOM | 5511 | O | HOH | W | 64 | 76.945 | 51.373 | 73.955 | 1.00 | 23.23 | W |
| ATOM | 5512 | O | HOH | W | 65 | 67.995 | 36.880 | 17.054 | 1.00 | 24.49 | W |
| ATOM | 5513 | O | HOH | W | 66 | 82.927 | 56.970 | 67.201 | 1.00 | 25.47 | W |
| ATOM | 5514 | O | HOH | W | 67 | 56.677 | 63.762 | 39.805 | 1.00 | 25.76 | W |
| ATOM | 5515 | O | HOH | W | 68 | 57.173 | 54.194 | 48.428 | 1.00 | 22.24 | W |

TABLE 1-continued

| ATOM | 5516 | O | HOH | W | 69 | 70.312 | 37.585 | 36.895 | 1.00 | 20.64 | W |
|---|---|---|---|---|---|---|---|---|---|---|---|
| ATOM | 5517 | O | HOH | W | 70 | 59.716 | 22.619 | 40.630 | 1.00 | 19.77 | W |
| ATOM | 5518 | O | HOH | W | 71 | 62.373 | 43.353 | 71.825 | 1.00 | 23.31 | W |
| ATOM | 5519 | O | HOH | W | 72 | 63.316 | 10.814 | 19.131 | 1.00 | 23.93 | W |
| ATOM | 5520 | O | HOH | W | 73 | 73.934 | 35.029 | 43.644 | 1.00 | 22.55 | W |
| ATOM | 5521 | O | HOH | W | 74 | 57.549 | 44.448 | 51.899 | 1.00 | 23.19 | W |
| ATOM | 5522 | O | HOH | W | 75 | 64.310 | 24.248 | 49.196 | 1.00 | 22.50 | W |
| ATOM | 5523 | O | HOH | W | 76 | 75.705 | 27.919 | 14.511 | 1.00 | 22.42 | W |
| ATOM | 5524 | O | HOH | W | 77 | 42.214 | 60.197 | 59.627 | 1.00 | 24.28 | W |
| ATOM | 5525 | O | HOH | W | 78 | 65.346 | 65.739 | 70.508 | 1.00 | 24.33 | W |
| ATOM | 5526 | O | HOH | W | 80 | 83.353 | 14.214 | 21.276 | 1.00 | 24.04 | W |
| ATOM | 5527 | O | HOH | W | 81 | 69.141 | 36.086 | 71.352 | 1.00 | 25.12 | W |
| ATOM | 5528 | O | HOH | W | 82 | 52.257 | 16.759 | 27.273 | 1.00 | 23.06 | W |
| ATOM | 5529 | O | HOH | W | 83 | 74.845 | 44.047 | 53.561 | 1.00 | 24.47 | W |
| ATOM | 5530 | O | HOH | W | 84 | 46.487 | 14.398 | 28.106 | 1.00 | 25.30 | W |
| ATOM | 5531 | O | HOH | W | 85 | 82.937 | 31.249 | 19.904 | 1.00 | 23.42 | W |
| ATOM | 5532 | O | HOH | W | 86 | 49.796 | 68.893 | 56.040 | 1.00 | 25.00 | W |
| ATOM | 5533 | O | HOH | W | 87 | 69.545 | 33.641 | 11.832 | 1.00 | 26.29 | W |
| ATOM | 5534 | O | HOH | W | 88 | 51.203 | 56.490 | 68.529 | 1.00 | 22.77 | W |
| ATOM | 5535 | O | HOH | W | 89 | 43.081 | 28.692 | 26.089 | 1.00 | 24.70 | W |
| ATOM | 5536 | O | HOH | W | 90 | 57.726 | 67.189 | 57.623 | 1.00 | 24.54 | W |
| ATOM | 5537 | O | HOH | W | 91 | 58.329 | 42.654 | 66.218 | 1.00 | 23.57 | W |
| ATOM | 5538 | O | HOH | W | 92 | 51.770 | 67.560 | 63.119 | 1.00 | 24.10 | W |
| ATOM | 5539 | O | HOH | W | 93 | 59.347 | 43.681 | 68.561 | 1.00 | 24.88 | W |
| ATOM | 5540 | O | HOH | W | 94 | 62.001 | 76.154 | 52.947 | 1.00 | 25.42 | W |
| ATOM | 5541 | O | HOH | W | 95 | 74.979 | 38.296 | 31.807 | 1.00 | 26.78 | W |
| ATOM | 5542 | O | HOH | W | 96 | 80.313 | 69.550 | 67.984 | 1.00 | 30.89 | W |
| ATOM | 5543 | O | HOH | W | 97 | 60.559 | 49.641 | 40.481 | 1.00 | 22.94 | W |
| ATOM | 5544 | O | HOH | W | 98 | 70.074 | 16.214 | 17.253 | 1.00 | 26.55 | W |
| ATOM | 5545 | O | HOH | W | 99 | 70.032 | 50.461 | 27.259 | 1.00 | 23.41 | W |
| ATOM | 5546 | O | HOH | W | 100 | 62.657 | 54.191 | 73.741 | 1.00 | 26.11 | W |
| ATOM | 5547 | O | HOH | W | 101 | 58.963 | 32.090 | 16.061 | 1.00 | 27.21 | W |
| ATOM | 5548 | O | HOH | W | 102 | 72.167 | 51.953 | 85.003 | 1.00 | 23.67 | W |
| ATOM | 5549 | O | HOH | W | 103 | 58.895 | 7.223 | 24.776 | 1.00 | 24.46 | W |
| ATOM | 5550 | O | HOH | W | 105 | 77.240 | 54.753 | 44.339 | 1.00 | 27.39 | W |
| ATOM | 5551 | O | HOH | W | 107 | 74.373 | 45.527 | 46.711 | 1.00 | 26.32 | W |
| ATOM | 5552 | O | HOH | W | 108 | 68.380 | 73.123 | 52.390 | 1.00 | 26.05 | W |
| ATOM | 5553 | O | HOH | W | 109 | 51.952 | 28.351 | 46.664 | 1.00 | 25.77 | W |
| ATOM | 5554 | O | HOH | W | 110 | 52.932 | 52.556 | 69.308 | 1.00 | 24.81 | W |
| ATOM | 5555 | O | HOH | W | 111 | 50.995 | 71.153 | 33.535 | 1.00 | 25.70 | W |
| ATOM | 5556 | O | HOH | W | 112 | 69.435 | 5.918 | 48.243 | 1.00 | 26.08 | W |
| ATOM | 5557 | O | HOH | W | 113 | 58.571 | 35.820 | 21.970 | 1.00 | 24.94 | W |
| ATOM | 5558 | O | HOH | W | 114 | 82.554 | 7.623 | 25.613 | 1.00 | 25.82 | W |
| ATOM | 5559 | O | HOH | W | 115 | 61.024 | 6.273 | 30.807 | 1.00 | 26.93 | W |
| ATOM | 5560 | O | HOH | W | 117 | 52.715 | −3.232 | 51.112 | 1.00 | 26.71 | W |
| ATOM | 5561 | O | HOH | W | 118 | 60.654 | 45.563 | 41.052 | 1.00 | 24.78 | W |
| ATOM | 5562 | O | HOH | W | 119 | 61.527 | 44.168 | 37.077 | 1.00 | 28.25 | W |
| ATOM | 5563 | O | HOH | W | 120 | 62.877 | 11.277 | 29.667 | 1.00 | 25.59 | W |
| ATOM | 5565 | O | HOH | W | 122 | 60.970 | 30.695 | 49.132 | 1.00 | 24.64 | W |
| ATOM | 5566 | O | HOH | W | 123 | 66.299 | 38.019 | 60.150 | 1.00 | 28.45 | W |
| ATOM | 5567 | O | HOH | W | 124 | 61.549 | 26.608 | 49.083 | 1.00 | 26.53 | W |
| ATOM | 5568 | O | HOH | W | 125 | 61.072 | 0.000 | 33.963 | 1.00 | 28.97 | W |
| ATOM | 5569 | O | HOH | W | 126 | 49.512 | 46.232 | 52.603 | 1.00 | 30.79 | W |
| ATOM | 5570 | O | HOH | W | 127 | 68.576 | 19.378 | 48.527 | 1.00 | 24.69 | W |
| ATOM | 5571 | O | HOH | W | 128 | 70.853 | 59.851 | 22.136 | 1.00 | 27.18 | W |
| ATOM | 5572 | O | HOH | W | 129 | 44.582 | 12.795 | 29.138 | 1.00 | 29.59 | W |
| ATOM | 5573 | O | HOH | W | 130 | 46.994 | 18.321 | 47.027 | 1.00 | 29.83 | W |
| ATOM | 5574 | O | HOH | W | 131 | 65.144 | 45.712 | 74.829 | 1.00 | 26.98 | W |
| ATOM | 5575 | O | HOH | W | 132 | 57.516 | 69.284 | 68.083 | 1.00 | 26.30 | W |
| ATOM | 5576 | O | HOH | W | 133 | 56.003 | 7.423 | 30.904 | 1.00 | 26.48 | W |
| ATOM | 5577 | O | HOH | W | 134 | 49.501 | −0.691 | 45.149 | 1.00 | 26.54 | W |
| ATOM | 5578 | O | HOH | W | 135 | 39.961 | 61.065 | 58.631 | 1.00 | 25.80 | W |
| ATOM | 5579 | O | HOH | W | 136 | 70.917 | 24.862 | 14.486 | 1.00 | 24.46 | W |
| ATOM | 5580 | O | HOH | W | 137 | 77.750 | 13.435 | 39.710 | 1.00 | 29.43 | W |
| ATOM | 5581 | O | HOH | W | 138 | 62.229 | 40.302 | 37.890 | 1.00 | 21.48 | W |
| ATOM | 5582 | O | HOH | W | 139 | 84.323 | 36.766 | 25.075 | 1.00 | 27.92 | W |
| ATOM | 5583 | O | HOH | W | 140 | 63.971 | 37.907 | 42.820 | 1.00 | 21.62 | W |
| ATOM | 5584 | O | HOH | W | 141 | 75.483 | 65.204 | 28.062 | 1.00 | 26.96 | W |
| ATOM | 5585 | O | HOH | W | 142 | 46.730 | 53.739 | 43.969 | 1.00 | 28.65 | W |
| ATOM | 5586 | O | HOH | W | 143 | 46.258 | 65.015 | 59.982 | 1.00 | 29.02 | W |
| ATOM | 5587 | O | HOH | W | 144 | 60.824 | 42.361 | 45.951 | 1.00 | 25.54 | W |
| ATOM | 5588 | O | HOH | W | 145 | 57.787 | 3.260 | 53.084 | 1.00 | 27.40 | W |
| ATOM | 5589 | O | HOH | W | 146 | 65.042 | 72.620 | 70.008 | 1.00 | 28.84 | W |
| ATOM | 5590 | O | HOH | W | 147 | 65.078 | 40.503 | 44.187 | 1.00 | 23.04 | W |
| ATOM | 5591 | O | HOH | W | 148 | 68.652 | 45.263 | 73.567 | 1.00 | 29.23 | W |
| ATOM | 5592 | O | HOH | W | 149 | 84.241 | 48.502 | 65.450 | 1.00 | 25.86 | W |
| ATOM | 5593 | O | HOH | W | 150 | 74.537 | 41.450 | 22.811 | 1.00 | 26.68 | W |
| ATOM | 5594 | O | HOH | W | 151 | 61.477 | 40.341 | 55.733 | 1.00 | 25.33 | W |
| ATOM | 5595 | O | HOH | W | 152 | 57.918 | 79.068 | 41.281 | 1.00 | 31.29 | W |

TABLE 1-continued

| ATOM | 5596 | O | HOH | W | 153 | 74.785 | 53.778 | 43.371 | 1.00 | 30.36 | W |
| --- | --- | --- | --- | --- | --- | --- | --- | --- | --- | --- | --- |
| ATOM | 5597 | O | HOH | W | 154 | 85.703 | 15.024 | 23.348 | 1.00 | 27.23 | W |
| ATOM | 5598 | O | HOH | W | 155 | 68.964 | 68.690 | 44.970 | 1.00 | 26.03 | W |
| ATOM | 5599 | O | HOH | W | 156 | 74.089 | 10.257 | 42.380 | 1.00 | 30.35 | W |
| ATOM | 5600 | O | HOH | W | 157 | 49.244 | 19.843 | 44.762 | 1.00 | 25.95 | W |
| ATOM | 5601 | O | HOH | W | 158 | 58.670 | 47.443 | 73.914 | 1.00 | 26.97 | W |
| ATOM | 5602 | O | HOH | W | 159 | 69.964 | 68.241 | 49.366 | 1.00 | 26.68 | W |
| ATOM | 5603 | O | HOH | W | 160 | 74.406 | 16.621 | 66.256 | 1.00 | 27.77 | W |
| ATOM | 5604 | O | HOH | W | 161 | 62.764 | 36.720 | 45.204 | 1.00 | 25.78 | W |
| ATOM | 5605 | O | HOH | W | 162 | 56.600 | 24.241 | 53.804 | 1.00 | 31.52 | W |
| ATOM | 5606 | O | HOH | W | 163 | 73.168 | 23.765 | 13.424 | 1.00 | 29.29 | W |
| ATOM | 5607 | O | HOH | W | 164 | 77.101 | 68.818 | 60.573 | 1.00 | 25.58 | W |
| ATOM | 5608 | O | HOH | W | 165 | 41.426 | 57.744 | 46.220 | 1.00 | 33.03 | W |
| ATOM | 5609 | O | HOH | W | 166 | 60.502 | 40.074 | 21.898 | 1.00 | 27.06 | W |
| ATOM | 5610 | O | HOH | W | 167 | 59.684 | 59.525 | 44.242 | 1.00 | 28.75 | W |
| ATOM | 5611 | O | HOH | W | 168 | 65.647 | 38.859 | 72.915 | 1.00 | 25.66 | W |
| ATOM | 5612 | O | HOH | W | 169 | 73.730 | 38.059 | 26.842 | 1.00 | 27.75 | W |
| ATOM | 5613 | O | HOH | W | 170 | 81.015 | 19.538 | 38.738 | 1.00 | 30.36 | W |
| ATOM | 5614 | O | HOH | W | 171 | 78.966 | 58.963 | 73.586 | 1.00 | 27.55 | W |
| ATOM | 5615 | O | HOH | W | 172 | 69.668 | 11.618 | 57.747 | 1.00 | 30.42 | W |
| ATOM | 5616 | O | HOH | W | 173 | 61.587 | 37.662 | 18.435 | 1.00 | 29.16 | W |
| ATOM | 5617 | O | HOH | W | 174 | 76.065 | 41.038 | 38.931 | 1.00 | 26.29 | W |
| ATOM | 5618 | O | HOH | W | 175 | 79.523 | 17.109 | 34.686 | 1.00 | 25.68 | W |
| ATOM | 5619 | O | HOH | W | 176 | 70.554 | 69.481 | 47.306 | 1.00 | 28.09 | W |
| ATOM | 5620 | O | HOH | W | 177 | 75.690 | 41.201 | 17.956 | 1.00 | 24.68 | W |
| ATOM | 5621 | O | HOH | W | 178 | 75.825 | 44.206 | 58.913 | 1.00 | 27.90 | W |
| ATOM | 5622 | O | HOH | W | 179 | 75.440 | 74.910 | 58.035 | 1.00 | 27.08 | W |
| ATOM | 5623 | O | HOH | W | 180 | 42.016 | 59.088 | 43.328 | 1.00 | 27.18 | W |
| ATOM | 5624 | O | HOH | W | 181 | 68.729 | 17.924 | 50.739 | 1.00 | 25.32 | W |
| ATOM | 5625 | O | HOH | W | 182 | 73.777 | 37.415 | 37.197 | 1.00 | 25.43 | W |
| ATOM | 5626 | O | HOH | W | 183 | 46.531 | 24.581 | 44.620 | 1.00 | 28.83 | W |
| ATOM | 5627 | O | HOH | W | 184 | 61.176 | 73.591 | 61.170 | 1.00 | 24.78 | W |
| ATOM | 5628 | O | HOH | W | 185 | 40.960 | 70.738 | 51.853 | 1.00 | 31.15 | W |
| ATOM | 5629 | O | HOH | W | 186 | 40.807 | 72.423 | 48.103 | 1.00 | 27.75 | W |
| ATOM | 5630 | O | HOH | W | 187 | 80.220 | 13.052 | 59.537 | 1.00 | 29.82 | W |
| ATOM | 5631 | O | HOH | W | 188 | 73.108 | 56.052 | 75.317 | 1.00 | 27.07 | W |
| ATOM | 5632 | O | HOH | W | 189 | 69.002 | 43.361 | 33.177 | 1.00 | 28.78 | W |
| ATOM | 5633 | O | HOH | W | 190 | 56.918 | 37.352 | 33.022 | 1.00 | 30.65 | W |
| ATOM | 5634 | O | HOH | W | 191 | 64.753 | 76.092 | 51.045 | 1.00 | 27.43 | W |
| ATOM | 5635 | O | HOH | W | 192 | 72.764 | 61.062 | 38.798 | 1.00 | 28.71 | W |
| ATOM | 5636 | O | HOH | W | 193 | 55.401 | 1.808 | 35.317 | 1.00 | 30.56 | W |
| ATOM | 5637 | O | HOH | W | 194 | 81.135 | 49.413 | 66.611 | 1.00 | 27.12 | W |
| ATOM | 5638 | O | HOH | W | 195 | 81.103 | 35.964 | 34.772 | 1.00 | 23.48 | W |
| ATOM | 5639 | O | HOH | W | 196 | 78.919 | 20.830 | 47.204 | 1.00 | 31.44 | W |
| ATOM | 5640 | O | HOH | W | 197 | 71.785 | 67.773 | 44.301 | 1.00 | 29.93 | W |
| ATOM | 5641 | O | HOH | W | 198 | 57.897 | 22.956 | 19.386 | 1.00 | 30.03 | W |
| ATOM | 5642 | O | HOH | W | 199 | 46.145 | 73.210 | 53.298 | 1.00 | 31.94 | W |
| ATOM | 5643 | O | HOH | W | 200 | 66.365 | 20.561 | 47.889 | 1.00 | 25.86 | W |
| ATOM | 5644 | O | HOH | W | 201 | 75.417 | 43.377 | 74.666 | 1.00 | 28.69 | W |
| ATOM | 5645 | O | HOH | W | 203 | 64.275 | 24.657 | 46.531 | 1.00 | 29.03 | W |
| ATOM | 5646 | O | HOH | W | 204 | 70.321 | 14.773 | 61.241 | 1.00 | 26.97 | W |
| ATOM | 5647 | O | HOH | W | 205 | 74.963 | 38.325 | 51.420 | 1.00 | 26.71 | W |
| ATOM | 5648 | O | HOH | W | 206 | 77.850 | 49.218 | 75.614 | 1.00 | 25.71 | W |
| ATOM | 5649 | O | HOH | W | 207 | 56.810 | 25.276 | 42.331 | 1.00 | 24.63 | W |
| ATOM | 5650 | O | HOH | W | 208 | 66.406 | 0.835 | 38.426 | 1.00 | 29.23 | W |
| ATOM | 5651 | O | HOH | W | 209 | 76.759 | 44.123 | 33.732 | 1.00 | 27.61 | W |
| ATOM | 5652 | O | HOH | W | 210 | 39.502 | 58.418 | 54.377 | 1.00 | 25.63 | W |
| ATOM | 5653 | O | HOH | W | 211 | 68.205 | 16.368 | 60.989 | 1.00 | 27.58 | W |
| ATOM | 5654 | O | HOH | W | 212 | 63.399 | 38.275 | 40.371 | 1.00 | 26.33 | W |
| ATOM | 5655 | O | HOH | W | 213 | 67.436 | 22.692 | 57.790 | 1.00 | 29.61 | W |
| ATOM | 5656 | O | HOH | W | 214 | 36.007 | 58.062 | 72.610 | 1.00 | 33.67 | W |
| ATOM | 5657 | O | HOH | W | 215 | 48.587 | 62.223 | 61.382 | 1.00 | 29.34 | W |
| ATOM | 5658 | O | HOH | W | 216 | 64.925 | 53.860 | 31.603 | 1.00 | 26.68 | W |
| ATOM | 5659 | O | HOH | W | 217 | 75.220 | 25.508 | 13.494 | 1.00 | 28.06 | W |
| ATOM | 5660 | O | HOH | W | 218 | 82.014 | 20.634 | 42.646 | 1.00 | 28.66 | W |
| ATOM | 5661 | O | HOH | W | 219 | 43.877 | 74.785 | 46.989 | 1.00 | 30.02 | W |
| ATOM | 5662 | O | HOH | W | 220 | 49.745 | 45.753 | 69.697 | 1.00 | 29.45 | W |
| ATOM | 5663 | O | HOH | W | 221 | 73.064 | 67.339 | 28.737 | 1.00 | 32.32 | W |
| ATOM | 5664 | O | HOH | W | 222 | 78.863 | 39.394 | 24.379 | 1.00 | 31.79 | W |
| ATOM | 5665 | O | HOH | W | 223 | 89.572 | 32.973 | 23.599 | 1.00 | 30.18 | W |
| ATOM | 5666 | O | HOH | W | 224 | 45.658 | 57.318 | 71.862 | 1.00 | 31.36 | W |
| ATOM | 5667 | O | HOH | W | 225 | 53.700 | 70.470 | 56.193 | 1.00 | 27.16 | W |
| ATOM | 5668 | O | HOH | W | 226 | 72.375 | 67.680 | 47.720 | 1.00 | 29.36 | W |
| ATOM | 5669 | O | HOH | W | 227 | 41.691 | 44.668 | 49.005 | 1.00 | 28.53 | W |
| ATOM | 5670 | O | HOH | W | 228 | 60.020 | 55.992 | 45.357 | 1.00 | 28.40 | W |
| ATOM | 5671 | O | HOH | W | 229 | 77.198 | 51.745 | 71.156 | 1.00 | 23.06 | W |
| ATOM | 5672 | O | HOH | W | 230 | 66.672 | 28.713 | 11.453 | 1.00 | 29.12 | W |
| ATOM | 5673 | O | HOH | W | 231 | 55.988 | 15.430 | 22.654 | 1.00 | 28.39 | W |
| ATOM | 5674 | O | HOH | W | 232 | 52.390 | 70.720 | 61.829 | 1.00 | 27.92 | W |

TABLE 1-continued

| | | | | | | | | | | |
|---|---|---|---|---|---|---|---|---|---|---|
| ATOM | 5675 | O | HOH | W | 233 | 71.858 | 26.637 | 62.357 | 1.00 | 32.81 | W |
| ATOM | 5676 | O | HOH | W | 234 | 49.795 | 74.365 | 52.433 | 1.00 | 29.36 | W |
| ATOM | 5677 | O | HOH | W | 235 | 64.184 | 51.855 | 43.054 | 1.00 | 26.39 | W |
| ATOM | 5678 | O | HOH | W | 236 | 66.442 | 34.520 | 58.627 | 1.00 | 31.27 | W |
| ATOM | 5679 | O | HOH | W | 237 | 76.545 | 34.823 | 56.994 | 1.00 | 28.47 | W |
| ATOM | 5680 | O | HOH | W | 238 | 38.881 | 59.114 | 56.826 | 1.00 | 30.63 | W |
| ATOM | 5681 | O | HOH | W | 239 | 60.976 | 68.353 | 70.927 | 1.00 | 32.25 | W |
| ATOM | 5682 | O | HOH | W | 240 | 51.945 | 7.734 | 51.708 | 1.00 | 27.85 | W |
| ATOM | 5683 | O | HOH | W | 241 | 47.145 | 46.227 | 69.422 | 1.00 | 29.12 | W |
| ATOM | 5684 | O | HOH | W | 242 | 58.822 | 22.414 | 56.487 | 1.00 | 32.89 | W |
| ATOM | 5685 | O | HOH | W | 243 | 57.845 | 1.076 | 33.438 | 1.00 | 27.35 | W |
| ATOM | 5686 | O | HOH | W | 244 | 61.403 | 31.848 | 53.249 | 1.00 | 27.09 | W |
| ATOM | 5687 | O | HOH | W | 245 | 51.680 | 45.763 | 42.936 | 1.00 | 29.13 | W |
| ATOM | 5688 | O | HOH | W | 246 | 73.753 | 51.662 | 34.311 | 1.00 | 28.21 | W |
| ATOM | 5689 | O | HOH | W | 247 | 77.659 | 62.276 | 49.770 | 1.00 | 32.45 | W |
| ATOM | 5690 | O | HOH | W | 248 | 58.663 | 52.302 | 75.507 | 1.00 | 29.27 | W |
| ATOM | 5691 | O | HOH | W | 249 | 57.070 | 51.226 | 72.660 | 1.00 | 30.39 | W |
| ATOM | 5692 | O | HOH | W | 250 | 42.629 | 64.169 | 50.085 | 1.00 | 28.09 | W |
| ATOM | 5693 | O | HOH | W | 251 | 54.157 | 63.726 | 66.937 | 1.00 | 27.20 | W |
| ATOM | 5694 | O | HOH | W | 252 | 85.096 | 16.633 | 18.808 | 1.00 | 31.78 | W |
| ATOM | 5695 | O | HOH | W | 253 | 51.723 | 10.808 | 26.932 | 1.00 | 28.39 | W |
| ATOM | 5696 | O | HOH | W | 254 | 45.305 | 65.496 | 63.968 | 1.00 | 31.30 | W |
| ATOM | 5697 | O | HOH | W | 255 | 64.503 | 52.819 | 78.235 | 1.00 | 30.69 | W |
| ATOM | 5698 | O | HOH | W | 256 | 41.667 | 53.864 | 67.154 | 1.00 | 31.99 | W |
| ATOM | 5699 | O | HOH | W | 257 | 75.413 | 12.104 | 37.946 | 1.00 | 27.16 | W |
| ATOM | 5700 | O | HOH | W | 258 | 43.381 | 14.777 | 33.518 | 1.00 | 29.08 | W |
| ATOM | 5701 | O | HOH | W | 259 | 47.695 | 73.987 | 50.495 | 1.00 | 28.82 | W |
| ATOM | 5702 | O | HOH | W | 260 | 43.621 | 19.310 | 24.167 | 1.00 | 34.31 | W |
| ATOM | 5703 | O | HOH | W | 261 | 67.804 | 44.306 | 30.239 | 1.00 | 31.10 | W |
| ATOM | 5704 | O | HOH | W | 262 | 47.866 | 30.670 | 20.342 | 1.00 | 27.71 | W |
| ATOM | 5705 | O | HOH | W | 263 | 42.804 | 19.146 | 37.484 | 1.00 | 30.70 | W |
| ATOM | 5706 | O | HOH | W | 264 | 41.444 | 74.101 | 41.897 | 1.00 | 28.92 | W |
| ATOM | 5707 | O | HOH | W | 265 | 65.591 | 45.630 | 29.635 | 1.00 | 33.71 | W |
| ATOM | 5708 | O | HOH | W | 266 | 74.406 | 64.628 | 32.170 | 1.00 | 31.47 | W |
| ATOM | 5709 | O | HOH | W | 267 | 67.472 | 46.632 | 75.428 | 1.00 | 28.28 | W |
| ATOM | 5710 | O | HOH | W | 268 | 77.508 | 38.587 | 28.109 | 1.00 | 30.04 | W |
| ATOM | 5711 | O | HOH | W | 270 | 75.311 | 26.948 | 55.187 | 1.00 | 30.83 | W |
| ATOM | 5712 | O | HOH | W | 271 | 65.229 | 37.820 | 56.571 | 1.00 | 30.93 | W |
| ATOM | 5713 | O | HOH | W | 272 | 73.280 | 39.878 | 15.712 | 1.00 | 30.10 | W |
| ATOM | 5714 | O | HOH | W | 273 | 78.268 | 59.662 | 48.058 | 1.00 | 29.57 | W |
| ATOM | 5715 | O | HOH | W | 274 | 60.734 | 53.549 | 71.838 | 1.00 | 27.03 | W |
| ATOM | 5716 | O | HOH | W | 275 | 54.568 | 54.013 | 67.979 | 1.00 | 27.83 | W |
| ATOM | 5717 | O | HOH | W | 276 | 74.611 | 42.685 | 55.688 | 1.00 | 28.19 | W |
| ATOM | 5718 | O | HOH | W | 277 | 59.388 | 75.806 | 40.928 | 1.00 | 33.13 | W |
| ATOM | 5719 | O | HOH | W | 278 | 69.463 | 67.984 | 33.824 | 1.00 | 32.45 | W |
| ATOM | 5720 | O | HOH | W | 279 | 74.512 | 9.720 | 54.383 | 1.00 | 31.41 | W |
| ATOM | 5721 | O | HOH | W | 280 | 42.579 | 57.947 | 67.286 | 1.00 | 32.19 | W |
| ATOM | 5722 | O | HOH | W | 281 | 64.827 | 21.473 | 54.787 | 1.00 | 28.93 | W |
| ATOM | 5723 | O | HOH | W | 282 | 45.808 | 25.843 | 14.464 | 1.00 | 29.21 | W |
| ATOM | 5724 | O | HOH | W | 283 | 71.565 | 2.926 | 32.664 | 1.00 | 31.89 | W |
| ATOM | 5725 | O | HOH | W | 284 | 41.770 | 52.505 | 56.626 | 1.00 | 32.45 | W |
| ATOM | 5726 | O | HOH | W | 285 | 87.293 | 26.262 | 19.876 | 1.00 | 28.06 | W |
| ATOM | 5727 | O | HOH | W | 286 | 81.321 | 33.767 | 21.275 | 1.00 | 32.23 | W |
| ATOM | 5728 | O | HOH | W | 287 | 69.846 | 12.148 | 60.348 | 1.00 | 30.73 | W |
| ATOM | 5729 | O | HOH | W | 288 | 60.964 | 8.948 | 49.107 | 1.00 | 29.21 | W |
| ATOM | 5730 | O | HOH | W | 289 | 58.950 | 61.830 | 51.401 | 1.00 | 30.81 | W |
| ATOM | 5731 | O | HOH | W | 290 | 62.407 | 56.365 | 30.766 | 1.00 | 30.19 | W |
| ATOM | 5732 | O | HOH | W | 291 | 61.796 | 48.435 | 75.769 | 1.00 | 29.55 | W |
| ATOM | 5733 | O | HOH | W | 292 | 75.268 | 5.714 | 14.226 | 1.00 | 31.55 | W |
| ATOM | 5734 | O | HOH | W | 293 | 44.515 | 23.741 | 42.985 | 1.00 | 28.69 | W |
| ATOM | 5735 | O | HOH | W | 294 | 76.682 | 26.413 | 45.954 | 1.00 | 30.45 | W |
| ATOM | 5736 | O | HOH | W | 295 | 64.258 | 2.397 | 56.682 | 1.00 | 30.13 | W |
| ATOM | 5737 | O | HOH | W | 297 | 77.206 | 10.071 | 18.415 | 1.00 | 30.09 | W |
| ATOM | 5738 | O | HOH | W | 298 | 42.058 | 61.924 | 43.815 | 1.00 | 31.20 | W |
| ATOM | 5739 | O | HOH | W | 299 | 68.976 | 33.493 | 57.382 | 1.00 | 33.71 | W |
| ATOM | 5740 | O | HOH | W | 300 | 56.209 | 24.456 | 21.199 | 1.00 | 28.52 | W |
| ATOM | 5741 | O | HOH | W | 301 | 71.705 | 7.433 | 56.476 | 1.00 | 31.61 | W |
| ATOM | 5742 | O | HOH | W | 302 | 56.440 | 62.051 | 67.237 | 1.00 | 29.21 | W |
| ATOM | 5743 | O | HOH | W | 303 | 42.273 | 38.834 | 66.808 | 1.00 | 34.44 | W |
| ATOM | 5744 | O | HOH | W | 304 | 64.199 | 49.444 | 20.009 | 1.00 | 33.99 | W |
| ATOM | 5745 | O | HOH | W | 305 | 69.072 | 45.610 | 19.588 | 1.00 | 28.20 | W |
| ATOM | 5746 | O | HOH | W | 306 | 68.919 | 35.614 | 56.073 | 1.00 | 32.66 | W |
| ATOM | 5747 | O | HOH | W | 307 | 76.902 | 15.459 | 53.866 | 1.00 | 28.55 | W |
| ATOM | 5748 | O | HOH | W | 308 | 76.913 | 23.882 | 52.941 | 1.00 | 33.45 | W |
| ATOM | 5749 | O | HOH | W | 309 | 78.766 | 55.553 | 46.227 | 1.00 | 30.18 | W |
| ATOM | 5750 | O | HOH | W | 310 | 74.360 | 54.202 | 35.783 | 1.00 | 31.72 | W |
| ATOM | 5751 | O | HOH | W | 311 | 56.524 | 46.901 | 35.255 | 1.00 | 34.16 | W |
| ATOM | 5752 | O | HOH | W | 312 | 44.676 | 70.416 | 58.335 | 1.00 | 34.21 | W |
| ATOM | 5753 | O | HOH | W | 313 | 71.884 | 10.478 | 57.404 | 1.00 | 31.30 | W |

TABLE 1-continued

| ATOM | 5754 | O | HOH | W | 314 | 76.916 | 12.018 | 45.911 | 1.00 | 28.73 | W |
|---|---|---|---|---|---|---|---|---|---|---|---|
| ATOM | 5755 | O | HOH | W | 315 | 63.110 | 58.895 | 31.419 | 1.00 | 32.64 | W |
| ATOM | 5756 | O | HOH | W | 316 | 64.675 | 72.380 | 46.743 | 1.00 | 31.30 | W |
| ATOM | 5757 | O | HOH | W | 318 | 74.556 | 39.933 | 25.103 | 1.00 | 28.35 | W |
| ATOM | 5758 | O | HOH | W | 319 | 69.370 | 30.913 | 61.997 | 1.00 | 31.48 | W |
| ATOM | 5759 | O | HOH | W | 320 | 65.576 | 48.553 | 26.319 | 1.00 | 30.03 | W |
| ATOM | 5760 | O | HOH | W | 322 | 73.498 | 11.638 | 60.639 | 1.00 | 32.06 | W |
| ATOM | 5761 | O | HOH | W | 323 | 53.622 | 35.468 | 19.545 | 1.00 | 30.39 | W |
| ATOM | 5762 | O | HOH | W | 324 | 75.381 | 60.008 | 41.281 | 1.00 | 31.72 | W |
| ATOM | 5763 | O | HOH | W | 325 | 84.900 | 63.351 | 68.628 | 1.00 | 31.55 | W |
| ATOM | 5764 | O | HOH | W | 326 | 56.204 | 26.594 | 17.464 | 1.00 | 31.39 | W |
| ATOM | 5765 | O | HOH | W | 327 | 45.244 | 48.437 | 44.476 | 1.00 | 28.97 | W |
| ATOM | 5766 | O | HOH | W | 329 | 55.378 | 56.019 | 69.611 | 1.00 | 28.06 | W |
| ATOM | 5767 | O | HOH | W | 330 | 74.385 | 24.992 | 64.652 | 1.00 | 29.27 | W |
| ATOM | 5768 | O | HOH | W | 331 | 79.017 | 26.230 | 44.976 | 1.00 | 29.13 | W |
| ATOM | 5769 | O | HOH | W | 332 | 45.280 | 71.142 | 56.006 | 1.00 | 28.82 | W |
| ATOM | 5770 | O | HOH | W | 333 | 84.528 | 60.486 | 69.657 | 1.00 | 31.99 | W |
| ATOM | 5771 | O | HOH | W | 334 | 71.275 | 6.614 | 49.967 | 1.00 | 30.95 | W |
| ATOM | 5772 | O | HOH | W | 335 | 64.006 | 62.993 | 75.549 | 1.00 | 33.11 | W |
| ATOM | 5773 | O | HOH | W | 336 | 75.642 | 50.256 | 69.897 | 1.00 | 27.46 | W |
| ATOM | 5774 | O | HOH | W | 337 | 75.213 | 7.248 | 34.079 | 1.00 | 31.06 | W |
| ATOM | 5775 | O | HOH | W | 338 | 42.191 | 20.708 | 35.462 | 1.00 | 27.83 | W |
| ATOM | 5776 | O | HOH | W | 339 | 46.143 | 13.143 | 43.918 | 1.00 | 30.25 | W |
| ATOM | 5777 | O | HOH | W | 340 | 55.092 | 50.392 | 47.083 | 1.00 | 26.20 | W |
| ATOM | 5778 | O | HOH | W | 341 | 49.664 | 54.653 | 76.262 | 1.00 | 32.65 | W |
| ATOM | 5779 | O | HOH | W | 342 | 39.303 | 68.113 | 43.834 | 1.00 | 30.55 | W |
| ATOM | 5780 | O | HOH | W | 343 | 58.261 | 28.206 | 16.838 | 1.00 | 33.31 | W |
| ATOM | 5781 | O | HOH | W | 344 | 51.167 | 31.548 | 40.969 | 1.00 | 34.14 | W |
| ATOM | 5782 | O | HOH | W | 345 | 87.942 | 36.558 | 20.152 | 1.00 | 32.63 | W |
| ATOM | 5783 | O | HOH | W | 346 | 59.595 | 44.427 | 38.736 | 1.00 | 33.78 | W |
| ATOM | 5784 | O | HOH | W | 347 | 38.419 | 23.811 | 24.459 | 1.00 | 29.98 | W |
| ATOM | 5785 | O | HOH | W | 348 | 70.824 | 9.768 | 16.729 | 1.00 | 27.88 | W |
| ATOM | 5786 | O | HOH | W | 349 | 67.576 | 4.444 | 21.537 | 1.00 | 31.48 | W |
| ATOM | 5787 | O | HOH | W | 350 | 54.095 | 28.209 | 50.426 | 1.00 | 29.84 | W |
| ATOM | 5788 | O | HOH | W | 351 | 60.494 | 34.637 | 45.382 | 1.00 | 32.35 | W |
| ATOM | 5789 | O | HOH | W | 352 | 50.465 | −1.152 | 50.669 | 1.00 | 33.34 | W |
| ATOM | 5790 | O | HOH | W | 353 | 44.232 | 31.267 | 40.817 | 1.00 | 33.86 | W |
| ATOM | 5791 | O | HOH | W | 354 | 72.874 | 77.776 | 55.446 | 1.00 | 30.84 | W |
| ATOM | 5792 | O | HOH | W | 355 | 78.305 | 66.385 | 49.370 | 1.00 | 33.77 | W |
| ATOM | 5793 | O | HOH | W | 356 | 62.547 | 24.715 | 13.827 | 1.00 | 31.14 | W |
| ATOM | 5794 | O | HOH | W | 357 | 79.098 | 28.800 | 45.028 | 1.00 | 32.57 | W |
| ATOM | 5795 | O | HOH | W | 358 | 43.176 | 63.541 | 37.365 | 1.00 | 28.99 | W |
| ATOM | 5796 | O | HOH | | 359 | 82.826 | 34.248 | 35.768 | 1.00 | 38.41 | |
| ATOM | 5797 | O | HOH | | 360 | 81.933 | 49.402 | 53.992 | 1.00 | 21.68 | |
| ATOM | 5798 | O | HOH | | 361 | 61.127 | 46.027 | 72.258 | 1.00 | 22.14 | |
| ATOM | 5799 | O | HOH | | 362 | 60.745 | 38.400 | 39.803 | 1.00 | 24.66 | |
| ATOM | 5800 | O | HOH | | 363 | 57.542 | 60.901 | 43.861 | 1.00 | 38.76 | |
| ATOM | 5801 | O | HOH | | 364 | 56.614 | 62.112 | 41.757 | 1.00 | 26.88 | |
| ATOM | 5802 | O | HOH | | 365 | 55.276 | 60.792 | 39.856 | 1.00 | 29.74 | |
| ATOM | 5803 | O | HOH | | 367 | 45.983 | 65.576 | 35.806 | 1.00 | 31.88 | |
| ATOM | 5804 | O | HOH | | 368 | 67.594 | 37.794 | 55.508 | 1.00 | 29.58 | |
| ATOM | 5805 | O | HOH | | 369 | 59.456 | 36.813 | 37.550 | 1.00 | 28.71 | |
| ATOM | 5806 | O | HOH | | 370 | 61.358 | 9.159 | 53.944 | 1.00 | 21.56 | |
| ATOM | 5807 | O | HOH | | 371 | 62.481 | 21.388 | 42.968 | 1.00 | 33.23 | |
| ATOM | 5808 | O | HOH | | 372 | 61.544 | 40.229 | 35.178 | 1.00 | 25.99 | |
| ATOM | 5809 | O | HOH | | 373 | 74.106 | 56.457 | 37.068 | 1.00 | 42.20 | |
| ATOM | 5810 | O | HOH | | 374 | 61.083 | 57.738 | 42.924 | 1.00 | 39.67 | |
| ATOM | 5811 | O | HOH | | 375 | 82.321 | 55.124 | 69.122 | 1.00 | 31.83 | |
| ATOM | 5812 | O | HOH | | 376 | 62.686 | 26.839 | 17.591 | 1.00 | 29.72 | |
| ATOM | 5813 | O | HOH | | 377 | 77.126 | 57.683 | 75.248 | 1.00 | 31.25 | |
| ATOM | 5814 | O | HOH | | 378 | 75.223 | 30.516 | 13.211 | 1.00 | 33.93 | |
| ATOM | 5815 | O | HOH | | 379 | 55.181 | 62.323 | 37.646 | 1.00 | 38.61 | |
| ATOM | 5816 | O | HOH | | 380 | 59.120 | 80.637 | 43.119 | 1.00 | 44.85 | |
| ATOM | 5817 | O | HOH | | 381 | 55.211 | 26.155 | 19.743 | 1.00 | 43.08 | |
| ATOM | 5818 | O | HOH | | 382 | 66.462 | 39.648 | 46.452 | 1.00 | 28.53 | |
| ATOM | 5819 | O | HOH | | 383 | 41.138 | 54.779 | 64.332 | 1.00 | 44.65 | |
| ATOM | 5820 | O | HOH | | 384 | 48.464 | 68.340 | 58.368 | 1.00 | 35.13 | |
| ATOM | 5821 | O | HOH | | 385 | 78.082 | 67.637 | 68.071 | 1.00 | 36.99 | |
| ATOM | 5822 | O | HOH | | 386 | 80.925 | 35.374 | 23.432 | 1.00 | 33.74 | |
| ATOM | 5823 | O | HOH | | 387 | 88.991 | 28.140 | 20.326 | 1.00 | 35.14 | |
| ATOM | 5824 | O | HOH | | 388 | 72.273 | 3.700 | 35.075 | 1.00 | 31.92 | |
| ATOM | 5825 | O | HOH | | 390 | 78.045 | 14.948 | 37.552 | 1.00 | 33.97 | |
| ATOM | 5826 | O | HOH | | 391 | 55.108 | 7.963 | 28.281 | 1.00 | 33.24 | |
| ATOM | 5827 | O | HOH | | 392 | 55.440 | 67.256 | 38.091 | 1.00 | 38.52 | |
| ATOM | 5828 | O | HOH | | 393 | 81.522 | 46.295 | 67.736 | 1.00 | 38.88 | |
| ATOM | 5829 | O | HOH | | 394 | 56.563 | 38.917 | 24.510 | 1.00 | 37.34 | |
| ATOM | 5830 | O | HOH | | 395 | 56.748 | 55.497 | 72.257 | 1.00 | 28.73 | |
| ATOM | 5831 | O | HOH | | 396 | 76.315 | 45.726 | 48.521 | 1.00 | 37.14 | |
| ATOM | 5832 | O | HOH | | 397 | 63.257 | 39.171 | 71.757 | 1.00 | 35.49 | |

TABLE 1-continued

| ATOM | 5833 | O | HOH | 398 | 48.673 | 73.275 | 54.707 | 1.00 | 35.47 |
|---|---|---|---|---|---|---|---|---|---|
| ATOM | 5834 | O | HOH | 399 | 68.398 | 49.981 | 25.035 | 1.00 | 29.93 |
| ATOM | 5835 | O | HOH | 400 | 74.510 | 42.399 | 68.883 | 1.00 | 41.78 |
| ATOM | 5836 | O | HOH | 401 | 48.691 | 66.095 | 60.584 | 1.00 | 37.28 |
| ATOM | 5837 | O | HOH | 402 | 73.079 | 66.521 | 49.991 | 1.00 | 35.56 |
| ATOM | 5838 | O | HOH | 403 | 68.935 | 36.920 | 58.417 | 1.00 | 34.53 |
| ATOM | 5839 | O | HOH | 404 | 64.176 | 18.821 | 46.569 | 1.00 | 31.46 |
| ATOM | 5840 | O | HOH | 405 | 75.827 | 14.862 | 36.054 | 1.00 | 41.48 |
| ATOM | 5841 | O | HOH | 406 | 68.996 | 42.645 | 28.371 | 1.00 | 34.47 |
| ATOM | 5842 | O | HOH | 407 | 63.289 | 71.642 | 38.965 | 1.00 | 41.30 |
| ATOM | 5843 | O | HOH | 408 | 58.661 | 24.821 | 16.774 | 1.00 | 33.66 |
| ATOM | 5844 | O | HOH | 409 | 66.656 | 36.001 | 14.873 | 1.00 | 36.95 |
| ATOM | 5845 | O | HOH | 410 | 50.369 | 71.556 | 30.930 | 1.00 | 37.95 |
| ATOM | 5846 | O | HOH | 411 | 79.270 | 49.475 | 68.969 | 1.00 | 32.68 |
| ATOM | 5847 | O | HOH | 412 | 62.790 | 8.541 | 30.282 | 1.00 | 35.69 |
| ATOM | 5848 | O | HOH | 413 | 81.274 | 51.642 | 51.639 | 1.00 | 39.18 |
| ATOM | 5849 | O | HOH | 414 | 40.490 | 22.826 | 35.751 | 1.00 | 33.63 |
| ATOM | 5850 | O | HOH | 415 | 45.278 | 59.272 | 37.800 | 1.00 | 46.31 |
| ATOM | 5851 | O | HOH | 416 | 85.987 | 13.185 | 21.433 | 1.00 | 45.56 |
| ATOM | 5852 | O | HOH | 417 | 59.377 | 57.538 | 73.836 | 1.00 | 35.62 |
| ATOM | 5853 | O | HOH | 418 | 58.467 | 65.156 | 28.611 | 1.00 | 40.79 |
| ATOM | 5854 | O | HOH | 419 | 51.700 | 70.827 | 57.927 | 1.00 | 39.11 |
| ATOM | 5855 | O | HOH | 420 | 71.151 | 66.528 | 52.084 | 1.00 | 28.40 |
| ATOM | 5856 | O | HOH | 421 | 83.586 | 19.765 | 37.431 | 1.00 | 45.66 |
| ATOM | 5857 | O | HOH | 422 | 62.829 | 61.888 | 31.168 | 1.00 | 39.07 |
| ATOM | 5858 | O | HOH | 423 | 67.870 | 19.503 | 66.639 | 1.00 | 38.53 |
| ATOM | 5859 | O | HOH | 424 | 50.558 | 40.114 | 24.997 | 1.00 | 39.96 |
| ATOM | 5860 | O | HOH | 425 | 65.626 | 32.889 | 60.678 | 1.00 | 36.63 |
| ATOM | 5861 | O | HOH | 426 | 78.350 | 34.226 | 40.475 | 1.00 | 43.31 |
| ATOM | 5862 | O | HOH | 427 | 61.852 | 57.639 | 25.627 | 1.00 | 35.62 |
| ATOM | 5863 | O | HOH | 428 | 75.183 | 9.113 | 36.157 | 1.00 | 33.77 |
| ATOM | 5864 | O | HOH | 429 | 81.080 | 13.591 | 19.976 | 1.00 | 35.61 |
| ATOM | 5865 | O | HOH | 430 | 80.166 | 12.031 | 39.210 | 1.00 | 44.47 |
| ATOM | 5866 | O | HOH | 431 | 55.682 | 41.627 | 30.125 | 1.00 | 35.50 |
| ATOM | 5867 | O | HOH | 432 | 58.165 | 6.304 | 29.538 | 1.00 | 41.91 |
| ATOM | 5868 | O | HOH | 433 | 73.703 | 41.273 | 50.591 | 1.00 | 39.46 |
| ATOM | 5869 | O | HOH | 434 | 57.671 | 39.231 | 34.914 | 1.00 | 38.36 |
| ATOM | 5870 | O | HOH | 435 | 42.003 | 27.364 | 40.674 | 1.00 | 41.11 |
| ATOM | 5871 | O | HOH | 436 | 78.733 | 40.594 | 56.235 | 1.00 | 35.96 |
| ATOM | 5872 | O | HOH | 437 | 51.664 | 75.960 | 56.960 | 1.00 | 45.87 |
| ATOM | 5873 | O | HOH | 438 | 64.725 | 27.318 | 15.787 | 1.00 | 32.68 |
| ATOM | 5874 | O | HOH | 439 | 80.741 | 44.141 | 54.513 | 1.00 | 43.67 |
| ATOM | 5875 | O | HOH | 440 | 63.634 | 68.995 | 69.742 | 1.00 | 39.88 |
| ATOM | 5876 | O | HOH | 441 | 65.951 | 18.194 | 12.943 | 1.00 | 40.81 |
| ATOM | 5877 | O | HOH | 442 | 41.548 | 54.467 | 48.215 | 1.00 | 37.45 |
| ATOM | 5878 | O | HOH | 443 | 79.373 | 13.864 | 55.732 | 1.00 | 37.40 |
| ATOM | 5879 | O | HOH | 444 | 36.744 | 49.942 | 59.322 | 1.00 | 40.35 |
| ATOM | 5880 | O | HOH | 445 | 74.773 | 64.848 | 53.376 | 1.00 | 34.89 |
| ATOM | 5881 | O | HOH | 446 | 68.851 | 42.859 | 52.867 | 1.00 | 34.72 |
| ATOM | 5882 | O | HOH | 447 | 80.068 | 47.501 | 75.134 | 1.00 | 46.72 |
| ATOM | 5883 | O | HOH | 448 | 57.519 | 40.184 | 58.304 | 1.00 | 40.13 |
| ATOM | 5884 | O | HOH | 449 | 58.887 | 42.261 | 47.875 | 1.00 | 33.05 |
| ATOM | 5885 | O | HOH | 450 | 61.103 | 41.207 | 19.437 | 1.00 | 37.85 |
| ATOM | 5886 | O | HOH | 451 | 65.161 | 71.594 | 36.948 | 1.00 | 38.68 |
| ATOM | 5887 | O | HOH | 452 | 54.321 | 63.380 | 69.881 | 1.00 | 39.06 |
| ATOM | 5888 | O | HOH | 453 | 67.510 | 1.511 | 41.613 | 1.00 | 46.46 |
| ATOM | 5889 | O | HOH | 454 | 61.658 | 38.048 | 52.750 | 1.00 | 36.51 |
| ATOM | 5890 | O | HOH | 455 | 68.915 | 2.897 | 33.229 | 1.00 | 45.17 |
| ATOM | 5891 | O | HOH | 456 | 53.559 | 56.777 | 28.753 | 1.00 | 45.82 |
| ATOM | 5892 | O | HOH | 457 | 77.672 | 52.145 | 48.833 | 1.00 | 42.57 |
| ATOM | 5893 | O | HOH | 458 | 60.689 | 60.353 | 25.313 | 1.00 | 47.87 |
| ATOM | 5894 | O | HOH | 459 | 42.683 | 46.135 | 63.662 | 1.00 | 46.19 |
| ATOM | 5895 | O | HOH | 460 | 55.482 | 23.886 | 51.309 | 1.00 | 40.01 |
| ATOM | 5896 | O | HOH | 461 | 78.986 | 29.549 | 40.993 | 1.00 | 44.58 |
| ATOM | 5897 | O | HOH | 462 | 62.690 | 44.354 | 30.696 | 1.00 | 37.40 |
| ATOM | 5898 | O | HOH | 463 | 75.061 | 38.781 | 29.137 | 1.00 | 32.56 |
| ATOM | 5899 | O | HOH | 464 | 76.832 | 30.118 | 47.179 | 1.00 | 46.44 |
| ATOM | 5900 | O | HOH | 465 | 57.535 | 35.324 | 38.962 | 1.00 | 44.49 |
| ATOM | 5901 | O | HOH | 466 | 44.037 | 53.130 | 43.517 | 1.00 | 42.37 |
| ATOM | 5902 | O | HOH | 467 | 54.621 | 10.002 | 26.204 | 1.00 | 38.80 |
| ATOM | 5903 | O | HOH | 468 | 71.161 | 6.743 | 40.383 | 1.00 | 38.21 |
| ATOM | 5904 | O | HOH | 469 | 77.359 | 32.899 | 14.744 | 1.00 | 39.32 |
| ATOM | 5905 | O | HOH | 470 | 49.766 | 5.511 | 51.108 | 1.00 | 38.93 |
| ATOM | 5906 | O | HOH | 471 | 76.569 | 27.256 | 48.641 | 1.00 | 47.06 |
| ATOM | 5907 | O | HOH | 472 | 38.160 | 68.860 | 57.427 | 1.00 | 45.03 |
| ATOM | 5908 | O | HOH | 473 | 77.858 | 71.395 | 66.714 | 1.00 | 41.36 |
| ATOM | 5909 | O | HOH | 474 | 44.098 | 45.702 | 43.292 | 1.00 | 39.55 |
| ATOM | 5910 | O | HOH | 475 | 78.199 | 52.110 | 45.473 | 1.00 | 39.95 |
| ATOM | 5911 | O | HOH | 476 | 48.226 | 2.443 | 35.328 | 1.00 | 38.56 |

TABLE 1-continued

| ATOM | 5912 | O | HOH | 477 | 62.030 | 49.807 | 29.564 | 1.00 | 42.74 |
|---|---|---|---|---|---|---|---|---|---|
| ATOM | 5913 | O | HOH | 478 | 58.753 | 20.056 | 58.924 | 1.00 | 40.93 |
| ATOM | 5914 | O | HOH | 479 | 71.194 | 14.486 | 63.804 | 1.00 | 42.59 |
| ATOM | 5916 | O | HOH | 481 | 66.412 | 2.543 | 29.264 | 1.00 | 42.49 |
| ATOM | 5917 | O | HOH | 482 | 76.906 | 12.204 | 43.119 | 1.00 | 37.07 |
| ATOM | 5918 | O | HOH | 483 | 38.762 | 22.347 | 29.394 | 1.00 | 44.90 |
| ATOM | 5919 | O | HOH | 484 | 73.875 | 6.246 | 38.334 | 1.00 | 41.96 |
| ATOM | 5920 | O | HOH | 485 | 72.806 | 63.185 | 34.291 | 1.00 | 36.43 |
| ATOM | 5921 | O | HOH | 486 | 54.217 | 52.040 | 71.835 | 1.00 | 38.87 |
| ATOM | 5922 | O | HOH | 487 | 54.320 | 21.537 | 19.772 | 1.00 | 39.67 |
| ATOM | 5923 | O | HOH | 488 | 63.692 | 22.057 | 14.004 | 1.00 | 42.09 |
| ATOM | 5924 | O | HOH | 489 | 70.347 | 41.729 | 31.565 | 1.00 | 45.05 |
| ATOM | 5925 | O | HOH | 490 | 71.373 | 37.710 | 64.729 | 1.00 | 43.39 |
| ATOM | 5926 | O | HOH | 491 | 78.748 | 61.365 | 75.320 | 1.00 | 47.25 |
| ATOM | 5927 | O | HOH | 492 | 61.762 | 20.981 | 57.359 | 1.00 | 46.08 |
| ATOM | 5928 | O | HOH | 493 | 47.619 | 52.318 | 34.533 | 1.00 | 41.60 |
| ATOM | 5929 | O | HOH | 494 | 83.816 | 59.306 | 71.918 | 1.00 | 42.77 |
| ATOM | 5930 | O | HOH | 495 | 85.187 | 14.338 | 16.925 | 1.00 | 42.09 |
| ATOM | 5931 | O | HOH | 496 | 42.784 | 48.557 | 45.621 | 1.00 | 40.70 |
| ATOM | 5932 | O | HOH | 497 | 51.709 | 36.646 | 63.299 | 1.00 | 33.30 |
| ATOM | 5933 | O | HOH | 498 | 49.605 | 27.712 | 16.622 | 1.00 | 40.75 |
| ATOM | 5934 | O | HOH | 499 | 84.431 | 37.642 | 28.179 | 1.00 | 31.21 |
| ATOM | 5935 | O | HOH | 500 | 58.262 | 40.034 | 67.330 | 1.00 | 40.85 |
| ATOM | 5936 | O | HOH | 501 | 62.807 | 41.249 | 15.518 | 1.00 | 44.78 |
| ATOM | 5937 | O | HOH | 502 | 38.992 | 49.328 | 53.016 | 1.00 | 40.00 |
| ATOM | 5938 | O | HOH | 503 | 59.651 | 45.161 | 46.822 | 1.00 | 44.76 |
| ATOM | 5939 | O | HOH | 504 | 60.008 | 76.322 | 44.324 | 1.00 | 47.51 |
| ATOM | 5940 | O | HOH | 505 | 74.216 | 41.166 | 13.594 | 1.00 | 46.75 |
| ATOM | 5941 | O | HOH | 506 | 50.037 | 63.427 | 63.232 | 1.00 | 44.82 |
| END | | | | | | | | | |

TABLE 2

```
REMARK  3
REMARK  3  REFINEMENT.
REMARK  3     PROGRAM     : REFMAC 5.1.25
REMARK  3     AUTHORS     : MURSHUDOV, VAGAIN, DODSON
REMARK  3
REMARK  3   REFINEMENT TARGET : MAXIMUM LIKELIHOOD
REMARK  3
REMARK  3  DATA USED IN REFINEMENT.
REMARK  3     RESOLUTION RANGE HIGH      (ANGSTROMS) :    2.23
REMARK  3     RESOLUTION RANGE LOW       (ANGSTROMS) :   70.71
REMARK  3     DATA CUTOFF                (SIGMA(F))  : NONE
REMARK  3     COMPLETENESS FOR RANGE          (%)    :   98.27
REMARK  3     NUMBER OF REFLECTIONS                  :   40941
REMARK  3
REMARK  3  FIT TO DATA USED IN REFINEMENT.
REMARK  3     CROSS-VALIDATION METHOD           : THROUGHOUT
REMARK  3     FREE R VALUE TEST SET SELECTION   : RANDOM
REMARK  3     R VALUE     (WORKING + TEST SET)  : 0.30246
REMARK  3     R VALUE            (WORKING SET)  : 0.30142
REMARK  3     FREE R VALUE                      : 0.32189
REMARK  3     FREE R VALUE TEST SET SIZE   (%)  : 5.1
REMARK  3     FREE R VALUE TEST SET COUNT       : 2179
REMARK  3
REMARK  3  FIT IN THE HIGHEST RESOLUTION BIN.
REMARK  3     TOTAL NUMBER OF BINS USED          :      20
REMARK  3     BIN RESOLUTION RANGE HIGH          :    2.230
REMARK  3     BIN RESOLUTION RANGE LOW           :    2.288
REMARK  3     REFLECTION IN BIN    (WORKING SET) :    3001
REMARK  3     BIN R VALUE          (WORKING SET) :    0.475
REMARK  3     BIN FREE R VALUE SET COUNT         :     149
REMARK  3     BIN FREE R VALUE                   :   0.486
REMARK  3
REMARK  3  NUMBER OF NON-HYDROGEN ATOMS USED IN REFINEMENT.
REMARK  3     ALL ATOMS         :    5343
REMARK  3
REMARK  3  B VALUES.
REMARK  3     FROM WILSON POLT          (A**2) : NULL
REMARK  3     MEAN B VALUE       (OVERALL, A**2) : 47.019
REMARK  3     OVERALL ANISOTROPIC B VALUE.
REMARK  3      B11 (A**2) :     -4.03
REMARK  3      B22 (A**2) :     -2.48
REMARK  3      B33 (A**2) :      6.51
REMARK  3      B12 (A**2) :      0.00
```

TABLE 2-continued

```
REMARK  3     B13 (A**2):         0.00
REMARK  3     B23 (A**2):         0.00
REMARK  3
REMARK  3    ESTIMATED OVERALL COORDINATE ERROR.
REMARK  3     ESU BASED ON R VALUE                              (A):    0.359
REMARK  3     ESU BASED ON FREE R VALUE                         (A):    0.265
REMARK  3     ESU BASED ON MAXIMUM LIKELIHOOD                   (A):    0.218
REMARK  3     ESU FOR B VALUES BASED ON MAXIMUM LIKELIHOOD   (A**2):    9.431
REMARK  3
REMARK  3    CORRELATION COEFFICIENTS.
REMARK  3     CORRELATION COEFFICIENT FO-FC           :  0.931
REMARK  3     CORRELATION COEFFICIENT FO-FC FREE      :  0.920
REMARK  3
REMARK  3    RMS DEVIATIONS FROM IDEAL VALUES                COUNT     RMS    WEIGHT
REMARK  3     BOND LENGTHS REFINED ATOMS         (A):        5389;   0.006;    0.021
REMARK  3     BOND LENGTHS OTHERS                (A):        4782;   0.002;    0.020
REMARK  3     BOND ANGLES REFINED ATOMS     (DEGREES):       7301;   1.037;    1.951
REMARK  3     BOND ANGLES OTHERS            (DEGREES):      11132;   0.988;    3.000
REMARK  3     TORSION ANGLES, PERIOD 1      (DEGREES):        642;   2.239;    5.000
REMARK  3     CHIRAL-CENTER RESTRAINTS         (A**3):        825;   0.065;    0.200
REMARK  3     GENERAL PLANES REFINED ATOMS       (A):        5946;   0.006;    0.020
REMARK  3     GENERAL PLANES OTHERS              (A):        1066;   0.003;    0.020
REMARK  3     NON-BONDED CONTACTS REFINED ATOMS  (A):        1349;   0.175;    0.200
REMARK  3     NON-BONDED CONTACTS OTHERS         (A):        5413;   0.194;    0.200
REMARK  3     NON-BONDED TORSION OTHERS          (A):        3010;   0.094;    0.200
REMARK  3     H-BOND (X...Y) REFINED ATOMS       (A):         131;   0.196;    0.200
REMARK  3     POTENTIAL METAL-ION REFINED ATOMS  (A):           9;   0.240;    0.200
REMARK  3     SYMMETRY VDW REFINED ATOMS         (A):          10;   0.130;    0.200
REMARK  3     SYMMETRY VDW OTHERS                (A):          36;   0.243;    0.200
REMARK  3     SYMMETRY H-BOND REFINED ATOMS      (A):           3;   0.112;    0.200
REMARK  3
REMARK  3    ISOTROPIC THERMAL FACTOR RESTRAINTS.            COUNT     RMS    WEIGHT
REMARK  3     MAIN-CHAIN BOND REFINED ATOMS    (A**2):       3228;   0.391;    1.500
REMARK  3     MAIN-CHAIN ANGLE REFINED ATOMS   (A**2):       5232;   0.751;    2.000
REMARK  3     SIDE-CHAIN BOND REFINED ATOMS    (A**2):       2161;   0.989;    3.000
REMARK  3     SIDE-CHAIN ANGLE REFINED ATOMS   (A**2):       2069;   1.689;    4.500
REMARK  3
REMARK  3    NCS RESTRAINTS STATISTICS
REMARK  3     NUMBER OF NCS GROUPS   : NULL
REMARK  3
REMARK  3
REMARK  3    TLS DETAILS
REMARK  3     NUMBER OF TLS GROUPS    : NULL
REMARK  3
REMARK  3
REMARK  3    BULK SOLVENT MODELLING.
REMARK  3     METHOD USED : BABINET MODEL WITH MASK
REMARK  3     PARAMETERS FOR MASK CALCULATION
REMARK  3     VDW PROBE RADIUS       :  1.40
REMARK  3     ION PROBE RADIUS       :  0.80
REMARK  3     SHRINKAGE RADIUS       :  0.80
REMARK  3
REMARK  3    OTHER REFINEMENT REMARKS:
REMARK  3    HYDROGENS HAVE BEEN ADDED IN THE RIDING POSITIONS
REMARK  3
CISPEP   1 GLN A  463    PRO A  464           0.00
CISPEP   2 GLN C  463    PRO C  464           0.00
CRYST1   89.282   93.946  105.658  90.00  90.00  90.00 P 21 21 21
SCALE1      0.011200  0.000000  0.000000        0.00000
SCALE2      0.000000  0.010644  0.000000        0.00000
SCALE3      0.000000  0.000000  0.009464        0.00000
ATOM     1   N    GLU  A   163     -16.830  18.878   8.071  1.00  61.06  N
ATOM     3   CA   GLU  A   163     -18.255  19.006   7.652  1.00  60.99  C
ATOM     5   CB   GLU  A   163     -18.346  19.684   6.276  1.00  61.20  C
ATOM     8   CG   GLU  A   163     -17.798  18.870   5.112  1.00  61.71  C
ATOM    11   CD   GLU  A   163     -18.050  19.537   3.773  1.00  62.25  C
ATOM    12   OE1  GLU  A   163     -19.232  19.766   3.437  1.00  62.47  O
ATOM    13   OE2  GLU  A   163     -17.069  19.832   3.057  1.00  62.55  O
ATOM    14   C    GLU  A   163     -18.957  17.641   7.655  1.00  60.65  C
ATOM    15   O    GLU  A   163     -18.363  16.631   8.035  1.00  60.63  O
ATOM    18   N    ASP  A   164     -20.222  17.630   7.237  1.00  60.25  N
ATOM    20   CA   ASP  A   164     -21.047  16.416   7.217  1.00  59.90  C
ATOM    22   CB   ASP  A   164     -22.476  16.752   6.765  1.00  60.00  C
ATOM    25   CG   ASP  A   164     -23.313  17.362   7.872  1.00  60.45  C
ATOM    26   OD1  ASP  A   164     -22.964  18.461   8.350  1.00  60.92  O
ATOM    27   OD2  ASP  A   164     -24.343  16.814   8.322  1.00  60.92  O
ATOM    28   C    ASP  A   164     -20.507  15.305   6.321  1.00  59.36  C
ATOM    29   O    ASP  A   164     -20.345  14.170   6.766  1.00  59.22  O
ATOM    30   N    HIS  A   165     -20.246  15.640   5.059  1.00  58.76  N
```

TABLE 2-continued

| | | | | | | | | | | | |
|---|---|---|---|---|---|---|---|---|---|---|---|
| ATOM | 32 | CA | HIS | A | 165 | −19.775 | 14.666 | 4.066 | 1.00 | 58.24 | C |
| ATOM | 34 | CB | HIS | A | 165 | −19.638 | 15.326 | 2.690 | 1.00 | 58.21 | C |
| ATOM | 37 | CG | HIS | A | 165 | −20.943 | 15.736 | 2.082 | 1.00 | 58.07 | C |
| ATOM | 38 | ND1 | HIS | A | 165 | −21.926 | 14.829 | 1.749 | 1.00 | 58.08 | N |
| ATOM | 40 | CE1 | HIS | A | 165 | −22.956 | 15.472 | 1.230 | 1.00 | 57.92 | C |
| ATOM | 42 | NE2 | HIS | A | 165 | −22.678 | 16.763 | 1.215 | 1.00 | 57.88 | N |
| ATOM | 44 | CD2 | HIS | A | 165 | −21.424 | 16.955 | 1.741 | 1.00 | 57.93 | C |
| ATOM | 46 | C | HIS | A | 165 | −18.454 | 13.990 | 4.438 | 1.00 | 57.75 | C |
| ATOM | 47 | O | HIS | A | 165 | −18.251 | 12.818 | 4.128 | 1.00 | 57.64 | O |
| ATOM | 48 | N | LEU | A | 166 | −17.563 | 14.732 | 5.090 | 1.00 | 57.24 | N |
| ATOM | 50 | CA | LEU | A | 166 | −16.269 | 14.199 | 5.509 | 1.00 | 56.81 | C |
| ATOM | 52 | CB | LEU | A | 166 | −15.365 | 15.328 | 6.018 | 1.00 | 56.67 | C |
| ATOM | 55 | CG | LEU | A | 166 | −13.925 | 14.980 | 6.412 | 1.00 | 56.20 | C |
| ATOM | 57 | CD1 | LEU | A | 166 | −13.205 | 14.182 | 5.322 | 1.00 | 55.63 | C |
| ATOM | 61 | CD2 | LEU | A | 166 | −13.161 | 16.257 | 6.741 | 1.00 | 55.85 | C |
| ATOM | 65 | C | LEU | A | 166 | −16.422 | 13.123 | 6.587 | 1.00 | 56.68 | C |
| ATOM | 66 | O | LEU | A | 166 | −15.760 | 12.088 | 6.525 | 1.00 | 56.65 | O |
| ATOM | 67 | N | ALA | A | 167 | −17.294 | 13.366 | 7.565 | 1.00 | 56.37 | N |
| ATOM | 69 | CA | ALA | A | 167 | −17.524 | 12.406 | 8.648 | 1.00 | 56.21 | C |
| ATOM | 71 | CB | ALA | A | 167 | −18.390 | 13.028 | 9.740 | 1.00 | 56.19 | C |
| ATOM | 75 | C | ALA | A | 167 | −18.163 | 11.113 | 8.132 | 1.00 | 55.96 | C |
| ATOM | 76 | O | ALA | A | 167 | −17.833 | 10.021 | 8.596 | 1.00 | 55.86 | O |
| ATOM | 77 | N | LYS | A | 168 | −19.070 | 11.248 | 7.168 | 1.00 | 55.77 | N |
| ATOM | 79 | CA | LYS | A | 168 | −19.753 | 10.104 | 6.562 | 1.00 | 55.66 | C |
| ATOM | 81 | CB | LYS | A | 168 | −20.855 | 10.588 | 5.608 | 1.00 | 55.77 | C |
| ATOM | 84 | CG | LYS | A | 168 | −21.823 | 9.500 | 5.139 | 1.00 | 56.58 | C |
| ATOM | 87 | CD | LYS | A | 168 | −22.499 | 9.881 | 3.824 | 1.00 | 57.56 | C |
| ATOM | 90 | CE | LYS | A | 168 | −23.490 | 8.815 | 3.372 | 1.00 | 58.16 | C |
| ATOM | 93 | NZ | LYS | A | 168 | −23.910 | 9.008 | 1.954 | 1.00 | 58.62 | N |
| ATOM | 97 | C | LYS | A | 168 | −18.760 | 9.224 | 5.806 | 1.00 | 55.17 | C |
| ATOM | 98 | O | LYS | A | 168 | −18.857 | 7.996 | 5.832 | 1.00 | 55.22 | O |
| ATOM | 99 | N | GLU | A | 169 | −17.806 | 9.864 | 5.138 | 1.00 | 54.61 | N |
| ATOM | 101 | CA | GLU | A | 169 | −16.789 | 9.160 | 4.366 | 1.00 | 54.17 | C |
| ATOM | 103 | CB | GLU | A | 169 | −16.037 | 10.147 | 3.468 | 1.00 | 54.13 | C |
| ATOM | 106 | CG | GLU | A | 169 | −15.343 | 9.506 | 2.280 | 1.00 | 54.34 | C |
| ATOM | 109 | CD | GLU | A | 169 | −16.319 | 8.876 | 1.310 | 1.00 | 54.42 | C |
| ATOM | 110 | OE1 | GLU | A | 169 | −16.249 | 7.645 | 1.110 | 1.00 | 54.73 | O |
| ATOM | 111 | OE2 | GLU | A | 169 | −17.160 | 9.614 | 0.760 | 1.00 | 54.56 | O |
| ATOM | 112 | C | GLU | A | 169 | −15.813 | 8.428 | 5.284 | 1.00 | 53.74 | C |
| ATOM | 113 | O | GLU | A | 169 | −15.351 | 7.337 | 4.956 | 1.00 | 53.68 | O |
| ATOM | 114 | N | LEU | A | 170 | −15.530 | 9.020 | 6.445 | 1.00 | 53.31 | N |
| ATOM | 116 | CA | LEU | A | 170 | −14.601 | 8.436 | 7.418 | 1.00 | 52.98 | C |
| ATOM | 118 | CB | LEU | A | 170 | −14.041 | 9.514 | 8.361 | 1.00 | 52.98 | C |
| ATOM | 121 | CG | LEU | A | 170 | −13.025 | 10.511 | 7.777 | 1.00 | 53.00 | C |
| ATOM | 123 | CD1 | LEU | A | 170 | −12.474 | 11.390 | 8.888 | 1.00 | 53.16 | C |
| ATOM | 127 | CD2 | LEU | A | 170 | −11.881 | 9.823 | 7.028 | 1.00 | 52.94 | C |
| ATOM | 131 | C | LEU | A | 170 | −15.206 | 7.284 | 8.229 | 1.00 | 52.59 | C |
| ATOM | 132 | O | LEU | A | 170 | −14.528 | 6.709 | 9.082 | 1.00 | 52.45 | O |
| ATOM | 133 | N | GLU | A | 171 | −16.470 | 6.951 | 7.970 | 1.00 | 52.24 | N |
| ATOM | 135 | CA | GLU | A | 171 | −17.118 | 5.811 | 8.617 | 1.00 | 52.00 | C |
| ATOM | 137 | CB | GLU | A | 171 | −18.628 | 5.806 | 8.352 | 1.00 | 52.14 | C |
| ATOM | 140 | CG | GLU | A | 171 | −19.402 | 6.888 | 9.090 | 1.00 | 52.73 | C |
| ATOM | 143 | CD | GLU | A | 171 | −20.908 | 6.770 | 8.909 | 1.00 | 53.61 | C |
| ATOM | 144 | OE1 | GLU | A | 171 | −21.374 | 5.766 | 8.322 | 1.00 | 54.18 | O |
| ATOM | 145 | OE2 | GLU | A | 171 | −21.631 | 7.688 | 9.356 | 1.00 | 54.23 | O |
| ATOM | 146 | C | GLU | A | 171 | −16.509 | 4.500 | 8.109 | 1.00 | 51.47 | C |
| ATOM | 147 | O | GLU | A | 171 | −16.590 | 3.474 | 8.785 | 1.00 | 51.56 | O |
| ATOM | 148 | N | ASP | A | 172 | −15.919 | 4.545 | 6.914 | 1.00 | 50.79 | N |
| ATOM | 150 | CA | ASP | A | 172 | −15.257 | 3.389 | 6.305 | 1.00 | 50.28 | C |
| ATOM | 152 | CB | ASP | A | 172 | −15.615 | 3.294 | 4.812 | 1.00 | 50.35 | C |
| ATOM | 155 | CG | ASP | A | 172 | −17.114 | 3.275 | 4.559 | 1.00 | 50.67 | C |
| ATOM | 156 | OD1 | ASP | A | 172 | −17.879 | 2.868 | 5.459 | 1.00 | 51.29 | O |
| ATOM | 157 | OD2 | ASP | A | 172 | −17.618 | 3.644 | 3.478 | 1.00 | 51.52 | O |
| ATOM | 158 | C | ASP | A | 172 | −13.731 | 3.478 | 6.453 | 1.00 | 49.61 | C |
| ATOM | 159 | O | ASP | A | 172 | −12.996 | 3.014 | 5.584 | 1.00 | 49.61 | O |
| ATOM | 160 | N | LEU | A | 173 | −13.263 | 4.067 | 7.554 | 1.00 | 48.78 | N |
| ATOM | 162 | CA | LEU | A | 173 | −11.828 | 4.225 | 7.818 | 1.00 | 48.08 | C |
| ATOM | 164 | CB | LEU | A | 173 | −11.611 | 5.049 | 9.096 | 1.00 | 48.01 | C |
| ATOM | 167 | CG | LEU | A | 173 | −10.177 | 5.283 | 9.594 | 1.00 | 47.75 | C |
| ATOM | 169 | CD1 | LEU | A | 173 | −9.436 | 6.256 | 8.704 | 1.00 | 47.36 | C |
| ATOM | 173 | CD2 | LEU | A | 173 | −10.178 | 5.789 | 11.038 | 1.00 | 48.04 | C |
| ATOM | 177 | C | LEU | A | 173 | −11.122 | 2.877 | 7.944 | 1.00 | 47.54 | C |
| ATOM | 178 | O | LEU | A | 173 | −9.994 | 2.723 | 7.478 | 1.00 | 47.30 | O |
| ATOM | 179 | N | ASN | A | 174 | −11.796 | 1.913 | 8.571 | 1.00 | 46.96 | N |
| ATOM | 181 | CA | ASN | A | 174 | −11.247 | 0.573 | 8.785 | 1.00 | 46.59 | C |
| ATOM | 183 | CB | ASN | A | 174 | −11.740 | 0.001 | 10.128 | 1.00 | 46.51 | C |
| ATOM | 186 | CG | ASN | A | 174 | −11.577 | 0.976 | 11.289 | 1.00 | 46.35 | C |
| ATOM | 187 | OD1 | ASN | A | 174 | −10.776 | 1.907 | 11.235 | 1.00 | 45.84 | O |
| ATOM | 188 | ND2 | ASN | A | 174 | −12.342 | 0.758 | 12.347 | 1.00 | 47.02 | N |

TABLE 2-continued

| | | | | | | | | | | | |
|---|---|---|---|---|---|---|---|---|---|---|---|
| ATOM | 191 | C | ASN | A | 174 | −11.597 | −0.413 | 7.667 | 1.00 | 46.30 | C |
| ATOM | 192 | O | ASN | A | 174 | −11.357 | −1.612 | 7.803 | 1.00 | 46.23 | O |
| ATOM | 193 | N | LYS | A | 175 | −12.147 | 0.088 | 6.564 | 1.00 | 46.16 | N |
| ATOM | 195 | CA | LYS | A | 175 | −12.570 | −0.761 | 5.452 | 1.00 | 46.17 | C |
| ATOM | 197 | CB | LYS | A | 175 | −14.060 | −0.546 | 5.164 | 1.00 | 46.40 | C |
| ATOM | 200 | CG | LYS | A | 175 | −14.991 | −0.929 | 6.321 | 1.00 | 47.27 | C |
| ATOM | 203 | CD | LYS | A | 175 | −15.999 | −2.014 | 5.931 | 1.00 | 48.32 | C |
| ATOM | 206 | CE | LYS | A | 175 | −17.223 | −1.996 | 6.840 | 1.00 | 48.87 | C |
| ATOM | 209 | NZ | LYS | A | 175 | −18.105 | −0.821 | 6.579 | 1.00 | 49.47 | N |
| ATOM | 213 | C | LYS | A | 175 | −11.776 | −0.526 | 4.168 | 1.00 | 45.71 | C |
| ATOM | 214 | O | LYS | A | 175 | −11.256 | 0.562 | 3.920 | 1.00 | 45.74 | O |
| ATOM | 215 | N | TRP | A | 176 | −11.716 | −1.571 | 3.352 | 1.00 | 45.26 | N |
| ATOM | 217 | CA | TRP | A | 176 | −11.020 | −1.551 | 2.070 | 1.00 | 44.84 | C |
| ATOM | 219 | CB | TRP | A | 176 | −10.932 | −2.981 | 1.520 | 1.00 | 44.58 | C |
| ATOM | 222 | CG | TRP | A | 176 | −9.822 | −3.210 | 0.553 | 1.00 | 43.13 | C |
| ATOM | 223 | CD1 | TRP | A | 176 | −9.936 | −3.464 | −0.786 | 1.00 | 41.96 | C |
| ATOM | 225 | NE1 | TRP | A | 176 | −8.691 | −3.630 | −1.342 | 1.00 | 41.20 | N |
| ATOM | 227 | CE2 | TRP | A | 176 | −7.743 | −3.491 | −0.363 | 1.00 | 40.36 | C |
| ATOM | 228 | CD2 | TRP | A | 176 | −8.423 | −3.227 | 0.846 | 1.00 | 41.11 | C |
| ATOM | 229 | CE3 | TRP | A | 176 | −7.667 | −3.037 | 2.012 | 1.00 | 39.95 | C |
| ATOM | 231 | CZ3 | TRP | A | 176 | −6.285 | −3.118 | 1.936 | 1.00 | 39.16 | C |
| ATOM | 233 | CH2 | TRP | A | 176 | −5.641 | −3.382 | 0.718 | 1.00 | 39.60 | C |
| ATOM | 235 | CZ2 | TRP | A | 176 | −6.350 | −3.569 | −0.440 | 1.00 | 39.60 | C |
| ATOM | 237 | C | TRP | A | 176 | −11.731 | −0.659 | 1.054 | 1.00 | 44.97 | C |
| ATOM | 238 | O | TRP | A | 176 | −11.098 | −0.117 | 0.152 | 1.00 | 45.06 | O |
| ATOM | 239 | N | GLY | A | 177 | −13.046 | −0.507 | 1.213 | 1.00 | 45.10 | N |
| ATOM | 241 | CA | GLY | A | 177 | −13.861 | 0.285 | 0.308 | 1.00 | 45.17 | C |
| ATOM | 244 | C | GLY | A | 177 | −13.919 | 1.781 | 0.567 | 1.00 | 45.35 | C |
| ATOM | 245 | O | GLY | A | 177 | −14.782 | 2.459 | 0.008 | 1.00 | 45.53 | O |
| ATOM | 246 | N | LEU | A | 178 | −13.024 | 2.305 | 1.405 | 1.00 | 45.48 | N |
| ATOM | 248 | CA | LEU | A | 178 | −12.985 | 3.742 | 1.671 | 1.00 | 45.45 | C |
| ATOM | 250 | CB | LEU | A | 178 | −11.938 | 4.088 | 2.730 | 1.00 | 45.37 | C |
| ATOM | 253 | CG | LEU | A | 178 | −11.779 | 5.590 | 3.025 | 1.00 | 45.63 | C |
| ATOM | 255 | CD1 | LEU | A | 178 | −11.974 | 5.894 | 4.501 | 1.00 | 45.83 | C |
| ATOM | 259 | CD2 | LEU | A | 178 | −10.426 | 6.102 | 2.557 | 1.00 | 45.46 | C |
| ATOM | 263 | C | LEU | A | 178 | −12.630 | 4.476 | 0.393 | 1.00 | 45.36 | C |
| ATOM | 264 | O | LEU | A | 178 | −11.776 | 4.024 | −0.366 | 1.00 | 45.36 | O |
| ATOM | 265 | N | ASN | A | 179 | −13.288 | 5.608 | 0.165 | 1.00 | 45.38 | N |
| ATOM | 267 | CA | ASN | A | 179 | −13.020 | 6.433 | −1.003 | 1.00 | 45.35 | C |
| ATOM | 269 | CB | ASN | A | 179 | −14.330 | 6.916 | −1.644 | 1.00 | 45.32 | C |
| ATOM | 272 | CG | ASN | A | 179 | −14.130 | 7.449 | −3.059 | 1.00 | 45.20 | C |
| ATOM | 273 | OD1 | ASN | A | 179 | −13.198 | 8.203 | −3.318 | 1.00 | 44.35 | O |
| ATOM | 274 | ND2 | ASN | A | 179 | −15.007 | 7.058 | −3.974 | 1.00 | 44.88 | N |
| ATOM | 277 | C | ASN | A | 179 | −12.137 | 7.607 | −0.595 | 1.00 | 45.28 | C |
| ATOM | 278 | O | ASN | A | 179 | −12.626 | 8.613 | −0.077 | 1.00 | 45.29 | O |
| ATOM | 279 | N | ILE | A | 180 | −10.832 | 7.463 | −0.827 | 1.00 | 45.17 | N |
| ATOM | 281 | CA | ILE | A | 180 | −9.857 | 8.501 | −0.490 | 1.00 | 45.07 | C |
| ATOM | 283 | CB | ILE | A | 180 | −8.412 | 7.934 | −0.553 | 1.00 | 45.00 | C |
| ATOM | 285 | CG1 | ILE | A | 180 | −7.448 | 8.802 | 0.260 | 1.00 | 45.02 | C |
| ATOM | 288 | CD1 | ILE | A | 180 | −7.627 | 8.691 | 1.764 | 1.00 | 45.45 | C |
| ATOM | 292 | CG2 | ILE | A | 180 | −7.939 | 7.815 | −1.995 | 1.00 | 44.91 | C |
| ATOM | 296 | C | ILE | A | 180 | −9.994 | 9.745 | −1.372 | 1.00 | 45.14 | C |
| ATOM | 297 | O | ILE | A | 180 | −9.584 | 10.834 | −0.972 | 1.00 | 45.00 | O |
| ATOM | 298 | N | PHE | A | 181 | −10.546 | 9.582 | −2.573 | 1.00 | 45.26 | N |
| ATOM | 300 | CA | PHE | A | 181 | −10.781 | 10.717 | −3.466 | 1.00 | 45.47 | C |
| ATOM | 302 | CB | PHE | A | 181 | −11.254 | 10.251 | −4.852 | 1.00 | 45.24 | C |
| ATOM | 305 | CG | PHE | A | 181 | −10.253 | 9.408 | −5.579 | 1.00 | 44.43 | C |
| ATOM | 306 | CD1 | PHE | A | 181 | −9.220 | 9.998 | −6.290 | 1.00 | 43.83 | C |
| ATOM | 308 | CE1 | PHE | A | 181 | −8.284 | 9.224 | −6.955 | 1.00 | 43.26 | C |
| ATOM | 310 | CZ | PHE | A | 181 | −8.374 | 7.843 | −6.917 | 1.00 | 43.11 | C |
| ATOM | 312 | CE2 | PHE | A | 181 | −9.398 | 7.239 | −6.211 | 1.00 | 43.29 | C |
| ATOM | 314 | CD2 | PHE | A | 181 | −10.332 | 8.022 | −5.545 | 1.00 | 44.02 | C |
| ATOM | 316 | C | PHE | A | 181 | −11.817 | 11.653 | −2.836 | 1.00 | 45.97 | C |
| ATOM | 317 | O | PHE | A | 181 | −11.716 | 12.873 | −2.956 | 1.00 | 45.85 | O |
| ATOM | 318 | N | ASN | A | 182 | −12.799 | 11.064 | −2.155 | 1.00 | 46.63 | N |
| ATOM | 320 | CA | ASN | A | 182 | −13.851 | 11.818 | −1.480 | 1.00 | 47.12 | C |
| ATOM | 322 | CB | ASN | A | 182 | −15.042 | 10.913 | −1.145 | 1.00 | 47.07 | C |
| ATOM | 325 | CG | ASN | A | 182 | −15.846 | 10.520 | −2.375 | 1.00 | 46.91 | C |
| ATOM | 326 | OD1 | ASN | A | 182 | −15.546 | 10.938 | −3.495 | 1.00 | 46.83 | O |
| ATOM | 327 | ND2 | ASN | A | 182 | −16.876 | 9.706 | −2.168 | 1.00 | 46.32 | N |
| ATOM | 330 | C | ASN | A | 182 | −13.357 | 12.525 | −0.217 | 1.00 | 47.65 | C |
| ATOM | 331 | O | ASN | A | 182 | −13.824 | 13.619 | 0.085 | 1.00 | 47.75 | O |
| ATOM | 332 | N | VAL | A | 183 | −12.422 | 11.917 | 0.516 | 1.00 | 48.31 | N |
| ATOM | 334 | CA | VAL | A | 183 | −11.870 | 12.569 | 1.710 | 1.00 | 48.94 | C |
| ATOM | 336 | CB | VAL | A | 183 | −11.077 | 11.600 | 2.656 | 1.00 | 48.99 | C |
| ATOM | 338 | CG1 | VAL | A | 183 | −11.827 | 10.285 | 2.861 | 1.00 | 49.24 | C |
| ATOM | 342 | CG2 | VAL | A | 183 | −9.668 | 11.328 | 2.159 | 1.00 | 49.36 | C |
| ATOM | 346 | C | VAL | A | 183 | −11.003 | 13.755 | 1.274 | 1.00 | 49.39 | C |
| ATOM | 347 | O | VAL | A | 183 | −10.885 | 14.742 | 1.996 | 1.00 | 49.34 | O |

TABLE 2-continued

| | | | | | | | | | | | |
|---|---|---|---|---|---|---|---|---|---|---|---|
| ATOM | 348 | N | ALA | A | 184 | −10.419 | 13.656 | 0.080 | 1.00 | 50.01 | N |
| ATOM | 350 | CA | ALA | A | 184 | −9.598 | 14.727 | −0.480 | 1.00 | 50.45 | C |
| ATOM | 352 | CB | ALA | A | 184 | −8.782 | 14.213 | −1.658 | 1.00 | 50.46 | C |
| ATOM | 356 | C | ALA | A | 184 | −10.475 | 15.896 | −0.915 | 1.00 | 50.86 | C |
| ATOM | 357 | O | ALA | A | 184 | −10.073 | 17.050 | −0.812 | 1.00 | 50.99 | O |
| ATOM | 358 | N | GLY | A | 185 | −11.679 | 15.592 | −1.393 | 1.00 | 51.41 | N |
| ATOM | 360 | CA | GLY | A | 185 | −12.610 | 16.612 | −1.838 | 1.00 | 51.80 | C |
| ATOM | 363 | C | GLY | A | 185 | −13.240 | 17.384 | −0.693 | 1.00 | 52.13 | C |
| ATOM | 364 | O | GLY | A | 185 | −13.343 | 18.609 | −0.754 | 1.00 | 52.25 | O |
| ATOM | 365 | N | TYR | A | 186 | −13.638 | 16.668 | 0.357 | 1.00 | 52.48 | N |
| ATOM | 367 | CA | TYR | A | 186 | −14.300 | 17.274 | 1.514 | 1.00 | 52.76 | C |
| ATOM | 369 | CB | TYR | A | 186 | −15.311 | 16.293 | 2.134 | 1.00 | 52.96 | C |
| ATOM | 372 | CG | TYR | A | 186 | −16.286 | 15.646 | 1.160 | 1.00 | 53.90 | C |
| ATOM | 373 | CD1 | TYR | A | 186 | −16.973 | 16.402 | 0.210 | 1.00 | 54.91 | C |
| ATOM | 375 | CE1 | TYR | A | 186 | −17.875 | 15.797 | −0.678 | 1.00 | 55.21 | C |
| ATOM | 377 | CZ | TYR | A | 186 | −18.091 | 14.428 | −0.607 | 1.00 | 55.52 | C |
| ATOM | 378 | OH | TYR | A | 186 | −18.971 | 13.809 | −1.465 | 1.00 | 56.47 | O |
| ATOM | 380 | CE2 | TYR | A | 186 | −17.422 | 13.666 | 0.329 | 1.00 | 55.22 | C |
| ATOM | 382 | CD2 | TYR | A | 186 | −16.533 | 14.275 | 1.208 | 1.00 | 54.72 | C |
| ATOM | 384 | C | TYR | A | 186 | −13.337 | 17.753 | 2.610 | 1.00 | 52.54 | C |
| ATOM | 385 | O | TYR | A | 186 | −13.789 | 18.146 | 3.686 | 1.00 | 52.65 | O |
| ATOM | 386 | N | SER | A | 187 | −12.028 | 17.725 | 2.358 | 1.00 | 52.26 | N |
| ATOM | 388 | CA | SER | A | 187 | −11.053 | 18.183 | 3.354 | 1.00 | 51.98 | C |
| ATOM | 390 | CB | SER | A | 187 | −10.240 | 17.003 | 3.892 | 1.00 | 52.07 | C |
| ATOM | 393 | OG | SER | A | 187 | −9.266 | 16.570 | 2.954 | 1.00 | 51.97 | O |
| ATOM | 395 | C | SER | A | 187 | −10.113 | 19.264 | 2.817 | 1.00 | 51.67 | C |
| ATOM | 396 | O | SER | A | 187 | −8.971 | 19.365 | 3.258 | 1.00 | 51.71 | O |
| ATOM | 397 | N | HIS | A | 188 | −10.602 | 20.077 | 1.880 | 1.00 | 51.31 | N |
| ATOM | 399 | CA | HIS | A | 188 | −9.818 | 21.160 | 1.277 | 1.00 | 51.01 | C |
| ATOM | 401 | CB | HIS | A | 188 | −9.604 | 22.301 | 2.280 | 1.00 | 51.09 | C |
| ATOM | 404 | CG | HIS | A | 188 | −9.730 | 23.736 | 1.290 | 1.00 | 46.66 | C |
| ATOM | 405 | ND1 | HIS | A | 188 | −8.385 | 24.002 | 1.101 | 1.00 | 46.29 | N |
| ATOM | 407 | CE1 | HIS | A | 188 | −8.225 | 25.166 | 0.500 | 1.00 | 45.96 | C |
| ATOM | 409 | NE2 | HIS | A | 188 | −9.416 | 25.695 | 0.291 | 1.00 | 45.96 | N |
| ATOM | 411 | CD2 | HIS | A | 188 | −10.375 | 24.809 | 0.776 | 1.00 | 46.29 | C |
| ATOM | 413 | C | HIS | A | 188 | −8.475 | 20.671 | 0.711 | 1.00 | 50.58 | C |
| ATOM | 414 | O | HIS | A | 188 | −7.445 | 21.332 | 0.855 | 1.00 | 50.59 | O |
| ATOM | 415 | N | ASN | A | 189 | −8.516 | 19.503 | 0.074 | 1.00 | 49.98 | N |
| ATOM | 417 | CA | ASN | A | 189 | −7.354 | 18.884 | −0.567 | 1.00 | 49.46 | C |
| ATOM | 419 | CB | ASN | A | 189 | −6.853 | 19.775 | −1.719 | 1.00 | 49.71 | C |
| ATOM | 422 | CG | ASN | A | 189 | −6.226 | 18.974 | −2.855 | 1.00 | 50.59 | C |
| ATOM | 423 | OD1 | ASN | A | 189 | −6.722 | 17.911 | −3.233 | 1.00 | 52.19 | O |
| ATOM | 424 | ND2 | ASN | A | 189 | −5.130 | 19.488 | −3.405 | 1.00 | 51.45 | N |
| ATOM | 427 | C | ASN | A | 189 | −6.210 | 18.508 | 0.390 | 1.00 | 48.47 | C |
| ATOM | 428 | O | ASN | A | 189 | −5.038 | 18.713 | 0.080 | 1.00 | 48.55 | O |
| ATOM | 429 | N | ARG | A | 190 | −6.571 | 17.923 | 1.534 | 1.00 | 47.13 | N |
| ATOM | 431 | CA | ARG | A | 190 | −5.612 | 17.472 | 2.544 | 1.00 | 46.13 | C |
| ATOM | 433 | CB | ARG | A | 190 | −5.776 | 18.304 | 3.817 | 1.00 | 46.15 | C |
| ATOM | 436 | CG | ARG | A | 190 | −5.306 | 19.738 | 3.687 | 1.00 | 46.71 | C |
| ATOM | 439 | CD | ARG | A | 190 | −4.022 | 20.016 | 4.439 | 1.00 | 47.39 | C |
| ATOM | 442 | NE | ARG | A | 190 | −3.221 | 21.056 | 3.803 | 1.00 | 47.69 | N |
| ATOM | 444 | CZ | ARG | A | 190 | −1.891 | 21.088 | 3.791 | 1.00 | 48.41 | C |
| ATOM | 445 | NH1 | ARG | A | 190 | −1.177 | 20.136 | 4.380 | 1.00 | 48.66 | N |
| ATOM | 448 | NH2 | ARG | A | 190 | −1.262 | 22.083 | 3.182 | 1.00 | 48.42 | N |
| ATOM | 451 | C | ARG | A | 190 | −5.825 | 15.991 | 2.882 | 1.00 | 45.03 | C |
| ATOM | 452 | O | ARG | A | 190 | −5.985 | 15.642 | 4.054 | 1.00 | 44.81 | O |
| ATOM | 453 | N | PRO | A | 191 | −5.802 | 15.116 | 1.875 | 1.00 | 43.70 | N |
| ATOM | 454 | CA | PRO | A | 191 | −6.073 | 13.687 | 2.096 | 1.00 | 42.98 | C |
| ATOM | 456 | CB | PRO | A | 191 | −5.907 | 13.073 | 0.695 | 1.00 | 42.98 | C |
| ATOM | 459 | CG | PRO | A | 191 | −5.126 | 14.063 | −0.080 | 1.00 | 43.15 | C |
| ATOM | 462 | CD | PRO | A | 191 | −5.505 | 15.398 | 0.460 | 1.00 | 43.63 | C |
| ATOM | 465 | C | PRO | A | 191 | −5.141 | 13.004 | 3.099 | 1.00 | 42.30 | C |
| ATOM | 466 | O | PRO | A | 191 | −5.622 | 12.230 | 3.931 | 1.00 | 42.05 | O |
| ATOM | 467 | N | LEU | A | 192 | −3.844 | 13.290 | 3.016 | 1.00 | 41.47 | N |
| ATOM | 469 | CA | LEU | A | 192 | −2.852 | 12.682 | 3.898 | 1.00 | 40.85 | C |
| ATOM | 471 | CB | LEU | A | 192 | −1.442 | 12.859 | 3.328 | 1.00 | 40.59 | C |
| ATOM | 474 | CG | LEU | A | 192 | −0.287 | 12.213 | 4.096 | 1.00 | 38.91 | C |
| ATOM | 476 | CD1 | LEU | A | 192 | −0.438 | 10.707 | 4.166 | 1.00 | 37.68 | C |
| ATOM | 480 | CD2 | LEU | A | 192 | 1.033 | 12.586 | 3.455 | 1.00 | 38.83 | C |
| ATOM | 484 | C | LEU | A | 192 | −2.912 | 13.214 | 5.332 | 1.00 | 41.07 | C |
| ATOM | 485 | O | LEU | A | 192 | −2.788 | 12.432 | 6.268 | 1.00 | 40.77 | O |
| ATOM | 486 | N | THR | A | 193 | −3.072 | 14.528 | 5.512 | 1.00 | 41.33 | N |
| ATOM | 488 | CA | THR | A | 193 | −3.175 | 15.086 | 6.864 | 1.00 | 41.55 | C |
| ATOM | 490 | CB | THR | A | 193 | −3.292 | 16.615 | 6.857 | 1.00 | 41.50 | C |
| ATOM | 492 | OG1 | THR | A | 193 | −2.126 | 17.174 | 6.245 | 1.00 | 40.56 | O |
| ATOM | 494 | CG2 | THR | A | 193 | −3.241 | 17.168 | 8.284 | 1.00 | 41.50 | C |
| ATOM | 498 | C | THR | A | 193 | −4.371 | 14.374 | 7.500 | 1.00 | 42.02 | C |
| ATOM | 499 | O | THR | A | 193 | −4.156 | 13.543 | 8.373 | 1.00 | 42.26 | O |
| ATOM | 500 | N | CME | A | 194 | −5.607 | 14.765 | 7.204 | 1.00 | 42.50 | N |

TABLE 2-continued

| ATOM | 503 | CA | CME | A | 194 | −6.888 | 14.115 | 7.401 | 1.00 | 42.83 | C |
| --- | --- | --- | --- | --- | --- | --- | --- | --- | --- | --- | --- |
| ATOM | 505 | CB | CME | A | 194 | −7.893 | 14.277 | 6.255 | 1.00 | 43.14 | C |
| ATOM | 508 | SG | CME | A | 194 | −9.493 | 13.981 | 6.949 | 1.00 | 45.79 | S |
| ATOM | 509 | S2 | CME | A | 194 | −9.864 | 15.262 | 8.466 | 1.00 | 49.58 | S |
| ATOM | 510 | C2 | CME | A | 194 | −10.684 | 14.582 | 9.873 | 1.00 | 50.91 | C |
| ATOM | 513 | C1 | CME | A | 194 | −9.760 | 13.698 | 10.675 | 1.00 | 51.26 | C |
| ATOM | 515 | O1 | CME | A | 194 | −10.220 | 13.054 | 11.606 | 1.00 | 51.94 | O |
| ATOM | 516 | C | CME | A | 194 | −6.833 | 12.681 | 7.898 | 1.00 | 42.57 | C |
| ATOM | 517 | O | CME | A | 194 | −6.708 | 12.448 | 9.082 | 1.00 | 42.62 | O |
| ATOM | 519 | N | ILE | A | 195 | −6.625 | 11.763 | 6.942 | 1.00 | 42.06 | N |
| ATOM | 521 | CA | ILE | A | 195 | −6.553 | 10.307 | 7.188 | 1.00 | 41.82 | C |
| ATOM | 523 | CB | ILE | A | 195 | −6.353 | 9.534 | 5.845 | 1.00 | 41.37 | C |
| ATOM | 525 | CG1 | ILE | A | 195 | −7.082 | 8.193 | 5.892 | 1.00 | 40.56 | C |
| ATOM | 528 | CD1 | ILE | A | 195 | −8.582 | 8.306 | 5.704 | 1.00 | 40.05 | C |
| ATOM | 532 | CG2 | ILE | A | 195 | −4.871 | 9.317 | 5.533 | 1.00 | 41.04 | C |
| ATOM | 536 | C | ILE | A | 195 | −5.501 | 9.851 | 8.207 | 1.00 | 42.00 | C |
| ATOM | 537 | O | ILE | A | 195 | −5.721 | 8.863 | 8.894 | 1.00 | 41.72 | O |
| ATOM | 538 | N | MET | A | 196 | −4.361 | 10.535 | 8.271 | 1.00 | 42.40 | N |
| ATOM | 540 | CA | MET | A | 196 | −3.313 | 10.188 | 9.233 | 1.00 | 42.95 | C |
| ATOM | 542 | CB | MET | A | 196 | −1.985 | 10.890 | 8.915 | 1.00 | 42.83 | C |
| ATOM | 545 | CG | MET | A | 196 | −1.170 | 10.242 | 7.798 | 1.00 | 42.63 | C |
| ATOM | 548 | SD | MET | A | 196 | −0.640 | 8.560 | 8.152 | 1.00 | 42.53 | S |
| ATOM | 549 | CE | MET | A | 196 | 0.776 | 8.847 | 9.170 | 1.00 | 43.39 | C |
| ATOM | 553 | C | MET | A | 196 | −3.770 | 10.557 | 10.641 | 1.00 | 43.54 | C |
| ATOM | 554 | O | MET | A | 196 | −3.472 | 9.852 | 11.597 | 1.00 | 43.54 | O |
| ATOM | 555 | N | TYR | A | 197 | −4.474 | 11.677 | 10.760 | 1.00 | 44.32 | N |
| ATOM | 557 | CA | TYR | A | 197 | −5.028 | 12.107 | 12.036 | 1.00 | 45.06 | C |
| ATOM | 559 | CB | TYR | A | 197 | −5.530 | 13.554 | 11.954 | 1.00 | 45.26 | C |
| ATOM | 562 | CG | TYR | A | 197 | −5.927 | 14.137 | 13.291 | 1.00 | 46.75 | C |
| ATOM | 563 | CD1 | TYR | A | 197 | −5.019 | 14.186 | 14.348 | 1.00 | 48.15 | C |
| ATOM | 565 | CE1 | TYR | A | 197 | −5.377 | 14.716 | 15.580 | 1.00 | 49.03 | C |
| ATOM | 567 | CZ | TYR | A | 197 | −6.657 | 15.207 | 15.766 | 1.00 | 49.70 | C |
| ATOM | 568 | OH | TYR | A | 197 | −7.011 | 15.728 | 16.988 | 1.00 | 50.40 | O |
| ATOM | 570 | CE2 | TYR | A | 197 | −7.582 | 15.170 | 14.731 | 1.00 | 49.35 | C |
| ATOM | 572 | CD2 | TYR | A | 197 | −7.213 | 14.637 | 13.504 | 1.00 | 48.29 | C |
| ATOM | 574 | C | TYR | A | 197 | −6.159 | 11.164 | 12.444 | 1.00 | 45.16 | C |
| ATOM | 575 | O | TYR | A | 197 | −6.329 | 10.878 | 13.626 | 1.00 | 45.27 | O |
| ATOM | 576 | N | ALA | A | 198 | −6.907 | 10.664 | 11.460 | 1.00 | 45.45 | N |
| ATOM | 578 | CA | ALA | A | 198 | −8.017 | 9.739 | 11.708 | 1.00 | 45.67 | C |
| ATOM | 580 | CB | ALA | A | 198 | −8.949 | 9.688 | 10.511 | 1.00 | 45.60 | C |
| ATOM | 584 | C | ALA | A | 198 | −7.527 | 8.334 | 12.050 | 1.00 | 46.02 | C |
| ATOM | 585 | O | ALA | A | 198 | −8.171 | 7.631 | 12.830 | 1.00 | 46.53 | O |
| ATOM | 586 | N | ILE | A | 199 | −6.391 | 7.932 | 11.481 | 1.00 | 46.14 | N |
| ATOM | 588 | CA | ILE | A | 199 | −5.823 | 6.603 | 11.728 | 1.00 | 46.31 | C |
| ATOM | 590 | CB | ILE | A | 199 | −4.763 | 6.239 | 10.640 | 1.00 | 46.16 | C |
| ATOM | 592 | CG1 | ILE | A | 199 | −5.447 | 5.840 | 9.328 | 1.00 | 46.13 | C |
| ATOM | 595 | CD1 | ILE | A | 199 | −4.556 | 5.994 | 8.091 | 1.00 | 45.58 | C |
| ATOM | 599 | CG2 | ILE | A | 199 | −3.853 | 5.099 | 11.096 | 1.00 | 45.98 | C |
| ATOM | 603 | C | ILE | A | 199 | −5.204 | 6.545 | 13.127 | 1.00 | 46.65 | C |
| ATOM | 604 | O | ILE | A | 199 | −5.358 | 5.555 | 13.835 | 1.00 | 46.58 | O |
| ATOM | 605 | N | PHE | A | 200 | −4.508 | 7.612 | 13.511 | 1.00 | 47.13 | N |
| ATOM | 607 | CA | PHE | A | 200 | −3.839 | 7.682 | 14.808 | 1.00 | 47.56 | C |
| ATOM | 609 | CB | PHE | A | 200 | −2.830 | 8.838 | 14.840 | 1.00 | 47.51 | C |
| ATOM | 612 | CG | PHE | A | 200 | −1.477 | 8.486 | 14.264 | 1.00 | 47.34 | C |
| ATOM | 613 | CD1 | PHE | A | 200 | −1.361 | 7.985 | 12.973 | 1.00 | 46.95 | C |
| ATOM | 615 | CE1 | PHE | A | 200 | −0.120 | 7.665 | 12.444 | 1.00 | 46.68 | C |
| ATOM | 617 | CZ | PHE | A | 200 | 1.022 | 7.840 | 13.197 | 1.00 | 46.85 | C |
| ATOM | 619 | CE2 | PHE | A | 200 | 0.925 | 8.336 | 14.482 | 1.00 | 47.13 | C |
| ATOM | 621 | CD2 | PHE | A | 200 | −0.321 | 8.659 | 15.011 | 1.00 | 47.40 | C |
| ATOM | 623 | C | PHE | A | 200 | −4.842 | 7.804 | 15.955 | 1.00 | 48.07 | C |
| ATOM | 624 | O | PHE | A | 200 | −4.608 | 7.275 | 17.038 | 1.00 | 48.28 | O |
| ATOM | 625 | N | GLN | A | 201 | −5.954 | 8.492 | 15.712 | 1.00 | 48.58 | N |
| ATOM | 627 | CA | GLN | A | 201 | −7.005 | 8.638 | 16.717 | 1.00 | 49.08 | C |
| ATOM | 629 | CB | GLN | A | 201 | −8.011 | 9.709 | 16.298 | 1.00 | 49.38 | C |
| ATOM | 632 | CG | GLN | A | 201 | −7.544 | 11.125 | 16.579 | 1.00 | 50.79 | C |
| ATOM | 635 | CD | GLN | A | 201 | −8.579 | 12.173 | 16.213 | 1.00 | 53.10 | C |
| ATOM | 636 | OE1 | GLN | A | 201 | −8.686 | 13.200 | 16.886 | 1.00 | 55.17 | O |
| ATOM | 637 | NE2 | GLN | A | 201 | −9.343 | 11.921 | 15.149 | 1.00 | 54.16 | N |
| ATOM | 640 | C | GLN | A | 201 | −7.727 | 7.308 | 16.930 | 1.00 | 49.01 | C |
| ATOM | 641 | O | GLN | A | 201 | −8.050 | 6.939 | 18.064 | 1.00 | 49.16 | O |
| ATOM | 642 | N | GLU | A | 202 | −7.978 | 6.604 | 15.829 | 1.00 | 48.80 | N |
| ATOM | 644 | CA | GLU | A | 202 | −8.640 | 5.299 | 15.847 | 1.00 | 48.69 | C |
| ATOM | 646 | CB | GLU | A | 202 | −8.862 | 4.812 | 14.403 | 1.00 | 48.68 | C |
| ATOM | 649 | CG | GLU | A | 202 | −9.205 | 3.331 | 14.228 | 1.00 | 48.41 | C |
| ATOM | 652 | CD | GLU | A | 202 | −10.651 | 2.996 | 14.546 | 1.00 | 48.57 | C |
| ATOM | 653 | OE1 | GLU | A | 202 | −11.478 | 3.927 | 14.672 | 1.00 | 48.89 | O |
| ATOM | 654 | OE2 | GLU | A | 202 | −10.966 | 1.791 | 14.657 | 1.00 | 48.02 | O |
| ATOM | 655 | C | GLU | A | 202 | −7.837 | 4.260 | 16.633 | 1.00 | 48.68 | C |
| ATOM | 656 | O | GLU | A | 202 | −8.417 | 3.394 | 17.285 | 1.00 | 48.82 | O |

TABLE 2-continued

| ATOM | 657 | N | ARG | A | 203 | −6.509 | 4.359 | 16.573 | 1.00 | 48.71 | N |
| --- | --- | --- | --- | --- | --- | --- | --- | --- | --- | --- | --- |
| ATOM | 659 | CA | ARG | A | 203 | −5.608 | 3.409 | 17.231 | 1.00 | 48.78 | C |
| ATOM | 661 | CB | ARG | A | 203 | −4.458 | 3.065 | 16.276 | 1.00 | 48.76 | C |
| ATOM | 664 | CG | ARG | A | 203 | −4.883 | 2.339 | 15.001 | 1.00 | 48.38 | C |
| ATOM | 667 | CD | ARG | A | 203 | −3.705 | 1.917 | 14.132 | 1.00 | 47.77 | C |
| ATOM | 670 | NE | ARG | A | 203 | −4.061 | 0.929 | 13.115 | 1.00 | 47.02 | N |
| ATOM | 672 | CZ | ARG | A | 203 | −4.309 | −0.358 | 13.354 | 1.00 | 46.27 | C |
| ATOM | 673 | NH1 | ARG | A | 203 | −4.239 | −0.858 | 14.585 | 1.00 | 45.99 | N |
| ATOM | 676 | NH2 | ARG | A | 203 | −4.629 | −1.156 | 12.346 | 1.00 | 45.30 | N |
| ATOM | 679 | C | ARG | A | 203 | −5.020 | 3.886 | 18.576 | 1.00 | 48.92 | C |
| ATOM | 680 | O | ARG | A | 203 | −4.244 | 3.159 | 19.198 | 1.00 | 48.76 | O |
| ATOM | 681 | N | ASP | A | 204 | −5.390 | 5.094 | 19.012 | 1.00 | 49.20 | N |
| ATOM | 683 | CA | ASP | A | 204 | −4.888 | 5.706 | 20.256 | 1.00 | 49.41 | C |
| ATOM | 685 | CB | ASP | A | 204 | −5.290 | 4.885 | 21.491 | 1.00 | 49.47 | C |
| ATOM | 688 | CG | ASP | A | 204 | −6.780 | 4.706 | 21.612 | 1.00 | 49.60 | C |
| ATOM | 689 | OD1 | ASP | A | 204 | −7.500 | 5.726 | 21.614 | 1.00 | 50.19 | O |
| ATOM | 690 | OD2 | ASP | A | 204 | −7.321 | 3.584 | 21.715 | 1.00 | 49.92 | O |
| ATOM | 691 | C | ASP | A | 204 | −3.371 | 5.913 | 20.261 | 1.00 | 49.54 | C |
| ATOM | 692 | O | ASP | A | 204 | −2.758 | 5.968 | 21.327 | 1.00 | 49.56 | O |
| ATOM | 693 | N | LEU | A | 205 | −2.776 | 6.034 | 19.074 | 1.00 | 49.68 | N |
| ATOM | 695 | CA | LEU | A | 205 | −1.330 | 6.202 | 18.931 | 1.00 | 49.83 | C |
| ATOM | 697 | CB | LEU | A | 205 | −0.917 | 6.112 | 17.450 | 1.00 | 49.78 | C |
| ATOM | 700 | CG | LEU | A | 205 | −1.067 | 4.749 | 16.765 | 1.00 | 49.46 | C |
| ATOM | 702 | CD1 | LEU | A | 205 | −0.778 | 4.867 | 15.272 | 1.00 | 49.43 | C |
| ATOM | 706 | CD2 | LEU | A | 205 | −0.163 | 3.703 | 17.401 | 1.00 | 49.17 | C |
| ATOM | 710 | C | LEU | A | 205 | −0.805 | 7.509 | 19.517 | 1.00 | 50.09 | C |
| ATOM | 711 | O | LEU | A | 205 | 0.342 | 7.563 | 19.955 | 1.00 | 50.06 | O |
| ATOM | 712 | N | LEU | A | 206 | −1.627 | 8.557 | 19.509 | 1.00 | 50.50 | N |
| ATOM | 714 | CA | LEU | A | 206 | −1.220 | 9.854 | 20.055 | 1.00 | 50.93 | C |
| ATOM | 716 | CB | LEU | A | 206 | −2.204 | 10.956 | 19.652 | 1.00 | 50.99 | C |
| ATOM | 719 | CG | LEU | A | 206 | −2.338 | 11.241 | 18.150 | 1.00 | 51.01 | C |
| ATOM | 721 | CD1 | LEU | A | 206 | −3.483 | 12.214 | 17.892 | 1.00 | 51.00 | C |
| ATOM | 725 | CD2 | LEU | A | 206 | −1.038 | 11.781 | 17.572 | 1.00 | 50.93 | C |
| ATOM | 729 | C | LEU | A | 206 | −1.081 | 9.798 | 21.581 | 1.00 | 51.35 | C |
| ATOM | 730 | O | LEU | A | 206 | −0.179 | 10.407 | 22.147 | 1.00 | 51.30 | O |
| ATOM | 731 | N | LYS | A | 207 | −1.971 | 9.064 | 22.239 | 1.00 | 51.86 | N |
| ATOM | 733 | CA | LYS | A | 207 | −1.911 | 8.917 | 23.691 | 1.00 | 52.34 | C |
| ATOM | 735 | CB | LYS | A | 207 | −3.286 | 8.529 | 24.244 | 1.00 | 52.50 | C |
| ATOM | 738 | CG | LYS | A | 207 | −4.328 | 9.635 | 24.120 | 1.00 | 53.08 | C |
| ATOM | 741 | CD | LYS | A | 207 | −5.731 | 9.116 | 24.385 | 1.00 | 53.90 | C |
| ATOM | 744 | CE | LYS | A | 207 | −6.745 | 10.249 | 24.373 | 1.00 | 54.40 | C |
| ATOM | 747 | NZ | LYS | A | 207 | −8.101 | 9.787 | 24.786 | 1.00 | 54.85 | N |
| ATOM | 751 | C | LYS | A | 207 | −0.861 | 7.879 | 24.103 | 1.00 | 52.46 | C |
| ATOM | 752 | O | LYS | A | 207 | −0.202 | 8.030 | 25.136 | 1.00 | 52.65 | O |
| ATOM | 753 | N | THR | A | 208 | −0.699 | 6.845 | 23.279 | 1.00 | 52.47 | N |
| ATOM | 755 | CA | THR | A | 208 | 0.237 | 5.752 | 23.551 | 1.00 | 52.47 | C |
| ATOM | 757 | CB | THR | A | 208 | −0.005 | 4.590 | 22.554 | 1.00 | 52.51 | C |
| ATOM | 759 | OG1 | THR | A | 208 | −1.349 | 4.108 | 22.678 | 1.00 | 52.37 | O |
| ATOM | 761 | CG2 | THR | A | 208 | 0.856 | 3.372 | 22.889 | 1.00 | 52.59 | C |
| ATOM | 765 | C | THR | A | 208 | 1.698 | 6.199 | 23.486 | 1.00 | 52.47 | C |
| ATOM | 766 | O | THR | A | 208 | 2.543 | 5.706 | 24.240 | 1.00 | 52.56 | O |
| ATOM | 767 | N | PHE | A | 209 | 1.985 | 7.134 | 22.584 | 1.00 | 52.41 | N |
| ATOM | 769 | CA | PHE | A | 209 | 3.336 | 7.656 | 22.393 | 1.00 | 52.30 | C |
| ATOM | 771 | CB | PHE | A | 209 | 3.773 | 7.426 | 20.944 | 1.00 | 52.16 | C |
| ATOM | 774 | CG | PHE | A | 209 | 3.934 | 5.974 | 20.593 | 1.00 | 51.30 | C |
| ATOM | 775 | CD1 | PHE | A | 209 | 5.000 | 5.243 | 21.098 | 1.00 | 50.43 | C |
| ATOM | 777 | CE1 | PHE | A | 209 | 5.154 | 3.902 | 20.788 | 1.00 | 49.98 | C |
| ATOM | 779 | CZ | PHE | A | 209 | 4.235 | 3.274 | 19.974 | 1.00 | 49.78 | C |
| ATOM | 781 | CE2 | PHE | A | 209 | 3.161 | 3.988 | 19.464 | 1.00 | 49.94 | C |
| ATOM | 783 | CD2 | PHE | A | 209 | 3.012 | 5.331 | 19.776 | 1.00 | 50.41 | C |
| ATOM | 785 | C | PHE | A | 209 | 3.433 | 9.140 | 22.771 | 1.00 | 52.57 | C |
| ATOM | 786 | O | PHE | A | 209 | 4.409 | 9.811 | 22.434 | 1.00 | 52.57 | O |
| ATOM | 787 | N | ARG | A | 210 | 2.418 | 9.633 | 23.481 | 1.00 | 52.88 | N |
| ATOM | 789 | CA | ARG | A | 210 | 2.358 | 11.016 | 23.957 | 1.00 | 53.17 | C |
| ATOM | 791 | CB | ARG | A | 210 | 3.204 | 11.172 | 25.227 | 1.00 | 53.33 | C |
| ATOM | 794 | CG | ARG | A | 210 | 2.703 | 10.341 | 26.407 | 1.00 | 54.23 | C |
| ATOM | 797 | CD | ARG | A | 210 | 3.812 | 9.801 | 27.291 | 1.00 | 55.42 | C |
| ATOM | 800 | NE | ARG | A | 210 | 4.661 | 10.884 | 27.786 | 1.00 | 56.41 | N |
| ATOM | 802 | CZ | ARG | A | 210 | 5.931 | 10.754 | 28.169 | 1.00 | 57.54 | C |
| ATOM | 803 | NH1 | ARG | A | 210 | 6.545 | 9.573 | 28.134 | 1.00 | 58.09 | N |
| ATOM | 806 | NH2 | ARG | A | 210 | 6.597 | 11.823 | 28.595 | 1.00 | 58.03 | N |
| ATOM | 809 | C | ARG | A | 210 | 2.762 | 12.037 | 22.891 | 1.00 | 53.15 | C |
| ATOM | 810 | O | ARG | A | 210 | 3.549 | 12.948 | 23.147 | 1.00 | 53.08 | O |
| ATOM | 811 | N | ILE | A | 211 | 2.218 | 11.863 | 21.689 | 1.00 | 53.27 | N |
| ATOM | 813 | CA | ILE | A | 211 | 2.469 | 12.770 | 20.581 | 1.00 | 53.30 | C |
| ATOM | 815 | CB | ILE | A | 211 | 2.290 | 12.051 | 19.223 | 1.00 | 53.31 | C |
| ATOM | 817 | CG1 | ILE | A | 211 | 3.225 | 10.842 | 19.120 | 1.00 | 53.44 | C |
| ATOM | 820 | CD1 | ILE | A | 211 | 2.813 | 9.839 | 18.067 | 1.00 | 53.63 | C |
| ATOM | 824 | CG2 | ILE | A | 211 | 2.535 | 13.024 | 18.069 | 1.00 | 53.28 | C |

TABLE 2-continued

| | | | | | | | | | | | |
|---|---|---|---|---|---|---|---|---|---|---|---|
| ATOM | 828 | C | ILE | A | 211 | 1.471 | 13.905 | 20.687 | 1.00 | 53.36 | C |
| ATOM | 829 | O | ILE | A | 211 | 0.263 | 13.671 | 20.698 | 1.00 | 53.40 | O |
| ATOM | 830 | N | SER | A | 212 | 1.970 | 15.132 | 20.771 | 1.00 | 53.52 | N |
| ATOM | 832 | CA | SER | A | 212 | 1.102 | 16.303 | 20.842 | 1.00 | 53.67 | C |
| ATOM | 834 | CB | SER | A | 212 | 1.935 | 17.576 | 21.028 | 1.00 | 53.69 | C |
| ATOM | 837 | OG | SER | A | 212 | 1.172 | 18.740 | 20.764 | 1.00 | 53.92 | O |
| ATOM | 839 | C | SER | A | 212 | 0.266 | 16.389 | 19.565 | 1.00 | 53.73 | C |
| ATOM | 840 | O | SER | A | 212 | 0.777 | 16.169 | 18.466 | 1.00 | 53.72 | O |
| ATOM | 841 | N | SER | A | 213 | −1.020 | 16.692 | 19.721 | 1.00 | 53.80 | N |
| ATOM | 843 | CA | SER | A | 213 | −1.941 | 16.812 | 18.591 | 1.00 | 53.86 | C |
| ATOM | 845 | CB | SER | A | 213 | −3.369 | 17.029 | 19.101 | 1.00 | 53.86 | C |
| ATOM | 848 | OG | SER | A | 213 | −4.316 | 16.928 | 18.056 | 1.00 | 54.05 | O |
| ATOM | 850 | C | SER | A | 213 | −1.538 | 17.960 | 17.663 | 1.00 | 53.86 | C |
| ATOM | 851 | O | SER | A | 213 | −1.748 | 17.894 | 16.453 | 1.00 | 53.78 | O |
| ATOM | 852 | N | ASP | A | 214 | −0.950 | 19.002 | 18.244 | 1.00 | 53.81 | N |
| ATOM | 854 | CA | ASP | A | 214 | −0.508 | 20.177 | 17.500 | 1.00 | 53.73 | C |
| ATOM | 856 | CB | ASP | A | 214 | −0.156 | 21.318 | 18.464 | 1.00 | 53.95 | C |
| ATOM | 859 | CG | ASP | A | 214 | −1.343 | 21.775 | 19.301 | 1.00 | 54.78 | C |
| ATOM | 860 | OD1 | ASP | A | 214 | −1.923 | 20.946 | 20.035 | 1.00 | 55.88 | O |
| ATOM | 861 | OD2 | ASP | A | 214 | −1.763 | 22.951 | 19.297 | 1.00 | 56.11 | O |
| ATOM | 862 | C | ASP | A | 214 | 0.714 | 19.844 | 16.653 | 1.00 | 53.21 | C |
| ATOM | 863 | O | ASP | A | 214 | 0.769 | 20.167 | 15.467 | 1.00 | 53.23 | O |
| ATOM | 864 | N | THR | A | 215 | 1.690 | 19.196 | 17.283 | 1.00 | 52.51 | N |
| ATOM | 866 | CA | THR | A | 215 | 2.936 | 18.809 | 16.625 | 1.00 | 52.01 | C |
| ATOM | 868 | CB | THR | A | 215 | 3.884 | 18.122 | 17.644 | 1.00 | 52.05 | C |
| ATOM | 870 | OG1 | THR | A | 215 | 4.088 | 18.966 | 18.788 | 1.00 | 52.32 | O |
| ATOM | 872 | CG2 | THR | A | 215 | 5.281 | 17.945 | 17.066 | 1.00 | 52.10 | C |
| ATOM | 876 | C | THR | A | 215 | 2.689 | 17.868 | 15.442 | 1.00 | 51.42 | C |
| ATOM | 877 | O | THR | A | 215 | 3.316 | 18.000 | 14.393 | 1.00 | 51.24 | O |
| ATOM | 878 | N | PHE | A | 216 | 1.768 | 16.926 | 15.632 | 1.00 | 50.71 | N |
| ATOM | 880 | CA | PHE | A | 216 | 1.422 | 15.934 | 14.624 | 1.00 | 50.09 | C |
| ATOM | 882 | CB | PHE | A | 216 | 0.424 | 14.933 | 15.207 | 1.00 | 50.21 | C |
| ATOM | 885 | CG | PHE | A | 216 | 0.079 | 13.802 | 14.279 | 1.00 | 50.42 | C |
| ATOM | 886 | CD1 | PHE | A | 216 | 0.917 | 12.704 | 14.164 | 1.00 | 50.54 | C |
| ATOM | 888 | CE1 | PHE | A | 216 | 0.599 | 11.655 | 13.317 | 1.00 | 50.73 | C |
| ATOM | 890 | CZ | PHE | A | 216 | −0.569 | 11.698 | 12.571 | 1.00 | 50.81 | C |
| ATOM | 892 | CE2 | PHE | A | 216 | −1.413 | 12.786 | 12.678 | 1.00 | 50.69 | C |
| ATOM | 894 | CD2 | PHE | A | 216 | −1.089 | 13.832 | 13.529 | 1.00 | 50.63 | C |
| ATOM | 896 | C | PHE | A | 216 | 0.823 | 16.569 | 13.381 | 1.00 | 49.47 | C |
| ATOM | 897 | O | PHE | A | 216 | 1.211 | 16.231 | 12.271 | 1.00 | 49.20 | O |
| ATOM | 898 | N | ILE | A | 217 | −0.124 | 17.484 | 13.579 | 1.00 | 48.67 | N |
| ATOM | 900 | CA | ILE | A | 217 | −0.801 | 18.156 | 12.472 | 1.00 | 48.03 | C |
| ATOM | 902 | CB | ILE | A | 217 | −2.002 | 19.002 | 12.991 | 1.00 | 48.09 | C |
| ATOM | 904 | CG1 | ILE | A | 217 | −3.106 | 18.089 | 13.550 | 1.00 | 48.26 | C |
| ATOM | 907 | CD1 | ILE | A | 217 | −3.942 | 17.367 | 12.498 | 1.00 | 48.63 | C |
| ATOM | 911 | CG2 | ILE | A | 217 | −2.560 | 19.920 | 11.894 | 1.00 | 47.92 | C |
| ATOM | 915 | C | ILE | A | 217 | 0.173 | 19.022 | 11.677 | 1.00 | 47.32 | C |
| ATOM | 916 | O | ILE | A | 217 | 0.101 | 19.070 | 10.458 | 1.00 | 47.35 | O |
| ATOM | 917 | N | THR | A | 218 | 1.089 | 19.690 | 12.367 | 1.00 | 46.49 | N |
| ATOM | 919 | CA | THR | A | 218 | 2.070 | 20.548 | 11.709 | 1.00 | 45.82 | C |
| ATOM | 921 | CB | THR | A | 218 | 2.842 | 21.385 | 12.749 | 1.00 | 45.85 | C |
| ATOM | 923 | OG1 | THR | A | 218 | 1.924 | 22.194 | 13.497 | 1.00 | 45.85 | O |
| ATOM | 925 | CG2 | THR | A | 218 | 3.763 | 22.398 | 12.070 | 1.00 | 45.83 | C |
| ATOM | 929 | C | THR | A | 218 | 3.042 | 19.730 | 10.866 | 1.00 | 45.15 | C |
| ATOM | 930 | O | THR | A | 218 | 3.393 | 20.134 | 9.755 | 1.00 | 45.08 | O |
| ATOM | 931 | N | TYR | A | 219 | 3.469 | 18.584 | 11.392 | 1.00 | 44.36 | N |
| ATOM | 933 | CA | TYR | A | 219 | 4.400 | 17.711 | 10.678 | 1.00 | 43.70 | C |
| ATOM | 935 | CB | TYR | A | 219 | 4.928 | 16.590 | 11.579 | 1.00 | 43.47 | C |
| ATOM | 938 | CG | TYR | A | 219 | 5.750 | 15.571 | 10.814 | 1.00 | 41.81 | C |
| ATOM | 939 | CD1 | TYR | A | 219 | 7.111 | 15.761 | 10.604 | 1.00 | 40.13 | C |
| ATOM | 941 | CE1 | TYR | A | 219 | 7.861 | 14.840 | 9.887 | 1.00 | 39.10 | C |
| ATOM | 943 | CZ | TYR | A | 219 | 7.251 | 13.719 | 9.365 | 1.00 | 38.51 | C |
| ATOM | 944 | OH | TYR | A | 219 | 7.997 | 12.804 | 8.664 | 1.00 | 37.26 | O |
| ATOM | 946 | CE2 | TYR | A | 219 | 5.902 | 13.508 | 9.552 | 1.00 | 39.23 | C |
| ATOM | 948 | CD2 | TYR | A | 219 | 5.157 | 14.433 | 10.271 | 1.00 | 40.39 | C |
| ATOM | 950 | C | TYR | A | 219 | 3.757 | 17.079 | 9.451 | 1.00 | 43.66 | C |
| ATOM | 951 | O | TYR | A | 219 | 4.393 | 16.981 | 8.403 | 1.00 | 43.34 | O |
| ATOM | 952 | N | MET | A | 220 | 2.511 | 16.632 | 9.602 | 1.00 | 43.57 | N |
| ATOM | 954 | CA | MET | A | 220 | 1.783 | 15.976 | 8.520 | 1.00 | 43.79 | C |
| ATOM | 956 | CB | MET | A | 220 | 0.527 | 15.271 | 9.047 | 1.00 | 43.80 | C |
| ATOM | 959 | CG | MET | A | 220 | 0.798 | 14.008 | 9.855 | 1.00 | 44.24 | C |
| ATOM | 962 | SD | MET | A | 220 | 1.697 | 12.719 | 8.969 | 1.00 | 44.31 | S |
| ATOM | 963 | CE | MET | A | 220 | 2.266 | 11.717 | 10.350 | 1.00 | 45.41 | C |
| ATOM | 967 | C | MET | A | 220 | 1.403 | 16.966 | 7.427 | 1.00 | 43.70 | C |
| ATOM | 968 | O | MET | A | 220 | 1.397 | 16.616 | 6.253 | 1.00 | 43.71 | O |
| ATOM | 969 | N | MET | A | 221 | 1.081 | 18.195 | 7.823 | 1.00 | 43.80 | N |
| ATOM | 971 | CA | MET | A | 221 | 0.725 | 19.244 | 6.876 | 1.00 | 43.73 | C |
| ATOM | 973 | CB | MET | A | 221 | 0.194 | 20.490 | 7.603 | 1.00 | 43.86 | C |
| ATOM | 976 | CG | MET | A | 221 | −1.299 | 20.441 | 7.923 | 1.00 | 44.39 | C |

TABLE 2-continued

| ATOM | 979 | SD | MET | A | 221 | −1.929 | 21.917 | 8.780 | 1.00 | 45.76 | S |
| --- | --- | --- | --- | --- | --- | --- | --- | --- | --- | --- | --- |
| ATOM | 980 | CE | MET | A | 221 | −2.034 | 23.088 | 7.430 | 1.00 | 45.53 | C |
| ATOM | 984 | C | MET | A | 221 | 1.949 | 19.594 | 6.031 | 1.00 | 43.47 | C |
| ATOM | 985 | O | MET | A | 221 | 1.848 | 19.763 | 4.820 | 1.00 | 43.68 | O |
| ATOM | 986 | N | THR | A | 222 | 3.107 | 19.672 | 6.677 | 1.00 | 43.17 | N |
| ATOM | 988 | CA | THR | A | 222 | 4.363 | 19.990 | 6.000 | 1.00 | 43.08 | C |
| ATOM | 990 | CB | THR | A | 222 | 5.436 | 20.360 | 7.038 | 1.00 | 42.99 | C |
| ATOM | 992 | OG1 | THR | A | 222 | 5.061 | 21.578 | 7.693 | 1.00 | 43.55 | O |
| ATOM | 994 | CG2 | THR | A | 222 | 6.769 | 20.690 | 6.379 | 1.00 | 43.14 | C |
| ATOM | 998 | C | THR | A | 222 | 4.832 | 18.828 | 5.121 | 1.00 | 42.81 | C |
| ATOM | 999 | O | THR | A | 222 | 5.371 | 19.044 | 4.039 | 1.00 | 42.88 | O |
| ATOM | 1000 | N | LEU | A | 223 | 4.613 | 17.605 | 5.596 | 1.00 | 42.51 | N |
| ATOM | 1002 | CA | LEU | A | 223 | 4.975 | 16.393 | 4.865 | 1.00 | 42.31 | C |
| ATOM | 1004 | CB | LEU | A | 223 | 4.708 | 15.159 | 5.729 | 1.00 | 42.14 | C |
| ATOM | 1007 | CG | LEU | A | 223 | 4.908 | 13.775 | 5.101 | 1.00 | 41.06 | C |
| ATOM | 1009 | CD1 | LEU | A | 223 | 6.380 | 13.413 | 5.067 | 1.00 | 40.93 | C |
| ATOM | 1013 | CD2 | LEU | A | 223 | 4.108 | 12.735 | 5.861 | 1.00 | 40.31 | C |
| ATOM | 1017 | C | LEU | A | 223 | 4.169 | 16.295 | 3.571 | 1.00 | 42.54 | C |
| ATOM | 1018 | O | LEU | A | 223 | 4.695 | 15.909 | 2.538 | 1.00 | 42.18 | O |
| ATOM | 1019 | N | GLU | A | 224 | 2.890 | 16.651 | 3.661 | 1.00 | 42.95 | N |
| ATOM | 1021 | CA | GLU | A | 224 | 1.963 | 16.639 | 2.533 | 1.00 | 43.45 | C |
| ATOM | 1023 | CB | GLU | A | 224 | 0.531 | 16.819 | 3.051 | 1.00 | 43.53 | C |
| ATOM | 1026 | CG | GLU | A | 224 | −0.524 | 16.994 | 1.974 | 1.00 | 43.55 | C |
| ATOM | 1029 | CD | GLU | A | 224 | −1.872 | 16.450 | 2.389 | 1.00 | 44.23 | C |
| ATOM | 1030 | OE1 | GLU | A | 224 | −2.303 | 16.722 | 3.534 | 1.00 | 43.53 | O |
| ATOM | 1031 | OE2 | GLU | A | 224 | −2.495 | 15.743 | 1.570 | 1.00 | 44.14 | O |
| ATOM | 1032 | C | GLU | A | 224 | 2.294 | 17.719 | 1.493 | 1.00 | 43.76 | C |
| ATOM | 1033 | O | GLU | A | 224 | 2.033 | 17.537 | 0.303 | 1.00 | 43.94 | O |
| ATOM | 1034 | N | ASP | A | 225 | 2.857 | 18.838 | 1.945 | 1.00 | 44.19 | N |
| ATOM | 1036 | CA | ASP | A | 225 | 3.262 | 19.928 | 1.050 | 1.00 | 44.46 | C |
| ATOM | 1038 | CB | ASP | A | 225 | 3.520 | 21.217 | 1.832 | 1.00 | 44.71 | C |
| ATOM | 1041 | CG | ASP | A | 225 | 2.256 | 21.981 | 2.119 | 1.00 | 45.77 | C |
| ATOM | 1042 | OD1 | ASP | A | 225 | 2.351 | 23.172 | 2.476 | 1.00 | 48.21 | O |
| ATOM | 1043 | OD2 | ASP | A | 225 | 1.120 | 21.475 | 2.007 | 1.00 | 47.39 | O |
| ATOM | 1044 | C | ASP | A | 225 | 4.518 | 19.558 | 0.277 | 1.00 | 44.39 | C |
| ATOM | 1045 | O | ASP | A | 225 | 4.821 | 20.162 | −0.755 | 1.00 | 44.22 | O |
| ATOM | 1046 | N | HIS | A | 226 | 5.262 | 18.584 | 0.799 | 1.00 | 44.27 | N |
| ATOM | 1048 | CA | HIS | A | 226 | 6.459 | 18.098 | 0.131 | 1.00 | 44.09 | C |
| ATOM | 1050 | CB | HIS | A | 226 | 7.463 | 17.549 | 1.145 | 1.00 | 44.15 | C |
| ATOM | 1053 | CG | HIS | A | 226 | 8.301 | 18.616 | 1.772 | 1.00 | 44.28 | C |
| ATOM | 1054 | ND1 | HIS | A | 226 | 7.753 | 19.718 | 2.391 | 1.00 | 45.17 | N |
| ATOM | 1056 | CE1 | HIS | A | 226 | 8.721 | 20.501 | 2.833 | 1.00 | 45.12 | C |
| ATOM | 1058 | NE2 | HIS | A | 226 | 9.877 | 19.947 | 2.519 | 1.00 | 45.16 | N |
| ATOM | 1060 | CD2 | HIS | A | 226 | 9.642 | 18.772 | 1.846 | 1.00 | 44.95 | C |
| ATOM | 1062 | C | HIS | A | 226 | 6.122 | 17.092 | −0.974 | 1.00 | 43.77 | C |
| ATOM | 1063 | O | HIS | A | 226 | 7.003 | 16.694 | −1.726 | 1.00 | 43.67 | O |
| ATOM | 1064 | N | TYR | A | 227 | 4.858 | 16.671 | −1.054 | 1.00 | 43.53 | N |
| ATOM | 1066 | CA | TYR | A | 227 | 4.386 | 15.843 | −2.166 | 1.00 | 43.24 | C |
| ATOM | 1068 | CB | TYR | A | 227 | 3.173 | 14.985 | −1.796 | 1.00 | 42.79 | C |
| ATOM | 1071 | CG | TYR | A | 227 | 3.492 | 13.715 | −1.038 | 1.00 | 41.44 | C |
| ATOM | 1072 | CD1 | TYR | A | 227 | 3.569 | 13.718 | 0.351 | 1.00 | 39.66 | C |
| ATOM | 1074 | CE1 | TYR | A | 227 | 3.848 | 12.562 | 1.061 | 1.00 | 38.83 | C |
| ATOM | 1076 | CZ | TYR | A | 227 | 4.058 | 11.380 | 0.384 | 1.00 | 38.29 | C |
| ATOM | 1077 | OH | TYR | A | 227 | 4.332 | 10.235 | 1.104 | 1.00 | 35.79 | O |
| ATOM | 1079 | CE2 | TYR | A | 227 | 3.975 | 11.345 | −1.002 | 1.00 | 38.34 | C |
| ATOM | 1081 | CD2 | TYR | A | 227 | 3.693 | 12.509 | −1.704 | 1.00 | 39.56 | C |
| ATOM | 1083 | C | TYR | A | 227 | 3.976 | 16.854 | −3.225 | 1.00 | 43.62 | C |
| ATOM | 1084 | O | TYR | A | 227 | 3.233 | 17.790 | −2.931 | 1.00 | 43.60 | O |
| ATOM | 1085 | N | HIS | A | 228 | 4.459 | 16.668 | −4.449 | 1.00 | 44.08 | N |
| ATOM | 1087 | CA | HIS | A | 228 | 4.188 | 17.600 | −5.540 | 1.00 | 44.32 | C |
| ATOM | 1089 | CB | HIS | A | 228 | 5.161 | 17.377 | −6.703 | 1.00 | 44.52 | C |
| ATOM | 1092 | CG | HIS | A | 228 | 6.608 | 17.434 | −6.313 | 1.00 | 45.44 | C |
| ATOM | 1093 | ND1 | HIS | A | 228 | 7.627 | 17.287 | −7.230 | 1.00 | 46.38 | N |
| ATOM | 1095 | CE1 | HIS | A | 228 | 8.791 | 17.370 | −6.610 | 1.00 | 46.96 | C |
| ATOM | 1097 | NE2 | HIS | A | 228 | 8.565 | 17.564 | −5.322 | 1.00 | 46.74 | N |
| ATOM | 1099 | CD2 | HIS | A | 228 | 7.208 | 17.607 | −5.110 | 1.00 | 46.26 | C |
| ATOM | 1101 | C | HIS | A | 228 | 2.759 | 17.453 | −6.039 | 1.00 | 44.35 | C |
| ATOM | 1102 | O | HIS | A | 228 | 2.387 | 16.414 | −6.577 | 1.00 | 44.16 | O |
| ATOM | 1103 | N | SER | A | 229 | 1.966 | 18.507 | −5.867 | 1.00 | 44.54 | N |
| ATOM | 1105 | CA | SER | A | 229 | 0.572 | 18.503 | −6.312 | 1.00 | 44.82 | C |
| ATOM | 1107 | CB | SER | A | 229 | −0.187 | 19.685 | −5.698 | 1.00 | 44.86 | C |
| ATOM | 1110 | OG | SER | A | 229 | 0.450 | 20.919 | −5.997 | 1.00 | 45.69 | O |
| ATOM | 1112 | C | SER | A | 229 | 0.419 | 18.516 | −7.846 | 1.00 | 44.72 | C |
| ATOM | 1113 | O | SER | A | 229 | −0.682 | 18.310 | −8.352 | 1.00 | 44.75 | O |
| ATOM | 1114 | N | ASP | A | 230 | 1.516 | 18.744 | −8.570 | 1.00 | 44.70 | N |
| ATOM | 1116 | CA | ASP | A | 230 | 1.507 | 18.766 | −10.045 | 1.00 | 44.73 | C |
| ATOM | 1118 | CB | ASP | A | 230 | 2.383 | 19.907 | −10.595 | 1.00 | 44.90 | C |
| ATOM | 1121 | CG | ASP | A | 230 | 3.764 | 19.950 | −9.969 | 1.00 | 46.30 | C |
| ATOM | 1122 | OD1 | ASP | A | 230 | 3.904 | 20.499 | −8.848 | 1.00 | 47.79 | O |

TABLE 2-continued

| | | | | | | | | | | |
|---|---|---|---|---|---|---|---|---|---|---|
| ATOM | 1123 | OD2 | ASP | A | 230 | 4.772 | 19.466 | −10.527 | 1.00 | 48.34 O |
| ATOM | 1124 | C | ASP | A | 230 | 1.930 | 17.422 | −10.652 | 1.00 | 44.19 C |
| ATOM | 1125 | O | ASP | A | 230 | 2.049 | 17.289 | −11.873 | 1.00 | 44.36 O |
| ATOM | 1126 | N | VAL | A | 231 | 2.159 | 16.433 | −9.792 | 1.00 | 43.41 N |
| ATOM | 1128 | CA | VAL | A | 231 | 2.500 | 15.083 | −10.220 | 1.00 | 42.73 C |
| ATOM | 1130 | CB | VAL | A | 231 | 3.620 | 14.493 | −9.357 | 1.00 | 42.78 C |
| ATOM | 1132 | CG1 | VAL | A | 231 | 3.800 | 13.019 | −9.634 | 1.00 | 43.05 C |
| ATOM | 1136 | CG2 | VAL | A | 231 | 4.926 | 15.243 | −9.617 | 1.00 | 42.73 C |
| ATOM | 1140 | C | VAL | A | 231 | 1.194 | 14.300 | −10.113 | 1.00 | 42.11 C |
| ATOM | 1141 | O | VAL | A | 231 | 0.569 | 14.272 | −9.048 | 1.00 | 42.23 O |
| ATOM | 1142 | N | ALA | A | 232 | 0.795 | 13.671 | −11.218 | 1.00 | 41.16 N |
| ATOM | 1144 | CA | ALA | A | 232 | −0.508 | 13.005 | −11.341 | 1.00 | 40.51 C |
| ATOM | 1146 | CB | ALA | A | 232 | −0.712 | 12.530 | −12.793 | 1.00 | 40.50 C |
| ATOM | 1150 | C | ALA | A | 232 | −0.825 | 11.858 | −10.377 | 1.00 | 39.79 C |
| ATOM | 1151 | O | ALA | A | 232 | −1.914 | 11.822 | −9.803 | 1.00 | 39.74 O |
| ATOM | 1152 | N | TYR | A | 233 | 0.098 | 10.911 | −10.233 | 1.00 | 38.94 N |
| ATOM | 1154 | CA | TYR | A | 233 | −0.115 | 9.748 | −9.370 | 1.00 | 38.26 C |
| ATOM | 1156 | CB | TYR | A | 233 | 0.329 | 8.471 | −10.088 | 1.00 | 38.08 C |
| ATOM | 1159 | CG | TYR | A | 233 | 0.103 | 7.202 | −9.292 | 1.00 | 37.62 C |
| ATOM | 1160 | CD1 | TYR | A | 233 | −1.056 | 6.453 | −9.455 | 1.00 | 36.44 C |
| ATOM | 1162 | CE1 | TYR | A | 233 | −1.266 | 5.288 | −8.731 | 1.00 | 36.92 C |
| ATOM | 1164 | CZ | TYR | A | 233 | −0.311 | 4.861 | −7.810 | 1.00 | 37.45 C |
| ATOM | 1165 | OH | TYR | A | 233 | −0.510 | 3.709 | −7.083 | 1.00 | 36.72 O |
| ATOM | 1167 | CE2 | TYR | A | 233 | 0.847 | 5.589 | −7.623 | 1.00 | 37.58 C |
| ATOM | 1169 | CD2 | TYR | A | 233 | 1.054 | 6.751 | −8.370 | 1.00 | 38.07 C |
| ATOM | 1171 | C | TYR | A | 233 | 0.620 | 9.851 | −8.035 | 1.00 | 37.84 C |
| ATOM | 1172 | O | TYR | A | 233 | 0.026 | 9.646 | −6.975 | 1.00 | 37.74 O |
| ATOM | 1173 | N | HIS | A | 234 | 1.909 | 10.170 | −8.101 | 1.00 | 37.30 N |
| ATOM | 1175 | CA | HIS | A | 234 | 2.772 | 10.219 | −6.930 | 1.00 | 37.12 C |
| ATOM | 1177 | CB | HIS | A | 234 | 4.214 | 9.921 | −7.365 | 1.00 | 36.96 C |
| ATOM | 1180 | CG | HIS | A | 234 | 4.437 | 8.483 | −7.717 | 1.00 | 36.63 C |
| ATOM | 1181 | ND1 | HIS | A | 234 | 4.502 | 8.028 | −9.016 | 1.00 | 36.47 N |
| ATOM | 1183 | CE1 | HIS | A | 234 | 4.689 | 6.722 | −9.017 | 1.00 | 36.00 C |
| ATOM | 1185 | NE2 | HIS | A | 234 | 4.736 | 6.310 | −7.764 | 1.00 | 37.64 N |
| ATOM | 1187 | CD2 | HIS | A | 234 | 4.581 | 7.391 | −6.932 | 1.00 | 37.22 C |
| ATOM | 1189 | C | HIS | A | 234 | 2.659 | 11.512 | −6.104 | 1.00 | 37.06 C |
| ATOM | 1190 | O | HIS | A | 234 | 3.658 | 12.167 | −5.801 | 1.00 | 37.08 O |
| ATOM | 1191 | N | ASN | A | 235 | 1.427 | 11.848 | −5.728 | 1.00 | 36.86 N |
| ATOM | 1193 | CA | ASN | A | 235 | 1.130 | 13.023 | −4.917 | 1.00 | 36.82 C |
| ATOM | 1195 | CB | ASN | A | 235 | 0.104 | 13.924 | −5.619 | 1.00 | 36.77 C |
| ATOM | 1198 | CG | ASN | A | 235 | −1.095 | 13.154 | −6.152 | 1.00 | 37.29 C |
| ATOM | 1199 | OD1 | ASN | A | 235 | −1.834 | 12.543 | −5.394 | 1.00 | 37.64 O |
| ATOM | 1200 | ND2 | ASN | A | 235 | −1.285 | 13.178 | −7.471 | 1.00 | 37.29 N |
| ATOM | 1203 | C | ASN | A | 235 | 0.640 | 12.546 | −3.540 | 1.00 | 36.67 C |
| ATOM | 1204 | O | ASN | A | 235 | 0.666 | 11.348 | −3.256 | 1.00 | 36.65 O |
| ATOM | 1205 | N | SER | A | 236 | 0.191 | 13.468 | −2.692 | 1.00 | 36.57 N |
| ATOM | 1207 | CA | SER | A | 236 | −0.251 | 13.114 | −1.338 | 1.00 | 36.47 C |
| ATOM | 1209 | CB | SER | A | 236 | −0.481 | 14.372 | −0.502 | 1.00 | 36.45 C |
| ATOM | 1212 | OG | SER | A | 236 | −1.721 | 14.982 | −0.814 | 1.00 | 37.06 O |
| ATOM | 1214 | C | SER | A | 236 | −1.505 | 12.238 | −1.294 | 1.00 | 36.20 C |
| ATOM | 1215 | O | SER | A | 236 | −1.801 | 11.647 | −0.259 | 1.00 | 36.67 O |
| ATOM | 1216 | N | LEU | A | 237 | −2.251 | 12.175 | −2.394 | 1.00 | 35.41 N |
| ATOM | 1218 | CA | LEU | A | 237 | −3.443 | 11.330 | −2.458 | 1.00 | 34.82 C |
| ATOM | 1220 | CB | LEU | A | 237 | −4.234 | 11.600 | −3.743 | 1.00 | 35.21 C |
| ATOM | 1223 | CG | LEU | A | 237 | −5.646 | 11.017 | −3.828 | 1.00 | 36.56 C |
| ATOM | 1225 | CD1 | LEU | A | 237 | −6.465 | 11.318 | −2.572 | 1.00 | 37.71 C |
| ATOM | 1229 | CD2 | LEU | A | 237 | −6.340 | 11.551 | −5.067 | 1.00 | 37.98 C |
| ATOM | 1233 | C | LEU | A | 237 | −3.051 | 9.857 | −2.389 | 1.00 | 33.51 C |
| ATOM | 1234 | O | LEU | A | 237 | −3.733 | 9.054 | −1.745 | 1.00 | 34.00 O |
| ATOM | 1235 | N | HIS | A | 238 | −1.958 | 9.512 | −3.067 | 1.00 | 31.61 N |
| ATOM | 1237 | CA | HIS | A | 238 | −1.416 | 8.149 | −3.080 | 1.00 | 29.63 C |
| ATOM | 1239 | CB | HIS | A | 238 | −0.419 | 8.011 | −4.240 | 1.00 | 28.40 C |
| ATOM | 1242 | CG | HIS | A | 238 | 0.382 | 6.746 | −4.232 | 1.00 | 21.68 C |
| ATOM | 1243 | ND1 | HIS | A | 238 | −0.191 | 5.496 | −4.252 | 1.00 | 16.97 N |
| ATOM | 1245 | CE1 | HIS | A | 238 | 0.757 | 4.575 | −4.259 | 1.00 | 16.82 C |
| ATOM | 1247 | NE2 | HIS | A | 238 | 1.930 | 5.184 | −4.242 | 1.00 | 14.83 N |
| ATOM | 1249 | CD2 | HIS | A | 238 | 1.719 | 6.543 | −4.258 | 1.00 | 18.63 C |
| ATOM | 1251 | C | HIS | A | 238 | −0.761 | 7.799 | −1.725 | 1.00 | 30.29 C |
| ATOM | 1252 | O | HIS | A | 238 | −0.797 | 6.655 | −1.292 | 1.00 | 29.86 O |
| ATOM | 1253 | N | ALA | A | 239 | −0.143 | 8.776 | −1.075 | 1.00 | 31.00 N |
| ATOM | 1255 | CA | ALA | A | 239 | 0.458 | 8.536 | 0.235 | 1.00 | 31.77 C |
| ATOM | 1257 | CB | ALA | A | 239 | 1.212 | 9.748 | 0.713 | 1.00 | 31.87 C |
| ATOM | 1261 | C | ALA | A | 239 | −0.670 | 8.201 | 1.189 | 1.00 | 32.18 C |
| ATOM | 1262 | O | ALA | A | 239 | −0.624 | 7.199 | 1.889 | 1.00 | 32.54 O |
| ATOM | 1263 | N | ALA | A | 240 | −1.701 | 9.035 | 1.162 | 1.00 | 32.71 N |
| ATOM | 1265 | CA | ALA | A | 240 | −2.882 | 8.868 | 1.992 | 1.00 | 33.16 C |
| ATOM | 1267 | CB | ALA | A | 240 | −3.892 | 9.964 | 1.673 | 1.00 | 33.31 C |
| ATOM | 1271 | C | ALA | A | 240 | −3.529 | 7.497 | 1.809 | 1.00 | 33.54 C |
| ATOM | 1272 | O | ALA | A | 240 | −3.883 | 6.833 | 2.790 | 1.00 | 33.41 O |

TABLE 2-continued

| | | | | | | | | | | |
|---|---|---|---|---|---|---|---|---|---|---|
| ATOM | 1273 | N | ASP | A | 241 | −3.681 | 7.084 | 0.551 | 1.00 | 33.56 N |
| ATOM | 1275 | CA | ASP | A | 241 | −4.313 | 5.811 | 0.219 | 1.00 | 33.55 C |
| ATOM | 1277 | CB | ASP | A | 241 | −4.584 | 5.734 | −1.284 | 1.00 | 33.89 C |
| ATOM | 1280 | CG | ASP | A | 241 | −4.777 | 4.321 | −1.768 | 1.00 | 33.86 C |
| ATOM | 1281 | OD1 | ASP | A | 241 | −5.819 | 3.708 | −1.454 | 1.00 | 34.76 O |
| ATOM | 1282 | OD2 | ASP | A | 241 | −3.931 | 3.747 | −2.474 | 1.00 | 35.46 O |
| ATOM | 1283 | C | ASP | A | 241 | −3.477 | 4.619 | 0.660 | 1.00 | 33.68 C |
| ATOM | 1284 | O | ASP | A | 241 | −4.024 | 3.626 | 1.133 | 1.00 | 34.18 O |
| ATOM | 1285 | N | VAL | A | 242 | −2.159 | 4.717 | 0.498 | 1.00 | 33.52 N |
| ATOM | 1287 | CA | VAL | A | 242 | −1.238 | 3.658 | 0.903 | 1.00 | 33.66 C |
| ATOM | 1289 | CB | VAL | A | 242 | 0.195 | 3.888 | 0.334 | 1.00 | 33.34 C |
| ATOM | 1291 | CG1 | VAL | A | 242 | 1.197 | 2.897 | 0.909 | 1.00 | 33.22 C |
| ATOM | 1295 | CG2 | VAL | A | 242 | 0.193 | 3.767 | −1.187 | 1.00 | 33.91 C |
| ATOM | 1299 | C | VAL | A | 242 | −1.207 | 3.529 | 2.441 | 1.00 | 33.97 C |
| ATOM | 1300 | O | VAL | A | 242 | −1.154 | 2.419 | 2.964 | 1.00 | 33.96 O |
| ATOM | 1301 | N | ALA | A | 243 | −1.256 | 4.654 | 3.150 | 1.00 | 34.47 N |
| ATOM | 1303 | CA | ALA | A | 243 | −1.254 | 4.655 | 4.621 | 1.00 | 35.06 C |
| ATOM | 1305 | CB | ALA | A | 243 | −1.073 | 6.065 | 5.159 | 1.00 | 34.83 C |
| ATOM | 1309 | C | ALA | A | 243 | −2.543 | 4.052 | 5.155 | 1.00 | 35.72 C |
| ATOM | 1310 | O | ALA | A | 243 | −2.510 | 3.234 | 6.064 | 1.00 | 36.09 O |
| ATOM | 1311 | N | GLN | A | 244 | −3.671 | 4.454 | 4.569 | 1.00 | 36.58 N |
| ATOM | 1313 | CA | GLN | A | 244 | −4.994 | 3.960 | 4.950 | 1.00 | 37.00 C |
| ATOM | 1315 | CB | GLN | A | 244 | −6.091 | 4.724 | 4.198 | 1.00 | 37.06 C |
| ATOM | 1318 | CG | GLN | A | 244 | −7.511 | 4.510 | 4.737 | 1.00 | 37.24 C |
| ATOM | 1321 | CD | GLN | A | 244 | −8.280 | 3.394 | 4.037 | 1.00 | 37.71 C |
| ATOM | 1322 | OE1 | GLN | A | 244 | −8.043 | 3.104 | 2.869 | 1.00 | 38.46 O |
| ATOM | 1323 | NE2 | GLN | A | 244 | −9.210 | 2.773 | 4.756 | 1.00 | 38.28 N |
| ATOM | 1326 | C | GLN | A | 244 | −5.128 | 2.467 | 4.670 | 1.00 | 37.54 C |
| ATOM | 1327 | O | GLN | A | 244 | −5.712 | 1.737 | 5.463 | 1.00 | 37.82 O |
| ATOM | 1328 | N | SER | A | 245 | −4.594 | 2.026 | 3.535 | 1.00 | 37.99 N |
| ATOM | 1330 | CA | SER | A | 245 | −4.630 | 0.620 | 3.147 | 1.00 | 38.25 C |
| ATOM | 1332 | CB | SER | A | 245 | −4.096 | 0.438 | 1.718 | 1.00 | 38.27 C |
| ATOM | 1335 | OG | SER | A | 245 | −4.938 | 1.064 | 0.764 | 1.00 | 38.27 O |
| ATOM | 1337 | C | SER | A | 245 | −3.800 | −0.220 | 4.110 | 1.00 | 38.50 C |
| ATOM | 1338 | O | SER | A | 245 | −4.148 | −1.354 | 4.397 | 1.00 | 38.55 O |
| ATOM | 1339 | N | THR | A | 246 | −2.692 | 0.344 | 4.585 | 1.00 | 39.00 N |
| ATOM | 1341 | CA | THR | A | 246 | −1.806 | −0.327 | 5.534 | 1.00 | 39.42 C |
| ATOM | 1343 | CB | THR | A | 246 | −0.465 | 0.443 | 5.646 | 1.00 | 39.49 C |
| ATOM | 1345 | OG1 | THR | A | 246 | 0.322 | 0.221 | 4.467 | 1.00 | 39.12 O |
| ATOM | 1347 | CG2 | THR | A | 246 | 0.409 | −0.098 | 6.784 | 1.00 | 39.23 C |
| ATOM | 1351 | C | THR | A | 246 | −2.501 | −0.433 | 6.898 | 1.00 | 39.71 C |
| ATOM | 1352 | O | THR | A | 246 | −2.271 | −1.375 | 7.652 | 1.00 | 39.75 O |
| ATOM | 1353 | N | HIS | A | 247 | −3.348 | 0.547 | 7.192 | 1.00 | 40.03 N |
| ATOM | 1355 | CA | HIS | A | 247 | −4.147 | 0.579 | 8.411 | 1.00 | 40.40 C |
| ATOM | 1357 | CB | HIS | A | 247 | −4.873 | 1.929 | 8.508 | 1.00 | 40.45 C |
| ATOM | 1360 | CG | HIS | A | 247 | −5.964 | 1.969 | 9.528 | 1.00 | 40.63 C |
| ATOM | 1361 | ND1 | HIS | A | 247 | −5.739 | 1.759 | 10.870 | 1.00 | 40.70 N |
| ATOM | 1363 | CE1 | HIS | A | 247 | −6.880 | 1.864 | 11.527 | 1.00 | 40.79 C |
| ATOM | 1365 | NE2 | HIS | A | 247 | −7.837 | 2.135 | 10.658 | 1.00 | 40.59 N |
| ATOM | 1367 | CD2 | HIS | A | 247 | −7.289 | 2.211 | 9.401 | 1.00 | 40.55 C |
| ATOM | 1369 | C | HIS | A | 247 | −5.144 | −0.588 | 8.412 | 1.00 | 40.59 C |
| ATOM | 1370 | O | HIS | A | 247 | −5.424 | −1.175 | 9.461 | 1.00 | 40.17 O |
| ATOM | 1371 | N | VAL | A | 248 | −5.657 | −0.933 | 7.231 | 1.00 | 40.80 N |
| ATOM | 1373 | CA | VAL | A | 248 | −6.620 | −2.026 | 7.097 | 1.00 | 41.19 C |
| ATOM | 1375 | CB | VAL | A | 248 | −7.479 | −1.892 | 5.806 | 1.00 | 41.13 C |
| ATOM | 1377 | CG1 | VAL | A | 248 | −8.454 | −3.064 | 5.669 | 1.00 | 40.98 C |
| ATOM | 1381 | CG2 | VAL | A | 248 | −8.242 | −0.573 | 5.801 | 1.00 | 40.63 C |
| ATOM | 1385 | C | VAL | A | 248 | −5.932 | −3.395 | 7.129 | 1.00 | 41.68 C |
| ATOM | 1386 | O | VAL | A | 248 | −6.497 | −4.358 | 7.643 | 1.00 | 42.21 O |
| ATOM | 1387 | N | LEU | A | 249 | −4.712 | −3.479 | 6.606 | 1.00 | 42.23 N |
| ATOM | 1389 | CA | LEU | A | 249 | −3.983 | −4.749 | 6.561 | 1.00 | 42.61 C |
| ATOM | 1391 | CB | LEU | A | 249 | −2.896 | −4.709 | 5.482 | 1.00 | 42.43 C |
| ATOM | 1394 | CG | LEU | A | 249 | −3.389 | −4.520 | 4.038 | 1.00 | 42.54 C |
| ATOM | 1396 | CD1 | LEU | A | 249 | −2.213 | −4.252 | 3.102 | 1.00 | 42.17 C |
| ATOM | 1400 | CD2 | LEU | A | 249 | −4.206 | −5.714 | 3.538 | 1.00 | 42.10 C |
| ATOM | 1404 | C | LEU | A | 249 | −3.382 | −5.128 | 7.921 | 1.00 | 43.23 C |
| ATOM | 1405 | O | LEU | A | 249 | −3.082 | −6.298 | 8.160 | 1.00 | 43.25 O |
| ATOM | 1406 | N | LEU | A | 250 | −3.216 | −4.144 | 8.803 | 1.00 | 43.93 N |
| ATOM | 1408 | CA | LEU | A | 250 | −2.680 | −4.382 | 10.142 | 1.00 | 44.55 C |
| ATOM | 1410 | CB | LEU | A | 250 | −2.126 | −3.086 | 10.746 | 1.00 | 44.45 C |
| ATOM | 1413 | CG | LEU | A | 250 | −0.780 | −2.599 | 10.208 | 1.00 | 43.66 C |
| ATOM | 1415 | CD1 | LEU | A | 250 | −0.559 | −1.138 | 10.560 | 1.00 | 43.42 C |
| ATOM | 1419 | CD2 | LEU | A | 250 | 0.361 | −3.451 | 10.727 | 1.00 | 43.27 C |
| ATOM | 1423 | C | LEU | A | 250 | −3.759 | −4.966 | 11.061 | 1.00 | 45.37 C |
| ATOM | 1424 | O | LEU | A | 250 | −3.443 | −5.575 | 12.080 | 1.00 | 45.48 O |
| ATOM | 1425 | N | SER | A | 251 | −5.023 | −4.760 | 10.688 | 1.00 | 46.38 N |
| ATOM | 1427 | CA | SER | A | 251 | −6.174 | −5.259 | 11.436 | 1.00 | 47.15 C |
| ATOM | 1429 | CB | SER | A | 251 | −7.338 | −4.273 | 11.326 | 1.00 | 47.15 C |
| ATOM | 1432 | OG | SER | A | 251 | −7.037 | −3.059 | 11.984 | 1.00 | 47.96 O |

TABLE 2-continued

| ATOM | 1434 | C | SER | A | 251 | −6.663 | −6.624 | 10.955 | 1.00 | 47.78 | C |
|---|---|---|---|---|---|---|---|---|---|---|---|
| ATOM | 1435 | O | SER | A | 251 | −7.558 | −7.198 | 11.573 | 1.00 | 47.99 | O |
| ATOM | 1436 | N | THR | A | 252 | −6.103 | −7.134 | 9.854 | 1.00 | 48.45 | N |
| ATOM | 1438 | CA | THR | A | 252 | −6.520 | −8.432 | 9.316 | 1.00 | 48.84 | C |
| ATOM | 1440 | CB | THR | A | 252 | −5.682 | −8.827 | 8.060 | 1.00 | 48.81 | C |
| ATOM | 1442 | OG1 | THR | A | 252 | −6.291 | −9.943 | 7.397 | 1.00 | 49.03 | O |
| ATOM | 1444 | CG2 | THR | A | 252 | −4.282 | −9.324 | 8.423 | 1.00 | 48.81 | C |
| ATOM | 1448 | C | THR | A | 252 | −6.438 | −9.488 | 10.432 | 1.00 | 49.05 | C |
| ATOM | 1449 | O | THR | A | 252 | −5.427 | −9.559 | 11.128 | 1.00 | 49.24 | O |
| ATOM | 1450 | N | PRO | A | 253 | −7.495 | −10.286 | 10.613 | 1.00 | 49.25 | N |
| ATOM | 1451 | CA | PRO | A | 253 | −7.556 | −11.265 | 11.714 | 1.00 | 49.26 | C |
| ATOM | 1453 | CB | PRO | A | 253 | −8.825 | −12.071 | 11.398 | 1.00 | 49.30 | C |
| ATOM | 1456 | CG | PRO | A | 253 | −9.673 | −11.153 | 10.594 | 1.00 | 49.34 | C |
| ATOM | 1459 | CD | PRO | A | 253 | −8.716 | −10.322 | 9.783 | 1.00 | 49.31 | C |
| ATOM | 1462 | C | PRO | A | 253 | −6.358 | −12.209 | 11.861 | 1.00 | 49.30 | C |
| ATOM | 1463 | O | PRO | A | 253 | −6.043 | −12.602 | 12.991 | 1.00 | 49.25 | O |
| ATOM | 1464 | N | ALA | A | 254 | −5.706 | −12.559 | 10.753 | 1.00 | 49.24 | N |
| ATOM | 1466 | CA | ALA | A | 254 | −4.566 | −13.477 | 10.782 | 1.00 | 49.18 | C |
| ATOM | 1468 | CB | ALA | A | 254 | −4.209 | −13.929 | 9.364 | 1.00 | 49.27 | C |
| ATOM | 1472 | C | ALA | A | 254 | −3.333 | −12.890 | 11.479 | 1.00 | 49.15 | C |
| ATOM | 1473 | O | ALA | A | 254 | −2.496 | −13.638 | 11.969 | 1.00 | 49.16 | O |
| ATOM | 1474 | N | LEU | A | 255 | −3.215 | −11.564 | 11.509 | 1.00 | 49.12 | N |
| ATOM | 1476 | CA | LEU | A | 255 | −2.086 | −10.888 | 12.159 | 1.00 | 49.13 | C |
| ATOM | 1478 | CB | LEU | A | 255 | −1.462 | −9.872 | 11.194 | 1.00 | 49.01 | C |
| ATOM | 1481 | CG | LEU | A | 255 | −1.130 | −10.391 | 9.790 | 1.00 | 48.91 | C |
| ATOM | 1483 | CD1 | LEU | A | 255 | −0.806 | −9.244 | 8.842 | 1.00 | 48.88 | C |
| ATOM | 1487 | CD2 | LEU | A | 255 | 0.024 | −11.376 | 9.847 | 1.00 | 48.71 | C |
| ATOM | 1491 | C | LEU | A | 255 | −2.504 | −10.186 | 13.461 | 1.00 | 49.16 | C |
| ATOM | 1492 | O | LEU | A | 255 | −1.832 | −9.264 | 13.920 | 1.00 | 49.01 | O |
| ATOM | 1493 | N | ASP | A | 256 | −3.601 | −10.647 | 14.056 | 1.00 | 49.25 | N |
| ATOM | 1495 | CA | ASP | A | 256 | −4.149 | −10.052 | 15.276 | 1.00 | 49.48 | C |
| ATOM | 1497 | CB | ASP | A | 256 | −5.536 | −10.643 | 15.567 | 1.00 | 49.63 | C |
| ATOM | 1500 | CG | ASP | A | 256 | −6.308 | −9.849 | 16.608 | 1.00 | 50.50 | C |
| ATOM | 1501 | OD1 | ASP | A | 256 | −6.528 | −8.636 | 16.394 | 1.00 | 51.45 | O |
| ATOM | 1502 | OD2 | ASP | A | 256 | −6.744 | −10.357 | 17.666 | 1.00 | 51.37 | O |
| ATOM | 1503 | C | ASP | A | 256 | −3.233 | −10.257 | 16.481 | 1.00 | 49.14 | C |
| ATOM | 1504 | O | ASP | A | 256 | −2.839 | −11.380 | 16.776 | 1.00 | 49.23 | O |
| ATOM | 1505 | N | ALA | A | 257 | −2.891 | −9.156 | 17.151 | 1.00 | 48.96 | N |
| ATOM | 1507 | CA | ALA | A | 257 | −2.042 | −9.154 | 18.356 | 1.00 | 48.83 | C |
| ATOM | 1509 | CB | ALA | A | 257 | −2.681 | −10.008 | 19.467 | 1.00 | 48.83 | C |
| ATOM | 1513 | C | ALA | A | 257 | −0.591 | −9.589 | 18.117 | 1.00 | 48.63 | C |
| ATOM | 1514 | O | ALA | A | 257 | 0.148 | −9.847 | 19.072 | 1.00 | 48.67 | O |
| ATOM | 1515 | N | VAL | A | 258 | −0.182 | −9.627 | 16.851 | 1.00 | 48.34 | N |
| ATOM | 1517 | CA | VAL | A | 258 | 1.157 | −10.065 | 16.462 | 1.00 | 48.03 | C |
| ATOM | 1519 | CB | VAL | A | 258 | 1.115 | −10.716 | 15.053 | 1.00 | 48.18 | C |
| ATOM | 1521 | CG1 | VAL | A | 258 | 2.520 | −10.919 | 14.472 | 1.00 | 48.36 | C |
| ATOM | 1525 | CG2 | VAL | A | 258 | 0.363 | −12.042 | 15.109 | 1.00 | 48.10 | C |
| ATOM | 1529 | C | VAL | A | 258 | 2.180 | −8.927 | 16.478 | 1.00 | 47.69 | C |
| ATOM | 1530 | O | VAL | A | 258 | 3.363 | −9.159 | 16.731 | 1.00 | 47.56 | O |
| ATOM | 1531 | N | PHE | A | 259 | 1.724 | −7.704 | 16.218 | 1.00 | 47.39 | N |
| ATOM | 1533 | CA | PHE | A | 259 | 2.615 | −6.549 | 16.150 | 1.00 | 47.11 | C |
| ATOM | 1535 | CB | PHE | A | 259 | 2.314 | −5.738 | 14.885 | 1.00 | 46.96 | C |
| ATOM | 1538 | CG | PHE | A | 259 | 2.557 | −6.498 | 13.608 | 1.00 | 45.91 | C |
| ATOM | 1539 | CD1 | PHE | A | 259 | 1.510 | −6.786 | 12.744 | 1.00 | 45.32 | C |
| ATOM | 1541 | CE1 | PHE | A | 259 | 1.735 | −7.495 | 11.571 | 1.00 | 44.77 | C |
| ATOM | 1543 | CZ | PHE | A | 259 | 3.013 | −7.922 | 11.256 | 1.00 | 44.42 | C |
| ATOM | 1545 | CE2 | PHE | A | 259 | 4.063 | −7.641 | 12.110 | 1.00 | 44.79 | C |
| ATOM | 1547 | CD2 | PHE | A | 259 | 3.833 | −6.934 | 13.279 | 1.00 | 45.12 | C |
| ATOM | 1549 | C | PHE | A | 259 | 2.512 | −5.646 | 17.370 | 1.00 | 47.27 | C |
| ATOM | 1550 | O | PHE | A | 259 | 1.424 | −5.425 | 17.907 | 1.00 | 47.28 | O |
| ATOM | 1551 | N | THR | A | 260 | 3.661 | −5.120 | 17.792 | 1.00 | 47.38 | N |
| ATOM | 1553 | CA | THR | A | 260 | 3.735 | −4.203 | 18.925 | 1.00 | 47.45 | C |
| ATOM | 1555 | CB | THR | A | 260 | 5.198 | −4.045 | 19.430 | 1.00 | 47.54 | C |
| ATOM | 1557 | OG1 | THR | A | 260 | 6.044 | −3.569 | 18.373 | 1.00 | 47.87 | O |
| ATOM | 1559 | CG2 | THR | A | 260 | 5.810 | −5.390 | 19.818 | 1.00 | 47.77 | C |
| ATOM | 1563 | C | THR | A | 260 | 3.202 | −2.843 | 18.495 | 1.00 | 47.31 | C |
| ATOM | 1564 | O | THR | A | 260 | 2.979 | −2.601 | 17.310 | 1.00 | 47.31 | O |
| ATOM | 1565 | N | ASP | A | 261 | 3.001 | −1.956 | 19.462 | 1.00 | 47.12 | N |
| ATOM | 1567 | CA | ASP | A | 261 | 2.509 | −0.613 | 19.177 | 1.00 | 46.99 | C |
| ATOM | 1569 | CB | ASP | A | 261 | 2.174 | 0.122 | 20.480 | 1.00 | 47.11 | C |
| ATOM | 1572 | CG | ASP | A | 261 | 0.960 | −0.455 | 21.179 | 1.00 | 47.96 | C |
| ATOM | 1573 | OD1 | ASP | A | 261 | 0.013 | −0.887 | 20.481 | 1.00 | 48.08 | O |
| ATOM | 1574 | OD2 | ASP | A | 261 | 0.864 | −0.514 | 22.427 | 1.00 | 49.47 | O |
| ATOM | 1575 | C | ASP | A | 261 | 3.531 | 0.194 | 18.376 | 1.00 | 46.49 | C |
| ATOM | 1576 | O | ASP | A | 261 | 3.161 | 1.061 | 17.586 | 1.00 | 46.45 | O |
| ATOM | 1577 | N | LEU | A | 262 | 4.812 | −0.086 | 18.603 | 1.00 | 45.94 | N |
| ATOM | 1579 | CA | LEU | A | 262 | 5.898 | 0.603 | 17.917 | 1.00 | 45.56 | C |
| ATOM | 1581 | CB | LEU | A | 262 | 7.225 | 0.309 | 18.622 | 1.00 | 45.48 | C |
| ATOM | 1584 | CG | LEU | A | 262 | 8.472 | 1.045 | 18.132 | 1.00 | 45.43 | C |

TABLE 2-continued

| ATOM | 1586 | CD1 | LEU | A | 262 | 8.329 | 2.559 | 18.256 | 1.00 | 45.27 | C |
| --- | --- | --- | --- | --- | --- | --- | --- | --- | --- | --- | --- |
| ATOM | 1590 | CD2 | LEU | A | 262 | 9.684 | 0.553 | 18.899 | 1.00 | 45.55 | C |
| ATOM | 1594 | C | LEU | A | 262 | 5.975 | 0.180 | 16.449 | 1.00 | 45.38 | C |
| ATOM | 1595 | O | LEU | A | 262 | 6.259 | 0.995 | 15.579 | 1.00 | 45.06 | O |
| ATOM | 1596 | N | GLU | A | 263 | 5.723 | −1.099 | 16.194 | 1.00 | 45.25 | N |
| ATOM | 1598 | CA | GLU | A | 263 | 5.747 | −1.649 | 14.843 | 1.00 | 45.20 | C |
| ATOM | 1600 | CB | GLU | A | 263 | 5.801 | −3.179 | 14.896 | 1.00 | 45.16 | C |
| ATOM | 1603 | CG | GLU | A | 263 | 7.156 | −3.687 | 15.367 | 1.00 | 45.10 | C |
| ATOM | 1606 | CD | GLU | A | 263 | 7.227 | −5.185 | 15.586 | 1.00 | 45.07 | C |
| ATOM | 1607 | OE1 | GLU | A | 263 | 6.177 | −5.853 | 15.685 | 1.00 | 45.51 | O |
| ATOM | 1608 | OE2 | GLU | A | 263 | 8.361 | −5.697 | 15.665 | 1.00 | 45.19 | O |
| ATOM | 1609 | C | GLU | A | 263 | 4.547 | −1.166 | 14.026 | 1.00 | 45.13 | C |
| ATOM | 1610 | O | GLU | A | 263 | 4.666 | −0.931 | 12.828 | 1.00 | 45.13 | O |
| ATOM | 1611 | N | ILE | A | 264 | 3.401 | −1.015 | 14.684 | 1.00 | 45.00 | N |
| ATOM | 1613 | CA | ILE | A | 264 | 2.186 | −0.522 | 14.039 | 1.00 | 44.84 | C |
| ATOM | 1615 | CB | ILE | A | 264 | 0.966 | −0.698 | 14.986 | 1.00 | 44.88 | C |
| ATOM | 1617 | CG1 | ILE | A | 264 | 0.514 | −2.162 | 14.982 | 1.00 | 45.14 | C |
| ATOM | 1620 | CD1 | ILE | A | 264 | −0.384 | −2.542 | 16.150 | 1.00 | 45.35 | C |
| ATOM | 1624 | CG2 | ILE | A | 264 | −0.196 | 0.218 | 14.588 | 1.00 | 44.98 | C |
| ATOM | 1628 | C | ILE | A | 264 | 2.381 | 0.944 | 13.641 | 1.00 | 44.59 | C |
| ATOM | 1629 | O | ILE | A | 264 | 1.931 | 1.372 | 12.577 | 1.00 | 44.75 | O |
| ATOM | 1630 | N | LEU | A | 265 | 3.062 | 1.694 | 14.503 | 1.00 | 44.09 | N |
| ATOM | 1632 | CA | LEU | A | 265 | 3.360 | 3.104 | 14.265 | 1.00 | 43.72 | C |
| ATOM | 1634 | CB | LEU | A | 265 | 3.950 | 3.735 | 15.531 | 1.00 | 43.80 | C |
| ATOM | 1637 | CG | LEU | A | 265 | 4.499 | 5.164 | 15.442 | 1.00 | 44.29 | C |
| ATOM | 1639 | CD1 | LEU | A | 265 | 3.364 | 6.163 | 15.323 | 1.00 | 44.75 | C |
| ATOM | 1643 | CD2 | LEU | A | 265 | 5.361 | 5.481 | 16.654 | 1.00 | 45.06 | C |
| ATOM | 1647 | C | LEU | A | 265 | 4.350 | 3.289 | 13.123 | 1.00 | 43.10 | C |
| ATOM | 1648 | O | LEU | A | 265 | 4.246 | 4.247 | 12.359 | 1.00 | 43.02 | O |
| ATOM | 1649 | N | ALA | A | 266 | 5.316 | 2.378 | 13.034 | 1.00 | 42.29 | N |
| ATOM | 1651 | CA | ALA | A | 266 | 6.370 | 2.442 | 12.028 | 1.00 | 41.65 | C |
| ATOM | 1653 | CB | ALA | A | 266 | 7.496 | 1.485 | 12.392 | 1.00 | 41.67 | C |
| ATOM | 1657 | C | ALA | A | 266 | 5.853 | 2.124 | 10.632 | 1.00 | 40.98 | C |
| ATOM | 1658 | O | ALA | A | 266 | 6.321 | 2.701 | 9.655 | 1.00 | 40.87 | O |
| ATOM | 1659 | N | ALA | A | 267 | 4.894 | 1.206 | 10.552 | 1.00 | 40.20 | N |
| ATOM | 1661 | CA | ALA | A | 267 | 4.314 | 0.783 | 9.283 | 1.00 | 39.76 | C |
| ATOM | 1663 | CB | ALA | A | 267 | 3.542 | −0.520 | 9.458 | 1.00 | 39.65 | C |
| ATOM | 1667 | C | ALA | A | 267 | 3.413 | 1.852 | 8.686 | 1.00 | 39.15 | C |
| ATOM | 1668 | O | ALA | A | 267 | 3.405 | 2.046 | 7.478 | 1.00 | 39.29 | O |
| ATOM | 1669 | N | ILE | A | 268 | 2.646 | 2.534 | 9.531 | 1.00 | 38.44 | N |
| ATOM | 1671 | CA | ILE | A | 268 | 1.746 | 3.586 | 9.061 | 1.00 | 37.82 | C |
| ATOM | 1673 | CB | ILE | A | 268 | 0.632 | 3.858 | 10.104 | 1.00 | 37.92 | C |
| ATOM | 1675 | CG1 | ILE | A | 268 | −0.323 | 2.659 | 10.165 | 1.00 | 38.53 | C |
| ATOM | 1678 | CD1 | ILE | A | 268 | −1.088 | 2.544 | 11.469 | 1.00 | 39.25 | C |
| ATOM | 1682 | CG2 | ILE | A | 268 | −0.158 | 5.123 | 9.758 | 1.00 | 37.92 | C |
| ATOM | 1686 | C | ILE | A | 268 | 2.548 | 4.846 | 8.722 | 1.00 | 36.81 | C |
| ATOM | 1687 | O | ILE | A | 268 | 2.243 | 5.542 | 7.757 | 1.00 | 36.57 | O |
| ATOM | 1688 | N | PHE | A | 269 | 3.576 | 5.125 | 9.517 | 1.00 | 35.60 | N |
| ATOM | 1690 | CA | PHE | A | 269 | 4.440 | 6.275 | 9.277 | 1.00 | 34.36 | C |
| ATOM | 1692 | CB | PHE | A | 269 | 5.388 | 6.520 | 10.448 | 1.00 | 33.57 | C |
| ATOM | 1695 | CG | PHE | A | 269 | 6.396 | 7.597 | 10.179 | 1.00 | 30.93 | C |
| ATOM | 1696 | CD1 | PHE | A | 269 | 6.007 | 8.926 | 10.149 | 1.00 | 29.26 | C |
| ATOM | 1698 | CE1 | PHE | A | 269 | 6.920 | 9.921 | 9.889 | 1.00 | 28.19 | C |
| ATOM | 1700 | CZ | PHE | A | 269 | 8.241 | 9.599 | 9.650 | 1.00 | 27.73 | C |
| ATOM | 1702 | CE2 | PHE | A | 269 | 8.641 | 8.277 | 9.667 | 1.00 | 27.56 | C |
| ATOM | 1704 | CD2 | PHE | A | 269 | 7.720 | 7.284 | 9.922 | 1.00 | 28.36 | C |
| ATOM | 1706 | C | PHE | A | 269 | 5.267 | 6.095 | 8.007 | 1.00 | 34.11 | C |
| ATOM | 1707 | O | PHE | A | 269 | 5.537 | 7.060 | 7.310 | 1.00 | 33.89 | O |
| ATOM | 1708 | N | ALA | A | 270 | 5.691 | 4.865 | 7.741 | 1.00 | 33.93 | N |
| ATOM | 1710 | CA | ALA | A | 270 | 6.483 | 4.554 | 6.557 | 1.00 | 33.85 | C |
| ATOM | 1712 | CB | ALA | A | 270 | 6.979 | 3.110 | 6.598 | 1.00 | 33.80 | C |
| ATOM | 1716 | C | ALA | A | 270 | 5.623 | 4.772 | 5.335 | 1.00 | 33.84 | C |
| ATOM | 1717 | O | ALA | A | 270 | 6.049 | 5.400 | 4.373 | 1.00 | 34.23 | O |
| ATOM | 1718 | N | ALA | A | 271 | 4.405 | 4.246 | 5.386 | 1.00 | 33.62 | N |
| ATOM | 1720 | CA | ALA | A | 271 | 3.443 | 4.405 | 4.310 | 1.00 | 33.18 | C |
| ATOM | 1722 | CB | ALA | A | 271 | 2.143 | 3.715 | 4.674 | 1.00 | 33.31 | C |
| ATOM | 1726 | C | ALA | A | 271 | 3.190 | 5.882 | 4.021 | 1.00 | 32.76 | C |
| ATOM | 1727 | O | ALA | A | 271 | 3.079 | 6.270 | 2.866 | 1.00 | 32.34 | O |
| ATOM | 1728 | N | ALA | A | 272 | 3.127 | 6.702 | 5.074 | 1.00 | 32.14 | N |
| ATOM | 1730 | CA | ALA | A | 272 | 2.860 | 8.143 | 4.934 | 1.00 | 31.67 | C |
| ATOM | 1732 | CB | ALA | A | 272 | 2.480 | 8.739 | 6.286 | 1.00 | 31.80 | C |
| ATOM | 1736 | C | ALA | A | 272 | 4.006 | 8.960 | 4.314 | 1.00 | 31.14 | C |
| ATOM | 1737 | O | ALA | A | 272 | 3.770 | 10.026 | 3.751 | 1.00 | 31.31 | O |
| ATOM | 1738 | N | ILE | A | 273 | 5.242 | 8.485 | 4.439 | 1.00 | 30.43 | N |
| ATOM | 1740 | CA | ILE | A | 273 | 6.398 | 9.197 | 3.885 | 1.00 | 29.79 | C |
| ATOM | 1742 | CB | ILE | A | 273 | 7.495 | 9.362 | 4.973 | 1.00 | 29.76 | C |
| ATOM | 1744 | CG1 | ILE | A | 273 | 8.187 | 8.026 | 5.253 | 1.00 | 30.89 | C |
| ATOM | 1747 | CD1 | ILE | A | 273 | 9.525 | 8.169 | 5.990 | 1.00 | 32.18 | C |
| ATOM | 1751 | CG2 | ILE | A | 273 | 6.927 | 9.962 | 6.272 | 1.00 | 30.27 | C |

TABLE 2-continued

| ATOM | 1755 | C | ILE | A | 273 | 7.051 | 8.481 | 2.695 | 1.00 | 28.69 | C |
| --- | --- | --- | --- | --- | --- | --- | --- | --- | --- | --- | --- |
| ATOM | 1756 | O | ILE | A | 273 | 8.000 | 9.001 | 2.119 | 1.00 | 28.40 | O |
| ATOM | 1757 | N | HIS | A | 274 | 6.545 | 7.306 | 2.340 | 1.00 | 27.27 | N |
| ATOM | 1759 | CA | HIS | A | 274 | 7.225 | 6.431 | 1.388 | 1.00 | 26.68 | C |
| ATOM | 1761 | CB | HIS | A | 274 | 6.569 | 5.038 | 1.369 | 1.00 | 25.99 | C |
| ATOM | 1764 | CG | HIS | A | 274 | 5.480 | 4.910 | 0.366 | 1.00 | 21.50 | C |
| ATOM | 1765 | ND1 | HIS | A | 274 | 4.276 | 5.576 | 0.490 | 1.00 | 18.68 | N |
| ATOM | 1767 | CE1 | HIS | A | 274 | 3.527 | 5.307 | −0.572 | 1.00 | 15.89 | C |
| ATOM | 1769 | NE2 | HIS | A | 274 | 4.201 | 4.485 | −1.359 | 1.00 | 2.00 | N |
| ATOM | 1771 | CD2 | HIS | A | 274 | 5.430 | 4.238 | −0.813 | 1.00 | 13.55 | C |
| ATOM | 1773 | C | HIS | A | 274 | 7.405 | 6.937 | −0.053 | 1.00 | 27.11 | C |
| ATOM | 1774 | O | HIS | A | 274 | 8.228 | 6.383 | −0.763 | 1.00 | 27.48 | O |
| ATOM | 1775 | N | ASP | A | 275 | 6.658 | 7.957 | −0.473 | 1.00 | 27.20 | N |
| ATOM | 1777 | CA | ASP | A | 275 | 6.772 | 8.509 | −1.838 | 1.00 | 27.62 | C |
| ATOM | 1779 | CB | ASP | A | 275 | 5.546 | 8.116 | −2.700 | 1.00 | 26.90 | C |
| ATOM | 1782 | CG | ASP | A | 275 | 5.738 | 6.804 | −3.471 | 1.00 | 27.14 | C |
| ATOM | 1783 | OD1 | ASP | A | 275 | 6.907 | 6.432 | −3.737 | 1.00 | 29.27 | O |
| ATOM | 1784 | OD2 | ASP | A | 275 | 4.773 | 6.056 | −3.844 | 1.00 | 18.91 | O |
| ATOM | 1785 | C | ASP | A | 275 | 6.924 | 10.045 | −1.812 | 1.00 | 27.97 | C |
| ATOM | 1786 | O | ASP | A | 275 | 6.750 | 10.699 | −2.845 | 1.00 | 27.71 | O |
| ATOM | 1787 | N | VAL | A | 276 | 7.284 | 10.601 | −0.648 | 1.00 | 28.24 | N |
| ATOM | 1789 | CA | VAL | A | 276 | 7.396 | 12.056 | −0.463 | 1.00 | 28.56 | C |
| ATOM | 1791 | CB | VAL | A | 276 | 7.656 | 12.438 | 1.027 | 1.00 | 28.39 | C |
| ATOM | 1793 | CG1 | VAL | A | 276 | 9.112 | 12.225 | 1.417 | 1.00 | 28.35 | C |
| ATOM | 1797 | CG2 | VAL | A | 276 | 7.260 | 13.878 | 1.276 | 1.00 | 28.52 | C |
| ATOM | 1801 | C | VAL | A | 276 | 8.462 | 12.733 | −1.326 | 1.00 | 29.01 | C |
| ATOM | 1802 | O | VAL | A | 276 | 9.580 | 12.248 | −1.451 | 1.00 | 28.63 | O |
| ATOM | 1803 | N | ASP | A | 277 | 8.114 | 13.900 | −1.856 | 1.00 | 29.91 | N |
| ATOM | 1805 | CA | ASP | A | 277 | 8.982 | 14.644 | −2.768 | 1.00 | 30.69 | C |
| ATOM | 1807 | CB | ASP | A | 277 | 10.264 | 15.097 | −2.061 | 1.00 | 30.79 | C |
| ATOM | 1810 | CG | ASP | A | 277 | 10.964 | 16.244 | −2.783 | 1.00 | 30.07 | C |
| ATOM | 1811 | OD1 | ASP | A | 277 | 10.302 | 17.240 | −3.121 | 1.00 | 29.78 | O |
| ATOM | 1812 | OD2 | ASP | A | 277 | 12.182 | 16.246 | −3.033 | 1.00 | 30.12 | O |
| ATOM | 1813 | C | ASP | A | 277 | 9.299 | 13.825 | −4.027 | 1.00 | 31.23 | C |
| ATOM | 1814 | O | ASP | A | 277 | 10.396 | 13.903 | −4.560 | 1.00 | 31.47 | O |
| ATOM | 1815 | N | HIS | A | 278 | 8.343 | 13.025 | −4.484 | 1.00 | 32.33 | N |
| ATOM | 1817 | CA | HIS | A | 278 | 8.527 | 12.238 | −5.713 | 1.00 | 33.45 | C |
| ATOM | 1819 | CB | HIS | A | 278 | 7.425 | 11.181 | −5.859 | 1.00 | 33.18 | C |
| ATOM | 1822 | CG | HIS | A | 278 | 7.755 | 10.069 | −6.807 | 1.00 | 33.55 | C |
| ATOM | 1823 | ND1 | HIS | A | 278 | 7.900 | 10.262 | −8.166 | 1.00 | 33.38 | N |
| ATOM | 1825 | CE1 | HIS | A | 278 | 8.169 | 9.107 | −8.747 | 1.00 | 33.33 | C |
| ATOM | 1827 | NE2 | HIS | A | 278 | 8.189 | 8.168 | −7.818 | 1.00 | 33.65 | N |
| ATOM | 1829 | CD2 | HIS | A | 278 | 7.928 | 8.743 | −6.597 | 1.00 | 33.20 | C |
| ATOM | 1831 | C | HIS | A | 278 | 8.483 | 13.225 | −6.881 | 1.00 | 34.25 | C |
| ATOM | 1832 | O | HIS | A | 278 | 7.529 | 13.986 | −6.987 | 1.00 | 34.30 | O |
| ATOM | 1833 | N | PRO | A | 279 | 9.509 | 13.240 | −7.733 | 1.00 | 35.86 | N |
| ATOM | 1834 | CA | PRO | A | 279 | 9.564 | 14.173 | −8.873 | 1.00 | 36.78 | C |
| ATOM | 1836 | CB | PRO | A | 279 | 10.998 | 14.004 | −9.395 | 1.00 | 36.58 | C |
| ATOM | 1839 | CG | PRO | A | 279 | 11.363 | 12.628 | −9.035 | 1.00 | 36.25 | C |
| ATOM | 1842 | CD | PRO | A | 279 | 10.696 | 12.370 | −7.699 | 1.00 | 35.96 | C |
| ATOM | 1845 | C | PRO | A | 279 | 8.564 | 13.884 | −9.991 | 1.00 | 37.60 | C |
| ATOM | 1846 | O | PRO | A | 279 | 8.178 | 14.820 | −10.684 | 1.00 | 38.30 | O |
| ATOM | 1847 | N | GLY | A | 280 | 8.163 | 12.626 | −10.156 | 1.00 | 38.65 | N |
| ATOM | 1849 | CA | GLY | A | 280 | 7.230 | 12.215 | −11.200 | 1.00 | 39.14 | C |
| ATOM | 1852 | C | GLY | A | 280 | 7.876 | 11.348 | −12.269 | 1.00 | 39.79 | C |
| ATOM | 1853 | O | GLY | A | 280 | 7.292 | 11.111 | −13.338 | 1.00 | 39.98 | O |
| ATOM | 1854 | N | VAL | A | 281 | 9.086 | 10.875 | −11.983 | 1.00 | 40.26 | N |
| ATOM | 1856 | CA | VAL | A | 281 | 9.839 | 10.030 | −12.906 | 1.00 | 40.57 | C |
| ATOM | 1858 | CB | VAL | A | 281 | 10.936 | 10.835 | −13.649 | 1.00 | 40.68 | C |
| ATOM | 1860 | CG1 | VAL | A | 281 | 10.307 | 11.741 | −14.692 | 1.00 | 41.03 | C |
| ATOM | 1864 | CG2 | VAL | A | 281 | 11.775 | 11.666 | −12.681 | 1.00 | 40.97 | C |
| ATOM | 1868 | C | VAL | A | 281 | 10.456 | 8.855 | −12.152 | 1.00 | 40.58 | C |
| ATOM | 1869 | O | VAL | A | 281 | 10.680 | 8.931 | −10.941 | 1.00 | 40.87 | O |
| ATOM | 1870 | N | SER | A | 282 | 10.727 | 7.774 | −12.874 | 1.00 | 40.51 | N |
| ATOM | 1872 | CA | SER | A | 282 | 11.288 | 6.555 | −12.290 | 1.00 | 40.46 | C |
| ATOM | 1874 | CB | SER | A | 282 | 11.163 | 5.407 | −13.292 | 1.00 | 40.61 | C |
| ATOM | 1877 | OG | SER | A | 282 | 11.937 | 5.663 | −14.458 | 1.00 | 40.57 | O |
| ATOM | 1879 | C | SER | A | 282 | 12.754 | 6.704 | −11.878 | 1.00 | 40.32 | C |
| ATOM | 1880 | O | SER | A | 282 | 13.380 | 7.735 | −12.124 | 1.00 | 40.59 | O |
| ATOM | 1881 | N | ASN | A | 283 | 13.291 | 5.665 | −11.244 | 1.00 | 40.11 | N |
| ATOM | 1883 | CA | ASN | A | 283 | 14.687 | 5.647 | −10.824 | 1.00 | 39.86 | C |
| ATOM | 1885 | CB | ASN | A | 283 | 14.980 | 4.425 | −9.944 | 1.00 | 39.38 | C |
| ATOM | 1888 | CG | ASN | A | 283 | 14.635 | 4.656 | −8.472 | 1.00 | 38.12 | C |
| ATOM | 1889 | OD1 | ASN | A | 283 | 14.676 | 5.782 | −7.980 | 1.00 | 34.02 | O |
| ATOM | 1890 | ND2 | ASN | A | 283 | 14.286 | 3.584 | −7.772 | 1.00 | 34.29 | N |
| ATOM | 1893 | C | ASN | A | 283 | 15.597 | 5.627 | −12.044 | 1.00 | 40.60 | C |
| ATOM | 1894 | O | ASN | A | 283 | 16.623 | 6.308 | −12.067 | 1.00 | 40.64 | O |
| ATOM | 1895 | N | GLN | A | 284 | 15.207 | 4.849 | −13.055 | 1.00 | 41.15 | N |
| ATOM | 1897 | CA | GLN | A | 284 | 15.984 | 4.734 | −14.288 | 1.00 | 41.88 | C |

TABLE 2-continued

| ATOM | 1899 | CB | GLN | A | 284 | 15.372 | 3.693 | −15.240 | 1.00 | 42.14 | C |
|---|---|---|---|---|---|---|---|---|---|---|---|
| ATOM | 1902 | CG | GLN | A | 284 | 16.369 | 3.089 | −16.221 | 1.00 | 43.42 | C |
| ATOM | 1905 | CD | GLN | A | 284 | 17.638 | 2.597 | −15.542 | 1.00 | 45.03 | C |
| ATOM | 1906 | OE1 | GLN | A | 284 | 17.589 | 1.706 | −14.690 | 1.00 | 46.51 | O |
| ATOM | 1907 | NE2 | GLN | A | 284 | 18.773 | 3.187 | −15.903 | 1.00 | 46.51 | N |
| ATOM | 1910 | C | GLN | A | 284 | 16.137 | 6.070 | −15.010 | 1.00 | 41.83 | C |
| ATOM | 1911 | O | GLN | A | 284 | 17.222 | 6.388 | −15.479 | 1.00 | 41.90 | O |
| ATOM | 1912 | N | PHE | A | 285 | 15.059 | 6.847 | −15.089 | 1.00 | 42.01 | N |
| ATOM | 1914 | CA | PHE | A | 285 | 15.093 | 8.149 | −15.755 | 1.00 | 42.09 | C |
| ATOM | 1916 | CB | PHE | A | 285 | 13.706 | 8.798 | −15.748 | 1.00 | 42.10 | C |
| ATOM | 1919 | CG | PHE | A | 285 | 13.661 | 10.140 | −16.427 | 1.00 | 41.86 | C |
| ATOM | 1920 | CD1 | PHE | A | 285 | 13.875 | 11.309 | −15.703 | 1.00 | 41.90 | C |
| ATOM | 1922 | CE1 | PHE | A | 285 | 13.837 | 12.550 | −16.326 | 1.00 | 41.81 | C |
| ATOM | 1924 | CZ | PHE | A | 285 | 13.582 | 12.632 | −17.684 | 1.00 | 41.87 | C |
| ATOM | 1926 | CE2 | PHE | A | 285 | 13.363 | 11.474 | −18.417 | 1.00 | 41.76 | C |
| ATOM | 1928 | CD2 | PHE | A | 285 | 13.405 | 10.235 | −17.788 | 1.00 | 41.83 | C |
| ATOM | 1930 | C | PHE | A | 285 | 16.097 | 9.088 | −15.092 | 1.00 | 42.27 | C |
| ATOM | 1931 | O | PHE | A | 285 | 16.845 | 9.784 | −15.777 | 1.00 | 42.20 | O |
| ATOM | 1932 | N | LEU | A | 286 | 16.089 | 9.112 | −13.759 | 1.00 | 42.48 | N |
| ATOM | 1934 | CA | LEU | A | 286 | 16.996 | 9.950 | −12.981 | 1.00 | 42.47 | C |
| ATOM | 1936 | CB | LEU | A | 286 | 16.649 | 9.866 | −11.492 | 1.00 | 42.52 | C |
| ATOM | 1939 | CG | LEU | A | 286 | 15.293 | 10.429 | −11.065 | 1.00 | 42.07 | C |
| ATOM | 1941 | CD1 | LEU | A | 286 | 15.045 | 10.112 | −9.598 | 1.00 | 42.39 | C |
| ATOM | 1945 | CD2 | LEU | A | 286 | 15.220 | 11.931 | −11.315 | 1.00 | 41.73 | C |
| ATOM | 1949 | C | LEU | A | 286 | 18.452 | 9.545 | −13.190 | 1.00 | 42.74 | C |
| ATOM | 1950 | O | LEU | A | 286 | 19.337 | 10.396 | −13.199 | 1.00 | 42.63 | O |
| ATOM | 1951 | N | LEU | A | 287 | 18.688 | 8.247 | −13.352 | 1.00 | 43.25 | N |
| ATOM | 1953 | CA | ILE | A | 287 | 20.030 | 7.713 | −13.579 | 1.00 | 43.83 | C |
| ATOM | 1955 | CB | ILE | A | 287 | 20.051 | 6.171 | −13.377 | 1.00 | 43.81 | C |
| ATOM | 1957 | CG1 | ILE | A | 287 | 19.840 | 5.817 | −11.900 | 1.00 | 43.80 | C |
| ATOM | 1960 | CD1 | ILE | A | 287 | 19.409 | 4.372 | −11.659 | 1.00 | 43.57 | C |
| ATOM | 1964 | CG2 | ILE | A | 287 | 21.371 | 5.571 | −13.870 | 1.00 | 43.78 | C |
| ATOM | 1968 | C | ILE | A | 287 | 20.549 | 8.066 | −14.978 | 1.00 | 44.43 | C |
| ATOM | 1969 | O | ILE | A | 287 | 21.702 | 8.477 | −15.122 | 1.00 | 44.55 | O |
| ATOM | 1970 | N | ASN | A | 288 | 19.703 | 7.903 | −15.996 | 1.00 | 45.03 | N |
| ATOM | 1972 | CA | ASN | A | 288 | 20.089 | 8.184 | −17.384 | 1.00 | 45.58 | C |
| ATOM | 1974 | CB | ASN | A | 288 | 19.033 | 7.673 | −18.373 | 1.00 | 45.51 | C |
| ATOM | 1977 | CG | ASN | A | 288 | 18.827 | 6.171 | −18.300 | 1.00 | 45.47 | C |
| ATOM | 1978 | OD1 | ASN | A | 288 | 19.749 | 5.415 | −18.006 | 1.00 | 46.21 | O |
| ATOM | 1979 | ND2 | ASN | A | 288 | 17.604 | 5.734 | −18.568 | 1.00 | 44.94 | N |
| ATOM | 1982 | C | ASN | A | 288 | 20.317 | 9.670 | −17.645 | 1.00 | 46.11 | C |
| ATOM | 1983 | O | ASN | A | 288 | 21.135 | 10.033 | −18.482 | 1.00 | 46.45 | O |
| ATOM | 1984 | N | THR | A | 289 | 19.597 | 10.523 | −16.922 | 1.00 | 46.75 | N |
| ATOM | 1986 | CA | THR | A | 289 | 19.708 | 11.974 | −17.093 | 1.00 | 47.24 | C |
| ATOM | 1988 | CB | THR | A | 289 | 18.339 | 12.649 | −16.859 | 1.00 | 47.34 | C |
| ATOM | 1990 | OG1 | THR | A | 289 | 17.790 | 12.243 | −15.598 | 1.00 | 47.85 | O |
| ATOM | 1992 | CG2 | THR | A | 289 | 17.318 | 12.174 | −17.880 | 1.00 | 47.52 | C |
| ATOM | 1996 | C | THR | A | 289 | 20.761 | 12.614 | −16.182 | 1.00 | 47.46 | C |
| ATOM | 1997 | O | THR | A | 289 | 20.898 | 13.838 | −16.161 | 1.00 | 47.53 | O |
| ATOM | 1998 | N | ASN | A | 290 | 21.500 | 11.792 | −15.438 | 1.00 | 47.75 | N |
| ATOM | 2000 | CA | ASN | A | 290 | 22.547 | 12.270 | −14.533 | 1.00 | 48.00 | C |
| ATOM | 2002 | CB | ASN | A | 290 | 23.756 | 12.790 | −15.328 | 1.00 | 48.10 | C |
| ATOM | 2005 | CG | ASN | A | 290 | 24.284 | 11.774 | −16.335 | 1.00 | 48.44 | C |
| ATOM | 2006 | OD1 | ASN | A | 290 | 24.489 | 10.605 | −16.008 | 1.00 | 48.46 | O |
| ATOM | 2007 | ND2 | ASN | A | 290 | 24.513 | 12.224 | −17.567 | 1.00 | 48.94 | N |
| ATOM | 2010 | C | ASN | A | 290 | 22.037 | 13.352 | −13.578 | 1.00 | 47.89 | C |
| ATOM | 2011 | O | ASN | A | 290 | 22.667 | 14.397 | −13.416 | 1.00 | 48.12 | O |
| ATOM | 2012 | N | SER | A | 291 | 20.890 | 13.095 | −12.954 | 1.00 | 47.70 | N |
| ATOM | 2014 | CA | SER | A | 291 | 20.280 | 14.046 | −12.027 | 1.00 | 47.60 | C |
| ATOM | 2016 | CB | SER | A | 291 | 18.821 | 13.679 | −11.766 | 1.00 | 47.62 | C |
| ATOM | 2019 | OG | SER | A | 291 | 18.734 | 12.526 | −10.949 | 1.00 | 48.18 | O |
| ATOM | 2021 | C | SER | A | 291 | 21.031 | 14.077 | −10.707 | 1.00 | 47.33 | C |
| ATOM | 2022 | O | SER | A | 291 | 21.709 | 13.119 | −10.351 | 1.00 | 47.23 | O |
| ATOM | 2023 | N | GLU | A | 292 | 20.885 | 15.176 | −9.974 | 1.00 | 47.16 | N |
| ATOM | 2025 | CA | GLU | A | 292 | 21.562 | 15.339 | −8.687 | 1.00 | 47.11 | C |
| ATOM | 2027 | CB | GLU | A | 292 | 21.273 | 16.726 | −8.086 | 1.00 | 47.37 | C |
| ATOM | 2030 | CG | GLU | A | 292 | 21.924 | 17.895 | −8.826 | 1.00 | 48.60 | C |
| ATOM | 2033 | CD | GLU | A | 292 | 23.444 | 17.932 | −8.700 | 1.00 | 50.01 | C |
| ATOM | 2034 | OE1 | OLU | A | 292 | 23.967 | 17.869 | −7.562 | 1.00 | 50.51 | O |
| ATOM | 2035 | OE2 | OLU | A | 292 | 24.125 | 18.031 | −9.747 | 1.00 | 51.24 | O |
| ATOM | 2036 | C | GLU | A | 292 | 21.207 | 14.237 | −7.679 | 1.00 | 46.52 | C |
| ATOM | 2037 | O | GLU | A | 292 | 22.021 | 13.910 | −6.816 | 1.00 | 46.44 | O |
| ATOM | 2038 | N | LEU | A | 293 | 20.003 | 13.672 | −7.792 | 1.00 | 45.86 | N |
| ATOM | 2040 | CA | LEU | A | 293 | 19.552 | 12.599 | −6.900 | 1.00 | 45.30 | C |
| ATOM | 2042 | CB | LEU | A | 293 | 18.052 | 12.346 | −7.066 | 1.00 | 45.31 | C |
| ATOM | 2045 | CG | LEU | A | 293 | 17.091 | 13.344 | −6.435 | 1.00 | 45.04 | C |
| ATOM | 2047 | CD1 | LEU | A | 293 | 15.683 | 13.077 | −6.944 | 1.00 | 44.92 | C |
| ATOM | 2051 | CD2 | LEU | A | 293 | 17.149 | 13.271 | −4.908 | 1.00 | 45.54 | C |
| ATOM | 2055 | C | LEU | A | 293 | 20.292 | 11.294 | −7.158 | 1.00 | 44.88 | C |

TABLE 2-continued

| ATOM | 2056 | O | LEU | A | 293 | 20.642 | 10.581 | −6.216 | 1.00 | 44.88 | O |
| --- | --- | --- | --- | --- | --- | --- | --- | --- | --- | --- | --- |
| ATOM | 2057 | N | ALA | A | 294 | 20.496 | 10.973 | −8.434 | 1.00 | 44.36 | N |
| ATOM | 2059 | CA | ALA | A | 294 | 21.212 | 9.763 | −8.835 | 1.00 | 43.86 | C |
| ATOM | 2061 | CB | ALA | A | 294 | 21.002 | 9.491 | −10.318 | 1.00 | 43.88 | C |
| ATOM | 2065 | C | ALA | A | 294 | 22.708 | 9.848 | −8.512 | 1.00 | 43.50 | C |
| ATOM | 2066 | O | ALA | A | 294 | 23.344 | 8.827 | −8.275 | 1.00 | 43.48 | O |
| ATOM | 2067 | N | LEU | A | 295 | 23.266 | 11.058 | −8.511 | 1.00 | 43.09 | N |
| ATOM | 2069 | CA | LEU | A | 295 | 24.673 | 11.255 | −8.175 | 1.00 | 42.84 | C |
| ATOM | 2071 | CB | LEU | A | 295 | 25.213 | 12.554 | −8.787 | 1.00 | 42.96 | C |
| ATOM | 2074 | CG | LEU | A | 295 | 25.094 | 12.698 | −10.319 | 1.00 | 43.48 | C |
| ATOM | 2076 | CD1 | LEU | A | 295 | 25.685 | 14.015 | −10.800 | 1.00 | 43.66 | C |
| ATOM | 2080 | CD2 | LEU | A | 295 | 25.747 | 11.537 | −11.048 | 1.00 | 43.57 | C |
| ATOM | 2084 | C | LEU | A | 295 | 24.842 | 11.253 | −6.651 | 1.00 | 42.61 | C |
| ATOM | 2085 | O | LEU | A | 295 | 25.905 | 10.925 | −6.135 | 1.00 | 42.50 | O |
| ATOM | 2086 | N | MET | A | 296 | 23.777 | 11.595 | −5.937 | 1.00 | 42.27 | N |
| ATOM | 2088 | CA | MET | A | 296 | 23.805 | 11.615 | −4.482 | 1.00 | 42.18 | C |
| ATOM | 2090 | CB | MET | A | 296 | 22.621 | 12.417 | −3.937 | 1.00 | 42.57 | C |
| ATOM | 2093 | CG | MET | A | 296 | 22.374 | 12.222 | −2.438 | 1.00 | 44.43 | C |
| ATOM | 2096 | SD | MET | A | 296 | 21.914 | 13.736 | −1.601 | 1.00 | 48.17 | S |
| ATOM | 2097 | CE | MET | A | 296 | 23.482 | 14.615 | −1.656 | 1.00 | 47.94 | C |
| ATOM | 2101 | C | MET | A | 296 | 23.771 | 10.195 | −3.920 | 1.00 | 41.37 | C |
| ATOM | 2102 | O | MET | A | 296 | 24.584 | 9.848 | −3.062 | 1.00 | 41.07 | O |
| ATOM | 2103 | N | TYR | A | 297 | 22.854 | 9.377 | −4.438 | 1.00 | 40.45 | N |
| ATOM | 2105 | CA | TYR | A | 297 | 22.639 | 8.014 | −3.947 | 1.00 | 39.58 | C |
| ATOM | 2107 | CB | TYR | A | 297 | 21.132 | 7.758 | −3.810 | 1.00 | 38.95 | C |
| ATOM | 2110 | CG | TYR | A | 297 | 20.537 | 8.611 | −2.721 | 1.00 | 36.11 | C |
| ATOM | 2111 | CD1 | TYR | A | 297 | 20.929 | 8.433 | −1.393 | 1.00 | 34.33 | C |
| ATOM | 2113 | CE1 | TYR | A | 297 | 20.416 | 9.221 | −0.381 | 1.00 | 31.97 | C |
| ATOM | 2115 | CZ | TYR | A | 297 | 19.504 | 10.207 | −0.686 | 1.00 | 31.51 | C |
| ATOM | 2116 | OH | TYR | A | 297 | 19.000 | 10.994 | 0.314 | 1.00 | 28.90 | O |
| ATOM | 2118 | CE2 | TYR | A | 297 | 19.107 | 10.416 | −2.008 | 1.00 | 31.67 | C |
| ATOM | 2120 | CD2 | TYR | A | 297 | 19.630 | 9.622 | −3.009 | 1.00 | 33.10 | C |
| ATOM | 2122 | C | TYR | A | 297 | 23.314 | 6.904 | −4.748 | 1.00 | 39.89 | C |
| ATOM | 2123 | O | TYR | A | 297 | 23.056 | 5.725 | −4.511 | 1.00 | 39.71 | O |
| ATOM | 2124 | N | ASN | A | 298 | 24.189 | 7.278 | −5.676 | 1.00 | 40.35 | N |
| ATOM | 2126 | CA | ASN | A | 298 | 24.947 | 6.305 | −6.464 | 1.00 | 40.54 | C |
| ATOM | 2128 | CB | ASN | A | 298 | 25.990 | 5.624 | −5.562 | 1.00 | 40.71 | C |
| ATOM | 2131 | CG | ASN | A | 298 | 26.780 | 6.619 | −4.726 | 1.00 | 41.06 | C |
| ATOM | 2132 | OD1 | ASN | A | 298 | 27.481 | 7.467 | −5.263 | 1.00 | 40.65 | O |
| ATOM | 2133 | ND2 | ASN | A | 298 | 26.662 | 6.519 | −3.400 | 1.00 | 41.63 | N |
| ATOM | 2136 | C | ASN | A | 298 | 24.090 | 5.254 | −7.195 | 1.00 | 40.47 | C |
| ATOM | 2137 | O | ASN | A | 298 | 24.424 | 4.068 | −7.213 | 1.00 | 40.32 | O |
| ATOM | 2138 | N | ASP | A | 299 | 22.974 | 5.701 | −7.765 | 1.00 | 40.66 | N |
| ATOM | 2140 | CA | ASP | A | 299 | 22.069 | 4.858 | −8.573 | 1.00 | 40.92 | C |
| ATOM | 2142 | CB | ASP | A | 299 | 22.798 | 4.309 | −9.812 | 1.00 | 40.91 | C |
| ATOM | 2145 | CG | ASP | A | 299 | 23.464 | 5.392 | −10.628 | 1.00 | 41.33 | C |
| ATOM | 2146 | OD1 | ASP | A | 299 | 23.025 | 6.554 | −10.550 | 1.00 | 41.32 | O |
| ATOM | 2147 | OD2 | ASP | A | 299 | 24.436 | 5.170 | −11.384 | 1.00 | 43.44 | O |
| ATOM | 2148 | C | ASP | A | 299 | 21.373 | 3.695 | −7.867 | 1.00 | 40.96 | C |
| ATOM | 2149 | O | ASP | A | 299 | 20.752 | 2.863 | −8.535 | 1.00 | 40.77 | O |
| ATOM | 2150 | N | GLU | A | 300 | 21.453 | 3.635 | −6.538 | 1.00 | 41.14 | N |
| ATOM | 2152 | CA | GLU | A | 300 | 20.826 | 2.555 | −5.781 | 1.00 | 41.29 | C |
| ATOM | 2154 | CB | GLU | A | 300 | 21.827 | 1.945 | −4.790 | 1.00 | 41.68 | C |
| ATOM | 2157 | CG | GLU | A | 300 | 21.297 | 0.799 | −3.926 | 1.00 | 43.60 | C |
| ATOM | 2160 | CD | GLU | A | 300 | 20.740 | −0.376 | −4.725 | 1.00 | 46.37 | C |
| ATOM | 2161 | OE1 | GLU | A | 300 | 21.137 | −0.561 | −5.899 | 1.00 | 48.85 | O |
| ATOM | 2162 | OE2 | GLU | A | 300 | 19.899 | −1.127 | −4.178 | 1.00 | 47.83 | O |
| ATOM | 2163 | C | GLU | A | 300 | 19.602 | 3.108 | −5.063 | 1.00 | 40.78 | C |
| ATOM | 2164 | O | GLU | A | 300 | 19.719 | 4.029 | −4.254 | 1.00 | 40.95 | O |
| ATOM | 2165 | N | SER | A | 301 | 18.430 | 2.562 | −5.384 | 1.00 | 40.10 | N |
| ATOM | 2167 | CA | SER | A | 301 | 17.176 | 2.994 | −4.777 | 1.00 | 39.62 | C |
| ATOM | 2169 | CB | SER | A | 301 | 16.966 | 2.262 | −3.446 | 1.00 | 39.57 | C |
| ATOM | 2172 | OG | SER | A | 301 | 16.719 | 0.884 | −3.664 | 1.00 | 38.97 | O |
| ATOM | 2174 | C | SER | A | 301 | 17.193 | 4.512 | −4.583 | 1.00 | 39.20 | C |
| ATOM | 2175 | O | SER | A | 301 | 17.052 | 5.012 | −3.465 | 1.00 | 39.18 | O |
| ATOM | 2176 | N | VAL | A | 302 | 17.367 | 5.229 | −5.693 | 1.00 | 38.61 | N |
| ATOM | 2178 | CA | VAL | A | 302 | 17.500 | 6.690 | −5.695 | 1.00 | 38.09 | C |
| ATOM | 2180 | CB | VAL | A | 302 | 17.682 | 7.250 | −7.144 | 1.00 | 38.01 | C |
| ATOM | 2182 | CG1 | VAL | A | 302 | 17.702 | 8.772 | −7.150 | 1.00 | 37.90 | C |
| ATOM | 2186 | CG2 | VAL | A | 302 | 18.961 | 6.722 | −7.769 | 1.00 | 38.29 | C |
| ATOM | 2190 | C | VAL | A | 302 | 16.328 | 7.385 | −5.014 | 1.00 | 37.65 | C |
| ATOM | 2191 | O | VAL | A | 302 | 16.505 | 8.041 | −3.989 | 1.00 | 38.03 | O |
| ATOM | 2192 | N | LEU | A | 303 | 15.140 | 7.226 | −5.589 | 1.00 | 36.98 | N |
| ATOM | 2194 | CA | LEU | A | 303 | 13.917 | 7.848 | −5.088 | 1.00 | 36.34 | C |
| ATOM | 2196 | CB | LEU | A | 303 | 12.733 | 7.466 | −5.982 | 1.00 | 36.31 | C |
| ATOM | 2199 | CG | LEU | A | 303 | 12.679 | 8.136 | −7.352 | 1.00 | 36.71 | C |
| ATOM | 2201 | CD1 | LEU | A | 303 | 11.960 | 7.286 | −8.394 | 1.00 | 36.88 | C |
| ATOM | 2205 | CD2 | LEU | A | 303 | 12.016 | 9.478 | −7.223 | 1.00 | 37.01 | C |
| ATOM | 2209 | C | LEU | A | 303 | 13.589 | 7.432 | −3.660 | 1.00 | 35.76 | C |

TABLE 2-continued

| ATOM | 2210 | O | LEU | A | 303 | 13.258 | 8.267 | −2.826 | 1.00 | 35.69 | O |
|---|---|---|---|---|---|---|---|---|---|---|---|
| ATOM | 2211 | N | GLU | A | 304 | 13.698 | 6.130 | −3.412 | 1.00 | 34.94 | N |
| ATOM | 2213 | CA | GLU | A | 304 | 13.355 | 5.509 | −2.138 | 1.00 | 34.29 | C |
| ATOM | 2215 | CB | GLU | A | 304 | 13.450 | 3.985 | −2.266 | 1.00 | 34.02 | C |
| ATOM | 2218 | CG | GLU | A | 304 | 12.350 | 3.359 | −3.111 | 1.00 | 32.76 | C |
| ATOM | 2221 | CD | GLU | A | 304 | 12.543 | 3.529 | −4.621 | 1.00 | 31.88 | C |
| ATOM | 2222 | OE1 | GLU | A | 304 | 13.701 | 3.571 | −5.107 | 1.00 | 28.63 | O |
| ATOM | 2223 | OE2 | GLU | A | 304 | 11.511 | 3.616 | −5.323 | 1.00 | 31.89 | O |
| ATOM | 2224 | C | GLU | A | 304 | 14.234 | 5.995 | −0.994 | 1.00 | 34.19 | C |
| ATOM | 2225 | O | GLU | A | 304 | 13.748 | 6.229 | 0.116 | 1.00 | 34.64 | O |
| ATOM | 2226 | N | ASN | A | 305 | 15.527 | 6.129 | −1.265 | 1.00 | 33.85 | N |
| ATOM | 2228 | CA | ASN | A | 305 | 16.472 | 6.642 | −0.286 | 1.00 | 33.36 | C |
| ATOM | 2230 | CB | ASN | A | 305 | 17.914 | 6.598 | −0.814 | 1.00 | 33.43 | C |
| ATOM | 2233 | CG | ASN | A | 305 | 18.649 | 5.332 | −0.427 | 1.00 | 33.58 | C |
| ATOM | 2234 | OD1 | ASN | A | 305 | 18.909 | 5.092 | 0.752 | 1.00 | 34.44 | O |
| ATOM | 2235 | ND2 | ASN | A | 305 | 19.016 | 4.526 | −1.422 | 1.00 | 33.37 | N |
| ATOM | 2238 | C | ASN | A | 305 | 16.101 | 8.085 | 0.029 | 1.00 | 33.03 | C |
| ATOM | 2239 | O | ASN | A | 305 | 16.128 | 8.500 | 1.195 | 1.00 | 32.88 | O |
| ATOM | 2240 | N | HIS | A | 306 | 15.748 | 8.836 | −1.018 | 1.00 | 32.12 | N |
| ATOM | 2242 | CA | HIS | A | 306 | 15.374 | 10.250 | −0.888 | 1.00 | 31.60 | C |
| ATOM | 2244 | CB | HIS | A | 306 | 15.305 | 10.928 | −2.268 | 1.00 | 31.07 | C |
| ATOM | 2247 | CG | HIS | A | 306 | 14.874 | 12.360 | −2.211 | 1.00 | 27.97 | C |
| ATOM | 2248 | ND1 | HIS | A | 306 | 15.725 | 13.379 | −1.844 | 1.00 | 25.57 | N |
| ATOM | 2250 | CE1 | HIS | A | 306 | 15.075 | 14.529 | −1.876 | 1.00 | 24.90 | C |
| ATOM | 2252 | NE2 | HIS | A | 306 | 13.827 | 14.291 | −2.237 | 1.00 | 25.27 | N |
| ATOM | 2254 | CD2 | HIS | A | 306 | 13.675 | 12.941 | −2.449 | 1.00 | 26.20 | C |
| ATOM | 2256 | C | HIS | A | 306 | 14.056 | 10.491 | −0.151 | 1.00 | 32.04 | C |
| ATOM | 2257 | O | HIS | A | 306 | 13.885 | 11.536 | 0.472 | 1.00 | 31.86 | O |
| ATOM | 2258 | N | HIS | A | 307 | 13.119 | 9.550 | −0.243 | 1.00 | 32.83 | N |
| ATOM | 2260 | CA | HIS | A | 307 | 11.830 | 9.680 | 0.435 | 1.00 | 33.53 | C |
| ATOM | 2262 | CB | HIS | A | 307 | 10.863 | 8.578 | −0.003 | 1.00 | 33.64 | C |
| ATOM | 2265 | CG | HIS | A | 307 | 10.507 | 8.618 | −1.460 | 1.00 | 33.44 | C |
| ATOM | 2266 | ND1 | HIS | A | 307 | 10.209 | 7.484 | −2.185 | 1.00 | 34.07 | N |
| ATOM | 2268 | CE1 | HIS | A | 307 | 9.933 | 7.820 | −3.433 | 1.00 | 33.65 | C |
| ATOM | 2270 | NE2 | HIS | A | 307 | 10.041 | 9.130 | −3.545 | 1.00 | 33.10 | N |
| ATOM | 2272 | CD2 | HIS | A | 307 | 10.403 | 9.652 | −2.327 | 1.00 | 33.40 | C |
| ATOM | 2274 | C | HIS | A | 307 | 12.065 | 9.599 | 1.947 | 1.00 | 34.42 | C |
| ATOM | 2275 | O | HIS | A | 307 | 11.456 | 10.331 | 2.723 | 1.00 | 34.45 | O |
| ATOM | 2276 | N | LEU | A | 308 | 12.977 | 8.713 | 2.339 | 1.00 | 35.33 | N |
| ATOM | 2278 | CA | LEU | A | 308 | 13.347 | 8.519 | 3.730 | 1.00 | 36.17 | C |
| ATOM | 2280 | CB | LEU | A | 308 | 14.188 | 7.254 | 3.877 | 1.00 | 36.08 | C |
| ATOM | 2283 | CG | LEU | A | 308 | 13.395 | 5.965 | 3.738 | 1.00 | 36.26 | C |
| ATOM | 2285 | CD1 | LEU | A | 308 | 14.320 | 4.805 | 3.405 | 1.00 | 36.46 | C |
| ATOM | 2289 | CD2 | LEU | A | 308 | 12.603 | 5.711 | 5.025 | 1.00 | 37.03 | C |
| ATOM | 2293 | C | LEU | A | 308 | 14.138 | 9.697 | 4.268 | 1.00 | 37.00 | C |
| ATOM | 2294 | O | LEU | A | 308 | 13.966 | 10.085 | 5.425 | 1.00 | 36.86 | O |
| ATOM | 2295 | N | ALA | A | 309 | 15.004 | 10.264 | 3.432 | 1.00 | 37.80 | N |
| ATOM | 2297 | CA | ALA | A | 309 | 15.835 | 11.389 | 3.849 | 1.00 | 38.43 | C |
| ATOM | 2299 | CB | ALA | A | 309 | 16.856 | 11.737 | 2.775 | 1.00 | 38.39 | C |
| ATOM | 2303 | C | ALA | A | 309 | 14.961 | 12.592 | 4.162 | 1.00 | 39.03 | C |
| ATOM | 2304 | O | ALA | A | 309 | 15.162 | 13.267 | 5.172 | 1.00 | 39.00 | O |
| ATOM | 2305 | N | VAL | A | 310 | 13.976 | 12.830 | 3.300 | 1.00 | 39.54 | N |
| ATOM | 2307 | CA | VAL | A | 310 | 13.052 | 13.953 | 3.441 | 1.00 | 39.92 | C |
| ATOM | 2309 | CB | VAL | A | 310 | 12.220 | 14.141 | 2.145 | 1.00 | 39.76 | C |
| ATOM | 2311 | CG1 | VAL | A | 310 | 11.101 | 15.162 | 2.338 | 1.00 | 39.55 | C |
| ATOM | 2315 | CG2 | VAL | A | 310 | 13.127 | 14.554 | 0.978 | 1.00 | 39.87 | C |
| ATOM | 2319 | C | VAL | A | 310 | 12.110 | 13.778 | 4.637 | 1.00 | 40.49 | C |
| ATOM | 2320 | O | VAL | A | 310 | 11.895 | 14.714 | 5.401 | 1.00 | 40.56 | O |
| ATOM | 2321 | N | GLY | A | 311 | 11.554 | 12.582 | 4.788 | 1.00 | 41.29 | N |
| ATOM | 2323 | CA | GLY | A | 311 | 10.617 | 12.294 | 5.858 | 1.00 | 42.08 | C |
| ATOM | 2326 | C | GLY | A | 311 | 11.232 | 12.420 | 7.239 | 1.00 | 42.78 | C |
| ATOM | 2327 | O | GLY | A | 311 | 10.602 | 12.947 | 8.151 | 1.00 | 42.87 | O |
| ATOM | 2328 | N | PHE | A | 312 | 12.464 | 11.941 | 7.380 | 1.00 | 43.75 | N |
| ATOM | 2330 | CA | PHE | A | 312 | 13.186 | 11.994 | 8.649 | 1.00 | 44.64 | C |
| ATOM | 2332 | CB | PHE | A | 312 | 14.261 | 10.899 | 8.712 | 1.00 | 44.43 | C |
| ATOM | 2335 | CG | PHE | A | 312 | 13.731 | 9.559 | 9.146 | 1.00 | 43.77 | C |
| ATOM | 2336 | CD1 | PHE | A | 312 | 13.533 | 9.283 | 10.495 | 1.00 | 43.48 | C |
| ATOM | 2338 | CE1 | PHE | A | 312 | 13.041 | 8.054 | 10.903 | 1.00 | 42.97 | C |
| ATOM | 2340 | CZ | PHE | A | 312 | 12.736 | 7.088 | 9.959 | 1.00 | 43.15 | C |
| ATOM | 2342 | CE2 | PHE | A | 312 | 12.926 | 7.353 | 8.612 | 1.00 | 42.95 | C |
| ATOM | 2344 | CD2 | PHE | A | 312 | 13.418 | 8.582 | 8.214 | 1.00 | 42.99 | C |
| ATOM | 2346 | C | PHE | A | 312 | 13.803 | 13.371 | 8.905 | 1.00 | 45.82 | C |
| ATOM | 2347 | O | PHE | A | 312 | 14.015 | 13.744 | 10.062 | 1.00 | 45.81 | O |
| ATOM | 2348 | N | LYS | A | 313 | 14.080 | 14.128 | 7.841 | 1.00 | 47.09 | N |
| ATOM | 2350 | CA | LYS | A | 313 | 14.645 | 15.475 | 7.989 | 1.00 | 48.33 | C |
| ATOM | 2352 | CB | LYS | A | 313 | 15.306 | 15.972 | 6.695 | 1.00 | 48.49 | C |
| ATOM | 2355 | CG | LYS | A | 313 | 16.785 | 15.598 | 6.571 | 1.00 | 49.29 | C |
| ATOM | 2358 | CD | LYS | A | 313 | 17.310 | 15.760 | 5.140 | 1.00 | 49.97 | C |
| ATOM | 2361 | CE | LYS | A | 313 | 18.686 | 15.126 | 4.982 | 1.00 | 50.25 | C |

TABLE 2-continued

| ATOM | 2364 | NZ | LYS | A | 313 | 19.291 | 15.413 | 3.652 | 1.00 | 50.61 | N |
| --- | --- | --- | --- | --- | --- | --- | --- | --- | --- | --- | --- |
| ATOM | 2368 | C | LYS | A | 313 | 13.580 | 16.474 | 8.444 | 1.00 | 49.20 | C |
| ATOM | 2369 | O | LYS | A | 313 | 13.912 | 17.545 | 8.944 | 1.00 | 49.36 | O |
| ATOM | 2370 | N | LEU | A | 314 | 12.308 | 16.130 | 8.260 | 1.00 | 50.39 | N |
| ATOM | 2372 | CA | LEU | A | 314 | 11.214 | 16.994 | 8.691 | 1.00 | 51.41 | C |
| ATOM | 2374 | CB | LEU | A | 314 | 9.948 | 16.719 | 7.875 | 1.00 | 51.32 | C |
| ATOM | 2377 | CG | LEU | A | 314 | 10.004 | 17.155 | 6.405 | 1.00 | 51.29 | C |
| ATOM | 2379 | CD1 | LEU | A | 314 | 8.762 | 16.675 | 5.663 | 1.00 | 51.18 | C |
| ATOM | 2383 | CD2 | LEU | A | 314 | 10.165 | 18.666 | 6.262 | 1.00 | 51.14 | C |
| ATOM | 2387 | C | LEU | A | 314 | 10.954 | 16.831 | 10.192 | 1.00 | 52.54 | C |
| ATOM | 2388 | O | LEU | A | 314 | 10.249 | 17.637 | 10.791 | 1.00 | 52.51 | O |
| ATOM | 2389 | N | LEU | A | 315 | 11.528 | 15.788 | 10.789 | 1.00 | 54.07 | N |
| ATOM | 2391 | CA | LEU | A | 315 | 11.427 | 15.549 | 12.227 | 1.00 | 55.42 | C |
| ATOM | 2393 | CB | LEU | A | 315 | 11.536 | 14.053 | 12.535 | 1.00 | 55.28 | C |
| ATOM | 2396 | CG | LEU | A | 315 | 10.596 | 13.085 | 11.809 | 1.00 | 54.94 | C |
| ATOM | 2398 | CD1 | LEU | A | 315 | 11.121 | 11.660 | 11.932 | 1.00 | 54.60 | C |
| ATOM | 2402 | CD2 | LEU | A | 315 | 9.176 | 13.176 | 12.353 | 1.00 | 54.60 | C |
| ATOM | 2406 | C | LEU | A | 315 | 12.524 | 16.296 | 13.000 | 1.00 | 56.87 | C |
| ATOM | 2407 | O | LEU | A | 315 | 12.544 | 16.257 | 14.229 | 1.00 | 57.08 | O |
| ATOM | 2408 | N | GLN | A | 316 | 13.434 | 16.958 | 12.282 | 1.00 | 58.60 | N |
| ATOM | 2410 | CA | GLN | A | 316 | 14.542 | 17.700 | 12.895 | 1.00 | 59.97 | C |
| ATOM | 2412 | CB | GLN | A | 316 | 15.462 | 18.281 | 11.815 | 1.00 | 60.13 | C |
| ATOM | 2415 | CG | GLN | A | 316 | 16.245 | 17.242 | 11.030 | 1.00 | 60.79 | C |
| ATOM | 2418 | CD | GLN | A | 316 | 17.404 | 16.667 | 11.814 | 1.00 | 61.76 | C |
| ATOM | 2419 | OE1 | GLN | A | 316 | 17.232 | 15.708 | 12.571 | 1.00 | 62.48 | O |
| ATOM | 2420 | NE2 | GLN | A | 316 | 18.589 | 17.245 | 11.635 | 1.00 | 62.08 | N |
| ATOM | 2423 | C | GLN | A | 316 | 14.060 | 18.835 | 13.795 | 1.00 | 60.95 | C |
| ATOM | 2424 | O | GLN | A | 316 | 14.456 | 18.923 | 14.957 | 1.00 | 61.19 | O |
| ATOM | 2425 | N | GLU | A | 317 | 13.215 | 19.700 | 13.241 | 1.00 | 62.15 | N |
| ATOM | 2427 | CA | GLU | A | 317 | 12.659 | 20.839 | 13.972 | 1.00 | 63.13 | C |
| ATOM | 2429 | CB | GLU | A | 317 | 11.803 | 21.684 | 13.027 | 1.00 | 63.38 | C |
| ATOM | 2432 | CG | GLU | A | 317 | 11.392 | 23.040 | 13.575 | 1.00 | 64.44 | C |
| ATOM | 2435 | CD | GLU | A | 317 | 12.506 | 24.074 | 13.552 | 1.00 | 65.83 | C |
| ATOM | 2436 | OE1 | GLU | A | 317 | 13.626 | 23.763 | 13.083 | 1.00 | 66.85 | O |
| ATOM | 2437 | OE2 | GLU | A | 317 | 12.252 | 25.212 | 14.005 | 1.00 | 66.75 | O |
| ATOM | 2438 | C | GLU | A | 317 | 11.821 | 20.350 | 15.157 | 1.00 | 63.62 | C |
| ATOM | 2439 | O | GLU | A | 317 | 10.996 | 19.455 | 14.997 | 1.00 | 63.69 | O |
| ATOM | 2440 | N | GLU | A | 318 | 12.024 | 20.949 | 16.331 | 1.00 | 64.26 | N |
| ATOM | 2442 | CA | GLU | A | 318 | 11.330 | 20.520 | 17.559 | 1.00 | 64.73 | C |
| ATOM | 2444 | CB | GLU | A | 318 | 11.926 | 21.206 | 18.807 | 1.00 | 64.92 | C |
| ATOM | 2447 | CG | GLU | A | 318 | 11.246 | 22.500 | 19.247 | 1.00 | 65.70 | C |
| ATOM | 2450 | CD | GLU | A | 318 | 9.946 | 22.266 | 20.006 | 1.00 | 66.66 | C |
| ATOM | 2451 | OE1 | GLU | A | 318 | 9.920 | 21.402 | 20.913 | 1.00 | 66.93 | O |
| ATOM | 2452 | OE2 | GLU | A | 318 | 8.942 | 22.943 | 19.686 | 1.00 | 67.17 | O |
| ATOM | 2453 | C | GLU | A | 318 | 9.793 | 20.651 | 17.519 | 1.00 | 64.78 | C |
| ATOM | 2454 | O | GLU | A | 318 | 9.097 | 19.802 | 18.081 | 1.00 | 64.79 | O |
| ATOM | 2455 | N | HIS | A | 319 | 9.264 | 21.694 | 16.870 | 1.00 | 64.86 | N |
| ATOM | 2457 | CA | HIS | A | 319 | 7.804 | 21.852 | 16.725 | 1.00 | 64.90 | C |
| ATOM | 2459 | CB | HIS | A | 319 | 7.411 | 23.331 | 16.548 | 1.00 | 65.08 | C |
| ATOM | 2462 | CG | HIS | A | 319 | 7.499 | 23.832 | 15.140 | 1.00 | 66.16 | C |
| ATOM | 2463 | ND1 | HIS | A | 319 | 8.676 | 24.273 | 14.577 | 1.00 | 67.19 | N |
| ATOM | 2465 | CE1 | HIS | A | 319 | 8.448 | 24.665 | 13.335 | 1.00 | 67.82 | C |
| ATOM | 2467 | NE2 | HIS | A | 319 | 7.164 | 24.497 | 13.074 | 1.00 | 67.83 | N |
| ATOM | 2469 | CD2 | HIS | A | 319 | 6.546 | 23.986 | 14.189 | 1.00 | 67.21 | C |
| ATOM | 2471 | C | HIS | A | 319 | 7.284 | 20.933 | 15.583 | 1.00 | 64.51 | C |
| ATOM | 2472 | O | HIS | A | 319 | 6.285 | 21.216 | 14.926 | 1.00 | 64.58 | O |
| ATOM | 2473 | N | CME | A | 320 | 7.960 | 19.791 | 15.458 | 1.00 | 64.09 | N |
| ATOM | 2476 | CA | CME | A | 320 | 7.529 | 18.882 | 14.377 | 1.00 | 63.88 | C |
| ATOM | 2478 | CB | CME | A | 320 | 8.210 | 19.242 | 13.047 | 1.00 | 64.00 | C |
| ATOM | 2481 | SG | CME | A | 320 | 7.168 | 20.279 | 12.064 | 1.00 | 64.69 | S |
| ATOM | 2482 | S2 | CME | A | 320 | 7.615 | 20.403 | 10.115 | 1.00 | 66.64 | S |
| ATOM | 2483 | C2 | CME | A | 320 | 9.348 | 20.529 | 9.821 | 1.00 | 67.24 | C |
| ATOM | 2486 | C1 | CME | A | 320 | 9.684 | 21.900 | 9.285 | 1.00 | 67.70 | C |
| ATOM | 2488 | O1 | CME | A | 320 | 10.483 | 22.595 | 9.893 | 1.00 | 68.26 | O |
| ATOM | 2489 | C | CME | A | 320 | 7.778 | 17.436 | 14.681 | 1.00 | 63.38 | C |
| ATOM | 2490 | O | CME | A | 320 | 6.883 | 16.623 | 14.628 | 1.00 | 63.58 | O |
| ATOM | 2492 | N | ASP | A | 321 | 8.941 | 17.202 | 15.305 | 1.00 | 62.54 | N |
| ATOM | 2494 | CA | ASP | A | 321 | 9.383 | 15.889 | 15.806 | 1.00 | 61.79 | C |
| ATOM | 2496 | CB | ASP | A | 321 | 10.564 | 16.091 | 16.774 | 1.00 | 61.72 | C |
| ATOM | 2499 | CG | ASP | A | 321 | 11.302 | 14.799 | 17.104 | 1.00 | 61.46 | C |
| ATOM | 2500 | OD1 | ASP | A | 321 | 10.735 | 13.699 | 16.940 | 1.00 | 61.10 | O |
| ATOM | 2501 | OD2 | ASP | A | 321 | 12.470 | 14.795 | 17.546 | 1.00 | 61.01 | O |
| ATOM | 2502 | C | ASP | A | 321 | 8.246 | 15.170 | 16.531 | 1.00 | 61.26 | C |
| ATOM | 2503 | O | ASP | A | 321 | 8.021 | 15.382 | 17.726 | 1.00 | 61.26 | O |
| ATOM | 2504 | N | ILE | A | 322 | 7.529 | 14.323 | 15.799 | 1.00 | 60.50 | N |
| ATOM | 2506 | CA | ILE | A | 322 | 6.413 | 13.569 | 16.369 | 1.00 | 59.95 | C |
| ATOM | 2508 | CB | ILE | A | 322 | 5.455 | 13.049 | 15.259 | 1.00 | 59.76 | C |
| ATOM | 2510 | CG1 | ILE | A | 322 | 6.204 | 12.234 | 14.199 | 1.00 | 59.22 | C |
| ATOM | 2513 | CD1 | ILE | A | 322 | 5.301 | 11.336 | 13.393 | 1.00 | 58.89 | C |

TABLE 2-continued

| | | | | | | | | | | |
|---|---|---|---|---|---|---|---|---|---|---|
| ATOM | 2517 | CG2 | ILE | A | 322 | 4.718 | 14.211 | 14.606 | 1.00 | 59.61 C |
| ATOM | 2521 | C | ILE | A | 322 | 6.880 | 12.417 | 17.270 | 1.00 | 59.70 C |
| ATOM | 2522 | O | ILE | A | 322 | 6.118 | 11.938 | 18.105 | 1.00 | 59.46 O |
| ATOM | 2523 | N | PHE | A | 323 | 8.130 | 11.986 | 17.100 | 1.00 | 59.47 N |
| ATOM | 2525 | CA | PHE | A | 323 | 8.709 | 10.903 | 17.901 | 1.00 | 59.35 C |
| ATOM | 2527 | CB | PHE | A | 323 | 9.540 | 9.972 | 17.004 | 1.00 | 59.24 C |
| ATOM | 2530 | CG | PHE | A | 323 | 8.821 | 9.508 | 15.756 | 1.00 | 58.85 C |
| ATOM | 2531 | CD1 | PHE | A | 323 | 7.504 | 9.064 | 15.813 | 1.00 | 58.41 C |
| ATOM | 2533 | CE1 | PHE | A | 323 | 6.849 | 8.636 | 14.668 | 1.00 | 58.22 C |
| ATOM | 2535 | CZ | PHE | A | 323 | 7.504 | 8.646 | 13.452 | 1.00 | 58.13 C |
| ATOM | 2537 | CE2 | PHE | A | 323 | 8.813 | 9.082 | 13.377 | 1.00 | 58.18 C |
| ATOM | 2539 | CD2 | PHE | A | 323 | 9.468 | 9.508 | 14.526 | 1.00 | 58.41 C |
| ATOM | 2541 | C | PHE | A | 323 | 9.584 | 11.434 | 19.050 | 1.00 | 59.40 C |
| ATOM | 2542 | O | PHE | A | 323 | 10.488 | 10.741 | 19.518 | 1.00 | 59.40 O |
| ATOM | 2543 | N | MET | A | 324 | 9.297 | 12.652 | 19.510 | 1.00 | 59.45 N |
| ATOM | 2545 | CA | MET | A | 324 | 10.067 | 13.298 | 20.574 | 1.00 | 59.58 C |
| ATOM | 2547 | CB | MET | A | 324 | 9.544 | 14.722 | 20.799 | 1.00 | 59.72 C |
| ATOM | 2550 | CG | MET | A | 324 | 10.326 | 15.531 | 21.830 | 1.00 | 60.51 C |
| ATOM | 2553 | SD | MET | A | 324 | 9.798 | 17.257 | 21.916 | 1.00 | 62.22 S |
| ATOM | 2554 | CE | MET | A | 324 | 11.269 | 18.102 | 21.255 | 1.00 | 62.21 C |
| ATOM | 2558 | C | MET | A | 324 | 10.027 | 12.533 | 21.897 | 1.00 | 59.42 C |
| ATOM | 2559 | O | MET | A | 324 | 11.061 | 12.305 | 22.524 | 1.00 | 59.29 O |
| ATOM | 2560 | N | ASN | A | 325 | 8.827 | 12.138 | 22.308 | 1.00 | 59.33 N |
| ATOM | 2562 | CA | ASN | A | 325 | 8.625 | 11.440 | 23.576 | 1.00 | 59.24 C |
| ATOM | 2564 | CB | ASN | A | 325 | 7.240 | 11.782 | 24.137 | 1.00 | 59.23 C |
| ATOM | 2567 | CG | ASN | A | 325 | 7.095 | 13.265 | 24.460 | 1.00 | 59.22 C |
| ATOM | 2568 | OD1 | ASN | A | 325 | 8.048 | 13.914 | 24.896 | 1.00 | 59.37 O |
| ATOM | 2569 | ND2 | ASN | A | 325 | 5.902 | 13.805 | 24.244 | 1.00 | 58.97 N |
| ATOM | 2572 | C | ASN | A | 325 | 8.852 | 9.926 | 23.562 | 1.00 | 59.21 C |
| ATOM | 2573 | O | ASN | A | 325 | 8.488 | 9.243 | 24.518 | 1.00 | 59.21 O |
| ATOM | 2574 | N | LEU | A | 326 | 9.440 | 9.397 | 22.490 | 1.00 | 59.22 N |
| ATOM | 2576 | CA | LEU | A | 326 | 9.812 | 7.985 | 22.444 | 1.00 | 59.24 C |
| ATOM | 2578 | CB | LEU | A | 326 | 9.954 | 7.474 | 21.005 | 1.00 | 59.15 C |
| ATOM | 2581 | CG | LEU | A | 326 | 8.815 | 7.620 | 19.991 | 1.00 | 58.88 C |
| ATOM | 2583 | CD1 | LEU | A | 326 | 8.921 | 6.532 | 18.924 | 1.00 | 58.51 C |
| ATOM | 2587 | CD2 | LEU | A | 326 | 7.458 | 7.581 | 20.657 | 1.00 | 58.66 C |
| ATOM | 2591 | C | LEU | A | 326 | 11.173 | 7.884 | 23.119 | 1.00 | 59.42 C |
| ATOM | 2592 | O | LEU | A | 326 | 11.877 | 8.889 | 23.237 | 1.00 | 59.45 O |
| ATOM | 2593 | N | THR | A | 327 | 11.549 | 6.683 | 23.554 | 1.00 | 59.64 N |
| ATOM | 2595 | CA | THR | A | 327 | 12.876 | 6.461 | 24.134 | 1.00 | 59.86 C |
| ATOM | 2597 | CB | THR | A | 327 | 12.958 | 5.091 | 24.857 | 1.00 | 59.88 C |
| ATOM | 2599 | OG1 | THR | A | 327 | 11.839 | 4.921 | 25.735 | 1.00 | 60.12 O |
| ATOM | 2601 | CG2 | THR | A | 327 | 14.171 | 5.026 | 25.793 | 1.00 | 60.15 C |
| ATOM | 2605 | C | THR | A | 327 | 13.865 | 6.488 | 22.976 | 1.00 | 59.95 C |
| ATOM | 2606 | O | THR | A | 327 | 13.460 | 6.351 | 21.825 | 1.00 | 59.92 O |
| ATOM | 2607 | N | LYS | A | 328 | 15.152 | 6.664 | 23.264 | 1.00 | 60.09 N |
| ATOM | 2609 | CA | LYS | A | 328 | 16.166 | 6.659 | 22.205 | 1.00 | 60.14 C |
| ATOM | 2611 | CB | LYS | A | 328 | 17.539 | 7.097 | 22.734 | 1.00 | 60.26 C |
| ATOM | 2614 | CG | LYS | A | 328 | 18.290 | 8.017 | 21.776 | 1.00 | 60.89 C |
| ATOM | 2617 | CD | LYS | A | 328 | 19.677 | 8.367 | 22.291 | 1.00 | 61.58 C |
| ATOM | 2620 | CE | LYS | A | 328 | 20.676 | 7.247 | 22.026 | 1.00 | 62.06 C |
| ATOM | 2623 | NZ | LYS | A | 328 | 22.083 | 7.698 | 22.221 | 1.00 | 62.16 N |
| ATOM | 2627 | C | LYS | A | 328 | 16.250 | 5.275 | 21.547 | 1.00 | 59.93 C |
| ATOM | 2628 | O | LYS | A | 328 | 16.610 | 5.160 | 20.373 | 1.00 | 60.00 O |
| ATOM | 2629 | N | LYS | A | 329 | 15.915 | 4.237 | 22.313 | 1.00 | 59.64 N |
| ATOM | 2631 | CA | LYS | A | 329 | 15.899 | 2.863 | 21.819 | 1.00 | 59.39 C |
| ATOM | 2633 | CB | LYS | A | 329 | 15.835 | 1.874 | 22.989 | 1.00 | 59.47 C |
| ATOM | 2636 | CG | LYS | A | 329 | 15.826 | 0.398 | 22.588 | 1.00 | 59.92 C |
| ATOM | 2639 | CD | LYS | A | 329 | 17.196 | −0.070 | 22.127 | 1.00 | 60.65 C |
| ATOM | 2642 | CE | LYS | A | 329 | 17.177 | −1.543 | 21.750 | 1.00 | 61.15 C |
| ATOM | 2645 | NZ | LYS | A | 329 | 18.424 | −1.952 | 21.045 | 1.00 | 61.60 N |
| ATOM | 2649 | C | LYS | A | 329 | 14.703 | 2.648 | 20.899 | 1.00 | 58.93 C |
| ATOM | 2650 | O | LYS | A | 329 | 14.825 | 2.005 | 19.863 | 1.00 | 58.89 O |
| ATOM | 2651 | N | GLN | A | 330 | 13.546 | 3.169 | 21.300 | 1.00 | 58.39 N |
| ATOM | 2653 | CA | GLN | A | 330 | 12.326 | 3.060 | 20.499 | 1.00 | 58.03 C |
| ATOM | 2655 | CB | GLN | A | 330 | 11.119 | 3.602 | 21.274 | 1.00 | 57.97 C |
| ATOM | 2658 | CG | GLN | A | 330 | 10.511 | 2.621 | 22.264 | 1.00 | 57.93 C |
| ATOM | 2661 | CD | GLN | A | 330 | 9.204 | 3.126 | 22.849 | 1.00 | 57.50 C |
| ATOM | 2662 | OE1 | GLN | A | 330 | 9.140 | 4.244 | 23.358 | 1.00 | 57.60 O |
| ATOM | 2663 | NE2 | GLN | A | 330 | 8.160 | 2.309 | 22.772 | 1.00 | 57.37 N |
| ATOM | 2666 | C | GLN | A | 330 | 12.455 | 3.815 | 19.172 | 1.00 | 57.60 C |
| ATOM | 2667 | O | GLN | A | 330 | 11.902 | 3.392 | 18.164 | 1.00 | 57.44 O |
| ATOM | 2668 | N | ARG | A | 331 | 13.183 | 4.930 | 19.195 | 1.00 | 57.20 N |
| ATOM | 2670 | CA | ARG | A | 331 | 13.399 | 5.769 | 18.014 | 1.00 | 57.01 C |
| ATOM | 2672 | CB | ARG | A | 331 | 13.988 | 7.133 | 18.417 | 1.00 | 57.34 C |
| ATOM | 2675 | CG | ARG | A | 331 | 13.172 | 8.343 | 17.970 | 1.00 | 58.80 C |
| ATOM | 2678 | CD | ARG | A | 331 | 13.877 | 9.678 | 18.190 | 1.00 | 60.72 C |
| ATOM | 2681 | NE | ARG | A | 331 | 14.005 | 9.993 | 19.616 | 1.00 | 62.49 N |
| ATOM | 2683 | CZ | ARG | A | 331 | 15.149 | 10.250 | 20.263 | 1.00 | 64.27 C |

TABLE 2-continued

| | | | | | | | | | | | |
|---|---|---|---|---|---|---|---|---|---|---|---|
| ATOM | 2684 | NH1 | ARG | A | 331 | 16.327 | 10.244 | 19.637 | 1.00 | 65.00 | N |
| ATOM | 2687 | NH2 | ARG | A | 331 | 15.112 | 10.518 | 21.565 | 1.00 | 64.63 | N |
| ATOM | 2690 | C | ARG | A | 331 | 14.337 | 5.083 | 17.026 | 1.00 | 56.15 | C |
| ATOM | 2691 | O | ARG | A | 331 | 14.177 | 5.221 | 15.820 | 1.00 | 56.21 | O |
| ATOM | 2692 | N | GLN | A | 332 | 15.318 | 4.354 | 17.552 | 1.00 | 55.23 | N |
| ATOM | 2694 | CA | GLN | A | 332 | 16.291 | 3.627 | 16.737 | 1.00 | 54.42 | C |
| ATOM | 2696 | CB | GLN | A | 332 | 17.467 | 3.161 | 17.606 | 1.00 | 54.56 | C |
| ATOM | 2699 | CG | GLN | A | 332 | 18.462 | 2.234 | 16.909 | 1.00 | 54.96 | C |
| ATOM | 2702 | CD | GLN | A | 332 | 19.528 | 1.715 | 17.856 | 1.00 | 55.68 | C |
| ATOM | 2703 | OE1 | GLN | A | 332 | 20.502 | 2.413 | 18.146 | 1.00 | 55.99 | O |
| ATOM | 2704 | NE2 | GLN | A | 332 | 19.349 | 0.490 | 18.339 | 1.00 | 55.92 | N |
| ATOM | 2707 | C | GLN | A | 332 | 15.641 | 2.425 | 16.062 | 1.00 | 53.41 | C |
| ATOM | 2708 | O | GLN | A | 332 | 15.898 | 2.144 | 14.892 | 1.00 | 53.07 | O |
| ATOM | 2709 | N | THR | A | 333 | 14.805 | 1.717 | 16.815 | 1.00 | 52.19 | N |
| ATOM | 2711 | CA | THR | A | 333 | 14.111 | 0.539 | 16.307 | 1.00 | 51.29 | C |
| ATOM | 2713 | CB | THR | A | 333 | 13.427 | −0.229 | 17.469 | 1.00 | 51.20 | C |
| ATOM | 2715 | OG1 | THR | A | 333 | 14.402 | −0.579 | 18.458 | 1.00 | 51.16 | O |
| ATOM | 2717 | CG2 | THR | A | 333 | 12.896 | −1.581 | 17.014 | 1.00 | 51.17 | C |
| ATOM | 2721 | C | THR | A | 333 | 13.098 | 0.940 | 15.229 | 1.00 | 50.38 | C |
| ATOM | 2722 | O | THR | A | 333 | 12.956 | 0.240 | 14.235 | 1.00 | 50.20 | O |
| ATOM | 2723 | N | LEU | A | 334 | 12.419 | 2.072 | 15.423 | 1.00 | 49.30 | N |
| ATOM | 2725 | CA | LEU | A | 334 | 11.433 | 2.559 | 14.462 | 1.00 | 48.59 | C |
| ATOM | 2727 | CB | LEU | A | 334 | 10.623 | 3.730 | 15.035 | 1.00 | 48.61 | C |
| ATOM | 2730 | CG | LEU | A | 334 | 9.557 | 4.324 | 14.093 | 1.00 | 48.20 | C |
| ATOM | 2732 | CD1 | LEU | A | 334 | 8.229 | 4.527 | 14.802 | 1.00 | 48.10 | C |
| ATOM | 2736 | CD2 | LEU | A | 334 | 10.021 | 5.638 | 13.487 | 1.00 | 48.25 | C |
| ATOM | 2740 | C | LEU | A | 334 | 12.119 | 2.992 | 13.174 | 1.00 | 47.92 | C |
| ATOM | 2741 | O | LEU | A | 334 | 11.666 | 2.649 | 12.090 | 1.00 | 47.78 | O |
| ATOM | 2742 | N | ARG | A | 335 | 13.210 | 3.743 | 13.319 | 1.00 | 47.14 | N |
| ATOM | 2744 | CA | ARG | A | 335 | 14.002 | 4.247 | 12.196 | 1.00 | 46.51 | C |
| ATOM | 2746 | CB | ARG | A | 335 | 15.190 | 5.055 | 12.722 | 1.00 | 46.44 | C |
| ATOM | 2749 | CG | ARG | A | 335 | 16.028 | 5.711 | 11.656 | 1.00 | 45.75 | C |
| ATOM | 2752 | CD | ARG | A | 335 | 16.974 | 6.782 | 12.186 | 1.00 | 45.12 | C |
| ATOM | 2755 | NE | ARG | A | 335 | 18.047 | 7.062 | 11.234 | 1.00 | 44.75 | N |
| ATOM | 2757 | CZ | ARG | A | 335 | 17.876 | 7.686 | 10.069 | 1.00 | 43.78 | C |
| ATOM | 2758 | NH1 | ARG | A | 335 | 16.682 | 8.139 | 9.704 | 1.00 | 43.31 | N |
| ATOM | 2761 | NH2 | ARG | A | 335 | 18.916 | 7.880 | 9.270 | 1.00 | 43.59 | N |
| ATOM | 2764 | C | ARG | A | 335 | 14.503 | 3.110 | 11.314 | 1.00 | 46.18 | C |
| ATOM | 2765 | O | ARG | A | 335 | 14.393 | 3.165 | 10.092 | 1.00 | 46.02 | O |
| ATOM | 2766 | N | LYS | A | 336 | 15.056 | 2.086 | 11.952 | 1.00 | 45.69 | N |
| ATOM | 2768 | CA | LYS | A | 336 | 15.544 | 0.900 | 11.262 | 1.00 | 45.47 | C |
| ATOM | 2770 | CB | LYS | A | 336 | 16.139 | −0.084 | 12.281 | 1.00 | 45.68 | C |
| ATOM | 2773 | CG | LYS | A | 336 | 16.468 | −1.474 | 11.740 | 1.00 | 46.69 | C |
| ATOM | 2776 | CD | LYS | A | 336 | 16.896 | −2.414 | 12.871 | 1.00 | 48.09 | C |
| ATOM | 2779 | CE | LYS | A | 336 | 17.626 | −3.649 | 12.343 | 1.00 | 48.73 | C |
| ATOM | 2782 | NZ | LYS | A | 336 | 17.211 | −4.895 | 13.049 | 1.00 | 49.53 | N |
| ATOM | 2786 | C | LYS | A | 336 | 14.404 | 0.238 | 10.489 | 1.00 | 44.79 | C |
| ATOM | 2787 | O | LYS | A | 336 | 14.580 | −0.173 | 9.347 | 1.00 | 44.89 | O |
| ATOM | 2788 | N | MET | A | 337 | 13.236 | 0.159 | 11.118 | 1.00 | 43.97 | N |
| ATOM | 2790 | CA | MET | A | 337 | 12.062 | −0.475 | 10.517 | 1.00 | 43.32 | C |
| ATOM | 2792 | CB | MET | A | 337 | 10.997 | −0.727 | 11.584 | 1.00 | 43.37 | C |
| ATOM | 2795 | CG | MET | A | 337 | 11.302 | −1.909 | 12.480 | 1.00 | 43.73 | C |
| ATOM | 2798 | SD | MET | A | 337 | 9.868 | −2.447 | 13.404 | 1.00 | 44.39 | S |
| ATOM | 2799 | CE | MET | A | 337 | 9.694 | −1.148 | 14.556 | 1.00 | 44.46 | C |
| ATOM | 2803 | C | MET | A | 337 | 11.438 | 0.319 | 9.375 | 1.00 | 42.50 | C |
| ATOM | 2804 | O | MET | A | 337 | 10.971 | −0.270 | 8.407 | 1.00 | 42.05 | O |
| ATOM | 2805 | N | VAL | A | 338 | 11.420 | 1.646 | 9.499 | 1.00 | 41.85 | N |
| ATOM | 2807 | CA | VAL | A | 338 | 10.834 | 2.515 | 8.480 | 1.00 | 41.32 | C |
| ATOM | 2809 | CB | VAL | A | 338 | 10.646 | 3.967 | 8.991 | 1.00 | 41.27 | C |
| ATOM | 2811 | CG1 | VAL | A | 338 | 10.203 | 4.900 | 7.852 | 1.00 | 40.93 | C |
| ATOM | 2815 | CG2 | VAL | A | 338 | 9.638 | 4.014 | 10.146 | 1.00 | 41.37 | C |
| ATOM | 2819 | C | VAL | A | 338 | 11.711 | 2.512 | 7.231 | 1.00 | 40.97 | C |
| ATOM | 2820 | O | VAL | A | 338 | 11.199 | 2.429 | 6.120 | 1.00 | 40.87 | O |
| ATOM | 2821 | N | ILE | A | 339 | 13.026 | 2.613 | 7.430 | 1.00 | 40.61 | N |
| ATOM | 2823 | CA | ILE | A | 339 | 13.999 | 2.584 | 6.340 | 1.00 | 40.44 | C |
| ATOM | 2825 | CB | ILE | A | 339 | 15.443 | 2.740 | 6.886 | 1.00 | 40.32 | C |
| ATOM | 2827 | CG1 | ILE | A | 339 | 15.696 | 4.190 | 7.305 | 1.00 | 40.20 | C |
| ATOM | 2830 | CD1 | ILE | A | 339 | 16.878 | 4.375 | 8.239 | 1.00 | 40.04 | C |
| ATOM | 2834 | CG2 | ILE | A | 339 | 16.478 | 2.299 | 5.842 | 1.00 | 40.23 | C |
| ATOM | 2838 | C | ILE | A | 339 | 13.863 | 1.272 | 5.577 | 1.00 | 40.46 | C |
| ATOM | 2839 | O | ILE | A | 339 | 13.877 | 1.251 | 4.352 | 1.00 | 40.13 | O |
| ATOM | 2840 | N | ASP | A | 340 | 13.731 | 0.183 | 6.325 | 1.00 | 40.43 | N |
| ATOM | 2842 | CA | ASP | A | 340 | 13.576 | −1.147 | 5.750 | 1.00 | 40.42 | C |
| ATOM | 2844 | CB | ASP | A | 340 | 13.509 | −2.187 | 6.877 | 1.00 | 40.54 | C |
| ATOM | 2847 | CG | ASP | A | 340 | 13.657 | −3.608 | 6.383 | 1.00 | 40.69 | C |
| ATOM | 2848 | OD1 | ASP | A | 340 | 12.635 | −4.203 | 6.007 | 1.00 | 41.57 | O |
| ATOM | 2849 | OD2 | ASP | A | 340 | 14.746 | −4.218 | 6.349 | 1.00 | 41.51 | O |
| ATOM | 2850 | C | ASP | A | 340 | 12.319 | −1.215 | 4.880 | 1.00 | 40.27 | C |
| ATOM | 2851 | O | ASP | A | 340 | 12.378 | −1.647 | 3.730 | 1.00 | 40.26 | O |

TABLE 2-continued

| ATOM | 2852 | N | MET | A | 341 | 11.195 | −0.751 | 5.422 | 1.00 | 40.04 | N |
|---|---|---|---|---|---|---|---|---|---|---|---|
| ATOM | 2854 | CA | MET | A | 341 | 9.913 | −0.803 | 4.717 | 1.00 | 39.91 | C |
| ATOM | 2856 | CB | MET | A | 341 | 8.760 | −0.432 | 5.664 | 1.00 | 39.89 | C |
| ATOM | 2859 | CG | MET | A | 341 | 8.352 | −1.563 | 6.610 | 1.00 | 40.26 | C |
| ATOM | 2862 | SD | MET | A | 341 | 6.991 | −1.161 | 7.760 | 1.00 | 40.19 | S |
| ATOM | 2863 | CE | MET | A | 341 | 7.900 | −0.486 | 9.111 | 1.00 | 40.09 | C |
| ATOM | 2867 | C | MET | A | 341 | 9.871 | 0.067 | 3.451 | 1.00 | 39.67 | C |
| ATOM | 2868 | O | MET | A | 341 | 9.410 | −0.389 | 2.413 | 1.00 | 39.56 | O |
| ATOM | 2869 | N | VAL | A | 342 | 10.368 | 1.300 | 3.537 | 1.00 | 39.52 | N |
| ATOM | 2871 | CA | VAL | A | 342 | 10.342 | 2.242 | 2.410 | 1.00 | 39.46 | C |
| ATOM | 2873 | CB | VAL | A | 342 | 10.695 | 3.678 | 2.866 | 1.00 | 39.41 | C |
| ATOM | 2875 | CG1 | VAL | A | 342 | 10.825 | 4.624 | 1.686 | 1.00 | 38.89 | C |
| ATOM | 2879 | CG2 | VAL | A | 342 | 9.642 | 4.203 | 3.840 | 1.00 | 39.71 | C |
| ATOM | 2883 | C | VAL | A | 342 | 11.273 | 1.806 | 1.274 | 1.00 | 39.55 | C |
| ATOM | 2884 | O | VAL | A | 342 | 10.933 | 1.946 | 0.096 | 1.00 | 39.76 | O |
| ATOM | 2885 | N | LEU | A | 343 | 12.451 | 1.301 | 1.632 | 1.00 | 39.40 | N |
| ATOM | 2887 | CA | LEU | A | 343 | 13.406 | 0.786 | 0.655 | 1.00 | 39.41 | C |
| ATOM | 2889 | CB | LEU | A | 343 | 14.733 | 0.400 | 1.324 | 1.00 | 39.20 | C |
| ATOM | 2892 | CG | LEU | A | 343 | 15.708 | 1.552 | 1.581 | 1.00 | 38.91 | C |
| ATOM | 2894 | CD1 | LEU | A | 343 | 16.816 | 1.120 | 2.540 | 1.00 | 38.70 | C |
| ATOM | 2898 | CD2 | LEU | A | 343 | 16.298 | 2.066 | 0.266 | 1.00 | 38.70 | C |
| ATOM | 2902 | C | LEU | A | 343 | 12.816 | −0.429 | −0.064 | 1.00 | 39.58 | C |
| ATOM | 2903 | O | LEU | A | 343 | 13.109 | −0.666 | −1.239 | 1.00 | 39.39 | O |
| ATOM | 2904 | N | ALA | A | 344 | 11.983 | −1.184 | 0.653 | 1.00 | 39.71 | N |
| ATOM | 2906 | CA | ALA | A | 344 | 11.307 | −2.360 | 0.107 | 1.00 | 39.91 | C |
| ATOM | 2908 | CB | ALA | A | 344 | 10.703 | −3.200 | 1.238 | 1.00 | 39.82 | C |
| ATOM | 2912 | C | ALA | A | 344 | 10.224 | −2.006 | −0.922 | 1.00 | 40.06 | C |
| ATOM | 2913 | O | ALA | A | 344 | 9.762 | −2.884 | −1.655 | 1.00 | 40.07 | O |
| ATOM | 2914 | N | THR | A | 345 | 9.808 | −0.738 | −0.969 | 1.00 | 40.23 | N |
| ATOM | 2916 | CA | THR | A | 345 | 8.817 | −0.296 | −1.956 | 1.00 | 40.48 | C |
| ATOM | 2918 | CB | THR | A | 345 | 8.091 | 1.012 | −1.532 | 1.00 | 40.16 | C |
| ATOM | 2920 | OG1 | THR | A | 345 | 8.975 | 2.134 | −1.649 | 1.00 | 39.46 | O |
| ATOM | 2922 | CG2 | THR | A | 345 | 7.682 | 0.993 | −0.066 | 1.00 | 40.47 | C |
| ATOM | 2926 | C | THR | A | 345 | 9.452 | −0.082 | −3.333 | 1.00 | 41.11 | C |
| ATOM | 2927 | O | THR | A | 345 | 8.770 | 0.344 | −4.256 | 1.00 | 40.81 | O |
| ATOM | 2928 | N | ASP | A | 346 | 10.756 | −0.341 | −3.449 | 1.00 | 42.09 | N |
| ATOM | 2930 | CA | ASP | A | 346 | 11.487 | −0.203 | −4.705 | 1.00 | 43.17 | C |
| ATOM | 2932 | CB | ASP | A | 346 | 13.000 | −0.237 | −4.442 | 1.00 | 43.17 | C |
| ATOM | 2935 | CG | ASP | A | 346 | 13.831 | 0.065 | −5.685 | 1.00 | 43.23 | C |
| ATOM | 2936 | OD1 | ASP | A | 346 | 13.266 | 0.138 | −6.794 | 1.00 | 42.38 | O |
| ATOM | 2937 | OD2 | ASP | A | 346 | 15.068 | 0.238 | −5.644 | 1.00 | 44.27 | O |
| ATOM | 2938 | C | ASP | A | 346 | 11.070 | −1.351 | −5.622 | 1.00 | 44.19 | C |
| ATOM | 2939 | O | ASP | A | 346 | 11.259 | −2.519 | −5.283 | 1.00 | 44.32 | O |
| ATOM | 2940 | N | MET | A | 347 | 10.516 | −1.011 | −6.781 | 1.00 | 45.54 | N |
| ATOM | 2942 | CA | MET | A | 347 | 9.997 | −2.016 | −7.721 | 1.00 | 46.71 | C |
| ATOM | 2944 | CB | MET | A | 347 | 9.191 | −1.356 | −8.850 | 1.00 | 46.78 | C |
| ATOM | 2947 | CG | MET | A | 347 | 7.685 | −1.396 | −8.628 | 1.00 | 47.64 | C |
| ATOM | 2950 | SD | MET | A | 347 | 7.036 | −3.076 | −8.460 | 1.00 | 49.80 | S |
| ATOM | 2951 | CE | MET | A | 347 | 6.238 | −3.274 | −10.064 | 1.00 | 50.00 | C |
| ATOM | 2955 | C | MET | A | 347 | 11.036 | −2.966 | −8.318 | 1.00 | 47.42 | C |
| ATOM | 2956 | O | MET | A | 347 | 10.681 | −4.064 | −8.748 | 1.00 | 47.60 | O |
| ATOM | 2957 | N | SER | A | 348 | 12.300 | −2.549 | −8.357 | 1.00 | 48.44 | N |
| ATOM | 2959 | CA | SER | A | 348 | 13.377 | −3.403 | −8.867 | 1.00 | 49.24 | C |
| ATOM | 2961 | CB | SER | A | 348 | 14.645 | −2.583 | −9.123 | 1.00 | 49.21 | C |
| ATOM | 2964 | OG | SER | A | 348 | 15.227 | −2.132 | −7.916 | 1.00 | 49.29 | O |
| ATOM | 2966 | C | SER | A | 348 | 13.669 | −4.573 | −7.912 | 1.00 | 50.03 | C |
| ATOM | 2967 | O | SER | A | 348 | 14.310 | −5.550 | −8.299 | 1.00 | 50.03 | O |
| ATOM | 2968 | N | LYS | A | 349 | 13.201 | −4.452 | −6.669 | 1.00 | 51.08 | N |
| ATOM | 2970 | CA | LYS | A | 349 | 13.341 | −5.489 | −5.645 | 1.00 | 51.93 | C |
| ATOM | 2972 | CB | LYS | A | 349 | 13.667 | −4.850 | −4.292 | 1.00 | 52.02 | C |
| ATOM | 2975 | CG | LYS | A | 349 | 14.768 | −3.812 | −4.341 | 1.00 | 52.97 | C |
| ATOM | 2978 | CD | LYS | A | 349 | 15.170 | −3.360 | −2.951 | 1.00 | 53.90 | C |
| ATOM | 2981 | CE | LYS | A | 349 | 16.448 | −2.538 | −2.990 | 1.00 | 54.59 | C |
| ATOM | 2984 | NZ | LYS | A | 349 | 17.608 | −3.333 | −3.492 | 1.00 | 55.18 | N |
| ATOM | 2988 | C | LYS | A | 349 | 12.062 | −6.322 | −5.487 | 1.00 | 52.50 | C |
| ATOM | 2989 | O | LYS | A | 349 | 11.959 | −7.116 | −4.556 | 1.00 | 52.47 | O |
| ATOM | 2990 | N | HIS | A | 350 | 11.100 | −6.152 | −6.394 | 1.00 | 53.22 | N |
| ATOM | 2992 | CA | HIS | A | 350 | 9.815 | −6.849 | −6.301 | 1.00 | 53.86 | C |
| ATOM | 2994 | CB | HIS | A | 350 | 8.856 | −6.405 | −7.409 | 1.00 | 53.91 | C |
| ATOM | 2997 | CG | HIS | A | 350 | 7.685 | −7.322 | −7.583 | 1.00 | 54.18 | C |
| ATOM | 2998 | ND1 | HIS | A | 350 | 6.683 | −7.433 | −6.643 | 1.00 | 54.33 | N |
| ATOM | 3000 | CE1 | HIS | A | 350 | 5.799 | −8.326 | −7.049 | 1.00 | 54.32 | C |
| ATOM | 3002 | NE2 | HIS | A | 350 | 6.194 | −8.802 | −8.216 | 1.00 | 54.39 | N |
| ATOM | 3004 | CD2 | HIS | A | 350 | 7.375 | −8.196 | −8.570 | 1.00 | 54.14 | C |
| ATOM | 3006 | C | HIS | A | 350 | 9.940 | −8.369 | −6.332 | 1.00 | 54.39 | C |
| ATOM | 3007 | O | HIS | A | 350 | 9.336 | −9.048 | −5.508 | 1.00 | 54.33 | O |
| ATOM | 3008 | N | MET | A | 351 | 10.702 | −8.893 | −7.291 | 1.00 | 55.07 | N |
| ATOM | 3010 | CA | MET | A | 351 | 10.891 | −10.343 | −7.428 | 1.00 | 55.60 | C |
| ATOM | 3012 | CB | MET | A | 351 | 11.734 | −10.671 | −8.667 | 1.00 | 55.91 | C |

TABLE 2-continued

| ATOM | 3015 | CG | MET | A | 351 | 11.031 | −10.438 | −10.002 | 1.00 | 57.23 | C |
| ATOM | 3018 | SD | MET | A | 351 | 9.501 | −11.391 | −10.253 | 1.00 | 60.16 | S |
| ATOM | 3019 | CE | MET | A | 351 | 9.928 | −13.013 | −9.526 | 1.00 | 60.75 | C |
| ATOM | 3023 | C | MET | A | 351 | 11.551 | −10.957 | −6.196 | 1.00 | 55.53 | C |
| ATOM | 3024 | O | MET | A | 351 | 11.156 | −12.032 | −5.755 | 1.00 | 55.69 | O |
| ATOM | 3025 | N | SER | A | 352 | 12.559 | −10.278 | −5.656 | 1.00 | 55.53 | N |
| ATOM | 3027 | CA | SER | A | 352 | 13.262 | −10.749 | −4.463 | 1.00 | 55.61 | C |
| ATOM | 3029 | CB | SER | A | 352 | 14.471 | −9.857 | −4.174 | 1.00 | 55.69 | C |
| ATOM | 3032 | OG | SER | A | 352 | 15.106 | −10.232 | −2.962 | 1.00 | 55.96 | O |
| ATOM | 3034 | C | SER | A | 352 | 12.346 | −10.783 | −3.235 | 1.00 | 55.49 | C |
| ATOM | 3035 | O | SER | A | 352 | 12.545 | −11.590 | −2.331 | 1.00 | 55.74 | O |
| ATOM | 3036 | N | LEU | A | 353 | 11.357 | −9.894 | −3.214 | 1.00 | 55.34 | N |
| ATOM | 3038 | CA | LEU | A | 353 | 10.386 | −9.801 | −2.127 | 1.00 | 55.18 | C |
| ATOM | 3040 | CB | LEU | A | 353 | 9.690 | −8.436 | −2.158 | 1.00 | 55.08 | C |
| ATOM | 3043 | CG | LEU | A | 353 | 10.165 | −7.402 | −1.143 | 1.00 | 54.83 | C |
| ATOM | 3045 | CD1 | LEU | A | 353 | 11.520 | −6.829 | −1.531 | 1.00 | 54.74 | C |
| ATOM | 3049 | CD2 | LEU | A | 353 | 9.127 | −6.304 | −1.030 | 1.00 | 54.61 | C |
| ATOM | 3053 | C | LEU | A | 353 | 9.326 | −10.892 | −2.235 | 1.00 | 55.25 | C |
| ATOM | 3054 | O | LEU | A | 353 | 8.891 | −11.443 | −1.229 | 1.00 | 55.16 | O |
| ATOM | 3055 | N | LEU | A | 354 | 8.907 | −11.172 | −3.468 | 1.00 | 55.43 | N |
| ATOM | 3057 | CA | LEU | A | 354 | 7.880 | −12.164 | −3.767 | 1.00 | 55.53 | C |
| ATOM | 3059 | CB | LEU | A | 354 | 7.412 | −12.000 | −5.221 | 1.00 | 55.45 | C |
| ATOM | 3062 | CG | LEU | A | 354 | 6.365 | −12.973 | −5.776 | 1.00 | 55.33 | C |
| ATOM | 3064 | CD1 | LEU | A | 354 | 5.124 | −13.000 | −4.900 | 1.00 | 54.95 | C |
| ATOM | 3068 | CD2 | LEU | A | 354 | 6.004 | −12.600 | −7.219 | 1.00 | 55.15 | C |
| ATOM | 3072 | C | LEU | A | 354 | 8.390 | −13.583 | −3.542 | 1.00 | 55.85 | C |
| ATOM | 3073 | O | LEU | A | 354 | 7.619 | −14.471 | −3.186 | 1.00 | 55.80 | O |
| ATOM | 3074 | N | ALA | A | 355 | 9.687 | −13.788 | −3.763 | 1.00 | 56.29 | N |
| ATOM | 3076 | CA | ALA | A | 355 | 10.316 | −15.092 | −3.577 | 1.00 | 56.60 | C |
| ATOM | 3078 | CB | ALA | A | 355 | 11.644 | −15.154 | −4.318 | 1.00 | 56.51 | C |
| ATOM | 3082 | C | ALA | A | 355 | 10.519 | −15.358 | −2.088 | 1.00 | 57.01 | C |
| ATOM | 3083 | O | ALA | A | 355 | 10.313 | −16.475 | −1.618 | 1.00 | 57.16 | O |
| ATOM | 3084 | N | ASP | A | 356 | 10.919 | −14.323 | −1.354 | 1.00 | 57.44 | N |
| ATOM | 3086 | CA | ASP | A | 356 | 11.127 | −14.427 | 0.092 | 1.00 | 57.85 | C |
| ATOM | 3088 | CB | ASP | A | 356 | 11.849 | −13.183 | 0.627 | 1.00 | 57.86 | C |
| ATOM | 3091 | CG | ASP | A | 356 | 13.356 | −13.304 | 0.550 | 1.00 | 58.11 | C |
| ATOM | 3092 | OD1 | ASP | A | 356 | 13.869 | −13.749 | −0.498 | 1.00 | 58.55 | O |
| ATOM | 3093 | OD2 | ASP | A | 356 | 14.110 | −12.971 | 1.488 | 1.00 | 58.40 | O |
| ATOM | 3094 | C | ASP | A | 356 | 9.800 | −14.604 | 0.824 | 1.00 | 58.14 | C |
| ATOM | 3095 | O | ASP | A | 356 | 9.741 | −15.258 | 1.866 | 1.00 | 58.15 | O |
| ATOM | 3096 | N | LEU | A | 357 | 8.742 | −14.015 | 0.270 | 1.00 | 58.53 | N |
| ATOM | 3098 | CA | LEU | A | 357 | 7.411 | −14.105 | 0.853 | 1.00 | 58.85 | C |
| ATOM | 3100 | CB | LEU | A | 357 | 6.485 | −13.038 | 0.262 | 1.00 | 58.70 | C |
| ATOM | 3103 | CG | LEU | A | 357 | 5.072 | −12.968 | 0.853 | 1.00 | 58.24 | C |
| ATOM | 3105 | CD1 | LEU | A | 357 | 5.116 | −12.631 | 2.343 | 1.00 | 57.97 | C |
| ATOM | 3109 | CD2 | LEU | A | 357 | 4.212 | −11.963 | 0.093 | 1.00 | 58.03 | C |
| ATOM | 3113 | C | LEU | A | 357 | 6.831 | −15.496 | 0.622 | 1.00 | 59.38 | C |
| ATOM | 3114 | O | LEU | A | 357 | 6.052 | −15.986 | 1.434 | 1.00 | 59.38 | O |
| ATOM | 3115 | N | LYS | A | 358 | 7.208 | −16.122 | −0.491 | 1.00 | 60.10 | N |
| ATOM | 3117 | CA | LYS | A | 358 | 6.755 | −17.475 | −0.811 | 1.00 | 60.58 | C |
| ATOM | 3119 | CB | LYS | A | 358 | 6.989 | −17.794 | −2.291 | 1.00 | 60.52 | C |
| ATOM | 3122 | CG | LYS | A | 358 | 5.872 | −17.325 | −3.210 | 1.00 | 60.17 | C |
| ATOM | 3125 | CD | LYS | A | 358 | 6.175 | −17.656 | −4.660 | 1.00 | 59.88 | C |
| ATOM | 3128 | CE | LYS | A | 358 | 5.301 | −16.852 | −5.609 | 1.00 | 59.80 | C |
| ATOM | 3131 | NZ | LYS | A | 358 | 5.505 | −17.260 | −7.026 | 1.00 | 59.79 | N |
| ATOM | 3135 | C | LYS | A | 358 | 7.469 | −18.502 | 0.072 | 1.00 | 61.29 | C |
| ATOM | 3136 | O | LYS | A | 358 | 6.919 | −19.568 | 0.352 | 1.00 | 61.49 | O |
| ATOM | 3137 | N | THR | A | 359 | 8.683 | −18.165 | 0.518 | 1.00 | 62.09 | N |
| ATOM | 3139 | CA | THR | A | 359 | 9.486 | −19.030 | 1.390 | 1.00 | 62.66 | C |
| ATOM | 3141 | CB | THR | A | 359 | 11.004 | −18.802 | 1.141 | 1.00 | 62.66 | C |
| ATOM | 3143 | OG1 | THR | A | 359 | 11.260 | −18.683 | −0.266 | 1.00 | 62.61 | O |
| ATOM | 3145 | CG2 | THR | A | 359 | 11.833 | −20.023 | 1.548 | 1.00 | 62.83 | C |
| ATOM | 3149 | C | THR | A | 359 | 9.132 | −18.792 | 2.867 | 1.00 | 63.21 | C |
| ATOM | 3150 | O | THR | A | 359 | 9.858 | −19.215 | 3.771 | 1.00 | 63.42 | O |
| ATOM | 3151 | N | MET | A | 360 | 8.025 | −18.084 | 3.087 | 1.00 | 63.75 | N |
| ATOM | 3153 | CA | MET | A | 360 | 7.477 | −17.811 | 4.413 | 1.00 | 64.19 | C |
| ATOM | 3155 | CB | MET | A | 360 | 7.380 | −16.303 | 4.641 | 1.00 | 64.35 | C |
| ATOM | 3158 | CG | MET | A | 360 | 6.677 | −15.914 | 5.930 | 1.00 | 65.15 | C |
| ATOM | 3161 | SD | MET | A | 360 | 7.393 | −14.457 | 6.691 | 1.00 | 66.79 | S |
| ATOM | 3162 | CE | MET | A | 360 | 8.602 | −15.221 | 7.783 | 1.00 | 66.86 | C |
| ATOM | 3166 | C | MET | A | 360 | 6.088 | −18.461 | 4.511 | 1.00 | 64.26 | C |
| ATOM | 3167 | O | MET | A | 360 | 5.694 | −18.944 | 5.574 | 1.00 | 64.28 | O |
| ATOM | 3168 | N | VAL | A | 361 | 5.357 | −18.443 | 3.394 | 1.00 | 64.36 | N |
| ATOM | 3170 | CA | VAL | A | 361 | 4.038 | −19.062 | 3.271 | 1.00 | 64.49 | C |
| ATOM | 3172 | CB | VAL | A | 361 | 3.395 | −18.723 | 1.896 | 1.00 | 64.48 | C |
| ATOM | 3174 | CG1 | VAL | A | 361 | 2.223 | −19.651 | 1.568 | 1.00 | 64.41 | C |
| ATOM | 3178 | CG2 | VAL | A | 361 | 2.948 | −17.270 | 1.860 | 1.00 | 64.49 | C |
| ATOM | 3182 | C | VAL | A | 361 | 4.166 | −20.576 | 3.405 | 1.00 | 64.64 | C |
| ATOM | 3183 | O | VAL | A | 361 | 3.276 | −21.238 | 3.940 | 1.00 | 64.75 | O |

TABLE 2-continued

| ATOM | 3184 | N | GLU | A | 362 | 5.277 | −21.111 | 2.901 | 1.00 | 64.76 | N |
|---|---|---|---|---|---|---|---|---|---|---|---|
| ATOM | 3186 | CA | GLU | A | 362 | 5.563 | −22.541 | 2.967 | 1.00 | 64.82 | C |
| ATOM | 3188 | CB | GLU | A | 362 | 6.795 | −22.880 | 2.120 | 1.00 | 64.87 | C |
| ATOM | 3191 | CG | GLU | A | 362 | 6.534 | −22.851 | 0.618 | 1.00 | 65.11 | C |
| ATOM | 3194 | CD | GLU | A | 362 | 7.805 | −22.815 | −0.220 | 1.00 | 65.64 | C |
| ATOM | 3195 | OE1 | GLU | A | 362 | 8.921 | −22.864 | 0.347 | 1.00 | 65.81 | O |
| ATOM | 3196 | OE2 | GLU | A | 362 | 7.686 | −22.736 | −1.461 | 1.00 | 65.97 | O |
| ATOM | 3197 | C | GLU | A | 362 | 5.779 | −22.980 | 4.413 | 1.00 | 64.76 | C |
| ATOM | 3198 | O | GLU | A | 362 | 5.172 | −23.949 | 4.863 | 1.00 | 64.96 | O |
| ATOM | 3199 | N | THR | A | 363 | 6.622 | −22.247 | 5.141 | 1.00 | 64.60 | N |
| ATOM | 3201 | CA | THR | A | 363 | 6.926 | −22.554 | 6.544 | 1.00 | 64.47 | C |
| ATOM | 3203 | CB | THR | A | 363 | 8.409 | −22.233 | 6.851 | 1.00 | 64.50 | C |
| ATOM | 3205 | OG1 | THR | A | 363 | 8.660 | −20.833 | 6.662 | 1.00 | 64.50 | O |
| ATOM | 3207 | CG2 | THR | A | 363 | 9.342 | −22.919 | 5.853 | 1.00 | 64.68 | C |
| ATOM | 3211 | C | THR | A | 363 | 6.019 | −21.786 | 7.513 | 1.00 | 64.31 | C |
| ATOM | 3212 | O | THR | A | 363 | 6.409 | −21.494 | 8.646 | 1.00 | 64.24 | O |
| ATOM | 3213 | N | LYS | A | 364 | 4.804 | −21.479 | 7.065 | 1.00 | 64.15 | N |
| ATOM | 3215 | CA | LYS | A | 364 | 3.841 | −20.729 | 7.862 | 1.00 | 63.99 | C |
| ATOM | 3217 | CB | LYS | A | 364 | 2.666 | −20.302 | 6.978 | 1.00 | 63.83 | C |
| ATOM | 3220 | CG | LYS | A | 364 | 1.662 | −19.363 | 7.642 | 1.00 | 63.30 | C |
| ATOM | 3223 | CD | LYS | A | 364 | 0.226 | −19.860 | 7.490 | 1.00 | 62.69 | C |
| ATOM | 3226 | CE | LYS | A | 364 | −0.197 | −19.958 | 6.030 | 1.00 | 62.25 | C |
| ATOM | 3229 | NZ | LYS | A | 364 | −1.662 | −19.764 | 5.870 | 1.00 | 61.94 | N |
| ATOM | 3233 | C | LYS | A | 364 | 3.321 | −21.544 | 9.046 | 1.00 | 64.13 | C |
| ATOM | 3234 | O | LYS | A | 364 | 2.816 | −22.654 | 8.872 | 1.00 | 64.18 | O |
| ATOM | 3235 | N | LYS | A | 365 | 3.462 | −20.985 | 10.244 | 1.00 | 64.19 | N |
| ATOM | 3237 | CA | LYS | A | 365 | 2.960 | −21.603 | 11.464 | 1.00 | 64.27 | C |
| ATOM | 3239 | CB | LYS | A | 365 | 4.058 | −21.691 | 12.522 | 1.00 | 64.25 | C |
| ATOM | 3242 | CG | LYS | A | 365 | 5.112 | −22.750 | 12.241 | 1.00 | 64.22 | C |
| ATOM | 3245 | CD | LYS | A | 365 | 6.011 | −22.966 | 13.447 | 1.00 | 64.32 | C |
| ATOM | 3248 | CE | LYS | A | 365 | 6.910 | −24.183 | 13.271 | 1.00 | 64.48 | C |
| ATOM | 3251 | NZ | LYS | A | 365 | 7.491 | −24.640 | 14.569 | 1.00 | 64.45 | N |
| ATOM | 3255 | C | LYS | A | 365 | 1.817 | −20.737 | 11.973 | 1.00 | 64.48 | C |
| ATOM | 3256 | O | LYS | A | 365 | 1.995 | −19.544 | 12.197 | 1.00 | 64.35 | O |
| ATOM | 3257 | N | VAL | A | 366 | 0.644 | −21.338 | 12.144 | 1.00 | 64.80 | N |
| ATOM | 3259 | CA | VAL | A | 366 | −0.539 | −20.622 | 12.629 | 1.00 | 65.07 | C |
| ATOM | 3261 | CB | VAL | A | 366 | −1.652 | −20.502 | 11.518 | 1.00 | 65.07 | C |
| ATOM | 3263 | CG1 | VAL | A | 366 | −1.543 | −21.618 | 10.487 | 1.00 | 65.09 | C |
| ATOM | 3267 | CG2 | VAL | A | 366 | −3.063 | −20.452 | 12.109 | 1.00 | 65.06 | C |
| ATOM | 3271 | C | VAL | A | 366 | −1.026 | −21.321 | 13.905 | 1.00 | 65.33 | C |
| ATOM | 3272 | O | VAL | A | 366 | −1.378 | −22.498 | 13.874 | 1.00 | 65.44 | O |
| ATOM | 3273 | N | THR | A | 367 | −1.025 | −20.587 | 15.020 | 1.00 | 65.62 | N |
| ATOM | 3275 | CA | THR | A | 367 | −1.420 | −21.117 | 16.337 | 1.00 | 65.84 | C |
| ATOM | 3277 | CB | THR | A | 367 | −1.222 | −20.041 | 17.451 | 1.00 | 65.79 | C |
| ATOM | 3279 | OG1 | THR | A | 367 | −2.157 | −18.966 | 17.283 | 1.00 | 65.81 | O |
| ATOM | 3281 | CG2 | THR | A | 367 | 0.149 | −19.372 | 17.358 | 1.00 | 65.81 | C |
| ATOM | 3285 | C | THR | A | 367 | −2.860 | −21.657 | 16.381 | 1.00 | 66.07 | C |
| ATOM | 3286 | O | THR | A | 367 | −3.570 | −21.642 | 15.372 | 1.00 | 66.10 | O |
| ATOM | 3287 | N | SER | A | 368 | −3.279 | −22.133 | 17.555 | 1.00 | 66.25 | N |
| ATOM | 3289 | CA | SER | A | 368 | −4.620 | −22.704 | 17.739 | 1.00 | 66.40 | C |
| ATOM | 3291 | CB | SER | A | 368 | −4.736 | −23.352 | 19.127 | 1.00 | 66.45 | C |
| ATOM | 3294 | OG | SER | A | 368 | −4.695 | −22.380 | 20.159 | 1.00 | 66.58 | O |
| ATOM | 3296 | C | SER | A | 368 | −5.778 | −21.713 | 17.527 | 1.00 | 66.44 | C |
| ATOM | 3297 | O | SER | A | 368 | −6.897 | −22.127 | 17.214 | 1.00 | 66.53 | O |
| ATOM | 3298 | N | SER | A | 369 | −5.511 | −20.419 | 17.691 | 1.00 | 66.51 | N |
| ATOM | 3300 | CA | SER | A | 369 | −6.534 | −19.380 | 17.518 | 1.00 | 66.52 | C |
| ATOM | 3302 | CB | SER | A | 369 | −6.180 | −18.148 | 18.357 | 1.00 | 66.55 | C |
| ATOM | 3305 | OG | SER | A | 369 | −6.442 | −18.381 | 19.729 | 1.00 | 66.65 | O |
| ATOM | 3307 | C | SER | A | 369 | −6.746 | −18.957 | 16.056 | 1.00 | 66.52 | C |
| ATOM | 3308 | O | SER | A | 369 | −7.733 | −18.291 | 15.741 | 1.00 | 66.60 | O |
| ATOM | 3309 | N | GLY | A | 370 | −5.822 | −19.338 | 15.176 | 1.00 | 66.42 | N |
| ATOM | 3311 | CA | GLY | A | 370 | −5.894 | −18.988 | 13.765 | 1.00 | 66.30 | C |
| ATOM | 3314 | C | GLY | A | 370 | −5.126 | −17.712 | 13.459 | 1.00 | 66.14 | C |
| ATOM | 3315 | O | GLY | A | 370 | −5.561 | −16.903 | 12.638 | 1.00 | 66.16 | O |
| ATOM | 3316 | N | VAL | A | 371 | −3.978 | −17.549 | 14.116 | 1.00 | 65.95 | N |
| ATOM | 3318 | CA | VAL | A | 371 | −3.133 | −16.363 | 13.971 | 1.00 | 65.84 | C |
| ATOM | 3320 | CB | VAL | A | 371 | −3.234 | −15.469 | 15.235 | 1.00 | 65.80 | C |
| ATOM | 3322 | CG1 | VAL | A | 371 | −2.175 | −14.362 | 15.234 | 1.00 | 65.65 | C |
| ATOM | 3326 | CG2 | VAL | A | 371 | −4.633 | −14.879 | 15.360 | 1.00 | 65.87 | C |
| ATOM | 3330 | C | VAL | A | 371 | −1.673 | −16.762 | 13.757 | 1.00 | 65.74 | C |
| ATOM | 3331 | O | VAL | A | 371 | −1.149 | −17.603 | 14.482 | 1.00 | 65.82 | O |
| ATOM | 3332 | N | LEU | A | 372 | −1.022 | −16.141 | 12.774 | 1.00 | 65.57 | N |
| ATOM | 3334 | CA | LEU | A | 372 | 0.381 | −16.412 | 12.463 | 1.00 | 65.39 | C |
| ATOM | 3336 | CB | LEU | A | 372 | 0.899 | −15.454 | 11.380 | 1.00 | 65.39 | C |
| ATOM | 3339 | CG | LEU | A | 372 | 0.294 | −15.515 | 9.973 | 1.00 | 65.31 | C |
| ATOM | 3341 | CD1 | LEU | A | 372 | 1.076 | −14.600 | 9.032 | 1.00 | 65.24 | C |
| ATOM | 3345 | CD2 | LEU | A | 372 | 0.259 | −16.943 | 9.442 | 1.00 | 65.29 | C |
| ATOM | 3349 | C | LEU | A | 372 | 1.285 | −16.286 | 13.683 | 1.00 | 65.30 | C |
| ATOM | 3350 | O | LEU | A | 372 | 1.074 | −15.437 | 14.550 | 1.00 | 65.28 | O |

TABLE 2-continued

| | | | | | | | | | | | |
|---|---|---|---|---|---|---|---|---|---|---|---|
| ATOM | 3351 | N | LEU | A | 373 | 2.303 | −17.136 | 13.720 | 1.00 | 65.25 | N |
| ATOM | 3353 | CA | LEU | A | 373 | 3.286 | −17.152 | 14.787 | 1.00 | 65.18 | C |
| ATOM | 3355 | CB | LEU | A | 373 | 3.489 | −18.580 | 15.312 | 1.00 | 65.21 | C |
| ATOM | 3358 | CG | LEU | A | 373 | 3.946 | −18.733 | 16.767 | 1.00 | 65.27 | C |
| ATOM | 3360 | CD1 | LEU | A | 373 | 4.024 | −20.207 | 17.145 | 1.00 | 65.41 | C |
| ATOM | 3364 | CD2 | LEU | A | 373 | 5.285 | −18.049 | 17.006 | 1.00 | 65.35 | C |
| ATOM | 3368 | C | LEU | A | 373 | 4.576 | −16.607 | 14.190 | 1.00 | 65.07 | C |
| ATOM | 3369 | O | LEU | A | 373 | 5.153 | −17.220 | 13.288 | 1.00 | 65.10 | O |
| ATOM | 3370 | N | LEU | A | 374 | 5.001 | −15.442 | 14.669 | 1.00 | 64.95 | N |
| ATOM | 3372 | CA | LEU | A | 374 | 6.238 | −14.818 | 14.216 | 1.00 | 64.79 | C |
| ATOM | 3374 | CB | LEU | A | 374 | 5.950 | −13.440 | 13.614 | 1.00 | 64.71 | C |
| ATOM | 3377 | CG | LEU | A | 374 | 4.887 | −13.420 | 12.504 | 1.00 | 64.35 | C |
| ATOM | 3379 | CD1 | LEU | A | 374 | 4.669 | −12.009 | 11.970 | 1.00 | 64.33 | C |
| ATOM | 3383 | CD2 | LEU | A | 374 | 5.253 | −14.356 | 11.363 | 1.00 | 64.07 | C |
| ATOM | 3387 | C | LEU | A | 374 | 7.178 | −14.734 | 15.418 | 1.00 | 64.81 | C |
| ATOM | 3388 | O | LEU | A | 374 | 6.819 | −14.163 | 16.449 | 1.00 | 64.73 | O |
| ATOM | 3389 | N | ASP | A | 375 | 8.366 | −15.328 | 15.279 | 1.00 | 64.83 | N |
| ATOM | 3391 | CA | ASP | A | 375 | 9.363 | −15.402 | 16.357 | 1.00 | 64.80 | C |
| ATOM | 3393 | CB | ASP | A | 375 | 10.583 | −16.224 | 15.910 | 1.00 | 64.92 | C |
| ATOM | 3396 | CG | ASP | A | 375 | 10.281 | −17.704 | 15.796 | 1.00 | 65.38 | C |
| ATOM | 3397 | OD1 | ASP | A | 375 | 9.802 | −18.293 | 16.789 | 1.00 | 66.10 | O |
| ATOM | 3398 | OD2 | ASP | A | 375 | 10.496 | −18.360 | 14.752 | 1.00 | 66.10 | O |
| ATOM | 3399 | C | ASP | A | 375 | 9.795 | −14.023 | 16.858 | 1.00 | 64.53 | C |
| ATOM | 3400 | O | ASP | A | 375 | 9.142 | −13.459 | 17.740 | 1.00 | 64.68 | O |
| ATOM | 3401 | N | ASN | A | 376 | 10.897 | −13.495 | 16.322 | 1.00 | 64.06 | N |
| ATOM | 3403 | CA | ASN | A | 376 | 11.366 | −12.159 | 16.689 | 1.00 | 63.62 | C |
| ATOM | 3405 | CB | ASN | A | 376 | 12.687 | −12.215 | 17.481 | 1.00 | 63.70 | C |
| ATOM | 3408 | CG | ASN | A | 376 | 12.801 | −11.092 | 18.529 | 1.00 | 63.83 | C |
| ATOM | 3409 | OD1 | ASN | A | 376 | 11.858 | −10.814 | 19.271 | 1.00 | 63.62 | O |
| ATOM | 3410 | ND2 | ASN | A | 376 | 13.959 | −10.443 | 18.576 | 1.00 | 64.12 | N |
| ATOM | 3413 | C | ASN | A | 376 | 11.474 | −11.288 | 15.435 | 1.00 | 62.99 | C |
| ATOM | 3414 | O | ASN | A | 376 | 10.898 | −11.622 | 14.397 | 1.00 | 62.85 | O |
| ATOM | 3415 | N | TYR | A | 377 | 12.200 | −10.179 | 15.548 | 1.00 | 62.24 | N |
| ATOM | 3417 | CA | TYR | A | 377 | 12.350 | −9.195 | 14.479 | 1.00 | 61.70 | C |
| ATOM | 3419 | CB | TYR | A | 377 | 13.623 | −8.366 | 14.698 | 1.00 | 61.88 | C |
| ATOM | 3422 | CG | TYR | A | 377 | 13.704 | −7.178 | 13.771 | 1.00 | 62.57 | C |
| ATOM | 3423 | CD1 | TYR | A | 377 | 12.900 | −6.062 | 13.976 | 1.00 | 63.01 | C |
| ATOM | 3425 | CE1 | TYR | A | 377 | 12.956 | −4.976 | 13.125 | 1.00 | 63.38 | C |
| ATOM | 3427 | CZ | TYR | A | 377 | 13.818 | −4.996 | 12.044 | 1.00 | 63.62 | C |
| ATOM | 3428 | OH | TYR | A | 377 | 13.879 | −3.920 | 11.192 | 1.00 | 64.56 | O |
| ATOM | 3430 | CE2 | TYR | A | 377 | 14.621 | −6.096 | 11.813 | 1.00 | 63.67 | C |
| ATOM | 3432 | CD2 | TYR | A | 377 | 14.559 | −7.181 | 12.674 | 1.00 | 63.25 | C |
| ATOM | 3434 | C | TYR | A | 377 | 12.335 | −9.708 | 13.033 | 1.00 | 60.81 | C |
| ATOM | 3435 | O | TYR | A | 377 | 11.502 | −9.278 | 12.247 | 1.00 | 60.79 | O |
| ATOM | 3436 | N | THR | A | 378 | 13.239 | −10.621 | 12.690 | 1.00 | 59.72 | N |
| ATOM | 3438 | CA | THR | A | 378 | 13.373 | −11.094 | 11.302 | 1.00 | 58.91 | C |
| ATOM | 3440 | CB | THR | A | 378 | 14.296 | −12.330 | 11.222 | 1.00 | 58.92 | C |
| ATOM | 3442 | OG1 | THR | A | 378 | 15.471 | −12.120 | 12.016 | 1.00 | 58.94 | O |
| ATOM | 3444 | CG2 | THR | A | 378 | 14.842 | −12.509 | 9.805 | 1.00 | 58.98 | C |
| ATOM | 3448 | C | THR | A | 378 | 12.056 | −11.401 | 10.584 | 1.00 | 58.03 | C |
| ATOM | 3449 | O | THR | A | 378 | 11.824 | −10.925 | 9.472 | 1.00 | 57.92 | O |
| ATOM | 3450 | N | ASP | A | 379 | 11.205 | −12.197 | 11.221 | 1.00 | 56.99 | N |
| ATOM | 3452 | CA | ASP | A | 379 | 9.938 | −12.609 | 10.614 | 1.00 | 56.14 | C |
| ATOM | 3454 | CB | ASP | A | 379 | 9.382 | −13.853 | 11.318 | 1.00 | 56.19 | C |
| ATOM | 3457 | CG | ASP | A | 379 | 10.389 | −14.991 | 11.377 | 1.00 | 56.72 | C |
| ATOM | 3458 | OD1 | ASP | A | 379 | 10.563 | −15.684 | 10.352 | 1.00 | 56.97 | O |
| ATOM | 3459 | OD2 | ASP | A | 379 | 11.057 | −15.258 | 12.402 | 1.00 | 57.18 | O |
| ATOM | 3460 | C | ASP | A | 379 | 8.887 | −11.498 | 10.608 | 1.00 | 55.16 | C |
| ATOM | 3461 | O | ASP | A | 379 | 8.153 | −11.347 | 9.633 | 1.00 | 55.02 | O |
| ATOM | 3462 | N | ARG | A | 380 | 8.821 | −10.728 | 11.690 | 1.00 | 54.06 | N |
| ATOM | 3464 | CA | ARG | A | 380 | 7.836 | −9.649 | 11.816 | 1.00 | 53.27 | C |
| ATOM | 3466 | CB | ARG | A | 380 | 7.828 | −9.089 | 13.241 | 1.00 | 53.30 | C |
| ATOM | 3469 | CG | ARG | A | 380 | 7.126 | −9.986 | 14.256 | 1.00 | 53.98 | C |
| ATOM | 3472 | CD | ARG | A | 380 | 6.680 | −9.256 | 15.507 | 1.00 | 54.82 | C |
| ATOM | 3475 | NE | ARG | A | 380 | 7.816 | −8.619 | 16.170 | 1.00 | 55.69 | N |
| ATOM | 3477 | CZ | ARG | A | 380 | 8.580 | −9.195 | 17.094 | 1.00 | 56.88 | C |
| ATOM | 3478 | NH1 | ARG | A | 380 | 8.355 | −10.444 | 17.493 | 1.00 | 57.59 | N |
| ATOM | 3481 | NH2 | ARG | A | 380 | 9.589 | −8.511 | 17.625 | 1.00 | 57.34 | N |
| ATOM | 3484 | C | ARG | A | 380 | 8.034 | −8.513 | 10.808 | 1.00 | 52.27 | C |
| ATOM | 3485 | O | ARG | A | 380 | 7.060 | −8.008 | 10.260 | 1.00 | 52.10 | O |
| ATOM | 3486 | N | ILE | A | 381 | 9.284 | −8.115 | 10.575 | 1.00 | 51.21 | N |
| ATOM | 3488 | CA | ILE | A | 381 | 9.596 | −7.048 | 9.622 | 1.00 | 50.48 | C |
| ATOM | 3490 | CB | ILE | A | 381 | 11.023 | −6.481 | 9.867 | 1.00 | 50.44 | C |
| ATOM | 3492 | CG1 | ILE | A | 381 | 11.188 | −5.096 | 9.228 | 1.00 | 50.07 | C |
| ATOM | 3495 | CD1 | ILE | A | 381 | 10.250 | −4.041 | 9.769 | 1.00 | 50.04 | C |
| ATOM | 3499 | CG2 | ILE | A | 381 | 12.096 | −7.423 | 9.315 | 1.00 | 50.36 | C |
| ATOM | 3503 | C | ILE | A | 381 | 9.457 | −7.512 | 8.173 | 1.00 | 49.88 | C |
| ATOM | 3504 | O | ILE | A | 381 | 9.327 | −6.687 | 7.277 | 1.00 | 49.73 | O |
| ATOM | 3505 | N | GLN | A | 382 | 9.512 | −8.823 | 7.948 | 1.00 | 49.32 | N |

TABLE 2-continued

| ATOM | 3507 | CA | GLN | A | 382 | 9.361 | −9.389 | 6.604 | 1.00 | 48.96 | C |
| --- | --- | --- | --- | --- | --- | --- | --- | --- | --- | --- | --- |
| ATOM | 3509 | CB | GLN | A | 382 | 9.874 | −10.833 | 6.550 | 1.00 | 49.03 | C |
| ATOM | 3512 | CG | GLN | A | 382 | 9.498 | −11.583 | 5.271 | 1.00 | 49.71 | C |
| ATOM | 3515 | CD | GLN | A | 382 | 10.366 | −12.798 | 5.018 | 1.00 | 50.87 | C |
| ATOM | 3516 | OE1 | GLN | A | 382 | 10.619 | −13.589 | 5.927 | 1.00 | 51.76 | O |
| ATOM | 3517 | NE2 | GLN | A | 382 | 10.821 | −12.953 | 3.781 | 1.00 | 51.90 | N |
| ATOM | 3520 | C | GLN | A | 382 | 7.901 | −9.330 | 6.158 | 1.00 | 48.39 | C |
| ATOM | 3521 | O | GLN | A | 382 | 7.617 | −9.186 | 4.967 | 1.00 | 48.24 | O |
| ATOM | 3522 | N | VAL | A | 383 | 6.982 | −9.458 | 7.114 | 1.00 | 47.74 | N |
| ATOM | 3524 | CA | VAL | A | 383 | 5.554 | −9.375 | 6.825 | 1.00 | 47.31 | C |
| ATOM | 3526 | CB | VAL | A | 383 | 4.690 | −10.020 | 7.940 | 1.00 | 47.37 | C |
| ATOM | 3528 | CG1 | VAL | A | 383 | 3.196 | −9.847 | 7.645 | 1.00 | 47.42 | C |
| ATOM | 3532 | CG2 | VAL | A | 383 | 5.027 | −11.498 | 8.095 | 1.00 | 47.50 | C |
| ATOM | 3536 | C | VAL | A | 383 | 5.173 | −7.907 | 6.660 | 1.00 | 46.82 | C |
| ATOM | 3537 | O | VAL | A | 383 | 4.283 | −7.583 | 5.881 | 1.00 | 46.84 | O |
| ATOM | 3538 | N | LEU | A | 384 | 5.846 | −7.029 | 7.402 | 1.00 | 46.26 | N |
| ATOM | 3540 | CA | LEU | A | 384 | 5.598 | −5.590 | 7.321 | 1.00 | 45.82 | C |
| ATOM | 3542 | CB | LEU | A | 384 | 6.181 | −4.864 | 8.539 | 1.00 | 45.65 | C |
| ATOM | 3545 | CG | LEU | A | 384 | 5.535 | −5.180 | 9.894 | 1.00 | 45.05 | C |
| ATOM | 3547 | CD1 | LEU | A | 384 | 6.395 | −4.643 | 11.026 | 1.00 | 44.71 | C |
| ATOM | 3551 | CD2 | LEU | A | 384 | 4.127 | −4.615 | 9.986 | 1.00 | 44.60 | C |
| ATOM | 3555 | C | LEU | A | 384 | 6.175 | −5.013 | 6.023 | 1.00 | 45.60 | C |
| ATOM | 3556 | O | LEU | A | 384 | 5.630 | −4.063 | 5.475 | 1.00 | 45.57 | O |
| ATOM | 3557 | N | ARG | A | 385 | 7.274 | −5.592 | 5.543 | 1.00 | 45.37 | N |
| ATOM | 3559 | CA | ARG | A | 385 | 7.894 | −5.175 | 4.284 | 1.00 | 45.25 | C |
| ATOM | 3561 | CB | ARG | A | 385 | 9.134 | −6.025 | 3.957 | 1.00 | 45.39 | C |
| ATOM | 3564 | CG | ARG | A | 385 | 10.461 | −5.417 | 4.341 | 1.00 | 46.64 | C |
| ATOM | 3567 | CD | ARG | A | 385 | 11.639 | −5.926 | 3.514 | 1.00 | 48.25 | C |
| ATOM | 3570 | NE | ARG | A | 385 | 11.772 | −7.384 | 3.538 | 1.00 | 49.59 | N |
| ATOM | 3572 | CZ | ARG | A | 385 | 12.315 | −8.095 | 4.528 | 1.00 | 50.79 | C |
| ATOM | 3573 | NH1 | ARG | A | 385 | 12.785 | −7.505 | 5.626 | 1.00 | 51.23 | N |
| ATOM | 3576 | NH2 | ARG | A | 385 | 12.380 | −9.420 | 4.422 | 1.00 | 50.95 | N |
| ATOM | 3579 | C | ARG | A | 385 | 6.876 | −5.390 | 3.184 | 1.00 | 44.69 | C |
| ATOM | 3580 | O | ARG | A | 385 | 6.533 | −4.463 | 2.460 | 1.00 | 44.67 | O |
| ATOM | 3581 | N | ASN | A | 386 | 6.392 | −6.627 | 3.088 | 1.00 | 44.18 | N |
| ATOM | 3583 | CA | ASN | A | 386 | 5.406 | −7.016 | 2.084 | 1.00 | 43.71 | C |
| ATOM | 3585 | CB | ASN | A | 386 | 5.260 | −8.544 | 2.036 | 1.00 | 43.83 | C |
| ATOM | 3588 | CG | ASN | A | 386 | 6.454 | −9.224 | 1.402 | 1.00 | 43.70 | C |
| ATOM | 3589 | OD1 | ASN | A | 386 | 6.476 | −9.467 | 0.191 | 1.00 | 44.67 | O |
| ATOM | 3590 | ND2 | ASN | A | 386 | 7.458 | −9.528 | 2.213 | 1.00 | 43.32 | N |
| ATOM | 3593 | C | ASN | A | 386 | 4.031 | −6.386 | 2.287 | 1.00 | 43.28 | C |
| ATOM | 3594 | O | ASN | A | 386 | 3.285 | −6.246 | 1.325 | 1.00 | 43.11 | O |
| ATOM | 3595 | N | MET | A | 387 | 3.694 | −6.015 | 3.521 | 1.00 | 42.73 | N |
| ATOM | 3597 | CA | MET | A | 387 | 2.392 | −5.408 | 3.809 | 1.00 | 42.45 | C |
| ATOM | 3599 | CB | MET | A | 387 | 2.137 | −5.317 | 5.321 | 1.00 | 42.47 | C |
| ATOM | 3602 | CG | MET | A | 387 | 0.832 | −4.620 | 5.700 | 1.00 | 42.67 | C |
| ATOM | 3605 | SD | MET | A | 387 | 0.604 | −4.461 | 7.501 | 1.00 | 44.12 | S |
| ATOM | 3606 | CE | MET | A | 387 | 0.251 | −6.152 | 7.931 | 1.00 | 44.14 | C |
| ATOM | 3610 | C | MET | A | 387 | 2.319 | −4.019 | 3.191 | 1.00 | 42.13 | C |
| ATOM | 3611 | O | MET | A | 387 | 1.305 | −3.650 | 2.603 | 1.00 | 41.95 | O |
| ATOM | 3612 | N | VAL | A | 388 | 3.398 | −3.254 | 3.341 | 1.00 | 41.82 | N |
| ATOM | 3614 | CA | VAL | A | 388 | 3.477 | −1.906 | 2.790 | 1.00 | 41.67 | C |
| ATOM | 3616 | CB | VAL | A | 388 | 4.652 | −1.112 | 3.405 | 1.00 | 41.63 | C |
| ATOM | 3618 | CG1 | VAL | A | 388 | 4.801 | 0.256 | 2.739 | 1.00 | 41.55 | C |
| ATOM | 3622 | CG2 | VAL | A | 388 | 4.460 | −0.950 | 4.913 | 1.00 | 41.76 | C |
| ATOM | 3626 | C | VAL | A | 388 | 3.633 | −1.987 | 1.269 | 1.00 | 41.46 | C |
| ATOM | 3627 | O | VAL | A | 388 | 3.160 | −1.115 | 0.548 | 1.00 | 41.48 | O |
| ATOM | 3628 | N | HIS | A | 389 | 4.285 | −3.046 | 0.800 | 1.00 | 41.23 | N |
| ATOM | 3630 | CA | HIS | A | 389 | 4.507 | −3.274 | −0.627 | 1.00 | 41.10 | C |
| ATOM | 3632 | CB | HIS | A | 389 | 5.523 | −4.412 | −0.824 | 1.00 | 40.86 | C |
| ATOM | 3635 | CG | HIS | A | 389 | 5.807 | −4.739 | −2.259 | 1.00 | 40.60 | C |
| ATOM | 3636 | ND1 | HIS | A | 389 | 6.008 | −3.773 | −3.220 | 1.00 | 39.95 | N |
| ATOM | 3638 | CE1 | HIS | A | 389 | 6.241 | −4.354 | −4.383 | 1.00 | 40.08 | C |
| ATOM | 3640 | NE2 | HIS | A | 389 | 6.200 | −5.663 | −4.212 | 1.00 | 40.52 | N |
| ATOM | 3642 | CD2 | HIS | A | 389 | 5.933 | −5.931 | −2.891 | 1.00 | 40.18 | C |
| ATOM | 3644 | C | HIS | A | 389 | 3.177 | −3.605 | −1.303 | 1.00 | 41.02 | C |
| ATOM | 3645 | O | HIS | A | 389 | 2.902 | −3.136 | −2.408 | 1.00 | 41.03 | O |
| ATOM | 3646 | N | CYS | A | 390 | 2.353 | −4.395 | −0.615 | 1.00 | 40.89 | N |
| ATOM | 3648 | CA | CYS | A | 390 | 1.032 | −4.787 | −1.103 | 1.00 | 40.62 | C |
| ATOM | 3650 | CB | CYS | A | 390 | 0.399 | −5.841 | −0.185 | 1.00 | 40.57 | C |
| ATOM | 3653 | SG | CYS | A | 390 | 1.059 | −7.520 | −0.334 | 1.00 | 41.97 | S |
| ATOM | 3654 | C | CYS | A | 390 | 0.143 | −3.554 | −1.147 | 1.00 | 40.02 | C |
| ATOM | 3655 | O | CYS | A | 390 | −0.599 | −3.340 | −2.105 | 1.00 | 39.93 | O |
| ATOM | 3656 | N | ALA | A | 391 | 0.230 | −2.745 | −0.096 | 1.00 | 39.44 | N |
| ATOM | 3658 | CA | ALA | A | 391 | −0.536 | −1.509 | 0.008 | 1.00 | 39.01 | C |
| ATOM | 3660 | CB | ALA | A | 391 | −0.318 | −0.855 | 1.378 | 1.00 | 38.87 | C |
| ATOM | 3664 | C | ALA | A | 391 | −0.168 | −0.544 | −1.115 | 1.00 | 38.55 | C |
| ATOM | 3665 | O | ALA | A | 391 | −1.033 | 0.152 | −1.626 | 1.00 | 38.72 | O |
| ATOM | 3666 | N | ASP | A | 392 | 1.109 | −0.512 | −1.492 | 1.00 | 38.27 | N |

TABLE 2-continued

| | | | | | | | | | | | |
|---|---|---|---|---|---|---|---|---|---|---|---|
| ATOM | 3668 | CA | ASP | A | 392 | 1.596 | 0.337 | −2.586 | 1.00 | 38.33 | C |
| ATOM | 3670 | CB | ASP | A | 392 | 3.137 | 0.357 | −2.605 | 1.00 | 37.78 | C |
| ATOM | 3673 | CG | ASP | A | 392 | 3.728 | 1.583 | −3.318 | 1.00 | 37.06 | C |
| ATOM | 3674 | OD1 | ASP | A | 392 | 4.924 | 1.527 | −3.675 | 1.00 | 36.40 | O |
| ATOM | 3675 | OD2 | ASP | A | 392 | 3.121 | 2.649 | −3.557 | 1.00 | 32.73 | O |
| ATOM | 3676 | C | ASP | A | 392 | 1.034 | −0.194 | −3.917 | 1.00 | 38.88 | C |
| ATOM | 3677 | O | ASP | A | 392 | 0.692 | 0.586 | −4.803 | 1.00 | 39.17 | O |
| ATOM | 3678 | N | LEU | A | 393 | 0.927 | −1.518 | −4.036 | 1.00 | 39.64 | N |
| ATOM | 3680 | CA | LEU | A | 393 | 0.384 | −2.179 | −5.231 | 1.00 | 40.17 | C |
| ATOM | 3682 | CB | LEU | A | 393 | 1.296 | −3.332 | −5.662 | 1.00 | 40.13 | C |
| ATOM | 3685 | CG | LEU | A | 393 | 2.778 | −3.012 | −5.860 | 1.00 | 40.50 | C |
| ATOM | 3687 | CD1 | LEU | A | 393 | 3.537 | −4.271 | −6.228 | 1.00 | 40.65 | C |
| ATOM | 3691 | CD2 | LEU | A | 393 | 2.963 | −1.949 | −6.927 | 1.00 | 41.08 | C |
| ATOM | 3695 | C | LEU | A | 393 | −1.031 | −2.719 | −4.991 | 1.00 | 40.58 | C |
| ATOM | 3696 | O | LEU | A | 393 | −1.344 | −3.837 | −5.391 | 1.00 | 40.89 | O |
| ATOM | 3697 | N | SER | A | 394 | −1.884 | −1.915 | −4.357 | 1.00 | 41.12 | N |
| ATOM | 3699 | CA | SER | A | 394 | −3.258 | −2.317 | −4.035 | 1.00 | 41.47 | C |
| ATOM | 3701 | CB | SER | A | 394 | −3.564 | −1.997 | −2.566 | 1.00 | 41.42 | C |
| ATOM | 3704 | OG | SER | A | 394 | −3.644 | −0.596 | −2.363 | 1.00 | 41.45 | O |
| ATOM | 3706 | C | SER | A | 394 | −4.333 | −1.666 | −4.898 | 1.00 | 41.75 | C |
| ATOM | 3707 | O | SER | A | 394 | −5.506 | −1.972 | −4.732 | 1.00 | 41.92 | O |
| ATOM | 3708 | N | ASN | A | 395 | −3.947 | −0.757 | −5.791 | 1.00 | 42.41 | N |
| ATOM | 3710 | CA | ASN | A | 395 | −4.900 | −0.065 | −6.675 | 1.00 | 42.79 | C |
| ATOM | 3712 | CB | ASN | A | 395 | −4.165 | 0.788 | −7.727 | 1.00 | 42.93 | C |
| ATOM | 3715 | CG | ASN | A | 395 | −3.454 | 1.991 | −7.137 | 1.00 | 43.32 | C |
| ATOM | 3716 | OD1 | ASN | A | 395 | −2.567 | 2.555 | −7.774 | 1.00 | 43.40 | O |
| ATOM | 3717 | ND2 | ASN | A | 395 | −3.835 | 2.392 | −5.929 | 1.00 | 43.70 | N |
| ATOM | 3720 | C | ASN | A | 395 | −5.899 | −0.982 | −7.407 | 1.00 | 43.00 | C |
| ATOM | 3721 | O | ASN | A | 395 | −7.091 | −0.680 | −7.431 | 1.00 | 42.89 | O |
| ATOM | 3722 | N | PRO | A | 396 | −5.430 | −2.075 | −8.016 | 1.00 | 43.44 | N |
| ATOM | 3723 | CA | PRO | A | 396 | −6.325 | −2.980 | −8.757 | 1.00 | 43.76 | C |
| ATOM | 3725 | CB | PRO | A | 396 | −5.350 | −3.863 | −9.552 | 1.00 | 43.61 | C |
| ATOM | 3728 | CG | PRO | A | 396 | −4.049 | −3.165 | −9.468 | 1.00 | 43.42 | C |
| ATOM | 3731 | CD | PRO | A | 396 | −4.035 | −2.540 | −8.100 | 1.00 | 43.46 | C |
| ATOM | 3734 | C | PRO | A | 396 | −7.234 | −3.847 | −7.888 | 1.00 | 44.16 | C |
| ATOM | 3735 | O | PRO | A | 396 | −8.130 | −4.492 | −8.431 | 1.00 | 44.22 | O |
| ATOM | 3736 | N | THR | A | 397 | −7.000 | −3.871 | −6.579 | 1.00 | 44.54 | N |
| ATOM | 3738 | CA | THR | A | 397 | −7.814 | −4.658 | −5.654 | 1.00 | 44.84 | C |
| ATOM | 3740 | CB | THR | A | 397 | −6.952 | −5.177 | −4.487 | 1.00 | 44.87 | C |
| ATOM | 3742 | OG1 | THR | A | 397 | −6.512 | −4.078 | −3.680 | 1.00 | 44.99 | O |
| ATOM | 3744 | CG2 | THR | A | 397 | −5.664 | −5.830 | −4.986 | 1.00 | 44.63 | C |
| ATOM | 3748 | C | THR | A | 397 | −8.992 | −3.871 | −5.076 | 1.00 | 45.05 | C |
| ATOM | 3749 | O | THR | A | 397 | −9.796 | −4.425 | −4.330 | 1.00 | 45.16 | O |
| ATOM | 3750 | N | LYS | A | 398 | −9.090 | −2.589 | −5.410 | 1.00 | 45.34 | N |
| ATOM | 3752 | CA | LYS | A | 398 | −10.167 | −1.741 | −4.912 | 1.00 | 45.60 | C |
| ATOM | 3754 | CB | LYS | A | 398 | −9.704 | −0.284 | −4.807 | 1.00 | 45.48 | C |
| ATOM | 3757 | CG | LYS | A | 398 | −8.381 | −0.077 | −4.076 | 1.00 | 45.11 | C |
| ATOM | 3760 | CD | LYS | A | 398 | −8.521 | −0.256 | −2.566 | 1.00 | 44.81 | C |
| ATOM | 3763 | CE | LYS | A | 398 | −7.158 | −0.283 | −1.900 | 1.00 | 44.33 | C |
| ATOM | 3766 | NZ | LYS | A | 398 | −7.192 | 0.252 | −0.520 | 1.00 | 45.17 | N |
| ATOM | 3770 | C | LYS | A | 398 | −11.360 | −1.841 | −5.852 | 1.00 | 46.15 | C |
| ATOM | 3771 | O | LYS | A | 398 | −11.270 | −2.472 | −6.907 | 1.00 | 46.33 | O |
| ATOM | 3772 | N | SER | A | 399 | −12.478 | −1.225 | −5.471 | 1.00 | 46.72 | N |
| ATOM | 3774 | CA | SER | A | 399 | −13.671 | −1.230 | −6.315 | 1.00 | 47.18 | C |
| ATOM | 3776 | CB | SER | A | 399 | −14.819 | −0.482 | −5.641 | 1.00 | 47.16 | C |
| ATOM | 3779 | OG | SER | A | 399 | −14.557 | 0.907 | −5.590 | 1.00 | 47.64 | O |
| ATOM | 3781 | C | SER | A | 399 | −13.319 | −0.574 | −7.650 | 1.00 | 47.59 | C |
| ATOM | 3782 | O | SER | A | 399 | −12.555 | 0.390 | −7.677 | 1.00 | 47.75 | O |
| ATOM | 3783 | N | LEU | A | 400 | −13.879 | −1.092 | −8.742 | 1.00 | 47.96 | N |
| ATOM | 3785 | CA | LEU | A | 400 | −13.570 | −0.606 | −10.095 | 1.00 | 48.22 | C |
| ATOM | 3787 | CB | LEU | A | 400 | −14.511 | −1.248 | −11.127 | 1.00 | 48.28 | C |
| ATOM | 3790 | CG | LEU | A | 400 | −14.167 | −1.051 | −12.611 | 1.00 | 48.36 | C |
| ATOM | 3792 | CD1 | LEU | A | 400 | −12.816 | −1.664 | −12.960 | 1.00 | 48.16 | C |
| ATOM | 3796 | CD2 | LEU | A | 400 | −15.261 | −1.644 | −13.491 | 1.00 | 48.58 | C |
| ATOM | 3800 | C | LEU | A | 400 | −13.580 | 0.920 | −10.252 | 1.00 | 48.54 | C |
| ATOM | 3801 | O | LEU | A | 400 | −12.779 | 1.461 | −11.012 | 1.00 | 48.59 | O |
| ATOM | 3802 | N | GLU | A | 401 | −14.472 | 1.609 | −9.541 | 1.00 | 48.80 | N |
| ATOM | 3804 | CA | GLU | A | 401 | −14.558 | 3.072 | −9.621 | 1.00 | 49.07 | C |
| ATOM | 3806 | CB | GLU | A | 401 | −15.691 | 3.601 | −8.733 | 1.00 | 49.32 | C |
| ATOM | 3809 | CG | GLU | A | 401 | −15.979 | 5.087 | −8.911 | 1.00 | 50.46 | C |
| ATOM | 3812 | CD | GLU | A | 401 | −17.019 | 5.614 | −7.936 | 1.00 | 52.36 | C |
| ATOM | 3813 | OE1 | GLU | A | 401 | −17.912 | 6.374 | −8.373 | 1.00 | 53.45 | O |
| ATOM | 3814 | OE2 | GLU | A | 401 | −16.943 | 5.281 | −6.730 | 1.00 | 53.64 | O |
| ATOM | 3815 | C | GLU | A | 401 | −13.239 | 3.757 | −9.240 | 1.00 | 48.88 | C |
| ATOM | 3816 | O | GLU | A | 401 | −12.774 | 4.647 | −9.952 | 1.00 | 49.05 | O |
| ATOM | 3817 | N | LEU | A | 402 | −12.656 | 3.344 | −8.114 | 1.00 | 48.57 | N |
| ATOM | 3819 | CA | LEU | A | 402 | −11.394 | 3.910 | −7.629 | 1.00 | 48.27 | C |
| ATOM | 3821 | CB | LEU | A | 402 | −11.127 | 3.503 | −6.167 | 1.00 | 48.36 | C |
| ATOM | 3824 | CG | LEU | A | 402 | −12.280 | 3.501 | −5.153 | 1.00 | 48.49 | C |

TABLE 2-continued

| ATOM | 3826 | CD1 | LEU | A | 402 | −11.745 | 3.347 | −3.738 | 1.00 | 48.50 | C |
| --- | --- | --- | --- | --- | --- | --- | --- | --- | --- | --- | --- |
| ATOM | 3830 | CD2 | LEU | A | 402 | −13.138 | 4.750 | −5.269 | 1.00 | 48.76 | C |
| ATOM | 3834 | C | LEU | A | 402 | −10.200 | 3.480 | −8.487 | 1.00 | 47.93 | C |
| ATOM | 3835 | O | LEU | A | 402 | −9.328 | 4.284 | −8.783 | 1.00 | 47.77 | O |
| ATOM | 3836 | N | TYR | A | 403 | −10.171 | 2.207 | −8.866 | 1.00 | 47.70 | N |
| ATOM | 3838 | CA | TYR | A | 403 | −9.087 | 1.641 | −9.663 | 1.00 | 47.65 | C |
| ATOM | 3840 | CB | TYR | A | 403 | −9.338 | 0.145 | −9.882 | 1.00 | 47.53 | C |
| ATOM | 3843 | CG | TYR | A | 403 | −8.309 | −0.587 | −10.725 | 1.00 | 47.11 | C |
| ATOM | 3844 | CD1 | TYR | A | 403 | −6.969 | −0.191 | −10.755 | 1.00 | 46.57 | C |
| ATOM | 3846 | CE1 | TYR | A | 403 | −6.041 | −0.869 | −11.524 | 1.00 | 46.35 | C |
| ATOM | 3848 | CZ | TYR | A | 403 | −6.436 | −1.963 | −12.265 | 1.00 | 45.90 | C |
| ATOM | 3849 | OH | TYR | A | 403 | −5.514 | −2.644 | −13.021 | 1.00 | 45.02 | O |
| ATOM | 3851 | CE2 | TYR | A | 403 | −7.749 | −2.384 | −12.241 | 1.00 | 46.31 | C |
| ATOM | 3853 | CD2 | TYR | A | 403 | −8.677 | −1.696 | −11.478 | 1.00 | 46.40 | C |
| ATOM | 3855 | C | TYR | A | 403 | −8.892 | 2.346 | −11.009 | 1.00 | 47.87 | C |
| ATOM | 3856 | O | TYR | A | 403 | −7.763 | 2.539 | −11.445 | 1.00 | 48.05 | O |
| ATOM | 3857 | N | ARG | A | 404 | −9.981 | 2.732 | −11.661 | 1.00 | 47.98 | N |
| ATOM | 3859 | CA | ARG | A | 404 | −9.888 | 3.410 | −12.955 | 1.00 | 48.10 | C |
| ATOM | 3861 | CB | ARG | A | 404 | −11.241 | 3.429 | −13.671 | 1.00 | 48.09 | C |
| ATOM | 3864 | CG | ARG | A | 404 | −11.697 | 2.057 | −14.138 | 1.00 | 48.48 | C |
| ATOM | 3867 | CD | ARG | A | 404 | −13.175 | 1.976 | −14.480 | 1.00 | 49.63 | C |
| ATOM | 3870 | NE | ARG | A | 404 | −13.572 | 2.967 | −15.480 | 1.00 | 50.59 | N |
| ATOM | 3872 | CZ | ARG | A | 404 | −14.813 | 3.126 | −15.936 | 1.00 | 51.74 | C |
| ATOM | 3873 | NH1 | ARG | A | 404 | −15.807 | 2.362 | −15.491 | 1.00 | 51.70 | N |
| ATOM | 3876 | NH2 | ARG | A | 404 | −15.064 | 4.058 | −16.849 | 1.00 | 52.64 | N |
| ATOM | 3879 | C | ARG | A | 404 | −9.344 | 4.825 | −12.785 | 1.00 | 47.93 | C |
| ATOM | 3880 | O | ARG | A | 404 | −8.649 | 5.326 | −13.664 | 1.00 | 47.98 | O |
| ATOM | 3881 | N | GLN | A | 405 | −9.674 | 5.466 | −11.665 | 1.00 | 47.72 | N |
| ATOM | 3883 | CA | GLN | A | 405 | −9.169 | 6.807 | −11.364 | 1.00 | 47.55 | C |
| ATOM | 3885 | CB | GLN | A | 405 | −9.894 | 7.415 | −10.156 | 1.00 | 47.65 | C |
| ATOM | 3888 | CG | GLN | A | 405 | −11.333 | 7.827 | −10.423 | 1.00 | 47.91 | C |
| ATOM | 3891 | CD | GLN | A | 405 | −12.033 | 8.333 | −9.171 | 1.00 | 48.34 | C |
| ATOM | 3892 | OE1 | GLN | A | 405 | −11.867 | 9.493 | −8.787 | 1.00 | 48.55 | O |
| ATOM | 3893 | NE2 | GLN | A | 405 | −12.814 | 7.468 | −8.535 | 1.00 | 48.06 | N |
| ATOM | 3896 | C | GLN | A | 405 | −7.667 | 6.750 | −11.086 | 1.00 | 47.17 | C |
| ATOM | 3897 | O | GLN | A | 405 | −6.938 | 7.686 | −11.401 | 1.00 | 47.21 | O |
| ATOM | 3898 | N | TRP | A | 406 | −7.217 | 5.647 | −10.492 | 1.00 | 46.86 | N |
| ATOM | 3900 | CA | TRP | A | 406 | −5.804 | 5.447 | −10.189 | 1.00 | 46.50 | C |
| ATOM | 3902 | CB | TRP | A | 406 | −5.606 | 4.261 | −9.242 | 1.00 | 46.25 | C |
| ATOM | 3905 | CG | TRP | A | 406 | −5.940 | 4.535 | −7.801 | 1.00 | 45.56 | C |
| ATOM | 3906 | CD1 | TRP | A | 406 | −6.770 | 3.802 | −7.006 | 1.00 | 44.81 | C |
| ATOM | 3908 | NE1 | TRP | A | 406 | −6.820 | 4.344 | −5.744 | 1.00 | 44.56 | N |
| ATOM | 3910 | CE2 | TRP | A | 406 | −6.009 | 5.446 | −5.699 | 1.00 | 44.23 | C |
| ATOM | 3911 | CD2 | TRP | A | 406 | −5.431 | 5.593 | −6.978 | 1.00 | 44.25 | C |
| ATOM | 3912 | CE3 | TRP | A | 406 | −4.548 | 6.661 | −7.194 | 1.00 | 43.97 | C |
| ATOM | 3914 | CZ3 | TRP | A | 406 | −4.277 | 7.533 | −6.141 | 1.00 | 43.95 | C |
| ATOM | 3916 | CH2 | TRP | A | 406 | −4.871 | 7.355 | −4.882 | 1.00 | 43.36 | C |
| ATOM | 3918 | CZ2 | TRP | A | 406 | −5.735 | 6.322 | −4.641 | 1.00 | 43.59 | C |
| ATOM | 3920 | C | TRP | A | 406 | −5.052 | 5.178 | −11.479 | 1.00 | 46.53 | C |
| ATOM | 3921 | O | TRP | A | 406 | −3.933 | 5.644 | −11.662 | 1.00 | 46.38 | O |
| ATOM | 3922 | N | THR | A | 407 | −5.683 | 4.414 | −12.365 | 1.00 | 46.63 | N |
| ATOM | 3924 | CA | THR | A | 407 | −5.099 | 4.060 | −13.650 | 1.00 | 46.70 | C |
| ATOM | 3926 | CB | THR | A | 407 | −6.005 | 3.060 | −14.384 | 1.00 | 46.72 | C |
| ATOM | 3928 | OG1 | THR | A | 407 | −5.963 | 1.793 | −13.713 | 1.00 | 46.85 | O |
| ATOM | 3930 | CG2 | THR | A | 407 | −5.482 | 2.762 | −15.796 | 1.00 | 46.53 | C |
| ATOM | 3934 | C | THR | A | 407 | −4.883 | 5.296 | −14.506 | 1.00 | 46.74 | C |
| ATOM | 3935 | O | THR | A | 407 | −3.832 | 5.449 | −15.109 | 1.00 | 46.88 | O |
| ATOM | 3936 | N | ASP | A | 408 | −5.874 | 6.181 | −14.546 | 1.00 | 46.80 | N |
| ATOM | 3938 | CA | ASP | A | 408 | −5.772 | 7.402 | −15.341 | 1.00 | 46.99 | C |
| ATOM | 3940 | CB | ASP | A | 408 | −7.091 | 8.189 | −15.323 | 1.00 | 47.06 | C |
| ATOM | 3943 | CG | ASP | A | 408 | −8.225 | 7.468 | −16.050 | 1.00 | 47.20 | C |
| ATOM | 3944 | OD1 | ASP | A | 408 | −7.998 | 6.370 | −16.609 | 1.00 | 47.26 | O |
| ATOM | 3945 | OD2 | ASP | A | 408 | −9.388 | 7.926 | −16.101 | 1.00 | 47.56 | O |
| ATOM | 3946 | C | ASP | A | 408 | −4.636 | 8.283 | −14.834 | 1.00 | 46.98 | C |
| ATOM | 3947 | O | ASP | A | 408 | −3.980 | 8.966 | −15.620 | 1.00 | 47.06 | O |
| ATOM | 3948 | N | ARG | A | 409 | −4.409 | 8.247 | −13.521 | 1.00 | 46.89 | N |
| ATOM | 3950 | CA | ARG | A | 409 | −3.362 | 9.036 | −12.876 | 1.00 | 46.74 | C |
| ATOM | 3952 | CB | ARG | A | 409 | −3.598 | 9.104 | −11.359 | 1.00 | 46.70 | C |
| ATOM | 3955 | CG | ARG | A | 409 | −4.569 | 10.198 | −10.952 | 1.00 | 46.75 | C |
| ATOM | 3958 | CD | ARG | A | 409 | −5.104 | 10.079 | −9.536 | 1.00 | 46.90 | C |
| ATOM | 3961 | NE | ARG | A | 409 | −6.104 | 11.112 | −9.271 | 1.00 | 46.89 | N |
| ATOM | 3963 | CZ | ARG | A | 409 | −5.948 | 12.159 | −8.464 | 1.00 | 47.19 | C |
| ATOM | 3964 | NH1 | ARG | A | 409 | −4.818 | 12.355 | −7.787 | 1.00 | 47.87 | N |
| ATOM | 3967 | NH2 | ARG | A | 409 | −6.945 | 13.023 | −8.323 | 1.00 | 46.98 | N |
| ATOM | 3970 | C | ARG | A | 409 | −1.953 | 8.511 | −13.169 | 1.00 | 46.70 | C |
| ATOM | 3971 | O | ARG | A | 409 | −1.062 | 9.299 | −13.478 | 1.00 | 46.44 | O |
| ATOM | 3972 | N | ILE | A | 410 | −1.752 | 7.197 | −13.063 | 1.00 | 46.71 | N |
| ATOM | 3974 | CA | ILE | A | 410 | −0.441 | 6.598 | −13.326 | 1.00 | 46.91 | C |
| ATOM | 3976 | CB | ILE | A | 410 | −0.370 | 5.110 | −12.858 | 1.00 | 46.87 | C |

TABLE 2-continued

| ATOM | 3978 | CG1 | ILE | A | 410 | 1.079 | 4.597 | −12.868 | 1.00 | 46.76 | C |
|---|---|---|---|---|---|---|---|---|---|---|---|
| ATOM | 3981 | CD1 | ILE | A | 410 | 1.978 | 5.210 | −11.796 | 1.00 | 46.43 | C |
| ATOM | 3985 | CG2 | ILE | A | 410 | −1.218 | 4.203 | −13.733 | 1.00 | 46.87 | C |
| ATOM | 3989 | C | ILE | A | 410 | −0.051 | 6.716 | −14.800 | 1.00 | 47.18 | C |
| ATOM | 3990 | O | ILE | A | 410 | 1.117 | 6.932 | −15.106 | 1.00 | 47.10 | O |
| ATOM | 3991 | N | MET | A | 411 | −1.026 | 6.579 | −15.697 | 1.00 | 47.39 | N |
| ATOM | 3993 | CA | MET | A | 411 | −0.770 | 6.674 | −17.133 | 1.00 | 47.63 | C |
| ATOM | 3995 | CB | MET | A | 411 | −1.945 | 6.117 | −17.944 | 1.00 | 47.77 | C |
| ATOM | 3998 | CG | MET | A | 411 | −2.099 | 4.606 | −17.864 | 1.00 | 48.04 | C |
| ATOM | 4001 | SD | MET | A | 411 | −0.578 | 3.715 | −18.224 | 1.00 | 49.46 | S |
| ATOM | 4002 | CE | MET | A | 411 | −0.926 | 2.147 | −17.470 | 1.00 | 49.79 | C |
| ATOM | 4006 | C | MET | A | 411 | −0.485 | 8.108 | −17.552 | 1.00 | 47.61 | C |
| ATOM | 4007 | O | MET | A | 411 | 0.245 | 8.333 | −18.510 | 1.00 | 47.55 | O |
| ATOM | 4008 | N | GLU | A | 412 | −1.060 | 9.072 | −16.838 | 1.00 | 47.57 | N |
| ATOM | 4010 | CA | GLU | A | 412 | −0.816 | 10.477 | −17.133 | 1.00 | 47.66 | C |
| ATOM | 4012 | CB | GLU | A | 412 | −1.809 | 11.377 | −16.394 | 1.00 | 47.82 | C |
| ATOM | 4015 | CG | GLU | A | 412 | −1.707 | 12.847 | −16.775 | 1.00 | 48.72 | C |
| ATOM | 4018 | CD | GLU | A | 412 | −2.785 | 13.707 | −16.141 | 1.00 | 50.24 | C |
| ATOM | 4019 | OE1 | GLU | A | 412 | −3.958 | 13.270 | −16.083 | 1.00 | 51.65 | O |
| ATOM | 4020 | OE2 | GLU | A | 412 | −2.458 | 14.832 | −15.704 | 1.00 | 51.24 | O |
| ATOM | 4021 | C | GLU | A | 412 | 0.618 | 10.831 | −16.741 | 1.00 | 47.48 | C |
| ATOM | 4022 | O | GLU | A | 412 | 1.302 | 11.545 | −17.470 | 1.00 | 47.55 | O |
| ATOM | 4023 | N | GLU | A | 413 | 1.056 | 10.320 | −15.589 | 1.00 | 47.16 | N |
| ATOM | 4025 | CA | GLU | A | 413 | 2.405 | 10.551 | −15.072 | 1.00 | 46.86 | C |
| ATOM | 4027 | CB | GLU | A | 413 | 2.486 | 10.115 | −13.599 | 1.00 | 46.63 | C |
| ATOM | 4030 | CG | GLU | A | 413 | 3.885 | 10.099 | −12.994 | 1.00 | 45.50 | C |
| ATOM | 4033 | CD | GLU | A | 413 | 3.868 | 9.987 | −11.476 | 1.00 | 45.25 | C |
| ATOM | 4034 | OE1 | GLU | A | 413 | 2.888 | 10.439 | −10.859 | 1.00 | 43.07 | O |
| ATOM | 4035 | OE2 | GLU | A | 413 | 4.834 | 9.448 | −10.894 | 1.00 | 43.56 | O |
| ATOM | 4036 | C | GLU | A | 413 | 3.442 | 9.802 | −15.906 | 1.00 | 46.93 | C |
| ATOM | 4037 | O | GLU | A | 413 | 4.545 | 10.296 | −16.122 | 1.00 | 46.92 | O |
| ATOM | 4038 | N | PHE | A | 414 | 3.070 | 8.611 | −16.363 | 1.00 | 47.23 | N |
| ATOM | 4040 | CA | PHE | A | 414 | 3.925 | 7.764 | −17.195 | 1.00 | 47.47 | C |
| ATOM | 4042 | CB | PHE | A | 414 | 3.280 | 6.383 | −17.400 | 1.00 | 47.64 | C |
| ATOM | 4045 | CG | PHE | A | 414 | 3.860 | 5.286 | −16.545 | 1.00 | 48.44 | C |
| ATOM | 4046 | CD1 | PHE | A | 414 | 4.274 | 5.522 | −15.236 | 1.00 | 49.79 | C |
| ATOM | 4048 | CE1 | PHE | A | 414 | 4.800 | 4.491 | −14.461 | 1.00 | 50.00 | C |
| ATOM | 4050 | CZ | PHE | A | 414 | 4.907 | 3.212 | −14.994 | 1.00 | 50.40 | C |
| ATOM | 4052 | CE2 | PHE | A | 414 | 4.490 | 2.968 | −16.291 | 1.00 | 50.03 | C |
| ATOM | 4054 | CD2 | PHE | A | 414 | 3.969 | 3.999 | −17.055 | 1.00 | 49.43 | C |
| ATOM | 4056 | C | PHE | A | 414 | 4.141 | 8.400 | −18.565 | 1.00 | 47.42 | C |
| ATOM | 4057 | O | PHE | A | 414 | 5.261 | 8.443 | −19.059 | 1.00 | 47.39 | O |
| ATOM | 4058 | N | PHE | A | 415 | 3.059 | 8.884 | −19.171 | 1.00 | 47.55 | N |
| ATOM | 4060 | CA | PHE | A | 415 | 3.119 | 9.508 | −20.498 | 1.00 | 47.55 | C |
| ATOM | 4062 | CB | PHE | A | 415 | 1.717 | 9.631 | −21.117 | 1.00 | 47.28 | C |
| ATOM | 4065 | CG | PHE | A | 415 | 1.092 | 8.313 | −21.529 | 1.00 | 45.72 | C |
| ATOM | 4066 | CD1 | PHE | A | 415 | −0.275 | 8.242 | −21.763 | 1.00 | 44.96 | C |
| ATOM | 4068 | CE1 | PHE | A | 415 | −0.876 | 7.047 | −22.150 | 1.00 | 44.54 | C |
| ATOM | 4070 | CZ | PHE | A | 415 | −0.110 | 5.905 | −22.303 | 1.00 | 44.42 | C |
| ATOM | 4072 | CE2 | PHE | A | 415 | 1.254 | 5.960 | −22.079 | 1.00 | 44.55 | C |
| ATOM | 4074 | CD2 | PHE | A | 415 | 1.850 | 7.159 | −21.696 | 1.00 | 44.76 | C |
| ATOM | 4076 | C | PHE | A | 415 | 3.794 | 10.878 | −20.452 | 1.00 | 48.13 | C |
| ATOM | 4077 | O | PHE | A | 415 | 4.299 | 11.351 | −21.467 | 1.00 | 47.97 | O |
| ATOM | 4078 | N | GLN | A | 416 | 3.801 | 11.510 | −19.278 | 1.00 | 48.82 | N |
| ATOM | 4080 | CA | GLN | A | 416 | 4.461 | 12.802 | −19.102 | 1.00 | 49.44 | C |
| ATOM | 4082 | CB | GLN | A | 416 | 3.986 | 13.508 | −17.829 | 1.00 | 49.75 | C |
| ATOM | 4085 | CG | GLN | A | 416 | 3.060 | 14.684 | −18.084 | 1.00 | 50.68 | C |
| ATOM | 4088 | CD | GLN | A | 416 | 2.864 | 15.532 | −16.844 | 1.00 | 52.13 | C |
| ATOM | 4089 | OE1 | GLN | A | 416 | 3.818 | 16.131 | −16.341 | 1.00 | 52.97 | O |
| ATOM | 4090 | NE2 | GLN | A | 416 | 1.631 | 15.581 | −16.342 | 1.00 | 52.95 | N |
| ATOM | 4093 | C | GLN | A | 416 | 5.972 | 12.594 | −19.053 | 1.00 | 49.73 | C |
| ATOM | 4094 | O | GLN | A | 416 | 6.730 | 13.489 | −19.418 | 1.00 | 49.70 | O |
| ATOM | 4095 | N | GLN | A | 417 | 6.397 | 11.426 | −18.572 | 1.00 | 50.19 | N |
| ATOM | 4097 | CA | GLN | A | 417 | 7.811 | 11.064 | −18.550 | 1.00 | 50.60 | C |
| ATOM | 4099 | CB | GLN | A | 417 | 8.080 | 9.859 | −17.632 | 1.00 | 50.55 | C |
| ATOM | 4102 | CG | GLN | A | 417 | 9.377 | 9.090 | −17.956 | 1.00 | 50.24 | C |
| ATOM | 4105 | CD | GLN | A | 417 | 9.777 | 8.081 | −16.891 | 1.00 | 50.18 | C |
| ATOM | 4106 | OE1 | GLN | A | 417 | 9.458 | 8.247 | −15.715 | 1.00 | 50.08 | O |
| ATOM | 4107 | NE2 | GLN | A | 417 | 10.490 | 7.039 | −17.302 | 1.00 | 49.51 | N |
| ATOM | 4110 | C | GLN | A | 417 | 8.235 | 10.746 | −19.982 | 1.00 | 51.10 | C |
| ATOM | 4111 | O | GLN | A | 417 | 9.357 | 11.040 | −20.382 | 1.00 | 51.03 | O |
| ATOM | 4112 | N | GLY | A | 418 | 7.333 | 10.130 | −20.742 | 1.00 | 51.81 | N |
| ATOM | 4114 | CA | GLY | A | 418 | 7.591 | 9.797 | −22.132 | 1.00 | 52.42 | C |
| ATOM | 4117 | C | GLY | A | 418 | 7.848 | 11.042 | −22.956 | 1.00 | 52.94 | C |
| ATOM | 4118 | O | GLY | A | 418 | 8.710 | 11.040 | −23.826 | 1.00 | 53.07 | O |
| ATOM | 4119 | N | ASP | A | 419 | 7.105 | 12.108 | −22.662 | 1.00 | 53.65 | N |
| ATOM | 4121 | CA | ASP | A | 419 | 7.252 | 13.378 | −23.363 | 1.00 | 54.24 | C |
| ATOM | 4123 | CB | ASP | A | 419 | 6.074 | 14.308 | −23.053 | 1.00 | 54.22 | C |
| ATOM | 4126 | CG | ASP | A | 419 | 4.769 | 13.835 | −23.682 | 1.00 | 54.27 | C |

TABLE 2-continued

| ATOM | 4127 | OD1 | ASP | A | 419 | 4.727 | 12.718 | −24.242 | 1.00 | 53.78 | O |
|---|---|---|---|---|---|---|---|---|---|---|---|
| ATOM | 4128 | OD2 | ASP | A | 419 | 3.725 | 14.517 | −23.659 | 1.00 | 54.56 | O |
| ATOM | 4129 | C | ASP | A | 419 | 8.574 | 14.054 | −22.999 | 1.00 | 54.84 | C |
| ATOM | 4130 | O | ASP | A | 419 | 9.187 | 14.700 | −23.848 | 1.00 | 54.92 | O |
| ATOM | 4131 | N | LYS | A | 420 | 8.999 | 13.906 | −21.741 | 1.00 | 55.43 | N |
| ATOM | 4133 | CA | LYS | A | 420 | 10.271 | 14.456 | −21.265 | 1.00 | 55.89 | C |
| ATOM | 4135 | CB | LYS | A | 420 | 10.380 | 14.351 | −19.735 | 1.00 | 55.96 | C |
| ATOM | 4138 | CG | LYS | A | 420 | 9.601 | 15.409 | −18.963 | 1.00 | 56.06 | C |
| ATOM | 4141 | CD | LYS | A | 420 | 9.907 | 15.339 | −17.467 | 1.00 | 56.44 | C |
| ATOM | 4144 | CE | LYS | A | 420 | 8.801 | 15.967 | −16.626 | 1.00 | 56.61 | C |
| ATOM | 4147 | NZ | LYS | A | 420 | 7.697 | 15.002 | −16.331 | 1.00 | 56.84 | N |
| ATOM | 4151 | C | LYS | A | 420 | 11.443 | 13.716 | −21.910 | 1.00 | 56.38 | C |
| ATOM | 4152 | O | LYS | A | 420 | 12.493 | 14.304 | −22.157 | 1.00 | 56.29 | O |
| ATOM | 4153 | N | GLU | A | 421 | 11.246 | 12.425 | −22.174 | 1.00 | 57.21 | N |
| ATOM | 4155 | CA | GLU | A | 421 | 12.256 | 11.578 | −22.806 | 1.00 | 57.91 | C |
| ATOM | 4157 | CB | GLU | A | 421 | 11.865 | 10.096 | −22.709 | 1.00 | 57.84 | C |
| ATOM | 4160 | CG | GLU | A | 421 | 12.102 | 9.455 | −21.346 | 1.00 | 57.32 | C |
| ATOM | 4163 | CD | GLU | A | 421 | 11.475 | 8.075 | −21.218 | 1.00 | 56.57 | C |
| ATOM | 4164 | OE1 | GLU | A | 421 | 10.549 | 7.762 | −21.989 | 1.00 | 55.95 | O |
| ATOM | 4165 | OE2 | GLU | A | 421 | 11.908 | 7.297 | −20.341 | 1.00 | 56.11 | O |
| ATOM | 4166 | C | GLU | A | 421 | 12.439 | 11.952 | −24.278 | 1.00 | 58.82 | C |
| ATOM | 4167 | O | GLU | A | 421 | 13.552 | 11.887 | −24.806 | 1.00 | 59.03 | O |
| ATOM | 4168 | N | ARG | A | 422 | 11.345 | 12.337 | −24.933 | 1.00 | 59.81 | N |
| ATOM | 4170 | CA | ARG | A | 422 | 11.375 | 12.720 | −26.346 | 1.00 | 60.67 | C |
| ATOM | 4172 | CB | ARG | A | 422 | 9.959 | 12.733 | −26.938 | 1.00 | 60.78 | C |
| ATOM | 4175 | CG | ARG | A | 422 | 9.929 | 12.691 | −28.464 | 1.00 | 61.41 | C |
| ATOM | 4178 | CD | ARG | A | 422 | 8.542 | 12.503 | −29.069 | 1.00 | 62.16 | C |
| ATOM | 4181 | NE | ARG | A | 422 | 7.904 | 11.259 | −28.626 | 1.00 | 62.73 | N |
| ATOM | 4183 | CZ | ARG | A | 422 | 6.915 | 11.169 | −27.728 | 1.00 | 63.52 | C |
| ATOM | 4184 | NH1 | ARG | A | 422 | 6.409 | 12.251 | −27.135 | 1.00 | 63.52 | N |
| ATOM | 4187 | NH2 | ARG | A | 422 | 6.426 | 9.971 | −27.415 | 1.00 | 63.67 | N |
| ATOM | 4190 | C | ARG | A | 422 | 12.035 | 14.087 | −26.543 | 1.00 | 61.15 | C |
| ATOM | 4191 | O | ARG | A | 422 | 12.720 | 14.309 | −27.542 | 1.00 | 61.33 | O |
| ATOM | 4192 | N | GLU | A | 423 | 11.836 | 14.990 | −25.584 | 1.00 | 61.67 | N |
| ATOM | 4194 | CA | GLU | A | 423 | 12.412 | 16.332 | −25.646 | 1.00 | 62.13 | C |
| ATOM | 4196 | CB | GLU | A | 423 | 11.727 | 17.264 | −24.642 | 1.00 | 62.27 | C |
| ATOM | 4199 | CG | GLU | A | 423 | 10.281 | 17.599 | −24.986 | 1.00 | 62.86 | C |
| ATOM | 4202 | CD | GLU | A | 423 | 9.526 | 18.250 | −23.835 | 1.00 | 63.81 | C |
| ATOM | 4203 | OE1 | GLU | A | 423 | 9.853 | 17.971 | −22.658 | 1.00 | 64.39 | O |
| ATOM | 4204 | OE2 | GLU | A | 423 | 8.597 | 19.045 | −24.107 | 1.00 | 64.18 | O |
| ATOM | 4205 | C | GLU | A | 423 | 13.918 | 16.317 | −25.383 | 1.00 | 62.30 | C |
| ATOM | 4206 | O | GLU | A | 423 | 14.601 | 17.307 | −25.647 | 1.00 | 62.55 | O |
| ATOM | 4207 | N | ARG | A | 424 | 14.425 | 15.203 | −24.855 | 1.00 | 62.40 | N |
| ATOM | 4209 | CA | ARG | A | 424 | 15.849 | 15.048 | −24.564 | 1.00 | 62.46 | C |
| ATOM | 4211 | CB | ARG | A | 424 | 16.031 | 14.602 | −23.109 | 1.00 | 62.43 | C |
| ATOM | 4214 | CG | ARG | A | 424 | 15.586 | 15.660 | −22.101 | 1.00 | 62.39 | C |
| ATOM | 4217 | CD | ARG | A | 424 | 15.702 | 15.243 | −20.644 | 1.00 | 62.26 | C |
| ATOM | 4220 | NE | ARG | A | 424 | 14.694 | 15.895 | −19.805 | 1.00 | 62.15 | N |
| ATOM | 4222 | CZ | ARG | A | 424 | 14.897 | 16.360 | −18.570 | 1.00 | 62.06 | C |
| ATOM | 4223 | NH1 | ARG | A | 424 | 16.087 | 16.268 | −17.980 | 1.00 | 61.98 | N |
| ATOM | 4226 | NH2 | ARG | A | 424 | 13.890 | 16.930 | −17.915 | 1.00 | 62.24 | N |
| ATOM | 4229 | C | ARG | A | 424 | 16.555 | 14.083 | −25.532 | 1.00 | 62.51 | C |
| ATOM | 4230 | O | ARG | A | 424 | 17.748 | 13.815 | −25.387 | 1.00 | 62.61 | O |
| ATOM | 4231 | N | GLY | A | 425 | 15.819 | 13.554 | −26.508 | 1.00 | 62.55 | N |
| ATOM | 4233 | CA | GLY | A | 425 | 16.389 | 12.675 | −27.518 | 1.00 | 62.59 | C |
| ATOM | 4236 | C | GLY | A | 425 | 16.656 | 11.233 | −27.120 | 1.00 | 62.63 | C |
| ATOM | 4237 | O | GLY | A | 425 | 16.930 | 10.403 | −27.990 | 1.00 | 62.66 | O |
| ATOM | 4238 | N | MET | A | 426 | 16.574 | 10.919 | −25.828 | 1.00 | 62.58 | N |
| ATOM | 4240 | CA | MET | A | 426 | 16.833 | 9.556 | −25.359 | 1.00 | 62.51 | C |
| ATOM | 4242 | CB | MET | A | 426 | 17.059 | 9.523 | −23.838 | 1.00 | 62.49 | C |
| ATOM | 4245 | CG | MET | A | 426 | 15.875 | 9.951 | −22.977 | 1.00 | 62.33 | C |
| ATOM | 4248 | SD | MET | A | 426 | 16.358 | 10.194 | −21.236 | 1.00 | 62.34 | S |
| ATOM | 4249 | CE | MET | A | 426 | 15.929 | 11.853 | −20.974 | 1.00 | 61.75 | C |
| ATOM | 4253 | C | MET | A | 426 | 15.716 | 8.594 | −25.768 | 1.00 | 62.47 | C |
| ATOM | 4254 | O | MET | A | 426 | 14.631 | 9.023 | −26.163 | 1.00 | 62.37 | O |
| ATOM | 4255 | N | GLU | A | 427 | 16.006 | 7.296 | −25.681 | 1.00 | 62.54 | N |
| ATOM | 4257 | CA | GLU | A | 427 | 15.052 | 6.243 | −26.047 | 1.00 | 62.60 | C |
| ATOM | 4259 | CB | GLU | A | 427 | 15.729 | 4.864 | −26.020 | 1.00 | 62.75 | C |
| ATOM | 4262 | CG | GLU | A | 427 | 16.459 | 4.490 | −27.307 | 1.00 | 63.44 | C |
| ATOM | 4265 | CD | GLU | A | 427 | 15.844 | 3.286 | −28.001 | 1.00 | 64.17 | C |
| ATOM | 4266 | OE1 | GLU | A | 427 | 16.438 | 2.187 | −27.927 | 1.00 | 64.74 | O |
| ATOM | 4267 | OE2 | GLU | A | 427 | 14.764 | 3.438 | −28.616 | 1.00 | 64.34 | O |
| ATOM | 4268 | C | GLU | A | 427 | 13.829 | 6.227 | −25.126 | 1.00 | 62.39 | C |
| ATOM | 4269 | O | GLU | A | 427 | 13.961 | 6.160 | −23.900 | 1.00 | 62.45 | O |
| ATOM | 4270 | N | ILE | A | 428 | 12.644 | 6.278 | −25.731 | 1.00 | 62.09 | N |
| ATOM | 4272 | CA | ILE | A | 428 | 11.383 | 6.288 | −24.990 | 1.00 | 61.72 | C |
| ATOM | 4274 | CB | ILE | A | 428 | 10.234 | 6.832 | −25.879 | 1.00 | 61.83 | C |
| ATOM | 4276 | CG1 | ILE | A | 428 | 10.507 | 8.288 | −26.285 | 1.00 | 62.06 | C |
| ATOM | 4279 | CD1 | ILE | A | 428 | 10.161 | 8.592 | −27.732 | 1.00 | 62.43 | C |

TABLE 2-continued

| ATOM | 4283 | CG2 | ILE | A | 428 | 8.884 | 6.720 | −25.162 | 1.00 | 61.94 | C |
|---|---|---|---|---|---|---|---|---|---|---|---|
| ATOM | 4287 | C | ILE | A | 428 | 11.040 | 4.888 | −24.493 | 1.00 | 61.17 | C |
| ATOM | 4288 | O | ILE | A | 428 | 11.125 | 3.917 | −25.244 | 1.00 | 61.23 | O |
| ATOM | 4289 | N | SER | A | 429 | 10.645 | 4.799 | −23.227 | 1.00 | 60.50 | N |
| ATOM | 4291 | CA | SER | A | 429 | 10.270 | 3.528 | −22.617 | 1.00 | 59.97 | C |
| ATOM | 4293 | CB | SER | A | 429 | 10.139 | 3.674 | −21.094 | 1.00 | 59.99 | C |
| ATOM | 4296 | OG | SER | A | 429 | 11.115 | 4.562 | −20.563 | 1.00 | 59.54 | O |
| ATOM | 4298 | C | SER | A | 429 | 8.937 | 3.080 | −23.227 | 1.00 | 59.49 | C |
| ATOM | 4299 | O | SER | A | 429 | 8.034 | 3.898 | −23.368 | 1.00 | 59.42 | O |
| ATOM | 4300 | N | PRO | A | 430 | 8.817 | 1.807 | −23.610 | 1.00 | 58.94 | N |
| ATOM | 4301 | CA | PRO | A | 430 | 7.578 | 1.295 | −24.218 | 1.00 | 58.56 | C |
| ATOM | 4303 | CB | PRO | A | 430 | 7.817 | −0.219 | −24.280 | 1.00 | 58.56 | C |
| ATOM | 4306 | CG | PRO | A | 430 | 9.291 | −0.368 | −24.340 | 1.00 | 58.73 | C |
| ATOM | 4309 | CD | PRO | A | 430 | 9.856 | 0.763 | −23.532 | 1.00 | 58.91 | C |
| ATOM | 4312 | C | PRO | A | 430 | 6.277 | 1.594 | −23.453 | 1.00 | 58.21 | C |
| ATOM | 4313 | O | PRO | A | 430 | 5.303 | 2.001 | −24.085 | 1.00 | 58.23 | O |
| ATOM | 4314 | N | MET | A | 431 | 6.259 | 1.407 | −22.135 | 1.00 | 57.64 | N |
| ATOM | 4316 | CA | MET | A | 431 | 5.034 | 1.626 | −21.355 | 1.00 | 57.24 | C |
| ATOM | 4318 | CB | MET | A | 431 | 5.089 | 0.855 | −20.032 | 1.00 | 57.53 | C |
| ATOM | 4321 | CG | MET | A | 431 | 3.717 | 0.458 | −19.497 | 1.00 | 58.63 | C |
| ATOM | 4324 | SD | MET | A | 431 | 3.747 | −1.110 | −18.599 | 1.00 | 61.12 | S |
| ATOM | 4325 | CE | MET | A | 431 | 3.644 | −0.542 | −16.897 | 1.00 | 61.43 | C |
| ATOM | 4329 | C | MET | A | 431 | 4.721 | 3.098 | −21.079 | 1.00 | 56.38 | C |
| ATOM | 4330 | O | MET | A | 431 | 3.605 | 3.425 | −20.670 | 1.00 | 56.17 | O |
| ATOM | 4331 | N | CYS | A | 432 | 5.704 | 3.972 | −21.292 | 1.00 | 55.44 | N |
| ATOM | 4333 | CA | CYS | A | 432 | 5.543 | 5.413 | −21.089 | 1.00 | 54.68 | C |
| ATOM | 4335 | CB | CYS | A | 432 | 6.784 | 5.973 | −20.382 | 1.00 | 54.73 | C |
| ATOM | 4338 | SG | CYS | A | 432 | 6.978 | 5.422 | −18.671 | 1.00 | 54.35 | S |
| ATOM | 4339 | C | CYS | A | 432 | 5.294 | 6.182 | −22.398 | 1.00 | 54.09 | C |
| ATOM | 4340 | O | CYS | A | 432 | 5.233 | 7.411 | −22.389 | 1.00 | 53.97 | O |
| ATOM | 4341 | N | ASP | A | 433 | 5.130 | 5.457 | −23.507 | 1.00 | 53.47 | N |
| ATOM | 4343 | CA | ASP | A | 433 | 4.914 | 6.042 | −24.839 | 1.00 | 52.93 | C |
| ATOM | 4345 | CB | ASP | A | 433 | 5.554 | 5.125 | −25.892 | 1.00 | 52.93 | C |
| ATOM | 4348 | CG | ASP | A | 433 | 5.599 | 5.739 | −27.288 | 1.00 | 52.84 | C |
| ATOM | 4349 | OD1 | ASP | A | 433 | 5.419 | 6.967 | −27.444 | 1.00 | 52.28 | O |
| ATOM | 4350 | OD2 | ASP | A | 433 | 5.823 | 5.044 | −28.300 | 1.00 | 53.03 | O |
| ATOM | 4351 | C | ASP | A | 433 | 3.421 | 6.213 | −25.132 | 1.00 | 52.52 | C |
| ATOM | 4352 | O | ASP | A | 433 | 2.707 | 5.235 | −25.324 | 1.00 | 52.44 | O |
| ATOM | 4353 | N | LYS | A | 434 | 2.953 | 7.456 | −25.182 | 1.00 | 52.04 | N |
| ATOM | 4355 | CA | LYS | A | 434 | 1.532 | 7.730 | −25.415 | 1.00 | 51.71 | C |
| ATOM | 4357 | CB | LYS | A | 434 | 1.192 | 9.178 | −25.033 | 1.00 | 51.58 | C |
| ATOM | 4360 | CG | LYS | A | 434 | 1.763 | 10.246 | −25.957 | 1.00 | 51.12 | C |
| ATOM | 4363 | CD | LYS | A | 434 | 1.209 | 11.609 | −25.603 | 1.00 | 50.27 | C |
| ATOM | 4366 | CE | LYS | A | 434 | 1.962 | 12.713 | −26.302 | 1.00 | 50.26 | C |
| ATOM | 4369 | NZ | LYS | A | 434 | 1.549 | 14.042 | −25.793 | 1.00 | 50.04 | N |
| ATOM | 4373 | C | LYS | A | 434 | 1.049 | 7.434 | −26.844 | 1.00 | 51.56 | C |
| ATOM | 4374 | O | LYS | A | 434 | −0.146 | 7.230 | −27.060 | 1.00 | 51.70 | O |
| ATOM | 4375 | N | HIS | A | 435 | 1.968 | 7.404 | −27.808 | 1.00 | 51.37 | N |
| ATOM | 4377 | CA | HIS | A | 435 | 1.614 | 7.154 | −29.212 | 1.00 | 51.18 | C |
| ATOM | 4379 | CB | HIS | A | 435 | 2.634 | 7.822 | −30.142 | 1.00 | 51.08 | C |
| ATOM | 4382 | CG | HIS | A | 435 | 2.726 | 9.306 | −29.975 | 1.00 | 50.93 | C |
| ATOM | 4383 | ND1 | HIS | A | 435 | 1.673 | 10.153 | −30.243 | 1.00 | 51.24 | N |
| ATOM | 4385 | CE1 | HIS | A | 435 | 2.043 | 11.400 | −30.011 | 1.00 | 51.20 | C |
| ATOM | 4387 | NE2 | HIS | A | 435 | 3.299 | 11.392 | −29.603 | 1.00 | 50.88 | N |
| ATOM | 4389 | CD2 | HIS | A | 435 | 3.751 | 10.095 | −29.575 | 1.00 | 50.81 | C |
| ATOM | 4391 | C | HIS | A | 435 | 1.541 | 5.673 | −29.576 | 1.00 | 51.13 | C |
| ATOM | 4392 | O | HIS | A | 435 | 1.160 | 5.334 | −30.701 | 1.00 | 51.19 | O |
| ATOM | 4393 | N | THR | A | 436 | 1.898 | 4.801 | −28.632 | 1.00 | 50.98 | N |
| ATOM | 4395 | CA | THR | A | 436 | 1.957 | 3.360 | −28.876 | 1.00 | 50.88 | C |
| ATOM | 4397 | CB | THR | A | 436 | 3.445 | 2.960 | −29.036 | 1.00 | 50.87 | C |
| ATOM | 4399 | OG1 | THR | A | 436 | 4.079 | 3.801 | −30.011 | 1.00 | 51.11 | O |
| ATOM | 4401 | CG2 | THR | A | 436 | 3.603 | 1.551 | −29.602 | 1.00 | 50.83 | C |
| ATOM | 4405 | C | THR | A | 436 | 1.316 | 2.493 | −27.781 | 1.00 | 50.95 | C |
| ATOM | 4406 | O | THR | A | 436 | 0.589 | 1.548 | −28.085 | 1.00 | 50.79 | O |
| ATOM | 4407 | N | ALA | A | 437 | 1.602 | 2.811 | −26.519 | 1.00 | 50.96 | N |
| ATOM | 4409 | CA | ALA | A | 437 | 1.132 | 2.029 | −25.369 | 1.00 | 50.91 | C |
| ATOM | 4411 | CB | ALA | A | 437 | 1.819 | 2.514 | −24.087 | 1.00 | 50.94 | C |
| ATOM | 4415 | C | ALA | A | 437 | −0.381 | 2.002 | −25.153 | 1.00 | 50.90 | C |
| ATOM | 4416 | O | ALA | A | 437 | −1.054 | 3.029 | −25.223 | 1.00 | 50.82 | O |
| ATOM | 4417 | N | SER | A | 438 | −0.888 | 0.807 | −24.863 | 1.00 | 50.97 | N |
| ATOM | 4419 | CA | SER | A | 438 | −2.295 | 0.582 | −24.569 | 1.00 | 51.05 | C |
| ATOM | 4421 | CB | SER | A | 438 | −2.714 | −0.820 | −25.011 | 1.00 | 51.08 | C |
| ATOM | 4424 | OG | SER | A | 438 | −4.088 | −1.051 | −24.749 | 1.00 | 51.04 | O |
| ATOM | 4426 | C | SER | A | 438 | −2.479 | 0.689 | −23.063 | 1.00 | 51.10 | C |
| ATOM | 4427 | O | SER | A | 438 | −1.849 | −0.052 | −22.313 | 1.00 | 50.99 | O |
| ATOM | 4428 | N | VAL | A | 439 | −3.334 | 1.604 | −22.618 | 1.00 | 51.31 | N |
| ATOM | 4430 | CA | VAL | A | 439 | −3.617 | 1.757 | −21.190 | 1.00 | 51.47 | C |
| ATOM | 4432 | CB | VAL | A | 439 | −4.579 | 2.948 | −20.927 | 1.00 | 51.42 | C |
| ATOM | 4434 | CG1 | VAL | A | 439 | −5.045 | 2.980 | −19.466 | 1.00 | 51.38 | C |

TABLE 2-continued

| | | | | | | | | | | |
|---|---|---|---|---|---|---|---|---|---|---|
| ATOM | 4438 | CG2 | VAL | A | 439 | −3.923 | 4.265 | −21.310 | 1.00 | 51.55 C |
| ATOM | 4442 | C | VAL | A | 439 | −4.250 | 0.467 | −20.652 | 1.00 | 51.62 C |
| ATOM | 4443 | O | VAL | A | 439 | −4.038 | 0.092 | −19.498 | 1.00 | 51.80 O |
| ATOM | 4444 | N | GLU | A | 440 | −4.994 | −0.216 | −21.519 | 1.00 | 51.78 N |
| ATOM | 4446 | CA | GLU | A | 440 | −5.741 | −1.417 | −21.159 | 1.00 | 51.91 C |
| ATOM | 4448 | CB | GLU | A | 440 | −6.828 | −1.701 | −22.206 | 1.00 | 51.97 C |
| ATOM | 4451 | CG | GLU | A | 440 | −7.998 | −0.720 | −22.176 | 1.00 | 52.11 C |
| ATOM | 4454 | CD | GLU | A | 440 | −7.604 | 0.706 | −22.528 | 1.00 | 52.37 C |
| ATOM | 4455 | OE1 | GLU | A | 440 | −6.925 | 0.910 | −23.557 | 1.00 | 53.33 O |
| ATOM | 4456 | OE2 | GLU | A | 440 | −7.969 | 1.629 | −21.776 | 1.00 | 52.82 O |
| ATOM | 4457 | C | GLU | A | 440 | −4.837 | −2.631 | −20.980 | 1.00 | 51.89 C |
| ATOM | 4458 | O | GLU | A | 440 | −4.959 | −3.349 | −19.987 | 1.00 | 52.18 O |
| ATOM | 4459 | N | LYS | A | 441 | −3.937 | −2.860 | −21.933 | 1.00 | 51.69 N |
| ATOM | 4461 | CA | LYS | A | 441 | −2.995 | −3.975 | −21.844 | 1.00 | 51.63 C |
| ATOM | 4463 | CB | LYS | A | 441 | −2.247 | −4.177 | −23.164 | 1.00 | 51.74 C |
| ATOM | 4466 | CG | LYS | A | 441 | −3.116 | −4.644 | −24.313 | 1.00 | 52.20 C |
| ATOM | 4469 | CD | LYS | A | 441 | −2.350 | −4.614 | −25.627 | 1.00 | 52.85 C |
| ATOM | 4472 | CE | LYS | A | 441 | −2.906 | −5.616 | −26.626 | 1.00 | 53.27 C |
| ATOM | 4475 | NZ | LYS | A | 441 | −2.185 | −5.551 | −27.926 | 1.00 | 53.67 N |
| ATOM | 4479 | C | LYS | A | 441 | −1.978 | −3.747 | −20.731 | 1.00 | 51.39 C |
| ATOM | 4480 | O | LYS | A | 441 | −1.370 | −4.694 | −20.244 | 1.00 | 51.39 O |
| ATOM | 4481 | N | SER | A | 442 | −1.782 | −2.489 | −20.348 | 1.00 | 51.21 N |
| ATOM | 4483 | CA | SER | A | 442 | −0.849 | −2.141 | −19.284 | 1.00 | 51.18 C |
| ATOM | 4485 | CB | SER | A | 442 | −0.562 | −0.638 | −19.287 | 1.00 | 51.27 C |
| ATOM | 4488 | OG | SER | A | 442 | 0.219 | −0.267 | −20.413 | 1.00 | 51.99 O |
| ATOM | 4490 | C | SER | A | 442 | −1.394 | −2.565 | −17.922 | 1.00 | 50.92 C |
| ATOM | 4491 | O | SER | A | 442 | −0.632 | −2.956 | −17.048 | 1.00 | 50.94 O |
| ATOM | 4492 | N | GLN | A | 443 | −2.709 | −2.484 | −17.746 | 1.00 | 50.63 N |
| ATOM | 4494 | CA | GLN | A | 443 | −3.338 | −2.885 | −16.489 | 1.00 | 50.41 C |
| ATOM | 4496 | CB | GLN | A | 443 | −4.665 | −2.148 | −16.292 | 1.00 | 50.31 C |
| ATOM | 4499 | CG | GLN | A | 443 | −4.499 | −0.660 | −16.001 | 1.00 | 50.37 C |
| ATOM | 4502 | CD | GLN | A | 443 | −3.508 | −0.386 | −14.874 | 1.00 | 50.65 C |
| ATOM | 4503 | OE1 | GLN | A | 443 | −3.482 | −1.109 | −13.877 | 1.00 | 50.10 O |
| ATOM | 4504 | NE2 | GLN | A | 443 | −2.692 | 0.652 | −15.035 | 1.00 | 50.58 N |
| ATOM | 4507 | C | GLN | A | 443 | −3.539 | −4.398 | −16.403 | 1.00 | 50.24 C |
| ATOM | 4508 | O | GLN | A | 443 | −3.546 | −4.958 | −15.306 | 1.00 | 50.04 O |
| ATOM | 4509 | N | VAL | A | 444 | −3.698 | −5.049 | −17.555 | 1.00 | 50.01 N |
| ATOM | 4511 | CA | VAL | A | 444 | −3.859 | −6.502 | −17.620 | 1.00 | 49.86 C |
| ATOM | 4513 | CB | VAL | A | 444 | −4.429 | −6.956 | −19.000 | 1.00 | 49.90 C |
| ATOM | 4515 | CG1 | VAL | A | 444 | −4.203 | −8.450 | −19.249 | 1.00 | 49.84 C |
| ATOM | 4519 | CG2 | VAL | A | 444 | −5.909 | −6.633 | −19.096 | 1.00 | 49.72 C |
| ATOM | 4523 | C | VAL | A | 444 | −2.511 | −7.172 | −17.352 | 1.00 | 49.82 C |
| ATOM | 4524 | O | VAL | A | 444 | −2.454 | −8.222 | −16.716 | 1.00 | 49.90 O |
| ATOM | 4525 | N | GLY | A | 445 | −1.434 | −6.560 | −17.842 | 1.00 | 49.78 N |
| ATOM | 4527 | CA | GLY | A | 445 | −0.087 | −7.074 | −17.649 | 1.00 | 49.75 C |
| ATOM | 4530 | C | GLY | A | 445 | 0.418 | −6.767 | −16.251 | 1.00 | 49.83 C |
| ATOM | 4531 | O | GLY | A | 445 | 1.207 | −7.520 | −15.685 | 1.00 | 49.63 O |
| ATOM | 4532 | N | PHE | A | 446 | −0.041 | −5.647 | −15.700 | 1.00 | 49.94 N |
| ATOM | 4534 | CA | PHE | A | 446 | 0.321 | −5.236 | −14.352 | 1.00 | 50.11 C |
| ATOM | 4536 | CB | PHE | A | 446 | −0.218 | −3.825 | −14.066 | 1.00 | 50.12 C |
| ATOM | 4539 | CG | PHE | A | 446 | 0.237 | −3.239 | −12.756 | 1.00 | 50.27 C |
| ATOM | 4540 | CD1 | PHE | A | 446 | 1.573 | −3.278 | −12.377 | 1.00 | 50.28 C |
| ATOM | 4542 | CE1 | PHE | A | 446 | 1.980 | −2.730 | −11.171 | 1.00 | 50.37 C |
| ATOM | 4544 | CZ | PHE | A | 446 | 1.054 | −2.124 | −10.336 | 1.00 | 50.13 C |
| ATOM | 4546 | CE2 | PHE | A | 446 | −0.272 | −2.073 | −10.703 | 1.00 | 50.12 C |
| ATOM | 4548 | CD2 | PHE | A | 446 | −0.677 | −2.622 | −11.908 | 1.00 | 50.48 C |
| ATOM | 4550 | C | PHE | A | 446 | −0.242 | −6.250 | −13.360 | 1.00 | 50.23 C |
| ATOM | 4551 | O | PHE | A | 446 | 0.449 | −6.654 | −12.436 | 1.00 | 49.99 O |
| ATOM | 4552 | N | ILE | A | 447 | −1.479 | −6.691 | −13.590 | 1.00 | 50.50 N |
| ATOM | 4554 | CA | ILE | A | 447 | −2.133 | −7.654 | −12.705 | 1.00 | 50.73 C |
| ATOM | 4556 | CB | ILE | A | 447 | −3.669 | −7.680 | −12.947 | 1.00 | 50.69 C |
| ATOM | 4558 | CG1 | ILE | A | 447 | −4.302 | −6.343 | −12.550 | 1.00 | 50.51 C |
| ATOM | 4561 | CD1 | ILE | A | 447 | −5.701 | −6.129 | −13.115 | 1.00 | 50.24 C |
| ATOM | 4565 | CG2 | ILE | A | 447 | −4.324 | −8.813 | −12.143 | 1.00 | 50.61 C |
| ATOM | 4569 | C | ILE | A | 447 | −1.561 | −9.067 | −12.836 | 1.00 | 51.01 C |
| ATOM | 4570 | O | ILE | A | 447 | −1.172 | −9.673 | −11.847 | 1.00 | 50.90 O |
| ATOM | 4571 | N | ASP | A | 448 | −1.500 | −9.581 | −14.058 | 1.00 | 51.43 N |
| ATOM | 4573 | CA | ASP | A | 448 | −1.051 | −10.957 | −14.300 | 1.00 | 51.79 C |
| ATOM | 4575 | CB | ASP | A | 448 | −1.155 | −11.299 | −15.798 | 1.00 | 51.81 C |
| ATOM | 4578 | CG | ASP | A | 448 | −2.587 | −11.336 | −16.295 | 1.00 | 52.06 C |
| ATOM | 4579 | OD1 | ASP | A | 448 | −3.493 | −11.641 | −15.491 | 1.00 | 52.17 O |
| ATOM | 4580 | OD2 | ASP | A | 448 | −2.901 | −11.072 | −17.478 | 1.00 | 52.64 O |
| ATOM | 4581 | C | ASP | A | 448 | 0.362 | −11.293 | −13.825 | 1.00 | 52.03 C |
| ATOM | 4582 | O | ASP | A | 448 | 0.588 | −12.374 | −13.284 | 1.00 | 52.12 O |
| ATOM | 4583 | N | TYR | A | 449 | 1.302 | −10.371 | −14.016 | 1.00 | 52.37 N |
| ATOM | 4585 | CA | TYR | A | 449 | 2.710 | −10.634 | −13.715 | 1.00 | 52.70 C |
| ATOM | 4587 | CB | TYR | A | 449 | 3.559 | −10.277 | −14.945 | 1.00 | 53.04 C |
| ATOM | 4590 | CG | TYR | A | 449 | 3.043 | −10.906 | −16.227 | 1.00 | 54.52 C |
| ATOM | 4591 | CD1 | TYR | A | 449 | 2.536 | −10.120 | −17.264 | 1.00 | 56.01 C |

TABLE 2-continued

| | | | | | | | | | | | |
|---|---|---|---|---|---|---|---|---|---|---|---|
| ATOM | 4593 | CE1 | TYR | A | 449 | 2.051 | −10.697 | −18.437 | 1.00 | 56.92 | C |
| ATOM | 4595 | CZ | TYR | A | 449 | 2.069 | −12.076 | −18.579 | 1.00 | 57.69 | C |
| ATOM | 4596 | OH | TYR | A | 449 | 1.593 | −12.657 | −19.732 | 1.00 | 59.09 | O |
| ATOM | 4598 | CE2 | TYR | A | 449 | 2.565 | −12.877 | −17.563 | 1.00 | 57.31 | C |
| ATOM | 4600 | CD2 | TYR | A | 449 | 3.044 | −12.289 | −16.392 | 1.00 | 56.24 | C |
| ATOM | 4602 | C | TYR | A | 449 | 3.289 | −9.948 | −12.476 | 1.00 | 52.43 | C |
| ATOM | 4603 | O | TYR | A | 449 | 4.420 | −10.249 | −12.097 | 1.00 | 52.33 | O |
| ATOM | 4604 | N | ILE | A | 450 | 2.532 | −9.053 | −11.838 | 1.00 | 52.24 | N |
| ATOM | 4606 | CA | ILE | A | 450 | 3.028 | −8.330 | −10.660 | 1.00 | 52.12 | C |
| ATOM | 4608 | CB | ILE | A | 450 | 3.402 | −6.868 | −11.042 | 1.00 | 52.13 | C |
| ATOM | 4610 | CG1 | ILE | A | 450 | 4.673 | −6.836 | −11.900 | 1.00 | 52.49 | C |
| ATOM | 4613 | CD1 | ILE | A | 450 | 4.636 | −5.795 | −13.007 | 1.00 | 52.62 | C |
| ATOM | 4617 | CG2 | ILE | A | 450 | 3.604 | −6.003 | −9.798 | 1.00 | 52.18 | C |
| ATOM | 4621 | C | ILE | A | 450 | 2.047 | −8.326 | −9.485 | 1.00 | 51.83 | C |
| ATOM | 4622 | O | ILE | A | 450 | 2.366 | −8.827 | −8.407 | 1.00 | 51.65 | O |
| ATOM | 4623 | N | VAL | A | 451 | 0.859 | −7.770 | −9.706 | 1.00 | 51.54 | N |
| ATOM | 4625 | CA | VAL | A | 451 | −0.145 | −7.610 | −8.654 | 1.00 | 51.42 | C |
| ATOM | 4627 | CB | VAL | A | 451 | −1.203 | −6.555 | −9.057 | 1.00 | 51.43 | C |
| ATOM | 4629 | CG1 | VAL | A | 451 | −2.246 | −6.374 | −7.962 | 1.00 | 51.53 | C |
| ATOM | 4633 | CG2 | VAL | A | 451 | −0.524 | −5.224 | −9.366 | 1.00 | 51.48 | C |
| ATOM | 4637 | C | VAL | A | 451 | −0.825 | −8.916 | −8.223 | 1.00 | 51.29 | C |
| ATOM | 4638 | O | VAL | A | 451 | −0.887 | −9.206 | −7.028 | 1.00 | 51.38 | O |
| ATOM | 4639 | N | HIS | A | 452 | −1.347 | −9.688 | −9.173 | 1.00 | 50.99 | N |
| ATOM | 4641 | CA | HIS | A | 452 | −2.001 | −10.963 | −8.845 | 1.00 | 50.90 | C |
| ATOM | 4643 | CB | HIS | A | 452 | −2.669 | −11.616 | −10.069 | 1.00 | 50.95 | C |
| ATOM | 4646 | CG | HIS | A | 452 | −3.394 | −12.891 | −9.757 | 1.00 | 51.14 | C |
| ATOM | 4647 | ND1 | HIS | A | 452 | −4.753 | −12.939 | −9.528 | 1.00 | 51.55 | N |
| ATOM | 4649 | CE1 | HIS | A | 452 | −5.112 | −14.187 | −9.282 | 1.00 | 51.60 | C |
| ATOM | 4651 | NE2 | HIS | A | 452 | −4.036 | −14.951 | −9.349 | 1.00 | 51.14 | N |
| ATOM | 4653 | CD2 | HIS | A | 452 | −2.949 | −14.166 | −9.647 | 1.00 | 51.14 | C |
| ATOM | 4655 | C | HIS | A | 452 | −1.042 | −11.936 | −8.151 | 1.00 | 50.68 | C |
| ATOM | 4656 | O | HIS | A | 452 | −1.400 | −12.481 | −7.115 | 1.00 | 50.66 | O |
| ATOM | 4657 | N | PRO | A | 453 | 0.150 | −12.172 | −8.706 | 1.00 | 50.40 | N |
| ATOM | 4658 | CA | PRO | A | 453 | 1.129 | −13.054 | −8.051 | 1.00 | 50.20 | C |
| ATOM | 4660 | CB | PRO | A | 453 | 2.365 | −12.928 | −8.947 | 1.00 | 50.22 | C |
| ATOM | 4663 | CG | PRO | A | 453 | 1.832 | −12.559 | −10.275 | 1.00 | 50.37 | C |
| ATOM | 4666 | CD | PRO | A | 453 | 0.650 | −11.682 | −10.005 | 1.00 | 50.39 | C |
| ATOM | 4669 | C | PRO | A | 453 | 1.482 | −12.651 | −6.613 | 1.00 | 50.06 | C |
| ATOM | 4670 | O | PRO | A | 453 | 1.709 | −13.528 | −5.775 | 1.00 | 50.11 | O |
| ATOM | 4671 | N | LEU | A | 454 | 1.529 | −11.348 | −6.338 | 1.00 | 49.81 | N |
| ATOM | 4673 | CA | LEU | A | 454 | 1.873 | −10.846 | −5.006 | 1.00 | 49.54 | C |
| ATOM | 4675 | CB | LEU | A | 454 | 2.265 | −9.366 | −5.066 | 1.00 | 49.57 | C |
| ATOM | 4678 | CG | LEU | A | 454 | 2.464 | −8.660 | −3.719 | 1.00 | 49.28 | C |
| ATOM | 4680 | CD1 | LEU | A | 454 | 3.642 | −9.252 | −2.969 | 1.00 | 49.03 | C |
| ATOM | 4684 | CD2 | LEU | A | 454 | 2.646 | −7.169 | −3.927 | 1.00 | 49.47 | C |
| ATOM | 4688 | C | LEU | A | 454 | 0.738 | −11.025 | −4.008 | 1.00 | 49.37 | C |
| ATOM | 4689 | O | LEU | A | 454 | 0.965 | −11.488 | −2.895 | 1.00 | 49.24 | O |
| ATOM | 4690 | N | TRP | A | 455 | −0.471 | −10.630 | −4.402 | 1.00 | 49.26 | N |
| ATOM | 4692 | CA | TRP | A | 455 | −1.648 | −10.747 | −3.538 | 1.00 | 49.35 | C |
| ATOM | 4694 | CB | TRP | A | 455 | −2.806 | −9.906 | −4.071 | 1.00 | 49.20 | C |
| ATOM | 4697 | CG | TRP | A | 455 | −2.719 | −8.485 | −3.644 | 1.00 | 48.71 | C |
| ATOM | 4698 | CD1 | TRP | A | 455 | −2.308 | −7.428 | −4.396 | 1.00 | 47.94 | C |
| ATOM | 4700 | NE1 | TRP | A | 455 | −2.356 | −6.273 | −3.654 | 1.00 | 47.76 | N |
| ATOM | 4702 | CE2 | TRP | A | 455 | −2.799 | −6.573 | −2.393 | 1.00 | 47.42 | C |
| ATOM | 4703 | CD2 | TRP | A | 455 | −3.035 | −7.959 | −2.350 | 1.00 | 47.97 | C |
| ATOM | 4704 | CE3 | TRP | A | 455 | −3.496 | −8.523 | −1.153 | 1.00 | 47.67 | C |
| ATOM | 4706 | CZ3 | TRP | A | 455 | −3.704 | −7.696 | −0.061 | 1.00 | 47.35 | C |
| ATOM | 4708 | CH2 | TRP | A | 455 | −3.460 | −6.323 | −0.141 | 1.00 | 47.35 | C |
| ATOM | 4710 | CZ2 | TRP | A | 455 | −3.011 | −5.744 | −1.296 | 1.00 | 47.21 | C |
| ATOM | 4712 | C | TRP | A | 455 | −2.089 | −12.196 | −3.369 | 1.00 | 49.57 | C |
| ATOM | 4713 | O | TRP | A | 455 | −2.665 | −12.551 | −2.344 | 1.00 | 49.63 | O |
| ATOM | 4714 | N | GLU | A | 456 | −1.818 | −13.021 | −4.377 | 1.00 | 49.72 | N |
| ATOM | 4716 | CA | GLU | A | 456 | −2.124 | −14.451 | −4.330 | 1.00 | 49.98 | C |
| ATOM | 4718 | CB | GLU | A | 456 | −1.800 | −15.105 | −5.681 | 1.00 | 50.16 | C |
| ATOM | 4721 | CG | GLU | A | 456 | −1.641 | −16.618 | −5.676 | 1.00 | 51.00 | C |
| ATOM | 4724 | CD | GLU | A | 456 | −1.545 | −17.186 | −7.085 | 1.00 | 52.00 | C |
| ATOM | 4725 | OE1 | GLU | A | 456 | −0.534 | −16.918 | −7.772 | 1.00 | 52.21 | O |
| ATOM | 4726 | OE2 | GLU | A | 456 | −2.483 | −17.897 | −7.506 | 1.00 | 52.28 | O |
| ATOM | 4727 | C | GLU | A | 456 | −1.303 | −15.087 | −3.213 | 1.00 | 49.79 | C |
| ATOM | 4728 | O | GLU | A | 456 | −1.754 | −16.022 | −2.560 | 1.00 | 49.93 | O |
| ATOM | 4729 | N | THR | A | 457 | −0.094 | −14.566 | −3.012 | 1.00 | 49.70 | N |
| ATOM | 4731 | CA | THR | A | 457 | 0.811 | −15.036 | −1.971 | 1.00 | 49.61 | C |
| ATOM | 4733 | CB | THR | A | 457 | 2.257 | −14.657 | −2.325 | 1.00 | 49.62 | C |
| ATOM | 4735 | OG1 | THR | A | 457 | 2.567 | −15.113 | −3.648 | 1.00 | 49.55 | O |
| ATOM | 4737 | CG2 | THR | A | 457 | 3.251 | −15.392 | −1.442 | 1.00 | 49.46 | C |
| ATOM | 4741 | C | THR | A | 457 | 0.438 | −14.458 | −0.605 | 1.00 | 49.62 | C |
| ATOM | 4742 | O | THR | A | 457 | 0.488 | −15.163 | 0.396 | 1.00 | 49.71 | O |
| ATOM | 4743 | N | TRP | A | 458 | 0.075 | −13.177 | −0.565 | 1.00 | 49.66 | N |
| ATOM | 4745 | CA | TRP | A | 458 | −0.327 | −12.528 | 0.681 | 1.00 | 49.64 | C |

TABLE 2-continued

| ATOM | 4747 | CB | TRP | A | 458 | −0.578 | −11.026 | 0.474 | 1.00 | 49.37 | C |
| ATOM | 4750 | CG | TRP | A | 458 | −1.144 | −10.352 | 1.689 | 1.00 | 47.69 | C |
| ATOM | 4751 | CD1 | TRP | A | 458 | −2.461 | −10.106 | 1.952 | 1.00 | 46.79 | C |
| ATOM | 4753 | NE1 | TRP | A | 458 | −2.594 | −9.488 | 3.173 | 1.00 | 46.06 | N |
| ATOM | 4755 | CE2 | TRP | A | 458 | −1.352 | −9.327 | 3.726 | 1.00 | 45.61 | C |
| ATOM | 4756 | CD2 | TRP | A | 458 | −0.415 | −9.863 | 2.818 | 1.00 | 45.98 | C |
| ATOM | 4757 | CE3 | TRP | A | 458 | 0.943 | −9.819 | 3.157 | 1.00 | 45.38 | C |
| ATOM | 4759 | CZ3 | TRP | A | 458 | 1.314 | −9.254 | 4.370 | 1.00 | 45.13 | C |
| ATOM | 4761 | CH2 | TRP | A | 458 | 0.359 | −8.731 | 5.247 | 1.00 | 45.05 | C |
| ATOM | 4763 | CZ2 | TRP | A | 458 | −0.976 | −8.757 | 4.945 | 1.00 | 45.47 | C |
| ATOM | 4765 | C | TRP | A | 458 | −1.587 | −13.203 | 1.214 | 1.00 | 50.27 | C |
| ATOM | 4766 | O | TRP | A | 458 | −1.758 | −13.344 | 2.427 | 1.00 | 50.29 | O |
| ATOM | 4767 | N | ALA | A | 459 | −2.455 | −13.619 | 0.293 | 1.00 | 50.90 | N |
| ATOM | 4769 | CA | ALA | A | 459 | −3.699 | −14.300 | 0.630 | 1.00 | 51.52 | C |
| ATOM | 4771 | CB | ALA | A | 459 | −4.600 | −14.417 | −0.597 | 1.00 | 51.53 | C |
| ATOM | 4775 | C | ALA | A | 459 | −3.418 | −15.677 | 1.217 | 1.00 | 52.09 | C |
| ATOM | 4776 | O | ALA | A | 459 | −4.101 | −16.090 | 2.141 | 1.00 | 52.33 | O |
| ATOM | 4777 | N | ASP | A | 460 | −2.418 | −16.381 | 0.682 | 1.00 | 52.75 | N |
| ATOM | 4779 | CA | ASP | A | 460 | −2.023 | −17.700 | 1.199 | 1.00 | 53.26 | C |
| ATOM | 4781 | CB | ASP | A | 460 | −0.900 | −18.318 | 0.346 | 1.00 | 53.44 | C |
| ATOM | 4784 | CG | ASP | A | 460 | −1.415 | −19.110 | −0.855 | 1.00 | 54.00 | C |
| ATOM | 4785 | OD1 | ASP | A | 460 | −2.501 | −18.788 | −1.387 | 1.00 | 54.34 | O |
| ATOM | 4786 | OD2 | ASP | A | 460 | −0.777 | −20.069 | −1.345 | 1.00 | 54.56 | O |
| ATOM | 4787 | C | ASP | A | 460 | −1.522 | −17.584 | 2.642 | 1.00 | 53.50 | C |
| ATOM | 4788 | O | ASP | A | 460 | −1.724 | −18.486 | 3.455 | 1.00 | 53.69 | O |
| ATOM | 4789 | N | LEU | A | 461 | −0.862 | −16.467 | 2.939 | 1.00 | 53.71 | N |
| ATOM | 4791 | CA | LEU | A | 461 | −0.291 | −16.198 | 4.254 | 1.00 | 53.90 | C |
| ATOM | 4793 | CB | LEU | A | 461 | 0.709 | −15.042 | 4.141 | 1.00 | 53.85 | C |
| ATOM | 4796 | CG | LEU | A | 461 | 1.504 | −14.650 | 5.389 | 1.00 | 53.59 | C |
| ATOM | 4798 | CD1 | LEU | A | 461 | 2.607 | −15.656 | 5.661 | 1.00 | 53.67 | C |
| ATOM | 4802 | CD2 | LEU | A | 461 | 2.080 | −13.254 | 5.232 | 1.00 | 53.36 | C |
| ATOM | 4806 | C | LEU | A | 461 | −1.344 | −15.841 | 5.300 | 1.00 | 54.27 | C |
| ATOM | 4807 | O | LEU | A | 461 | −1.165 | −16.120 | 6.487 | 1.00 | 54.16 | O |
| ATOM | 4808 | N | VAL | A | 462 | −2.439 | −15.231 | 4.854 | 1.00 | 54.66 | N |
| ATOM | 4810 | CA | VAL | A | 462 | −3.486 | −14.759 | 5.756 | 1.00 | 55.00 | C |
| ATOM | 4812 | CB | VAL | A | 462 | −3.504 | −13.201 | 5.781 | 1.00 | 54.94 | C |
| ATOM | 4814 | CG1 | VAL | A | 462 | −2.113 | −12.649 | 6.059 | 1.00 | 54.88 | C |
| ATOM | 4818 | CG2 | VAL | A | 462 | −4.060 | −12.624 | 4.470 | 1.00 | 54.78 | C |
| ATOM | 4822 | C | VAL | A | 462 | −4.894 | −15.259 | 5.412 | 1.00 | 55.38 | C |
| ATOM | 4823 | O | VAL | A | 462 | −5.874 | −14.654 | 5.836 | 1.00 | 55.45 | O |
| ATOM | 4824 | N | GLN | A | 463 | −5.006 | −16.370 | 4.687 | 1.00 | 55.87 | N |
| ATOM | 4826 | CA | GLN | A | 463 | −6.325 | −16.863 | 4.268 | 1.00 | 56.23 | C |
| ATOM | 4828 | CB | GLN | A | 463 | −6.210 | −18.049 | 3.300 | 1.00 | 56.36 | C |
| ATOM | 4831 | CG | GLN | A | 463 | −5.558 | −19.300 | 3.860 | 1.00 | 56.87 | C |
| ATOM | 4834 | CD | GLN | A | 463 | −5.398 | −20.376 | 2.801 | 1.00 | 57.65 | C |
| ATOM | 4835 | OE1 | GLN | A | 463 | −4.334 | −20.992 | 2.685 | 1.00 | 58.29 | O |
| ATOM | 4836 | NE2 | GLN | A | 463 | −6.453 | −20.604 | 2.023 | 1.00 | 57.50 | N |
| ATOM | 4839 | C | GLN | A | 463 | −7.222 | −17.244 | 5.449 | 1.00 | 56.38 | C |
| ATOM | 4840 | O | GLN | A | 463 | −6.721 | −17.650 | 6.502 | 1.00 | 56.32 | O |
| ATOM | 4841 | N | PRO | A | 464 | −8.541 | −17.113 | 5.287 | 1.00 | 56.68 | N |
| ATOM | 4842 | CA | PRO | A | 464 | −9.194 | −16.621 | 4.061 | 1.00 | 56.84 | C |
| ATOM | 4844 | CB | PRO | A | 464 | −10.473 | −17.461 | 4.026 | 1.00 | 56.87 | C |
| ATOM | 4847 | CG | PRO | A | 464 | −10.822 | −17.661 | 5.506 | 1.00 | 56.79 | C |
| ATOM | 4850 | CD | PRO | A | 464 | −9.539 | −17.484 | 6.307 | 1.00 | 56.67 | C |
| ATOM | 4853 | C | PRO | A | 464 | −9.546 | −15.123 | 4.120 | 1.00 | 57.04 | C |
| ATOM | 4854 | O | PRO | A | 464 | −10.538 | −14.695 | 3.527 | 1.00 | 57.00 | O |
| ATOM | 4855 | N | ASP | A | 465 | −8.719 | −14.337 | 4.806 | 1.00 | 57.36 | N |
| ATOM | 4857 | CA | ASP | A | 465 | −8.976 | −12.909 | 5.011 | 1.00 | 57.58 | C |
| ATOM | 4859 | CB | ASP | A | 465 | −8.052 | −12.349 | 6.102 | 1.00 | 57.63 | C |
| ATOM | 4862 | CG | ASP | A | 465 | −8.050 | −13.199 | 7.365 | 1.00 | 57.91 | C |
| ATOM | 4863 | OD1 | ASP | A | 465 | −9.039 | −13.924 | 7.610 | 1.00 | 58.07 | O |
| ATOM | 4864 | OD2 | ASP | A | 465 | −7.095 | −13.210 | 8.168 | 1.00 | 58.10 | O |
| ATOM | 4865 | C | ASP | A | 465 | −8.847 | −12.053 | 3.751 | 1.00 | 57.63 | C |
| ATOM | 4866 | O | ASP | A | 465 | −9.487 | −11.008 | 3.654 | 1.00 | 57.59 | O |
| ATOM | 4867 | N | ALA | A | 466 | −8.030 | −12.492 | 2.797 | 1.00 | 57.84 | N |
| ATOM | 4869 | CA | ALA | A | 466 | −7.823 | −11.743 | 1.557 | 1.00 | 58.00 | C |
| ATOM | 4871 | CB | ALA | A | 466 | −6.337 | −11.607 | 1.283 | 1.00 | 58.01 | C |
| ATOM | 4875 | C | ALA | A | 466 | −8.527 | −12.385 | 0.362 | 1.00 | 58.21 | C |
| ATOM | 4876 | O | ALA | A | 466 | −8.075 | −12.243 | −0.777 | 1.00 | 58.25 | O |
| ATOM | 4877 | N | GLN | A | 467 | −9.638 | −13.073 | 0.617 | 1.00 | 58.45 | N |
| ATOM | 4879 | CA | GLN | A | 467 | −10.388 | −13.745 | −0.443 | 1.00 | 58.58 | C |
| ATOM | 4881 | CB | GLN | A | 467 | −11.300 | −14.835 | 0.139 | 1.00 | 58.70 | C |
| ATOM | 4884 | CG | GLN | A | 467 | −12.004 | −15.711 | −0.905 | 1.00 | 59.03 | C |
| ATOM | 4887 | CD | GLN | A | 467 | −11.093 | −16.120 | −2.058 | 1.00 | 59.58 | C |
| ATOM | 4888 | OE1 | GLN | A | 467 | −10.013 | −16.672 | −1.839 | 1.00 | 59.94 | O |
| ATOM | 4889 | NE2 | GLN | A | 467 | −11.524 | −15.840 | −3.285 | 1.00 | 59.78 | N |
| ATOM | 4892 | C | GLN | A | 467 | −11.208 | −12.755 | −1.267 | 1.00 | 58.53 | C |
| ATOM | 4893 | O | GLN | A | 467 | −11.224 | −12.837 | −2.493 | 1.00 | 58.57 | O |
| ATOM | 4894 | N | ASP | A | 468 | −11.892 | −11.832 | −0.595 | 1.00 | 58.49 | N |

TABLE 2-continued

| | | | | | | | | | | |
|---|---|---|---|---|---|---|---|---|---|---|
| ATOM | 4896 | CA | ASP | A | 468 | −12.687 | −10.810 | −1.280 | 1.00 | 58.47 | C |
| ATOM | 4898 | CB | ASP | A | 468 | −13.433 | −9.932 | −0.269 | 1.00 | 58.58 | C |
| ATOM | 4901 | CG | ASP | A | 468 | −14.639 | −10.630 | 0.335 | 1.00 | 58.90 | C |
| ATOM | 4902 | OD1 | ASP | A | 468 | −15.637 | −9.939 | 0.625 | 1.00 | 59.07 | O |
| ATOM | 4903 | OD2 | ASP | A | 468 | −14.681 | −11.860 | 0.556 | 1.00 | 59.55 | O |
| ATOM | 4904 | C | ASP | A | 468 | −11.810 | −9.932 | −2.176 | 1.00 | 58.35 | C |
| ATOM | 4905 | O | ASP | A | 468 | −12.260 | −9.456 | −3.218 | 1.00 | 58.35 | O |
| ATOM | 4906 | N | ILE | A | 469 | −10.565 | −9.718 | −1.755 | 1.00 | 58.12 | N |
| ATOM | 4908 | CA | ILE | A | 469 | −9.604 | −8.925 | −2.516 | 1.00 | 57.94 | C |
| ATOM | 4910 | CB | ILE | A | 469 | −8.367 | −8.593 | −1.633 | 1.00 | 57.83 | C |
| ATOM | 4912 | CG1 | ILE | A | 469 | −8.709 | −7.460 | −0.657 | 1.00 | 57.58 | C |
| ATOM | 4915 | CD1 | ILE | A | 469 | −7.757 | −7.339 | 0.519 | 1.00 | 57.20 | C |
| ATOM | 4919 | CG2 | ILE | A | 469 | −7.151 | −8.217 | −2.483 | 1.00 | 57.73 | C |
| ATOM | 4923 | C | ILE | A | 469 | −9.190 | −9.651 | −3.800 | 1.00 | 57.93 | C |
| ATOM | 4924 | O | ILE | A | 469 | −9.044 | −9.026 | −4.845 | 1.00 | 57.74 | O |
| ATOM | 4925 | N | LEU | A | 470 | −9.005 | −10.965 | −3.711 | 1.00 | 58.05 | N |
| ATOM | 4927 | CA | LEU | A | 470 | −8.609 | −11.778 | −4.864 | 1.00 | 58.17 | C |
| ATOM | 4929 | CB | LEU | A | 470 | −8.149 | −13.176 | −4.418 | 1.00 | 58.20 | C |
| ATOM | 4932 | CG | LEU | A | 470 | −6.687 | −13.554 | −4.685 | 1.00 | 58.32 | C |
| ATOM | 4934 | CD1 | LEU | A | 470 | −5.722 | −12.490 | −4.181 | 1.00 | 58.21 | C |
| ATOM | 4938 | CD2 | LEU | A | 470 | −6.365 | −14.910 | −4.054 | 1.00 | 58.38 | C |
| ATOM | 4942 | C | LEU | A | 470 | −9.726 | −11.893 | −5.908 | 1.00 | 58.28 | C |
| ATOM | 4943 | O | LEU | A | 470 | −9.444 | −12.003 | −7.101 | 1.00 | 58.35 | O |
| ATOM | 4944 | N | ASP | A | 471 | −10.981 | −11.868 | −5.457 | 1.00 | 58.37 | N |
| ATOM | 4946 | CA | ASP | A | 471 | −12.140 | −11.935 | −6.354 | 1.00 | 58.33 | C |
| ATOM | 4948 | CB | ASP | A | 471 | −13.412 | −12.328 | −5.590 | 1.00 | 58.45 | C |
| ATOM | 4951 | CG | ASP | A | 471 | −13.399 | −13.772 | −5.130 | 1.00 | 58.77 | C |
| ATOM | 4952 | OD1 | ASP | A | 471 | −13.207 | −14.667 | −5.983 | 1.00 | 59.01 | O |
| ATOM | 4953 | OD2 | ASP | A | 471 | −13.573 | −14.104 | −3.935 | 1.00 | 59.44 | O |
| ATOM | 4954 | C | ASP | A | 471 | −12.361 | −10.587 | −7.033 | 1.00 | 58.16 | C |
| ATOM | 4955 | O | ASP | A | 471 | −12.790 | −10.534 | −8.181 | 1.00 | 58.25 | O |
| ATOM | 4956 | N | THR | A | 472 | −12.079 | −9.506 | −6.307 | 1.00 | 57.97 | N |
| ATOM | 4958 | CA | THR | A | 472 | −12.212 | −8.145 | −6.830 | 1.00 | 57.83 | C |
| ATOM | 4960 | CB | THR | A | 472 | −12.116 | −7.101 | −5.685 | 1.00 | 57.75 | C |
| ATOM | 4962 | OG1 | THR | A | 472 | −13.130 | −7.343 | −4.702 | 1.00 | 57.68 | O |
| ATOM | 4964 | CG2 | THR | A | 472 | −12.425 | −5.692 | −6.188 | 1.00 | 57.70 | C |
| ATOM | 4968 | C | THR | A | 472 | −11.113 | −7.877 | −7.850 | 1.00 | 57.71 | C |
| ATOM | 4969 | O | THR | A | 472 | −11.299 | −7.101 | −8.779 | 1.00 | 57.71 | O |
| ATOM | 4970 | N | LEU | A | 473 | −9.969 | −8.530 | −7.657 | 1.00 | 57.64 | N |
| ATOM | 4972 | CA | LEU | A | 473 | −8.810 | −8.388 | −8.530 | 1.00 | 57.61 | C |
| ATOM | 4974 | CB | LEU | A | 473 | −7.582 | −9.002 | −7.851 | 1.00 | 57.55 | C |
| ATOM | 4977 | CG | LEU | A | 473 | −6.205 | −8.815 | −8.484 | 1.00 | 57.36 | C |
| ATOM | 4979 | CD1 | LEU | A | 473 | −5.943 | −7.360 | −8.832 | 1.00 | 57.43 | C |
| ATOM | 4983 | CD2 | LEU | A | 473 | −5.138 | −9.337 | −7.534 | 1.00 | 57.34 | C |
| ATOM | 4987 | C | LEU | A | 473 | −9.068 | −9.067 | −9.871 | 1.00 | 57.72 | C |
| ATOM | 4988 | O | LEU | A | 473 | −8.728 | −8.527 | −10.918 | 1.00 | 57.64 | O |
| ATOM | 4989 | N | GLU | A | 474 | −9.673 | −10.252 | −9.822 | 1.00 | 57.84 | N |
| ATOM | 4991 | CA | GLU | A | 474 | −10.012 | −11.019 | −11.018 | 1.00 | 57.97 | C |
| ATOM | 4993 | CB | GLU | A | 474 | −10.500 | −12.416 | −10.620 | 1.00 | 58.21 | C |
| ATOM | 4996 | CG | GLU | A | 474 | −10.906 | −13.312 | −11.781 | 1.00 | 59.11 | C |
| ATOM | 4999 | CD | GLU | A | 474 | −11.284 | −14.707 | −11.322 | 1.00 | 60.27 | C |
| ATOM | 5000 | OE1 | GLU | A | 474 | −12.453 | −15.110 | −11.519 | 1.00 | 60.85 | O |
| ATOM | 5001 | OE2 | GLU | A | 474 | −10.411 | −15.398 | −10.753 | 1.00 | 61.40 | O |
| ATOM | 5002 | C | GLU | A | 474 | −11.083 | −10.312 | −11.852 | 1.00 | 57.68 | C |
| ATOM | 5003 | O | GLU | A | 474 | −11.037 | −10.345 | −13.078 | 1.00 | 57.78 | O |
| ATOM | 5004 | N | ASP | A | 475 | −12.039 | −9.678 | −11.177 | 1.00 | 57.33 | N |
| ATOM | 5006 | CA | ASP | A | 475 | −13.127 | −8.963 | −11.841 | 1.00 | 56.95 | C |
| ATOM | 5008 | CB | ASP | A | 475 | −14.223 | −8.604 | −10.833 | 1.00 | 56.90 | C |
| ATOM | 5011 | CG | ASP | A | 475 | −15.024 | −9.813 | −10.379 | 1.00 | 56.92 | C |
| ATOM | 5012 | OD1 | ASP | A | 475 | −14.562 | −10.962 | −10.570 | 1.00 | 56.90 | O |
| ATOM | 5013 | OD2 | ASP | A | 475 | −16.132 | −9.707 | −9.817 | 1.00 | 56.64 | O |
| ATOM | 5014 | C | ASP | A | 475 | −12.627 | −7.698 | −12.521 | 1.00 | 56.67 | C |
| ATOM | 5015 | O | ASP | A | 475 | −13.067 | −7.362 | −13.618 | 1.00 | 56.71 | O |
| ATOM | 5016 | N | ASN | A | 476 | −11.716 | −6.994 | −11.858 | 1.00 | 56.37 | N |
| ATOM | 5018 | CA | ASN | A | 476 | −11.133 | −5.773 | −12.407 | 1.00 | 56.06 | C |
| ATOM | 5020 | CB | ASN | A | 476 | −10.356 | −5.018 | −11.323 | 1.00 | 55.93 | C |
| ATOM | 5023 | CG | ASN | A | 476 | −11.263 | −4.451 | −10.238 | 1.00 | 55.60 | C |
| ATOM | 5024 | OD1 | ASN | A | 476 | −12.457 | −4.238 | −10.454 | 1.00 | 54.94 | O |
| ATOM | 5025 | ND2 | ASN | A | 476 | −10.695 | −4.205 | −9.062 | 1.00 | 54.97 | N |
| ATOM | 5028 | C | ASN | A | 476 | −10.223 | −6.100 | −13.591 | 1.00 | 55.95 | C |
| ATOM | 5029 | O | ASN | A | 476 | −10.105 | −5.317 | −14.531 | 1.00 | 55.77 | O |
| ATOM | 5030 | N | ARG | A | 477 | −9.600 | −7.273 | −13.534 | 1.00 | 55.98 | N |
| ATOM | 5032 | CA | ARG | A | 477 | −8.718 | −7.753 | −14.588 | 1.00 | 56.16 | C |
| ATOM | 5034 | CB | ARG | A | 477 | −7.960 | −8.996 | −14.109 | 1.00 | 56.25 | C |
| ATOM | 5037 | CG | ARG | A | 477 | −6.829 | −9.454 | −15.025 | 1.00 | 56.76 | C |
| ATOM | 5040 | CD | ARG | A | 477 | −7.284 | −10.262 | −16.230 | 1.00 | 57.39 | C |
| ATOM | 5043 | NE | ARG | A | 477 | −6.302 | −11.265 | −16.636 | 1.00 | 58.10 | N |
| ATOM | 5045 | CZ | ARG | A | 477 | −6.266 | −11.842 | −17.838 | 1.00 | 58.64 | C |
| ATOM | 5046 | NH1 | ARG | A | 477 | −7.169 | −11.545 | −18.769 | 1.00 | 58.60 | N |

TABLE 2-continued

| | | | | | | | | | | |
|---|---|---|---|---|---|---|---|---|---|---|
| ATOM | 5049 | NH2 | ARG | A | 477 | −5.322 | −12.736 | −18.109 | 1.00 | 58.74 N |
| ATOM | 5052 | C | ARG | A | 477 | −9.540 | −8.091 | −15.827 | 1.00 | 56.20 C |
| ATOM | 5053 | O | ARG | A | 477 | −9.149 | −7.772 | −16.948 | 1.00 | 56.18 O |
| ATOM | 5054 | N | ASN | A | 478 | −10.688 | −8.729 | −15.607 | 1.00 | 56.19 N |
| ATOM | 5056 | CA | ASN | A | 478 | −11.581 | −9.124 | −16.690 | 1.00 | 56.07 C |
| ATOM | 5058 | CB | ASN | A | 478 | −12.692 | −10.051 | −16.169 | 1.00 | 56.09 C |
| ATOM | 5061 | CG | ASN | A | 478 | −12.182 | −11.436 | −15.777 | 1.00 | 56.01 C |
| ATOM | 5062 | OD1 | ASN | A | 478 | −12.960 | −12.289 | −15.349 | 1.00 | 55.76 O |
| ATOM | 5063 | ND2 | ASN | A | 478 | −10.880 | −11.663 | −15.918 | 1.00 | 56.43 N |
| ATOM | 5066 | C | ASN | A | 478 | −12.203 | −7.914 | −17.381 | 1.00 | 55.97 C |
| ATOM | 5067 | O | ASN | A | 478 | −12.505 | −7.974 | −18.572 | 1.00 | 56.08 O |
| ATOM | 5068 | N | TRP | A | 479 | −12.382 | −6.821 | −16.641 | 1.00 | 55.72 N |
| ATOM | 5070 | CA | TRP | A | 479 | −12.974 | −5.603 | −17.194 | 1.00 | 55.49 C |
| ATOM | 5072 | CB | TRP | A | 479 | −13.414 | −4.653 | −16.079 | 1.00 | 55.28 C |
| ATOM | 5075 | CG | TRP | A | 479 | −14.202 | −3.491 | −16.592 | 1.00 | 54.29 C |
| ATOM | 5076 | CD1 | TRP | A | 479 | −15.553 | −3.429 | −16.765 | 1.00 | 53.63 C |
| ATOM | 5078 | NE1 | TRP | A | 479 | −15.912 | −2.200 | −17.264 | 1.00 | 53.36 N |
| ATOM | 5080 | CE2 | TRP | A | 479 | −14.783 | −1.441 | −17.431 | 1.00 | 53.11 C |
| ATOM | 5081 | CD2 | TRP | A | 479 | −13.686 | −2.224 | −17.019 | 1.00 | 53.46 C |
| ATOM | 5082 | CE3 | TRP | A | 479 | −12.402 | −1.668 | −17.094 | 1.00 | 53.34 C |
| ATOM | 5084 | CZ3 | TRP | A | 479 | −12.259 | −0.372 | −17.570 | 1.00 | 52.93 C |
| ATOM | 5086 | CH2 | TRP | A | 479 | −13.370 | 0.378 | −17.969 | 1.00 | 52.84 C |
| ATOM | 5088 | CZ2 | TRP | A | 479 | −14.637 | −0.136 | −17.908 | 1.00 | 52.99 C |
| ATOM | 5090 | C | TRP | A | 479 | −12.017 | −4.867 | −18.127 | 1.00 | 55.62 C |
| ATOM | 5091 | O | TRP | A | 479 | −12.441 | −4.313 | −19.142 | 1.00 | 55.73 O |
| ATOM | 5092 | N | TYR | A | 480 | −10.737 | −4.837 | −17.766 | 1.00 | 55.82 N |
| ATOM | 5094 | CA | TYR | A | 480 | −9.730 | −4.172 | −18.590 | 1.00 | 55.91 C |
| ATOM | 5096 | CB | TYR | A | 480 | −8.438 | −3.914 | −17.802 | 1.00 | 55.76 C |
| ATOM | 5099 | CG | TYR | A | 480 | −8.406 | −2.541 | −17.169 | 1.00 | 55.19 C |
| ATOM | 5100 | CD1 | TYR | A | 480 | −8.230 | −1.403 | −17.949 | 1.00 | 54.43 C |
| ATOM | 5102 | CE1 | TYR | A | 480 | −8.213 | −0.140 | −17.382 | 1.00 | 54.45 C |
| ATOM | 5104 | CZ | TYR | A | 480 | −8.378 | −0.003 | −16.014 | 1.00 | 54.55 C |
| ATOM | 5105 | OH | TYR | A | 480 | −8.361 | 1.247 | −15.444 | 1.00 | 55.01 O |
| ATOM | 5107 | CE2 | TYR | A | 480 | −8.560 | −1.114 | −15.217 | 1.00 | 54.40 C |
| ATOM | 5109 | CD2 | TYR | A | 480 | −8.579 | −2.376 | −15.795 | 1.00 | 54.93 C |
| ATOM | 5111 | C | TYR | A | 480 | −9.464 | −5.002 | −19.839 | 1.00 | 56.30 C |
| ATOM | 5112 | O | TYR | A | 480 | −9.216 | −4.451 | −20.910 | 1.00 | 56.35 O |
| ATOM | 5113 | N | GLN | A | 481 | −9.537 | −6.324 | −19.690 | 1.00 | 56.77 N |
| ATOM | 5115 | CA | GLN | A | 481 | −9.365 | −7.260 | −20.798 | 1.00 | 57.12 C |
| ATOM | 5117 | CB | GLN | A | 481 | −9.203 | −8.690 | −20.259 | 1.00 | 57.15 C |
| ATOM | 5120 | CG | GLN | A | 481 | −9.064 | −9.791 | −21.319 | 1.00 | 57.13 C |
| ATOM | 5123 | CD | GLN | A | 481 | −7.628 | −10.044 | −21.736 | 1.00 | 57.15 C |
| ATOM | 5124 | OE1 | GLN | A | 481 | −7.214 | −11.195 | −21.864 | 1.00 | 57.53 O |
| ATOM | 5125 | NE2 | GLN | A | 481 | −6.869 | −8.977 | −21.956 | 1.00 | 56.82 N |
| ATOM | 5128 | C | GLN | A | 481 | −10.568 | −7.175 | −21.740 | 1.00 | 57.46 C |
| ATOM | 5129 | O | GLN | A | 481 | −10.434 | −7.409 | −22.938 | 1.00 | 57.65 O |
| ATOM | 5130 | N | SER | A | 482 | −11.732 | −6.820 | −21.194 | 1.00 | 57.81 N |
| ATOM | 5132 | CA | SER | A | 482 | −12.960 | −6.689 | −21.983 | 1.00 | 58.01 C |
| ATOM | 5134 | CB | SER | A | 482 | −14.204 | −6.701 | −21.078 | 1.00 | 57.99 C |
| ATOM | 5137 | OG | SER | A | 482 | −14.489 | −5.410 | −20.555 | 1.00 | 57.61 O |
| ATOM | 5139 | C | SER | A | 482 | −12.956 | −5.415 | −22.827 | 1.00 | 58.26 C |
| ATOM | 5140 | O | SER | A | 482 | −13.729 | −5.300 | −23.776 | 1.00 | 58.28 O |
| ATOM | 5141 | N | MET | A | 483 | −12.101 | −4.459 | −22.467 | 1.00 | 58.53 N |
| ATOM | 5143 | CA | MET | A | 483 | −11.991 | −3.196 | −23.196 | 1.00 | 58.78 C |
| ATOM | 5145 | CB | MET | A | 483 | −11.874 | −2.027 | −22.212 | 1.00 | 59.07 C |
| ATOM | 5148 | CG | MET | A | 483 | −13.204 | −1.672 | −21.536 | 1.00 | 59.83 C |
| ATOM | 5151 | SD | MET | A | 483 | −13.875 | −0.097 | −22.111 | 1.00 | 62.00 S |
| ATOM | 5152 | CE | MET | A | 483 | −15.625 | −0.208 | −21.576 | 1.00 | 62.03 C |
| ATOM | 5156 | C | MET | A | 483 | −10.843 | −3.198 | −24.220 | 1.00 | 58.60 C |
| ATOM | 5157 | O | MET | A | 483 | −10.438 | −2.142 | −24.703 | 1.00 | 58.50 O |
| ATOM | 5158 | N | ILE | A | 484 | −10.322 | −4.387 | −24.526 | 1.00 | 58.58 N |
| ATOM | 5160 | CA | ILE | A | 484 | −9.331 | −4.577 | −25.585 | 1.00 | 58.54 C |
| ATOM | 5162 | CB | ILE | A | 484 | −8.078 | −5.341 | −25.100 | 1.00 | 58.55 C |
| ATOM | 5164 | CG1 | ILE | A | 484 | −7.482 | −4.705 | −23.845 | 1.00 | 58.59 C |
| ATOM | 5167 | CD1 | ILE | A | 484 | −6.525 | −5.626 | −23.102 | 1.00 | 58.50 C |
| ATOM | 5171 | CG2 | ILE | A | 484 | −7.016 | −5.368 | −26.204 | 1.00 | 58.47 C |
| ATOM | 5175 | C | ILE | A | 484 | −10.050 | −5.411 | −26.651 | 1.00 | 58.54 C |
| ATOM | 5176 | O | ILE | A | 484 | −10.428 | −6.554 | −26.378 | 1.00 | 58.53 O |
| ATOM | 5177 | N | PRO | A | 485 | −10.263 | −4.842 | −27.841 | 1.00 | 58.55 N |
| ATOM | 5178 | CA | PRO | A | 485 | −10.957 | −5.537 | −28.941 | 1.00 | 58.49 C |
| ATOM | 5180 | CB | PRO | A | 485 | −10.619 | −4.670 | −30.154 | 1.00 | 58.53 C |
| ATOM | 5183 | CG | PRO | A | 485 | −10.474 | −3.295 | −29.594 | 1.00 | 58.43 C |
| ATOM | 5186 | CD | PRO | A | 485 | −9.884 | −3.468 | −28.223 | 1.00 | 58.55 C |
| ATOM | 5189 | C | PRO | A | 485 | −10.529 | −6.991 | −29.191 | 1.00 | 58.43 C |
| ATOM | 5190 | O | PRO | A | 485 | −9.341 | −7.283 | −29.313 | 1.00 | 58.32 O |
| ATOM | 5191 | ZN | ZN | A | 1001 | 3.889 | 4.378 | −3.843 | 1.00 | 22.75 ZN |
| ATOM | 5192 | MG | MG | A | 1002 | 7.674 | 4.704 | −4.983 | 1.00 | 11.41 MG |
| ATOM | 5193 | O | HOH | A | 1003 | 9.241 | 5.292 | −5.207 | 1.00 | 7.87 O |
| ATOM | 5196 | O | HOH | A | 1004 | 8.472 | 4.740 | −2.622 | 1.00 | 9.57 O |

TABLE 2-continued

| ATOM | 5199 | O | HOH | A | 1005 | 8.919 | 3.206 | −4.952 | 1.00 | 19.26 | O |
|---|---|---|---|---|---|---|---|---|---|---|---|
| ATOM | 5202 | O | HOH | A | 1006 | 5.993 | 4.344 | −6.564 | 1.00 | 23.03 | O |
| ATOM | 5205 | O | HOH | A | 1007 | 5.410 | 4.034 | −3.859 | 1.00 | 7.95 | O |
| ATOM | 5208 | O | HOH | A | 1008 | 4.084 | 4.122 | −6.406 | 1.00 | 4.50 | O |
| ATOM | 5211 | N | GLU | C | 163 | 61.842 | 20.332 | −7.001 | 1.00 | 67.23 | N |
| ATOM | 5213 | CA | GLU | C | 163 | 63.216 | 19.888 | −6.621 | 1.00 | 67.23 | C |
| ATOM | 5215 | CB | GLU | C | 163 | 63.376 | 19.840 | −5.089 | 1.00 | 67.32 | C |
| ATOM | 5218 | CG | GLU | C | 163 | 62.187 | 19.271 | −4.324 | 1.00 | 67.78 | C |
| ATOM | 5221 | CD | GLU | C | 163 | 61.887 | 20.031 | −3.042 | 1.00 | 68.11 | C |
| ATOM | 5222 | OE1 | GLU | C | 163 | 62.687 | 19.929 | −2.084 | 1.00 | 68.42 | O |
| ATOM | 5223 | OE2 | GLU | C | 163 | 60.850 | 20.727 | −2.991 | 1.00 | 68.22 | O |
| ATOM | 5224 | C | GLU | C | 163 | 63.559 | 18.536 | −7.257 | 1.00 | 66.96 | C |
| ATOM | 5225 | O | GLU | C | 163 | 62.697 | 17.874 | −7.840 | 1.00 | 66.88 | O |
| ATOM | 5228 | N | ASP | C | 164 | 64.825 | 18.141 | −7.139 | 1.00 | 66.66 | N |
| ATOM | 5230 | CA | ASP | C | 164 | 65.317 | 16.887 | −7.729 | 1.00 | 66.40 | C |
| ATOM | 5232 | CB | ASP | C | 164 | 66.826 | 16.962 | −8.071 | 1.00 | 66.58 | C |
| ATOM | 5235 | CG | ASP | C | 164 | 67.620 | 17.865 | −7.126 | 1.00 | 67.08 | C |
| ATOM | 5236 | OD1 | ASP | C | 164 | 67.779 | 19.066 | −7.439 | 1.00 | 67.70 | O |
| ATOM | 5237 | OD2 | ASP | C | 164 | 68.136 | 17.459 | −6.062 | 1.00 | 67.94 | O |
| ATOM | 5238 | C | ASP | C | 164 | 65.024 | 15.645 | −6.873 | 1.00 | 65.87 | C |
| ATOM | 5239 | O | ASP | C | 164 | 65.053 | 14.523 | −7.387 | 1.00 | 65.74 | O |
| ATOM | 5240 | N | HIS | C | 165 | 64.740 | 15.845 | −5.584 | 1.00 | 65.20 | N |
| ATOM | 5242 | CA | HIS | C | 165 | 64.427 | 14.738 | −4.674 | 1.00 | 64.66 | C |
| ATOM | 5244 | CB | HIS | C | 165 | 64.326 | 15.224 | −3.223 | 1.00 | 64.69 | C |
| ATOM | 5247 | CG | HIS | C | 165 | 65.586 | 15.832 | −2.695 | 1.00 | 64.91 | C |
| ATOM | 5248 | ND1 | HIS | C | 165 | 66.693 | 15.081 | −2.362 | 1.00 | 65.02 | N |
| ATOM | 5250 | CE1 | HIS | C | 165 | 67.648 | 15.881 | −1.924 | 1.00 | 65.23 | C |
| ATOM | 5252 | NE2 | HIS | C | 165 | 67.200 | 17.123 | −1.957 | 1.00 | 65.30 | N |
| ATOM | 5254 | CD2 | HIS | C | 165 | 65.912 | 17.120 | −2.434 | 1.00 | 65.16 | C |
| ATOM | 5256 | C | HIS | C | 165 | 63.111 | 14.055 | −5.047 | 1.00 | 64.05 | C |
| ATOM | 5257 | O | HIS | C | 165 | 62.930 | 12.865 | −4.789 | 1.00 | 63.87 | O |
| ATOM | 5258 | N | LEU | C | 166 | 62.194 | 14.822 | −5.634 | 1.00 | 63.32 | N |
| ATOM | 5260 | CA | LEU | C | 166 | 60.894 | 14.306 | −6.049 | 1.00 | 62.72 | C |
| ATOM | 5262 | CB | LEU | C | 166 | 60.002 | 15.452 | −6.543 | 1.00 | 62.60 | C |
| ATOM | 5265 | CG | LEU | C | 166 | 58.573 | 15.129 | −6.995 | 1.00 | 62.36 | C |
| ATOM | 5267 | CD1 | LEU | C | 166 | 57.884 | 14.135 | −6.066 | 1.00 | 62.18 | C |
| ATOM | 5271 | CD2 | LEU | C | 166 | 57.762 | 16.416 | −7.092 | 1.00 | 62.16 | C |
| ATOM | 5275 | C | LEU | C | 166 | 61.040 | 13.243 | −7.134 | 1.00 | 62.29 | C |
| ATOM | 5276 | O | LEU | C | 166 | 60.397 | 12.198 | −7.067 | 1.00 | 62.20 | O |
| ATOM | 5277 | N | ALA | C | 167 | 61.895 | 13.508 | −8.120 | 1.00 | 61.69 | N |
| ATOM | 5279 | CA | ALA | C | 167 | 62.127 | 12.565 | −9.217 | 1.00 | 61.23 | C |
| ATOM | 5281 | CB | ALA | C | 167 | 62.961 | 13.220 | −10.312 | 1.00 | 61.20 | C |
| ATOM | 5285 | C | ALA | C | 167 | 62.801 | 11.275 | −8.737 | 1.00 | 60.71 | C |
| ATOM | 5286 | O | ALA | C | 167 | 62.513 | 10.191 | −9.248 | 1.00 | 60.66 | O |
| ATOM | 5287 | N | LYS | C | 168 | 63.694 | 11.399 | −7.758 | 1.00 | 60.10 | N |
| ATOM | 5289 | CA | LYS | C | 168 | 64.409 | 10.251 | −7.198 | 1.00 | 59.69 | C |
| ATOM | 5291 | CB | LYS | C | 168 | 65.511 | 10.730 | −6.238 | 1.00 | 59.76 | C |
| ATOM | 5294 | CG | LYS | C | 168 | 66.385 | 9.626 | −5.630 | 1.00 | 60.16 | C |
| ATOM | 5297 | CD | LYS | C | 168 | 67.425 | 9.106 | −6.612 | 1.00 | 60.57 | C |
| ATOM | 5300 | CE | LYS | C | 168 | 68.133 | 7.872 | −6.066 | 1.00 | 60.66 | C |
| ATOM | 5303 | NZ | LYS | C | 168 | 69.412 | 7.601 | −6.782 | 1.00 | 60.80 | N |
| ATOM | 5307 | C | LYS | C | 168 | 63.448 | 9.308 | −6.474 | 1.00 | 59.08 | C |
| ATOM | 5308 | O | LYS | C | 168 | 63.562 | 8.088 | −6.585 | 1.00 | 59.00 | O |
| ATOM | 5309 | N | GLU | C | 169 | 62.502 | 9.885 | −5.740 | 1.00 | 58.44 | N |
| ATOM | 5311 | CA | GLU | C | 169 | 61.522 | 9.110 | −4.987 | 1.00 | 57.93 | C |
| ATOM | 5313 | CB | GLU | C | 169 | 60.785 | 10.013 | −3.992 | 1.00 | 57.84 | C |
| ATOM | 5316 | CG | GLU | C | 169 | 60.011 | 9.267 | −2.918 | 1.00 | 57.80 | C |
| ATOM | 5319 | CD | GLU | C | 169 | 60.915 | 8.505 | −1.972 | 1.00 | 57.67 | C |
| ATOM | 5320 | OE1 | GLU | C | 169 | 60.835 | 7.256 | −1.948 | 1.00 | 57.33 | O |
| ATOM | 5321 | OE2 | GLU | C | 169 | 61.707 | 9.156 | −1.259 | 1.00 | 57.03 | O |
| ATOM | 5322 | C | GLU | C | 169 | 60.522 | 8.415 | −5.911 | 1.00 | 57.45 | C |
| ATOM | 5323 | O | GLU | C | 169 | 60.034 | 7.331 | −5.592 | 1.00 | 57.36 | O |
| ATOM | 5324 | N | LEU | C | 170 | 60.241 | 9.032 | −7.060 | 1.00 | 56.91 | N |
| ATOM | 5326 | CA | LEU | C | 170 | 59.293 | 8.481 | −8.035 | 1.00 | 56.52 | C |
| ATOM | 5328 | CB | LEU | C | 170 | 58.771 | 9.577 | −8.979 | 1.00 | 56.50 | C |
| ATOM | 5331 | CG | LEU | C | 170 | 57.731 | 10.556 | −8.410 | 1.00 | 56.69 | C |
| ATOM | 5333 | CD1 | LEU | C | 170 | 57.119 | 11.380 | −9.538 | 1.00 | 56.74 | C |
| ATOM | 5337 | CD2 | LEU | C | 170 | 56.635 | 9.851 | −7.607 | 1.00 | 56.63 | C |
| ATOM | 5341 | C | LEU | C | 170 | 59.853 | 7.302 | −8.842 | 1.00 | 56.03 | C |
| ATOM | 5342 | O | LEU | C | 170 | 59.129 | 6.695 | −9.630 | 1.00 | 55.98 | O |
| ATOM | 5343 | N | GLU | C | 171 | 61.134 | 6.990 | −8.655 | 1.00 | 55.58 | N |
| ATOM | 5345 | CA | GLU | C | 171 | 61.748 | 5.825 | −9.294 | 1.00 | 55.22 | C |
| ATOM | 5347 | CB | GLU | C | 171 | 63.253 | 5.777 | −9.020 | 1.00 | 55.33 | C |
| ATOM | 5350 | CG | GLU | C | 171 | 64.068 | 6.800 | −9.793 | 1.00 | 55.62 | C |
| ATOM | 5353 | CD | GLU | C | 171 | 65.565 | 6.548 | −9.706 | 1.00 | 56.12 | C |
| ATOM | 5354 | OE1 | GLU | C | 171 | 65.983 | 5.368 | −9.645 | 1.00 | 56.00 | O |
| ATOM | 5355 | OE2 | GLU | C | 171 | 66.328 | 7.538 | −9.702 | 1.00 | 56.45 | O |
| ATOM | 5356 | C | GLU | C | 171 | 61.106 | 4.533 | −8.777 | 1.00 | 54.69 | C |
| ATOM | 5357 | O | GLU | C | 171 | 61.085 | 3.523 | −9.482 | 1.00 | 54.74 | O |

TABLE 2-continued

| ATOM | 5358 | N | ASP | C | 172 | 60.602 | 4.577 | −7.539 | 1.00 | 53.99 | N |
| --- | --- | --- | --- | --- | --- | --- | --- | --- | --- | --- | --- |
| ATOM | 5360 | CA | ASP | C | 172 | 59.916 | 3.445 | −6.911 | 1.00 | 53.46 | C |
| ATOM | 5362 | CB | ASP | C | 172 | 60.214 | 3.400 | −5.401 | 1.00 | 53.50 | C |
| ATOM | 5365 | CG | ASP | C | 172 | 61.700 | 3.398 | −5.081 | 1.00 | 53.71 | C |
| ATOM | 5366 | OD1 | ASP | C | 172 | 62.504 | 2.904 | −5.902 | 1.00 | 53.49 | O |
| ATOM | 5367 | OD2 | ASP | C | 172 | 62.147 | 3.861 | −4.007 | 1.00 | 53.93 | O |
| ATOM | 5368 | C | ASP | C | 172 | 58.390 | 3.524 | −7.099 | 1.00 | 52.85 | C |
| ATOM | 5369 | O | ASP | C | 172 | 57.638 | 3.063 | −6.240 | 1.00 | 52.98 | O |
| ATOM | 5370 | N | LEU | C | 173 | 57.932 | 4.095 | −8.214 | 1.00 | 52.04 | N |
| ATOM | 5372 | CA | LEU | C | 173 | 56.497 | 4.245 | −8.483 | 1.00 | 51.24 | C |
| ATOM | 5374 | CB | LEU | C | 173 | 56.277 | 5.038 | −9.777 | 1.00 | 51.21 | C |
| ATOM | 5377 | CG | LEU | C | 173 | 54.834 | 5.356 | −10.192 | 1.00 | 51.06 | C |
| ATOM | 5379 | CD1 | LEU | C | 173 | 54.193 | 6.329 | −9.224 | 1.00 | 50.66 | C |
| ATOM | 5383 | CD2 | LEU | C | 173 | 54.786 | 5.914 | −11.617 | 1.00 | 50.99 | C |
| ATOM | 5387 | C | LEU | C | 173 | 55.776 | 2.901 | −8.570 | 1.00 | 50.55 | C |
| ATOM | 5388 | O | LEU | C | 173 | 54.657 | 2.764 | −8.077 | 1.00 | 50.59 | O |
| ATOM | 5389 | N | ASN | C | 174 | 56.431 | 1.916 | −9.178 | 1.00 | 49.72 | N |
| ATOM | 5391 | CA | ASN | C | 174 | 55.858 | 0.580 | −9.353 | 1.00 | 49.12 | C |
| ATOM | 5393 | CB | ASN | C | 174 | 56.300 | −0.008 | −10.700 | 1.00 | 49.08 | C |
| ATOM | 5396 | CG | ASN | C | 174 | 56.172 | 0.979 | −11.847 | 1.00 | 48.91 | C |
| ATOM | 5397 | OD1 | ASN | C | 174 | 55.475 | 1.990 | −11.745 | 1.00 | 48.48 | O |
| ATOM | 5398 | ND2 | ASN | C | 174 | 56.849 | 0.687 | −12.949 | 1.00 | 49.29 | N |
| ATOM | 5401 | C | ASN | C | 174 | 56.231 | −0.405 | −8.242 | 1.00 | 48.65 | C |
| ATOM | 5402 | O | ASN | C | 174 | 56.010 | −1.608 | −8.387 | 1.00 | 48.67 | O |
| ATOM | 5403 | N | LYS | C | 175 | 56.772 | 0.099 | −7.136 | 1.00 | 48.07 | N |
| ATOM | 5405 | CA | LYS | C | 175 | 57.222 | −0.753 | −6.039 | 1.00 | 47.77 | C |
| ATOM | 5407 | CB | LYS | C | 175 | 58.717 | −0.532 | −5.786 | 1.00 | 47.88 | C |
| ATOM | 5410 | CG | LYS | C | 175 | 59.612 | −0.812 | −6.985 | 1.00 | 48.35 | C |
| ATOM | 5413 | CD | LYS | C | 175 | 61.069 | −0.929 | −6.564 | 1.00 | 49.15 | C |
| ATOM | 5416 | CE | LYS | C | 175 | 62.002 | −0.966 | −7.760 | 1.00 | 49.54 | C |
| ATOM | 5419 | NZ | LYS | C | 175 | 63.411 | −1.185 | −7.340 | 1.00 | 49.76 | N |
| ATOM | 5423 | C | LYS | C | 175 | 56.459 | −0.518 | −4.740 | 1.00 | 47.17 | C |
| ATOM | 5424 | O | LYS | C | 175 | 56.002 | 0.588 | −4.457 | 1.00 | 47.14 | O |
| ATOM | 5425 | N | TRP | C | 176 | 56.355 | −1.578 | −3.947 | 1.00 | 46.56 | N |
| ATOM | 5427 | CA | TRP | C | 176 | 55.682 | −1.542 | −2.651 | 1.00 | 46.02 | C |
| ATOM | 5429 | CB | TRP | C | 176 | 55.606 | −2.960 | −2.068 | 1.00 | 45.83 | C |
| ATOM | 5432 | CG | TRP | C | 176 | 54.448 | −3.194 | −1.157 | 1.00 | 45.15 | C |
| ATOM | 5433 | CD1 | TRP | C | 176 | 54.500 | −3.530 | 0.170 | 1.00 | 44.64 | C |
| ATOM | 5435 | NE1 | TRP | C | 176 | 53.228 | −3.669 | 0.671 | 1.00 | 44.03 | N |
| ATOM | 5437 | CE2 | TRP | C | 176 | 52.323 | −3.422 | −0.329 | 1.00 | 43.19 | C |
| ATOM | 5438 | CD2 | TRP | C | 176 | 53.058 | −3.124 | −1.497 | 1.00 | 43.57 | C |
| ATOM | 5439 | CE3 | TRP | C | 176 | 52.355 | −2.830 | −2.673 | 1.00 | 42.34 | C |
| ATOM | 5441 | CZ3 | TRP | C | 176 | 50.970 | −2.847 | −2.646 | 1.00 | 41.76 | C |
| ATOM | 5443 | CH2 | TRP | C | 176 | 50.270 | −3.146 | −1.471 | 1.00 | 42.18 | C |
| ATOM | 5445 | CZ2 | TRP | C | 176 | 50.925 | −3.437 | −0.304 | 1.00 | 42.45 | C |
| ATOM | 5447 | C | TRP | C | 176 | 56.405 | −0.621 | −1.667 | 1.00 | 45.81 | C |
| ATOM | 5448 | O | TRP | C | 176 | 55.787 | −0.070 | −0.761 | 1.00 | 45.76 | O |
| ATOM | 5449 | N | GLY | C | 177 | 57.712 | −0.455 | −1.864 | 1.00 | 45.67 | N |
| ATOM | 5451 | CA | GLY | C | 177 | 58.545 | 0.363 | −1.001 | 1.00 | 45.47 | C |
| ATOM | 5454 | C | GLY | C | 177 | 58.526 | 1.869 | −1.213 | 1.00 | 45.42 | C |
| ATOM | 5455 | O | GLY | C | 177 | 59.265 | 2.581 | −0.524 | 1.00 | 45.61 | O |
| ATOM | 5456 | N | LEU | C | 178 | 57.711 | 2.369 | −2.142 | 1.00 | 45.11 | N |
| ATOM | 5458 | CA | LEU | C | 178 | 57.619 | 3.814 | −2.367 | 1.00 | 44.90 | C |
| ATOM | 5460 | CB | LEU | C | 178 | 56.562 | 4.153 | −3.417 | 1.00 | 44.80 | C |
| ATOM | 5463 | CG | LEU | C | 178 | 56.394 | 5.656 | −3.696 | 1.00 | 44.86 | C |
| ATOM | 5465 | CD1 | LEU | C | 178 | 56.417 | 5.960 | −5.186 | 1.00 | 45.03 | C |
| ATOM | 5469 | CD2 | LEU | C | 178 | 55.107 | 6.191 | −3.074 | 1.00 | 44.90 | C |
| ATOM | 5473 | C | LEU | C | 178 | 57.249 | 4.528 | −1.075 | 1.00 | 44.74 | C |
| ATOM | 5474 | O | LEU | C | 178 | 56.391 | 4.061 | −0.327 | 1.00 | 44.76 | O |
| ATOM | 5475 | N | ASN | C | 179 | 57.896 | 5.662 | −0.828 | 1.00 | 44.60 | N |
| ATOM | 5477 | CA | ASN | C | 179 | 57.624 | 6.467 | 0.354 | 1.00 | 44.49 | C |
| ATOM | 5479 | CB | ASN | C | 179 | 58.938 | 6.952 | 0.984 | 1.00 | 44.41 | C |
| ATOM | 5482 | CG | ASN | C | 179 | 58.777 | 7.351 | 2.448 | 1.00 | 44.43 | C |
| ATOM | 5483 | OD1 | ASN | C | 179 | 57.820 | 8.030 | 2.817 | 1.00 | 43.77 | O |
| ATOM | 5484 | ND2 | ASN | C | 179 | 59.716 | 6.927 | 3.284 | 1.00 | 43.59 | N |
| ATOM | 5487 | C | ASN | C | 179 | 56.729 | 7.638 | −0.039 | 1.00 | 44.37 | C |
| ATOM | 5488 | O | ASN | C | 179 | 57.207 | 8.632 | −0.583 | 1.00 | 44.33 | O |
| ATOM | 5489 | N | ILE | C | 180 | 55.428 | 7.509 | 0.227 | 1.00 | 44.25 | N |
| ATOM | 5491 | CA | ILE | C | 180 | 54.461 | 8.553 | −0.121 | 1.00 | 44.28 | C |
| ATOM | 5493 | CB | ILE | C | 180 | 53.011 | 8.004 | −0.076 | 1.00 | 44.19 | C |
| ATOM | 5495 | CG1 | ILE | C | 180 | 52.080 | 8.864 | −0.940 | 1.00 | 44.08 | C |
| ATOM | 5498 | CD1 | ILE | C | 180 | 52.465 | 8.907 | −2.413 | 1.00 | 44.19 | C |
| ATOM | 5502 | CG2 | ILE | C | 180 | 52.498 | 7.926 | 1.348 | 1.00 | 44.04 | C |
| ATOM | 5506 | C | ILE | C | 180 | 54.599 | 9.809 | 0.741 | 1.00 | 44.57 | C |
| ATOM | 5507 | O | ILE | C | 180 | 54.196 | 10.892 | 0.325 | 1.00 | 44.54 | O |
| ATOM | 5508 | N | PHE | C | 181 | 55.155 | 9.658 | 1.940 | 1.00 | 45.01 | N |
| ATOM | 5510 | CA | PHE | C | 181 | 55.387 | 10.797 | 2.824 | 1.00 | 45.39 | C |
| ATOM | 5512 | CB | PHE | C | 181 | 55.814 | 10.345 | 4.228 | 1.00 | 45.27 | C |
| ATOM | 5515 | CG | PHE | C | 181 | 54.801 | 9.491 | 4.920 | 1.00 | 44.59 | C |

TABLE 2-continued

| ATOM | 5516 | CD1 | PHE | C | 181 | 53.779 | 10.067 | 5.650 | 1.00 | 44.11 | C |
| --- | --- | --- | --- | --- | --- | --- | --- | --- | --- | --- | --- |
| ATOM | 5518 | CE1 | PHE | C | 181 | 52.834 | 9.283 | 6.280 | 1.00 | 43.66 | C |
| ATOM | 5520 | CZ | PHE | C | 181 | 52.907 | 7.905 | 6.190 | 1.00 | 43.64 | C |
| ATOM | 5522 | CE2 | PHE | C | 181 | 53.919 | 7.316 | 5.465 | 1.00 | 43.79 | C |
| ATOM | 5524 | CD2 | PHE | C | 181 | 54.863 | 8.108 | 4.834 | 1.00 | 44.48 | C |
| ATOM | 5526 | C | PHE | C | 181 | 56.469 | 11.681 | 2.209 | 1.00 | 45.93 | C |
| ATOM | 5527 | O | PHE | C | 181 | 56.417 | 12.904 | 2.328 | 1.00 | 45.85 | O |
| ATOM | 5528 | N | ASN | C | 182 | 57.440 | 11.046 | 1.552 | 1.00 | 46.68 | N |
| ATOM | 5530 | CA | ASN | C | 182 | 58.528 | 11.762 | 0.888 | 1.00 | 47.36 | C |
| ATOM | 5532 | CB | ASN | C | 182 | 59.673 | 10.811 | 0.495 | 1.00 | 47.27 | C |
| ATOM | 5535 | CG | ASN | C | 182 | 60.525 | 10.384 | 1.690 | 1.00 | 47.68 | C |
| ATOM | 5536 | OD1 | ASN | C | 182 | 60.417 | 10.948 | 2.779 | 1.00 | 47.51 | O |
| ATOM | 5537 | ND2 | ASN | C | 182 | 61.375 | 9.381 | 1.486 | 1.00 | 47.78 | N |
| ATOM | 5540 | C | ASN | C | 182 | 58.044 | 12.555 | −0.327 | 1.00 | 47.90 | C |
| ATOM | 5541 | O | ASN | C | 182 | 58.461 | 13.698 | −0.510 | 1.00 | 47.96 | O |
| ATOM | 5542 | N | VAL | C | 183 | 57.160 | 11.974 | −1.143 | 1.00 | 48.64 | N |
| ATOM | 5544 | CA | VAL | C | 183 | 56.646 | 12.696 | −2.320 | 1.00 | 49.30 | C |
| ATOM | 5546 | CB | VAL | C | 183 | 55.926 | 11.792 | −3.407 | 1.00 | 49.30 | C |
| ATOM | 5548 | CG1 | VAL | C | 183 | 56.246 | 10.299 | −3.248 | 1.00 | 49.49 | C |
| ATOM | 5552 | CG2 | VAL | C | 183 | 54.414 | 12.025 | −3.446 | 1.00 | 49.39 | C |
| ATOM | 5556 | C | VAL | C | 183 | 55.743 | 13.851 | −1.875 | 1.00 | 49.88 | C |
| ATOM | 5557 | O | VAL | C | 183 | 55.611 | 14.843 | −2.586 | 1.00 | 49.90 | O |
| ATOM | 5558 | N | ALA | C | 184 | 55.135 | 13.720 | −0.695 | 1.00 | 50.64 | N |
| ATOM | 5560 | CA | ALA | C | 184 | 54.277 | 14.768 | −0.151 | 1.00 | 51.17 | C |
| ATOM | 5562 | CB | ALA | C | 184 | 53.482 | 14.246 | 1.035 | 1.00 | 51.20 | C |
| ATOM | 5566 | C | ALA | C | 184 | 55.112 | 15.979 | 0.258 | 1.00 | 51.72 | C |
| ATOM | 5567 | O | ALA | C | 184 | 54.665 | 17.112 | 0.136 | 1.00 | 51.70 | O |
| ATOM | 5568 | N | GLY | C | 185 | 56.329 | 15.730 | 0.734 | 1.00 | 52.52 | N |
| ATOM | 5570 | CA | GLY | C | 185 | 57.226 | 16.791 | 1.158 | 1.00 | 53.10 | C |
| ATOM | 5573 | C | GLY | C | 185 | 57.872 | 17.549 | 0.012 | 1.00 | 53.68 | C |
| ATOM | 5574 | O | GLY | C | 185 | 58.057 | 18.765 | 0.101 | 1.00 | 53.74 | O |
| ATOM | 5575 | N | TYR | C | 186 | 58.200 | 16.838 | −1.067 | 1.00 | 54.31 | N |
| ATOM | 5577 | CA | TYR | C | 186 | 58.876 | 17.435 | −2.223 | 1.00 | 54.88 | C |
| ATOM | 5579 | CB | TYR | C | 186 | 59.816 | 16.412 | −2.877 | 1.00 | 55.06 | C |
| ATOM | 5582 | CG | TYR | C | 186 | 60.808 | 15.764 | −1.921 | 1.00 | 56.04 | C |
| ATOM | 5583 | CD1 | TYR | C | 186 | 61.538 | 16.528 | −1.008 | 1.00 | 56.86 | C |
| ATOM | 5585 | CE1 | TYR | C | 186 | 62.446 | 15.933 | −0.135 | 1.00 | 57.17 | C |
| ATOM | 5587 | CZ | TYR | C | 186 | 62.632 | 14.563 | −0.171 | 1.00 | 57.30 | C |
| ATOM | 5588 | OH | TYR | C | 186 | 63.525 | 13.967 | 0.689 | 1.00 | 57.70 | O |
| ATOM | 5590 | CE2 | TYR | C | 186 | 61.922 | 13.785 | −1.067 | 1.00 | 57.02 | C |
| ATOM | 5592 | CD2 | TYR | C | 186 | 61.020 | 14.385 | −1.936 | 1.00 | 56.68 | C |
| ATOM | 5594 | C | TYR | C | 186 | 57.925 | 18.011 | −3.280 | 1.00 | 54.97 | C |
| ATOM | 5595 | O | TYR | C | 186 | 58.360 | 18.758 | −4.156 | 1.00 | 55.21 | O |
| ATOM | 5596 | N | SER | C | 187 | 56.640 | 17.671 | −3.197 | 1.00 | 55.10 | N |
| ATOM | 5598 | CA | SER | C | 187 | 55.643 | 18.157 | −4.155 | 1.00 | 55.10 | C |
| ATOM | 5600 | CB | SER | C | 187 | 54.702 | 17.021 | −4.557 | 1.00 | 55.21 | C |
| ATOM | 5603 | OG | SER | C | 187 | 53.898 | 16.618 | −3.461 | 1.00 | 55.35 | O |
| ATOM | 5605 | C | SER | C | 187 | 54.828 | 19.317 | −3.584 | 1.00 | 54.98 | C |
| ATOM | 5606 | O | SER | C | 187 | 53.789 | 19.686 | −4.142 | 1.00 | 54.94 | O |
| ATOM | 5607 | N | HIS | C | 188 | 55.317 | 19.887 | −2.480 | 1.00 | 54.82 | N |
| ATOM | 5609 | CA | HIS | C | 188 | 54.668 | 20.998 | −1.776 | 1.00 | 54.62 | C |
| ATOM | 5611 | CB | HIS | C | 188 | 54.700 | 22.294 | −2.612 | 1.00 | 54.90 | C |
| ATOM | 5614 | CG | HIS | C | 188 | 56.039 | 22.976 | −2.614 | 1.00 | 56.16 | C |
| ATOM | 5615 | ND1 | HIS | C | 188 | 57.230 | 22.283 | −2.699 | 1.00 | 57.62 | N |
| ATOM | 5617 | CE1 | HIS | C | 188 | 58.239 | 23.137 | −2.673 | 1.00 | 58.00 | C |
| ATOM | 5619 | NE2 | HIS | C | 188 | 57.747 | 24.359 | −2.571 | 1.00 | 57.87 | N |
| ATOM | 5621 | CD2 | HIS | C | 188 | 56.375 | 24.286 | −2.531 | 1.00 | 57.12 | C |
| ATOM | 5623 | C | HIS | C | 188 | 53.259 | 20.609 | −1.301 | 1.00 | 53.86 | C |
| ATOM | 5624 | O | HIS | C | 188 | 52.272 | 21.313 | −1.525 | 1.00 | 53.86 | O |
| ATOM | 5625 | N | ASN | C | 189 | 53.213 | 19.459 | −0.635 | 1.00 | 52.96 | N |
| ATOM | 5627 | CA | ASN | C | 189 | 52.001 | 18.895 | −0.041 | 1.00 | 52.22 | C |
| ATOM | 5629 | CB | ASN | C | 189 | 51.520 | 19.796 | 1.110 | 1.00 | 52.30 | C |
| ATOM | 5632 | CG | ASN | C | 189 | 50.671 | 19.050 | 2.132 | 1.00 | 52.99 | C |
| ATOM | 5633 | OD1 | ASN | C | 189 | 50.792 | 17.834 | 2.307 | 1.00 | 53.78 | O |
| ATOM | 5634 | ND2 | ASN | C | 189 | 49.801 | 19.786 | 2.813 | 1.00 | 53.66 | N |
| ATOM | 5637 | C | ASN | C | 189 | 50.864 | 18.586 | −1.027 | 1.00 | 51.14 | C |
| ATOM | 5638 | O | ASN | C | 189 | 49.703 | 18.904 | −0.770 | 1.00 | 51.21 | O |
| ATOM | 5639 | N | ARG | C | 190 | 51.214 | 17.945 | −2.143 | 1.00 | 49.83 | N |
| ATOM | 5641 | CA | ARG | C | 190 | 50.243 | 17.509 | −3.154 | 1.00 | 48.85 | C |
| ATOM | 5643 | CB | ARG | C | 190 | 50.349 | 18.375 | −4.425 | 1.00 | 48.87 | C |
| ATOM | 5646 | CG | ARG | C | 190 | 49.593 | 19.725 | −4.443 | 1.00 | 49.53 | C |
| ATOM | 5649 | CD | ARG | C | 190 | 48.422 | 19.872 | −3.475 | 1.00 | 50.59 | C |
| ATOM | 5652 | NE | ARG | C | 190 | 47.177 | 20.355 | −4.079 | 1.00 | 51.28 | N |
| ATOM | 5654 | CZ | ARG | C | 190 | 46.982 | 21.569 | −4.588 | 1.00 | 51.67 | C |
| ATOM | 5655 | NH1 | ARG | C | 190 | 47.963 | 22.469 | −4.622 | 1.00 | 52.33 | N |
| ATOM | 5658 | NH2 | ARG | C | 190 | 45.789 | 21.885 | −5.077 | 1.00 | 51.55 | N |
| ATOM | 5661 | C | ARG | C | 190 | 50.467 | 16.028 | −3.503 | 1.00 | 47.76 | C |
| ATOM | 5662 | O | ARG | C | 190 | 50.606 | 15.678 | −4.677 | 1.00 | 47.58 | O |
| ATOM | 5663 | N | PRO | C | 191 | 50.479 | 15.154 | −2.495 | 1.00 | 46.55 | N |

TABLE 2-continued

| | | | | | | | | | | |
|---|---|---|---|---|---|---|---|---|---|---|
| ATOM | 5664 | CA | PRO | C | 191 | 50.740 | 13.727 | −2.722 | 1.00 | 45.93 | C |
| ATOM | 5666 | CB | PRO | C | 191 | 50.654 | 13.120 | −1.311 | 1.00 | 46.00 | C |
| ATOM | 5669 | CG | PRO | C | 191 | 49.891 | 14.105 | −0.505 | 1.00 | 45.99 | C |
| ATOM | 5672 | CD | PRO | C | 191 | 50.245 | 15.438 | −1.066 | 1.00 | 46.50 | C |
| ATOM | 5675 | C | PRO | C | 191 | 49.745 | 13.048 | −3.658 | 1.00 | 45.33 | C |
| ATOM | 5676 | O | PRO | C | 191 | 50.166 | 12.213 | −4.459 | 1.00 | 45.28 | O |
| ATOM | 5677 | N | LEU | C | 192 | 48.464 | 13.399 | −3.562 | 1.00 | 44.63 | N |
| ATOM | 5679 | CA | LEU | C | 192 | 47.445 | 12.790 | −4.416 | 1.00 | 44.20 | C |
| ATOM | 5681 | CB | LEU | C | 192 | 46.038 | 13.034 | −3.863 | 1.00 | 43.96 | C |
| ATOM | 5684 | CG | LEU | C | 192 | 44.885 | 12.362 | −4.621 | 1.00 | 42.67 | C |
| ATOM | 5686 | CD1 | LEU | C | 192 | 45.011 | 10.839 | −4.622 | 1.00 | 41.32 | C |
| ATOM | 5690 | CD2 | LEU | C | 192 | 43.557 | 12.798 | −4.030 | 1.00 | 42.62 | C |
| ATOM | 5694 | C | LEU | C | 192 | 47.532 | 13.251 | −5.876 | 1.00 | 44.26 | C |
| ATOM | 5695 | O | LEU | C | 192 | 47.451 | 12.419 | −6.775 | 1.00 | 44.14 | O |
| ATOM | 5696 | N | THR | C | 193 | 47.675 | 14.558 | −6.108 | 1.00 | 44.43 | N |
| ATOM | 5698 | CA | THR | C | 193 | 47.801 | 15.088 | −7.477 | 1.00 | 44.58 | C |
| ATOM | 5700 | CB | THR | C | 193 | 47.955 | 16.627 | −7.489 | 1.00 | 44.54 | C |
| ATOM | 5702 | OG1 | THR | C | 193 | 46.848 | 17.228 | −6.804 | 1.00 | 44.10 | O |
| ATOM | 5704 | CG2 | THR | C | 193 | 47.842 | 17.179 | −8.911 | 1.00 | 44.42 | C |
| ATOM | 5708 | C | THR | C | 193 | 48.996 | 14.355 | −8.092 | 1.00 | 44.79 | C |
| ATOM | 5709 | O | THR | C | 193 | 48.781 | 13.472 | −8.910 | 1.00 | 44.93 | O |
| ATOM | 5710 | N | CME | C | 194 | 50.229 | 14.786 | −7.838 | 1.00 | 45.18 | N |
| ATOM | 5713 | CA | CME | C | 194 | 51.528 | 14.157 | −8.006 | 1.00 | 45.40 | C |
| ATOM | 5715 | CB | CME | C | 194 | 52.486 | 14.371 | −6.828 | 1.00 | 45.72 | C |
| ATOM | 5718 | SG | CME | C | 194 | 54.127 | 14.000 | −7.375 | 1.00 | 47.44 | S |
| ATOM | 5719 | S2 | CME | C | 194 | 54.622 | 15.014 | −9.041 | 1.00 | 51.92 | S |
| ATOM | 5720 | C2 | CME | C | 194 | 54.183 | 14.145 | −10.514 | 1.00 | 53.16 | C |
| ATOM | 5723 | C1 | CME | C | 194 | 55.315 | 14.191 | −11.515 | 1.00 | 54.09 | C |
| ATOM | 5725 | O1 | CME | C | 194 | 55.154 | 13.690 | −12.617 | 1.00 | 55.63 | O |
| ATOM | 5726 | C | CME | C | 194 | 51.499 | 12.710 | −8.452 | 1.00 | 45.12 | C |
| ATOM | 5727 | O | CME | C | 194 | 51.398 | 12.444 | −9.625 | 1.00 | 45.36 | O |
| ATOM | 5729 | N | ILE | C | 195 | 51.283 | 11.818 | −7.473 | 1.00 | 44.67 | N |
| ATOM | 5731 | CA | ILE | C | 195 | 51.234 | 10.356 | −7.677 | 1.00 | 44.38 | C |
| ATOM | 5733 | CB | ILE | C | 195 | 51.054 | 9.613 | −6.315 | 1.00 | 44.11 | C |
| ATOM | 5735 | CG1 | ILE | C | 195 | 51.752 | 8.253 | −6.361 | 1.00 | 43.74 | C |
| ATOM | 5738 | CD1 | ILE | C | 195 | 53.262 | 8.343 | −6.223 | 1.00 | 43.79 | C |
| ATOM | 5742 | CG2 | ILE | C | 195 | 49.575 | 9.426 | −5.951 | 1.00 | 43.86 | C |
| ATOM | 5746 | C | ILE | C | 195 | 50.189 | 9.861 | −8.678 | 1.00 | 44.34 | C |
| ATOM | 5747 | O | ILE | C | 195 | 50.434 | 8.880 | −9.365 | 1.00 | 43.88 | O |
| ATOM | 5748 | N | MET | C | 196 | 49.024 | 10.502 | −8.728 | 1.00 | 44.56 | N |
| ATOM | 5750 | CA | MET | C | 196 | 47.985 | 10.114 | −9.687 | 1.00 | 44.95 | C |
| ATOM | 5752 | CB | MET | C | 196 | 46.639 | 10.764 | −9.352 | 1.00 | 44.93 | C |
| ATOM | 5755 | CG | MET | C | 196 | 45.877 | 10.048 | −8.250 | 1.00 | 44.85 | C |
| ATOM | 5758 | SD | MET | C | 196 | 45.247 | 8.458 | −8.792 | 1.00 | 44.47 | S |
| ATOM | 5759 | CE | MET | C | 196 | 43.795 | 8.956 | −9.677 | 1.00 | 44.67 | C |
| ATOM | 5763 | C | MET | C | 196 | 48.401 | 10.484 | −11.110 | 1.00 | 45.29 | C |
| ATOM | 5764 | O | MET | C | 196 | 48.032 | 9.806 | −12.065 | 1.00 | 45.29 | O |
| ATOM | 5765 | N | TYR | C | 197 | 49.152 | 11.573 | −11.239 | 1.00 | 45.77 | N |
| ATOM | 5767 | CA | TYR | C | 197 | 49.669 | 12.020 | −12.530 | 1.00 | 46.27 | C |
| ATOM | 5769 | CB | TYR | C | 197 | 50.157 | 13.474 | −12.439 | 1.00 | 46.48 | C |
| ATOM | 5772 | CG | TYR | C | 197 | 50.513 | 14.106 | −13.768 | 1.00 | 47.90 | C |
| ATOM | 5773 | CD1 | TYR | C | 197 | 49.616 | 14.090 | −14.835 | 1.00 | 49.24 | C |
| ATOM | 5775 | CE1 | TYR | C | 197 | 49.938 | 14.666 | −16.052 | 1.00 | 49.99 | C |
| ATOM | 5777 | CZ | TYR | C | 197 | 51.166 | 15.275 | −16.215 | 1.00 | 50.61 | C |
| ATOM | 5778 | OH | TYR | C | 197 | 51.486 | 15.841 | −17.424 | 1.00 | 51.70 | O |
| ATOM | 5780 | CE2 | TYR | C | 197 | 52.077 | 15.311 | −15.170 | 1.00 | 50.40 | C |
| ATOM | 5782 | CD2 | TYR | C | 197 | 51.747 | 14.728 | −13.957 | 1.00 | 49.35 | C |
| ATOM | 5784 | C | TYR | C | 197 | 50.796 | 11.090 | −12.974 | 1.00 | 46.08 | C |
| ATOM | 5785 | O | TYR | C | 197 | 50.895 | 10.754 | −14.148 | 1.00 | 45.91 | O |
| ATOM | 5786 | N | ALA | C | 198 | 51.623 | 10.658 | −12.025 | 1.00 | 46.07 | N |
| ATOM | 5788 | CA | ALA | C | 198 | 52.729 | 9.750 | −12.315 | 1.00 | 46.08 | C |
| ATOM | 5790 | CB | ALA | C | 198 | 53.699 | 9.707 | −11.149 | 1.00 | 45.96 | C |
| ATOM | 5794 | C | ALA | C | 198 | 52.222 | 8.348 | −12.638 | 1.00 | 46.26 | C |
| ATOM | 5795 | O | ALA | C | 198 | 52.827 | 7.644 | −13.440 | 1.00 | 46.70 | O |
| ATOM | 5796 | N | ILE | C | 199 | 51.103 | 7.957 | −12.030 | 1.00 | 46.36 | N |
| ATOM | 5798 | CA | ILE | C | 199 | 50.512 | 6.636 | −12.249 | 1.00 | 46.49 | C |
| ATOM | 5800 | CB | ILE | C | 199 | 49.489 | 6.291 | −11.119 | 1.00 | 46.22 | C |
| ATOM | 5802 | CG1 | ILE | C | 199 | 50.218 | 5.918 | −9.825 | 1.00 | 46.02 | C |
| ATOM | 5805 | CD1 | ILE | C | 199 | 49.363 | 6.073 | −8.560 | 1.00 | 45.16 | C |
| ATOM | 5809 | CG2 | ILE | C | 199 | 48.575 | 5.133 | −11.515 | 1.00 | 45.98 | C |
| ATOM | 5813 | C | ILE | C | 199 | 49.847 | 6.577 | −13.625 | 1.00 | 47.00 | C |
| ATOM | 5814 | O | ILE | C | 199 | 49.909 | 5.551 | −14.300 | 1.00 | 47.05 | O |
| ATOM | 5815 | N | PHE | C | 200 | 49.224 | 7.680 | −14.034 | 1.00 | 47.66 | N |
| ATOM | 5817 | CA | PHE | C | 200 | 48.523 | 7.752 | −15.318 | 1.00 | 48.29 | C |
| ATOM | 5819 | CB | PHE | C | 200 | 47.544 | 8.936 | −15.343 | 1.00 | 48.28 | C |
| ATOM | 5822 | CG | PHE | C | 200 | 46.139 | 8.576 | −14.926 | 1.00 | 48.52 | C |
| ATOM | 5823 | CD1 | PHE | C | 200 | 45.907 | 7.699 | −13.869 | 1.00 | 49.25 | C |
| ATOM | 5825 | CE1 | PHE | C | 200 | 44.611 | 7.370 | −13.489 | 1.00 | 49.29 | C |
| ATOM | 5827 | CZ | PHE | C | 200 | 43.535 | 7.919 | −14.159 | 1.00 | 49.18 | C |

TABLE 2-continued

| ATOM | 5829 | CE2 | PHE | C | 200 | 43.753 | 8.795 | −15.207 | 1.00 | 49.06 | C |
| --- | --- | --- | --- | --- | --- | --- | --- | --- | --- | --- | --- |
| ATOM | 5831 | CD2 | PHE | C | 200 | 45.049 | 9.121 | −15.584 | 1.00 | 48.87 | C |
| ATOM | 5833 | C | PHE | C | 200 | 49.487 | 7.814 | −16.507 | 1.00 | 48.79 | C |
| ATOM | 5834 | O | PHE | C | 200 | 49.206 | 7.240 | −17.553 | 1.00 | 48.96 | O |
| ATOM | 5835 | N | GLN | C | 201 | 50.616 | 8.502 | −16.342 | 1.00 | 49.40 | N |
| ATOM | 5837 | CA | GLN | C | 201 | 51.638 | 8.595 | −17.389 | 1.00 | 49.85 | C |
| ATOM | 5839 | CB | GLN | C | 201 | 52.680 | 9.661 | −17.044 | 1.00 | 49.99 | C |
| ATOM | 5842 | CG | GLN | C | 201 | 52.220 | 11.087 | −17.270 | 1.00 | 50.68 | C |
| ATOM | 5845 | CD | GLN | C | 201 | 53.304 | 12.116 | −16.973 | 1.00 | 51.96 | C |
| ATOM | 5846 | OE1 | GLN | C | 201 | 53.067 | 13.317 | −17.100 | 1.00 | 53.03 | O |
| ATOM | 5847 | NE2 | GLN | C | 201 | 54.491 | 11.652 | −16.583 | 1.00 | 52.58 | N |
| ATOM | 5850 | C | GLN | C | 201 | 52.347 | 7.253 | −17.574 | 1.00 | 50.00 | C |
| ATOM | 5851 | O | GLN | C | 201 | 52.661 | 6.858 | −18.696 | 1.00 | 50.17 | O |
| ATOM | 5852 | N | GLU | C | 202 | 52.605 | 6.571 | −16.460 | 1.00 | 50.20 | N |
| ATOM | 5854 | CA | GLU | C | 202 | 53.255 | 5.258 | −16.459 | 1.00 | 50.33 | C |
| ATOM | 5856 | CB | GLU | C | 202 | 53.504 | 4.804 | −15.008 | 1.00 | 50.41 | C |
| ATOM | 5859 | CG | GLU | C | 202 | 53.830 | 3.324 | −14.799 | 1.00 | 50.80 | C |
| ATOM | 5862 | CD | GLU | C | 202 | 55.253 | 2.943 | −15.173 | 1.00 | 51.48 | C |
| ATOM | 5863 | OE1 | GLU | C | 202 | 56.076 | 3.843 | −15.450 | 1.00 | 52.39 | O |
| ATOM | 5864 | OE2 | GLU | C | 202 | 55.554 | 1.730 | −15.180 | 1.00 | 51.72 | O |
| ATOM | 5865 | C | GLU | C | 202 | 52.434 | 4.206 | −17.217 | 1.00 | 50.29 | C |
| ATOM | 5866 | O | GLU | C | 202 | 53.002 | 3.314 | −17.846 | 1.00 | 50.26 | O |
| ATOM | 5867 | N | ARG | C | 203 | 51.107 | 4.323 | −17.161 | 1.00 | 50.34 | N |
| ATOM | 5869 | CA | ARG | C | 203 | 50.198 | 3.366 | −17.801 | 1.00 | 50.39 | C |
| ATOM | 5871 | CB | ARG | C | 203 | 49.046 | 3.044 | −16.843 | 1.00 | 50.37 | C |
| ATOM | 5874 | CG | ARG | C | 203 | 49.427 | 2.162 | −15.679 | 1.00 | 49.80 | C |
| ATOM | 5877 | CD | ARG | C | 203 | 48.231 | 1.696 | −14.880 | 1.00 | 49.34 | C |
| ATOM | 5880 | NE | ARG | C | 203 | 48.610 | 0.768 | −13.822 | 1.00 | 48.56 | N |
| ATOM | 5882 | CZ | ARG | C | 203 | 48.915 | −0.516 | −14.008 | 1.00 | 47.83 | C |
| ATOM | 5883 | NH1 | ARG | C | 203 | 48.877 | −1.074 | −15.219 | 1.00 | 47.00 | N |
| ATOM | 5886 | NH2 | ARG | C | 203 | 49.258 | −1.253 | −12.960 | 1.00 | 47.00 | N |
| ATOM | 5889 | C | ARG | C | 203 | 49.605 | 3.825 | −19.144 | 1.00 | 50.59 | C |
| ATOM | 5890 | O | ARG | C | 203 | 48.826 | 3.089 | −19.752 | 1.00 | 50.54 | O |
| ATOM | 5891 | N | ASP | C | 204 | 49.968 | 5.024 | −19.599 | 1.00 | 50.82 | N |
| ATOM | 5893 | CA | ASP | C | 204 | 49.446 | 5.596 | −20.846 | 1.00 | 51.00 | C |
| ATOM | 5895 | CB | ASP | C | 204 | 49.857 | 4.758 | −22.071 | 1.00 | 51.15 | C |
| ATOM | 5898 | CG | ASP | C | 204 | 51.353 | 4.609 | −22.203 | 1.00 | 51.51 | C |
| ATOM | 5899 | OD1 | ASP | C | 204 | 51.819 | 3.473 | −22.441 | 1.00 | 52.26 | O |
| ATOM | 5900 | OD2 | ASP | C | 204 | 52.140 | 5.571 | −22.089 | 1.00 | 52.32 | O |
| ATOM | 5901 | C | ASP | C | 204 | 47.924 | 5.734 | −20.815 | 1.00 | 50.93 | C |
| ATOM | 5902 | O | ASP | C | 204 | 47.262 | 5.526 | −21.832 | 1.00 | 51.03 | O |
| ATOM | 5903 | N | LEU | C | 205 | 47.376 | 6.074 | −19.650 | 1.00 | 50.69 | N |
| ATOM | 5905 | CA | LEU | C | 205 | 45.932 | 6.230 | −19.491 | 1.00 | 50.57 | C |
| ATOM | 5907 | CB | LEU | C | 205 | 45.529 | 6.088 | −18.019 | 1.00 | 50.52 | C |
| ATOM | 5910 | CG | LEU | C | 205 | 45.635 | 4.673 | −17.449 | 1.00 | 50.07 | C |
| ATOM | 5912 | CD1 | LEU | C | 205 | 45.531 | 4.711 | −15.933 | 1.00 | 49.96 | C |
| ATOM | 5916 | CD2 | LEU | C | 205 | 44.572 | 3.758 | −18.041 | 1.00 | 49.59 | C |
| ATOM | 5920 | C | LEU | C | 205 | 45.428 | 7.560 | −20.038 | 1.00 | 50.61 | C |
| ATOM | 5921 | O | LEU | C | 205 | 44.264 | 7.662 | −20.424 | 1.00 | 50.45 | O |
| ATOM | 5922 | N | LEU | C | 206 | 46.289 | 8.576 | −20.051 | 1.00 | 50.85 | N |
| ATOM | 5924 | CA | LEU | C | 206 | 45.922 | 9.885 | −20.594 | 1.00 | 51.16 | C |
| ATOM | 5926 | CB | LEU | C | 206 | 46.972 | 10.944 | −20.237 | 1.00 | 51.15 | C |
| ATOM | 5929 | CG | LEU | C | 206 | 47.101 | 11.331 | −18.757 | 1.00 | 51.17 | C |
| ATOM | 5931 | CD1 | LEU | C | 206 | 48.286 | 12.264 | −18.546 | 1.00 | 50.85 | C |
| ATOM | 5935 | CD2 | LEU | C | 206 | 45.825 | 11.975 | −18.238 | 1.00 | 51.27 | C |
| ATOM | 5939 | C | LEU | C | 206 | 45.749 | 9.810 | −22.119 | 1.00 | 51.55 | C |
| ATOM | 5940 | O | LEU | C | 206 | 44.866 | 10.454 | −22.682 | 1.00 | 51.42 | O |
| ATOM | 5941 | N | LYS | C | 207 | 46.598 | 9.021 | −22.775 | 1.00 | 51.99 | N |
| ATOM | 5943 | CA | LYS | C | 207 | 46.535 | 8.842 | −24.223 | 1.00 | 52.40 | C |
| ATOM | 5945 | CB | LYS | C | 207 | 47.833 | 8.211 | −24.741 | 1.00 | 52.54 | C |
| ATOM | 5948 | CG | LYS | C | 207 | 49.088 | 9.055 | −24.555 | 1.00 | 53.19 | C |
| ATOM | 5951 | CD | LYS | C | 207 | 50.290 | 8.376 | −25.210 | 1.00 | 53.91 | C |
| ATOM | 5954 | CE | LYS | C | 207 | 51.537 | 9.245 | −25.163 | 1.00 | 54.55 | C |
| ATOM | 5957 | NZ | LYS | C | 207 | 52.789 | 8.430 | −25.163 | 1.00 | 54.93 | N |
| ATOM | 5961 | C | LYS | C | 207 | 45.370 | 7.934 | −24.611 | 1.00 | 52.50 | C |
| ATOM | 5962 | O | LYS | C | 207 | 44.579 | 8.262 | −25.498 | 1.00 | 52.58 | O |
| ATOM | 5963 | N | THR | C | 208 | 45.279 | 6.797 | −23.924 | 1.00 | 52.57 | N |
| ATOM | 5965 | CA | THR | C | 208 | 44.272 | 5.768 | −24.193 | 1.00 | 52.57 | C |
| ATOM | 5967 | CB | THR | C | 208 | 44.516 | 4.542 | −23.275 | 1.00 | 52.56 | C |
| ATOM | 5969 | OG1 | THR | C | 208 | 45.868 | 4.089 | −23.408 | 1.00 | 52.55 | O |
| ATOM | 5971 | CG2 | THR | C | 208 | 43.697 | 3.339 | −23.717 | 1.00 | 52.79 | C |
| ATOM | 5975 | C | THR | C | 208 | 42.830 | 6.246 | −24.036 | 1.00 | 52.62 | C |
| ATOM | 5976 | O | THR | C | 208 | 41.927 | 5.711 | −24.681 | 1.00 | 52.63 | O |
| ATOM | 5977 | N | PHE | C | 209 | 42.618 | 7.249 | −23.186 | 1.00 | 52.68 | N |
| ATOM | 5979 | CA | PHE | C | 209 | 41.280 | 7.782 | −22.928 | 1.00 | 52.68 | C |
| ATOM | 5981 | CB | PHE | C | 209 | 40.894 | 7.497 | −21.473 | 1.00 | 52.54 | C |
| ATOM | 5984 | CG | PHE | C | 209 | 40.733 | 6.031 | −21.171 | 1.00 | 51.75 | C |
| ATOM | 5985 | CD1 | PHE | C | 209 | 39.734 | 5.290 | −21.794 | 1.00 | 50.85 | C |
| ATOM | 5987 | CE1 | PHE | C | 209 | 39.577 | 3.941 | −21.525 | 1.00 | 50.49 | C |

TABLE 2-continued

| | | | | | | | | | | |
|---|---|---|---|---|---|---|---|---|---|---|
| ATOM | 5989 | CZ | PHE | C | 209 | 40.424 | 3.312 | −20.630 | 1.00 | 50.27 C |
| ATOM | 5991 | CE2 | PHE | C | 209 | 41.430 | 4.035 | −20.003 | 1.00 | 50.21 C |
| ATOM | 5993 | CD2 | PHE | C | 209 | 41.581 | 5.387 | −20.273 | 1.00 | 50.93 C |
| ATOM | 5995 | C | PHE | C | 209 | 41.139 | 9.275 | −23.252 | 1.00 | 53.01 C |
| ATOM | 5996 | O | PHE | C | 209 | 40.145 | 9.900 | −22.885 | 1.00 | 53.04 O |
| ATOM | 5997 | N | ARG | C | 210 | 42.131 | 9.830 | −23.947 | 1.00 | 53.46 N |
| ATOM | 5999 | CA | ARG | C | 210 | 42.122 | 11.224 | −24.393 | 1.00 | 53.87 C |
| ATOM | 6001 | CB | ARG | C | 210 | 41.114 | 11.414 | −25.534 | 1.00 | 54.21 C |
| ATOM | 6004 | CG | ARG | C | 210 | 41.236 | 10.431 | −26.691 | 1.00 | 55.90 C |
| ATOM | 6007 | CD | ARG | C | 210 | 39.937 | 10.269 | −27.477 | 1.00 | 58.26 C |
| ATOM | 6010 | NE | ARG | C | 210 | 40.156 | 10.181 | −28.919 | 1.00 | 60.17 N |
| ATOM | 6012 | CZ | ARG | C | 210 | 39.203 | 10.313 | −29.842 | 1.00 | 61.94 C |
| ATOM | 6013 | NH1 | ARG | C | 210 | 37.939 | 10.544 | −29.494 | 1.00 | 62.54 N |
| ATOM | 6016 | NH2 | ARG | C | 210 | 39.517 | 10.212 | −31.129 | 1.00 | 62.43 N |
| ATOM | 6019 | C | ARG | C | 210 | 41.813 | 12.213 | −23.277 | 1.00 | 53.64 C |
| ATOM | 6020 | O | ARG | C | 210 | 41.002 | 13.124 | −23.445 | 1.00 | 53.55 O |
| ATOM | 6021 | N | ILE | C | 211 | 42.455 | 12.026 | −22.132 | 1.00 | 53.59 N |
| ATOM | 6023 | CA | ILE | C | 211 | 42.267 | 12.922 | −21.004 | 1.00 | 53.50 C |
| ATOM | 6025 | CB | ILE | C | 211 | 42.413 | 12.168 | −19.663 | 1.00 | 53.44 C |
| ATOM | 6027 | CG1 | ILE | C | 211 | 41.492 | 10.944 | −19.637 | 1.00 | 53.48 C |
| ATOM | 6030 | CD1 | ILE | C | 211 | 41.709 | 10.023 | −18.454 | 1.00 | 53.48 C |
| ATOM | 6034 | CG2 | ILE | C | 211 | 42.097 | 13.096 | −18.491 | 1.00 | 53.45 C |
| ATOM | 6038 | C | ILE | C | 211 | 43.308 | 14.026 | −21.123 | 1.00 | 53.50 C |
| ATOM | 6039 | O | ILE | C | 211 | 44.508 | 13.755 | −21.120 | 1.00 | 53.48 O |
| ATOM | 6040 | N | SER | C | 212 | 42.844 | 15.264 | −21.258 | 1.00 | 53.54 N |
| ATOM | 6042 | CA | SER | C | 212 | 43.740 | 16.415 | −21.338 | 1.00 | 53.63 C |
| ATOM | 6044 | CB | SER | C | 212 | 42.942 | 17.699 | −21.599 | 1.00 | 53.62 C |
| ATOM | 6047 | OG | SER | C | 212 | 43.642 | 18.849 | −21.151 | 1.00 | 53.78 O |
| ATOM | 6049 | C | SER | C | 212 | 44.515 | 16.531 | −20.025 | 1.00 | 53.66 C |
| ATOM | 6050 | O | SER | C | 212 | 43.955 | 16.290 | −18.954 | 1.00 | 53.76 O |
| ATOM | 6051 | N | SER | C | 213 | 45.794 | 16.888 | −20.108 | 1.00 | 53.66 N |
| ATOM | 6053 | CA | SER | C | 213 | 46.636 | 17.025 | −18.916 | 1.00 | 53.65 C |
| ATOM | 6055 | CB | SER | C | 213 | 48.095 | 17.308 | −19.292 | 1.00 | 53.67 C |
| ATOM | 6058 | OG | SER | C | 213 | 48.832 | 16.102 | −19.394 | 1.00 | 53.99 O |
| ATOM | 6060 | C | SER | C | 213 | 46.119 | 18.128 | −17.996 | 1.00 | 53.60 C |
| ATOM | 6061 | O | SER | C | 213 | 46.173 | 17.995 | −16.773 | 1.00 | 53.52 O |
| ATOM | 6062 | N | ASP | C | 214 | 45.622 | 19.209 | −18.592 | 1.00 | 53.45 N |
| ATOM | 6064 | CA | ASP | C | 214 | 45.080 | 20.334 | −17.836 | 1.00 | 53.37 C |
| ATOM | 6066 | CB | ASP | C | 214 | 44.760 | 21.511 | −18.765 | 1.00 | 53.56 C |
| ATOM | 6069 | CG | ASP | C | 214 | 45.995 | 22.096 | −19.422 | 1.00 | 53.90 C |
| ATOM | 6070 | OD1 | ASP | C | 214 | 45.854 | 22.684 | −20.514 | 1.00 | 54.90 O |
| ATOM | 6071 | OD2 | ASP | C | 214 | 47.141 | 22.019 | −18.930 | 1.00 | 54.45 O |
| ATOM | 6072 | C | ASP | C | 214 | 43.817 | 19.938 | −17.077 | 1.00 | 53.01 C |
| ATOM | 6073 | O | ASP | C | 214 | 43.659 | 20.287 | −15.908 | 1.00 | 53.08 O |
| ATOM | 6074 | N | THR | C | 215 | 42.918 | 19.222 | −17.751 | 1.00 | 52.41 N |
| ATOM | 6076 | CA | THR | C | 215 | 41.669 | 18.777 | −17.135 | 1.00 | 51.94 C |
| ATOM | 6078 | CB | THR | C | 215 | 40.781 | 18.028 | −18.168 | 1.00 | 51.98 C |
| ATOM | 6080 | OG1 | THR | C | 215 | 40.535 | 18.856 | −19.316 | 1.00 | 52.00 O |
| ATOM | 6082 | CG2 | THR | C | 215 | 39.388 | 17.769 | −17.608 | 1.00 | 52.02 C |
| ATOM | 6086 | C | THR | C | 215 | 41.960 | 17.867 | −15.941 | 1.00 | 51.48 C |
| ATOM | 6087 | O | THR | C | 215 | 41.379 | 18.026 | −14.868 | 1.00 | 51.25 O |
| ATOM | 6088 | N | PHE | C | 216 | 42.884 | 16.932 | −16.143 | 1.00 | 50.88 N |
| ATOM | 6090 | CA | PHE | C | 216 | 43.265 | 15.960 | −15.131 | 1.00 | 50.35 C |
| ATOM | 6092 | CB | PHE | C | 216 | 44.269 | 14.969 | −15.715 | 1.00 | 50.31 C |
| ATOM | 6095 | CG | PHE | C | 216 | 44.603 | 13.839 | −14.793 | 1.00 | 49.88 C |
| ATOM | 6096 | CD1 | PHE | C | 216 | 43.694 | 12.813 | −14.582 | 1.00 | 49.76 C |
| ATOM | 6098 | CE1 | PHE | C | 216 | 43.994 | 11.763 | −13.728 | 1.00 | 49.70 C |
| ATOM | 6100 | CZ | PHE | C | 216 | 45.212 | 11.735 | −13.072 | 1.00 | 49.71 C |
| ATOM | 6102 | CE2 | PHE | C | 216 | 46.125 | 12.755 | −13.272 | 1.00 | 49.76 C |
| ATOM | 6104 | CD2 | PHE | C | 216 | 45.819 | 13.802 | −14.129 | 1.00 | 49.74 C |
| ATOM | 6106 | C | PHE | C | 216 | 43.860 | 16.609 | −13.891 | 1.00 | 50.14 C |
| ATOM | 6107 | O | PHE | C | 216 | 43.480 | 16.270 | −12.773 | 1.00 | 50.03 O |
| ATOM | 6108 | N | ILE | C | 217 | 44.788 | 17.540 | −14.097 | 1.00 | 49.66 N |
| ATOM | 6110 | CA | ILE | C | 217 | 45.452 | 18.229 | −12.995 | 1.00 | 49.29 C |
| ATOM | 6112 | CB | ILE | C | 217 | 46.633 | 19.101 | −13.516 | 1.00 | 49.29 C |
| ATOM | 6114 | CG1 | ILE | C | 217 | 47.746 | 18.222 | −14.106 | 1.00 | 49.34 C |
| ATOM | 6117 | CD1 | ILE | C | 217 | 48.641 | 17.541 | −13.080 | 1.00 | 49.64 C |
| ATOM | 6121 | CG2 | ILE | C | 217 | 47.193 | 19.998 | −12.399 | 1.00 | 49.50 C |
| ATOM | 6125 | C | ILE | C | 217 | 44.451 | 19.086 | −12.223 | 1.00 | 48.91 C |
| ATOM | 6126 | O | ILE | C | 217 | 44.489 | 19.138 | −10.996 | 1.00 | 48.95 O |
| ATOM | 6127 | N | THR | C | 218 | 43.552 | 19.745 | −12.945 | 1.00 | 48.35 N |
| ATOM | 6129 | CA | THR | C | 218 | 42.553 | 20.614 | −12.328 | 1.00 | 47.98 C |
| ATOM | 6131 | CB | THR | C | 218 | 41.791 | 21.415 | −13.409 | 1.00 | 48.02 C |
| ATOM | 6133 | OG1 | THR | C | 218 | 42.722 | 22.139 | −14.223 | 1.00 | 48.25 O |
| ATOM | 6135 | CG2 | THR | C | 218 | 40.934 | 22.512 | −12.788 | 1.00 | 48.21 C |
| ATOM | 6139 | C | THR | C | 218 | 41.578 | 19.815 | −11.467 | 1.00 | 47.51 C |
| ATOM | 6140 | O | THR | C | 218 | 41.156 | 20.285 | −10.405 | 1.00 | 47.70 O |
| ATOM | 6141 | N | TYR | C | 219 | 41.244 | 18.605 | −11.914 | 1.00 | 46.79 N |
| ATOM | 6143 | CA | TYR | C | 219 | 40.321 | 17.739 | −11.188 | 1.00 | 46.22 C |

TABLE 2-continued

| | | | | | | | | | | |
|---|---|---|---|---|---|---|---|---|---|---|
| ATOM | 6145 | CB | TYR | C | 219 | 39.793 | 16.613 | −12.084 | 1.00 | 46.13 C |
| ATOM | 6148 | CG | TYR | C | 219 | 38.949 | 15.611 | −11.324 | 1.00 | 45.60 C |
| ATOM | 6149 | CD1 | TYR | C | 219 | 37.596 | 15.842 | −11.102 | 1.00 | 44.98 C |
| ATOM | 6151 | CE1 | TYR | C | 219 | 36.822 | 14.941 | −10.390 | 1.00 | 44.74 C |
| ATOM | 6153 | CZ | TYR | C | 219 | 37.398 | 13.793 | −9.880 | 1.00 | 44.75 C |
| ATOM | 6154 | OH | TYR | C | 219 | 36.621 | 12.902 | −9.177 | 1.00 | 43.63 O |
| ATOM | 6156 | CE2 | TYR | C | 219 | 38.744 | 13.541 | −10.079 | 1.00 | 44.97 C |
| ATOM | 6158 | CD2 | TYR | C | 219 | 39.512 | 14.451 | −10.797 | 1.00 | 45.10 C |
| ATOM | 6160 | C | TYR | C | 219 | 40.968 | 17.117 | −9.953 | 1.00 | 45.95 C |
| ATOM | 6161 | O | TYR | C | 219 | 40.353 | 17.070 | −8.888 | 1.00 | 45.67 O |
| ATOM | 6162 | N | MET | C | 220 | 42.196 | 16.626 | −10.116 | 1.00 | 45.61 N |
| ATOM | 6164 | CA | MET | C | 220 | 42.919 | 15.958 | −9.041 | 1.00 | 45.49 C |
| ATOM | 6166 | CB | MET | C | 220 | 44.193 | 15.281 | −9.564 | 1.00 | 45.39 C |
| ATOM | 6169 | CG | MET | C | 220 | 43.969 | 13.998 | −10.378 | 1.00 | 45.51 C |
| ATOM | 6172 | SD | MET | C | 220 | 42.898 | 12.741 | −9.627 | 1.00 | 45.03 S |
| ATOM | 6173 | CE | MET | C | 220 | 43.466 | 12.757 | −7.923 | 1.00 | 45.63 C |
| ATOM | 6177 | C | MET | C | 220 | 43.265 | 16.936 | −7.930 | 1.00 | 45.53 C |
| ATOM | 6178 | O | MET | C | 220 | 43.178 | 16.594 | −6.751 | 1.00 | 45.38 O |
| ATOM | 6179 | N | MET | C | 221 | 43.659 | 18.147 | −8.314 | 1.00 | 45.48 N |
| ATOM | 6181 | CA | MET | C | 221 | 43.980 | 19.193 | −7.357 | 1.00 | 45.47 C |
| ATOM | 6183 | CB | MET | C | 221 | 44.467 | 20.459 | −8.073 | 1.00 | 45.61 C |
| ATOM | 6186 | CG | MET | C | 221 | 45.942 | 20.433 | −8.436 | 1.00 | 46.23 C |
| ATOM | 6189 | SD | MET | C | 221 | 46.501 | 21.952 | −9.245 | 1.00 | 47.75 S |
| ATOM | 6190 | CE | MET | C | 221 | 47.178 | 22.843 | −7.879 | 1.00 | 47.61 C |
| ATOM | 6194 | C | MET | C | 221 | 42.741 | 19.504 | −6.522 | 1.00 | 45.33 C |
| ATOM | 6195 | O | MET | C | 221 | 42.828 | 19.627 | −5.297 | 1.00 | 45.36 O |
| ATOM | 6196 | N | THR | C | 222 | 41.592 | 19.612 | −7.193 | 1.00 | 44.98 N |
| ATOM | 6198 | CA | THR | C | 222 | 40.320 | 19.914 | −6.531 | 1.00 | 44.84 C |
| ATOM | 6200 | CB | THR | C | 222 | 39.249 | 20.285 | −7.580 | 1.00 | 44.86 C |
| ATOM | 6202 | OG1 | THR | C | 222 | 39.665 | 21.451 | −8.305 | 1.00 | 44.74 O |
| ATOM | 6204 | CG2 | THR | C | 222 | 37.940 | 20.709 | −6.913 | 1.00 | 44.93 C |
| ATOM | 6208 | C | THR | C | 222 | 39.827 | 18.760 | −5.652 | 1.00 | 44.56 C |
| ATOM | 6209 | O | THR | C | 222 | 39.216 | 18.986 | −4.605 | 1.00 | 44.60 O |
| ATOM | 6210 | N | LEU | C | 223 | 40.095 | 17.532 | −6.082 | 1.00 | 44.14 N |
| ATOM | 6212 | CA | LEU | C | 223 | 39.714 | 16.345 | −5.329 | 1.00 | 43.85 C |
| ATOM | 6214 | CB | LEU | C | 223 | 39.988 | 15.092 | −6.155 | 1.00 | 43.76 C |
| ATOM | 6217 | CG | LEU | C | 223 | 39.594 | 13.752 | −5.537 | 1.00 | 43.05 C |
| ATOM | 6219 | CD1 | LEU | C | 223 | 38.087 | 13.556 | −5.590 | 1.00 | 42.82 C |
| ATOM | 6223 | CD2 | LEU | C | 223 | 40.322 | 12.624 | −6.245 | 1.00 | 42.79 C |
| ATOM | 6227 | C | LEU | C | 223 | 40.517 | 16.310 | −4.032 | 1.00 | 43.98 C |
| ATOM | 6228 | O | LEU | C | 223 | 39.992 | 15.976 | −2.969 | 1.00 | 43.83 O |
| ATOM | 6229 | N | GLU | C | 224 | 41.791 | 16.677 | −4.146 | 1.00 | 44.06 N |
| ATOM | 6231 | CA | GLU | C | 224 | 42.721 | 16.735 | −3.028 | 1.00 | 44.22 C |
| ATOM | 6233 | CB | GLU | C | 224 | 44.140 | 16.923 | −3.564 | 1.00 | 44.26 C |
| ATOM | 6236 | CG | GLU | C | 224 | 45.211 | 17.028 | −2.496 | 1.00 | 43.93 C |
| ATOM | 6239 | CD | GLU | C | 224 | 46.561 | 16.553 | −2.985 | 1.00 | 43.68 C |
| ATOM | 6240 | OE1 | GLU | C | 224 | 46.882 | 16.766 | −4.173 | 1.00 | 43.06 O |
| ATOM | 6241 | OE2 | GLU | C | 224 | 47.297 | 15.963 | −2.179 | 1.00 | 43.49 O |
| ATOM | 6242 | C | GLU | C | 224 | 42.362 | 17.862 | −2.053 | 1.00 | 44.40 C |
| ATOM | 6243 | O | GLU | C | 224 | 42.620 | 17.753 | −0.852 | 1.00 | 44.51 O |
| ATOM | 6244 | N | ASP | C | 225 | 41.772 | 18.936 | −2.579 | 1.00 | 44.53 N |
| ATOM | 6246 | CA | ASP | C | 225 | 41.309 | 20.059 | −1.764 | 1.00 | 44.57 C |
| ATOM | 6248 | CB | ASP | C | 225 | 40.810 | 21.209 | −2.643 | 1.00 | 44.53 C |
| ATOM | 6251 | CG | ASP | C | 225 | 41.928 | 21.980 | −3.298 | 1.00 | 44.63 C |
| ATOM | 6252 | OD1 | ASP | C | 225 | 41.607 | 22.879 | −4.105 | 1.00 | 45.04 O |
| ATOM | 6253 | OD2 | ASP | C | 225 | 43.141 | 21.775 | −3.072 | 1.00 | 44.20 O |
| ATOM | 6254 | C | ASP | C | 225 | 40.147 | 19.617 | −0.888 | 1.00 | 44.65 C |
| ATOM | 6255 | O | ASP | C | 225 | 39.939 | 20.157 | 0.201 | 1.00 | 44.65 O |
| ATOM | 6256 | N | HIS | C | 226 | 39.376 | 18.654 | −1.388 | 1.00 | 44.59 N |
| ATOM | 6258 | CA | HIS | C | 226 | 38.216 | 18.145 | −0.667 | 1.00 | 44.53 C |
| ATOM | 6260 | CB | HIS | C | 226 | 37.178 | 17.591 | −1.646 | 1.00 | 44.60 C |
| ATOM | 6263 | CG | HIS | C | 226 | 36.337 | 18.661 | −2.265 | 1.00 | 44.99 C |
| ATOM | 6264 | ND1 | HIS | C | 226 | 36.881 | 19.714 | −2.968 | 1.00 | 46.04 N |
| ATOM | 6266 | CE1 | HIS | C | 226 | 35.914 | 20.517 | −3.374 | 1.00 | 46.24 C |
| ATOM | 6268 | NE2 | HIS | C | 226 | 34.763 | 20.028 | −2.950 | 1.00 | 46.14 N |
| ATOM | 6270 | CD2 | HIS | C | 226 | 35.001 | 18.872 | −2.247 | 1.00 | 45.76 C |
| ATOM | 6272 | C | HIS | C | 226 | 38.570 | 17.151 | 0.439 | 1.00 | 44.27 C |
| ATOM | 6273 | O | HIS | C | 226 | 37.703 | 16.791 | 1.233 | 1.00 | 44.32 O |
| ATOM | 6274 | N | TYR | C | 227 | 39.825 | 16.706 | 0.487 | 1.00 | 43.96 N |
| ATOM | 6276 | CA | TYR | C | 227 | 40.295 | 15.872 | 1.590 | 1.00 | 43.82 C |
| ATOM | 6278 | CB | TYR | C | 227 | 41.498 | 15.012 | 1.200 | 1.00 | 43.41 C |
| ATOM | 6281 | CG | TYR | C | 227 | 41.154 | 13.724 | 0.475 | 1.00 | 42.01 C |
| ATOM | 6282 | CD1 | TYR | C | 227 | 41.058 | 13.689 | −0.914 | 1.00 | 40.02 C |
| ATOM | 6284 | CE1 | TYR | C | 227 | 40.759 | 12.515 | −1.588 | 1.00 | 39.24 C |
| ATOM | 6286 | CZ | TYR | C | 227 | 40.546 | 11.352 | −0.879 | 1.00 | 38.80 C |
| ATOM | 6287 | OH | TYR | C | 227 | 40.254 | 10.184 | −1.552 | 1.00 | 36.24 O |
| ATOM | 6289 | CE2 | TYR | C | 227 | 40.644 | 11.353 | 0.502 | 1.00 | 39.28 C |
| ATOM | 6291 | CD2 | TYR | C | 227 | 40.946 | 12.539 | 1.172 | 1.00 | 40.62 C |
| ATOM | 6293 | C | TYR | C | 227 | 40.673 | 16.849 | 2.713 | 1.00 | 44.34 C |

TABLE 2-continued

| | | | | | | | | | | | |
|---|---|---|---|---|---|---|---|---|---|---|---|
| ATOM | 6294 | O | TYR | C | 227 | 41.419 | 17.806 | 2.502 | 1.00 | 44.07 | O |
| ATOM | 6295 | N | HIS | C | 228 | 40.144 | 16.597 | 3.902 | 1.00 | 45.00 | N |
| ATOM | 6297 | CA | HIS | C | 228 | 40.368 | 17.464 | 5.051 | 1.00 | 45.52 | C |
| ATOM | 6299 | CB | HIS | C | 228 | 39.366 | 17.142 | 6.163 | 1.00 | 45.72 | C |
| ATOM | 6302 | CG | HIS | C | 228 | 37.932 | 17.270 | 5.743 | 1.00 | 46.71 | C |
| ATOM | 6303 | ND1 | HIS | C | 228 | 36.884 | 17.154 | 6.631 | 1.00 | 47.87 | N |
| ATOM | 6305 | CE1 | HIS | C | 228 | 35.742 | 17.306 | 5.984 | 1.00 | 48.40 | C |
| ATOM | 6307 | NE2 | HIS | C | 228 | 36.010 | 17.517 | 4.707 | 1.00 | 47.85 | N |
| ATOM | 6309 | CD2 | HIS | C | 228 | 37.372 | 17.500 | 4.530 | 1.00 | 47.37 | C |
| ATOM | 6311 | C | HIS | C | 228 | 41.790 | 17.323 | 5.569 | 1.00 | 45.59 | C |
| ATOM | 6312 | O | HIS | C | 228 | 42.174 | 16.270 | 6.073 | 1.00 | 45.64 | O |
| ATOM | 6313 | N | SER | C | 229 | 42.563 | 18.396 | 5.435 | 1.00 | 45.84 | N |
| ATOM | 6315 | CA | SER | C | 229 | 43.949 | 18.421 | 5.889 | 1.00 | 46.17 | C |
| ATOM | 6317 | CB | SER | C | 229 | 44.676 | 19.615 | 5.281 | 1.00 | 46.16 | C |
| ATOM | 6320 | OG | SER | C | 229 | 46.074 | 19.460 | 5.428 | 1.00 | 47.28 | O |
| ATOM | 6322 | C | SER | C | 229 | 44.060 | 18.466 | 7.420 | 1.00 | 46.12 | C |
| ATOM | 6323 | O | SER | C | 229 | 45.104 | 18.132 | 7.981 | 1.00 | 46.12 | O |
| ATOM | 6324 | N | ASP | C | 230 | 42.976 | 18.873 | 8.079 | 1.00 | 46.05 | N |
| ATOM | 6326 | CA | ASP | C | 230 | 42.908 | 18.933 | 9.545 | 1.00 | 46.02 | C |
| ATOM | 6328 | CB | ASP | C | 230 | 41.845 | 19.947 | 10.008 | 1.00 | 46.25 | C |
| ATOM | 6331 | CG | ASP | C | 230 | 40.685 | 20.075 | 9.031 | 1.00 | 47.43 | C |
| ATOM | 6332 | OD1 | ASP | C | 230 | 39.818 | 19.173 | 9.007 | 1.00 | 48.83 | O |
| ATOM | 6333 | OD2 | ASP | C | 230 | 40.567 | 21.038 | 8.239 | 1.00 | 48.99 | O |
| ATOM | 6334 | C | ASP | C | 230 | 42.621 | 17.553 | 10.150 | 1.00 | 45.35 | C |
| ATOM | 6335 | O | ASP | C | 230 | 42.593 | 17.401 | 11.373 | 1.00 | 45.51 | O |
| ATOM | 6336 | N | VAL | C | 231 | 42.393 | 16.561 | 9.289 | 1.00 | 44.48 | N |
| ATOM | 6338 | CA | VAL | C | 231 | 42.138 | 15.185 | 9.707 | 1.00 | 43.68 | C |
| ATOM | 6340 | CB | VAL | C | 231 | 41.009 | 14.560 | 8.873 | 1.00 | 43.70 | C |
| ATOM | 6342 | CG1 | VAL | C | 231 | 40.842 | 13.093 | 9.194 | 1.00 | 43.76 | C |
| ATOM | 6346 | CG2 | VAL | C | 231 | 39.700 | 15.308 | 9.127 | 1.00 | 43.71 | C |
| ATOM | 6350 | C | VAL | C | 231 | 43.449 | 14.402 | 9.586 | 1.00 | 43.04 | C |
| ATOM | 6351 | O | VAL | C | 231 | 44.041 | 14.317 | 8.505 | 1.00 | 43.03 | O |
| ATOM | 6352 | N | ALA | C | 232 | 43.881 | 13.827 | 10.707 | 1.00 | 42.15 | N |
| ATOM | 6354 | CA | ALA | C | 232 | 45.178 | 13.146 | 10.827 | 1.00 | 41.57 | C |
| ATOM | 6356 | CB | ALA | C | 232 | 45.358 | 12.648 | 12.271 | 1.00 | 41.65 | C |
| ATOM | 6360 | C | ALA | C | 232 | 45.499 | 12.001 | 9.854 | 1.00 | 40.79 | C |
| ATOM | 6361 | O | ALA | C | 232 | 46.596 | 11.952 | 9.297 | 1.00 | 40.53 | O |
| ATOM | 6362 | N | TYR | C | 233 | 44.565 | 11.072 | 9.684 | 1.00 | 39.95 | N |
| ATOM | 6364 | CA | TYR | C | 233 | 44.800 | 9.896 | 8.847 | 1.00 | 39.34 | C |
| ATOM | 6366 | CB | TYR | C | 233 | 44.392 | 8.632 | 9.601 | 1.00 | 39.13 | C |
| ATOM | 6369 | CG | TYR | C | 233 | 44.595 | 7.351 | 8.812 | 1.00 | 39.15 | C |
| ATOM | 6370 | CD1 | TYR | C | 233 | 45.775 | 6.621 | 8.925 | 1.00 | 38.64 | C |
| ATOM | 6372 | CE1 | TYR | C | 233 | 45.964 | 5.453 | 8.208 | 1.00 | 38.61 | C |
| ATOM | 6374 | CZ | TYR | C | 233 | 44.965 | 5.000 | 7.359 | 1.00 | 38.23 | C |
| ATOM | 6375 | OH | TYR | C | 233 | 45.146 | 3.837 | 6.659 | 1.00 | 36.96 | O |
| ATOM | 6377 | CE2 | TYR | C | 233 | 43.789 | 5.703 | 7.225 | 1.00 | 38.20 | C |
| ATOM | 6379 | CD2 | TYR | C | 233 | 43.605 | 6.869 | 7.952 | 1.00 | 38.73 | C |
| ATOM | 6381 | C | TYR | C | 233 | 44.068 | 9.901 | 7.519 | 1.00 | 38.76 | C |
| ATOM | 6382 | O | TYR | C | 233 | 44.649 | 9.573 | 6.489 | 1.00 | 38.59 | O |
| ATOM | 6383 | N | HIS | C | 234 | 42.789 | 10.256 | 7.559 | 1.00 | 38.20 | N |
| ATOM | 6385 | CA | HIS | C | 234 | 41.921 | 10.196 | 6.392 | 1.00 | 37.88 | C |
| ATOM | 6387 | CB | HIS | C | 234 | 40.486 | 9.886 | 6.861 | 1.00 | 37.63 | C |
| ATOM | 6390 | CG | HIS | C | 234 | 40.236 | 8.423 | 7.055 | 1.00 | 36.65 | C |
| ATOM | 6391 | ND1 | HIS | C | 234 | 40.214 | 7.816 | 8.293 | 1.00 | 35.05 | N |
| ATOM | 6393 | CE1 | HIS | C | 234 | 39.996 | 6.521 | 8.145 | 1.00 | 34.45 | C |
| ATOM | 6395 | NE2 | HIS | C | 234 | 39.879 | 6.266 | 6.853 | 1.00 | 35.90 | N |
| ATOM | 6397 | CD2 | HIS | C | 234 | 40.030 | 7.437 | 6.151 | 1.00 | 36.09 | C |
| ATOM | 6399 | C | HIS | C | 234 | 42.012 | 11.438 | 5.492 | 1.00 | 37.73 | C |
| ATOM | 6400 | O | HIS | C | 234 | 41.001 | 11.994 | 5.066 | 1.00 | 37.73 | O |
| ATOM | 6401 | N | ASN | C | 235 | 43.247 | 11.839 | 5.193 | 1.00 | 37.57 | N |
| ATOM | 6403 | CA | ASN | C | 235 | 43.537 | 13.004 | 4.361 | 1.00 | 37.65 | C |
| ATOM | 6405 | CB | ASN | C | 235 | 44.569 | 13.919 | 5.052 | 1.00 | 37.66 | C |
| ATOM | 6408 | CG | ASN | C | 235 | 45.793 | 13.162 | 5.564 | 1.00 | 38.46 | C |
| ATOM | 6409 | OD1 | ASN | C | 235 | 46.501 | 12.522 | 4.795 | 1.00 | 39.20 | O |
| ATOM | 6410 | ND2 | ASN | C | 235 | 46.037 | 13.230 | 6.874 | 1.00 | 38.51 | N |
| ATOM | 6413 | C | ASN | C | 235 | 44.002 | 12.534 | 2.970 | 1.00 | 37.41 | C |
| ATOM | 6414 | O | ASN | C | 235 | 43.931 | 11.344 | 2.670 | 1.00 | 37.43 | O |
| ATOM | 6415 | N | SER | C | 236 | 44.477 | 13.452 | 2.131 | 1.00 | 37.22 | N |
| ATOM | 6417 | CA | SER | C | 236 | 44.903 | 13.109 | 0.763 | 1.00 | 37.08 | C |
| ATOM | 6419 | CB | SER | C | 236 | 45.146 | 14.381 | −0.047 | 1.00 | 36.95 | C |
| ATOM | 6422 | OG | SER | C | 236 | 46.390 | 14.973 | 0.287 | 1.00 | 36.99 | O |
| ATOM | 6424 | C | SER | C | 236 | 46.148 | 12.213 | 0.678 | 1.00 | 36.90 | C |
| ATOM | 6425 | O | SER | C | 236 | 46.450 | 11.673 | −0.388 | 1.00 | 37.09 | O |
| ATOM | 6426 | N | LEU | C | 237 | 46.876 | 12.090 | 1.786 | 1.00 | 36.26 | N |
| ATOM | 6428 | CA | LEU | C | 237 | 48.072 | 11.254 | 1.858 | 1.00 | 35.89 | C |
| ATOM | 6430 | CB | LEU | C | 237 | 48.837 | 11.558 | 3.151 | 1.00 | 36.22 | C |
| ATOM | 6433 | CG | LEU | C | 237 | 50.278 | 11.072 | 3.287 | 1.00 | 37.39 | C |
| ATOM | 6435 | CD1 | LEU | C | 237 | 51.170 | 11.649 | 2.194 | 1.00 | 38.17 | C |
| ATOM | 6439 | CD2 | LEU | C | 237 | 50.794 | 11.456 | 4.668 | 1.00 | 38.80 | C |

TABLE 2-continued

| | | | | | | | | | | |
|---|---|---|---|---|---|---|---|---|---|---|
| ATOM | 6443 | C | LEU | C | 237 | 47.698 | 9.773 | 1.813 | 1.00 | 34.90 C |
| ATOM | 6444 | O | LEU | C | 237 | 48.410 | 8.959 | 1.224 | 1.00 | 35.00 O |
| ATOM | 6445 | N | HIS | C | 238 | 46.589 | 9.437 | 2.466 | 1.00 | 33.58 N |
| ATOM | 6447 | CA | HIS | C | 238 | 46.063 | 8.075 | 2.487 | 1.00 | 32.25 C |
| ATOM | 6449 | CB | HIS | C | 238 | 45.036 | 7.933 | 3.598 | 1.00 | 31.37 C |
| ATOM | 6452 | CG | HIS | C | 238 | 44.313 | 6.621 | 3.611 | 1.00 | 27.29 C |
| ATOM | 6453 | ND1 | HIS | C | 238 | 44.808 | 5.506 | 4.247 | 1.00 | 23.03 N |
| ATOM | 6455 | CE1 | HIS | C | 238 | 43.951 | 4.509 | 4.114 | 1.00 | 22.81 C |
| ATOM | 6457 | NE2 | HIS | C | 238 | 42.908 | 4.941 | 3.428 | 1.00 | 22.03 N |
| ATOM | 6459 | CD2 | HIS | C | 238 | 43.112 | 6.258 | 3.096 | 1.00 | 25.71 C |
| ATOM | 6461 | C | HIS | C | 238 | 45.404 | 7.737 | 1.161 | 1.00 | 32.61 C |
| ATOM | 6462 | O | HIS | C | 238 | 45.409 | 6.592 | 0.750 | 1.00 | 32.51 O |
| ATOM | 6463 | N | ALA | C | 239 | 44.786 | 8.724 | 0.527 | 1.00 | 33.08 N |
| ATOM | 6465 | CA | ALA | C | 239 | 44.172 | 8.510 | -0.780 | 1.00 | 33.62 C |
| ATOM | 6467 | CB | ALA | C | 239 | 43.445 | 9.746 | -1.242 | 1.00 | 33.58 C |
| ATOM | 6471 | C | ALA | C | 239 | 45.293 | 8.159 | -1.736 | 1.00 | 33.82 C |
| ATOM | 6472 | O | ALA | C | 239 | 45.240 | 7.141 | -2.404 | 1.00 | 34.31 O |
| ATOM | 6473 | N | ALA | C | 240 | 46.329 | 8.991 | -1.737 | 1.00 | 34.22 N |
| ATOM | 6475 | CA | ALA | C | 240 | 47.509 | 8.814 | -2.576 | 1.00 | 34.55 C |
| ATOM | 6477 | CB | ALA | C | 240 | 48.505 | 9.937 | -2.297 | 1.00 | 34.65 C |
| ATOM | 6481 | C | ALA | C | 240 | 48.189 | 7.464 | -2.366 | 1.00 | 34.85 C |
| ATOM | 6482 | O | ALA | C | 240 | 48.625 | 6.827 | -3.325 | 1.00 | 34.80 O |
| ATOM | 6483 | N | ASP | C | 241 | 48.284 | 7.045 | -1.105 | 1.00 | 34.96 N |
| ATOM | 6485 | CA | ASP | C | 241 | 48.917 | 5.782 | -0.741 | 1.00 | 35.01 C |
| ATOM | 6487 | CB | ASP | C | 241 | 49.154 | 5.735 | 0.771 | 1.00 | 35.25 C |
| ATOM | 6490 | CG | ASP | C | 241 | 49.313 | 4.332 | 1.295 | 1.00 | 35.57 C |
| ATOM | 6491 | OD1 | ASP | C | 241 | 50.326 | 3.678 | 0.963 | 1.00 | 35.94 O |
| ATOM | 6492 | OD2 | ASP | C | 241 | 48.471 | 3.806 | 2.051 | 1.00 | 37.88 O |
| ATOM | 6493 | C | ASP | C | 241 | 48.091 | 4.577 | -1.180 | 1.00 | 35.06 C |
| ATOM | 6494 | O | ASP | C | 241 | 48.647 | 3.565 | -1.596 | 1.00 | 35.22 O |
| ATOM | 6495 | N | VAL | C | 242 | 46.768 | 4.690 | -1.072 | 1.00 | 35.07 N |
| ATOM | 6497 | CA | VAL | C | 242 | 45.857 | 3.622 | -1.469 | 1.00 | 35.20 C |
| ATOM | 6499 | CB | VAL | C | 242 | 44.427 | 3.844 | -0.890 | 1.00 | 35.04 C |
| ATOM | 6501 | CG1 | VAL | C | 242 | 43.424 | 2.832 | -1.448 | 1.00 | 34.72 C |
| ATOM | 6505 | CG2 | VAL | C | 242 | 44.447 | 3.756 | 0.644 | 1.00 | 35.58 C |
| ATOM | 6509 | C | VAL | C | 242 | 45.833 | 3.517 | -3.003 | 1.00 | 35.50 C |
| ATOM | 6510 | O | VAL | C | 242 | 45.724 | 2.423 | -3.546 | 1.00 | 35.47 O |
| ATOM | 6511 | N | ALA | C | 243 | 45.968 | 4.651 | -3.687 | 1.00 | 36.01 N |
| ATOM | 6513 | CA | ALA | C | 243 | 45.976 | 4.687 | -5.154 | 1.00 | 36.54 C |
| ATOM | 6515 | CB | ALA | C | 243 | 45.825 | 6.112 | -5.649 | 1.00 | 36.33 C |
| ATOM | 6519 | C | ALA | C | 243 | 47.252 | 4.057 | -5.718 | 1.00 | 37.07 C |
| ATOM | 6520 | O | ALA | C | 243 | 47.182 | 3.237 | -6.627 | 1.00 | 37.23 O |
| ATOM | 6521 | N | GLN | C | 244 | 48.407 | 4.436 | -5.169 | 1.00 | 37.75 N |
| ATOM | 6523 | CA | GLN | C | 244 | 49.699 | 3.896 | -5.602 | 1.00 | 38.10 C |
| ATOM | 6525 | CB | GLN | C | 244 | 50.855 | 4.640 | -4.919 | 1.00 | 38.21 C |
| ATOM | 6528 | CG | GLN | C | 244 | 52.252 | 4.316 | -5.484 | 1.00 | 38.19 C |
| ATOM | 6531 | CD | GLN | C | 244 | 53.047 | 3.317 | -4.640 | 1.00 | 38.71 C |
| ATOM | 6532 | OE1 | GLN | C | 244 | 52.812 | 3.181 | -3.438 | 1.00 | 37.76 O |
| ATOM | 6533 | NE2 | GLN | C | 244 | 53.998 | 2.624 | -5.273 | 1.00 | 38.19 N |
| ATOM | 6536 | C | GLN | C | 244 | 49.796 | 2.402 | -5.300 | 1.00 | 38.54 C |
| ATOM | 6537 | O | GLN | C | 244 | 50.328 | 1.637 | -6.101 | 1.00 | 38.77 O |
| ATOM | 6538 | N | SER | C | 245 | 49.280 | 1.999 | -4.141 | 1.00 | 38.82 N |
| ATOM | 6540 | CA | SER | C | 245 | 49.274 | 0.602 | -3.718 | 1.00 | 38.95 C |
| ATOM | 6542 | CB | SER | C | 245 | 48.741 | 0.479 | -2.282 | 1.00 | 39.02 C |
| ATOM | 6545 | OG | SER | C | 245 | 49.623 | 1.083 | -1.351 | 1.00 | 38.97 O |
| ATOM | 6547 | C | SER | C | 245 | 48.427 | -0.256 | -4.655 | 1.00 | 39.11 C |
| ATOM | 6548 | O | SER | C | 245 | 48.741 | -1.417 | -4.884 | 1.00 | 39.01 O |
| ATOM | 6549 | N | THR | C | 246 | 47.345 | 0.324 | -5.171 | 1.00 | 39.61 N |
| ATOM | 6551 | CA | THR | C | 246 | 46.441 | -0.347 | -6.113 | 1.00 | 39.86 C |
| ATOM | 6553 | CB | THR | C | 246 | 45.116 | 0.457 | -6.241 | 1.00 | 39.91 C |
| ATOM | 6555 | OG1 | THR | C | 246 | 44.335 | 0.314 | -5.044 | 1.00 | 39.32 O |
| ATOM | 6557 | CG2 | THR | C | 246 | 44.214 | -0.100 | -7.354 | 1.00 | 39.57 C |
| ATOM | 6561 | C | THR | C | 246 | 47.111 | -0.485 | -7.486 | 1.00 | 40.15 C |
| ATOM | 6562 | O | THR | C | 246 | 46.846 | -1.434 | -8.221 | 1.00 | 40.19 O |
| ATOM | 6563 | N | HIS | C | 247 | 47.969 | 0.478 | -7.813 | 1.00 | 40.51 N |
| ATOM | 6565 | CA | HIS | C | 247 | 48.735 | 0.493 | -9.064 | 1.00 | 40.81 C |
| ATOM | 6567 | CB | HIS | C | 247 | 49.396 | 1.875 | -9.230 | 1.00 | 40.81 C |
| ATOM | 6570 | CG | HIS | C | 247 | 50.511 | 1.923 | -10.228 | 1.00 | 40.74 C |
| ATOM | 6571 | ND1 | HIS | C | 247 | 50.306 | 1.796 | -11.584 | 1.00 | 40.45 N |
| ATOM | 6573 | CE1 | HIS | C | 247 | 51.463 | 1.897 | -12.213 | 1.00 | 40.57 C |
| ATOM | 6575 | NE2 | HIS | C | 247 | 52.409 | 2.101 | -11.315 | 1.00 | 40.30 N |
| ATOM | 6577 | CD2 | HIS | C | 247 | 51.839 | 2.131 | -10.067 | 1.00 | 40.57 C |
| ATOM | 6579 | C | HIS | C | 247 | 49.765 | -0.645 | -9.077 | 1.00 | 41.13 C |
| ATOM | 6580 | O | HIS | C | 247 | 50.039 | -1.217 | -10.125 | 1.00 | 40.70 O |
| ATOM | 6581 | N | VAL | C | 248 | 50.310 | -0.994 | -7.911 | 1.00 | 41.66 N |
| ATOM | 6583 | CA | VAL | C | 248 | 51.289 | -2.083 | -7.826 | 1.00 | 42.24 C |
| ATOM | 6585 | CB | VAL | C | 248 | 52.193 | -1.971 | -6.561 | 1.00 | 42.34 C |
| ATOM | 6587 | CG1 | VAL | C | 248 | 53.267 | -3.070 | -6.555 | 1.00 | 42.18 C |
| ATOM | 6591 | CG2 | VAL | C | 248 | 52.838 | -0.586 | -6.475 | 1.00 | 42.11 C |

TABLE 2-continued

| ATOM | 6595 | C | VAL | C | 248 | 50.592 | −3.452 | −7.855 | 1.00 | 42.73 | C |
| --- | --- | --- | --- | --- | --- | --- | --- | --- | --- | --- | --- |
| ATOM | 6596 | O | VAL | C | 248 | 51.123 | −4.402 | −8.426 | 1.00 | 42.90 | O |
| ATOM | 6597 | N | LEU | C | 249 | 49.408 | −3.546 | −7.249 | 1.00 | 43.39 | N |
| ATOM | 6599 | CA | LEU | C | 249 | 48.653 | −4.803 | −7.208 | 1.00 | 43.84 | C |
| ATOM | 6601 | CB | LEU | C | 249 | 47.557 | −4.754 | −6.135 | 1.00 | 43.67 | C |
| ATOM | 6604 | CG | LEU | C | 249 | 48.004 | −4.549 | −4.679 | 1.00 | 43.72 | C |
| ATOM | 6606 | CD1 | LEU | C | 249 | 46.789 | −4.374 | −3.775 | 1.00 | 43.68 | C |
| ATOM | 6610 | CD2 | LEU | C | 249 | 48.885 | −5.683 | −4.163 | 1.00 | 43.55 | C |
| ATOM | 6614 | C | LEU | C | 249 | 48.045 | −5.153 | −8.570 | 1.00 | 44.45 | C |
| ATOM | 6615 | O | LEU | C | 249 | 47.777 | −6.320 | −8.847 | 1.00 | 44.52 | O |
| ATOM | 6616 | N | LEU | C | 250 | 47.829 | −4.144 | −9.411 | 1.00 | 45.23 | N |
| ATOM | 6618 | CA | LEU | C | 250 | 47.300 | −4.356 | −10.761 | 1.00 | 45.89 | C |
| ATOM | 6620 | CB | LEU | C | 250 | 46.793 | −3.042 | −11.364 | 1.00 | 45.77 | C |
| ATOM | 6623 | CG | LEU | C | 250 | 45.421 | −2.547 | −10.911 | 1.00 | 45.32 | C |
| ATOM | 6625 | CD1 | LEU | C | 250 | 45.237 | −1.079 | −11.280 | 1.00 | 44.96 | C |
| ATOM | 6629 | CD2 | LEU | C | 250 | 44.310 | −3.398 | −11.500 | 1.00 | 45.01 | C |
| ATOM | 6633 | C | LEU | C | 250 | 48.379 | −4.942 | −11.676 | 1.00 | 46.71 | C |
| ATOM | 6634 | O | LEU | C | 250 | 48.062 | −5.584 | −12.678 | 1.00 | 47.00 | O |
| ATOM | 6635 | N | SER | C | 251 | 49.644 | −4.702 | −11.328 | 1.00 | 47.61 | N |
| ATOM | 6637 | CA | SER | C | 251 | 50.792 | −5.195 | −12.090 | 1.00 | 48.27 | C |
| ATOM | 6639 | CB | SER | C | 251 | 51.943 | −4.184 | −12.020 | 1.00 | 48.31 | C |
| ATOM | 6642 | OG | SER | C | 251 | 51.815 | −3.201 | −13.033 | 1.00 | 48.93 | O |
| ATOM | 6644 | C | SER | C | 251 | 51.294 | −6.562 | −11.614 | 1.00 | 48.76 | C |
| ATOM | 6645 | O | SER | C | 251 | 52.215 | −7.120 | −12.213 | 1.00 | 48.95 | O |
| ATOM | 6646 | N | THR | C | 252 | 50.701 | −7.096 | −10.545 | 1.00 | 49.40 | N |
| ATOM | 6648 | CA | THR | C | 252 | 51.111 | −8.394 | −10.003 | 1.00 | 49.71 | C |
| ATOM | 6650 | CB | THR | C | 252 | 50.258 | −8.775 | −8.752 | 1.00 | 49.73 | C |
| ATOM | 6652 | OG1 | THR | C | 252 | 50.889 | −9.839 | −8.029 | 1.00 | 49.93 | O |
| ATOM | 6654 | CG2 | THR | C | 252 | 48.890 | −9.334 | −9.132 | 1.00 | 49.80 | C |
| ATOM | 6658 | C | THR | C | 252 | 51.038 | −9.465 | −11.107 | 1.00 | 49.88 | C |
| ATOM | 6659 | O | THR | C | 252 | 50.049 | −9.525 | −11.838 | 1.00 | 49.98 | O |
| ATOM | 6660 | N | PRO | C | 253 | 52.091 | −10.278 | −11.248 | 1.00 | 50.02 | N |
| ATOM | 6661 | CA | PRO | C | 253 | 52.162 | −11.305 | −12.303 | 1.00 | 50.00 | C |
| ATOM | 6663 | CB | PRO | C | 253 | 53.399 | −12.125 | −11.907 | 1.00 | 50.03 | C |
| ATOM | 6666 | CG | PRO | C | 253 | 54.262 | −11.175 | −11.168 | 1.00 | 49.95 | C |
| ATOM | 6669 | CD | PRO | C | 253 | 53.321 | −10.258 | −10.430 | 1.00 | 50.07 | C |
| ATOM | 6672 | C | PRO | C | 253 | 50.950 | −12.230 | −12.458 | 1.00 | 49.99 | C |
| ATOM | 6673 | O | PRO | C | 253 | 50.689 | −12.680 | −13.574 | 1.00 | 49.84 | O |
| ATOM | 6674 | N | ALA | C | 254 | 50.223 | −12.497 | −11.378 | 1.00 | 50.03 | N |
| ATOM | 6676 | CA | ALA | C | 254 | 49.081 | −13.412 | −11.427 | 1.00 | 50.07 | C |
| ATOM | 6678 | CB | ALA | C | 254 | 48.764 | −13.934 | −10.033 | 1.00 | 50.10 | C |
| ATOM | 6682 | C | ALA | C | 254 | 47.832 | −12.795 | −12.056 | 1.00 | 50.09 | C |
| ATOM | 6683 | O | ALA | C | 254 | 46.899 | −13.514 | −12.395 | 1.00 | 50.09 | O |
| ATOM | 6684 | N | LEU | C | 255 | 47.803 | −11.471 | −12.187 | 1.00 | 50.17 | N |
| ATOM | 6686 | CA | LEU | C | 255 | 46.677 | −10.774 | −12.806 | 1.00 | 50.32 | C |
| ATOM | 6688 | CB | LEU | C | 255 | 46.108 | −9.737 | −11.837 | 1.00 | 50.27 | C |
| ATOM | 6691 | CG | LEU | C | 255 | 45.810 | −10.244 | −10.418 | 1.00 | 50.17 | C |
| ATOM | 6693 | CD1 | LEU | C | 255 | 45.551 | −9.090 | −9.471 | 1.00 | 50.15 | C |
| ATOM | 6697 | CD2 | LEU | C | 255 | 44.624 | −11.191 | −10.429 | 1.00 | 50.08 | C |
| ATOM | 6701 | C | LEU | C | 255 | 47.111 | −10.104 | −14.116 | 1.00 | 50.48 | C |
| ATOM | 6702 | O | LEU | C | 255 | 46.502 | −9.128 | −14.555 | 1.00 | 50.41 | O |
| ATOM | 6703 | N | ASP | C | 256 | 48.152 | −10.653 | −14.739 | 1.00 | 50.67 | N |
| ATOM | 6705 | CA | ASP | C | 256 | 48.718 | −10.118 | −15.980 | 1.00 | 50.96 | C |
| ATOM | 6707 | CB | ASP | C | 256 | 50.048 | −10.830 | −16.287 | 1.00 | 51.10 | C |
| ATOM | 6710 | CG | ASP | C | 256 | 50.791 | −10.230 | −17.476 | 1.00 | 51.50 | C |
| ATOM | 6711 | OD1 | ASP | C | 256 | 50.845 | −8.989 | −17.606 | 1.00 | 51.92 | O |
| ATOM | 6712 | OD2 | ASP | C | 256 | 51.372 | −10.935 | −18.328 | 1.00 | 52.14 | O |
| ATOM | 6713 | C | ASP | C | 256 | 47.758 | −10.261 | −17.162 | 1.00 | 50.88 | C |
| ATOM | 6714 | O | ASP | C | 256 | 47.258 | −11.351 | −17.437 | 1.00 | 50.89 | O |
| ATOM | 6715 | N | ALA | C | 257 | 47.492 | −9.140 | −17.834 | 1.00 | 50.92 | N |
| ATOM | 6717 | CA | ALA | C | 257 | 46.615 | −9.084 | −19.014 | 1.00 | 50.96 | C |
| ATOM | 6719 | CB | ALA | C | 257 | 47.203 | −9.926 | −20.155 | 1.00 | 50.97 | C |
| ATOM | 6723 | C | ALA | C | 257 | 45.158 | −9.487 | −18.753 | 1.00 | 50.85 | C |
| ATOM | 6724 | O | ALA | C | 257 | 44.379 | −9.640 | −19.696 | 1.00 | 50.82 | O |
| ATOM | 6725 | N | VAL | C | 258 | 44.790 | −9.628 | −17.482 | 1.00 | 50.62 | N |
| ATOM | 6727 | CA | VAL | C | 258 | 43.441 | −10.039 | −17.100 | 1.00 | 50.44 | C |
| ATOM | 6729 | CB | VAL | C | 258 | 43.446 | −10.635 | −15.663 | 1.00 | 50.59 | C |
| ATOM | 6731 | CG1 | VAL | C | 258 | 42.086 | −10.486 | −14.964 | 1.00 | 50.73 | C |
| ATOM | 6735 | CG2 | VAL | C | 258 | 43.874 | −12.097 | −15.700 | 1.00 | 50.48 | C |
| ATOM | 6739 | C | VAL | C | 258 | 42.443 | −8.883 | −17.201 | 1.00 | 50.22 | C |
| ATOM | 6740 | O | VAL | C | 258 | 41.283 | −9.087 | −17.571 | 1.00 | 50.09 | O |
| ATOM | 6741 | N | PHE | C | 259 | 42.901 | −7.673 | −16.886 | 1.00 | 50.02 | N |
| ATOM | 6743 | CA | PHE | C | 259 | 42.034 | −6.497 | −16.877 | 1.00 | 49.79 | C |
| ATOM | 6745 | CB | PHE | C | 259 | 42.310 | −5.669 | −15.617 | 1.00 | 49.69 | C |
| ATOM | 6748 | CG | PHE | C | 259 | 42.099 | −6.430 | −14.338 | 1.00 | 48.71 | C |
| ATOM | 6749 | CD1 | PHE | C | 259 | 40.831 | −6.868 | −13.983 | 1.00 | 48.08 | C |
| ATOM | 6751 | CE1 | PHE | C | 259 | 40.626 | −7.576 | −12.813 | 1.00 | 47.77 | C |
| ATOM | 6753 | CZ | PHE | C | 259 | 41.697 | −7.855 | −11.984 | 1.00 | 47.65 | C |
| ATOM | 6755 | CE2 | PHE | C | 259 | 42.968 | −7.427 | −12.329 | 1.00 | 47.73 | C |

TABLE 2-continued

| | | | | | | | | | | | |
|---|---|---|---|---|---|---|---|---|---|---|---|
| ATOM | 6757 | CD2 | PHE | C | 259 | 43.164 | −6.719 | −13.500 | 1.00 | 47.87 | C |
| ATOM | 6759 | C | PHE | C | 259 | 42.182 | −5.611 | −18.110 | 1.00 | 49.86 | C |
| ATOM | 6760 | O | PHE | C | 259 | 43.283 | −5.425 | −18.634 | 1.00 | 49.84 | O |
| ATOM | 6761 | N | THR | C | 260 | 41.055 | −5.059 | −18.554 | 1.00 | 49.85 | N |
| ATOM | 6763 | CA | THR | C | 260 | 41.027 | −4.140 | −19.686 | 1.00 | 49.89 | C |
| ATOM | 6765 | CB | THR | C | 260 | 39.600 | −4.005 | −20.264 | 1.00 | 50.00 | C |
| ATOM | 6767 | OG1 | THR | C | 260 | 38.715 | −3.474 | −19.267 | 1.00 | 50.43 | O |
| ATOM | 6769 | CG2 | THR | C | 260 | 38.998 | −5.366 | −20.616 | 1.00 | 50.11 | C |
| ATOM | 6773 | C | THR | C | 260 | 41.497 | −2.777 | −19.196 | 1.00 | 49.71 | C |
| ATOM | 6774 | O | THR | C | 260 | 41.664 | −2.570 | −17.994 | 1.00 | 49.80 | O |
| ATOM | 6775 | N | ASP | C | 261 | 41.696 | −1.848 | −20.123 | 1.00 | 49.46 | N |
| ATOM | 6777 | CA | ASP | C | 261 | 42.139 | −0.499 | −19.775 | 1.00 | 49.19 | C |
| ATOM | 6779 | CB | ASP | C | 261 | 42.477 | 0.301 | −21.039 | 1.00 | 49.38 | C |
| ATOM | 6782 | CG | ASP | C | 261 | 43.730 | −0.201 | −21.736 | 1.00 | 50.09 | C |
| ATOM | 6783 | OD1 | ASP | C | 261 | 44.650 | −0.700 | −21.048 | 1.00 | 50.38 | O |
| ATOM | 6784 | OD2 | ASP | C | 261 | 43.884 | −0.126 | −22.976 | 1.00 | 51.63 | O |
| ATOM | 6785 | C | ASP | C | 261 | 41.095 | 0.265 | −18.953 | 1.00 | 48.62 | C |
| ATOM | 6786 | O | ASP | C | 261 | 41.453 | 1.073 | −18.093 | 1.00 | 48.72 | O |
| ATOM | 6787 | N | LEU | C | 262 | 39.814 | 0.021 | −19.230 | 1.00 | 47.78 | N |
| ATOM | 6789 | CA | LEU | C | 262 | 38.718 | 0.688 | −18.523 | 1.00 | 47.02 | C |
| ATOM | 6791 | CB | LEU | C | 262 | 37.383 | 0.415 | −19.224 | 1.00 | 46.88 | C |
| ATOM | 6794 | CG | LEU | C | 262 | 36.160 | 1.195 | −18.737 | 1.00 | 46.22 | C |
| ATOM | 6796 | CD1 | LEU | C | 262 | 36.235 | 2.660 | −19.134 | 1.00 | 45.77 | C |
| ATOM | 6800 | CD2 | LEU | C | 262 | 34.893 | 0.566 | −19.274 | 1.00 | 46.08 | C |
| ATOM | 6804 | C | LEU | C | 262 | 38.642 | 0.231 | −17.072 | 1.00 | 46.69 | C |
| ATOM | 6805 | O | LEU | C | 262 | 38.325 | 1.016 | −16.185 | 1.00 | 46.67 | O |
| ATOM | 6806 | N | GLU | C | 263 | 38.925 | −1.045 | −16.847 | 1.00 | 46.21 | N |
| ATOM | 6808 | CA | GLU | C | 263 | 38.899 | −1.621 | −15.512 | 1.00 | 45.84 | C |
| ATOM | 6810 | CB | GLU | C | 263 | 38.869 | −3.146 | −15.607 | 1.00 | 45.79 | C |
| ATOM | 6813 | CG | GLU | C | 263 | 37.585 | −3.650 | −16.240 | 1.00 | 45.43 | C |
| ATOM | 6816 | CD | GLU | C | 263 | 37.507 | −5.154 | −16.348 | 1.00 | 45.13 | C |
| ATOM | 6817 | OE1 | GLU | C | 263 | 38.553 | −5.813 | −16.506 | 1.00 | 45.20 | O |
| ATOM | 6818 | OE2 | GLU | C | 263 | 36.379 | −5.675 | −16.279 | 1.00 | 45.31 | O |
| ATOM | 6819 | C | GLU | C | 263 | 40.093 | −1.147 | −14.692 | 1.00 | 45.67 | C |
| ATOM | 6820 | O | GLU | C | 263 | 39.985 | −0.953 | −13.482 | 1.00 | 45.72 | O |
| ATOM | 6821 | N | ILE | C | 264 | 41.228 | −0.960 | −15.357 | 1.00 | 45.32 | N |
| ATOM | 6823 | CA | ILE | C | 264 | 42.431 | −0.464 | −14.706 | 1.00 | 45.04 | C |
| ATOM | 6825 | CB | ILE | C | 264 | 43.638 | −0.551 | −15.673 | 1.00 | 45.05 | C |
| ATOM | 6827 | CG1 | ILE | C | 264 | 44.112 | −2.004 | −15.775 | 1.00 | 45.27 | C |
| ATOM | 6830 | CD1 | ILE | C | 264 | 45.172 | −2.249 | −16.832 | 1.00 | 45.10 | C |
| ATOM | 6834 | CG2 | ILE | C | 264 | 44.784 | 0.353 | −15.219 | 1.00 | 45.21 | C |
| ATOM | 6838 | C | ILE | C | 264 | 42.187 | 0.974 | −14.237 | 1.00 | 44.74 | C |
| ATOM | 6839 | O | ILE | C | 264 | 42.580 | 1.347 | −13.126 | 1.00 | 44.91 | O |
| ATOM | 6840 | N | LEU | C | 265 | 41.519 | 1.758 | −15.081 | 1.00 | 44.03 | N |
| ATOM | 6842 | CA | LEU | C | 265 | 41.197 | 3.157 | −14.798 | 1.00 | 43.59 | C |
| ATOM | 6844 | CB | LEU | C | 265 | 40.559 | 3.802 | −16.034 | 1.00 | 43.73 | C |
| ATOM | 6847 | CG | LEU | C | 265 | 40.204 | 5.295 | −16.012 | 1.00 | 43.94 | C |
| ATOM | 6849 | CD1 | LEU | C | 265 | 41.453 | 6.152 | −16.047 | 1.00 | 44.13 | C |
| ATOM | 6853 | CD2 | LEU | C | 265 | 39.293 | 5.643 | −17.187 | 1.00 | 44.03 | C |
| ATOM | 6857 | C | LEU | C | 265 | 40.253 | 3.301 | −13.605 | 1.00 | 43.14 | C |
| ATOM | 6858 | O | LEU | C | 265 | 40.457 | 4.159 | −12.743 | 1.00 | 42.93 | O |
| ATOM | 6859 | N | ALA | C | 266 | 39.225 | 2.458 | −13.569 | 1.00 | 42.37 | N |
| ATOM | 6861 | CA | ALA | C | 266 | 38.222 | 2.487 | −12.513 | 1.00 | 41.81 | C |
| ATOM | 6863 | CB | ALA | C | 266 | 37.115 | 1.503 | −12.827 | 1.00 | 41.86 | C |
| ATOM | 6867 | C | ALA | C | 266 | 38.820 | 2.173 | −11.145 | 1.00 | 41.24 | C |
| ATOM | 6868 | O | ALA | C | 266 | 38.486 | 2.821 | −10.153 | 1.00 | 41.32 | O |
| ATOM | 6869 | N | ALA | C | 267 | 39.697 | 1.175 | −11.108 | 1.00 | 40.37 | N |
| ATOM | 6871 | CA | ALA | C | 267 | 40.346 | 0.741 | −9.879 | 1.00 | 39.87 | C |
| ATOM | 6873 | CB | ALA | C | 267 | 41.170 | −0.511 | −10.134 | 1.00 | 39.85 | C |
| ATOM | 6877 | C | ALA | C | 267 | 41.220 | 1.833 | −9.284 | 1.00 | 39.30 | C |
| ATOM | 6878 | O | ALA | C | 267 | 41.232 | 2.030 | −8.068 | 1.00 | 39.35 | O |
| ATOM | 6879 | N | ILE | C | 268 | 41.949 | 2.542 | −10.139 | 1.00 | 38.37 | N |
| ATOM | 6881 | CA | ILE | C | 268 | 42.834 | 3.612 | −9.681 | 1.00 | 37.75 | C |
| ATOM | 6883 | CB | ILE | C | 268 | 43.947 | 3.879 | −10.733 | 1.00 | 37.71 | C |
| ATOM | 6885 | CG1 | ILE | C | 268 | 44.908 | 2.684 | −10.782 | 1.00 | 38.10 | C |
| ATOM | 6888 | CD1 | ILE | C | 268 | 45.637 | 2.525 | −12.104 | 1.00 | 38.91 | C |
| ATOM | 6892 | CG2 | ILE | C | 268 | 44.729 | 5.152 | −10.409 | 1.00 | 37.47 | C |
| ATOM | 6896 | C | ILE | C | 268 | 42.039 | 4.877 | −9.323 | 1.00 | 36.87 | C |
| ATOM | 6897 | O | ILE | C | 268 | 42.432 | 5.631 | −8.435 | 1.00 | 36.91 | O |
| ATOM | 6898 | N | PHE | C | 269 | 40.911 | 5.085 | −9.994 | 1.00 | 35.80 | N |
| ATOM | 6900 | CA | PHE | C | 269 | 40.057 | 6.241 | −9.742 | 1.00 | 34.66 | C |
| ATOM | 6902 | CB | PHE | C | 269 | 39.068 | 6.439 | −10.885 | 1.00 | 34.11 | C |
| ATOM | 6905 | CG | PHE | C | 269 | 38.152 | 7.613 | −10.695 | 1.00 | 31.89 | C |
| ATOM | 6906 | CD1 | PHE | C | 269 | 38.654 | 8.901 | −10.698 | 1.00 | 30.41 | C |
| ATOM | 6908 | CE1 | PHE | C | 269 | 37.821 | 9.983 | −10.526 | 1.00 | 29.83 | C |
| ATOM | 6910 | CZ | PHE | C | 269 | 36.467 | 9.790 | −10.346 | 1.00 | 29.63 | C |
| ATOM | 6912 | CE2 | PHE | C | 269 | 35.952 | 8.512 | −10.340 | 1.00 | 29.46 | C |
| ATOM | 6914 | CD2 | PHE | C | 269 | 36.793 | 7.430 | −10.511 | 1.00 | 30.21 | C |
| ATOM | 6916 | C | PHE | C | 269 | 39.284 | 6.073 | −8.439 | 1.00 | 34.56 | C |

TABLE 2-continued

| ATOM | 6917 | O | PHE | C | 269 | 39.051 | 7.044 | −7.731 | 1.00 | 34.54 | O |
|---|---|---|---|---|---|---|---|---|---|---|---|
| ATOM | 6918 | N | ALA | C | 270 | 38.875 | 4.839 | −8.154 | 1.00 | 34.29 | N |
| ATOM | 6920 | CA | ALA | C | 270 | 38.134 | 4.509 | −6.948 | 1.00 | 34.08 | C |
| ATOM | 6922 | CB | ALA | C | 270 | 37.664 | 3.065 | −6.996 | 1.00 | 34.08 | C |
| ATOM | 6926 | C | ALA | C | 270 | 39.036 | 4.722 | −5.750 | 1.00 | 34.00 | C |
| ATOM | 6927 | O | ALA | C | 270 | 38.621 | 5.278 | −4.738 | 1.00 | 34.13 | O |
| ATOM | 6928 | N | ALA | C | 271 | 40.274 | 4.258 | −5.880 | 1.00 | 33.75 | N |
| ATOM | 6930 | CA | ALA | C | 271 | 41.277 | 4.404 | −4.841 | 1.00 | 33.43 | C |
| ATOM | 6932 | CB | ALA | C | 271 | 42.574 | 3.766 | −5.289 | 1.00 | 33.51 | C |
| ATOM | 6936 | C | ALA | C | 271 | 41.503 | 5.876 | −4.505 | 1.00 | 33.08 | C |
| ATOM | 6937 | O | ALA | C | 271 | 41.579 | 6.245 | −3.336 | 1.00 | 32.96 | O |
| ATOM | 6938 | N | ALA | C | 272 | 41.583 | 6.715 | −5.535 | 1.00 | 32.56 | N |
| ATOM | 6940 | CA | ALA | C | 272 | 41.824 | 8.150 | −5.351 | 1.00 | 32.16 | C |
| ATOM | 6942 | CB | ALA | C | 272 | 42.199 | 8.786 | −6.683 | 1.00 | 32.23 | C |
| ATOM | 6946 | C | ALA | C | 272 | 40.666 | 8.933 | −4.715 | 1.00 | 31.62 | C |
| ATOM | 6947 | O | ALA | C | 272 | 40.895 | 9.982 | −4.119 | 1.00 | 31.91 | O |
| ATOM | 6948 | N | ILE | C | 273 | 39.436 | 8.444 | −4.857 | 1.00 | 30.92 | N |
| ATOM | 6950 | CA | ILE | C | 273 | 38.253 | 9.137 | −4.329 | 1.00 | 30.25 | C |
| ATOM | 6952 | CB | ILE | C | 273 | 37.181 | 9.313 | −5.460 | 1.00 | 29.97 | C |
| ATOM | 6954 | CG1 | ILE | C | 273 | 36.590 | 7.963 | −5.879 | 1.00 | 30.04 | C |
| ATOM | 6957 | CD1 | ILE | C | 273 | 35.103 | 8.010 | −6.208 | 1.00 | 30.36 | C |
| ATOM | 6961 | CG2 | ILE | C | 273 | 37.757 | 10.034 | −6.685 | 1.00 | 30.61 | C |
| ATOM | 6965 | C | ILE | C | 273 | 37.570 | 8.419 | −3.155 | 1.00 | 29.46 | C |
| ATOM | 6966 | O | ILE | C | 273 | 36.569 | 8.907 | −2.652 | 1.00 | 29.43 | O |
| ATOM | 6967 | N | HIS | C | 274 | 38.113 | 7.283 | −2.731 | 1.00 | 28.58 | N |
| ATOM | 6969 | CA | HIS | C | 274 | 37.455 | 6.410 | −1.749 | 1.00 | 28.36 | C |
| ATOM | 6971 | CB | HIS | C | 274 | 38.168 | 5.048 | −1.697 | 1.00 | 27.75 | C |
| ATOM | 6974 | CG | HIS | C | 274 | 39.288 | 4.998 | −0.713 | 1.00 | 27.24 | C |
| ATOM | 6975 | ND1 | HIS | C | 274 | 40.455 | 5.719 | −0.872 | 1.00 | 26.57 | N |
| ATOM | 6977 | CE1 | HIS | C | 274 | 41.242 | 5.491 | 0.169 | 1.00 | 24.89 | C |
| ATOM | 6979 | NE2 | HIS | C | 274 | 40.638 | 4.635 | 0.973 | 1.00 | 17.75 | N |
| ATOM | 6981 | CD2 | HIS | C | 274 | 39.407 | 4.334 | 0.465 | 1.00 | 21.11 | C |
| ATOM | 6983 | C | HIS | C | 274 | 37.262 | 6.926 | −0.309 | 1.00 | 28.32 | C |
| ATOM | 6984 | O | HIS | C | 274 | 36.473 | 6.346 | 0.442 | 1.00 | 28.84 | O |
| ATOM | 6985 | N | ASP | C | 275 | 37.975 | 7.976 | 0.087 | 1.00 | 27.86 | N |
| ATOM | 6987 | CA | ASP | C | 275 | 37.831 | 8.525 | 1.448 | 1.00 | 27.50 | C |
| ATOM | 6989 | CB | ASP | C | 275 | 39.004 | 8.084 | 2.357 | 1.00 | 26.52 | C |
| ATOM | 6992 | CG | ASP | C | 275 | 38.791 | 6.703 | 3.016 | 1.00 | 24.95 | C |
| ATOM | 6993 | OD1 | ASP | C | 275 | 37.629 | 6.310 | 3.296 | 1.00 | 24.29 | O |
| ATOM | 6994 | OD2 | ASP | C | 275 | 39.751 | 5.926 | 3.305 | 1.00 | 13.37 | O |
| ATOM | 6995 | C | ASP | C | 275 | 37.724 | 10.065 | 1.413 | 1.00 | 27.98 | C |
| ATOM | 6996 | O | ASP | C | 275 | 37.952 | 10.729 | 2.428 | 1.00 | 27.72 | O |
| ATOM | 6997 | N | VAL | C | 276 | 37.342 | 10.621 | 0.258 | 1.00 | 28.21 | N |
| ATOM | 6999 | CA | VAL | C | 276 | 37.250 | 12.077 | 0.079 | 1.00 | 28.49 | C |
| ATOM | 7001 | CB | VAL | C | 276 | 37.006 | 12.458 | −1.409 | 1.00 | 28.28 | C |
| ATOM | 7003 | CG1 | VAL | C | 276 | 35.567 | 12.190 | −1.805 | 1.00 | 28.05 | C |
| ATOM | 7007 | CG2 | VAL | C | 276 | 37.358 | 13.917 | −1.647 | 1.00 | 28.08 | C |
| ATOM | 7011 | C | VAL | C | 276 | 36.168 | 12.752 | 0.930 | 1.00 | 29.11 | C |
| ATOM | 7012 | O | VAL | C | 276 | 35.064 | 12.243 | 1.075 | 1.00 | 28.74 | O |
| ATOM | 7013 | N | ASP | C | 277 | 36.483 | 13.939 | 1.431 | 1.00 | 30.07 | N |
| ATOM | 7015 | CA | ASP | C | 277 | 35.590 | 14.666 | 2.326 | 1.00 | 30.97 | C |
| ATOM | 7017 | CB | ASP | C | 277 | 34.289 | 15.028 | 1.607 | 1.00 | 31.03 | C |
| ATOM | 7020 | CG | ASP | C | 277 | 33.596 | 16.237 | 2.215 | 1.00 | 30.63 | C |
| ATOM | 7021 | OD1 | ASP | C | 277 | 34.282 | 17.203 | 2.597 | 1.00 | 30.25 | O |
| ATOM | 7022 | OD2 | ASP | C | 277 | 32.361 | 16.315 | 2.334 | 1.00 | 31.25 | O |
| ATOM | 7023 | C | ASP | C | 277 | 35.315 | 13.864 | 3.617 | 1.00 | 31.77 | C |
| ATOM | 7024 | O | ASP | C | 277 | 34.241 | 13.966 | 4.204 | 1.00 | 31.94 | O |
| ATOM | 7025 | N | HIS | C | 278 | 36.278 | 13.052 | 4.039 | 1.00 | 32.94 | N |
| ATOM | 7027 | CA | HIS | C | 278 | 36.134 | 12.276 | 5.271 | 1.00 | 34.14 | C |
| ATOM | 7029 | CB | HIS | C | 278 | 37.234 | 11.221 | 5.377 | 1.00 | 33.94 | C |
| ATOM | 7032 | CG | HIS | C | 278 | 36.891 | 10.073 | 6.272 | 1.00 | 34.46 | C |
| ATOM | 7033 | ND1 | HIS | C | 278 | 36.858 | 10.183 | 7.648 | 1.00 | 34.45 | N |
| ATOM | 7035 | CE1 | HIS | C | 278 | 36.541 | 9.013 | 8.173 | 1.00 | 34.50 | C |
| ATOM | 7037 | NE2 | HIS | C | 278 | 36.368 | 8.149 | 7.188 | 1.00 | 34.68 | N |
| ATOM | 7039 | CD2 | HIS | C | 278 | 36.587 | 8.786 | 5.990 | 1.00 | 34.16 | C |
| ATOM | 7041 | C | HIS | C | 278 | 36.223 | 13.263 | 6.442 | 1.00 | 34.99 | C |
| ATOM | 7042 | O | HIS | C | 278 | 37.221 | 13.956 | 6.573 | 1.00 | 35.09 | O |
| ATOM | 7043 | N | PRO | C | 279 | 35.189 | 13.343 | 7.276 | 1.00 | 36.43 | N |
| ATOM | 7044 | CA | PRO | C | 279 | 35.183 | 14.273 | 8.413 | 1.00 | 37.44 | C |
| ATOM | 7046 | CB | PRO | C | 279 | 33.715 | 14.274 | 8.853 | 1.00 | 37.36 | C |
| ATOM | 7049 | CG | PRO | C | 279 | 33.213 | 12.934 | 8.475 | 1.00 | 37.02 | C |
| ATOM | 7052 | CD | PRO | C | 279 | 33.955 | 12.544 | 7.226 | 1.00 | 36.56 | C |
| ATOM | 7055 | C | PRO | C | 279 | 36.090 | 13.861 | 9.577 | 1.00 | 38.30 | C |
| ATOM | 7056 | O | PRO | C | 279 | 36.245 | 14.640 | 10.512 | 1.00 | 38.95 | O |
| ATOM | 7057 | N | GLY | C | 280 | 36.668 | 12.665 | 9.524 | 1.00 | 39.18 | N |
| ATOM | 7059 | CA | GLY | C | 280 | 37.557 | 12.188 | 10.566 | 1.00 | 39.84 | C |
| ATOM | 7062 | C | GLY | C | 280 | 36.841 | 11.400 | 11.643 | 1.00 | 40.42 | C |
| ATOM | 7063 | O | GLY | C | 280 | 37.403 | 11.148 | 12.712 | 1.00 | 40.56 | O |
| ATOM | 7064 | N | VAL | C | 281 | 35.604 | 11.008 | 11.357 | 1.00 | 41.00 | N |

TABLE 2-continued

| ATOM | 7066 | CA | VAL | C | 281 | 34.800 | 10.229 | 12.291 | 1.00 | 41.48 | C |
| --- | --- | --- | --- | --- | --- | --- | --- | --- | --- | --- | --- |
| ATOM | 7068 | CB | VAL | C | 281 | 33.712 | 11.104 | 12.966 | 1.00 | 41.61 | C |
| ATOM | 7070 | CG1 | VAL | C | 281 | 34.359 | 12.104 | 13.914 | 1.00 | 41.75 | C |
| ATOM | 7074 | CG2 | VAL | C | 281 | 32.867 | 11.844 | 11.932 | 1.00 | 41.61 | C |
| ATOM | 7078 | C | VAL | C | 281 | 34.190 | 9.021 | 11.575 | 1.00 | 41.69 | C |
| ATOM | 7079 | O | VAL | C | 281 | 33.939 | 9.069 | 10.374 | 1.00 | 41.83 | O |
| ATOM | 7080 | N | SER | C | 282 | 33.968 | 7.940 | 12.319 | 1.00 | 41.89 | N |
| ATOM | 7082 | CA | SER | C | 282 | 33.423 | 6.693 | 11.774 | 1.00 | 41.96 | C |
| ATOM | 7084 | CB | SER | C | 282 | 33.602 | 5.562 | 12.788 | 1.00 | 42.06 | C |
| ATOM | 7087 | OG | SER | C | 282 | 32.854 | 5.818 | 13.972 | 1.00 | 42.25 | O |
| ATOM | 7089 | C | SER | C | 282 | 31.944 | 6.788 | 11.411 | 1.00 | 41.90 | C |
| ATOM | 7090 | O | SER | C | 282 | 31.271 | 7.758 | 11.748 | 1.00 | 41.95 | O |
| ATOM | 7091 | N | ASN | C | 283 | 31.447 | 5.761 | 10.730 | 1.00 | 42.00 | N |
| ATOM | 7093 | CA | ASN | C | 283 | 30.045 | 5.702 | 10.329 | 1.00 | 41.86 | C |
| ATOM | 7095 | CB | ASN | C | 283 | 29.790 | 4.494 | 9.418 | 1.00 | 41.51 | C |
| ATOM | 7098 | CG | ASN | C | 283 | 30.077 | 4.796 | 7.953 | 1.00 | 40.00 | C |
| ATOM | 7099 | OD1 | ASN | C | 283 | 29.983 | 5.937 | 7.523 | 1.00 | 36.93 | O |
| ATOM | 7100 | ND2 | ASN | C | 283 | 30.431 | 3.771 | 7.191 | 1.00 | 36.05 | N |
| ATOM | 7103 | C | ASN | C | 283 | 29.115 | 5.636 | 11.529 | 1.00 | 42.59 | C |
| ATOM | 7104 | O | ASN | C | 283 | 28.049 | 6.253 | 11.525 | 1.00 | 42.71 | O |
| ATOM | 7105 | N | GLN | C | 284 | 29.527 | 4.893 | 12.555 | 1.00 | 43.14 | N |
| ATOM | 7107 | CA | GLN | C | 284 | 28.725 | 4.737 | 13.762 | 1.00 | 43.66 | C |
| ATOM | 7109 | CB | GLN | C | 284 | 29.326 | 3.668 | 14.687 | 1.00 | 43.95 | C |
| ATOM | 7112 | CG | GLN | C | 284 | 28.371 | 3.158 | 15.771 | 1.00 | 45.00 | C |
| ATOM | 7115 | CD | GLN | C | 284 | 27.046 | 2.664 | 15.205 | 1.00 | 46.22 | C |
| ATOM | 7116 | OE1 | GLN | C | 284 | 27.015 | 1.707 | 14.433 | 1.00 | 47.52 | O |
| ATOM | 7117 | NE2 | GLN | C | 284 | 25.955 | 3.324 | 15.579 | 1.00 | 47.37 | N |
| ATOM | 7120 | C | GLN | C | 284 | 28.568 | 6.057 | 14.510 | 1.00 | 43.62 | C |
| ATOM | 7121 | O | GLN | C | 284 | 27.525 | 6.303 | 15.102 | 1.00 | 43.77 | O |
| ATOM | 7122 | N | PHE | C | 285 | 29.599 | 6.898 | 14.478 | 1.00 | 43.68 | N |
| ATOM | 7124 | CA | PHE | C | 285 | 29.555 | 8.204 | 15.132 | 1.00 | 43.67 | C |
| ATOM | 7126 | CB | PHE | C | 285 | 30.928 | 8.881 | 15.087 | 1.00 | 43.60 | C |
| ATOM | 7129 | CG | PHE | C | 285 | 30.953 | 10.238 | 15.737 | 1.00 | 43.39 | C |
| ATOM | 7130 | CD1 | PHE | C | 285 | 30.765 | 11.389 | 14.983 | 1.00 | 42.95 | C |
| ATOM | 7132 | CE1 | PHE | C | 285 | 30.782 | 12.642 | 15.581 | 1.00 | 43.15 | C |
| ATOM | 7134 | CZ | PHE | C | 285 | 30.983 | 12.754 | 16.947 | 1.00 | 43.13 | C |
| ATOM | 7136 | CE2 | PHE | C | 285 | 31.167 | 11.611 | 17.714 | 1.00 | 43.41 | C |
| ATOM | 7138 | CD2 | PHE | C | 285 | 31.149 | 10.360 | 17.109 | 1.00 | 43.40 | C |
| ATOM | 7140 | C | PHE | C | 285 | 28.532 | 9.123 | 14.476 | 1.00 | 43.83 | C |
| ATOM | 7141 | O | PHE | C | 285 | 27.789 | 9.823 | 15.159 | 1.00 | 43.94 | O |
| ATOM | 7142 | N | LEU | C | 286 | 28.517 | 9.128 | 13.146 | 1.00 | 44.01 | N |
| ATOM | 7144 | CA | LEU | C | 286 | 27.596 | 9.957 | 12.379 | 1.00 | 44.15 | C |
| ATOM | 7146 | CB | LEU | C | 286 | 27.935 | 9.874 | 10.886 | 1.00 | 44.19 | C |
| ATOM | 7149 | CG | LEU | C | 286 | 29.305 | 10.451 | 10.507 | 1.00 | 43.98 | C |
| ATOM | 7151 | CD1 | LEU | C | 286 | 29.804 | 9.842 | 9.216 | 1.00 | 44.22 | C |
| ATOM | 7155 | CD2 | LEU | C | 286 | 29.254 | 11.968 | 10.400 | 1.00 | 43.94 | C |
| ATOM | 7159 | C | LEU | C | 286 | 26.144 | 9.545 | 12.615 | 1.00 | 44.35 | C |
| ATOM | 7160 | O | LEU | C | 286 | 25.259 | 10.392 | 12.663 | 1.00 | 44.52 | O |
| ATOM | 7161 | N | ILE | C | 287 | 25.905 | 8.246 | 12.767 | 1.00 | 44.58 | N |
| ATOM | 7163 | CA | ILE | C | 287 | 24.557 | 7.734 | 13.006 | 1.00 | 44.86 | C |
| ATOM | 7165 | CB | ILE | C | 287 | 24.500 | 6.197 | 12.774 | 1.00 | 44.82 | C |
| ATOM | 7167 | CG1 | ILE | C | 287 | 24.805 | 5.856 | 11.307 | 1.00 | 44.77 | C |
| ATOM | 7170 | CD1 | ILE | C | 287 | 25.275 | 4.424 | 11.087 | 1.00 | 44.52 | C |
| ATOM | 7174 | CG2 | ILE | C | 287 | 23.130 | 5.633 | 13.171 | 1.00 | 44.70 | C |
| ATOM | 7178 | C | ILE | C | 287 | 24.079 | 8.089 | 14.426 | 1.00 | 45.30 | C |
| ATOM | 7179 | O | ILE | C | 287 | 22.939 | 8.522 | 14.605 | 1.00 | 45.27 | O |
| ATOM | 7180 | N | ASN | C | 288 | 24.954 | 7.919 | 15.420 | 1.00 | 45.62 | N |
| ATOM | 7182 | CA | ASN | C | 288 | 24.615 | 8.198 | 16.822 | 1.00 | 46.00 | C |
| ATOM | 7184 | CB | ASN | C | 288 | 25.712 | 7.685 | 17.767 | 1.00 | 46.00 | C |
| ATOM | 7187 | CG | ASN | C | 288 | 25.862 | 6.174 | 17.738 | 1.00 | 46.04 | C |
| ATOM | 7188 | OD1 | ASN | C | 288 | 24.956 | 5.449 | 17.324 | 1.00 | 46.59 | O |
| ATOM | 7189 | ND2 | ASN | C | 288 | 27.021 | 5.692 | 18.173 | 1.00 | 45.40 | N |
| ATOM | 7192 | C | ASN | C | 288 | 24.368 | 9.679 | 17.111 | 1.00 | 46.27 | C |
| ATOM | 7193 | O | ASN | C | 288 | 23.579 | 10.012 | 17.990 | 1.00 | 46.41 | O |
| ATOM | 7194 | N | THR | C | 289 | 25.035 | 10.561 | 16.368 | 1.00 | 46.66 | N |
| ATOM | 7196 | CA | THR | C | 289 | 24.886 | 12.010 | 16.557 | 1.00 | 46.85 | C |
| ATOM | 7198 | CB | THR | C | 289 | 26.236 | 12.730 | 16.346 | 1.00 | 46.93 | C |
| ATOM | 7200 | OG1 | THR | C | 289 | 26.803 | 12.358 | 15.082 | 1.00 | 46.95 | O |
| ATOM | 7202 | CG2 | THR | C | 289 | 27.261 | 12.277 | 17.374 | 1.00 | 47.06 | C |
| ATOM | 7206 | C | THR | C | 289 | 23.841 | 12.625 | 15.631 | 1.00 | 46.85 | C |
| ATOM | 7207 | O | THR | C | 289 | 23.689 | 13.847 | 15.592 | 1.00 | 46.85 | O |
| ATOM | 7208 | N | ASN | C | 290 | 23.125 | 11.779 | 14.894 | 1.00 | 47.00 | N |
| ATOM | 7210 | CA | ASN | C | 290 | 22.097 | 12.218 | 13.951 | 1.00 | 47.09 | C |
| ATOM | 7212 | CB | ASN | C | 290 | 20.851 | 12.713 | 14.698 | 1.00 | 47.21 | C |
| ATOM | 7215 | CG | ASN | C | 290 | 20.303 | 11.681 | 15.671 | 1.00 | 47.56 | C |
| ATOM | 7216 | OD1 | ASN | C | 290 | 19.847 | 10.614 | 15.263 | 1.00 | 48.04 | O |
| ATOM | 7217 | ND2 | ASN | C | 290 | 20.346 | 11.996 | 16.965 | 1.00 | 47.58 | N |
| ATOM | 7220 | C | ASN | C | 290 | 22.617 | 13.290 | 12.994 | 1.00 | 46.85 | C |
| ATOM | 7221 | O | ASN | C | 290 | 21.938 | 14.278 | 12.724 | 1.00 | 47.08 | O |

TABLE 2-continued

| ATOM | 7222 | N | SER | C | 291 | 23.834 | 13.091 | 12.501 | 1.00 | 46.59 | N |
|---|---|---|---|---|---|---|---|---|---|---|---|
| ATOM | 7224 | CA | SER | C | 291 | 24.457 | 14.021 | 11.560 | 1.00 | 46.58 | C |
| ATOM | 7226 | CB | SER | C | 291 | 25.882 | 13.575 | 11.236 | 1.00 | 46.55 | C |
| ATOM | 7229 | OG | SER | C | 291 | 25.869 | 12.311 | 10.597 | 1.00 | 46.98 | O |
| ATOM | 7231 | C | SER | C | 291 | 23.655 | 14.092 | 10.269 | 1.00 | 46.23 | C |
| ATOM | 7232 | O | SER | C | 291 | 22.884 | 13.191 | 9.966 | 1.00 | 45.98 | O |
| ATOM | 7233 | N | GLU | C | 292 | 23.845 | 15.167 | 9.512 | 1.00 | 46.16 | N |
| ATOM | 7235 | CA | GLU | C | 292 | 23.128 | 15.351 | 8.249 | 1.00 | 46.20 | C |
| ATOM | 7237 | CB | GLU | C | 292 | 23.453 | 16.715 | 7.618 | 1.00 | 46.46 | C |
| ATOM | 7240 | CG | GLU | C | 292 | 22.682 | 17.882 | 8.230 | 1.00 | 47.74 | C |
| ATOM | 7243 | CD | GLU | C | 292 | 21.204 | 17.888 | 7.858 | 1.00 | 48.97 | C |
| ATOM | 7244 | OE1 | GLU | C | 292 | 20.884 | 17.892 | 6.646 | 1.00 | 49.52 | O |
| ATOM | 7245 | OE2 | GLU | C | 292 | 20.359 | 17.893 | 8.781 | 1.00 | 49.48 | O |
| ATOM | 7246 | C | GLU | C | 292 | 23.404 | 14.223 | 7.250 | 1.00 | 45.53 | C |
| ATOM | 7247 | O | GLU | C | 292 | 22.518 | 13.845 | 6.493 | 1.00 | 45.49 | O |
| ATOM | 7248 | N | LEU | C | 293 | 24.624 | 13.687 | 7.269 | 1.00 | 45.05 | N |
| ATOM | 7250 | CA | LEU | C | 293 | 25.021 | 12.607 | 6.361 | 1.00 | 44.52 | C |
| ATOM | 7252 | CB | LEU | C | 293 | 26.541 | 12.391 | 6.406 | 1.00 | 44.52 | C |
| ATOM | 7255 | CG | LEU | C | 293 | 27.404 | 13.329 | 5.567 | 1.00 | 44.49 | C |
| ATOM | 7257 | CD1 | LEU | C | 293 | 28.869 | 13.092 | 5.884 | 1.00 | 44.54 | C |
| ATOM | 7261 | CD2 | LEU | C | 293 | 27.134 | 13.149 | 4.062 | 1.00 | 44.38 | C |
| ATOM | 7265 | C | LEU | C | 293 | 24.320 | 11.286 | 6.658 | 1.00 | 44.15 | C |
| ATOM | 7266 | O | LEU | C | 293 | 23.975 | 10.549 | 5.737 | 1.00 | 44.02 | O |
| ATOM | 7267 | N | ALA | C | 294 | 24.136 | 10.976 | 7.940 | 1.00 | 43.71 | N |
| ATOM | 7269 | CA | ALA | C | 294 | 23.461 | 9.746 | 8.343 | 1.00 | 43.31 | C |
| ATOM | 7271 | CB | ALA | C | 294 | 23.651 | 9.496 | 9.827 | 1.00 | 43.44 | C |
| ATOM | 7275 | C | ALA | C | 294 | 21.975 | 9.803 | 7.989 | 1.00 | 43.07 | C |
| ATOM | 7276 | O | ALA | C | 294 | 21.386 | 8.794 | 7.620 | 1.00 | 42.99 | O |
| ATOM | 7277 | N | LEU | C | 295 | 21.379 | 10.988 | 8.105 | 1.00 | 42.85 | N |
| ATOM | 7279 | CA | LEU | C | 295 | 19.973 | 11.186 | 7.760 | 1.00 | 42.88 | C |
| ATOM | 7281 | CB | LEU | C | 295 | 19.463 | 12.538 | 8.284 | 1.00 | 43.00 | C |
| ATOM | 7284 | CG | LEU | C | 295 | 18.885 | 12.624 | 9.711 | 1.00 | 43.85 | C |
| ATOM | 7286 | CD1 | LEU | C | 295 | 19.431 | 11.555 | 10.654 | 1.00 | 44.54 | C |
| ATOM | 7290 | CD2 | LEU | C | 295 | 19.136 | 14.009 | 10.296 | 1.00 | 44.21 | C |
| ATOM | 7294 | C | LEU | C | 295 | 19.795 | 11.111 | 6.240 | 1.00 | 42.66 | C |
| ATOM | 7295 | O | LEU | C | 295 | 18.785 | 10.612 | 5.746 | 1.00 | 42.51 | O |
| ATOM | 7296 | N | MET | C | 296 | 20.797 | 11.582 | 5.511 | 1.00 | 42.36 | N |
| ATOM | 7298 | CA | MET | C | 296 | 20.763 | 11.585 | 4.055 | 1.00 | 42.40 | C |
| ATOM | 7300 | CB | MET | C | 296 | 21.942 | 12.393 | 3.519 | 1.00 | 42.75 | C |
| ATOM | 7303 | CG | MET | C | 296 | 22.106 | 12.335 | 2.012 | 1.00 | 44.57 | C |
| ATOM | 7306 | SD | MET | C | 296 | 23.038 | 13.737 | 1.425 | 1.00 | 48.52 | S |
| ATOM | 7307 | CE | MET | C | 296 | 21.800 | 15.050 | 1.609 | 1.00 | 48.38 | C |
| ATOM | 7311 | C | MET | C | 296 | 20.808 | 10.175 | 3.476 | 1.00 | 41.57 | C |
| ATOM | 7312 | O | MET | C | 296 | 20.010 | 9.835 | 2.610 | 1.00 | 41.26 | O |
| ATOM | 7313 | N | TYR | C | 297 | 21.719 | 9.356 | 3.996 | 1.00 | 40.79 | N |
| ATOM | 7315 | CA | TYR | C | 297 | 21.948 | 7.998 | 3.499 | 1.00 | 39.94 | C |
| ATOM | 7317 | CB | TYR | C | 297 | 23.457 | 7.761 | 3.388 | 1.00 | 39.38 | C |
| ATOM | 7320 | CG | TYR | C | 297 | 24.065 | 8.604 | 2.303 | 1.00 | 36.92 | C |
| ATOM | 7321 | CD1 | TYR | C | 297 | 23.717 | 8.395 | 0.972 | 1.00 | 34.93 | C |
| ATOM | 7323 | CE1 | TYR | C | 297 | 24.244 | 9.169 | −0.040 | 1.00 | 33.03 | C |
| ATOM | 7325 | CZ | TYR | C | 297 | 25.137 | 10.171 | 0.267 | 1.00 | 32.57 | C |
| ATOM | 7326 | OH | TYR | C | 297 | 25.658 | 10.938 | −0.737 | 1.00 | 30.75 | O |
| ATOM | 7328 | CE2 | TYR | C | 297 | 25.501 | 10.410 | 1.587 | 1.00 | 33.01 | C |
| ATOM | 7330 | CD2 | TYR | C | 297 | 24.957 | 9.629 | 2.596 | 1.00 | 34.70 | C |
| ATOM | 7332 | C | TYR | C | 297 | 21.282 | 6.880 | 4.302 | 1.00 | 40.13 | C |
| ATOM | 7333 | O | TYR | C | 297 | 21.551 | 5.702 | 4.071 | 1.00 | 39.99 | O |
| ATOM | 7334 | N | ASN | C | 298 | 20.402 | 7.247 | 5.227 | 1.00 | 40.34 | N |
| ATOM | 7336 | CA | ASN | C | 298 | 19.657 | 6.268 | 6.014 | 1.00 | 40.45 | C |
| ATOM | 7338 | CB | ASN | C | 298 | 18.629 | 5.566 | 5.105 | 1.00 | 40.37 | C |
| ATOM | 7341 | CG | ASN | C | 298 | 17.889 | 6.539 | 4.184 | 1.00 | 40.08 | C |
| ATOM | 7342 | OD1 | ASN | C | 298 | 17.216 | 7.457 | 4.640 | 1.00 | 38.42 | O |
| ATOM | 7343 | ND2 | ASN | C | 298 | 18.014 | 6.331 | 2.878 | 1.00 | 40.93 | N |
| ATOM | 7346 | C | ASN | C | 298 | 20.528 | 5.234 | 6.774 | 1.00 | 40.54 | C |
| ATOM | 7347 | O | ASN | C | 298 | 20.181 | 4.055 | 6.850 | 1.00 | 40.61 | O |
| ATOM | 7348 | N | ASP | C | 299 | 21.659 | 5.690 | 7.314 | 1.00 | 40.61 | N |
| ATOM | 7350 | CA | ASP | C | 299 | 22.582 | 4.862 | 8.117 | 1.00 | 40.81 | C |
| ATOM | 7352 | CB | ASP | C | 299 | 21.875 | 4.288 | 9.360 | 1.00 | 40.81 | C |
| ATOM | 7355 | CG | ASP | C | 299 | 21.113 | 5.333 | 10.145 | 1.00 | 40.65 | C |
| ATOM | 7356 | OD1 | ASP | C | 299 | 21.604 | 6.469 | 10.280 | 1.00 | 39.79 | O |
| ATOM | 7357 | OD2 | ASP | C | 299 | 20.006 | 5.099 | 10.672 | 1.00 | 42.16 | O |
| ATOM | 7358 | C | ASP | C | 299 | 23.294 | 3.710 | 7.393 | 1.00 | 40.98 | C |
| ATOM | 7359 | O | ASP | C | 299 | 23.932 | 2.884 | 8.050 | 1.00 | 40.70 | O |
| ATOM | 7360 | N | GLU | C | 300 | 23.206 | 3.663 | 6.063 | 1.00 | 41.25 | N |
| ATOM | 7362 | CA | GLU | C | 300 | 23.824 | 2.595 | 5.273 | 1.00 | 41.57 | C |
| ATOM | 7364 | CB | GLU | C | 300 | 22.787 | 1.985 | 4.317 | 1.00 | 41.91 | C |
| ATOM | 7367 | CG | GLU | C | 300 | 23.295 | 0.884 | 3.386 | 1.00 | 43.68 | C |
| ATOM | 7370 | CD | GLU | C | 300 | 24.024 | −0.242 | 4.105 | 1.00 | 46.21 | C |
| ATOM | 7371 | OE1 | GLU | C | 300 | 23.554 | −0.674 | 5.180 | 1.00 | 47.85 | O |
| ATOM | 7372 | OE2 | GLU | C | 300 | 25.070 | −0.704 | 3.593 | 1.00 | 48.46 | O |

TABLE 2-continued

| ATOM | 7373 | C | GLU | C | 300 | 25.026 | 3.134 | 4.498 | 1.00 | 41.19 | C |
| ATOM | 7374 | O | GLU | C | 300 | 24.870 | 3.965 | 3.601 | 1.00 | 41.40 | O |
| ATOM | 7375 | N | SER | C | 301 | 26.221 | 2.654 | 4.848 | 1.00 | 40.67 | N |
| ATOM | 7377 | CA | SER | C | 301 | 27.461 | 3.093 | 4.211 | 1.00 | 40.35 | C |
| ATOM | 7379 | CB | SER | C | 301 | 27.664 | 2.374 | 2.870 | 1.00 | 40.29 | C |
| ATOM | 7382 | OG | SER | C | 301 | 27.932 | 0.995 | 3.067 | 1.00 | 40.23 | O |
| ATOM | 7384 | C | SER | C | 301 | 27.425 | 4.609 | 4.024 | 1.00 | 40.02 | C |
| ATOM | 7385 | O | SER | C | 301 | 27.569 | 5.121 | 2.910 | 1.00 | 40.05 | O |
| ATOM | 7386 | N | VAL | C | 302 | 27.229 | 5.314 | 5.135 | 1.00 | 39.31 | N |
| ATOM | 7388 | CA | VAL | C | 302 | 27.085 | 6.768 | 5.142 | 1.00 | 38.93 | C |
| ATOM | 7390 | CB | VAL | C | 302 | 26.894 | 7.311 | 6.589 | 1.00 | 38.89 | C |
| ATOM | 7392 | CG1 | VAL | C | 302 | 26.868 | 8.835 | 6.608 | 1.00 | 38.97 | C |
| ATOM | 7396 | CG2 | VAL | C | 302 | 25.614 | 6.758 | 7.201 | 1.00 | 39.29 | C |
| ATOM | 7400 | C | VAL | C | 302 | 28.265 | 7.475 | 4.492 | 1.00 | 38.45 | C |
| ATOM | 7401 | O | VAL | C | 302 | 28.094 | 8.223 | 3.530 | 1.00 | 38.70 | O |
| ATOM | 7402 | N | LEU | C | 303 | 29.459 | 7.220 | 5.014 | 1.00 | 37.78 | N |
| ATOM | 7404 | CA | LEU | C | 303 | 30.675 | 7.866 | 4.531 | 1.00 | 37.28 | C |
| ATOM | 7406 | CB | LEU | C | 303 | 31.852 | 7.555 | 5.458 | 1.00 | 37.19 | C |
| ATOM | 7409 | CG | LEU | C | 303 | 31.878 | 8.397 | 6.728 | 1.00 | 38.37 | C |
| ATOM | 7411 | CD1 | LEU | C | 303 | 32.596 | 7.696 | 7.884 | 1.00 | 38.92 | C |
| ATOM | 7415 | CD2 | LEU | C | 303 | 32.508 | 9.742 | 6.439 | 1.00 | 39.29 | C |
| ATOM | 7419 | C | LEU | C | 303 | 31.049 | 7.449 | 3.120 | 1.00 | 36.52 | C |
| ATOM | 7420 | O | LEU | C | 303 | 31.500 | 8.267 | 2.335 | 1.00 | 36.50 | O |
| ATOM | 7421 | N | GLU | C | 304 | 30.832 | 6.176 | 2.812 | 1.00 | 35.64 | N |
| ATOM | 7423 | CA | GLU | C | 304 | 31.240 | 5.589 | 1.542 | 1.00 | 34.93 | C |
| ATOM | 7425 | CB | GLU | C | 304 | 31.252 | 4.059 | 1.654 | 1.00 | 34.56 | C |
| ATOM | 7428 | CG | GLU | C | 304 | 32.380 | 3.516 | 2.530 | 1.00 | 33.33 | C |
| ATOM | 7431 | CD | GLU | C | 304 | 32.169 | 3.720 | 4.037 | 1.00 | 31.98 | C |
| ATOM | 7432 | OE1 | GLU | C | 304 | 31.005 | 3.811 | 4.492 | 1.00 | 28.83 | O |
| ATOM | 7433 | OE2 | GLU | C | 304 | 33.183 | 3.780 | 4.773 | 1.00 | 30.24 | O |
| ATOM | 7434 | C | GLU | C | 304 | 30.375 | 6.064 | 0.379 | 1.00 | 34.71 | C |
| ATOM | 7435 | O | GLU | C | 304 | 30.880 | 6.298 | −0.720 | 1.00 | 34.88 | O |
| ATOM | 7436 | N | ASN | C | 305 | 29.072 | 6.183 | 0.622 | 1.00 | 34.33 | N |
| ATOM | 7438 | CA | ASN | C | 305 | 28.152 | 6.710 | −0.372 | 1.00 | 33.81 | C |
| ATOM | 7440 | CB | ASN | C | 305 | 26.699 | 6.658 | 0.111 | 1.00 | 33.84 | C |
| ATOM | 7443 | CG | ASN | C | 305 | 26.002 | 5.369 | −0.247 | 1.00 | 33.67 | C |
| ATOM | 7444 | OD1 | ASN | C | 305 | 25.724 | 5.107 | −1.415 | 1.00 | 34.39 | O |
| ATOM | 7445 | ND2 | ASN | C | 305 | 25.687 | 4.565 | 0.762 | 1.00 | 33.83 | N |
| ATOM | 7448 | C | ASN | C | 305 | 28.523 | 8.162 | −0.646 | 1.00 | 33.61 | C |
| ATOM | 7449 | O | ASN | C | 305 | 28.505 | 8.602 | −1.801 | 1.00 | 33.66 | O |
| ATOM | 7450 | N | HIS | C | 306 | 28.864 | 8.893 | 0.418 | 1.00 | 32.76 | N |
| ATOM | 7452 | CA | HIS | C | 306 | 29.229 | 10.308 | 0.311 | 1.00 | 32.30 | C |
| ATOM | 7454 | CB | HIS | C | 306 | 29.320 | 10.977 | 1.688 | 1.00 | 31.90 | C |
| ATOM | 7457 | CG | HIS | C | 306 | 29.805 | 12.392 | 1.627 | 1.00 | 29.40 | C |
| ATOM | 7458 | ND1 | HIS | C | 306 | 28.991 | 13.440 | 1.255 | 1.00 | 26.58 | N |
| ATOM | 7460 | CE1 | HIS | C | 306 | 29.684 | 14.564 | 1.277 | 1.00 | 26.22 | C |
| ATOM | 7462 | NE2 | HIS | C | 306 | 30.925 | 14.281 | 1.629 | 1.00 | 26.89 | N |
| ATOM | 7464 | CD2 | HIS | C | 306 | 31.029 | 12.927 | 1.844 | 1.00 | 28.03 | C |
| ATOM | 7466 | C | HIS | C | 306 | 30.543 | 10.544 | −0.409 | 1.00 | 32.52 | C |
| ATOM | 7467 | O | HIS | C | 306 | 30.719 | 11.584 | −1.034 | 1.00 | 32.43 | O |
| ATOM | 7468 | N | HIS | C | 307 | 31.475 | 9.605 | −0.281 | 1.00 | 33.04 | N |
| ATOM | 7470 | CA | HIS | C | 307 | 32.770 | 9.706 | −0.949 | 1.00 | 33.48 | C |
| ATOM | 7472 | CB | HIS | C | 307 | 33.719 | 8.609 | −0.462 | 1.00 | 33.52 | C |
| ATOM | 7475 | CG | HIS | C | 307 | 34.078 | 8.708 | 0.991 | 1.00 | 33.22 | C |
| ATOM | 7476 | ND1 | HIS | C | 307 | 34.431 | 7.611 | 1.747 | 1.00 | 33.37 | N |
| ATOM | 7478 | CE1 | HIS | C | 307 | 34.697 | 7.995 | 2.982 | 1.00 | 33.07 | C |
| ATOM | 7480 | NE2 | HIS | C | 307 | 34.524 | 9.301 | 3.057 | 1.00 | 32.68 | N |
| ATOM | 7482 | CD2 | HIS | C | 307 | 34.132 | 9.769 | 1.828 | 1.00 | 32.75 | C |
| ATOM | 7484 | C | HIS | C | 307 | 32.566 | 9.572 | −2.465 | 1.00 | 34.16 | C |
| ATOM | 7485 | O | HIS | C | 307 | 33.229 | 10.246 | −3.252 | 1.00 | 34.36 | O |
| ATOM | 7486 | N | LEU | C | 308 | 31.639 | 8.703 | −2.856 | 1.00 | 34.73 | N |
| ATOM | 7488 | CA | LEU | C | 308 | 31.320 | 8.476 | −4.263 | 1.00 | 35.43 | C |
| ATOM | 7490 | CB | LEU | C | 308 | 30.479 | 7.212 | −4.433 | 1.00 | 35.19 | C |
| ATOM | 7493 | CG | LEU | C | 308 | 31.228 | 5.888 | −4.383 | 1.00 | 35.33 | C |
| ATOM | 7495 | CD1 | LEU | C | 308 | 30.259 | 4.752 | −4.083 | 1.00 | 35.06 | C |
| ATOM | 7499 | CD2 | LEU | C | 308 | 31.962 | 5.653 | −5.704 | 1.00 | 35.92 | C |
| ATOM | 7503 | C | LEU | C | 308 | 30.552 | 9.652 | −4.837 | 1.00 | 35.92 | C |
| ATOM | 7504 | O | LEU | C | 308 | 30.723 | 9.991 | −6.000 | 1.00 | 35.88 | O |
| ATOM | 7505 | N | ALA | C | 309 | 29.712 | 10.274 | −4.011 | 1.00 | 36.58 | N |
| ATOM | 7507 | CA | ALA | C | 309 | 28.884 | 11.398 | −4.448 | 1.00 | 36.93 | C |
| ATOM | 7509 | CB | ALA | C | 309 | 27.789 | 11.692 | −3.425 | 1.00 | 36.75 | C |
| ATOM | 7513 | C | ALA | C | 309 | 29.724 | 12.642 | −4.703 | 1.00 | 37.40 | C |
| ATOM | 7514 | O | ALA | C | 309 | 29.457 | 13.386 | −5.642 | 1.00 | 37.64 | O |
| ATOM | 7515 | N | VAL | C | 310 | 30.742 | 12.852 | −3.874 | 1.00 | 37.88 | N |
| ATOM | 7517 | CA | VAL | C | 310 | 31.627 | 14.003 | −4.006 | 1.00 | 38.21 | C |
| ATOM | 7519 | CB | VAL | C | 310 | 32.440 | 14.230 | −2.719 | 1.00 | 38.02 | C |
| ATOM | 7521 | CG1 | VAL | C | 310 | 33.495 | 15.315 | −2.916 | 1.00 | 37.60 | C |
| ATOM | 7525 | CG2 | VAL | C | 310 | 31.513 | 14.593 | −1.552 | 1.00 | 38.30 | C |
| ATOM | 7529 | C | VAL | C | 310 | 32.590 | 13.824 | −5.178 | 1.00 | 38.79 | C |

TABLE 2-continued

| | | | | | | | | | | | |
|---|---|---|---|---|---|---|---|---|---|---|---|
| ATOM | 7530 | O | VAL | C | 310 | 32.941 | 14.792 | −5.850 | 1.00 | 38.57 | O |
| ATOM | 7531 | N | GLY | C | 311 | 33.023 | 12.590 | −5.405 | 1.00 | 39.58 | N |
| ATOM | 7533 | CA | GLY | C | 311 | 33.960 | 12.285 | −6.469 | 1.00 | 40.42 | C |
| ATOM | 7536 | C | GLY | C | 311 | 33.363 | 12.466 | −7.849 | 1.00 | 41.14 | C |
| ATOM | 7537 | O | GLY | C | 311 | 34.014 | 12.998 | −8.742 | 1.00 | 41.16 | O |
| ATOM | 7538 | N | PHE | C | 312 | 32.115 | 12.040 | −8.007 | 1.00 | 42.30 | N |
| ATOM | 7540 | CA | PHE | C | 312 | 31.411 | 12.129 | −9.285 | 1.00 | 43.36 | C |
| ATOM | 7542 | CB | PHE | C | 312 | 30.340 | 11.039 | −9.385 | 1.00 | 43.18 | C |
| ATOM | 7545 | CG | PHE | C | 312 | 30.879 | 9.707 | −9.816 | 1.00 | 42.56 | C |
| ATOM | 7546 | CD1 | PHE | C | 312 | 31.077 | 9.429 | −11.163 | 1.00 | 41.53 | C |
| ATOM | 7548 | CE1 | PHE | C | 312 | 31.573 | 8.206 | −11.567 | 1.00 | 41.20 | C |
| ATOM | 7550 | CZ | PHE | C | 312 | 31.888 | 7.243 | −10.628 | 1.00 | 41.59 | C |
| ATOM | 7552 | CE2 | PHE | C | 312 | 31.699 | 7.507 | −9.278 | 1.00 | 41.92 | C |
| ATOM | 7554 | CD2 | PHE | C | 312 | 31.200 | 8.734 | −8.880 | 1.00 | 41.71 | C |
| ATOM | 7556 | C | PHE | C | 312 | 30.795 | 13.503 | −9.529 | 1.00 | 44.65 | C |
| ATOM | 7557 | O | PHE | C | 312 | 30.605 | 13.892 | −10.678 | 1.00 | 44.44 | O |
| ATOM | 7558 | N | LYS | C | 313 | 30.480 | 14.235 | −8.458 | 1.00 | 46.23 | N |
| ATOM | 7560 | CA | LYS | C | 313 | 29.914 | 15.578 | −8.602 | 1.00 | 47.65 | C |
| ATOM | 7562 | CB | LYS | C | 313 | 29.261 | 16.067 | −7.305 | 1.00 | 47.87 | C |
| ATOM | 7565 | CG | LYS | C | 313 | 27.795 | 15.660 | −7.169 | 1.00 | 48.99 | C |
| ATOM | 7568 | CD | LYS | C | 313 | 27.288 | 15.794 | −5.729 | 1.00 | 49.91 | C |
| ATOM | 7571 | CE | LYS | C | 313 | 25.987 | 15.027 | −5.526 | 1.00 | 50.26 | C |
| ATOM | 7574 | NZ | LYS | C | 313 | 25.460 | 15.192 | −4.146 | 1.00 | 50.71 | N |
| ATOM | 7578 | C | LYS | C | 313 | 30.984 | 16.568 | −9.056 | 1.00 | 48.57 | C |
| ATOM | 7579 | O | LYS | C | 313 | 30.662 | 17.611 | −9.621 | 1.00 | 48.65 | O |
| ATOM | 7580 | N | LEU | C | 314 | 32.250 | 16.239 | −8.806 | 1.00 | 49.82 | N |
| ATOM | 7582 | CA | LEU | C | 314 | 33.362 | 17.091 | −9.221 | 1.00 | 50.88 | C |
| ATOM | 7584 | CB | LEU | C | 314 | 34.608 | 16.798 | −8.381 | 1.00 | 50.82 | C |
| ATOM | 7587 | CG | LEU | C | 314 | 34.552 | 17.328 | −6.944 | 1.00 | 50.90 | C |
| ATOM | 7589 | CD1 | LEU | C | 314 | 35.683 | 16.737 | −6.114 | 1.00 | 50.97 | C |
| ATOM | 7593 | CD2 | LEU | C | 314 | 34.598 | 18.851 | −6.901 | 1.00 | 50.98 | C |
| ATOM | 7597 | C | LEU | C | 314 | 33.671 | 16.965 | −10.722 | 1.00 | 51.92 | C |
| ATOM | 7598 | O | LEU | C | 314 | 34.411 | 17.781 | −11.271 | 1.00 | 52.05 | O |
| ATOM | 7599 | N | LEU | C | 315 | 33.104 | 15.948 | −11.373 | 1.00 | 53.27 | N |
| ATOM | 7601 | CA | LEU | C | 315 | 33.257 | 15.746 | −12.818 | 1.00 | 54.42 | C |
| ATOM | 7603 | CB | LEU | C | 315 | 33.228 | 14.251 | −13.156 | 1.00 | 54.25 | C |
| ATOM | 7606 | CG | LEU | C | 315 | 34.231 | 13.324 | −12.473 | 1.00 | 53.79 | C |
| ATOM | 7608 | CD1 | LEU | C | 315 | 33.753 | 11.884 | −12.583 | 1.00 | 53.39 | C |
| ATOM | 7612 | CD2 | LEU | C | 315 | 35.610 | 13.479 | −13.085 | 1.00 | 53.23 | C |
| ATOM | 7616 | C | LEU | C | 315 | 32.144 | 16.431 | −13.622 | 1.00 | 55.72 | C |
| ATOM | 7617 | O | LEU | C | 315 | 32.034 | 16.219 | −14.833 | 1.00 | 55.97 | O |
| ATOM | 7618 | N | GLN | C | 316 | 31.321 | 17.243 | −12.957 | 1.00 | 57.20 | N |
| ATOM | 7620 | CA | GLN | C | 316 | 30.200 | 17.919 | −13.614 | 1.00 | 58.35 | C |
| ATOM | 7622 | CB | GLN | C | 316 | 29.225 | 18.496 | −12.575 | 1.00 | 58.50 | C |
| ATOM | 7625 | CG | GLN | C | 316 | 28.307 | 17.462 | −11.939 | 1.00 | 59.06 | C |
| ATOM | 7628 | CD | GLN | C | 316 | 27.301 | 16.884 | −12.918 | 1.00 | 60.00 | C |
| ATOM | 7629 | OE1 | GLN | C | 316 | 26.286 | 17.517 | −13.218 | 1.00 | 60.90 | O |
| ATOM | 7630 | NE2 | GLN | C | 316 | 27.576 | 15.681 | −13.417 | 1.00 | 59.97 | N |
| ATOM | 7633 | C | GLN | C | 316 | 30.643 | 19.023 | −14.571 | 1.00 | 59.16 | C |
| ATOM | 7634 | O | GLN | C | 316 | 30.273 | 19.004 | −15.743 | 1.00 | 59.31 | O |
| ATOM | 7635 | N | GLU | C | 317 | 31.426 | 19.979 | −14.070 | 1.00 | 60.16 | N |
| ATOM | 7637 | CA | GLU | C | 317 | 31.892 | 21.102 | −14.890 | 1.00 | 60.96 | C |
| ATOM | 7639 | CB | GLU | C | 317 | 32.574 | 22.165 | −14.026 | 1.00 | 61.14 | C |
| ATOM | 7642 | CG | GLU | C | 317 | 31.623 | 22.878 | −13.069 | 1.00 | 61.99 | C |
| ATOM | 7645 | CD | GLU | C | 317 | 32.056 | 24.299 | −12.736 | 1.00 | 62.86 | C |
| ATOM | 7646 | OE1 | GLU | C | 317 | 33.260 | 24.615 | −12.860 | 1.00 | 63.57 | O |
| ATOM | 7647 | OE2 | GLU | C | 317 | 31.185 | 25.105 | −12.344 | 1.00 | 63.40 | O |
| ATOM | 7648 | C | GLU | C | 317 | 32.835 | 20.642 | −15.999 | 1.00 | 61.38 | C |
| ATOM | 7649 | O | GLU | C | 317 | 33.643 | 19.738 | −15.793 | 1.00 | 61.45 | O |
| ATOM | 7650 | N | GLU | C | 318 | 32.728 | 21.288 | −17.162 | 1.00 | 61.91 | N |
| ATOM | 7652 | CA | GLU | C | 318 | 33.512 | 20.937 | −18.353 | 1.00 | 62.23 | C |
| ATOM | 7654 | CB | GLU | C | 318 | 33.111 | 21.822 | −19.539 | 1.00 | 62.29 | C |
| ATOM | 7657 | CG | GLU | C | 318 | 33.265 | 20.395 | −20.984 | 0.00 | 51.13 | C |
| ATOM | 7660 | CD | GLU | C | 318 | 32.108 | 19.419 | −21.051 | 0.00 | 49.71 | C |
| ATOM | 7661 | OE1 | GLU | C | 318 | 30.944 | 19.870 | −20.989 | 0.00 | 48.63 | O |
| ATOM | 7662 | OE2 | GLU | C | 318 | 32.361 | 18.202 | −21.165 | 0.00 | 48.63 | O |
| ATOM | 7663 | C | GLU | C | 318 | 35.026 | 21.001 | −18.162 | 1.00 | 62.47 | C |
| ATOM | 7664 | O | GLU | C | 318 | 35.743 | 20.121 | −18.645 | 1.00 | 62.54 | O |
| ATOM | 7665 | N | HIS | C | 319 | 35.513 | 22.029 | −17.466 | 1.00 | 62.71 | N |
| ATOM | 7667 | CA | HIS | C | 319 | 36.957 | 22.175 | −17.213 | 1.00 | 62.99 | C |
| ATOM | 7669 | CB | HIS | C | 319 | 37.332 | 23.659 | −17.001 | 1.00 | 63.19 | C |
| ATOM | 7672 | CG | HIS | C | 319 | 37.332 | 24.106 | −15.571 | 1.00 | 64.23 | C |
| ATOM | 7673 | ND1 | HIS | C | 319 | 36.224 | 24.010 | −14.756 | 1.00 | 65.36 | N |
| ATOM | 7675 | CE1 | HIS | C | 319 | 36.520 | 24.484 | −13.558 | 1.00 | 65.91 | C |
| ATOM | 7677 | NE2 | HIS | C | 319 | 37.777 | 24.892 | −13.569 | 1.00 | 65.94 | N |
| ATOM | 7679 | CD2 | HIS | C | 319 | 38.306 | 24.671 | −14.817 | 1.00 | 65.37 | C |
| ATOM | 7681 | C | HIS | C | 319 | 37.432 | 21.239 | −16.064 | 1.00 | 62.81 | C |
| ATOM | 7682 | O | HIS | C | 319 | 38.410 | 21.519 | −15.371 | 1.00 | 62.96 | O |
| ATOM | 7683 | N | CME | C | 320 | 36.756 | 20.091 | −15.971 | 1.00 | 62.58 | N |

TABLE 2-continued

| ATOM | 7686 | CA | CME | C | 320 | 37.162 | 19.176 | −14.877 | 1.00 | 62.44 | C |
|---|---|---|---|---|---|---|---|---|---|---|---|
| ATOM | 7688 | CB | CME | C | 320 | 36.458 | 19.544 | −13.561 | 1.00 | 62.59 | C |
| ATOM | 7691 | SG | CME | C | 320 | 37.439 | 20.698 | −12.652 | 1.00 | 63.49 | S |
| ATOM | 7692 | S2 | CME | C | 320 | 37.265 | 20.647 | −10.660 | 1.00 | 65.76 | S |
| ATOM | 7693 | C2 | CME | C | 320 | 36.174 | 21.907 | −10.084 | 1.00 | 66.11 | C |
| ATOM | 7696 | C1 | CME | C | 320 | 35.010 | 22.038 | −11.037 | 1.00 | 66.45 | C |
| ATOM | 7698 | O1 | CME | C | 320 | 34.382 | 21.041 | −11.357 | 1.00 | 66.86 | O |
| ATOM | 7699 | C | CME | C | 320 | 36.919 | 17.724 | −15.149 | 1.00 | 61.97 | C |
| ATOM | 7700 | O | CME | C | 320 | 37.789 | 16.902 | −14.985 | 1.00 | 62.13 | O |
| ATOM | 7702 | N | ASP | C | 321 | 35.810 | 17.485 | −15.860 | 1.00 | 61.25 | N |
| ATOM | 7704 | CA | ASP | C | 321 | 35.369 | 16.162 | −16.340 | 1.00 | 60.62 | C |
| ATOM | 7706 | CB | ASP | C | 321 | 34.199 | 16.377 | −17.312 | 1.00 | 60.53 | C |
| ATOM | 7709 | CG | ASP | C | 321 | 33.427 | 15.110 | −17.610 | 1.00 | 60.29 | C |
| ATOM | 7710 | OD1 | ASP | C | 321 | 33.991 | 14.001 | −17.509 | 1.00 | 59.69 | O |
| ATOM | 7711 | OD2 | ASP | C | 321 | 32.232 | 15.144 | −17.964 | 1.00 | 59.82 | O |
| ATOM | 7712 | C | ASP | C | 321 | 36.491 | 15.395 | −17.051 | 1.00 | 60.21 | C |
| ATOM | 7713 | O | ASP | C | 321 | 36.714 | 15.573 | −18.250 | 1.00 | 60.28 | O |
| ATOM | 7714 | N | ILE | C | 322 | 37.185 | 14.533 | −16.308 | 1.00 | 59.65 | N |
| ATOM | 7716 | CA | ILE | C | 322 | 38.294 | 13.745 | −16.864 | 1.00 | 59.18 | C |
| ATOM | 7718 | CB | ILE | C | 322 | 39.255 | 13.243 | −15.744 | 1.00 | 59.06 | C |
| ATOM | 7720 | CG1 | ILE | C | 322 | 38.531 | 12.339 | −14.735 | 1.00 | 58.57 | C |
| ATOM | 7723 | CD1 | ILE | C | 322 | 39.467 | 11.477 | −13.915 | 1.00 | 58.15 | C |
| ATOM | 7727 | CG2 | ILE | C | 322 | 39.904 | 14.420 | −15.035 | 1.00 | 58.94 | C |
| ATOM | 7731 | C | ILE | C | 322 | 37.855 | 12.563 | −17.732 | 1.00 | 58.94 | C |
| ATOM | 7732 | O | ILE | C | 322 | 38.690 | 11.941 | −18.375 | 1.00 | 58.81 | O |
| ATOM | 7733 | N | PHE | C | 323 | 36.563 | 12.240 | −17.728 | 1.00 | 58.82 | N |
| ATOM | 7735 | CA | PHE | C | 323 | 36.027 | 11.142 | −18.537 | 1.00 | 58.80 | C |
| ATOM | 7737 | CB | PHE | C | 323 | 35.169 | 10.217 | −17.668 | 1.00 | 58.78 | C |
| ATOM | 7740 | CG | PHE | C | 323 | 35.857 | 9.751 | −16.410 | 1.00 | 59.15 | C |
| ATOM | 7741 | CD1 | PHE | C | 323 | 37.135 | 9.203 | −16.458 | 1.00 | 59.50 | C |
| ATOM | 7743 | CE1 | PHE | C | 323 | 37.772 | 8.774 | −15.297 | 1.00 | 59.73 | C |
| ATOM | 7745 | CZ | PHE | C | 323 | 37.131 | 8.887 | −14.071 | 1.00 | 59.50 | C |
| ATOM | 7747 | CE2 | PHE | C | 323 | 35.858 | 9.430 | −14.008 | 1.00 | 59.55 | C |
| ATOM | 7749 | CD2 | PHE | C | 323 | 35.225 | 9.858 | −15.176 | 1.00 | 59.20 | C |
| ATOM | 7751 | C | PHE | C | 323 | 35.199 | 11.662 | −19.716 | 1.00 | 58.73 | C |
| ATOM | 7752 | O | PHE | C | 323 | 34.312 | 10.968 | −20.207 | 1.00 | 58.66 | O |
| ATOM | 7753 | N | MET | C | 324 | 35.508 | 12.876 | −20.170 | 1.00 | 58.70 | N |
| ATOM | 7755 | CA | MET | C | 324 | 34.797 | 13.526 | −21.276 | 1.00 | 58.85 | C |
| ATOM | 7757 | CB | MET | C | 324 | 35.423 | 14.904 | −21.553 | 1.00 | 58.98 | C |
| ATOM | 7760 | CG | MET | C | 324 | 34.862 | 15.643 | −22.773 | 1.00 | 59.59 | C |
| ATOM | 7763 | SD | MET | C | 324 | 35.243 | 17.419 | −22.769 | 1.00 | 60.75 | S |
| ATOM | 7764 | CE | MET | C | 324 | 37.040 | 17.413 | −22.473 | 1.00 | 60.73 | C |
| ATOM | 7768 | C | MET | C | 324 | 34.786 | 12.703 | −22.570 | 1.00 | 58.62 | C |
| ATOM | 7769 | O | MET | C | 324 | 33.731 | 12.482 | −23.160 | 1.00 | 58.40 | O |
| ATOM | 7770 | N | ASN | C | 325 | 35.961 | 12.245 | −22.993 | 1.00 | 58.60 | N |
| ATOM | 7772 | CA | ASN | C | 325 | 36.104 | 11.500 | −24.246 | 1.00 | 58.66 | C |
| ATOM | 7774 | CB | ASN | C | 325 | 37.459 | 11.825 | −24.889 | 1.00 | 58.58 | C |
| ATOM | 7777 | CG | ASN | C | 325 | 37.610 | 13.307 | −25.217 | 1.00 | 58.25 | C |
| ATOM | 7778 | OD1 | ASN | C | 325 | 36.644 | 13.976 | −25.584 | 1.00 | 58.02 | O |
| ATOM | 7779 | ND2 | ASN | C | 325 | 38.825 | 13.823 | −25.082 | 1.00 | 57.81 | N |
| ATOM | 7782 | C | ASN | C | 325 | 35.890 | 9.984 | −24.161 | 1.00 | 58.76 | C |
| ATOM | 7783 | O | ASN | C | 325 | 36.366 | 9.242 | −25.018 | 1.00 | 58.78 | O |
| ATOM | 7784 | N | LEU | C | 326 | 35.179 | 9.528 | −23.135 | 1.00 | 58.93 | N |
| ATOM | 7786 | CA | LEU | C | 326 | 34.810 | 8.121 | −23.023 | 1.00 | 59.09 | C |
| ATOM | 7788 | CB | LEU | C | 326 | 34.630 | 7.698 | −21.559 | 1.00 | 59.04 | C |
| ATOM | 7791 | CG | LEU | C | 326 | 35.824 | 7.695 | −20.599 | 1.00 | 58.84 | C |
| ATOM | 7793 | CD1 | LEU | C | 326 | 35.448 | 6.975 | −19.312 | 1.00 | 58.84 | C |
| ATOM | 7797 | CD2 | LEU | C | 326 | 37.043 | 7.049 | −21.215 | 1.00 | 58.64 | C |
| ATOM | 7801 | C | LEU | C | 326 | 33.474 | 7.978 | −23.747 | 1.00 | 59.35 | C |
| ATOM | 7802 | O | LEU | C | 326 | 32.792 | 8.974 | −23.993 | 1.00 | 59.35 | O |
| ATOM | 7803 | N | THR | C | 327 | 33.100 | 6.747 | −24.085 | 1.00 | 59.70 | N |
| ATOM | 7805 | CA | THR | C | 327 | 31.810 | 6.479 | −24.725 | 1.00 | 60.05 | C |
| ATOM | 7807 | CB | THR | C | 327 | 31.789 | 5.061 | −25.360 | 1.00 | 60.06 | C |
| ATOM | 7809 | OG1 | THR | C | 327 | 33.012 | 4.809 | −26.063 | 1.00 | 60.45 | O |
| ATOM | 7811 | CG2 | THR | C | 327 | 30.711 | 4.944 | −26.445 | 1.00 | 60.36 | C |
| ATOM | 7815 | C | THR | C | 327 | 30.732 | 6.560 | −23.652 | 1.00 | 60.29 | C |
| ATOM | 7816 | O | THR | C | 327 | 31.044 | 6.568 | −22.462 | 1.00 | 60.37 | O |
| ATOM | 7817 | N | LYS | C | 328 | 29.469 | 6.636 | −24.062 | 1.00 | 60.53 | N |
| ATOM | 7819 | CA | LYS | C | 328 | 28.364 | 6.638 | −23.105 | 1.00 | 60.66 | C |
| ATOM | 7821 | CB | LYS | C | 328 | 27.029 | 6.925 | −23.799 | 1.00 | 60.82 | C |
| ATOM | 7824 | CG | LYS | C | 328 | 25.923 | 7.400 | −22.856 | 1.00 | 61.35 | C |
| ATOM | 7827 | CD | LYS | C | 328 | 24.540 | 6.917 | −23.301 | 1.00 | 61.92 | C |
| ATOM | 7830 | CE | LYS | C | 328 | 23.496 | 7.145 | −22.215 | 1.00 | 62.21 | C |
| ATOM | 7833 | NZ | LYS | C | 328 | 22.125 | 6.768 | −22.656 | 1.00 | 62.10 | N |
| ATOM | 7837 | C | LYS | C | 328 | 28.324 | 5.278 | −22.399 | 1.00 | 60.59 | C |
| ATOM | 7838 | O | LYS | C | 328 | 27.944 | 5.189 | −21.231 | 1.00 | 60.77 | O |
| ATOM | 7839 | N | LYS | C | 329 | 28.724 | 4.230 | −23.120 | 1.00 | 60.34 | N |
| ATOM | 7841 | CA | LYS | C | 329 | 28.786 | 2.872 | −22.581 | 1.00 | 60.18 | C |
| ATOM | 7843 | CB | LYS | C | 329 | 28.908 | 1.857 | −23.727 | 1.00 | 60.26 | C |

TABLE 2-continued

| | | | | | | | | | | |
|---|---|---|---|---|---|---|---|---|---|---|
| ATOM | 7846 | CG | LYS | C | 329 | 29.061 | 0.392 | −23.299 | 1.00 | 60.92 C |
| ATOM | 7849 | CD | LYS | C | 329 | 27.733 | −0.357 | −23.270 | 1.00 | 61.76 C |
| ATOM | 7852 | CE | LYS | C | 329 | 27.960 | −1.864 | −23.172 | 1.00 | 62.08 C |
| ATOM | 7855 | NZ | LYS | C | 329 | 26.682 | −2.628 | −23.120 | 1.00 | 62.59 N |
| ATOM | 7859 | C | LYS | C | 329 | 29.957 | 2.718 | −21.605 | 1.00 | 59.72 C |
| ATOM | 7860 | O | LYS | C | 329 | 29.829 | 2.044 | −20.586 | 1.00 | 59.79 O |
| ATOM | 7861 | N | GLN | C | 330 | 31.094 | 3.334 | −21.926 | 1.00 | 59.12 N |
| ATOM | 7863 | CA | GLN | C | 330 | 32.279 | 3.276 | −21.068 | 1.00 | 58.72 C |
| ATOM | 7865 | CB | GLN | C | 330 | 33.493 | 3.875 | −21.782 | 1.00 | 58.73 C |
| ATOM | 7868 | CG | GLN | C | 330 | 34.030 | 3.031 | −22.930 | 1.00 | 58.82 C |
| ATOM | 7871 | CD | GLN | C | 330 | 35.374 | 3.531 | −23.434 | 1.00 | 58.71 C |
| ATOM | 7872 | OE1 | GLN | C | 330 | 35.520 | 4.710 | −23.757 | 1.00 | 58.79 O |
| ATOM | 7873 | NE2 | GLN | C | 330 | 36.357 | 2.640 | −23.496 | 1.00 | 58.49 N |
| ATOM | 7876 | C | GLN | C | 330 | 32.056 | 4.008 | −19.737 | 1.00 | 58.22 C |
| ATOM | 7877 | O | GLN | C | 330 | 32.572 | 3.589 | −18.706 | 1.00 | 58.07 O |
| ATOM | 7878 | N | ARG | C | 331 | 31.304 | 5.106 | −19.781 | 1.00 | 57.66 N |
| ATOM | 7880 | CA | ARG | C | 331 | 30.966 | 5.892 | −18.596 | 1.00 | 57.32 C |
| ATOM | 7882 | CB | ARG | C | 331 | 30.092 | 7.085 | −18.976 | 1.00 | 57.65 C |
| ATOM | 7885 | CG | ARG | C | 331 | 30.824 | 8.322 | −19.415 | 1.00 | 58.84 C |
| ATOM | 7888 | CD | ARG | C | 331 | 29.920 | 9.547 | −19.461 | 1.00 | 60.82 C |
| ATOM | 7891 | NE | ARG | C | 331 | 30.586 | 10.718 | −18.902 | 1.00 | 62.72 N |
| ATOM | 7893 | CZ | ARG | C | 331 | 31.295 | 11.600 | −19.603 | 1.00 | 64.37 C |
| ATOM | 7894 | NH1 | ARG | C | 331 | 31.449 | 11.472 | −20.921 | 1.00 | 65.14 N |
| ATOM | 7897 | NH2 | ARG | C | 331 | 31.861 | 12.625 | −18.979 | 1.00 | 64.74 N |
| ATOM | 7900 | C | ARG | C | 331 | 30.157 | 5.041 | −17.634 | 1.00 | 56.44 C |
| ATOM | 7901 | O | ARG | C | 331 | 30.453 | 4.973 | −16.446 | 1.00 | 56.37 O |
| ATOM | 7902 | N | GLN | C | 332 | 29.114 | 4.422 | −18.180 | 1.00 | 55.36 N |
| ATOM | 7904 | CA | GLN | C | 332 | 28.191 | 3.573 | −17.437 | 1.00 | 54.47 C |
| ATOM | 7906 | CB | GLN | C | 332 | 27.152 | 2.998 | −18.402 | 1.00 | 54.63 C |
| ATOM | 7909 | CG | GLN | C | 332 | 26.043 | 2.189 | −17.759 | 1.00 | 55.30 C |
| ATOM | 7912 | CD | GLN | C | 332 | 25.093 | 1.607 | −18.791 | 1.00 | 55.84 C |
| ATOM | 7913 | OE1 | GLN | C | 332 | 25.381 | 0.569 | −19.387 | 1.00 | 55.94 O |
| ATOM | 7914 | NE2 | GLN | C | 332 | 23.965 | 2.275 | −19.007 | 1.00 | 56.04 N |
| ATOM | 7917 | C | GLN | C | 332 | 28.903 | 2.437 | −16.713 | 1.00 | 53.35 C |
| ATOM | 7918 | O | GLN | C | 332 | 28.651 | 2.192 | −15.531 | 1.00 | 53.33 O |
| ATOM | 7919 | N | THR | C | 333 | 29.791 | 1.751 | −17.424 | 1.00 | 51.83 N |
| ATOM | 7921 | CA | THR | C | 333 | 30.525 | 0.627 | −16.853 | 1.00 | 50.72 C |
| ATOM | 7923 | CB | THR | C | 333 | 31.215 | −0.190 | −17.968 | 1.00 | 50.63 C |
| ATOM | 7925 | OG1 | THR | C | 333 | 30.233 | −0.656 | −18.901 | 1.00 | 50.29 O |
| ATOM | 7927 | CG2 | THR | C | 333 | 31.829 | −1.472 | −17.419 | 1.00 | 50.44 C |
| ATOM | 7931 | C | THR | C | 333 | 31.539 | 1.092 | −15.804 | 1.00 | 49.73 C |
| ATOM | 7932 | O | THR | C | 333 | 31.709 | 0.436 | −14.783 | 1.00 | 49.50 O |
| ATOM | 7933 | N | LEU | C | 334 | 32.189 | 2.228 | −16.052 | 1.00 | 48.46 N |
| ATOM | 7935 | CA | LEU | C | 334 | 33.175 | 2.778 | −15.123 | 1.00 | 47.54 C |
| ATOM | 7937 | CB | LEU | C | 334 | 33.914 | 3.964 | −15.754 | 1.00 | 47.43 C |
| ATOM | 7940 | CG | LEU | C | 334 | 34.864 | 4.772 | −14.852 | 1.00 | 46.96 C |
| ATOM | 7942 | CD1 | LEU | C | 334 | 36.309 | 4.379 | −15.065 | 1.00 | 46.59 C |
| ATOM | 7946 | CD2 | LEU | C | 334 | 34.689 | 6.261 | −15.097 | 1.00 | 46.85 C |
| ATOM | 7950 | C | LEU | C | 334 | 32.499 | 3.206 | −13.822 | 1.00 | 46.80 C |
| ATOM | 7951 | O | LEU | C | 334 | 32.998 | 2.918 | −12.739 | 1.00 | 46.62 O |
| ATOM | 7952 | N | ARG | C | 335 | 31.361 | 3.881 | −13.945 | 1.00 | 45.92 N |
| ATOM | 7954 | CA | ARG | C | 335 | 30.590 | 4.357 | −12.800 | 1.00 | 45.36 C |
| ATOM | 7956 | CB | ARG | C | 335 | 29.400 | 5.192 | −13.280 | 1.00 | 45.23 C |
| ATOM | 7959 | CG | ARG | C | 335 | 28.598 | 5.828 | −12.164 | 1.00 | 44.29 C |
| ATOM | 7962 | CD | ARG | C | 335 | 27.593 | 6.871 | −12.632 | 1.00 | 43.21 C |
| ATOM | 7965 | NE | ARG | C | 335 | 26.584 | 7.126 | −11.607 | 1.00 | 42.48 N |
| ATOM | 7967 | CZ | ARG | C | 335 | 26.813 | 7.784 | −10.469 | 1.00 | 41.59 C |
| ATOM | 7968 | NH1 | ARG | C | 335 | 28.010 | 8.292 | −10.198 | 1.00 | 40.59 N |
| ATOM | 7971 | NH2 | ARG | C | 335 | 25.825 | 7.947 | −9.600 | 1.00 | 41.86 N |
| ATOM | 7974 | C | ARG | C | 335 | 30.100 | 3.184 | −11.955 | 1.00 | 45.12 C |
| ATOM | 7975 | O | ARG | C | 335 | 30.137 | 3.227 | −10.723 | 1.00 | 45.15 O |
| ATOM | 7976 | N | LYS | C | 336 | 29.645 | 2.142 | −12.639 | 1.00 | 44.64 N |
| ATOM | 7978 | CA | LYS | C | 336 | 29.163 | 0.927 | −12.005 | 1.00 | 44.50 C |
| ATOM | 7980 | CB | LYS | C | 336 | 28.626 | −0.028 | −13.079 | 1.00 | 44.54 C |
| ATOM | 7983 | CG | LYS | C | 336 | 28.175 | −1.398 | −12.589 | 1.00 | 45.49 C |
| ATOM | 7986 | CD | LYS | C | 336 | 27.954 | −2.355 | −13.776 | 1.00 | 46.27 C |
| ATOM | 7989 | CE | LYS | C | 336 | 26.965 | −3.473 | −13.452 | 1.00 | 46.60 C |
| ATOM | 7992 | NZ | LYS | C | 336 | 27.505 | −4.825 | −13.796 | 1.00 | 47.19 N |
| ATOM | 7996 | C | LYS | C | 336 | 30.280 | 0.259 | −11.208 | 1.00 | 44.07 C |
| ATOM | 7997 | O | LYS | C | 336 | 30.065 | −0.169 | −10.078 | 1.00 | 44.30 O |
| ATOM | 7998 | N | MET | C | 337 | 31.472 | 0.194 | −11.793 | 1.00 | 43.37 N |
| ATOM | 8000 | CA | MET | C | 337 | 32.609 | −0.470 | −11.162 | 1.00 | 43.03 C |
| ATOM | 8002 | CB | MET | C | 337 | 33.713 | −0.731 | −12.188 | 1.00 | 43.08 C |
| ATOM | 8005 | CG | MET | C | 337 | 33.361 | −1.791 | −13.227 | 1.00 | 43.51 C |
| ATOM | 8008 | SD | MET | C | 337 | 34.771 | −2.243 | −14.247 | 1.00 | 43.88 S |
| ATOM | 8009 | CE | MET | C | 337 | 35.101 | −0.723 | −15.059 | 1.00 | 43.83 C |
| ATOM | 8013 | C | MET | C | 337 | 33.194 | 0.309 | −9.990 | 1.00 | 42.49 C |
| ATOM | 8014 | O | MET | C | 337 | 33.581 | −0.290 | −8.996 | 1.00 | 42.18 O |
| ATOM | 8015 | N | VAL | C | 338 | 33.265 | 1.633 | −10.122 | 1.00 | 41.95 N |

TABLE 2-continued

| | | | | | | | | | | | |
|---|---|---|---|---|---|---|---|---|---|---|---|
| ATOM | 8017 | CA | VAL | C | 338 | 33.819 | 2.493 | −9.085 | 1.00 | 41.58 | C |
| ATOM | 8019 | CB | VAL | C | 338 | 34.001 | 3.956 | −9.578 | 1.00 | 41.59 | C |
| ATOM | 8021 | CG1 | VAL | C | 338 | 34.361 | 4.891 | −8.417 | 1.00 | 41.34 | C |
| ATOM | 8025 | CG2 | VAL | C | 338 | 35.067 | 4.038 | −10.671 | 1.00 | 41.29 | C |
| ATOM | 8029 | C | VAL | C | 338 | 32.912 | 2.469 | −7.861 | 1.00 | 41.42 | C |
| ATOM | 8030 | O | VAL | C | 338 | 33.394 | 2.355 | −6.739 | 1.00 | 41.59 | O |
| ATOM | 8031 | N | ILE | C | 339 | 31.605 | 2.583 | −8.088 | 1.00 | 41.10 | N |
| ATOM | 8033 | CA | ILE | C | 339 | 30.617 | 2.562 | −7.016 | 1.00 | 40.80 | C |
| ATOM | 8035 | CB | ILE | C | 339 | 29.184 | 2.715 | −7.584 | 1.00 | 40.71 | C |
| ATOM | 8037 | CG1 | ILE | C | 339 | 28.888 | 4.192 | −7.861 | 1.00 | 40.60 | C |
| ATOM | 8040 | CD1 | ILE | C | 339 | 27.723 | 4.429 | −8.801 | 1.00 | 39.94 | C |
| ATOM | 8044 | CG2 | ILE | C | 339 | 28.141 | 2.140 | −6.625 | 1.00 | 40.58 | C |
| ATOM | 8048 | C | ILE | C | 339 | 30.750 | 1.270 | −6.228 | 1.00 | 40.93 | C |
| ATOM | 8049 | O | ILE | C | 339 | 30.768 | 1.279 | −4.997 | 1.00 | 40.58 | O |
| ATOM | 8050 | N | ASP | C | 340 | 30.847 | 0.164 | −6.955 | 1.00 | 40.93 | N |
| ATOM | 8052 | CA | ASP | C | 340 | 30.986 | −1.154 | −6.349 | 1.00 | 40.91 | C |
| ATOM | 8054 | CB | ASP | C | 340 | 30.994 | −2.213 | −7.454 | 1.00 | 40.99 | C |
| ATOM | 8057 | CG | ASP | C | 340 | 30.916 | −3.619 | −6.921 | 1.00 | 41.20 | C |
| ATOM | 8058 | OD1 | ASP | C | 340 | 31.926 | −4.081 | −6.367 | 1.00 | 41.73 | O |
| ATOM | 8059 | OD2 | ASP | C | 340 | 29.904 | −4.355 | −7.027 | 1.00 | 41.88 | O |
| ATOM | 8060 | C | ASP | C | 340 | 32.247 | −1.255 | −5.472 | 1.00 | 40.85 | C |
| ATOM | 8061 | O | ASP | C | 340 | 32.184 | −1.769 | −4.348 | 1.00 | 40.95 | O |
| ATOM | 8062 | N | MET | C | 341 | 33.372 | −0.741 | −5.971 | 1.00 | 40.50 | N |
| ATOM | 8064 | CA | MET | C | 341 | 34.650 | −0.812 | −5.251 | 1.00 | 40.35 | C |
| ATOM | 8066 | CB | MET | C | 341 | 35.816 | −0.462 | −6.187 | 1.00 | 40.45 | C |
| ATOM | 8069 | CG | MET | C | 341 | 36.178 | −1.560 | −7.186 | 1.00 | 40.70 | C |
| ATOM | 8072 | SD | MET | C | 341 | 37.584 | −1.118 | −8.254 | 1.00 | 41.03 | S |
| ATOM | 8073 | CE | MET | C | 341 | 36.735 | −0.315 | −9.567 | 1.00 | 40.89 | C |
| ATOM | 8077 | C | MET | C | 341 | 34.712 | 0.070 | −3.993 | 1.00 | 39.99 | C |
| ATOM | 8078 | O | MET | C | 341 | 35.180 | −0.381 | −2.950 | 1.00 | 40.06 | O |
| ATOM | 8079 | N | VAL | C | 342 | 34.247 | 1.315 | −4.089 | 1.00 | 39.48 | N |
| ATOM | 8081 | CA | VAL | C | 342 | 34.279 | 2.245 | −2.951 | 1.00 | 39.07 | C |
| ATOM | 8083 | CB | VAL | C | 342 | 33.940 | 3.697 | −3.377 | 1.00 | 39.02 | C |
| ATOM | 8085 | CG1 | VAL | C | 342 | 33.829 | 4.613 | −2.169 | 1.00 | 38.63 | C |
| ATOM | 8089 | CG2 | VAL | C | 342 | 34.994 | 4.232 | −4.341 | 1.00 | 38.86 | C |
| ATOM | 8093 | C | VAL | C | 342 | 33.329 | 1.792 | −1.848 | 1.00 | 38.93 | C |
| ATOM | 8094 | O | VAL | C | 342 | 33.631 | 1.936 | −0.654 | 1.00 | 39.11 | O |
| ATOM | 8095 | N | LEU | C | 343 | 32.175 | 1.264 | −2.248 | 1.00 | 38.50 | N |
| ATOM | 8097 | CA | LEU | C | 343 | 31.206 | 0.730 | −1.299 | 1.00 | 38.34 | C |
| ATOM | 8099 | CB | LEU | C | 343 | 29.913 | 0.305 | −2.007 | 1.00 | 38.19 | C |
| ATOM | 8102 | CG | LEU | C | 343 | 28.916 | 1.419 | −2.338 | 1.00 | 37.92 | C |
| ATOM | 8104 | CD1 | LEU | C | 343 | 27.685 | 0.821 | −2.999 | 1.00 | 37.48 | C |
| ATOM | 8108 | CD2 | LEU | C | 343 | 28.531 | 2.224 | −1.091 | 1.00 | 38.11 | C |
| ATOM | 8112 | C | LEU | C | 343 | 31.815 | −0.458 | −0.554 | 1.00 | 38.26 | C |
| ATOM | 8113 | O | LEU | C | 343 | 31.541 | −0.661 | 0.633 | 1.00 | 38.13 | O |
| ATOM | 8114 | N | ALA | C | 344 | 32.653 | −1.222 | −1.255 | 1.00 | 38.18 | N |
| ATOM | 8116 | CA | ALA | C | 344 | 33.342 | −2.376 | −0.677 | 1.00 | 38.28 | C |
| ATOM | 8118 | CB | ALA | C | 344 | 33.933 | −3.252 | −1.776 | 1.00 | 38.17 | C |
| ATOM | 8122 | C | ALA | C | 344 | 34.434 | −2.015 | 0.344 | 1.00 | 38.41 | C |
| ATOM | 8123 | O | ALA | C | 344 | 34.933 | −2.908 | 1.027 | 1.00 | 38.46 | O |
| ATOM | 8124 | N | THR | C | 345 | 34.819 | −0.738 | 0.436 | 1.00 | 38.48 | N |
| ATOM | 8126 | CA | THR | C | 345 | 35.816 | −0.304 | 1.431 | 1.00 | 38.87 | C |
| ATOM | 8128 | CB | THR | C | 345 | 36.579 | 0.959 | 0.974 | 1.00 | 38.61 | C |
| ATOM | 8130 | OG1 | THR | C | 345 | 35.701 | 2.094 | 0.957 | 1.00 | 38.81 | O |
| ATOM | 8132 | CG2 | THR | C | 345 | 37.066 | 0.829 | −0.465 | 1.00 | 38.96 | C |
| ATOM | 8136 | C | THR | C | 345 | 35.183 | −0.045 | 2.809 | 1.00 | 39.34 | C |
| ATOM | 8137 | O | THR | C | 345 | 35.868 | 0.373 | 3.737 | 1.00 | 38.97 | O |
| ATOM | 8138 | N | ASP | C | 346 | 33.875 | −0.262 | 2.917 | 1.00 | 40.24 | N |
| ATOM | 8140 | CA | ASP | C | 346 | 33.147 | −0.102 | 4.163 | 1.00 | 41.21 | C |
| ATOM | 8142 | CB | ASP | C | 346 | 31.638 | −0.109 | 3.888 | 1.00 | 41.15 | C |
| ATOM | 8145 | CG | ASP | C | 346 | 30.805 | 0.155 | 5.132 | 1.00 | 41.23 | C |
| ATOM | 8146 | OD1 | ASP | C | 346 | 31.383 | 0.322 | 6.227 | 1.00 | 40.89 | O |
| ATOM | 8147 | OD2 | ASP | C | 346 | 29.556 | 0.215 | 5.106 | 1.00 | 41.84 | O |
| ATOM | 8148 | C | ASP | C | 346 | 33.544 | −1.281 | 5.041 | 1.00 | 42.25 | C |
| ATOM | 8149 | O | ASP | C | 346 | 33.293 | −2.430 | 4.680 | 1.00 | 42.26 | O |
| ATOM | 8150 | N | MET | C | 347 | 34.168 | −0.996 | 6.182 | 1.00 | 43.52 | N |
| ATOM | 8152 | CA | MET | C | 347 | 34.655 | −2.051 | 7.082 | 1.00 | 44.73 | C |
| ATOM | 8154 | CB | MET | C | 347 | 35.427 | −1.457 | 8.267 | 1.00 | 44.83 | C |
| ATOM | 8157 | CG | MET | C | 347 | 36.898 | −1.191 | 7.989 | 1.00 | 45.92 | C |
| ATOM | 8160 | SD | MET | C | 347 | 37.828 | −2.555 | 7.241 | 1.00 | 48.14 | S |
| ATOM | 8161 | CE | MET | C | 347 | 37.538 | −3.872 | 8.407 | 1.00 | 48.05 | C |
| ATOM | 8165 | C | MET | C | 347 | 33.585 | −3.005 | 7.610 | 1.00 | 45.46 | C |
| ATOM | 8166 | O | MET | C | 347 | 33.908 | −4.125 | 8.005 | 1.00 | 45.60 | O |
| ATOM | 8167 | N | SER | C | 348 | 32.328 | −2.566 | 7.635 | 1.00 | 46.51 | N |
| ATOM | 8169 | CA | SER | C | 348 | 31.224 | −3.419 | 8.080 | 1.00 | 47.34 | C |
| ATOM | 8171 | CB | SER | C | 348 | 29.926 | −2.611 | 8.190 | 1.00 | 47.35 | C |
| ATOM | 8174 | OG | SER | C | 348 | 29.369 | −2.362 | 6.910 | 1.00 | 48.07 | O |
| ATOM | 8176 | C | SER | C | 348 | 31.025 | −4.609 | 7.133 | 1.00 | 48.00 | C |
| ATOM | 8177 | O | SER | C | 348 | 30.488 | −5.643 | 7.533 | 1.00 | 48.23 | O |

TABLE 2-continued

| | | | | | | | | | | | |
|---|---|---|---|---|---|---|---|---|---|---|---|
| ATOM | 8178 | N | LYS | C | 349 | 31.460 | −4.440 | 5.883 | 1.00 | 48.76 | N |
| ATOM | 8180 | CA | LYS | C | 349 | 31.374 | −5.465 | 4.839 | 1.00 | 49.37 | C |
| ATOM | 8182 | CB | LYS | C | 349 | 31.198 | −4.804 | 3.459 | 1.00 | 49.38 | C |
| ATOM | 8185 | CG | LYS | C | 349 | 30.166 | −3.678 | 3.376 | 1.00 | 49.50 | C |
| ATOM | 8188 | CD | LYS | C | 349 | 28.790 | −4.199 | 3.013 | 1.00 | 50.04 | C |
| ATOM | 8191 | CE | LYS | C | 349 | 27.729 | −3.118 | 3.162 | 1.00 | 50.49 | C |
| ATOM | 8194 | NZ | LYS | C | 349 | 26.916 | −3.306 | 4.395 | 1.00 | 50.86 | N |
| ATOM | 8198 | C | LYS | C | 349 | 32.615 | −6.373 | 4.764 | 1.00 | 49.92 | C |
| ATOM | 8199 | O | LYS | C | 349 | 32.652 | −7.295 | 3.955 | 1.00 | 50.02 | O |
| ATOM | 8200 | N | HIS | C | 350 | 33.622 | −6.108 | 5.592 | 1.00 | 50.61 | N |
| ATOM | 8202 | CA | HIS | C | 350 | 34.879 | −6.859 | 5.573 | 1.00 | 51.27 | C |
| ATOM | 8204 | CB | HIS | C | 350 | 35.762 | −6.456 | 6.762 | 1.00 | 51.37 | C |
| ATOM | 8207 | CG | HIS | C | 350 | 36.987 | −7.304 | 6.918 | 1.00 | 51.74 | C |
| ATOM | 8208 | ND1 | HIS | C | 350 | 38.103 | −7.154 | 6.123 | 1.00 | 52.07 | N |
| ATOM | 8210 | CE1 | HIS | C | 350 | 39.015 | −8.042 | 6.475 | 1.00 | 52.13 | C |
| ATOM | 8212 | NE2 | HIS | C | 350 | 38.532 | −8.762 | 7.471 | 1.00 | 52.30 | N |
| ATOM | 8214 | CD2 | HIS | C | 350 | 37.264 | −8.323 | 7.765 | 1.00 | 52.15 | C |
| ATOM | 8216 | C | HIS | C | 350 | 34.709 | −8.376 | 5.575 | 1.00 | 51.72 | C |
| ATOM | 8217 | O | HIS | C | 350 | 35.286 | −9.059 | 4.734 | 1.00 | 51.60 | O |
| ATOM | 8218 | N | MET | C | 351 | 33.921 | −8.883 | 6.522 | 1.00 | 52.31 | N |
| ATOM | 8220 | CA | MET | C | 351 | 33.701 | −10.326 | 6.687 | 1.00 | 52.77 | C |
| ATOM | 8222 | CB | MET | C | 351 | 32.852 | −10.610 | 7.937 | 1.00 | 53.07 | C |
| ATOM | 8225 | CG | MET | C | 351 | 33.453 | −10.124 | 9.252 | 1.00 | 54.31 | C |
| ATOM | 8228 | SD | MET | C | 351 | 35.089 | −10.804 | 9.583 | 1.00 | 57.51 | S |
| ATOM | 8229 | CE | MET | C | 351 | 35.096 | −10.837 | 11.405 | 1.00 | 57.91 | C |
| ATOM | 8233 | C | MET | C | 351 | 33.041 | −10.993 | 5.482 | 1.00 | 52.69 | C |
| ATOM | 8234 | O | MET | C | 351 | 33.455 | −12.076 | 5.077 | 1.00 | 52.73 | O |
| ATOM | 8235 | N | SER | C | 352 | 32.011 | −10.358 | 4.929 | 1.00 | 52.68 | N |
| ATOM | 8237 | CA | SER | C | 352 | 31.299 | −10.895 | 3.765 | 1.00 | 52.72 | C |
| ATOM | 8239 | CB | SER | C | 352 | 30.050 | −10.060 | 3.468 | 1.00 | 52.76 | C |
| ATOM | 8242 | OG | SER | C | 352 | 30.406 | −8.764 | 3.009 | 1.00 | 53.14 | O |
| ATOM | 8244 | C | SER | C | 352 | 32.191 | −10.931 | 2.522 | 1.00 | 52.60 | C |
| ATOM | 8245 | O | SER | C | 352 | 32.022 | −11.786 | 1.652 | 1.00 | 52.70 | O |
| ATOM | 8246 | N | LEU | C | 353 | 33.129 | −9.990 | 2.451 | 1.00 | 52.35 | N |
| ATOM | 8248 | CA | LEU | C | 353 | 34.071 | −9.893 | 1.343 | 1.00 | 52.12 | C |
| ATOM | 8250 | CB | LEU | C | 353 | 34.636 | −8.468 | 1.248 | 1.00 | 52.04 | C |
| ATOM | 8253 | CG | LEU | C | 353 | 34.641 | −7.832 | −0.144 | 1.00 | 51.52 | C |
| ATOM | 8255 | CD1 | LEU | C | 353 | 33.223 | −7.614 | −0.656 | 1.00 | 51.24 | C |
| ATOM | 8259 | CD2 | LEU | C | 353 | 35.406 | −6.522 | −0.105 | 1.00 | 51.29 | C |
| ATOM | 8263 | C | LEU | C | 353 | 35.210 | −10.901 | 1.511 | 1.00 | 52.07 | C |
| ATOM | 8264 | O | LEU | C | 353 | 35.725 | −11.419 | 0.525 | 1.00 | 51.86 | O |
| ATOM | 8265 | N | LEU | C | 354 | 35.588 | −11.172 | 2.762 | 1.00 | 52.07 | N |
| ATOM | 8267 | CA | LEU | C | 354 | 36.661 | −12.110 | 3.091 | 1.00 | 52.14 | C |
| ATOM | 8269 | CB | LEU | C | 354 | 37.082 | −11.946 | 4.559 | 1.00 | 52.10 | C |
| ATOM | 8272 | CG | LEU | C | 354 | 38.167 | −12.882 | 5.111 | 1.00 | 51.97 | C |
| ATOM | 8274 | CD1 | LEU | C | 354 | 39.434 | −12.809 | 4.275 | 1.00 | 51.85 | C |
| ATOM | 8278 | CD2 | LEU | C | 354 | 38.473 | −12.555 | 6.573 | 1.00 | 52.11 | C |
| ATOM | 8282 | C | LEU | C | 354 | 36.218 | −13.549 | 2.835 | 1.00 | 52.44 | C |
| ATOM | 8283 | O | LEU | C | 354 | 37.029 | −14.398 | 2.469 | 1.00 | 52.28 | O |
| ATOM | 8284 | N | ALA | C | 355 | 34.927 | −13.809 | 3.038 | 1.00 | 52.90 | N |
| ATOM | 8286 | CA | ALA | C | 355 | 34.348 | −15.128 | 2.814 | 1.00 | 53.30 | C |
| ATOM | 8288 | CB | ALA | C | 355 | 33.008 | −15.245 | 3.519 | 1.00 | 53.19 | C |
| ATOM | 8292 | C | ALA | C | 355 | 34.186 | −15.376 | 1.316 | 1.00 | 53.82 | C |
| ATOM | 8293 | O | ALA | C | 355 | 34.440 | −16.482 | 0.839 | 1.00 | 53.87 | O |
| ATOM | 8294 | N | ASP | C | 356 | 33.765 | −14.345 | 0.585 | 1.00 | 54.43 | N |
| ATOM | 8296 | CA | ASP | C | 356 | 33.584 | −14.435 | −0.869 | 1.00 | 55.04 | C |
| ATOM | 8298 | CB | ASP | C | 356 | 32.877 | −13.186 | −1.417 | 1.00 | 55.03 | C |
| ATOM | 8301 | CG | ASP | C | 356 | 31.379 | −13.198 | −1.178 | 1.00 | 55.19 | C |
| ATOM | 8302 | OD1 | ASP | C | 356 | 30.796 | −14.293 | −1.045 | 1.00 | 55.81 | O |
| ATOM | 8303 | OD2 | ASP | C | 356 | 30.697 | −12.153 | −1.119 | 1.00 | 55.50 | O |
| ATOM | 8304 | C | ASP | C | 356 | 34.926 | −14.600 | −1.578 | 1.00 | 55.49 | C |
| ATOM | 8305 | O | ASP | C | 356 | 35.007 | −15.239 | −2.627 | 1.00 | 55.58 | O |
| ATOM | 8306 | N | LEU | C | 357 | 35.972 | −14.020 | −0.996 | 1.00 | 56.17 | N |
| ATOM | 8308 | CA | LEU | C | 357 | 37.316 | −14.108 | −1.548 | 1.00 | 56.62 | C |
| ATOM | 8310 | CB | LEU | C | 357 | 38.246 | −13.094 | −0.873 | 1.00 | 56.43 | C |
| ATOM | 8313 | CG | LEU | C | 357 | 39.656 | −12.973 | −1.459 | 1.00 | 56.10 | C |
| ATOM | 8315 | CD1 | LEU | C | 357 | 39.618 | −12.579 | −2.937 | 1.00 | 55.76 | C |
| ATOM | 8319 | CD2 | LEU | C | 357 | 40.489 | −11.986 | −0.651 | 1.00 | 55.85 | C |
| ATOM | 8323 | C | LEU | C | 357 | 37.857 | −15.521 | −1.366 | 1.00 | 57.26 | C |
| ATOM | 8324 | O | LEU | C | 357 | 38.574 | −16.022 | −2.225 | 1.00 | 57.29 | O |
| ATOM | 8325 | N | LYS | C | 358 | 37.509 | −16.149 | −0.244 | 1.00 | 58.10 | N |
| ATOM | 8327 | CA | LYS | C | 358 | 37.935 | −17.517 | 0.050 | 1.00 | 58.75 | C |
| ATOM | 8329 | CB | LYS | C | 358 | 37.630 | −17.885 | 1.508 | 1.00 | 58.55 | C |
| ATOM | 8332 | CG | LYS | C | 358 | 38.673 | −17.387 | 2.500 | 1.00 | 57.98 | C |
| ATOM | 8335 | CD | LYS | C | 358 | 38.242 | −17.630 | 3.936 | 1.00 | 57.09 | C |
| ATOM | 8338 | CE | LYS | C | 358 | 39.298 | −17.155 | 4.920 | 1.00 | 56.71 | C |
| ATOM | 8341 | NZ | LYS | C | 358 | 38.829 | −17.252 | 6.327 | 1.00 | 56.41 | N |
| ATOM | 8345 | C | LYS | C | 358 | 37.266 | −18.520 | −0.893 | 1.00 | 59.64 | C |
| ATOM | 8346 | O | LYS | C | 358 | 37.865 | −19.534 | −1.243 | 1.00 | 59.70 | O |

TABLE 2-continued

| ATOM | 8347 | N | THR | C | 359 | 36.033 | −18.223 | −1.303 | 1.00 | 60.79 | N |
|---|---|---|---|---|---|---|---|---|---|---|---|
| ATOM | 8349 | CA | THR | C | 359 | 35.275 | −19.087 | −2.209 | 1.00 | 61.69 | C |
| ATOM | 8351 | CB | THR | C | 359 | 33.763 | −18.765 | −2.126 | 1.00 | 61.71 | C |
| ATOM | 8353 | OG1 | THR | C | 359 | 33.348 | −18.721 | −0.753 | 1.00 | 61.48 | O |
| ATOM | 8355 | CG2 | THR | C | 359 | 32.919 | −19.893 | −2.720 | 1.00 | 61.77 | C |
| ATOM | 8359 | C | THR | C | 359 | 35.788 | −18.953 | −3.651 | 1.00 | 62.67 | C |
| ATOM | 8360 | O | THR | C | 359 | 35.503 | −19.798 | −4.501 | 1.00 | 62.78 | O |
| ATOM | 8361 | N | MET | C | 360 | 36.529 | −17.877 | −3.916 | 1.00 | 63.74 | N |
| ATOM | 8363 | CA | MET | C | 360 | 37.159 | −17.645 | −5.212 | 1.00 | 64.53 | C |
| ATOM | 8365 | CB | MET | C | 360 | 37.279 | −16.139 | −5.476 | 1.00 | 64.76 | C |
| ATOM | 8368 | CG | MET | C | 360 | 37.843 | −15.767 | −6.848 | 1.00 | 65.88 | C |
| ATOM | 8371 | SD | MET | C | 360 | 36.629 | −14.989 | −7.940 | 1.00 | 68.24 | S |
| ATOM | 8372 | CE | MET | C | 360 | 35.530 | −16.396 | −8.298 | 1.00 | 68.42 | C |
| ATOM | 8376 | C | MET | C | 360 | 38.546 | −18.304 | −5.242 | 1.00 | 64.86 | C |
| ATOM | 8377 | O | MET | C | 360 | 39.009 | −18.735 | −6.299 | 1.00 | 64.91 | O |
| ATOM | 8378 | N | VAL | C | 361 | 39.194 | −18.388 | −4.079 | 1.00 | 65.27 | N |
| ATOM | 8380 | CA | VAL | C | 361 | 40.524 | −18.990 | −3.951 | 1.00 | 65.66 | C |
| ATOM | 8382 | CB | VAL | C | 361 | 41.150 | −18.689 | −2.557 | 1.00 | 65.65 | C |
| ATOM | 8384 | CG1 | VAL | C | 361 | 42.261 | −19.686 | −2.199 | 1.00 | 65.71 | C |
| ATOM | 8388 | CG2 | VAL | C | 361 | 41.685 | −17.271 | −2.513 | 1.00 | 65.63 | C |
| ATOM | 8392 | C | VAL | C | 361 | 40.463 | −20.501 | −4.155 | 1.00 | 66.01 | C |
| ATOM | 8393 | O | VAL | C | 361 | 41.333 | −21.083 | −4.803 | 1.00 | 66.06 | O |
| ATOM | 8394 | N | GLU | C | 362 | 39.428 | −21.122 | −3.595 | 1.00 | 66.41 | N |
| ATOM | 8396 | CA | GLU | C | 362 | 39.244 | −22.570 | −3.679 | 1.00 | 66.69 | C |
| ATOM | 8398 | CB | GLU | C | 362 | 38.438 | −23.084 | −2.476 | 1.00 | 66.72 | C |
| ATOM | 8401 | CG | GLU | C | 362 | 37.000 | −22.594 | −2.365 | 1.00 | 66.82 | C |
| ATOM | 8404 | CD | GLU | C | 362 | 36.442 | −22.717 | −0.953 | 1.00 | 67.08 | C |
| ATOM | 8405 | OE1 | GLU | C | 362 | 37.220 | −22.609 | 0.023 | 1.00 | 67.17 | O |
| ATOM | 8406 | OE2 | GLU | C | 362 | 35.217 | −22.918 | −0.814 | 1.00 | 66.96 | O |
| ATOM | 8407 | C | GLU | C | 362 | 38.639 | −23.052 | −5.007 | 1.00 | 66.87 | C |
| ATOM | 8408 | O | GLU | C | 362 | 38.488 | −24.254 | −5.215 | 1.00 | 67.06 | O |
| ATOM | 8409 | N | THR | C | 363 | 38.287 | −22.118 | −5.888 | 1.00 | 67.09 | N |
| ATOM | 8411 | CA | THR | C | 363 | 37.798 | −22.443 | −7.231 | 1.00 | 67.26 | C |
| ATOM | 8413 | CB | THR | C | 363 | 36.309 | −22.062 | −7.399 | 1.00 | 67.26 | C |
| ATOM | 8415 | OG1 | THR | C | 363 | 36.105 | −20.687 | −7.045 | 1.00 | 67.31 | O |
| ATOM | 8417 | CG2 | THR | C | 363 | 35.430 | −22.838 | −6.428 | 1.00 | 67.28 | C |
| ATOM | 8421 | C | THR | C | 363 | 38.669 | −21.685 | −8.235 | 1.00 | 67.43 | C |
| ATOM | 8422 | O | THR | C | 363 | 38.208 | −21.273 | −9.303 | 1.00 | 67.37 | O |
| ATOM | 8423 | N | LYS | C | 364 | 39.941 | −21.520 | −7.872 | 1.00 | 67.70 | N |
| ATOM | 8425 | CA | LYS | C | 364 | 40.910 | −20.799 | −8.686 | 1.00 | 67.82 | C |
| ATOM | 8427 | CB | LYS | C | 364 | 42.153 | −20.471 | −7.850 | 1.00 | 67.77 | C |
| ATOM | 8430 | CG | LYS | C | 364 | 43.204 | −19.629 | −8.567 | 1.00 | 67.86 | C |
| ATOM | 8433 | CD | LYS | C | 364 | 44.625 | −20.108 | −8.286 | 1.00 | 67.90 | C |
| ATOM | 8436 | CE | LYS | C | 364 | 45.067 | −19.750 | −6.877 | 1.00 | 67.84 | C |
| ATOM | 8439 | NZ | LYS | C | 364 | 46.543 | −19.836 | −6.720 | 1.00 | 67.76 | N |
| ATOM | 8443 | C | LYS | C | 364 | 41.309 | −21.627 | −9.897 | 1.00 | 68.00 | C |
| ATOM | 8444 | O | LYS | C | 364 | 41.739 | −22.768 | −9.758 | 1.00 | 68.00 | O |
| ATOM | 8445 | N | LYS | C | 365 | 41.147 | −21.041 | −11.078 | 1.00 | 68.29 | N |
| ATOM | 8447 | CA | LYS | C | 365 | 41.527 | −21.673 | −12.333 | 1.00 | 68.51 | C |
| ATOM | 8449 | CB | LYS | C | 365 | 40.323 | −21.778 | −13.270 | 1.00 | 68.47 | C |
| ATOM | 8452 | CG | LYS | C | 365 | 39.318 | −22.849 | −12.873 | 1.00 | 68.34 | C |
| ATOM | 8455 | CD | LYS | C | 365 | 38.321 | −23.113 | −13.991 | 1.00 | 68.30 | C |
| ATOM | 8458 | CE | LYS | C | 365 | 37.089 | −23.855 | −13.490 | 1.00 | 68.37 | C |
| ATOM | 8461 | NZ | LYS | C | 365 | 37.440 | −25.106 | −12.762 | 1.00 | 68.50 | N |
| ATOM | 8465 | C | LYS | C | 365 | 42.615 | −20.815 | −12.969 | 1.00 | 68.87 | C |
| ATOM | 8466 | O | LYS | C | 365 | 42.434 | −19.612 | −13.137 | 1.00 | 68.93 | O |
| ATOM | 8467 | N | VAL | C | 366 | 43.749 | −21.430 | −13.293 | 1.00 | 69.27 | N |
| ATOM | 8469 | CA | VAL | C | 366 | 44.871 | −20.730 | −13.918 | 1.00 | 69.50 | C |
| ATOM | 8471 | CB | VAL | C | 366 | 46.137 | −20.764 | −13.017 | 1.00 | 69.45 | C |
| ATOM | 8473 | CG1 | VAL | C | 366 | 45.809 | −20.287 | −11.611 | 1.00 | 69.56 | C |
| ATOM | 8477 | CG2 | VAL | C | 366 | 46.759 | −22.162 | −12.969 | 1.00 | 69.45 | C |
| ATOM | 8481 | C | VAL | C | 366 | 45.222 | −21.341 | −15.273 | 1.00 | 69.81 | C |
| ATOM | 8482 | O | VAL | C | 366 | 45.024 | −22.539 | −15.497 | 1.00 | 69.95 | O |
| ATOM | 8483 | N | THR | C | 367 | 45.733 | −20.507 | −16.176 | 1.00 | 70.04 | N |
| ATOM | 8485 | CA | THR | C | 367 | 46.201 | −20.973 | −17.476 | 1.00 | 70.22 | C |
| ATOM | 8487 | CB | THR | C | 367 | 46.420 | −19.792 | −18.462 | 1.00 | 70.28 | C |
| ATOM | 8489 | OG1 | THR | C | 367 | 47.380 | −18.867 | −17.930 | 1.00 | 70.39 | O |
| ATOM | 8491 | CG2 | THR | C | 367 | 45.147 | −18.956 | −18.635 | 1.00 | 70.26 | C |
| ATOM | 8495 | C | THR | C | 367 | 47.515 | −21.715 | −17.232 | 1.00 | 70.30 | C |
| ATOM | 8496 | O | THR | C | 367 | 48.024 | −21.731 | −16.109 | 1.00 | 70.37 | O |
| ATOM | 8497 | N | SER | C | 368 | 48.063 | −22.331 | −18.274 | 1.00 | 70.35 | N |
| ATOM | 8499 | CA | SER | C | 368 | 49.325 | −23.065 | −18.147 | 1.00 | 70.30 | C |
| ATOM | 8501 | CB | SER | C | 368 | 49.604 | −23.871 | −19.419 | 1.00 | 70.34 | C |
| ATOM | 8504 | OG | SER | C | 368 | 49.760 | −23.019 | −20.542 | 1.00 | 70.34 | O |
| ATOM | 8506 | C | SER | C | 368 | 50.515 | −22.143 | −17.834 | 1.00 | 70.26 | C |
| ATOM | 8507 | O | SER | C | 368 | 51.518 | −22.591 | −17.275 | 1.00 | 70.29 | O |
| ATOM | 8508 | N | SER | C | 369 | 50.390 | −20.861 | −18.183 | 1.00 | 70.16 | N |
| ATOM | 8510 | CA | SER | C | 369 | 51.451 | −19.871 | −17.958 | 1.00 | 70.05 | C |
| ATOM | 8512 | CB | SER | C | 369 | 51.199 | −18.623 | −18.812 | 1.00 | 70.02 | C |

TABLE 2-continued

| ATOM | 8515 | OG | SER | C | 369 | 50.923 | −18.963 | −20.157 | 1.00 | 70.05 | O |
| --- | --- | --- | --- | --- | --- | --- | --- | --- | --- | --- | --- |
| ATOM | 8517 | C | SER | C | 369 | 51.607 | −19.438 | −16.496 | 1.00 | 69.91 | C |
| ATOM | 8518 | O | SER | C | 369 | 52.636 | −18.869 | −16.128 | 1.00 | 70.02 | O |
| ATOM | 8519 | N | GLY | C | 370 | 50.592 | −19.698 | −15.675 | 1.00 | 69.71 | N |
| ATOM | 8521 | CA | GLY | C | 370 | 50.600 | −19.315 | −14.271 | 1.00 | 69.47 | C |
| ATOM | 8524 | C | GLY | C | 370 | 49.868 | −18.005 | −14.027 | 1.00 | 69.25 | C |
| ATOM | 8525 | O | GLY | C | 370 | 50.161 | −17.299 | −13.057 | 1.00 | 69.24 | O |
| ATOM | 8526 | N | VAL | C | 371 | 48.913 | −17.691 | −14.905 | 1.00 | 68.94 | N |
| ATOM | 8528 | CA | VAL | C | 371 | 48.118 | −16.466 | −14.824 | 1.00 | 68.67 | C |
| ATOM | 8530 | CB | VAL | C | 371 | 48.241 | −15.638 | −16.130 | 1.00 | 68.70 | C |
| ATOM | 8532 | CG1 | VAL | C | 371 | 47.112 | −14.611 | −16.269 | 1.00 | 68.75 | C |
| ATOM | 8536 | CG2 | VAL | C | 371 | 49.597 | −14.945 | −16.193 | 1.00 | 68.71 | C |
| ATOM | 8540 | C | VAL | C | 371 | 46.656 | −16.823 | −14.547 | 1.00 | 68.35 | C |
| ATOM | 8541 | O | VAL | C | 371 | 46.122 | −17.771 | −15.112 | 1.00 | 68.41 | O |
| ATOM | 8542 | N | LEU | C | 372 | 46.018 | −16.042 | −13.683 | 1.00 | 67.95 | N |
| ATOM | 8544 | CA | LEU | C | 372 | 44.630 | −16.269 | −13.287 | 1.00 | 67.54 | C |
| ATOM | 8546 | CB | LEU | C | 372 | 44.235 | −15.300 | −12.170 | 1.00 | 67.54 | C |
| ATOM | 8549 | CG | LEU | C | 372 | 43.126 | −15.796 | −11.246 | 1.00 | 67.28 | C |
| ATOM | 8551 | CD1 | LEU | C | 372 | 43.692 | −16.754 | −10.215 | 1.00 | 67.17 | C |
| ATOM | 8555 | CD2 | LEU | C | 372 | 42.430 | −14.624 | −10.572 | 1.00 | 67.32 | C |
| ATOM | 8559 | C | LEU | C | 372 | 43.639 | −16.146 | −14.446 | 1.00 | 67.27 | C |
| ATOM | 8560 | O | LEU | C | 372 | 43.785 | −15.296 | −15.326 | 1.00 | 67.18 | O |
| ATOM | 8561 | N | LEU | C | 373 | 42.620 | −16.998 | −14.404 | 1.00 | 66.97 | N |
| ATOM | 8563 | CA | LEU | C | 373 | 41.573 | −17.066 | −15.414 | 1.00 | 66.73 | C |
| ATOM | 8565 | CB | LEU | C | 373 | 41.402 | −18.520 | −15.879 | 1.00 | 66.71 | C |
| ATOM | 8568 | CG | LEU | C | 373 | 40.796 | −18.796 | −17.261 | 1.00 | 66.65 | C |
| ATOM | 8570 | CD1 | LEU | C | 373 | 41.154 | −20.207 | −17.723 | 1.00 | 66.57 | C |
| ATOM | 8574 | CD2 | LEU | C | 373 | 39.282 | −18.610 | −17.258 | 1.00 | 66.69 | C |
| ATOM | 8578 | C | LEU | C | 373 | 40.276 | −16.561 | −14.797 | 1.00 | 66.55 | C |
| ATOM | 8579 | O | LEU | C | 373 | 39.854 | −17.050 | −13.747 | 1.00 | 66.60 | O |
| ATOM | 8580 | N | LEU | C | 374 | 39.660 | −15.572 | −15.441 | 1.00 | 66.29 | N |
| ATOM | 8582 | CA | LEU | C | 374 | 38.396 | −15.005 | −14.977 | 1.00 | 66.07 | C |
| ATOM | 8584 | CB | LEU | C | 374 | 38.621 | −13.614 | −14.381 | 1.00 | 65.99 | C |
| ATOM | 8587 | CG | LEU | C | 374 | 39.613 | −13.549 | −13.211 | 1.00 | 65.61 | C |
| ATOM | 8589 | CD1 | LEU | C | 374 | 39.906 | −12.110 | −12.826 | 1.00 | 65.57 | C |
| ATOM | 8593 | CD2 | LEU | C | 374 | 39.101 | −14.313 | −11.998 | 1.00 | 65.43 | C |
| ATOM | 8597 | C | LEU | C | 374 | 37.416 | −14.953 | −16.148 | 1.00 | 66.02 | C |
| ATOM | 8598 | O | LEU | C | 374 | 37.714 | −14.358 | −17.183 | 1.00 | 66.05 | O |
| ATOM | 8599 | N | ASP | C | 375 | 36.252 | −15.579 | −15.969 | 1.00 | 65.95 | N |
| ATOM | 8601 | CA | ASP | C | 375 | 35.231 | −15.681 | −17.021 | 1.00 | 65.85 | C |
| ATOM | 8603 | CB | ASP | C | 375 | 34.046 | −16.541 | −16.545 | 1.00 | 65.91 | C |
| ATOM | 8606 | CG | ASP | C | 375 | 34.436 | −17.989 | −16.272 | 1.00 | 66.20 | C |
| ATOM | 8607 | OD1 | ASP | C | 375 | 35.315 | −18.526 | −16.982 | 1.00 | 66.55 | O |
| ATOM | 8608 | OD2 | ASP | C | 375 | 33.913 | −18.671 | −15.363 | 1.00 | 66.67 | O |
| ATOM | 8609 | C | ASP | C | 375 | 34.744 | −14.317 | −17.530 | 1.00 | 65.59 | C |
| ATOM | 8610 | O | ASP | C | 375 | 35.212 | −13.849 | −18.572 | 1.00 | 65.70 | O |
| ATOM | 8611 | N | ASN | C | 376 | 33.804 | −13.696 | −16.813 | 1.00 | 65.15 | N |
| ATOM | 8613 | CA | ASN | C | 376 | 33.282 | −12.377 | −17.188 | 1.00 | 64.75 | C |
| ATOM | 8615 | CB | ASN | C | 376 | 31.937 | −12.507 | −17.936 | 1.00 | 64.86 | C |
| ATOM | 8618 | CG | ASN | C | 376 | 31.730 | −11.414 | −19.003 | 1.00 | 65.05 | C |
| ATOM | 8619 | OD1 | ASN | C | 376 | 32.643 | −11.072 | −19.757 | 1.00 | 65.07 | O |
| ATOM | 8620 | ND2 | ASN | C | 376 | 30.522 | −10.863 | −19.055 | 1.00 | 65.19 | N |
| ATOM | 8623 | C | ASN | C | 376 | 33.165 | −11.453 | −15.963 | 1.00 | 64.16 | C |
| ATOM | 8624 | O | ASN | C | 376 | 33.637 | −11.789 | −14.875 | 1.00 | 64.09 | O |
| ATOM | 8625 | N | TYR | C | 377 | 32.548 | −10.292 | −16.166 | 1.00 | 63.37 | N |
| ATOM | 8627 | CA | TYR | C | 377 | 32.385 | −9.257 | −15.145 | 1.00 | 62.77 | C |
| ATOM | 8629 | CB | TYR | C | 377 | 31.145 | −8.406 | −15.456 | 1.00 | 62.89 | C |
| ATOM | 8632 | CG | TYR | C | 377 | 31.042 | −7.182 | −14.580 | 1.00 | 63.42 | C |
| ATOM | 8633 | CD1 | TYR | C | 377 | 31.678 | −5.995 | −14.933 | 1.00 | 63.79 | C |
| ATOM | 8635 | CE1 | TYR | C | 377 | 31.595 | −4.872 | −14.123 | 1.00 | 64.11 | C |
| ATOM | 8637 | CZ | TYR | C | 377 | 30.875 | −4.934 | −12.942 | 1.00 | 64.23 | C |
| ATOM | 8638 | OH | TYR | C | 377 | 30.787 | −3.831 | −12.132 | 1.00 | 64.41 | O |
| ATOM | 8640 | CE2 | TYR | C | 377 | 30.239 | −6.103 | −12.570 | 1.00 | 64.31 | C |
| ATOM | 8642 | CD2 | TYR | C | 377 | 30.327 | −7.218 | −13.386 | 1.00 | 63.96 | C |
| ATOM | 8644 | C | TYR | C | 377 | 32.336 | −9.701 | −13.674 | 1.00 | 61.94 | C |
| ATOM | 8645 | O | TYR | C | 377 | 33.120 | −9.218 | −12.866 | 1.00 | 61.87 | O |
| ATOM | 8646 | N | THR | C | 378 | 31.426 | −10.609 | −13.333 | 1.00 | 60.90 | N |
| ATOM | 8648 | CA | THR | C | 378 | 31.245 | −11.041 | −11.938 | 1.00 | 60.16 | C |
| ATOM | 8650 | CB | THR | C | 378 | 30.278 | −12.240 | −11.863 | 1.00 | 60.20 | C |
| ATOM | 8652 | OG1 | THR | C | 378 | 29.013 | −11.883 | −12.432 | 1.00 | 60.34 | O |
| ATOM | 8654 | CG2 | THR | C | 378 | 29.942 | −12.586 | −10.410 | 1.00 | 60.36 | C |
| ATOM | 8658 | C | THR | C | 378 | 32.537 | −11.401 | −11.202 | 1.00 | 59.29 | C |
| ATOM | 8659 | O | THR | C | 378 | 32.734 | −11.009 | −10.050 | 1.00 | 59.20 | O |
| ATOM | 8660 | N | ASP | C | 379 | 33.404 | −12.154 | −11.869 | 1.00 | 58.22 | N |
| ATOM | 8662 | CA | ASP | C | 379 | 34.659 | −12.601 | −11.270 | 1.00 | 57.37 | C |
| ATOM | 8664 | CB | ASP | C | 379 | 35.196 | −13.838 | −12.005 | 1.00 | 57.51 | C |
| ATOM | 8667 | CG | ASP | C | 379 | 34.142 | −14.924 | −12.178 | 1.00 | 58.02 | C |
| ATOM | 8668 | OD1 | ASP | C | 379 | 33.879 | −15.666 | −11.208 | 1.00 | 58.50 | O |
| ATOM | 8669 | OD2 | ASP | C | 379 | 33.524 | −15.102 | −13.251 | 1.00 | 58.98 | O |

TABLE 2-continued

| ATOM | 8670 | C | ASP | C | 379 | 35.723 | −11.504 | −11.247 | 1.00 | 56.25 | C |
| ATOM | 8671 | O | ASP | C | 379 | 36.489 | −11.404 | −10.291 | 1.00 | 56.09 | O |
| ATOM | 8672 | N | ARG | C | 380 | 35.769 | −10.686 | −12.296 | 1.00 | 54.99 | N |
| ATOM | 8674 | CA | ARG | C | 380 | 36.763 | −9.615 | −12.391 | 1.00 | 54.00 | C |
| ATOM | 8676 | CB | ARG | C | 380 | 36.781 | −9.017 | −13.800 | 1.00 | 54.02 | C |
| ATOM | 8679 | CG | ARG | C | 380 | 37.427 | −9.925 | −14.845 | 1.00 | 54.28 | C |
| ATOM | 8682 | CD | ARG | C | 380 | 37.899 | −9.195 | −16.092 | 1.00 | 54.62 | C |
| ATOM | 8685 | NE | ARG | C | 380 | 36.781 | −8.552 | −16.781 | 1.00 | 55.01 | N |
| ATOM | 8687 | CZ | ARG | C | 380 | 36.005 | −9.137 | −17.695 | 1.00 | 55.36 | C |
| ATOM | 8688 | NH1 | ARG | C | 380 | 36.196 | −10.404 | −18.058 | 1.00 | 55.47 | N |
| ATOM | 8691 | NH2 | ARG | C | 380 | 35.015 | −8.442 | −18.248 | 1.00 | 55.28 | N |
| ATOM | 8694 | C | ARG | C | 380 | 36.573 | −8.510 | −11.343 | 1.00 | 52.97 | C |
| ATOM | 8695 | O | ARG | C | 380 | 37.541 | −8.106 | −10.705 | 1.00 | 52.84 | O |
| ATOM | 8696 | N | ILE | C | 381 | 35.340 | −8.032 | −11.169 | 1.00 | 51.68 | N |
| ATOM | 8698 | CA | ILE | C | 381 | 35.040 | −6.977 | −10.193 | 1.00 | 50.67 | C |
| ATOM | 8700 | CB | ILE | C | 381 | 33.628 | −6.367 | −10.439 | 1.00 | 50.54 | C |
| ATOM | 8702 | CG1 | ILE | C | 381 | 33.477 | −5.002 | −9.749 | 1.00 | 50.14 | C |
| ATOM | 8705 | CD1 | ILE | C | 381 | 34.328 | −3.890 | −10.339 | 1.00 | 49.70 | C |
| ATOM | 8709 | CG2 | ILE | C | 381 | 32.529 | −7.313 | −9.954 | 1.00 | 50.45 | C |
| ATOM | 8713 | C | ILE | C | 381 | 35.165 | −7.483 | −8.752 | 1.00 | 50.03 | C |
| ATOM | 8714 | O | ILE | C | 381 | 35.314 | −6.688 | −7.829 | 1.00 | 49.58 | O |
| ATOM | 8715 | N | GLN | C | 382 | 35.080 | −8.799 | −8.566 | 1.00 | 49.26 | N |
| ATOM | 8717 | CA | GLN | C | 382 | 35.247 | −9.397 | −7.249 | 1.00 | 48.80 | C |
| ATOM | 8719 | CB | GLN | C | 382 | 34.777 | −10.853 | −7.241 | 1.00 | 48.92 | C |
| ATOM | 8722 | CG | GLN | C | 382 | 34.958 | −11.548 | −5.896 | 1.00 | 49.41 | C |
| ATOM | 8725 | CD | GLN | C | 382 | 34.239 | −12.882 | −5.808 | 1.00 | 50.48 | C |
| ATOM | 8726 | OE1 | GLN | C | 382 | 33.693 | −13.376 | −6.800 | 1.00 | 50.88 | O |
| ATOM | 8727 | NE2 | GLN | C | 382 | 34.239 | −13.473 | −4.616 | 1.00 | 50.51 | N |
| ATOM | 8730 | C | GLN | C | 382 | 36.714 | −9.310 | −6.847 | 1.00 | 48.20 | C |
| ATOM | 8731 | O | GLN | C | 382 | 37.028 | −9.129 | −5.670 | 1.00 | 48.13 | O |
| ATOM | 8732 | N | VAL | C | 383 | 37.603 | −9.449 | −7.829 | 1.00 | 47.40 | N |
| ATOM | 8734 | CA | VAL | C | 383 | 39.041 | −9.348 | −7.596 | 1.00 | 46.86 | C |
| ATOM | 8736 | CB | VAL | C | 383 | 39.867 | −9.983 | −8.747 | 1.00 | 46.76 | C |
| ATOM | 8738 | CG1 | VAL | C | 383 | 41.360 | −9.710 | −8.568 | 1.00 | 46.63 | C |
| ATOM | 8742 | CG2 | VAL | C | 383 | 39.616 | −11.487 | −8.823 | 1.00 | 46.58 | C |
| ATOM | 8746 | C | VAL | C | 383 | 39.433 | −7.882 | −7.412 | 1.00 | 46.43 | C |
| ATOM | 8747 | O | VAL | C | 383 | 40.311 | −7.574 | −6.607 | 1.00 | 46.76 | O |
| ATOM | 8748 | N | LEU | C | 384 | 38.786 | −6.985 | −8.155 | 1.00 | 45.71 | N |
| ATOM | 8750 | CA | LEU | C | 384 | 39.054 | −5.552 | −8.047 | 1.00 | 45.25 | C |
| ATOM | 8752 | CB | LEU | C | 384 | 38.442 | −4.789 | −9.227 | 1.00 | 45.12 | C |
| ATOM | 8755 | CG | LEU | C | 384 | 39.014 | −5.089 | −10.621 | 1.00 | 44.86 | C |
| ATOM | 8757 | CD1 | LEU | C | 384 | 38.145 | −4.459 | −11.702 | 1.00 | 44.46 | C |
| ATOM | 8761 | CD2 | LEU | C | 384 | 40.452 | −4.604 | −10.745 | 1.00 | 44.63 | C |
| ATOM | 8765 | C | LEU | C | 384 | 38.506 | −5.011 | −6.720 | 1.00 | 44.91 | C |
| ATOM | 8766 | O | LEU | C | 384 | 39.087 | −4.111 | −6.129 | 1.00 | 44.99 | O |
| ATOM | 8767 | N | ARG | C | 385 | 37.392 | −5.579 | −6.264 | 1.00 | 44.48 | N |
| ATOM | 8769 | CA | ARG | C | 385 | 36.760 | −5.201 | −5.004 | 1.00 | 44.21 | C |
| ATOM | 8771 | CB | ARG | C | 385 | 35.509 | −6.051 | −4.750 | 1.00 | 44.36 | C |
| ATOM | 8774 | CG | ARG | C | 385 | 34.194 | −5.391 | −5.075 | 1.00 | 45.27 | C |
| ATOM | 8777 | CD | ARG | C | 385 | 33.032 | −5.893 | −4.221 | 1.00 | 46.54 | C |
| ATOM | 8780 | NE | ARG | C | 385 | 32.879 | −7.347 | −4.252 | 1.00 | 47.63 | N |
| ATOM | 8782 | CZ | ARG | C | 385 | 32.316 | −8.045 | −5.241 | 1.00 | 48.44 | C |
| ATOM | 8783 | NH1 | ARG | C | 385 | 31.847 | −7.445 | −6.333 | 1.00 | 48.72 | N |
| ATOM | 8786 | NH2 | ARG | C | 385 | 32.232 | −9.367 | −5.138 | 1.00 | 48.73 | N |
| ATOM | 8789 | C | ARG | C | 385 | 37.726 | −5.454 | −3.861 | 1.00 | 43.68 | C |
| ATOM | 8790 | O | ARG | C | 385 | 37.962 | −4.584 | −3.032 | 1.00 | 43.59 | O |
| ATOM | 8791 | N | ASN | C | 386 | 38.272 | −6.665 | −3.836 | 1.00 | 43.18 | N |
| ATOM | 8793 | CA | ASN | C | 386 | 39.202 | −7.091 | −2.799 | 1.00 | 42.75 | C |
| ATOM | 8795 | CB | ASN | C | 386 | 39.315 | −8.619 | −2.787 | 1.00 | 42.79 | C |
| ATOM | 8798 | CG | ASN | C | 386 | 38.055 | −9.289 | −2.278 | 1.00 | 42.66 | C |
| ATOM | 8799 | OD1 | ASN | C | 386 | 37.999 | −9.722 | −1.137 | 1.00 | 43.37 | O |
| ATOM | 8800 | ND2 | ASN | C | 386 | 37.034 | −9.365 | −3.121 | 1.00 | 42.81 | N |
| ATOM | 8803 | C | ASN | C | 386 | 40.584 | −6.469 | −2.939 | 1.00 | 42.33 | C |
| ATOM | 8804 | O | ASN | C | 386 | 41.313 | −6.373 | −1.954 | 1.00 | 42.30 | O |
| ATOM | 8805 | N | MET | C | 387 | 40.932 | −6.038 | −4.152 | 1.00 | 41.80 | N |
| ATOM | 8807 | CA | MET | C | 387 | 42.233 | −5.423 | −4.421 | 1.00 | 41.42 | C |
| ATOM | 8809 | CB | MET | C | 387 | 42.515 | −5.365 | −5.932 | 1.00 | 41.35 | C |
| ATOM | 8812 | CG | MET | C | 387 | 43.833 | −4.675 | −6.323 | 1.00 | 41.19 | C |
| ATOM | 8815 | SD | MET | C | 387 | 44.036 | −4.487 | −8.134 | 1.00 | 42.06 | S |
| ATOM | 8816 | CE | MET | C | 387 | 44.142 | −6.180 | −8.617 | 1.00 | 41.58 | C |
| ATOM | 8820 | C | MET | C | 387 | 42.297 | −4.021 | −3.834 | 1.00 | 41.17 | C |
| ATOM | 8821 | O | MET | C | 387 | 43.324 | −3.627 | −3.288 | 1.00 | 41.19 | O |
| ATOM | 8822 | N | VAL | C | 388 | 41.211 | −3.264 | −3.974 | 1.00 | 40.96 | N |
| ATOM | 8824 | CA | VAL | C | 388 | 41.136 | −1.908 | −3.432 | 1.00 | 40.88 | C |
| ATOM | 8826 | CB | VAL | C | 388 | 39.958 | −1.110 | −4.037 | 1.00 | 40.81 | C |
| ATOM | 8828 | CG1 | VAL | C | 388 | 39.812 | 0.253 | −3.356 | 1.00 | 40.45 | C |
| ATOM | 8832 | CG2 | VAL | C | 388 | 40.149 | −0.928 | −5.540 | 1.00 | 40.75 | C |
| ATOM | 8836 | C | VAL | C | 388 | 40.985 | −1.992 | −1.914 | 1.00 | 40.90 | C |
| ATOM | 8837 | O | VAL | C | 388 | 41.508 | −1.153 | −1.182 | 1.00 | 41.04 | O |

TABLE 2-continued

| | | | | | | | | | | | |
|---|---|---|---|---|---|---|---|---|---|---|---|
| ATOM | 8838 | N | HIS | C | 389 | 40.272 | −3.014 | −1.452 | 1.00 | 40.89 | N |
| ATOM | 8840 | CA | HIS | C | 389 | 40.066 | −3.237 | −0.028 | 1.00 | 40.97 | C |
| ATOM | 8842 | CB | HIS | C | 389 | 39.042 | −4.356 | 0.189 | 1.00 | 40.93 | C |
| ATOM | 8845 | CG | HIS | C | 389 | 38.825 | −4.712 | 1.626 | 1.00 | 40.69 | C |
| ATOM | 8846 | ND1 | HIS | C | 389 | 38.750 | −3.767 | 2.625 | 1.00 | 40.75 | N |
| ATOM | 8848 | CE1 | HIS | C | 389 | 38.558 | −4.369 | 3.785 | 1.00 | 40.71 | C |
| ATOM | 8850 | NE2 | HIS | C | 389 | 38.501 | −5.672 | 3.574 | 1.00 | 41.28 | N |
| ATOM | 8852 | CD2 | HIS | C | 389 | 38.662 | −5.913 | 2.231 | 1.00 | 40.94 | C |
| ATOM | 8854 | C | HIS | C | 389 | 41.405 | −3.581 | 0.611 | 1.00 | 41.10 | C |
| ATOM | 8855 | O | HIS | C | 389 | 41.711 | −3.116 | 1.707 | 1.00 | 41.46 | O |
| ATOM | 8856 | N | CYS | C | 390 | 42.209 | −4.371 | −0.101 | 1.00 | 41.10 | N |
| ATOM | 8858 | CA | CYS | C | 390 | 43.534 | −4.776 | 0.367 | 1.00 | 40.92 | C |
| ATOM | 8860 | CB | CYS | C | 390 | 44.148 | −5.825 | −0.568 | 1.00 | 40.93 | C |
| ATOM | 8863 | SG | CYS | C | 390 | 43.612 | −7.524 | −0.252 | 1.00 | 41.88 | S |
| ATOM | 8864 | C | CYS | C | 390 | 44.452 | −3.563 | 0.445 | 1.00 | 40.47 | C |
| ATOM | 8865 | O | CYS | C | 390 | 45.206 | −3.404 | 1.406 | 1.00 | 40.67 | O |
| ATOM | 8866 | N | ALA | C | 391 | 44.376 | −2.711 | −0.573 | 1.00 | 39.80 | N |
| ATOM | 8868 | CA | ALA | C | 391 | 45.180 | −1.494 | −0.638 | 1.00 | 39.38 | C |
| ATOM | 8870 | CB | ALA | C | 391 | 44.993 | −0.803 | −1.992 | 1.00 | 39.22 | C |
| ATOM | 8874 | C | ALA | C | 391 | 44.835 | −0.536 | 0.500 | 1.00 | 38.91 | C |
| ATOM | 8875 | O | ALA | C | 391 | 45.713 | 0.143 | 1.013 | 1.00 | 38.94 | O |
| ATOM | 8876 | N | ASP | C | 392 | 43.557 | −0.486 | 0.875 | 1.00 | 38.61 | N |
| ATOM | 8878 | CA | ASP | C | 392 | 43.079 | 0.352 | 1.975 | 1.00 | 38.70 | C |
| ATOM | 8880 | CB | ASP | C | 392 | 41.537 | 0.382 | 1.989 | 1.00 | 38.48 | C |
| ATOM | 8883 | CG | ASP | C | 392 | 40.955 | 1.624 | 2.678 | 1.00 | 38.85 | C |
| ATOM | 8884 | OD1 | ASP | C | 392 | 39.742 | 1.608 | 2.981 | 1.00 | 39.47 | O |
| ATOM | 8885 | OD2 | ASP | C | 392 | 41.593 | 2.661 | 2.957 | 1.00 | 36.83 | O |
| ATOM | 8886 | C | ASP | C | 392 | 43.637 | −0.203 | 3.297 | 1.00 | 38.84 | C |
| ATOM | 8887 | O | ASP | C | 392 | 44.023 | 0.559 | 4.178 | 1.00 | 39.28 | O |
| ATOM | 8888 | N | LEU | C | 393 | 43.695 | −1.528 | 3.411 | 1.00 | 39.02 | N |
| ATOM | 8890 | CA | LEU | C | 393 | 44.230 | −2.205 | 4.593 | 1.00 | 39.26 | C |
| ATOM | 8892 | CB | LEU | C | 393 | 43.334 | −3.385 | 4.981 | 1.00 | 39.17 | C |
| ATOM | 8895 | CG | LEU | C | 393 | 41.839 | −3.111 | 5.157 | 1.00 | 39.37 | C |
| ATOM | 8897 | CD1 | LEU | C | 393 | 41.172 | −4.310 | 5.801 | 1.00 | 39.33 | C |
| ATOM | 8901 | CD2 | LEU | C | 393 | 41.600 | −1.858 | 5.974 | 1.00 | 39.76 | C |
| ATOM | 8905 | C | LEU | C | 393 | 45.648 | −2.717 | 4.346 | 1.00 | 39.38 | C |
| ATOM | 8906 | O | LEU | C | 393 | 45.969 | −3.843 | 4.713 | 1.00 | 39.51 | O |
| ATOM | 8907 | N | SER | C | 394 | 46.498 | −1.884 | 3.751 | 1.00 | 39.70 | N |
| ATOM | 8909 | CA | SER | C | 394 | 47.878 | −2.272 | 3.423 | 1.00 | 39.87 | C |
| ATOM | 8911 | CB | SER | C | 394 | 48.180 | −1.914 | 1.962 | 1.00 | 39.70 | C |
| ATOM | 8914 | OG | SER | C | 394 | 48.310 | −0.514 | 1.807 | 1.00 | 38.90 | O |
| ATOM | 8916 | C | SER | C | 394 | 48.961 | −1.642 | 4.304 | 1.00 | 40.28 | C |
| ATOM | 8917 | O | SER | C | 394 | 50.136 | −1.951 | 4.142 | 1.00 | 40.41 | O |
| ATOM | 8918 | N | ASN | C | 395 | 48.586 | −0.753 | 5.216 | 1.00 | 41.04 | N |
| ATOM | 8920 | CA | ASN | C | 395 | 49.567 | −0.086 | 6.078 | 1.00 | 41.65 | C |
| ATOM | 8922 | CB | ASN | C | 395 | 48.870 | 0.834 | 7.094 | 1.00 | 41.82 | C |
| ATOM | 8925 | CG | ASN | C | 395 | 48.228 | 2.053 | 6.449 | 1.00 | 41.99 | C |
| ATOM | 8926 | OD1 | ASN | C | 395 | 47.400 | 2.721 | 7.062 | 1.00 | 42.09 | O |
| ATOM | 8927 | ND2 | ASN | C | 395 | 48.602 | 2.342 | 5.211 | 1.00 | 41.93 | N |
| ATOM | 8930 | C | ASN | C | 395 | 50.533 | −1.038 | 6.804 | 1.00 | 42.10 | C |
| ATOM | 8931 | O | ASN | C | 395 | 51.732 | −0.759 | 6.867 | 1.00 | 42.06 | O |
| ATOM | 8932 | N | PRO | C | 396 | 50.030 | −2.139 | 7.365 | 1.00 | 42.81 | N |
| ATOM | 8933 | CA | PRO | C | 396 | 50.893 | −3.105 | 8.064 | 1.00 | 43.24 | C |
| ATOM | 8935 | CB | PRO | C | 396 | 49.885 | −4.010 | 8.780 | 1.00 | 43.23 | C |
| ATOM | 8938 | CG | PRO | C | 396 | 48.626 | −3.237 | 8.781 | 1.00 | 43.04 | C |
| ATOM | 8941 | CD | PRO | C | 396 | 48.615 | −2.538 | 7.458 | 1.00 | 42.78 | C |
| ATOM | 8944 | C | PRO | C | 396 | 51.820 | −3.938 | 7.171 | 1.00 | 43.81 | C |
| ATOM | 8945 | O | PRO | C | 396 | 52.739 | −4.569 | 7.701 | 1.00 | 43.60 | O |
| ATOM | 8946 | N | THR | C | 397 | 51.578 | −3.939 | 5.860 | 1.00 | 44.45 | N |
| ATOM | 8948 | CA | THR | C | 397 | 52.394 | −4.689 | 4.903 | 1.00 | 44.97 | C |
| ATOM | 8950 | CB | THR | C | 397 | 51.535 | −5.162 | 3.703 | 1.00 | 45.03 | C |
| ATOM | 8952 | OG1 | THR | C | 397 | 51.065 | −4.032 | 2.959 | 1.00 | 44.78 | O |
| ATOM | 8954 | CG2 | THR | C | 397 | 50.262 | −5.863 | 4.162 | 1.00 | 45.07 | C |
| ATOM | 8958 | C | THR | C | 397 | 53.587 | −3.896 | 4.361 | 1.00 | 45.49 | C |
| ATOM | 8959 | O | THR | C | 397 | 54.430 | −4.458 | 3.665 | 1.00 | 45.34 | O |
| ATOM | 8960 | N | LYS | C | 398 | 53.647 | −2.601 | 4.663 | 1.00 | 46.23 | N |
| ATOM | 8962 | CA | LYS | C | 398 | 54.735 | −1.745 | 4.196 | 1.00 | 46.84 | C |
| ATOM | 8964 | CB | LYS | C | 398 | 54.279 | −0.283 | 4.129 | 1.00 | 46.83 | C |
| ATOM | 8967 | CG | LYS | C | 398 | 53.024 | −0.038 | 3.301 | 1.00 | 46.89 | C |
| ATOM | 8970 | CD | LYS | C | 398 | 53.224 | −0.418 | 1.836 | 1.00 | 46.68 | C |
| ATOM | 8973 | CE | LYS | C | 398 | 51.947 | −0.242 | 1.032 | 1.00 | 46.40 | C |
| ATOM | 8976 | NZ | LYS | C | 398 | 51.540 | 1.184 | 0.952 | 1.00 | 46.59 | N |
| ATOM | 8980 | C | LYS | C | 398 | 55.934 | −1.864 | 5.126 | 1.00 | 47.64 | C |
| ATOM | 8981 | O | LYS | C | 398 | 55.848 | −2.511 | 6.175 | 1.00 | 47.81 | O |
| ATOM | 8982 | N | SER | C | 399 | 57.052 | −1.242 | 4.745 | 1.00 | 48.37 | N |
| ATOM | 8984 | CA | SER | C | 399 | 58.262 | −1.262 | 5.572 | 1.00 | 49.08 | C |
| ATOM | 8986 | CB | SER | C | 399 | 59.383 | −0.437 | 4.934 | 1.00 | 49.05 | C |
| ATOM | 8989 | OG | SER | C | 399 | 59.010 | 0.923 | 4.785 | 1.00 | 49.56 | O |
| ATOM | 8991 | C | SER | C | 399 | 57.905 | −0.718 | 6.953 | 1.00 | 49.56 | C |

TABLE 2-continued

| ATOM | 8992 | O | SER | C | 399 | 57.018 | 0.122 | 7.063 | 1.00 | 49.70 | O |
| --- | --- | --- | --- | --- | --- | --- | --- | --- | --- | --- | --- |
| ATOM | 8993 | N | LEU | C | 400 | 58.578 | −1.198 | 7.998 | 1.00 | 50.24 | N |
| ATOM | 8995 | CA | LEU | C | 400 | 58.261 | −0.782 | 9.371 | 1.00 | 50.66 | C |
| ATOM | 8997 | CB | LEU | C | 400 | 59.206 | −1.444 | 10.381 | 1.00 | 50.88 | C |
| ATOM | 9000 | CG | LEU | C | 400 | 58.887 | −1.222 | 11.868 | 1.00 | 51.42 | C |
| ATOM | 9002 | CD1 | LEU | C | 400 | 57.507 | −1.757 | 12.222 | 1.00 | 51.68 | C |
| ATOM | 9006 | CD2 | LEU | C | 400 | 59.948 | −1.870 | 12.751 | 1.00 | 52.00 | C |
| ATOM | 9010 | C | LEU | C | 400 | 58.269 | 0.733 | 9.562 | 1.00 | 50.99 | C |
| ATOM | 9011 | O | LEU | C | 400 | 57.466 | 1.259 | 10.328 | 1.00 | 51.24 | O |
| ATOM | 9012 | N | GLU | C | 401 | 59.169 | 1.427 | 8.867 | 1.00 | 51.32 | N |
| ATOM | 9014 | CA | GLU | C | 401 | 59.269 | 2.886 | 8.951 | 1.00 | 51.57 | C |
| ATOM | 9016 | CB | GLU | C | 401 | 60.437 | 3.395 | 8.099 | 1.00 | 51.94 | C |
| ATOM | 9019 | CG | GLU | C | 401 | 60.854 | 4.828 | 8.412 | 1.00 | 53.33 | C |
| ATOM | 9022 | CD | GLU | C | 401 | 61.798 | 5.416 | 7.375 | 1.00 | 55.07 | C |
| ATOM | 9023 | OE1 | GLU | C | 401 | 62.806 | 6.040 | 7.774 | 1.00 | 56.15 | O |
| ATOM | 9024 | OE2 | GLU | C | 401 | 61.530 | 5.263 | 6.162 | 1.00 | 56.44 | O |
| ATOM | 9025 | C | GLU | C | 401 | 57.979 | 3.590 | 8.517 | 1.00 | 51.29 | C |
| ATOM | 9026 | O | GLU | C | 401 | 57.582 | 4.588 | 9.119 | 1.00 | 51.27 | O |
| ATOM | 9027 | N | LEU | C | 402 | 57.350 | 3.081 | 7.458 | 1.00 | 50.93 | N |
| ATOM | 9029 | CA | LEU | C | 402 | 56.100 | 3.643 | 6.944 | 1.00 | 50.62 | C |
| ATOM | 9031 | CB | LEU | C | 402 | 55.841 | 3.152 | 5.516 | 1.00 | 50.64 | C |
| ATOM | 9034 | CG | LEU | C | 402 | 56.851 | 3.600 | 4.455 | 1.00 | 50.71 | C |
| ATOM | 9036 | CD1 | LEU | C | 402 | 56.729 | 2.756 | 3.191 | 1.00 | 50.54 | C |
| ATOM | 9040 | CD2 | LEU | C | 402 | 56.663 | 5.073 | 4.136 | 1.00 | 50.87 | C |
| ATOM | 9044 | C | LEU | C | 402 | 54.902 | 3.278 | 7.823 | 1.00 | 50.29 | C |
| ATOM | 9045 | O | LEU | C | 402 | 54.048 | 4.114 | 8.091 | 1.00 | 50.28 | O |
| ATOM | 9046 | N | TYR | C | 403 | 54.851 | 2.024 | 8.260 | 1.00 | 49.91 | N |
| ATOM | 9048 | CA | TYR | C | 403 | 53.763 | 1.507 | 9.088 | 1.00 | 49.63 | C |
| ATOM | 9050 | CB | TYR | C | 403 | 53.987 | 0.007 | 9.329 | 1.00 | 49.40 | C |
| ATOM | 9053 | CG | TYR | C | 403 | 52.902 | −0.739 | 10.091 | 1.00 | 48.38 | C |
| ATOM | 9054 | CD1 | TYR | C | 403 | 51.585 | −0.279 | 10.149 | 1.00 | 47.14 | C |
| ATOM | 9056 | CE1 | TYR | C | 403 | 50.614 | −0.982 | 10.843 | 1.00 | 46.69 | C |
| ATOM | 9058 | CZ | TYR | C | 403 | 50.943 | −2.163 | 11.478 | 1.00 | 46.12 | C |
| ATOM | 9059 | OH | TYR | C | 403 | 49.988 | −2.873 | 12.167 | 1.00 | 45.11 | O |
| ATOM | 9061 | CE2 | TYR | C | 403 | 52.230 | −2.645 | 11.421 | 1.00 | 46.63 | C |
| ATOM | 9063 | CD2 | TYR | C | 403 | 53.200 | −1.935 | 10.736 | 1.00 | 46.96 | C |
| ATOM | 9065 | C | TYR | C | 403 | 53.617 | 2.248 | 10.423 | 1.00 | 49.88 | C |
| ATOM | 9066 | O | TYR | C | 403 | 52.506 | 2.411 | 10.918 | 1.00 | 49.98 | O |
| ATOM | 9067 | N | ARG | C | 404 | 54.727 | 2.705 | 10.994 | 1.00 | 49.94 | N |
| ATOM | 9069 | CA | ARG | C | 404 | 54.684 | 3.417 | 12.272 | 1.00 | 50.12 | C |
| ATOM | 9071 | CB | ARG | C | 404 | 56.073 | 3.479 | 12.920 | 1.00 | 50.33 | C |
| ATOM | 9074 | CG | ARG | C | 404 | 56.433 | 2.215 | 13.685 | 1.00 | 51.36 | C |
| ATOM | 9077 | CD | ARG | C | 404 | 57.917 | 2.052 | 13.951 | 1.00 | 52.94 | C |
| ATOM | 9080 | NE | ARG | C | 404 | 58.433 | 3.088 | 14.845 | 1.00 | 54.34 | N |
| ATOM | 9082 | CZ | ARG | C | 404 | 59.702 | 3.185 | 15.237 | 1.00 | 55.94 | C |
| ATOM | 9083 | NH1 | ARG | C | 404 | 60.614 | 2.311 | 14.817 | 1.00 | 56.60 | N |
| ATOM | 9086 | NH2 | ARG | C | 404 | 60.068 | 4.165 | 16.054 | 1.00 | 56.65 | N |
| ATOM | 9089 | C | ARG | C | 404 | 54.102 | 4.816 | 12.110 | 1.00 | 49.73 | C |
| ATOM | 9090 | O | ARG | C | 404 | 53.430 | 5.314 | 13.013 | 1.00 | 49.64 | O |
| ATOM | 9091 | N | GLN | C | 405 | 54.368 | 5.448 | 10.967 | 1.00 | 49.28 | N |
| ATOM | 9093 | CA | GLN | C | 405 | 53.834 | 6.782 | 10.680 | 1.00 | 48.84 | C |
| ATOM | 9095 | CB | GLN | C | 405 | 54.519 | 7.403 | 9.459 | 1.00 | 48.95 | C |
| ATOM | 9098 | CG | GLN | C | 405 | 55.872 | 8.026 | 9.768 | 1.00 | 49.16 | C |
| ATOM | 9101 | CD | GLN | C | 405 | 56.615 | 8.460 | 8.519 | 1.00 | 49.05 | C |
| ATOM | 9102 | OE1 | GLN | C | 405 | 56.403 | 9.562 | 8.015 | 1.00 | 49.23 | O |
| ATOM | 9103 | NE2 | GLN | C | 405 | 57.493 | 7.598 | 8.024 | 1.00 | 48.53 | N |
| ATOM | 9106 | C | GLN | C | 405 | 52.325 | 6.715 | 10.460 | 1.00 | 48.28 | C |
| ATOM | 9107 | O | GLN | C | 405 | 51.593 | 7.614 | 10.875 | 1.00 | 48.43 | O |
| ATOM | 9108 | N | TRP | C | 406 | 51.870 | 5.647 | 9.808 | 1.00 | 47.54 | N |
| ATOM | 9110 | CA | TRP | C | 406 | 50.448 | 5.431 | 9.556 | 1.00 | 46.90 | C |
| ATOM | 9112 | CB | TRP | C | 406 | 50.231 | 4.250 | 8.603 | 1.00 | 46.63 | C |
| ATOM | 9115 | CG | TRP | C | 406 | 50.608 | 4.502 | 7.166 | 1.00 | 45.51 | C |
| ATOM | 9116 | CD1 | TRP | C | 406 | 51.450 | 3.749 | 6.400 | 1.00 | 44.30 | C |
| ATOM | 9118 | NE1 | TRP | C | 406 | 51.541 | 4.275 | 5.135 | 1.00 | 43.72 | N |
| ATOM | 9120 | CE2 | TRP | C | 406 | 50.740 | 5.384 | 5.056 | 1.00 | 43.65 | C |
| ATOM | 9121 | CD2 | TRP | C | 406 | 50.132 | 5.553 | 6.319 | 1.00 | 43.70 | C |
| ATOM | 9122 | CE3 | TRP | C | 406 | 49.257 | 6.634 | 6.500 | 1.00 | 43.36 | C |
| ATOM | 9124 | CZ3 | TRP | C | 406 | 49.020 | 7.493 | 5.430 | 1.00 | 42.77 | C |
| ATOM | 9126 | CH2 | TRP | C | 406 | 49.646 | 7.296 | 4.192 | 1.00 | 42.14 | C |
| ATOM | 9128 | CZ2 | TRP | C | 406 | 50.505 | 6.252 | 3.986 | 1.00 | 42.48 | C |
| ATOM | 9130 | C | TRP | C | 406 | 49.727 | 5.135 | 10.866 | 1.00 | 46.76 | C |
| ATOM | 9131 | O | TRP | C | 406 | 48.616 | 5.603 | 11.091 | 1.00 | 46.65 | O |
| ATOM | 9132 | N | THR | C | 407 | 50.374 | 4.348 | 11.719 | 1.00 | 46.54 | N |
| ATOM | 9134 | CA | THR | C | 407 | 49.810 | 3.954 | 13.003 | 1.00 | 46.40 | C |
| ATOM | 9136 | CB | THR | C | 407 | 50.734 | 2.940 | 13.702 | 1.00 | 46.42 | C |
| ATOM | 9138 | OG1 | THR | C | 407 | 50.680 | 1.683 | 13.012 | 1.00 | 46.50 | O |
| ATOM | 9140 | CG2 | THR | C | 407 | 50.242 | 2.614 | 15.118 | 1.00 | 46.22 | C |
| ATOM | 9144 | C | THR | C | 407 | 49.579 | 5.164 | 13.895 | 1.00 | 46.24 | C |
| ATOM | 9145 | O | THR | C | 407 | 48.549 | 5.261 | 14.548 | 1.00 | 46.13 | O |

TABLE 2-continued

| ATOM | 9146 | N | ASP | C | 408 | 50.527 | 6.093 | 13.900 | 1.00 | 46.19 | N |
|---|---|---|---|---|---|---|---|---|---|---|---|
| ATOM | 9148 | CA | ASP | C | 408 | 50.413 | 7.292 | 14.725 | 1.00 | 46.30 | C |
| ATOM | 9150 | CB | ASP | C | 408 | 51.749 | 8.047 | 14.770 | 1.00 | 46.44 | C |
| ATOM | 9153 | CG | ASP | C | 408 | 52.854 | 7.258 | 15.466 | 1.00 | 46.80 | C |
| ATOM | 9154 | OD1 | ASP | C | 408 | 52.596 | 6.134 | 15.958 | 1.00 | 47.20 | O |
| ATOM | 9155 | OD2 | ASP | C | 408 | 54.022 | 7.689 | 15.559 | 1.00 | 47.71 | O |
| ATOM | 9156 | C | ASP | C | 408 | 49.302 | 8.222 | 14.233 | 1.00 | 46.11 | C |
| ATOM | 9157 | O | ASP | C | 408 | 48.694 | 8.939 | 15.026 | 1.00 | 46.07 | O |
| ATOM | 9158 | N | ARG | C | 409 | 49.042 | 8.198 | 12.928 | 1.00 | 45.87 | N |
| ATOM | 9160 | CA | ARG | C | 409 | 48.013 | 9.040 | 12.321 | 1.00 | 45.60 | C |
| ATOM | 9162 | CB | ARG | C | 409 | 48.230 | 9.134 | 10.807 | 1.00 | 45.56 | C |
| ATOM | 9165 | CG | ARG | C | 409 | 49.307 | 10.123 | 10.409 | 1.00 | 45.53 | C |
| ATOM | 9168 | CD | ARG | C | 409 | 49.700 | 10.060 | 8.937 | 1.00 | 45.01 | C |
| ATOM | 9171 | NE | ARG | C | 409 | 50.702 | 11.077 | 8.631 | 1.00 | 44.67 | N |
| ATOM | 9173 | CZ | ARG | C | 409 | 50.491 | 12.195 | 7.941 | 1.00 | 44.39 | C |
| ATOM | 9174 | NH1 | ARG | C | 409 | 49.297 | 12.486 | 7.431 | 1.00 | 44.70 | N |
| ATOM | 9177 | NH2 | ARG | C | 409 | 51.498 | 13.036 | 7.751 | 1.00 | 44.09 | N |
| ATOM | 9180 | C | ARG | C | 409 | 46.595 | 8.538 | 12.596 | 1.00 | 45.47 | C |
| ATOM | 9181 | O | ARG | C | 409 | 45.702 | 9.331 | 12.887 | 1.00 | 45.19 | O |
| ATOM | 9182 | N | ILE | C | 410 | 46.388 | 7.230 | 12.472 | 1.00 | 45.44 | N |
| ATOM | 9184 | CA | ILE | C | 410 | 45.073 | 6.637 | 12.696 | 1.00 | 45.62 | C |
| ATOM | 9186 | CB | ILE | C | 410 | 45.009 | 5.179 | 12.147 | 1.00 | 45.59 | C |
| ATOM | 9188 | CG1 | ILE | C | 410 | 43.564 | 4.667 | 12.098 | 1.00 | 45.47 | C |
| ATOM | 9191 | CD1 | ILE | C | 410 | 42.605 | 5.523 | 11.287 | 1.00 | 45.08 | C |
| ATOM | 9195 | CG2 | ILE | C | 410 | 45.845 | 4.220 | 12.987 | 1.00 | 45.75 | C |
| ATOM | 9199 | C | ILE | C | 410 | 44.692 | 6.697 | 14.177 | 1.00 | 45.92 | C |
| ATOM | 9200 | O | ILE | C | 410 | 43.524 | 6.895 | 14.510 | 1.00 | 45.69 | O |
| ATOM | 9201 | N | MET | C | 411 | 45.679 | 6.536 | 15.057 | 1.00 | 46.30 | N |
| ATOM | 9203 | CA | MET | C | 411 | 45.438 | 6.598 | 16.494 | 1.00 | 46.58 | C |
| ATOM | 9205 | CB | MET | C | 411 | 46.594 | 5.973 | 17.282 | 1.00 | 46.81 | C |
| ATOM | 9208 | CG | MET | C | 411 | 46.697 | 4.446 | 17.186 | 1.00 | 47.31 | C |
| ATOM | 9211 | SD | MET | C | 411 | 45.136 | 3.570 | 16.946 | 1.00 | 49.11 | S |
| ATOM | 9212 | CE | MET | C | 411 | 44.666 | 3.263 | 18.662 | 1.00 | 49.05 | C |
| ATOM | 9216 | C | MET | C | 411 | 45.201 | 8.039 | 16.935 | 1.00 | 46.62 | C |
| ATOM | 9217 | O | MET | C | 411 | 44.523 | 8.270 | 17.932 | 1.00 | 46.67 | O |
| ATOM | 9218 | N | GLU | C | 412 | 45.750 | 9.003 | 16.199 | 1.00 | 46.53 | N |
| ATOM | 9220 | CA | GLU | C | 412 | 45.518 | 10.412 | 16.509 | 1.00 | 46.60 | C |
| ATOM | 9222 | CB | GLU | C | 412 | 46.504 | 11.315 | 15.768 | 1.00 | 46.75 | C |
| ATOM | 9225 | CG | GLU | C | 412 | 46.448 | 12.778 | 16.187 | 1.00 | 47.59 | C |
| ATOM | 9228 | CD | GLU | C | 412 | 47.519 | 13.627 | 15.519 | 1.00 | 49.12 | C |
| ATOM | 9229 | OE1 | GLU | C | 412 | 48.714 | 13.260 | 15.604 | 1.00 | 50.57 | O |
| ATOM | 9230 | OE2 | GLU | C | 412 | 47.170 | 14.665 | 14.911 | 1.00 | 49.43 | O |
| ATOM | 9231 | C | GLU | C | 412 | 44.078 | 10.773 | 16.134 | 1.00 | 46.47 | C |
| ATOM | 9232 | O | GLU | C | 412 | 43.381 | 11.430 | 16.904 | 1.00 | 46.69 | O |
| ATOM | 9233 | N | GLU | C | 413 | 43.646 | 10.330 | 14.953 | 1.00 | 46.07 | N |
| ATOM | 9235 | CA | GLU | C | 413 | 42.289 | 10.567 | 14.455 | 1.00 | 45.74 | C |
| ATOM | 9237 | CB | GLU | C | 413 | 42.176 | 10.098 | 12.996 | 1.00 | 45.42 | C |
| ATOM | 9240 | CG | GLU | C | 413 | 40.762 | 10.037 | 12.427 | 1.00 | 44.08 | C |
| ATOM | 9243 | CD | GLU | C | 413 | 40.741 | 9.966 | 10.902 | 1.00 | 42.84 | C |
| ATOM | 9244 | OE1 | GLU | C | 413 | 41.680 | 10.480 | 10.275 | 1.00 | 40.16 | O |
| ATOM | 9245 | OE2 | GLU | C | 413 | 39.789 | 9.399 | 10.326 | 1.00 | 40.45 | O |
| ATOM | 9246 | C | GLU | C | 413 | 41.263 | 9.845 | 15.325 | 1.00 | 45.99 | C |
| ATOM | 9247 | O | GLU | C | 413 | 40.177 | 10.358 | 15.569 | 1.00 | 45.98 | O |
| ATOM | 9248 | N | PHE | C | 414 | 41.626 | 8.654 | 15.783 | 1.00 | 46.40 | N |
| ATOM | 9250 | CA | PHE | C | 414 | 40.776 | 7.838 | 16.645 | 1.00 | 46.79 | C |
| ATOM | 9252 | CB | PHE | C | 414 | 41.372 | 6.431 | 16.804 | 1.00 | 46.92 | C |
| ATOM | 9255 | CG | PHE | C | 414 | 40.825 | 5.408 | 15.840 | 1.00 | 47.36 | C |
| ATOM | 9256 | CD1 | PHE | C | 414 | 40.319 | 5.768 | 14.591 | 1.00 | 48.39 | C |
| ATOM | 9258 | CE1 | PHE | C | 414 | 39.820 | 4.801 | 13.724 | 1.00 | 48.60 | C |
| ATOM | 9260 | CZ | PHE | C | 414 | 39.828 | 3.466 | 14.103 | 1.00 | 48.96 | C |
| ATOM | 9262 | CE2 | PHE | C | 414 | 40.334 | 3.103 | 15.340 | 1.00 | 48.50 | C |
| ATOM | 9264 | CD2 | PHE | C | 414 | 40.827 | 4.068 | 16.194 | 1.00 | 48.13 | C |
| ATOM | 9266 | C | PHE | C | 414 | 40.611 | 8.475 | 18.029 | 1.00 | 47.06 | C |
| ATOM | 9267 | O | PHE | C | 414 | 39.514 | 8.491 | 18.572 | 1.00 | 47.02 | O |
| ATOM | 9268 | N | PHE | C | 415 | 41.695 | 8.996 | 18.597 | 1.00 | 47.43 | N |
| ATOM | 9270 | CA | PHE | C | 415 | 41.628 | 9.636 | 19.914 | 1.00 | 47.76 | C |
| ATOM | 9272 | CB | PHE | C | 415 | 43.024 | 9.822 | 20.531 | 1.00 | 47.63 | C |
| ATOM | 9275 | CG | PHE | C | 415 | 43.716 | 8.532 | 20.905 | 1.00 | 46.87 | C |
| ATOM | 9276 | CD1 | PHE | C | 415 | 42.997 | 7.377 | 21.199 | 1.00 | 46.55 | C |
| ATOM | 9278 | CE1 | PHE | C | 415 | 43.647 | 6.201 | 21.536 | 1.00 | 46.83 | C |
| ATOM | 9280 | CZ | PHE | C | 415 | 45.029 | 6.167 | 21.592 | 1.00 | 47.03 | C |
| ATOM | 9282 | CE2 | PHE | C | 415 | 45.756 | 7.309 | 21.307 | 1.00 | 47.07 | C |
| ATOM | 9284 | CD2 | PHE | C | 415 | 45.100 | 8.483 | 20.967 | 1.00 | 46.70 | C |
| ATOM | 9286 | C | PHE | C | 415 | 40.892 | 10.973 | 19.840 | 1.00 | 48.36 | C |
| ATOM | 9287 | O | PHE | C | 415 | 40.366 | 11.440 | 20.849 | 1.00 | 48.27 | O |
| ATOM | 9288 | N | GLN | C | 416 | 40.858 | 11.579 | 18.650 | 1.00 | 48.96 | N |
| ATOM | 9290 | CA | GLN | C | 416 | 40.137 | 12.833 | 18.439 | 1.00 | 49.54 | C |
| ATOM | 9292 | CB | GLN | C | 416 | 40.536 | 13.498 | 17.112 | 1.00 | 49.65 | C |
| ATOM | 9295 | CG | GLN | C | 416 | 41.731 | 14.444 | 17.222 | 1.00 | 50.28 | C |

TABLE 2-continued

| | | | | | | | | | | | |
|---|---|---|---|---|---|---|---|---|---|---|---|
| ATOM | 9298 | CD | GLN | C | 416 | 41.760 | 15.495 | 16.123 | 1.00 | 51.30 | C |
| ATOM | 9299 | OE1 | GLN | C | 416 | 40.772 | 16.206 | 15.909 | 1.00 | 51.67 | O |
| ATOM | 9300 | NE2 | GLN | C | 416 | 42.894 | 15.602 | 15.429 | 1.00 | 51.53 | N |
| ATOM | 9303 | C | GLN | C | 416 | 38.633 | 12.565 | 18.463 | 1.00 | 49.86 | C |
| ATOM | 9304 | O | GLN | C | 416 | 37.862 | 13.403 | 18.923 | 1.00 | 49.89 | O |
| ATOM | 9305 | N | GLN | C | 417 | 38.226 | 11.401 | 17.956 | 1.00 | 50.33 | N |
| ATOM | 9307 | CA | GLN | C | 417 | 36.820 | 10.999 | 17.970 | 1.00 | 50.71 | C |
| ATOM | 9309 | CB | GLN | C | 417 | 36.570 | 9.808 | 17.037 | 1.00 | 50.53 | C |
| ATOM | 9312 | CG | GLN | C | 417 | 35.227 | 9.097 | 17.270 | 1.00 | 50.13 | C |
| ATOM | 9315 | CD | GLN | C | 417 | 34.799 | 8.221 | 16.111 | 1.00 | 49.69 | C |
| ATOM | 9316 | OE1 | GLN | C | 417 | 35.175 | 8.471 | 14.970 | 1.00 | 49.20 | O |
| ATOM | 9317 | NE2 | GLN | C | 417 | 34.005 | 7.195 | 16.400 | 1.00 | 48.99 | N |
| ATOM | 9320 | C | GLN | C | 417 | 36.401 | 10.647 | 19.399 | 1.00 | 51.27 | C |
| ATOM | 9321 | O | GLN | C | 417 | 35.252 | 10.857 | 19.783 | 1.00 | 51.28 | O |
| ATOM | 9322 | N | GLY | C | 418 | 37.331 | 10.095 | 20.174 | 1.00 | 51.97 | N |
| ATOM | 9324 | CA | GLY | C | 418 | 37.069 | 9.755 | 21.561 | 1.00 | 52.62 | C |
| ATOM | 9327 | C | GLY | C | 418 | 36.817 | 11.013 | 22.364 | 1.00 | 53.21 | C |
| ATOM | 9328 | O | GLY | C | 418 | 35.943 | 11.034 | 23.223 | 1.00 | 53.30 | O |
| ATOM | 9329 | N | ASP | C | 419 | 37.575 | 12.065 | 22.054 | 1.00 | 54.08 | N |
| ATOM | 9331 | CA | ASP | C | 419 | 37.450 | 13.355 | 22.723 | 1.00 | 54.83 | C |
| ATOM | 9333 | CB | ASP | C | 419 | 38.607 | 14.282 | 22.328 | 1.00 | 54.86 | C |
| ATOM | 9336 | CG | ASP | C | 419 | 39.961 | 13.789 | 22.825 | 1.00 | 55.13 | C |
| ATOM | 9337 | OD1 | ASP | C | 419 | 40.029 | 12.691 | 23.420 | 1.00 | 55.26 | O |
| ATOM | 9338 | OD2 | ASP | C | 419 | 41.019 | 14.435 | 22.657 | 1.00 | 55.32 | O |
| ATOM | 9339 | C | ASP | C | 419 | 36.117 | 14.027 | 22.394 | 1.00 | 55.57 | C |
| ATOM | 9340 | O | ASP | C | 419 | 35.500 | 14.638 | 23.266 | 1.00 | 55.68 | O |
| ATOM | 9341 | N | LYS | C | 420 | 35.681 | 13.908 | 21.139 | 1.00 | 56.37 | N |
| ATOM | 9343 | CA | LYS | C | 420 | 34.415 | 14.491 | 20.690 | 1.00 | 57.01 | C |
| ATOM | 9345 | CB | LYS | C | 420 | 34.304 | 14.455 | 19.158 | 1.00 | 57.06 | C |
| ATOM | 9348 | CG | LYS | C | 420 | 35.152 | 15.507 | 18.444 | 1.00 | 57.47 | C |
| ATOM | 9351 | CD | LYS | C | 420 | 34.435 | 16.083 | 17.225 | 1.00 | 58.09 | C |
| ATOM | 9354 | CE | LYS | C | 420 | 35.287 | 17.119 | 16.505 | 1.00 | 58.26 | C |
| ATOM | 9357 | NZ | LYS | C | 420 | 36.156 | 16.497 | 15.469 | 1.00 | 58.25 | N |
| ATOM | 9361 | C | LYS | C | 420 | 33.224 | 13.770 | 21.320 | 1.00 | 57.57 | C |
| ATOM | 9362 | O | LYS | C | 420 | 32.223 | 14.401 | 21.650 | 1.00 | 57.69 | O |
| ATOM | 9363 | N | GLU | C | 421 | 33.340 | 12.453 | 21.481 | 1.00 | 58.31 | N |
| ATOM | 9365 | CA | GLU | C | 421 | 32.295 | 11.645 | 22.106 | 1.00 | 58.97 | C |
| ATOM | 9367 | CB | GLU | C | 421 | 32.628 | 10.149 | 22.009 | 1.00 | 58.97 | C |
| ATOM | 9370 | CG | GLU | C | 421 | 32.414 | 9.533 | 20.630 | 1.00 | 58.79 | C |
| ATOM | 9373 | CD | GLU | C | 421 | 33.078 | 8.172 | 20.470 | 1.00 | 58.47 | C |
| ATOM | 9374 | OE1 | GLU | C | 421 | 33.972 | 7.833 | 21.273 | 1.00 | 58.05 | O |
| ATOM | 9375 | OE2 | GLU | C | 421 | 32.708 | 7.433 | 19.533 | 1.00 | 58.22 | O |
| ATOM | 9376 | C | GLU | C | 421 | 32.136 | 12.034 | 23.577 | 1.00 | 59.75 | C |
| ATOM | 9377 | O | GLU | C | 421 | 31.021 | 12.078 | 24.093 | 1.00 | 59.86 | O |
| ATOM | 9378 | N | ARG | C | 422 | 33.256 | 12.320 | 24.242 | 1.00 | 60.61 | N |
| ATOM | 9380 | CA | ARG | C | 422 | 33.246 | 12.705 | 25.655 | 1.00 | 61.38 | C |
| ATOM | 9382 | CB | ARG | C | 422 | 34.670 | 12.703 | 26.233 | 1.00 | 61.51 | C |
| ATOM | 9385 | CG | ARG | C | 422 | 34.726 | 12.442 | 27.739 | 1.00 | 62.06 | C |
| ATOM | 9388 | CD | ARG | C | 422 | 36.135 | 12.323 | 28.316 | 1.00 | 62.80 | C |
| ATOM | 9391 | NE | ARG | C | 422 | 36.920 | 11.262 | 27.676 | 1.00 | 63.55 | N |
| ATOM | 9393 | CZ | ARG | C | 422 | 37.868 | 11.446 | 26.747 | 1.00 | 64.53 | C |
| ATOM | 9394 | NH1 | ARG | C | 422 | 38.189 | 12.664 | 26.307 | 1.00 | 64.57 | N |
| ATOM | 9397 | NH2 | ARG | C | 422 | 38.506 | 10.391 | 26.247 | 1.00 | 64.86 | N |
| ATOM | 9400 | C | ARG | C | 422 | 32.599 | 14.077 | 25.856 | 1.00 | 61.82 | C |
| ATOM | 9401 | O | ARG | C | 422 | 31.935 | 14.310 | 26.865 | 1.00 | 62.00 | O |
| ATOM | 9402 | N | GLU | C | 423 | 32.792 | 14.973 | 24.890 | 1.00 | 62.37 | N |
| ATOM | 9404 | CA | GLU | C | 423 | 32.221 | 16.316 | 24.945 | 1.00 | 62.85 | C |
| ATOM | 9406 | CB | GLU | C | 423 | 32.779 | 17.192 | 23.818 | 1.00 | 62.91 | C |
| ATOM | 9409 | CG | GLU | C | 423 | 34.210 | 17.665 | 24.036 | 1.00 | 63.32 | C |
| ATOM | 9412 | CD | GLU | C | 423 | 34.809 | 18.343 | 22.812 | 1.00 | 63.91 | C |
| ATOM | 9413 | OE1 | GLU | C | 423 | 34.319 | 18.115 | 21.683 | 1.00 | 64.12 | O |
| ATOM | 9414 | OE2 | GLU | C | 423 | 35.782 | 19.108 | 22.981 | 1.00 | 64.32 | O |
| ATOM | 9415 | C | GLU | C | 423 | 30.703 | 16.268 | 24.830 | 1.00 | 63.15 | C |
| ATOM | 9416 | O | GLU | C | 423 | 30.001 | 17.016 | 25.510 | 1.00 | 63.35 | O |
| ATOM | 9417 | N | ARG | C | 424 | 30.208 | 15.378 | 23.973 | 1.00 | 63.47 | N |
| ATOM | 9419 | CA | ARG | C | 424 | 28.773 | 15.238 | 23.725 | 1.00 | 63.72 | C |
| ATOM | 9421 | CB | ARG | C | 424 | 28.540 | 14.714 | 22.300 | 1.00 | 63.75 | C |
| ATOM | 9424 | CG | ARG | C | 424 | 29.077 | 15.617 | 21.188 | 1.00 | 64.06 | C |
| ATOM | 9427 | CD | ARG | C | 424 | 29.459 | 14.860 | 19.920 | 1.00 | 64.59 | C |
| ATOM | 9430 | NE | ARG | C | 424 | 29.945 | 15.737 | 18.852 | 1.00 | 64.95 | N |
| ATOM | 9432 | CZ | ARG | C | 424 | 29.173 | 16.402 | 17.992 | 1.00 | 65.34 | C |
| ATOM | 9433 | NH1 | ARG | C | 424 | 27.845 | 16.322 | 18.057 | 1.00 | 65.36 | N |
| ATOM | 9436 | NH2 | ARG | C | 424 | 29.735 | 17.161 | 17.056 | 1.00 | 65.56 | N |
| ATOM | 9439 | C | ARG | C | 424 | 28.056 | 14.328 | 24.735 | 1.00 | 63.85 | C |
| ATOM | 9440 | O | ARG | C | 424 | 26.847 | 14.117 | 24.626 | 1.00 | 63.95 | O |
| ATOM | 9441 | N | GLY | C | 425 | 28.793 | 13.782 | 25.703 | 1.00 | 64.02 | N |
| ATOM | 9443 | CA | GLY | C | 425 | 28.214 | 12.911 | 26.716 | 1.00 | 64.06 | C |
| ATOM | 9446 | C | GLY | C | 425 | 27.877 | 11.509 | 26.229 | 1.00 | 64.16 | C |
| ATOM | 9447 | O | GLY | C | 425 | 27.233 | 10.740 | 26.946 | 1.00 | 64.15 | O |

TABLE 2-continued

| ATOM | 9448 | N | MET | C | 426 | 28.317 | 11.173 | 25.018 | 1.00 | 64.28 | N |
|---|---|---|---|---|---|---|---|---|---|---|---|
| ATOM | 9450 | CA | MET | C | 426 | 28.071 | 9.858 | 24.432 | 1.00 | 64.27 | C |
| ATOM | 9452 | CB | MET | C | 426 | 28.346 | 9.874 | 22.927 | 1.00 | 64.18 | C |
| ATOM | 9455 | CG | MET | C | 426 | 27.587 | 10.920 | 22.129 | 1.00 | 63.98 | C |
| ATOM | 9458 | SD | MET | C | 426 | 28.346 | 11.160 | 20.514 | 1.00 | 63.16 | S |
| ATOM | 9459 | CE | MET | C | 426 | 28.097 | 9.544 | 19.802 | 1.00 | 63.27 | C |
| ATOM | 9463 | C | MET | C | 426 | 28.987 | 8.823 | 25.056 | 1.00 | 64.41 | C |
| ATOM | 9464 | O | MET | C | 426 | 29.941 | 9.165 | 25.756 | 1.00 | 64.40 | O |
| ATOM | 9465 | N | GLU | C | 427 | 28.699 | 7.554 | 24.779 | 1.00 | 64.63 | N |
| ATOM | 9467 | CA | GLU | C | 427 | 29.527 | 6.454 | 25.260 | 1.00 | 64.79 | C |
| ATOM | 9469 | CB | GLU | C | 427 | 28.773 | 5.127 | 25.162 | 1.00 | 64.89 | C |
| ATOM | 9472 | CG | GLU | C | 427 | 29.598 | 3.915 | 25.571 | 1.00 | 65.45 | C |
| ATOM | 9475 | CD | GLU | C | 427 | 28.753 | 2.762 | 26.082 | 1.00 | 66.22 | C |
| ATOM | 9476 | OE1 | GLU | C | 427 | 27.620 | 2.573 | 25.583 | 1.00 | 66.72 | O |
| ATOM | 9477 | OE2 | GLU | C | 427 | 29.229 | 2.040 | 26.984 | 1.00 | 66.57 | O |
| ATOM | 9478 | C | GLU | C | 427 | 30.810 | 6.414 | 24.423 | 1.00 | 64.75 | C |
| ATOM | 9479 | O | GLU | C | 427 | 30.759 | 6.513 | 23.197 | 1.00 | 64.80 | O |
| ATOM | 9480 | N | ILE | C | 428 | 31.952 | 6.269 | 25.093 | 1.00 | 64.74 | N |
| ATOM | 9482 | CA | ILE | C | 428 | 33.258 | 6.258 | 24.430 | 1.00 | 64.61 | C |
| ATOM | 9484 | CB | ILE | C | 428 | 34.386 | 6.618 | 25.434 | 1.00 | 64.60 | C |
| ATOM | 9486 | CG1 | ILE | C | 428 | 34.109 | 7.954 | 26.140 | 1.00 | 64.67 | C |
| ATOM | 9489 | CD1 | ILE | C | 428 | 34.156 | 9.172 | 25.240 | 1.00 | 64.84 | C |
| ATOM | 9493 | CG2 | ILE | C | 428 | 35.746 | 6.656 | 24.732 | 1.00 | 64.78 | C |
| ATOM | 9497 | C | ILE | C | 428 | 33.555 | 4.893 | 23.816 | 1.00 | 64.50 | C |
| ATOM | 9498 | O | ILE | C | 428 | 33.379 | 3.865 | 24.469 | 1.00 | 64.48 | O |
| ATOM | 9499 | N | SER | C | 429 | 34.015 | 4.891 | 22.566 | 1.00 | 64.40 | N |
| ATOM | 9501 | CA | SER | C | 429 | 34.384 | 3.652 | 21.885 | 1.00 | 64.36 | C |
| ATOM | 9503 | CB | SER | C | 429 | 34.485 | 3.858 | 20.368 | 1.00 | 64.35 | C |
| ATOM | 9506 | OG | SER | C | 429 | 33.410 | 4.642 | 19.873 | 1.00 | 63.98 | O |
| ATOM | 9508 | C | SER | C | 429 | 35.728 | 3.203 | 22.474 | 1.00 | 64.40 | C |
| ATOM | 9509 | O | SER | C | 429 | 36.631 | 4.023 | 22.622 | 1.00 | 64.27 | O |
| ATOM | 9510 | N | PRO | C | 430 | 35.867 | 1.921 | 22.811 | 1.00 | 64.54 | N |
| ATOM | 9511 | CA | PRO | C | 430 | 37.090 | 1.421 | 23.463 | 1.00 | 64.74 | C |
| ATOM | 9513 | CB | PRO | C | 430 | 36.814 | −0.084 | 23.631 | 1.00 | 64.69 | C |
| ATOM | 9516 | CG | PRO | C | 430 | 35.347 | −0.241 | 23.506 | 1.00 | 64.63 | C |
| ATOM | 9519 | CD | PRO | C | 430 | 34.879 | 0.846 | 22.601 | 1.00 | 64.54 | C |
| ATOM | 9522 | C | PRO | C | 430 | 38.417 | 1.617 | 22.715 | 1.00 | 65.07 | C |
| ATOM | 9523 | O | PRO | C | 430 | 39.335 | 2.217 | 23.279 | 1.00 | 65.01 | O |
| ATOM | 9524 | N | MET | C | 431 | 38.503 | 1.127 | 21.479 | 1.00 | 65.41 | N |
| ATOM | 9526 | CA | MET | C | 431 | 39.751 | 1.147 | 20.707 | 1.00 | 65.68 | C |
| ATOM | 9528 | CB | MET | C | 431 | 39.612 | 0.243 | 19.479 | 1.00 | 65.76 | C |
| ATOM | 9531 | CG | MET | C | 431 | 40.929 | −0.092 | 18.813 | 1.00 | 66.22 | C |
| ATOM | 9534 | SD | MET | C | 431 | 40.726 | −1.357 | 17.555 | 1.00 | 67.25 | S |
| ATOM | 9535 | CE | MET | C | 431 | 41.420 | −0.553 | 16.155 | 1.00 | 67.26 | C |
| ATOM | 9539 | C | MET | C | 431 | 40.228 | 2.534 | 20.274 | 1.00 | 65.76 | C |
| ATOM | 9540 | O | MET | C | 431 | 40.801 | 3.307 | 21.039 | 1.00 | 65.78 | O |
| ATOM | 9541 | OXT | MET | C | 431 | 40.092 | 2.957 | 19.129 | 1.00 | 66.08 | O |
| ATOM | 9542 | N | CME | B | 432 | 38.490 | 4.359 | 20.846 | 1.00 | 52.58 | N |
| ATOM | 9545 | CA | CME | B | 432 | 38.907 | 5.674 | 20.403 | 1.00 | 52.73 | C |
| ATOM | 9547 | CB | CME | B | 432 | 37.705 | 6.350 | 19.753 | 1.00 | 52.90 | C |
| ATOM | 9550 | SG | CME | B | 432 | 37.679 | 5.928 | 18.040 | 1.00 | 53.64 | S |
| ATOM | 9551 | S2 | CME | B | 432 | 37.254 | 3.998 | 17.735 | 1.00 | 56.00 | S |
| ATOM | 9552 | C2 | CME | B | 432 | 35.630 | 3.776 | 17.081 | 1.00 | 56.30 | C |
| ATOM | 9555 | C1 | CME | B | 432 | 35.709 | 3.429 | 15.612 | 1.00 | 56.90 | C |
| ATOM | 9557 | O1 | CME | B | 432 | 36.216 | 4.211 | 14.823 | 1.00 | 57.30 | O |
| ATOM | 9558 | C | CME | B | 432 | 39.423 | 6.440 | 21.594 | 1.00 | 52.54 | C |
| ATOM | 9559 | O | CME | B | 432 | 39.507 | 7.650 | 21.643 | 1.00 | 52.35 | O |
| ATOM | 9562 | N | ASP | C | 433 | 39.443 | 5.142 | 23.409 | 1.00 | 49.37 | N |
| ATOM | 9564 | CA | ASP | C | 433 | 39.717 | 5.923 | 24.636 | 1.00 | 49.37 | C |
| ATOM | 9566 | CB | ASP | C | 433 | 39.204 | 5.127 | 25.835 | 1.00 | 49.52 | C |
| ATOM | 9569 | CG | ASP | C | 433 | 39.105 | 5.950 | 27.093 | 1.00 | 49.90 | C |
| ATOM | 9570 | OD1 | ASP | C | 433 | 39.309 | 7.181 | 27.045 | 1.00 | 50.98 | O |
| ATOM | 9571 | OD2 | ASP | C | 433 | 38.817 | 5.437 | 28.190 | 1.00 | 51.53 | O |
| ATOM | 9572 | C | ASP | C | 433 | 41.223 | 6.162 | 24.737 | 1.00 | 49.22 | C |
| ATOM | 9573 | O | ASP | C | 433 | 41.992 | 5.210 | 24.791 | 1.00 | 49.30 | O |
| ATOM | 9576 | N | LYS | C | 434 | 41.652 | 7.421 | 24.741 | 1.00 | 48.98 | N |
| ATOM | 9578 | CA | LYS | C | 434 | 43.083 | 7.718 | 24.831 | 1.00 | 48.95 | C |
| ATOM | 9580 | CB | LYS | C | 434 | 43.388 | 9.154 | 24.376 | 1.00 | 48.79 | C |
| ATOM | 9583 | CG | LYS | C | 434 | 42.938 | 10.258 | 25.322 | 1.00 | 48.65 | C |
| ATOM | 9586 | CD | LYS | C | 434 | 43.343 | 11.622 | 24.788 | 1.00 | 48.05 | C |
| ATOM | 9589 | CE | LYS | C | 434 | 42.690 | 12.743 | 25.566 | 1.00 | 47.94 | C |
| ATOM | 9592 | NZ | LYS | C | 434 | 43.219 | 14.074 | 25.174 | 1.00 | 47.61 | N |
| ATOM | 9596 | C | LYS | C | 434 | 43.643 | 7.444 | 26.238 | 1.00 | 49.13 | C |
| ATOM | 9597 | O | LYS | C | 434 | 44.845 | 7.219 | 26.396 | 1.00 | 49.15 | O |
| ATOM | 9598 | N | HIS | C | 435 | 42.764 | 7.446 | 27.242 | 1.00 | 49.23 | N |
| ATOM | 9600 | CA | HIS | C | 435 | 43.147 | 7.191 | 28.633 | 1.00 | 49.32 | C |
| ATOM | 9602 | CB | HIS | C | 435 | 42.175 | 7.898 | 29.589 | 1.00 | 49.23 | C |
| ATOM | 9605 | CG | HIS | C | 435 | 42.007 | 9.360 | 29.317 | 1.00 | 49.13 | C |
| ATOM | 9606 | ND1 | HIS | C | 435 | 43.057 | 10.252 | 29.354 | 1.00 | 49.51 | N |

TABLE 2-continued

| | | | | | | | | | | | |
|---|---|---|---|---|---|---|---|---|---|---|---|
| ATOM | 9608 | CE1 | HIS | C | 435 | 42.612 | 11.466 | 29.081 | 1.00 | 49.40 | C |
| ATOM | 9610 | NE2 | HIS | C | 435 | 41.311 | 11.394 | 28.871 | 1.00 | 49.28 | N |
| ATOM | 9612 | CD2 | HIS | C | 435 | 40.907 | 10.089 | 29.014 | 1.00 | 49.20 | C |
| ATOM | 9614 | C | HIS | C | 435 | 43.169 | 5.700 | 28.993 | 1.00 | 49.52 | C |
| ATOM | 9615 | O | HIS | C | 435 | 43.555 | 5.348 | 30.111 | 1.00 | 49.68 | O |
| ATOM | 9616 | N | THR | C | 436 | 42.758 | 4.836 | 28.061 | 1.00 | 49.63 | N |
| ATOM | 9618 | CA | THR | C | 436 | 42.686 | 3.390 | 28.304 | 1.00 | 49.79 | C |
| ATOM | 9620 | CB | THR | C | 436 | 41.196 | 2.977 | 28.456 | 1.00 | 49.83 | C |
| ATOM | 9622 | OG1 | THR | C | 436 | 40.664 | 3.505 | 29.678 | 1.00 | 50.29 | O |
| ATOM | 9624 | CG2 | THR | C | 436 | 41.034 | 1.468 | 28.614 | 1.00 | 49.91 | C |
| ATOM | 9628 | C | THR | C | 436 | 43.352 | 2.519 | 27.225 | 1.00 | 49.91 | C |
| ATOM | 9629 | O | THR | C | 436 | 44.107 | 1.605 | 27.549 | 1.00 | 49.92 | O |
| ATOM | 9630 | N | ALA | C | 437 | 43.060 | 2.799 | 25.956 | 1.00 | 49.96 | N |
| ATOM | 9632 | CA | ALA | C | 437 | 43.561 | 2.001 | 24.828 | 1.00 | 50.03 | C |
| ATOM | 9634 | CB | ALA | C | 437 | 42.815 | 2.383 | 23.547 | 1.00 | 50.04 | C |
| ATOM | 9638 | C | ALA | C | 437 | 45.070 | 2.055 | 24.570 | 1.00 | 50.06 | C |
| ATOM | 9639 | O | ALA | C | 437 | 45.673 | 3.130 | 24.524 | 1.00 | 50.02 | O |
| ATOM | 9640 | N | SER | C | 438 | 45.655 | 0.873 | 24.376 | 1.00 | 50.18 | N |
| ATOM | 9642 | CA | SER | C | 438 | 47.072 | 0.714 | 24.062 | 1.00 | 50.28 | C |
| ATOM | 9644 | CB | SER | C | 438 | 47.596 | −0.628 | 24.584 | 1.00 | 50.21 | C |
| ATOM | 9647 | OG | SER | C | 438 | 48.883 | −0.922 | 24.068 | 1.00 | 50.16 | O |
| ATOM | 9649 | C | SER | C | 438 | 47.232 | 0.756 | 22.546 | 1.00 | 50.38 | C |
| ATOM | 9650 | O | SER | C | 438 | 46.625 | −0.043 | 21.839 | 1.00 | 50.24 | O |
| ATOM | 9651 | N | VAL | C | 439 | 48.056 | 1.683 | 22.063 | 1.00 | 50.68 | N |
| ATOM | 9653 | CA | VAL | C | 439 | 48.317 | 1.846 | 20.629 | 1.00 | 50.86 | C |
| ATOM | 9655 | CB | VAL | C | 439 | 49.274 | 3.049 | 20.374 | 1.00 | 50.85 | C |
| ATOM | 9657 | CG1 | VAL | C | 439 | 49.694 | 3.129 | 18.904 | 1.00 | 50.98 | C |
| ATOM | 9661 | CG2 | VAL | C | 439 | 48.626 | 4.355 | 20.818 | 1.00 | 50.95 | C |
| ATOM | 9665 | C | VAL | C | 439 | 48.930 | 0.581 | 20.020 | 1.00 | 50.95 | C |
| ATOM | 9666 | O | VAL | C | 439 | 48.681 | 0.257 | 18.857 | 1.00 | 51.20 | O |
| ATOM | 9667 | N | GLU | C | 440 | 49.713 | −0.135 | 20.823 | 1.00 | 50.93 | N |
| ATOM | 9669 | CA | GLU | C | 440 | 50.412 | −1.336 | 20.378 | 1.00 | 50.88 | C |
| ATOM | 9671 | CB | GLU | C | 440 | 51.581 | −1.660 | 21.318 | 1.00 | 50.92 | C |
| ATOM | 9674 | CG | GLU | C | 440 | 52.740 | −0.668 | 21.237 | 1.00 | 51.08 | C |
| ATOM | 9677 | CD | GLU | C | 440 | 52.389 | 0.719 | 21.756 | 1.00 | 51.58 | C |
| ATOM | 9678 | OE1 | GLU | C | 440 | 51.870 | 0.827 | 22.887 | 1.00 | 52.60 | O |
| ATOM | 9679 | OE2 | GLU | C | 440 | 52.624 | 1.711 | 21.035 | 1.00 | 52.06 | O |
| ATOM | 9680 | C | GLU | C | 440 | 49.455 | −2.519 | 20.272 | 1.00 | 50.77 | C |
| ATOM | 9681 | O | GLU | C | 440 | 49.489 | −3.261 | 19.290 | 1.00 | 50.97 | O |
| ATOM | 9682 | N | LYS | C | 441 | 48.596 | −2.690 | 21.274 | 1.00 | 50.44 | N |
| ATOM | 9684 | CA | LYS | C | 441 | 47.610 | −3.770 | 21.254 | 1.00 | 50.17 | C |
| ATOM | 9686 | CB | LYS | C | 441 | 46.866 | −3.864 | 22.587 | 1.00 | 50.23 | C |
| ATOM | 9689 | CG | LYS | C | 441 | 47.678 | −4.496 | 23.699 | 1.00 | 50.69 | C |
| ATOM | 9692 | CD | LYS | C | 441 | 46.877 | −4.571 | 24.985 | 1.00 | 51.29 | C |
| ATOM | 9695 | CE | LYS | C | 441 | 47.543 | −5.483 | 26.003 | 1.00 | 51.78 | C |
| ATOM | 9698 | NZ | LYS | C | 441 | 47.025 | −5.250 | 27.375 | 1.00 | 51.97 | N |
| ATOM | 9702 | C | LYS | C | 441 | 46.603 | −3.590 | 20.118 | 1.00 | 49.71 | C |
| ATOM | 9703 | O | LYS | C | 441 | 45.996 | −4.561 | 19.675 | 1.00 | 49.56 | O |
| ATOM | 9704 | N | SER | C | 442 | 46.417 | −2.351 | 19.664 | 1.00 | 49.30 | N |
| ATOM | 9706 | CA | SER | C | 442 | 45.501 | −2.063 | 18.559 | 1.00 | 49.14 | C |
| ATOM | 9708 | CB | ASER | C | 442 | 45.279 | −0.551 | 18.404 | 0.50 | 49.15 | C |
| ATOM | 9709 | CB | BSER | C | 442 | 45.287 | −0.553 | 18.394 | 0.50 | 49.15 | C |
| ATOM | 9714 | OG | ASER | C | 442 | 46.261 | 0.042 | 17.564 | 0.50 | 49.12 | O |
| ATOM | 9715 | OG | BSER | C | 442 | 44.321 | −0.063 | 19.308 | 0.50 | 49.04 | O |
| ATOM | 9718 | C | SER | C | 442 | 46.039 | −2.651 | 17.258 | 1.00 | 48.88 | C |
| ATOM | 9719 | O | SER | C | 442 | 45.292 | −3.250 | 16.495 | 1.00 | 48.84 | O |
| ATOM | 9720 | N | GLN | C | 443 | 47.339 | −2.485 | 17.029 | 1.00 | 48.68 | N |
| ATOM | 9722 | CA | GLN | C | 443 | 47.985 | −2.964 | 15.806 | 1.00 | 48.52 | C |
| ATOM | 9724 | CB | GLN | C | 443 | 49.323 | −2.247 | 15.599 | 1.00 | 48.40 | C |
| ATOM | 9727 | CG | GLN | C | 443 | 49.178 | −0.755 | 15.337 | 1.00 | 48.01 | C |
| ATOM | 9730 | CD | GLN | C | 443 | 48.136 | −0.450 | 14.272 | 1.00 | 47.60 | C |
| ATOM | 9731 | OE1 | GLN | C | 443 | 48.168 | −1.033 | 13.190 | 1.00 | 48.05 | O |
| ATOM | 9732 | NE2 | GLN | C | 443 | 47.209 | 0.449 | 14.579 | 1.00 | 47.32 | N |
| ATOM | 9735 | C | GLN | C | 443 | 48.184 | −4.474 | 15.749 | 1.00 | 48.56 | C |
| ATOM | 9736 | O | GLN | C | 443 | 48.205 | −5.050 | 14.662 | 1.00 | 48.45 | O |
| ATOM | 9737 | N | VAL | C | 444 | 48.334 | −5.114 | 16.906 | 1.00 | 48.59 | N |
| ATOM | 9739 | CA | VAL | C | 444 | 48.500 | −6.562 | 16.955 | 1.00 | 48.61 | C |
| ATOM | 9741 | CB | VAL | C | 444 | 49.131 | −7.027 | 18.286 | 1.00 | 48.76 | C |
| ATOM | 9743 | CG1 | VAL | C | 444 | 49.207 | −8.552 | 18.353 | 1.00 | 48.81 | C |
| ATOM | 9747 | CG2 | VAL | C | 444 | 50.520 | −6.426 | 18.449 | 1.00 | 48.72 | C |
| ATOM | 9751 | C | VAL | C | 444 | 47.139 | −7.217 | 16.741 | 1.00 | 48.65 | C |
| ATOM | 9752 | O | VAL | C | 444 | 47.049 | −8.291 | 16.155 | 1.00 | 48.79 | O |
| ATOM | 9753 | N | GLY | C | 445 | 46.081 | −6.560 | 17.210 | 1.00 | 48.83 | N |
| ATOM | 9755 | CA | GLY | C | 445 | 44.725 | −7.051 | 17.035 | 1.00 | 48.94 | C |
| ATOM | 9758 | C | GLY | C | 445 | 44.228 | −6.778 | 15.623 | 1.00 | 49.11 | C |
| ATOM | 9759 | O | GLY | C | 445 | 43.451 | −7.553 | 15.070 | 1.00 | 48.86 | O |
| ATOM | 9760 | N | PHE | C | 446 | 44.690 | −5.673 | 15.042 | 1.00 | 49.40 | N |
| ATOM | 9762 | CA | PHE | C | 446 | 44.317 | −5.275 | 13.688 | 1.00 | 49.73 | C |
| ATOM | 9764 | CB | PHE | C | 446 | 44.809 | −3.844 | 13.401 | 1.00 | 49.71 | C |

TABLE 2-continued

| ATOM | 9767 | CG | PHE | C | 446 | 44.334 | -3.269 | 12.084 | 1.00 | 49.75 | C |
| --- | --- | --- | --- | --- | --- | --- | --- | --- | --- | --- | --- |
| ATOM | 9768 | CD1 | PHE | C | 446 | 43.013 | -3.397 | 11.675 | 1.00 | 49.75 | C |
| ATOM | 9770 | CE1 | PHE | C | 446 | 42.590 | -2.855 | 10.467 | 1.00 | 49.80 | C |
| ATOM | 9772 | CZ | PHE | C | 446 | 43.483 | -2.170 | 9.664 | 1.00 | 49.68 | C |
| ATOM | 9774 | CE2 | PHE | C | 446 | 44.795 | -2.028 | 10.062 | 1.00 | 49.74 | C |
| ATOM | 9776 | CD2 | PHE | C | 446 | 45.216 | -2.570 | 11.267 | 1.00 | 49.83 | C |
| ATOM | 9778 | C | PHE | C | 446 | 44.884 | -6.277 | 12.678 | 1.00 | 49.94 | C |
| ATOM | 9779 | O | PHE | C | 446 | 44.170 | -6.731 | 11.801 | 1.00 | 49.91 | O |
| ATOM | 9780 | N | ILE | C | 447 | 46.153 | -6.649 | 12.836 | 1.00 | 50.34 | N |
| ATOM | 9782 | CA | ILE | C | 447 | 46.799 | -7.614 | 11.943 | 1.00 | 50.60 | C |
| ATOM | 9784 | CB | ILE | C | 447 | 48.328 | -7.680 | 12.215 | 1.00 | 50.50 | C |
| ATOM | 9786 | CG1 | ILE | C | 447 | 49.011 | -6.374 | 11.801 | 1.00 | 50.31 | C |
| ATOM | 9789 | CD1 | ILE | C | 447 | 50.408 | -6.204 | 12.379 | 1.00 | 49.99 | C |
| ATOM | 9793 | CG2 | ILE | C | 447 | 48.965 | -8.861 | 11.472 | 1.00 | 50.39 | C |
| ATOM | 9797 | C | ILE | C | 447 | 46.202 | -9.020 | 12.076 | 1.00 | 50.98 | C |
| ATOM | 9798 | O | ILE | C | 447 | 45.780 | -9.617 | 11.093 | 1.00 | 50.91 | O |
| ATOM | 9799 | N | ASP | C | 448 | 46.176 | -9.533 | 13.300 | 1.00 | 51.55 | N |
| ATOM | 9801 | CA | ASP | C | 448 | 45.717 | -10.898 | 13.574 | 1.00 | 52.02 | C |
| ATOM | 9803 | CB | ASP | C | 448 | 45.871 | -11.214 | 15.072 | 1.00 | 52.12 | C |
| ATOM | 9806 | CG | ASP | C | 448 | 47.323 | -11.346 | 15.503 | 1.00 | 52.72 | C |
| ATOM | 9807 | OD1 | ASP | C | 448 | 48.145 | -11.838 | 14.700 | 1.00 | 53.22 | O |
| ATOM | 9808 | OD2 | ASP | C | 448 | 47.731 | -10.991 | 16.634 | 1.00 | 53.35 | O |
| ATOM | 9809 | C | ASP | C | 448 | 44.280 | -11.211 | 13.163 | 1.00 | 52.29 | C |
| ATOM | 9810 | O | ASP | C | 448 | 44.003 | -12.300 | 12.661 | 1.00 | 52.33 | O |
| ATOM | 9811 | N | TYR | C | 449 | 43.376 | -10.260 | 13.369 | 1.00 | 52.77 | N |
| ATOM | 9813 | CA | TYR | C | 449 | 41.952 | -10.481 | 13.123 | 1.00 | 53.15 | C |
| ATOM | 9815 | CB | TYR | C | 449 | 41.156 | -10.028 | 14.357 | 1.00 | 53.50 | C |
| ATOM | 9818 | CG | TYR | C | 449 | 41.613 | -10.710 | 15.635 | 1.00 | 54.98 | C |
| ATOM | 9819 | CD1 | TYR | C | 449 | 42.138 | -9.976 | 16.695 | 1.00 | 56.52 | C |
| ATOM | 9821 | CE1 | TYR | C | 449 | 42.571 | -10.602 | 17.863 | 1.00 | 57.72 | C |
| ATOM | 9823 | CZ | TYR | C | 449 | 42.482 | -11.979 | 17.974 | 1.00 | 58.21 | C |
| ATOM | 9824 | OH | TYR | C | 449 | 42.907 | -12.602 | 19.125 | 1.00 | 59.20 | O |
| ATOM | 9826 | CE2 | TYR | C | 449 | 41.967 | -12.731 | 16.931 | 1.00 | 57.69 | C |
| ATOM | 9828 | CD2 | TYR | C | 449 | 41.539 | -12.094 | 15.770 | 1.00 | 56.60 | C |
| ATOM | 9830 | C | TYR | C | 449 | 41.378 | -9.835 | 11.859 | 1.00 | 52.87 | C |
| ATOM | 9831 | O | TYR | C | 449 | 40.247 | -10.145 | 11.482 | 1.00 | 52.83 | O |
| ATOM | 9832 | N | ILE | C | 450 | 42.149 | -8.972 | 11.194 | 1.00 | 52.67 | N |
| ATOM | 9834 | CA | ILE | C | 450 | 41.671 | -8.270 | 9.995 | 1.00 | 52.51 | C |
| ATOM | 9836 | CB | ILE | C | 450 | 41.355 | -6.776 | 10.317 | 1.00 | 52.56 | C |
| ATOM | 9838 | CG1 | ILE | C | 450 | 40.347 | -6.647 | 11.470 | 1.00 | 52.74 | C |
| ATOM | 9841 | CD1 | ILE | C | 450 | 38.931 | -7.116 | 11.140 | 1.00 | 52.96 | C |
| ATOM | 9845 | CG2 | ILE | C | 450 | 40.842 | -6.047 | 9.070 | 1.00 | 52.56 | C |
| ATOM | 9849 | C | ILE | C | 450 | 42.636 | -8.328 | 8.811 | 1.00 | 52.16 | C |
| ATOM | 9850 | O | ILE | C | 450 | 42.315 | -8.904 | 7.774 | 1.00 | 51.99 | O |
| ATOM | 9851 | N | VAL | C | 451 | 43.818 | -7.741 | 8.978 | 1.00 | 51.83 | N |
| ATOM | 9853 | CA | VAL | C | 451 | 44.790 | -7.617 | 7.887 | 1.00 | 51.62 | C |
| ATOM | 9855 | CB | VAL | C | 451 | 45.861 | -6.544 | 8.216 | 1.00 | 51.65 | C |
| ATOM | 9857 | CG1 | VAL | C | 451 | 46.767 | -6.286 | 7.020 | 1.00 | 51.44 | C |
| ATOM | 9861 | CG2 | VAL | C | 451 | 45.182 | -5.242 | 8.663 | 1.00 | 51.85 | C |
| ATOM | 9865 | C | VAL | C | 451 | 45.459 | -8.929 | 7.442 | 1.00 | 51.31 | C |
| ATOM | 9866 | O | VAL | C | 451 | 45.508 | -9.202 | 6.245 | 1.00 | 51.41 | O |
| ATOM | 9867 | N | HIS | C | 452 | 45.987 | -9.724 | 8.372 | 1.00 | 50.90 | N |
| ATOM | 9869 | CA | HIS | C | 452 | 46.628 | -10.989 | 7.992 | 1.00 | 50.63 | C |
| ATOM | 9871 | CB | HIS | C | 452 | 47.380 | -11.665 | 9.147 | 1.00 | 50.72 | C |
| ATOM | 9874 | CG | HIS | C | 452 | 47.996 | -12.979 | 8.763 | 1.00 | 51.18 | C |
| ATOM | 9875 | ND1 | HIS | C | 452 | 49.299 | -13.092 | 8.327 | 1.00 | 51.63 | N |
| ATOM | 9877 | CE1 | HIS | C | 452 | 49.559 | -14.355 | 8.042 | 1.00 | 51.63 | C |
| ATOM | 9879 | NE2 | HIS | C | 452 | 48.468 | -15.065 | 8.266 | 1.00 | 51.73 | N |
| ATOM | 9881 | CD2 | HIS | C | 452 | 47.475 | -14.228 | 8.714 | 1.00 | 51.44 | C |
| ATOM | 9883 | C | HIS | C | 452 | 45.649 | -11.971 | 7.348 | 1.00 | 50.22 | C |
| ATOM | 9884 | O | HIS | C | 452 | 45.975 | -12.542 | 6.316 | 1.00 | 50.21 | O |
| ATOM | 9885 | N | PRO | C | 453 | 44.484 | -12.209 | 7.955 | 1.00 | 49.75 | N |
| ATOM | 9886 | CA | PRO | C | 453 | 43.480 | -13.089 | 7.342 | 1.00 | 49.41 | C |
| ATOM | 9888 | CB | PRO | C | 453 | 42.261 | -12.906 | 8.252 | 1.00 | 49.52 | C |
| ATOM | 9891 | CG | PRO | C | 453 | 42.832 | -12.551 | 9.579 | 1.00 | 49.54 | C |
| ATOM | 9894 | CD | PRO | C | 453 | 44.048 | -11.731 | 9.283 | 1.00 | 49.72 | C |
| ATOM | 9897 | C | PRO | C | 453 | 43.128 | -12.706 | 5.898 | 1.00 | 49.17 | C |
| ATOM | 9898 | O | PRO | C | 453 | 42.890 | -13.583 | 5.064 | 1.00 | 48.97 | O |
| ATOM | 9899 | N | LEU | C | 454 | 43.104 | -11.405 | 5.619 | 1.00 | 48.95 | N |
| ATOM | 9901 | CA | LEU | C | 454 | 42.775 | -10.891 | 4.294 | 1.00 | 48.64 | C |
| ATOM | 9903 | CB | LEU | C | 454 | 42.381 | -9.413 | 4.381 | 1.00 | 48.57 | C |
| ATOM | 9906 | CG | LEU | C | 454 | 42.094 | -8.704 | 3.054 | 1.00 | 47.91 | C |
| ATOM | 9908 | CD1 | LEU | C | 454 | 40.774 | -9.165 | 2.482 | 1.00 | 47.57 | C |
| ATOM | 9912 | CD2 | LEU | C | 454 | 42.102 | -7.201 | 3.250 | 1.00 | 48.00 | C |
| ATOM | 9916 | C | LEU | C | 454 | 43.921 | -11.064 | 3.298 | 1.00 | 48.56 | C |
| ATOM | 9917 | O | LEU | C | 454 | 43.706 | -11.564 | 2.200 | 1.00 | 48.36 | O |
| ATOM | 9918 | N | TRP | C | 455 | 45.124 | -10.640 | 3.678 | 1.00 | 48.63 | N |
| ATOM | 9920 | CA | TRP | C | 455 | 46.300 | -10.732 | 2.800 | 1.00 | 48.66 | C |
| ATOM | 9922 | CB | TRP | C | 455 | 47.465 | -9.905 | 3.346 | 1.00 | 48.53 | C |

TABLE 2-continued

| | | | | | | | | | | | |
|---|---|---|---|---|---|---|---|---|---|---|---|
| ATOM | 9925 | CG | TRP | C | 455 | 47.414 | −8.472 | 2.935 | 1.00 | 48.02 | C |
| ATOM | 9926 | CD1 | TRP | C | 455 | 47.057 | −7.411 | 3.711 | 1.00 | 47.60 | C |
| ATOM | 9928 | NE1 | TRP | C | 455 | 47.132 | −6.246 | 2.988 | 1.00 | 47.05 | N |
| ATOM | 9930 | CE2 | TRP | C | 455 | 47.539 | −6.541 | 1.713 | 1.00 | 46.93 | C |
| ATOM | 9931 | CD2 | TRP | C | 455 | 47.728 | −7.936 | 1.645 | 1.00 | 47.17 | C |
| ATOM | 9932 | CE3 | TRP | C | 455 | 48.150 | −8.495 | 0.432 | 1.00 | 46.82 | C |
| ATOM | 9934 | CZ3 | TRP | C | 455 | 48.368 | −7.656 | −0.653 | 1.00 | 46.66 | C |
| ATOM | 9936 | CH2 | TRP | C | 455 | 48.174 | −6.273 | −0.548 | 1.00 | 46.58 | C |
| ATOM | 9938 | CZ2 | TRP | C | 455 | 47.760 | −5.698 | 0.623 | 1.00 | 46.72 | C |
| ATOM | 9940 | C | TRP | C | 455 | 46.757 | −12.172 | 2.582 | 1.00 | 48.99 | C |
| ATOM | 9941 | O | TRP | C | 455 | 47.337 | −12.487 | 1.545 | 1.00 | 49.27 | O |
| ATOM | 9942 | N | GLU | C | 456 | 46.498 | −13.030 | 3.563 | 1.00 | 49.13 | N |
| ATOM | 9944 | CA | GLU | C | 456 | 46.825 | −14.452 | 3.478 | 1.00 | 49.36 | C |
| ATOM | 9946 | CB | GLU | C | 456 | 46.553 | −15.135 | 4.822 | 1.00 | 49.59 | C |
| ATOM | 9949 | CG | GLU | C | 456 | 46.326 | −16.636 | 4.775 | 1.00 | 50.53 | C |
| ATOM | 9952 | CD | GLU | C | 456 | 46.050 | −17.198 | 6.156 | 1.00 | 52.13 | C |
| ATOM | 9953 | OE1 | GLU | C | 456 | 45.040 | −16.790 | 6.767 | 1.00 | 52.84 | O |
| ATOM | 9954 | OE2 | GLU | C | 456 | 46.845 | −18.036 | 6.634 | 1.00 | 53.25 | O |
| ATOM | 9955 | C | GLU | C | 456 | 45.984 | −15.090 | 2.383 | 1.00 | 49.21 | C |
| ATOM | 9956 | O | GLU | C | 456 | 46.450 | −15.977 | 1.668 | 1.00 | 49.20 | O |
| ATOM | 9957 | N | THR | C | 457 | 44.737 | −14.638 | 2.279 | 1.00 | 49.09 | N |
| ATOM | 9959 | CA | THR | C | 457 | 43.810 | −15.117 | 1.264 | 1.00 | 49.11 | C |
| ATOM | 9961 | CB | THR | C | 457 | 42.366 | −14.750 | 1.654 | 1.00 | 49.09 | C |
| ATOM | 9963 | OG1 | THR | C | 457 | 42.084 | −15.218 | 2.979 | 1.00 | 49.00 | O |
| ATOM | 9965 | CG2 | THR | C | 457 | 41.360 | −15.487 | 0.788 | 1.00 | 48.91 | C |
| ATOM | 9969 | C | THR | C | 457 | 44.163 | −14.528 | −0.107 | 1.00 | 49.24 | C |
| ATOM | 9970 | O | THR | C | 457 | 44.073 | −15.218 | −1.117 | 1.00 | 49.20 | O |
| ATOM | 9971 | N | TRP | C | 458 | 44.560 | −13.255 | −0.131 | 1.00 | 49.46 | N |
| ATOM | 9973 | CA | TRP | C | 458 | 44.950 | −12.581 | −1.368 | 1.00 | 49.63 | C |
| ATOM | 9975 | CB | TRP | C | 458 | 45.182 | −11.078 | −1.134 | 1.00 | 49.45 | C |
| ATOM | 9978 | CG | TRP | C | 458 | 45.735 | −10.373 | −2.343 | 1.00 | 47.94 | C |
| ATOM | 9979 | CD1 | TRP | C | 458 | 47.047 | −10.127 | −2.617 | 1.00 | 46.96 | C |
| ATOM | 9981 | NE1 | TRP | C | 458 | 47.168 | −9.477 | −3.822 | 1.00 | 46.62 | N |
| ATOM | 9983 | CE2 | TRP | C | 458 | 45.920 | −9.295 | −4.355 | 1.00 | 46.10 | C |
| ATOM | 9984 | CD2 | TRP | C | 458 | 44.993 | −9.851 | −3.451 | 1.00 | 46.56 | C |
| ATOM | 9985 | CE3 | TRP | C | 458 | 43.631 | −9.793 | −3.772 | 1.00 | 45.95 | C |
| ATOM | 9987 | CZ3 | TRP | C | 458 | 43.248 | −9.193 | −4.962 | 1.00 | 45.50 | C |
| ATOM | 9989 | CH2 | TRP | C | 458 | 44.196 | −8.650 | −5.837 | 1.00 | 45.57 | C |
| ATOM | 9991 | CZ2 | TRP | C | 458 | 45.533 | −8.691 | −5.553 | 1.00 | 45.76 | C |
| ATOM | 9993 | C | TRP | C | 458 | 46.220 | −13.223 | −1.913 | 1.00 | 50.23 | C |
| ATOM | 9994 | O | TRP | C | 458 | 46.373 | −13.378 | −3.120 | 1.00 | 50.19 | O |
| ATOM | 9995 | N | ALA | C | 459 | 47.115 | −13.595 | −1.002 | 1.00 | 50.99 | N |
| ATOM | 9997 | CA | ALA | C | 459 | 48.373 | −14.250 | −1.342 | 1.00 | 51.67 | C |
| ATOM | 9999 | CB | ALA | C | 459 | 49.248 | −14.388 | −0.101 | 1.00 | 51.69 | C |
| ATOM | 10003 | C | ALA | C | 459 | 48.102 | −15.619 | −1.948 | 1.00 | 52.34 | C |
| ATOM | 10004 | O | ALA | C | 459 | 48.828 | −16.060 | −2.826 | 1.00 | 52.49 | O |
| ATOM | 10005 | N | ASP | C | 460 | 47.052 | −16.277 | −1.464 | 1.00 | 53.18 | N |
| ATOM | 10007 | CA | ASP | C | 460 | 46.634 | −17.592 | −1.955 | 1.00 | 53.86 | C |
| ATOM | 10009 | CB | ASP | C | 460 | 45.521 | −18.154 | −1.054 | 1.00 | 54.00 | C |
| ATOM | 10012 | CG | ASP | C | 460 | 45.941 | −19.389 | −0.282 | 1.00 | 54.61 | C |
| ATOM | 10013 | OD1 | ASP | C | 460 | 47.065 | −19.411 | 0.269 | 1.00 | 55.26 | O |
| ATOM | 10014 | OD2 | ASP | C | 460 | 45.192 | −20.382 | −0.159 | 1.00 | 55.58 | O |
| ATOM | 10015 | C | ASP | C | 460 | 46.110 | −17.522 | −3.394 | 1.00 | 54.34 | C |
| ATOM | 10016 | O | ASP | C | 460 | 46.252 | −18.478 | −4.159 | 1.00 | 54.59 | O |
| ATOM | 10017 | N | LEU | C | 461 | 45.494 | −16.392 | −3.740 | 1.00 | 54.75 | N |
| ATOM | 10019 | CA | LEU | C | 461 | 44.899 | −16.172 | −5.061 | 1.00 | 55.15 | C |
| ATOM | 10021 | CB | LEU | C | 461 | 43.840 | −15.063 | −4.964 | 1.00 | 55.16 | C |
| ATOM | 10024 | CG | LEU | C | 461 | 43.262 | −14.458 | −6.247 | 1.00 | 55.12 | C |
| ATOM | 10026 | CD1 | LEU | C | 461 | 42.222 | −15.378 | −6.853 | 1.00 | 55.52 | C |
| ATOM | 10030 | CD2 | LEU | C | 461 | 42.670 | −13.087 | −5.967 | 1.00 | 55.05 | C |
| ATOM | 10034 | C | LEU | C | 461 | 45.918 | −15.809 | −6.144 | 1.00 | 55.52 | C |
| ATOM | 10035 | O | LEU | C | 461 | 45.693 | −16.086 | −7.324 | 1.00 | 55.49 | O |
| ATOM | 10036 | N | VAL | C | 462 | 47.029 | −15.194 | −5.740 | 1.00 | 56.03 | N |
| ATOM | 10038 | CA | VAL | C | 462 | 48.061 | −14.739 | −6.676 | 1.00 | 56.35 | C |
| ATOM | 10040 | CB | VAL | C | 462 | 48.151 | −13.182 | −6.684 | 1.00 | 56.34 | C |
| ATOM | 10042 | CG1 | VAL | C | 462 | 46.811 | −12.564 | −7.048 | 1.00 | 56.37 | C |
| ATOM | 10046 | CG2 | VAL | C | 462 | 48.644 | −12.638 | −5.338 | 1.00 | 56.28 | C |
| ATOM | 10050 | C | VAL | C | 462 | 49.459 | −15.294 | −6.378 | 1.00 | 56.73 | C |
| ATOM | 10051 | O | VAL | C | 462 | 50.443 | −14.779 | −6.904 | 1.00 | 56.81 | O |
| ATOM | 10052 | N | GLN | C | 463 | 49.548 | −16.357 | −5.577 | 1.00 | 57.17 | N |
| ATOM | 10054 | CA | GLN | C | 463 | 50.847 | −16.910 | −5.163 | 1.00 | 57.51 | C |
| ATOM | 10056 | CB | GLN | C | 463 | 50.656 | −18.136 | −4.252 | 1.00 | 57.59 | C |
| ATOM | 10059 | CG | GLN | C | 463 | 50.286 | −19.434 | −4.963 | 1.00 | 58.28 | C |
| ATOM | 10062 | CD | GLN | C | 463 | 51.434 | −20.423 | −4.973 | 1.00 | 59.31 | C |
| ATOM | 10063 | OE1 | GLN | C | 463 | 51.712 | −21.062 | −3.957 | 1.00 | 60.12 | O |
| ATOM | 10064 | NE2 | GLN | C | 463 | 52.113 | −20.544 | −6.112 | 1.00 | 59.69 | N |
| ATOM | 10067 | C | GLN | C | 463 | 51.776 | −17.260 | −6.333 | 1.00 | 57.53 | C |
| ATOM | 10068 | O | GLN | C | 463 | 51.298 | −17.642 | −7.401 | 1.00 | 57.58 | O |
| ATOM | 10069 | N | PRO | C | 464 | 53.094 | −17.124 | −6.151 | 1.00 | 57.66 | N |

TABLE 2-continued

| ATOM | 10070 | CA | PRO | C | 464 | 53.729 | −16.651 | −4.911 | 1.00 | 57.72 | C |
| --- | --- | --- | --- | --- | --- | --- | --- | --- | --- | --- | --- |
| ATOM | 10072 | CB | PRO | C | 464 | 55.012 | −17.480 | −4.880 | 1.00 | 57.70 | C |
| ATOM | 10075 | CG | PRO | C | 464 | 55.391 | −17.610 | −6.348 | 1.00 | 57.67 | C |
| ATOM | 10078 | CD | PRO | C | 464 | 54.109 | −17.469 | −7.162 | 1.00 | 57.62 | C |
| ATOM | 10081 | C | PRO | C | 464 | 54.076 | −15.153 | −4.946 | 1.00 | 57.83 | C |
| ATOM | 10082 | O | PRO | C | 464 | 55.073 | −14.733 | −4.354 | 1.00 | 57.88 | O |
| ATOM | 10083 | N | ASP | C | 465 | 53.249 | −14.357 | −5.616 | 1.00 | 58.03 | N |
| ATOM | 10085 | CA | ASP | C | 465 | 53.499 | −12.924 | −5.781 | 1.00 | 58.13 | C |
| ATOM | 10087 | CB | ASP | C | 465 | 52.466 | −12.305 | −6.729 | 1.00 | 58.16 | C |
| ATOM | 10090 | CG | ASP | C | 465 | 52.462 | −12.952 | −8.110 | 1.00 | 58.55 | C |
| ATOM | 10091 | OD1 | ASP | C | 465 | 53.357 | −13.773 | −8.413 | 1.00 | 58.82 | O |
| ATOM | 10092 | OD2 | ASP | C | 465 | 51.587 | −12.699 | −8.959 | 1.00 | 58.68 | O |
| ATOM | 10093 | C | ASP | C | 465 | 53.509 | −12.137 | −4.471 | 1.00 | 58.17 | C |
| ATOM | 10094 | O | ASP | C | 465 | 54.345 | −11.252 | −4.293 | 1.00 | 58.25 | O |
| ATOM | 10095 | N | ALA | C | 466 | 52.592 | −12.458 | −3.561 | 1.00 | 58.30 | N |
| ATOM | 10097 | CA | ALA | C | 466 | 52.488 | −11.748 | −2.282 | 1.00 | 58.50 | C |
| ATOM | 10099 | CB | ALA | C | 466 | 51.020 | −11.541 | −1.919 | 1.00 | 58.48 | C |
| ATOM | 10103 | C | ALA | C | 466 | 53.226 | −12.436 | −1.133 | 1.00 | 58.69 | C |
| ATOM | 10104 | O | ALA | C | 466 | 52.819 | −12.318 | 0.022 | 1.00 | 58.78 | O |
| ATOM | 10105 | N | GLN | C | 467 | 54.313 | −13.136 | −1.446 | 1.00 | 59.02 | N |
| ATOM | 10107 | CA | GLN | C | 467 | 55.107 | −13.831 | −0.436 | 1.00 | 59.33 | C |
| ATOM | 10109 | CB | GLN | C | 467 | 56.060 | −14.833 | −1.097 | 1.00 | 59.47 | C |
| ATOM | 10112 | CG | GLN | C | 467 | 56.888 | −15.681 | −0.119 | 1.00 | 60.09 | C |
| ATOM | 10115 | CD | GLN | C | 467 | 58.333 | −15.896 | −0.577 | 1.00 | 61.04 | C |
| ATOM | 10116 | OE1 | GLN | C | 467 | 59.057 | −14.937 | −0.847 | 1.00 | 61.88 | O |
| ATOM | 10117 | NE2 | GLN | C | 467 | 58.751 | −17.156 | −0.652 | 1.00 | 61.64 | N |
| ATOM | 10120 | C | GLN | C | 467 | 55.897 | −12.822 | 0.393 | 1.00 | 59.42 | C |
| ATOM | 10121 | O | GLN | C | 467 | 55.916 | −12.910 | 1.618 | 1.00 | 59.29 | O |
| ATOM | 10122 | N | ASP | C | 468 | 56.544 | −11.872 | −0.284 | 1.00 | 59.58 | N |
| ATOM | 10124 | CA | ASP | C | 468 | 57.344 | −10.833 | 0.379 | 1.00 | 59.71 | C |
| ATOM | 10126 | CB | ASP | C | 468 | 58.078 | −9.966 | −0.657 | 1.00 | 59.83 | C |
| ATOM | 10129 | CG | ASP | C | 468 | 59.145 | −10.736 | −1.431 | 1.00 | 60.19 | C |
| ATOM | 10130 | OD1 | ASP | C | 468 | 59.883 | −10.096 | −2.211 | 1.00 | 60.83 | O |
| ATOM | 10131 | OD2 | ASP | C | 468 | 59.323 | −11.971 | −1.330 | 1.00 | 60.38 | O |
| ATOM | 10132 | C | ASP | C | 468 | 56.490 | −9.934 | 1.284 | 1.00 | 59.64 | C |
| ATOM | 10133 | O | ASP | C | 468 | 56.956 | −9.473 | 2.326 | 1.00 | 59.79 | O |
| ATOM | 10134 | N | ILE | C | 469 | 55.250 | −9.680 | 0.870 | 1.00 | 59.47 | N |
| ATOM | 10136 | CA | ILE | C | 469 | 54.312 | −8.869 | 1.645 | 1.00 | 59.31 | C |
| ATOM | 10138 | CB | ILE | C | 469 | 53.064 | −8.531 | 0.787 | 1.00 | 59.27 | C |
| ATOM | 10140 | CG1 | ILE | C | 469 | 53.388 | −7.404 | −0.200 | 1.00 | 59.21 | C |
| ATOM | 10143 | CD1 | ILE | C | 469 | 52.454 | −7.339 | −1.399 | 1.00 | 58.88 | C |
| ATOM | 10147 | CG2 | ILE | C | 469 | 51.870 | −8.153 | 1.665 | 1.00 | 59.27 | C |
| ATOM | 10151 | C | ILE | C | 469 | 53.900 | −9.604 | 2.921 | 1.00 | 59.20 | C |
| ATOM | 10152 | O | ILE | C | 469 | 53.812 | −9.005 | 3.991 | 1.00 | 59.19 | O |
| ATOM | 10153 | N | LEU | C | 470 | 53.650 | −10.903 | 2.792 | 1.00 | 59.12 | N |
| ATOM | 10155 | CA | LEU | C | 470 | 53.246 | −11.740 | 3.919 | 1.00 | 59.05 | C |
| ATOM | 10157 | CB | LEU | C | 470 | 52.826 | −13.134 | 3.429 | 1.00 | 59.10 | C |
| ATOM | 10160 | CG | LEU | C | 470 | 51.643 | −13.811 | 4.126 | 1.00 | 59.38 | C |
| ATOM | 10162 | CD1 | LEU | C | 470 | 50.361 | −13.004 | 3.966 | 1.00 | 59.51 | C |
| ATOM | 10166 | CD2 | LEU | C | 470 | 51.459 | −15.224 | 3.576 | 1.00 | 59.50 | C |
| ATOM | 10170 | C | LEU | C | 470 | 54.366 | −11.854 | 4.955 | 1.00 | 58.98 | C |
| ATOM | 10171 | O | LEU | C | 470 | 54.094 | −11.952 | 6.152 | 1.00 | 58.99 | O |
| ATOM | 10172 | N | ASP | C | 471 | 55.616 | −11.833 | 4.488 | 1.00 | 58.85 | N |
| ATOM | 10174 | CA | ASP | C | 471 | 56.788 | −11.903 | 5.362 | 1.00 | 58.71 | C |
| ATOM | 10176 | CB | ASP | C | 471 | 58.065 | −12.189 | 4.554 | 1.00 | 58.81 | C |
| ATOM | 10179 | CG | ASP | C | 471 | 58.142 | −13.626 | 4.054 | 1.00 | 58.89 | C |
| ATOM | 10180 | OD1 | ASP | C | 471 | 57.520 | −14.519 | 4.667 | 1.00 | 59.50 | O |
| ATOM | 10181 | OD2 | ASP | C | 471 | 58.810 | −13.959 | 3.053 | 1.00 | 58.88 | O |
| ATOM | 10182 | C | ASP | C | 471 | 56.957 | −10.596 | 6.132 | 1.00 | 58.48 | C |
| ATOM | 10183 | O | ASP | C | 471 | 57.325 | −10.608 | 7.305 | 1.00 | 58.56 | O |
| ATOM | 10184 | N | THR | C | 472 | 56.690 | −9.473 | 5.465 | 1.00 | 58.17 | N |
| ATOM | 10186 | CA | THR | C | 472 | 56.788 | −8.153 | 6.087 | 1.00 | 57.95 | C |
| ATOM | 10188 | CB | THR | C | 472 | 56.752 | −7.036 | 5.014 | 1.00 | 57.84 | C |
| ATOM | 10190 | OG1 | THR | C | 472 | 57.840 | −7.200 | 4.098 | 1.00 | 57.85 | O |
| ATOM | 10192 | CG2 | THR | C | 472 | 57.007 | −5.666 | 5.630 | 1.00 | 57.79 | C |
| ATOM | 10196 | C | THR | C | 472 | 55.653 | −7.945 | 7.088 | 1.00 | 57.80 | C |
| ATOM | 10197 | O | THR | C | 472 | 55.771 | −7.126 | 7.997 | 1.00 | 57.85 | O |
| ATOM | 10198 | N | LEU | C | 473 | 54.562 | −8.689 | 6.912 | 1.00 | 57.59 | N |
| ATOM | 10200 | CA | LEU | C | 473 | 53.401 | −8.609 | 7.792 | 1.00 | 57.43 | C |
| ATOM | 10202 | CB | LEU | C | 473 | 52.182 | −9.251 | 7.120 | 1.00 | 57.34 | C |
| ATOM | 10205 | CG | LEU | C | 473 | 50.799 | −8.800 | 7.586 | 1.00 | 56.79 | C |
| ATOM | 10207 | CD1 | LEU | C | 473 | 50.675 | −7.284 | 7.574 | 1.00 | 56.61 | C |
| ATOM | 10211 | CD2 | LEU | C | 473 | 49.736 | −9.433 | 6.710 | 1.00 | 56.59 | C |
| ATOM | 10215 | C | LEU | C | 473 | 53.689 | −9.298 | 9.122 | 1.00 | 57.52 | C |
| ATOM | 10216 | O | LEU | C | 473 | 53.346 | −8.776 | 10.179 | 1.00 | 57.54 | O |
| ATOM | 10217 | N | GLU | C | 474 | 54.315 | −10.473 | 9.057 | 1.00 | 57.52 | N |
| ATOM | 10219 | CA | GLU | C | 474 | 54.684 | −11.231 | 10.250 | 1.00 | 57.51 | C |
| ATOM | 10221 | CB | GLU | C | 474 | 55.224 | −12.616 | 9.864 | 1.00 | 57.67 | C |
| ATOM | 10224 | CG | GLU | C | 474 | 55.821 | −13.410 | 11.021 | 1.00 | 58.13 | C |

TABLE 2-continued

| ATOM | 10227 | CD | GLU | C | 474 | 55.972 | −14.889 | 10.709 | 1.00 | 58.69 | C |
|---|---|---|---|---|---|---|---|---|---|---|---|
| ATOM | 10228 | OE1 | GLU | C | 474 | 54.940 | −15.577 | 10.565 | 1.00 | 59.26 | O |
| ATOM | 10229 | OE2 | GLU | C | 474 | 57.124 | −15.367 | 10.611 | 1.00 | 58.97 | O |
| ATOM | 10230 | C | GLU | C | 474 | 55.729 | −10.473 | 11.066 | 1.00 | 57.29 | C |
| ATOM | 10231 | O | GLU | C | 474 | 55.670 | −10.461 | 12.293 | 1.00 | 57.47 | O |
| ATOM | 10232 | N | ASP | C | 475 | 56.678 | −9.846 | 10.376 | 1.00 | 56.99 | N |
| ATOM | 10234 | CA | ASP | C | 475 | 57.750 | −9.094 | 11.027 | 1.00 | 56.71 | C |
| ATOM | 10236 | CB | ASP | C | 475 | 58.809 | −8.682 | 10.004 | 1.00 | 56.78 | C |
| ATOM | 10239 | CG | ASP | C | 475 | 59.672 | −9.847 | 9.555 | 1.00 | 57.01 | C |
| ATOM | 10240 | OD1 | ASP | C | 475 | 59.194 | −11.002 | 9.579 | 1.00 | 57.30 | O |
| ATOM | 10241 | OD2 | ASP | C | 475 | 60.845 | −9.698 | 9.161 | 1.00 | 57.43 | O |
| ATOM | 10242 | C | ASP | C | 475 | 57.219 | −7.861 | 11.743 | 1.00 | 56.37 | C |
| ATOM | 10243 | O | ASP | C | 475 | 57.588 | −7.596 | 12.885 | 1.00 | 56.33 | O |
| ATOM | 10244 | N | ASN | C | 476 | 56.361 | −7.107 | 11.062 | 1.00 | 55.96 | N |
| ATOM | 10246 | CA | ASN | C | 476 | 55.755 | −5.910 | 11.640 | 1.00 | 55.63 | C |
| ATOM | 10248 | CB | ASN | C | 476 | 54.927 | −5.167 | 10.584 | 1.00 | 55.61 | C |
| ATOM | 10251 | CG | ASN | C | 476 | 55.787 | −4.381 | 9.600 | 1.00 | 55.29 | C |
| ATOM | 10252 | OD1 | ASN | C | 476 | 57.005 | −4.291 | 9.746 | 1.00 | 55.21 | O |
| ATOM | 10253 | ND2 | ASN | C | 476 | 55.144 | −3.801 | 8.594 | 1.00 | 54.36 | N |
| ATOM | 10256 | C | ASN | C | 476 | 54.875 | −6.254 | 12.845 | 1.00 | 55.38 | C |
| ATOM | 10257 | O | ASN | C | 476 | 54.816 | −5.501 | 13.815 | 1.00 | 55.09 | O |
| ATOM | 10258 | N | ARG | C | 477 | 54.205 | −7.401 | 12.771 | 1.00 | 55.26 | N |
| ATOM | 10260 | CA | ARG | C | 477 | 53.333 | −7.879 | 13.839 | 1.00 | 55.26 | C |
| ATOM | 10262 | CB | ARG | C | 477 | 52.589 | −9.143 | 13.390 | 1.00 | 55.28 | C |
| ATOM | 10265 | CG | ARG | C | 477 | 51.478 | −9.600 | 14.332 | 1.00 | 55.35 | C |
| ATOM | 10268 | CD | ARG | C | 477 | 51.965 | −10.348 | 15.565 | 1.00 | 55.45 | C |
| ATOM | 10271 | NE | ARG | C | 477 | 50.994 | −11.329 | 16.049 | 1.00 | 55.47 | N |
| ATOM | 10273 | CZ | ARG | C | 477 | 50.917 | −11.760 | 17.310 | 1.00 | 55.81 | C |
| ATOM | 10274 | NH1 | ARG | C | 477 | 51.761 | −11.319 | 18.241 | 1.00 | 55.47 | N |
| ATOM | 10277 | NH2 | ARG | C | 477 | 49.989 | −12.652 | 17.643 | 1.00 | 55.94 | N |
| ATOM | 10280 | C | ARG | C | 477 | 54.154 | −8.177 | 15.087 | 1.00 | 55.26 | C |
| ATOM | 10281 | O | ARG | C | 477 | 53.810 | −7.740 | 16.183 | 1.00 | 55.24 | O |
| ATOM | 10282 | N | ASN | C | 478 | 55.246 | −8.916 | 14.902 | 1.00 | 55.19 | N |
| ATOM | 10284 | CA | ASN | C | 478 | 56.137 | −9.291 | 15.995 | 1.00 | 55.10 | C |
| ATOM | 10286 | CB | ASN | C | 478 | 57.224 | −10.257 | 15.504 | 1.00 | 55.17 | C |
| ATOM | 10289 | CG | ASN | C | 478 | 56.679 | −11.634 | 15.157 | 1.00 | 55.50 | C |
| ATOM | 10290 | OD1 | ASN | C | 478 | 57.358 | −12.427 | 14.504 | 1.00 | 56.14 | O |
| ATOM | 10291 | ND2 | ASN | C | 478 | 55.454 | −11.925 | 15.593 | 1.00 | 55.79 | N |
| ATOM | 10294 | C | ASN | C | 478 | 56.787 | −8.086 | 16.662 | 1.00 | 54.88 | C |
| ATOM | 10295 | O | ASN | C | 478 | 57.125 | −8.143 | 17.846 | 1.00 | 54.89 | O |
| ATOM | 10296 | N | TRP | C | 479 | 56.951 | −6.996 | 15.912 | 1.00 | 54.47 | N |
| ATOM | 10298 | CA | TRP | C | 479 | 57.546 | −5.782 | 16.453 | 1.00 | 54.16 | C |
| ATOM | 10300 | CB | TRP | C | 479 | 57.887 | −4.797 | 15.338 | 1.00 | 53.85 | C |
| ATOM | 10303 | CG | TRP | C | 479 | 58.712 | −3.646 | 15.820 | 1.00 | 52.34 | C |
| ATOM | 10304 | CD1 | TRP | C | 479 | 60.067 | −3.616 | 15.965 | 1.00 | 51.42 | C |
| ATOM | 10306 | NE1 | TRP | C | 479 | 60.467 | −2.388 | 16.435 | 1.00 | 51.01 | N |
| ATOM | 10308 | CE2 | TRP | C | 479 | 59.362 | −1.598 | 16.611 | 1.00 | 50.53 | C |
| ATOM | 10309 | CD2 | TRP | C | 479 | 58.237 | −2.360 | 16.232 | 1.00 | 50.73 | C |
| ATOM | 10310 | CE3 | TRP | C | 479 | 56.972 | −1.770 | 16.319 | 1.00 | 50.26 | C |
| ATOM | 10312 | CZ3 | TRP | C | 479 | 56.872 | −0.460 | 16.772 | 1.00 | 49.85 | C |
| ATOM | 10314 | CH2 | TRP | C | 479 | 58.010 | 0.269 | 17.139 | 1.00 | 49.92 | C |
| ATOM | 10316 | CZ2 | TRP | C | 479 | 59.261 | −0.280 | 17.065 | 1.00 | 50.23 | C |
| ATOM | 10318 | C | TRP | C | 479 | 56.616 | −5.101 | 17.449 | 1.00 | 54.47 | C |
| ATOM | 10319 | O | TRP | C | 479 | 57.057 | −4.650 | 18.507 | 1.00 | 54.55 | O |
| ATOM | 10320 | N | TYR | C | 480 | 55.335 | −5.014 | 17.099 | 1.00 | 54.70 | N |
| ATOM | 10322 | CA | TYR | C | 480 | 54.348 | −4.362 | 17.957 | 1.00 | 54.82 | C |
| ATOM | 10324 | CB | TYR | C | 480 | 53.046 | −4.088 | 17.188 | 1.00 | 54.65 | C |
| ATOM | 10327 | CG | TYR | C | 480 | 53.038 | −2.744 | 16.482 | 1.00 | 53.66 | C |
| ATOM | 10328 | CD1 | TYR | C | 480 | 52.920 | −1.561 | 17.206 | 1.00 | 52.52 | C |
| ATOM | 10330 | CE1 | TYR | C | 480 | 52.917 | −0.327 | 16.572 | 1.00 | 52.29 | C |
| ATOM | 10332 | CZ | TYR | C | 480 | 53.031 | −0.262 | 15.194 | 1.00 | 52.28 | C |
| ATOM | 10333 | OH | TYR | C | 480 | 53.026 | 0.961 | 14.566 | 1.00 | 52.25 | O |
| ATOM | 10335 | CE2 | TYR | C | 480 | 53.150 | −1.419 | 14.449 | 1.00 | 52.31 | C |
| ATOM | 10337 | CD2 | TYR | C | 480 | 53.156 | −2.655 | 15.094 | 1.00 | 53.01 | C |
| ATOM | 10339 | C | TYR | C | 480 | 54.088 | −5.178 | 19.224 | 1.00 | 55.35 | C |
| ATOM | 10340 | O | TYR | C | 480 | 53.839 | −4.609 | 20.288 | 1.00 | 55.39 | O |
| ATOM | 10341 | N | GLN | C | 481 | 54.162 | −6.503 | 19.105 | 1.00 | 55.90 | N |
| ATOM | 10343 | CA | GLN | C | 481 | 53.993 | −7.403 | 20.242 | 1.00 | 56.41 | C |
| ATOM | 10345 | CB | GLN | C | 481 | 53.826 | −8.852 | 19.764 | 1.00 | 56.53 | C |
| ATOM | 10348 | CG | GLN | C | 481 | 53.620 | −9.904 | 20.873 | 1.00 | 57.15 | C |
| ATOM | 10351 | CD | GLN | C | 481 | 52.372 | −9.672 | 21.723 | 1.00 | 58.01 | C |
| ATOM | 10352 | OE1 | GLN | C | 481 | 52.411 | −9.827 | 22.946 | 1.00 | 58.79 | O |
| ATOM | 10353 | NE2 | GLN | C | 481 | 51.269 | −9.313 | 21.080 | 1.00 | 58.12 | N |
| ATOM | 10356 | C | GLN | C | 481 | 55.199 | −7.269 | 21.174 | 1.00 | 56.66 | C |
| ATOM | 10357 | O | GLN | C | 481 | 55.073 | −7.460 | 22.382 | 1.00 | 56.83 | O |
| ATOM | 10358 | N | SER | C | 482 | 56.357 | −6.932 | 20.604 | 1.00 | 56.93 | N |
| ATOM | 10360 | CA | SER | C | 482 | 57.589 | −6.730 | 21.369 | 1.00 | 57.08 | C |
| ATOM | 10362 | CB | SER | C | 482 | 58.821 | −6.738 | 20.449 | 1.00 | 57.04 | C |
| ATOM | 10365 | OG | SER | C | 482 | 59.159 | −5.429 | 20.009 | 1.00 | 56.64 | O |

TABLE 2-continued

| ATOM | 10367 | C | SER | C | 482 | 57.542 | -5.419 | 22.154 | 1.00 | 57.30 | C |
|---|---|---|---|---|---|---|---|---|---|---|---|
| ATOM | 10368 | O | SER | C | 482 | 58.301 | -5.233 | 23.106 | 1.00 | 57.37 | O |
| ATOM | 10369 | N | MET | C | 483 | 56.670 | -4.506 | 21.731 | 1.00 | 57.50 | N |
| ATOM | 10371 | CA | MET | C | 483 | 56.491 | -3.219 | 22.403 | 1.00 | 57.71 | C |
| ATOM | 10373 | CB | MET | C | 483 | 56.123 | -2.136 | 21.381 | 1.00 | 57.90 | C |
| ATOM | 10376 | CG | MET | C | 483 | 57.232 | -1.820 | 20.385 | 1.00 | 58.56 | C |
| ATOM | 10379 | SD | MET | C | 483 | 58.654 | -1.007 | 21.141 | 1.00 | 59.92 | S |
| ATOM | 10380 | CE | MET | C | 483 | 58.089 | 0.711 | 21.210 | 1.00 | 59.99 | C |
| ATOM | 10384 | C | MET | C | 483 | 55.428 | -3.275 | 23.514 | 1.00 | 57.52 | C |
| ATOM | 10385 | O | MET | C | 483 | 55.150 | -2.260 | 24.151 | 1.00 | 57.46 | O |
| ATOM | 10386 | N | ILE | C | 484 | 54.836 | -4.452 | 23.727 | 1.00 | 57.35 | N |
| ATOM | 10388 | CA | ILE | C | 484 | 53.844 | -4.661 | 24.780 | 1.00 | 57.29 | C |
| ATOM | 10390 | CB | ILE | C | 484 | 52.687 | -5.564 | 24.279 | 1.00 | 57.32 | C |
| ATOM | 10392 | CG1 | ILE | C | 484 | 51.912 | -4.877 | 23.149 | 1.00 | 57.36 | C |
| ATOM | 10395 | CD1 | ILE | C | 484 | 51.001 | -5.814 | 22.369 | 1.00 | 57.27 | C |
| ATOM | 10399 | CG2 | ILE | C | 484 | 51.735 | -5.919 | 25.432 | 1.00 | 57.28 | C |
| ATOM | 10403 | C | ILE | C | 484 | 54.524 | -5.322 | 25.989 | 1.00 | 57.17 | C |
| ATOM | 10404 | O | ILE | C | 484 | 54.985 | -6.461 | 25.885 | 1.00 | 57.11 | O |
| ATOM | 10405 | N | PRO | C | 485 | 54.613 | -4.620 | 27.119 | 1.00 | 57.02 | N |
| ATOM | 10406 | CA | PRO | C | 485 | 55.197 | -5.204 | 28.335 | 1.00 | 56.90 | C |
| ATOM | 10408 | CB | PRO | C | 485 | 55.333 | -4.000 | 29.276 | 1.00 | 56.95 | C |
| ATOM | 10411 | CG | PRO | C | 485 | 55.123 | -2.794 | 28.421 | 1.00 | 56.99 | C |
| ATOM | 10414 | CD | PRO | C | 485 | 54.212 | -3.217 | 27.328 | 1.00 | 56.97 | C |
| ATOM | 10417 | C | PRO | C | 485 | 54.298 | -6.267 | 28.969 | 1.00 | 56.81 | C |
| ATOM | 10418 | O | PRO | C | 485 | 54.417 | -7.451 | 28.650 | 1.00 | 56.64 | O |
| ATOM | 10419 | ZN | ZN | C | 1001 | 40.738 | 4.428 | 3.314 | 1.00 | 24.61 | ZN |
| ATOM | 10420 | MG | MG | C | 1002 | 36.994 | 4.524 | 4.060 | 1.00 | 25.37 | MG |
| ATOM | 10421 | O | HOH | C | 1003 | 35.496 | 5.461 | 4.783 | 1.00 | 34.06 | O |
| ATOM | 10424 | O | HOH | C | 1004 | 36.061 | 4.446 | 2.033 | 1.00 | 28.89 | O |
| ATOM | 10427 | O | HOH | C | 1005 | 35.562 | 3.025 | 4.585 | 1.00 | 27.07 | O |
| ATOM | 10430 | O | HOH | C | 1006 | 38.085 | 4.535 | 6.123 | 1.00 | 33.63 | O |
| ATOM | 10433 | O | HOH | C | 1007 | 39.102 | 4.152 | 3.344 | 1.00 | 2.00 | O |
| ATOM | 10436 | O | HOH | C | 1008 | 40.474 | 4.323 | 5.884 | 1.00 | 2.56 | O |
| ATOM | 10439 | C17 | LIG | L | 1 | -2.623 | 1.858 | -11.199 | 1.00 | 52.36 | C |
| ATOM | 10443 | O16 | LIG | L | 1 | -1.652 | 0.924 | -11.700 | 1.00 | 53.04 | O |
| ATOM | 10444 | C15 | LIG | L | 1 | -0.303 | 1.146 | -11.404 | 1.00 | 53.99 | C |
| ATOM | 10445 | C18 | LIG | L | 1 | 0.099 | 1.716 | -10.189 | 1.00 | 54.48 | C |
| ATOM | 10447 | C19 | LIG | L | 1 | 1.458 | 1.917 | -9.920 | 1.00 | 55.75 | C |
| ATOM | 10449 | C12 | LIG | L | 1 | 0.658 | 0.758 | -12.349 | 1.00 | 54.64 | C |
| ATOM | 10450 | O13 | LIG | L | 1 | 0.198 | 0.177 | -13.544 | 1.00 | 54.19 | O |
| ATOM | 10451 | C14 | LIG | L | 1 | 1.079 | 0.145 | -14.681 | 1.00 | 53.56 | C |
| ATOM | 10455 | C11 | LIG | L | 1 | 2.025 | 0.952 | -12.069 | 1.00 | 55.78 | C |
| ATOM | 10457 | C1 | LIG | L | 1 | 2.436 | 1.532 | -10.852 | 1.00 | 56.76 | C |
| ATOM | 10458 | C2 | LIG | L | 1 | 3.889 | 1.745 | -10.576 | 1.00 | 59.02 | C |
| ATOM | 10459 | C3 | LIG | L | 1 | 4.767 | 2.220 | -11.565 | 1.00 | 59.77 | C |
| ATOM | 10461 | C4 | LIG | L | 1 | 6.136 | 2.422 | -11.300 | 1.00 | 60.39 | C |
| ATOM | 10463 | N5 | LIG | L | 1 | 6.661 | 2.168 | -10.074 | 1.00 | 60.82 | N |
| ATOM | 10464 | C6 | LIG | L | 1 | 5.844 | 1.714 | -9.102 | 1.00 | 60.82 | C |
| ATOM | 10465 | N7 | LIG | L | 1 | 6.094 | 1.384 | -7.819 | 1.00 | 61.50 | N |
| ATOM | 10467 | C10 | LIG | L | 1 | 4.487 | 1.503 | -9.332 | 1.00 | 60.62 | C |
| ATOM | 10468 | C9 | LIG | L | 1 | 4.024 | 1.009 | -7.985 | 1.00 | 61.47 | C |
| ATOM | 10470 | C8 | LIG | L | 1 | 5.060 | 0.973 | -7.138 | 1.00 | 61.59 | C |
| ATOM | 10472 | C17 | LIG | L | 2 | 47.387 | 1.989 | 10.542 | 1.00 | 50.91 | C |
| ATOM | 10476 | O16 | LIG | L | 2 | 46.440 | 0.999 | 10.986 | 1.00 | 51.24 | O |
| ATOM | 10477 | C15 | LIG | L | 2 | 45.093 | 1.232 | 10.694 | 1.00 | 51.49 | C |
| ATOM | 10478 | C18 | LIG | L | 2 | 44.692 | 1.759 | 9.460 | 1.00 | 51.78 | C |
| ATOM | 10480 | C19 | LIG | L | 2 | 43.332 | 1.973 | 9.192 | 1.00 | 52.63 | C |
| ATOM | 10482 | C12 | LIG | L | 2 | 44.134 | 0.907 | 11.660 | 1.00 | 51.70 | C |
| ATOM | 10483 | O13 | LIG | L | 2 | 44.605 | 0.371 | 12.868 | 1.00 | 51.43 | O |
| ATOM | 10484 | C14 | LIG | L | 2 | 43.764 | 0.428 | 14.029 | 1.00 | 50.89 | C |
| ATOM | 10488 | C11 | LIG | L | 2 | 42.767 | 1.113 | 11.386 | 1.00 | 52.59 | C |
| ATOM | 10490 | C1 | LIG | L | 2 | 42.355 | 1.642 | 10.145 | 1.00 | 53.46 | C |
| ATOM | 10491 | C2 | LIG | L | 2 | 40.912 | 1.896 | 9.856 | 1.00 | 55.11 | C |
| ATOM | 10492 | C3 | LIG | L | 2 | 40.098 | 2.500 | 10.824 | 1.00 | 55.69 | C |
| ATOM | 10494 | C4 | LIG | L | 2 | 38.739 | 2.770 | 10.581 | 1.00 | 56.33 | C |
| ATOM | 10496 | N5 | LIG | L | 2 | 38.163 | 2.465 | 9.390 | 1.00 | 56.81 | N |
| ATOM | 10497 | C6 | LIG | L | 2 | 38.919 | 1.893 | 8.430 | 1.00 | 56.69 | C |
| ATOM | 10498 | N7 | LIG | L | 2 | 38.603 | 1.494 | 7.177 | 1.00 | 56.84 | N |
| ATOM | 10500 | C10 | LIG | L | 2 | 40.268 | 1.613 | 8.642 | 1.00 | 56.38 | C |
| ATOM | 10501 | C9 | LIG | L | 2 | 40.653 | 0.996 | 7.324 | 1.00 | 56.91 | C |
| ATOM | 10503 | C8 | LIG | L | 2 | 39.591 | 0.968 | 6.505 | 1.00 | 56.97 | C |
| ATOM | 10505 | O | HOH | X | 1 | 36.071 | 5.373 | 7.700 | 1.00 | 35.86 | O |
| ATOM | 10508 | O | HOH | X | 2 | 5.133 | 13.984 | -4.862 | 1.00 | 34.72 | O |
| ATOM | 10511 | O | HOH | X | 3 | 4.638 | 1.240 | -26.598 | 1.00 | 43.32 | O |
| ATOM | 10514 | O | HOH | X | 4 | -1.039 | 0.223 | -6.862 | 1.00 | 36.83 | O |
| ATOM | 10517 | O | HOH | X | 5 | 10.699 | 4.151 | -7.655 | 1.00 | 49.64 | O |
| ATOM | 10520 | O | HOH | X | 6 | 17.023 | 9.154 | 6.875 | 1.00 | 31.61 | O |
| ATOM | 10523 | O | HOH | X | 7 | 8.200 | 5.023 | -7.753 | 1.00 | 23.65 | O |
| ATOM | 10526 | O | HOH | X | 8 | 26.781 | 3.496 | 7.716 | 1.00 | 31.90 | O |

TABLE 2-continued

| | | | | | | | | | | |
|---|---|---|---|---|---|---|---|---|---|---|
| ATOM | 10529 | O | HOH | X | 9 | 42.094 | 3.021 | 5.899 | 1.00 | 37.70 O |
| ATOM | 10532 | O | HOH | X | 10 | −14.368 | 6.688 | 11.729 | 1.00 | 45.94 O |
| ATOM | 10535 | O | HOH | X | 11 | 27.688 | 8.901 | −7.347 | 1.00 | 26.43 O |
| ATOM | 10538 | O | HOH | X | 12 | −8.011 | 3.468 | −2.950 | 1.00 | 38.88 O |
| ATOM | 10541 | O | HOH | X | 13 | 51.318 | −15.323 | −2.358 | 1.00 | 40.66 O |
| ATOM | 10544 | O | HOH | X | 14 | 33.538 | 4.507 | 7.210 | 1.00 | 46.18 O |
| ATOM | 10547 | O | HOH | X | 15 | 49.682 | 1.570 | 2.917 | 1.00 | 33.83 O |
| ATOM | 10550 | O | HOH | X | 16 | 6.399 | −1.165 | −4.073 | 1.00 | 35.16 O |
| ATOM | 10553 | O | HOH | X | 17 | 3.049 | −7.009 | 21.450 | 1.00 | 47.54 O |
| ATOM | 10556 | O | HOH | X | 18 | 26.269 | 2.793 | −14.389 | 1.00 | 34.79 O |
| ATOM | 10559 | O | HOH | X | 19 | 47.876 | 16.676 | −22.600 | 1.00 | 48.36 O |
| ATOM | 10562 | O | HOH | X | 20 | 39.363 | 13.818 | 4.650 | 1.00 | 35.25 O |
| ATOM | 10565 | O | HOH | X | 21 | −3.577 | −0.123 | 17.433 | 1.00 | 41.95 O |
| ATOM | 10568 | O | HOH | X | 22 | 31.602 | 2.504 | 12.250 | 1.00 | 42.34 O |
| ATOM | 10571 | O | HOH | X | 23 | 61.708 | 4.369 | −1.233 | 1.00 | 45.14 O |
| ATOM | 10574 | O | HOH | X | 24 | 17.823 | 3.500 | −8.260 | 1.00 | 38.10 O |
| ATOM | 10577 | O | HOH | X | 25 | 47.335 | 4.973 | 4.313 | 1.00 | 40.48 O |
| ATOM | 10580 | O | HOH | X | 26 | 50.152 | −9.005 | −5.138 | 1.00 | 55.75 O |
| ATOM | 10583 | O | HOH | X | 27 | 52.705 | 3.493 | 2.239 | 1.00 | 40.28 O |
| ATOM | 10586 | O | HOH | X | 28 | 30.325 | 7.237 | 18.493 | 1.00 | 49.75 O |
| ATOM | 10589 | O | HOH | X | 29 | −2.726 | 4.905 | −4.700 | 1.00 | 38.74 O |
| ATOM | 10592 | O | HOH | X | 30 | 52.077 | 4.500 | −1.174 | 1.00 | 41.04 O |
| ATOM | 10595 | O | HOH | X | 31 | 17.788 | 13.455 | −0.253 | 1.00 | 37.79 O |
| ATOM | 10598 | O | HOH | X | 32 | 9.320 | 1.868 | −7.191 | 1.00 | 38.65 O |
| ATOM | 10601 | O | HOH | X | 33 | 26.832 | 13.395 | −0.030 | 1.00 | 38.82 O |
| ATOM | 10604 | O | HOH | X | 34 | 6.238 | 11.596 | 20.745 | 1.00 | 37.65 O |
| ATOM | 10607 | O | HOH | X | 35 | 16.964 | −0.750 | 8.251 | 1.00 | 33.92 O |
| ATOM | 10610 | O | HOH | X | 36 | 27.678 | −0.518 | −9.026 | 1.00 | 50.06 O |
| ATOM | 10613 | O | HOH | X | 37 | 18.796 | 2.756 | 11.150 | 1.00 | 41.74 O |
| ATOM | 10616 | O | HOH | X | 38 | 25.808 | 2.882 | −11.787 | 1.00 | 40.17 O |
| ATOM | 10619 | O | HOH | X | 39 | 36.461 | 0.037 | −23.198 | 1.00 | 48.01 O |
| ATOM | 10622 | O | HOH | X | 40 | 38.221 | 11.604 | −20.943 | 1.00 | 36.91 O |
| ATOM | 10625 | O | HOH | X | 41 | 10.714 | −18.310 | −3.552 | 1.00 | 46.23 O |
| ATOM | 10628 | O | HOH | X | 42 | −4.845 | 1.464 | −3.658 | 1.00 | 42.52 O |
| ATOM | 10631 | O | HOH | X | 43 | 45.775 | 0.269 | 6.130 | 1.00 | 38.64 O |
| ATOM | 10634 | O | HOH | X | 44 | 43.641 | −1.075 | 21.556 | 1.00 | 62.35 O |
| ATOM | 10637 | O | HOH | X | 45 | 40.300 | 10.136 | 23.315 | 1.00 | 56.76 O |
| ATOM | 10640 | O | HOH | X | 46 | 35.739 | 2.311 | 10.495 | 1.00 | 37.29 O |
| ATOM | 10643 | O | HOH | X | 47 | 4.440 | 10.114 | −23.806 | 1.00 | 34.83 O |
| ATOM | 10646 | O | HOH | X | 48 | 17.078 | −1.257 | 5.582 | 1.00 | 41.76 O |
| ATOM | 10649 | O | HOH | X | 49 | 11.151 | 4.027 | −10.073 | 1.00 | 33.65 O |

TABLE 3

PDE4B in pET15S

*Homo sapiens* phosphodiesterase 4B, cAMP-specific (phosphodiesterase E4
dunce homolog, Drosophila) (PDE4B), mRNA, SEQ ID NO:4
Domains within the query sequence of 564 residues
PCR from Human Brain, hippocampus QUICK-Clone cDNA (Clontech, #7169-1)
Full-length protein in pET15S:
398 aa Mass: 45599.2 pI: 5.03 Ext. Coefficiency (280 nm) = 0.949

```
    MGSSHHHHHH SSGLVPRGSH MSISRFGVNT ENEDHLAKEL EDLNKWGLNI FNVAGYSHNR
    PLTCIMYAIF QERDLLKTFR ISSDTFITYM MTLEDHYHSD VAYHNSLHAA DVAQSTHVLL
    STPALDAVFT DLEILAAIFA AAIHDVDHPG VSNQFLINTN SELALMYNDE SVLENHHLAV
    GFKLLQEEHC DIFMNLTKKQ RQTLRKMVID MVLATDMSKH MSLLADLKTM VETKKVTSSG
    VLLLDNYTDR IQVLRNMVHC ADLSNPTKSL ELYRQWTDRI MEEFFQQGDK ERERGMEISP
    MCDKHTASVE KSQVGFIDYI VHPLWETWAD LVQPDAQDIL DTLEDNRNWY QSMIPQSPSP
    PLDEQNRDCQ GLMEKFQFEL TLDEEDSEGP EKEGEGHS (SEQ ID NO: 14)
```

PDE4B-S:    5'-CCGAATT CATATG AGCATCTCACGCTTTGGAGTC-3' 34 mer    (SEQ ID NO: 7)
PDE4B-A:    5'-TGTGCT CTCGAG TTA GCTGTGTCCCTCTCCCTCC-3' 34 mer    (SEQ ID NO: 8)
PDE4B-NDE1: 5'-GATATGTCTAAACACATGAGCCTGCTGGC-3' 29 mer              (SEQ ID NO: 9)
PDE4B-NDE2: 5'-GCCAGCAGGCTCATGTGTTTAGACATATC-3' 29 mer              (SEQ ID NO: 10)

pET15S sequence (PCR product; 1159 bp) (SEQ ID NO: 29)
ATATACCATGGGCAGCAGCCATCATCATCATCATCACAGCAGCGGCCTGGTGCCGCGCGGCAGCCATATG
          ag catctcacgc tttggagtca acactgaaaa tgaagatcac
     1261 ctggccaagg agctggaaga cctgaacaaa tggggtctta acatctttaa tgtggctgga
     1321 tattctcaca atagacccct aacatgcatc atgtatgcta tattccagga agagacctc
     1381 ctaaagacat tcagaatctc atctgacaca tttataacct acatgatgac tttagaagac
     1441 cattaccatt ctgacgtggc atatcacaac agcctgcacg ctgctgatgt agcccagtcg
     1501 acccatgttc tcctttctac accagcatta gacgctgtct tcacagattt ggaaatcctg
     1561 gctgccattt ttgcagctgc catccatgac gttgatcatc ctggagtctc aatcagttt
     1621 ctcatcaaca caaattcaga acttgctttg atgtataatg atgaatctgt gttggaaaat TABLE 3-continued PDE4B in pET15S

```
1681 catcaccttg ctgtgggttt caaactgctg caagaagaac actgtgacat cttcatgaat
1741 ctcaccaaga agcagcgtca gacactcagg aagatggtta ttgacatggt gttagcaact
1801 gatatgtcta aacacatgag cctgctggca gacctgaaga caatggtaga aacgaagaaa
1861 gttacaagtt caggcgttct tctcctagac aactataccg atcgcattca ggtccttcgc
1921 aacatggtac actgtgcaga cctgagcaac cccaccaagt ccttggaatt gtatcggcaa
1981 tggacagacc gcatcatgga ggaatttttc cagcagggag acaaagagcg ggagagggga
2041 atggaaatta gcccaatgtg tgataaacac acagcttctg tggaaaaatc ccaggttggt
2101 ttcatcgact acattgtcca tccattgtgg gagacatggg cagatttggt acagcctgat
2161 gctcaggaca ttctcgatac cttagaagat aacaggaact ggtatcagag catgataacc
2221 caaagtccct caccaccact ggacgagcag aacaggact gccagggtct gatggagaag
2281 tttcagtttg aactgactct cgatgaggaa gattctgaag gacctgagaa ggagggagag
2341 ggacacagct aa (NdeI site mutated)
CTCGACTAGAGCCTGCAGTCTCGACCATCATCATCATCATTAATAAAAGGGCGAATTCCAGCACACT
```

TABLE 4

Catalytic domain alignment of PDE4B (SEQ ID NO: 30) and PDE4D (SEQ ID NO: 31) with selectivity sites indicated by filled boxes.

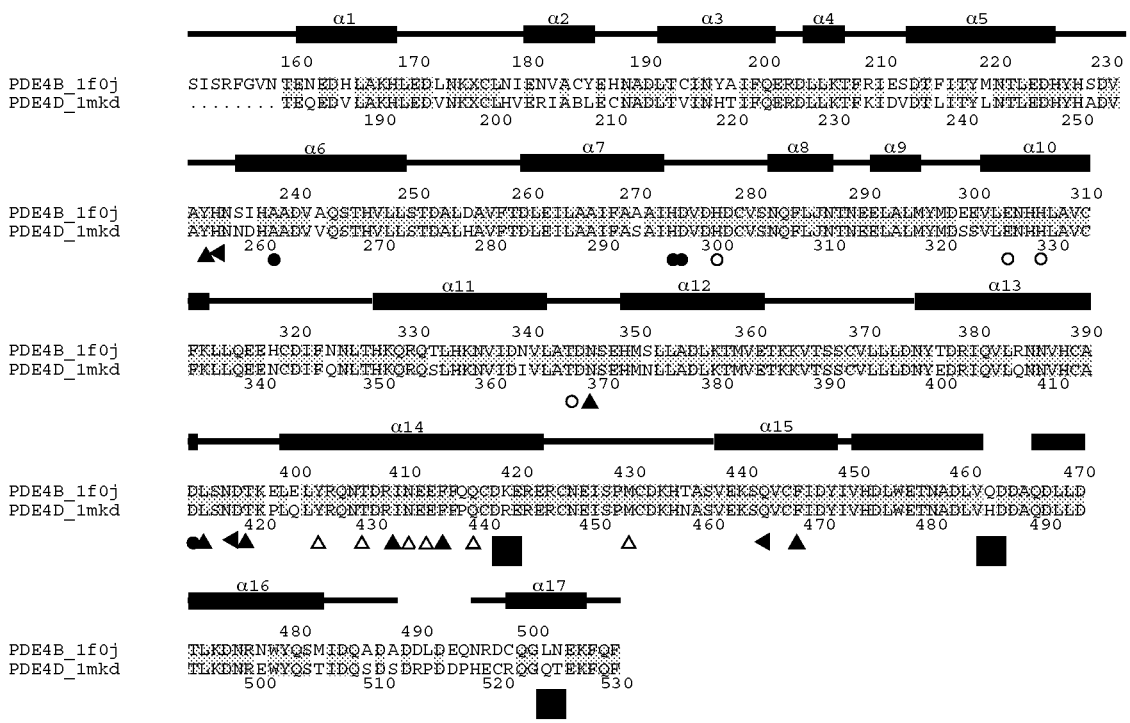

TABLE 5

Activity of the compounds assayed as described in Examples 145-147.

| Compound number | % inhibition rTNFα | hTNFα | PDE4B | PDE4B2 | PDE4D | PDE4D5 |
|---|---|---|---|---|---|---|
| 1 | | + | + | + | + | + |
| 5 | | + | + | + | + | + |
| 7 | + 50 mg/kg po or ip | + | + | + | | + |
| 8 | | + | + | + | | + |
| 9 | | + | + | + | | + |
| 10 | | | + | + | | + |
| 11 | | + | + | + | | + |
| 12 | − | | + | + | | + |
| 13 | | | + | + | | + |
| 14 | + | | + | + | | + |
| 15 | | | + | + | | + |
| 16 | + | | + | + | | + |
| 17 | + | | + | + | + | + |
| 18 | + | | + | + | + | + |
| 19 | | | + | + | | + |
| 21 | + | | + | + | | + |

TABLE 5-continued

Activity of the compounds assayed as described in Examples 145-147.

| Compound number | % inhibition r TNFα | h TNFα | PDE4B | PDE4B2 | PDE4D | PDE4D5 |
|---|---|---|---|---|---|---|
| 24 |  | + | + | + | + | + |
| 25 |  |  | + | + |  | + |
| 26 |  | + | + | + |  | + |
| 27 |  | + | + | + |  | + |
| 28 |  |  | + | + | + | + |
| 29 |  | + | + | + |  | + |
| 30 |  |  | + | + | + | + |
| 31 |  | + | + | + | + | + |
| 32 |  | − | + | + | + | + |
| 33 |  |  | + | + | + | − |
| 34 |  | + | + | + |  | + |
| 35 |  |  | − | − |  | − |
| 36 |  | − | + | + | + | + |
| 37 |  | + | + | + |  | + |
| 38 |  | − | + | + |  | − |
| 39 |  |  | + | + |  | − |
| 40 |  |  | + | + |  | + |
| 41 |  | + | + | + |  | + |
| 42 |  | − | + | + | + | + |
| 43 |  | + | + | + |  | + |
| 45 |  |  | + | + |  | + |
| 46 |  |  | + | + |  | + |
| 48 | + 5 mg/kg po | + | + | + |  | + |
| 50 |  | + | + | + | + | + |
| 51 |  | − | + | + |  | + |
| 52 | + 5 mg/kg po | + | + | + | + | + |
| 53 |  | + | + | + | + | + |
| 54 |  | − | + | + |  | + |
| 55 |  | + | + | + |  | + |
| 56 |  | + | + | + | + | + |
| 57 |  | − | + | + |  | + |
| 58 |  | + | + | + |  | + |
| 59 |  | + | + | + |  | + |
| 60 |  |  | + | + |  | + |
| 61 | + 5 mg/kg po | + | + | + | + | + |
| 62 |  | + | + | + | + | + |
| 63 |  | + | + | + | + | + |
| 64 |  | + | + | + | + | + |
| 65 |  | + | + | + | + | + |
| 66 |  | + | + | + | + | + |
| 67 |  | + | + | + |  | + |
| 68 |  | + | + | + |  | + |
| 69 |  | + | + | + | + | + |
| 70 |  | + | + | + |  | + |
| 72 |  | + | + | + |  | + |
| 73 |  | + | + | + |  | + |
| 74 |  | + | + | + | + | + |
| 75 |  | + | + | + |  | + |
| 76 |  | + | + | + |  | + |
| 77 |  | + | + | + |  | + |
| 78 |  | + | + | + |  | + |
| 79 |  | + | + | + |  | + |
| 80 |  | − | + | + |  | + |
| 82 |  | + | + | + |  | + |
| 83 | + 5 mg/kg po | + | + | + |  | + |
| 84 |  | + |  | + |  | + |
| 86 |  | + |  | + |  | + |
| 87 |  | + |  | + |  | + |
| 88 |  | + | + | + | + | + |
| 89 |  | + |  | + |  | + |
| 90 |  | − | − | − |  | − |
| 91 |  | − | + | + |  | + |
| 92 |  | + |  | + |  | + |
| 93 |  | + | + | + |  | + |
| 94 |  |  |  | + |  | + |
| 95 |  | + | + | + | + | + |
| 96 |  | + | + | + | + | + |
| 97 |  |  | + | + | + | − |
| 98 |  |  |  | + |  | + |
| 99 |  |  | + | + |  | + |
| 100 |  | + | + | + | + | + |
| 101 |  | + | + | + | + | + |
| 102 |  | + | + | + | + | + |
| 103 |  |  | + | + | + | + |
| 104 |  |  | + | + | + | + |
| 105 | + | + | + | + |  | + |
| 106 | + |  | + | + |  | + |
| 107 |  |  | + | + |  | + |
| 108 |  |  | + | + |  | + |
| 109 |  | + | + | + | + | + |
| 110 | + 5 mg/kg po | + | + | + |  | + |
| 111 |  |  | + | + |  | + |
| 112 | + 3 mg/kg po |  | + |  |  | + |
| 113 |  | + | + | + | + | + |
| 114 |  | + | + | + |  | + |
| 115 |  | + | + | + | + | + |
| 116 |  | + | + | + | + | + |
| 117 |  | − | + | + |  | + |
| 118 |  |  |  | + |  | + |
| 119 |  | + |  | + |  | + |
| 120 |  |  |  | + |  | + |
| 121 |  | + |  | + |  | + |
| 122 |  | + |  | + |  | + |
| 123 |  |  |  | + |  | + |
| 124 |  |  | + | + | + | + |
| 125 |  |  |  | + |  | + |
| 126 | + 5 mg/kg po | + | + | + |  | + |
| 127 |  | + | + | + |  | + |
| 128 |  | + |  | + |  | + |
| 129 |  | + |  | + |  | + |
| 130 |  | + |  | + |  | + |
| 131 |  | + |  | + |  | + |
| 132 |  | + |  | + |  | + |
| 135 |  |  |  | + |  |  |
| 136 |  |  |  | + |  | + |
| 137 |  |  |  | + |  | + |
| 138 |  | + |  | + |  | + |
| 139 |  | − |  | + |  | + |
| 140 |  | − |  | + |  | + |
| 141 |  |  |  | + |  | + |
| 142 |  |  | + | − |  | − |
| 143 |  |  | + |  | + |  |
| 144 |  | + | + | + | + | + |
| 145 |  | + | + | + | + | + |

For hTNFα and PDE4 biochemical assays, compounds with IC$_{50}$ of ≦10 μM indicated with +, those with >10 μM with −.
For rTNFa assay, compounds with % inhibition of ≧20% are indicated with +, those with <20% with −.
Cells without + or − were not run in that assay.
Compound numbers are as indicated in the Examples section.

| SEQUENCE IDENTIFICATION NOS. |
| --- |

SEQ ID NO: 1 Phosphodiester PDE4B (GenBank JC1519)

```
  1 mkehggtfss tgisggsgds amdslqplqp nympvclfae esyqklamet leeldwcldq
 61 letiqtyrsv semasnkfkr mlnrelthls emsrsgnqvs eyisntfldk qndveipspt
121 qkdrekkkkq qlmtqisgvk klmhssslnn tsisrfgvnt enedhlakel edlnkwglni
181 fnvagyshnr pltcimyaif qerdllktfr issdtfitym mtledhyhsd vayhnslhaa
241 dvaqsthvll stpaldavft dleilaaifa aaihdvdhpg vsnqflintn selalmynde
301 svlenhhlav gfkllqeehc difmnltkkq rqtlrkmvid mvlatdmskh mslladlktm
361 vetkkvtssg vllldnytdr iqvlrnmvhc adlsnptksl elyrqwtdri meeffqqgdk
421 erergmeisp mcdkhtasve ksqvgfidyi vhplwetwad lvqpdaqdil dtlednrnwy
481 qsmipqspsp pldeqnrdcq glmekfqfel tldeedsegp ekegeghsyf sstktlcvid
541 penrdslget didiatedks pvdt
```

SEQ ID NO:2 Phosphodiester PDE4D (GenBank NP_006194)

```
  1 mmhvnnfpfr rhswicfdvd ngtsagrspl dpmtspgsgl ilqanfvhsq rresflyrsd
 61 sdydlspksm srnssiasdi hgddlivtpf aqvlaslrtv rnnfaaltnl qdrapskrsp
121 mcnqpsinka titeeayqkl asetleeldw cldqletlqt rhsvsemasn kfkrmlnrel
181 thlsemsrsg nqvsefisnt fldkqhevei psptqkekek kkrpmsqisg vkklmhsssl
241 nnssiprfgv kteqedvlak eledvnkwgl hvfriaelsg nrpltvimht ifqerdllkt
301 fkipvdtlit ylmtledhyh advayhnnih aadvvqsthv llstpaleav ftdleilaai
361 fasaihdvdh pgvsnqflin tnselalmyn dssvlenhhl avgfkllqee ncdifqnltk
421 kqrqslrkmv idivlatdms khmnlladlk tmvetkkvts sgvllldnys driqvlqnmv
481 hcadlsnptk plqlyrqwtd rimeeffrqg drerergmei spmcdkhnas veksqvgfid
541 yivhplwetw adlvhpdaqd ildtlednre wyqstipqsp spapddpeeg rqgqtekfqf
601 eltleedges dtekdsgsqv eedtscsdsk tlctqdsest eipldeqvee eavgeeeesq
661 peacviddrs pdt
```

SEQ ID NO:3 Phosphodiester PDE4D (GenBank NP_002591)

```
  1 mkksrsvmtv maddnvkdyf ecslsksyss ssntlgidlw rgrrccsgnl qlpplsqrqs
 61 erartpegdg isrpttlplt tlpsiaittv sqecfdveng pspgrspldp qasssaglvl
121 hatfpghsqr resflyrsds dydlspkams rnsslpseqh gddlivtpfa qvlaslrsvr
181 nnftiltnlh gtsnkrspaa sqppvsrvnp qeesyqklam etleeldwcl dqletiqtyr
241 svsemasnkf krmlnrelth lsemsrsgnq vseyisntfl dkqndveips ptqkdrekkk
301 kqqlmtqisg vkklmhsssl nntsisrfgv ntenedhlak eledlnkwgl nifnvagysh
361 nrpltcimya ifqerdllkt frissdtfit ymmtledhyh sdvayhnslh aadvaqsthv
421 llstpaldav ftdleilaai faaaihdvdh pgvsnqflin tnselalmyn desvlenhhl
481 avgfkllqee hcdifmnltk kqrqtlrkmv idmvlatdms khmslladlk tmvetkkvts
541 sgvllldnyt driqvlrnmv hcadlsnptk slelyrqwtd rimeeffqqg dkerergmei
601 spmcdkhtas veksqvgfid yivhplwetw adlvqpdaqd ildtlednrn wyqsmipqsp
661 sppldeqnrd cqglmekfqf eltldeedse gpekegeghs yfsstktlcv idpenrdslg
721 etdidiated kspvdt
```

SEQ ID NO:4 Phosphodiester PDE4D (GenBank NM_002600)

```
   1 gcggccgcgg cggtgcagca gaggcgcctc gggcaggagg agggcggctt ctgcgagggc
  61 agcctgaggt attaaaaagt gtcagcaaac tgcattgaat aacagacatc ctaagagggg
 121 atattttcca cctctataat gaagaaaagc aggagtgtga tgacggtgat ggctgatgat
 181 aatgttaaag attattttga atgtagcttt agtaaatcct acagttcttc cagtaacaca
 241 cttgggatcg acctctggag agggagaagg tgttgctcag gaaacttaca gttaccacca
 301 ctgtctcaaa gacagagtga aagggcaagg actcctgagg gagatggtat ttccaggccg
 361 accacactgc ctttgacaac gcttccaagc attgctatta caactgtaag ccaggagtgc
 421 tttgatgtgg aaaatggccc ttccccaggt cggagtccac tggatcccca ggccagctct
 481 tccgctgggc tggtacttca cgccaccttt cctgggcaca gccagcgcag agagtcattt
 541 ctctacagat cagacagcga ctatgacttg tcaccaaagg cgatgtcgaa aaactcttct
 601 cttccaagcg agcaacacgg cgatgacttg attgtaactc cttttgccca ggtccttgcc
 661 agcttgcgaa gtgtgagaaa caacttcact atactgacaa accttcatgg tacatctaac
 721 aagaggtccc cagctgctag tcagcctcct gtctccagag tcaacccaca agaagaatct
 781 tatcaaaaat tagcaatgga aacgctggag gaattagact ggtgtttaga coagotagag
 841 accatacaga cctaccggtc tgtcagtgag atggcttcta acaagttcaa aagaatgctg
 901 aaccgggagc tgacacacct ctcagagatg agccgatcag gaaccaggt gtctgaatac
 961 atttcaaata ctttcttaga caagcagaat gatgtggaga tcccatctcc tacccagaaa
1021 gacagggaga aaaagaaaaa gcagcagctc atgacccaga taagtggagt gaagaaatta
1081 atgcatagtt caagcctaaa caatacaagc atctcacgct ttggagtcaa cactgaaaat
1141 gaagatcacc tggccaagga gctggaagac ctgaacaaat ggggtcttaa catctttaat
1201 gtggctggat attctcacaa tagaccccta acatgcatca tgtatgctat attccaggaa
1261 agagacctcc taaagacatt cagaatctca tctgcacacat ttataaccta catgatgact
1321 ttagaagacc attaccattc tgacgtggca tatcacaaca gcctgcacgc tgctgatgta
1381 gcccagtcga cccatgttct cctttctaca ccagcattag acgctgtctt cacagatttg
1441 gagatcctgg ctgccatttt tgcagctgcc atccatgacg ttgatcatcc tggagtctcc
1501 aatcagtttc tcatcaacac aaattcagaa cttgctttga tgtataatga tgaatctgtg
1561 ttggaaaatc atcaccttgc tgtgggtttc aaactgctgc aagaagaaca ctgtgacatc
1621 ttcatgaatc tcaccaagaa gcagcgtcag acactcagga gatggttat tgacatggtg
1681 ttagcaactg atatgtctaa acatatgagc ctgctggcag acctgaagac aatggtagaa
1741 acgaagaaag ttacaagttc aggcgttctt ctcctagaca actataccga tcgcattcag
1801 gtccttcgca acatggtaca ctgtgcagac ctgagcaacc ccaccaagtc cttggaattg
1861 tatcggcaat ggacagaccg catcatggag gaatttttcc agcagggaga caaagagcgg
1921 gagaggggaa tggaaattag cccaatgtgt gataaacaca gcttctgt ggaaaaatcc
1981 caggttggtt tcatcgacta cattgtccat ccattgtggg agacatgggc agatttggta
2041 cagcctgatg ctcaggacat tctcgatacc ttagaagata caggaactg gtatcagagc
```

-continued

| SEQUENCE IDENTIFICATION NOS. |
|---|
| 2101 atgatacctc aaagtccctc accaccactg gacgagcaga acagggactg ccagggtctg |
| 2161 atggagaagt tcagtttga actgactctc gatgaggaag attctgaagg acctgagaag |
| 2221 gagggagagc gacacagota tttcagcagc acaaagacgc tttgtgtgat tgatccagaa |
| 2281 aacagagatt ccctgggaga gactgacata gacattgcaa cagaagacaa gtccccgtg |
| 2341 gatacataat ccccctctcc ctgtggagat gaacattcta tccttgatga gcatgccagc |
| 2401 tatgtggtag ggccagccca ccatgggggc caagacctgc acaggacaag ggccacctgg |
| 2461 cctttcagtt acttgagttt ggagtcagaa agcaagacca ggaagcaaat agcagctcag |
| 2521 gaaatcccac ggttgacttg ccttgatggc aagcttggtg gagagggctg aagctgttgc |
| 2581 tgggggccga ttctgatcaa gacacatggc ttgaaaatgg aagacacaaa actgagagat |
| 2641 cattctgcac taagtttcgg gaacttatcc ccgacagtga ctgaactcac tgactaataa |
| 2701 cttcatttat gaatcttctc acttgtccct ttgtctgcca acctgtgtgc ctttttgta |
| 2761 aaacattttc atgtctttaa aatgcctgtt gaataccctgg agtttagtat caactttctac |
| 2821 acagataagc tttcaaagtt gacaaacttt tttgactctt tctggaaaag ggaaagaaaa |
| 2881 tagtcttcct tctttcttgg gcaatatcct tcacttact acagttactt ttgcaaacag |
| 2941 acagaaagga tacacttcta accacatttt acttccttcc cctgttgtcc agtccaactc |
| 3001 cacagtcact cttaaaactt ctctctgttt gcctgcctcc aacagtactt ttaactttt |
| 3061 gctgtaaaca gaataaaatt gaacaaatta gggggtagaa aggagcagtg gtgtcgttca |
| 3121 ccgtgagagt ctgcatagaa ctcagcagtg tgccctgctg tgtcttggac cctgcaatgc |
| 3181 ggccgc |

SEQ ID NO:5 Phosphodiester PDE4D (GenBank AAB96381)
```
  1 mtakdsskel tasepevcik tfkeqmhlel elprlpgnrp tspkisprss prnspcffrk
 61 llvnksirqr rrftvahtcf dvengpspgr spldpqasss aglvlhatfp ghsqrresfl
121 yrsdsdydls pkamsrnssl pseqhgddli vtpfaqvlas lrsvrnnfti ltnlhgtsnk
181 rspaasqppv srvnpqeesy qklametlee ldwcldqlet iqtyrsvsem asnkfkrmln
241 relthlsems rsgnqvseyi sntfldkqnd veipsptqkd rekkkqqlm tqisgvkklm
301 hssslnntsi srfgvntene dhlakeledl nkwglnifnv agyshnrplt cimyaifqer
361 dllktfriss dtfitymmtl edhyhsdvay hnslhaadva qsthvllstp aldavftdle
421 ilaaifaaai hdvdhpgvsn qflintnsel almyndesvl enhhlavgfk llqeehcdif
481 mnltkkqrqt lrkmvidmvl atdmskhmsl ladlktmvet kkvtssgvll ldnytdriqv
541 lrnmvhcadl snptkslely rqwtdrimee ffqqgdkere rgmeispmcd khtasveksq
601 vgfidyivhp lwetwadlvq pdaqdildtl ednrnwyqsm ipqspsppld eqnrdcqglm
661 ekfqfeltld eedsegpeke geghsyfsst ktlcvidpen rdslgetdid iatedkspvd
721 t
```

SEQ ID NO:6 Phosphodiester PDE4D (AAA35643)
```
  1 itdtssrrgv ggklgtshpr qsttvicspg geswkegasv qimkehggtf sstgisggsg
 61 dsamdslqpl qpnympvclf aeesyqklam etleeldwcl dqletiqtyr svsemasnkf
121 krmlnrelth lsemsrsgnq vseyisntfl dkqndveips ptqkdrekkk qqlmtqisg
181 vkklmhsssl nntsisrfgv ntenedhlak eledlnkwgl nifnvagysh nrpltcimya
241 ifqerdllkt frissdtfit ymmtledhyh sdvayhnslh aadvaqsthv llstpaldav
301 ftdleilaai faaaihdvdh pgvsnqflin tnselalmyn desvlenhhl avgfkllqee
361 hcdifmnltk kqrqtlrkmv idmvlatdms khmslladlk tmvetkkvts sgvllldnyt
421 driqvlrnmv hcadlsnptk slelyrqwtd rimeeffqqg dkerergmei spmcdkhtas
481 veksqvgfid yivhplwetw adlvqpdaqd ildtlednrn wyqsmipqsp sppldeqnrd
541 cqglmekfqf eltldeedse gpekegeghs yfsstktlcv idpenrdslg etdidiated
601 kspvdt
```

---

What is claimed is:

1. A compound having the chemical structure

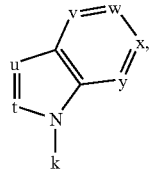

all salts, prodrugs, tautomers and isomers thereof,
wherein:
k is selected from the group consisting of $-CR^6R^7R^{19}$, $-C(Z)R^8$, $-C(Z)NR^{12}R^{13}$, $-S(O)_2NR^{12}R^{13}$, and $-S(O)_2R^{14}$;
Z is O, S, or $NR^9$;
t is CH;
y is N or CH;
one of u, v, w, and x is C-A and the others of u, v, w and x are CH;

A has a structure selected from the group consisting of

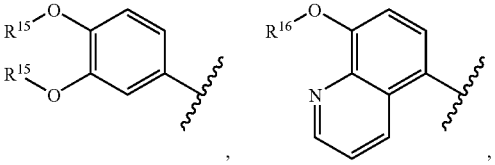

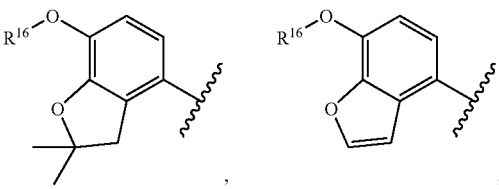

-continued

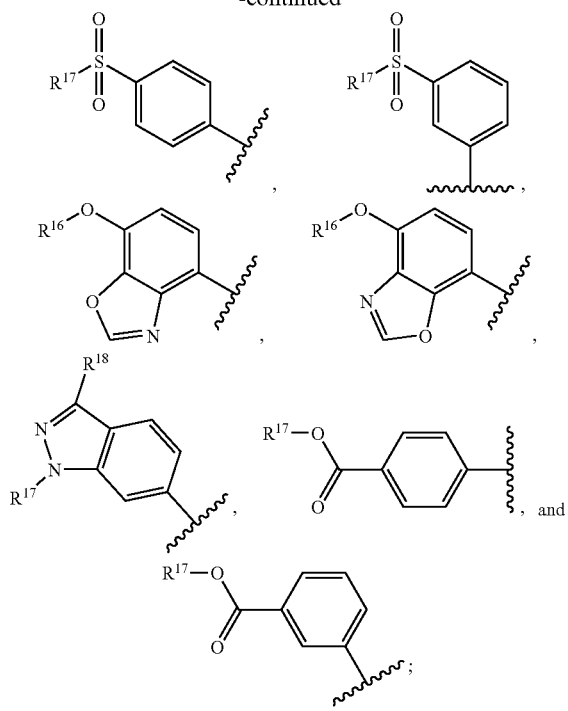

R[6] and R[7] are independently selected from the group consisting of hydrogen, optionally substituted lower alkyl, optionally substituted lower alkenyl, optionally substituted lower alkynyl, optionally substituted cycloalkyl, optionally substituted cycloalkylalkyl, optionally substituted heterocycloalkyl, optionally substituted heterocycloalkylakyl, optionally substituted aryl, optionally substituted aralkyl, optionally substituted heteroaryl, and optionally substituted heteroaralkyl;

R[8] at each occurrence is independently selected from the group consisting of —OR[9], optionally substituted lower alkyl, optionally substituted lower alkenyl, provided, however, that when R[8] is alkenyl, no alkene carbon thereof is bound to C(Z), optionally substituted lower alkynyl, provided, however, that when R[8] is alkynyl, no alkyne carbon thereof is bound to C(Z), optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, and optionally substituted heteroaralkyl;

R[9] at each occurrence is independently selected from the group consisting of hydrogen, optionally substituted lower alkyl, optionally substituted lower alkenyl, provided, however, that when R[9] is alkenyl, no alkene carbon thereof is bound to O, N or S, optionally substituted lower alkynyl, provided, however, that when R[9] is alkynyl, no alkyne carbon thereof is bound to O, N or S, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, and optionally substituted heteroaralkyl;

R[10] and R[11] at each occurrence are independently selected from the group consisting of hydrogen, optionally substituted lower alkyl, optionally substituted lower alkenyl, provided, however, that when R[10] and/or R[11] are alkenyl, no alkene carbon thereof is bound to nitrogen, optionally substituted lower alkynyl, provided, however, that when R[10] and/or R[11] are alkynyl, no alkyne carbon thereof is bound to nitrogen, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, optionally substituted heteroaralkyl, —C(Z)R[8], —C(Z)NR[12]R[13], —S(O)$_2$NR[12]R[13], and —S(O)$_2$R[14]; or R[10] and R[11] together with the nitrogen to which they are attached form a 5-7 membered optionally substituted heterocycloalkyl or optionally substituted heteroaryl ring;

R[12] and R[13] at each occurrence are independently selected from the group consisting of hydrogen, optionally substituted lower alkyl, optionally substituted lower alkenyl, provided, however, that when R[12] and/or R[13] are alkenyl, no alkene carbon thereof is bound to nitrogen, optionally substituted lower alkynyl, provided, however, that when R[12] and/or R[13] are alkynyl, no alkyne carbon thereof is bound to nitrogen, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, and optionally substituted heteroaralkyl; or R[12] and R[13] together with the nitrogen to which they are attached form a 5-7 membered optionally substituted heterocycloalkyl or optionally substituted heteroaryl ring;

R[14] at each occurrence is independently selected from the group consisting of optionally substituted lower alkyl, optionally substituted lower alkenyl, provided, however, that when R[14] is alkenyl, no alkene carbon thereof is bound to —S(O)$_2$—, optionally substituted lower alkynyl, provided, however, that when R[14] is alkynyl, no alkyne carbon thereof is bound to —S(O)$_2$—, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, and optionally substituted heteroaralkyl;

R[15] at each occurrence is independently selected from the group consisting of optionally substituted lower alkyl, optionally substituted lower alkenyl, provided, however, that when R[15] is alkenyl, no alkene carbon thereof is bound to oxygen, optionally substituted lower alkynyl, provided, however, that when R[15] is alkynyl, no alkyne carbon thereof is bound to oxygen, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, optionally substituted heteroaralkyl, —C(Z)R[8], and —C(Z)NR[12]R[13];

R[16] is selected from the group consisting of optionally substituted lower alkyl, optionally substituted lower alkenyl provided, however, that when R[16] is alkenyl, no alkene carbon thereof is bound to oxygen, optionally substituted lower alkynyl provided, however, that when R[16] is alkynyl, no alkyne carbon thereof is bound to oxygen, optionally substituted cycloalkyl, optionally substituted cycloalkylalkyl, optionally substituted heterocycloalkyl, optionally substituted heterocycloalkyl alkyl, optionally substituted aryl, optionally substituted aralkyl, optionally substituted heteroaryl, optionally substituted heteroaralkyl, —C(Z)R⁸, and —C(Z)NR¹²R¹³;

R¹⁷ is selected from the group consisting of optionally substituted lower alkyl, optionally substituted lower alkenyl provided, however, that when R¹⁷ is alkenyl, no alkene carbon thereof is bound to N, O, or S, optionally substituted lower alkynyl, provided, however, that when R¹⁷ is alkynyl, no alkyne carbon thereof is bound to N, O, or S, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, and optionally substituted heteroaralkyl;

R¹⁸ is selected from the group consisting of optionally substituted lower alkyl, optionally substituted lower alkenyl, optionally substituted lower alkynyl, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, optionally substituted heteroaralkyl, —C(Z)R⁸, —OR⁹, —SR⁹, —NR¹⁰R¹¹, —C(Z)NR¹²R¹³, —S(O)₂NR¹²R¹³, and —S(O)₂R¹⁴;

R¹⁹ is selected from the group consisting of optionally substituted lower alkyl, optionally substituted lower alkenyl, optionally substituted lower alkynyl, optionally substituted cycloalkyl, optionally substituted cycloalkylalkyl, optionally substituted heterocycloalkyl, optionally substituted heterocycloalkylalkyl, optionally substituted aryl, optionally substituted aralkyl, optionally substituted heteroaryl, and optionally substituted heteroaralkyl.

2. The compound of claim 1, wherein y is CH.
3. The compound of claim 1, wherein y is N.
4. The compound of claim 3,
wherein k is selected from the group consisting of —CH₂R¹⁹, —C(Z)R⁸, —C(Z)NR¹²R¹³, —S(O)₂NR¹²R¹³, and —S(O)₂R¹⁴;
wherein R⁸, R¹², R¹³, R¹⁴, and R¹⁹ are selected from the group consisting of optionally substituted lower alkyl, aryl and heteroaryl,
wherein aryl and heteroaryl are optionally substituted with 1-3 substituents selected from the group consisting of halogen, optionally substituted lower alkyl, optionally substituted lower alkoxy, optionally substituted lower thioalkyl, optionally substituted aryloxy, optionally substituted heteroaryloxy, optionally substituted amino, optionally substituted carboxyl, optionally substituted alkylsulfonylamino, cyano and nitro.

5. The compound of claim 3, wherein A has the structure

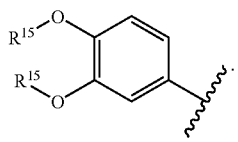

6. The compound of claim 5,
wherein u, w, and x are each CH, and v is C-A, thereby providing a compound having the structure

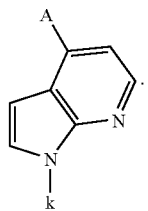

7. The compound of claim 5,
wherein u, v, and x are each CH, and w is C-A, thereby providing a compound having the structure

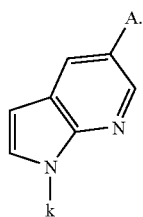

8. The compound of claim 1,
wherein v, w, and x are CH, u is C-A, and y is N; and wherein A has the structure

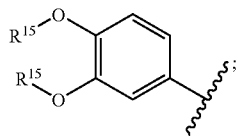

thereby providing a compound having the chemical structure

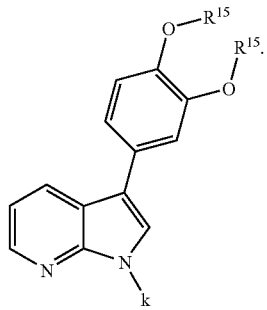

9. The compound of claim 8,
wherein k is selected from the group consisting of —CH₂R¹⁹, —C(Z)R⁸, —C(Z)NR¹²R¹³, —S(O)₂NR¹²R¹³, and —S(O)₂R¹⁴,
wherein R⁸, R¹², R¹³, R¹⁴, and R¹⁹ are selected from the group consisting of optionally substituted lower alkyl, aryl and heteroaryl;
wherein aryl and heteroaryl are optionally substituted with 1-3 substituents selected from the group consisting of halogen, optionally substituted lower alkyl, optionally substituted lower alkoxy, optionally substituted lower thioalkyl, optionally substituted aryloxy, optionally substituted heteroaryloxy, optionally substituted amino, optionally substituted carboxyl, optionally substituted alkylsulfonylamino, cyano and nitro.

10. The compound of claim 9, wherein each occurrence of R¹⁵ is independently selected from the group consisting of optionally substituted lower alkyl, optionally substituted cycloalkyl, optionally substituted heterocycloalkyl, optionally substituted aryl, and optionally substituted heteroaryl.

11. The compound of claim 10, wherein when $R^{15}$ is optionally substituted lower alkyl, the lower alkyl is optionally substituted with 1-3 substituents selected from the group consisting of fluoro, optionally substituted cycloalkyl, optionally substituted heterocycloalkyl, optionally substituted aryl and optionally substituted heteroaryl.

12. A composition comprising:
a compound according to claim 1; and
a pharmaceutically acceptable carrier.

13. A method for treating a subject suffering from or at risk of a disease or condition for which PDE4B modulation provides a therapeutic benefit, said method comprising administering to said patient an effective amount of a compound according to claim 1 wherein said disease or condition is selected from the group consisting of asthma, chronic obstructive pulmonary disease, Alzheimer's disease, diffuse large-cell B cell lymphoma, and chronic lymphocytic leukemia.

14. The method of claim 13, wherein said compound is approved for administration to a human.

15. The method of claim 14, wherein said disease or condition is a PDE4B-mediated disease or condition.

16. A kit comprising a composition of claim 12.

* * * * *

UNITED STATES PATENT AND TRADEMARK OFFICE
CERTIFICATE OF CORRECTION

PATENT NO. : 7,605,168 B2
APPLICATION NO. : 11/219635
DATED : October 20, 2009
INVENTOR(S) : Ibrahim et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 991 days.

Signed and Sealed this

Fifth Day of October, 2010

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,605,168 B2 |
| APPLICATION NO. | : 11/219635 |
| DATED | : October 20, 2009 |
| INVENTOR(S) | : Prabha N. Ibrahim et al. |

It is certified that error appears in the above-identified patent and that said Letters Patent is hereby corrected as shown below:

On the Title Page:

Item "(73) Assignee:    Plexxikon, Inc., Berkeley, CA (US)"

should read

Item --(73) Assignee:    Plexxikon Inc., Berkeley, CA (US)--

Signed and Sealed this
Twenty-ninth Day of May, 2012

David J. Kappos
*Director of the United States Patent and Trademark Office*